US00RE49582E

(19) United States
(12) Reissued Patent
Salituro et al.

(10) Patent Number: US RE49,582 E
(45) Date of Reissued Patent: *Jul. 18, 2023

(54) THERAPEUTIC COMPOUNDS AND COMPOSITIONS

(71) Applicant: Agios Pharmaceuticals, Inc., Cambridge, MA (US)

(72) Inventors: Francesco G. Salituro, Marlborough, MA (US); Jeffrey O. Saunders, Lincoln, MA (US); Shunqi Yan, Irvine, CA (US)

(73) Assignee: AGIOS PHARMACEUTICALS, INC., Cambridge, MA (US)

( * ) Notice: This patent is subject to a terminal disclaimer.

(21) Appl. No.: 17/131,562

(22) Filed: Dec. 22, 2020

Related U.S. Patent Documents

Reissue of:
(64) Patent No.: 8,785,450
Issued: Jul. 22, 2014
Appl. No.: 12/826,630
Filed: Jun. 29, 2010

U.S. Applications:
(60) Provisional application No. 61/292,360, filed on Jan. 5, 2010, provisional application No. 61/221,430, filed on Jun. 29, 2009.

(51) Int. Cl.

| | |
|---|---|
| ***C07D 215/36*** | (2006.01) |
| ***A61K 31/497*** | (2006.01) |
| ***A61K 31/5513*** | (2006.01) |
| ***C07D 215/40*** | (2006.01) |
| ***C07D 239/42*** | (2006.01) |
| ***C07D 241/20*** | (2006.01) |
| ***C07D 243/08*** | (2006.01) |
| ***C07D 271/12*** | (2006.01) |
| ***C07D 277/64*** | (2006.01) |
| ***C07D 277/68*** | (2006.01) |
| ***C07D 295/192*** | (2006.01) |
| ***C07D 319/18*** | (2006.01) |
| ***C07D 401/12*** | (2006.01) |
| ***C07D 401/14*** | (2006.01) |
| ***C07D 403/12*** | (2006.01) |
| ***C07D 407/12*** | (2006.01) |
| ***C07D 409/12*** | (2006.01) |
| ***C07D 417/12*** | (2006.01) |
| ***C07D 417/14*** | (2006.01) |

(52) U.S. Cl.
CPC ..... *C07D 215/36* (2013.01); *A61K 31/497* (2013.01); *A61K 31/5513* (2013.01); *C07D 215/40* (2013.01); *C07D 239/42* (2013.01); *C07D 241/20* (2013.01); *C07D 243/08* (2013.01); *C07D 271/12* (2013.01); *C07D 277/64* (2013.01); *C07D 277/68* (2013.01); *C07D 295/192* (2013.01); *C07D 319/18* (2013.01); *C07D 401/12* (2013.01); *C07D 401/14* (2013.01); *C07D 403/12* (2013.01); *C07D 407/12* (2013.01); *C07D 409/12* (2013.01); *C07D 417/12* (2013.01); *C07D 417/14* (2013.01); *Y02P 20/582* (2015.11)

(58) Field of Classification Search
CPC .. C07D 215/36; C07D 215/40; C07D 239/42; C07D 241/20; C07D 243/08; C07D 271/12; C07D 277/64; C07D 277/68; C07D 295/192; C07D 319/18; C07D 401/12; C07D 401/14; C07D 403/12; C07D 407/12; C07D 409/12; C07D 417/12; C07D 417/14; C07D 405/12; C07D 241/22; A61K 31/497; A61K 31/5513; Y02P 20/582; A61P 9/00; A61P 35/00; A61P 9/10
See application file for complete search history.

(56) References Cited

U.S. PATENT DOCUMENTS

| | | | |
|---|---|---|---|
| 2,390,529 | A | 12/1945 | Friedheim |
| 3,046,122 | A | 7/1962 | Siis et al. |
| 3,097,210 | A | 7/1963 | Bicking |
| 3,755,322 | A | 8/1973 | Winter et al. |
| 3,867,383 | A | 2/1975 | Winter |
| 3,998,828 | A | 12/1976 | Wiedermann |
| 4,084,053 | A | 4/1978 | Desai et al. |
| 4,235,871 | A | 11/1980 | Papahadjopoulos et al. |
| 4,315,940 | A | 2/1982 | Hitzel et al. |
| 4,474,599 | A | 10/1984 | Rogers et al. |
| 4,501,728 | A | 2/1985 | Geho et al. |
| 4,591,548 | A | 5/1986 | Delprato |
| 4,593,102 | A | 6/1986 | Shanklin, Jr. |
| 4,775,762 | A | 10/1988 | Knox et al. |

(Continued)

FOREIGN PATENT DOCUMENTS

| | | | |
|---|---|---|---|
| AU | 2008345225 | A1 | 7/2009 |
| CA | 2235621 | A1 | 5/1997 |

(Continued)

OTHER PUBLICATIONS

Aghili et al., "Hydroxyglutaric aciduria and malignant brain tumor: a case report and literature review", J Neurooncol (2009) 91:233-236.

Anastasiou et al., "Pyruvate kinase M2 activators promote tetramer formation and suppress tumorigenesis," Nat Chem Biol. Oct. 2012; 8(10):839-847.

Ansell et al., "The interactions of artificial coenzymes with alcohol dehydrogenase and other NAD(P)(H) dependent enzymes," Journal of Molecular Catalysis B: Enzymatic (1999) vol. 6, No. 1-2, pp. 111-123.

(Continued)

*Primary Examiner* — Alan D Diamond
(74) *Attorney, Agent, or Firm* — Finnegan, Henderson, Farabow, Garrett & Dunner, LLP

(57) ABSTRACT

Compounds and compositions comprising compounds that modulate pyruvate kinase M2 (PKM2) are described herein. Also described herein are methods of using the compounds that modulate PKM2 in the treatment of cancer.

57 Claims, 70 Drawing Sheets

(56) References Cited

U.S. PATENT DOCUMENTS 4,837,028 A 6/1989 Allen
4,849,424 A 7/1989 Ikeda et al.
4,881,965 A 11/1989 Yamamoto et al.
4,889,553 A 12/1989 Rowson et al.
4,959,094 A 9/1990 Wegner et al.
5,019,369 A 5/1991 Presant et al.
5,021,421 A 6/1991 Hino et al.
5,122,530 A 6/1992 Tomioka et al.
5,180,732 A 1/1993 Tomioka et al.
5,220,028 A 6/1993 Iwasawa et al.
5,252,590 A 10/1993 Tomioka et al.
5,489,591 A 2/1996 Kobayashi et al.
5,556,866 A 9/1996 Aga et al.
5,807,876 A 9/1998 Armistead et al.
5,834,485 A 11/1998 Dyke et al.
5,843,485 A 12/1998 Fernandez et al.
5,962,490 A 10/1999 Chan et al.
5,965,559 A 10/1999 Faull et al.
5,965,569 A 10/1999 Camps Garcia et al.
5,984,882 A 11/1999 Rosenschein et al.
6,020,357 A 2/2000 Pinto et al.
6,106,849 A 8/2000 Malkan et al.
6,150,356 A 11/2000 Lloyd et al.
6,172,005 B1 1/2001 Selby
6,262,113 B1 7/2001 Widdowson et al.
6,265,588 B1 7/2001 Mullner et al.
6,274,620 B1 8/2001 Labrecque et al.
6,313,127 B1 11/2001 Waterson et al.
6,359,134 B1 3/2002 Tawada et al.
6,399,358 B1 6/2002 Williams et al.
6,492,368 B1 12/2002 Dorsch et al.
6,511,977 B1 1/2003 Lloyd et al.
6,515,013 B2 2/2003 Bennani et al.
6,525,091 B2 2/2003 Robinson et al.
6,723,730 B2 4/2004 Bakthavatchalam et al.
6,818,631 B1 11/2004 Nakagawa et al.
6,878,196 B2 4/2005 Harada et al.
6,979,675 B2 12/2005 Tidmarsh
7,173,025 B1 2/2007 Stocker et al.
7,235,664 B2 6/2007 Brendel et al.
7,241,759 B2 7/2007 Allison et al.
7,288,554 B2 10/2007 Finkelstein et al.
7,358,262 B2 4/2008 Stockwell
7,452,888 B2 11/2008 Ahmed et al.
7,524,848 B2 4/2009 Powers et al.
7,572,913 B2 8/2009 McKerracher et al.
7,595,322 B2 9/2009 Morgan et al.
7,615,553 B2 11/2009 Van Emelen et al.
7,820,654 B2 10/2010 Pal et al.
7,858,782 B2 12/2010 Tao et al.
7,863,444 B2 1/2011 Calderwood et al.
8,058,313 B2 11/2011 Reddy et al.
8,133,900 B2 3/2012 Hood et al.
8,258,295 B2 9/2012 Zacharie et al.
8,278,038 B2 10/2012 Bryant et al.
8,465,673 B2 6/2013 Yasuda et al.
8,501,953 B2 8/2013 Salituro et al.
8,603,469 B2 12/2013 Teeling et al.
8,642,660 B2 2/2014 Goldfarb
8,652,534 B2 2/2014 Berry
8,673,891 B2 3/2014 Fujihara et al.
8,735,392 B2 5/2014 Wang et al.
8,742,119 B2 6/2014 Salituro et al.
8,785,450 B2 7/2014 Salituro et al.
8,877,791 B2 11/2014 Cantley et al.
8,883,438 B2 11/2014 Cantley et al.
8,889,667 B2 11/2014 Salituro et al.
9,115,086 B2 8/2015 Salituro et al.
9,150,505 B2 * 10/2015 Yasuda ..... C07D 271/10
9,193,701 B2 11/2015 Su
9,199,968 B2 12/2015 Salituro et al.
9,221,792 B2 12/2015 Salituro et al.
9,328,077 B2 5/2016 Salituro et al.
9,404,081 B2 8/2016 Su
9,434,979 B2 9/2016 Su et al.
9,474,779 B2 10/2016 Lemieux et al.
9,487,815 B2 11/2016 Balss et al.
9,579,324 B2 2/2017 Konteatis et al.
9,662,327 B2 5/2017 Cao et al.
9,682,080 B2 6/2017 Su
9,732,062 B2 8/2017 Cianchetta et al.
9,980,961 B2 5/2018 Su et al.
10,029,987 B2 7/2018 Salituro et al.
10,202,339 B2 2/2019 Popovici-Muller et al.
10,632,114 B2 4/2020 Su et al.
11,234,976 B2 * 2/2022 Agresta ..... A61P 7/06
11,254,652 B2 * 2/2022 Sizemore ..... C07D 215/36
2003/0082877 A1 5/2003 Ootsuka et al.
2003/0095958 A1 5/2003 Bhisetti et al.
2003/0106381 A1 6/2003 Krouth et al.
2003/0109527 A1 6/2003 Jin et al.
2003/0158232 A1 8/2003 Cheng et al.
2003/0187001 A1 10/2003 Calderwood et al.
2003/0207882 A1 11/2003 Stocker et al.
2004/0048283 A1 3/2004 Pau et al.
2004/0067234 A1 4/2004 Einat et al.
2004/0152648 A1 8/2004 Ullrich et al.
2004/0198979 A1 10/2004 Dhanak et al.
2004/0235755 A1 11/2004 Eigenbrodt et al.
2005/0176675 A1 8/2005 Gorny
2007/0032418 A1 2/2007 Shapiro et al.
2007/0032520 A1 2/2007 Vidal et al.
2007/0127505 A1 6/2007 Laurila et al.
2007/0244088 A1 10/2007 Brickmann et al.
2007/0280918 A1 12/2007 Schwartz et al.
2008/0004269 A1 1/2008 Xu et al.
2008/0021116 A1 1/2008 Ullrich et al.
2008/0044833 A1 2/2008 Connors
2008/0051414 A1 2/2008 Hurley et al.
2008/0214495 A1 9/2008 Alstermark et al.
2008/0300208 A1 12/2008 Einat et al.
2009/0048227 A1 2/2009 Chakravarty et al.
2009/0054453 A1 2/2009 Alcaraz et al.
2009/0093526 A1 4/2009 Miller et al.
2009/0163508 A1 6/2009 Kori et al.
2009/0163545 A1 6/2009 Goldfarb
2009/0247499 A1 10/2009 Fletcher et al.
2009/0270454 A1 10/2009 Weingarten et al.
2010/0105657 A1 4/2010 Nordvall et al.
2010/0144722 A1 6/2010 Alexander et al.
2010/0179150 A1 7/2010 Basarab et al.
2010/0273808 A1 10/2010 Armitage et al.
2010/0331307 A1 12/2010 Salituro et al.
2011/0046083 A1 2/2011 Cantley et al.
2011/0224252 A1 9/2011 Dumeunier et al.
2011/0312931 A1 12/2011 Cioffi et al.
2012/0121515 A1 5/2012 Dang et al.
2012/0202818 A1 8/2012 Tao et al.
2012/0238576 A1 9/2012 Tao et al.
2012/0277233 A1 11/2012 Tao et al.
2013/0035329 A1 2/2013 Saunders et al.
2013/0109643 A1 5/2013 Riggins et al.
2013/0184222 A1 7/2013 Popovici-Muller et al.
2013/0197106 A1 8/2013 Fantin et al.
2013/0288284 A1 10/2013 Dang et al.
2014/0187435 A1 7/2014 Dang et al.
2014/0213580 A1 7/2014 Cao et al.
2014/0249150 A1 9/2014 Kung
2014/0323467 A1 10/2014 Salituro et al.
2014/0323729 A1 10/2014 Salituro et al.
2015/0031627 A1 1/2015 Lemieux et al.
2015/0087600 A1 3/2015 Popovici-Muller et al.
2015/0240286 A1 8/2015 Dang et al.
2017/0166541 A1 6/2017 Saunders et al.
2019/0241523 A1 8/2019 Salituro et al.
2019/0345109 A1 11/2019 Salituro et al.
2020/0030322 A1 1/2020 Agresta et al.

FOREIGN PATENT DOCUMENTS

CA 2709784 A1 7/2009
CN 101296909 A 10/2008
CN 101575408 A 11/2009
CN 102481300 A 5/2012

(56) References Cited

FOREIGN PATENT DOCUMENTS

| | | | |
|---|---|---|---|
| CN | 102659765 | A | 9/2012 |
| CN | 103097340 | A | 5/2013 |
| DE | 3314663 | A1 | 10/1983 |
| DE | 3512630 | A1 | 10/1986 |
| DE | 3813886 | A1 | 11/1989 |
| DE | 19841985 | A1 | 3/2000 |
| EP | 0022958 | A1 | 1/1981 |
| EP | 0189069 | A2 | 7/1986 |
| EP | 0246749 | A2 | 11/1987 |
| EP | 0384228 | A1 | 8/1990 |
| EP | 0385237 | A2 | 9/1990 |
| EP | 0628551 | A1 | 12/1994 |
| EP | 0945446 | A1 | 9/1999 |
| EP | 1586558 | A2 | 10/2005 |
| EP | 2219646 | | 8/2010 |
| EP | 2417123 | | 2/2012 |
| EP | 2824099 | A1 | 1/2015 |
| FR | 2735127 | A1 | 12/1996 |
| GB | 1274436 | A | 5/1972 |
| IT | 1176770 | B | 8/1987 |
| JP | S 61129129 | A | 6/1986 |
| JP | H 04099768 | A | 3/1992 |
| JP | H 06-025177 | A | 2/1994 |
| JP | H 07165708 | A | 6/1995 |
| JP | H 9291034 | A | 11/1997 |
| JP | H 11158073 | A | 6/1999 |
| JP | 2002506859 | A | 3/2002 |
| JP | 2002193710 | A | 7/2002 |
| JP | 2004107220 | A | 4/2004 |
| JP | 2004534017 | A | 11/2004 |
| JP | 2006515337 | A | 5/2006 |
| JP | 2007519631 | A | 7/2007 |
| JP | 2007/238458 | A | 9/2007 |
| JP | 2008514590 | A | 5/2008 |
| JP | 4099768 | B2 | 6/2008 |
| JP | 2009237115 | A | 10/2009 |
| JP | 2010506122 | A | 2/2010 |
| JP | 2010079130 | A | 4/2010 |
| JP | 2010181540 | A | 8/2010 |
| JP | 2011507910 | A | 3/2011 |
| JP | 4753336 | B2 | 8/2011 |
| JP | 2012532137 | A5 | 8/2013 |
| JP | 2014509458 | A | 4/2014 |
| JP | 2014509459 | A | 4/2014 |
| JP | 2015028083 | A | 2/2015 |
| TW | 201103913 | A1 | 2/2011 |
| TW | I472522 | B | 2/2015 |
| TW | I598337 | B | 9/2017 |
| WO | 8501289 | A1 | 3/1985 |
| WO | WO 1992011761 | A1 | 7/1992 |
| WO | 93/13072 | A1 | 7/1993 |
| WO | 9630343 | A1 | 10/1996 |
| WO | 97/28129 | A1 | 8/1997 |
| WO | WO 9728128 | A1 | 8/1997 |
| WO | WO 9728141 | A1 | 8/1997 |
| WO | 9744322 | A1 | 11/1997 |
| WO | 98/03350 | A1 | 1/1998 |
| WO | WO 1998002434 | A1 | 1/1998 |
| WO | WO 199916751 | A1 | 4/1999 |
| WO | WO 9932463 | A1 | 7/1999 |
| WO | WO 9947508 | A1 | 9/1999 |
| WO | WO 1999048490 | A1 | 9/1999 |
| WO | WO 99062506 | A1 | 12/1999 |
| WO | WO 0017202 | A1 | 3/2000 |
| WO | 00/53596 | A2 | 9/2000 |
| WO | WO 0107440 | A1 | 2/2001 |
| WO | 0119788 | A2 | 3/2001 |
| WO | WO 2001016097 | A1 | 3/2001 |
| WO | WO 2001019798 | A2 | 3/2001 |
| WO | 0164642 | A2 | 9/2001 |
| WO | 0164643 | A2 | 9/2001 |
| WO | 02/072077 | A2 | 9/2002 |
| WO | 02/095063 | A1 | 11/2002 |
| WO | WO 2002088101 | A2 | 11/2002 |
| WO | 02100822 | A1 | 12/2002 |
| WO | WO 2002102313 | A2 | 12/2002 |
| WO | WO 03016289 | A1 | 2/2003 |
| WO | WO 2003016300 | A1 | 2/2003 |
| WO | 03022277 | A1 | 3/2003 |
| WO | 03037252 | A2 | 5/2003 |
| WO | 03/062235 | A1 | 7/2003 |
| WO | 03/073999 | A2 | 9/2003 |
| WO | WO 03076422 | A1 | 9/2003 |
| WO | WO 2003093297 | A2 | 11/2003 |
| WO | 2004/004730 | A2 | 1/2004 |
| WO | WO 2004009562 | A1 | 1/2004 |
| WO | 2004014851 | A2 | 2/2004 |
| WO | 2004/037251 | A1 | 5/2004 |
| WO | WO 2004046120 | A2 | 6/2004 |
| WO | WO 2004050033 | A2 | 6/2004 |
| WO | 2004/073619 | A2 | 9/2004 |
| WO | 2004/074438 | A2 | 9/2004 |
| WO | WO 2004074288 | A1 | 9/2004 |
| WO | 2004089470 | A2 | 10/2004 |
| WO | 2004/110375 | A2 | 12/2004 |
| WO | WO 2005035507 | A2 | 4/2005 |
| WO | WO 2005060956 | A1 | 7/2005 |
| WO | WO 2005065691 | A1 | 7/2005 |
| WO | WO 2005066126 | A1 | 7/2005 |
| WO | 2005/072642 | A1 | 8/2005 |
| WO | 2005/117591 | A2 | 12/2005 |
| WO | 2005120474 | A2 | 12/2005 |
| WO | 2006/004195 | A1 | 1/2006 |
| WO | 2006/016062 | A1 | 2/2006 |
| WO | 2006033628 | A1 | 3/2006 |
| WO | 2006034341 | A2 | 3/2006 |
| WO | 2006-038594 | A1 | 4/2006 |
| WO | 2006043950 | A1 | 4/2006 |
| WO | 2006052190 | A1 | 5/2006 |
| WO | WO 2006063294 | A2 | 6/2006 |
| WO | 2006070198 | A1 | 7/2006 |
| WO | WO 2006077821 | A1 | 7/2006 |
| WO | WO 2006079791 | A1 | 8/2006 |
| WO | 2006/122546 | A1 | 11/2006 |
| WO | WO 2006117762 | A2 | 11/2006 |
| WO | 2007003934 | A2 | 1/2007 |
| WO | 2007023186 | A1 | 3/2007 |
| WO | WO 2007117465 | A2 | 10/2007 |
| WO | 2007/127505 | A2 | 11/2007 |
| WO | 2008/019139 | A2 | 2/2008 |
| WO | WO 2008024284 | A2 | 2/2008 |
| WO | 2008/026658 | A1 | 3/2008 |
| WO | WO 2008043381 | A1 | 4/2008 |
| WO | WO 2008047198 | A1 | 4/2008 |
| WO | 2008/050168 | A1 | 5/2008 |
| WO | 2008052190 | A2 | 5/2008 |
| WO | 2008073670 | A2 | 6/2008 |
| WO | WO 2008070661 | A1 | 6/2008 |
| WO | WO 2008076883 | A2 | 6/2008 |
| WO | WO 2008131547 | A1 | 11/2008 |
| WO | WO 2008154026 | A1 | 12/2008 |
| WO | 2009012430 | A1 | 1/2009 |
| WO | 2009013126 | A1 | 1/2009 |
| WO | 2009/025781 | A1 | 2/2009 |
| WO | WO 2009016410 | A2 | 2/2009 |
| WO | WO 2009053102 | A1 | 4/2009 |
| WO | WO 2009086303 | A2 | 7/2009 |
| WO | WO 2009118567 | A2 | 10/2009 |
| WO | WO 2009126863 | A2 | 10/2009 |
| WO | WO 2009150248 | A1 | 12/2009 |
| WO | WO 2010007756 | A1 | 1/2010 |
| WO | WO 2010023445 | A1 | 3/2010 |
| WO | WO 2010028099 | A1 | 3/2010 |
| WO | 2010/042867 | A2 | 4/2010 |
| WO | 2010105243 | A1 | 9/2010 |
| WO | 2010118063 | A2 | 10/2010 |
| WO | 2010/129596 | A1 | 11/2010 |
| WO | 2010130638 | A1 | 11/2010 |
| WO | WO 2010144338 | A1 | 12/2010 |
| WO | WO 2010144404 | A1 | 12/2010 |
| WO | 2011002817 | A1 | 1/2011 |
| WO | WO 2011002816 | A1 | 1/2011 |
| WO | WO 2011002817 | A1 | 1/2011 |
| WO | 2011032169 | A2 | 3/2011 |

(56) References Cited

FOREIGN PATENT DOCUMENTS

| | | | |
|---|---|---|---|
| WO | 2011047432 | A1 | 4/2011 |
| WO | WO 2011050210 | A1 | 4/2011 |
| WO | 2011/072174 | A1 | 6/2011 |
| WO | WO 2011109441 | A1 | 9/2011 |
| WO | 2011137089 | A1 | 11/2011 |
| WO | WO 2012009678 | A1 | 1/2012 |
| WO | WO 2012069503 | A1 | 5/2012 |
| WO | WO 2012074999 | A1 | 6/2012 |
| WO | 2012/092442 | A1 | 7/2012 |
| WO | WO 2012151451 | A1 | 11/2012 |
| WO | WO 2012151452 | A1 | 11/2012 |
| WO | WO 2012160034 | A1 | 11/2012 |
| WO | WO 2012171506 | A1 | 12/2012 |
| WO | WO 2013102431 | A1 | 7/2013 |
| WO | WO 2013107291 | A1 | 7/2013 |
| WO | WO 2013107405 | A1 | 7/2013 |
| WO | WO 2013133367 | A1 | 9/2013 |
| WO | WO 2014015422 | A1 | 1/2014 |

OTHER PUBLICATIONS

Benner et al., "Evolution, language and analogy in functional genomics", Trends in Genetics (2001) vol. 17, No. 7, pp. 414-418.
Beutler et al., "Elevated Pyruvate Kinase Activity in Patients with Hemolytic Anemia Due to Red Cell Pyruvate Kinase 'Deficiency'," The American Journal of Medicine (1987) vol. 83, pp. 899-904.
Bhushan et al., "Reversed-phase liquid chromatographic resolution of diastereomers of protein and non-protein amino acids prepared with newly synthesized chiral derivatizing reagents based on cyanuric chloride," Amino Acids (2011) vol. 40, pp. 403-409.
Bleeker et al., "IDH1 Mutations at Residue p. R132 (IDH1 (R132)) Occur Frequently in High-Grade Gliomas But Not in Other Solid Tumors," Human Mutation, (2009), vol. 30, No. 1, pp. 7-11.
Braun et al., "Triazine-based polymers: 4. MALDI-MS of triazine-based polyamines," Polymer (1996) vol. 37, No. 5, pp. 777-783.
Cairns et al., "Oncogenic Isocitrate Dehydrogenase Mutations: Mechanisms, Models, and Clinical Opportunities," Cancer Discovery (2013) vol. 3, Iss. 7, pp. 730-741.
Chan et al., "Multi-domain hydrogen-bond forming metal chelates: X-ray crystal structures of dicyclopalladated 2,3-bis[6-(2-amino-4-phenylamino-1,3,5-triazinyl)]pyrazine(H2L) [Pd2Br2L] and 2,6-bis[6-(2-amino-4-phenylamino-1,3,5-triazinylium)]-pyridine dichloride," Chem. Commun. (1996) No. 1, pp. 81-83.
Chapman et al., "Substituted aminopyrimidine protein kinase B (PknB) inhibitors show activity against *Mycobacterium* tuberculosis," Bioorganic & Medicinal Chemistry Letters 22 (2012), pp. 3349-3353.
Charache et al., "Effect of 2,3-Diphosphoglycerate on Oxygen Affinity of Blood in Sickle Cell Anemia," The Journal of Clinical Investigation (1970) vol. 49, pp. 806-812.
Chen et al., "Cytotoxicity, Hemolysis, and Acute in Vivo Toxicity of Dendrimers Based on Melamine, Candidate Vehicles for Delivery," J. Am. Chem. Soc. (2004) vol. 126, No. 32, pp. 10044-10048.
Chilean Patent Office First Office Action and English Translation for Application No. 3350-2011 dated Feb. 5, 2014.
Chilean Patent Office Second Office Action and English Translation for Application No. 3350-2011 dated Jan. 28, 2015.
Chinese Patent Office Notice on the First Review Opinion and English Translation for Application No. 201080037700.8 dated Jan. 17, 2013.
Chinese Patent Office Notice on the First Review Opinion and English Translation for Application No. 201180068645.3 dated Sep. 2, 2014.
Chinese Patent Office Second Review Opinion Notice and English Translation for Application No. 201180068645.3 dated Jun. 23, 2015.
Cocco et al., "Synthesis of Triflouromethylated Pyridinecarbonitriles," J. Heterocyclic Chem. (1995), vol. 32, pp. 543-545.
Conti et al., "Su alcuni analoghi ossigenati della benzo-tiazine: 2-3-diidro-3-cheto-benzo-1-4-ossazine 6-sostitute," Bollettino Scientifico Della Facolta Di Chimica Industriale Di Bologna (1957) vol. XV, No. 2, pp. 33-36.
Dang et al., "Cancer-associated IDH1 mutations produce 2-hydroxyglutarate," Nature, Dec. 10, 2009, vol. 462, No. 7274, pp. 739-744.
Dang et al., "IDH mutations in glioma and acute myeloid leukemia," Trends in Molecular Medicine (2010) vol. 16, No. 9, pp. 387-397.
Davis et al., "Biochemical, Cellular, and Biophysical Characterization of a Potent Inhibitor of Mutant Isocitrate Dehydrogenase IDH1," The Journal of Biological Chemistry (2014) vol. 289, No. 20, pp. 13717-13725.
Denham et al., "Blood diseases in the elderly," Moscow, Medicine, 1989, Chapter 15.
Docoslis et al., "Characterization of the Distribution, Polymorphism, and Stability of Nimodipine in Its Solid Dispersions in Polyethylene Glycol by Micro-Raman Spectroscopy and Powder X-Ray Diffraction," The AAPS Journal 2007; 9 (3) Article 43, E361-E370.
Dohner et al., "Impact of Genetic Features on Treatment Decisions in AML," American Society of Hematology (2011) pp. 36-42.
Dong et al., "PKM2 and cancer: The function of PKM2 beyond glycolysis," Oncology Letters (2016), 11:1980-1986.
Duanmu et al., "Dendron-Functionalized Superparamagnetic Nanoparticles with Switchable Solubility in Organic and Aqueous Media: Matrices for Homogeneous Catalysis and Potential MRI Contrast Agents," Chem. Mater. (2006) vol. 18, No. 25, pp. 5973-5981.
Ecuador Patent Office Action and English Translation for Application No. SP 2011-11567 dated Apr. 17, 2019.
Egyptian Patent Office Decision and English Translation for Application No. 2011122168 dated Nov. 8, 2017.
Egyptian Patent Office Action and English Translation for Application No. 2011122168 dated Apr. 28, 2019.
European Search Report for European Application No. 10825706.4 dated Apr. 5, 2013.
European Communication pursuant to EP Article 94(3) EPC for European Application No. 10714131.9 dated Oct. 17, 2014.
European Supplementary European Search Report for European Application No. 10825707.2 dated Jun. 28, 2013.
European Patent Office Communication for European Application No. 10794668.3 dated Feb. 26, 2014.
European Patent Office Communication for European Application No. 10794668.3 dated Nov. 18, 2014.
European Patent Office Communication for European Application No. 10794668.3 dated Sep. 16, 2015.
European Search Report for EP Application No. 10751525.6 dated Dec. 14, 2012.
European Search Report for European Application No. 11808773.3 dated Apr. 9, 2014.
European Search Report for European Application No. 11811257.2 dated Apr. 23, 2014.
European Search Report for European Application No. 12799802.9 dated Oct. 9, 2014.
European Search Report for European Application No. 12800001.5 dated Oct. 21, 2014.
European Search Report for EP Application No. 11763425.3 dated Sep. 23, 2013.
Extended European Search Report for European Application No. 07836571.5 dated Oct. 18, 2010.
Extended European Search Report for European Application No. 16152308.9 dated Jul. 18, 2016.
Extended European Search Report for European Application No. 17000407.1 dated Aug. 4, 2017.
Extended European Search Report for European Application No. 20153827.9 dated Jun. 15, 2020.
Ge et al., "Anaplasma phagocytophilum inhibits human neutrophil apoptosis via upregulation of bfl-1, maintenance of mitochondrial membrane potential and prevention of caspase 3 activation," Cellular Microbiology (2005) 7(1), 29-38.

(56) References Cited

OTHER PUBLICATIONS

Genetics Home Reference, "L2HGDH," accessed at <http://ghr.nlm.nih.gov/gene/L2HGDH> on Sep. 4, 2015.
Gewald et al., "Discovery of triazines as potent, selective and orally active PDE4 inhibitors," Bioorganic & Medicinal Chemistry Letters 23 (2013), pp. 4308-4314.
Hartmann et al., "Type and frequency of IDH1 and IDH2 mutations are related to astrocytic and oligodendroglial differentiation and age: a study of 1,010 diffuse gliomas," Acta Neuropathol (2009) 118:469-474.
Holmes et al., "750 MHz $^{1}$H NMR spectroscopy characterisation of the complex metabolic pattern of urine from patients with inborn errors of metabolism: 2-hydroxyglutaric aciduria and maple syrup urine disease," Journal of Pharmaceutical and Biomedical Analysis 15 (1997), pp. 1647-1659.
Indian Patent Office Examination Report for Indian Application No. 471/DELNP/2012 dated Sep. 7, 2018.
Indian Patent Office Hearing Notice for Indian Application No. 471/DELNP/2012 dated Nov. 13, 2019.
Indian First Examination Report for Application No. 201918008568 dated Dec. 26, 2019.
International Preliminary Report on Patentability for PCT/CN2012/000841 dated Dec. 17, 2013.
International Preliminary Report on Patentability for PCT/CN2012/077096 dated Dec. 17, 2013.
International Preliminary Report on Patentability for PCT/US2010/027253 dated Sep. 13, 2011.
International Preliminary Report on Patentability for PCT/US2010/053623 dated Apr. 24, 2012.
International Preliminary Report on Patentability for PCT/US2010/053624 dated Apr. 24, 2012.
International Preliminary Report on Patentability for PCT/US2011/030692 dated Oct. 2, 2012.
International Search Report and Written Opinion for PCT/CN2013/070755 dated Apr. 25, 2013.
International Search Report and Written Opinion for International Application No. PCT/US2013/064601 dated Feb. 24, 2014.
International Search Report and Written Opinion for International Application No. PCT/CN2013/080105 dated Jul. 11, 2014.
International Search Report and Written Opinion for International Application No. PCT/CN2013/081170 dated Apr. 30, 2014.
International Search Report and Written Opinion for International Application No. PCT/CN2014/081957 dated Sep. 30, 2014.
International Search Report and Written Opinion for International Application No. PCT/CN2014/081958 dated Sep. 29, 2014.
International Search Report and Written Opinion for International Application No. PCT/US2015/020349 dated Jun. 15, 2015.
International Search Report and Written Opinion for International Application No. PCT/US2012/036412 dated Jul. 6, 2012.
International Search Report and Written Opinion for International Application No. PCT/US2012/036413 dated Jul. 6, 2012.
International Search Report and Written Opinion for International Application No. PCT/US2014/046202 dated Sep. 30, 2014.
International Search Report and Written Opinion for International Application No. PCT/US2014/049469 dated Jan. 22, 2015.
International Search Report and Written Opinion for International Application No. PCT/US2015/020346 dated Jun. 18, 2015.
International Search Report for International Application No. PCT/CN2013/079184 dated Jan. 12, 2015.
International Search Report for International Application No. PCT/CN2013/079200 dated Jan. 12, 2015.
International Search Report and Written Opinion for International Application No. PCT/CN2014/082869 dated Sep. 30, 2014.
International Search Report for International Application No. PCT/US2014/046204 dated Oct. 1, 2014.
International Search Report for PCT/CN2012/000841 dated Sep. 27, 2012.
International Search Report for PCT/CN2012/077096 dated Oct. 4, 2012.
International Search Report and Written Opinion for PCT/CN2013/000009 dated Apr. 18, 2013.
International Search Report for PCT/CN2013/000068 dated Apr. 25, 2013.
International Search Report for PCT/US2011/030692 dated Jun. 27, 2011.
International Search Report for PCT/US2010/027253 dated Aug. 19, 2010.
International Search Report for PCT/US2010/53623 dated Jan. 18, 2011.
International Search Report and Written Opinion for PCT/US2010/053624 dated Apr. 7, 2011.
International Search Report and Written Opinion for PCT/US2011/044254 dated Oct. 5, 2011.
Irikura et al., "New s-Triazine Derivatives as Depressants for Reticuloendothelial Hyperfunction Induced by Bacterial Endotoxin," Journal of Medicinal Chemistry (1970) vol. 31, pp. 1081-1089.
Japanese Patent Office Notification of Reasons for Rejection and English Translation for Application No. 2012-518591 dated Aug. 1, 2014.
Japanese Patent Office Decision of Rejection and English Translation for Application No. 2012-518591 dated Apr. 30, 2015.
Jennings et al., "Expression and Mutagenesis of Mammalian Cytosolic NADP+-Specific Isocitrate Dehydrogenase," Biochemistry (1997) vol. 36, pp. 13743-13747.
Kaila et al., "A convenient one-pot synthesis of trisubstituted 1,3,5-triazines through intermediary amidinothioureas," Tetrahedron Letters 51 (2010) pp. 1486-1489.
Kelarev et al., "Synthesis and properties of sym-triazines. 10 Synthesis of 2,4-diamino-sym-triazines containing a sterically hindered phenol substituent," Chemistry of Heterocyclic Compounds (1992) vol. 28, No. 10, pp. 1189-1193.
Kim et al., "Ser$^{95}$, Asn$^{97}$, and Thr$^{78}$ are important for the catalytic function of porcine NADP-dependent isocitrate dehydrogenase," Protein Science (2005) 14:140-147.
Kim et al., "Identification and Functional Characterization of a Novel, Tissue-specific NAD+-dependent Isocitrate Dehydrogenase β Subunit Isoform," The Journal of Biological Chemistry, Dec. 24, 1999, vol. 274, No. 52, p. 36866-36875.
Koshelev et al.,"Synthesis of N-Substituted 2,4-Diamino-1,3,5-triazines Containing Pyridyl Groups," Russian Journal of Organic Chemistry (1995) vol. 31, No. 2, pp. 260-263.
Kranendijk et al., "IDH2 Mutations in Patients with D-2-Hydroxyglutaric Aciduria," Science (2010) vol. 330, p. 336.
Krell et al., "IDH mutations in tumorigenesis and their potential role as novel therapeutic targets," Future Oncol. (2013) 9(12), pp. 1923-1935.
Kung, Charles et al., "AG-348 Activation of Pyruvate Kinase in Vivo Enhances Red Cell Glycolosis in Mice," Database Biosis [Online], database accession No. PREV201500280942, vol. 124, No. 21, 56th Annual Meeting of the American-Society-of-Hematology, San Francisco, CA, 2014.
Kusakabe et al., Chemical Abstracts vol. 152, No. 191956, Abstract for WO2010007756 (2010).
Lee et al., "Combinatorial Solid-Phase Synthesis of 6-Aryl-1,3,4-triazines via Suzuki Coupling," Aust. J. Chem. (2011) 64, pp. 540-544.
Liu et al., "Inhibition of Cancer-Associated Mutant Isocitrate Dehydrogenases: Synthesis, Structure—Activity Relationship, and Selective Antitumor Activity," J. Med. Chem. (2014), vol. 57, pp. 8307-8318.
Lou, "IDH1: function follows form," SciBX, 2009, pp. 1-2.
Luo et al., "Synthesis and Fungicidal Activity of N-Benzo[b][1,4]oxazin-6-y1-2,4-dimethylthiazole-5-carboxamides," Agrochemicals (2009) vol. 48, No. 1, pp. 19-22.
Lutker et al., "Crystal Polymorphism in a Carbamazepine Derivative: Oxcarbazepine," NIH Public Access, J Pharm Sci. Feb. 2010; 99(2): 794-803. doi:10.1002/jps.21873.
Madsen-Duggan et al., "Lead optimization of 5,6-diarylpyridines as CB1 receptor inverse agonists," Bioorganic & Medicinal Chemistry Letters 17 (2007) pp. 2031-2035.
Marry et al., "Human Biochemistry," Moscow, Mir, 1993, Chapter 18.

(56) References Cited

OTHER PUBLICATIONS

May, "How Many Species Are There on Earth," Science (1988) vol. 241, p. 1441.
Moreno et al., "Identification of diamine linkers with differing reactivity and their application in the synthesis of melamine dendrimers," Tetrahedron Letters 49 (2008), pp. 1152-1154.
Moreno et al., "Molecular recognition in dendrimers based on melamine," Polymer Preprints (2005) vol. 46, No. 2, p. 1127.
Morshed et al., "Computational approach to the identification of novel Aurora-A inhibitors," Bioorganic & Medicinal Chemistry (2011) vol. 19, No. 2, pp. 907-916.
Pan et al., "Research Status of Pyruvate Deficiency," Chinese Journal of Hematology (1999) vol. 20, No. 4, pp. 223.
Paraguay Office Action and English Translation for Application No. 25374/2010 dated Sep. 18, 2019.
Paronikyan et al., "Synthesis and biological activity of 3-piperazinyl-substituted pyrano [3,4-C] pyridines," Armyanskii Khimicheskii Zhurnal (1990) vol. 43, No. 8, pp. 518-523.
Parsons et al., "An Integrated Genomic Analysis of Human Glioblastoma Multiforme," Science, vol. 321 (2008) pp. 1807-1812 and Supplemental Data.
Petz et al., "Increased IgG Molecules Bound to the Surface of Red Blood Cells of Patients With Sickle Cell Anemia," Blood (1984) vol. 64, No. 1, pp. 301-304.
Pollard et al., "Cancer. Puzzling patterns of predisposition," Science, Apr. 10, 2009, vol. 324, 1-5, 15-16, 18-22, 35-38, No. 5924, pp. 192-194.
Popovici-Muller, Janeta et al., "Discovery of the First Potent Inhibitors of Mutant IDH1 That Lower Tumor 2-HG in Vivo," ACS Medicinal Chemistry Letters, Sep. 17, 2012, vol. 3, No. 10, pp. 850-855.
Pubchem CID 4078245 [online]; Sep. 13, 2005 [retrieved on Feb. 4, 2012]; retrieved from http://pubchem.ncbi.nlm.nih.gov/; 2d-structure.
Pubchem CID 4854170 [online]; Sep. 17, 2005 [retrieved on Feb. 4, 2012]; retrieved from http://pubchem.ncbi.nlm.nih.gov/; 2d-structure.
Rao et al., "Polymorphism in Drugs and its Significance in Therapeutics," Journal of Scientific & Industrial Research, vol. 46, Oct. 1987, pp. 450-455.
Raynaud et al., "Absence of R140Q mutation of isocitrate dehydrogenase 2 in gliomas and breast cancers," Oncology Letters (2010) vol. 1, No. 5, pp. 883-884.
Registry (STN) [online], Aug. 23, 2006 [Retrieved on Jan. 29, 2016] CAS Registration No. 903862-76-0.
Registry (STN) [online], Aug. 23, 2006 [Retrieved on Jan. 29, 2016] CAS Registration No. 903869-26-1.
Registry (STN) [online], Apr. 13, 2007 [Retrieved on Jan. 29, 2016] CAS Registration No. 929819-92-1.
Registry (STN) [online], Apr. 13, 2007 [Retrieved on Jan. 29, 2016] CAS Registration No. 929971-43-7.
Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Reitman et al., "Isocitrate Dehydrogenase 1 and 2 Mutations in Cancer: Alterations at a Crossroads of Cellular Metabolism," Journal of the National Cancer Institute (2010), vol. 102, No. 13, pp. 932-941.
Rohle et al., "An Inhibitor of Mutant IDH1 Delays Growth and Promotes Differentiation of Glioma Cells," Science (2013), vol. 340, No. 6132, pp. 626-630.
Scharn et al., "Spatially Addressed Synthesis of Amino- and Amino-Oxy-Substituted 1,3,5-Triazine Arrays on Polymeric Membranes," J. Comb. Chem. (2000) vol. 2, No. 4, pp. 361-369.
Shih et al., "The role of mutations in epigenetic regulators in myeloid malignancies," Nature Reviews Cancer (2012) vol. 12, No. 9, pp. 599-612.
Sirakanyan, S.N. et al., "Synthesis of new derivatives of piperazine-substituted pyrano[3,4-c]pyridines," Hayastani Kimiakan Handes 2009, vol. 62, No. 3-4, pp. 378-385. English Abstract Only.
Sonoda et al., "Analysis of IDH1 and IDH2 mutations in Japanese glioma patients," Cancer Science (2009), vol. 100, No. 10, pp. 1996-1998.
Sosnovik et al., "Emerging concepts in molecular MRI," Current Opinion in Biotechnology 2007, 18:4-10.
Steiner et al., "Synthesis and Antihypertensive Activity of New 6-Heteroaryl-3-hydrazinopyridazine Derivatives," J. Med. Chem. (1981), vol. 24, No. 1, pp. 59-63.
STN File CA, Registry No. 134538-28-6, entered STN on Jun. 28, 1991, Chemical Abstracts Index Name "1H-Pyrano[3,4-c]pyridine-5-carbonitrile,3,4-dihydro-3,3-dimethyl-6-[4-(1-oxobutyl)-1-piperazinyl]-8-phenyl-", disclosed in Paronikyan et al. Armyanskii Khimicheskii Zhurnal, 1990, vol. 43, No. 8.
STN File CA, Registry No. 134538-29-7, entered STN on Jun. 28, 1991, Chemical Abstracts Index Name "1H-Pyrano[3,4-c]pyridine-5-carbonitrile,3,4-dihydro-3,3-dimethyl-6-[4-(2-methyl-1-oxopropyl)-1-piperazinyl]-8-phenyl-", disclosed in Paronikyan et al. Armyanskii Khimicheskii Zhurnal, 1990, vol. 43, No. 8.
STN File CA, Registry No. 134538-30-0, entered STN on Jun. 28, 1991, Chemical Abstracts Index Name "1H-Pyrano[3,4-c]pyridine-5-carbonitrile,6-(4-benzoyl-1-piperazinyl)-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 134538-31-1, entered STN on Jun. 28, 1991, Chemical Abstracts Index Name "1H-Pyrano[3,4-c]pyridine-5-carbonitrile,6-[4-(2-furanylcarbonyl)-1-piperazinyl]-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 321433-63-0, entered STN on Feb. 12, 2001, Chemical Abstracts Index Name "1H-Pyrrole-2-sulfonamide, 1-[3-chloro-5-(trifluoromethyl)-2-pyridinyl]-N-phenyl" Available through Key Organics (under the Bionet brand) Jan. 1994.
STN File CA, Registry No. 321433-64-1, entered STN on Feb. 12, 2001, Chemical Abstracts Index Name "1H-Pyrrole-2-sulfonamide, 1-[3-chloro-5-(trifluoromethyl)-2-pyridinyl]-N-(4-methphenyl)" Available through Key Organics (under the Bionet brand) Jan. 1994.
STN File CA, Registry No. 321433-65-2, entered STN on Feb. 12, 2001, Chemical Abstracts Index Name "1H-Pyrrole-2-sulfonamide, 1-[3-chloro-5-(trifluoromethyl)-2-pyridinyl]-N-(3,5-dimethylphenyl)" Available through Key Organics (under the Bionet brand) Jan. 1994.
STN File CA, Registry No. 321433-66-3, entered STN on Feb. 12, 2001, Chemical Abstracts Index Name "1H-Pyrrole-2-sulfonamide, 1-[3-chloro-5-(trifluoromethyl)-2-pyridinyl]-N-(4-methoxyphenyl)" Available through Key Organics (under the Bionet brand) Jan. 1994.
STN File CA, Registry No. 321433-68-5, entered STN on Feb. 12, 2001, Chemical Abstracts Index Name "1H-Pyrrole-2-sulfonamide, 1-[3-chloro-5-(trifluoromethyl)-2-pyridinyl]-N-propyl" Available through Key Organics (under the Bionet brand) Jan. 1994.
STN File CA, Registry No. 321433-69-6, entered STN on Feb. 12, 2001, Chemical Abstracts Index Name "1H-Pyrrole-2-sulfonamide, 1-[3-chloro-5-(trifluoromethyl)-2-pyridinyl]-N-(2-methoxyethyl)" Available through Key Organics (under the Bionet brand) Jan. 1994.
STN File CA, Registry No. 338397-92-5, entered STN on May 25, 2001, Chemical Abstracts Index Name "1H-Pyrrole-2-sulfonamide, 1-[3-chloro-5-(trifluoromethyl)-2-pyridinyl]-N,N-dimethyl" Available through Key Organics (under the Bionet brand) Feb. 1993.
STN File CA, Registry No. 338397-95-8, entered STN on May 25, 2001, Chemical Abstracts Index Name "1H-Pyrrole-2-sulfonamide, N-[(4-chlorophenyl)-1-[3-chloro-5-(trifluoromethyl)-2-pyridinyl]" Available through Key Organics (under the Bionet brand) Feb. 1993.
STN File CA, Registry No. 338397-96-9, entered STN on May 25, 2001, Chemical Abstracts Index Name "1H-Pyrrole-2-sulfonic acid, 1-[3-chloro-5-(trifluoromethyl)-2-pyridinyl]-4-chlorophenyl ester" Available through Key Organics (under the Bionet brand) Feb. 1993.
STN File CA, Registry No. 338406-58-9, entered STN on May 25, 2001, Chemical Abstracts Index Name "1H-Pyrrole-2-sulfonamide,

(56) References Cited

OTHER PUBLICATIONS

1-[3-chloro-5-(trifluoromethyl)-2-pyridinyl]-N-[2-(trifluoromethyl)phenyl]" Available through Key Organics (under the Bionet brand) Mar. 1993.
STN File CA, Registry No. 338406-64-7, entered STN on May 25, 2001, Chemical Abstracts Index Name "1H-Pyrrole-2-sulfonamide, 1-[3-chloro-5-(trifluoromethyl)-2-pyridinyl]-N-(3-pyridinylmethyl)" Available through Key Organics (under the Bionet brand) Mar. 1993.
STN File CA, Registry No. 338406-72-7, entered STN on May 25, 2001, Chemical Abstracts Index Name "1H-Pyrrole-2-sulfonamide, N-[(4-chlorophenyl)methyl]-1-[3-chloro-5-(trifluoromethyl)-2-pyridinyl]" Available through Key Organics (under the Bionet brand) Mar. 1993.
STN File CA, Registry No. 338407-11-7, entered STN on May 25, 2001, Chemical Abstracts Index Name "1H=Pyrrole-2-sulfonamide, 1-[3-chloro-5-(trifluoromethyl)-2-pyridinyl]-N-[3-chloro-4-[[5-(trifluoromethyl)-2-pyridinyl]oxy]phenyl]" Available through Key Organics (under the Bionet brand) Mar. 1993.
STN File CA, Registry No. 338407-13-9, entered STN on May 25, 2001, Chemical Abstracts Index Name "Benzoic acid, 3-[[[1-[3-chloro-5-(trifluoromethyl)-2-pyridinyl]-1H-pyrrol-2-yl]sulfonyl]amino]" Available through Key Organics (under the Bionet brand) Mar. 1993.
STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".
STN Registry, L23 Answer 2 of 3 (Cas No. 1032450-21-7), Database: ASINEX Ltd., Entered STN: Jul. 3, 2008 (Jul. 3, 2008).
STN Registry. L23 Answer 1 of 3 (Cas No. 1038821-72-5), Database: ChemDB (University of California Irvine), Entered STN: Aug. 5, 2008 (Aug. 5, 2008).
STN Tokyo, Registry No. 1001833-18-6, Entered STN on Feb. 6, 2008, Chemical Abstracts Index Name "1,4-Benzodioxin-6-sulfonamide, 2,3-dihydro-N-[4- [(4-methyl-1-piperazinyl)carbonyl]phenyl]--".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4- [[4-[(5-methyl-3-isoxazolyl)methyl]-1-piperazinyl]carbonyl]phenyl]-".
STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4- [[4-(2-pyridinyl)-1-piperazinyl]carbonyl]phenyl]-".
STN Tokyo, Registry No. 1240875-00-6, entered STN on Sep. 14, 2010, Chemical Abstracts Index Name "1,4-Benzodioxin-6-sulfonamide, 2,3-dihydro-N-[4-[[4-(2-thiazolyl)-1-piperazinyl] carbonyl]phenyl]-".
STN Tokyo, Registry No. 748791-86-8, Entered STN on Sep. 21, 2004, Chemical Abstracts Index Name "1,4-Benzodioxin-6-sulfonamide, N-[4- [[4-(2-furanylcarbonyl)-1-piperazinyl]carbonyl]phenyl]-2,3-dihydro-".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".
STN Tokyo, Registry No. 878474-39-6, Entered STN on Mar. 29, 2006, Chemical Abstracts Index Name "1,4-Benzodioxin-6-sulfonamide, 2,3-dihydro-N-[4[(4-phenyl-1-piperazinyl)carbonyl]phenyl]-".
STN Tokyo, Registry No. 878590-33-1, Entered STN on Mar. 30, 2006, Chemical Abstracts Index Name "1,4-Benzodioxin-6-sulfonamide, 2,3-dihydro-N-[4-{{4-(tetrahydro-2-furanyl)methyl]-1-piperazinyl]carbonyl]phenyl]-".
STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl)carbonyl]phenyl]-".
STN Tokyo, Registry No. 878956-06-0, Entered STN on Apr. 2, 2006, Chemical Abstracts Index Name "1,4-Benzodioxin-6-sulfonamide, N-[4- [[4-(cyclopropylcarbonyl)-1-piperazinyl]carbonyl]phenyl]-2,3 -dihydro-".
STN Tokyo, Registry No. 920679-46-5, Entered STN on Feb. 13, 2007, Chemical Abstracts Index Name "1,4-Benzodioxin-6-sulfonamide, 2,3-dihydro-N-[4- [[4-(4-pyridinyl)-1-piperazinyl]carbonyl]phenyl]-".
STN Tokyo, Registry No. 920822-52-2, Entered STN on Feb. 14, 2007, Chemical Abstracts Index Name "1,4-Benzodioxin-6-sulfonamide, N-[4- [[4-(4-fluoropheyl)-1-piperazinyl]carbonyl]phenyl]-2,3dihydro-".
STN Tokyo, Registry No. 920824-56-2, Entered STN on Feb. 14, 2007, Chemical Abstracts Index Name "1,4-Benzodioxin-6-sulfonamide, 2,3-dihydro-N-[4- [[4-(3-thienylmethyl)-1-piperazinyl]carbonyl]phenyl]-".
STN Tokyo, Registry No. 920847-34-3, Entered STN on Feb. 14, 2007, Chemical Abstracts Index Name "1,4-Benzodioxin-6-sulfonamide, 2,3-dihydro-N-[4- [[4-(2-methylphenyl)-1-piperazinyl]carbonyl]phenyl]-".
STN Tokyo, Registry No. 920875-39-4, Entered STN on Feb. 14, 2007, Chemical Abstracts Index Name "1,4-Benzodioxin-6-sulfonamide, 2,3-dihydro-N-[4- [[4-(2-hydroxyphenyl)-1-piperazinyl]carbonyl]phenyl]-".
STN Tokyo, Registry No. 920902-88-1, Entered STN on Feb. 14, 2007, Chemical Abstracts Index Name "1,4-Benzodioxin-6-sulfonamide, 2,3-dihydro-N-[4- [[4-(2-thienylmethyl)-1-piperazinyl]carbonyl]phenyl]-".
STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]-".
STN Tokyo, Registry No. 920924-42-1, Entered STN on Feb. 14, 2007, Chemical Abstracts Index Name "1,4-Benzodioxin-6-sulfonamide, 2,3-dihydro-N-[4- [[4-(2-pyridinylmethyl)-1-piperazinyl]carbonyl]phenyl]-".
STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-1-piperazinyl)carbonyl]phenyl]-".
Struys et al., Investigations by mass isotopomer analysis of the formation of D-2-hydroxyglutarate by cultured lymphoblasts from two patients with D-2-hydroxyglutaric aciduria, FEBS Letters 557 (2004), pp. 115-120.
Struys et al., "Mutations in the D-2-Hydroxyglutarate Dehydrogenase Gene Cause D-2-Hydroxyglutaric Aciduria," Am. J. Hum. Genet. (2005), 76:358-360.
Struys, et al., "Measurement of Urinary D- and L-2-Hydroxyglutarate Enantiomers by Stable-Isotope-Dilution Liquid Chromatography-Tandem Mass Spectrometry after Derivatization with Diacetyl-L-Tartaric Anhydride," Clinical Chemistry (2004), 50:8, pp. 1391-1395.
Takagi et al., "Synthesis of poly(triazinylstyrene) containing nitrogen-based ligand and function as metal ion adsorbent and oxidation catalyst," Reactive & Functional Polymers 66 (2006) vol. 31, pp. 1718-1724.
The radiation fact sheet published by the National Cancer Institute, http://www.cancer.gov/about-cancer/treatment/types/radiation-therapy/radiation-fact-sheet, reviewed Jun. 30, 2010.
Thompson, "Metabolic Enzymes as Oncogenes or Tumor Suppressors," The New England Journal of Medicine, Feb. 19, 2009, vol. 360, No. 8, pp. 813-815, col. 1; Fig. 1.
Tsujino, Kumiko et al., "CBA-Pk-$1^{slc}$/Pk-$1^{slc}$ mutant mouse in Newborn period does not exhibit hemolytic anemia," Japanese Society of Animal Models for Human Diseases, 1998, vol. 14, p. 24.
Van Emelen et al., Caplus am 2003:737742.

(56) References Cited

OTHER PUBLICATIONS

Van Schaftingen, et al., "L-2-Hydroxyglutaric aciduria, a disorder of metabolite repair," J Inherit. Metab. Dis. (2009) vol. 32, pp. 135-142.
Wang et al., "Facile Synthesis of 2,4-Diamino-6-alkyl- or 6-Aryl-Pyrimidine Derivatives," J. Heterocyclic Chem. (2010) vol. 47 pp. 1056-1061.
Wang et al., "A novel ligand N,N'-di(2-pyridyl)-2,4-diamino-6-phenyl-1,3,5-triazine (dpdapt) and its complexes: [Cu(dpdapt)$Cl_2$] and [Cu(dpdapt)($NO_3$)($H_2O$)] $NO_3$ $H_2O$," Polyhedron (2006) vol. 25, Issue 1, pp. 195-202.
Ward et al., "The Common Feature of Leukemia-Associated IDH1 and IDH2 Mutations Is a Neomorphic Enzyme Activity Converting [alpha]-Ketoglutarate to 2-Hydroxyglutarate," Cancer Cell (2010), vol. 17, No. 3, pp. 225-234.
Watanabe et al., "IDH1 Mutations Are Early Events in the Development of Astrocytomas and Oligodendrogliomas," The American Journal of Pathology, Apr. 2009 (published online Feb. 26, 2009, vol. 174, No. 4, pp. 1149-1153; Abstract, p. 1150, col. 1.
Wong et al., "PKM2, a Central Point of Regulation in Cancer Metabolism," International Journal of Cell Biology (2013), vol. 2013, pp. 1-11.
Written Opinion for PCT/US2010/027253 dated Aug. 19, 2010.
Written Opinion of Search Authority for PCT/US2010/53623 dated Jan. 18, 2011.
Written Opinion of the International Searching Authority for PCT/US2011/067752 dated Mar. 5, 2012.
Yamaoka, Takashi, Adenosine deaminase hyperkinasia, Nihon Rinsho (supplementary volume) series of Syndrome for each area 20 Blood Syndrome I, Aug. 12, 1998, p. 308-311.
Yang, Hua et al., "Phase I Single (SAD) and Multiple Ascending Dose (MAD) Studies of the Safety, Tolerability, Pharmacokinetics (PK) and Pharmacodynamics (PD) of AG-348, a First-in-Class Allosteric Activator of Pyruvate Kinase-R, in Healthy Subjects," Database Biosis [Online], database accession No. PREV201500280858, vol. 124, No. 21, 56$^{th}$ Annual Meeting of the American-Society-of-Hematology, San Francisco, CA, 2014.
Zhao et al., "Glioma-Derived Mutations in IDH1 Dominantly Inhibit IDH1 Catalytic Activity and Induce HIF-1alpha," Science, vol. 324, No. 5924, Apr. 10, 2009 (Apr. 10, 2009), pp. 261-265.
Zheng et al., "Synthesis and antitumor evaluation of a novel series of triaminotriazine derivatives," Bioorganic & Medicinal Chemistry 15 (2007), pp. 1815-1827.
Adveenko, et al., "Thiocyanation of N-arylsulfonyl-, N-aroyl-, and N-[(N-arylsulfonyl)benzimidoyl]-1,4-benzoquinone imines" Russian Journal of Organic Chemistry, vol. 45, No. 3, (2009), 408-416.
Baxter I et al: "Preparation and some reactions of 6-arylsulphonimidobenzoxazol-2(3H)-one" Journal of the Chemical Society, Section C: Organic Chemistry, Chemical Society Letchworth, GB LNKD-DOI:10.1039/J39700000850, Jan. 1, 1970, pp. 850-853.
Benesch et al., "The clinicopathological and prognostic relevance of pyruvate kinase M2 and pAkt expression in breast cancer." Anticancer Res.; 30(5):1689-94 (2010).
Bonuccelli et al., "The reverse Warburg effect: Glycolysis inhibitors prevent the tumor promiting effects of caveolin-1 deficient cancer associated fibroblasts." Cell Cycle.;9(10)(2010).
Boxer, et al., "Evaluation of Substituted N,N?-Diarylsulfonamides as Activators of the Tumor Cell Specific M2 Isoform of Pruvate Kinase", J Med Chem. Feb. 11, 2010; 53(3):1048.
Boxer, et al., "Identification of activators for the M2 isoform of human pyruvate kinase Version 3", Sep. 2009, Probe Reports from the NIH Molecular Libraries Program [Internet]. Bethesda (MD): National Center for Biotechnology Information (US).
Buschow et al., "MHC class II-associated proteins in B-cell exosomes and potential functional implications for exosome biogenesis." Immunol Cell Biol. (2010).
Database Chemcats, Chemical Abstracts Service, Columbus, OH, US "Bionet Screening Compounds" Key Organics Ltd., Camelford, Cornwall (2001).
Dombrauckas, et al., Structural Basis for Tumor Pyruvate Kinasa M2 Allosteric Regulation and Catalysis, Biochemistry, vol. 44, p. 9717-9429 (2005).
Engelman et al., "Allelic Dilution Obscures Detection of a Biologically Significant Resistance Mutation in EGFR-Amplified Lung Cancer," J Clin Invest. 116: 2695-2706 (2006).
Eswaran et al., "Crystal Structures and Inhibitor Identifcation for PTPN5, PTPRR and PTPN7: A Family of Human MAPK-Specific Protien Tyrosine Phosphatases," Biochem J. 395: 483-491 (2006).
European Patent Office Communication (European Application No. 07836571.5), dated Oct. 18, 2010.
Friedman et al., "Leptin and the regulation of body weight in mammals" Nature. vol. 395, 1996.
Gupta et al., "Dominant negative mutations affect oligomerisation of human pyruvate kinase M2 isozyme and promote cellular growth and polyploidy." J Biol Chem. (2010).
Hitosugi T et al: "Tyrosine Phosphorylation Inhibits PKM2 to Promote the Warburg Effect and Tumor Growth" Science Signaling, American Association for the Advancement of Science, US LNKD-DOI:10.1126/SCISIGNAL.2000431, vol. 2, No. 97, Nov. 17, 2009, pp. RA73-RA1.
Hitosugi, et al., "Tyrosine Phosphorylation Ingibits PKM2 to Promote the Warburg Effect and Tumor Growth" Sci. Signal., Nov. 17, 2009, vol. 2, Issue 97, p. ra73.
Inglese et al., "Quantitative high-throughput screening: A titration-based approach that efficiently identifies biological activities in large chemical libraries," ProC. Natl. Acad. Sci., 103 (31), 11473-11478 (2006).
International Preliminary Report on patentability for International Application No. PCT/US2007/017519, issued Feb. 10, 2009.
International Preliminary Report on Patentability for PCT/US2008/009828, dated Feb. 16, 2010.
International Search Report & Written Opinion for PCT/US10/030139 dated Dec. 10, 2010.
International Search Report & Written Opinion for PCT/US10/40485 dated Aug. 11, 2010.
International Search Report and the Written Opinion of the International Search Authority (PCT/US07/17519), mailed Jul. 8, 2008.
International Search Report dated Mar. 5, 2012 for related international application No. PCT/US2011/067752.
International Search Report for PCT/US10/40486 dated Sep. 1, 2010.
International Search Report for PCT/US2008/009828, dated Dec. 5, 2008.
International Search Report for PCT/US2010/033610 dated Jul. 22, 2010.
International Search Report, Application No. PCT/US2011/033852, dated Aug. 3, 2011.
Jiang et al., "Evaluation of theino [3,2-b]pyrrole[3,2-djpyridazinones as activators of the tumor cell specific M2 isoform of pyruvate kinase." Bioorg. Med. Chern. Lett., 20(11), 3387-3393 (2010).
Joshi et al., "Age-related faecal calprotectin, lactoferrin and tumour M2-PK concentrations in healthy volunteers." Ann Clin Biochem. ;47(Pt 3):259-63 (2010).
Kao et al., "A Small-Molecule Inhibitor of the Ribonucleolytic Activity of Human Angiogenin That Possesses Antitumor Activity," Proc. Nat!. Acad. Sci. USA, 99(15): 10066-10071 (2002).
Kumar et al., "In vivo factors influencing tumour M2-pyruvate kinase level in human pancreatic cancer cell lines." Tumour Biol. ;31(2):69-77 (2010).
Li et al., "Quantitative proteome analysis of multidrug resistance in human ovarian cancer cell line." J Cell Biochem.;109(4):625-33 (2010).
Li et al., "Screening and identification of interactive proteins of SH2D4A." Yi Chuan.;32(7):712-8 (2010).
Park, "Prevention of type 2 diabetes mellitus from the viewpoint of genetics." Diabetes Research and Clinical Practice 2004; 66S: S33-S35.
Ruan et al., "HSP60, a protein downregulated by IGFBP7 in colorectal carcinoma." J Exp Clin Cancer Res.;29-41 (2010).
Sabatine et al., "Metabolomic Identification of Novel Biomarkers of Myocardial Ischemia," Circulation 112: 3868-3875 (2005).

(56) References Cited

OTHER PUBLICATIONS

Shi, et al., "Silencing of pkm2 increases the efficacy of docetaxel in human lung cancer xenografts in mice." Cancer Science, vol. 101, #6, 1447-1453, Jun. 2010.
Tawaka, et al., Caplus an 1998:794998, 1998.
Vander Heiden et al., "Growth Factors Can Influence Cell Growth and Survival Through Effects on Glucose Metabolism," Mol Cell Bioi. 21: 5899-5912 (2001).
Vander Hedien et al., "Identification of Small Molecule Inhibitors of Pyruvate Kinase M2," Biochemical Pharmacology. 79(8): 1118-1124 (2010).
Villen et al., "Large-Scale Phosphorylation Analysis of Mouse Liver," Proc Nat!Acad Sci USA 104: 1488-1493 (2007).
Written Opinion of the International Searching Authority for PCT/US2008/009828, dated Dec. 5, 2008.
Yamada and Noguchi, "Nutrient and Hormonal Regulation of Pyruvate Kinase Gene Expression," Biochem J. 337: 1-11 (1999).
Behun et al., "The Chemistry of Pyrazine and Its Derivatives. IV. The Alkylation and Arylation of Methylpyrazine," J Org. Chern., 26(9),3379-3382 (1961).
Beger, et. al., "Treatment of Pancreatic Cancer: Challenge of the Facts" World J. Surg., Societe Internationale de Chirurgie, vol. 27, pp. 1075-1083, 2003
Budinger et al., "Cellular Energy Utilization and Supply During Hypoxia in Embryonic Cardiac Myocytes," Am J Physiol. 270: L44-53 (1996).
Chabner, et al., "Chemotherapy and the war on cancer", Nature Rev. Cancer, Nature Publishing Group, vol. 5, pp. 65-72, 2005.
Chan et al., "Synthesis and characterization of poly(amide sulfonamide)s (PASAs)," J Polymer. Sci., 33(15), 2525-2531 (1995).
Christofk et al., "pyruvate Kinase M2 is a Phosphotyrosine-Binding Protein," Nature 452: 181-186 (2008).
Christofk et al. , "The M2 Splice Isoform of Pyruvate Kinase is Important for Cancer Metbolism and Tumour Growth," Nature 452: 230-233 (2008).
Clement, et. al., "Production of Intracellular Superoxide Mediates Dithiothreitol-Dependent Inhibition of Apoptotic Cell Death" Antioxidants and Redox Signaling, Mary Ann Liebert, vol. 7, issues 3-4, pp. 456-464, 2005.
Cuzick, et. al., "Overview of the main outcomes in breast-cancer prevention trials" The Lancet, The Lancet Publishing Group, vol. 361, pp. 296-300, 2003.
Eigenbrodt et al., "Double Role for Pyruvate Kinase Type M2 in the Expansion of Phosphometabolite Pools Found in Tumor Cells," Crit Rev Oncog. 3: 91-115 (1992). (Abstract only).
Hulleman, et al., "Pyruvate kinase M2 and prednisolone resistance in acute lymphoblastic leukemia." Haematologica. Sep. 2009; 94(9): 1322-1324.
International Preliminary Report on Patentability, Application No. PCT/US2009/060237, dated Apr. 12, 2011.
International Search Report, Application No. PCT/US2009/060237, dated Jun. 16, 2010.
Jurica et al., "The Allosteric Regulation of Pyruvate Kinase by Fructose-1 ,6-Bisphosphate," Structure 6: 195-210 (1998).
Kharalkar et al., "Identification of Novel Allosteric Regulators of Human-Erythrocyte Pyruvate Kinase," Chem Biodivers. 4: 2603-2617 (2007).
Klapars et al., "A General and Efficient Copper Catalyst for the Amidation of Aryl Halides and the N-Arylation of Nitrogen Heterocycles," J. Am. Chem. Soc., 123 (31), 7727-7729 (2001).
Lee et al., "An Efficient Synthesis of 2,8-Diazabicyclo[4.3.0]-Nonane Derivatives Via Intramolecular Cyclization Reaction," Synth. Comm., 25 (23), 3741-3746 (1995).
Lee, "Consolidation Effect of Phenylalanine-administration of Antitumor Activity of A 5 Fluorouracil," Med. J. Kagoshima Univ. 37(3-4): 285-308 (1985).
Lee, et al., "Pyruvate kinase isozyme type M2 (PKM2) interacts and cooperates with Oct-4 in regulating transcription" International J. Biochem. & Cell Biol., vol. 40, # 5,2008, 1043-1054.
Oeda, "On some 2,5-Dialikl-piperazines," Bull. Chem. Soc., 13, 465-470 (1938).
Paudler et al., "3,7-Disubstituted octahydro-1,5-diazocines. Their converstion into tetrahydro-1 ,5-diazocines and into ring-contracted products," J. Org. Chern., 32 (8), 2425-2430 (1967).
Pollard et al., "Some Amides of Piperazines," J. Am. Chem. Soc., 75(2), 491 (1953).
Pujol, et. al., "Is there a case for cisplatin in the treatment of smallcell lung cancer? A meta-analysis of randomized trials of a cisplatin-containing regimen versus a regimen without this alkylating agent" British Journal of Cancer, Cancer Research Campaign, vol. 83, issue 1, pp. 8-15, 2000.
Remington's, "Structure Activity Relationship and Drug Design," Pharmaceutical Sciences, pp. 420-425, 1980.
Rich, et. al., "Development of novel targeted therapies in the treatment of malignant glioma" Nature Rev. Drug Disc., Nature Publishing Group, vol. 3, pp. 430-446, 2004.
Root et al., "Genome-Scale Loss-of-Function Screening with a Lentiviral RNAi Library," Nat Methods 3: 715-719 (2006).
Schneider, et al., "Tumor M2-pyruvate kinase in the follow-up of inoperable lung cancer patients: a pilot study." Cancer Letters, Elsevier, vol. 193, pp. 91-98, 2003.
Schroth et al., "RingschluBreaktion von Diacetylen mit Diaminen: Eine Ciniache von 2,3-Dihydro-1 ,4-diazepinen," Zeitschritt Fur Chemie., 6 (4), 143 (1969).
Seibel et al., "Synthesis and evaluation of B-lactams (piperazones) as elastase inhibitors," Bioorg. Med. Chern. Ltrs., 13 (3),387-389 (2003).
Stewart et al., "Piperazines. I. Derivavtives of Piperazine-1-Carboxylic and -1,4-Dicarboxylic Acid,", J. Org. Chern., 18(1),1478-1483 (1953).
Surh, "Cancer Chemoprevention with Dietary Phytochemicals", Nature Reviews Cancer, Nature Publishing Group, vol. 3, p. 768-780, 2003.
Szoka et al., "Comparative properties and methods of preparation of lipid vesicles (liposomes )," Ann. Rev. Biophys. Bioeng., 9, 467-508 (1980).
Uozumi et al., "Catalytic asymmetric construction of morpholines and piperazines by palladium-catalyzed tandem allylic substitution reactions," J. Org. Chem., 58 (24),6826-6832 (1993).
Yar et al., "An Annulation Reaction for the Synthesis of Morpholines, Thiomorpholines, and Piperazines from !3-Heteroatom Amino Compounds and Vinyl Sulfonium Salts," Angewandte Chemie., 47(20),3784-3786 (2008).
International Search Report dated Sep. 1, 2010 in related application—PCT/US10/40486.
Supplementary Search Report for EP10794668 Mailed Oct. 18, 2012.
Cecil Textbook of Medicine, edited by Bennet, J.C., and Plum F., 20th edition, vol. 1, 1004-1010, 1996.
Cohen et al., "The development and therapeutic potential of protein kinase inhibitors", Current Opinion in Chemical Biology, 3,459-465, 1999.
Dermer et al., "Another Anniversary for the War on Cancer", Bio/Technology, 1994, 12:320.
Fabbro et al. "Protein kinases as targets for anticancer agents: from inhibitors to useful drugs." Pharmacology & Therapeutics 93, 79-98, 2002.
Freshney et al.,Culture of Animal Cells, a Manual of Basic Technique, Alan R. Liss, Inc., 1983, New York, p. 4
Golub et al., "Molecular Classification of Cancer: Class Discovery and Class Prediction by Gene Expression Monitoring", Science, 286, 531-537, 1999.
Mass, R. D., "The HER receptor family: a rich target for therapeutic development", Int. J. Radiation Oncology Bio. Phys.vol. 58(3): 932-940, 2004.
Balss, "Analysis of the IDH1 codon 132 mutation in brain tumors", Acata Neuropathol (2008) vol. 116, pp. 597-602.
International Preliminary Report for related application No. PCT/US2010/059778 dated Jun. 12, 2012.
International Preliminary Report for related application No. PCT/US2011/067752 dated Apr. 11, 2013.

(56) References Cited

OTHER PUBLICATIONS

International Search Report dated Apr. 4, 2012 for related Application PCT/US2011/065633.
International Search Report dated May 3, 2012 for related application PCT/US2011/066595.
STN File CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".
STN File CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5- [[(4-ethoxyphenyl)methylamino]sulfonyl]-2-methylbenzoyl]-".
Walsh et al. "2-oxo-N-aryl-1,2,3,4-tetrahydroquinoline-6-sulfonamides as activators of the tumor cell specific M2 isoform of pyruvate kinase" Bioorg Med Chem Lett. Nov. 1, 2011; 21(21):6322-6327.
Yan et al., "IDH1 and IDH2 Mutations in Gliomas." The New England Journal of Medicine, 19 Feb. 18-22, 2009, vol. 360, No. 8, pp. 765-773.
Crawford et al., Caplus an 2010:1218943, Sep. 30, 2010.
European Search report for EP Application No. 10 794 667.5 dated Oct. 9, 2013.
Furuya et al., Inactiveation of the 3-phosphoglycerate dehydrogenase gene in mice: changes in gene expression and associated regulatory networks resulting from serive deficiency. Funct Integr Genomics (2008) 8:235-249.
International Preliminary Report on Patenability for PCT/US2010/040486 dated Jan. 12, 2012.
International Search Report for Application No. PCT/US12/60099 dated Jan. 8, 2013.
International Search Report for PCT/US2011/065633 dated Jun. 18, 2013.
Komoriya et al. "Design, synthesis, and biological activity of non-basic compounds as factor Xa inhibitors: SAR Study of S1 and aryl binding sites" Bioorganic & Medicinal Chemistry 13 (2005) 3927-3954.
Kung et al. "Small Molecule Activation of PKM2 in Cancer Cells Induces Serine Auxotrophy" Chemistry & Biology, 19, 1187-1198, Sep. 21, 2012.
Patel et al. "Synthesis of some new idolinone derivatives containing piperazine moiety" Bulgarian Chemical Communications, 2003 Bol 35 No. 4 pp. 242-244.
Proisy et al. "Rapid Synthesis of 3-Aminoisoquinoline-5-sulfonamides Using the Buchwald_Hartwig Reaction" Synthesis 2009, No. 4, pp. 0561-0566.
Villoutreix et al., Caplus an 2010:20993, Jan. 7, 2010.
Web posting, Pyruvate kinase M2 isozyme (PKM2), SciBX 5(42), Published online Oct. 25, 2012, Abstract only.
Ye et al., Pyruvate kinase M2 promotes de novo serive synthesis to sustain mTORC1 activity and cell proliferation, PNAS 109(18), 2012, pp. 6904-6909.
International Search Report for PCT/US2010/059778 dated Mar. 17, 2011.
Supplemental EP Search Report & Written Opinion for EP 10 79 4667, Jan. 22, 2013.

* cited by examiner

| Compound | $AC_{50}$ |
|---|---|
|  | C |
|  | B |
|  | B |
|  | C |
|  | C |
|  | A |
|  | C |
|  | C |
|  | B |

| Compound | $AC_{50}$ |
|---|---|
|  | B |
|  | C |
|  | B |
|  | B |
|  | B |
|  | A |
|  | C |
|  | C |
|  | C |
|  | C |

| Compound | $AC_{50}$ |
|---|---|
|  | C |
|  | C |
|  | B |
|  | C |
|  | A |
|  | B |
|  | C |
|  | C |
|  | A |
|  | C |

| Compound | $AC_{50}$ |
|---|---|
|  | B |
|  | C |
|  | C |
|  | B |
|  | B |
|  | C |
|  | A |
|  | C |
|  | C |
|  | A |
|  | C |

| Compound | $AC_{50}$ |
|---|---|
|  | C |
|  | C |
|  | C |
|  | C |
|  | C |
|  | C |
|  | B |
|  | C |
|  | B |
|  | B |

| Compound | $AC_{50}$ |
|---|---|
|  | B |
|  | A |
|  | A |
|  | B |
|  | B |
|  | A |
|  | A |
|  | C |
|  | A |
|  | A |
|  | A |

| Compound | $AC_{50}$ |
|---|---|
|  | B |
|  | A |
|  | B |
|  | B |
|  | B |
|  | A |
|  | A |
|  | A |
|  | B |
|  | B |
|  | B |

| Compound | $AC_{50}$ |
|---|---|
|  | B |
|  | A |
|  | A |
|  | A |
|  | A |
|  | A |
|  | A |
|  | A |
|  | B |
|  | E |
|  | B |

| Compound | $AC_{50}$ |
|---|---|
|  | A |
|  | A |
|  | A |
|  | B |
|  | A |
|  | A |
|  | A |
|  | A |
|  | B |
|  | A |

| Compound | $AC_{50}$ |
|---|---|
|  | E |
|  | E |
|  | D |
|  | E |
|  | D |
|  | C |
|  | E |
|  | E |
|  | D |

| Compound | $AC_{50}$ |
|---|---|
|  | E |
|  | E |
|  | E |
|  | A |
|  | D |
|  | D |
|  | B |
|  | B |
|  | A |
|  | B |

| Compound | $AC_{50}$ |
|---|---|
|  | A |
|  | C |
|  | C |
|  | D |
|  | B |
|  | E |
|  | E |
|  | D |
|  | C |

| Compound | $AC_{50}$ |
|---|---|
|  | B |
|  | A |
|  | B |
|  | A |
|  | A |
|  | A |
|  | A |
|  | A |
|  | E |

| Compound | $AC_{50}$ |
|---|---|
|  | E |
|  | A |
|  | A |
|  | A |
|  | A |
|  | A |
|  | A |
|  | A |

| Compound | $AC_{50}$ |
|---|---|
|  | B |
|  | A |
|  | B |
|  | A |
|  | A |
|  | A |
|  | A |
|  | A |

| Compound | $AC_{50}$ |
|---|---|
|  | A |
|  | A |
|  | A |
|  | A |
|  | A |
|  | B |
|  | C |
|  | D |

| Compound | $AC_{50}$ |
|---|---|
|  | D |
|  | B |
|  | B |
|  | D |
|  | C |
|  | B |
|  | C |
|  | D |

| Compound | $AC_{50}$ |
|---|---|
|  | C |
|  | B |
|  | B |
|  | B |
|  | D |
|  | B |
|  | B |
|  | B |

| Compound | $AC_{50}$ |
|---|---|
|  | B |
|  | B |
|  | C |
|  | A |
|  | B |
|  | A |
|  | B |
|  | B |

| Compound | $AC_{50}$ |
|---|---|
|  | B |
|  | B |
|  | B |
|  | B |
|  | A |
|  | B |
|  | B |
|  | B |

| Compound | $AC_{50}$ |
|---|---|
|  | B |
|  | B |
|  | A |
|  | B |
|  | B |
|  | A |
|  | B |
|  | A |

| Compound | $AC_{50}$ |
|---|---|
|  | B |
|  | A |
|  | A |
|  | C |
|  | B |
|  | B |
|  | A |
|  | A |

| Compound | $AC_{50}$ |
|---|---|
|  | A |
|  | B |
|  | B |
|  | A |
|  | B |
|  | B |
|  | B |
|  | B |

| Compound | $AC_{50}$ |
|---|---|
|  | B |
|  | B |
|  | B |
|  | B |
|  | B |
|  | B |
|  | B |
|  | B |

| Compound | $AC_{50}$ |
|---|---|
|  | B |
|  | E |
|  | B |
|  | A |
|  | B |
|  | D |
|  | D |
|  | D |

| Compound | $AC_{50}$ |
|---|---|
|  | B |
|  | E |
|  | D |
|  | D |
|  | D |
|  | |
|  | B |
|  | C |

FIG. 1A-1
| Compound | $AC_{50}$ |
|---|---|
| 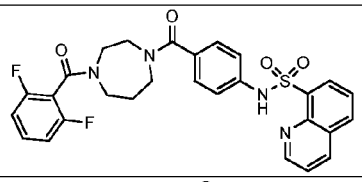 | A |
| 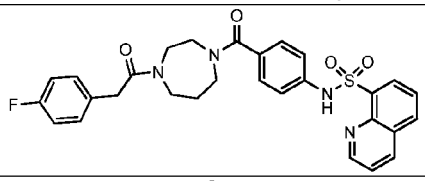 | B |
| 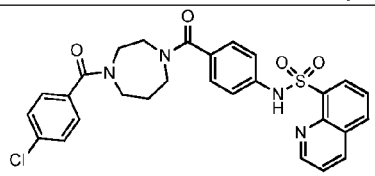 | B |
| 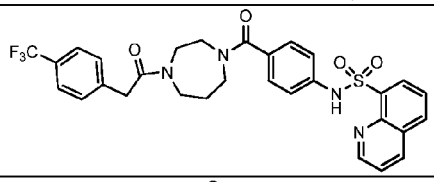 | E |
| 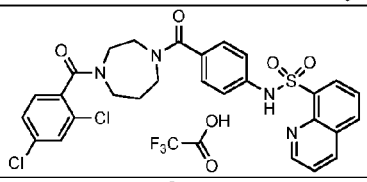 | B |
| 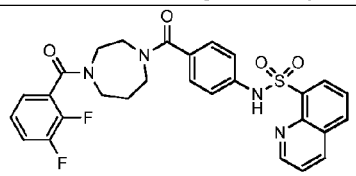 | A |
| 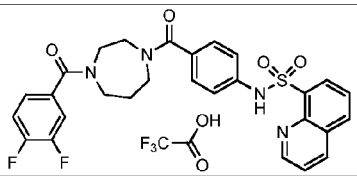 | B |
| 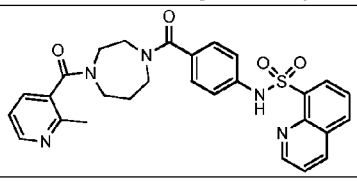 | B |

FIG. 1A-2
| Compound | $AC_{50}$ |
|---|---|
| 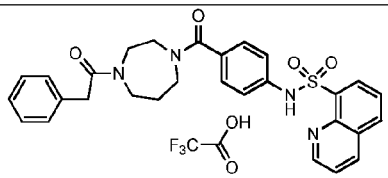 | B |
| 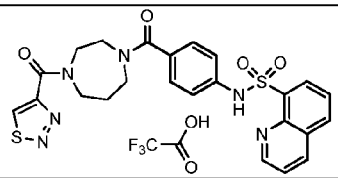 | B |
| 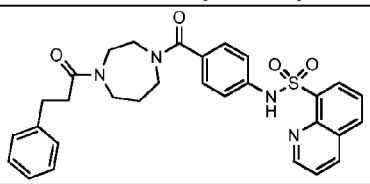 | B |
| 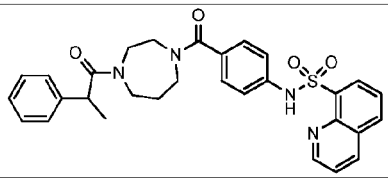 | B |
| 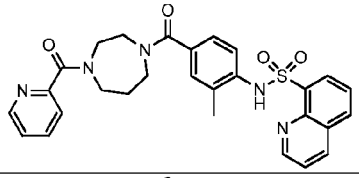 | B |
| 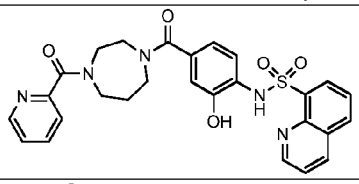 | A |
| 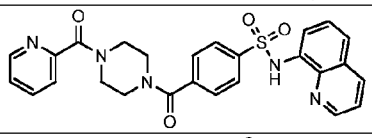 | A |
| 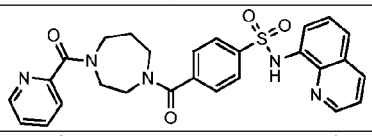 | D |
| 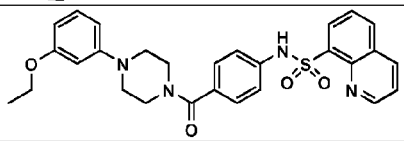 | A |

FIG. 1A-3
| Compound | $AC_{50}$ |
|---|---|
| 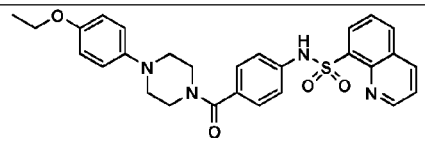 | B |
| 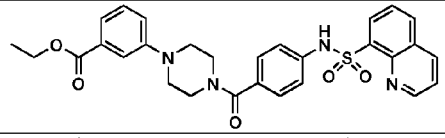 | B |
| 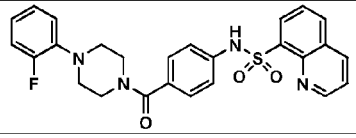 | A |
| 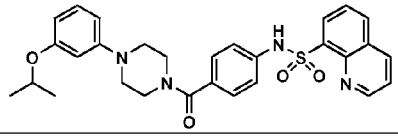 | B |
| 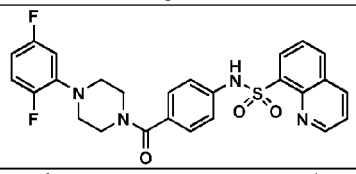 | A |
| 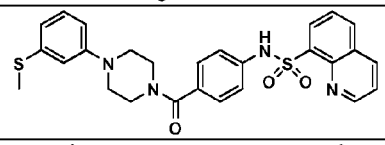 | A |
| 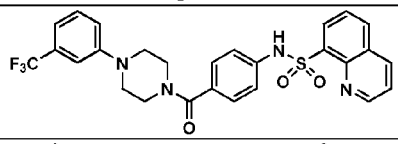 | B |
| 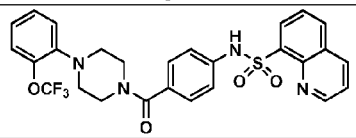 | A |
| 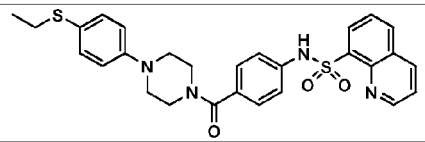 | B |
| 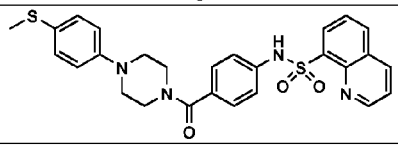 | B |

FIG. 1A-4
| Compound | $AC_{50}$ |
|---|---|
| 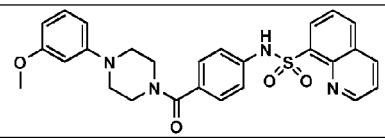 | A |
| 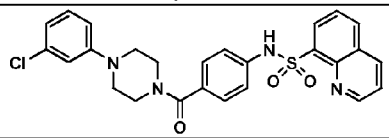 | A |
| 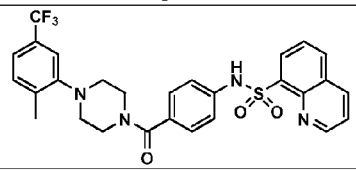 | B |
| 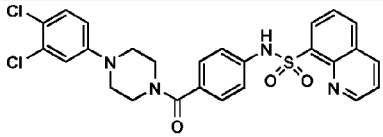 | B |
| 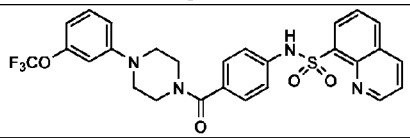 | B |
| 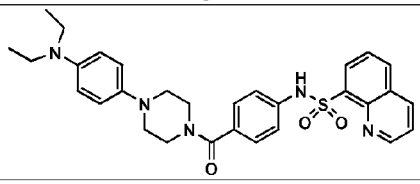 | D |
| 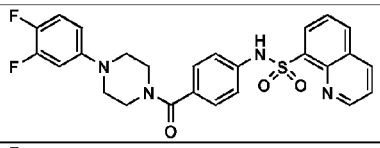 | A |
| 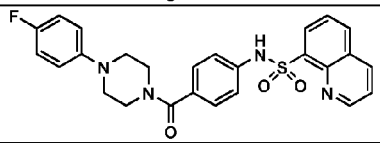 | A |
| 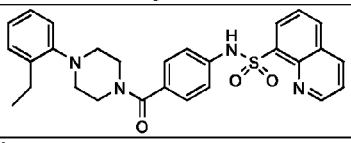 | A |
| 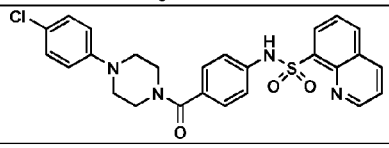 | A |

FIG. 1A-5
| Compound | $AC_{50}$ |
|---|---|
| 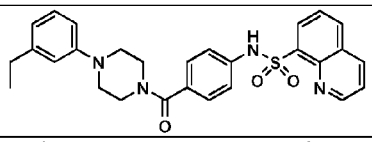 | A |
| 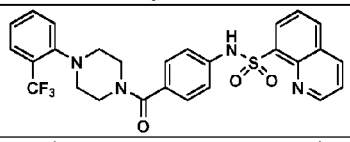 | A |
| 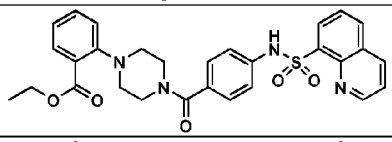 | A |
| 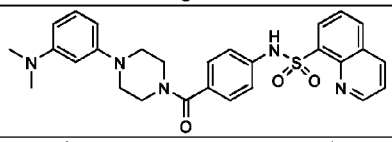 | A |
| 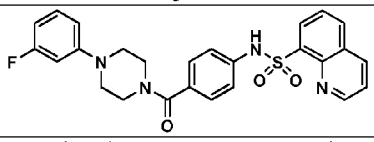 | A |
| 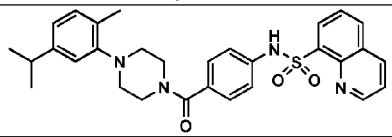 | B |
| 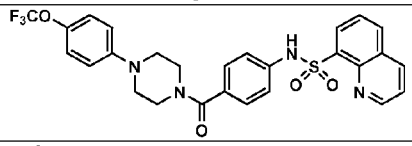 | B |
| 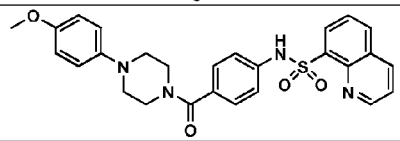 | B |
| 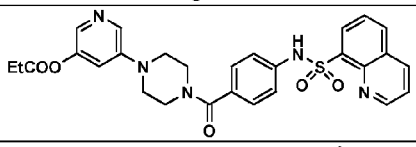 | E |
| 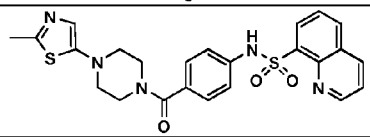 | D |
| 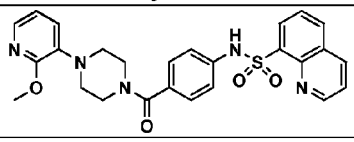 | A |

FIG. 1A-6
| Compound | $AC_{50}$ |
|---|---|
| 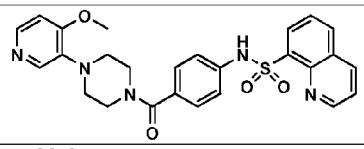 | B |
| 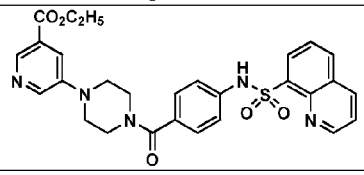 | D |
| 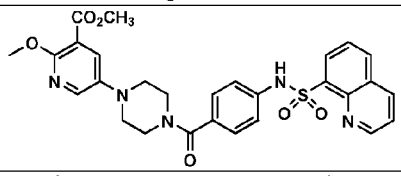 | A |
| 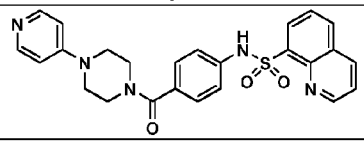 | E |
| 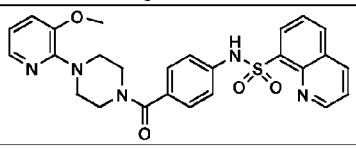 | A |
| 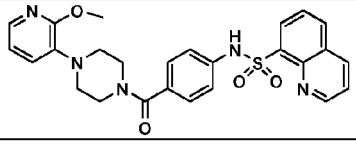 | A |
| 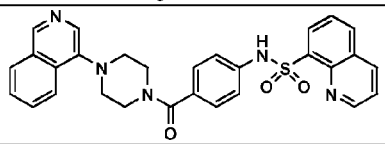 | A |
| 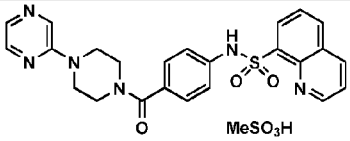 | A |
| 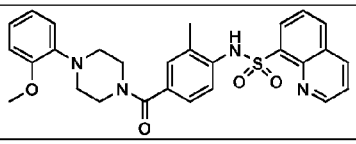 | A |
| 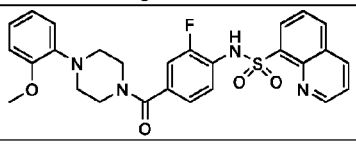 | B |

FIG. 1A-7
| Compound | $AC_{50}$ |
|---|---|
| 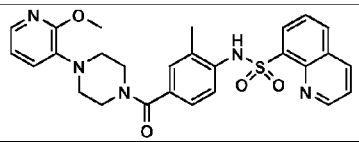 | A |
| 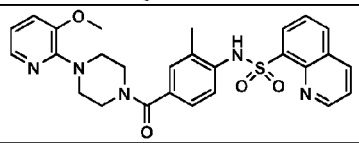 | A |
| 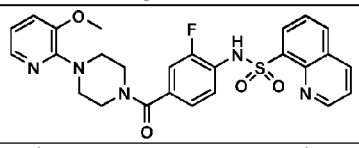 | E |
| 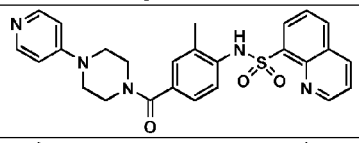 | E |
| 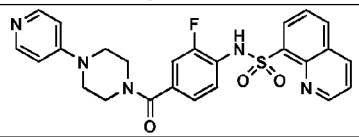 | D |
| 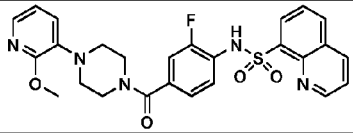 | E |
| 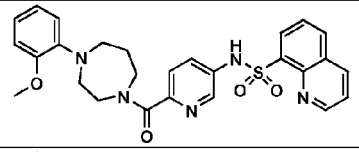 | C |
| 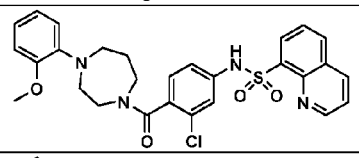 | B |
| 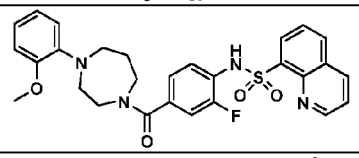 | B |
| 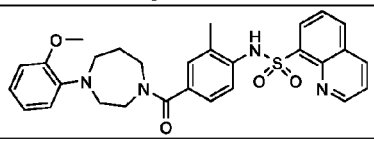 | A |

FIG. 1A-8
| Compound | $AC_{50}$ |
|---|---|
| 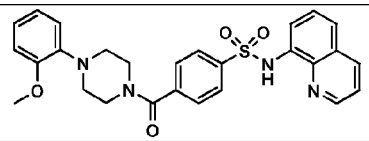 | A |
| 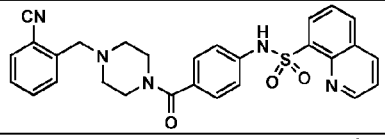 | A |
| 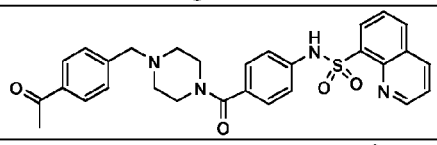 | B |
| 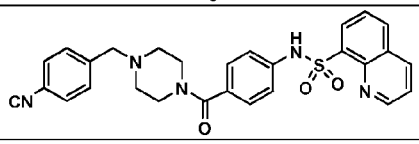 | A |
| 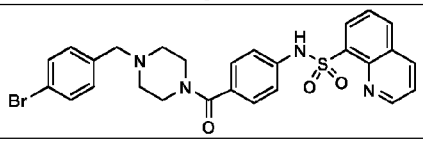 | A |
| 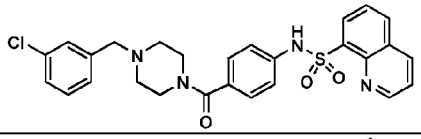 | A |
| 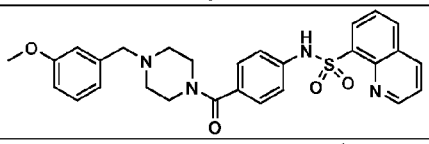 | A |
| 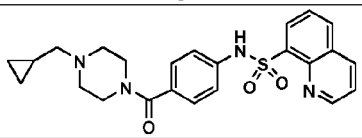 | A |
| 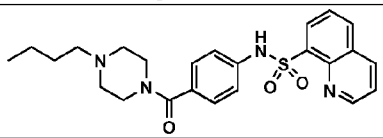 | A |
| 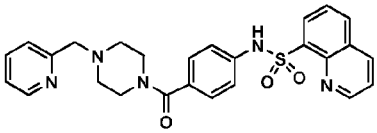 | A |
| 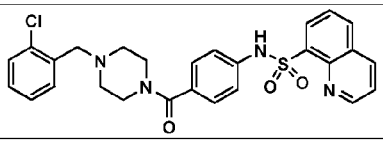 | A |

FIG. 1A-9
| Compound | $AC_{50}$ |
|---|---|
| 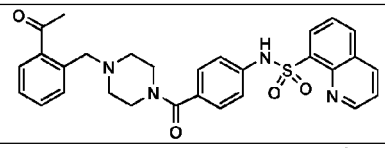 | A |
| 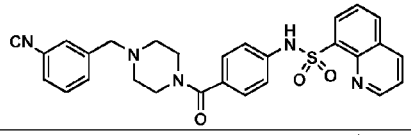 | A |
| 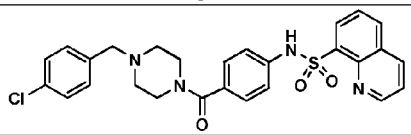 | A |
| 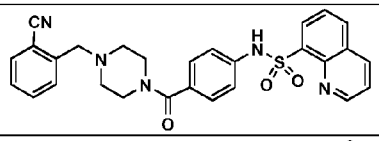 | A |
| 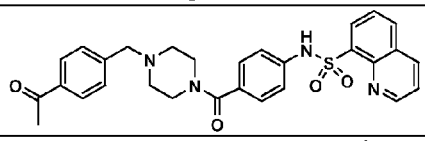 | B |
| 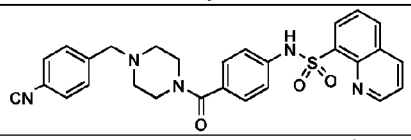 | A |
| 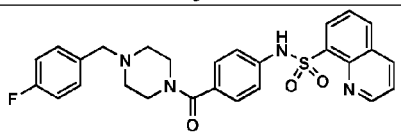 | A |
| 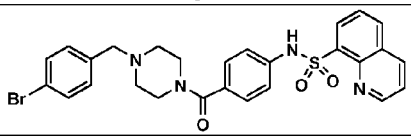 | A |
| 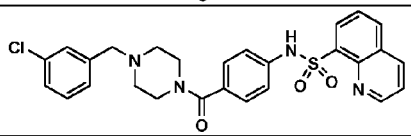 | A |
| 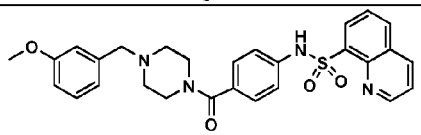 | A |
| 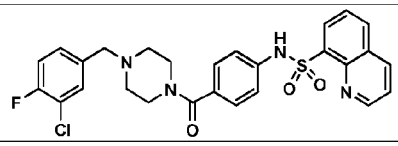 | A |

| Compound | $AC_{50}$ |
|---|---|
|  | B |
|  | B |
|  | A |
|  | B |
|  | A |
|  | B |
|  | B |
|  | A |
|  | B |
|  | B |
|  | A |

FIG. 1A-11
| Compound | $AC_{50}$ |
|---|---|
| 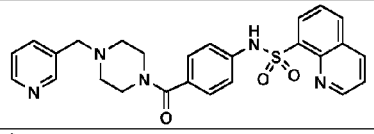 | A |
| 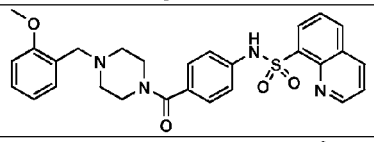 | A |
| 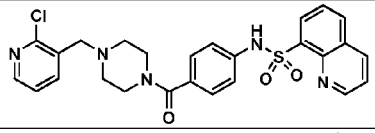 | A |
| 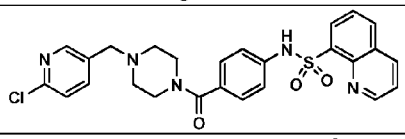 | A |
| 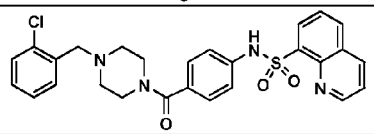 | A |
| 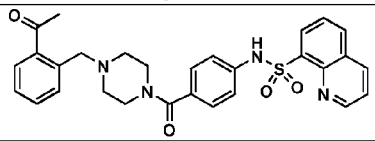 | A |
| 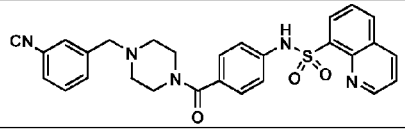 | A |
| 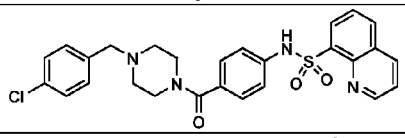 | A |
| 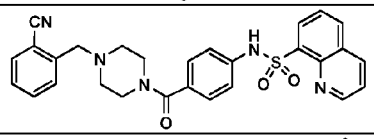 | A |
| 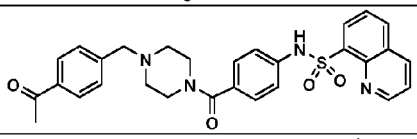 | B |
| 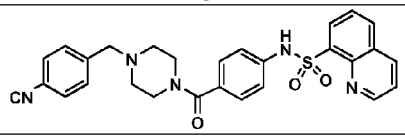 | A |

FIG. 1A-12
| Compound | $AC_{50}$ |
|---|---|
| 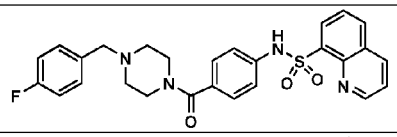 | A |
| 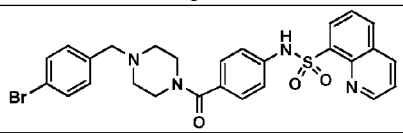 | A |
| 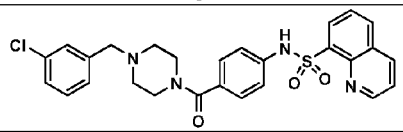 | A |
| 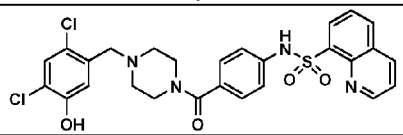 | A |
| 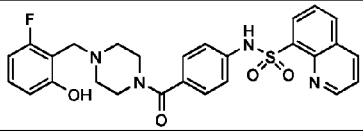 | A |
| 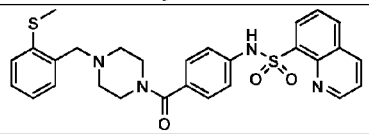 | A |
| 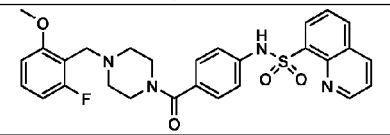 | A |
| 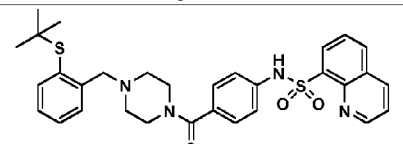 | B |
| 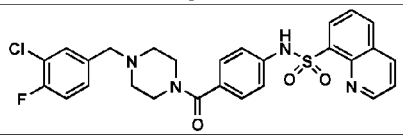 | A |
| 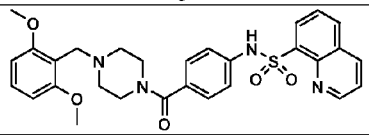 | A |
| 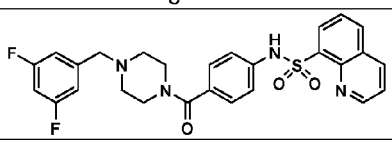 | A |

FIG. 1A-13
| Compound | $AC_{50}$ |
|---|---|
| 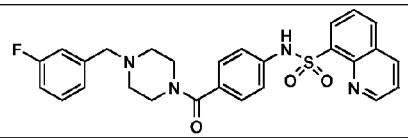 | A |
| 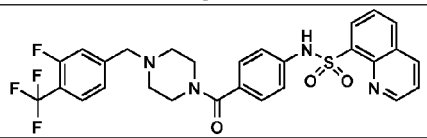 | A |
| 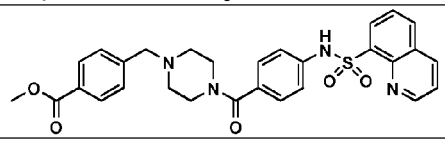 | B |
| 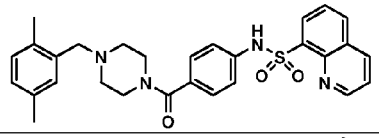 | A |
| 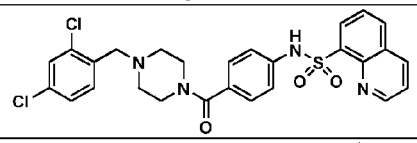 | A |
| 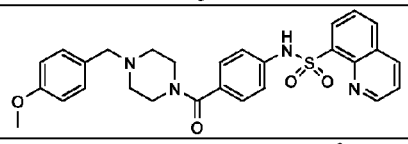 | A |
| 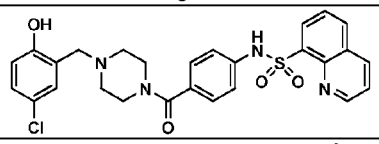 | A |
| 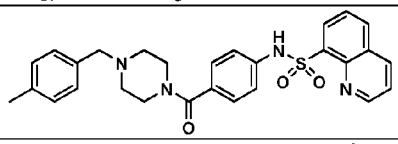 | A |
| 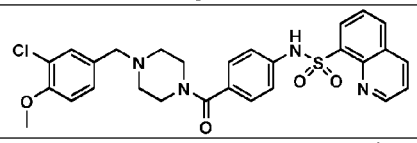 | A |
| 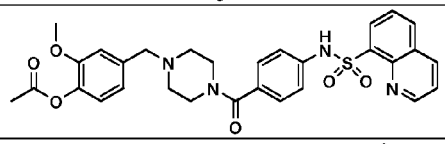 | B |
| 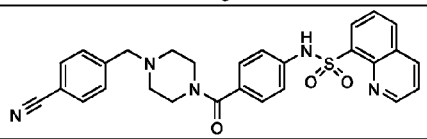 | A |

FIG. 1A-14
| Compound | $AC_{50}$ |
|---|---|
| 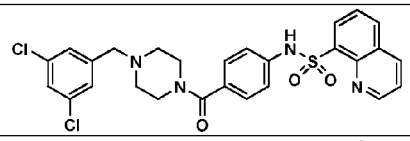 | A |
| 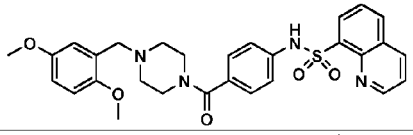 | A |
| 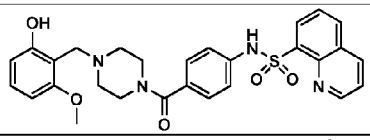 | A |
| 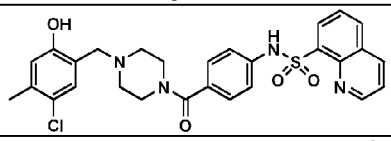 | A |
| 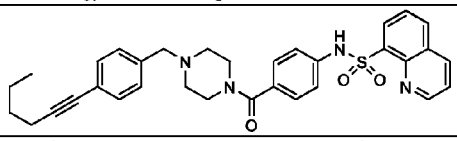 | B |
| 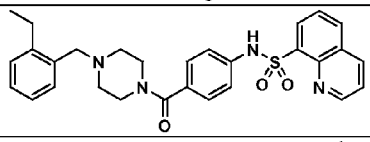 | B |
| 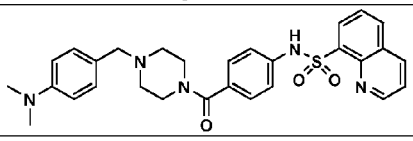 | B |
| 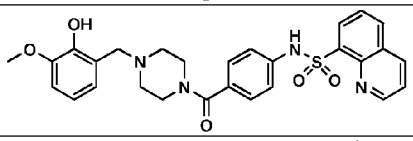 | A |
| 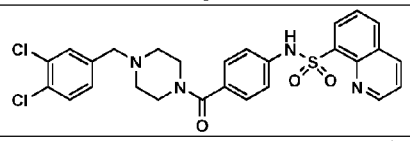 | A |
| 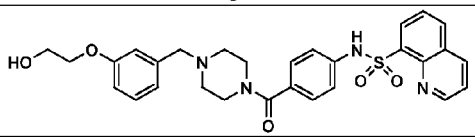 | A |
| 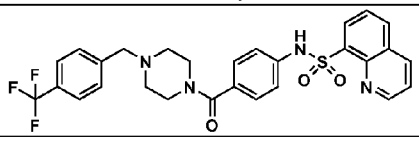 | B |

FIG. 1A-15
| Compound | $AC_{50}$ |
|---|---|
| 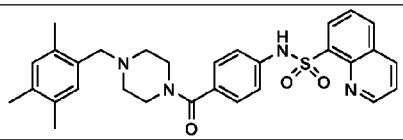 | B |
| 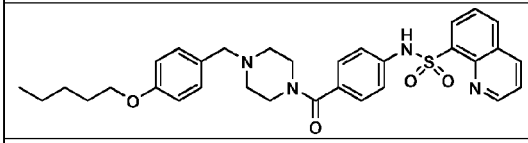 | B |
| 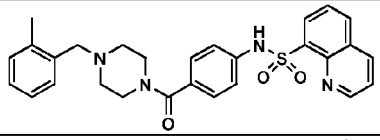 | A |
| 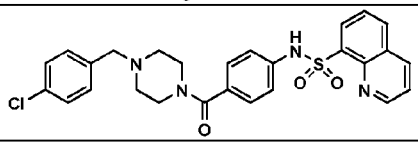 | A |
| 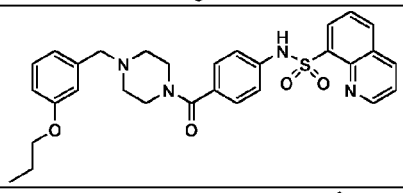 | B |
| 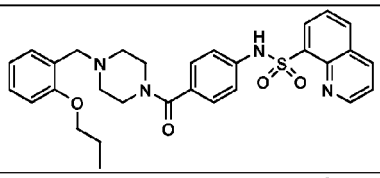 | B |
| 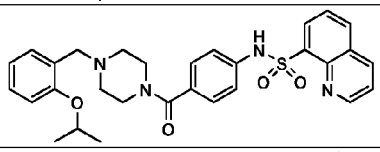 | B |
| 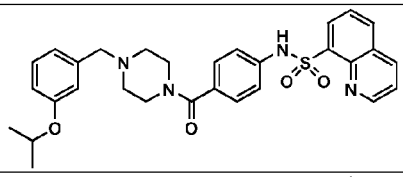 | B |
| 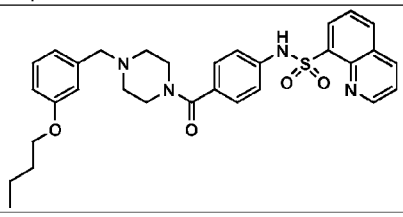 | B |

FIG. 1A-16
| Compound | $AC_{50}$ |
|---|---|
| 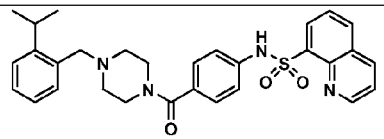 | B |
| 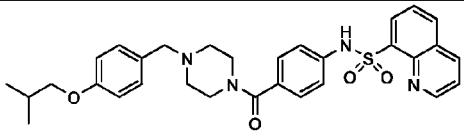 | C |
| 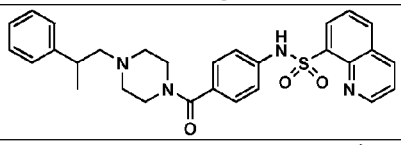 | A |
| 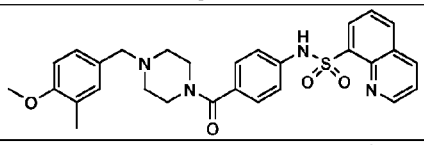 | B |
| 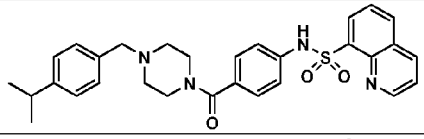 | B |
| 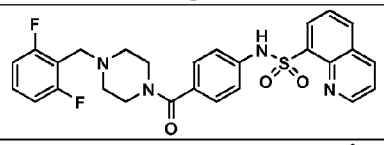 | A |
| 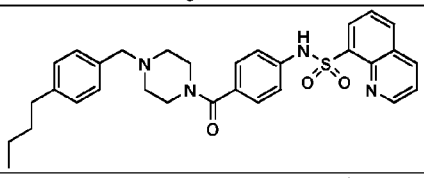 | B |
| 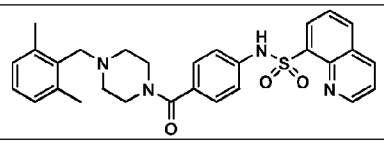 | A |
| 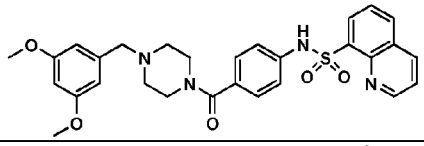 | A |
| 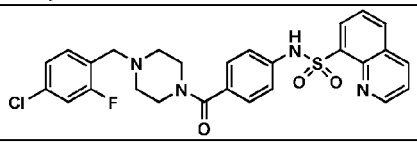 | A |

FIG. 1A-17
| Compound | $AC_{50}$ |
|---|---|
| 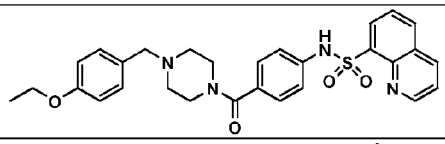 | B |
| 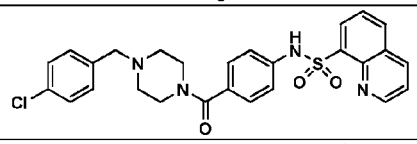 | A |
| 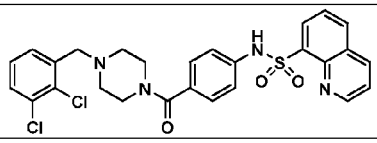 | A |
| 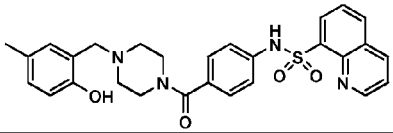 | A |
| 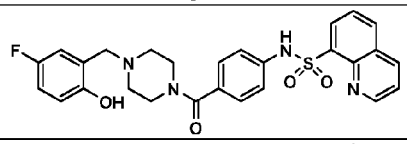 | A |
| 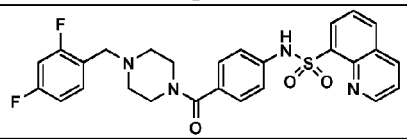 | A |
| 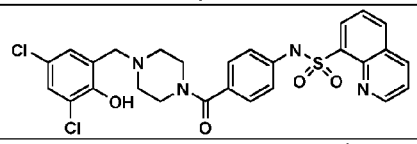 | A |
| 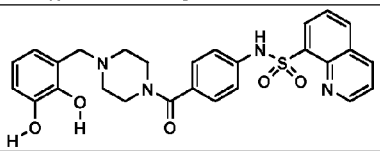 | A |
| 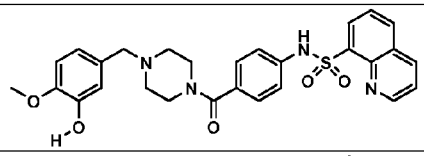 | B |
| 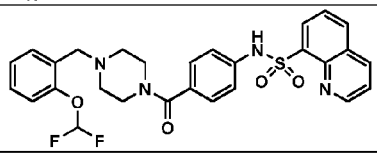 | A |

FIG. 1A-18
| Compound | $AC_{50}$ |
|---|---|
| 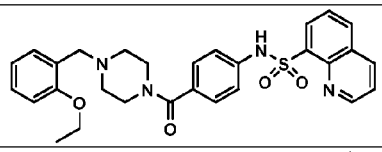 | A |
| 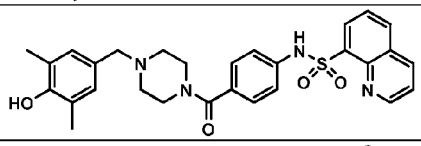 | A |
| 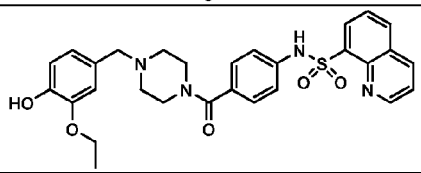 | A |
| 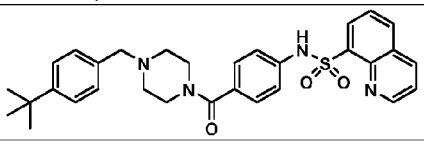 | B |
| 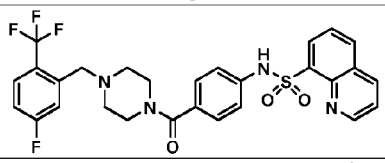 | A |
| 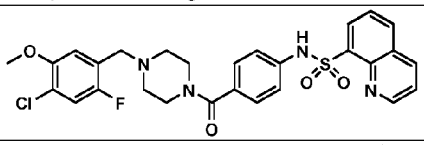 | A |
| 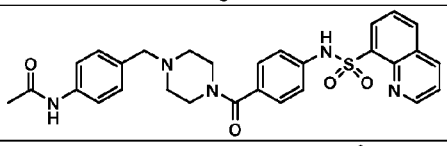 | B |
| 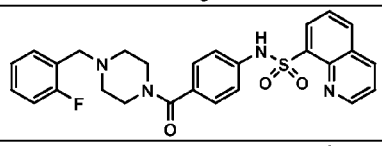 | A |
| 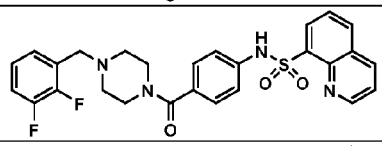 | A |
| 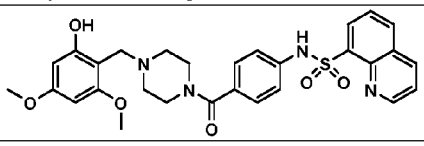 | B |

FIG. 1A-19
| Compound | $AC_{50}$ |
|---|---|
| 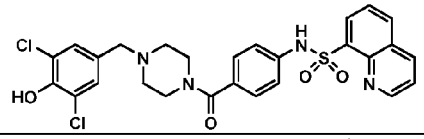 | A |
| 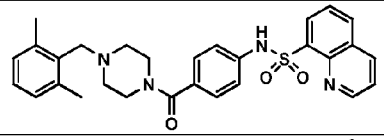 | A |
| 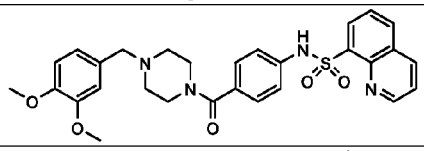 | B |
| 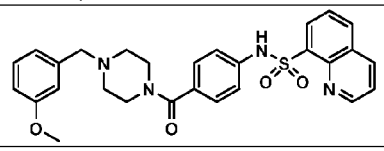 | A |
| 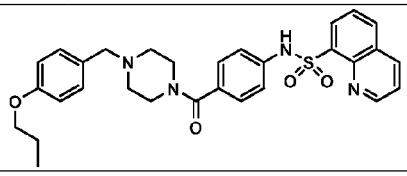 | B |
| 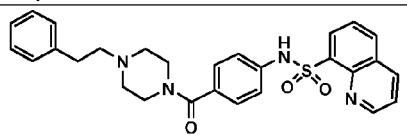 | A |
| 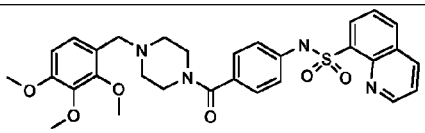 | D |
| 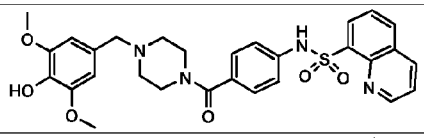 | B |
| 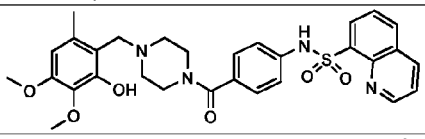 | C |
| 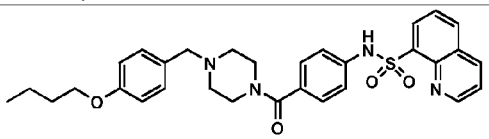 | B |
| 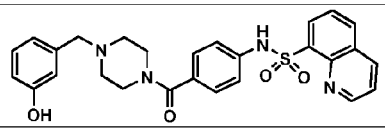 | A |

FIG. 1A-20
| Compound | $AC_{50}$ |
|---|---|
| 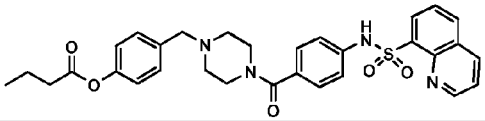 | A |
| 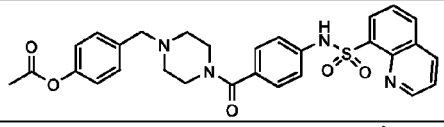 | A |
| 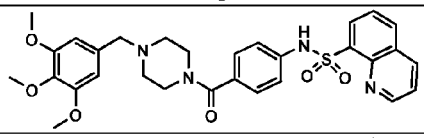 | D |
| 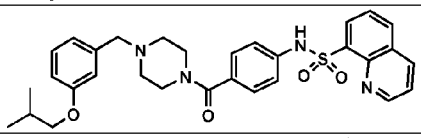 | B |
| 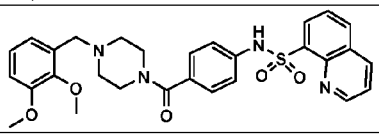 | B |
| 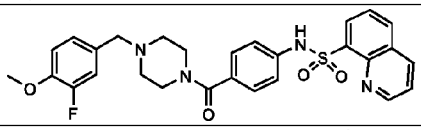 | A |
| 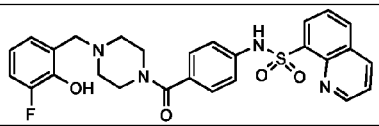 | A |
| 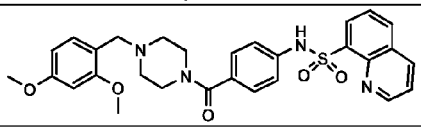 | B |
| 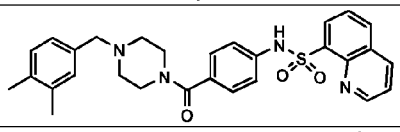 | A |
| 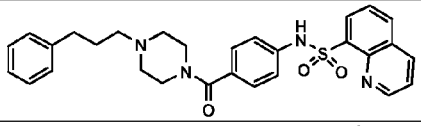 | A |
| 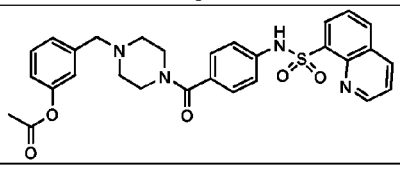 | A |

FIG. 1A-21
| Compound | $AC_{50}$ |
|---|---|
| 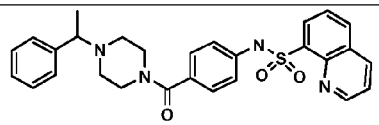 | A |
| 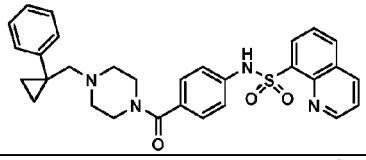 | A |
| 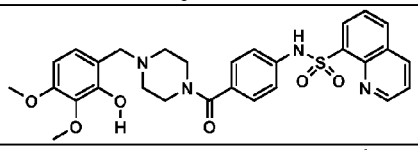 | B |
| 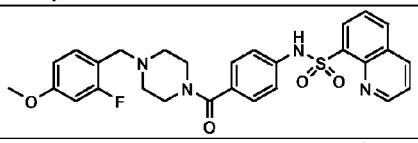 | A |
| 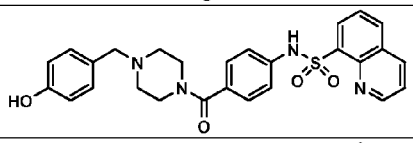 | A |
| 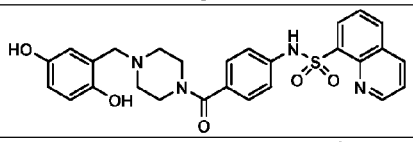 | A |
| 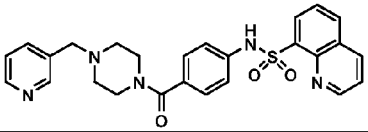 | A |
| 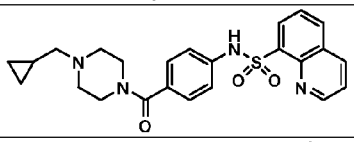 | A |
| 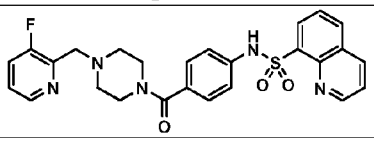 | A |
| 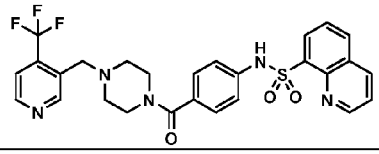 | A |

FIG. 1A-22
| Compound | $AC_{50}$ |
|---|---|
| 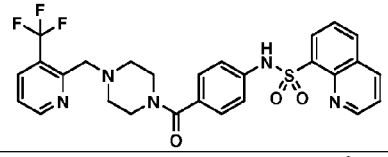 | A |
| 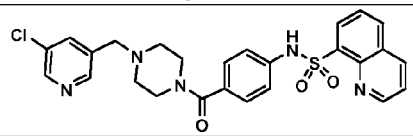 | A |
| 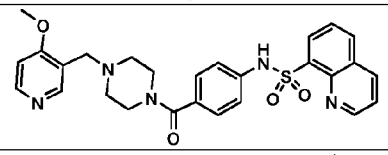 | A |
| 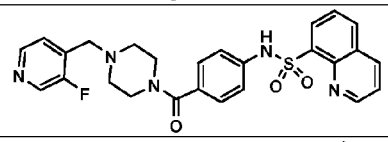 | A |
| 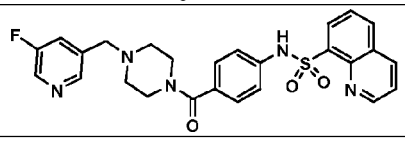 | A |
| 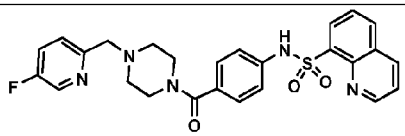 | A |
| 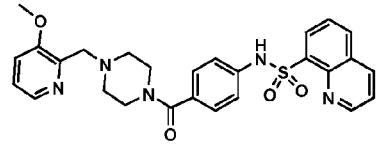 | A |
| 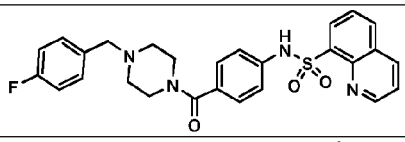 | A |
| 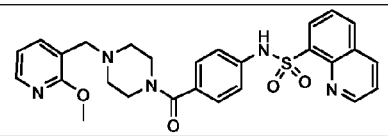 | A |
| 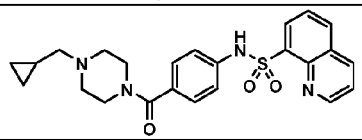 | A |
| 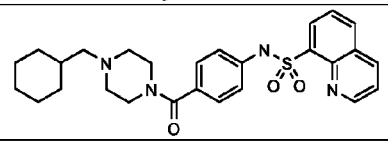 | A |

FIG. 1A-23
| Compound | $AC_{50}$ |
|---|---|
| 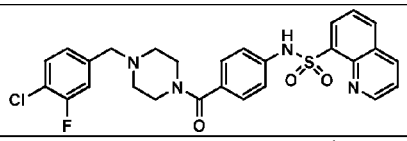 | A |
| 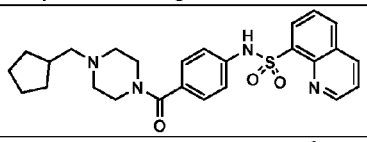 | A |
| 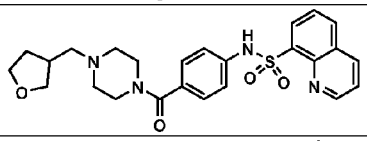 | A |
| 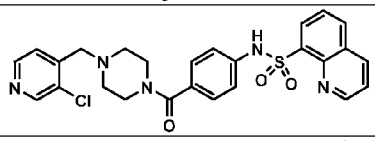 | A |
| 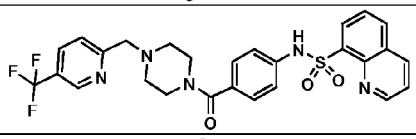 | B |
| 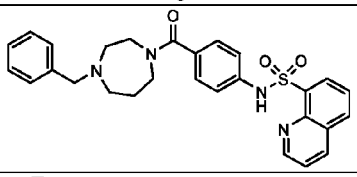 | A |
| 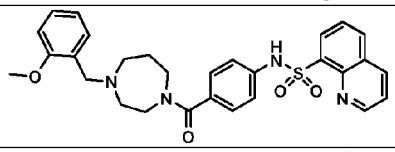 | A |
| 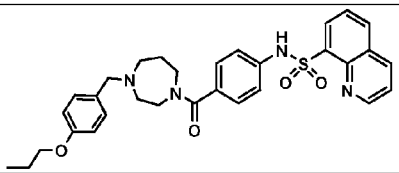 | B |
| 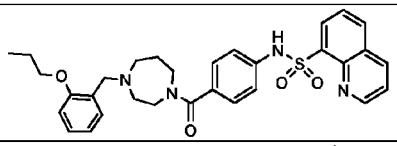 | B |
| 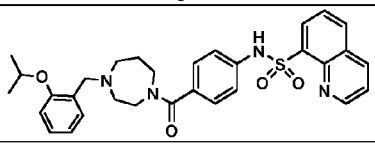 | B |

FIG. 1A-24
| Compound | $AC_{50}$ |
|---|---|
| 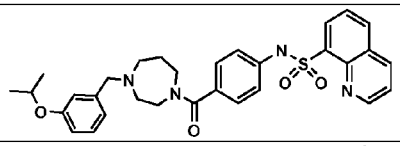 | D |
| 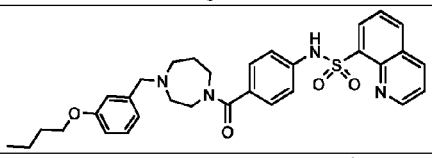 | D |
| 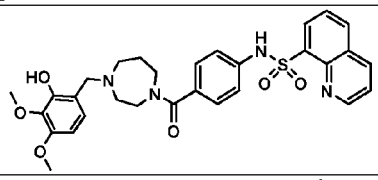 | D |
| 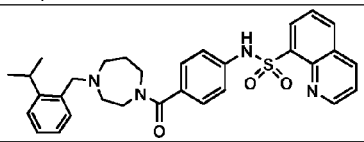 | B |
| 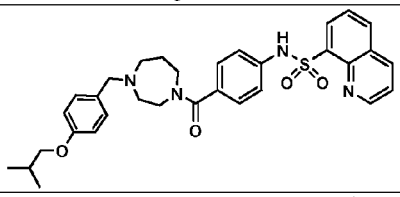 | D |
| 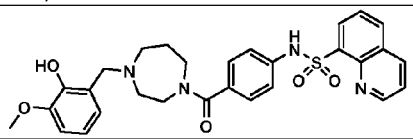 | B |
| 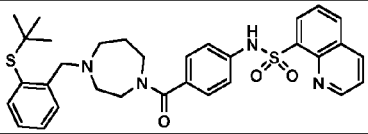 | A |
| 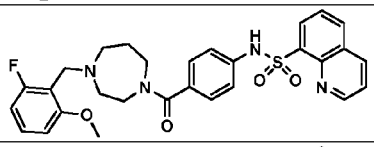 | A |
| 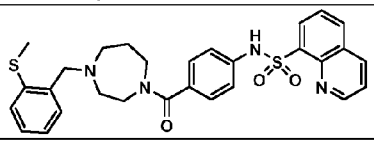 | B |

FIG. 1A-25
| Compound | $AC_{50}$ |
|---|---|
| 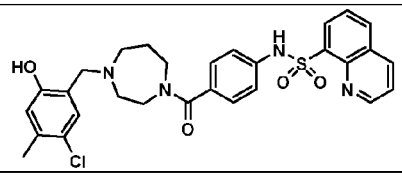 | C |
| 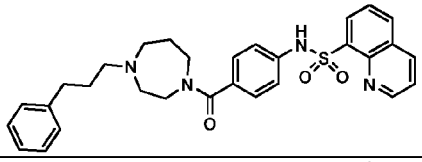 | D |
| 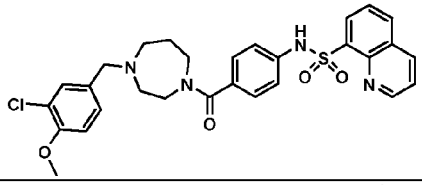 | D |
| 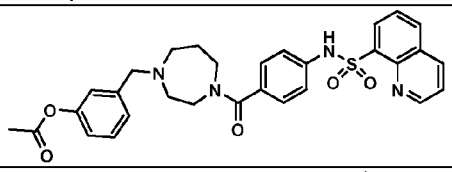 | B |
| 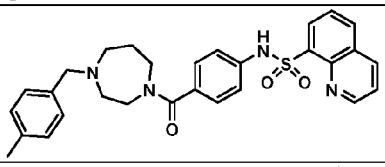 | D |
| 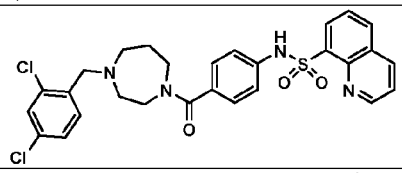 | A |
| 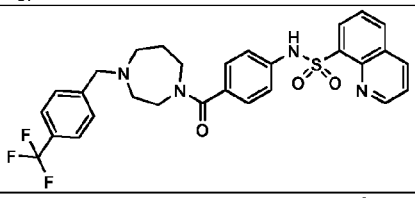 | B |
| 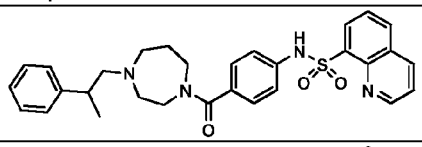 | B |
| 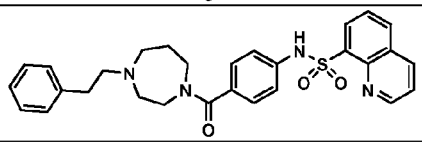 | A |

FIG. 1A-26
| Compound | $AC_{50}$ |
|---|---|
| 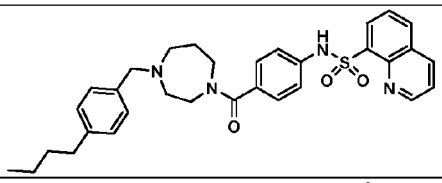 | D |
| 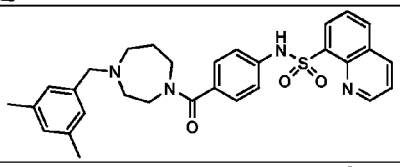 | B |
| 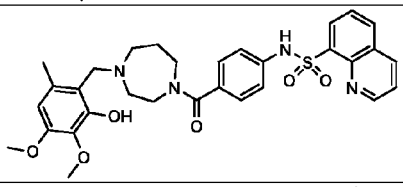 | D |
| 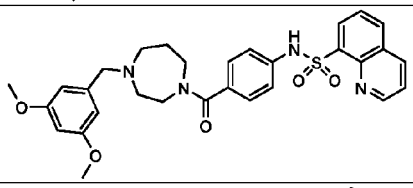 | D |
| 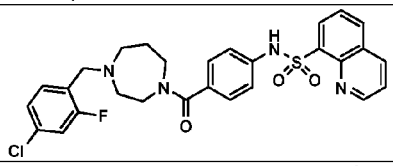 | B |
| 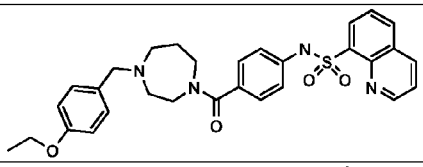 | D |
| 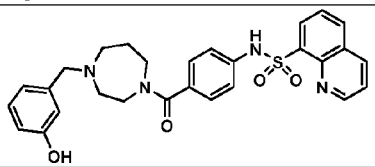 | A |
| 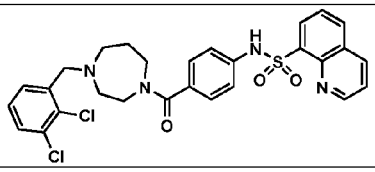 | B |

FIG. 1A-27
| Compound | $AC_{50}$ |
|---|---|
| 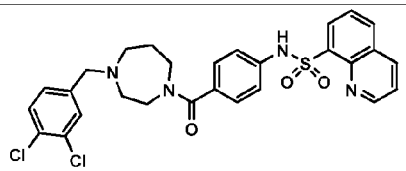 | B |
| 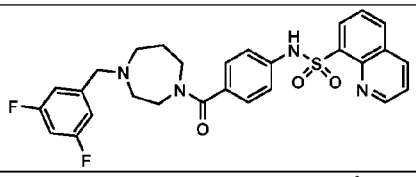 | A |
| 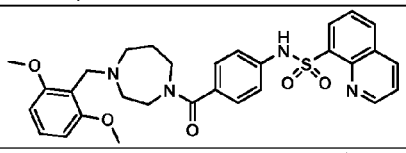 | E |
| 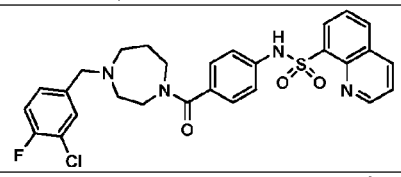 | A |
| 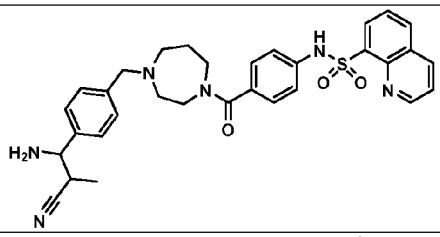 | D |
| 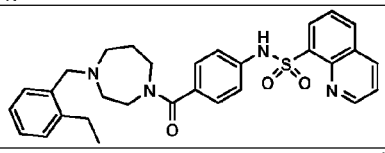 | A |
| 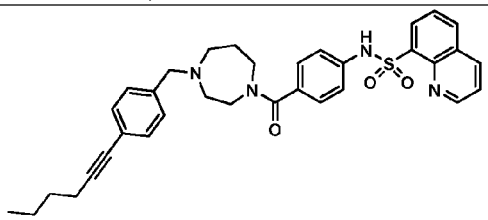 | B |
| 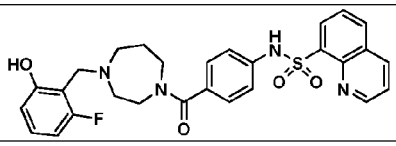 | A |

FIG. 1A-28
| Compound | $AC_{50}$ |
|---|---|
| 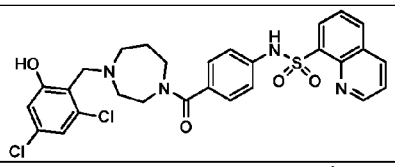 | B |
| 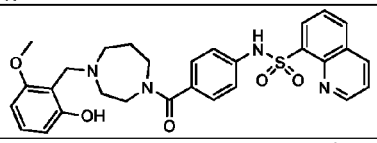 | E |
| 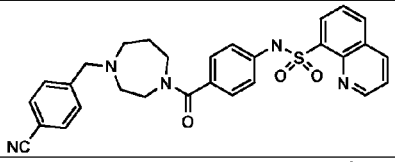 | B |
| 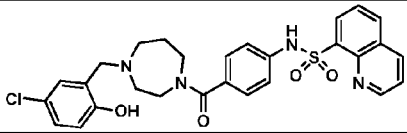 | A |
| 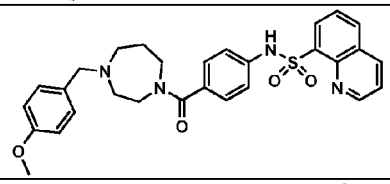 | B |
| 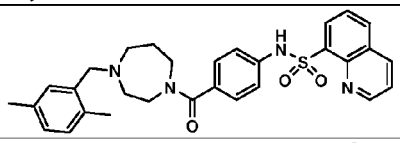 | B |
| 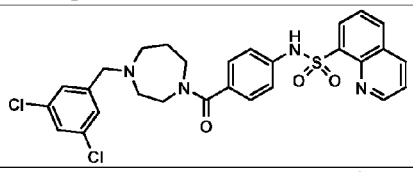 | D |
| 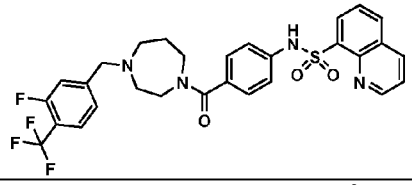 | D |
| 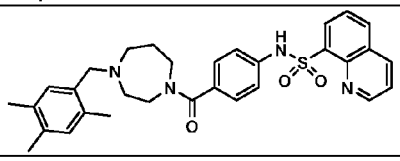 | D |

FIG. 1A-29
| Compound | $AC_{50}$ |
|---|---|
| 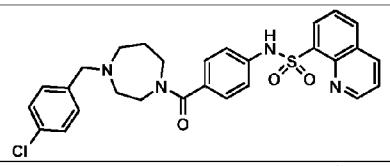 | B |
| 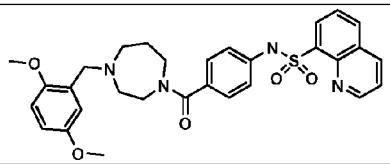 | B |
| 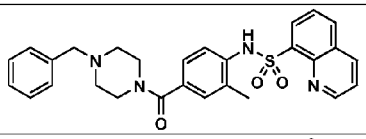 | A |
| 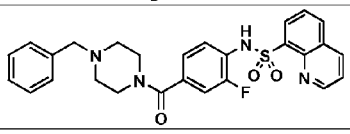 | B |
| 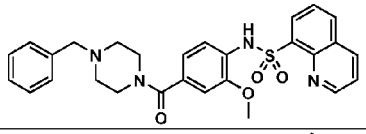 | A |
| 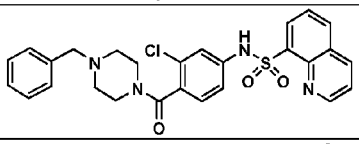 | A |
| 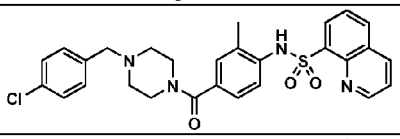 | A |
| 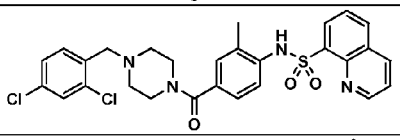 | A |
| 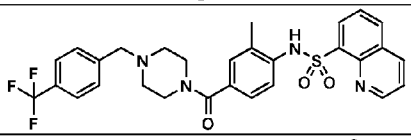 | A |
| 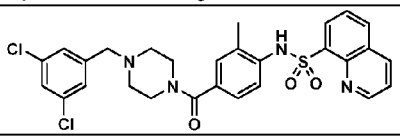 | A |

FIG. 1A-30
| Compound | $AC_{50}$ |
|---|---|
| 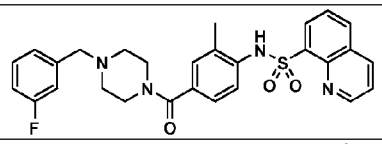 | A |
| 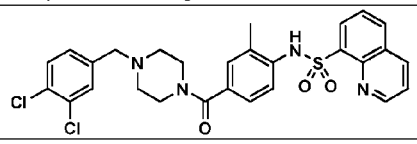 | A |
| 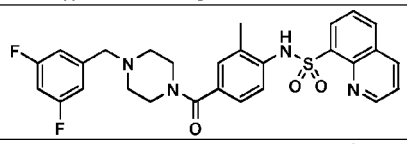 | A |
| 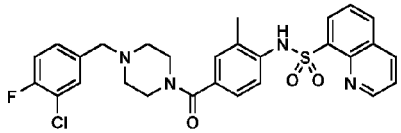 | A |
| 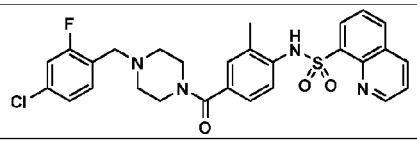 | A |
| 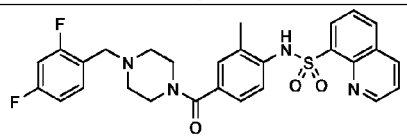 | A |
| 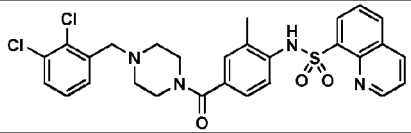 | A |
| 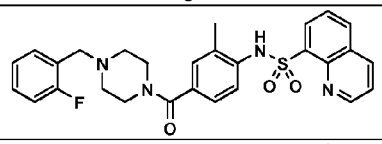 | A |
| 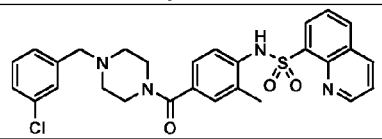 | A |
| 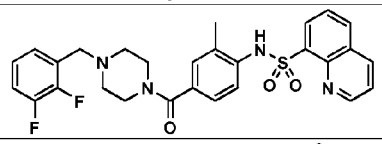 | A |
| 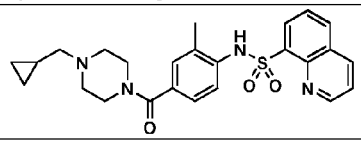 | A |

FIG. 1A-31
| Compound | $AC_{50}$ |
|---|---|
| 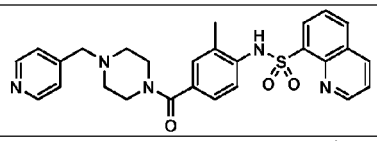 | A |
| 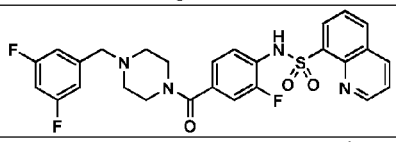 | A |
| 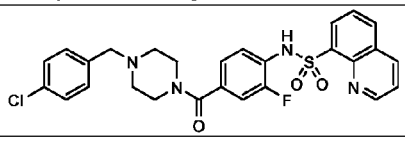 | B |
| 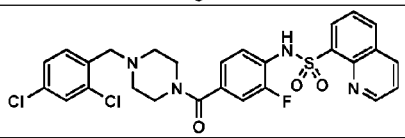 | B |
| 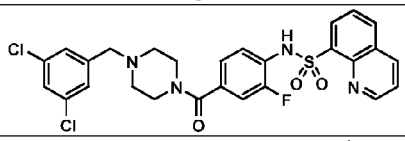 | B |
| 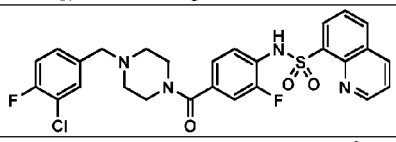 | A |
| 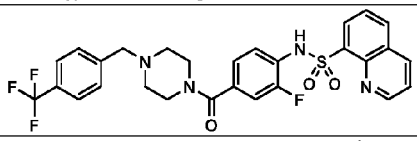 | B |
| 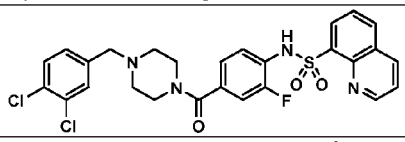 | A |
| 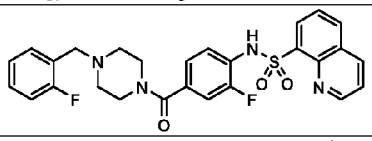 | B |
| 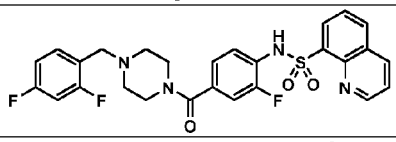 | B |
| 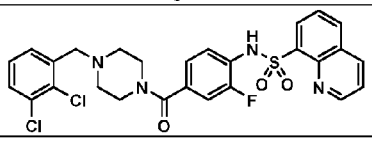 | A |

FIG. 1A-32
| Compound | $AC_{50}$ |
|---|---|
| 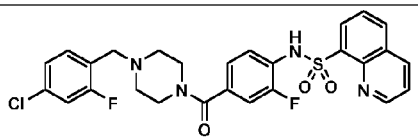 | B |
| 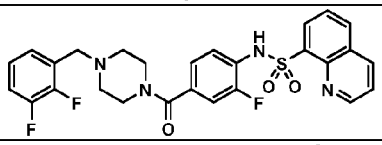 | A |
| 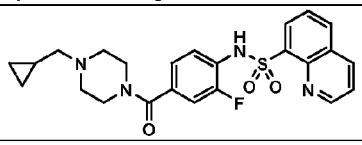 | B |
| 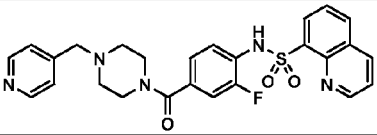 | B |
| 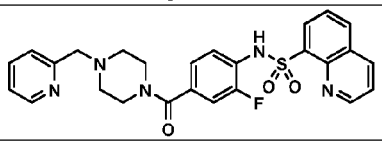 | B |
| 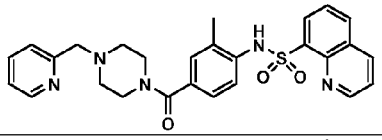 | A |
| 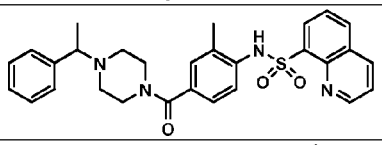 | A |
| 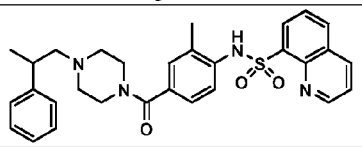 | A |
| 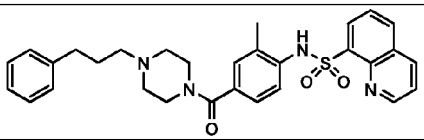 | A |
| 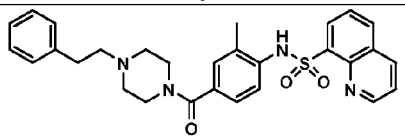 | A |
| 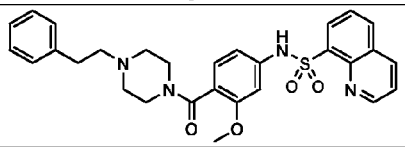 | A |

FIG. 1A-33
| Compound | $AC_{50}$ |
|---|---|
| 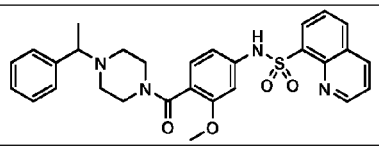 | A |
| 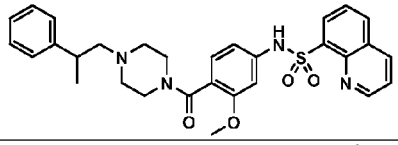 | A |
| 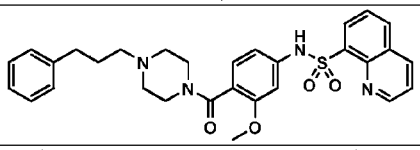 | A |
| 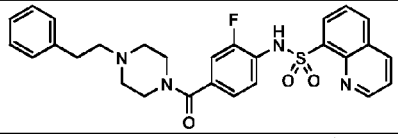 | B |
| 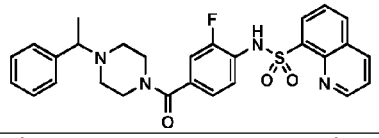 | B |
| 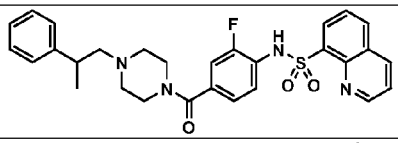 | B |
| 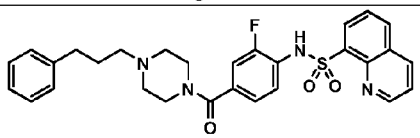 | B |
| 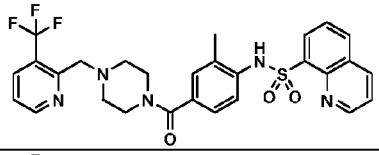 | A |
| 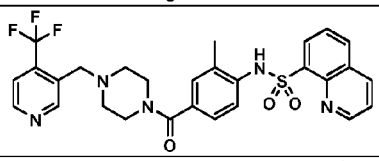 | A |
| 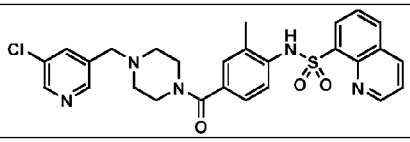 | A |

FIG. 1A-34
| Compound | $AC_{50}$ |
|---|---|
| 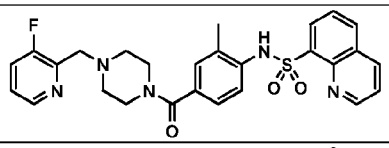 | A |
| 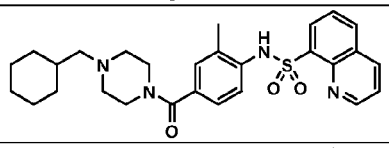 | A |
| 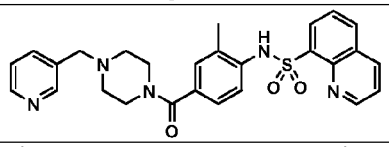 | A |
| 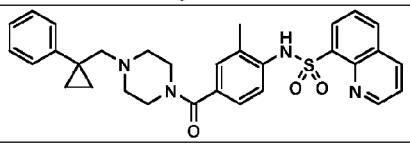 | A |
| 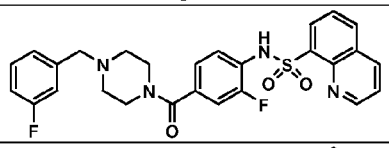 | A |
| 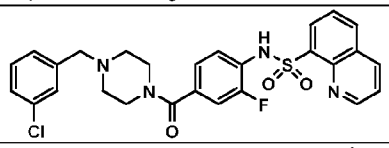 | A |
| 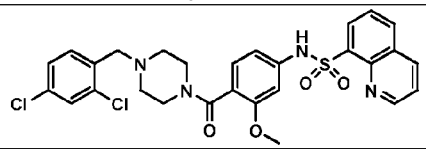 | B |
| 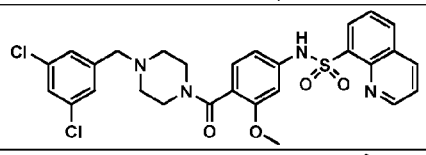 | A |
| 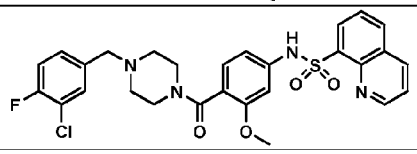 | A |
| 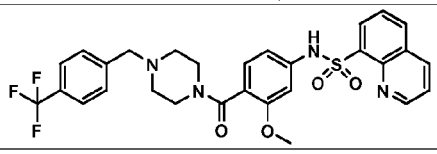 | A |

FIG. 1A-35
| Compound | $AC_{50}$ |
|---|---|
| 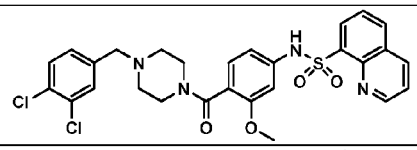 | A |
| 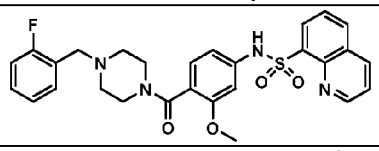 | A |
| 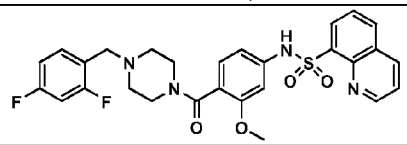 | A |
| 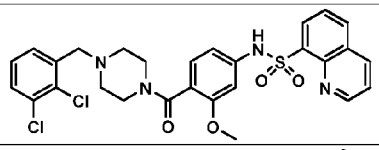 | A |
| 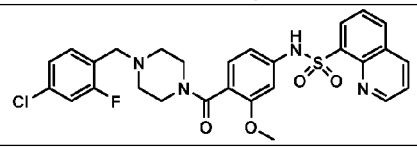 | A |
| 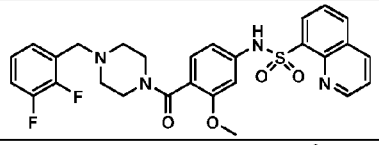 | A |
| 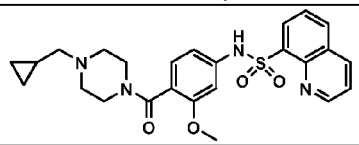 | A |
| 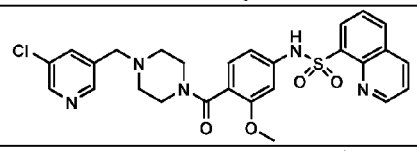 | A |
| 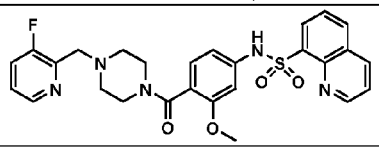 | B |
| 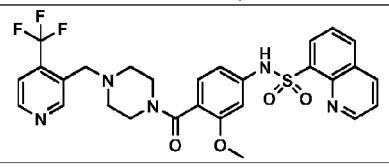 | A |

FIG. 1A-36
| Compound | $AC_{50}$ |
|---|---|
| 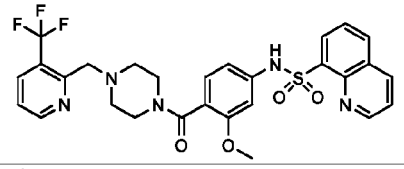 | A |
| 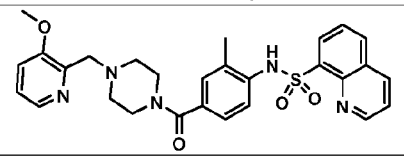 | A |
| 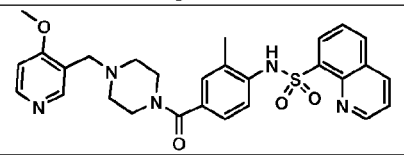 | A |
| 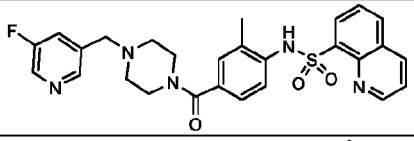 | A |
| 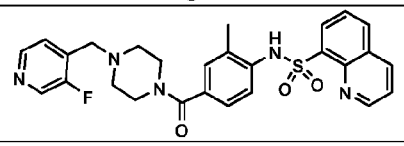 | A |
| 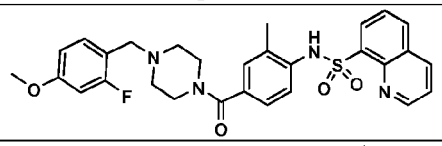 | A |
| 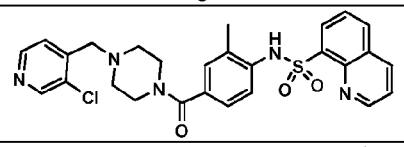 | A |
| 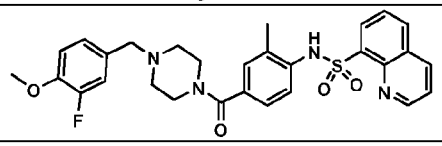 | A |
| 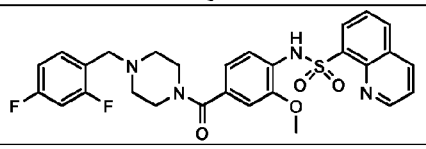 | A |
| 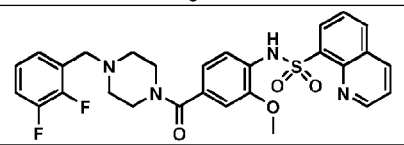 | A |
| 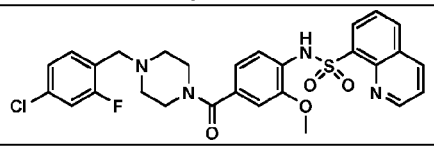 | A |

FIG. 1A-37
| Compound | $AC_{50}$ |
|---|---|
| 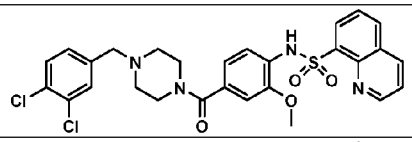 | A |
| 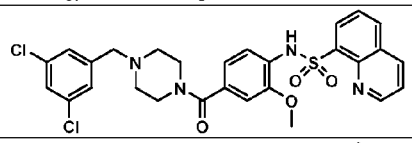 | B |
| 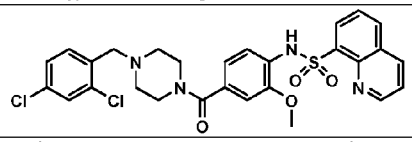 | A |
| 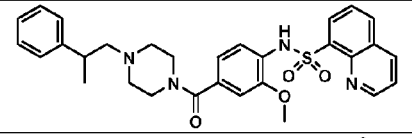 | A |
| 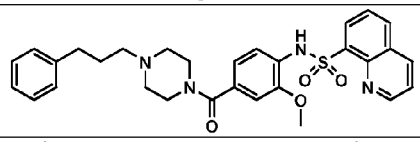 | B |
| 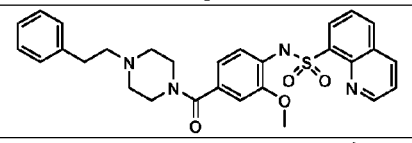 | A |
| 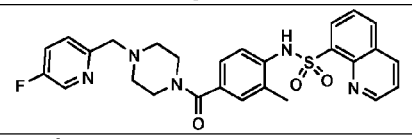 | A |
| 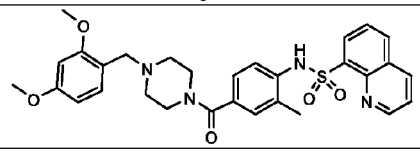 | A |
| 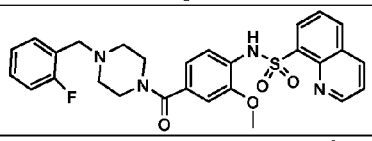 | A |
| 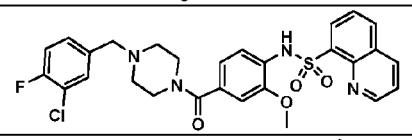 | A |
| 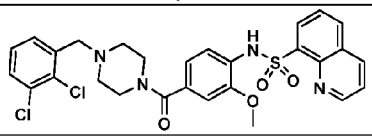 | A |

FIG. 1A-38
| Compound | $AC_{50}$ |
|---|---|
| 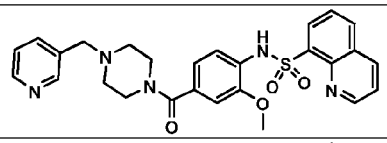 | A |
| 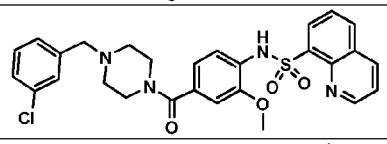 | A |
| 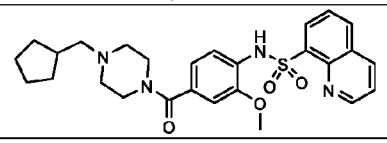 | A |
| 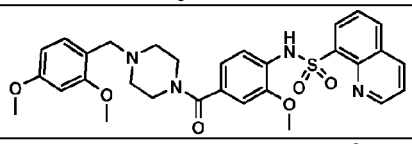 | B |
| 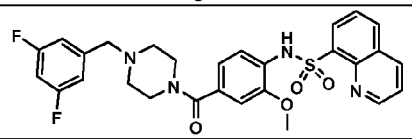 | A |
| 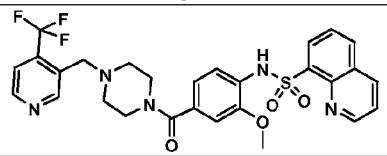 | B |
| 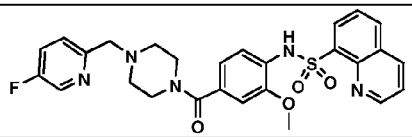 | A |
| 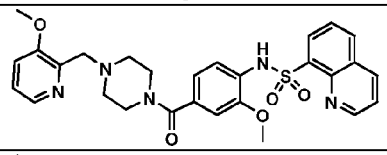 | B |
| 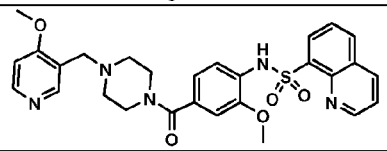 | B |
| 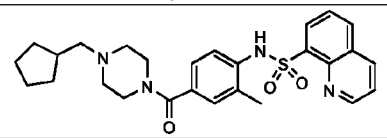 | B |
| 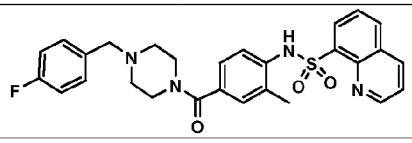 | B |

FIG. 1A-39
| Compound | $AC_{50}$ |
|---|---|
| 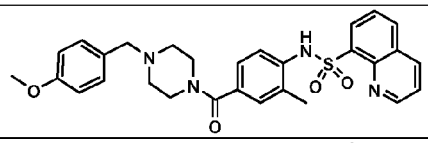 | B |
| 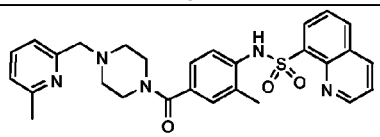 | D |
| 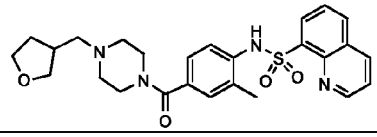 | A |
| 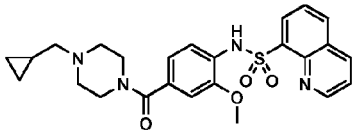 | A |
| 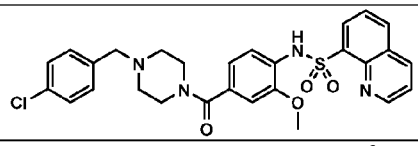 | A |
| 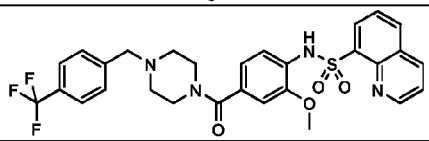 | A |
| 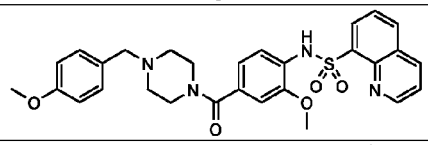 | A |
| 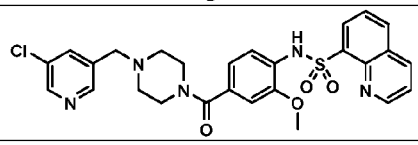 | A |
| 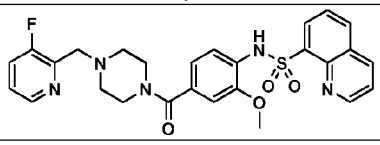 | A |
| 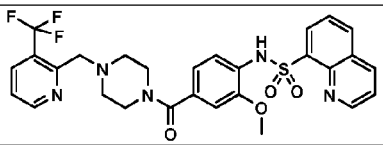 | A |
| 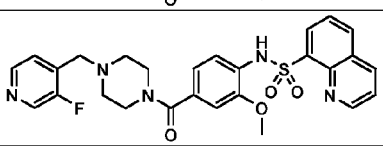 | A |

FIG. 1A-40
| Compound | $AC_{50}$ |
|---|---|
| 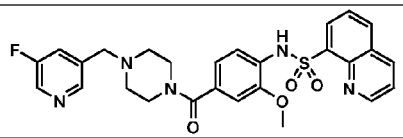 | A |
| 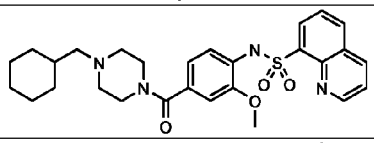 | A |
| 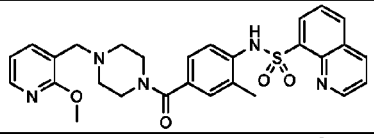 | A |
| 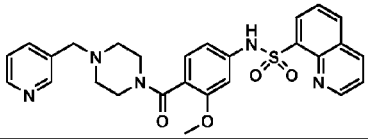 | A |
| 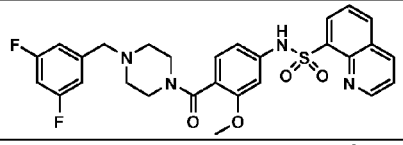 | A |
| 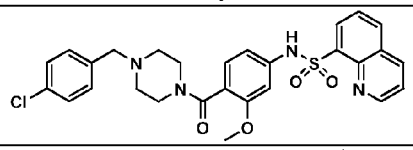 | A |
| 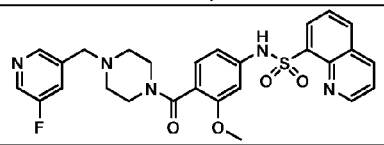 | A |
| 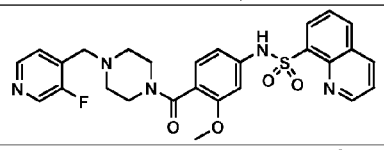 | B |
| 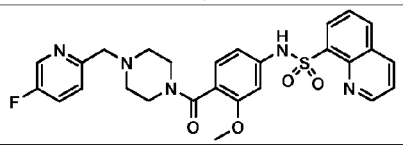 | B |
| 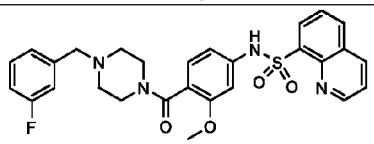 | A |

FIG. 1A-41
| Compound | $AC_{50}$ |
|---|---|
| 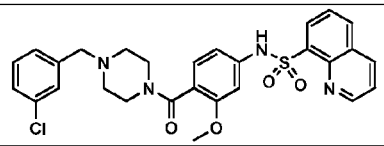 | A |
| 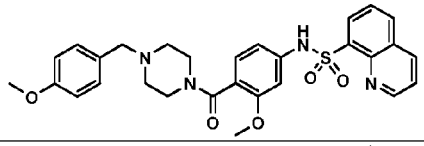 | B |
| 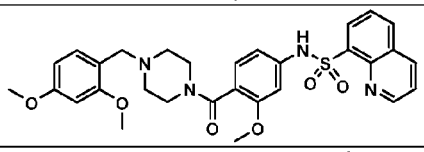 | A |
| 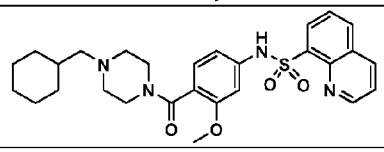 | B |
| 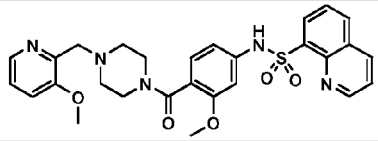 | B |
| 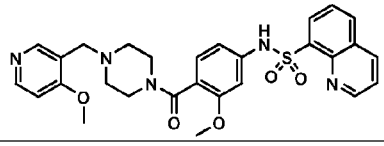 | B |
| 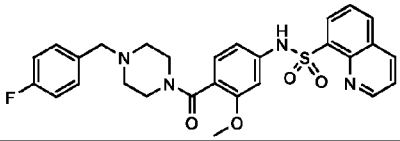 | A |
| 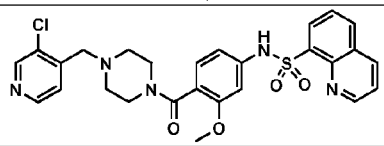 | A |
| 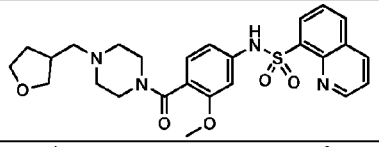 | B |
| 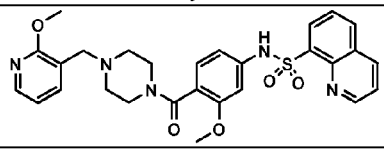 | B |

FIG. 1A-42
| Compound | $AC_{50}$ |
|---|---|
| 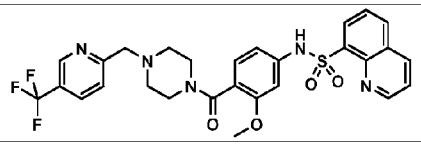 | B |
| 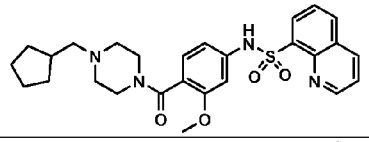 | B |
| 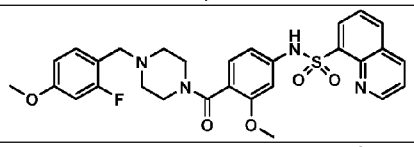 | A |
| 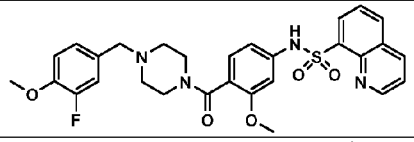 | A |
| 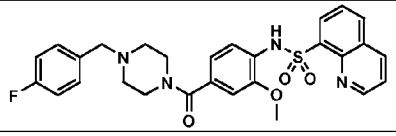 | A |
| 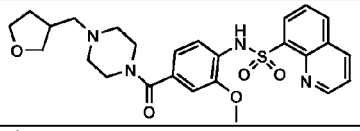 | B |
| 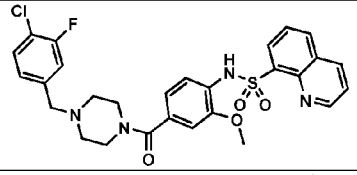 | A |
| 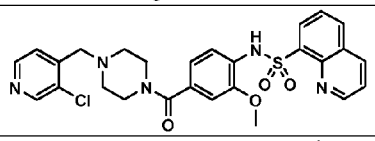 | A |
| 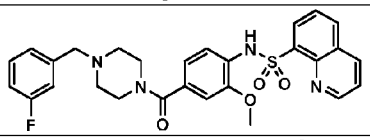 | A |
| 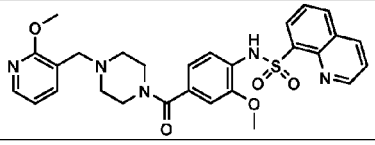 | A |

FIG. 1A-43
| Compound | $AC_{50}$ |
|---|---|
| 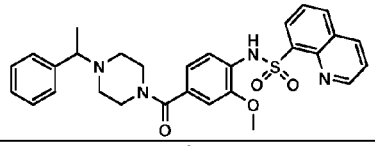 | A |
| 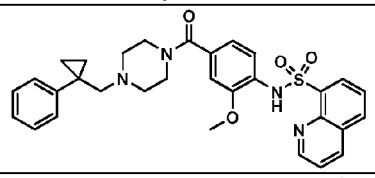 | A |
| 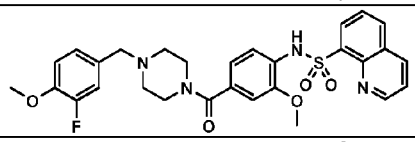 | B |
| 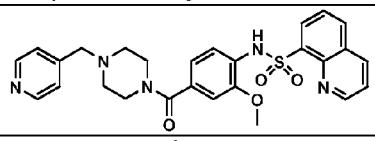 | B |
| 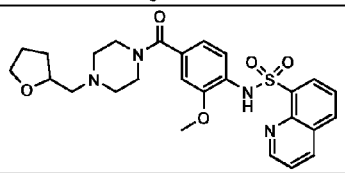 | B |
| 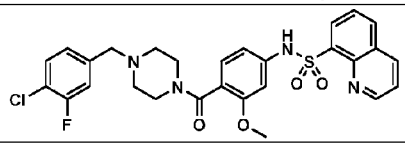 | A |
| 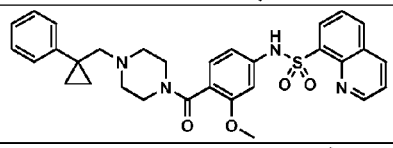 | B |
| 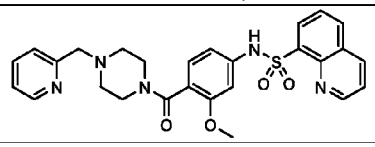 | A |
| 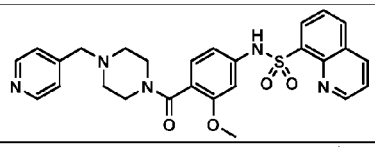 | B |
| 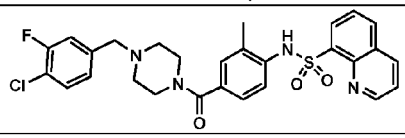 | A |

FIG. 1A-44
| Compound | $AC_{50}$ |
|---|---|
| 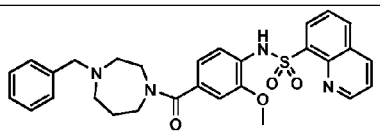 | B |
| 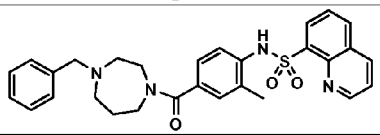 | A |
| 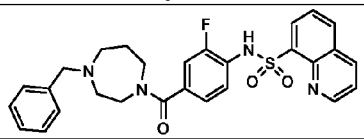 | C |
| 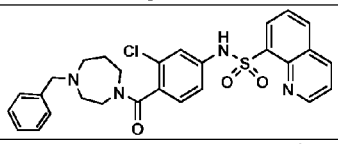 | C |
| 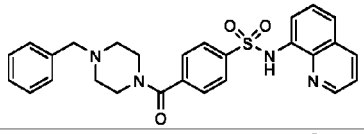 | A |
| 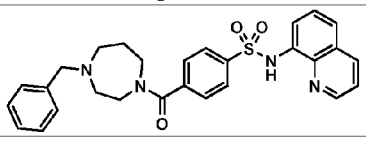 | A |

THERAPEUTIC COMPOUNDS AND COMPOSITIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CLAIM OF PRIORITY

This [application] *is a reissue of U.S. Pat. No. 8,785,450, issued on Jul. 22, 2014 from U.S. patent application Ser. No. 12/826,630, which* claims priority from U.S. Ser. No. 61/221,430, filed Jun. 29, 2009 and U.S. Ser. No. 61/292,360, filed Jan. 5, 2010, each of which is incorporated herein by reference in its entirety.

BACKGROUND OF INVENTION

Cancer cells rely primarily on glycolysis to generate cellular energy and biochemical intermediates for biosynthesis of lipids and nucleotides, while the majority of "normal" cells in adult tissues utilize aerobic respiration. This fundamental difference in cellular metabolism between cancer cells and normal cells, termed the Warburg Effect, has been exploited for diagnostic purposes, but has not yet been exploited for therapeutic benefit.

Pyruvate kinase (PK) is a metabolic enzyme that converts phosphoenolpyruvate to pyruvate during glycolysis. Four PK isoforms exist in mammals: the L and R isoforms are expressed in liver and red blood cells, the M1 isoform is expressed in most adult tissues, and the M2 isoform is a splice variant of M1 expressed during embryonic development. All tumor cells exclusively express the embryonic M2 isoform. A well-known difference between the M1 and M2 isoforms of PK is that M2 is a low-activity enzyme that relies on allosteric activation by the upstream glycolytic intermediate, fructose-1,6-bisphosphate (FBP), whereas M1 is a constitutively active enzyme.

All tumor cells exclusively express the embryonic M2 isoform of pyruvate kinase, suggesting PKM2 as a potential target for cancer therapy. PKM2 is also expressed in adipose tissue and activated T-cells. Thus, the modulation (e.g. inhibition or activation) of PKM2 may be effective in the treatment of, e.g., obesity, diabetes, autoimmune conditions, and proliferation-dependent diseases, e.g., benign prostatic hyperplasia (BPH). Current inhibitors of pyruvate kinase are not selective, making it difficult to treat disease related to pyruvate kinase function.

Furthermore, phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation will lead to the loss of allosteric control of PKM2 needed for shunting biochemical intermediates from glycolysis into biosynthesis of nucleotides and lipids. Thus, the activation of PKM2 (i.e., activators of PKM2) can also inhibit the growth and proliferation of cancer cells, activated immune cells, and fat cells.

There is a continuing need for novel treatments of diseases such as cancer, diabetes, obesity, autoimmune conditions, proliferation-dependent diseases (e.g., BPH), and other diseases related to the function of pyruvate kinase (e.g., PKM2).

SUMMARY OF INVENTION

Described herein are compounds that modulate pyruvate kinase M2 (PKM2) and pharmaceutically acceptable salts, solvates, and hydrates thereof, for example, compounds that activate PKM2. Also provided are pharmaceutical compositions comprising a compound provided herewith and the use of such compositions in methods of treating diseases and conditions that are related to pyruvate kinase function (e.g., PKM2 function), including, e.g., cancer, diabetes, obesity, autoimmune disorders, and benign prostatic hyperplasia (BPH).

In one embodiment, provided is a pharmaceutical composition comprising a compound or a pharmaceutically acceptable salt of formula (I):

(I)

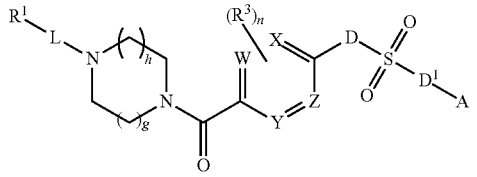

wherein:

W, X, Y and Z are each independently selected from CH or N;

D and $D^1$ are independently selected from a bond or $NR^b$;

A is optionally substituted aryl or optionally substituted heteroaryl;

L is a bond, —C(O)—, —$(CR^cR^c)_m$—, —OC(O)—, —$(CR^cR^c)_m$—OC(O)—, —$(CR^cR^c)_m$—C(O—, $NR^bC$(S)—, or —$NR^bC$(O)— (wherein the point of the attachment to $R^1$ is on the left-hand side);

$R^1$ is selected from alkyl, cycloalkyl, aryl, heteroaryl, and heterocyclyl; each of which is substituted with 0-5 occurrences of $R^d$;

each $R^3$ is independently selected from halo, haloalkyl, alkyl, hydroxyl and —$OR^a$, or two adjacent $R^3$ taken together with the carbon atoms to which they are attached form an optionally substituted heterocyclyl; each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —C(O)$R^a$, —OC(O)$R^a$, —C(O)O$R^a$, —S$R^a$, $NR^aR^b$ and —O$R^a$, or two $R^d$ taken together with the carbon atoms to which they are attached form an optionally substituted heterocyclyl;

n is 0, 1, or 2;

m is 1, 2 or 3;

h is 0, 1, 2; and g is 0, 1 or 2.

In another embodiment, provided is a method for treating or preventing a disease, condition or disorder as described (e.g., treating) herein comprising administering a compound provided herein, a pharmaceutically acceptable salt thereof, or pharmaceutical composition thereof.

In another embodiments, provided is a method of modulating (e.g., increasing or decreasing) the level of PKM2 activity and/or glycolysis (e.g., modulating the endogenous ability of a cell in the patient to down regulate PKM2) in a patient in need thereof. The method comprises the step of administering an effective amount of a compound described herein to the patient in need thereof, thereby modulating (e.g., increasing or decreasing) the level of PKM2 activity and/or glycolysis in the patient. In some embodiments, a compound or a composition described herein is used to maintain PKM2 in its active conformation or activate pyruvate kinase activity in proliferating cells as a means to divert glucose metabolites into catabolic rather than anabolic processes in the patient.

In another embodiment, provided is a method of inhibiting cell proliferation in a patient in need thereof. The method comprises the step of administering an effective amount of a compound described herein to the patient in need thereof, thereby inhibiting cell proliferation in the patient. E.g., this method can inhibiting growth of a transformed cell, e.g., a cancer cell, or generally inhibiting growth in a PKM2-dependent cell that undergoes aerobic glycolysis.

In another embodiment, provided is a method of treating a patient suffering from or susceptible to a disease or disorder associated with the function of PKM2 in a patient in need thereof. The method comprises the step of administering an effective amount of a compound described herein to the patient in need thereof, thereby treating, preventing or ameliorating the disease or disorder in the patient. In certain embodiment the modulator is provided in a pharmaceutical composition. In certain embodiment, the method includes identifying or selecting a patient who would benefit from modulation (e.g., activation) of PKM2. E.g., the patient can be identified on the basis of the level of PKM2 activity in a cell of the patient for treatment of cancer associated with PKM2 function. In another embodiment, the selected patient is a patient suffering from or susceptible to a disorder or disease identified herein, e.g., a disorder characterized by unwanted cell growth or proliferation, e.g., cancer, obesity, diabetes, atherosclerosis, restenosis, and autoimmune diseases.

In another embodiment, the compound described herein is administered at a dosage and frequency sufficient to increase lactate production or oxidative phosphorylation.

BRIEF DESCRIPTION OF THE FIGURES

FIGA. 1A-1A-44 represent a table of exemplary compounds and the corresponding activity of the compound.

DETAILED DESCRIPTION

Figure 1A:
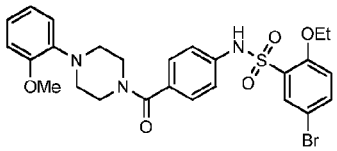
Figure 1A:
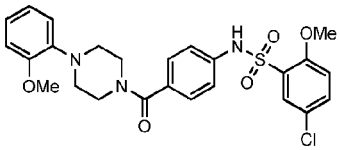
Figure 1A:
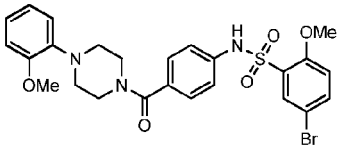
Figure 1A:
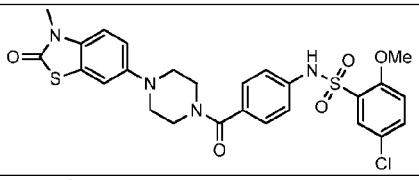
Figure 1A:
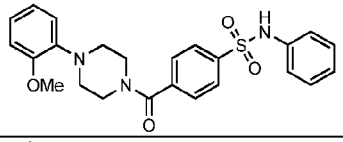
Figure 1A:
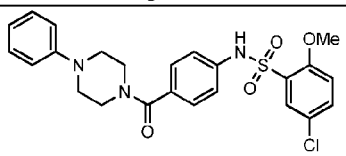
Figure 1A:
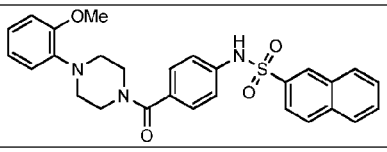
Figure 1A:
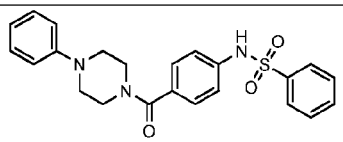
Figure 1A:
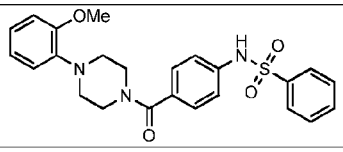
Figure 1B:
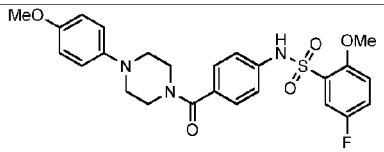
Figure 1B:
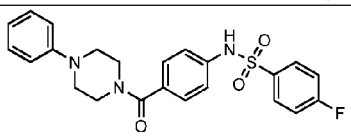
Figure 1B:
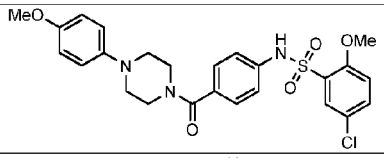
Figure 1B:
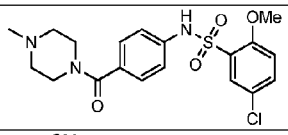
Figure 1B:
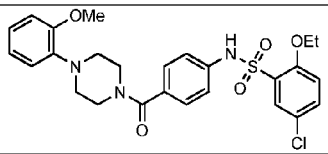
Figure 1B:
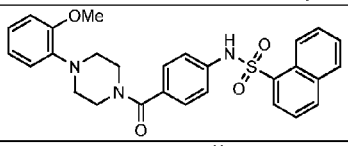
Figure 1B:
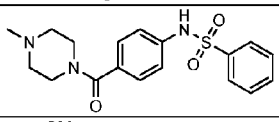
Figure 1B:
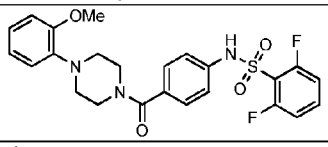
Figure 1B:
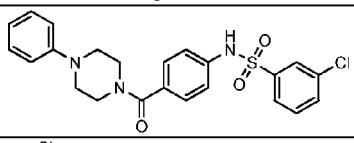
Figure 1B:
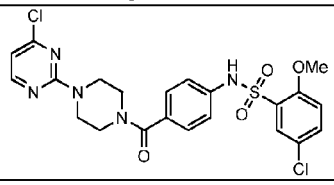
Figure 1C:
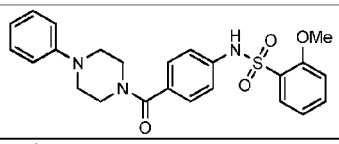
Figure 1C:
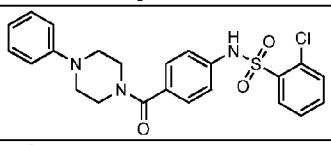
Figure 1C:
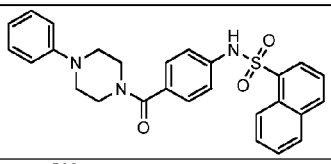
Figure 1C:
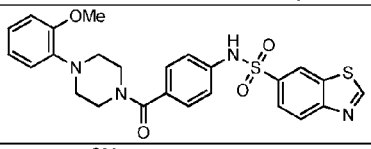
Figure 1C:
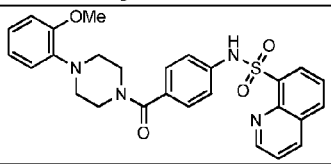
Figure 1C:
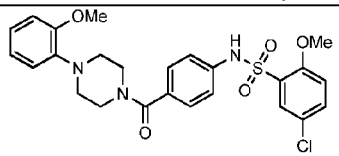
Figure 1C:
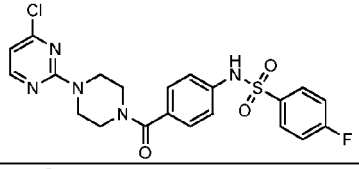
Figure 1C:
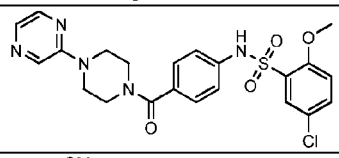
Figure 1C:
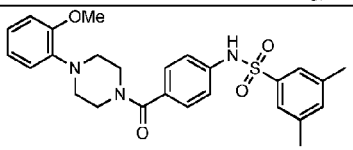
Figure 1C:
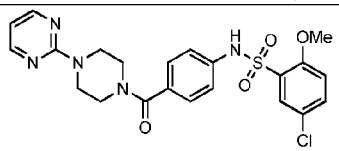
Figure 1D:
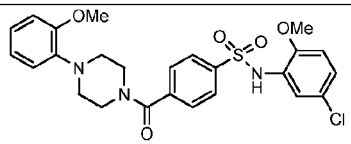
Figure 1D:
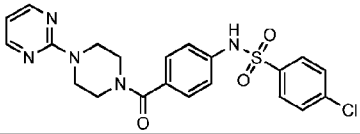
Figure 1D:
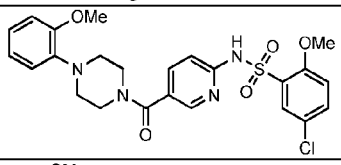
Figure 1D:
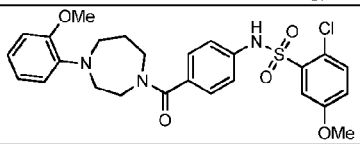
Figure 1D:
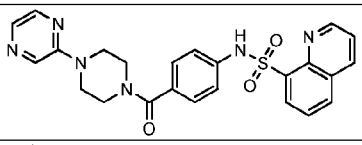
Figure 1D:
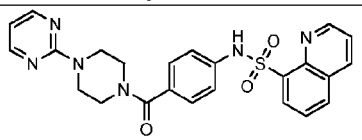
Figure 1D:
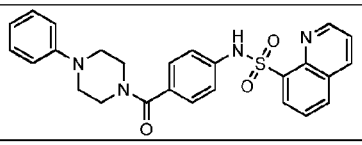
Figure 1D:
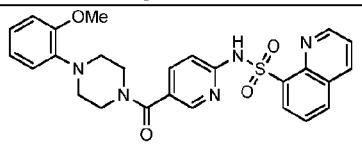
Figure 1D:
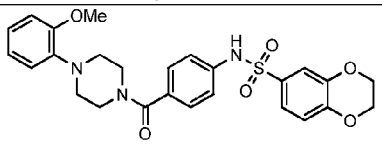
Figure 1D:
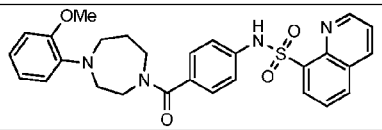
Figure 1D:
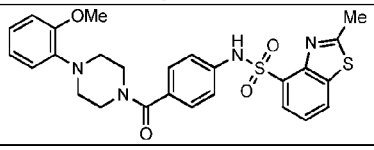
Figure 1E:
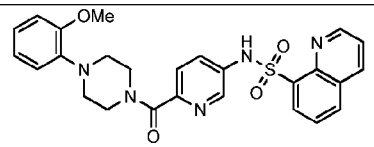
Figure 1E:
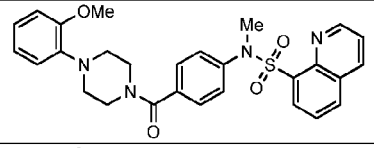
Figure 1E:
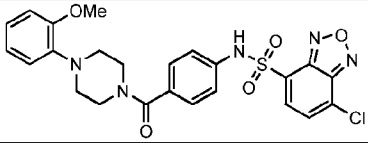
Figure 1E:
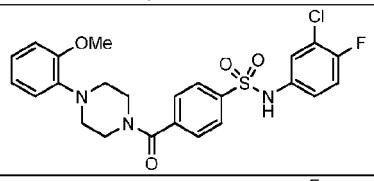
Figure 1E:
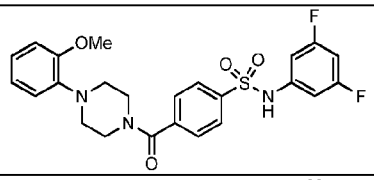
Figure 1E:
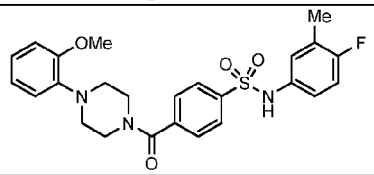
Figure 1E:
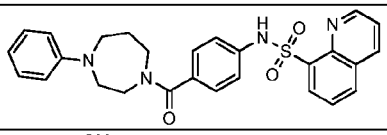
Figure 1E:
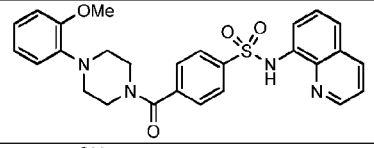
Figure 1E:
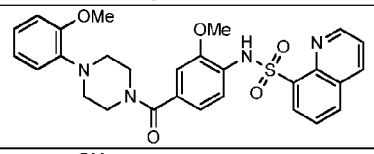
Figure 1E:
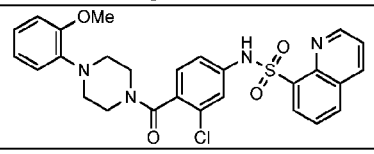
Figure 1F:
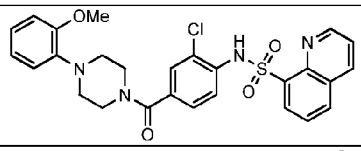
Figure 1F:
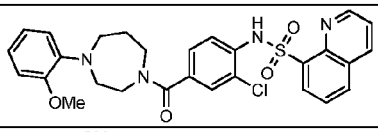
Figure 1F:
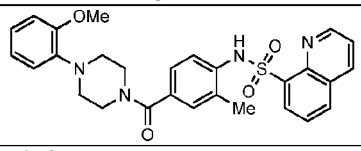
Figure 1F:
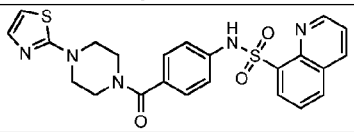
Figure 1F:
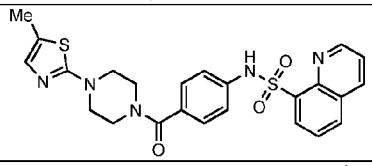
Figure 1F:
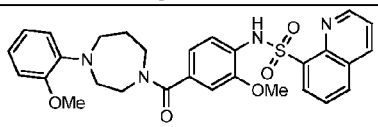
Figure 1F:
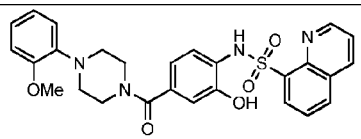
Figure 1F:
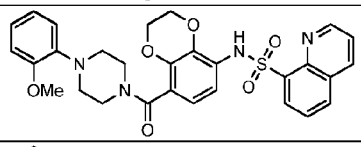
Figure 1F:
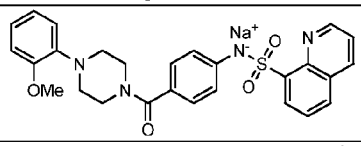
Figure 1F:
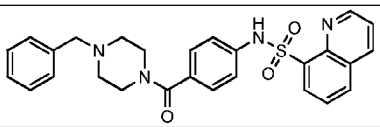
Figure 1F:
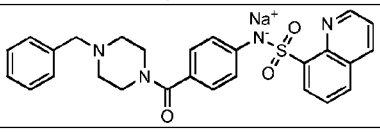
Figure 1G:
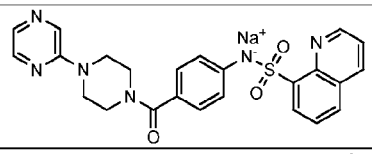
Figure 1G:
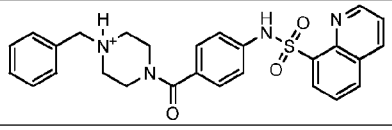
Figure 1G:
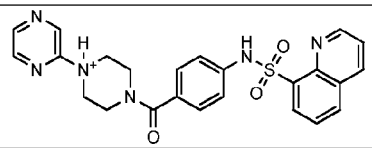
Figure 1G:
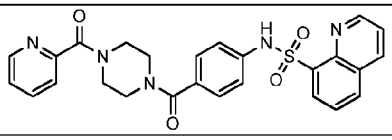
Figure 1G:
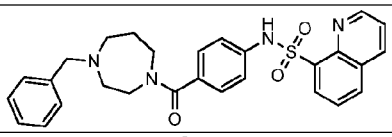
Figure 1G:
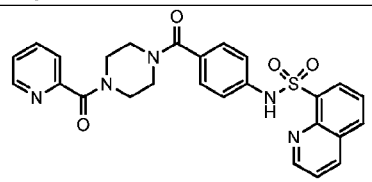
Figure 1G:
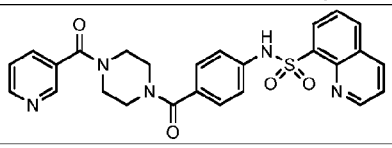
Figure 1G:
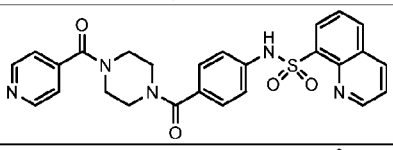
Figure 1G:
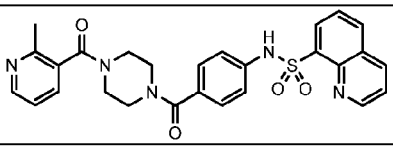
Figure 1G:
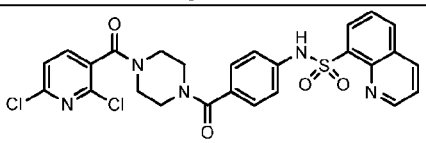
Figure 1G:
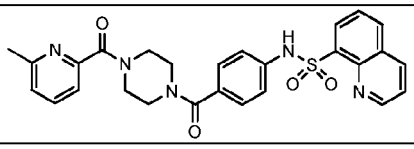
Figure 1H:
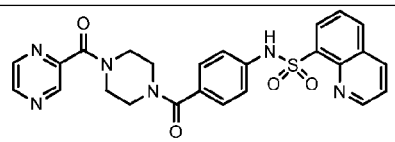
Figure 1H:
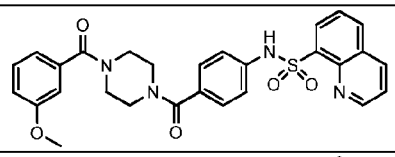
Figure 1H:
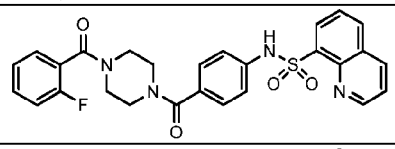
Figure 1H:
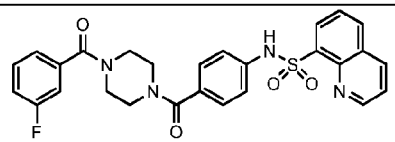
Figure 1H:
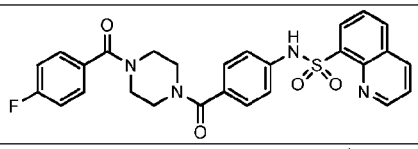
Figure 1H:
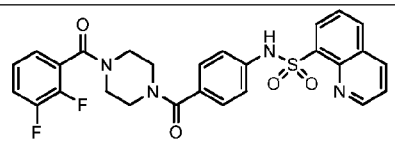
Figure 1H:
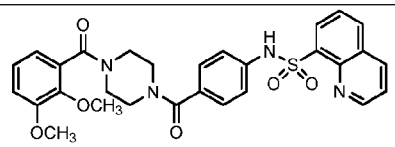
Figure 1H:
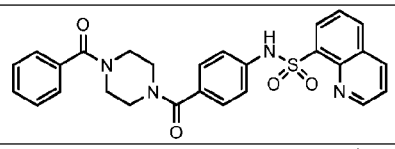
Figure 1H:
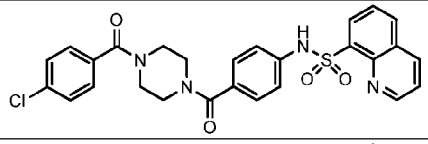
Figure 1H:
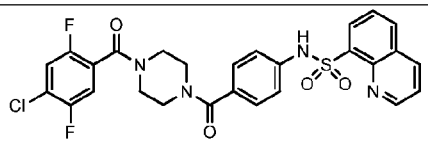
Figure 1H:
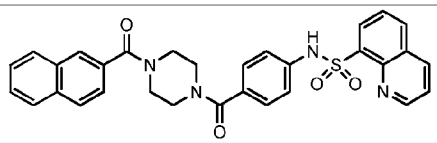
Figure 1I:
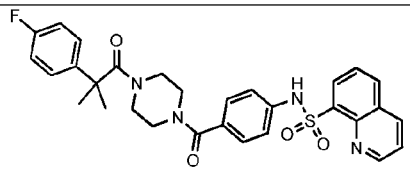
Figure 1I:
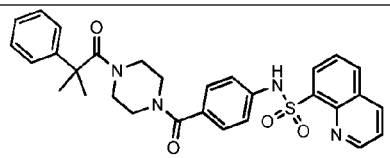
Figure 1I:
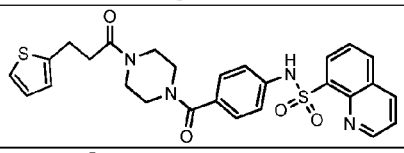
Figure 1I:
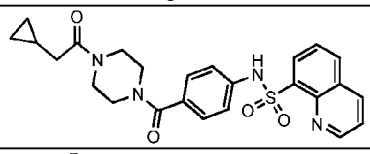
Figure 1I:
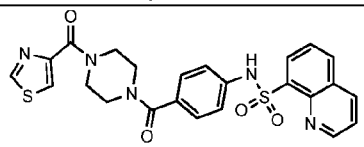
Figure 1I:
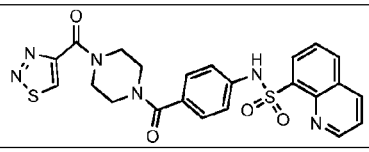
Figure 1I:
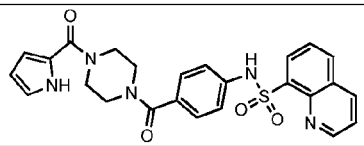
Figure 1I:
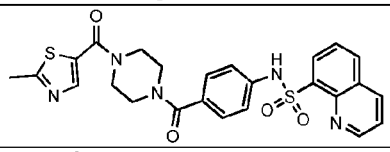
Figure 1I:
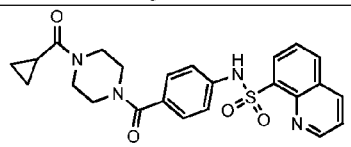
Figure 1I:
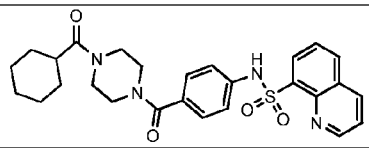
Figure 1J:
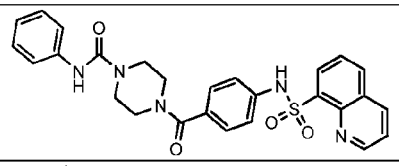
Figure 1J:
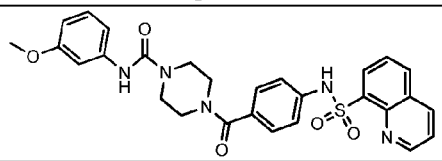
Figure 1J:
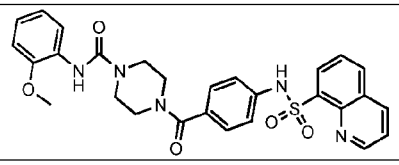
Figure 1J:
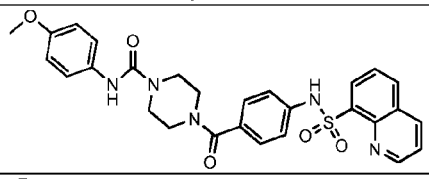
Figure 1J:
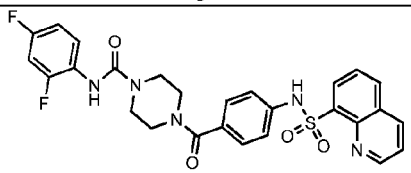
Figure 1J:
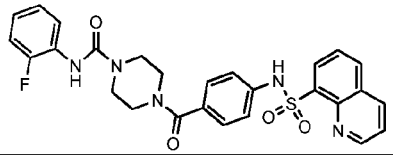
Figure 1J:
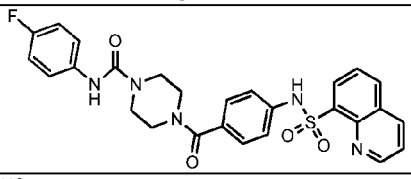
Figure 1J:
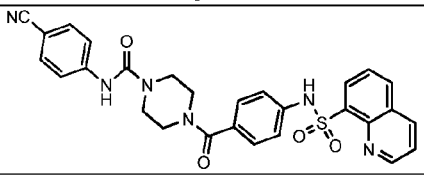
Figure 1J:
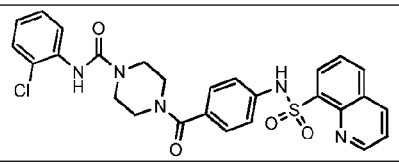
Figure 1K:
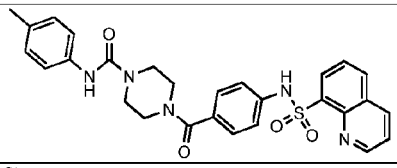
Figure 1K:
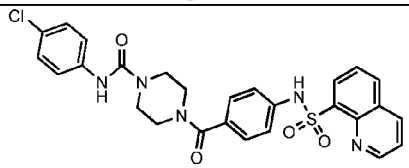
Figure 1K:
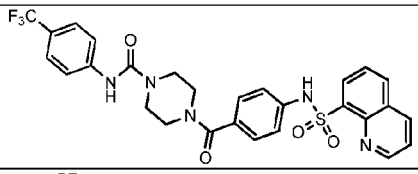
Figure 1K:
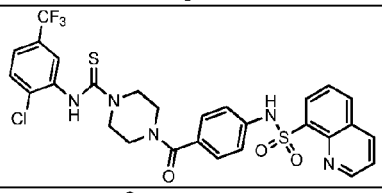
Figure 1K:
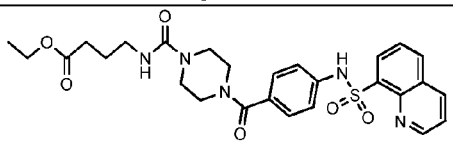
Figure 1K:
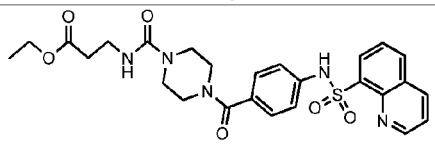
Figure 1K:
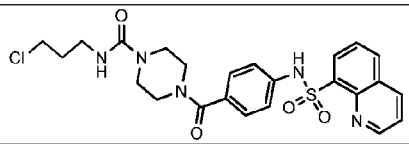
Figure 1K:
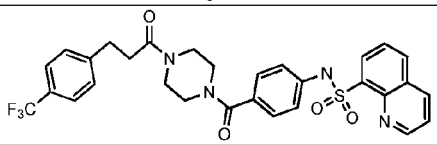
Figure 1K:
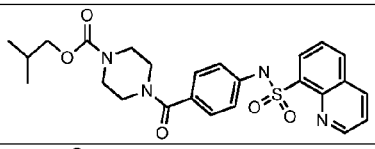
Figure 1K:
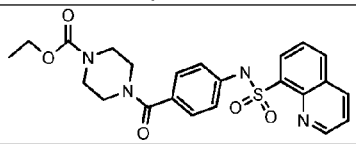
Figure 1L:
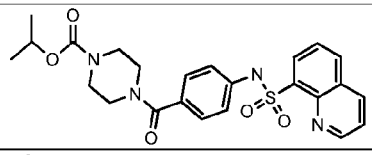
Figure 1L:
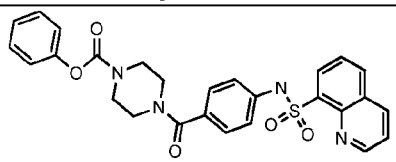
Figure 1L:
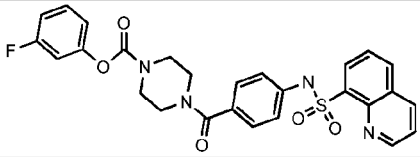
Figure 1L:
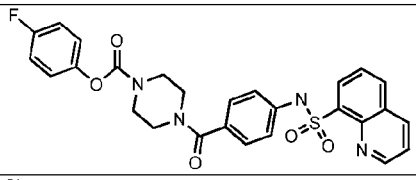
Figure 1L:
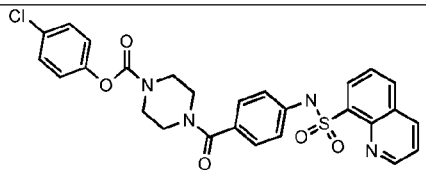
Figure 1L:
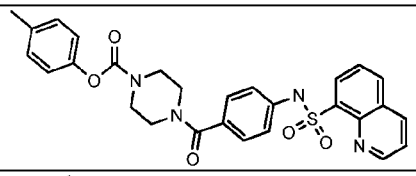
Figure 1L:
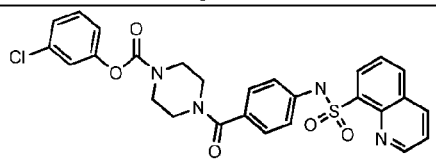
Figure 1L:
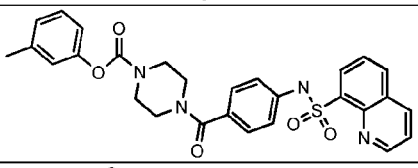
Figure 1L:
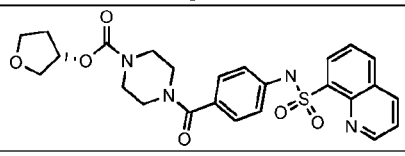
Figure 1M:
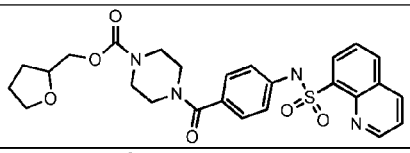
Figure 1M:
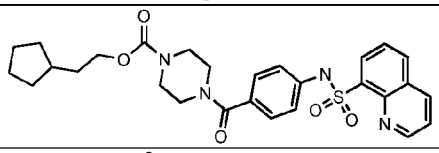
Figure 1M:
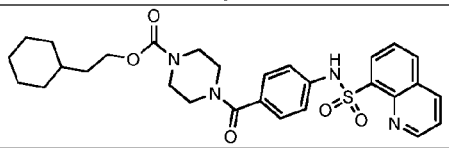
Figure 1M:
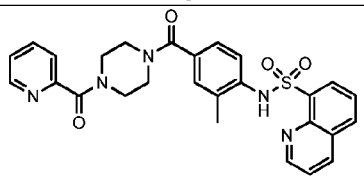
Figure 1M:
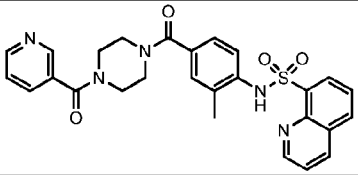
Figure 1M:
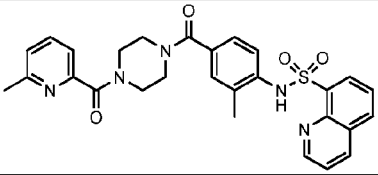
Figure 1M:
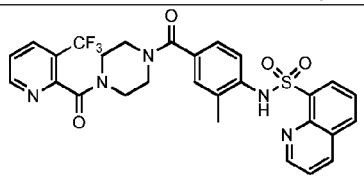
Figure 1M:
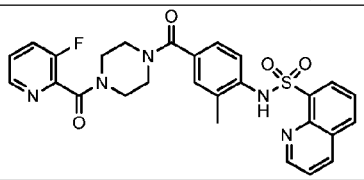
Figure 1M:
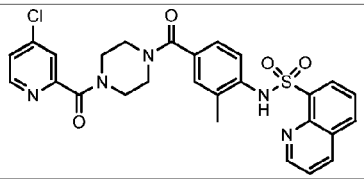
Figure 1N:
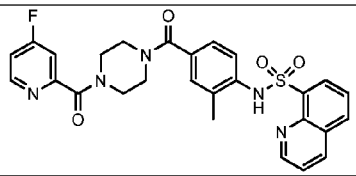
Figure 1N:
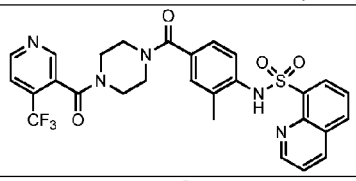
Figure 1N:
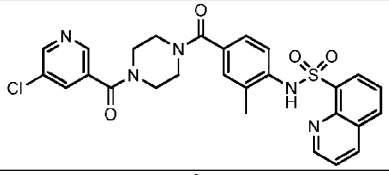
Figure 1N:
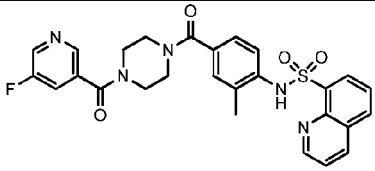
Figure 1N:
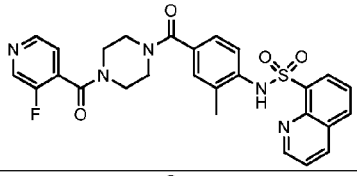
Figure 1N:
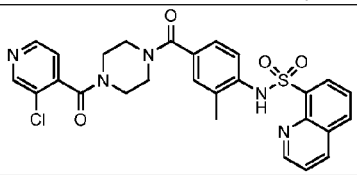
Figure 1N:
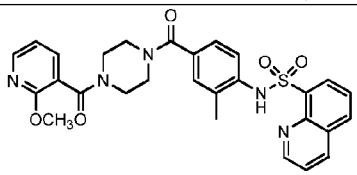
Figure 1N:
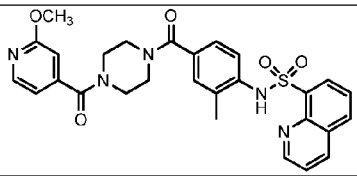
Figure 1O:
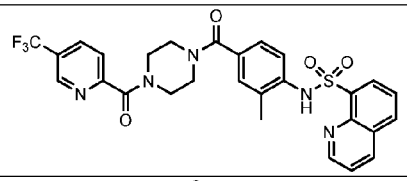
Figure 1O:
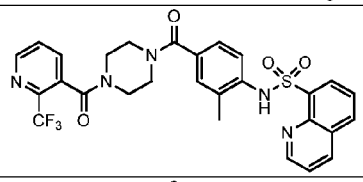
Figure 1O:
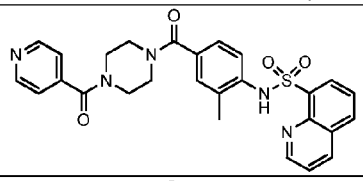
Figure 1O:
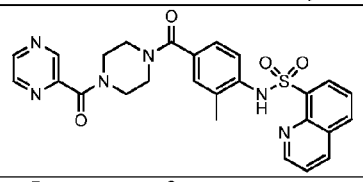
Figure 1O:
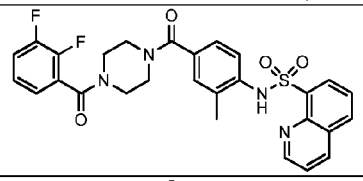
Figure 1O:
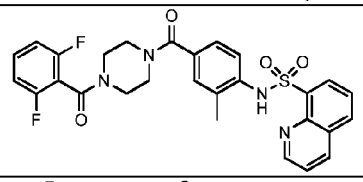
Figure 1O:
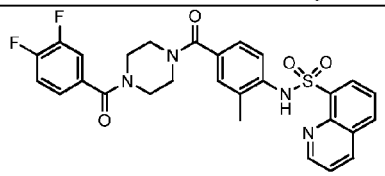
Figure 1O:
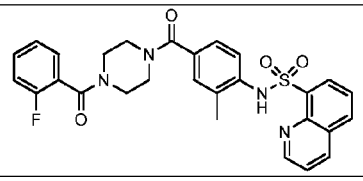
Figure 1P:
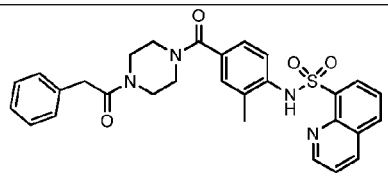
Figure 1P:
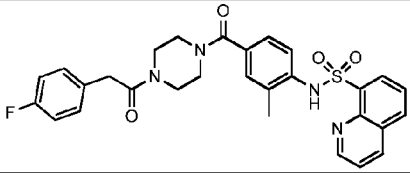
Figure 1P:
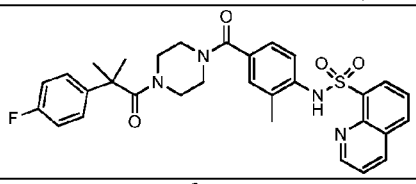
Figure 1P:
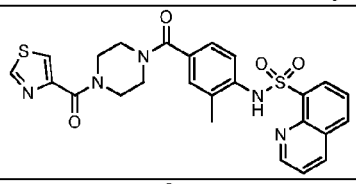
Figure 1P:
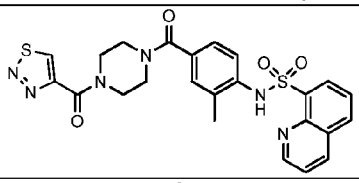
Figure 1P:
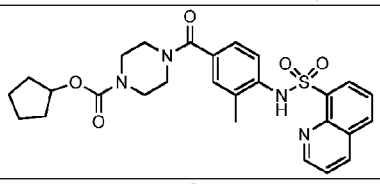
Figure 1P:
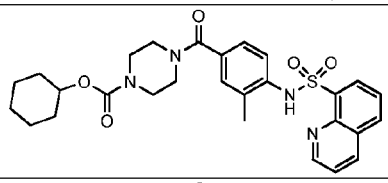
Figure 1P:
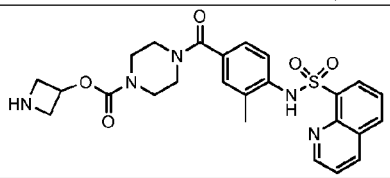
Figure 1Q:
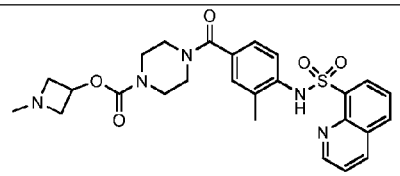
Figure 1Q:
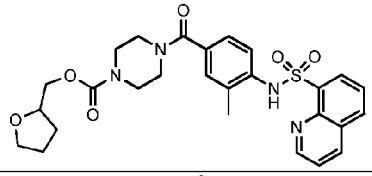
Figure 1Q:
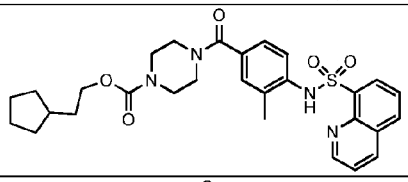
Figure 1Q:
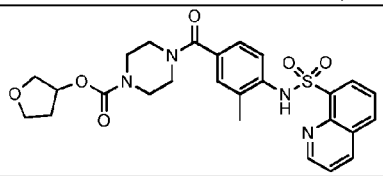
Figure 1Q:
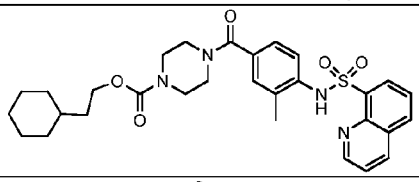
Figure 1Q:
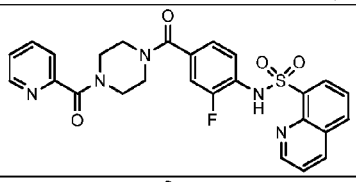
Figure 1Q:
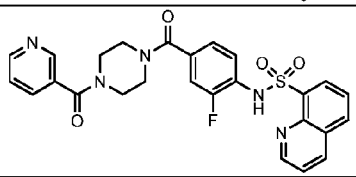
Figure 1Q:
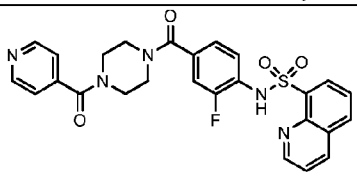
Figure 1R:
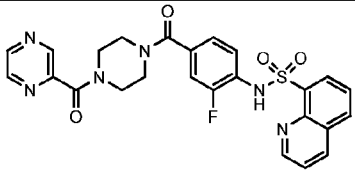
Figure 1R:
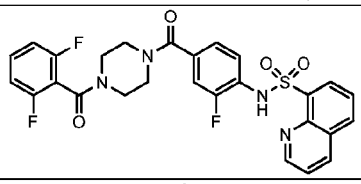
Figure 1R:
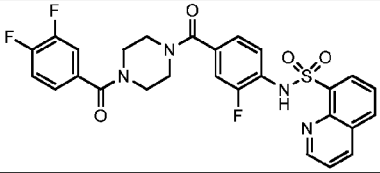
Figure 1R:
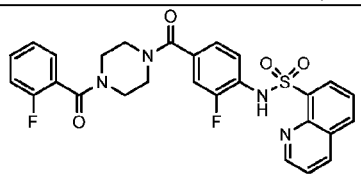
Figure 1R:
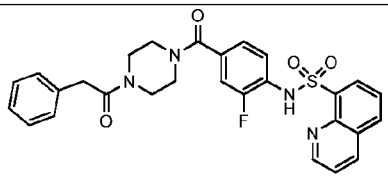
Figure 1R:
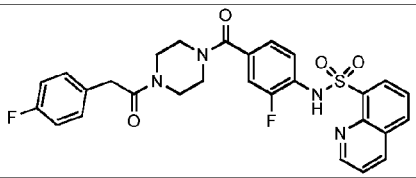
Figure 1R:
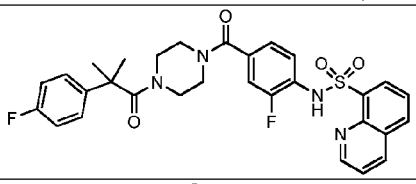
Figure 1R:
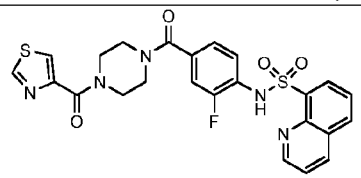
Figure 1S:
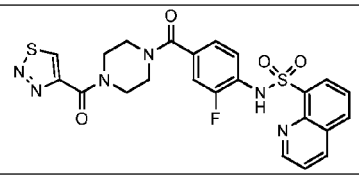
Figure 1S:
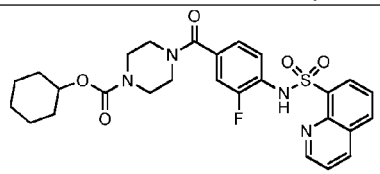
Figure 1S:
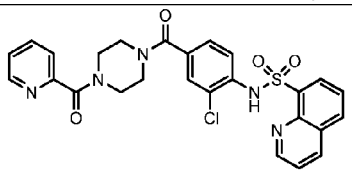
Figure 1S:
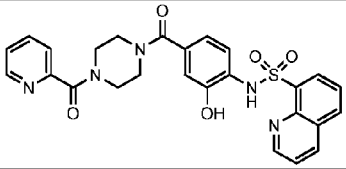
Figure 1S:
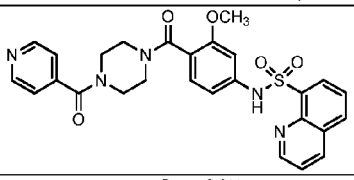
Figure 1S:
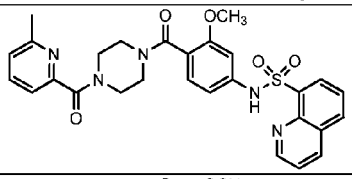
Figure 1S:
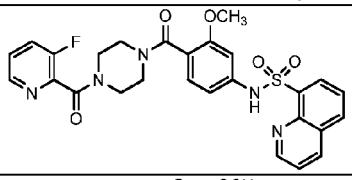
Figure 1S:
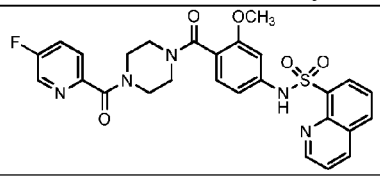
Figure 1T:
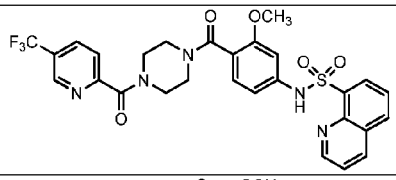
Figure 1T:
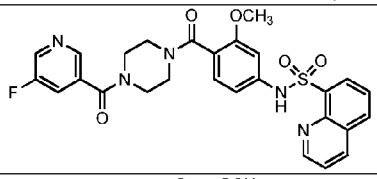
Figure 1T:
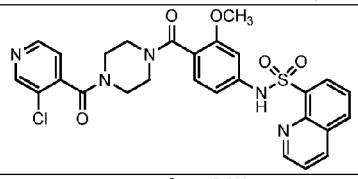
Figure 1T:
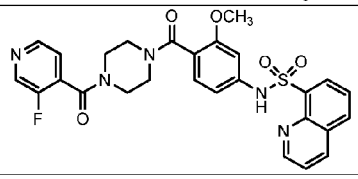
Figure 1T:
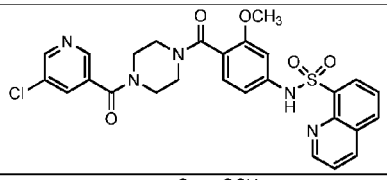
Figure 1T:
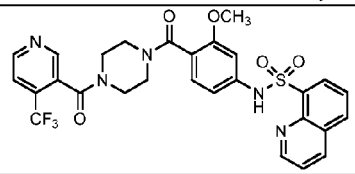
Figure 1T:
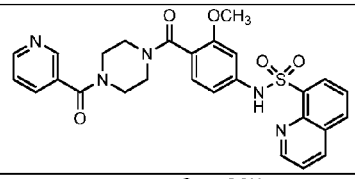
Figure 1T:
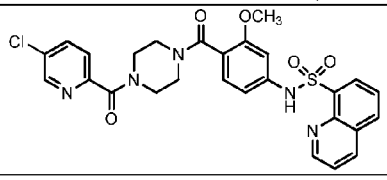
Figure 1U:
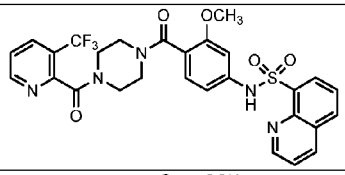
Figure 1U:
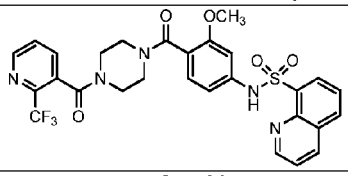
Figure 1U:
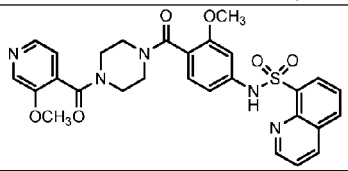
Figure 1U:
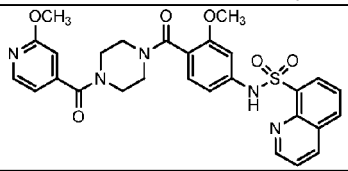
Figure 1U:
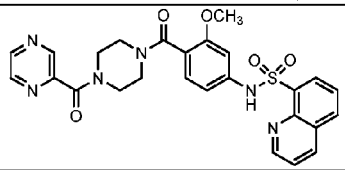
Figure 1U:
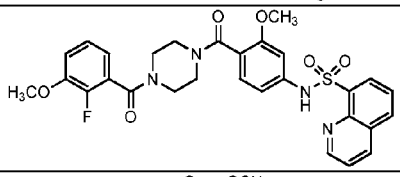
Figure 1U:
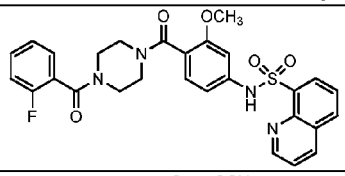
Figure 1U:
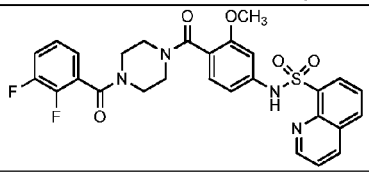
Figure 1V:
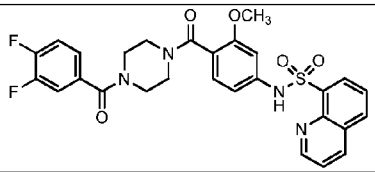
Figure 1V:
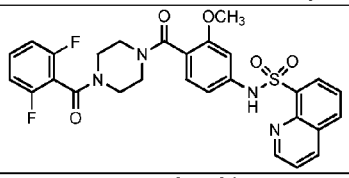
Figure 1V:
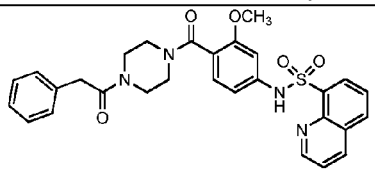
Figure 1V:
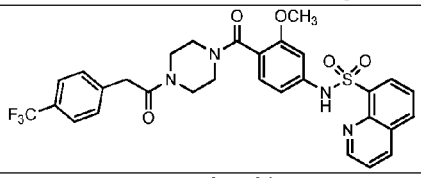
Figure 1V:
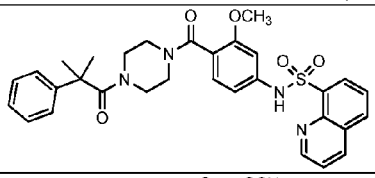
Figure 1V:
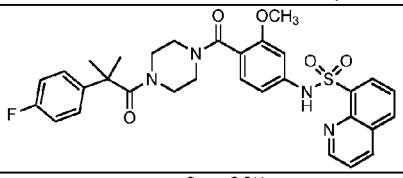
Figure 1V:
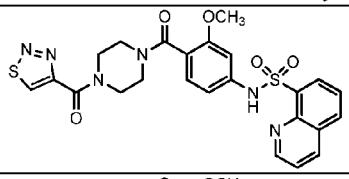
Figure 1V:
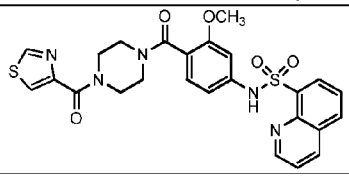
Figure 1W:
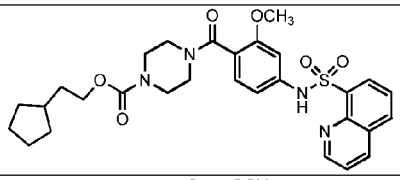
Figure 1W:
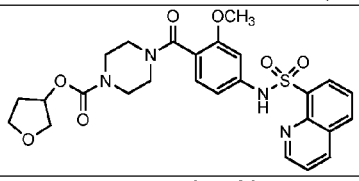
Figure 1W:
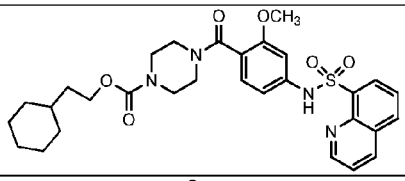
Figure 1W:
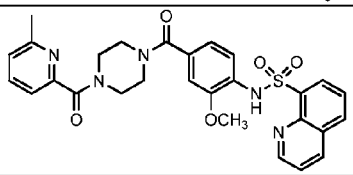
Figure 1W:
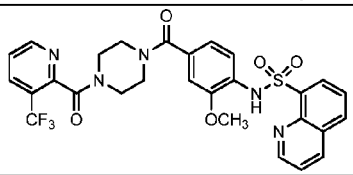
Figure 1W:
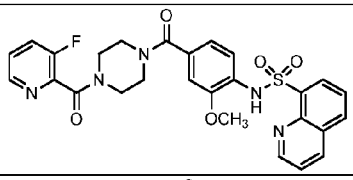
Figure 1W:
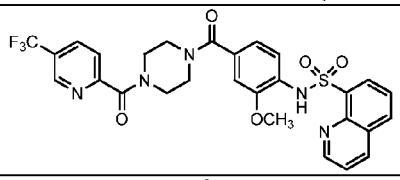
Figure 1W:
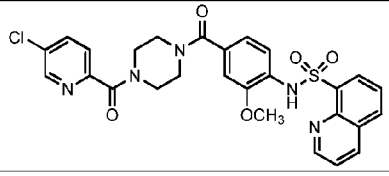
Figure 1X:
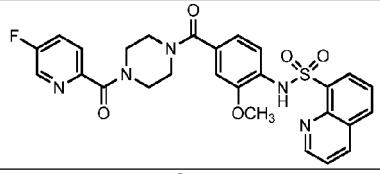
Figure 1X:
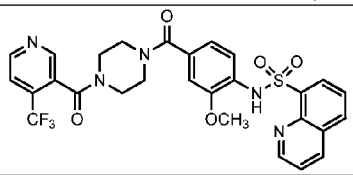
Figure 1X:
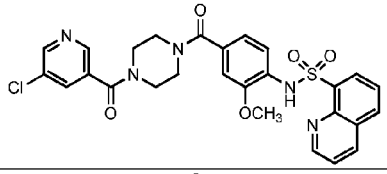
Figure 1X:
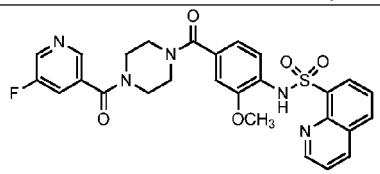
Figure 1X:
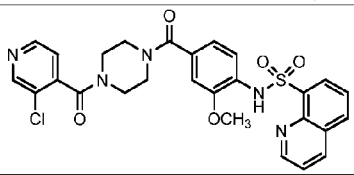
Figure 1X:
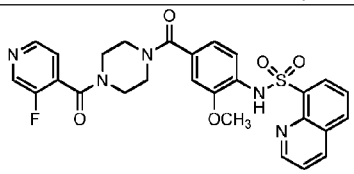
Figure 1X:
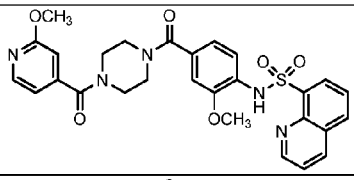
Figure 1X:
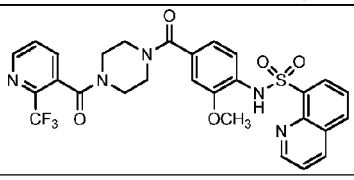
Figure 1Y:
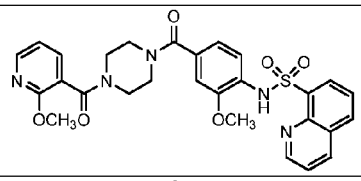
Figure 1Y:
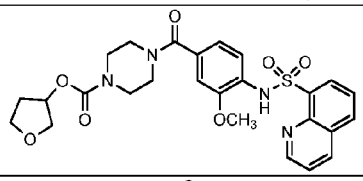
Figure 1Y:
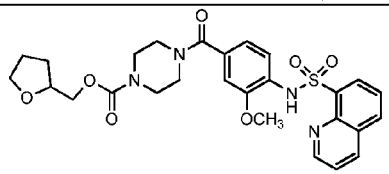
Figure 1Y:
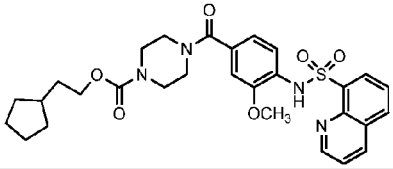
Figure 1Y:
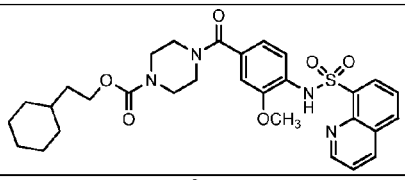
Figure 1Y:
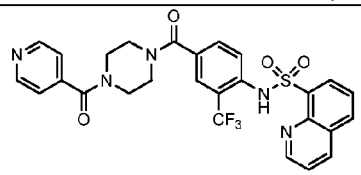
Figure 1Y:
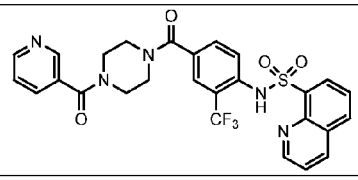
Figure 1Y:
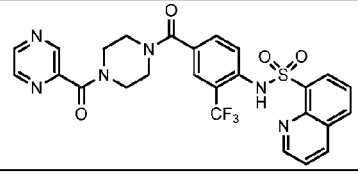
Figure 1Z:
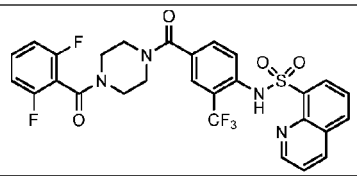
Figure 1Z:
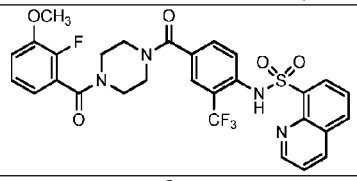
Figure 1Z:
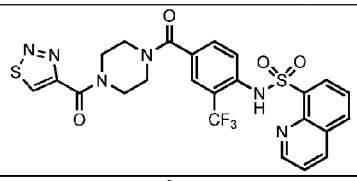
Figure 1Z:
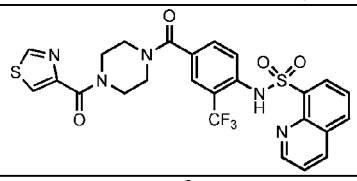
Figure 1Z:
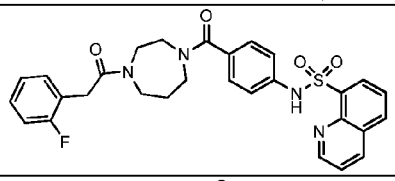
Figure 1Z:
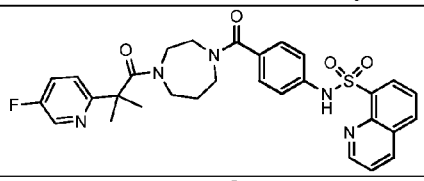
Figure 1Z:
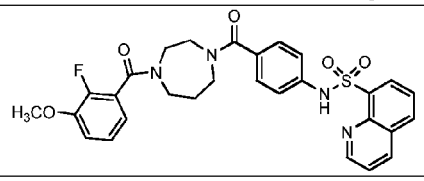
Figure 1Z:
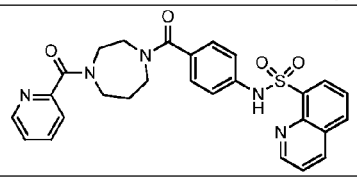
Figure 1A:
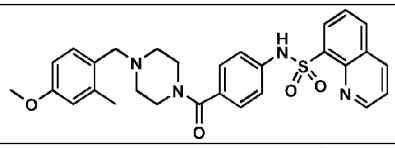
Figure 1:
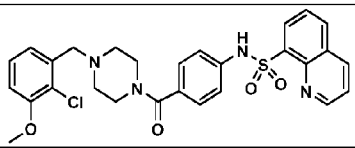
Figure 2:
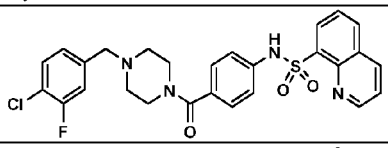
Figure 3:
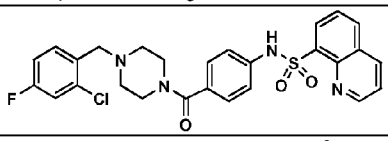
Figure 4:
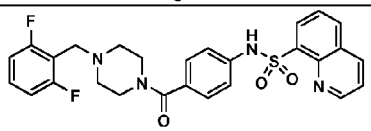
Figure 5:
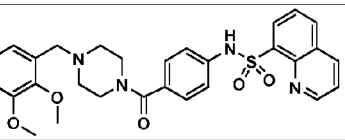
Figure 6:
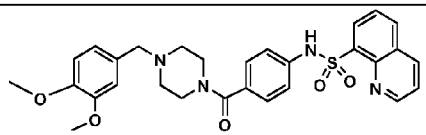
Figure 7:
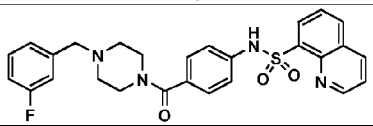
Figure 8:
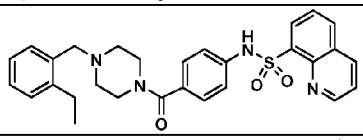
Figure 9:
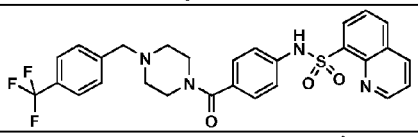
Figure 10:
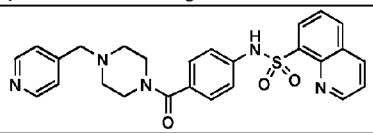

The details of construction and the arrangement of components set forth in the following description or illustrated in the drawings are not meant to be limiting. Embodiments can be practiced or carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Compounds

Described herein are compounds and compositions that modulate PKM2, for example, activate PKM2. Compounds that modulate PKM2, e.g., activate PKM2, can be used to treat disorders such as neoplastic disorders (e.g., cancer) or fat related disorders (e.g., obesity).

In one embodiment, provided is a compound of formula (I) or a pharmaceutically acceptable salt thereof, or a pharmaceutical composition comprising a compound of formula (I) or a pharmaceutically acceptable salt thereof:

(I)

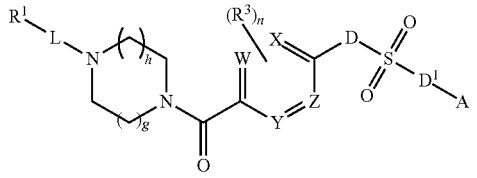

wherein:

W, X, Y and Z are each independently selected from CH or N;

D and $D^1$ are independently selected from a bond or $NR^b$;

A is optionally substituted aryl or optionally substituted heteroaryl;

L is a bond, —C(O)—, —$(CR^cR^c)_m$—, —OC(O)—, —$(CR^cR^c)_m$—OC(O)—, —$(CR^cR^c)_m$—C(O)—, —$NR^bC$(S)—, or —$NR^bC$(O)— (wherein the point of the attachment to $R^1$ is on the left-hand side);

$R^1$ is selected from alkyl, cyclalkyl, aryl, heteroaryl, and heterocyclyl; each of which is substituted with 0-5 occurrences of $R^d$;

each $R^3$ is independently selected from halo, haloalkyl, alkyl, hydroxyl and —$OR^a$, or two adjacent $R^3$ taken together with the carbon atoms to which they are attached form an optionally substituted heterocyclyl;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —C(O)$R^a$, —OC(O)$R^a$, —C(O)O$R^a$, —S$R^a$, —$NR^aR^b$ and —$OR^a$, or two $R^d$ taken together with the carbon atoms to which they are attached form an optionally substituted heterocyclyl;

n is 0, 1, or 2;

m is 1, 2 or 3;

h is 0, 1, 2; and g is 0, 1 or 2. In certain embodiments, provided is a compound of formula (I) or a pharmaceutically acceptable salt thereof:

(I)

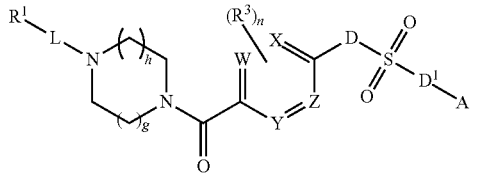

wherein:

W, X, Y and Z are each independently selected from CH or N;

D and $D^1$ are independently selected from a bond or $NR^b$;

A is optionally substituted bicyclic heteroaryl;

L is a bond, —C(O)—, —$(CR^cR^c)_m$—, —OC(O)—, —$(CR^cR^c)_m$—OC(O)—, —$(CR^cR^c)_m$—C(O)—, —$NR^bC(S)$—, or —$NR^bC(O)$;

$R^1$ is selected from alkyl, cycloalkyl, aryl, heteroaryl, and heterocyclyl; each of which is substituted with 0-5 occurrences of $R^d$;

each $R^3$ is independently selected from halo, haloalkyl, alkyl, hydroxyl and —$OR^a$ or two adjacent $R^3$ taken together with the carbon atoms to which they are attached form an optionally substituted cyclyl; each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —C(O)$R^a$, —OC(O)$R^a$, —C(O)$OR^a$, —$SR^a$, $NR^aR^b$ and —$OR^a$, or two $R^d$ taken together with the carbon atoms to which they are attached form an optionally substituted heterocyclyl;

n is 0, 1, or 2;

m is 1, 2 or 3;

h is 0, 1, 2; and g is 0, 1 or 2. In some embodiments, h is 1. In some embodiments, h is 2.

In some embodiments, g is 1. In some embodiments, g is 2.

In some embodiments, both h and g are 1. In some embodiments, h is 1 and g is 2. In some embodiments, g is 1 and h is 2.

In some embodiments, W, X, Y and Z are CH. In some embodiments, at least one of W, X, Y and Z is N. In some embodiments, at least two of W, X, Y and Z are N. In some embodiments, at least three of W, X, Y and Z are N.

In some embodiments, W, X, Y, Z and the carbons to which they are attached form a pyridyl ring. In some embodiments, W, X, Y, Z and the carbon atoms to which they are attached form a pyrimidyl ring. In some embodiments, W, X, Y, Z and the carbon atoms to which they are attached form a pyridazinyl ring.

In some embodiments, W, X and Y are CH and Z is N.

In some embodiments, X, Y and Z are CH and W is N.

In some embodiments, D is $NR^b$ and $D^1$ is a bond. In some embodiments, D is a bond and $D^1$ is $NR^b$. In some embodiments, both D and $D^1$ are $NR^b$. In some embodiments, $R^b$ is alkyl (e.g., methyl or ethyl). In some embodiments, $R^b$ is hydrogen (H).

In some embodiments, A is a 9-10 membered bicyclic heteroaryl (e.g., quinazolinyl, quinoxalinyl, cinnolinyl, isoquinolyl, indolyl, benzoxazolyl, pyrrolopyridyl, pyrrolopyrimidyl, benzimidazolyl, benzthiazolyl, or benzoxazolyl). In some embodiments, A is a N-containing 9-10 membered bicyclic heteroaryl. In some embodiments, A is optionally substituted quinazolinyl (e.g., 8-quinazolinyl or 4-quinazolinyl), optionally substituted quinoxalinyl (e.g., 5-quinoxalinyl), optionally substituted quinolinyl (e.g., 4-quinolinyl or 8-quinolinyl), optionally substituted cinnolinyl (e.g., 8-cinnolinyl), optionally substituted isoquinolinyl, optionally substituted indolyl (7-indolyl), optionally substituted benzoxazolyl (e.g., 7-benzoxazolyl), optionally substituted pyrrolopyridyl (e.g., 4-pyrrolopyridyl), optionally substituted pyrrolopyrimidyl (e.g., 4-pyrrolopyrimidyl), optionally substituted benzimidazolyl (e.g., 7-benzimidazolyl), optionally substituted benzthiazolyl (e.g., 4-benzthiazolyl, 2-methyl-4-benzthiazolyl or 7-benzthiazolyl), or optionally substituted benzoxazolyl (e.g., 4-benzoxazolyl). In some embodiments, A is optionally substituted with halo. In some embodiments, A is

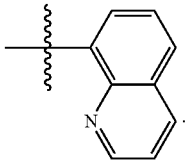

In some embodiments, A is

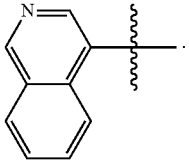

In some embodiments, A is optionally substituted

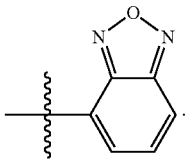

In some embodiments, A is

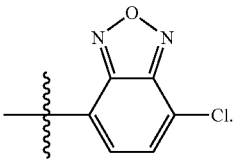

In some embodiments, L is a bond.

In some embodiments, L is —$(CR^cR^c)_m$— and m is 1. In some aspects of these embodiments, each $R^c$ is hydrogen. In some aspects of these embodiments, one $R^c$ is alkyl (e.g., methyl or ethyl) and the other $R^c$ is hydrogen. In some aspects of these embodiments, one $R^c$ is halo (e.g., fluoro) and one $R^c$ is hydrogen. In some aspects of these embodiments, both $R^c$ are halo (e.g., fluoro). In some aspects of these embodiments, one $R^c$ is alkoxy (e.g., methoxy or ethoxy) and one $R^c$ is hydrogen. In some aspects of these embodiments, both $R^c$ are alkoxy (e.g., methoxy or ethoxy). In some aspects of these embodiments, two $R^c$ taken together with the carbon to which they are attached form a cycloalkyl (e.g., cyclopropyl).

In some embodiments, L is —$(CR^cR^c)_m$— and m is 2. In some aspects of these embodiments, each $R^c$ is hydrogen. In some aspects of these embodiments, $1R^c$ is alkyl (e.g., methyl or ethyl) and each of the other $R^c$ are hydrogen. In some aspects of these embodiments, two $R^c$s taken together with the carbon to which they are attached form a cycloalkyl (e.g., cyclopropyl) and each of the other two $R^c$s are hydrogen.

In some embodiments, L is —$(CR^cR^c)_m$— and m is 3. In some aspects of these embodiments each $R^c$ is hydrogen.

In some embodiments, L is —C(O)—.

In some embodiments, L is —O—(O)—.

In some embodiments, L is $NR^bC(O)$— and $R^b$ is H. In some embodiments, L is $NR^bC(S)$— and $R^b$ is H.

In some embodiments, L is —$(CR^cR^c)_m$—C(O)— and m is 1. In some aspects of these embodiments, each $R^c$ is hydrogen. In some aspects of these embodiments, one $R^c$ is alkyl (e.g., methyl or ethyl) and one $R^c$ is hydrogen. In some aspects of these embodiments, both $R^c$ are alkyl (e.g., methyl or ethyl).

In some embodiments, L is —$(CR^cR^c)_m$—C(O)— and m is 2. In some aspects of these embodiments, each $R^c$ is hydrogen.

In some embodiments, L is (—$(CR^cR^c)_m$—C(O)— and m is 3. In some aspects of these embodiments, each $R^c$ is hydrogen.

In some embodiments, $R^1$ is alkyl substituted with 0-5 occurrences of $R^d$ (e.g., methyl, ethyl, n-propyl, i-propyl, or n-butyl). In some embodiments, $R^1$ is methyl, ethyl, n-propyl, i-propyl, or n-butyl. In some embodiments, $R^1$ is ethyl or propyl (n-propyl or i-propyl). In some aspects of these embodiments, L is a bond, —$CH_2$—, —C(O)—, or —O(CO)—. In some aspects of these embodiments, L is —O(CO)—.

In some embodiments, $R^1$ is alkyl substituted with 1 occurrence of $R^d$ (e.g., methyl, ethyl, n-propyl, i-propyl, or n-butyl). In some embodiments, $R^1$ is methyl, ethyl, or n-propyl substituted with 1 occurrence of $R^d$. In some aspects of these embodiments, $R^d$ is halo (e.g., fluorine or chlorine). In some aspects of these embodiments, $R^d$ is —$C(O)OR^a$. In some aspects of these embodiments, $R^a$ is alkyl (e.g., methyl or ethyl). In some aspects of these embodiments, L is —NHC (O)—.

In some embodiments, $R^1$ is alkyl substituted with 2 occurrences of $R^d$ (e.g., methyl, ethyl, n-propyl, i-propyl, or n-butyl). In some embodiments, $R^1$ is methyl, ethyl, or n-propyl substituted with 2 occurrences of $R^d$. In some embodiments, $R^1$ is n-propyl substituted with 2 occurrences of $R^d$. In some aspects of these embodiments, $1R^d$ is cyano and the other $R^d$ is —$NR^aR^b$. In some aspects of these embodiments, $R^a$ and $R^b$ are hydrogen. In some aspects of these embodiments, L is —$CH_2$—.

In some embodiments, $R^1$ is heteroaryl substituted with 0-5 occurrences of $R^d$ (e.g., S-containing monocyclic heteroaryl, N-containing monocyclic heteroaryl or N-containing bicyclic heteroaryl). In some embodiments, $R^1$ is a 5-8 membered monocyclic heteroaryl substituted with 0-5 occurrences of $R^d$ (e.g., thiophenyl, pyridyl, pyrimidyl or pyrazyl). In some embodiments, $R^1$ is pyridyl substituted with 0-5 occurrences of $R^d$ (e.g., 2-pyridyl, 3-pyridyl or 4-pyridyl), pyrimidyl substituted with 0-5 occurrences of $R^d$ (e.g., 2-pyrimidyl or 5-pyrimidyl) or pyrazinyl substituted with 0-5 occurrences of $R^d$ (e.g., 2-pyrazinyl). In some embodiments, $R^1$ is thiazolyl substituted with 0-5 occurrences of $R^d$ (e.g., 2-thiazolyl or 5-thiazolyl). In some embodiments, $R^1$ is pyrimidyl substituted with 0-5 occurrences of $R^d$ (e.g., 2-pyrimidyl). In some embodiments, $R^1$ is thiadiazolyl substituted with 0-5 occurrences of $R^d$ (e.g., 4-thiadiazolyl). In some embodiments, $R^1$ is pyrrolyl substituted with 0-5 occurrences of $R^d$ (e.g., 2-pyrrolyl). In some aspects of these embodiments, L is a bond, —$CH_2$—, —C(O)—, or —O(CO)—. In some embodiments, $R^1$ is pyridyl (e.g., 2-pyridyl, 3-pyridyl or 4-pyridyl).

In some embodiments, $R^1$ is pyridyl (e.g., 2-pyridyl, 3-pyridyl or 4-pyridyl) substituted with 1 occurrence of $R^d$. In some aspects of these embodiments, $R^d$ is —$OC(O)R^a$. In some aspects of these embodiments, $R^d$ is —$OR^a$. In some aspects of these embodiments, $R^d$ is —$C(O)OR^a$. In some aspects of these embodiments, $R^d$ is alkyl (e.g., methyl or ethyl). In some aspects of these embodiments, $R^d$ is haloalkyl (e.g., trifluoromethyl). In some aspects of these embodiments, $R^d$ is halo (e.g., fluorine or chlorine). In some aspects of these embodiments, $R^a$ is alkyl (e.g., methyl or ethyl). In some aspects of these embodiments, L is —$CH_2$—. In some embodiments, $R^1$ is pyridyl (e.g., 2-pyridyl, 3-pyridyl or 4-pyridyl) substituted with 2 occurrences of $R^d$. In some aspects of these embodiments, one $R^d$ is —$C(O)OR^a$ and the other $R^d$ is —$OR^a$. In some aspects of these embodiments, $R^a$ is alkyl (e.g., methyl or ethyl). In some aspects of these embodiments, both $R^d$ are halo (e.g., fluoro or chloro). In some aspects of these embodiments, L is —$CH_2$—.

In some embodiments, $R^1$ is pyrimidyl (e.g., 2-pyrimidyl or 5-pyrimidyl). In some aspects of these embodiments, L is a bond.

In some embodiments, $R^1$ is pyrimidyl (e.g., 2-pyrimidyl or 5-pyrimidyl) substituted with 1 occurrence of $R^d$. In some aspects of these embodiments, $R^d$ is halo (e.g., fluoro or chloro).

In some embodiments, $R^1$ is pyrazinyl (e.g., 2-pyrazinyl). In some aspects of these embodiments, L is a bond.

In some embodiments, $R^1$ is thiazolyl (e.g., 2-thiazolyl, 4-thiazolyl, or 5-thiazolyl). In some aspects of these embodiments, L is —C(O)—.

In some embodiments, $R^1$ is thiazolyl (e.g., 2-thiazolyl, 4-thiazolyl, or 5-thiazolyl) substituted with 1 occurrences of $R^d$. In some aspects of these embodiments, $R^d$ is alkyl (e.g, methyl or ethyl). In some aspects of these embodiments, L is —C(O)—.

In some embodiments, $R^1$ is thiophenyl substituted with 0-5 occurrences of $R^d$ (e.g., 2-thiophenyl). In some embodiments, $R^1$ is thiophenyl.

In some embodiments, $R^1$ is thiadiazolyl (e.g., 4-thiadiazolyl).

In some embodiments, $R^1$ is pyrrolyl (e.g., 2-pyrrolyl).

In some embodiments, $R^1$ is cycloalkyl substituted with 0-5 occurrences of $R^d$ (e.g., cyclopropyl, cyclopentyl or cyclohexyl). In some embodiments, $R^1$ is cyclopropyl. In some embodiments, $R^1$ is cyclohexyl. In some embodiments, $R^1$ is cyclopentyl. In some aspect of these embodiments, L is —$CH_2$—C(O)—. In some embodiment, $R^1$ is aryl substituted with 0-5 occurrences of $R^d$. In some aspects of these embodiments, L is a bond, —$CH_2$—, —C(O)—, or —O(CO)—.

In some embodiments $R^1$ is aryl (e.g., phenyl). In some embodiments, $R^1$ is phenyl. In some aspects of these embodiments, L is a bond, —$CH_2$—, —C(O)—, or —O(CO)—.

In some embodiments, $R^1$ is phenyl substituted with 1 occurrence of $R^d$. In some aspects of these embodiments, $R^d$ is ortho substituted. In some aspects of these embodiments, $R^d$ is meta substituted. In some aspects of these embodiments, $R^d$ is para substituted. In some aspects of these embodiments, $R^d$ is halo (e.g., fluorine, bromine or chlorine). In some aspects of these embodiments, $R^d$ is alkyl (e.g., methyl, ethyl, isopropyl, t-butyl, n-butyl or n-pentyl). In some aspects of these embodiments, $R^d$ is haloalkyl (e.g., trifluoromethyl). In some aspects of these embodiments, $R^d$ is —$OR^a$. In some aspects of these embodiments, $R^d$ is —$C(O)R^a$. In some aspects of these embodiments, $R^d$ is —$SR^a$. In some aspects of these embodiments, $R^d$ is —C(O) $OR^a$. In some aspects of these embodiments, $R^d$ is cyano. In some aspects of these embodiments, $R^d$ is —$NR^aR^b$. In some aspects of these embodiments, $R^d$ is haloalkoxy (e.g., difluoromethoxy or trifluoromethoxy). In some aspects of these embodiments, $R^d$ is hydroxyl. In some aspects of these embodiments, $R^d$ is —OC (O)$R^a$. In some aspects of these embodiments, $R^d$ is alkynyl (e.g., 1-hexynyl). In some aspects of these embodiments, $R^d$ is haloalkyl (e.g., trifluoromethyl). In some aspects of these embodiments, $R^a$ is alkyl (e.g., methyl, ethyl, n-propyl, isopropyl, n-butyl, isobutyl, t-butyl or n-pentyl). In some aspects of these embodiments, $R^a$ is hydroxyalkyl (e.g., 2-hydroxylethyl). In some aspects of these embodiments, $R^a$ and $R^b$ are alkyl (e.g., methyl or ethyl). In some aspects of these embodiments, $R^a$ is acyl (e.g., acetyl) and $R^b$ is hydrogen. In some aspects of these embodiments, L is a bond, —$CH_2$—, —C(O)—, or —O(CO)—.

In some embodiments, $R^1$ is phenyl substituted with 2 occurrences of $R^d$. In some aspects of these embodiments, both $R^d$ are halo (e.g., fluorine or chlorine). In some aspects of these embodiments, both $R^d$ are alkyl (e.g., methyl or ethyl). In some aspects of these embodiments, 1$R^d$ is alkyl (e.g., methyl or ethyl) and the other is —$OR^a$. In some aspects of these embodiments, 1 $R^d$ is halo (e.g., fluorine or chlorine) and the other $R^d$ is —$OR^a$. In some aspects of these embodiments, both $R^d$ are —$OR^a$. In some aspects of these embodiments, 1 $R^d$ is halo (e.g., fluorine or chlorine) and the other $R^d$ is hydroxyl. In some aspects of these embodiments, 1 $R^d$ is halo (e.g., fluorine or chlorine) and the other is haloalkyl (e.g., trifluoromethyl). In some aspects of these embodiments, 1 $R^d$ is —$OR^a$ and the other $R^d$ is —C(O) $OR^a$. In some aspects of these embodiments, 1 $R^d$ is —$OR^a$ and the other $R^d$ is hydroxyl. In some aspects of these embodiments, 1 $R^d$ is alkyl (e.g., methyl or ethyl) and the other $R^d$ is hydroxyl. In some aspects of these embodiments, both $R^d$ are hydroxyl. In some aspects of these embodiments, 1 $R^d$ is halo (e.g., fluorine) and the other $R^d$ is haloalkyl (e.g., trifluoromethyl). In some aspects of these embodiments, both $R^d$ are hydroxyl. In some aspects of these embodiments, one $R^d$ is haloalkyl (e.g., trifluoromethyl) and the other $R^d$ is alkyl (e.g., methyl). In some aspects of these embodiments, two $R^d$, together with the carbon atoms to which they are attached, form an optionally substituted heterocyclyl. In some aspects of these embodiments, two $R^d$, together with the carbon atoms to which they are attached, form an optionally substituted 5-7 membered heterocyclyl. In some aspects of these embodiments, two $R^d$, together with the phenyl ring to which they are attached, form the following structure:

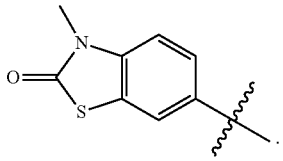

In some aspects of these embodiments, $R^a$ is alkyl (e.g., methyl or ethyl). In some aspects of these embodiments, L is a bond, —$CH_2$—, —C(O)—, or —O(CO)—.

In some embodiments, $R^1$ is phenyl substituted with 3 occurrences of $R^d$. In some aspects of these embodiments, 3 $R^d$ are halo (e.g., fluorine or chlorine). In some aspects of these embodiments, 2 $R^d$ are halo (e.g., fluorine or chlorine) and 1 $R^d$ is hydroxyl. In some aspects of these embodiments, 1 $R^d$ is halo (e.g., fluorine or chlorine), 1 $R^d$ is alkyl (e.g., methyl) and 1 $R^d$ is hydroxyl. In some aspects of these embodiments, 3 $R^d$ are alkyl (e.g., methyl or ethyl). In some aspects of these embodiments, 2 $R^d$ are alkyl (e.g., methyl or ethyl) and 1 $R^d$ is hydroxyl. In some aspects of these embodiments, 2 $R^d$ are halo (e.g., fluorine or chlorine) and 1 $R^d$ is —$OR^a$. In some aspects of these embodiments, $R^a$ is alkyl (e.g., methyl or ethyl). In some aspects of these embodiments, 1 $R^d$ is hydroxyl and 2 $R^d$ are —$OR^a$. In some aspects of these embodiments, $R^a$ is alkyl (e.g., methyl or ethyl). In some aspects of these embodiments, 3 $R^d$ are —$OR^a$. In some aspects of these embodiments, 3 $R^d$ are halo (e.g., fluorine or chlorine). In some aspects of these embodiments, $R^a$ is alkyl (e.g., methyl or ethyl). In some aspects of these embodiments, L is a bond, —$CH_2$—, —C(O)—, or —O(CO)—.

In some embodiments, $R^1$ is phenyl substituted with 4 occurrences of $R^d$. In some aspects of these embodiments, 1 $R^d$ is jhydroxyl, 1 $R^d$ is alkyl (e.g., methyl or ethyl) and 2 $R^d$ are —$OR^a$. In some aspects of these embodiments, $R^a$ is alkyl (e.g., methyl or ethyl). In some aspects of these embodiments, L is a bond, —$CH_2$—, —C(O)—, or —O(CO)—.

In some embodiments, $R^1$ is heterocyclyl substituted with 0-5 occurrences of $R^d$.

In some embodiments, $R^1$ is tetrahydrofuranyl substituted with 0-5 occurrences of $R^d$ (e.g., 2-tetrahydrofuranyl or 3-tetrahydrofuranyl). In some aspects of these embodiments, $R^1$ is tetrahydrofuranyl (e.g., 2-tetrahydrofuranyl or 3-tetrahydrofuranyl). In some aspects of these embodiments, L is —C(O)—.

In some embodiments, $R^1$ is azetidinyl substituted with 0-5 occurrences of $R^d$ (e.g., 3-azetidinyl). In some embodiments, $R^1$ is azetidinyl (e.g., 3-azetidinyl). In some embodiments, $R^1$ is azetidinyl (e.g., 3-azetidinyl) substituted with 1 occurrence of $R^d$. In some aspects of these embodiments, $R^d$ is alkyl (e.g., methyl or ethyl). In some aspects of these embodiments, L is —C(O)—.

In some embodiments, $R^1$ is 10-14 membered bicyclic aryl substituted with 0-5 occurrences of $R^d$. In some embodiments, $R^d$ is naphthyl substituted with 0-5 occurrences of $R^d$. In some embodiments, $R^d$ is naphthyl.

In some embodiments, L is a bond, —$(CR^cR^c)_m$—, —$NR^bC(O)$—, —$(CR^cR^c)_m$—C(O)—, —C(O)—, or —O(CO)—.

In some embodiments, L is a bond and $R^1$ is alkyl, aryl or heteroaryl substituted with 0-5 occurrences of $R^d$. In some aspects of these embodiments, alkyl, aryl or heteroaryl of $R^1$ is as described in any one of the embodiments and aspects above.

In some embodiments, L is —$(CR^cR^c)_m$— and $R^1$ is cycloalkyl, aryl, heteroaryl or heterocyclyl substituted with 0-5 occurrences of $R^d$. In some aspects of these embodiments, cycloalkyl, aryl, heteroaryl or heterocyclyl of $R^1$ is as described in any one of the embodiments and aspects above.

In some embodiments, L is —$NR^bC(O)$— and $R^b$ is hydrogen; and $R^1$ is aryl substituted with 0-5 occurrences of $R^d$. In some aspects of these embodiments, aryl of $R^1$ is as described in any one of the embodiments and aspects above. In some embodiments, L is —$(CR^cR^c)_m$—C(O)— and $R^1$ is cycloalkyl, aryl or heteroaryl substituted with 0-5 occurrences of $R^d$. In some aspects of these embodiments, cycloalkyl, aryl, or heteroaryl of $R^1$ is as described in any one of the embodiments and aspects above.

In some embodiments, L is —C(O)— and $R^1$ is aryl, alkyl, or heteroaryl substituted with 0-5 occurrences of $R^d$. In some aspects of these embodiments, aryl, alkyl, or heteroaryl of $R^1$ is as described in any one of the embodiments and aspects above.

In some embodiments, L is —OC(O)— and $R^1$ is alkyl, aryl or heterocyclyl substituted with 0-5 occurrences of $R^d$. In some aspects of these embodiments, alkyl, aryl, or heterocyclyl of $R^1$ is as described in any one of the embodiments and aspects above.

In some embodiments, L is $—(CR^cR^c)_m—OC(O)—$ and $R^1$ is heterocyclyl or cycloalkyl substituted with 0-5 occurrences of $R^d$. In some aspects of these embodiments, heterocyclyl or cycloalkyl of $R^1$ is as described in any one of the embodiments and aspects above.

In some embodiments, n is 0. In some embodiments, n is 1.

In some embodiments, $R^3$ is alkyl (e.g., methyl or ethyl). In some embodiments, $R^3$ is $—OR^a$. In some aspects of these embodiments, $R^a$ is alkyl (e.g., methyl or ethyl). In some embodiments, $R^3$ is halo (e.g., fluorine or chlorine). In some embodiments, $R^3$ is hydroxyl. In some embodiments, $R^3$ is haloalkyl (e.g., trifluoromethyl).

In some embodiments, n is 2.

In some embodiments, two adjacent $R^3$ taken together with the carbon atoms to which they are attached form a heterocyclyl ring. In some embodiments, both $R^3$ are $—OR^a$. In some embodiments, two adjacent $R^3$ taken together with the carbon atoms to which they are attached form

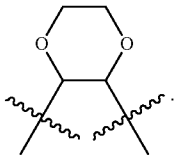

In certain embodiments, a compound is of formula (II) or a pharmaceutical acceptable salt thereof:

(II)

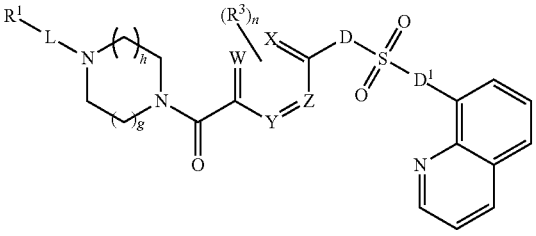

wherein L, $R^1$, $R^3$, $R^a$, $R^b$, $R^c$, $R^d$, Y, Z, m, h and g are as defined above in formula (I) or any one of the embodiments or aspects described herein.

In certain embodiments, A is aryl (e.g., phenyl or naphthyl) optionally substituted with 1 or 2 occurrences of $R^2$, wherein each $R^2$ is independently selected from halo, haloalkyl, aryl, heteroaryl, alkyl, $—OR^a$, $—COOR^c$, or $—CONR^cR^c$; and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some aspect of these embodiments, D and $D^1$ are N. In some aspect of these embodiments, at least one of W, X, Y and Z is N. In some aspect of these embodiments, one of W, Y and Z is N; his 1 and g is 1.

In certain embodiments, A is heteroaryl (e.g., N-containing monocyclic heteroaryl or N-containing bicyclic heteroaryl); and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some embodiments, A is a 5-8 membered monocyclic heteroaryl (e.g., pyridyl, pyrimidyl, or pyrazyl); and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some embodiments, A is a 5-8 membered N-containing monocyclic heteroaryl; and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some embodiments, A is optionally substituted pyridyl (e.g., 2-pyridyl, 3-pyridyl or 4-pyridyl), optionally substituted pyrimidyl (e.g., 2-pyrimidyl or 5-pyrimidyl), or optionally substituted pyrazyl (e.g., 2-pyrazyl); and L, $R^1$, $R^3$, $R^a$, $R^b$, $R^c$, $R^d$, Y, Z, m, h and g are as defined above in formula (I) or any one of the embodiments or aspects described herein.

In some embodiments, A is substituted with 1 occurrence of $R^2$; and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some aspects of these embodiments, $R^2$ is alkyl (e.g., methyl or ethyl). In some aspects of these embodiments, $R^2$ is halo. In some aspects of these embodiments, $R^2$ is fluorine (F). In some aspects of these embodiments, $R^2$ is bromine (Br). In some aspects of these embodiments, $R^2$ is chlorine (Cl). In some aspects of these embodiments, $R^2$ is $—OR^a$. In some aspects of these embodiments, $R^a$ is alkyl (e.g., methyl).

In some embodiments, A is substituted with 2 occurrences of $R^2$; and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some aspects of these embodiments, both $R^2$ are halo (e.g., fluorine or fluorine and chlorine). In some aspects of these embodiments, both $R^2$ are alkyl (e.g, methyl). In some aspects of these embodiments, both $R^2$ are $—OR^a$. In some aspects of these embodiments, one $R^2$ is halo and the other is $—OR^a$. In some aspects of these embodiments, one $R^2$ is bromine (BR) and the other is $—OR^a$. In some aspects of these embodiments, one $R^2$ is chlorine (Cl) and the other is $—OR^a$. In some aspects of these embodiments, one $R^2$ is fluorine (F) and the other is $—OR^a$. In some aspects of these embodiments, $R^a$ is alkyl (e.g., methyl or ethyl). In some aspects of these embodiments, both $R^2$ are $—OR^a$. In some aspects of these embodiments, two $—OR^a$ taken together with the carbon atoms to which they are attached form a heterocyclyl. In some embodiments, A is

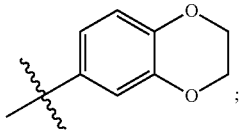

and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein.

In another embodiment, provided is a compound of formula (I) or a pharmaceutically acceptable salt thereof, or a pharmaceutical composition comprising a compound of formula (I) or a pharmaceutically acceptable salt thereof:

(I)

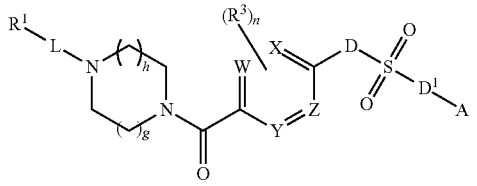

wherein:

W, X, Y and Z are each independently selected from CH or N;

D and $D^1$ are independently selected from a bond or $NR^b$;

A is optionally substituted aryl or optionally substituted heteroaryl;

L is a bond, —C(O)—, —$(CR^cR^c)_m$—, —OC(O)—, of —C(O)$NR^b$—;

$R^1$ is independently selected from alkyl, cycloalkyl, aryl, heteroaryl, and heterocyclyl; each of which are substituted with 0-3 occurrences of $R^d$;

each $R^3$ is independently selected from halo, haloalkyl, alkyl, hydroxyl and —$OR^a$ or two adjacent $R^3$ taken together with the carbon atoms to which they are attached form an optionally substituted cyclyl;

each $R^a$ is independently selected from alkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, alkyl, nitro, cyano and —$OR^a$, or two $R^d$ taken together with the carbon atoms to which they are attached form an optionally substituted heterocyclyl;

n is 0, 1, or 2;

m is 1, 2 or 3;

h is 0, 1, 2; and g is 0, 1 or 2. In some aspects of this embodiment, A, D, $D^1$, L, $R^1$, $R^3$, $R^a$, $R^b$, $R^c$, $R^d$, X, Y, Z, W, n, m, h and g are as defined in any one of the embodiments or aspects described herein.

In another embodiment, provided is a compound of formula (I) or a pharmaceutically acceptable salt thereof, or a pharmaceutical composition comprising a compound of formula (I) or a pharmaceutically acceptable salt thereof:

(I)

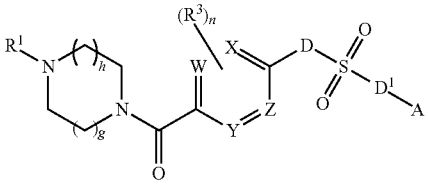

wherein:

W, X, Y and Z are each independently selected from CH or N;

D and $D^1$ are independently selected from a bond or $NR^c$;

A is optionally substituted aryl or optionally substituted heteroaryl;

$R^1$ is independently selected from alkyl, optionally substituted aryl, and optionally substituted heteroaryl;

each $R^3$ is independently selected from halo, haloalkyl, alkyl, and —$OR^a$;

each $R^a$ is independently selected from alkyl, haloalkyl and optionally substituted heteroaryl;

each $R^b$ is independently alkyl;

each $R^c$ is independently selected from hydrogen or alkyl;

n is 0, 1, or 2;

h is 0, 1, 2; and g is 0, 1 or 2. In some aspects of this embodiment, A, D, $D^1$, L, $R^1$, $R^3$, $R^a$, $R^b$, $R^c$, $R^d$, X, Y, Z, W, n, m, h and g are as defined in any one of the embodiments or aspects described herein.

In another embodiment, provided is a compound or pharmaceutically acceptable salt of formula (Ib) or a pharmaceutical composition comprising a compound or pharmaceutically acceptable salt of formula (Ib):

(Ib)

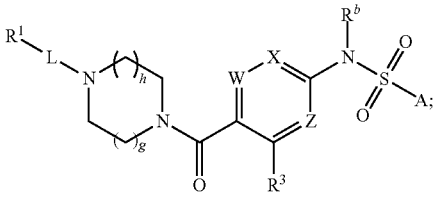

wherein A, L, $R^1$, $R^3$, $R^a$, $R^b$, $R^c$, $R^d$, W, X, Z, m, h and g are as defined above in formula (I) or any one of the embodiments or aspects described herein.

In some embodiments, X, W $_{an}$d Z are CH. In some embodiments, one of X, W and Z is N and the other two of X, W and Z are CH.

In another embodiment, provided is a pharmaceutical composition comprising a compound or pharmaceutically acceptable salt of formula (Ic) or a pharmaceutical composition comprising a compound or pharmaceutically acceptable salt of formula (Ic):

(Ic)

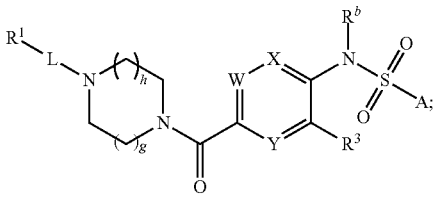

wherein A, L, $R^1$, $R^3$, $R^a$, $R^b$, $R^c$, $R^d$, W, X, Y, m, h and g are as defined above in formula (I) or any one of the embodiments or aspects described herein.

In some embodiments, X, Y and W are CH. In some embodiments, one o f X, Y and W is N and the other two of X, Y and W are CH.

In another embodiment, provided is a compound or pharmaceutically acceptable salt of formula (Id) or a pharmaceutical composition comprising a compound or pharmaceutically acceptable salt of formula (Id):

(Id)

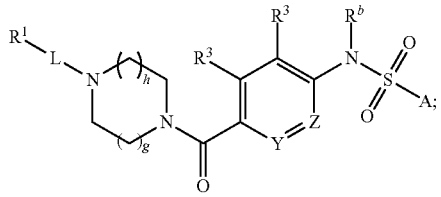

wherein A, L, $R^1$, $R^3$, $R^a$, $R^b$, $R^c$, $R^d$, Y, Z, m, h and g are as defined above in formula (I) or any one of the embodiments or aspects described herein.

In some embodiments, Y and Z are CH. In some embodiments, one of Y and Z is N and one of Y and Z is CH.

In another embodiment, provided is a compound or pharmaceutically acceptable salt of formula (Ie) or a pharmaceutical composition comprising a compound or pharmaceutically acceptable salt of formula (Ie):

(Ie)

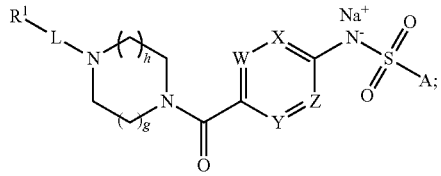

wherein A, L, $R^1$, $R^3$, $R^a$, $R^b$, $R^c$, $R^d$, W, X, Y, Z, m, h and g are as defined above in formula (I) or any one of the embodiments or aspects described herein.

In certain embodiments, exemplary compounds of Formula I include the compounds described in FIGS. 1A-1A-44 and in the Examples. In some embodiments, a compound described herein modulates PKM2 by interacting (e.g., binding) with the FBP binding pocket. For example, a compound described herein can compete with FBP binding in PKM2.

In some embodiments a compound described herein has one or more properties described herein, e.g., one or more of the following properties: it is an allosteric modulator (e.g., activator); it modulates the release of FBP (e.g., promotes); it is a modulator (e.g., agonist) of FBP, e.g., an agonist which binds with a lower, about the same, or higher affinity than does FBP; it modulates (e.g., promotes) the dissolution of tetrameric PKM2; it modulates (e.g., promotes) the assembly of tetrameric PKM2; it selectively modulates (e.g., activates) PKM2 over at least one other isoform of PK, e.g., it is selective for PKM2 over PKR, PKM1, or PKL; is has an affinity for PKM2 which is greater than its affinity for at least one other isoform of PK, e.g., PKR, PKM1, or PKL.

In another embodiment, the activator of PKM2 utilized in the methods and compositions described herein operates by or has one or more of the following mechanisms or properties:

a. it is an allosteric activator of PKM2;
b. it modulates (e.g., stabilizes) the binding of FBP in a binding pocket of PKM2;
c. it modulates (e.g., promotes) the release of FBP from a binding pocket of PKM2;
d. it is a modulator (e.g., an agonist), e.g., an analog, of FBP, e.g., an agonist which binds PKM2 with a lower, about the same, or higher affinity than does FBP;
e. it modulates (e.g., promotes) the dissolution of tetrameric PKM2;
f. it modulates (e.g., promotes) the assembly of tetrameric PKM2;
g. it modulates (e.g., stabilizes) the tetrameric conformation of PKM2;
h. it modulates (e.g., promotes) the binding of a phosphotyrosine containing polypeptide to PKM2;
i. it modulates (e.g., promotes) the ability of a phosphotyrosine containing polypeptide to induce release of FBP from PKM2, e.g., by inducing a change in the conformation of PKM2, e.g., in the position of Lys 433, thereby hindering the release of FBP;
k. it binds to or changes the position of Lys 433 relative to the FBP binding pocket;
l. it selectively modulates (e.g., activates) PKM2 over at least one other isoform of PK, e.g., it is selective for PKM2 over one or more of PKR, PKM1, or PKL;
m. it has an affinity for PKM2 which is greater than its affinity for at least one other isoform of PK, e.g., PKR, PKM1, or PKL. A compound described herein may be tested for its ability to activate PKM2. For simplicity, the activation activity of these compounds is represented as an $AC_{50}$ in FIGS. 1A-1A-44 and throughout the application. Exemplary compounds are shown in FIGS. 1A-1A-44. As shown in FIGS. 1A-1A-44, "A" refers to an activator of PKM2 with an $EC_{50}$<100 nM. "B" refers to an activator of PKM2 with an $EC_{50}$ between 100 nM and 500 nM. "C" refers to an activator of PKM2 with an $EC_{50}$ between 500 nM and 1000 nM. "D" refers to an activator of PKM2 with an $EC_{50}$ between 1 μM and 10 μM. "E" refers to data that is not available.

The compounds described herein can be made using a variety of synthetic techniques.

Scheme 1.

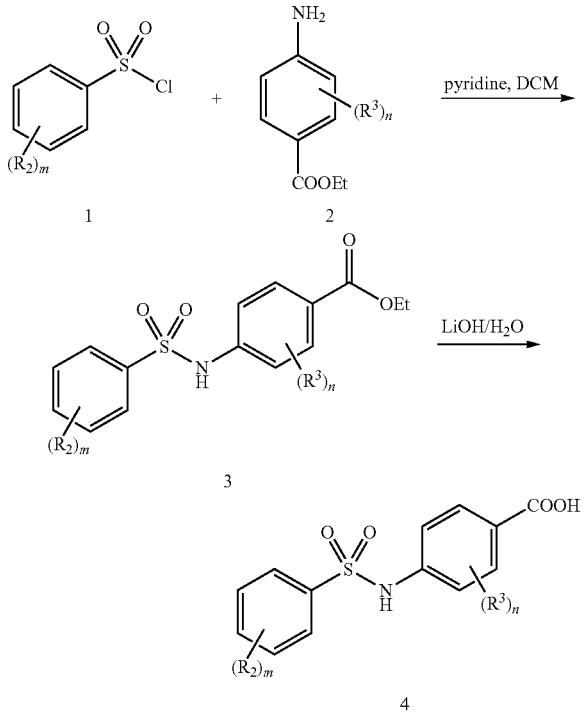

-continued

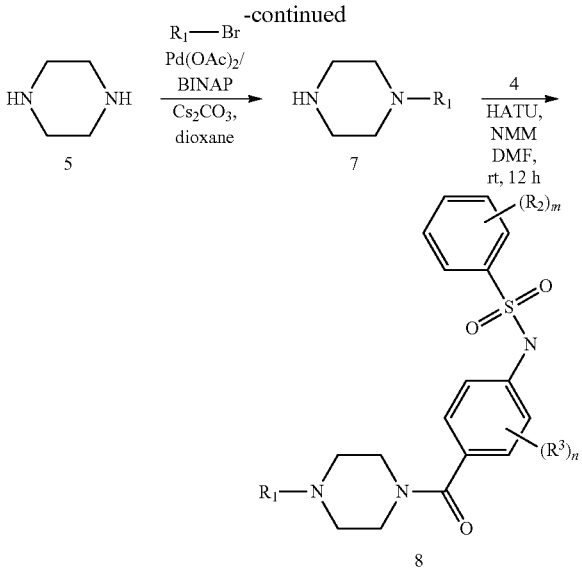

$R^1$, $R^2$, $R^3$, m and n = as defined herein

Scheme 1 above is an exemplary scheme that depicts a representative synthesis of certain copounds described herein. Sulfonyl chloride 1 is reacted with amine 1 under standard coupling conditions to produce ester 3. Hydrolysis of 3 using lithium hydroxide generates carboxylic acid 4. Piperazine (5) is with the appropriate bromide under standard palladium coupling conditions to provide 7. Carboxylic acid 4 is then treated with piperazine derivative 7 to produce final compound 8.

As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds provided herein may contain one or more asymmetric centers and thus occur as racemates and racemic mixtures, single enantiomers, individual diastereomers and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds) or substituents that can restrict bond rotation, e.g. restriction resulting from the presence of a ring or double bond. Accordingly, all cis/trans and E/Z isomers are expressly included.

The compounds provided herein (e.g. of Formula I) may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; and the like. The compounds provided herein may also be represented in multiple tautomeric forms, in such instances, expressly includes all tauto- meric forms of the compounds described herein, even though only a single tautomeric form may be represented (e.g., alkylation of a ring system may result in alkylation at multiple sites; all such reaction products are expressly included). All such isomeric forms of such compounds are expressly included. All crystal forms of the compounds described herein are expressly included.

The compounds provided herein include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds provided herein may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

In an alternate embodiment, the compounds described herein may be used as platforms or scaffolds that may be utilized in combinatorial chemistry techniques for preparation of derivatives and/or chemical libraries of compounds. Such derivatives and libraries of compounds have biological activity and are useful for identifying and designing compounds possessing a particular activity. Combinatorial techniques suitable for utilizing the compounds described herein are known in the art as exemplified by Obrecht, D. and Villalgrodo, J. M., Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, A. W., Curr. Opin. Chem. Bio., (1997) 1, 60. Thus, one embodiment relates to a method of using the compounds described herein for generating derivatives or chemical libraries comprising: 1) providing a body comprising a plurality of wells; 2) providing one or more compounds identified by methods described herein in each well; 3) providing an additional one or more chemicals in each well; 4) isolating the resulting one or more products from each well. An alternate embodiment relates to a method of using the compounds described herein for generating derivatives or chemical libraries comprising: 1) providing one or more compounds described herein attached to a solid support; 2) treating the one or more compounds identified by methods described herein attached to a solid support with one or more additional chemicals; 3) isolating the resulting one or more products from the solid support. In the methods described above, "tags" or identifier or labeling moieties may be attached to and/or detached from the compounds described herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

Definitions

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —$CH_2$—, —$CH_2CH_2$—, and —$CH_2CH_2CH_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH (alkyl) and —NH$(alkyl)_2$ radicals respectively. The term "aralkylamino" refers to a —NH(aralkyl) radical. The term alkylaminoalkyl refers to a (alkyl)NH-alkyl-radical; the term dialkylaminoalkyl refers to a $(alkyl)_2$N-alkyl-radical The term "alkoxy" refers to an —O-alkyl radical. The term "mercapto" refers to an SH radical. The term "thioalkoxy" refers to an S-alkyl radical. The term thioaryloxy refers to an —S-aryl radical.

The term "aryl" refers to a monocyclic, bicyclic, or tricyclic aromatic hydrocarbon ring system, wherein any ring atom capable of substitution can be substituted (e.g., by one or more substituents). Examples of aryl moieties include, but are not limited to, phenyl, naphthyl, and anthracenyl.

The term "cycloalkyl" as employed herein includes cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

The terms "heterocyclyl" or "heterocyclic group" refer to 3- to 14-membered non-aromatic ring structures (e.g., 3- to 14-membered rings, more preferably 3- to 7-membered rings), whose ring structures include one to four heteroatoms independently selected from O, N and S. The heterocyclyl or heterocyclic groups can contain fused or spiro rings. Heterocycles can also be polycycles, with each group having, e.g., 5-7 ring members. The term "heterocyclyl" or "heterocyclic group" includes saturated and partially saturated heterocyclyl structures. The term "heteroaryl" refers to a 5-14 membered (i.e., a 5-8 membered monocyclic, 8-12 membered bicyclic, or 11-14 membered tricyclic) aromatic ring system having 1-3 ring heteroatoms if monocyclic, 1-6 ring heteroatoms if bicyclic, or 1-9 ring heteroatoms if tricyclic, said ring heteroatoms independently selected from O, N, and S (e.g., 1-3, 1-6, or 1-9 ring heteroatoms of N, O or S if monocyclic, bicyclic, or tricyclic, respectively). Any substitutable ring atom can be substituted (e.g., by one or more substituents). Heterocyclyl and heteroaryl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic or heteroaryl ring can be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heterocyclylalkyl", as used herein, refers to an alkyl group substituted with a heterocycle group.

The term "cycloalkenyl" refers to partially unsaturated, nonaromatic, monocyclic, bicyclic, or tricyclic hydrocarbon groups having 5 to 12 carbons, preferably 5 to 8 carbons. The unsaturated carbon may optionally be the point of attachment of the cycloalkenyl substituent. Any substitutable ring atom can be substituted (e.g., by one or more substituents). The cycloalkenyl groups can contain fused or spiro rings. Fused rings are rings that share a common carbon atom. Examples of cycloalkenyl moieties include, but are not limited to, cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, and S (e.g., 1-3, 1-6, or 1-9 ring heteroatoms of N, O, or S if monocyclic, bicyclic, or tricyclic, respectively). The unsaturated carbon or the heteroatom may optionally be the point of attachment of the heterocycloalkenyl substituent. Any substitutable ring atom can be substituted (e.g., by one or more substituents). The heterocycloalkenyl groups can contain fused rings. Fused rings are rings that share a common carbon atom. Examples of heterocycloalkenyl include but are not limited to tetrahydropyridyl and dihydropyranyl.

The terms "hetaralkyl" and "heteroaralkyl", as used herein, refers to an alkyl group substituted with a heteroaryl group. The ring heteroatoms of the compounds provided herein include N—O, S(O), and $S(O)_2$.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

The term "substituents" refers to a group "substituted" on an alkyl, cycloalkyl, alkenyl, alkynyl, heterocyclyl, heterocycloalkenyl, cycloalkenyl, aryl, or heteroaryl group at any substitutable atom of that group. Any substitutable atom can be substituted. Unless otherwise specified, such substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O— wherein oxygens are attached to vicinal atoms), ethylenedioxy, oxo (not a substituent on heteroaryl), thioxo (e.g., C═S) (not a substituent on heteroaryl), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The term "selective" is meant at least 2-fold, 3-fold, 4-fold, 5-fold, 6-fold, or 10-fold greater modulation (e.g., activation) of PKM2 than PKM1.

The term "activator" as used herein means an agent that (measurably) increases the activity of a pyruvate kinase (e.g., PKM2) or causes pyruvate kinase (e.g., PKM2) activity to increase to a level that is greater than PKM2's basal levels of activity. For example, the activator may mimic the effect caused by a natural ligand (e.g., FBP). The activator effect caused by a compound provided herein may be to the same, or to a greater, or to a lesser extent than the activating effect caused by a natural ligand, but the same type of effect is caused. A compound provided herein can be evaluated to determine if it is an activator by measuring either directly or indirectly the activity of the pyruvate kinase when subjected to said compound. The activity of a compound provided herein can be measured, for example, against a control substance. In some instances, the activity measured of the test compound is for activation of PKM2. The activity of PKM2 can be measured, for example, by monitoring the concentration of a substrate such as ATP or NADH.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Methods of Evaluating Compounds

The compounds described herein can be evaluated for ability to modulate PKM2 (e.g., activate PKM2) by methods known in the art. In some embodiments, compounds described herein are evaluated for ability to modulate PKM2 (e.g. activate PKM2) in serine deficient conditions. In some embodiments, exemplary methods include contacting the compound with a cell-based assay which allows assessment of the ability to modulate (e.g., activate) PKM2. E.g., the candidate compound can be contacted with a cell and measuring the consumption of oxygen or production of lactate. A change in cellular phosphoenolpyruvate, a change in glycerol-phosphate, a change in ribose or deoxyribose, a change in lipid synthesis, or a change in glucose conversion to lipid or nucleic acids or amino acids or protein can also be used to evaluate a compound for its ability to modulate PKM2 (e.g., activate PKM2). The evaluation could also include measuring a change in pyruvate or a determination of an alteration in mitochondrial membrane potential, e.g., as measured by fluorescent potentiometric dyes.

The activity of the PKM enzyme measured in the screening/testing assay may be measured by, e.g., monitoring the concentration of a substrate (e.g., ATP or NADH) present in the reaction mixture. Pyruvate, produced by the enzymatic activity of pyruvate kinase, is converted into lactate by lactate dehydrogenase, which requires the consumption of NADH (NADH→NAD+). Thus, the activity of PKM2 can be indirectly measured by monitoring the consumption of NADH through, e.g., fluorescence assays. Additionally, the activity of the PKM2 enzyme can be directly monitored by measuring the production of ATP, as ATP is produced when phosphoenolpyruvate is converted to pyruvate. Methods for monitoring the amount of substrate in a reaction mixture include, e.g., absorbance, fluorescence, Raman scattering, phosphorescence, luminescence, luciferase assays, and radioactivity.

The screening procedure requires the presence of specific components in the reaction mixture. Components utilized in the assay include, e.g., a nucleoside diphosphate (e.g., ADP), phosphoenolpyruvate, NADH, lactate dehydrogenase, FBP, a reducing agent (e.g., dithiothreitol), a detergent (e.g., Brij 35), glycerol, and a solvent (e.g., DMSO). Exemplary reaction conditions are found in Table 1.

TABLE 1

| Component of Reaction Condition | Amount in Activation Assay |
|---|---|
| ADP | 0.1-5.0 mM |
| Phosphoenolpyruvate | 0.1-5.0 mM |
| NADH | 10-1000 μM |
| Lactate dehydrogenase | 0.1-10 units |
| Fructose-1,6-bisphosphate | 0 |
| DTT | 0.1-50 mM |
| Brij 35 | 0.01-1% |
| Glycerol | 0.1-10% |
| Pyruvate Kinase M2 (used for screen) | 1-100 pg |
| DMSO | 1-10% |

In some embodiments, a compound such as a compound described herein, can be evaluated in a cellular/ex vivo assay. For example, a cell is treated with a compound described herein (i.e., a PKM2 activator), and the compound is evaluated, for example for its ability to enter the cell and bind to PKM2, inducing an activated conformation of PKM2. The excess unbound compound can then be washed away with PBS, and the cells lysed, for example, by snap-freezing on dry ice, followed by addition of a detergent-containing lysis buffer. The lysate, in which activated PKM2 remains intact, can then be removed and added to a chemical cocktail including the chemicals necessary to measure pyruvate kinase activity. The assay can be coupled to another assay such as an assay that is coupled to the LDHa enzyme. The amount of pyruvate kinase activity that is measured can then be normalized to the total protein content in the lysate, and related to the concentration of PKM2 activator that was added to the cell. This can allow an $AC_{50}$ (concentration at which PKM2 is activated 50%) value to be derived. The total fold-increase in activity over mock-treated cells can also be calculated, and the "maximum level of activation" can be used to distinguish between compounds that fully activate PKM2 and compounds that can only partially activate PKM2. In the case of measuring PKM2 activity from tissue (for example, in a cell tumor), animals harboring the tissue/tumor of interest can be dosed with a compound. After a specified period of time in which exposure has been achieved in the target tissue/tumor of interest, the tissue/tumor can then be harvested from the animal, snap-frozen, and then lysed and homogenized. The amount of pyruvate kinase activity in this lysate can then be quantitated as described above.

PKM1 and PKM2 for use in the screening/testing methods described herein may be produced by any method known in the art for expression of recombinant proteins. For example, nucleic acids that encode the desired polypeptide may be introduced into various cell types or cell-free systems for expression. Eukaryotic (e.g., COS, HEK293T, CHO, and NIH cell lines) and prokaryotic (e.g., E. coli) expression systems may be generated in which a PKM sequence is introduced into a plasmid or other vector, which is then used to transform living cells. Constructs in which the PKM cDNA contains the entire open reading frame, or biologically active fragment thereof, are inserted in the correct orientation into an expression plasmid and may be used for protein expression. Prokaryotic and eukaryotic expression systems allow for the expression and recovery of fusion proteins in which the PKM protein is covalently linked to a tag molecule on either the amino terminal or carboxy terminal side, which facilitates identification and/or purification. Examples of tags that can be used include hexahistidine, HA, FLAG, and c-myc epitope tags. An enzymatic or chemical cleavage site can be engineered between the PKM protein and the tag molecule so that the tag can be removed following purification.

Compounds useful as PKM2 activators are those demonstrate specificity and activation of PKM2 enzyme in the absence of FBP to a level greater than that of 10, 15, 20, 25, 30, 35, 40, 45, 50, 55, 60, 65, 70, 75, 80, 85, 90, 95, 99, or 100% in the presence of FBP. Furthermore, compounds can be evaluated in the presence or absence of a phosphotyrosine peptide. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation even in the presence of a phosphotyrosine peptide will lead to the loss of allosteric control of PKM2 needed for shunting the biochemical intermediates from glycolysis into biosynthesis of other intermediates. This, in turn, will lead to inhibition of growth of cancer cells, activated immune cells and fat cells.

Methods of Treatment

In one embodiment, provided is a method for treating or preventing a disease, condition or disorder as described herein (e.g., treating) comprising administering a compound, a pharmaceutically acceptable salt of a compound or pharmaceutical composition comprising a compound described herein (e.g., a compound of formula (I), (I-a), (II) or in FIGS. 1A-1A-44).

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Other exemplary cancers include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated or prevented in accordance with the methods described herein.

Cancer Combination Therapies

In some embodiments, a compound described herein is administered together with one or more additional cancer treatments. Exemplary cancer treatments include, for example: chemotherapy, targeted therapies such as antibody therapies, immunotherapy, and hormonal therapy. Examples of each of these treatments are provided below.

Chemotherapy

In some embodiments, a compound described herein is administered with one or more chemotherapies. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Satraplatin, Streptozocin, Talaporfin, Tegafur-uracil, Temoporfin, Temozolomide, Teniposide, Tesetaxel, Testolactone, Tetranitrate, Thiotepa, Tiazofurin, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

In some embodiments, a compound described herein is administered with one or more targeted therapies. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound described herein is administered with one or more immunotherapies. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with one or more hormonal therapies. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Obesity and Fat Disorders

A compound or composition described herein can be used to treat or prevent obesity, e.g., in a human subject, e.g. a child or adult subject. "Obesity" refers to a condition in which a subject has a body mass index of greater than or equal to 30. Many compounds described herein can be used to treat or prevent an over-weight condition. "Over-weight" refers to a condition in which a subject has a body mass index of greater or equal to 25.0. The body mass index (BMI) and other definitions are according to the "NIH Clinical Guidelines on the Identification and Evaluation, and Treatment of Overweight and Obesity in Adults" (1998). Treatment with the compound may be in an amount effective to alter the weight of the subject, e.g., by at least 2, 5, 7, 10, 12, 15, 20, 25, 30, 25, 40, 45, 50, or 55%. Treatment with a compound may be in an amount effective to reduce the body mass index of the subject, e.g., to less than 30, 28, 27, 25, 22, 20, or 18. The compounds can be used to treat or prevent aberrant or inappropriate weight gain, metabolic rate, or fat deposition, e.g., anorexia, bulimia, obesity, diabetes, or hyperlipidemia (e.g., elevated triglycerides and/or elevated cholesterol), as well as disorders of fat or lipid metabolism.

A compound or composition described herein can be administered to treat obesity associated with Prader-Willi Syndrome (PWS). PWS is a genetic disorder associated with obesity (e.g., morbid obesity).

A compound or composition described herein can be used to reduce body fat, prevent increased body fat, reduce cholesterol (e.g., total cholesterol and/or ratios of total cholesterol to HDL cholesterol), and/or reduce appetite in individuals having PWS associated obesity, and/or reduce comorbidities such as diabetes, cardiovascular disease, and stroke.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions provided herewith may also be administered in the form of suppositories for rectal administration. These compositions can be prepared by mixing a compound provided herewith a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions provided herewith is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds provided herewith include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herewith may also be topically applied to the lower intestinal tract by rectal suppository formulation or in a suitable enema formulation. Topically-transdermal patches are also included.

The pharmaceutical compositions provided herewith may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can modulate PKM2. Accordingly, a patient and/or subject can be selected for treatment using a compound described herein by first evaluating the patient and/or subject to determine whether the subject is in need of modulation of PKM2, and if the subject is determined to be in need of modulation of PKM2, then administering to the subject a compound described herein.

A subject can be evaluated as being in need of modulation of PKM2 using methods known in the art, e.g., by measuring the presence and/or activity of PKM2 in the patient. In some embodiments, the activity and/or level of PKM2 is evaluated in the cancer.

A patient receiving a compound described herein can be monitored, for example, for improvement in the condition and/or adverse effects. Improvement of a patient's condition can be evaluated, for example, by monitoring the growth, absence of growth, or regression of the cancer (e.g., a tumor). In some embodiments, the patient is evaluated using a radiological assay or evaluation of hemolytic parameters.

EXAMPLES

Example 1

PKM2 Assay

Procedure:

- PKM2 stock enzyme solution was diluted in Reaction Buffer
- 2 μL of compound was added into each well first, and then 180 μL of the Reaction Mix was added.
- Reaction mixture with compound (without ADP) were incubated for 30 minutes at 4° C.
- Plates were re-equilibrated to room temperature prior to adding 20 μL ADP to initiate the reaction.
- Reaction progress was measured as changes in absorbance at 340 nm wavelength at room temperature (25° C.)

Reaction Mix:

PKM2 (50 ng/well), ADP (0.7 mM), PEP (0.15 mM), NADH (180 μM), LDH (2 units) in Reaction Buffer Reaction Buffer:

100 mM KCl, 50 mM Tris pH 7.5, 5 mM MgCl2, 1 mM DTT, 0.03% BSA.

Example 2

Compounds and Their Preparation

Scheme 2:

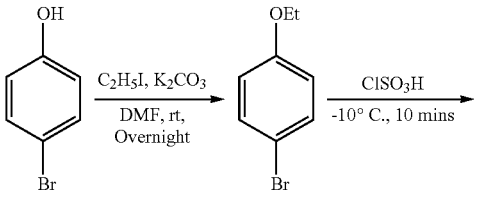

1

-continued

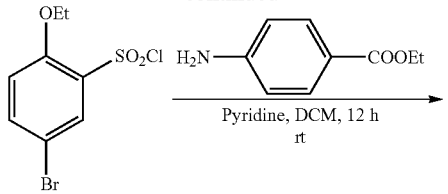

2

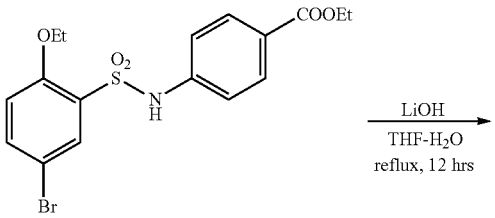

3

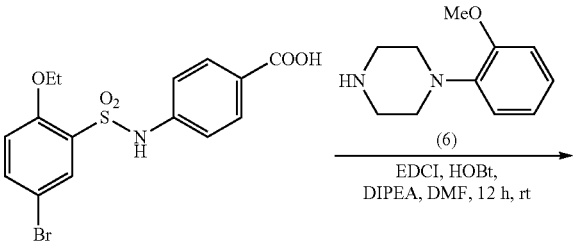

4

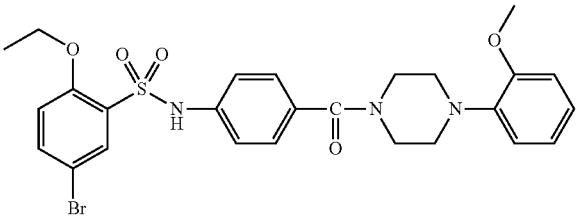

7

Compound 6:

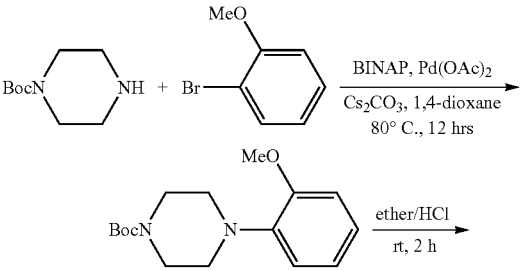

5

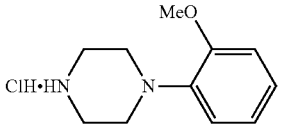

6

General Procedure for Compound 1:

To a solution of 4-bromo phenol (5.0, 0.0289 moles, 1 eq) in DMF (50 mL), potassium carbonate (9.970 g, 0.0722 moles, 2.5 eq) was added followed by the addition of ethyl iodide (4.70 ml, 0.0578 moles, 2 eq) and stirred for overnight. The progress of the reaction was monitored by TLC. After completion of starting material, the reaction mixture was quenched with water (25 mL) and extracted with ethylacetate (2×50 mL). The combined organic layers were washed with brine (40 ml) solution. Ethylacetate layer was dried over $Na_2SO_4$ and concentrated under reduced pressure. The crude product was purified by column chromatography (9:1, ethyl acetate/hexane) to obtain compound 1 (5.0 g, 86.2%). MS (201.06) 202.1 (M+1).

General Procedure for Compound 2:

Compound 1 was taken in a two necked flask (2.00 g, 0.0099 moles, 1 eq). Chlorosulfonic acid (25 mL, 0.358 moles, 36 eq) was added slowly over a period of 10 min at −10° C. The resulting mixture was stirred at the same temperature for 10 min. After completion of the starting material, the reaction mixture was poured into ice cold water (100 mL) and extracted with ethyl acetate. The organic layer was washed with $H_2O$, dried over $Na_2SO_4$ and concentrated under reduced pressure. The desired product 2 was obtained by column purification (60-120 mesh silica gel, 5% ethyl acetate-hexane) as a solid (3 g, 43.3%).

General Procedure for Compound 3:

To a solution of ethyl-4-aminobenzoate (300 mg, 1.81 mmole, 1 eq) in 1:1 mixture of DCM/pyridine (5 mL/5 mL) was added a solution of 5-bromo-2-ethoxybenzene-1-sulfonyl chloride (compound 2, 654 mg, 2.17 mmole, 1.2 eq) in DCM (5 mL/5 mL) at 0° C. The reaction mixture was then allowed to stir at room temperature for overnight. After completion of the reaction, the reaction mixture was diluted with DCM and washed with water, dried over sodium sulphate and concentrated under reduced pressure. The crude product was then washed with diethyl ether followed by n-hexane and dried to yield compound 3 as an off white solid (0.600 g, 77%).

$^1$H NMR (200 MHz, DMSO-$d_6$) 1.30 (t, 3H), 1.58 (t, 3H), 4.20-4.40 (m, 4H), 6.82 (d, 1H), 7.10-7.20 (m, 2H), 7.56-7.60 (dd, 1H), 7.90-8.00 (m, 3H).

General Procedure for Compound 4:

Ethyl 4-(5-bromo-2-ethoxyphenylslulfonamido) benzoate (compound 3, 600 mg, 0.0014 moles, 1 eq) was taken in THF—$H_2O$ (1:1, 30 mL/30 mL). LiOH.$H_2O$ (0.293 g, 0.007 moles, 5 eq) was then added to the above reaction mixture and stirred at reflux for overnight. After completion of the starting material, the solvent was removed under reduced pressure to obtain the crude product. The crude product was washed with ethyl acetate. The aqueous layer was acidified with citric acid (pH=4) and extracted again with ethyl acetate (2×25 mL). The combined organic layer was dried over $Na_2SO_4$ and concentrated under reduced pressure. The resultant acid was further washed with hexane to get pure compound 4 (0.500 g, 89%).

MS (400.24) 397.9 (M−2 peak, negative mode); $^1$H NMR (200 MHz, DMSO-$d_6$) 1.20 (t, 3H), 4.18 (q, 2H), 7.10 (d, 1H), 7.10-7.20 (d, 3H), 7.60-8.0 (m, 4H), 10.6 (s, 1H), 12.6 (bs, 1H).

General Procedure for Compound 7:

To a solution of 4-(5-bromo-2-ethoxyphenylsulfonamido) benzoic acid (compound 4, 0.300 g, 0.00074 moles, 1 eq) in DMF (25 mL), EDCI (0.157 g, 0.00082 moles, 1.1 eq), HOBt (0.126 g, 0.00082 moles, 1.1 eq) and DIPEA (0.48 mL, 0.0026 moles, 3.5 eq) were added at 0° C. and stirred for 15 minutes. A solution of 1-2-(methoxyphenyl)piperazine (Compound 6, 0.171 g, 0.00074 moles, 1 eq) was then added at 0° C. and then the resulting mixture was allowed to stir at room temperature for overnight. After completion of the reaction, water (30 mL) was added and extracted with ethyl acetate (2×30 mL). The combined organic layer was dried over anhydrous $Na_2SO_4$ and concentrated under reduced pressure. The crude product was dissolved in EtOAc and to this pentane was added to yield compound 7 as a white solid which was filtered and dried (200 mg, 46.5% yield).

7

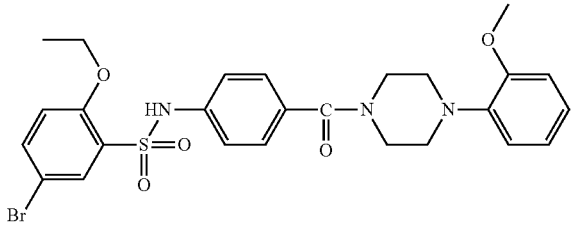

$^1$H NMR (500 MHz, DMSO-$d_6$) 1.30 (t, 3H), 2.80-3.0 (bs, 4H), 3.30-3.60 (bm, 4H), 3.78 (s, 3H), 4.20 (q, 2H), 6.80-7.00 (m, 4H), 7.10-7.20 (m, 3H), 7.30-7.34 (d, 2H), 7.70-7.75 (dd, 1H), 7.80 (d, 1H), 10.35 (s, 1H); MS 574.0; MS base peak at 574.0; HPLC purity 97.80%.

Synthesis of Compound 6:

Scheme 3:

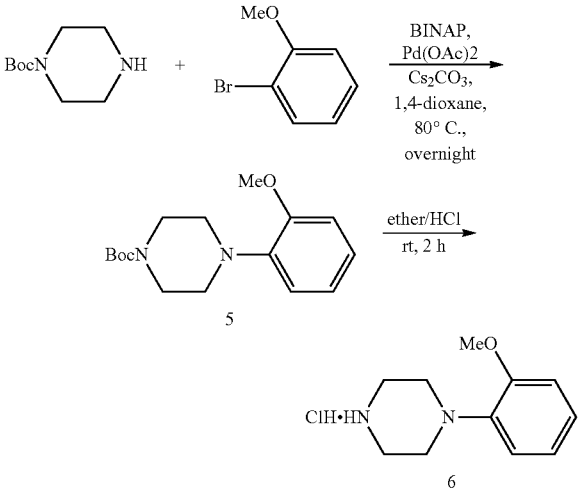

General Procedure for Compound 5:

In a two neck round bottom flask, tert-butyl piperazine-1-carboxylate (4.97 g, 0.0267 moles, 1 eq), 2-bromo anisole (5.0 g, 0.0267 moles, 1 eq) and $CS_2CO_3$ (21.7 g, 0.0668 moles, 2.5 eq) were charged in degassed 1,4-dioxane (100 mL) under $N_2$ atmosphere. BINAP (1.49 g, 0.00240 moles, 0.09 eq) and Pd $(OAc)_2$ (0.96 g, 0.00042 moles, 0.016 eq) were then added to the reaction mixture under $N_2$ atmosphere and stirred at 80° C. for overnight. The progress of the reaction was monitored by TLC. After completion of the starting material, the excess of solvent was distilled off under reduced pressure and the residue was diluted with water and extracted with ethyl acetate. The organic layer was separated, dried over $Na_2SO_4$ and concentrated under reduced pressure. The crude product was purified by column chromatography (silica gel 60-120, 5-6%, ethyl acetate/hexane) to yield the desired product 5 as viscous oil (2.8 g, 36%).

$^1$H NMR (500 MHz, $CDCl_3$): 1.42 (s, 9H), 3.0 (m, 4H), 3.60 (m, 4H), 3.84 (s, 3H), 6.80-7.00 (m, 4H); MS 293.1 (M+1 peak).

General Procedure for Compound 6:

In a two neck RB flask, tert-butyl-4-(2-methoxyphenyl) piperazine-1-carboxylate (compound 5, 0.600 g, 0.00205 moles, 1 eq) was treated with ether-HCl (10 mL). The resulting mixture was stirred for overnight. After completion of the starting material as indicated by TLC, ether was removed under reduced pressure and a solid material was obtained. The solid material was washed with ethyl acetate and dried to obtain the amine compound 6 as a white solid (0.425 g, 90.08%).

The following analogs were prepared utilizing the above procedure with various sulfonyl chlorides in place of compound 2.

5-Chloro-2-methoxy-N-(4-(4-(2-methoxyphenyl) piperazine-1-carbonyl)phenyl)benzene-sulfonamide (8)

8

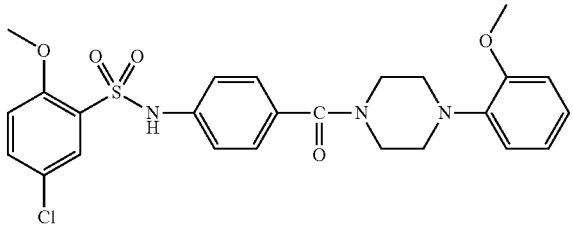

Compound 8 was prepared from commercially available 2-Methoxy-5-chlorobenzenesulfonyl chloride as shown in Scheme 2.

$^1$H NMR (500 MHz, DMSO-$d_6$) 2.8-3.0 (bm, 4H), 3.40-3.78 (m, 4H), 3.80 (s, 3H), 3.84 (s, 3H), 6.80-7.00 (m, 4H), 7.12 (d, 2H), 7.21 (d, 1H), 7.30 (d, 2H), 7.65 (dd, 1H), 7.74 (d, 1H); MS base peak at m/z 516; HPLC purity: 94.33%

5-Bromo-2-methoxy-N-(4-(4-(2-methoxyphenyl) piperazine-1-carbonyl)phenyl)benzene-sulfonamide (9)

9

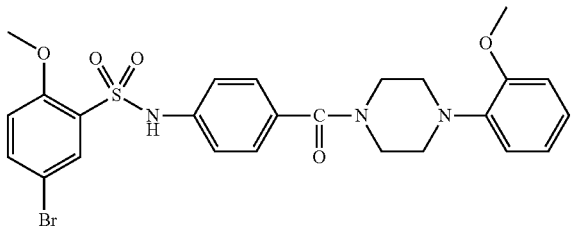

The corresponding sulfonyl chloride was prepared from 4-bromophenol. O-Methylation of 4-bromophenol followed by chlorosulfonic acid reaction gave 2-methoxy-5-bromobenzenesulfonyl chloride which was utilized to produce compound 9 as provided in Scheme 2.

$^1$H NMR (500 MHz, DMSO-$d_6$) 2.90-3.00 (bm, 4H), 3.40-3.78 (m, 4H), 3.80 (s, 3H), 3.84 (s, 3H), 6.80-7.00 (m, 4H), 7.10-7.18 (m, 3H), 7.30 (d, 2H), 7.70 (dd, 1H), 7.74 (d, 1H); MS base peak at 562.0; HPLC purity: 94.36%

N-(4-(4-(2-methoxyphenyl)piperazine-1-carbonyl) phenyl)naphthalene-2-sulfonamide (10)

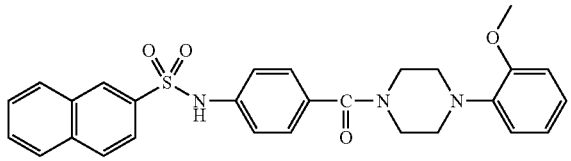

Commercially available naphthalene-2-sulfonyl chloride was utilized in place of compound 2 used to provide 10.

$^1$H NMR (500 MHz, DMSO-$d_6$) 2.80-3.00 (bm, 4H), 3.40-3.78 (m, 4H), 3.80 (s, 3H), 6.80-7.00 (m, 4H), 7.10-7.30 (m, 4H), 7.60-7.80 (m, 3H), 8.00-8.20 (m, 3H), 8.50 (s, 1H), 10.7 (s, 1H); MS base peak at 504.2; HPLC purity: 93.65% (HPLC)

5-Chloro-2-ethoxy-N-(4-(4-(2-methoxyphenyl)piperazine-1-carbonyl)phenyl)benzene-sulfonamide (11)

11

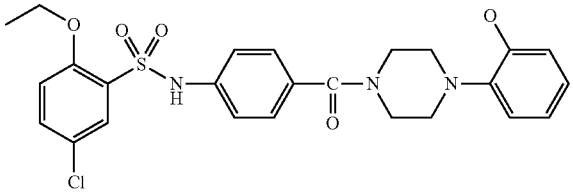

The corresponding sulfonyl chloride was prepared from 4-chlorophenol. O-Ethylation of 4-chlorophenol followed by a chlorosulfonic acid reaction under the appropriate conditions provided 2-ethoxy-5-chlorobenzenesulfonyl chloride which was utilized to prepare compound 11 as shown in Scheme 2.

$^1$H NMR (500 MHz, DMSO-$d_6$) 1.30 (t, 3H), 2.80-3.0 (bs, 4H), 3.40-3.78 (bm, 4H), 3.80 (s, 3H), 4.20 (q, 2H), 6.80-7.00 (m, 4H), 7.16 (d, 2H), 7.20 (d, 1H), 7.38 (d, 2H), 7.60 (d, 1H), 7.80 (s, 1H), 10.20 (s, 1H); MS base peak at 530.1; HPLC purity 97.48%

N-(4-(4-(2-methoxyphenyl)piperazine-1-carbonyl) phenyl)benzene-sulfonamide (12)

12

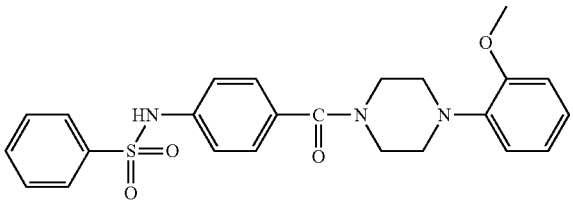

Compound 12 was prepared following Scheme 2 using benzenesulfonyl chloride.

$^1$H NMR (500 MHz, DMSO-$d_6$) 2.90-3.00 (bs, 4H), 3.40-3.78 (bm, 4H), 3.80 (s, 3H), 6.84-6.98 (m, 4H), 7.15 (d, 2H), 7.30 (d, 2H), 7.56-7.64 (m, 3H), 7.80 (d, 2H), 10.6 (s, 1H); MS base peak at 452.6; HPLC purity 96.90%.

N-(4-(4-(2-methoxyphenyl)piperazine-1-carbonyl) phenyl)naphthalene-1-sulfonamide (13)

13

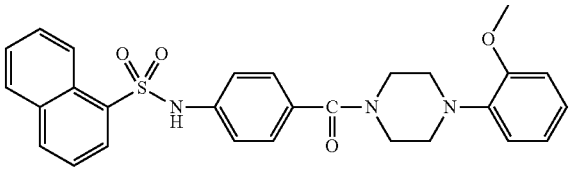

Compound 13 was prepared following Scheme 2 using commercially available naphthalene-1-sulfonyl chloride.

$^1$H NMR (500 MHz, DMSO-$d_6$) 2.90-3.00 (bs, 4H), 3.40-3.78 (bm, 4H), 3.80 (s, 3H), 6.84-6.98 (m, 4H), 7.10 (d, 2H), 7.24 (d, 2H), 7.62-7.78 (m, 3H), 8.08 (d, 1H), 8.23 (d, 1H), 8.28 (d, 1H), 8.72 (d, 1H), 10.98 (s, 1H); MS base peak at 502.1; HPLC purity 96.59%.

2,6-Difluoro-N-(4-(4-(2-methoxyphenyl)piperazine-1-carbonyl)phenyl)benzene-sulfonamide (14)

14

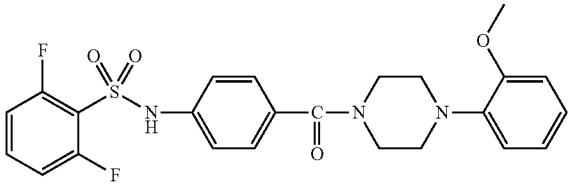

Compound 14 was prepared following Scheme 2 using commercially available 2,6-difluorobenzenesulfonyl chloride.

$^1$H NMR (500 MHz, DMSO-$d_6$) 2.90-3.00 (bs, 4H), 3.40-3.78 (bm, 4H), 3.80 (s, 3H), 6.84-7.00 (m, 4H), 7.20 (d, 2H), 7.30 (t, 2H), 7.38 (d, 2H), 7.68-7.74 (m, 1H), 11.2 (s, 1H); MS base peak at 488.1; HPLC purity 97.16%.

N-(4-(4-(2-methoxyphenyl)piperazine-1-carbonyl) phenyl)quinoline-8-sulfonamide (15)

15

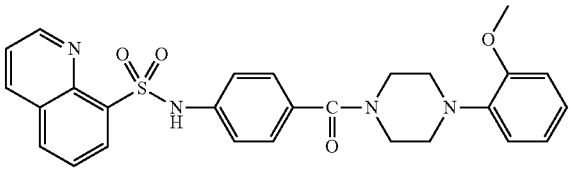

Compound 15 was prepared following Scheme 2 using commercially available quinoline-8-sulfonyl chloride.

$^1$H NMR (500 MHz, DMSO-$d_6$) 2.90-3.00 (bs, 4H), 3.40-3.78 (bm, 4H), 3.80 (s, 3H), 6.82 (d, 2H), 6.90-7.00 (m, 2H), 7.15-7.20 (2 doublets, 4H), 7.70-7.78 (m, 2H), 8.24 (d, 1H), 8.40 (d, 1H), 8.50 (d, 1H), 9.15 (bs, 1H), 10.42 (s, 1H); MS base peak at 503.2; HPLC purity 97.11%.

N-(4-(4-(2-methoxyphenyl)piperazine-1-carbonyl) phenyl)benzo[d]thiazole-5-sulfonamide (17)

17

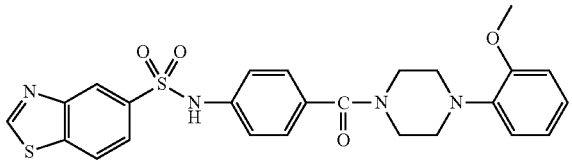

Compound 17 was prepared from commercially available benzthiazole-6-sulfonyl chloride following the Scheme 2 protocol.

$^1$H NMR (500 MHz, DMSO-$d_6$) 2.90-3.00 (bs, 4H), 3.40-3.78 (bm, 4H), 3.80 (s, 3H), 6.82-7.00 (m, 4H), 7.20 (d, 2H), 7.38 (d, 2H), 7.90 (d, 1H), 8.22 (d, 1H), 8.78 (s, 1H), 9.60 (s, 1H), 10.70 (s, 1H); MS base peak at 509.1; HPLC purity 97.29%.

N-(4-(4-(2-methoxyphenyl)piperazine-1-carbonyl) phenyl)-3,5-dimethylbenzene-sulfonamide (18)

18

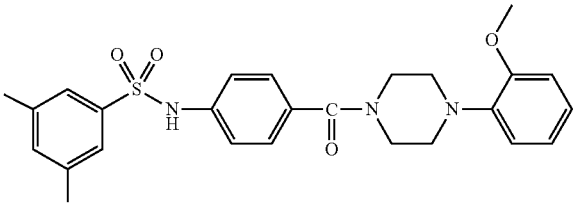

Compound 18 was prepared from commercially available 3,5-dimethylbenzenesulfonyl chloride following the protocol provided in Scheme 2.

$^1$H NMR (500 MHz, DMSO-$d_6$) 2.35 (s, 6H), 2.80-2.90 (m, 4H), 3.42-3.78 (bm, 4H), 3.80 (s, 3H), 6.88 (bs, 2H), 6.92-7.00 (m, 2H), 7.15 (d, 2H), 7.26 (s, 1H), 7.33 (d, 2H), 7.42 (s, 2H), 10.5 (s, 1H); MS base peak at 480.3; HPLC purity 98.56%.

N-(4-(4-(2-methoxyphenyl)piperazine-1-carbonyl) phenyl)2,3-dihydrobenzo[b][1,4]dioxin-6-sulfonamide (19)

19

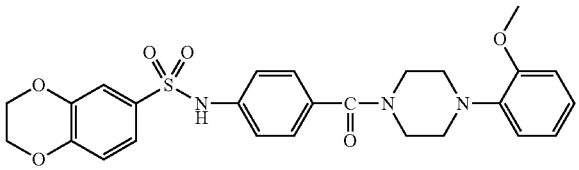

Compound 19 was prepared from commercially available 2,3-dihydrobenzodioxo-6-sulfonyl chloride following the protocol provided in Scheme 2.

$^1$H NMR (500 MHz, DMSO-$d_6$) 2.80-3.00 (m, 4H), 3.42-3.78 (bm, 4H), 3.80 (s, 3H), 4.25 (m, 4H), 6.86-6.88 (m, 2H), 6.92-6.98 (m, 2H), 7.00 (d, 1H), 7.15 (d, 2H), 7.24 (s, 1H), 7.26-7.30 (dd, 1H), 7.34 (d, 2H), 10.5 (s, 1H); MS base peak at 510.3; HPLC purity 97.02%.

5-Chloro-2-methoxy-N-(4-(4-(2-methoxyphenyl)-1, 4-diazepane-1-carbonyl)phenyl)benzene-sulfonamide (19a)

19a

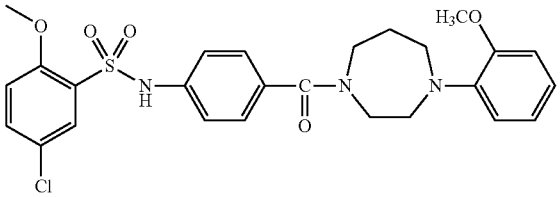

Compound 19a was prepared according to Scheme 2. N-boc-homopiperazine was utilized in place of N-Boc-piperazine to prepare the N-2-methoxyphenyl-homopiperazine intermediate through a Buchwald reaction as provided in Scheme 3.

$^1$H NMR (500 MHz, DMSO-$d_6$) 1.70 (s, 1H), 1.90 (s, 1H), 3.10-3.40 (m, 9H), 3.60-3.80 (m, 2H), 3.82 (s, 3H), 6.70-6.82 (m, 4H), 6.96-7.30 (m, 5H), 7.66 (t, 1H), 7.74 (s, 1H), 10.40 (d, 1H); MS base peak at 530.1; HPLC purity 95.89%.

N-(4-(4-(2-methoxyphenyl)-1,4-diazepane-1-carbonyl)phenyl)quinoline-8-sulfonamide (19b)

19b

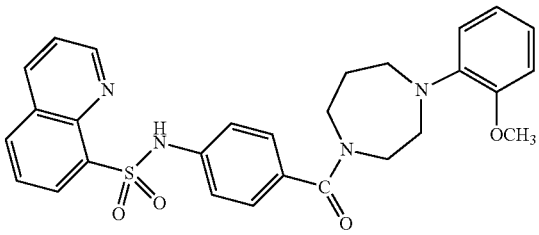

$^1$H NMR (500 MHz, DMSO-$d_6$) 1.70 (s, 1H), 1.90 (s, 1H), 3.10-3.40 (m, 8H), 3.58-3.80 (m, 3H), 6.58 (d, 1H), 6.70-7.20 (m, 7H), 7.80 (m, 2H), 8.30 (t, 1H), 8.40 (d, 1H), 8.56 (t, 1H), 9.18 (s, 1H), 10.40 (d, 1H); MS base peak at 517.2; HPLC purity 97.60%.

N-(4-(4-(2-methoxyphenyl)piperazine-1-carbonyl) phenyl)-2-methylbenzo[d]thiazole-4-sulfonamide (35)

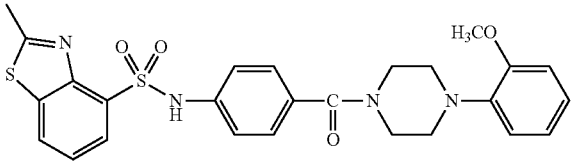

2-methylbenzothiazole-4-sulfonyl chloride was prepared according to U.S. Pat. No. 4,643,759. Compound 35 was prepared following the general procedure described in Scheme 2.

$^1$H NMR (500 MHz, DMSO-$d_6$) 2.80 (s, 3H), 3.00 (bs, 4H), 3.40-3.78 (m, 4H), 3.80 (s, 3H), 6.90 (s, 2H), 6.90-7.0 (m, 2H), 7.18 (d, 2H), 7.30 (d, 2H), 7.82 (d, 1H), 8.04 (d, 1H), 8.60 (s, 1H), 10.6 (1H); MS base peak at 523.4; LCMS purity 97.38%

N-(4-(4-(2-methoxyphenyl)piperazine-1-carbonyl) phenyl)thiophene-2-sulfonamide (36)

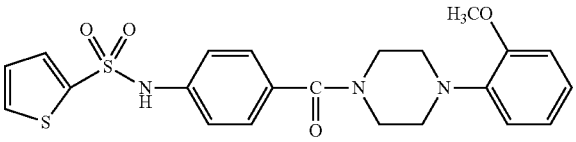

Compound 36 was prepared from commercially available thiophene-2-sulfonyl chloride according to the general procedure described in Scheme 2.

$^1$H NMR (500 MHz, DMSO-$d_6$) 2.90-3.00 (bs, 4H), 3.30-3.78 (bm, 4H), 3.80 (s, 3H), 6.80-6.90 (m, 2H), 6.90-7.0 (m, 2H), 7.18 (d, 1H), 7.20 (d, 2H), 7.40 (d, 2H), 7.60 (s, 1H), 7.94 (d, 1H), 10.70 (s, 1H); MS base peak at 458.2; HPLC purity 95.02%.

Synthesis of Phenyl Analogues

Scheme 4

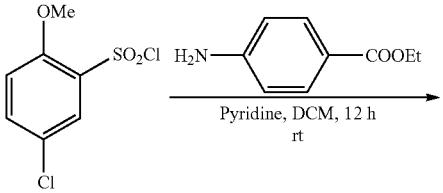

-continued

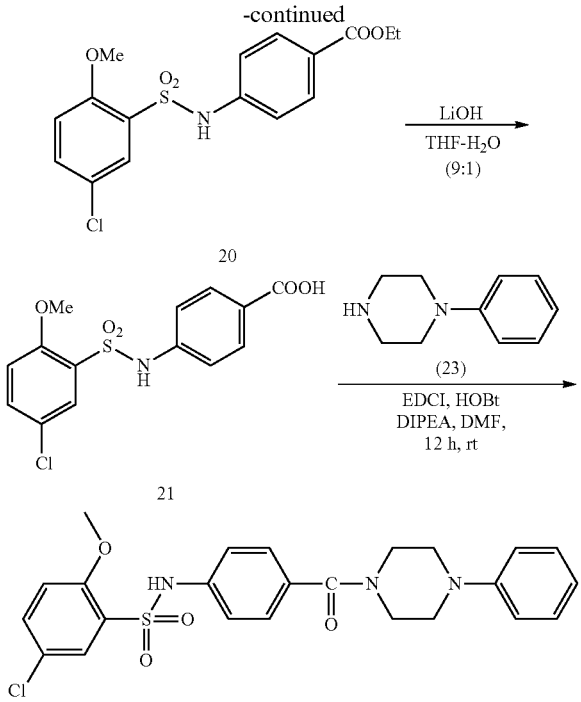

Compound 22:

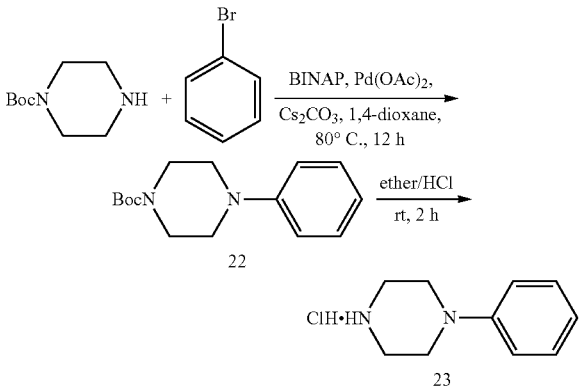

Procedure for the Synthesis of Compound 20:

To a solution of 2-methoxy-5-chlorobenzenesulfonyl chloride (878 mg, 0.00362 moles, 1.5 eq) in dichloromethane was added a solution of ethyl 4-aminobenzoate (400 mg, 0.00242 moles, 1 eq) in 1:1 ratio of pyridine and DCM (5 mL/5 mL) under nitrogen atmosphere at 0° C. The reaction mixture was stirred at room temperature overnight. The progress of the reaction was monitored by TLC. Upon completion, the reaction mixture was diluted with DCM, washed twice with water, and dried with anhydrous sodium sulphate. The organic layer was concentrated, dried, washed with ether followed by n-hexane and dried to provide 20 as an off-white solid (0.8 g, 89% yield).

$^1$H NMR (500 MHz, $CDCl_3$) 1.34 (t, 3H), 4.0 (s, 3H), 4.22-4.32 (q, 2H), 6.90 (d, 1H), 7.16 (d, 2H), 7.20 (s, 1H), 7.84 (s, 1H), 7.92 (d, 2H).

Procedure for the Synthesis of Compound 21:

LiOH (226 mg, 0.0049 moles, 4 eq) was added to a stirred solution of compound 20 (500 mg, 0.0013 moles, 1 eq) in THF—$H_2O$ mixture (1:1 ration, 30 ml/30 ml) and heated at reflux overnight. The progress of the reaction was monitored by TLC. Upon completion, the reaction mixture was acidified with citric acid to pH 4 and extracted with ethyl acetate. The ethyl acetate layer was washed with water, dried over sodium sulfate and distilled. The resulting solid 21 was dried and used without purification in the following step (400 mg, 87% yield).

$^1$H NMR (500 MHz, DMSO-$d_6$) 3.82 (s, 3H), 7.10-7.22 (m, 3H), 7.62 (d, 1H), 7.88-7.92 (m, 3H), 10.64 (s, 1H), 12.70 (s, 1H).

Procedure for the Synthesis of Compound 22:

The synthesis of compound 22 was carried out following a procedure similar to compound 5 utilizing bromobenzene in place of 2-bromoanisole. MS 263 (M+1 peak)

Procedure for the Synthesis of Compound 23:

Compound 22 (500 mg) was dissolved in 30 ml of ether/HCl and stirred for 2 hrs at room temperature under a nitrogen atmosphere. The reaction mixture was distilled under reduced pressure to remove ether, washed with pentane and dried over sodium sulfate to obtain compound 23 (300 mg, 97% yield).

$^1$H NMR (500 MHz, DMSO-$d_6$) 3.10-3.20 (m, 4H), 3.40-3.42 (m, 4H), 6.80 (t, 1H), 7.00 (d, 2H), 7.22 (t, 2H), 9.0 (bs, 1H), 9.40 (bs, 2H).

Procedure for the Synthesis of Compound 24:

To a stirred solution of compound 21 (100 mg, 0.00029 moles, 1 eq) in DMF (10 mL) was added EDCI (62 mg, 0.00032 moles, 1.1 eq), HOBt (50 mg, 0.00032 moles, 1.1 eq) and DIPEA (0.16 ml, 0.00088 moles, 3 eq) at 0° C. under a nitrogen atmosphere. The reaction mixture was stirred for 5 minutes at 0° C. and then at room temperature for 30 minutes. A solution of compound 23 (59 mg, 0.00029 moles, 1 eq) dissolved in DMF and half equivalent of DIPEA was added slowly to the above reaction mixture at 0° C. and allowed to stir at room temperature overnight. The reaction was monitored by TLC. Upon completion, the reaction mixture was washed with water and extracted with ethyl acetate. The organic layer was dried over sodium sulfate and concentrated under vacuum. The crude product was purified by crystallization with an ethyl acetate/hexane solvent mixture to obtain compound 24 in 24.6% yield (35 mg).

24

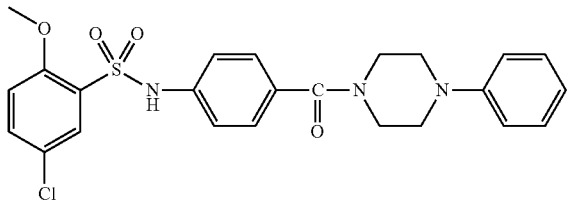

$^1$H NMR (500 MHz, DMSO-$d_6$) 3.10-3.20 (bs, 4H), 3.40-3.78 (bm, 4H), 3.82 (s, 3H), 6.80 (t, 1H), 6.90 (d, 2H), 7.14 (d, 2H), 7.20 (t, 3H), 7.30 (d, 2H), 7.62-7.66 (dd, 1H), 7.74 (d, 1H), 10.40 (s, 1H); MS base peak at 486.0; HPLC purity 97.34%.

**Compounds 25 to 30 were prepared following a protocol similar to that described in Scheme 4.

N-(4-(4-phenylpiperazine-1-carbonyl)phenyl)benzenesulfonamide (25)

25

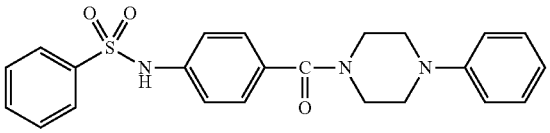

Compound 25 was prepared using benzenesulfonyl chloride following a protocol similar to that shown in Scheme 4.

$^1$H NMR (500 MHz, DMSO-$d_6$) 3.10-3.20 (bs, 4H), 3.40-3.78 (bm, 4H), 6.80 (t, 1H), 6.92 (d, 2H), 7.10-7.35 (m, 6H), 7.50-7.70 (m, 3H), 7.80 (d, 2H), 10.60 (s, 1H); MS base peak at 422.0; HPLC purity 97.92%.

4-Fluoro-N-(4-(4-phenylpiperazine-1-carbonyl)phenyl)benzenesulfonamide (26)

26

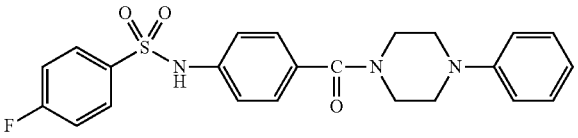

Compound 26 was made using 4-fluorobenzenesulfonyl chloride following a similar procedure as provided in Scheme 4.

$^1$H NMR (500 MHz, DMSO-$d_6$) 3.10-3.20 (bs, 4H), 3.40-3.80 (bm, 4H), 6.80 (t 1H), 6.94 (d, 2H), 7.14 (d, 2H), 7.20 (t, 2H), 7.32 (d, 2H), 7.35 (t, 2H), 7.80-7.90 (m, 2H), 10.6 (s, 1H); MS base peak at 440.1; HPLC purity 96.72%.

3-Chloro-N-(4-(4-phenylpiperazine-1-carbonyl)phenyl)benzenesulfonamide (27)

27

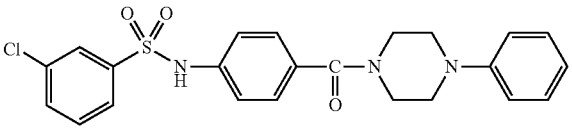

Compound 27 was prepared using commercial 3-chlorobenzenesulfonyl chloride following a similar procedure as provided in Scheme 4.

$^1$H NMR (500 MHz, DMSO-$d_6$) 3.10-3.20 (bs, 4H), 3.40-13.80 (bm, 4H), 6.80 (t, 1H), 7.00 (d, 2H), 7.18-7.22 (m, 4H), 7.38 (d, 2H), 7.60 (t, 1H), 7.70-7.80 (m, 3H), 10.6 (s, 1H); MS base peak at 456.2; HPLC purity 97.25%.

3-Methoxy-N-(4-(4-phenylpiperazine-1-carbonyl)phenyl)benzenesulfonamide (28)

28

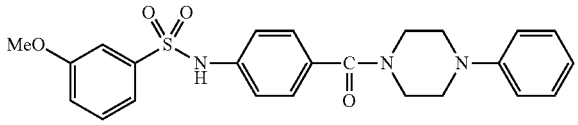

Compound 28 was prepared using 3-methoxybenzenesulfonyl chloride according to the general procedure provided in Scheme 4.

$^1$H NMR (500 MHz, DMSO-$d_6$) 3.10-3.20 (bs, 4H), 3.40-3.78 (bm, 4H), 3.80 (s, 3H), 6.80 (t, 1H), 6.95 (d, 2H), 7.14-7.24 (m, 5H), 7.28 (bs, 1H), 7.32-7.40 (m, 3H), 7.50 (t, 1H), 10.6 (s, 1H); MS base peak at 452.2; HPLC purity 93.60%.

2-Chloro-N-(4-(4-phenylpiperazine-1-carbonyl)phenyl)benzenesulfonamide (29)

29

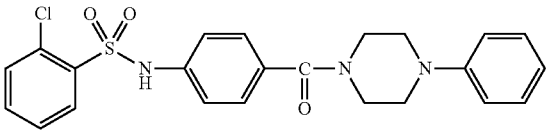

Compound 29 was prepared using commercially available 2-chlorobenzenesulfonyl chloride according to the general procedure provided in Scheme 4.

$^1$H NMR (500 MHz, DMSO-$d_6$) 3.10-3.20 (bs, 4H), 3.40-3.78 (bm, 4H), 6.80 (t,r 1H), 6.95 (d, 2H), 7.16-7.38 (m, 6H), 7.58 (t, 1H), 7.64 (d, 2H), 8.10 (d, 1H), 10.90 (s, 1H); MS base peak at 456.2; HPLC purity 99.21%. cl N-(4-(4-phenylpiperazine-1-carbonyl)phenyl)naphthalene-1-sulfonamide (30)

30

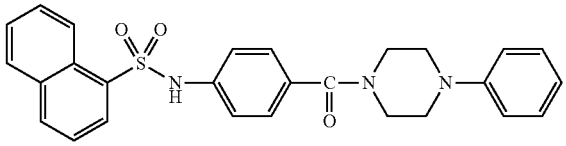

Compound 30 was prepared using commercially available is naphthalene-1-sulfonyl chloride according to the general procedure provided in Scheme 4.

$^1$H NMR (500 MHz, DMSO-$d_6$) 3.10-3.20 (bs, 4H), 3.40-3.78 (bm, 4H), 6.80 (t, 1H), 6.95 (d, 2H), 7.08 (d, 2H), 7.10-7.30 (m, 4H), 7.70-7.80 (m, 3H), 8.10 (d, 1H), 8.20-8.30 (m, 2H), 8.76 (d, 1H), 11.0 (s, 1H); MS base peak at 472.3; HPLC purity 99.14%.

N-(4-(4-phenylpiperazine-1-carbonyl)phenyl)quinoline-8-sulfonamide (30a)

30a

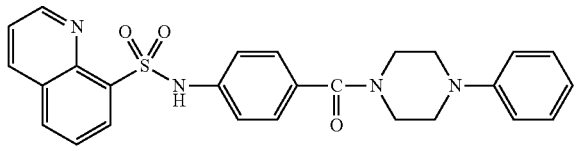

$^1$H NMR (500 MHz, DMSO-$d_6$) 3.00-3.20 (bm, 4H), 3.30-3.70 (bs, 4H), 6.80 (t, 1H), 6.90 (d, 2H), 7.10-7.22 (m, 6H), 7.70-7.80 (m, 2H), 8.30 (d, 1H), 8.44 (d, 1H), 8.56 (d, 1H), 9.18 (d, 1H), 10.42 (s, 1H); MS base peak at 473.2; HPLC purity 98.50%.

Synthesis of 4-Methoxy Phenyl Analogues

Scheme 5:

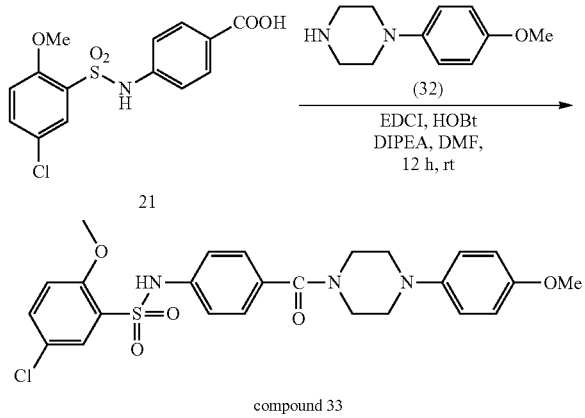

Compound 31:

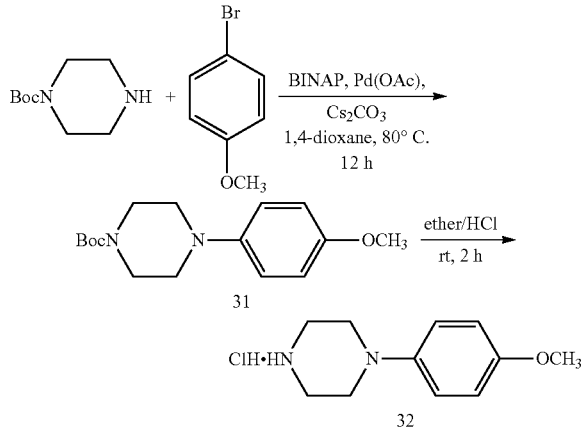

Synthesis of Compound 31:

To a solution of 4-bromoanisole (2.0 g, 0.0106 moles, 1 eq) in 1,4-dioxane (30 mL), $N_2$ gas was purged for 30 minutes at room temperature followed by the addition of $Cs_2CO_3$ (7.64 g, 0.023 moles, 2.2 eq), BINAP (598 mg, 0.00096 moles, 0.09 eq), $Pd(OAc)_2$ (38 mg, 0.00017 moles, 0.016 eq) and tetrabutylammonium iodide (15 mg). The reaction mixture was purged with nitrogen again for another 15 minutes followed by addition of N-Boc-piperazine (2.38 g, 0.0128 moles, 1.2 eq). The reaction mixture was heated at 80° C. overnight and monitored by TLC. The excess solvent was distilled off under reduced pressure and the residue was diluted with water and extracted with ethyl acetate. The organic layer was separated, washed once again with water, dried over sodium sulfate and concentrated. The crude material was purified by column chromatography using 60-120 mesh silica gel (15% Ethyl acetate/hexane) to afford 1.5 g (48.3% yield) of compound 31.

Synthesis of Compound 32:

Compound 31 was stirred at room temperature for 2 hrs in 60 ml of ether/HCl. The excess of solvent was removed under reduced pressure and the resultant solid was washed with n-hexane and dried to obtain 780 mg (99.7% yield) of compound 32.

5-Chloro-2-methoxy-N-(4-(4-(4-methoxyphenyl) piperazine-1-carbonyl)phenyl)benzene-sulfonamide (33)

33

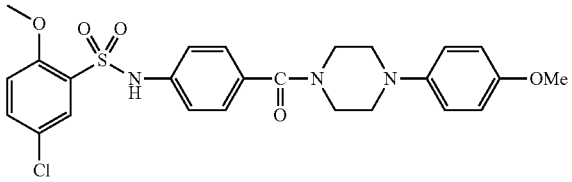

Compound 33 was prepared following the protocol described for compound 24 in Scheme 4.

$^1$H NMR (500 MHz, DMSO-$d_6$) 3.00 (bs, 4H), 3.40-3.70 (m, 7H), 3.80 (s, 3H), 6.80-6.90 (dd, 4H), 7.14 (d, 2H), 7.22 (d, 1H), 7.30 (d, 2H), 7.62-7.66 (dd, 1H), 7.74 (d, 1H), 10.4 (s, 1H); MS base peak at 557.1; HPLC purity 94.14%.

5-Fluoro-2-methoxy-N-(4-(4-(4-methoxyphenyl) piperazine-1-carbonyl)phenyl)benzene-sulfonamide (34)

34

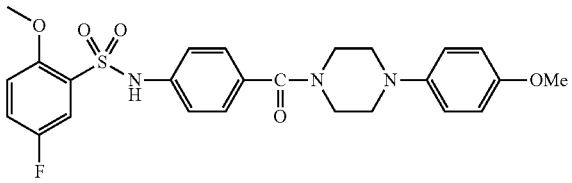

Compound 34 was prepared following the general protocol provided in Scheme 4 starting from 2-methoxy-4-fluorobenzenesulfonyl chloride.

$^1$H NMR (500 MHz, DMSO-$d_6$) 3.00 (bs, 4H), 3.40-3.70 (m, 7H), 3.82 (s, 3H), 6.80-6.90 (dd, 4H), 7.14 (d, 2H), 7.20 (dd, 1H), 7.30 (d, 2H), 7.46-7.49 (m, 1H), 7.60 (dd, 1H), 10.4 (s, 1H); MS base peak at 500.2; HPLC purity 95.48%.

Synthesis of 4-Chloro Pyrimidine Analogues

Scheme 6:

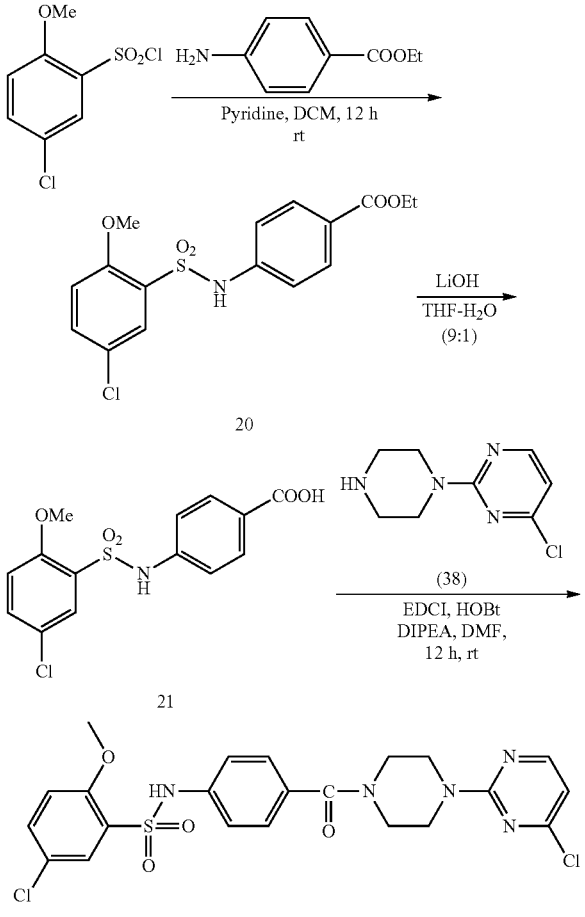

Compound 38:

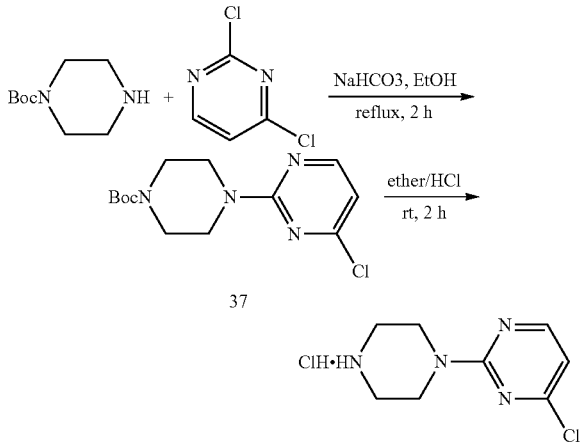

Preparation of Compound 37:

2,4-dichloropyrimidine (801 mg, 0.0053 mole, 1 eq), N-Boc-piperazine (1.0 gm, 0.0053 mole, 1 eq) and sodium bicarbonate (903 mg, 0.0107 mole, 2 eq) were dissolved in ethanol (50 ml) and stirred at reflux for 1 h. Progress of the reaction was monitored by TLC. The excess solvent was removed, dissolved in water and extracted with DCM. The organic layer was washed with water, dried with sodium sulfate and concentrated under reduced pressure. The crude product was purified on silica gel (60-120 mesh) using 15% ethyl acetate-hexane to afford coupled product compound 37 (230 mg).

$^1$H NMR (500 MHz, $CDCl_3$) 1.5 (s, 9H), 3.5 (m, 4H), 3.80 (m, 4H), 6.80 (d, 1H), 8.20 (d, 1H).

Preparation of Compound 38:

A solution of compound 37 in 20 ml of ether/HCl was allowed to stir at room temperature under nitrogen atmosphere for 1 h. The excess solvent was distilled off under reduced pressure and the crude material was washed with n-pentane and dried to yield 180 mg of compound 38 in quantitative yield.

Preparation of Compound 39:

To a stirred solution of compound 21 (109 mg, 0.31 mmole, 1.0 eq) in DMF (15 mL), was added EDCI (67 mg, 0.35 mmoles, 1.1 eq), HOBt (53.7 mg, 0.35, 1.1 eq) and DIPEA (2.0 eq) at 0° C. under a nitrogen atmosphere. The reaction mixture was allowed to stir at room temperature for 30 minutes. A solution of compound 38 (75 mg, 0.319 mmoles, 1 eq) in 5 ml of DMF and 1.5 eq of DIPEA was added slowly to reaction mixture at 0° C. and stirred at room temperature for 12 h. The reaction was monitored by TLC. After completion, the reaction mixture was quenched with water and extracted with ethyl acetate. The organic layer was separated, dried over sodium sulfate and concentrated under reduced pressure. The crude product was purified on silica gel column (60-120 mesh) using 2% MeOH-DCM to afford 30 mg of compound 39 in 18% yield.

5-Chloro-N-(4-(4-(4-Chloropyrimidin-2-yl)piperazine-1-carbonyl)phenyl)-2-methoxy benzenesulfonamide (39)

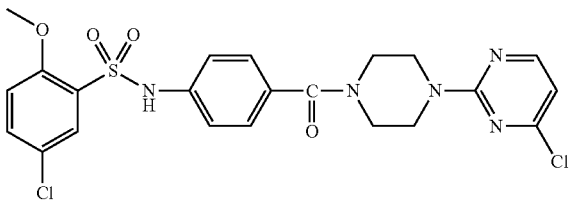

$^1$H NMR (500 MHz, DMSO-$d_6$) 3.35-3.60 (bs, 4H), 3.70-3.78 (bm, 4H), 3.80 (s, 3H), 6.78 (d, 1H), 7.16 (d, 2H), 7.22 (d, 1H), 7.36 (d, 2H), 7.66 (d, 1H), 7.80 (s, 1H), 8.18 (s, 1H), 10.50 (s, 1H); MS base peak at 522.1; HPLC purity 96.50%.

N-(4-(4-(4-Chloropyrimidin-2-yl)piperazine-1-carbonyl)phenyl)-4-fluoro benzenesulfonamide (40)

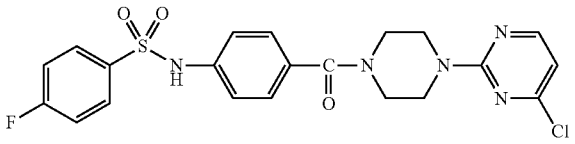

Compound 40 was prepared in-part by following the protocols established for the compound 38 coupling of pyrimidine as provided in Scheme 6 and subsequently by following general procedures as described in Scheme 4 starting from 4-fluorobenzenesulfonyl chloride.

$^1$H NMR (500 MHz, DMSO-$d_6$) 3.35-3.60 (bs, 4H), 3.70-3.78 (bm, 4H), 6.78 (d, 1H), 7.18 (d, 2H), 7.38 (d, 2H), 7.42 (d, 2H), 7.82 (d, 2H), 8.38 (d, 1H), 10.60 (s, 1H); MS base peak at 476.2; HPLC purity 97.89%.

Synthesis of 2-Pyrimidine Analogues

Scheme 7:

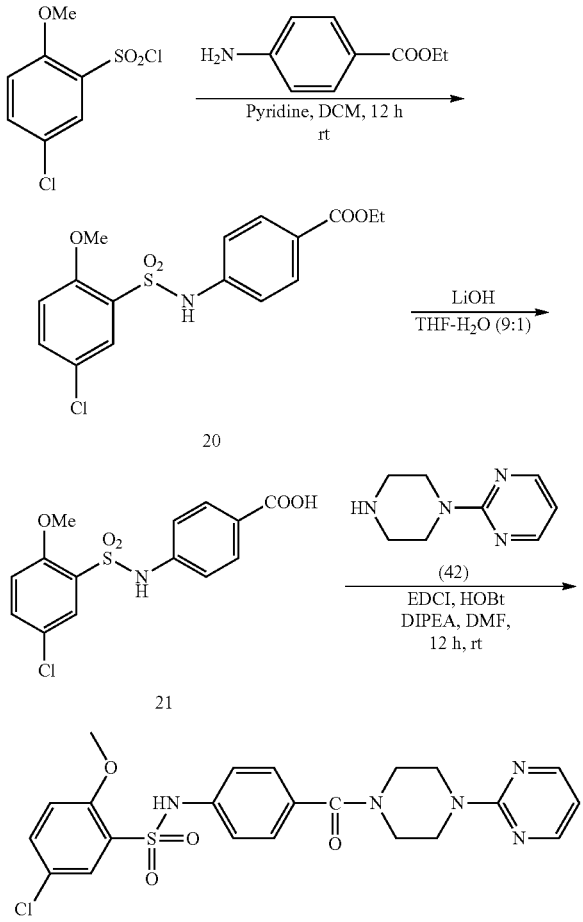

Compound 42:

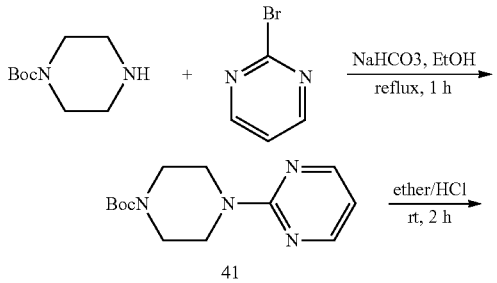

-continued

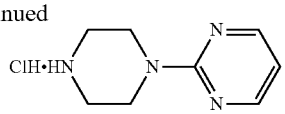

42

Preparation of Compound 41:

To a solution of 2-bromopyrimidine (500 mg, 0.003144 moles, 1 eq) in ethanol (50 ml) was added sodium bicarbonate (528 mg, 0.0062 moles, 2 eq) followed by N-Boc-piperazine (585 mg, 0.0031 moles, 1.0 eq). The reaction mixture was allowed to stir at reflux for 1 h and monitored by TLC. Upon completion, the excess solvent was removed under reduced pressure. The crude material was diluted with water and extracted with ethyl acetate. The organic layer was dried over sodium sulphate and concentrated. The crude material was washed with hexane and dried to obtain 400 mg of compound 41 (48% yield).

Preparation of Compound 42:

A solution of compound 41 (400 mg) in ether/HCl (30 ml) was stirred at room temperature for 2 hrs and monitored by TLC. After 2 hrs, the reaction mixture was concentrated under reduced pressure to yield compound 42 (300 mg, 98% yield) which was subsequently washed with hexane and used without purification.

Preparation of Compound 43:

To a solution of compound 21 (100 mg, 0.00029 moles, 1 eq) in DMF (15 mL) was added EDCI (61.5 mg, 0.00032 moles, 1.1), HOBt (49.28 mg, 0.00032 moles, 1.1 eq) and 1.5 equivalents of DIPEA at 0° C. and stirred at room temperature for 30 minutes. To this, a solution of compound 42 in DMF (5 ml) and 2 eq of DIPEA was added at 0° C. and stirred at room temperature overnight. The reaction mixture was quenched with water and extracted with ethyl acetate. The organic layer was washed with water, dried over sodium sulfate and concentrated under reduced pressure to provide the crude product. The crude material was purified on a silica gel (230-400 mesh) column with 3% MeOH/DCM to yield compound 43 in 31.6% yield (45 mg).

5-Chloro-2-methoxy-N-(4-(4-(pyrimidin-2-yl)piperazine-1-carbonyl)phenyl)benzene-sulfonamide (43)

43

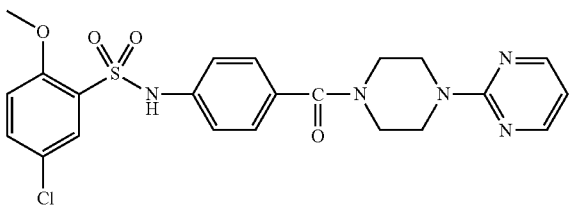

$^1$H NMR (500 MHz, DMSO-$d_6$) 3.35-3.70 (bm, 4H), 3.70-3.80 (bm, 4H), 3.82 (s, 3H), 6.62 (d, 1H), 7.15 (d, 2H), 7.22 (d, 1H), 7.34 (d, 2H), 7.62-7.66 (dd, 1H), 7.75 (d, 1H), 8.40 (s, 2H), 10.5 (s, 1H); MS base peak at 488.3; HPLC purity 97.47%.

4-Chloro-N-(4-(4-(pyrimidin-2-yl)piperazine-1-carbonyl)phenyl)benzenesulfonamide (44) 30

44

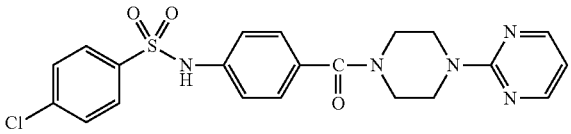

Compound 44 was prepared from 4-chlorobenzenesulfonyl chloride following the protocol described in Scheme 7 and utilizing the general procedure described in Scheme 4.

$^1$H NMR (500 MHz, DMSO-$d_6$) 3.35-3.70 (bm, 4H), 3.70-3.80 (bm, 4H), 6.62 (t, 1H), 7.18 (d, 2H), 7.38 (d, 2H), 7.62 (d, 2H), 7.80 (d, 2H), 8.40 (d, 2H), 10.62 (s, 1H); MS base peak at 458.2; HPLC purity 98.41%.

N-(4-(4-(pyrimidin-2-yl)piperazine-1-carbonyl)phenyl)quinoline-8-sulfonamide (45)

45

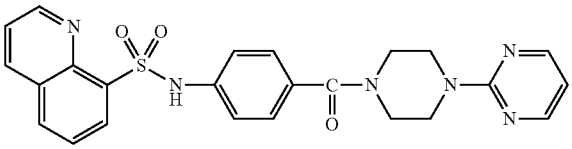

Compound 45 was prepared from 4-chlorobenzenesulfonyl chloride following the protocol described in Scheme 7 using the general procedure provided in Scheme 4.

$^1$H NMR (500 MHz, DMSO-$d_6$) 3.30-3.80 (bm, 8H), 6.62 (t, 1H), 7.18 (d, 2H), 7.22 (d, 2H), 7.64-7.80 (m, 2H), 8.30 (d, 1H), 8.38 (d, 2H), 8.42 (d, 1H), 8.58 (d, 1H), 9.18 (d, 1H), 10.42 (s, 1H); MS base peak at 475.2; HPLC purity 99.52%.

Synthesis of Pyrazine Analogues:

Scheme 8:

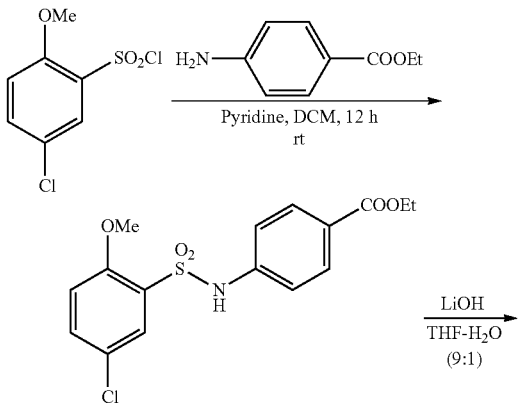

-continued

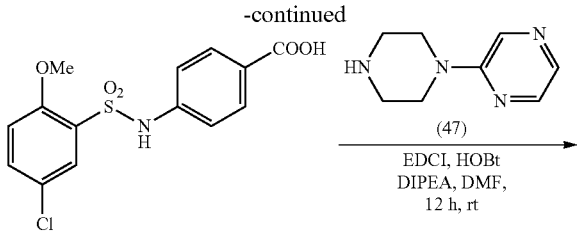

21

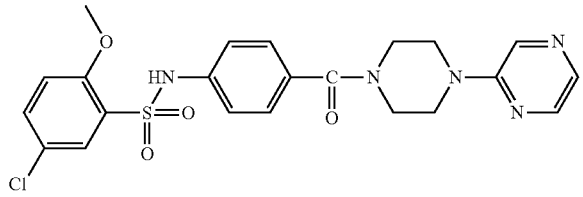

compound 48

Compound 47:

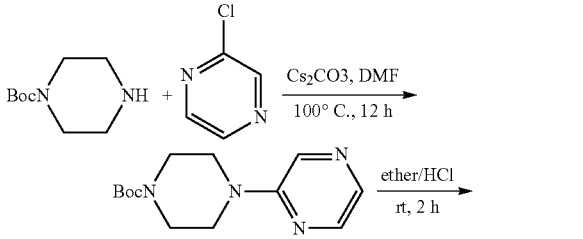

46

47

Preparation of Compound 46:

To a solution of 2-chloropyrazine (500 mg, 0.0027 moles, 1 eq) in DMF (20 ml) was added cesium carbonate (1.7 g, 0.0052 moles, 2 eq) followed by N-Boc-piperazine (506.8 mg, 0.0027 moles, 1.0 eq). The reaction mixture was heated at 100° C. for 12 hrs and monitored by TLC. Upon completion, the excess solvent was removed under reduced pressure and the crude material was diluted with water and extracted with ethyl acetate. The organic layer was dried over sodium sulfate and concentrated. The crude material was washed, purified on silica gel (60-120 mesh) using 30% ethylacetate-hexane to provide 400 mg of compound 46 (44.1% yield).

Preparation of Compound 47:

A solution of compound 46 (250 mg) in ether/HCl (30 ml) was stirred at room temperature for 1 h and monitored by TLC. After 1 h, the reaction mixture was concentrated under reduced pressure to yield compound 47 (200 mg, 98% yield) which was washed with hexane and used without further purification.

Preparation of Compound 48:

To a solution of compound 21 (100 mg, 0.00029 moles, 1 eq) in DMF (15 mL) was added EDCI (61.5 mg, 0.00032 moles, 1.1), HOBt (49.28 mg, 0.00032 moles, 1.1 eq) and 1.5 equivalents of DIPEA at 0° C. and stirred at room temperature for 30 minutes. To this, a solution of compound 47 (58.7 mg, 0.00029 moles, 1 eq) in DMF (5 ml) and 3 eq. of DIPEA was added at 0° C. and stirred at room temperature for 12 h. The reaction mixture was quenched with water and extracted with ethyl acetate. The organic layer was washed with water, dried over sodium sulfate and concentrated under reduced pressure to provide the crude product. The crude material was subsequently purified on silica gel (60-120 mesh) with ethyl acetate to yield compound 48 in 31.6% yield (45 mg).

5-Chloro-2-methoxy-N-(4-(4-(pyrazin-2-yl)piperazine-1-carbonyl)phenyl)benzene-sulfonamide (48)

48

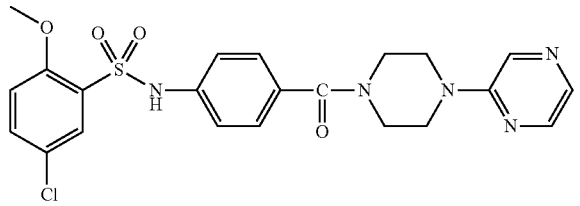

$^1$H NMR (500 MHz, DMSO-$d_6$) 3.35-3.70 (bm, 8H), 3.82 (s, 3H), 7.14 (d, 2H), 7.22 (d, 1H), 7.33 (d, 2H), 7.62-7.68 (dd, 1H), 7.74 (d, 1H), 7.86 (d, 1H), 8.10 (bs, 1H), 8.30 (s, 1H), 10.56 (s, 1H); MS base peak at 488.2; HPLC purity 92.55%.

N-(4-(4-(pyrazin-2-yl)piperazine-1-carbonyl)phenyl) quinoline-8-sulfonamide (49)

49

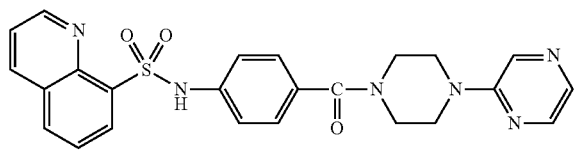

Compound 49 was prepared from quinoline-8-sulfonyl chloride as described in Scheme 8 using the general procedure provided in Scheme 4.

$^1$H NMR (500 MHz, DMSO-$d_6$) 3.35-3.70 (bm, 8H), 7.12 (d, 2H), 7.22 (d, 2H), 7.68-7.78 (m, 2H), 7.84 (s, 1H), 8.08 (s, 1H), 8.24 (d, 2H), 8.42 (d, 1H), 8.52 (d, 1H), 9.19 (s, 1H), 10.50 (s, 1H); MS base peak at 475.2; HPLC purity 98.10%.

Synthesis of Pyridine Analogues

Scheme 9:

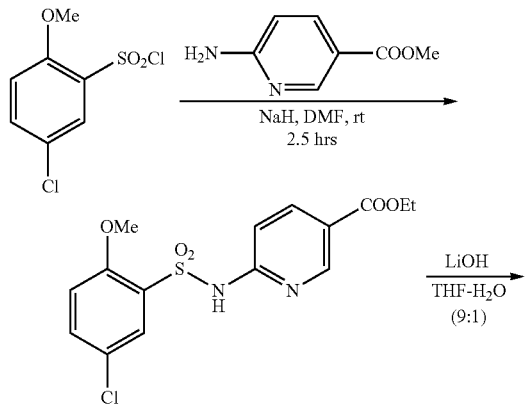

50

-continued

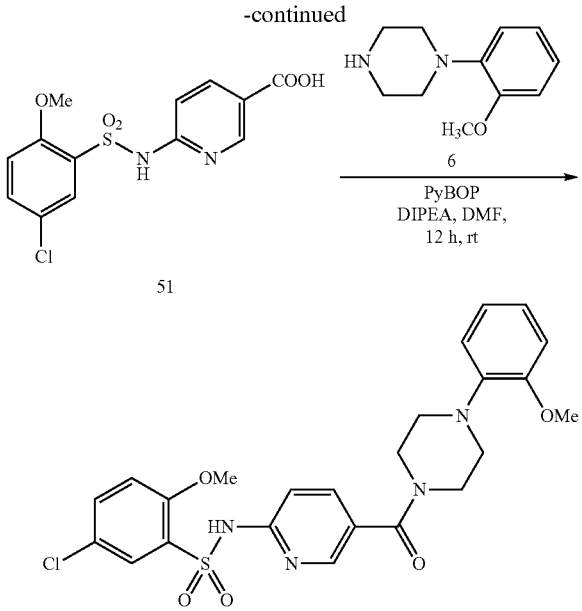

Preparation of Compound 50:

To a suspension of NaH (94 mg, 3.94 mmole, 2 eq) in DMF (20 mL) was added methyl-2-amino-pyridine-5-carboxylate (300 mg, 1.97 mmole, 1 eq) and stirred at room temperature for 30 minutes. A solution of 5-chloro-2-methoxybenzenesulfonyl chloride (570 mg, 2.36 mmole, 1.2 eq) was added slowly at room temperature and stirred for an additional 2 hrs. The reaction was monitored by TLC which showed 50% of the starting material remaining and continuation of the reaction failed to show improvement. The reaction mixture was quenched with water and extracted with ethyl acetate. The organic layer was separated, dried over sodium sulfate and concentrated under reduced pressure. The crude product 50 containing 50% of the starting ester was used without further purifications for the next step.

Preparation of Compound 51:

To a solution of compound 50 (270 mg) in THF/$H_2O$ was added lithium hydroxide (0.160 g, 5 eq, 3.786 mmole). The resulting reaction mixture was heated to reflux and stirred for 4 hrs. Upon completion, the reaction mixture was diluted with water and extracted with ethyl. The aqueous layer was acidified with citric acid and extracted with ethyl acetate. The organic layer was separated and dried over sodium sulfate and concentrated under reduced pressure. The crude acid 51 (90 mg, 36% yield) used without further purification.

Preparation of Compound 52:

To a solution of compound 51 (90 mg, 0.263 mmole, 1 eq) in DMF (15 mL) was added PyBOP (205 mg, 0.395 mmole, 1.5 eq) at 0° C. and stirred for 5 minutes. To this, a solution of compound 6 (60.2 mg, 0.2635 mmole, 1 eq) in 5 ml of DMF and 3 eq of DIPEA was added at 0° C. and stirred at room temperature overnight. Upon completion, the excess solvent was removed in vacuo and the residue was diluted with water and extracted with ethyl acetate. The organic layer was separated, washed with water and dried over sodium sulfate and concentrated under reduced pressure. The crude product was purified by silica gel column chromatography (60-120 mesh) using 1-2% MeOH/DCM to yield compound 52 in 33% yield (45 mg).

5-Chloro-2-methoxy-N-(5-(4-(2-methoxyphenyl) piperazine-1-carbonyl)pyridin-2-yl)benzenesulfonamide (52)

52

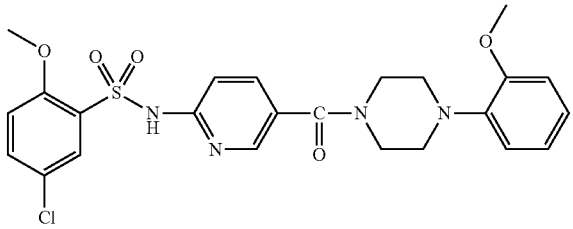

$^1$H NMR (500 MHz, DMSO-$d_6$) 3.00 (bs, 4H), 3.40-3.78 (bm, 4H), 3.9 (s, 6H), 6.90 (s, 2H), 6.92-7.00 (m, 2H), 7.20 (d, 1H), 7.60-7.62 (m, 1H), 7.80-7.82 (m, 2H), 8.18 (s, 1H), 11.4 (bs, 1H); MS base peak at 517.2; HPLC purity 97.65%.

N-(5-(4-(2-methoxyphenyl)piperazine-1-carbonyl) pyridin-2-yl)quinoline-8-sulfonamide (53)

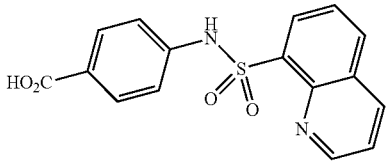

[$^1$H NMR (500 MHz, DMSO-$d_6$) 2.90 (bs, 4H), 3.40-3.70 (bm, 4H), 3.80 (s, 3H), 6.80-7.20 (m, 5H), 7.60-7.80 (m, 3H), 8.10 (s, 1H), 8.30 (d, 1H), 8.50 (d, 2H), 9.0 (s, 1H);] MS base peak at 504.2; HPLC purity 98.92%.

Synthesis of Benzyul Analogs

Scheme 10

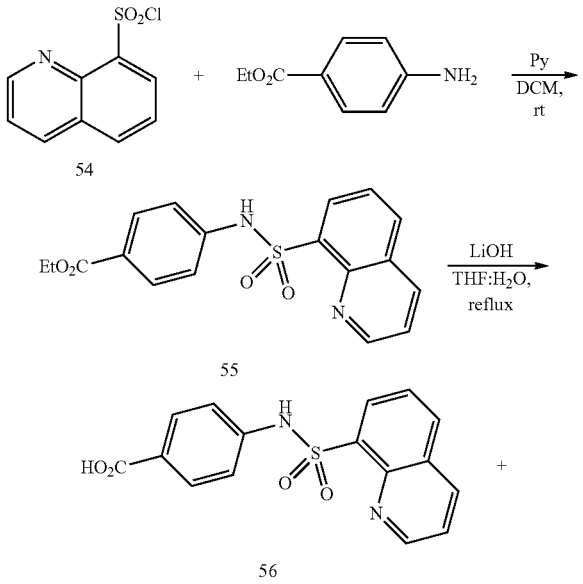

-continued
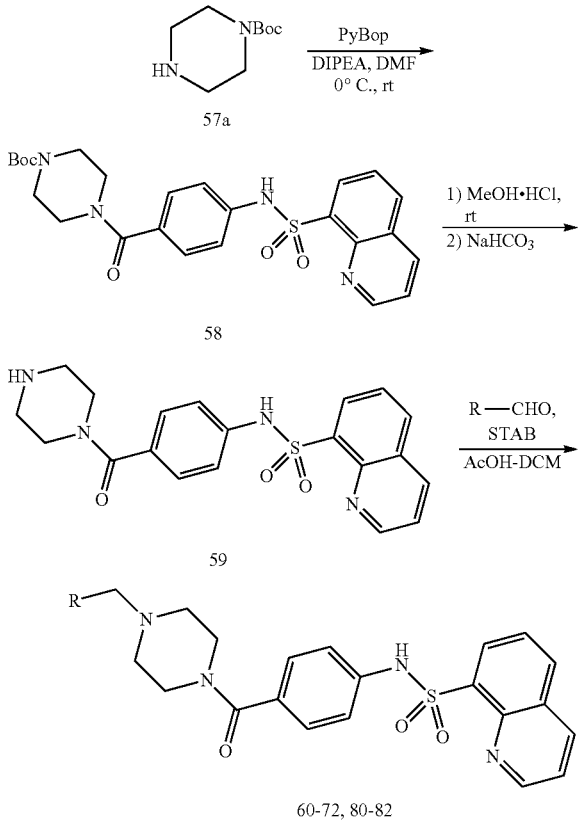
STAB - Sodium tri-acetoxyborohydride
Scheme 11
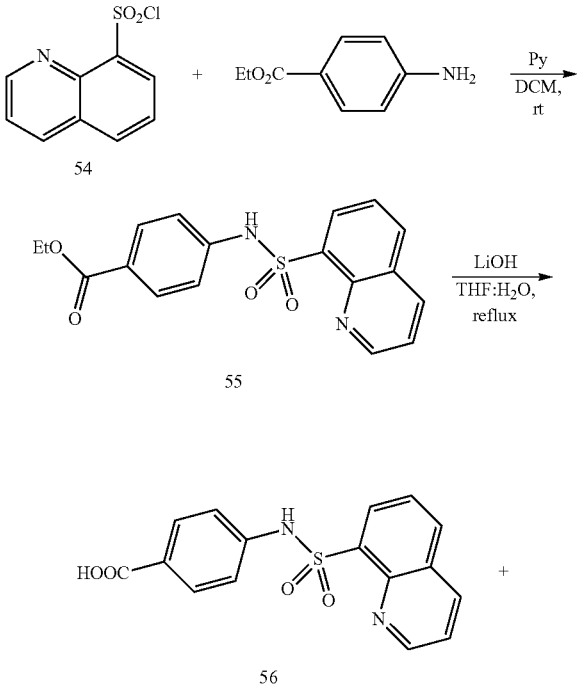
-continued
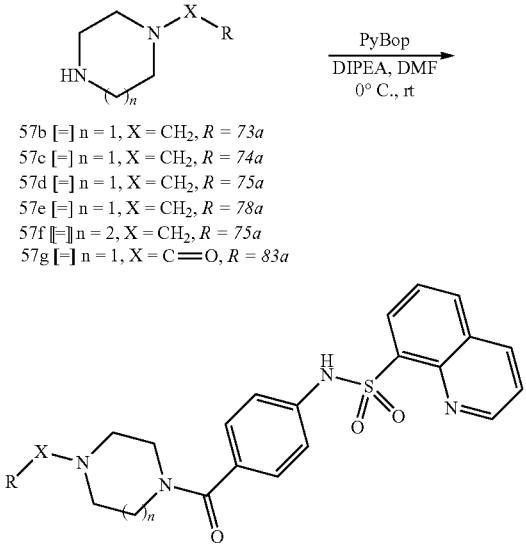
57b [=] n = 1, X = $CH_2$, *R = 73a*
57c [=] n = 1, X = $CH_2$, *R = 74a*
57d [=] n = 1, X = $CH_2$, *R = 75a*
57e [=] n = 1, X = $CH_2$, *R = 78a*
57f [=] n = 2, X = $CH_2$, *R = 75a*
57g [=] n = 1, X = C═O, *R = 83a*
73-78 [=] n = 1, X = $CH_2$
79 [=] n = 2, X = $CH_2$
83 [=] n = 1, X = C═O
TABLE 2
| S. No. | R | [R'] | [n] |
|---|---|---|---|
| 60 | 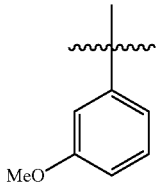 60a | [H] | [1] |
| 61 | 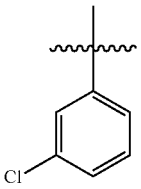 61a | [H] | [1] |
| 62 | 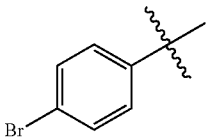 62a | [H] | [1] |
| 63 | 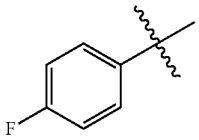 62a | [H] | [1] |

TABLE 2-continued
| S. No. | R | [R'] | [n] |
|---|---|---|---|
| 64 | 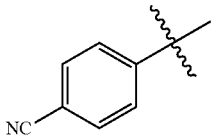 64a | [H] | [1] |
| 65 | 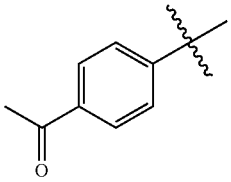 65a | [H] | [1] |
| 66 | 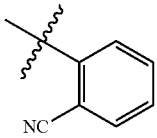 66a | [H] | [1] |
| 67 | 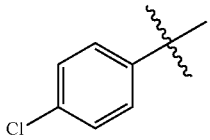 67a | [H] | [1] |
| 68 | 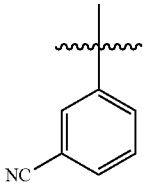 68a | [H] | [1] |
| 69 | 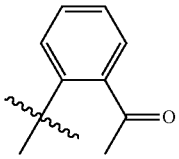 69a | [H] | [1] |
| 70 | 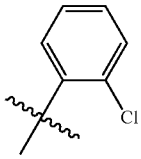 70a | [H] | [1] |
| 71 | 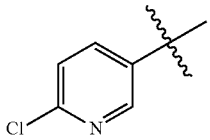 71a | [H] | [1] |
TABLE 2-continued
| S. No. | R | [R'] | [n] |
|---|---|---|---|
| 72 | 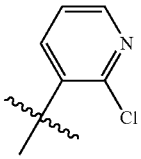 72a | [H] | [1] |
| 73 | 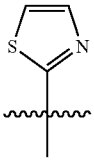 73a | [H] | [1] |
| 74 | 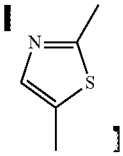 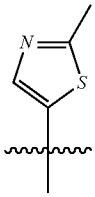 74a | [H] | [1] |
| 75 | 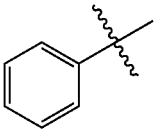 75a | [H] | [1] |
| 76 | 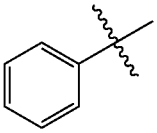 75a | [$Na^+$] | [1] |
| 77 | 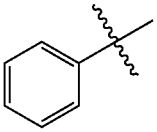 75a | [$CH_3SO_3^-$] | [1] |
| 78 | 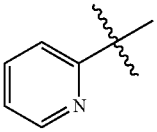 78a | [H] | [1] |

TABLE 2-continued

| S. No. | R | [R'] | [n] |
|---|---|---|---|
| 79 | 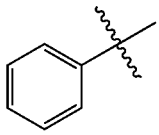 75a | [H] | [2] |
| 80 | 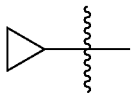 80a | [H] | [1] |
| 81 | 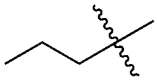 81a | [H] | [1] |
| 82 | 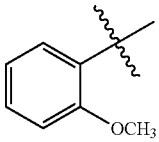 82a | [H] | [1] |
| 83 | 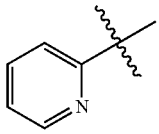 83a | [H] | [1] |

Preparation of Compound 55:

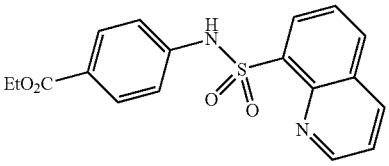

To a solution of ethyl 4-aminobenzoate (16 g, 96.85 mmol) in a mixture (1:1) of DCM and pyridine, sulfonyl chloride 54 (27.56 g, 121.07 mmol) was added at room temperature under an $N_2$ atmosphere. The resulting mixture was allowed to stir for 16 hrs. Upon completion of the reaction, the crude mixture was diluted with DCM, washed with water followed by 1N HCl. The resulting organic layer was then dried over $Na_2SO_4$ and concentrated under reduced pressure to afford product 55 in 98% yield (34 g).

Preparation of Compound 56:

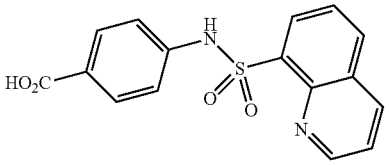

To a solution of sulfonamide 55 (34 g, 95.5 mmol) in THF and water (1:1) was added LiOH *monohydrate* (20 g, 47.66 mmol). The resulting mixture was allowed to stir at 80° C. overnight. After completion of the reaction, the crude mixture was washed with EtOAc. The aqueous layer was acidified with citric acid and filtered. The obtained solid was then washed with $Et_2O$ and azeotroped with toluene under reduced pressure to afford acid product 56 (30 g, 95.8% yield).

General Procedure for Compound 57b-57f (Scheme 11):

To a solution of N-Boc piperazine in DMF, corresponding bromide[, R-Br (R=20-23, see Table 1)] was added followed by addition of $K_2CO_3$. The resulting mixture was allowed to stir at 80° C. for 3 days. After completion of the reaction, DMF was removed under reduced pressure, the resulting residue was diluted with water and extracted with EtOAc. The organic layer was washed with water, dried over $Na_2SO_4$ and concentrated. The residue was purified by column chromatography to afford [products] *Boc-protected* 57b-57f in good yields. *Standard deprotection of the Boc-protected 57b-57f afforded copounds 57b-57f.*

Preparation of Compound 57g[(Scheme 2)]:

The synthesis of compound 57g was done from 2-picolinic acid (1.0 g, 8.12 mmol) by following a similar procedure as described for the preparation of compound 58 in scheme 10 by using amine N-Boc piperazine to afford [product] *Boc-protected* 57g in 76.10% yield (1.80 g). *Standard deprotection of the Boc-protected 57b-57f afforded copounds 57g.*

Preparation of Compound 58:

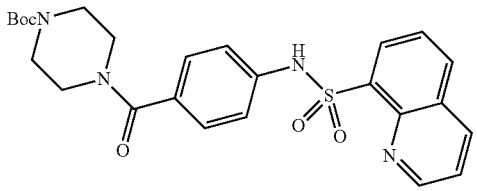

To a solution of acid 56 (2.0 g, 6.09 mmol) in DMF, PyBoP (Benzotriazole-1-yl-oxy-tris-(dimethylamino)-phosphonium hexafluorophosphate) (4.75 g, 9.14 mmol) was added at 0° C. and allowed to stir for 5 minutes. This was followed by addition of amine 57a (1.13 g, 6.09 mmol) *and catalytic amount DIPEA* at 0° C. under $N_2$ atmosphere and stirred overnight at room temperature. After completion of reaction, the resulting mixture was diluted with water and extracted with EtOAc. The organic layer was washed with water, dried over $Na_2SO_4$, and evaporated under reduced pressure. The residue was purified by column chromatography (silica gel, 60-120 mesh; MeOH-DCM, 2:8) to afford product 58 in 66% yield (2.0 g).

Preparation of Compound [6] *59*:

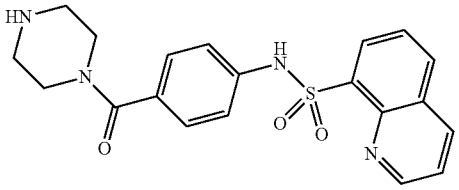

To a solution of MeOH.HCl, Boc protected amine [5] *58* (2 g[m], 4.03 mmol) was added and the resulting mixture was stirred for 1 hr. After completion of reaction, solvent was removed under reduced pressure, washed with water followed by addition of $NaHCO_3$ and extracted with DCM.

The organic layer was dried over $Na_2SO_4$ and evaporated under reduced pressure to afford product [6] *59* (1.5 g*m*, 94.30% yield).

Preparation of Compound 60:

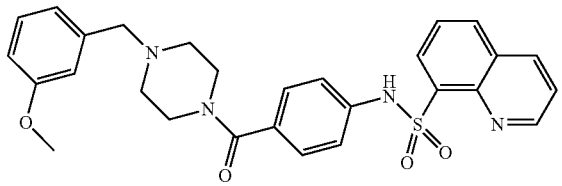

To a solution of amine 59 (0.1 g, 0.25 mmoles) and *the corresponding* aldehyde [60a] (0.04 g, 0.27 mmol) in DCM, acetic acid (0.2 mL) was added at room temperature and the resulting mixture was allowed to stir for 30 min. Then STAB (0.26 g, 1.26 mmol) was added and the resulting mixture was allowed to stir at 50° C. for 1 hr. After completion of reaction, the crude mixture was diluted with DCM, washed with water, dried over $Na_2SO_4$ and concentrated under reduced pressure. The residue was purified by column chromatography (silica gel, 60-120 mesh; MeOH-DCM, 2:8) to afford product 60 (0.05 g, 38.40% yield). [$^1$H NMR (400 MHz, $CDCl_3$) δ 2.40 (br d, 4H), 3.38 (br s, 2H), 3.48 (s, 2H), 3.68 (br s, 2H), 3.80 (s, 3H), 6.79 (d, 1H), 6.84 (s, 2H), 7.04 (d, 2H), 7.18 (d, 2H), 7.20-7.28 (m, 2H), 7.59-7.64 (m, 2H), 8.03 (d, 1H), 8.28 (d, 1H), 8.36 (d, 1H), 8.58 (s, 1H), 9.18 (s, 1H);] MS: 517 (M+1 peak).

Preparation of Compound 61:

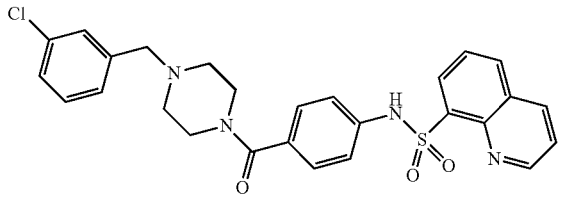

The synthesis of compound 61 was carried out using compound 59 (0.10 g, 0.25 mmol) and following a similar procedure as described for compound 60 by using *the corresponding* aldehyde [61a] to afford product 61 in 30.40% yield (0.040 g). [$^1$H NMR (400 MHz, $CDCl_3$) δ 2.40 (br d, 4H), 3.38 (br s, 2H), 3.56 (s, 2H), 3.68 (br s, 2H), 7.06 (d, 2H), 7.18 (d, 3H), 7.25 (d, 4H), 7.42 (d, 2H), 7.59-7.66 (m, 2H), 8.03 (d, 1H), 8.27 (d, 1H), 8.35 (d, 1H), 8.58 (s, 1H), 9.18 (s, 1H);] MS: 521 (M+1 peak).

Preparation of Compound 62:

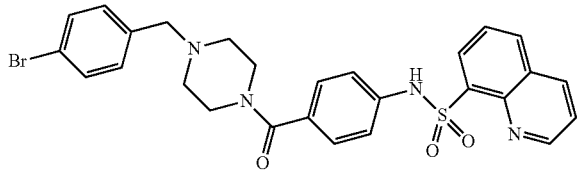

The synthesis of compound 62 was carried out utilizing compound 59 (0.08 g, 0.20 mmol) by following a similar procedure as described for compound 60 by using *the corresponding* aldehyde [62a] to afford product 62 in 35.00% yield (0.040 g). [$^1$H NMR (400 MHz, $CDCl_3$) δ 2.40 (br d, 4H), 3.39 (br s, 2H), 3.43 (s, 2H), 3.67 (br s, 2H), 7.02 (d, 2H), 7.15-7.21 (m, 2H), 7.48-7.63 (m, 2H), 8.03 (d, 1H), 8.31 (d, 2H), 8.39 (d, 1H), 8.58 (s, 1H), 9.18 (s, 1H); MS: 567 (M+2 peak).]

Preparation of Compound 63:

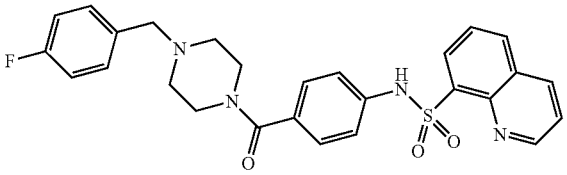

The synthesis of compound 63 was carried by following a similar procedure as described for compound 60 using *the corresponding* aldehyde [63a] to afford product 63 in 59.00% yield (0.06 g) from compound 59 (0.08 g, 0.20 mmol). [$^1$H NMR (400 MHz, $CDCl_3$) δ 2.40 (br d, 4H), 3.39 (br s, 2H), 3.43 (s, 2H), 3.67 (br s, 2H), 7.02 (t, 2H), 7.05 (d, 2H), 7.19 (d, 2H), 7.21 (s, 2H), 7.49-7.63 (m, 2H), 7.51-7.66 (m, 5H), 8.03 (d, 1H), 8.31 (d, 2H), 8.39 (d, 1H), 8.58 (s, 1H), 9.18 (s, 1H);] MS: 505 (M+1 peak).

Preparation of Compound 64:

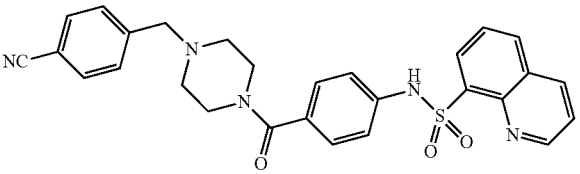

The synthesis of compound 64 was carried out following a similar procedure as described for compound 60 using *the corresponding* aldehyde [64a] to afford product 64 in 48.54% yield (0.05 g) from compound 59 (0.08 g, 0.20 mmol). [$^1$H NMR (400 MHz, $CDCl_3$) δ 2.40 (br s, 4H), 3.39 (br s, 2H), 3.58 (s, 2H), 3.71 (br s, 2H), 7.08 (d, 2H), 7.16 (d, 2H), 7.43 (d, 1H), 7.51 (d, 1H), 7.59-7.68 (m, 4H), 8.04 (d, 1H), 8.31 (d, 2H), 8.39 (d, 1H), 8.58 (s, 1H), 9.18 (s, 1H);] MS: 512 (M+1 peak).

Preparation of Compound 65:

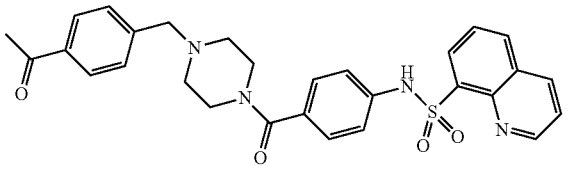

The synthesis of compound 65 was carried out following a similar procedure as described for compound 60 using *the corresponding* aldehyde [65a] to afford product 65 in 28.00% yield (0.03 g) from compound 59 (0.08 g, 0.20 mmol). [$^1$H NMR (400 MHz, $CDCl_3$) δ 2.39 (br d, 4H), 2.58 (s, 3H), 3.29 (br s, 2H), 3.59 (s, 2H), 3.76 (br s, 2H), 7.06 (d, 2H), 7.21 (d, 2H), 7.51-7.68 (m, 2H), 7.80 (d, 2H), 8.03 (d, 1H), 8.31 (d, 2H), 8.39 (d, 1H), 8.58 (s, 1H), 9.18 (s, 1H);] MS: 529 (M+1peak).

Preparation of Compound 66:

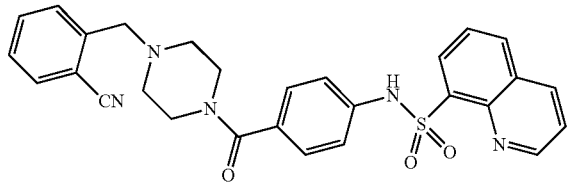

The synthesis of compound 66 was done by following the similar procedure as mentioned for compound 60 by using *the corresponding* aldehyde [66a] to afford product in 38.80% yield (0.04 g) from compound 59 (0.08 g, 0.20 mmol). [$^1$H NMR (400 MHz, $CDCl_3$) δ 2.40 (br s, 4H), 3.39 (br s, 2H), 3.53 (s, 2H), 3.71 (br s, 2H), 7.06 (d, 2H), 7.15 (d, 2H), 7.43 (t, 1H), 7.51-7.66 (m, 5H), 8.03 (d, 1H), 8.31 (d, 2H), 8.39 (d, 1H), 8.58 (s, 1H), 9.18 (s, 1H);] MS: 512 (M+1 peak).

Preparation of Compound 67:

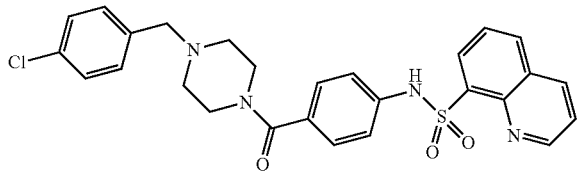

The synthesis of compound 67 was carried out following a similar procedure as described for compound 60 by using *the corresponding* aldehyde [67a] to afford product 38% yield (0.04 g) from compound 59 (0.08 g, 0.20 mmol). [$^1$H NMR (400 MHz, $CDCl_3$) δ 2.42 (br d, 4H), 3.38 (br s, 2H), 3.56 (s, 2H), 3.68 (br s, 2H), 7.06 (d, 2H), 7.18 (D, 2H), 7.42 (d, 2H), 7.49 (d, 1H), 7.59-7.68 (m, 4H), 8.03 (d, 1H), 8.27 (d, 1H), 8.35 (d, 1H), 8.58 (s, 1H), 9.18 (s, 1H);] MS: 521 (M+1 peak).

Preparation of Compound 68:

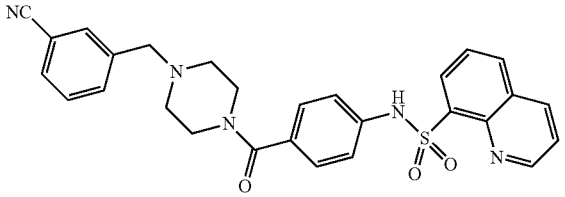

The synthesis of compound 68 was carried out by following a similar procedure described for compound 60 by using *the corresponding* aldehyde [68a] to afford the required product in 38% yield (0.04 g) from compound 59 (0.08 g, 0.20 mmol). [$^1$H NMR (400 MHz, $CDCl_3$) δ 2.43 (br d, 4H), 3.41 (br s, 2H), 3.68 (br s, 4H), 7.06 (d, 2H), 7.15 (d, 2H), 7.35-7.42 (m, 1H), 7.507.69 (m, 5H), 8.03 (d, 1H), 8.31 (d, 2H), 8.39 (d, 1H), 8.58 (s, 1H), 9.18 (s, 1H);] MS: 512 (M+1 peak).

reparation of Compound 69:

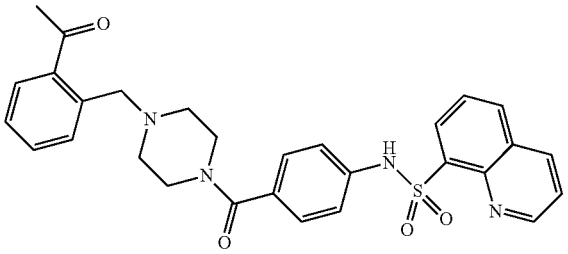

The synthesis of compound 69 was done by following the similar procedure as mentioned for compound 60 by using *the corresponding* aldehyde [69a] to afford the required product in 37.70% yield (0.04 g) from compound 59 (0.08 g, 0.20 mmol). [$^1$H NMR (400 MHz, $CDCl_3$) δ 2.39 (br s, 4H), 2.52 (s, 3H), 3.26 (br s, 2H), 3.61 (br s, 2H), 3.65 (s, 2H), 7.06 (d, 2H), 7.15 (d, 2H), 7.29-7.39 (m, 3H), 7.58-7.63 (m, 2H), 7.80 (d, 1H), 8.03 (d, 1H), 8.31 (d, 2H), 8.39 (d, 1H), 8.58 (s, 1H), 9.18 (s, 1H);] MS: 529 (M+1 peak).

Preparation of Compound 70:

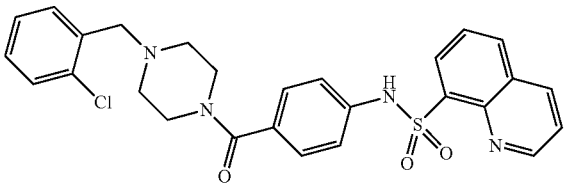

The synthesis of compound 70 was carried out following a similar procedure as described for compound 60 by using *the corresponding* aldehyde [70a] to afford the product in 28.50% yield (0.03 gm) from compound 6 (0.08 gm, 0.20 mmol). $^1$H NMR (400 MHz, $CDCl_3$) δ 2.42 (br d, 4H), 3.35 (br s, 2H), 3.60 (s, 2H), 3.68 (br s, 2H), 7.03 (d, 2H), 7.08-7.26 (m, 4H), 7.32 (d, 1H), 7.39 (d, 1H), 7.54-7.60 (m, 2H), 8.03 (d, 1H), 8.28 (d, 1H), 8.37 (d, 1H), 8.58 (s, 1H), 9.18 (s, 1H); MS: 521 (M+1 peak).

Preparation of Compound 71

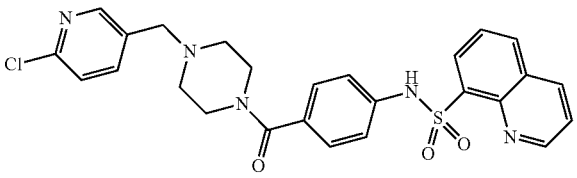

The synthesis of compound 71 was carried out following a 60 similar procedure as described for compound 60 by using *the corresponding* aldehyde [71a] to afford the [required] product in 57.00% yield (0.06 g) from compound 59 (0.08 g, 0.20 mmol). [$^1$H NMR (400 MHz, $CDCl_3$) δ 2.39 (br d, 4H), 3.38 (br s, 2H), 3.43 (s, 2H), 3.63 (br s, 2H), 7.06 (d, 2H), 7.17 (d, 2H), 7.21-7.29 (m, 65 2H), 7.58-7.63 (m, 3H), 8.03 (d, 1H), 8.31 (d, 2H), 8.39 (d, 1H), 8.58 (s, 1H), 9.18 (s, 1H);] MS: [522 (M+peak)] *522* (*M+1 peak*).

Synthesis of Compound 72:

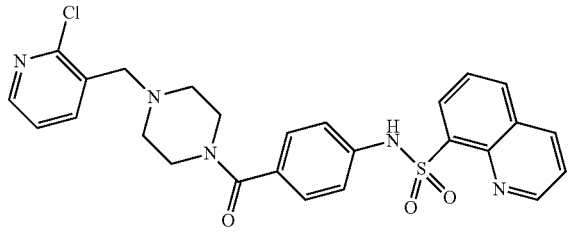

The synthesis of compound 72 was carried out following a similar procedure as described for compound [7a] *60* by using *the corresponding* aldehyde [72a] to afford the product in 38.80% yield (0.04 g) from compound 59 (0.08 g, 0.20 mmol). $^1$H NMR (400 MHz, $CDCl_3$): δ 2.45 (br s, 4H), 3.41 (br s, 2H), 3.60 (s, 2H), 3.68 20 (br s, 2H), 7.06 (d, 2H), 7.15 (d, 2H), 7.21-7.29 (m, 1H), 7.58-7.63 (m, 2H), 7.80 (d, 1H), 8.03 (d, 1H), 8.31 (d, 2H), 8.39 (d, 1H), 8.58 (s, 1H), 9.18 (s, 1H); MS: [522 (M+ peak)] *522* (*M+1 peak*).

Preparation of Compound 73:

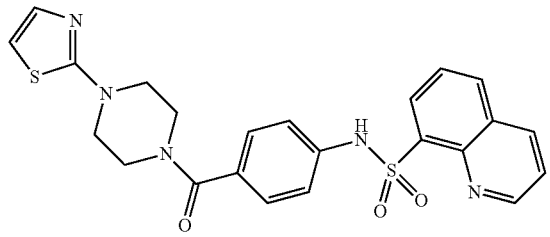

The synthesis of compound 73 was carried out following a similar procedure as described for compound 58 in scheme 10 by using amine 57b to afford product 73 in 73.27% yield (0.08 g) from compound 56 (0.08 g, 0.24 mmoles). [$^1$H NMR (400 MHz, $CDCl_3$): δ 3.44 (br s, 4H), 3.62 (s, 2H), 3.76 (br s, 4H), 6.84 (d, 1H), 7.12 (d, 2H), 7.21 (d, 2H), 7.37 (d, 1H), 7.60-7.66 (m, 2H), 8.04 (d, 1H), 8.32 (d, 1H), 8.39 (d, 1H), 9.18 (d, 45 1H);] MS: 480 (M+1 peak).

Preparation of Compound 74:

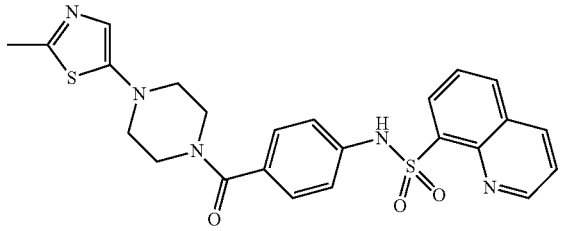

The synthesis of compound 74 was carried out following a similar procedure as described for compound 58 in scheme 10 by using amine 57c to afford product 74 in 33.45% yield (0.09 g) from compound 56 (0.18 g, 0.54 mmol). [$^1$H NMR (400 MHz, DMSO-$d_6$): δ 2.45 (s, 3H), 2.99 (br s, 4H), 3.55 (br s, 4H), 6.78 (s, 1H), 7.14 (dd, 4H), 7.66-7.75 (m, 2H), 8.26 (d, 1H), 8.41 (d, 1H), 8.50 (d, 1H), 9.16 (d, 1H); MS: 480 (M+1 peak).]

Preparation of Compound 75:

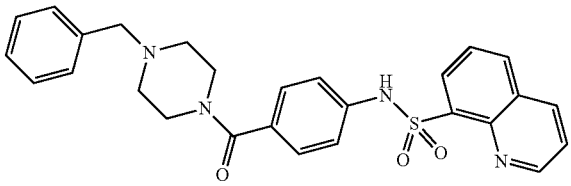

The synthesis of compound 75 was done by following the similar procedure as mentioned for compound 58 in scheme 10 by using amine 57d to afford product 75 in 43.85% yield (0.10 g) from compound 56 (0.15 g, 0.47 mmol). [$^1$H NMR (400 MHz, $CDl_3$):δ 2.40 (br d, 4H), 3.38 (br s, 2H), 3.52 (s, 2H), 3.73 (br s, 2H), 7.07 (d, 2H), 7.18 (d, 2H), 7.22-7.38 (m, 8H), 7.59-7.63 (m, 2H), 8.02 (d, 1H), 8.32 (d, 1H), 8.39 (d, 1H), 9.18 (d, 1H), 8.58 (s, 1H), 9.18 (s, 1H);] MS: 487 (M+1 peak).

Preparation of Compound [76] *78*:

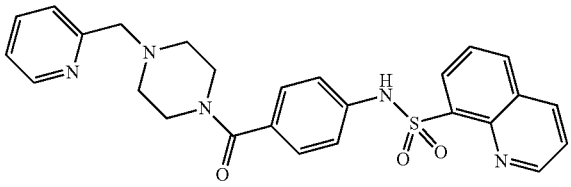

The synthesis of compound [76] *78* was carried out following a similar procedure as described for compound 58 in scheme 10 by using amine 57e to afford product [76] *78* in 26.31% yield (0.06 g) from compound 56 (0.23 g, 0.70 mmol). $^1$H NMR (400 MHz, $CDCl_3$): δ 3.15 (br s, 4H), 3.82 (br s, 4H), 4.21 (s, 2H), 7.12 (dd, 4H), 7.41 (t, 1H), 7.52-7.67 (m, 3H), 7.82 (t, 1H), 8.04 (d, 1H), 8.31 (d, 1H), 8.39 (d, 1H), 8.63 (d, 2H), 9.16 (d, 1H); [MS: 480 (M+1 peak);] MS: 488 (M+1 peak).

Preparation of Compound [77] *79*:

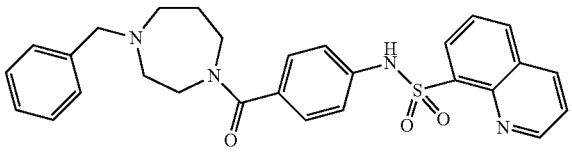

The synthesis of compound [77] *79* was carried out following a similar procedure as described for compound 58 in scheme 10 by using amine 57f to afford product [77] *79* in 21.14% yield (0.07 g) from compound 56 (0.17 g, 0.51 mmol). [$^1$H NMR (400 MHz, $CDCl_3$): δ 1.71 (br s, 1H), 1.80 (br s, 1H), 2.53 (br d, 2H), 2.71 (br d, 2H), 3.38 (br s, 2H), 3.57-3.69 (m, 4H), 7.02 (t, 2H), 7.16 (t, 2H), 7.59-7.63 (m, 2H), 8.01 (d, 1H), 8.31 (d, 1H), 8.39 (d, 1H), 8.48 (s, 1H), 9.16 (d, 1H); MS: 480 (M+1 peak);] MS: 501 (M+1 peak).

Preparation of Compound [78] *80*:

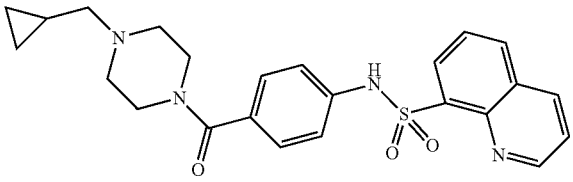

The synthesis of compound [78] *80* was carried out following a similar procedure as described for compound 60 in scheme 10 by using *the corresponding* aldehyde [24] to afford the required product in 48.61% yield (0.035 g) from compound 59 (0.07 g, 0.16 mmol). $^1$H NMR (400 MHz, $CDCl_3$): δ 0.04 (d, 2H), 0.54 (d, 2H), 0.80-0.90 (m 1H), 2.24 (d, 2H), 2.48 (br d, 4H), 3.39 (br s, 2H), 3.78 (br s, 2H), 7.12 (dd, 4H), 7.49-7.64 (m, 2H), 8.04 (d, 1H), 8.31 (d, 1H), 8.39 (d, 1H), 8.58 (s, 1H), 9.16 (d, 1H); [MS: 480 (M+1 peak);] MS: 451 (M+1 peak).

Preparation of Compound 81:

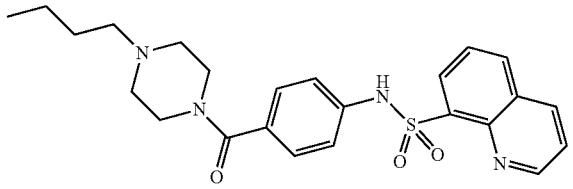

The synthesis of compound 81 was carried out following a similar procedure as described for compound 60 in scheme 10 by using *the corresponding* aldehyde [81a] to afford product 81 in 43.26% yield (0.045 g) from compound [6] *59* (0.1 g, 0.23 mmol). $^1$H NMR (400 MHz, $CDCl_3$): δ 0.91 (t, 3H), 1.25-1.39 (m, 2H), 1.40-1.49 (m, 2H), 2.30 (t, 2H), 2.42 (br s, 4H), 3.39 (br s, 2H), 3.70 (br s, 2H), 7.05 (d, 2H), 7.16 (d, 2H), 7.59-7.64 (m, 2H), 8.02 (d, 1H), 8.32 (d, 1H), 8.38 (d, 1H), 8.58 (br s, 1H), 9.16 (d, 1H); [MS: 480 (M+1 peak);] MS: 453 (M+1 peak).

Preparation of Compound 82:

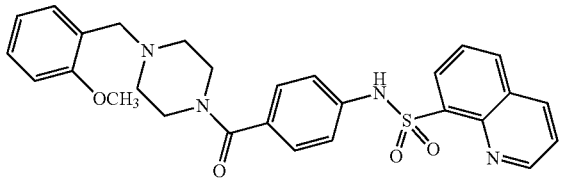

The synthesis of compound 82 was carried out following a similar procedure as described for compound 60 in scheme 10 by using *the corresponding* aldehyde [82a] to afford product in 48.73% yield (0.06 g) from compound 59 (0.08 g, 0.20 mmol). [$^1$H NMR (400 MHz, $CDCl_3$): δ 2.39 (br s, 2H), 2.56 (br s, 2H), 3.39 (br s, 2H), 3.59 (s, 2H), 3.75 (br s, 2H), 3.81 (s, 3H), 6.85 (d, 1H), 6.92 (t 1H), 7.08 (d, 2H), 7.17 (d, 2H), 7.24-7.31 (m, 2H), 8.02 (d, 1H), 8.32 (d, 1H), 8.38 (d, 1H), 8.58 (br s, 1H), 9.17 (d, 1H); MS: 480 (M+1 peak);] MS: 517 (M+1 peak).

Preparation of Compound 83:

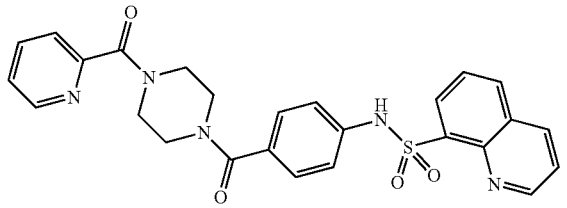

The synthesis of compound 83 was carried out following a similar procedure as described for compound 58 in scheme 10 by using amine 57g to afford product in 22.72% yield (0.05 gm) from compound 56 (0.14 gm, 0.43 mmol). [$^1$H NMR (400 MHz, $CDCl_3$): δ 3.62 (br s, 8H), 7.05 (d, 2H), 7.19 (d, 2H), 7.38 (t, 1H), 7.59-7.64 (m, 2H), 7.69 (d, 1H), 7.80 (t, 1H), 8.02 (d, 1H), 8.32 (d, 1H), 8.38 (d, 1H), 8.58 (br s, 1H), 9.17 (d, 1H); MS: 480 (M+1 peak);] MS: 502 (M+1 peak).

Preparation of Sodium Salt 76:

To a solution of sulfonamide 75 (0.05 g, 0.10 mmol) in Methanol, NaOH (0.04 g, 0.10 mmol) was added at room temperature and the resulting mixture was allowed to stir for 2 hrs. After completion of the reaction, the corresponding solvent was removed under reduced pressure. This was followed by the addition of $Et_2O$ (5 mL) and its subsequent removal. The addition and removal of $Et_2O$ was carried out several times to afford the desired product as a solid in 84.61% yield (0.04 g). [$^1$H NMR (400 MHz, DMSO-$d_6$): δ 3.40 (br s, 2H), 3.59 (br s, 8H), 6.77 (d, 1H), 6.89 (d, 1H), 7.18-7.29 (m, 2H), 7.50-7.60 (m, 2H), 7.99 (d, 1H), 8.25-8.32 (m, 2H), 8.98 (d, 1H);] MS: 509 (M+1 peak).

Preparation of Mesylate Salt 77:

To a solution of sulfonamide 75 (0.05 g, 0.10 mmol) in DCM, $CH_3SO_3H$ (0.10 g, 0.10 mmol) was added at room temperature and the resulting mixture was allowed to stir for 2 hrs. After completion of the reaction, the corresponding solvent was removed under reduced pressure followed by the addition of $Et_2O$ was added (5 mL) and it subsequent removal. The addition and removal of $Et_2O$ was carried out several times (3×5 mL) to afford the desired product in 59.32% yield (0.035 gm). [$^1$H NMR (400 MHz, $CDCl_3$): δ 3.02 (br s, 3H), 3.25 (br s, 3H), 4.23 (s, 2H), 7.17 (dd, 4H), 7.62-7.69 (m, 2H), 8.22 (d, 1H), 8.32 (d, 1H), 8.38 (d, 1H), 9.10 (d, 1H); MS: 487 (M+ peak).]

Synthesis of $N^4$-Aryl/Heteroaryl Piperazine Analogues

Scheme 12

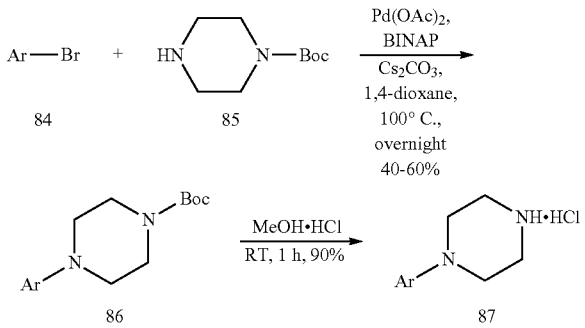

-continued

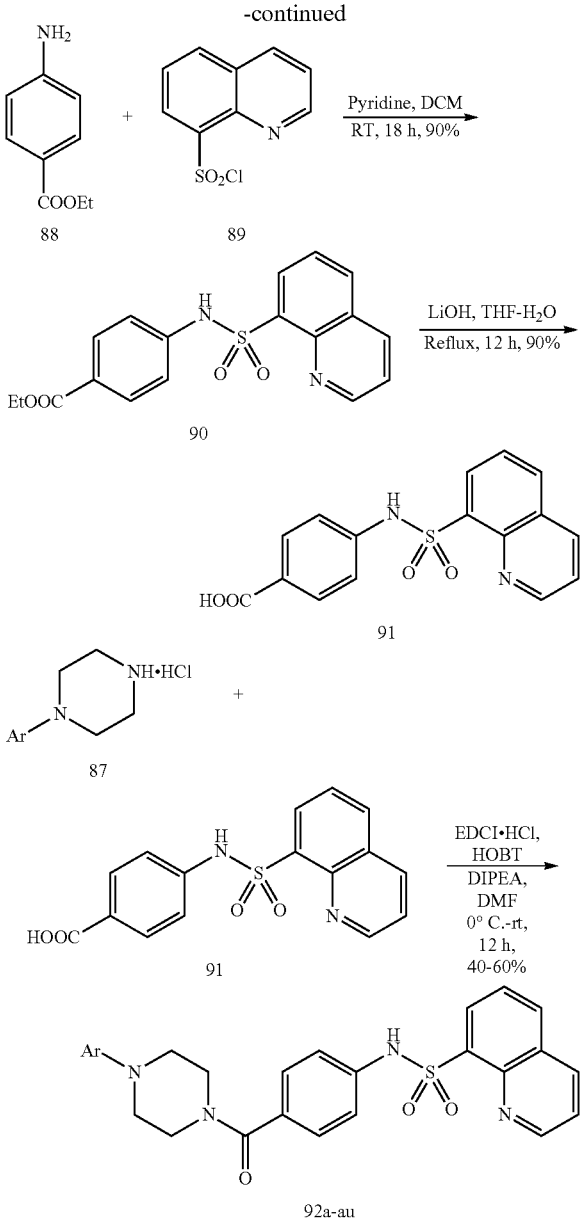

Where Ar = Substituted Aryl or Heteroaryl

General Procedure for Compound 86:

Nitrogen was purged through a stirred solution of arylbromide (84, 2.15 mmol) in 1,4-dioxane (20 ml) at room temperature for 30 min BINAP (0.134 g, 0.215 mmol), palladium acetate (0.0096 g, 0.043 mmol) and cesium carbonate (1.40 g, 4.3 mmol) were added to the reaction mixture and the nitrogen purging was continued for another 20 min and finally N-Boc piperazine (85, 0.4 g, 2.15 mmol) was added and stirred at 100° C. overnight under nitrogen atmosphere. After completion of the reaction (monitored by TLC), the reaction mixture was concentrated under vacuum. The residue was dissolved in water, extracted with ethyl acetate (3×50 ml). Combined organic extracts were washed with brine (20 ml), dried over anhydrous Sodium sulfate, filtered and concen65 trated under reduced pressure. The crude product was then purified by column chromatography (60-120 silica gel) using 10% ethyl acetate-hexane to yield compound 86 (40-60%).

General Procedure for Compound 87:

$N^1$-Boc-$N^4$-arylpiperazine (86, 1.075 mmol) was taken into a round bottomed flask and was added methanolic-HCl (20 ml, 20%) which resulted in formation of a homogeneous solution and was stirred for 1 h at room temperature. After completion of the reaction (monitored by TLC), the solvent was removed under vacuum. The crude product was washed with ethyl acetate repeatedly and then dried well to obtain compound 87 (90%) as a white solid.

Procedure for Preparation of Ethyl 4-(Quinoline-8-Sulfonamido)Benzoate 90:

To a solution of ethyl-4-amino benzoate (88, 5.0 g, 30.16 mmol) in a 1:1 mixture of DCM-pyridine (50:50 ml) was added quinoline-8-sulfonyl chloride (89, 8.24 g, 36.19 mmol) under nitrogen atmosphere. The resultant solution was stirred overnight at room temperature. On completion of the reaction (monitored by TLC), the reaction mixture was diluted with dichloromethane (150 ml), washed with water (3×50 ml), 1N HCl solution (3×50 ml) and brine (50 ml. The combined organic extracts were dried over anhydrous sodium sulfate, filtered and concentrated under vacuum. Crude product was co-distilled with toluene to remove the remnants of pyridine and dried to yield sulfonamide 90 (11.58 g, 90%) as an off-white solid and was used as such for the next step without further purification.

Analytical Data for Compound 90:

$^1$H NMR (500 MHz, $CDCl_3$) δ: 1.20 (3H, t), 4.19 (2H, q), 7.20 (2H, m), 7.60-7.80 (4H, m), 8.30 (1H, m), 8.40-8.50 (2H, m), 9.10 (1H, m), 10.8 (1H, s); MS: m/z 357.4 $(M+1)^+$.

Procedure for Preparation of 4-(Quinoline-8-Sulfonamido) Benzoic Acid 91:

Ethyl 4-(quinoline-8-sulfonamido)benzoate (90, 10 g, 28.08 mmol) was dissolved in a mixture of THF-water (100:100 ml) and maintained at room temperature. To this solution was added LiOH (5.89 g, 14.0 mmol) and the resultant solution was refluxed overnight. The reaction mixture was then washed with ethyl acetate (3×50 ml) and then acidified with dilute HCl. The resultant suspension was filtered and residue was co-distilled with toluene. This product was then dried under vacuum to yield carboxylic acid 91 (8.28 g, 90%) as an off-white solid.

Analytical Data for Compound 91:

$^1$H NMR (500 MHz, $CDCl_3$) δ: 7.10 (2H, m), 7.60-7.80 (4H, m), 8.25 (1H, m), 8.40-8.60 (2H, m), 9.10 (1H, m), 10.7 (1H, bs), 12.6 (1H, bs); MS: m/z 329.3 $(M+1)^+$.

General Procedure for Compound 92:

To a stirred solution of the carboxylic acid (91, 0.61 mmol) in DMF at 0° C. under nitrogen atmosphere, EDCI (0.129 gm, 0.671 mmol), HOBt (0.91 gm, 0.671 mmol) and DIPEA (0.31 ml, 1.83 mmol) were added and the resultant solution was stirred at room temperature for 30 min Amine hydrochloride (87, 0.61 mmol) was then added at 0° C. and stirred overnight at room temperature. After completion of the reaction (monitored by TLC), the reaction mixture was poured into 1.0 M HCl and extracted with EtOAc. The organic layer was washed with saturated $NaHCO_3$ solution, dried over $NaSO_4$ and filtered. The solvent was removed by rotary evaporation and the product was isolated by chromatography on silica gel (60-120 silica gel, 2% MeOH-DCM) or preparative HPLC to yield amide (92a-as) (40-60%) as an off-white solid.

General Procedure for Compound (92 at, 92au & 92av):

To a solution of $N^4$-aryl piperazine analogue (0.39 mmol) in methanol-DCM mixture (for Sodium salt) or DCM (for mesylate salt) was added sodium hydroxide in methanol (0.39 mmol) or methanesulfonylchloride (0.39 mmol). The reaction mixture was stirred over night and evaporated the solvent under reduced pressure. The crude residue was then washed sequentially with ether and n-pentane to yield desired salt as white solid.

N-(4-(4-(2-methoxyphenyl)piperazine-1-carbonyl) phenyl)quinoline-8-sulfonamide (92a)

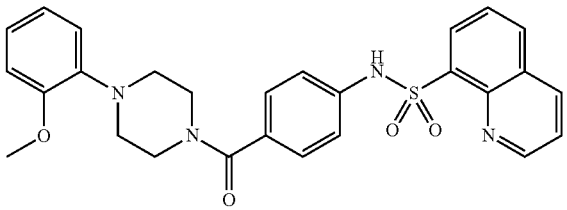

$^1$H NMR (500 MHz, DMSO-$d_6$) δ: 10.42 (s, 1H), 9.15 (bs, 1H), 8.50 (d, 1H), 8.40 (d, 1H), 8.24 (d, 1H), 7.70-7.80 (m, 2H), 7.15-7.20 (dd, 4H), 6.90-7.00 (m, 2H), 6.82 (d, 2H), 3.80 (s, 3H), 3.40-3.78 (bm, 4H), 2.80-3.00 (bs, 4H); HPLC purity: 97.11%; MS, m/z found 503.2 $(M+1)^+$.

N-(4-(4-phenylpiperazine-1-carbonyl)phenyl)quinoline-8-sulfonamide (92b)

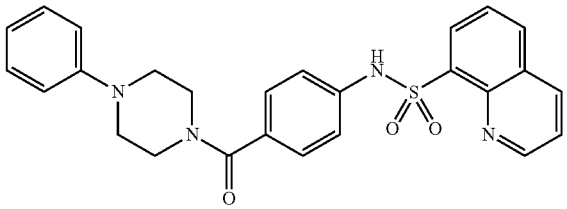

$^1$H NMR (500 MHz, DMSO-$d_6$) δ: 10.42 (s, 1H), 9.18 (d, 1H), 8.56 (d, 1H), 8.44 (d, 1H), 8.30 (d, 1H), 7.70-7.80 (m, 2H), 7.10-7.22 (m, 6H), 6.90 (d, 2H), 6.80 (t, 1H), 3.30-3.70 (bs, 4H), 3.00-3.20 (bm, 4H); HPLC purity 98.50%: MS, m/z found 473.2 $(M+1)^+$.

N-(4-(4-(3-ethoxyphenyl)piperazine-1-carbonyl) phenyl)quinoline-8-sulfonamide (92c)

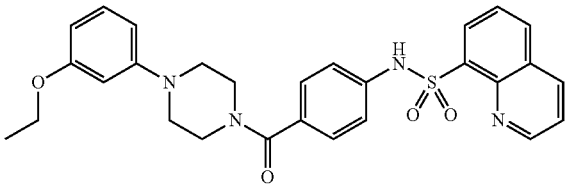

$^1$H NMR (400 MHz, $CDCl_3$) δ: 9.18 (d, 1H), 8.60 (s, 1H), 8.35 (d, 1H), 8.30 (d, 1H), 8.10 (d, 1H), 7.65 (m, 2H), 7.05-7.20 (m, 5H), 6.50 (m, 3H), 4.00 (q, 2H), 3.40-3.90 (bs, 4H), 3.00-3.20 (bm, 4H), 1.40 (t, 3H); HPLC purity 99.74%: MS, m/z found 517.40 $(M+1)^+$.

N-(4-(4-(4-ethoxyphenyl)piperazine-1-carbonyl)phenyl) quinoline-8-sulfonamide (92d)

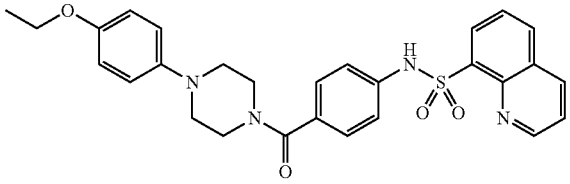

$^1$H NMR (400 MHz, $CDCl_3$) δ: 9.18 (d, 1H), 8.60 (s, 1H), 8.35 (d, 1H), 8.30 (d, 1H), 8.05 (d, 1H), 7.60 (m, 2H), 7.20 (d, 2H), 7.10 (d, 2H), 6.85 (m, 4H), 4.00 (q, 2H), 3.40-3.90 (bm, 4H), 3.00 (bm, 4H), 1.4 (t, 3H); HPLC purity 99.36%: MS, m/z found 517.40 $(M+1)^+$.

Ethyl 3-(4-(4-(quinoline-8-sulfonamido)benzoyl) piperazin-1-yl)benzoate (92e)

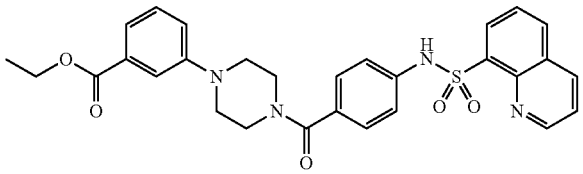

$^1$H NMR (400 MHz, $CDCl_3$) δ: 9.20 (d, 1H), 8.60 (s, 1H), 8.40 (d, 1H), 8.30 (d, 1H), 8.05 (d, 1H), 7.60 (m, 4H), 7.30 (m, 1H), 7.20 (d, 2H), 7.10 (m, 3H), 4.40 (q, 2H), 3.40-3.90 (bm, 4H), 3.20 (bm, 4H), 1.4 (t, 3H); HPLC purity 99.65%: MS, m/z found 545.35 $(M+1)^+$.

N-(4-(4-(2-fluorophenyl)piperazine-1-carbonyl)phenyl)quinoline-8-sulfonamide (92f)

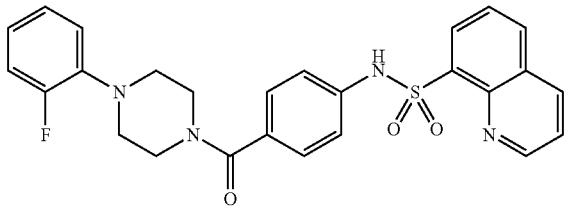

$^1$H NMR (400 MHz, $CDCl_3$) δ: 9.15 (d, 1H), 8.60 (s, 1H), 8.40 (d, 1H), 8.30 (d, 1H), 8.05 (d, 1H), 7.60 (m, 2H), 7.20 (m, 3H), 7.10 (d, 2H), 6.65 (d, 1H), 6.55 (m, 2H), 3.40-3.80 (bm, 4H), 3.15 (bm, 4H); HPLC purity 99.16%: MS, m/z found 491.35 $(M+1)^+$.

N-(4-(4-(3-isopropoxyphenyl)piperazine-1-carbonyl) phenyl)quinoline-8-sulfonamide (92g)

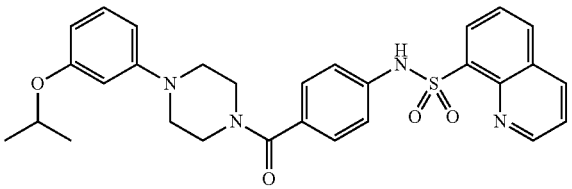

[$^1$H NMR (400 MHz, $CDCl_3$) δ: 9.15 (d, 1H), 8.60 (s, 1H), 8.40 (d, 1H), 8.30 (d, 1H), 8.05 (d, 1H), 7.60 (m, 2H), 7.20 (m, 2H), 7.15 (m, 1H), 7.10 (d, 2H), 6.45 (m, 3H), 3.40-3.80 (bm, 4H), 3.15 (bm, 4H);] HPLC purity 99.45%: MS, m/z found 531.40 $(M+1)^+$.

N-(4-(4-(2,5-difluorophenyl)piperazine-1-carbonyl) phenyl)quinoline-8-sulfonamide (92h)

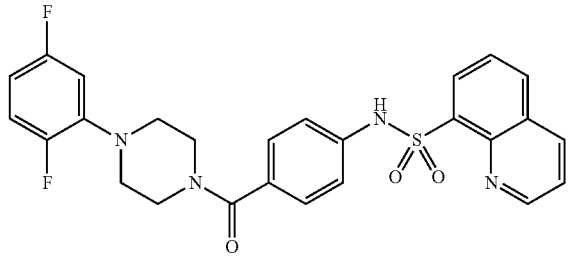

$^1$H NMR (400 MHz, $CDCl_3$) δ: 9.15 (d, 1H), 8.60 (s, 1H), 8.35 (d, 1H), 8.30 (d, 1H), 8.05 (d, 1H), 7.60 (m, 2H), 7.20 (m, 2H), 7.10 (d, 2H), 6.95 (m, 1H), 6.60 (m, 2H), 3.45-3.90 (bm, 4H), 3.00 (bm, 4H); HPLC purity 99.94%: MS, m/z found 509.30 $(M+1)^+$.

N-(4-(4-(3-(methylthio)phenyl)piperazine-1-carbonyl)phenyl)quinoline-8-sulfonamide (92i)

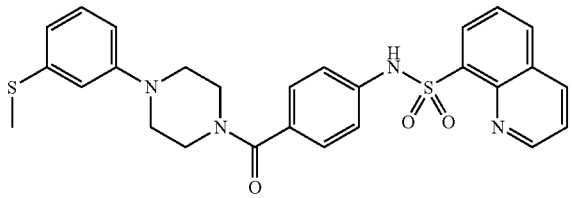

$^1$H NMR (400 MHz, $CDCl_3$) δ: 9.15 (d, 1H), 8.60 (s, 1H), 8.35 (d, 1H), 8.30 (d, 1H), 8.05 (d, 1H), 7.60 (m, 2H), 7.20 (m, 3H), 7.10 (d, 2H), 6.80 (m, 2H), 6.65 (d, 1H), 3.45-3.90 (bm, 4H), 3.10 (bm, 4H), 2.45 (s, 3H); HPLC purity 99.98%: MS, m/z found 519.30 $(M+1)^+$.

N-(4-(4-(3-(trifluoromethyl)phenyl)piperazine-1carbonyl)phenyl)quinoline-8-sulfonamide (92j)

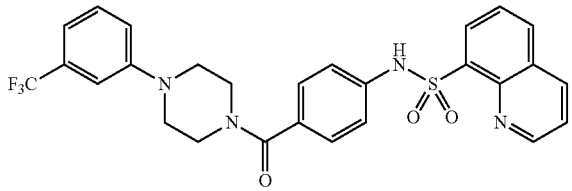

$^1$H NMR (400 MHz, $CDCl_3$) δ: 9.15 (d, 1H), 8.60 (s, 1H), 8.35 (d, 1H), 8.30 (d, 1H), 8.05 (d, 1H), 7.60 (m, 2H), 7.50 (d, 2H), 7.20 (m, 2H), 7.10 (d, 2H), 6.90 (d, 2H), 3.45-3.90 (bm, 4H), 3.10 (bm, 4H); HPLC purity 99.63%: MS, m/z found 541.25 $(M+1)^+$.

N-(4-(4-(2-(trifluoromethoxy)phenyl)piperazine-1-carbonyl)phenyl)quinoline-8-sulfon-amide (92k)

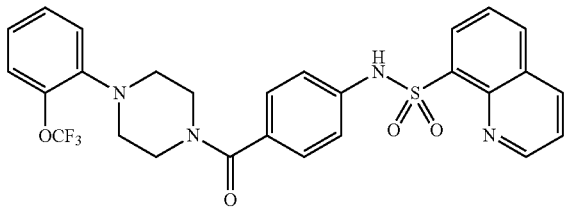

$^1$H NMR (400 MHz, $CDCl_3$) δ: 9.15 (d, 1H), 8.55 (s, 1H), 8.35 (d, 1H), 8.30 (d, 1H), 8.05 (d, 1H), 7.60 (m, 2H), 7.20 (m, 4H), 6.95-7.15 (m, 4H), 3.45-3.90 (bm, 4H), 3.10 (bm, 4H); HPLC purity 99.89%: MS, m/z found 557.35 $(M+1)^+$.

N-(4-(4-(4-(ethylthio)phenyl)piperazine-1-carbonyl) phenyl)quinoline-8-sulfonamide (92l)

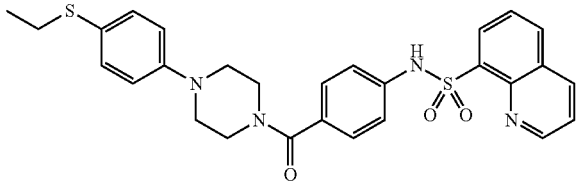

$^1$H NMR (400 MHz, $CDCl_3$) δ: 9.15 (d, 1H), 8.55 (s, 1H), 8.35 (d, 1H), 8.30 (d, 1H), 8.05 (d, 1H), 7.60 (m, 2H), 7.3 (d, 2H), 7.20 (d, 2H), 7.10 (d, 2H), 6.80 (d, 2H), 3.45-3.90 (bm, 4H), 3.10 (bm, 4H), 2.90 (q, 2H), 1.15 (t, 3H); HPLC purity 98.53%: MS, m/z found 533.35 $(M+1)^+$.

N-(4-(4-(4-(methylthio)phenyl)piperazine-1-carbonyl)phenyl)quinoline-8-sulfonamide (92m)

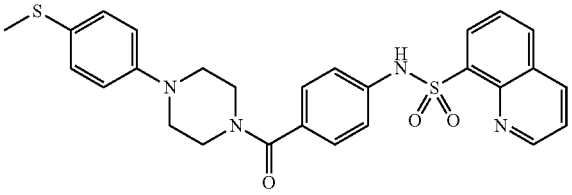

$^1$H NMR (400 MHz, DMSO-$d_6$) δ: 10.40 (s, 1H), 9.15 (s, 1H), 8.50 (d, 1H), 8.40 (d, 1H), 8.30 (d, 1H), 7.70 (m, 2H), 7.20 (m, 6H), 6.85 (d, 2H), 3.20-3.70 (bm, 4H), 3.05 (bm, 4H), 2.35 (s, 3H); HPLC purity 91.00%: MS, m/z found 518.50 $(M+1)^+$.

N-(4-(4-(3-(methoxy)phenyl)piperazine-1-carbonyl) phenyl)quinoline-8-sulfonamide (92n)

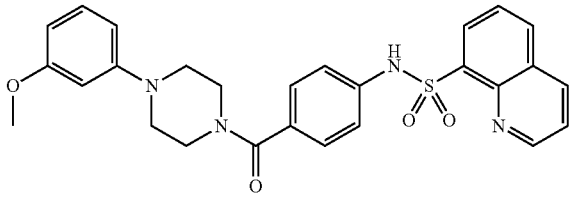

$^1$H NMR (400 MHz, DMSO-$d_6$) δ: 10.45 (s, 1H), 9.05 (d, 1H), 8.50 (d, 1H), 8.45 (d, 1H), 8.30 (d, 1H), 7.70 (m, 2H), 7.00-7.20 (m, 5H), 6.50 (d, 1H), 6.40 (s, 1H), 6.35 (d, 1H), 3.65 (s, 3H), 3.20-3.70 (bm, 4H), 3.05 (bm, 4H); LCMS purity 100.00%: MS, m/z found 503.35 $(M+1)^+$.

N-(4-(4-(3-(chloro)phenyl)piperazine-1-carbonyl) phenyl)quinoline-8-sulfonamide (92o)

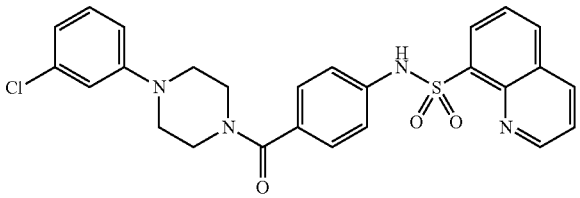

$^1$H NMR (400 MHz, $CDCl_3$) δ: 9.15 (s, 1H), 8.60 (s, 1H), 8.35 (d, 1H), 8.30 (d, 1H), 8.05 (d, 1H), 7.60 (m, 2H), 7.10-7.20 (m, 5H), 6.85 (m, 2H), 6.75 (d, 1H), 3.40-3.85 (bm, 4H), 3.10 (bm, 4H); LCMS purity 97.15%: MS, m/z found 507.30 $(M+1)^+$.

N-(4-(4-(3-(methyl)-5-(trifluoromethyl)phenyl)piperazine-1-carbonyl)phenyl)quinoline-8-sulfonamide (92p)

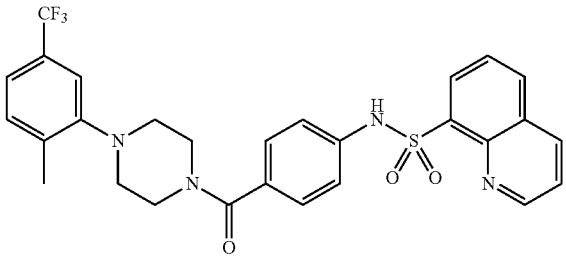

$^1$H NMR (400 MHz, $CDCl_3$) δ: 9.15 (d, 1H), 8.55 (s, 1H), 8.35 (d, 1H), 8.30 (d, 1H), 8.05 (d, 1H), 7.60 (m, 2H), 7.20-7.30 (m, 4H), 7.15 (s, 1H), 7.10 (d, 2H), 3.40-3.85 (bm, 4H), 2.85 (bm, 4H), 2.35 (s, 3H); LCMS purity 99.65%: MS, m/z found 555.35 $(M+1)^+$.

N-(4-(4-(3,4-(dichloro)phenyl)piperazine-1-carbonyl)phenyl)quinoline-8-sulfonamide (92q)

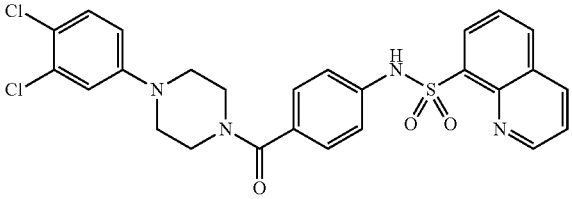

$^1$H NMR (400 MHz, DMSO-$d_6$) δ: 10.45 (s, 1H), 9.15 (s, 1H), 8.50 (d, 1H), 8.40 (d, 1H), 8.30 (d, 1H), 7.75 (m, 2H), 7.4 (d, 1H), 7.10-7.20 (m, 5H), 6.90 (d, 1H), 3.20-3.65 (bm, 4H), 3.10 (bs, 4H); HPLC purity 93.48%: MS, m/z found 542.35 $(M+1)^+$.

N-(4-(4-(3-(trifluoromethoxy)phenyl)piperazine-1-carbonyl)phenyl)quinoline-8-sulfon-amide (92r)

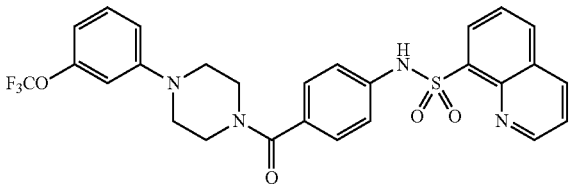

$^1$H NMR (400 MHz, $CDCl_3$) δ: 9.15 (d, 1H), 8.55 (s, 1H), 8.35 (d, 1H), 8.30 (d, 1H), 8.05 (d, 1H), 7.60 (m, 2H), 7.20 (d, 2H), 7.10 (m, 4H), 6.85 (d, 2H), 3.40-3.90 (bm, 4H), 3.10 (bs, 4H); HPLC purity 90.37%: MS, m/z found 557.50 $(M+1)^+$.

N-(4-(4-(4-(N,N-diethylamino)phenyl)piperazine-1-carbonyl)phenyl)quinoline-8-sulfon-amide (92s)

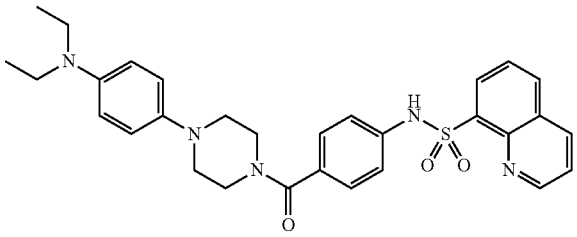

$^1$H NMR (400 MHz, $CDCl_3$) δ: 9.15 (d, 1H), 8.55 (s, 1H), 8.35 (d, 1H), 8.30 (d, 1H), 8.05 (d, 1H), 7.60 (m, 2H), 7.20 (d, 2H), 7.10 (d, 2H), 6.85 (d, 2H), 6.65 (d, 2H), 3.40-3.90 (bm, 4H), 3.3 (q, 4H), 2.80-3.10 (bm, 4H), 1.1 (t, 6H); HPLC purity 97.59%: MS, m/z found 544.50 $(M+1)^+$.

N-(4-(4-(3,4-(difluoro)phenyl)piperazine-1-carbonyl)phenyl)quinoline-8-sulfonamide (92t)

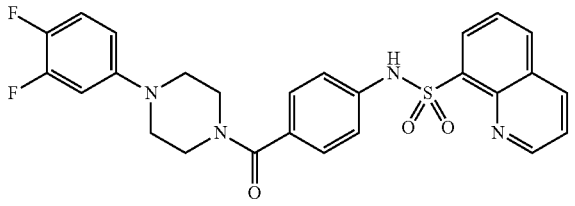

$^1$H NMR (400 MHz, $CDCl_3$) δ: 9.15 (d, 1H), 8.55 (s, 1H), 8.35 (d, 1H), 8.30 (d, 1H), 8.05 (d, 1H), 7.60 (m, 2H), 7.20 (d, 2H), 7.10 (d, 2H), 7.05 (m, 1H), 6.65 (m, 1H), 6.55 (d, 1H), 3.40-3.90 (bm, 4H), 3.00 (bs, 4H); HPLC purity 99.73%: MS, m/z found 509.55 $(M+1)^+$.

N-(4-(4-(4-(fluoro)phenyl)piperazine-1-carbonyl)phenyl)quinoline-8-sulfonamide (92u)

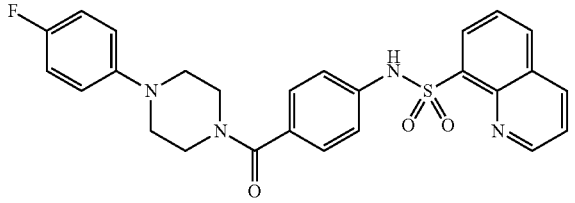

$^1$H NMR (400 MHz, $CDCl_3$) δ: 9.15 (d, 1H), 8.55 (s, 1H), 8.35 (d, 1H), 8.30 (d, 1H), 8.05 (d, 1H), 7.60 (m, 2H), 7.20 (d, 2H), 7.10 (d, 2H), 6.95 (m, 2H), 6.85 (m, 2H), 3.40-3.90 (bm, 4H), 3.00 (bs, 4H); HPLC purity 97.39%: MS, m/z found 491.25 $(M+1)^+$.

N-(4-(4-(2-(ethyl)phenyl)piperazine-1-carbonyl)phenyl)quinoline-8-sulfonamide (92v)

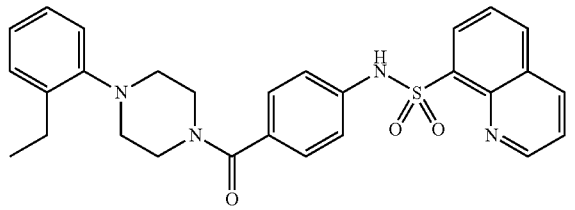

$^1$H NMR (400 MHz, $CDCl_3$) δ8: 9.15 (d, 1H), 8.55 (s, 1H), 8.35 (d, 1H), 8.30 (d, 1H), 8.05 (d, 1H), 7.60 (m, 2H), 7.05-7.30 (m, 7H), 7.00 (d, 1H), 3.40-3.90 (bm, 4H), 2.80 (bm, 4H), 2.7 (q, 2H), 1.20 (t, 3H); HPLC purity 98.85%: MS, m/z found 501.05 $(M+1)^+$.

N-(4-(4-(4-(chloro)phenyl)piperazine-1-carbonyl)phenyl)quinoline-8-sulfonamide (92w)

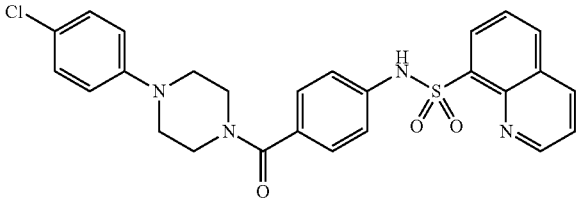

$^1$H NMR (400 MHz, $CDCl_3$) δ: 9.15 (d, 1H), 8.55 (s, 1H), 8.35 (d, 1H), 8.30 (d, 1H), 8.05 (d, 1H), 7.60 (m, 2H), 7.20 (m, 4H), 7.10 (d, 2H), 6.80 (d, 2H), 3.40-3.90 (bm, 4H), 3.10 (bm, 4H); LCMS purity 99.88%: MS, m/z found 507.25 $(M+1)^+$.

N-(4-(4-(3-(ethyl)phenyl)piperazine-1-carbonyl)phenyl)quinoline-8-sulfonamide (92x)

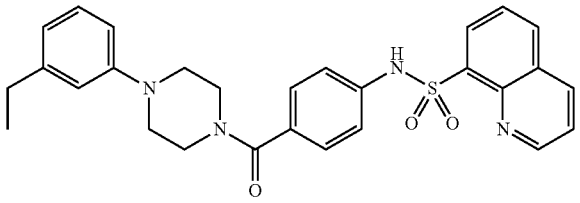

$^1$H NMR (400 MHz, $CDCl_3$) δ: 9.15 (d, 1H), 8.55 (s, 1H), 8.35 (d, 1H), 8.30 (d, 1H), 8.05 (d, 1H), 7.60 (m, 2H), 7.20 (m, 3H), 7.10 (d, 2H), 6.75 (m, 3H), 3.40-3.90 (bm, 4H), 3.10 (bm, 4H), 2.6 (q, 2H), 1.2 (t, 3H); LCMS purity 96.79%: MS, m/z found 501.30 $(M+1)^+$.

N-(4-(4-(3-(trifluoromethyl)phenyl)piperazine-1-carbonyl)phenyl)quinoline-8-sulfonamide (92y)

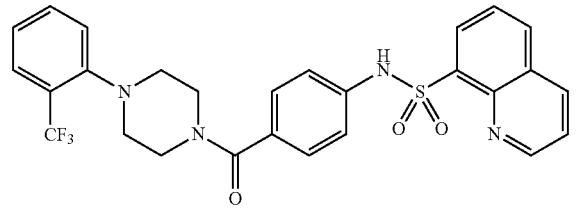

$^1$H NMR (400 MHz, $CDCl_3$) δ: 9.15 (d, 1H), 8.55 (s, 1H), 8.35 (d, 1H), 8.30 (d, 1H), 8.05 (d, 1H), 7.60 (m, 2H), 7.50 (m, 2H), 7.25 (m, 2H), 7.20 (m, 2H), 7.10 (d, 2H) 3.40-3.90 (bm, 4H), 2.90 (bm, 4H); HPLC purity 99.65%: MS, m/z found 541.15 $(M+1)^+$.

N-(4-(4-(2-methoxyphenyl)piperazine-1-carbonyl)phenyl)-N-methylquinoline-8-sulfo-namide (92z)

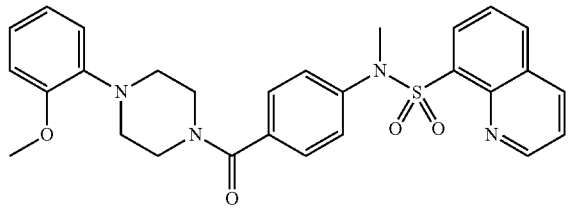

hu 1H NMR (500 MHz, DMSO-$d_6$) δ: 9.05 (s, 1H), 8.55 (m, 1H), 8.3 (m, 2H), 7.7 (m, 2H), 7.25 (m, 4H), 6.95 (m, 2H), 6.85 (m, 2H), 3.78 (s, 3H), 3.6 (s, 3H), 3.30-3.80 (bm, 4H), 2.80-3.00 (bm, 4H); HPLC purity 97.68%: MS, m/z found 517.3 $(M+1)^+$.

Ethyl 2-(4-(4-(N-methylquinoline-8-sulfonamido)benzoyl)piperazin-1-yl)benzoate (92aa)

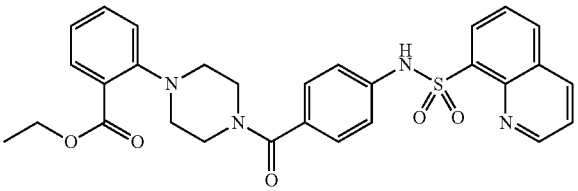

$^1$H NMR (400 MHz, DMSO-$d_6$) δ: 10.43 (s, 1H), 9.18 (s, 1H), 8.55 (d, 1H), 8.41 (d, 1H), 8.23 (d, 1H), 7.7 (m, 2H), 7.55 (m, 1H), 7.41 (m, 1H), 7.25 (m, 6H), 4.22 (q, 2H), 3.30-3.80 (bm, 4H), 2.80-3.00 (bm, 4H), 1.25 (t, 3H); LCMS purity 97.43%: MS, m/z found 545.1 $(M+1)^+$, 567.1 (M+23).

N-(4-(4-(3-(dimethylamino)phenyl)piperazine-1-carbonyl)phenyl)quinoline-8-sulfonamide (92ab)

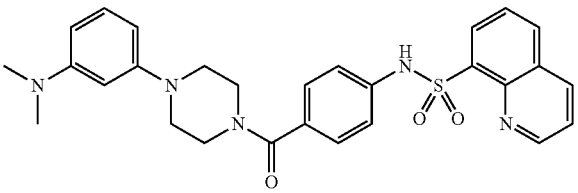

$^1$H NMR (400 MHz, DMSO-$d_6$) δ: 9.11-9.16 (d, 1H), 8.54 (bs, 1H), 8.22-8.55 (d, 2H), 8.02-8.06 (d, 1H), 7.55-7.64 (m, 2H), 7.02-7.32 (m, 6H), 6.20-6.54 (m, 2H), 3.20-3.94 (m, 4H), 3.00-3.22 (bs, 4H), 2.84-2.94 (s, 6H); LCMS purity 98.33%: MS, m/z found 516.3 $(M+1)^+$, 538.3 (M+23).

N-(4-(4-(3-fluorophenyl)piperazine-1-carbonyl)phenyl)quinoline-8-sulfonamide (92ac)

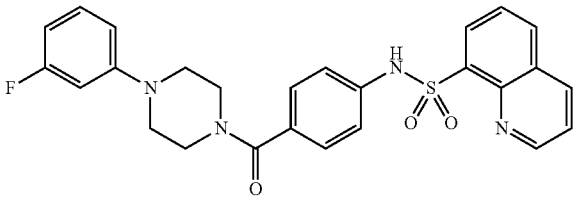

$^1$H NMR (400 MHz, DMSO-$d_6$) δ: 9.10-9.15 (d, 1H), 8.22-8.40 (m, 2H), 7.98-8.11 (d, 1H), 7.52-7.66 (m, 2H), 7.02-7.28 (m, 6H), 6.42-6.64 (m, 3H), 3.42-3.84 (bd, 4H), 3.00-3.22 (m, 4H); LCMS purity 93.74%: MS, m/z found 491.3 $(M+1)^+$.

N-(4-(4-(5-isopropyl-2-methylphenyl)piperazine-1-carbonyl)phenyl)quinoline-8-sulfona-mide (92ad)

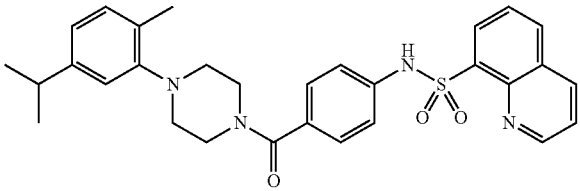

$^1$H NMR (400 MHz, DMSO-$d_6$) δ: 9.18 (d, 1H), 8.54 (bs, 1H), 8.24-8.38 (dd, 2H), 8.00-8.15 (d, 1H), 7.54-7.66 (m, 2H), 7.18-7.26 (m, 2H), 7.02-7.14 (m, 3H), 6.86-6.94 (m, 2H), 3.42-3.92 (bd, 4H), 2.80-2.98 (m, 2H), 2.22 (s, 3H), 1.14-1.24 (d, 6H), 0.80-0.92 (m, 1H); HPLC purity 98.76%:

N-(4-(4-(4-(trifluoromethoxy)phenyl)piperazine-1-carbonyl)phenyl)quinoline-8-sulfona-mide (92ae)

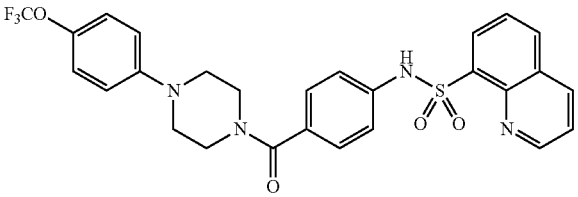

$^1$H NMR (400 MHz, DMSO-$d_6$) δ: 9.18 (d, 1H), 8.58 (bs, 1H), 8.23-8.38 (dd, 2H), 8.00-8.15 (d, 1H), 7.52-7.68 (m, 2H), 7.14-7.24 (m, 6H), 6.80-6.89 (d, 2H), 3.42-3.92 (bd, 4H), 3.00-3.18 (bs, 4H); HPLC purity 98.77%:

N-(4-(4-(4-methoxyphenyl)piperazine-1-carbonyl)phenyl)quinoline-8-sulfonamide (92af)

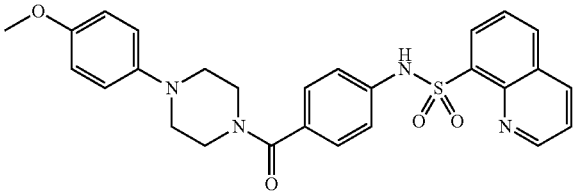

$^1$H NMR (400 MHz, DMSO-$d_6$) δ: 10.41 (s, 1H), 9.17 (s, 1H), 8.21-8.45 (ddd, 3H), 7.63-7.78 (m, 2H), 7.12-7.24 (m, 4H), 6.78-6.94 (d, 4H), 3.82 (s, 3H), 3.22-3.54 (m, 4H), 2.84-3.08 (m, 4H); LCMS purity=93.70%: MS, m/z found 503.1 $(M+1)^+$.

5-(4-(4-(quinoline-8-sulfonamido)benzoyl)piperazin-1-yl)pyridin-3-yl propionate (92ag)

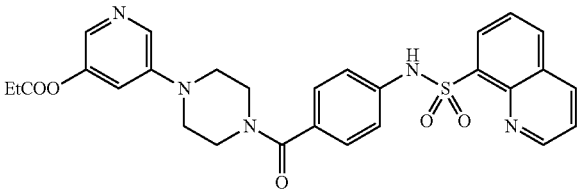

$^1$H NMR (400 MHz, $CDCl_3$) δ: 10.42 (s, 1H), 9.15 (s, 1H), 8.40-8.54 (dt, 2H), 8.24-8.28 (d, 1H), 7.60-7.72 (m, 3H), 7.05-7.22 (m, 4H), 4.21-4.38 (q, 2H), 3.3-3.8 (m, 8H), 1.25 (t, 3H); LCMS purity: 98.85%; MS, m/z found 546.3 $(M+1)^+$.

N-(4-(4-(thiazol-2-yl)piperazine-1-carbonyl)phenyl)quinoline-8-sulfonamide (92ah)

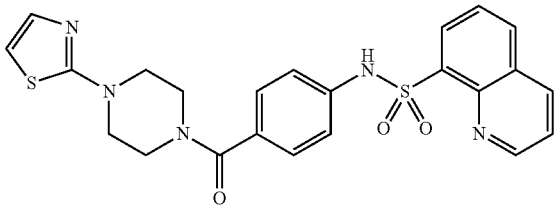

[$^1$H NMR (400 MHz, $CDCl_3$) δ: 9.15 (d, 1H), 8.40 (d, 1H), 8.30 (d, 1H), 8.05 (d, 1H), 7.60 (m, 2H), 7.35 (d, 1H), 7.20 (d, 2H), 7.10 (d, 2H), 6.7 (d, 1H), 3.3-3.8 (m, 8H);] HPLC purity: 99.79%; MS, m/z found 480.2 $(M+1)^+$.

N-(4-(4-(2-methylthiazol-5-yl)piperazine-1-carbonyl)phenyl)quinoline-8-sulfonamide (92ai)

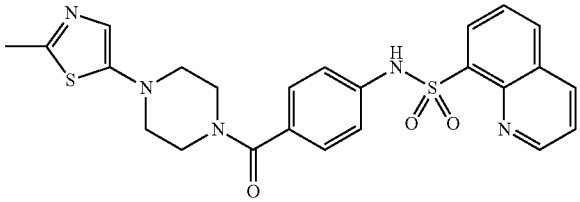

$^1$H NMR (400 MHz, $CDCl_3$) δ: 10.42 (s, 1H), 9.15 (d, 1H), 8.45 (d, 1H), 8.40 (d, 1H), 8.15 (d, 1H), 7.70 (m, 2H), 7.20 (d, 2H), 7.15 (d, 2H), 6.8 (s, 1H), 3.5 (bm, 4H), 2.95 (bm, 4H), 2.4 (s, 3H); HPLC purity: 95.78%; MS, m/z found 494.3 $(M+1)^+$.

N-(4-(4-(pyrazin-2-yl)piperazine-1-carbonyl)phenyl)quinoline-8-sulfonamide (92aj)

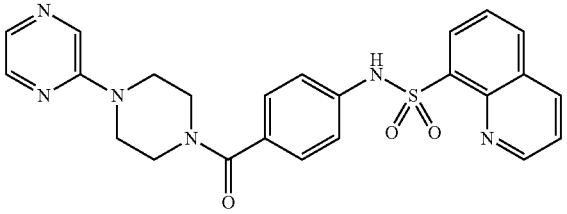

$^1$H NMR (500 MHz, DMSO-$d_6$) δ: 10.42 (s, 1H), 9.15 (s, 1H), 8.52 (d, 1H), 8.44 (d, 1H), 8.3 (m, 2H), 8.1 (s, 1H), 7.86 (s, 1H), 7.74 (m, 2H), 7.23 (d, 2H), 7.14 (d, 2H), 3.3-3.7 (m, 8H); HPLC purity: 98.10%; MS, m/z found 475.2 $(M+1)^+$.

N-(4-(4-(pyrimidin-2-yl)piperazine-1-carbonyl)phenyl)quinoline-8-sulfonamide (92ak)

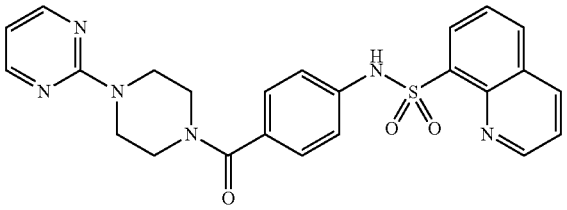

$^1$H NMR (500 MHz, DMSO-$d_6$) δ: 10.42 (s, 1H), 9.15 (s, 1H), 8.52 (d, 1H), 8.45 (d, 1H), 8.35 (d, 2H), 8.30 (d, 1H), 7.75 (m, 2H), 7.20 (d, 2H), 7.15 (d, 2H), 7.80 (t, 1H), 3.3-3.8 (m, 8H); HPLC purity: 99.52%; MS, m/z found 475.2 $(M+1)^+$.

N-(4-(4-(2-methoxypyridin-3-yl)piperazine-1-carbonyl)phenyl)quinoline-8-sulfonamide (92a1)

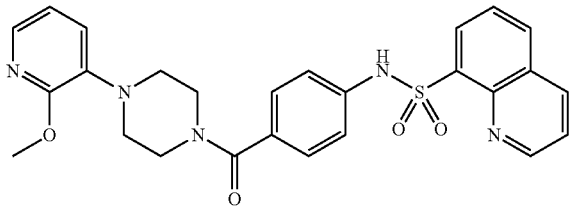

$^1$H NMR (500 MHz, DMSO-$d_6$) 2.80-3.00 (4H, m), 3.40-3.85 (4H, m), 3.85 (3H, s), 6.91(1H, m), 7.11-7.20 (5H, m), 7.70-7.75 (3H, m), 8.27-8.29 (1H, m), 8.41-8.53 (2H, m), 9.12 (1H, m), 10.44 (1H, s). MS 504.1 $(M+1)^+$.

N-4-(4-(4-methoxypyridin-3-yl)piperazine-1-carbonyl)phenyl)quinoline-8-sulfonamide (92 am)

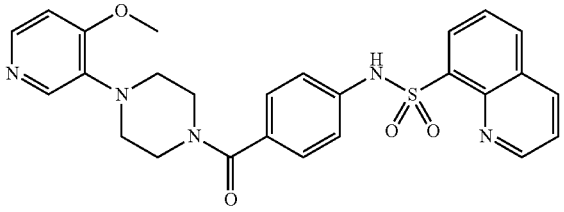

$^1$H NMR (400 MHz, $CDCl_3$) δ: 9.18 (d, 1H), 8.60 (bs, 1H), 8.25-8.40 (m, 3H), 8.05 (d, 1H), 7.65 (m, 2H), 7.20 (d, 2H), 7.15 (d, 2H), 7.10 (d, 1H), 4.10 (s, 3H), 3.40-3.80 (bm, 4H), 3.10 (bm, 4H); HPLC purity: 97.14%; LCMS, m/z found 504.35 $(M+1)^+$.

N-(4-(4-(5-(ethoxycarbonyl)pyridin-3-yl)piperazine-1-carbonyl)phenyl)quinoline-8-sulfon-amide (92an)

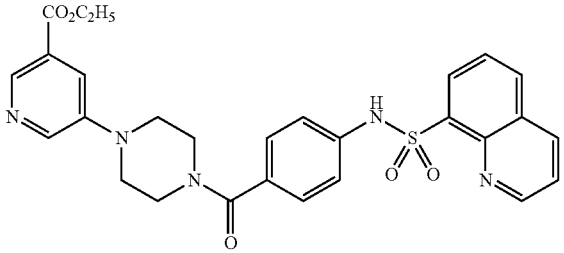

$^1$H NMR (400 MHz, DMSO-$d_6$) δ: 10.45 (s, 1H), 9.15 (d, 1H), 8.55 (m, 3H), 8.45 (d, 1H), 8.30 (d, 1H), 7.70 (m, 2H), 7.65 (s, 1H), 7.20 (d, 2H), 7.10 (d, 2H), 4.30 (q, 2H), 3.4-3.8 (bm, 4H), 3.1 (bm, 4H), 1.3 (t, 3H); LCMS purity: 98.85%; MS, m/z found 546.35 $(M+1)^+$.

N-(4-(4-(5-(methoxycarbonyl)-6-methoxy)pyridin-3-yl)piperazine-1-carbonyl)phenyl) quinoline-8-sulfonamide (92ao)

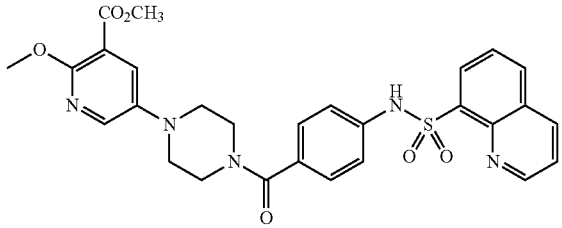

$^1$H NMR (400 MHz, $CDCl_3$) δ: 9.18 (d, 1H), 8.60 (bs, 1H), 8.35 (d, 1H), 8.30 (d, 1H), 8.05 (d, 1H), 7.95 (d, 1H), 7.80 (d, 1H), 7.60 (m, 2H), 7.20 (d, 2H), 7.10 (d, 2H), 4.00 (s, 3H), 3.9 (s, 3H), 3.4-3.8 (bm, 4H), 3.1 (bm, 4H); HPLC purity: 94.72%; MS, m/z found 562.18 $(M+1)^+$.

N-(4-(4-(pyridin-4-yl)piperazine-1-carbonyl)phenyl) quinoline-8-sulfonamide (92ap)

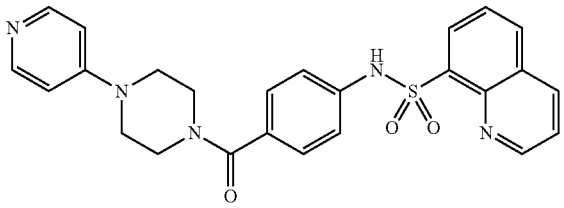

[$^1$H NMR (400 MHz, $CDCl_3$) δ: 9.2 (s, 1H), 8.22-8.40 (m, 4H), 8.00-8.04 (m, 1H), 7.54-7.62 (m, 2H), 7.05-7.22 (dd, 4H), 6.60-6.68 (d, 1H), 3.2-3.8 (m, 8H);] LCMS purity: 97.37%; LCMS, m/z found 474.05 $(M+1)^+$.

N-(4-(4-(3-methoxypyridin-2-yl)piperazine-1-carbonyl)phenyl)quinoline-8-sulfonamide (92aq)

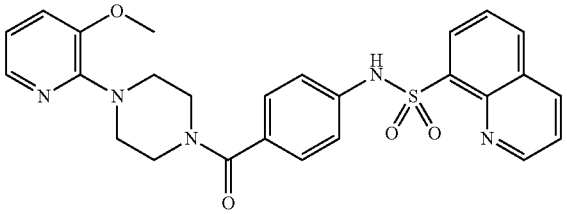

$^1$H NMR (400 MHz, $CDCl_3$) δ: 10.22 (s, 1H), 9.14 (d, 1H), 8.22-8.50 (ddd, 3H), 7.62-7.78 (m, 3H), 7.11-7.22 (m, 5H), 6.82-6.86 (d, 1H), 3.7 (s, 3H), 3.2-3.8 (m, 8H); LCMS purity: 97.96%; LCMS, m/z found 504.3 $(M+1)^+$.

N-(4-(4-(2-methoxypyridin-3-yl)piperazine-1-carbonyl)phenyl)quinoline-8-sulfonamide (92ar)

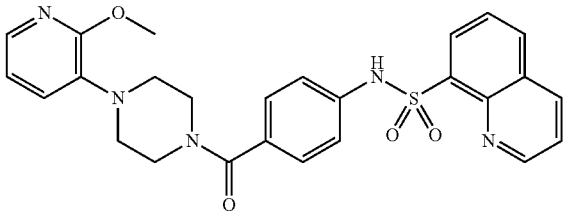

$^1$H NMR (400 MHz, $CDCl_3$) δ: 10.21 (s, 1H), 9.12-9.13 (d, 1H), 8.27-8.53 (ddd, 3H), 7.70-7.75 (m, 3H), 7.13-7.20 (m, 5H), 6.87-6.90 (dd, 1H), 3.85 (s, 3H), 3.29-3.50 (m, 4H), 2.92 (bm, 4H); LCMS purity 97.11%; LCMS, m/z found 504.3 $(M+1)^+$.

N-(4-(4-(isoquinolin-4-yl)piperazine-1-carbonyl)phenyl)quinoline-8-sulfonamide (92 as)

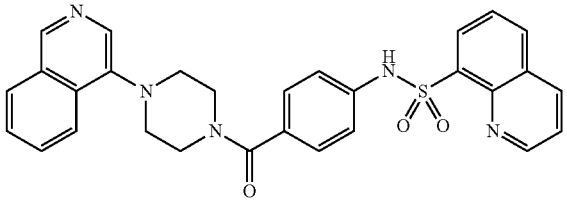

$^1$H NMR (400 MHz, DMSO-$d_6$) δ: 9.18 (d, 1H), 9.01 (s, 1H), 8.52-8.58 (s, 1H), 8.25-8.41 (dd, 2H), 7.98-8.18 (m, 4H), 7.54-7.78 (m, 4H), 7.22-7.28 (d, 2H), 7.02-7.16 (d, 2H), 3.82-3.98 (m, 4H), 2.94-3.22 (bs, 4H); HPLC purity 94.23%; MS m/z found 524.25 $(M+1)^+$.

Sodium (4-(4-(2-methoxyphenyl)piperazine-1-carbonyl)phenyl)(quinolin-8-ylsulfonyl) amide (92 at)

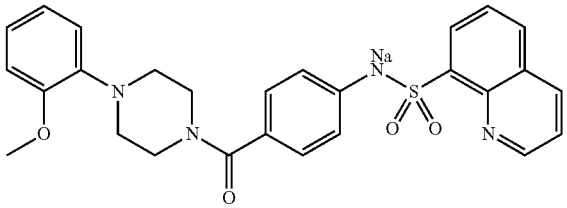

$^1$H NMR (400 MHz, DMSO-$d_6$) δ: 9.00 (s, 1H), 8.40 (m, 2H), 8.00 (d, 1H), 7.60 (m, 2H), 6.90-7.00 (m, 4H), 6.80 (m, 4H), 3.75 (s, 3H), 3.55 (bs, 4H), 2.90 (bs, 4H); LCMS purity: 95.17%; MS, m/z found 503.25 $(M+1)^+$.

Sodium (4-(4-(pyrazin-2-yl)piperazine-1-carbonyl)phenyl)(quinolin-8-ylsulfonyl)amide (92au)

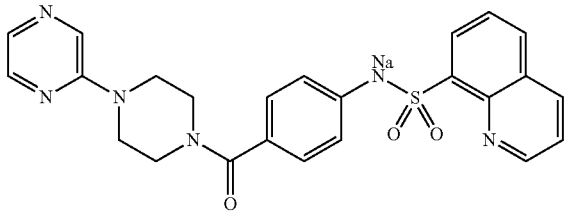

$^1$H NMR (400 MHz, DMSO-$d_6$) δ: 9.05 (s, 1H), 8.40 (m, 2H), 8.30 (s, 1H), 8.10 (m, 2H), 7.85 (s, 1H), 7.60 (m, 2H), 7.05 (d, 2H), 6.85 (d, 2H), 3.50 (bs, 8H); LCMS purity: 98.60%; MS, m/z found 475.15 $(M-Na+1)^+$.

N-(4-(4-(pyrazin-2-yl)piperazine-1-carbonyl)phenyl)quinoline-8-sulfonamide methane-sulfonate (92av)

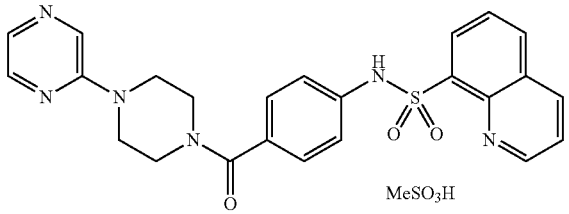

$^1$H NMR (400 MHz, DMSO-$d_6$) δ: 10.45 (s, 1H), 9.05 (d, 1H), 8.52 (d, 1H), 8.40 (d, 1H), 8.30 (m, 2H), 8.10 (s, 1H), 7.85 (s, 1H), 7.70 (m, 2H), 7.20 (d, 2H), 7.10 (d, 2H), 3.50 (bm, 8H), 2.4 (s, 3H); LCMS purity: 98.41%; MS, m/z found 475.15 $(M-MsSO_3H+1)^+$.

Synthesis of N4-Aryl/Heteroaryl Piperazine Analogues with Substituted Phenyl Central Ring Scheme 13

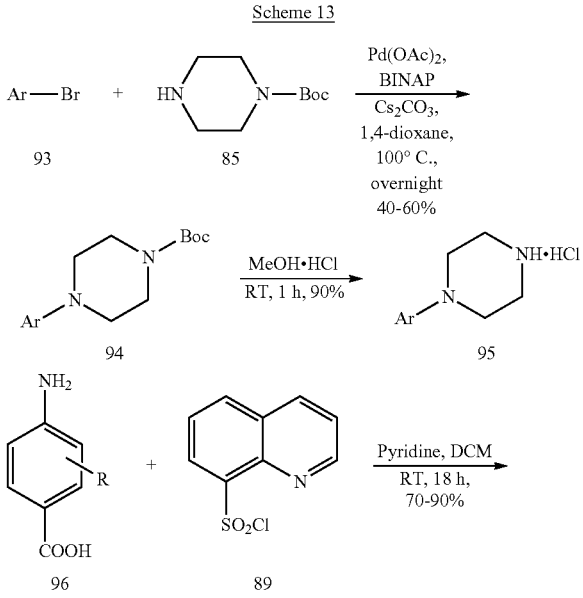

-continued

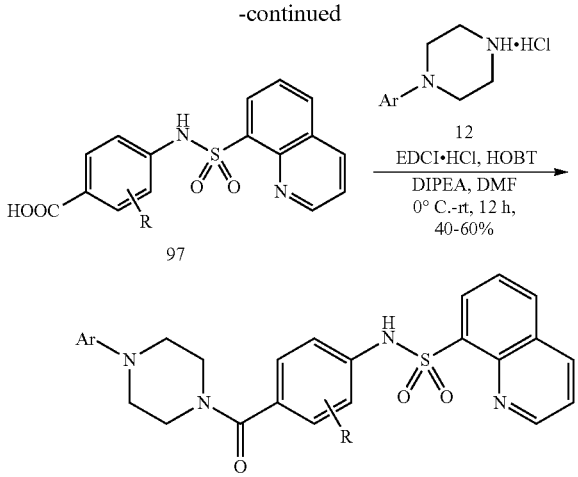

Where Ar = Substituted Aryl and Heteroaryl
R = Me, OH, OMe, Cl, F

General Procedure for Compound 94:

Nitrogen was purged through a stirred solution of arylbromide (93, 2.15 mmol) in 1,4-dioxane (20 ml) at room temperature for 30 min BINAP (0.134 g, 0.215 mmol), palladium acetate (0.0096 g, 0.043 mmol) and cesium carbonate (1.40 g, 4.3 mmol) were added to the reaction mixture and the nitrogen purging was continued for another 20 min and finally N-Boc piperazine (85, 0.4 g, 2.15 mmol) was added and stirred at 100° C. overnight under nitrogen atmosphere. After completion of the reaction (monitored by TLC), the reaction mixture was concentrated under vacuum. The residue was dissolved in water, extracted with ethyl acetate (3×50 ml). Combined organic extracts were washed with brine (20 ml), dried over anhydrous Sodium sulfate, filtered and concentrated under reduced pressure. The crude product was then purified by column chromatography (60-120 silica gel) using 10% ethyl acetate-hexane to yield compound (94) (40-60%).

General Procedure for Compound (95):

$N^1$-Boc-$N^4$-arylpiperazine (94, 1.075 mmol) was taken into a round bottomed flask and was added methanolic-HCl (20 ml, 20%) which resulted in formation of a homogeneous solution and was stirred for 1 h at room temperature. After completion of the reaction (monitored by TLC), the solvent was removed under vacuum. The crude product was washed with ethyl acetate repeatedly and then dried well to obtain hydrochloride salt (95) (90%) as a white solid.

General Procedure for Compound 97:

To a solution of amine (96, 30.16 mmol) in a 1:1 mixture of DCM-pyridine (50:50 ml) was added quinoline-8-sulfonyl chloride (89, 8.24 g, 36.19 mmol) under nitrogen atmosphere. The resultant solution was stirred overnight at room temperature. On completion of the reaction (monitored by TLC), the reaction mixture was diluted with dichloromethane (150 ml), washed with water (3×50 ml), 1N HCl solution (3×50 ml) and brine (50 ml. The combined organic extracts were dried over anhydrous sodium sulfate, filtered and concentrated under vacuum. Crude product was co-distilled with toluene to remove the remnants of pyridine and dried to yield sulfonamide (97) (70-90%) as an off-white solid and was used as such for the next step without further purification.

General Procedure for Compounds 98a-1:

To a stirred solution of the carboxylic acid (97, 0.61 mmol) in DMF at 0° C. under nitrogen atmosphere, EDCI (0.129 gm, 0.671 mmol), HOBt (0.91 gm, 0.671 mmol) and DIPEA (0.31 ml, 1.83 mmol) were added and the resultant solution was stirred at room temperature for 30 min Amine hydrochloride (95, 0.61 mmol) was then added at 0° C. and stirred overnight at room temperature. After completion of the reaction (monitored by TLC), the reaction mixture was poured into 1.0 M HCl and extracted with EtOAc. The organic layer was washed with saturated $NaHCO_3$ solution, dried over $NaSO_4$ and filtered. The solvent was removed by rotary evaporation and the product was isolated by chromatography on silica gel (60-120 silica gel, 2% MeOH-DCM) or preparative HPLC to yield amide (98a-1) (40-60%) as an off-white solid.

N-(4-(4-(2-methoxyphenyl)piperazine-1-carbonyl)-2-methoxyphenyl)quinoline-8-sulfona-mide (98a)

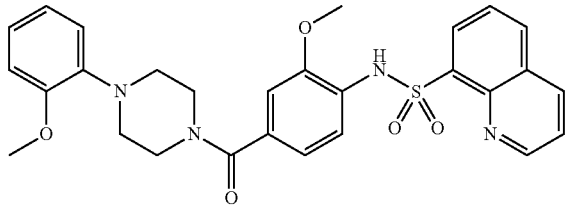

$^1$H NMR (400 MHz, DMSO-$d_6$) δ: 10.30 (s, 1H), 9.10 (d, 1H), 8.52 (d, 1H), 8.45 (d, 1H), 8.30 (d, 1H), 7.72 (m, 2H), 6.95 (m, 5H), 6.80 (s, 1H), 6.65 (d, 1H), 3.80 (s, 3H), 3.65 (bs, 2H), 3.60 (s, 3H), 3.10 (bs, 2H), 2.95 (bs, 2H), 2.80 (bs, 2H); HPLC purity 99.73%; MS, m/z found 533.30 $(M+1)^+$.

N-(4-(4-(2-methoxyphenyl)piperazine-1-carbonyl)-3-chlorophenyl)quinoline-8-sulfona-mide (98b)

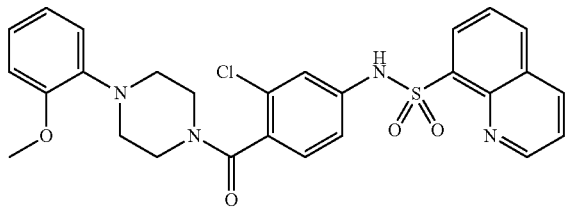

$^1$H NMR (400 MHz, DMSO-$d_6$) δ: 10.60 (s, 1H), 9.10 (d, 1H), 8.55 (d, 1H), 8.45 (d, 1H), 8.30 (d, 1H), 7.75 (m, 2H), 7.20 (m, 3H), 6.95 (m, 4H), 3.80 (s, 3H), 3.70 (bs, 2H), 3.10 (bs, 2H), 2.95 (bs, 2H), 2.80 (bs, 2H); HPLC purity 94.42%; MS, m/z found 537.25 $(M+1)^+$.

N-(4-(4-(2-methoxyphenyl)piperazine-1-carbonyl)-2-chlorophenyl)quinoline-8-sulfona-mide (98c)

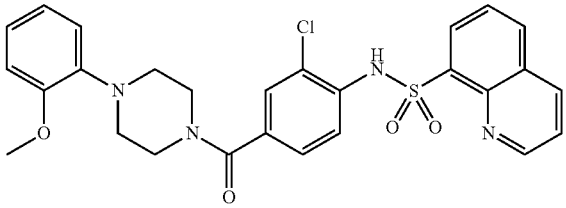

$^1$H NMR (400 MHz, DMSO-$d_6$) δ: 10.50 (bs, 1H), 9.10 (d, 1H), 8.58 (d, 1H), 8.35 (m, 2H), 7.75 (m, 2H), 7.50 (d, 1H), 7.40 (s, 1H), 7.30 (d, 1H), 6.95 (m, 3H), 6.85 (m, 1H), 3.80 (s, 3H), 3.30-3.75 (bm, 4H), 2.95 (bm, 4H); LCMS purity 97.99%; MS, m/z found 537.20 $(M+1)^+$.

N-(4-(4-(2-methoxyphenyl)piperazine-1-carbonyl)-2-methylphenyl)quinoline-8-sulfon-amide (98d)

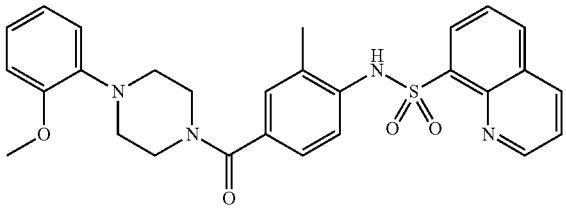

$^1$H NMR (400 MHz, DMSO-$d_6$) δ: 9.40 (s, 1H), 9.14 (d, 1H), 8.56 (d, 1H), 8.30 (d, 1H), 8.25 (d, 1H), 7.70 (m, 2H), 7.15 (s, 1H), 6.90-7.10 (m, 4H), 6.83 (m, 2H), 3.75 (s, 3H), 3.30-3.75 (bm, 4H), 2.95 (bm, 4H), 2.05 (s, 3H); HPLC purity 99.11%; MS, m/z found 517.14 $(M+1)^+$.

N-(4-(4-(2-methoxyphenyl)piperazine-1-carbonyl)-2-hydroxyphenyl)quinoline-8-sulfon-amide (98e)

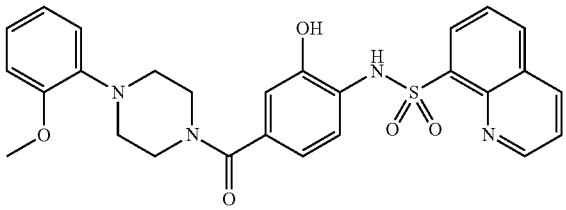

$^1$H NMR (400 MHz, DMSO-$d_6$) δ: 10.2 (s, 1H), 9.98 (s, 1H), 9.15 (d, 1H), 8.52 (d, 1H), 8.40 (d, 1H), 8.30 (d, 1H), 7.70 (m, 2H), 6.80-6.98 (m, 5H), 6.70 (s, 1H), 6.55 (d, 1H), 3.75 (s, 3H), 3.30-3.60 (bm, 4H), 2.85 (bm, 4H); HPLC purity 95.25%; MS, m/z found 519.14 $(M+1)^+$.

N-(4-(4-(2-methoxyphenyl)piperazine-1-carbonyl)-2-fluorophenyl)quinoline-8-sulfonamide (98f)

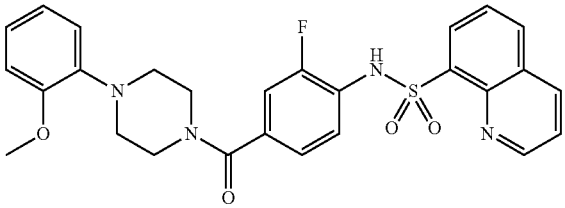

$^1$H NMR (400 MHz, $CDCl_3$) δ: 9.15 (d, 1H), 8.40 (d, 1H), 8.30 (d, 1H), 8.05 (d, 1H), 7.80 (t, 1H), 7.60 (m, 2H), 7.13-7.25 (m, 3H), 7.10 (d, 1H), 6.95 (m, 3H), 3.90 (s, 3H), 3.65-4.05 (bm, 4H), 3.30 (bm, 4H); LCMS purity 99.50%; MS, m/z found 521.10 $(M+1)^+$.

N-(4-(4-(2-methoxypyridin-3-yl)piperazine-1-carbonyl)-2-methylphenyl)quinoline-8-sulfo-namide (98g)

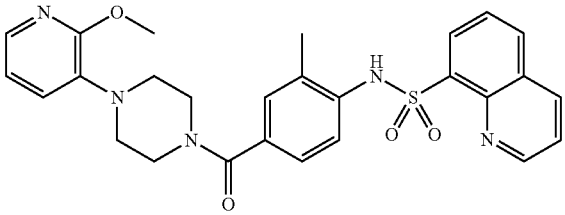

$^1$NH MR (400 MHz, DMSO-$d_6$) δ: 9.16 (s, 1H), 8.40-8.51 (d, 1H), 8.20-8.38 (m, 2H), 8.02-8.11 (d, 1H), 7.82-8.88 (d, 1H), 7.56-7.66 (m, 2H), 7.34-7.38 (m, 2H), 7.02-7.18 (d, 2H), 6.84-6.88 (d, 1H), 4.02 (s, 3H), 3.78-3.96 (bs, 2H), 3.58-3.62 (bs, 2H), 2.84-3.12 (bs, 4H), 2.22 (s, 3H); HPLC purity 90.41%; MS, m/z found 518.20 $(M+1)^+$.

N-(4-(4-(3-methoxypyridin-2-yl)piperazine-1-carbonyl)-2-methylphenyl)quinoline-8-sulfo-namide (98h)

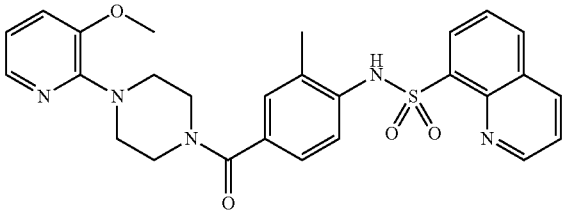

[$^1$H NMR (400 MHz, DMSO-$d_6$) δ: 9.16 (d, 1H), 8.40-8.51 (d, 1H), 8.23-8.31 (d, 1H), 8.19 (s, 1H), 8.02-8.11 (d, 1H), 7.82-8.84 (m, 1H), 7.52-7.64 (m, 2H), 7.28-7.32 (m, 1H), 7.11-7.18 (s, 1H), 6.98-7.02 (t, 1H), 6.82-6.88 (m, 1H), 3.88 (s, 3H), 3.78-3.84 (bs, 2H), 3.26-3.64 (bs, 6H), 2.24 (s, 3H);] LCMS purity 96.68%, LCMS, m/z found 518.2 $(M+1)^+$.

N-(2-fluoro-4-(4-(3-methoxypyridin-2-yl)piperazine-1-carbonyl)phenyl)quinoline-8-sulfon-amide (98i)

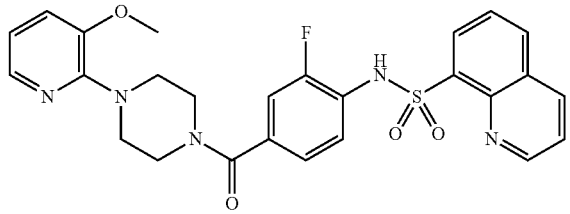

$^1$H NMR (400 MHz, DMSO-$d_6$) δ: 9.18 (d, 1H), 8.88 (s, 1H), 8.38-8.42 (d, 1H), 8.20-8.28 (m, 2H), 8.02-8.13 (d, 2H), 7.72-7.80 (t, 1H), 7.56-7.62 (m, 2H), 6.84-2.12 (dd, 2H), 6.70-6.78 (d, 1H), 3.92 (s, 3H), 3.48-3.82 (bs, 4H), 3.00-3.18 (bs, 4H); LCMS purity 96.76%, LCMS, m/z found 522.2 $(M+1)^+$.

N-(4-(4-(pyridin-4-yl)piperazine-1-carbonyl)-2-methylphenyl)quinoline-8-sulfonamide (98j)

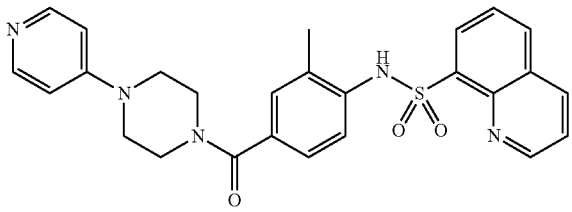

$^1$H NMR (400 MHz, $CDCl_3$) δ: 9.10 (d, 1H), 8.45 (d, 1H), 8.30 (m, 4H), 8.15 (d, 1H), 7.60 (m, 2H), 7.35 (d, 1H), 7.15 (d, 1H), 7.05 (d, 1H), 6.65 (d, 2H), 3.45-3.90 (bm, 4H), 3.30 (bm, 4H), 2.22 (s, 3H); LCMS purity 100.00%; MS, m/z found 488.30 $(M+1)^+$.

N-(4-(4-(2-methoxypyridin-3-yl)piperazine-1-carbonyl)-2-fluorophenyl)quinoline-8-sulfo-namide (98k)

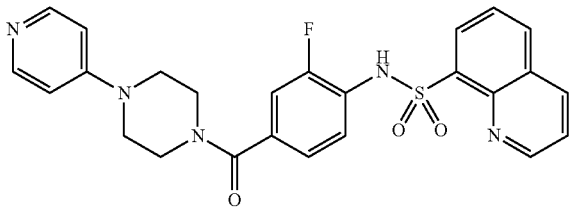

$^1$H NMR (400 MHz, $CDCl_3$) δ: 9.10 (d, 1H), 8.40 (d, 1H), 8.30 (m, 3H), 8.05 (d, 1H), 7.80 (m, 1H), 7.60 (m, 2H), 7.05 (d, 1H), 6.95 (d, 1H), 6.80 (d, 2H), 3.45-3.90 (bm, 4H), 3.30 (bm, 4H); LCMS purity 99.81%; MS, m/z found 492.30 $(M+1)^+$.

N-(4-(4-(2-methoxypyridin-3-yl)piperazine-1-carbonyl)-2-fluorophenyl)quinoline-8-sulfo-namide (98l)

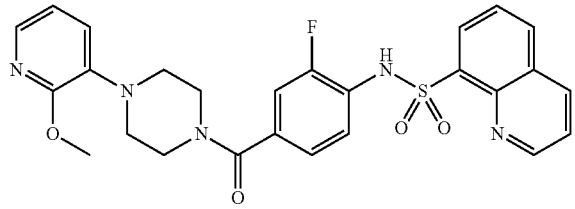

$^1$H NMR (400 MHz, $CDCl_3$) δ: 9.18 (d, 1H), 8.90 (bs, 1H), 8.40 (d, 1H), 8.30 (d, 1H), 8.05 (d, 1H), 7.85 (m, 1H), 7.75 (m, 1H), 7.60 (m, 2H), 7.05 (m, 1H), 6.95 (d, 1H), 6.80 (m, 1H), 4.00 (s, 3H), 3.45-3.90 (bm, 4H), 3.00 (bm, 4H); HPLC purity 96.60%; MS, m/z found 522.25 $(M+1)^+$.

Synthesis of N4-Aryl/Heteroaryl Homopiperazine Analogues

Scheme 14

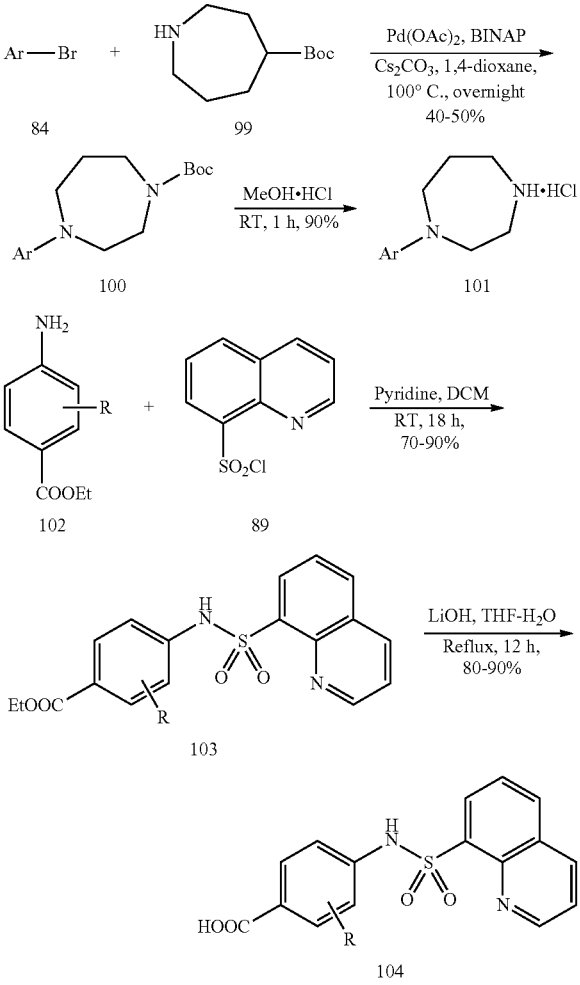

-continued

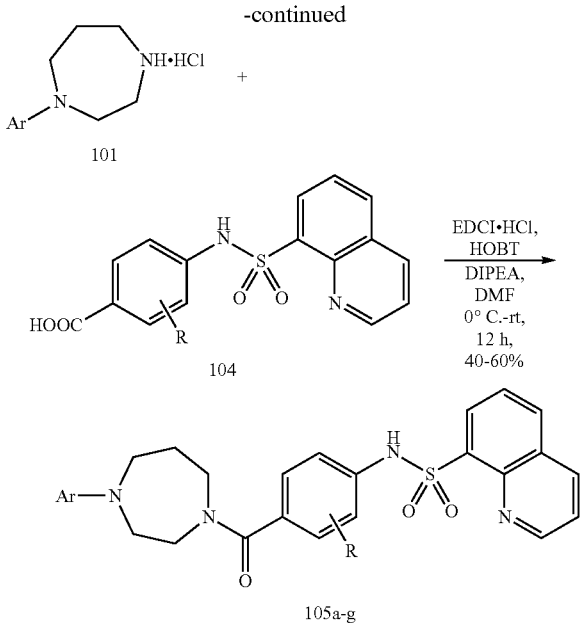

Where Ar = Substituted Aryl or heteroaryl
R = H, Cl, F, Me, OMe

General Procedure for Compound (100):

Nitrogen was purged through a stirred solution of arylbromide (84, 2.15 mmol) in 1,4-dioxane (20 ml) at room temperature for 30 min BINAP (0.134 g, 0.215 mmol), palladium acetate (0.0096 g, 0.043 mmol) and cesium carbonate (1.40 g, 4.3 mmol) were added to the reaction mixture and the nitrogen purging was continued for another 20 min and finally N-Boc homopiperazine (99, 0.428 g, 2.15 mmol) was added and stirred at 100° C. overnight under nitrogen atmosphere. After completion of the reaction (monitored by TLC), the reaction mixture was concentrated under vacuum. The residue was dissolved in water, extracted with ethyl acetate (3×50 ml). Combined organic extracts were washed with brine (20 ml), dried over anhydrous Sodium sulfate, filtered and concentrated under reduced pressure. The crude product was then purified by column chromatography (60-120 silica gel) using 10% ethyl acetate-hexane to yield compound (100) (40-50%).

General Procedure for Compound (101):

$N^1$-Boc-$N^4$-arylhomopiperazine (100, 1.070 mmol) was taken into a round bottomed flask and was added methanolic-HCl (20 ml, 20%) which resulted in formation of a homogeneous solution and was stirred for 1 h at room temperature. After completion of the reaction (monitored by TLC), the solvent was removed under vacuum. The crude product was washed with ethyl acetate repeatedly and then dried well to obtain compound (101) (90%) as a white solid.

General Procedure for Compound 103:

To a solution of amine (102, 30.16 mmol) in a 1:1 mixture of DCM-pyridine (50:50 ml) was added quinoline-8-sulfonyl chloride (89, 8.24 g, 36.19 mmol) under nitrogen atmosphere. The resultant solution was stirred overnight at room temperature. On completion of the reaction (monitored by TLC), the reaction mixture was diluted with dichloromethane (150 ml), washed with water (3×50 ml), 1N HCl solution (3×50 ml) and brine (50 ml. The combined organic extracts were dried over anhydrous sodium sulfate, filtered and concentrated under vacuum. Crude product was co-distilled with toluene to remove the remnants of pyridine and dried to yield sulfonamide (103) (70-90%) as an off-white solid and was used as such for the next step without further purification.

Procedure for Preparation of 4-(Quinoline-8-Sulfonamido) Benzoic Acid (104):

Ester (103, 5 g, 14.04 mmol) was dissolved in a mixture of THF-water (100:100 ml) and maintained at room temperature. To this solution was added LiOH (3.0 g, 7.0 mmol) and the resultant solution was refluxed overnight. The reaction mixture was then washed with ethyl acetate (3×50 ml) and then acidified with dilute HCl. The resultant suspension was filtered and residue was co-distilled with toluene. This product was then dried under vacuum to yield carboxylic acid (104) (80-90%) as an off-white solid.

General Procedure for Compound 105a-g:

To a stirred solution of the carboxylic acid (104, 0.61 mmol) in DMF at 0° C. under nitrogen atmosphere, EDCI (0.129 gm, 0.671 mmol), HOBt (0.91 gm, 0.671 mmol) and DIPEA (0.31 ml, 1.83 mmol) were added and the resultant solution was stirred at room temperature for 30 min Amine hydrochloride (101, 0.61 mmol) was then added at 0° C. and stirred overnight at room temperature. After completion of the reaction (monitored by TLC), the reaction mixture was poured into 1.0 M HCl and extracted with EtOAc. The organic layer was washed with saturated $NaHCO_3$ solution, dried over $NaSO_4$ and filtered. The solvent was removed by rotary evaporation and the product was isolated by chromatography on silica gel (60-120 silica gel, 2% MeOH-DCM) or preparative HPLC to yield amide (105a-g) (40-60%) as an off-white solid.

N-(4-(4-phenyl-1,4-diazepane-1-carbonyl)phenyl) quinoline-8-sulfonamide (105a)

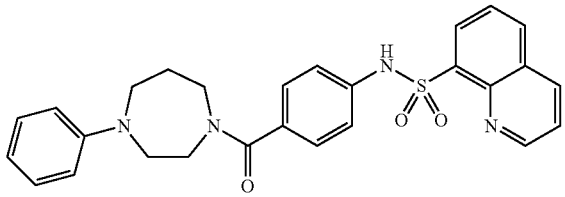

$^1$H NMR (400 MHz, DMSO-$d_6$) δ: 10.20 (s, 1H), 9.10 (s, 1H), 8.52 (d, 1H), 8.40 (d, 1H), 8.30 (d, 1H), 7.70 (m, 2H), 6.85-7.20 (m, 5H), 6.40-6.75 (m, 4H), 3.10-3.70 (m, 8H), 1.82 (bm, 2H); HPLC purity: 95.19%; MS, m/z found 487.30 $(M+1)^+$.

N-(6-(4-(2-methoxyphenyl)-1,4-diazepane-1-carbonyl)pyridin-3-yl)quinoline-8-sulfon-amide (105b)

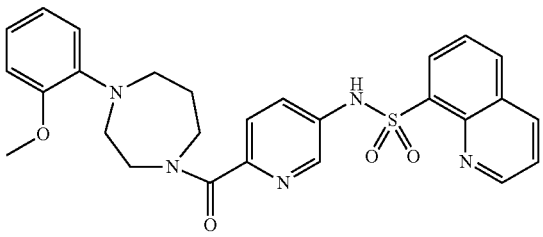

[$^1$H NMR (400 MHz, DMSO-$d_6$) δ: 9.15-9.19 (m, 1H), 8.32-8.42 (m, 2H), 8.20-8.26 (d, 1H), 8.10-8.16 (m, 1H), 7.58-7.74 (m, 5H), 7.20-7.28 (m, 1H), 6.92-7-18 (m, 2H), 4.15-4.20 (m, 4H), 3.81-3.88 (m, 4H), 3.82 (s, 3H), 2.42-2.58 (m, 2H);] LCMS purity 99.92%; MS, m/z found 518.5 $(M+1)^+$.

N-(2-chloro-4-(4-(2-methoxyphenyl)-1,4-diazepane-1-carbonyl)phenyl)quinoline-8-sulfona-mide (105c)

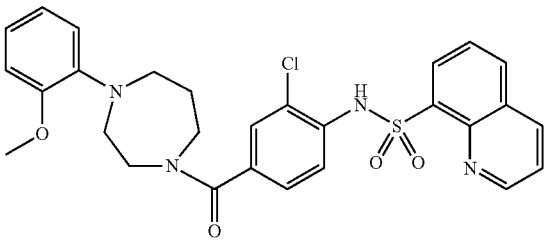

[$^1$H NMR (400 MHz, DMSO-$d_6$) δ: 9.15 (d, 1H), 8080-8.92 (m, 1H), 8.40-8.52 (m, 1H), 8.20-8.26 (d, 1H), 8.02-8.06 (d, 1H), 7.68-7.82 (dd, 1H), 7.54-7.62 (m, 2H), 6.84-7.05 (m, 5H), 6.66-6.68 (d, 1H), 3.82 (s, 3H), 3.74-3.78 (m, 2H), 3.41-3.54 (m, 2H), 3.21-3.36 (m, 3H), 3.16-3.19 (bs, 3H), 2.00-2.11 (bs, 1H), 1.82-1.98 (bs, 1H);] LCMS purity 97.10%; LCMS, m/z found 551.4 $(M+1)^+$.

N-(3-chloro-4-(4-(2-methoxyphenyl)-1,4-diazepane-1-carbonyl)phenyl)quinoline-8-sulfona-mide (105d)

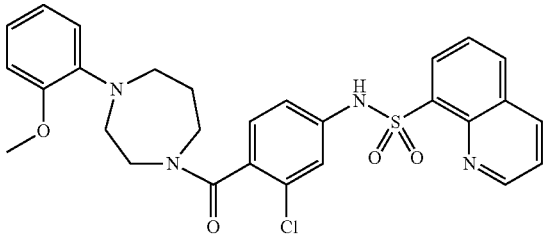

$^1$H NMR (400 MHz, DMSO-$d_6$) δ: 9.15 (s, 1H), 8.32-8.44 (m, 3H), 8.05-8.10 (m, 1H), 7.60-7.72 (m, 2H), 7.22-7.32 (m, 2H), 7.12 (s, 1H), 6.88-7.05 (m, 3H), 6.80-6.84 (m, 1H), 3.74-3.91 (m, 2H), 3.41 (s, 3H), 3.14-3.42 (m, 6H), 1.82-1.86 (m, 2H); LCMS purity 99.47%; MS, m/z found 551.4 $(M+1)^+$.

N-(2-fluoro-4-(4-(2-methoxyphenyl)-1,4-diazepane-1-carbonyl)phenyl)quinoline-8-sulfon-amide (105e)

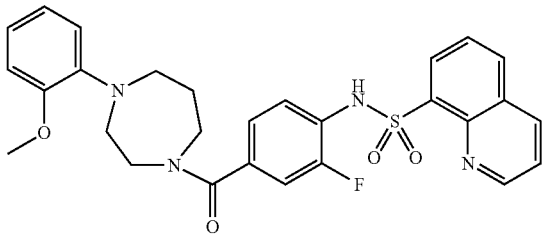

$^1$H NMR (400 MHz, DMSO-$d_6$) δ: 9.15 (s, 1H), 8.32-8.44 (d, 2H), 8.02-8.07 (t, 1H), 7.70-7.84 (m, 1H), 7.51-7.62 (m, 3H), 7.37-7-40 (m, 2H), 6.82-7.10 (m, 4H), 3.91-4.15 (m, 2H), 3.78-3.88 (m, 2H), 3.82 (s, 3H), 3.62-3.70 (m, 2H), 3.52-3.58 (m, 2H), 2.35-42 (m, 2H); LCMS purity 99.01%; MS, m/z found 535.5 $(M+1)^+$.

N-(4-(4-(2-methoxyphenyl)-1,4-diazepane-1-carbonyl)-2-methylphenyl)quinoline-8-sulfona-mide (105f)

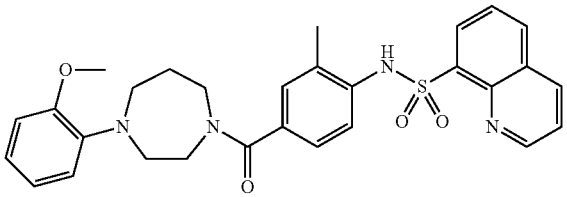

65

$^1$H NMR (400 MHz, DMSO-$d_6$) δ: 9.25 (s, 1H), 9.10 (d, 1H), 8.54-8.58 (d, 1H), 8.22-8.30 (dd, 2H), 7.68-7.76 (m, 2H, 6.78-7.18 (m, 7H), 3.81 (s, 3H), 3.20-3.64 (m, 8H), 2.15 (s, 3H), 1.82 (bm, 2H), LCMS purity: 99.67%; MS, M/z found 531.4 $(M+1)^+$.

N-(2-methoxy-4-(4-(2-methoxyphenyl)-1,4-diazepane-1-carbonyl)phenyl)quinoline-8-sulfo-namide (105g)

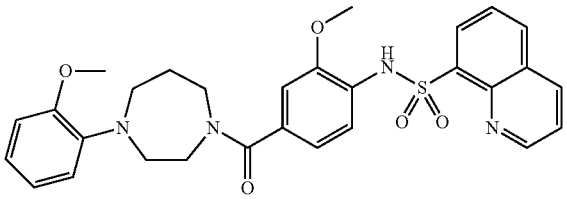

$^1$H NMR (400 MHz, DMSO-$d_6$) δ: 9.17 (d, 1H), 8.44 (s, 1H), 8.34-8.58 (dd, 2H), 8.02-8.10 (d, 1H), 7.56-7.64 (t, 2H), 6.82-6.94 (m, 4H), 6.66-6.68 (m, 1H), 6.24-6.38 (m, 1H), 3.81 (s, 3H), 3.64 (s, 3H), 3.58-3.60 (m, 2H), 3.24-3.40 (m, 4H), 3.04-3.22 (m, 2H), 1.82 (bm, 2H); LCMS purity: 94.21%; MS, m/z found 547.3 $(M+1)^+$.

Synthesis of N4-Aryl/Heteroaryl Piperazine/Homopiperazine Reverse Sulfonamide Analogues.

Scheme 15

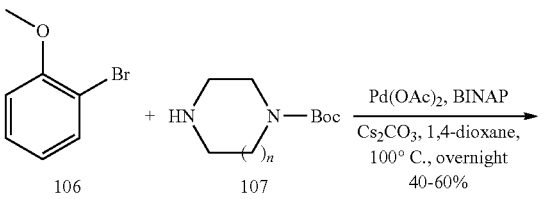

-continued

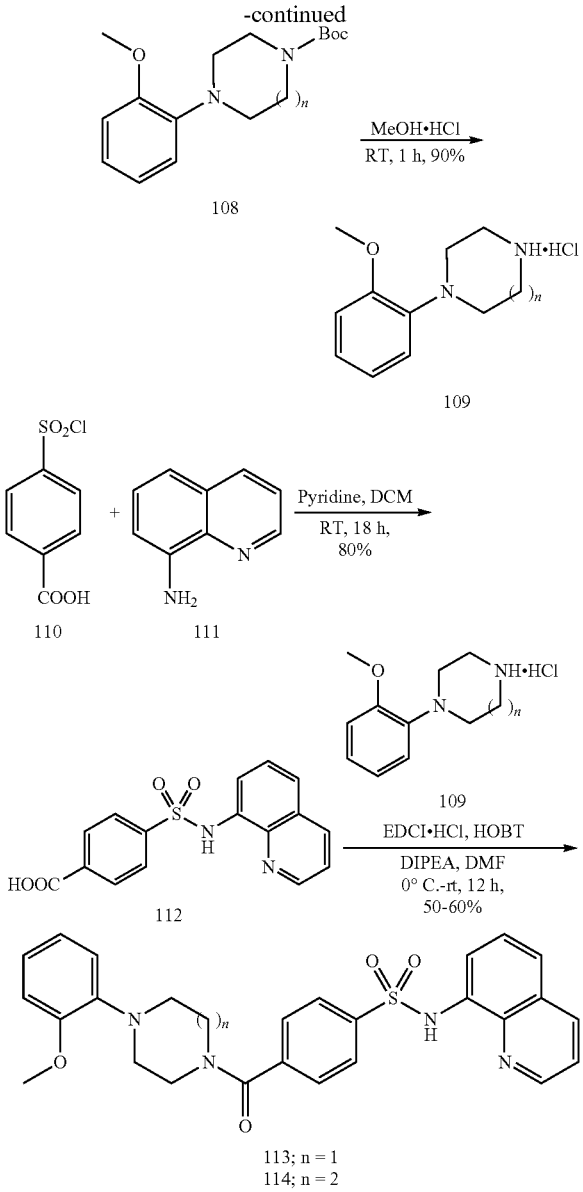

General Procedure for Compound (108):

Nitrogen was purged through a stirred solution of arylbromide (106, 0.4 g, 2.15 mmol) in 1,4-dioxane (20 ml) at room temperature for 30 min BINAP (0.134 g, 0.215 mmol), palladium acetate (0.0096 g, 0.043 mmol) and cesium carbonate (1.40 g, 4.3 mmol) were added to the reaction mixture and the nitrogen purging was continued for another 20 min and finally N-Boc amine (107, 2.15 mmol) was added and stirred at 100° C. overnight under nitrogen atmosphere. After completion of the reaction (monitored by TLC), the reaction mixture was concentrated under vacuum. The residue was dissolved in water, extracted with ethyl acetate (3×50 ml). Combined organic extracts were washed with brine (20 ml), dried over anhydrous Sodium sulfate, filtered and concentrated under reduced pressure. The crude product was then purified by column chromatography (60-120 silica gel) using 10% ethyl acetate-hexane to yield compound (108) (40-60%).

General Procedure for Compound (109):

Compound 108 (1.075 mmol) was taken into a round bottomed flask and was added methanolic-HCl (20 ml, 20%) which resulted in formation of a homogeneous solution and was stirred for 1 h at room temperature. After completion of the reaction (monitored by TLC), the solvent was removed under vacuum. The crude product was washed with ethyl acetate repeatedly and then dried well to obtain compound (109) (90%) as a white solid.

General Procedure for Compound 112:

To a solution of (4-chlorosulfonyl)benzoic acid (110, 1.6 g, 7.27 mmol) in a 1:1 mixture of DCM-pyridine (50:50 ml) was added 8-aminoquinoline (111, 1.15 g, 8.0 mmol) under nitrogen atmosphere. The resultant solution was stirred overnight at room temperature. On completion of the reaction (monitored by TLC), the reaction mixture was diluted with dichloromethane (150 ml), washed with water (3×50 ml), 1N HCl solution (3×50 ml) and brine (50 ml. The combined organic extracts were dried over anhydrous sodium sulfate, filtered and concentrated under vacuum. Crude product was co-distilled with toluene to remove the remnants of pyridine and dried to yield sulfonamide (112) (1.9 g, 80%) as an off-white solid and was used as such for the next step without further purification.

General Procedure for Compound 113/114:

To a stirred solution of the carboxylic acid (112, 0.61 mmol) in DMF at 0° C. under nitrogen atmosphere, EDCI (0.129 gm, 0.671 mmol), HOBt (0.91 gm, 0.671 mmol) and DIPEA (0.31 ml, 1.83 mmol) were added and the resultant solution was stirred at room temperature for 30 min Amine hydrochloride (109, 0.61 mmol) was then added at 0° C. and stirred overnight at room temperature. After completion of the reaction (monitored by TLC), the reaction mixture was poured into 1.0 M HCl and extracted with EtOAc. The organic layer was washed with saturated $NaHCO_3$ solution, dried over $NaSO_4$ and filtered. The solvent was removed by rotary evaporation and the product was isolated by chromatography on silica gel (60-120 silica gel, 2% MeO H-DCM) or preparative HPLC to yield amide (113/114) (50-60%) as an off-white solid.

4-(4-(2-methoxyphenyl)piperazine-1-carbonyl)-N-(quinolin-8-yl)benzenesulfonamide (113)

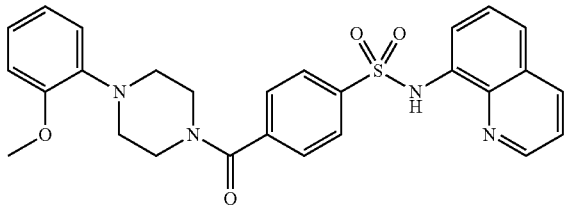

$^1$H NMR (400 MHz, DMSO-$d_6$) δ: 10.18 (s, 1H), 8.92 (s, 1H), 8.54-8.56 (d, 1H), 7.89-7.93 (d, 2H), 7.66-7.94 (m, 2H), 7.44-7.57 (m, 4H), 6.94-6.98 (m, 2H), 6.83-6.86 (m, 2H), 3.78 (s, 3H), 3.61-3.69 (m, 2H), 3.20-3.54 (m, 2H), 2.91-2.94 (bs, 2H), 1.82-1.86 (bs, 2H); HPLC purity 99.01%; MS, m/z found 503.3 $(M+1)^+$.

4-(4-(2-methoxyphenyl)-1,4-diazepane-1-carbonyl)-N-(quinolin-8-yl)benzenesulfonamide (114)

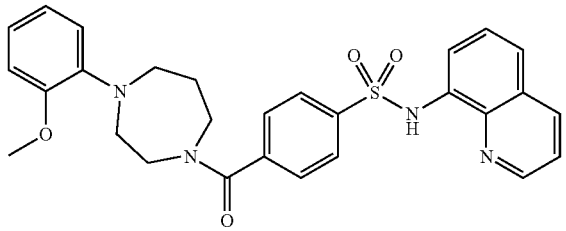

$^1$H NMR (400 MHz, DMSO-$d_6$) δ: 9.25 (s, 1H), 8.78 (s, 1H), 8.15 (d, 1H), 7.80-7.99 (m, 3H), 7.38-7.59 (m, 4H), 7.15-7.27 (m, 2H), 6.80-7.00 (m, 3H), 3.74-3.91 (m, 2H), 3.41 (s, 3H), 3.14-3.42 (m, 6H), 1.82-1.86 (m, 2H); LCMS purity 99.97%; MS, m/z found 517.3 $(M+1)^+$.

Synthesis of Piperazine Based Compounds with Substituted Phenyl Rings

Scheme 16

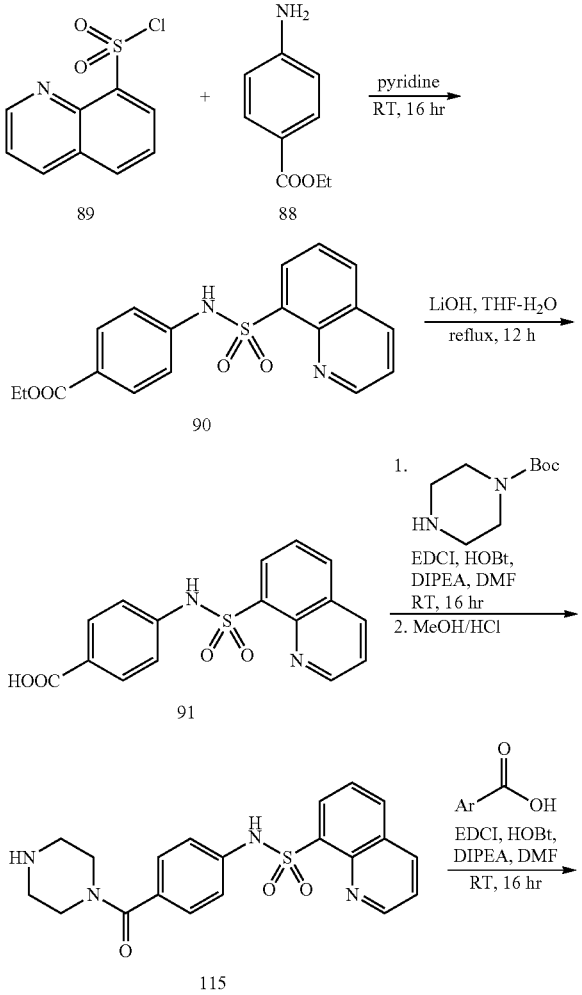

-continued

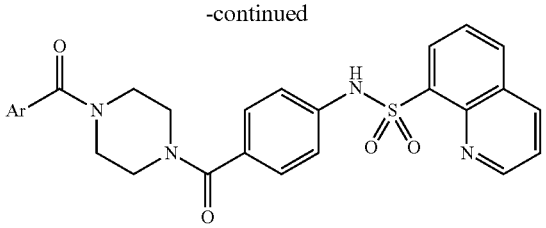

116a-bg

Ethyl 4-(quinoline-8-sulfonamido)benzoate (90)

To a stirred solution of ethyl 4-aminobenzoate (5 gm, 30.3 mmol) under nitrogen atmosphere was added pyridine (50 ml) at 0° C. and stirred for 10 min. Quinoline-8-sulfonyl chloride 89 (8.94 gm, 39.4 mmol) was then added to the reaction mixture at the same temperature. The resulting mixture was stirred for 16 hr at RT. After completion of the reaction, the solvent was removed under low pressure. The traces of pyridine were removed by co-distillation with toluene. Diethylether was added to the resulting residue, and the solid product was filtered out and air-dried. The resulting crude product (8.0 gm, 74%) was taken to the next step without further purification.

4-(Quinoline-8-sulfonamido)benzoic acid (91)

To a stirred solution of ethyl 4-(quinoline-8-sulfonamido) benzoate 90 (8 gm, 22.4 mmol) in THF:$H_2O$ (1:1) under nitrogen atmosphere was added solid LiOH (9.4 gm, 224 mmol) at RT. The solution was then refluxed for 6 hr. After completion of the reaction, the reaction mixture was washed with ethyl acetate (2×100 ml) to remove non polar impurities. The aqueous layer was acidified (pH 4) with citric acid solution. The resultant precipitate was filtered out and air-dried. The traces of water were removed by co-distillation with toluene. The resultant off white solid (5.9 gm, 80%) was taken to the next step without further purification.

N-(4-(piperazine-1-carbonyl)phenyl)quinoline-8-sulfonamide (115)

EDCI (3.8 g, 19.8 mmol) and HOBT (2.67 g, 19.8 mmol) were added to a stirred solution of the acid 91 (6.5 g, 19.8 mmol) in anhydrous DMF. The temperature of the mixture was reduced to 0° C., at which time DIPEA (11 ml, 59.45 mmol) was added under nitrogen atmosphere and the resultant solution (or suspension) was stirred at room temperature for 30 min. Boc-piperazine (3.68 g, 19.8 mmol) was then added at 0° C. The reaction mixture was then brought to room temperature and stirred overnight. After completion of the reaction, the reaction mixture was diluted with water and extracted with ethyl acetate (3×70 ml). The organic layer was washed with water (3×50 ml), dried over anhydrous sodium sulfate, filtered and concentrated over the rotary evaporator to get the crude product. Crude product was purified by column chromatography (60-120 silica gel, 2% MeOH-DCM) to get pure product, Boc-115 (8.0 g, 82%) as an off-white solid, which was subjected to the treatment with methanolic HCl (100 ml) for 2 hr at RT. After the complete cleavage of Boc-group, the solvent was removed under low pressure, to give the crude product as an HCl salt. The aqueous solution of the salt was washed with diethylether and basified with $NaHCO_3$ (pH 10). The desired product was then partitioned into ethyl acetate, dried with anhydrous $Na_2SO_4$ and the solvent removed under low pressure to get the free amine 115 as off white solid (6.0 g, 95%).

General Procedure for the Synthesis of Amides 116a-Bg:

EDCI (48 mg, 0.2525 mmol) and HOBT (34 mg, 0.2525 mmol) were added to a stirred solution of the Ar—COOH (0.2525 mmol) in anhydrous DMF. The temperature of the mixture was reduced to 0° C., at which time DIPEA (139 μl, 0.7575 mmol) was added under nitrogen atmosphere and the resultant solution (or suspension) was stirred at room temperature for 30 min Amine 115 (100 mg, 0.2525 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (3×10 ml), dried over anhydrous sodium sulfate, filtered and concentrated over the rotary evaporator to get the crude product. Crude product was purified by either by silica column chromatography or preparative HPLC to obtain the pure products in 55-69% yields.

N-(4-(4-Picolinoylpiperazine-1-carbonyl)phenyl) quinoline-8-sulfonamide (116a)

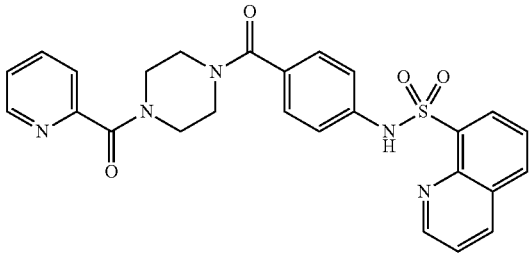

$^1$H NMR (400 MHz, DMSO-$d_6$) δ: 3.2-3.8 (m, 8H), 7.0-7.2 (m, 4H), 7.4-7.6 (m, 2H), 7.7 (m, 2H), 7.9 (m, 1H), 8.3 (m, 1H), 8.4-8.6 (m, 3H), 9.1 (d, 1H), 10.2-10.4 (s, 1H); HPLC Purity: 95.7%; LCMS, m/z found 502.1 $(M+1)^+$.

N-(4-(4-Nicotinoylpiperazine-1-carbonyl)phenyl) quinoline-8-sulfonamide (116b)

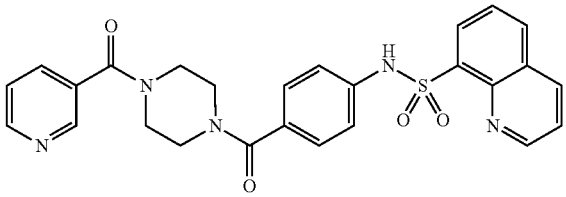

$^1$H NMR (400 MHz, $CDCl_3$) δ: 3.2-3.8 (m, 8H), 7.0-7.2 (m, 4H), 7.4 (m, 1H), 7.6-7.8 (m, 3H), 8.0 (m, 1H), 8.3 (m, 2H), 8.4-8.6 (m, 3H), 9.1 (d, 1H), 10.2-10.4 (s, 1H); HPLC Purity: 96.7%; LCMS, m/z found 502.2 $(M+1)^+$.

N-(4-(4-Isonicotinoylpiperazine-1-carbonyl)phenyl) quinoline-8-sulfonamide (116c)

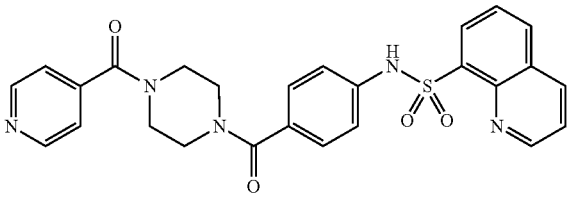

$^1$H NMR (400 MHz, $CDCl_3$) δ: 3.2-3.8 (m, 8H), 7.0-7.2 (m, 4H), 7.6 (m, 2H), 8.0 (m, 1H), 8.2-8.4 (m, 2H), 8.6 (m, 3H), 9.1 (m, 2H), 10.2-10.4 (s, 1H); HPLC Purity: 98.8%; LCMS, m/z found 502.1 $(M+1)^+$.

N-(4-(4-(2-Methylnicotinoyl)piperazine-1-carbonyl) phenyl)quinoline-8-sulfonamide (116d)

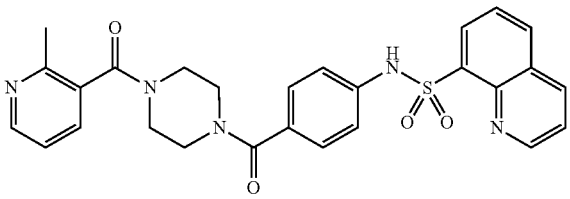

$^1$H NMR (400 MHz, DMSO-$d_6$) δ: 3.2 (s, 3H), 3.3-3.8 (m, 8H), 7.0-7.2 (m, 4H), 7.4 (m, 1H), 7.6-7.9 (m, 3H), 8.2 (m, 1H), 8.4-8.6 (m, 3H), 9.1 (m, 1H), 10.4 (s, 1H); HPLC Purity: 99.2%; LCMS, m/z found 516.4 $(M+1)^+$.

N-(4-(4-(2,6-Dichloronicotinoyl)piperazine-1-carbonyl)phenyl)quinoline-8-sulfonamide (116e)

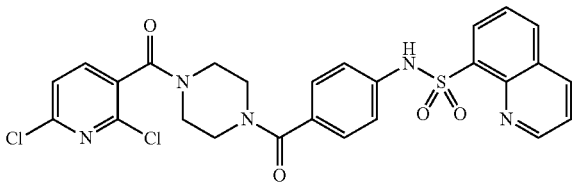

$^1$H NMR (400 MHz, DMSO-$d_6$) δ: 3.2 (s, 3H), 3.3-3.8 (m, 8H), 7.0-7.4 (m, 4H), 7.6 (m, 3H), 8.0 (m, 1H), 8.2 (m, 2H), 8.6 (m, 1H), 9.1 (m, 1H), 10.4 (s, 1H); HPLC Purity: 98.8%; LCMS, m/z found 570.3 $(M+1)^+$.

N-(4-(4-(6-Methylpicolinoyl)piperazine-1-carbonyl) phenyl)quinoline-8-sulfonamide (116f)

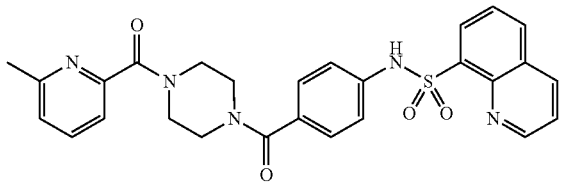

[$^1$H NMR (400 MHz, DMSO-$d_6$) δ: 2.5 (s, 3H), 3.3-3.8 (m, 8H), 7.0-7.3 (m, 5H), 7.4 (m, 1H), 7.6-7.8 (m, 3H), 8.0 (m, 1H), 8.2-8.4 (m, 1H), 8.6 (m, 1H), 10.4 (s, 1H);] HPLC Purity: 99.9%; LCMS, m/z found 516.1 $(M+1)^+$.

N-(4-(4-(Pyrazine-2-carbonyl)piperazine-1-carbonyl)phenyl)quinoline-8-sulfonamide (116g)

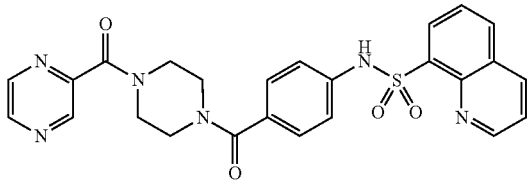

$^1$H NMR (400 MHz, $CDCl_3$) δ: 3.3-3.8 (m, 8H), 7.0-7.2 (m, 4H), 7.6 (m, 2H), 8.0 (m, 1H), 8.2-8.4 (m, 2H), 8.2-8.4 (m, 1H), 8.6 (m, 2H), 9.0 (s, 1H), 9.2 (m, 1H); HPLC Purity: 97.5%; LCMS, m/z found 503.2 $(M+1)^+$.

N-(4-(4-(3-Methoxybenzoyl)piperazine-1-carbonyl)phenyl)quinoline-8-sulfonamide (116h)

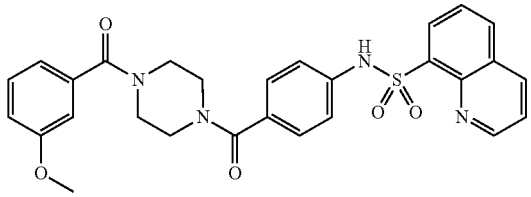

$^1$H NMR (400 MHz, DMSO-$d_6$) δ: 3.3-3.8 (m, 8H), 3.9 (s, 3H), 6.9-7.0 (m, 3H), 7.2 (m, 4H), 7.4 (m, 1H), 7.9 (m, 2H), 8.2 (m, 1H), 8.4-8.6 (m, 2H), 9.1 (s, 1H), 10.5 (s, 1H); HPLC Purity: 97.3%; LCMS, m/z found 531.3 $(M+1)^+$.

N-(4-(4-(2-Fluorobenzoyl)piperazine-1-carbonyl)phenyl)quinoline-8-sulfonamide (116i)

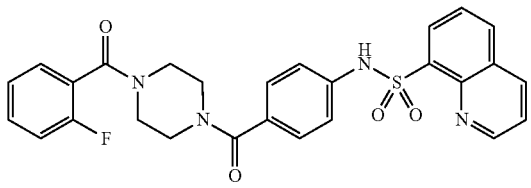

$^1$H NMR (400 MHz, DMSO-$d_6$) δ: 3.2 (m, 4H), 3.4 (m, 2H), 3.6 (m, 2H) 7.0-7.5 (m, 8H), 7.7 (m, 2H), 8.2 (m, 1H), 8.4-8.6 (m, 2H), 9.1 (m, 1H), 10.5 (s, 1H); HPLC Purity: 97.3%; LCMS, m/z found 519.3 $(M+1)^+$.

N-(4-(4-(3-Fluorobenzoyl)piperazine-1-carbonyl)phenyl)quinoline-8-sulfonamide (116j)

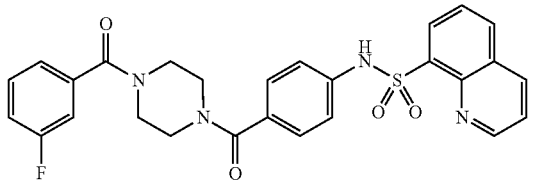

$^1$H NMR (400 MHz, DMSO-$d_6$) δ: 3.2-3.8 (m, 8H), 7.0-7.2 (m, 6H), 7.4 (m, 2H), 7.8 (m, 2H), 8.2-8.5 (m, 3H), 9.1 (m, 1H), 10.5 (s, 1H); HPLC Purity: 97.3%; LCMS, m/z found 519.3 $(M+1)^+$.

N-(4-(4-(4-Fluorobenzoyl)piperazine-1-carbonyl)phenyl)quinoline-8-sulfonamide (116k)

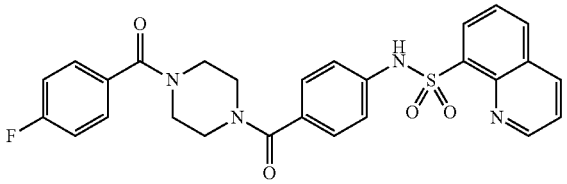

$^1$H NMR (400 MHz, DMSO-$d_6$) δ: 3.2-3.8 (m, 8H), 7.0-7.2 (m, 6H), 7.4 (m, 2H), 7.8 (m, 2H), 8.2-8.5 (m, 3H), 9.1 (m, 1H), 10.5 (s, 1H); HPLC Purity: 97.3%; LCMS, m/z found 45 519.3 $(M+1)^+$.

N-(4-(4-(2,3-Difluorobenzoyl)piperazine-1-carbonyl)phenyl)quinoline-8-sulfonamide (116l)

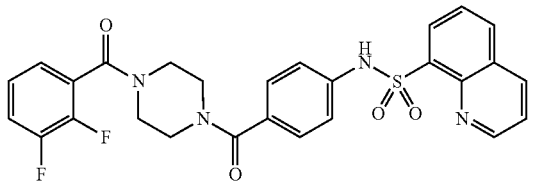

$^1$H NMR (400 MHz, DMSO-$d_6$) δ: 3.2 (m, 4H), 3.6 (m, 4H), 7.0-7.4 (m, 6H), 7.5-7.8 (m, 3H), 8.2 (m, 1H), 8.4-8.6 (m, 2H), 9.1 (m, 1H), 10.5 (s, 1H); HPLC Purity: 94.3%; LCMS, m/z found 537.3 $(M+1)^+$.

N-(4-(4-(2,3-Dimethoxybenzoyl)piperazine-1-carbonyl)phenyl)quinoline-8-sulfonamide (116m)

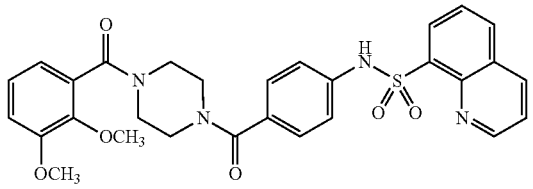

$^1$H NMR (400 MHz, DMSO-$d_6$) δ: 3.2 (m, 4H), 3.6 (m, 4H), 3.7 (s, 3H), 3.8 (s, 3H), 6.8 (m, 1H), 7.0-7.2 (m, 6H), 7.6-7.8 (m, 2H), 8.2 (m, 1H), 8.4-8.6 (m, 2H) 9.1 (m, 1H), 10.5 (s, 1H); HPLC Purity: 97.2%; LCMS, m/z found 561.1 $(M+1)^+$.

N-(4-(4-Benzoylpiperazine-1-carbonyl)phenyl)quinoline-8-sulfonamide (116n)

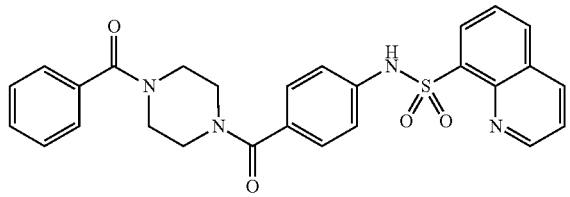

$^1$H NMR (400 MHz, DMSO-$d_6$) δ: 3.2-3.8 (s, 8H), 6.8 (m, 1H), 7.0-7.2 (m, 6H), 7.6-7.8 (m, 2H), 8.2 (m, 2H), 8.4-8.6 (m, 2H), 9.1 (m, 1H), 10.5 (s, 1H); HPLC Purity: 98.2%; LCMS, m/z found 501.2 $(M+1)^+$.

N-(4-(4-(4-Chlorobenzoyl)piperazine-1-carbonyl)phenyl)quinoline-8-sulfonamide (116o)

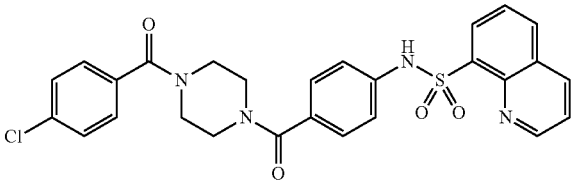

$^1$H NMR (400 MHz, DMSO-$d_6$) δ: 3.2-3.8 (m, 8H), 7.0-7.2 (m, 4H), 7.2-7.6 (m, 4H), 7.6-7.8 (m, 2H), 8.2-8.6 (m, 3H), 9.1 (m, 1H), 10.5 (s, 1H); HPLC Purity: 99.7%; LCMS, m/z found 535.0 $(M+1)^+$.

N-(4-(4-(4-Chloro-2,5-difluorobenzoyl)piperazine-1-carbonyl)phenyl)quinoline-8-sulfonamide (116p)

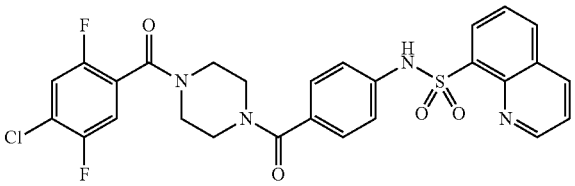

$^1$H NMR (400 MHz, DMSO-$d_6$) δ: 3.2-3.8 (m, 8H), 7.0-7.2 (m, 4H), 7.6-7.8 (m, 4H), 8.2-8.6 (m, 3H), 9.1 (m, 1H), 10.5 (s, 1H); HPLC Purity: 99.7%; LCMS, m/z found 555.4 $(M+1)^+$.

N-(4-(4-(2-Naphthoyl)piperazine-1-carbonyl)phenyl)quinoline-8-sulfonamide (116r)

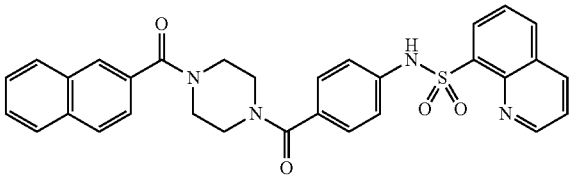

$^1$H NMR (400 MHz, $CDCl_3$) δ: 3.2-3.8 (m, 8H), 7.0-7.2 (m, 4H), 7.4-7.6 (m, 5H), 7.8 (m, 4H), 8.0 (m, 1H), 8.2-8.4 (m, 2H), 9.1 (m, 1H), 10.5 (s, 1H); HPLC Purity: 98.4%; LCMS, m/z found 551.4 $(M+1)^+$.

N-(4-(4-(2-(4-Fluorophenyl)-2-methylpropanoyl)piperazine-1-carbonyl)phenyl)quinoline-8-sulfonamide (116s)

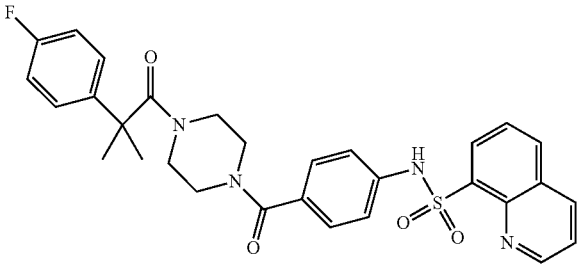

$^1$H NMR (400 MHz, DMSO-$d_6$) δ: 1.2 (s, 6H), 3.2-3.8 (m, 8H), 7.0-7.2 (m, 8H), 7.6-7.8 (m, 2H), 8.2-8.6 (m, 3H), 9.1 (m, 1H), 10.5 (s, 1H); HPLC Purity: 98.4%; LCMS, m/z found 561.4 $(M+1)^+$.

N-(4-(4-(2-Methyl-2-phenylpropanoyl)piperazine-1-carbonyl)phenyl)quinoline-8-sulfonamide (116t)

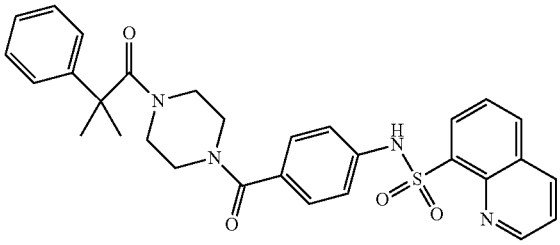

$^1$H NMR (400 MHz, $CD_3OD$) δ: 3.2-3.8 (m, 8H), 3.9 (s, 2H), 7.2-7.4 (m, 9H), 7.6-7.8 (m, 2H), 8.2 (m, 1H), 8.4 (m, 2H), 9.1 (m, 1H), 10.5 (s, 1H), HPLC Purity: 99.4%; LCMS, m/z found 515.3 $(M+1)^+$.

N-(4-(4-(3-(Thiophen-2-yl)propanoyl)piperazine-1-carbonyl)phenyl)quinoline-8-sulfonamide (116u)

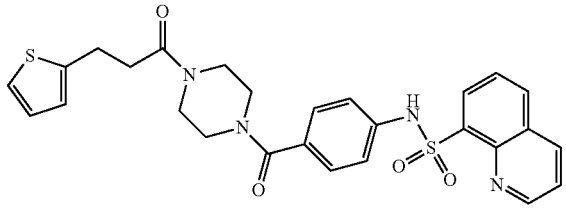

$^1$H NMR (400 MHz, DMSO-$d_6$) δ: 2.4-2.6 (m, 3H), 2.7 (m, 2H), 3.0 (m, 2H), 3.2-3.6 (m, 5H), 6.9 (m, 2H), 7.0-7.2 (m, 4H), 7.4 (m, 1H), 7.8 (m, 2H), 8.2-8.6 (m, 3H), 9.1 (m, 1H), 10.5 (s, 1H); HPLC Purity: 98.0%; LCMS, m/z found 535.1 $(M+1)^+$.

N-(4-(4-(2-Cyclopropylacetyl)piperazine-1-carbonyl)phenyl)quinoline-8-sulfonamide (116v)

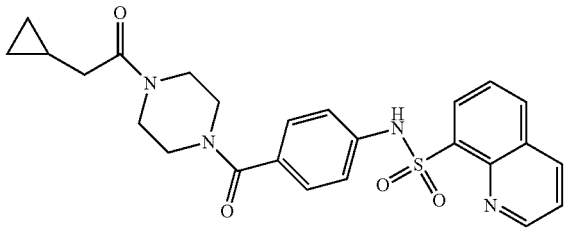

$^1$H NMR (400 MHz, $CDCl_3$) δ: 0.2 (m, 2H), 0.6 (m, 2H), 1.0 (m, 1H), 3.3-3.8 (m, 8H), 7.0-7.2 (m, 4H), 7.6 (m, 2H), 8.0 (m, 1H), 8.2-8.4 (m, 2H), 9.1 (m, 1H), 10.5 (s, 1H); HPLC Purity: 99.9%; LCMS, m/z found 479.4 $(M+1)^+$.

N-(4-(4-(Thiazole-4-carbonyl)piperazine-1-carbonyl)phenyl)quinoline-8-sulfonamide (116w)

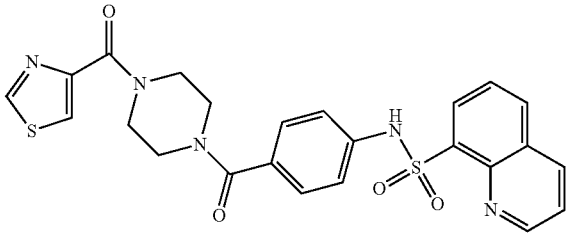

$^1$H NMR (400 MHz, $CDCl_3$) δ: 3.3-3.8 (m, 8H), 7.0-7.2 (m, 4H), 7.6-7.8 (m, 2H), 8.0-8.2 (m, 2H), 8.4-8.6 (m, 2H), 9.1 (m, 2H), 10.5 (s, 1H); HPLC Purity: 98.2%; LCMS, m/z found 508.1 $(M+1)^+$.

N-(4-(4-(1,2,3-Thiadiazole-4-carbonyl)piperazine-1-carbonyl)phenyl)quinoline-8-sulfonamide (116x)

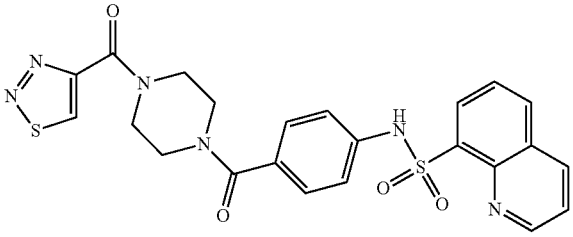

$^1$H NMR (400 MHz, DMSO-$d_6$) δ: 3.3-3.8 (m, 8H), 7.0-7.2 (m, 4H), 7.6-7.8 (m, 2H), 8.2-8.6 (m, 3H), 9.1 (m, 1H), 9.6 (s, 1H), 10.5 (s, 1H); HPLC Purity: 98.2%; LCMS, m/z found 508.1 $(M+1)^+$.

N-(4-(4-(1H-Pyrrole-2-carbonyl)piperazine-1-carbonyl)phenyl)quinoline-8-sulfonamide (116y)

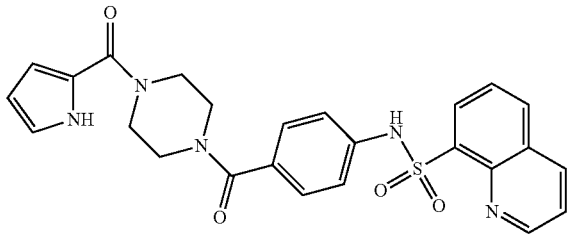

$^1$H NMR (400 MHz, DMSO-$d_6$) δ: 3.2-3.8 (m, 8H), 6.0 (m, 1H), 6.4 (m, 1H), 6.8 (m, 1H), 7.0-7.2 (m, 4H), 7.6-7.8 (m, 2H), 8.2 (m, 1H), 8.4-8.6 (m, 2H), 9.1 (m, 1H), 10.5 (s, 1H), 11.4 (s, 1H); HPLC Purity: 99.2%; LCMS, m/z found 490.3 $(M+1)^+$.

N-(4-(4-(2-Methylthiazole-5-carbonyl)piperazine-1-carbonyl)phenyl)quinoline-8-sulfonamide (116z)

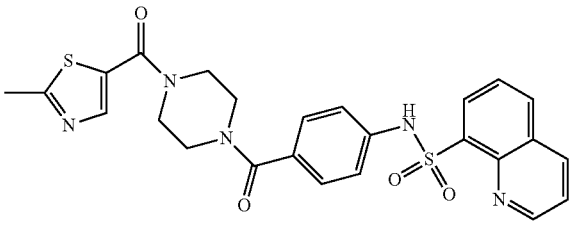

$^1$H NMR (400 MHz, $CDCl_3$) δ: 2.3 (s, 3H), 3.6-3.8 (m, 8H), 7.0-7.2 (m, 5H), 7.6 (m, 2H), 8.0 (m, 1H), 8.2-8.4 (m, 2H), 9.1 (m, 1H); HPLC Purity: 99.7%; LCMS, m/z found 521.6 $(M+1)^+$.

N-(4-(4-(Cyclopropanecarbonyl)piperazine-1-carbonyl)phenyl)quinoline-8-sulfonamide (116aa)

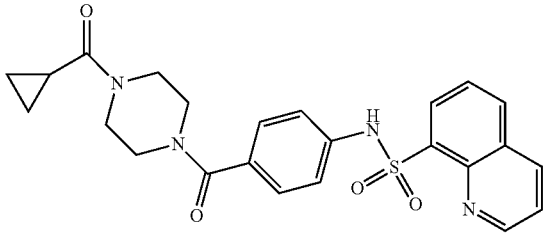

[$^1$H NMR (400 MHz, DMSO-$d_6$) δ: 0.6-0.8 (m, 2H), 2.0 (m, 1H), 3.2-3.8 (m, 8H), 7.0-7.2 (m, 4H), 7.6-7.8 (m, 2H), 8.2 (m, 1H), 8.4-8.6 (m, 2H), 9.1 (m, 1H), 10.5 (s, 1H);] HPLC Purity: 99.0%; LCMS, m/z found 465.35 $(M+1)^+$.

N-(4-(4-(Cyclohexanecarbonyl)piperazine-1-carbonyl)phenyl)quinoline-8-sulfonamide (116ab)

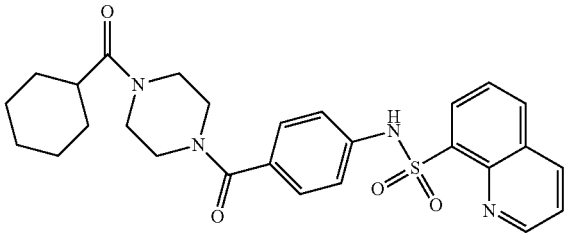

$^1$H NMR (400 MHz, DMSO-$d_6$) δ: 1.0-1.2 (m, 5H), 1.6-1.8 (m, 5H), 2.5 (m, 1H), 3.2-3.8 (m, 8H), 7.0-7.2 (m, 4H), 7.6-7.8 (m, 2H), 8.2 (m, 1H), 8.4-8.6 (m, 2H), 9.1 (m, 1H), 10.5 (s, 1H); HPLC Purity: 93.0%; LCMS, m/z found 507.15 $(M+1)^+$.

N-Phenyl-4-(4-(quinoline-8-sulfonamido)benzoyl) piperazine-1-carboxamide (116ac)

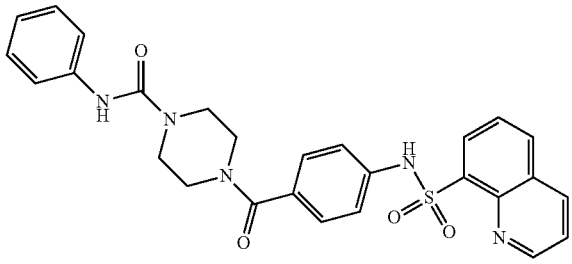

$^1$H NMR (400 MHz, DMSO-$d_6$) δ: 3.2-3.8 (m, 8H), 7.0-7.2 (m, 6H), 7.4 (m, 2H), 7.6 (m, 2H), 8.2 (m, 2H), 8.4-8.6 (m, 2H), 9.1 (m, 1H), 10.5 (s, 1H); HPLC Purity: 99.4%; LCMS, m/z found 516.4 $(M+1)^+$.

N-(3-Methoxyphenyl)-4-(4-(quinoline-8-sulfonamido)benzoyl)piperazine-1-carboxamide (116ad)

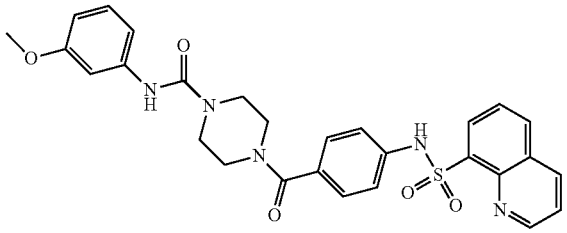

$^1$H NMR (400 MHz, DMSO-$d_6$) δ: 3.8 (m 8H), 3.9 (s, 3H), 6.48 (s, 1H), 7.23 (m, 7H), 7.9 (m, 2H), 8.3 (s, 1H), 8.4-8.6 (d, 2H), 8.72 (s, 1H), 9.24 (s, 1H), 10.53 (s, 1H); HPLC Purity: 95.27%; MS, m/z found 546.16 $(M+1)^+$.

N-(2-Methoxyphenyl)-4-(4-(quinoline-8-sulfonamido)benzoyl)piperazine-1-carboxamide (116ae)

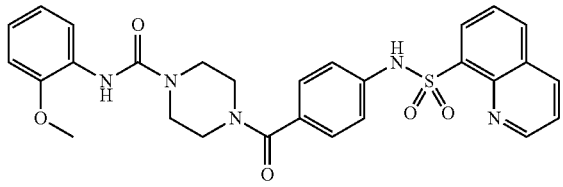

$^1$H NMR (400 MHz, DMSO-$d_6$) δ: 3.8 (m 8H), 3.9 (s, 3H), 6.8 (d 2H), 6.98 (d, 2H), 7.23 (m, 4H), 7.9 (m, 4H), 8.42 (d, 1H), 8.6 (d, 1H), 8.72 (d, 1H), 9.24 (s, 1H), 10.53 (s, 1H); HPLC Purity: 97.73%; MS, m/z found 546.14 $(M+1)^+$.

N-(4-Methoxyphenyl)-4-(4-(quinoline-8-sulfonamido)benzoyl)piperazine-1-carboxamide (116af)

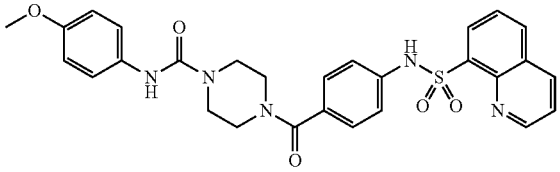

$^1$H NMR (400 MHz, DMSO-$d_6$) δ: 3.8 (m 8H), 3.9 (s, 3H), 5.9 (S 1H), 6.8 (d 2H), 6.98 (d, 2H), 7.23 (m, 6H), 7.9 (m, 2H), 8.2-8.6 (m, 4H), 9.24 (s, 1H), 10.53 (s, 1H); HPLC Purity: 98.22%; MS, m/z found 546.17 $(M+1)^+$.

N-(2,4-Difluorophenyl)-4-(4-(quinoline-8-sulfonamido)benzoyl)piperazine-1-carboxamide (116ag)

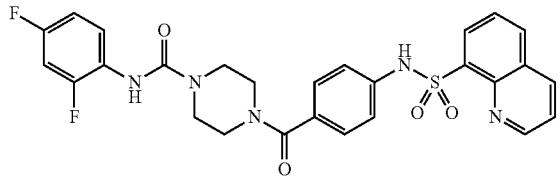

$^1$H NMR (400 MHz, DMSO-$d_6$) δ: 3.4 (m 8H), 7.9 (m 7H), 7.5 (m, 2H), 8.2-8.5 (d, 3H), 9.24 (s, 1H); HPLC Purity: 95.79%; MS, m/z found 552.19 $(M+1)^+$.

N-(2-Fluorophenyl)-4-(4-(quinoline-8-sulfonamido)benzoyl)piperazine-1-carboxamide (116ah)

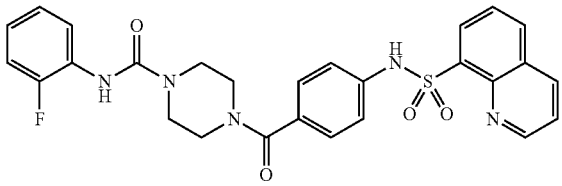

$^1$H NMR (400 MHz, DMSO-$d_6$) δ: 3.8 (m 8H), 7.2 (m, 7H), 7.6 (S, 1H), 7.9 (d, 2H), 8.2-8.6 (d, 4H), 9.24 (s, 1H), 10.53 (s, 1H); HPLC Purity: 95.38%; MS, m/z found 534.22 $(M+1)^+$.

N-(4-Fluorophenyl)-4-(4-(quinoline-8-sulfonamido)benzoyl)piperazine-1-carboxamide (116ai)

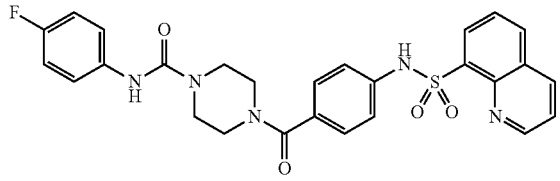

[$^1$H NMR (400 MHz, DMSO-$d_6$) δ: 3.8 (m 8H), 7.2 (m, 5H), 7.42 (d, 2H), 7.6 (d, 2H), 8.2-8.6 (d, 4H), 10.53 (s, 1H), 9.24 (s, 1H);] HPLC Purity: 98.92%[; MS, m/z found 532.42 $(M+1)^+$].

N-(4-Cyanophenyl)-4-(4-(quinoline-8-sulfonamido)benzoyl)piperazine-1-carboxamide (116aj)

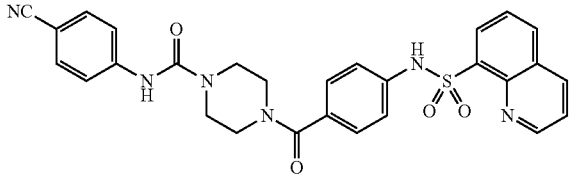

$^1$H NMR (400 MHz, DMSO-$d_6$) δ: 3.8 (m 8H), 7.23 (d, 4H), 7.9 (m, 6H), 8.42 (d, 1H), 8.2 (d, 1H), 8.15 (d, 1H), 9.23 (S, 1H), 9.1 (s, 1H), 10.53 (s, 1H), HPLC Purity: 97.97%; MS, m/z found 541.30 $(M+1)^+$.

N-(2-Chlorophenyl)-4-(4-(quinoline-8-sulfonamido)benzoyl)piperazine-1-carboxamide (116ak)

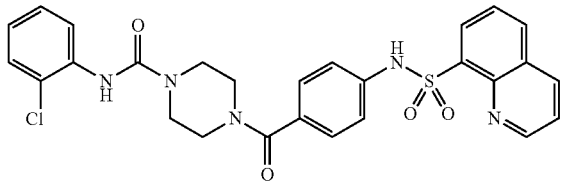

$^1$H NMR (400 MHz, DMSO-$d_6$) δ: 3.3 (m 8H), 7.2 (m, 6H), 7.3 (d, 4H), 7.9 (m, 2H), 8.42 (d, 2H), 8.5 (d, 1H), 8.52 (d, 1H), 9.24 (s, 1H), 10.53 (s, 1H); HPLC Purity: 97.73%; MS, m/z found 546.14 $(M+1)^+$.

4-(4-(Quinoline-8-sulfonamido)benzoyl)-N-(p-tolyl)piperazine-1-carboxamide (116al)

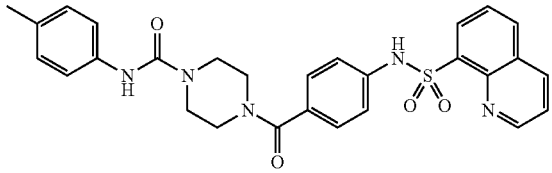

$^1$H NMR (400 MHz, DMSO-$d_6$) δ: 2.2 (S 3H), 3.8 (m, 8H), 7.1-7.3 (m, 7H), 7.9 (m, 2H), 8.23-8.4 (d, 4H), 9.1 (s, 1H), 8.62 (d, 10.53 (s, 1H), HPLC Purity: 98.27%; MS, m/z found 530.19 $(M+1)^+$.

N-(4-Chlorophenyl)-4-(4-(quinoline-8-sulfonamido)benzoyl)piperazine-1-carboxamide (116 am)

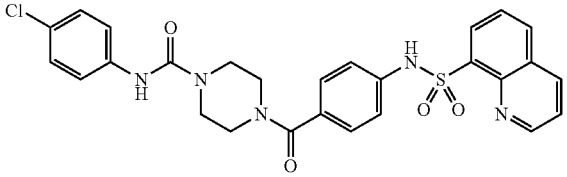

$^1$H NMR (400 MHz, DMSO-$d_6$) δ: 3.3 (m 8H), 7.2 (m, 6H), 7.4 (d, 2H), 7.9 (m, 2H), 8.42 (d, 2H), 8.5 (d, 1H), 8.62 (d, 1H), 9.24 (s, 1H), 10.43 (s, 1H); HPLC Purity: 97.92%; MS, m/z found 550.14 $(M+1)^+$.

4-(4-(Quinoline-8-sulfonamido)benzoyl)-N-(4-(trifluoromethyl)phenyl)piperazine-1-carboxamide (116an)

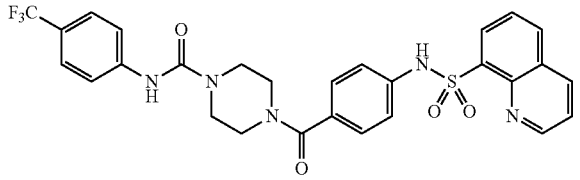

$^1$H NMR (400 MHz, DMSO-$d_6$) δ: 3.3 (m 8H), 7.4 (m, 6H), 7.5 (d, 2H), 8.0 (m, 2H), 8.6 (d, 2H), 8.7 (d, 1H), 8.8 (d, 1H), 9.24 (s, 1H), 10.43 (s, 1H); HPLC Purity: 97.90%; MS, m/z found 584.05 $(M+1)^+$.

N-(2-Chloro-5-(trifluoromethyl)phenyl)-4-(4-(quinoline-8-sulfonamido)benzoyl)piperazine-1-carbothioamide (116ao)

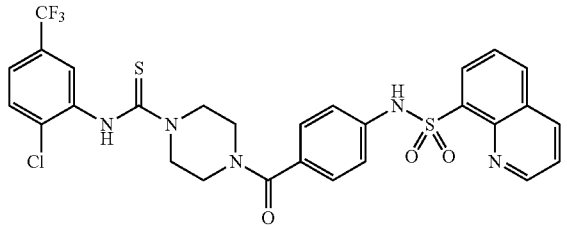

$^1$H NMR (400 MHz, DMSO-$d_6$) δ: 3.2-3.8 (m, 8H), 7.0-7.2 (m, 4H), 7.6-7.8 (m, 5H), 8.2 (m, 1H), 8.4-8.6 (m, 2H), 9.1 (m, 1H), 9.4 (m, 1H), 10.5 (s, 1H); HPLC Purity: 96.1%; LCMS, m/z found 634.17 $(M+1)^+$.

Ethyl 4-(4-(4-(quinoline-8-sulfonamido)benzoyl)piperazine-1-carboxamido)butanoate (116ap)

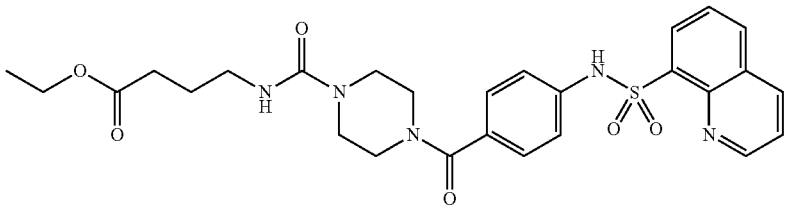

$^1$H NMR (400 MHz, $CDCl_3$) δ: 1.2 (t, 3H), 1.8 (q, 2H), 2.4 (t, 2H), 3.2-3.8 (m, 8H), 3.6 (m, 2H), 4.1 (m, 2H), 5.0 (m, 1H), 7.0-7.2 (m, 4H), 7.6 (m, 2H), 8.0 (m, 1H), 8.4 (m, 2H), 8.6 (m, 1H), 9.1 (m, 1H); HPLC Purity: 98.7%; LCMS, m/z found 554.19 $(M+1)^+$.

Ethyl 3-(4-(4-(quinoline-8-sulfonamido)benzoyl)piperazine-1-carboxamido)propanoate (116aq)

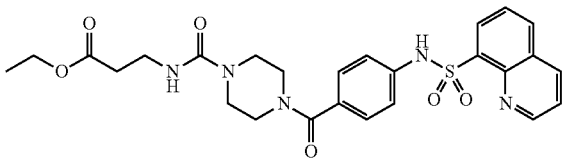

$^1$NMR (400 MHz, $CD_3OD$) δ: 1.2 (t, 3H), 2.5 (t, 2H), 3.2-3.8 (m, 8H), 3.6 (m, 2H), 4.1 (m, 2H), 7.2 (m, 4H), 7.6 (m, 2H), 8.2 (m, 1H), 8.4 (m, 2H), 9.1 (m, 1H); HPLC Purity: 99.3%; LCMS, m/z found 540.1 $(M+1)^+$.

N-(3-Chloropropyl)-4-(4-(quinoline-8-sulfonamido)benzoyl)piperazine-1-carboxamide (116ar)

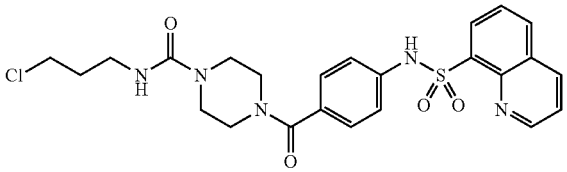

$^1$H NMR (400 MHz, $CD_3OD$) δ: 2.5 (m, 2H), 3.6 (t, 2H), 3.8 (t, 3H), 3.2-3.8 (m, 8H), 7.2 (m, 4H), 7.6 (m, 2H), 8.2 (m, 1H), 8.4 (m, 2H), 9.1 (m, 1H); HPLC Purity: 98.3%; LCMS, m/z found 517.1 $(M+1)^+$.

N-(4-(4-(3-(4-(Trifluoromethyl)phenyl)propanoyl) piperazine-1-carbonyl)phenyl)quinoline-8-sulfonamide (116 as)

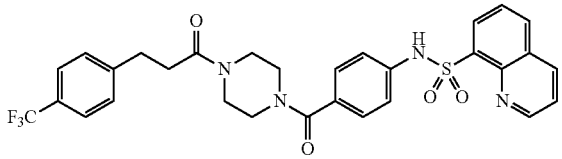

$^1$H NMR (400 MHz, DMSO-$d_6$) δ: 2.7 (t, 2H), 2.9 (t, 2H), 3.2-3.8 (m, 8H), 7.2 (m, 4H), 7.5 (m, 2H), 7.6-7.8 (m, 4H), 8.3 (m, 1H), 8.4-8.6 (m, 2H), 9.1 (m, 1H), 10.5 (s, 1H); HPLC Purity: 99.0%; LCMS, m/z found 597.45 $(M+1)^+$.

Isobutyl 4-(4-(quinoline-8-sulfonamido)benzoyl) piperazine-1-carboxylate (116 at)

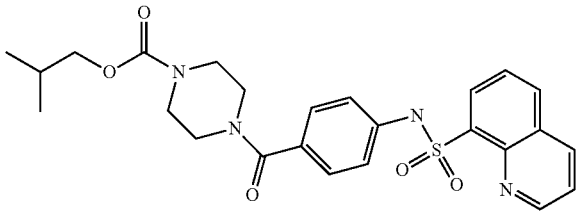

$^1$H NMR (400 MHz, DMSO-$d_6$) δ: 0.8-0.91 (t, 6H), 1.90 (m, 1H), 3.4-3.6 (m, 8H), 3.8 (d, 2H), 7.0-7.2 (m, 4H), 7.6-7.8 (m, 2H), 8.2 (m, 1H), 8.4-8.6 (m, 2H), 9.1 (m, 1H), 10.5 (s, 1H); HPLC Purity: 99.91%; LCMS, m/z found 497.18 $(M+1)^+$.

Ethyl 4-(4-(quinoline-8-sulfonamido)benzoyl)piperazine-1-carboxylate (116au)

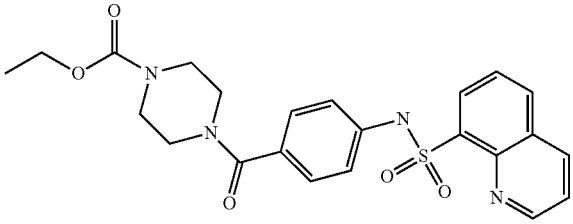

$^1$H NMR (400 MHz, DMSO-$d_6$) δ: 1.3 (t, 3H), 3.4-3.6 (m, 8H), 4.1 (q, 2H), 7.2 (m, 4H), 7.7-7.8 (m, 2H), 8.2 (m, 1H), 8.5-8.6 (m, 2H), 9.2 (m, 1H), 10.4 (s, 1H); HPLC Purity: 99.65%; LCMS, m/z found 469.10 $(M+1)^+$.

Isopropyl 4-(4-(quinoline-8-sulfonamido)benzoyl) piperazine-1-carboxylate (116av)

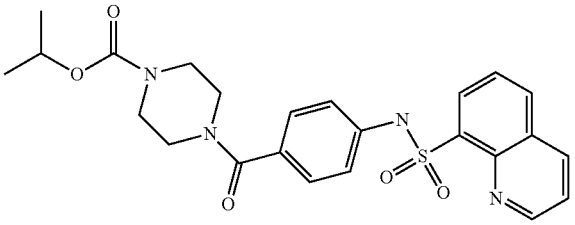

$^1$H NMR (400 MHz, DMSO-$d_6$) δ: 1.02-1-21. (m, 6H), 4.81-4.9 (m, 1H), 7.0-7.2 (m, 4H), 7.6-7.8 (m, 2H), 8.2 (m, 1H), 8.4-8.6 (m, 2H), 9.1 (m, 1H), 10.5 (s, 1H); HPLC Purity: 94.12%; LCMS, m/z found 481.51 $(M+1)^+$.

Phenyl 4-(4-(quinoline-8-sulfonamido)benzoyl)piperazine-1-carboxylate (116aw)

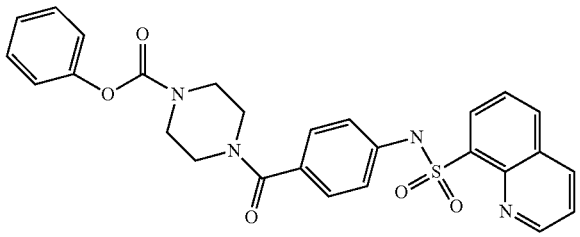

$^1$H NMR (400 MHz, DMSO-$d_6$) δ: 3.4-3.8 (m, 8H), 7.0-7.2 (m, 7H), 7.4-7.6 (m, 2H), 7.8.-7.85 (m, 2H), 8.2-8.6 (m, 3H), 9.1 (m, 1H), 10.5 (s, 1H); HPLC Purity: 99.71%; LCMS, m/z found 517.25 $(M+1)^+$.

3-Fluorophenyl 4-(4-(quinoline-8-sulfonamido)benzoyl)piperazine-1-carboxylate (116ax)

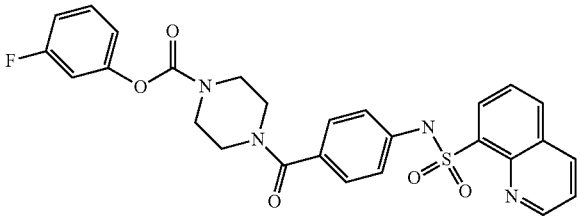

$^1$H NMR (400 MHz, DMSO-$d_6$) δ: 3.4-3.8. (m, 8H), 7.0-7.2 (m, 7H), 7.4-7.6 (m, 1H), 7.8.-7.85 (m, 2H), 8.2-8.6 (m, 3H), 9.1 (m, 1H), 10.5 (s, 1H); HPLC Purity: 95.75%; LCMS, m/z found 535.25 $(M+1)^+$.

4-Fluorophenyl 4-(4-(quinoline-8-sulfonamido)benzoyl)piperazine-1-carboxylate (116ay)

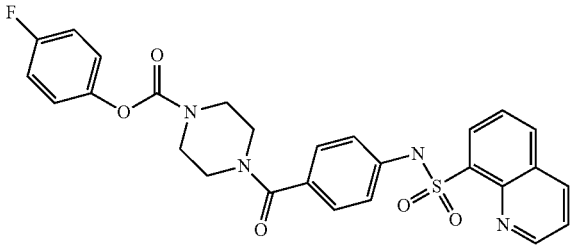

$^1$H NMR (400 MHz, DMSO-$d_6$) δ: 3.4-3.8 (m, 8H), 7.0-7.2 (m, 8H), 7.8-7.85 (m, 2H), 8.2-8.6 (m, 3H), 9.1 (m, 1H), 10.5 (s, 1H); HPLC Purity: 95.05%; LCMS, m/z found 535.27 $(M+1)^+$.

4-Chlorophenyl 4-(4-(quinoline-8-sulfonamido)benzoyl)piperazine-1-carboxylate (116az)

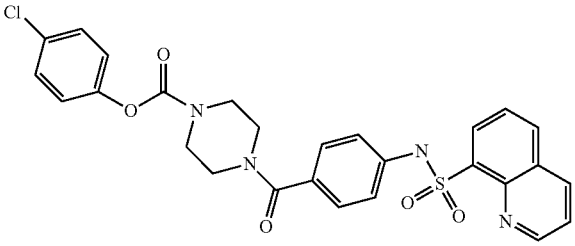

$^1$H NMR (400 MHz, DMSO-$d_6$) δ: 3.4-3.8 (m, 8H), 7.0-7.2 (m, 6H), 7.4 (d, 2H), 7.7 (m, 2H), 8.3-8.5 (m, 3H), 9.2 (m, 1H), 10.5 (s, 1H); HPLC Purity: 99.41%; LCMS, m/z found 549.56 $(M)^+$.

p-Tolyl 4-(4-(quinoline-8-sulfonamido)benzoyl)piperazine-1-carboxylate (116ba)

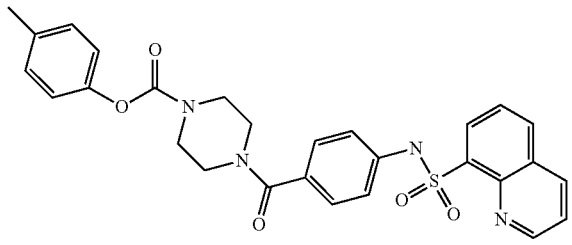

$^1$H NMR (400 MHz, DMSO-$d_6$) δ: 2.2 (s, 3H), 3.2-3.8 (m, 8H), 7.0 (m, 2H), 7.2 (m, 6H), 7.6-7.8 (m, 2H), 8.3 (m, 1H), 8.4-8.6 (m, 2H), 9.1 (m, 1H), 10.5 (s, 1H); HPLC Purity: 99.5%; LCMS, m/z found 531.58 $(M+1)^+$.

3-Chlorophenyl 4-(4-(quinoline-8-sulfonamido)benzoyl)piperazine-1-carboxylate (116bb)

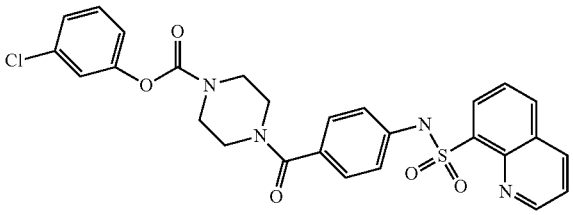

$^1$H NMR (400 MHz, DMSO-$d_6$) δ: 3.4-3.8 (m, 8H), 7.0-7.2 (m, 8H), 7.6-7.8 (m, 2H), 8.2-8.6 (m, 3H), 9.1 (m, 1H), HPLC Purity: 99.79%; LCMS, m/z found 549.58 $(M)^+$.

m-Tolyl 4-(4-(quinoline-8-sulfonamido)benzoyl)piperazine-1-carboxylate (116bc)

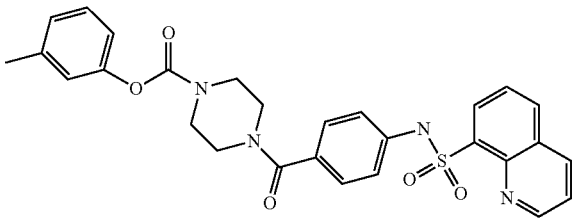

$^1$H NMR (400 MHz, DMSO-$d_6$) δ: 2.23-2.4 (t, 3H), 3.4-3.8. (t, 8H), 6.82-6.98 (m, 6H), 7.0-7.2 (m, 6H), 7.6-7.8 (m, 2H), 8.2-8.6 (m, 3H), 9.1 (m, 1H); HPLC Purity: 99.26%; LCMS, m/z found 531.16 $(M+1)^+$.

(S)-Tetrahydrofuran-3-yl 4-(4-(quinoline-8-sulfonamido)benzoyl)piperazine-1-carboxylate (116bd)

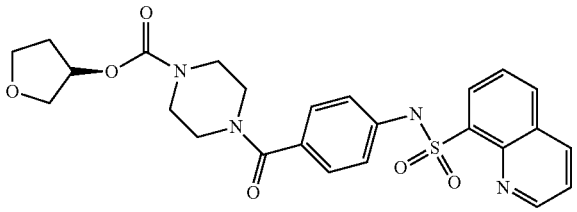

$^1$H NMR (400 MHz, DMSO-$d_6$) δ: 2.23-2.4 (m, 2H), 2.6-2.98 (m, 4H), 3.4-3.8 (t, 8H), 3.8-3.95 (m, 4H), 5.23-5.35 (m, 1H), 7.0-7.2 (m, 4H), 7.6-7.8 (m, 2H), 8.0-8.1 (d, 2H), 8.32-8.45 (dd, 2H), 9.1 (m, H); HPLC Purity: 96.89%; LCMS, m/z found 533.05 $(M+23)^+$.

(Tetrahydrofuran-2-yl)methyl 4-(4-(quinoline-8-sulfonamido)benzoyl)piperazine-1-carboxylate (116be)

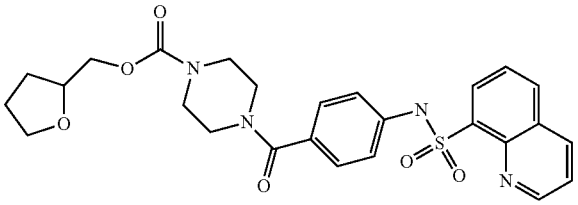

$^1$H NMR (400 MHz, DMSO-$d_6$) δ: 2.23-2.4 (m, 3H), 3.4-3.8 (t, 8H), 3.8-3.95 (m, 4H), 7.0-7.2 (m, 4H), 7.6-7.8 (m, 2H), 8.0-8.1 (d, 2H), 8.32-8.45 (dd, 3H), 9.1 (m, 1H); HPLC Purity: 99.84%; LCMS, m/z found 525.10 $(M+1)^+$.

2-Cyclopentylethyl 4-(4-(quinoline-8-sulfonamido) benzoyl)piperazine-1-carboxylate (116bf)

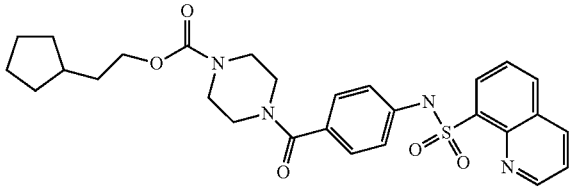

$^1$H NMR (400 MHz, DMSO-$d_6$) δ: 1.2-1.32 (d, 4H), 2.0-2.12 (m, 8H), 3.4-3.8 (t, 8H), 4.62-4.72 (m, 1H), 7.0-7.2 (m, 6H), 7.6-7.8 (m, 2H), 8.0-8.1 (d, 2H), 8.32-8.45 (dd, 3H), 9.1 (m, 1H); HPLC Purity: 99.89%; LCMS, m/z found 537.10 $(M+1)^+$.

2-Cyclohexylethyl 4-(4-(quinoline-8-sulfonamido) benzoyl)piperazine-1-carboxylate (116bg)

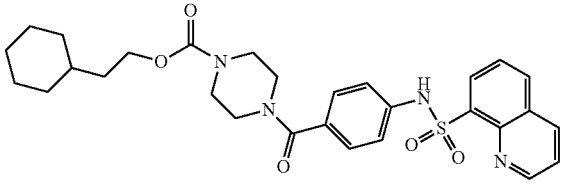

[$^1$H NMR (400 MHz, $CDCl_3$) δ: 1.0 (m, 2H), 1.2 (m, 7H), 1.5 (m, 1H), 1.6 (m, 5H), 3.2-3.8 (m, 8H), 7.0-7.2 (m, 4H), 7.6-7.8 (m, 2H), 8.0 (m, 1H), 8.2-8.4 (m, 2H), 8.6 (m, 2H), 9.1 (m, 1H);] HPLC Purity: 99.6%; LCMS, m/z found 551.45 $(M+1)^+$.

Synthesis of piperazine Derivatives with 3-methyl, 2-methyl, 3-fluoro, 3-chloro, 3-hydroxy or 3-methoxy Substituted Phenyl Rings Scheme 17

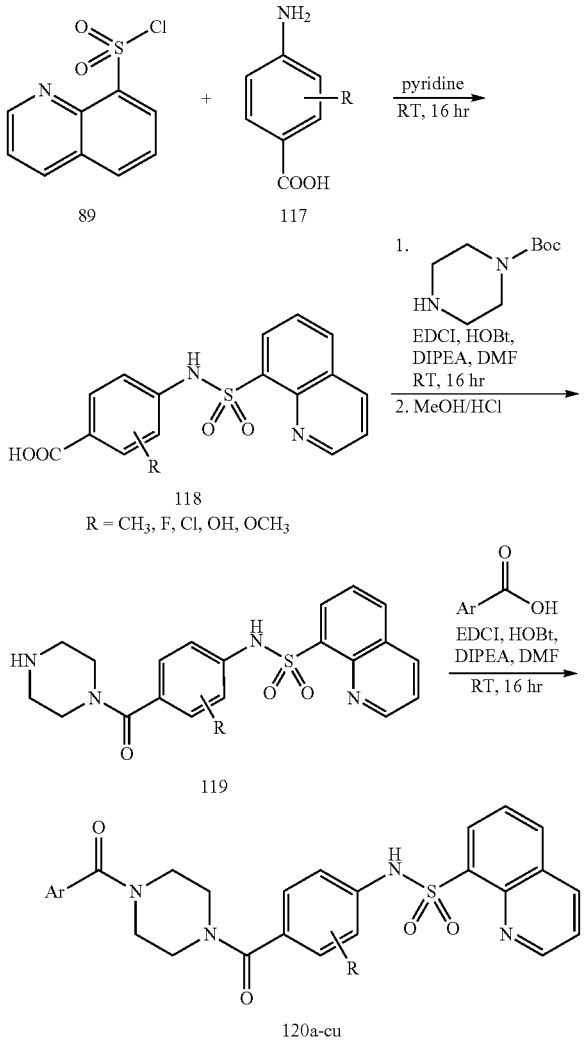

General Procedure for the Synthesis of Sulfonamide 118:

To a stirred solution of amine 7 (30.3 mmol) under nitrogen atmosphere was added pyridine (50 ml) at 0° C. and stirred for 10 min Quinoline-8-sulfonyl chloride 89 (8.94 gm, 39.4 mmol) was then added to the reaction mixture at the same temperature. The resulting mixture was stirred for 16 hr at RT. After completion of the reaction, the solvent was removed under low pressure. The traces of pyridine were removed by co-distillation with toluene. Diethylether was added to the resulting residue, and the solid product was filtered out and air-dried. The resulting crude product (8.0 gm, 74%) was then to the next step without further purification.

General Procedure for the Synthesis of Sulfonamide 119:

EDCI (3.8 g, 19.8 mmol) and HOBT (2.67 g, 19.8 mmol) were added to a stirred solution of the acid 118 (19.8 mmol) in anhydrous DMF. The temperature of the mixture was reduced to 0° C., at which time DIPEA (11 ml, 59.45 mmol)

was added under nitrogen atmosphere and the resultant solution (or suspension) was stirred at room temperature for 30 min Boc-piperazine (3.68 g, 19.8 mmol) was then added at 0° C. The reaction mixture was then brought to room temperature and stirred overnight. After completion of the reaction, the reaction mixture was diluted with water and extracted with ethyl acetate (3×70 ml). The organic layer was washed with water (3×50 ml), dried over anhydrous sodium sulfate, filtered and concentrated over the rotary evaporator to get the crude product. Crude product was purified by column chromatography (60-120 silica gel, 2% MeOH-DCM) to get pure product, Boc-119 (81%) as an off-white solid, which was subjected to the treatment with methanolic HCl (100 ml) for 2 hr at RT. After the complete cleavage of Boc-group, the solvent was removed under low pressure, to give the crude product as an HCl salt. The aqueous solution of the salt was washed with diethylether and basified with $NaHCO_3$ (pH 10). The desired product was then partitioned into ethyl acetate, dried with anhydrous $Na_2SO_4$ and the solvent removed under low pressure to get the free amine 119 as off white solid (95%).

General Procedure for the Synthesis of Amides 120a-cu:

EDCI (48 mg, 0.2525 mmol) and HOBT (34 mg, 0.2525 mmol) were added to a stirred solution of the Ar—COOH (0.2525 mmol) in anhydrous DMF. The temperature of the mixture was reduced to 0° C., at which time DIPEA (139 μl, 0.7575 mmol) was added under nitrogen atmosphere and the resultant solution (or suspension) was stirred at room temperature for 30 min Amine 119 (100 mg, 0.2525 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (3×10 ml), dried over anhydrous sodium sulfate, filtered and concentrated over the rotary evaporator to get the crude product. Crude product was purified by either by silica column chromatography or preparative HPLC to obtain the pure products in 52-68% yields.

N-(2-Methyl-4-(4-picolinoylpiperazine-1-carbonyl) phenyl)quinoline-8-sulfonamide (120a)

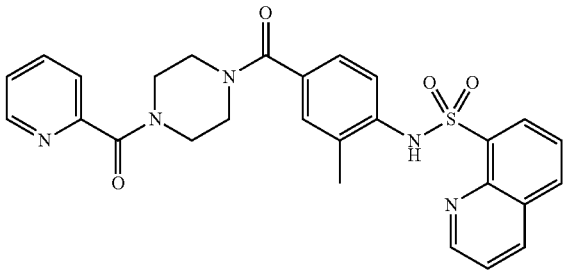

[$^1$H NMR (400 MHz, $CD_3OD$) δ: 2.1 (s, 3H), 3.2-3.8 (m, 8H), 7.0-7.2 (m, 3H), 7.6-7.8 (m, 4H), 8.0 (m, 1H), 8.2-8.4 (m, 2H), 8.6 (m, 2H), 9.1 (m, 1H);] HPLC Purity: 97.9%; LCMS, m/z found 516.1 $(M+1)^+$.

N-(2-Methyl-4-(4-nicotinoylpiperazine-1-carbonyl) phenyl)quinoline-8-sulfonamide (120b)

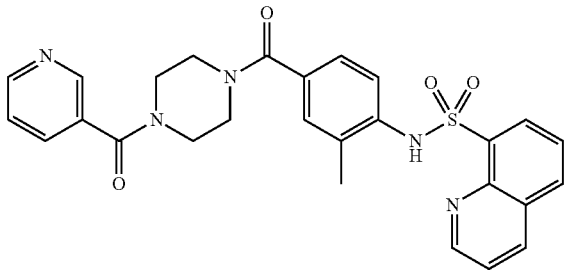

$^1$H NMR (400 MHz, $CDCl_3$) δ: 2.1 (s, 3H), 3.2-3.8 (m, 8H), 7.0-7.2 (m, 3H), 7.6-7.8 (m, 4H), 8.2 (m, 1H), 8.6 (m, 2H), 8.9 (m, 2H), 9.1 (m, 1H), 10.5 (s, 1H); HPLC Purity: 99.3%; LCMS, m/z found 516.1 $(M+1)^+$.

N-(2-Methyl-4-(4-(6-methylpicolinoyl)piperazine-1-carbonyl)phenyl)quinoline-8-sulfonamide (120c)

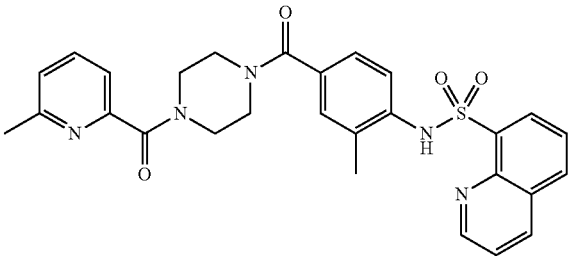

$^1$H NMR (400 MHz, $CDCl_3$) δ: 2.1 (s, 3H), 2.3 (s, 3H), 3.2-3.8 (m, 8H), 7.0-7.2 (m, 3H), 7.6-7.8 (m, 4H), 8.2 (m, 1H), 8.6 (m, 1H), 8.9 (m, 2H), 9.1 (m, 1H), 10.5 (s, 1H); HPLC Purity: 95.5.0%; LCMS, m/z found 530.2 $(M+1)^+$.

N-(2-Methyl-4-(4-(3-(trifluoromethyl)picolinoyl) piperazine-1-carbonyl)phenyl)quinoline-8-sulfonamide (120d)

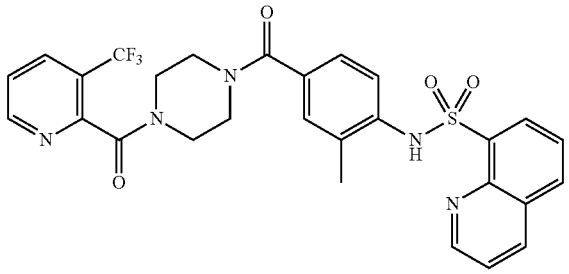

$^1$H NMR (400 MHz, $CDCl_3$) δ: 2.1 (s, 3H), 3.2-3.8 (m, 8H), 7.0-7.2 (m, 2H), 7.4-7.6 (m, 4H), 8.2 (m, 2H), 8.4 (m, 2H), 8.6-8.8 (m, 2H), 9.1 (m, 1H); HPLC Purity: 97.2.0%; LCMS, m/z found 584.1 $(M+1)^+$.

N-(4-(4-(3-Fluoropicolinoyl)piperazine-1-carbonyl)-2-methylphenyl)quinoline-8-sulfonamide (120e)

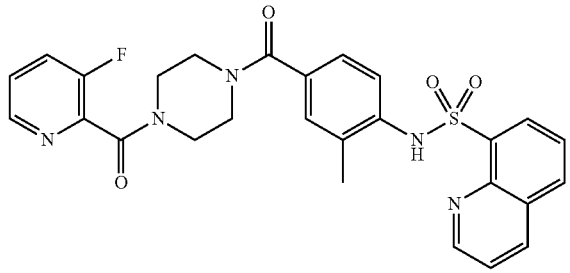

$^1$H NMR (400 MHz, $CDCl_3$) δ: 2.1 (s, 3H), 3.2-3.8 (m, 8H), 7.0-7.2 (m, 2H), 7.4-7.6 (m, 5H), 8.2 (m, 1H), 8.4 (m, 3H), 9.1 (m, 1H); HPLC Purity: 99.6.0%; LCMS, m/z found 534.1 $(M+1)^+$.

N-(4-(4-(4-Chloropicolinoyl)piperazine-1-carbonyl)-2-methylphenyl)quinoline-8-sulfonamide (120f)

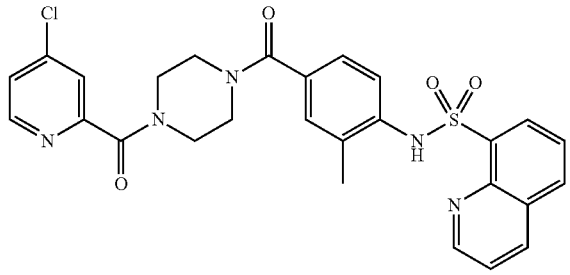

[$^1$H NMR (400 MHz, $CDCl_3$) δ: 2.1 (s, 3H), 3.2-3.8 (m, 8H), 7.0-7.2 (m, 2H), 7.4 (m, 1H), 7.5-7.8 (m, 4H), 8.0 (m, 1H), 8.2 (m, 2H), 8.6 (m, 1H), 9.1 (m, 1H);] HPLC Purity: 93.4%; LCMS, m/z found 550.1 $(M+1)^+$.

N-(4-(4-(4-Fluoropicolinoyl)piperazine-1-carbonyl)-2-methylphenyl)quinoline-8-sulfonamide (120g)

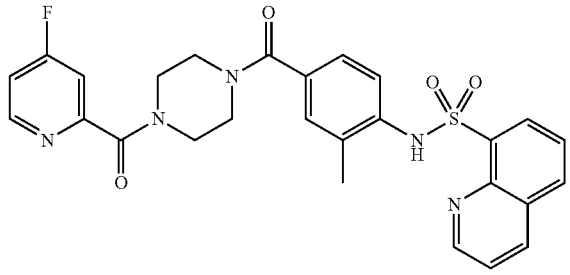

[$^1$H NMR (400 MHz, $CDCl_3$) δ: 2.1 (s, 3H), 3.2-3.8 (m, 8H), 7.0 (m, 2H), 7.4 (m, 1H), 7.5-7.8 (m, 4H), 8.0 (m, 1H), 8.2-8.4 (m, 3H), 9.1 (m, 1H);] HPLC Purity: 99.2%; LCMS, m/z found 534.1 $(M+1)^+$.

N-(2-Methyl-4-(4-(4-(trifluoromethyl)nicotinoyl)piperazine-1-carbonyl)phenyl)quinoline-8-sulfonamide (120h)

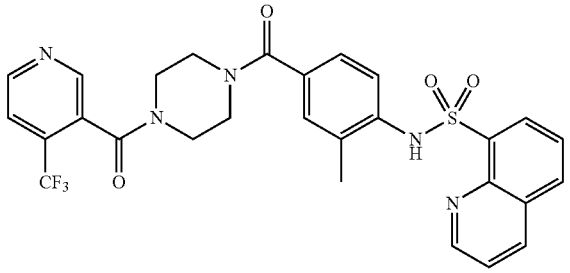

$^1$H NMR (400 MHz, $CDCl_3$) δ: 2.1 (s, 3H), 3.2-3.8 (m, 8H), 7.0 (m, 2H), 7.4 (m, 1H), 7.5-7.6 (m, 3H), 8.4 (m, 3H), 8.7 (s, 1H), 8.8 (m, 1H), 9.1 (m, 1H); HPLC Purity: 95.0%; LCMS, m/z found 584.1 $(M+1)^+$, N-(4-(4-(5-Chloronicotinoyl)piperazine-1-carbonyl)-2-methylphenyl)quinoline-8-sulfonamide (120i)

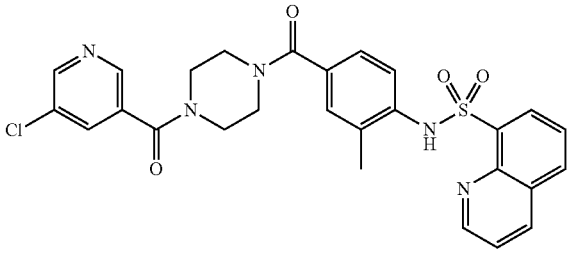

$^1$H NMR (400 MHz, $CDCl_3$) δ: 2.1 (s, 3H), 3.2-3.8 (m, 8H), 7.0 (m, 3H), 7.4 (m, 1H), 7.6-7.8 (m, 2H), 8.1 (m, 1H), 8.2 (m, 2H), 8.8 (m, 2H), 9.1 (m, 1H); HPLC Purity: 98.1%; LCMS, m/z found 550.1 $(M+1)^+$.

N-(4-(4-(5-Fluoronicotinoyl)piperazine-1-carbonyl)-2-methylphenyl)quinoline-8-sulfonamide (120j)

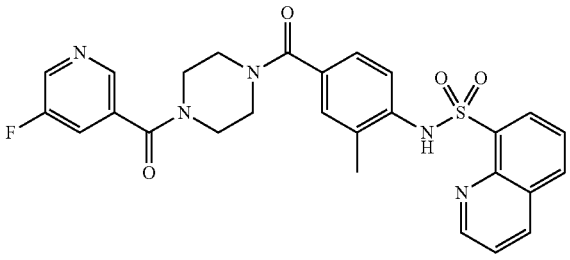

$^1$H NMR (400 MHz, $CDCl_3$) δ: 2.1 (s, 3H), 3.2-3.8 (m, 8H), 7.0 (m, 2H), 7.2-7.4 (m, 2H), 7.6-7.8 (m, 2H), 8.0-8.6 (m, 5H), 9.1 (m, 1H); HPLC Purity: 99.1%; LCMS, m/z found 534.3 $(M+1)^+$.

N-(4-(4-(3-Fluoroisonicotinoyl)piperazine-1-carbonyl)-2-methylphenyl)quinoline-8-sulfonamide (120k)

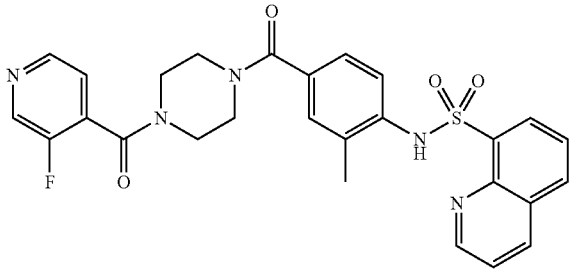

$^1$H NMR (400 MHz, $CDCl_3$) 67 : 2.1 (s, 3H), 3.2-3.8 (m, 8H), 7.0 (m, 2H), 7.2-7.4 (m, 2H), 7.6-7.8 (m, 2H), 8.0 (m, 1H), 8.2-8.6 (m, 4H), 9.1 (m, 1H); HPLC Purity: 95.3%; LCMS, m/z found 534.1 $(M+1)^+$.

N-(4-(4-(3-Chloroisonicotinoyl)piperazine-1-carbonyl)-2-methylphenyl)quinoline-8-sulfonamide (120l)

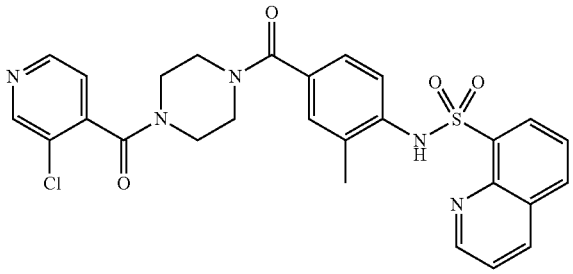

$^1$H NMR (400 MHz, $CDCl_3$) δ: 2.1 (s, 3H), 3.2-3.8 (m, 8H), 7.0 (m, 1H), 7.2-7.4 (m, 4H), 7.6-7.8 (m, 2H), 8.0 (m, 1H), 8.2-8.6 (m, 3H), 9.1 (m, 1H); HPLC Purity: 99.8%; LCMS, m/z found 550.3 $(M+1)^+$.

N-(4-(4-(2-Methoxynicotinoyl)piperazine-1-carbonyl)-2-methylphenyl)quinoline-8-sulfonamide (120m)

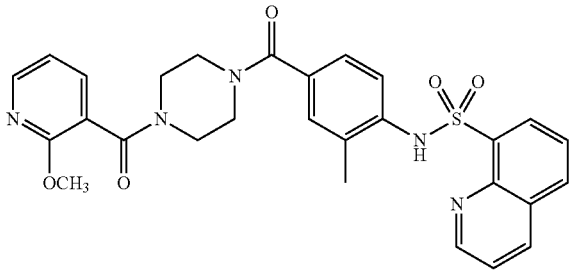

$^1$H NMR (400 MHz, $CDCl_3$) δ: 2.1 (s, 3H), 3.2-3.8 (m, 8H), 7.2-7.4 (m, 4H), 7.6-7.8 (m, 3H), 8.0 (m, 1H), 8.2-8.6 (m, 3H), 9.1 (m, 1H); HPLC Purity: 99.3%; LCMS, m/z found 546.3 $(M+1)^+$.

N-(4-(4-(2-Methoxyisonicotinoyl)piperazine-1-carbonyl)-2-methylphenyl)quinoline-8-sulfonamide (120n)

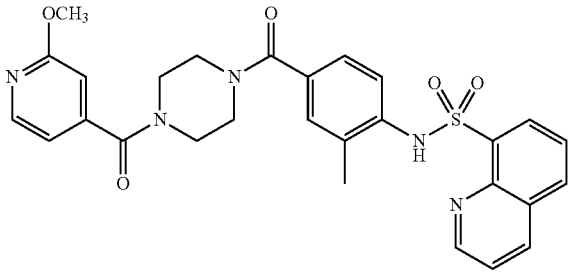

[$^1$H NMR (400 MHz, $CDCl_3$) δ: 2.1 (s, 3H), 3.2-3.8 (m, 8H), 6.7-7.0 (m, 4H), 7.2 (m, 1H), 7.6 (m, 2H), 8.0 (m, 1H), 8.2-8.6 (m, 3H), 9.1 (m, 1H);] HPLC Purity: 98.8%; LCMS, m/z found 546.3 $(M+1)^+$.

N-(2-Methyl-4-(4-(5-(trifluoromethyl)picolinoyl)piperazine-1-carbonyl)phenyl)quinoline-8-sulfonamide (120o)

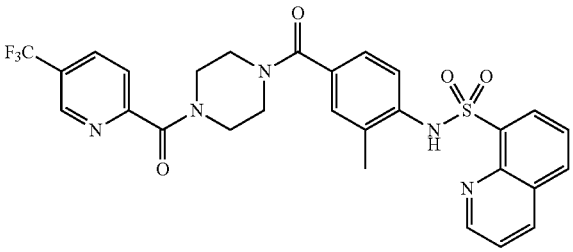

$^1$H NMR (400 MHz, $CDCl_3$) δ: 2.1 (s, 3H), 3.2-3.8 (m, 8H), 7.0 (m, 2H), 7.2 (m, 1H), 7.6 (m, 2H), 7.8 (m, 1H), 8.0 (m, 2H), 8.3-8.5 (m, 2H), 8.8 (s, 1H), 9.1 (m, 1H); HPLC Purity: 91.8%; LCMS, m/z found 584.4 $(M+1)^+$.

N-(2-Methyl-4-(4-(2-(trifluoromethyl)nicotinoyl)piperazine-1-carbonyl)phenyl)quinoline-8-sulfonamide (120p)

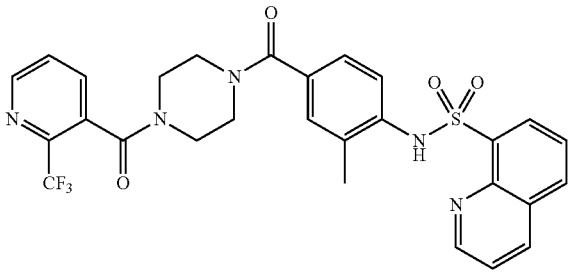

[$^1$H NMR (400 MHz, $CDCl_3$) δ: 2.1 (s, 3H), 3.2-3.8 (m, 8H), 7.0 (m, 3H), 7.4 (m, 1H), 7.6 (m, 4H), 8.0 (m, 1H), 8.3-8.5 (m, 1H), 8.8 (s, 1H), 9.1 (m, 1H);] HPLC Purity: 99.2%; LCMS, m/z found 584.3 $(M+1)^+$.

N-(4-(4-Isonicotinoylpiperazine-1-carbonyl)-2-methylphenyl)quinoline-8-sulfonamide (120q)

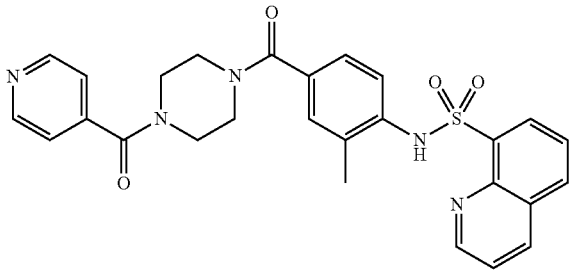

$^1$H NMR (400 MHz, $CDCl_3$) δ: 2.1 (s, 3H), 3.2-3.8 (m, 8H), 7.0 (m, 3H), 7.4 (m, 2H), 7.6 (m, 2H), 8.3 (m, 2H), 8.5 (m, 2H), 9.1 (m, 1H); HPLC Purity: 94.5%; LCMS, m/z found 516.34 $(M+1)^+$.

N-(2-Methyl-4-(4-(pyrazine-2-carbonyl)piperazine-1-carbonyl)phenyl)quinoline-8-sulfonamide (120r)

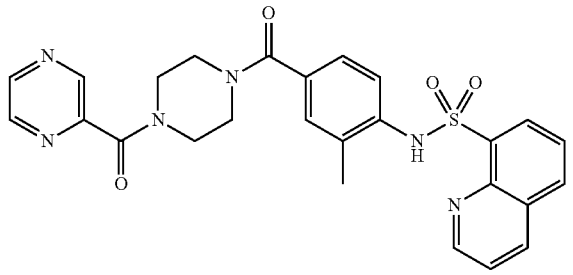

$^1$H NMR (400 MHz, $CDCl_3$) δ: 2.1 (s, 3H), 3.2-3.8 (m, 8H), 7.0-7.2 (m, 2H), 7.4 (m, 1H), 7.6 (m, 2H), 8.0 (m, 1H), 8.3 (m, 2H), 8.6 (m, 1H), 8.8 (m, 1H), 9.0 (s, 1H), 9.1 (m, 1H); HPLC Purity: 99.4%; LCMS, m/z found 517.15 $(M+1)^+$.

N-(4-(4-(2,3-Difluorobenzoyl)piperazine-1-carbonyl)-2-methylphenyl)quinoline-8-sulfonamide (120s)

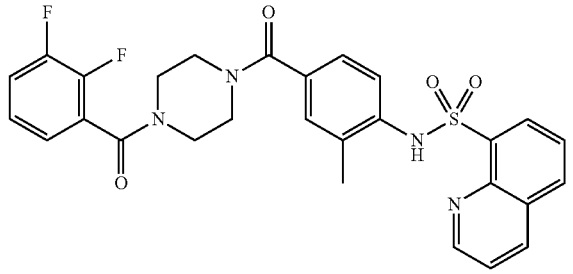

[$^1$H NMR (400 MHz, $CD_3OD$) δ: 2.1 (s, 3H), 3.2-3.8 (m, 8H), 7.0 (m, 1H), 7.2 (m, 4H), 7.4 (m, 1H), 8.7 (m, 2H), 8.2-8.5 (m, 3H), 9.1 (m, 1H);] HPLC Purity: 98.6%; LCMS, m/z found 551.35 $(M+1)^+$.

N-(4-(4-(2,6-Difluorobenzoyl)piperazine-1-carbonyl)-2-methylphenyl)quinoline-8-sulfonamide (120t)

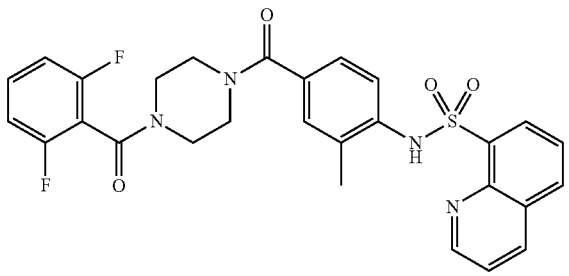

$^1$H NMR (400 MHz, $CD_3OD$) δ: 2.1 (s, 3H), 3.2-3.8 (m, 8H), 7.0-7.2 (m, 5H), 7.5 (m, 2H), 7.7 (m, 2H), 8.2-8.5 (m, 3H), 9.1 (m, 1H); HPLC Purity: 96.4%; LCMS, m/z found 551.35 $(M+1)^+$.

N-(4-(4-(3,4-Difluorobenzoyl)piperazine-1-carbonyl)-2-methylphenyl)quinoline-8-sulfonamide (120u)

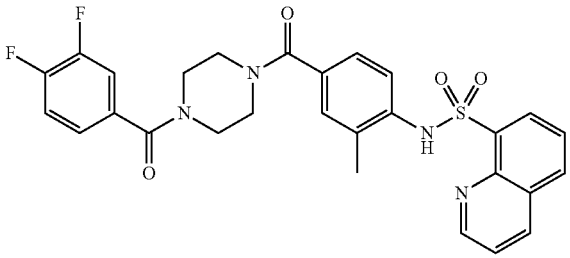

$^1$H NMR (400 MHz, $CD_3OD$) δ: 2.1 (s, 3H), 3.2-3.8 (m, 8H), 7.0 (m, 2H), 7.2-7.5 (m, 5H), 7.7 (m, 2H), 8.2-8.5 (m, 3H), 9.1 (m, 1H); HPLC Purity: 97.9%; LCMS, m/z found 551.35 $(M+1)^+$.

N-(4-(4-(2-Fluorobenzoyl)piperazine-1-carbonyl)-2-methylphenyl)quinoline-8-sulfonamide (120v)

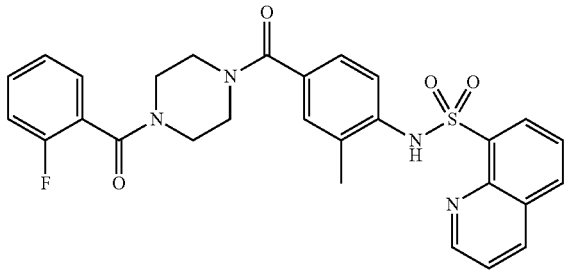

$^1$H NMR (400 MHz, $CDCl_3$) δ: 2.1 (s, 3H), 3.2-3.8 (m, 8H), 7.0-7.2 (m, 4H), 7.2-7.5 (m, 3H), 7.7 (m, 2H), 8.0-8.5 (m, 3H), 9.1 (m, 1H); HPLC Purity: 93.6%; LCMS, m/z found 533.27 $(M+1)^+$.

N-(2-Methyl-4-(4-(2-phenylacetyl)piperazine-1-carbonyl)phenyl)quinoline-8-sulfonamide (120w)

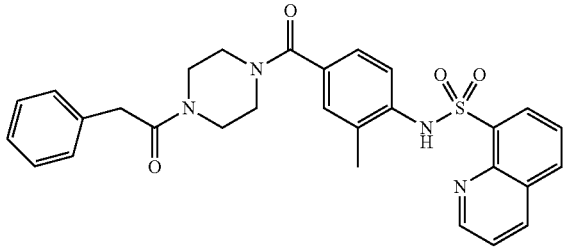

$^1$H NMR (400 MHz, $CDCl_3$) δ: 2.1 (s, 3H), 3.2-3.8 (m, 8H), 3.9 (m, 2H), 7.0 (m, 1H), 7.2-7.5 (m, 7H), 7.7 (m, 2H), 8.2-8.5 (m, 4H), 9.1 (m, 1H); HPLC Purity: 94.6%; LCMS, m/z found 529.35 $(M+1)^+$.

N-(4-(4-(2-(4-Fluorophenyl)acetyl)piperazine-1-carbonyl)-2-methylphenyl)quinoline-8-sulfonamide

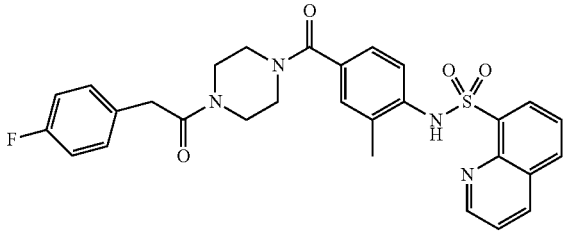

$^1$H NMR (400 MHz, $CD_3OD$) δ: 2.1 (s, 3H), 3.2-3.8 (m, 8H), 7.0-7.5 (m, 7H), 7.7 (m, 2H), 8.2-8.5 (m, 3H), 9.1 (m, 1H); HPLC Purity: 95.1%; LCMS, m/z found 547.0 $(M+1)^+$.

N-(4-(4-(2-(4-Fluorophenyl)-2-methylpropanoyl) piperazine-1-carbonyl)-2-methylphenyl)quinoline-8-sulfonamide (120y)

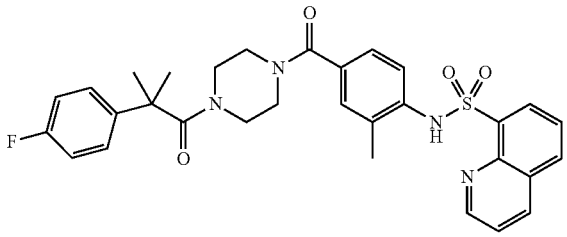

$^1$H NMR (400 MHz, $CDCl_3$) δ: 1.6 (s, 6H), 2.1 (s, 3H), 3.2-3.8 (m, 8H), 6.9-7.0 (m, 3H), 7.2-7.5 (m, 3H), 7.7 (m, 2H), 8.2-8.5 (m, 4H), 9.1 (m, 1H); HPLC Purity: 99.1%; LCMS, m/z found 575.1 $(M+1)^+$.

N-(2-Methyl-4-(4-(thiazole-4-carbonyl)piperazine-1-carbonyl)phenyl)quinoline-8-sulfonamide (120z)

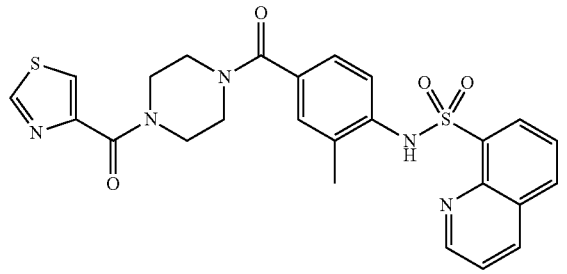

$^1$H NMR (400 MHz, $CD_3OD$) δ: 2.1 (s, 3H), 3.2-3.8 (m, 8H), 7.0-7.2 (m, 3H), 7.6-7.8 (m, 2H), 8.1-8.5 (m, 4H), 9.1 (m, 2H); HPLC Purity: 98.6%; LCMS, m/z found 522.05 $(M+1)^+$.

N-(4-(4-(1,2,3-Thiadiazole-4-carbonyl)piperazine-1-carbonyl)-2-methylphenyl)quinoline-8-sulfonamide (120aa)

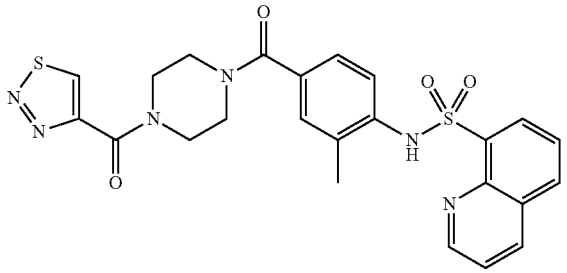

[$^1$H NMR (400 MHz, DMSO-$d_6$) δ: 2.1 (s, 3H), 3.2-3.8 (m, 8H), 7.0-7.2 (m, 3H), 7.4-7.6 (m, 2H), 7.7 (m, 2H), 8.2-8.5 (m, 3H), 9.1 (m, 1H), 9.4 (s, 1H), 9.6 (s, 1H);] HPLC Purity: 99.1%; LCMS, m/z found 523.15 $(M+1)^+$.

Cyclopentyl 4-(3-methyl-4-(quinoline-8-sulfonamido)benzoyl)piperazine-1-carboxylate (120ab)

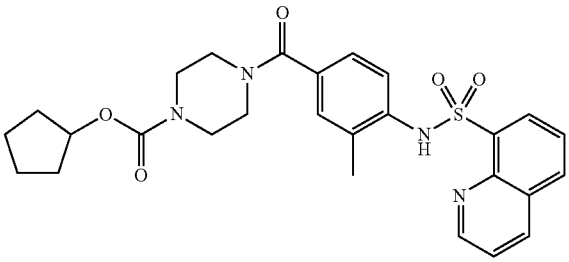

$^1$H NMR (400 MHz, $CDCl_3$) δ: 1.4-1.9 (m, 8H), 2.1 (s, 3H), 3.2-3.8 (m, 8H), 5.1 (s, 1H), 7.0-7.2 (m, 1H), 7.4 (m, 3H), 7.7 (m, 1H), 8.2 (m, 1H), 8.2-8.4 (m, 2H), 9.1 (m, 1H); HPLC Purity: 97.4%; LCMS, m/z found 523.30 $(M+1)^+$.

Cyclohexyl 4-(3-methyl-4-(quinoline-8-sulfonamido)benzoyl)piperazine-1-carboxylate (120ac)

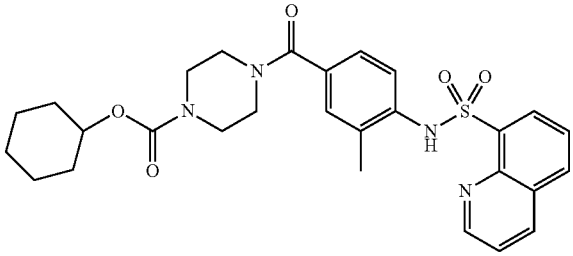

$^1$H NMR (400 MHz, $CDCl_3$) δ: 0.9 (m, 1H), 1.2-1.7 (m, 10H), 2.1 (s, 3H), 3.2-3.8 (m, 8H), 5.1 (s, 1H), 7.0-7.4 (m, 3H), 7.6 (m, 2H), 8.1 (m, 1H), 8.2-8.4 (m, 2H), 9.1 (m, 1H); HPLC Purity: 99.0%; LCMS, m/z found 537.19 $(M+1)^+$.

Azetidin-3-yl-4-(3-methyl-4-(quinoline-8-sulfonamido)benzoyl)piperazine-1-carboxylate (120ad)

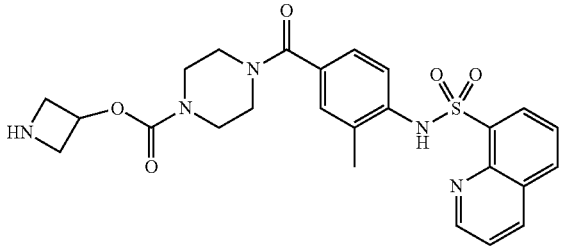

$^1$H NMR (400 MHz, DMSO-$d_6$) δ: 0.9 (m, 1H), 1.2-1.7 (m, 4H), 2.1 (s, 3H), 3.2-3.8 (m, 8H), 5.1 (s, 1H), 7.0-7.4 (m, 3H), 7.6 (m, 2H), 8.3 (m, 2H), 8.6 (m, 1H), 9.1 (m, 1H); HPLC Purity: 92.9%; LCMS, m/z found 510.31 $(M+1)^+$.

1-Methylazetidin-3-yl 4-(3-methyl-4-(quinoline-8-sulfonamido)benzoyl)piperazine-1-carboxylate (120ae)

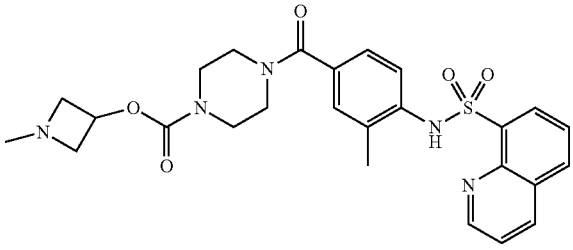

$^1$H NMR (400 MHz, DMSO-$d_6$) δ: 2.0 (s, 3H), 2.1 (s, 3H), 2.9 (m, 4H), 3.2-3.8 (m, 8H), 5.1 (s, 1H), 7.0-7.4 (m, 3H), 7.8 (m, 2H), 8.3 (m, 2H), 8.6 (m, 1H), 9.1 (m, 1H), 9.4 (s, 1H); HPLC Purity: 92.0%; LCMS, m/z found 524.05 $(M+1)^+$.

(Tetrahydrofuran-2-yl)methyl 4-(3-methyl-4-(quinoline-8-sulfonamido)benzoyl)piperazine-1-carboxylate (120af)

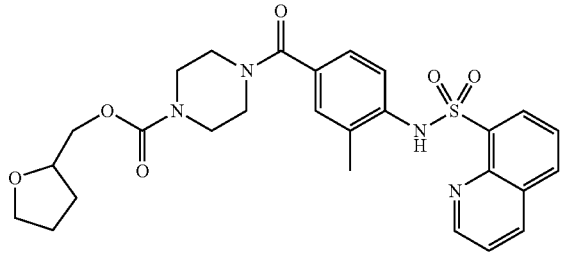

$^1$H NMR (400 MHz, $CDCl_3$) δ: 1.1 (m, 2H), 1.8-2.0 (m, 4H), 2.1 (s, 3H), 2.9 (m, 4H), 3.2-3.8 (m, 8H), 5.1 (s, 1H), 7.0-7.2 (m, 2H), 7.2-7.4 (m, 1H), 7.6 (m, 2H), 8.0-8.4 (m, 3H), 9.1 (m, 1H); HPLC Purity: 99.40%; LCMS, m/z found 539.15 $(M+1)^+$.

2-Cyclopentylethyl 4-(3-methyl-4-(quinoline-8-sulfonamido)benzoyl)piperazine-1-carboxylate (120ag)

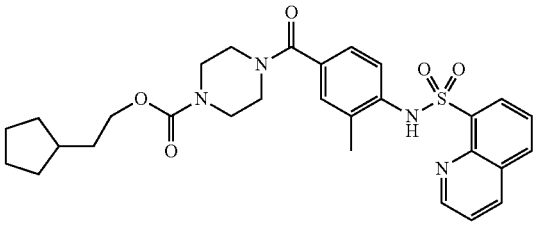

$^1$H NMR (400 MHz, $CDCl_3$) δ: 1.2 (m, 4H), 1.4-1.6 (m, 8H), 2.0 (m, 1H), 2.1 (s, 3H), 3.2-3.8 (m, 8H), 5.1 (s, 1H), 7.0-7.2 (m, 2H), 7.2-7.4 (m, 1H), 7.6 (m, 2H), 8.0-8.4 (m, 3H), 9.1 (m, 1H); HPLC Purity: 99.50%; LCMS, m/z found 551.1 $(M+1)^+$.

Tetrahydrofuran-3-yl 4-(3-methyl-4-(quinoline-8-sulfonamido)benzoyl)piperazine-1-carboxylate (120ah)

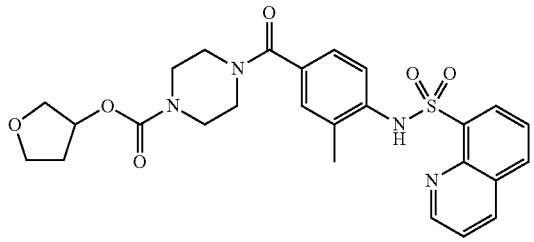

$^1$H NMR (400 MHz, $CDCl_3$) δ: 2.0 (m, 2H), 2.2 (s, 3H), 2.5 (s, 1H), 3.2-3.8 (m, 8H), 4.0 (m, 4H), 5.1 (s, 1H), 7.0-7.2 (m, 1H), 7.2-7.4 (m, 2H), 7.6 (m, 2H), 8.0-8.4 (m, 3H), 9.1 (m, 1H); HPLC Purity: 99.50%; LCMS, m/z found 525.05 $(M+1)^+$.

2-Cyclohexylethyl 4-(3-methyl-4-(quinoline-8-sulfonamido)benzoyl)piperazine-1-carboxylate (120ai)

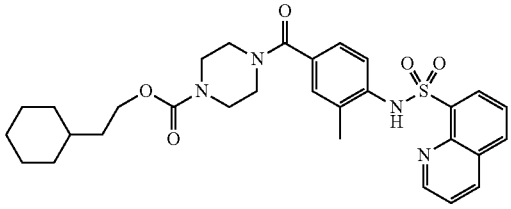

[$^1$H NMR (400 MHz, $CDCl_3$) δ: 2.0 (m, 2H), 2.2 (s, 3H), 2.5 (s, 1H), 3.2-3.8 (m, 8H), 4.0 (m, 4H), 5.1 (s, 1H), 7.0-7.2 (m, 1H), 7.2-7.4 (m, 2H), 7.6 (m, 2H), 8.0-8.4 (m, 3H), 9.1 (m, 1H);] HPLC Purity: 99.50[%; LCMS, m/z found 525.05 $(M+1)^+$].

N-(2-Fluoro-4-(4-picolinoylpiperazine-1-carbonyl)phenyl)quinoline-8-sulfonamide (120aj)

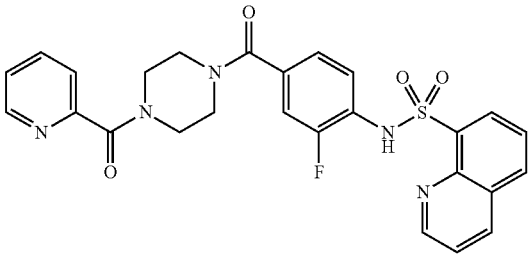

$^1$H NMR (400 MHz, $CDCl_3$) δ: 1.1 (m, 7H), 1.6-1.8 (m, 5H), 2.1 (s, 3H), 3.2-3.8 (m, 8H), 4.7 (m, 1H), 7.0-7.2 (m, 2H), 7.4-7.6 (m, 3H), 8.0-8.4 (m, 3H), 9.1 (m, 1H); HPLC Purity: 99.60%; LCMS, m/z found 565.45 $(M+1)^+$.

N-(2-Fluoro-4-(4-nicotinoylpiperazine-1-carbonyl)phenyl)quinoline-8-sulfonamide (120ak)

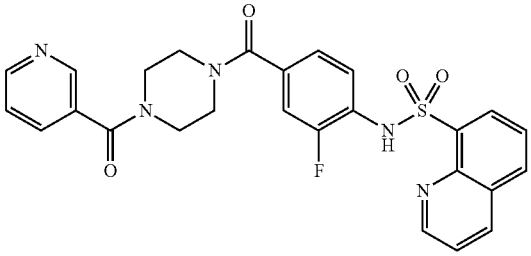

$^1$H NMR (400 MHz, DMSO-$d_6$) δ: 3.2-3.8 (m, 8H), 7.0-7.2 (m, 2H), 7.4-7.6 (m, 3H), 8.0-8.4 (m, 3H), 8.7 (m, 3H), 8.9 (m, 1H), 9.1 (m, 1H); HPLC Purity: 94.6%; LCMS, m/z found 520.25 $(M+1)^+$.

N-(2-Fluoro-4-(4-isonicotinoylpiperazine-1-carbonyl)phenyl)quinoline-8-sulfonamide (120al)

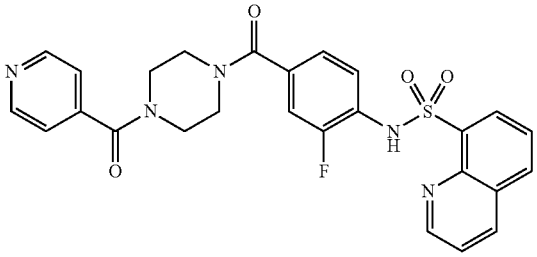

$^1$H NMR (400 MHz, DMSO-$d_6$) δ: 3.2-3.8 (m, 8H), 7.0-7.2 (m, 2H), 7.4-7.6 (m, 3H), 8.0-8.4 (m, 3H), 8.7 (m, 3H), 8.9 (m, 1H), 9.1 (m, 1H), 10.5 (s 1H); HPLC Purity: 93.8%; LCMS, m/z found 518.46 $(M+1)^+$.

N-(2-Fluoro-4-(4-(pyrazine-2-carbonyl)piperazine-1-carbonyl)phenyl)quinoline-8-sulfonamide (120 am)

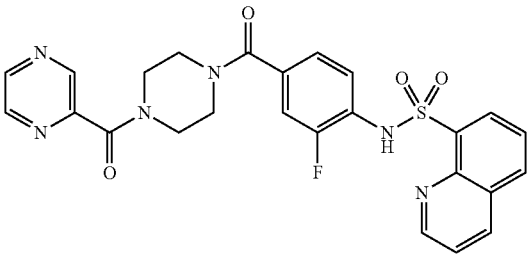

$^1$H NMR (400 MHz, DMSO-$d_6$) δ: 3.2-3.8 (m, 8H), 7.0-7.4 (m, 3H), 7.6-7.8 (m, 2H), 8.0-8.4 (m, 2H), 8.7 (m, 3H), 9.1 (m, 1H), 10.0 (s 1H); HPLC Purity: 99.8%; LCMS, m/z found 521.24 $(M+1)^+$

.

N-(4-(4-(2,6-Difluorobenzoyl)piperazine-1-carbonyl)-2-fluorophenyl)quinoline-8-sulfonamide (120an)

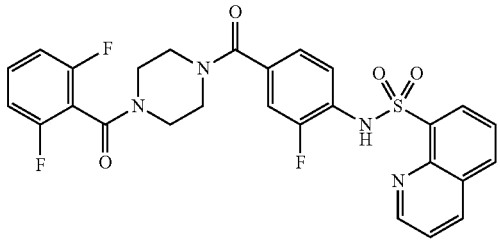

$^1$H NMR (400 MHz, DMSO-$d_6$) δ: 3.2-3.8 (m, 8H), 7.0-7.4 (m, 3H), 7.6-7.8 (m, 5H), 8.0-8.4 (m, 3H), 9.1 (m, 1H), 10.0 (s, 1H); HPLC Purity: 99.8%; LCMS, m/z found 555.21 $(M+1)^+$.

N-(4-(4-(3,4-Difluorobenzoyl)piperazine-1-carbonyl)-2-fluorophenyl)quinoline-8-sulfonamide (120ao)

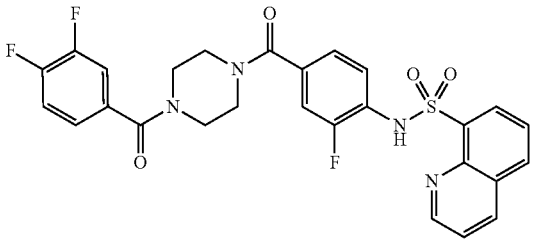

$^1$H NMR (400 MHz, DMSO-$d_6$) δ: 3.2-3.8 (m, 8H), 7.0-7.4 (m, 4H), 7.6-7.8 (m, 4H), 8.0-8.4 (m, 2H), 8.7 (m, 1H), 9.1 (m, 1H), 10.0 (s 1H); HPLC Purity: 97.9%; LCMS, m/z found 555.14 $(M+1)^+$.

N-(2-Fluoro-4-(4-(2-fluorobenzoyl)piperazine-1-carbonyl)phenyl)quinoline-8-sulfonamide (120ap): 108

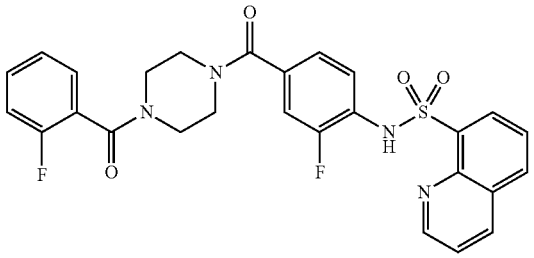

$^1$H NMR (400 MHz, $CDCl_3$) δ: 3.2-3.8 (m, 8H), 7.0-7.2 (m, 3H), 7.2-7.4 (m, 4H), 7.6-7.8 (m, 2H), 8.0-8.4 (m, 2H), 8.9 (s, 1H), 9.1 (m, 1H); HPLC Purity: 97.8%; LCMS, m/z found 537.21 $(M+1)^+$.

N-(2-Fluoro-4-(4-(2-phenylacetyl)piperazine-1-carbonyl)phenyl)quinoline-8-sulfonamide (120aq)

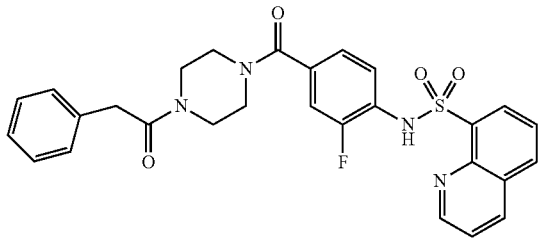

$^1$H NMR (400 MHz, $CDCl_3$) δ: 2.4 (s, 2H), 7.0-7.2 (m, 3H), 7.2-7.4 (m, 4H), 7.6-7.8 (m, 4H), 8.0-8.4 (m, 2H), 9.1 (m, 1H); HPLC Purity: 98.4%; LCMS, m/z found 533.26 $(M+1)^+$.

N-(2-Fluoro-4-(4-(2-(4-fluorophenyl)acetyl)piperazine-1-carbonyl)phenyl)quinoline-8-sulfonamide (120ar)

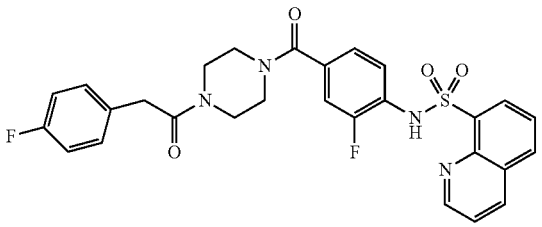

$^1$H NMR (400 MHz, $CD_3OD$) δ: 3.2-3.8 (m, 8H), 3.9 (s, 2H), 7.0-7.2 (m, 4H), 7.2-7.4 (m, 2H), 7.6-7.8 (m, 3H), 8.2 (m, 1H), 8.4 (m, 2H), 9.1 (m, 1H); HPLC Purity: 93.1%; LCMS, m/z found 551.23 $(M+1)^+$.

N-(2-Fluoro-4-(4-(2-(4-fluorophenyl)-2-methylpropanoyl)piperazine-1-carbonyl)phenyl)quinoline-8-sulfonamide (120 as)

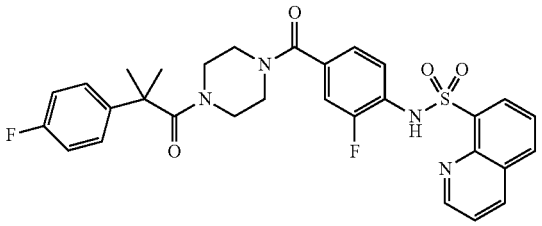

$^1$H NMR (400 MHz, $CDCl_3$) δ: 1.3 (s, 6H), 3.2-3.8 (m, 8H), 7.0-7.2 (m, 3H), 7.2-7.4 (m, 2H), 7.6-7.8 (m, 3H), 8.2 (m, 1H), 8.4 (m, 2H), 8.9 (s, 1H), 9.1 (m, 1H); HPLC Purity: 98.3%; LCMS, m/z found 579.22 $(M+1)^+$.

N-(2-Fluoro-4-(4-(Thiazole-4-carbonyl)piperazine-1-carbonyl)phenyl)quinoline-8-sulfonamide (120 at)

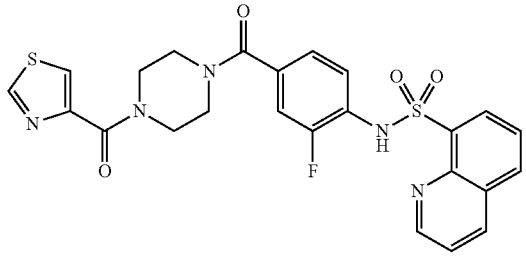

[$^1$H NMR (400 MHz, DMSO-$d_6$) δ: 3.2-3.8 (m, 8H), 7.0-7.2 (m, 3H), 7.2-7.4 (m, 2H), 7.6-7.8 (m, 3H), 8.2 (m, 1H), 8.9 (m, 2H), 9.0 (s, 1H), 9.5 (d, 1H);] HPLC Purity: 91.6%; LCMS, m/z found 526.19 $(M+1)^+$.

N-(4-(4-(1,2,3-Thiadiazole-4-carbonyl)piperazine-1-carbonyl)-2-fluorophenyl)quinoline-8-sulfonamide (120au)

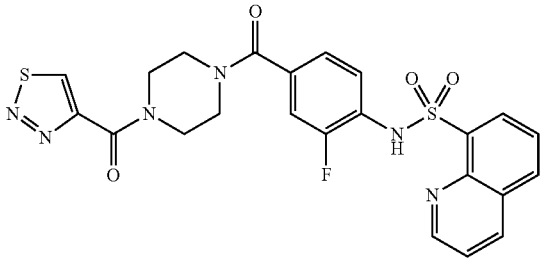

$^1$H NMR (400 MHz, DMSO-$d_6$) δ: 3.2-3.8 (m, 8H), 7.0-7.2 (m, 3H), 7.6-7.8 (m, 2H), 8.2-8.4 (m, 3H), 9.0 (m, 1H), 9.5 (s, 1H); HPLC Purity: 91.6%; LCMS, m/z found 526.19 $(M+1)^+$.

Cyclohexyl 4-(3-fluoro-4-(quinoline-8-sulfonamido) benzoyl)piperazine-1-carboxylate (120av)

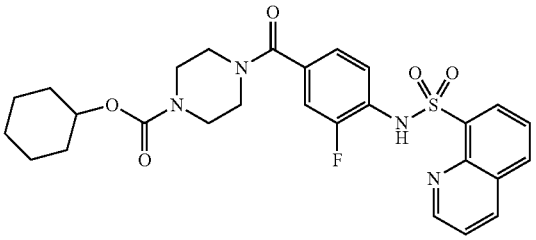

$^1$H NMR (400 MHz, DMSO-$d_6$) δ: 1.2-1.8 (m, 10H), 3.2-3.8 (m, 8H), 4.8 (m, 1H), 7.0-7.2 (m, 2H), 7.6-7.8 (m, 3H), 8.2 (m, 1H), 8.2-8.4 (m, 2H), 8.9 (m, 1H), 9.0 (s, 1H), 9.5 (d, 1H); HPLC Purity: 91.6%; LCMS, m/z found 526.19 $(M+1)^+$.

N-(2-Chloro-4-(4-picolinoylpiperazine-1-carbonyl) phenyl)quinoline-8-sulfonamide (120aw)

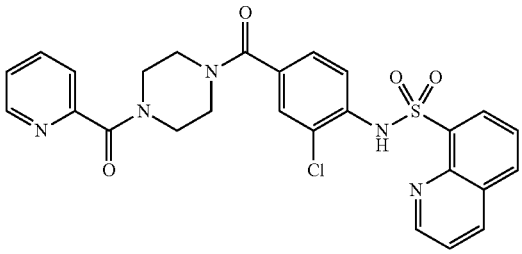

$^1$H NMR (400 MHz, DMSO-$d_6$) δ: 3.2-3.8 (m, 8H), 7.0-7.2 (m, 2H), 7.6-7.8 (m, 3H), 8.2 (m, 3H), 8.2-8.4 (m, 2H), 8.9 (m, 1H), 9.0 (s, 1H), 10.5 (s, 1H); HPLC Purity: 99.1%; LCMS, m/z found 537.1 $(M+1)^1$.

N-(2-Hydroxy-4-(4-picolinoylpiperazine-1-carbonyl) phenyl)quinoline-8-sulfonamide (120ax)

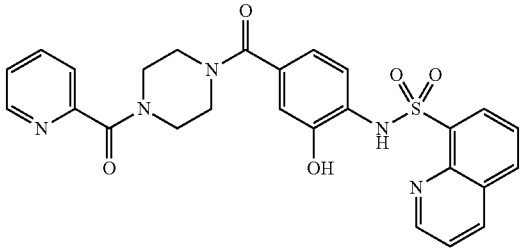

$^1$H NMR (400 MHz, DMSO-$d_6$) δ: 3.2-3.8 (m, 8H), 4.8 (s, 1H), 7.0-7.2 (m, 2H), 7.6-7.8 (m, 3H), 8.2 (m, 3H), 8.2-8.4 (m, 2H), 8.9 (m, 1H), 9.0 (s, 1H), 10.5 (s, 1H); HPLC Purity: 98.1%; LCMS, m/z found 518.2 $(M+1)^+$.

N-(4-(4-Isonicotinoylpiperazine-1-carbonyl)-3-methoxyphenyl)quinoline-8-sulfonamide (120ay)

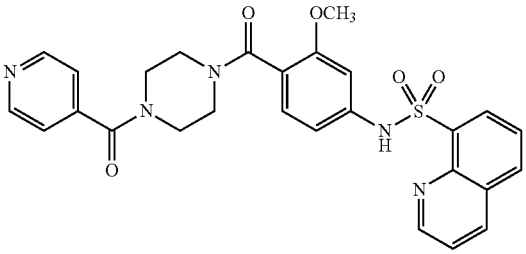

[$^1$H NMR (400 MHz, DMSO-$d_6$) δ: 3.2-3.8 (m, 8H), 6.4 (m, 1H), 7.0-7.2 (m, 2H), 7.6-7.8 (m, 2H), 8.0 (m, 1H), 8.2-8.4 (m, 3H), 8.8 (s, 1H), 8.9 (s, 1H), 9.0 (s, 1H);] HPLC Purity: 95.0%; LCMS, m/z found 532.2 $(M+1)^+$.

N-(3-Methoxy-4-(4-(6-methylpicolinoyl)piperazine-1-carbonyl)phenyl)quinoline-8-sulfonamide (120az)

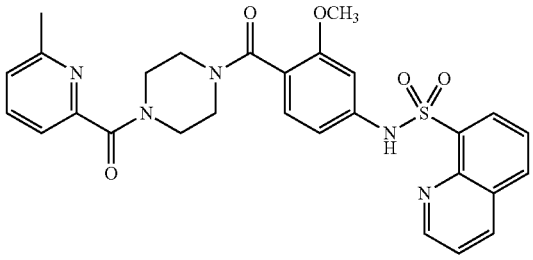

$^1$H NMR (400 MHz, $CD_3OD$) δ: 2.2 (s, 3H), 3.2-3.8 (m, 8H), 3.9 (s, 3H), 6.7 (m, 3H), 7.2 (m, 2H), 7.6-7.8 (m, 3H), 8.0 (m, 1H), 8.2-8.4 (m, 2H), 9.0 (s, 1H); HPLC Purity: 98.8%; LCMS, m/z found 546.2 $(M+1)^+$.

N-(4-(4-(3-Fluoropicolinoyl)piperazine-1-carbonyl)-3-methoxyphenyl)quinoline-8-sulfonamide (120ba)

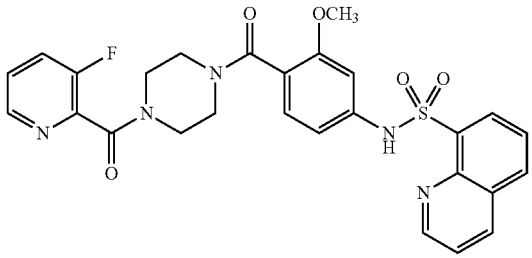

$^1$H NMR (400 MHz, DMSO-$d_6$)) δ: 3.2-3.8 (m, 8H), 3.9 (s, 3H), 6.7-7.0 (m, 3H), 7.2 (m, 2H), 7.6-7.8 (m, 3H), 8.1 (s, 1H), 8.4 (m, 2H), 9.0 (s, 1H); HPLC Purity: 98.8%; LCMS, m/z found 550.2 $(M+1)^+$.

N-(4-(4-(5-Fluoropicolinoyl)piperazine-1-carbonyl)-3-methoxyphenyl)quinoline-8-sulfonamide (120bb)

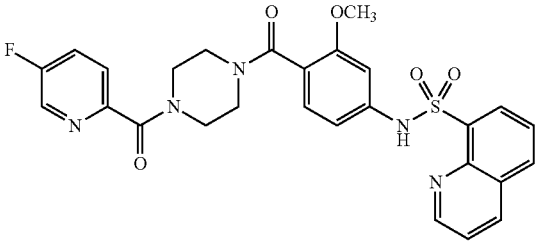

$^1$H NMR (400 MHz, $CDCl_3$) δ: 3.2-3.8 (m, 8H), 3.9 (s, 3H), 6.7-7.0 (m, 3H), 7.2 (m, 2H), 7.6-7.8 (m, 3H), 8.1 (s, 1H), 8.4 (m, 1H), 9.0 (s, 1H), 9.3 (s, 1H), 10.5 (s, 1H); HPLC Purity: 98.9%; LCMS, m/z found 550.2 $(M+1)^+$.

N-(3-Methoxy-4-(4-(5-(trifluoromethyl)picolinoyl) piperazine-1-carbonyl)phenyl)quinoline-8-sulfonamide (120bc)

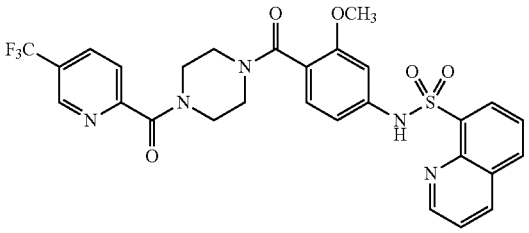

$^1$H NMR (400 MHz, $CDCl_3$) δ: 3.2-3.8 (m, 8H), 3.9 (s, 3H), 6.6-6.9 (m, 3H), 7.2 (m, 2H), 7.6-7.8 (m, 3H), 8.2-8.4 (m, 2H), 8.9 (m, 1H), 9.0 (s, 1H); HPLC Purity: 99.2%; LCMS, m/z found 600.3 $(M+1)^+$.

N-(4-(4-(5-Fluoronicotinoyl)piperazine-1-carbonyl)-3-methoxyphenyl)quinoline-8-sulfonamide (120bd)

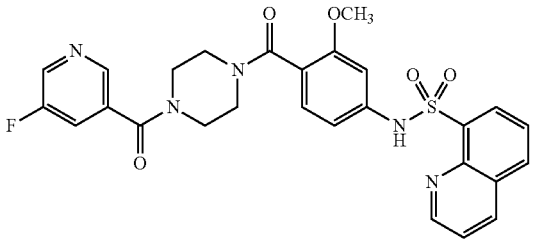

$^1$H NMR (400 MHz, $CDCl_3$) δ: 3.2-3.8 (m, 8H), 3.9 (s, 3H), 6.4 (m, 1H), 7.0 (m, 2H), 7.6 (m, 3H), 8.0 (m, 1H), 8.2-8.6 (m, 4H), 9.1 (m, 1H); HPLC Purity: 99.5%; LCMS, m/z found 550.3 $(M+1)^+$.

N-(4-(4-(3-Chloroisonicotinoyl)piperazine-1-carbonyl)-3-methoxyphenyl)quinoline-8-sulfonamide (120be)

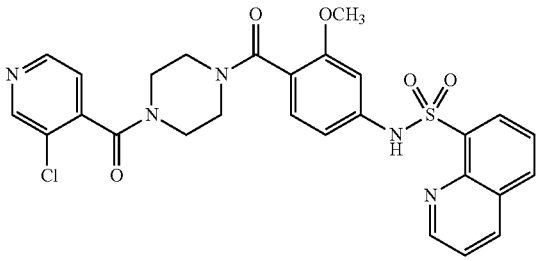

$^1$H NMR (400 MHz, $CDCl_3$) δ: 3.2-3.8 (m, 8H), 3.9 (s, 3H), 6.4 (m, 1H), 7.0 (m, 2H), 7.6 (m, 3H), 8.0 (m, 1H), 8.2-8.4 (m, 2H), 8.6-8.8 (m, 2H), 9.1 (m, 1H); HPLC Purity: 98.2%; LCMS, m/z found 566.25 $(M+1)^+$.

N-(4-(4-(3-Fluoroisonicotinoyl)piperazine-1-carbonyl)-3-methoxyphenyl)quinoline-8-sulfonamide (120bf)

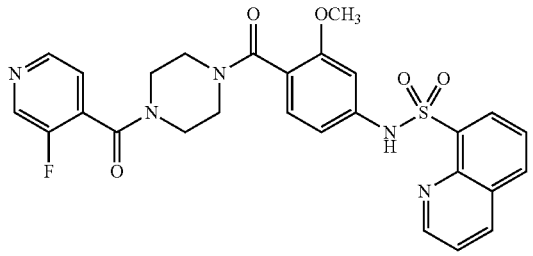

[$^1$H NMR (400 MHz, $CDCl_3$) δ: 3.2-3.8 (m, 8H), 3.9 (s, 3H), 6.4 (m, 1H), 7.0 (m, 2H), 7.6 (m, 3H), 8.0 (m, 1H), 8.2-8.4 (m, 2H), 8.6-8.8 (m, 2H), 9.1 (m, 1H);] HPLC Purity: 98.9%; LCMS, m/z found 550.35 $(M+1)^+$.

N-(4-(4-(5-Chloronicotinoyl)piperazine-1-carbonyl)-3-methoxyphenyl)quinoline-8-sulfonamide (120bg)

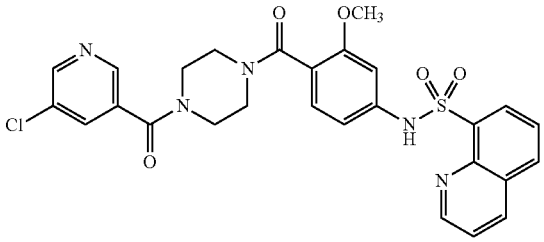

$^1$H NMR (400 MHz, $CDCl_3$) δ: 3.2-3.8 (m, 8H), 3.9 (s, 3H), 6.4 (m, 1H), 7.0 (m, 2H), 7.3 (m, 2H), 7.6 (m, 2H), 8.0 (m, 1H), 8.2-8.4 (m, 2H), 8.6-8.8 (m, 2H), 9.1 (m, 1H); HPLC Purity: 98.5%; LCMS, m/z found 566.3 $(M+1)^+$.

N-(3-Methoxy-4-(4-(4-(trifluoromethyl)nicotinoyl)piperazine-1-carbonyl)phenyl)quinoline-8-sulfonamide (120bh)

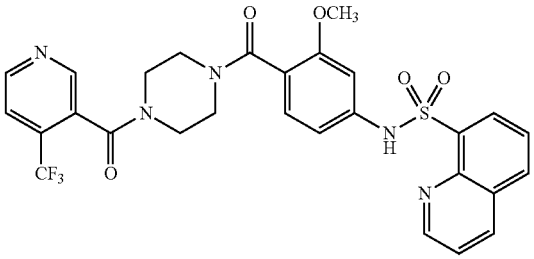

$^1$H NMR (400 MHz, $CDCl_3$) δ: 3.2-3.8 (m, 8H), 3.9 (s, 3H), 6.4 (m, 1H), 7.0 (m, 2H), 7.6 (m, 2H), 8.0 (m, 1H), 8.2-8.4 (m, 2H), 8.4-8.6 (m, 2H), 8.9 (m, 1H), 9.1 (m, 1H); HPLC Purity: 90.6%; LCMS, m/z found 600.35 $(M+1)^+$.

N-(3-Methoxy-4-(4-nicotinoylpiperazine-1-carbonyl)phenyl)quinoline-8-sulfonamide (120bi)

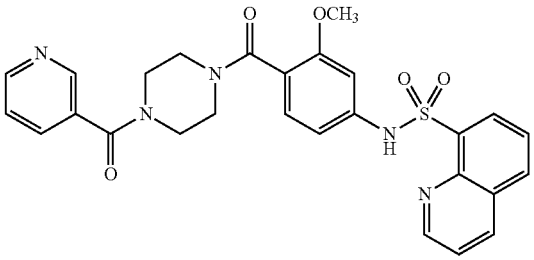

$^1$H NMR (400 MHz, $CDCl_3$) δ: 3.2-3.8 (m, 8H), 3.9 (s, 3H), 6.4 (m, 1H), 7.0 (m, 2H), 7.2-7.6 (m, 3H), 8.0 (m, 1H), 8.2-8.4 (m, 2H), 8.6-8.6 (m, 2H), 8.9 (m, 1H), 9.1 (m, 1H); HPLC Purity: 96.5%; LCMS, m/z found 532.35 $(M+1)^+$.

N-(4-(4-(5-Chloropicolinoyl)piperazine-1-carbonyl)-3-methoxyphenyl)quinoline-8-sulfonamide (120bj)

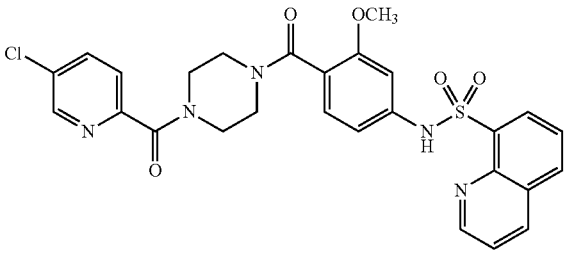

$^1$H NMR (400 MHz, $CDCl_3$) δ: 3.2-3.8 (m, 8H), 3.9 (s, 3H), 6.4 (m, 1H), 7.0 (m, 2H), 7.6-7.8 (m, 4H), 8.0 (m, 1H), 8.2-8.4 (m, 3H), 9.1 (m, 1H); HPLC Purity: 92.08%; LCMS, m/z found 566.3 $(M+1)^+$.

N-(3-Methoxy-4-(4-(3-(trifluoromethyl)picolinoyl)piperazine-1-carbonyl)phenyl)quinoline-8-sulfonamide (120bk)

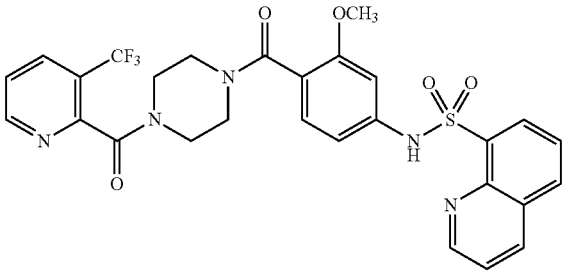

$^1$H NMR (400 MHz, $CDCl_3$) δ: 3.2-3.8 (m, 8H), 3.9 (s, 3H), 6.4 (m, 1H), 7.0 (m, 2H), 7.6-7.8 (m, 3H), 8.0 (m, 1H), 8.2-8.4 (m, 2H), 8.8 (m, 1H), 9.1 (m, 1H); HPLC Purity: 92.08%; LCMS, m/z found 566.3 $(M+1)^+$.

N-(3-Methoxy-4-(4-(2-(trifluoromethyl)nicotinoyl)piperazine-1-carbonyl)phenyl)quinoline-8-sulfonamide (120bl)

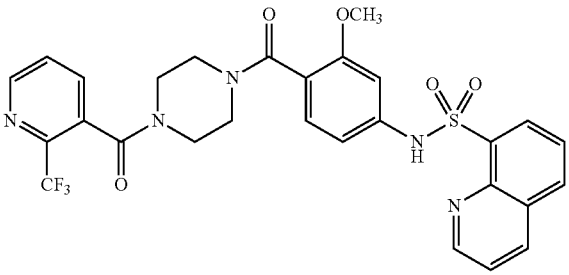

$^1$H NMR (400 MHz, $CDCl_3$) δ: 3.2-3.8 (m, 8H), 3.9 (s, 3H), 6.4 (m, 1H), 7.0 (m, 2H), 7.6-7.8 (m, 4H), 8.0 (m, 1H), 8.2-8.4 (m, 2H), 8.8 (m, 1H), 9.1 (m, 1H); HPLC Purity: 96.5%; LCMS, m/z found 600.3 $(M+1)^+$.

N-(3-Methoxy-4-(4-(3-methoxyisonicotinoyl)piperazine-1-carbonyl)phenyl)quinoline-8-sulfonamide (120bm)

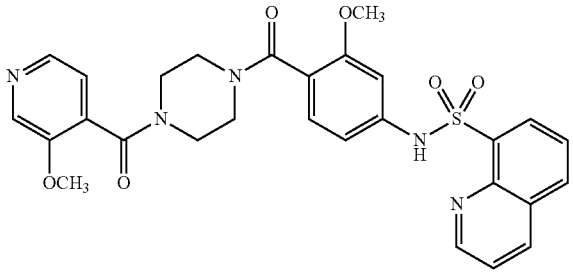

[$^1$H NMR (400 MHz, $CDCl_3$) δ: 3.2-3.8 (m, 8H), 3.9 (s, 3H), 6.4 (m, 1H), 7.0 (m, 3H), 7.6-7.8 (m, 3H), 8.0 (m, 1H), 8.2-8.4 (m, 2H), 8.8 (m, 1H), 9.1 (m, 1H);] HPLC Purity: 93.2%; LCMS, m/z found 562.3 $(M+1)^+$.

N-(3-Methoxy-4-(4-(2-methoxyisonicotinoyl)piperazine-1-carbonyl)phenyl)quinoline-8-sulfonamide (120bn)

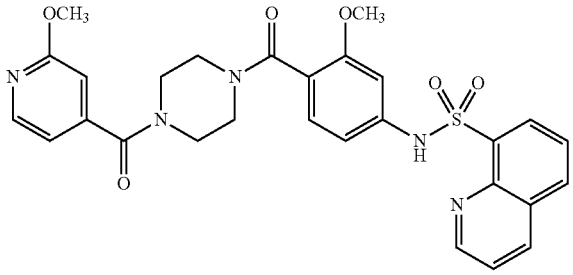

$^1$H NMR (400 MHz, $CDCl_3$) δ: 3.2-3.8 (m, 8H), 3.9 (s, 3H), 6.4 (m, 1H), 7.0 (m, 3H), 7.6-7.8 (m, 2H), 8.0 (m, 1H), 8.2-8.4 (m, 3H), 8.8 (m, 1H), 9.1 (m, 1H); HPLC Purity: 98.5%; LCMS, m/z found 562.4 $(M+1)^+$.

N-(3-Methoxy-4-(4-(pyrazine-2-carbonyl)piperazine-1-carbonyl)phenyl)quinoline-8-sulfonamide (120bo)

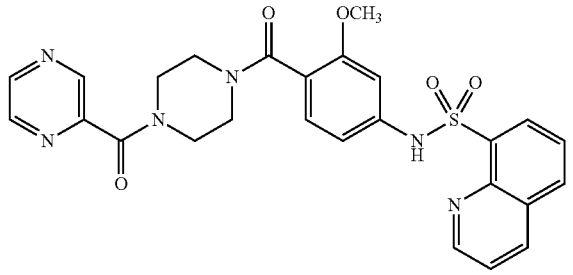

$^1$H NMR (400 MHz, $CDCl_3$) δ: 3.2-3.8 (m, 8H), 3.9 (s, 3H), 6.4 (m, 1H), 7.0 (m, 2H), 7.6-7.8 (m, 2H), 8.0 (m, 1H), 8.2-8.4 (m, 4H), 9.1 (s, 1H), 9.2 (s, 1H); HPLC Purity: 98.9%; LCMS, m/z found 533.1 $(M+1)^+$.

N-(4-(4-(2-Fluoro-3-methoxybenzoyl)piperazine-1-carbonyl)-3-methoxyphenyl)quinoline-8-sulfomide (120 bp)

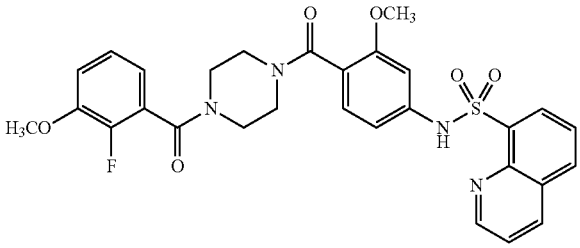

$^1$H NMR (400 MHz, $CDCl_3$) δ: 3.2-3.8 (m, 8H), 3.9 (s, 3H), 4.0 (s, 3H), 6.4 (m, 1H), 7.0 (m, 3H), 7.2 (m, 2H), 7.6 (m, 2H), 8.0 (m, 1H), 8.4 (m, 2H), 9.1 (s, 1H); HPLC Purity: 99.3%; LCMS, m/z found 579.2 $(M+1)^+$.

N-(4-(4-(2-Fluorobenzoyl)piperazine-1-carbonyl)-3-methoxyphenyl)quinoline-8-sulfonamide (120bq)

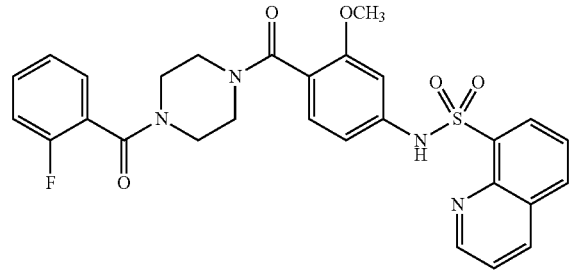

$^1$H NMR (400 MHz, $CDCl_3$) δ: 3.2-3.8 (m, 8H), 3.9 (s, 3H), 6.4 (m, 1H), 7.2-7.4 (m, 6H), 8.8 (m, 1H), 8.0 (m, 3H), 8.6 (s, 1H), 9.1 (s, 1H); HPLC Purity: 99.5%; LCMS, m/z found 549.2 $(M+1)^+$.

N-(4-(4-(2,3-Difluorobenzoyl)piperazine-1-carbonyl)-3-methoxyphenyl)quinoline-8-sulfonamide (120br)

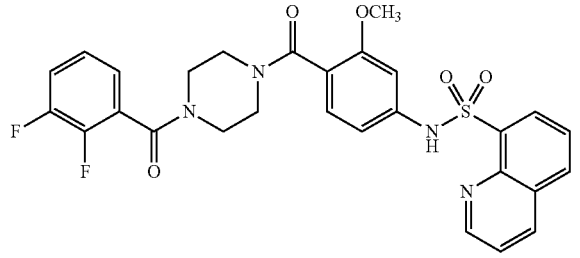

$^1$H NMR (400 MHz, $CDCl_3$) δ: 3.2-3.8 (m, 8H), 3.9 (s, 3H), 6.4 (m, 1H), 7.0-7.4 (m, 5H), 7.6 (m, 2H), 8.0 (m, 1H), 8.4 (m, 2H), 8.6 (s, 1H), 9.1 (s, 1H); HPLC Purity: 96.1%; LCMS, m/z found 567.1 $(M+1)^+$.

N-(4-(4-(3,4-Difluorobenzoyl)piperazine-1-carbonyl)-3-methoxyphenyl)quinoline-8-sulfonamide (120bs)

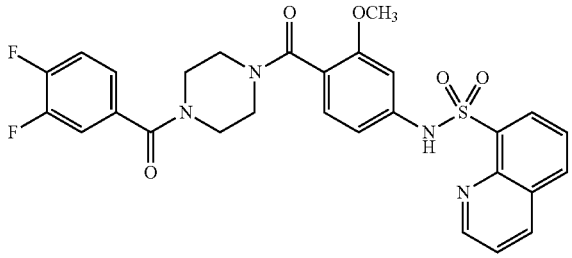

$^1$H NMR (400 MHz, $CDCl_3$) δ: 3.2-3.8 (m, 8H), 3.9 (s, 3H), 6.4 (m, 1H), 7.0-7.4 (m, 5H), 7.6 (m, 2H), 8.0 (m, 1H), 8.4 (m, 2H), 8.6 (s, 1H), 9.1 (s, 1H); HPLC Purity: 98.9%; LCMS, m/z found 567.1 $(M+1)^+$.

N-(4-(4-(2,6-Difluorobenzoyl)piperazine-1-carbonyl)-3-methoxyphenyl)quinoline-8-sulfonamide (120bt)

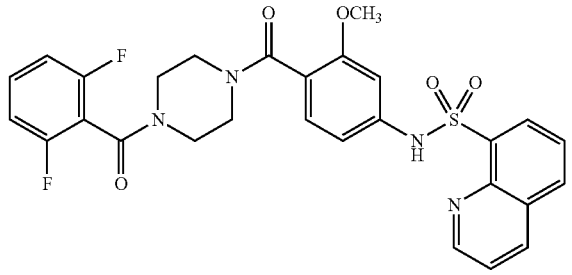

$^1$H NMR (400 MHz, $CDCl_3$) δ: 3.2-3.8 (m, 8H), 3.9 (s, 3H), 6.4 (m, 1H), 7.0-7.4 (m, 4H), 7.6 (m, 3H), 8.0 (m, 1H), 8.4 (m, 2H), 9.1 (s, 1H); HPLC Purity: 98.4%; LCMS, m/z found 567.0 $(M+1)^+$.

N-(3-Methoxy-4-(4-(2-phenylacetyl)piperazine-1-carbonyl)phenyl)quinoline-8-sulfonamide (120bu)

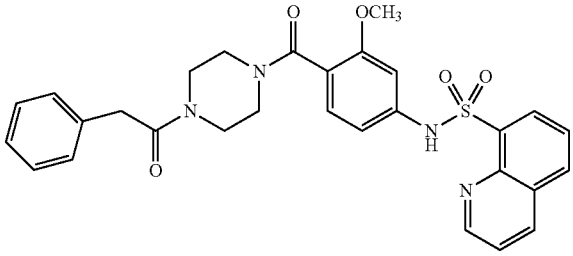

$^1$H NMR (400 MHz, $CDCl_3$) δ: 3.2-3.8 (m, 8H), 3.9 (s, 3H), 6.4 (m, 1H), 7.0 (m, 2H), 7.2-7.4 (m, 5H), 7.6 (m, 2H), 8.0 (m, 1H), 8.4 (m, 2H), 9.1 (s, 1H); HPLC Purity: 99.7%; LCMS, m/z found 545.2 $(M+1)^+$.

N-(3-Methoxy-4-(4-(2-(4-(trifluoromethyl)phenyl)acetyl)piperazine-1 -carbonyl)phenyl)quinoline-8-sulfonamide (120bv)

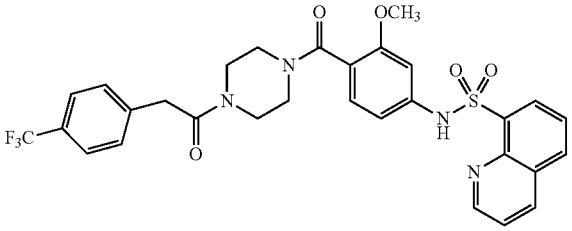

$^1$H NMR (400 MHz, $CDCl_3$) δ: 3.2-3.8 (m, 8H), 3.9 (s, 3H), 6.4 (m, 1H), 7.0 (m, 3H), 7.2-7.4 (m, 2H), 7.6 (m, 3H), 8.0 (m, 1H), 8.4 (m, 2H), 8.6 (s, 1H), 9.1 (s, 1H); HPLC Purity: 99.1%; LCMS, m/z found 613.1 $(M+1)^+$.

N-(3-Methoxy-4-(4-(2-methyl-2-phenylpropanoyl)piperazine-1-carbonyl)phenyl)quinoline-8-sulfonamide (120bw)

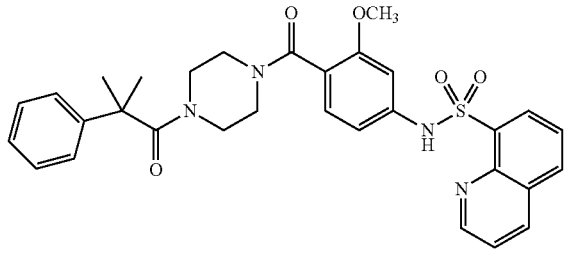

$^1$H NMR (400 MHz, $CDCl_3$) δ: 3.2-3.8 (m, 8H), 3.9 (s, 3H), 6.4 (m, 1H), 6.9-7.0 (m, 2H), 7.2-7.4 (m, 4H), 7.6 (m, 2H), 8.0 (m, 1H), 8.4 (m, 2H), 8.6 (s, 1H), 9.1 (s, 1H); HPLC Purity: 95.3%; LCMS, m/z found 573.45 $(M+1)^+$.

N-(4-(4-(2-(4-Fluorophenyl)-2-methylpropanoyl)piperazine-1-carbonyl)-3-methoxyphenyl)quinoline-8-sulfonamide (120bx)

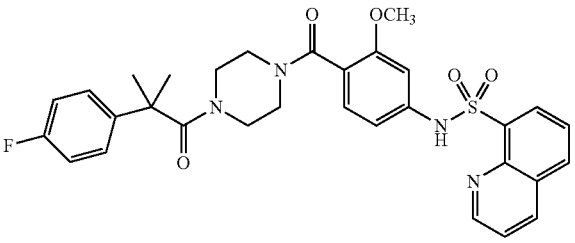

$^1$H NMR (400 MHz, $CDCl_3$) δ: 3.2-3.8 (m, 8H), 3.9 (s, 3H), 6.4 (m, 1H), 6.9-7.2 (m, 5H), 7.6 (m, 2H), 8.0 (m, 1H), 8.4 (m, 2H), 8.6 (s, 1H), 9.1 (s, 1H); HPLC Purity: 99.1%; LCMS, m/z found 591.3 $(M+1)^+$.

N-(4-(4-(1,2,3-Thiadiazole-4-carbonyl)piperazine-1-carbonyl)-3-methoxyphenyl)quinoline-8-sulfonamide (120by)

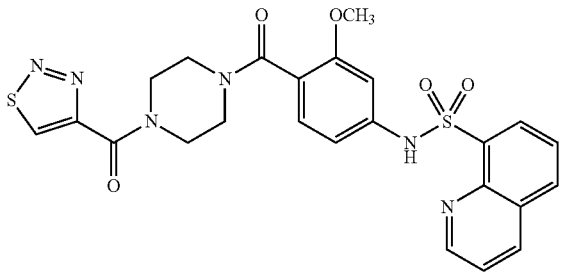

[$^1$H NMR (400 MHz, $CDCl_3$) δ: 3.2-3.8 (m, 8H), 3.9 (s, 3H), 6.4 (m, 1H), 6.9-7.2 (m, 2H), 7.6 (m, 2H), 8.0 (m, 1H), 8.4 (m, 2H), 8.6 (s, 1H), 9.1 (m, 1H);] HPLC Purity: 99.0%; LCMS, m/z found 539.3 $(M+1)^+$.

N-(3-Methoxy-4-(4-(thiazole-4-carbonyl)piperazine-1-carbonyl)phenyl)quinoline-8-sulfonamide (120bz)

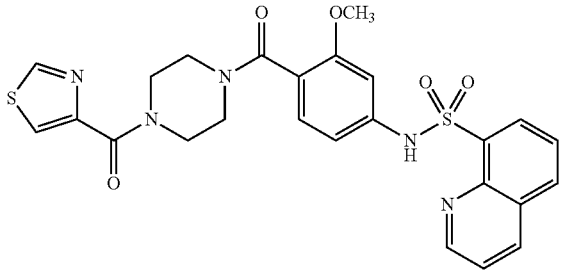

$^1$H NMR (400 MHz, $CDCl_3$) δ: 3.2-3.8 (m, 8H), 3.9 (s, 3H), 6.4 (m, 1H), 6.9-7.2 (m, 2H), 7.6 (m, 2H), 8.0 (m, 1H), 8.4 (m, 1H), 8.6 (s, 1H), 8.8 (s, 1H), 9.1 (m, 1H); HPLC Purity: 99.6%; LCMS, m/z found 538.3 $(M+1)^+$.

2-Cyclopentylethyl 4-(2-methoxy-4-(quinoline-8-sulfonamido)benzoyl)piperazine-1-carboxylate (120ca)

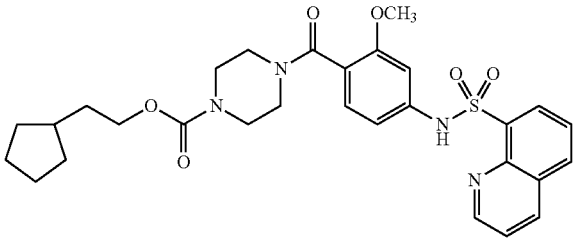

$^1$H NMR (400 MHz, $CDCl_3$) δ: 1.2 (m, 4H), 1.6 (m, 8H), 3.2-3.8 (m, 8H), 3.9 (s, 3H), 4.7 (m, 1H), 6.4 (m, 1H), 6.9-7.2 (m, 2H), 7.6 (m, 2H), 8.0 (m, 1H), 8.4 (m, 1H), 8.6 (s, 1H), 8.8 (s, 1H), 9.1 (m, 1H); HPLC Purity: 99.8%; LCMS, m/z found 567.1 $(M+1)^+$.

Tetrahydrofuran-3-yl 4-(2-methoxy-4-(quinoline-8-sulfonamido)benzoyl)piperazine-1-carboxylate (120cb)

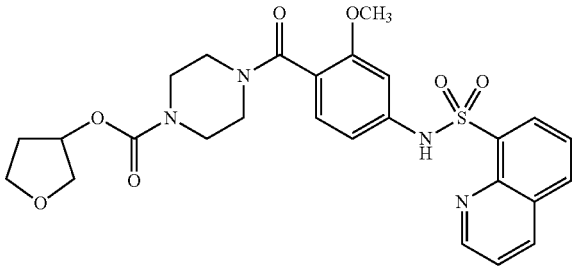

$^1$H NMR (400 MHz, $CDCl_3$) δ: 2.0 (m, 2H), 2.2 (m, 1H), 3.0-3.6 (m, 4H), 3.2-3.8 (m, 8H), 3.9 (s, 3H), 5.2 (s, 1H), 6.4 (m, 1H), 6.9-7.2 (m, 2H), 7.6 (m, 2H), 8.0 (m, 1H), 8.4 (m, 1H), 8.6 (s, 1H), 8.8 (s, 1H), 9.1 (m, 1H); HPLC Purity: 96.2%; LCMS, m/z found 541.05 $(M+1)^+$.

2-Cyclohexylethyl 4-(2-methoxy-4-(quinoline-8-sulfonamido)benzoyl)piperazine-1-carboxylate (120cc)

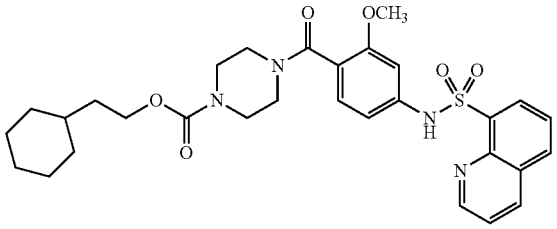

$^1$H NMR (400 MHz, $CDCl_3$) δ: 1.2 (m, 10H), 1.6-1.8 (m, 4H), 3.2-3.8 (m, 8H), 3.9 (s, 3H), 4.7 (s, 1H), 6.4 (m, 1H), 6.9-7.0 (m, 2H), 7.6 (m, 2H), 8.0 (m, 1H), 8.2-8.4 (m, 2H), 8.6 (s, 1H), 9.1 (m, 1H); HPLC Purity: 97.7%; LCMS, m/z found 581.4 $(M+1)^+$.

N-(2-Methoxy-4-(4-(6-methylpicolinoyl)piperazine-1-carbonyl)phenyl)quinoline-8-sulfonamide (120cd)

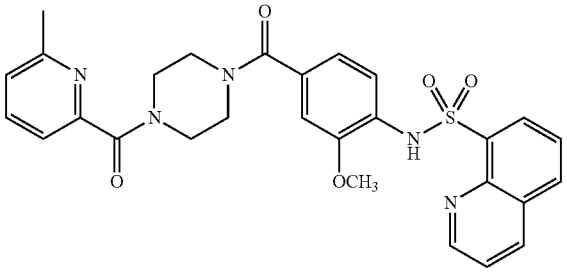

$^1$H NMR (400 MHz, $CDCl_3$) δ: 2.1 (s, 3H), 3.2-3.8 (m, 8H), 3.9 (s, 3H), 6.7 (s, 1H), 6.9 (m, 1H), 7.2 (m, 1H), 7.4-7.8 (m, 5H), 8.0 (m, 1H), 8.2-8.4 (m, 2H), 8.8 (s, 1H), 9.1 (m, 1H); HPLC Purity: 99.6%; LCMS, m/z found 546.3 $(M+1)^+$.

N-(2-Methoxy-4-(4-(3-(trifluoromethyl)picolinoyl) piperazme-1-carbonyl)phenyl)quinoline-8-sulfonamide (120ce)

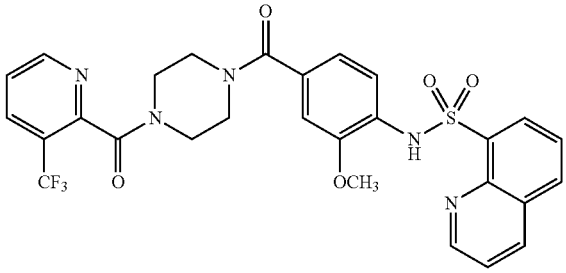

[$^1$H NMR (400 MHz, $CDCl_3$) δ: 3.2-3.8 (m, 8H), 3.9 (s, 3H), 6.7 (s, 1H), 6.9 (m, 1H), 7.4-7.7 (m, 4H), 8.0 (m, 2H), 8.2-8.4 (m, 2H), 8.8 (s, 1H), 9.1 (m, 1H);] HPLC Purity: 99.9%; LCMS, m/z found 600.3 $(M+1)^+$.

N-(4-(4-(3-Fluoropicolinoyl)piperazine-1-carbonyl)-2-methoxyphenyl)quinoline-8-sulfonamide (120cf)

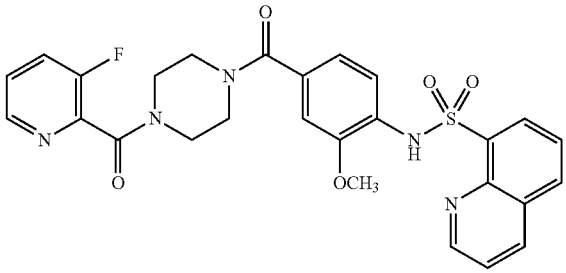

$^1$H NMR (400 MHz, $CDCl_3$) δ: 3.2-3.8 (m, 8H), 3.9 (s, 3H), 6.9 (m, 2H), 7.4-7.7 (m, 5H), 8.0 (m, 2H), 8.2-8.4 (m, 2H), 8.8 (s, 1H), 9.1 (m, 1H); HPLC Purity: 99.8%; LCMS, m/z found 550.3 $(M+1)^+$.

N-(2-Methoxy-4-(4-(5-(trifluoromethyl)picolinoyl) piperazine-1-carbonyl)phenyl)quinoline-8-sulfonamide (120cg)

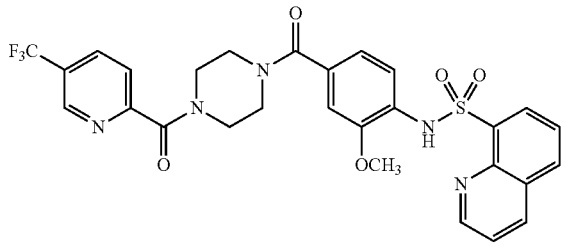

$^1$H NMR (400 MHz, $CDCl_3$) δ: 3.2-3.8 (m, 8H), 3.9 (s, 3H), 6.9 (m, 2H), 7.6-7.8 (m, 4H), 8.0 (m, 2H), 8.2-8.4 (m, 2H), 8.8 (s, 1H), 8.9 (m, 1H), 9.1 (m, 1H); HPLC Purity: 99.6%; LCMS, m/z found 600.3 $(M+1)^+$.

N-(4-(4-(5-Chloropicolinoyl)piperazine-1-carbonyl)-2-methoxyphenyl)quinoline-8-sulfonamide (120ch)

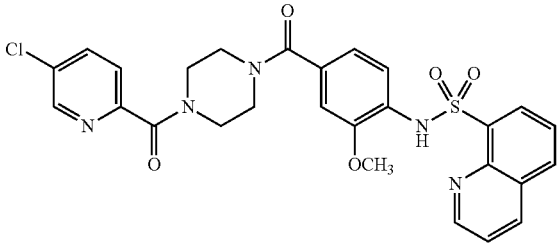

$^1$H NMR (400 MHz, $CDCl_3$) δ: 3.2-3.8 (m, 8H), 3.9 (s, 3H), 6.9 (m, 2H), 7.6-7.8 (m, 5H), 8.0 (m, 1H), 8.2-8.4 (m, 2H), 8.8 (s, 1H), 8.9 (m, 1H), 9.1 (m, 1H); HPLC Purity: 99.3%; LCMS, m/z found 566.3 $(M+1)^+$.

N-(4-(4-(5-Fluoropicolinoyl)piperazine-1-carbonyl)-2-methoxyphenyl)quinoline-8-sulfonamide (120ci)

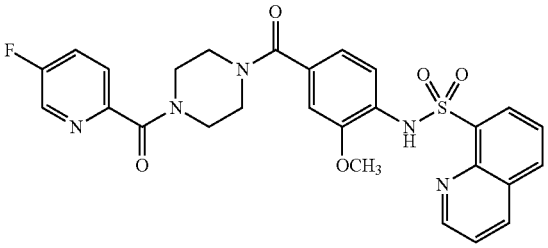

$^1$H NMR (400 MHz, $CDCl_3$) δ: 3.2-3.8 (m, 8H), 3.9 (s, 3H), 6.9 (m, 2H), 7.6-7.8 (m, 5H), 8.0 (m, 1H), 8.2-8.4 (m, 3H), 8.8 (s, 1H), 9.1 (m, 1H); HPLC Purity: 99.4%; LCMS, m/z found 550.3 $(M+1)^+$.

N-(2-Methoxy-4-(4-(4-(trifluoromethyl)nicotinoyl) piperazine-1-carbonyl)phenyl)quinoline-8-sulfonamide (120cj)

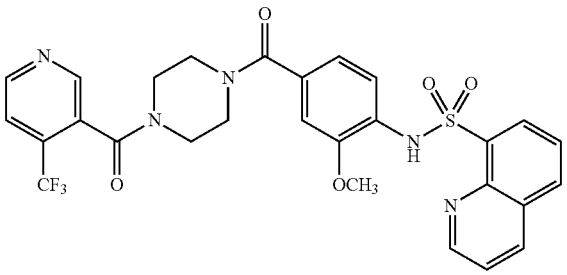

$^1$H NMR (400 MHz, $CDCl_3$) δ: 3.2-3.8 (m, 8H), 3.9 (s, 3H), 6.9 (m, 2H), 7.6-7.8 (m, 4H), 8.2-8.4 (m, 2H), 8.6 (s, 1H), 8.8 (m, 2H), 9.1 (m, 1H); HPLC Purity: 99.9%; LCMS, m/z found 600.3 $(M+1)^+$.

N-(4-(4-(5-Chloronicotinoyl)piperazine-1-carbonyl)-2-methoxyphenyl)quinoline-8-sulfonamide (120ck)

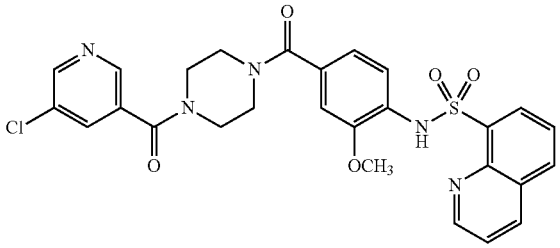

$^1$H NMR (400 MHz, $CDCl_3$) δ: 3.2-3.8 (m, 8H), 3.9 (s, 3H), 6.9 (m, 2H), 7.6-7.8 (m, 4H), 8.0 (m, 1H), 8.4-8.6 (m, 2H), 8.7 (s, 1H), 8.8 (s, 1H), 9.1 (m, 1H); HPLC Purity: 95.7%; LCMS, m/z found 566.3 $(M+1)^+$.

N-(4-(4-(5-Fluoronicotinoyl)piperazine-1-carbonyl)-2-methoxyphenyl)quinoline-8-sulfonamide (120cl)

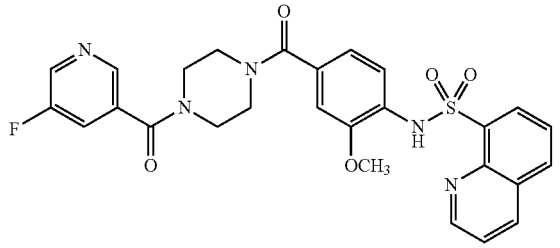

$^1$H NMR (400 MHz, $CDCl_3$) δ: 3.2-3.8 (m, 8H), 3.9 (s, 3H), 6.9 (m, 2H), 7.6-7.8 (m, 4H), 8.0 (m, 1H), 8.4-8.6(m, 2H), 8.7 (s, 1H), 8.8 (s, 1H), 9.1 (m, 1H); HPLC Purity: 89.4%; LCMS, m/z found 550.3 $(M+1)^+$.

N-(4-(4-(3-Chloroisonicotinoyl)piperazine-1-carbonyl)-2-methoxyphenyl)quinoline-8-sulfonamide (120cm)

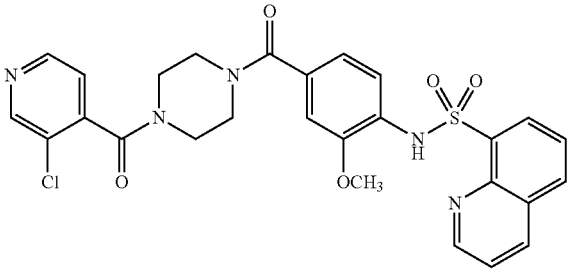

$^1$H NMR (400 MHz, $CDCl_3$) δ: 3.2-3.8 (m, 8H), 3.9 (s, 3H), 6.9 (m, 2H), 7.6-7.8 (m, 3H), 8.0 (m, 1H), 8.4-8.6 (m, 4H), 8.9 (s, 1H), 9.1 (m, 1H); HPLC Purity: 98.5%; LCMS, m/z found 566.3 $(M+1)^+$.

N-(4-(4-(3-Fluoroisonicotinoyl)piperazine-1-carbonyl)-2-methoxyphenyl)quinoline-8-sulfonamide (120cn)

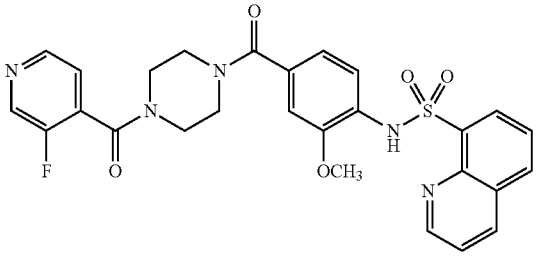

$^1$H NMR (400 MHz, $CDCl_3$) δ: 3.2-3.8 (m, 8H), 3.9 (s, 3H), 6.9 (m, 2H), 7.6-7.8 (m, 4H), 8.0 (m, 1H), 8.4-8.6 (m, 3H), 8.9 (s, 1H), 9.1 (m, 1H); HPLC Purity: 94.9%; LCMS, m/z found 550.3 $(M+1)^+$.

N-(2-Methoxy-4-(4-(2-methoxyisonicotinoyl)piperazine-1-carbonyl)phenyl)quinoline-8-sulfonamide (120co)

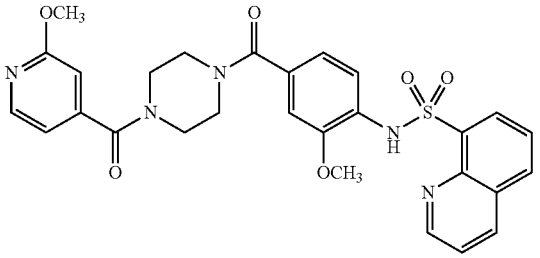

$^1$H NMR (400 MHz, $CDCl_3$) δ: 3.2-3.8 (m, 8H), 3.8 (s, 3H), 3.9 (s, 3H), 6.6-6.9 (m, 4H), 7.6-7.8 (m, 3H), 8.0 (m, 1H), 8.2-8.4 (m, 3H), 8.9 (s, 1H), 9.1 (m, 1H); HPLC Purity: 97.3%; LCMS, m/z found 562.3 $(M+1)^+$.

N-(2-Methoxy-4-(4-(2-(trifluoromethyl)nicotinoyl)piperazine-1-carbonyl)phenyl)quinoline-8-sulfonamide (120 cp)

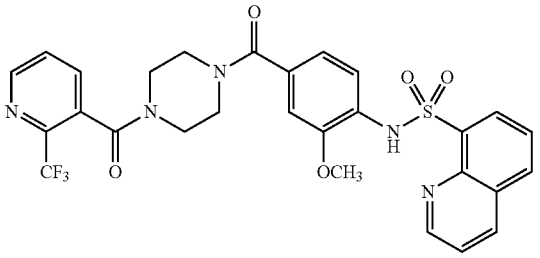

$^1$H NMR (400 MHz, $CDCl_3$) δ: 3.2-3.8 (m, 8H), 3.9 (s, 3H), 6.6 (s, 1H), 6.9 (m, 1H), 7.6-7.8 (m, 5H), 8.0 (m, 1H), 8.2-8.4 (m, 2H), 8.9 (s, 1H), 9.1 (m, 1H); HPLC Purity: 99.7%; LCMS, m/z found 600.3 $(M+1)^+$.

N-(2-Methoxy-4-(4-(2-methoxynicotinoyl)piperazine-1-carbonyl)phenyl)quinoline-8-sulfonamide (120cq)

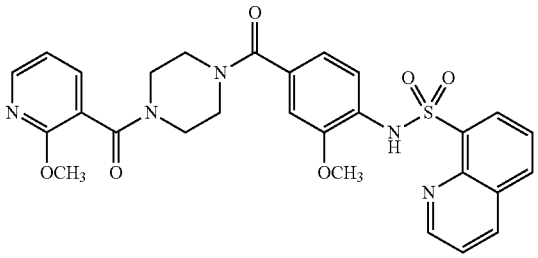

$^1$H NMR (400 MHz, $CDCl_3$) δ: 3.2-3.8 (m, 8H), 3.8 (s, 3H), 3.9 (s, 3H), 6.6 (s, 1H), 6.9 (m, 1H), 7.6-7.8 (m, 4H), 8.0 (m, 1H), 8.2-8.4 (m, 3H), 8.9 (s, 1H), 9.1 (m, 1H); HPLC Purity: 99.8%; LCMS, m/z found 562.4 $(M+1)^+$.

Tetrahydrofuran-3-yl 4-(3-methoxy-4-(quinoline-8-ulfonamido)benzoyl)piperazine-1-carboxylate (120cr)

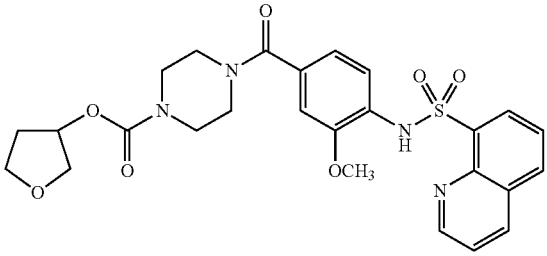

$^1$H NMR (400 MHz, $CDCl_3$) δ: 2.2 (m, 2H), 3.2-3.8 (m, 8H), 3.9 (s, 3H), 4.0 (m, 2H), 5.0 (m, 1H), 6.9 (m, 2H), 7.6-7.8 (m, 3H), 8.0 (m, 1H), 8.2-8.4 (m, 2H), 9.1 (m, 1H); HPLC Purity: 98.1%; LCMS, m/z found 541.0 $(M+1)^+$.

(Tetrahydrofuran-2-yl)methyl 4-(3-methoxy-4-(quinoline-8-sulfonamido)benzoyl)piperazine-1-carboxylate (120cs)

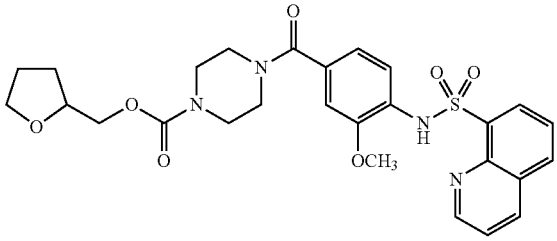

$^1$H NMR (400 MHz, $CDCl_3$) δ: 1.2 (m, 2H), 1.2 (m, 2H), 1.6 (m, 1H), 2.0 (m, 2H), 3.2-3.8 (m, 8H), 3.9 (s, 3H), 4.0 (m, 2H), 6.9-7.0 (m, 2H), 7.6-7.8 (m, 3H), 8.0 (m, 1H), 8.2-8.4 (m, 2H), 9.1 (m, 1H); HPLC Purity: 99.0%; LCMS, m/z found 555.1 $(M+1)^+$.

2-Cyclopentylethyl 4-(3-methoxy-4-(quinoline-8-sulfonamido)benzoyl)piperazine-1-carboxylate (120ct)

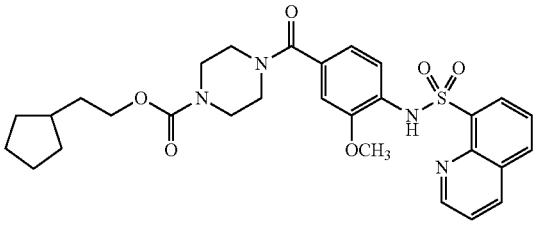

$^1$H NMR (400 MHz, $CDCl_3$) δ: 1.2 (m, 6H), 1.6 (m, 12H), 2.0 (m, 2H), 3.2-3.8 (m, 8H), 3.9 (s, 3H), 4.0 (m, 2H), 6.9-7.0 (m, 2H), 7.6-7.8 (m, 3H), 8.0 (m, 1H), 8.2-8.4 (m, 2H), 9.1 (m, 1H); HPLC Purity: 99.0%; LCMS, m/z found 589.1 $(M+1)^+$.

2-Cyclohexylethyl 4-(3-methoxy-4-(quinoline-8-sulfonamido)benzoyl)piperazine-1-carboxylate (120cu)

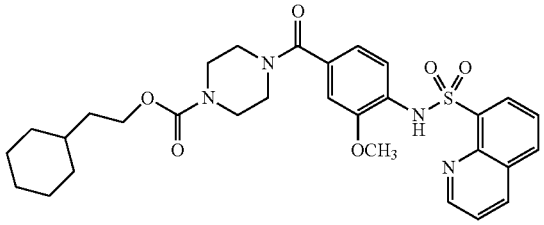

$^1$H NMR (400 MHz, $CDCl_3$) δ: 1.0 (m, 2H), 1.2 (m, 6H), 1.6 (m, 6H), 3.2-3.8 (m, 8H), 3.9 (s, 3H), 4.6 (m, 1H), 6.9-7.0 (m, 2H), 7.6-7.8 (m, 3H), 8.0 (m, 1H), 8.2-8.4 (m, 2H), 9.1 (m, 1H); HPLC Purity: 98.3%; LCMS, m/z found 581.4 $(M+1)^+$.

Synthesis of Piperazine Derivatives with 3-Trifluoromethyl or 3-Trifluoromethoxy Substituted Phenyl Rings Scheme 18

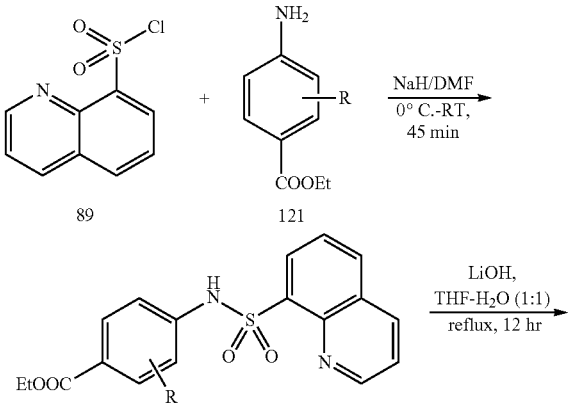

-continued

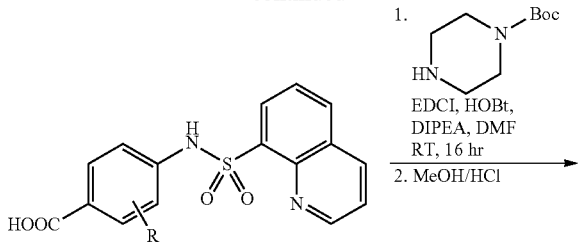

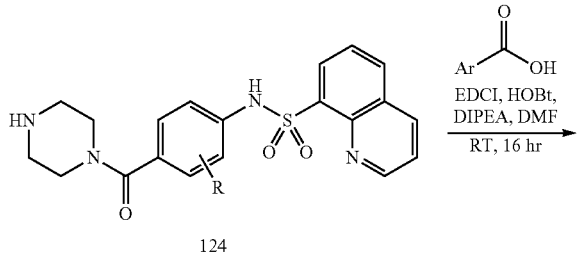

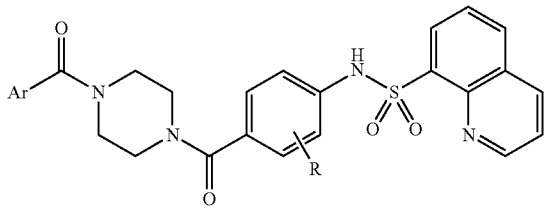

General Procedure for the Synthesis of Sulfonamide 122:

To a stirred solution of amine 121 (30.3 mmol) in DMF (20 ml per gm) under nitrogen atmosphere was added sodium hydride (90.9 mmol) portion-wise at 0° C. and stirred for 10 min at RT. Quinoline-8-sulfonyl chloride 89 (8.94 gm, 39.4 mmol) was then added to the reaction mixture at 0° C. The resulting mixture was stirred for further 30 min at RT. After completion of the reaction, most of the solvent was removed under low pressure. The residue was diluted with ice water-EtOAc mixture and the pH was brought to 7.0 using saturated solution of $NaH_2PO_4$. The product was then extracted in EtOAc, washed with water and brine, dried over sodium sulphate and the solvent removed under low pressure. The General Procedure for the Synthesis of Hydrolysis Product 12

To a stirred solution of sulfonamide 122 (22.4 mmol) in THF:$H_2O$ (1:1) under nitrogen atmosphere was added solid LiOH (9.4 gm, 224 mmol) at RT. The solution was then refluxed for 6 hr. After completion of the reaction, the reaction mixture was washed with ethyl acetate (2×100 ml) to remove non polar impurities. The aqueous layer was acidified (pH 4) with citric acid solution. The resultant precipitate was filtered out and air-dried. The traces of water were removed by co-distillation with toluene. The resultant off white solid (80%) was taken to the next step without further purification.

General Procedure for the Synthesis of Sulfonamide 124:

EDCI (3.8 g, 19.8 mmol) and HOBT (2.67 g, 19.8 mmol) were added to a stirred solution of the acid 123 (19.8 mmol) in anhydrous DMF. The temperature of the mixture was reduced to 0° C., at which time DIPEA (11 ml, 59.45 mmol) was added under nitrogen atmosphere and the resultant solution (or suspension) was stirred at room temperature for 30 min Boc-piperazine (3.68 g, 19.8 mmol) was then added at 0° C. The reaction mixture was then brought to room temperature and stirred overnight. After completion of the reaction, the reaction mixture was diluted with water and extracted with ethyl acetate (3×70 ml). The organic layer was washed with water (3×50 ml), dried over anhydrous sodium sulfate, filtered and concentrated over the rotary evaporator to get the crude product. Crude product was purified by column chromatography (60-120 silica gel, 2% MeOH-DCM) to get pure product, Boc-125 (8.0 g, 82%) as an off-white solid, which was subjected to the treatment with methanolic HCl (100 ml) for 2 hr at RT. After the complete cleavage of Boc-group, the solvent was removed under low pressure, to give the crude product as an HCl salt. The aqueous solution of the salt was washed with diethylether and basified with $NaHCO_3$ (pH 10). The desired product was then partitioned into ethyl acetate, dried with anhydrous $Na_2SO_4$ and the solvent removed under low pressure to get the free amine 125 as off white solid (6.0 g, 95%).

General Procedure for the Synthesis of Amides 125a-g:

EDCI (48 mg, 0.2525 mmol) and HOBT (34 mg, 0.2525 mmol) were added to a stirred solution of the Ar—COOH (0.2525 mmol) in anhydrous DMF. The temperature of the mixture was reduced to 0° C., at which time DIPEA (139 μl, 0.7575 mmol) was added under nitrogen atmosphere and the resultant solution (or suspension) was stirred at room temperature for 30 min Amine 124 (100 mg, 0.2525 mmol) was then added at 0° C. The reaction mixture was then brought to room temperature and stirred overnight. After completion of the reaction, the reaction mixture was diluted with water and extracted with ethyl acetate (333 15 ml). The organic layer was washed with water (3×10 ml), dried over anhydrous sodium sulfate, filtered and concentrated over the rotary evaporator to get the crude product. Crude product was purified by either by silica column chromatography or preparative HPLC to obtain the pure products in 52-70% yields.

N-(4-(4-Isonicotinoylpiperazine-1-carbonyl)-2-(trifluoromethyl)phenyl)quinoline-8-sulfonamide (125a)

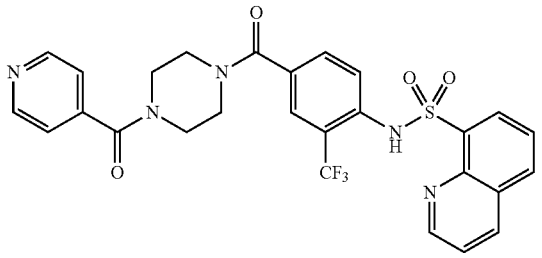

[$^1$H NMR (400 MHz, $CDCl_3$) δ: 3.2-3.8 (m, 8H), 7.2 (m, 2H), 7.4-7.7 (m, 4H), 8.0 (m, 2H), 8.4-8.8 (m, 4H), 9.1 (m, 1H);] HPLC Purity: 99.0%; LCMS, m/z found 570.1 $(M+1)^+$.

N-(4-(4-Nicotinoylpiperazine-1-carbonyl)-2-(trifluoromethyl)phenyl)quinoline-8-sulfonamide (125b)

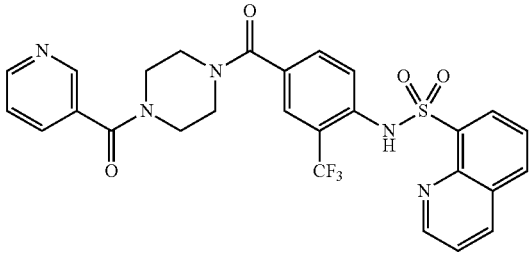

$^1$H NMR (400 MHz, $CDCl_3$) δ: 3.2-3.8 (m, 8H), 7.2 (m, 2H), 7.4-7.9 (m, 5H), 8.0-8.4 (m, 2H), 8.4-8.8 (m, 3H), 9.1 (m, 1H); HPLC Purity: 98.4%; LCMS, m/z found 570.1 $(M+1)^+$.

N-(4-(4-(Pyrazine-2-carbonyl)piperazine-1-carbonyl)-2-(trifluoromethyl)phenyl)quinoline-8-sulfonamide (125c)

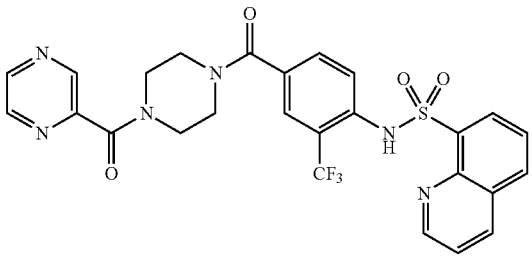

$^1$H NMR (400 MHz, $CDCl_3$) δ: 3.2-3.8 (m, 8H), 7.4-7.9 (m, 5H), 8.0-8.4 (m, 2H), 8.4-8.8 (m, 3H), 9.1 (m, 2H); HPLC Purity: 90.0%; LCMS, m/z found 571.1 $(M+1)^+$.

N-(4-(4-(2,6-Difluorobenzoyl)piperazine-1-carbonyl)-2-(trifluoromethyl)phenyl)quinoline-8-sulfonamide (125d)

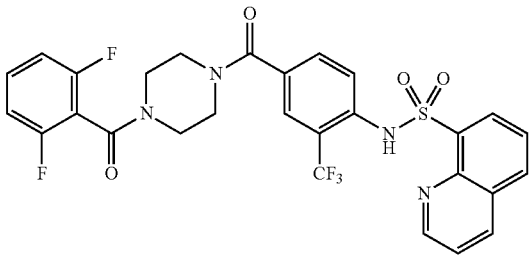

$^1$H NMR (400 MHz, $CDCl_3$) δ: 3.2-3.8 (m, 8H), 7.0 (m, 1H), 7.2-7.9 (m, 6H), 8.2-8.8 (m, 3H), 9.1 (m, 2H); HPLC Purity: 90.0%; LCMS, m/z found 571.1 $(M+1)^+$.

N-(4-(4-(2-Fluoro-3-methoxybenzoyl)piperazine-1-carbonyl)-2-(trifluoromethyl)phenyl)quinoline-8-sulfonamide (125e)

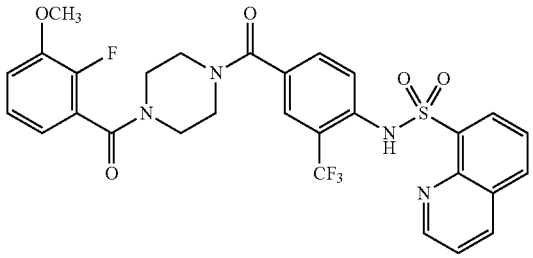

$^1$H NMR (400 MHz, $CDCl_3$) δ: 3.2-3.8 (m, 8H), 3.9 (s, 3H), 6.9-7.2 (m, 2H), 7.4-7.9 (m, 5H), 8.0-8.6 (m, 3H), 9.1 (m, 2H); HPLC Purity: 99.0%; LCMS, m/z found 617.1 $(M+1)^+$.

N-(4-(4-(1,2,3-Thiadiazole-4-carbonyl)piperazine-1-carbonyl)-2-(trifluoromethyl)phenyl)quinoline-8-sulfonamide (125f)

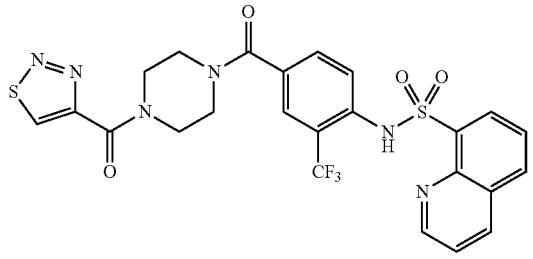

[$^1$H NMR (400 MHz, $CDCl_3$) δ: 3.2-3.8 (m, 8H), 7.4-7.9 (m, 4H), 8.1-8.6 (m, 3H), 9.0 (m, 2H), 9.2 (s, 1H);] HPLC Purity: 99.0[%; LCMS, m/z found 557.1 $(M+1)^+$].

N-(4-(4-(Thiazole-4-carbonyl)piperazine-1-carbonyl)-2-(trifluoromethyl)phenyl)quinoline-8-sulfonamide (125g)

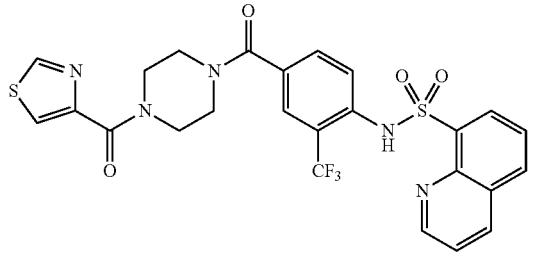

[$^1$H NMR (400 MHz, $CDCl_3$) δ: 3.2-3.8 (m, 8H), 7.4-7.9 (m, 3H), 8.1-8.6 (m, 4H), 8.8 (s, 1H), 9.0 (m, 1H);] HPLC Purity: 99.3%; LCMS, m/z found 576.1 $(M+1)^+$.

Synthesis Homopiperazine Compounds

Scheme 19

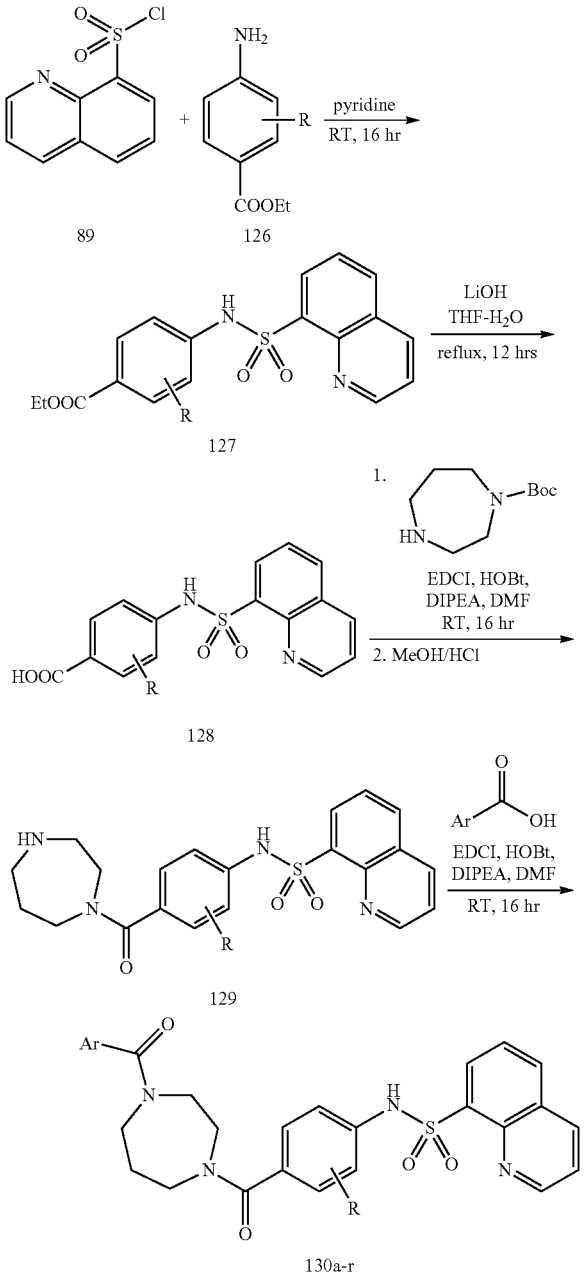

General Procedure for the Synthesis of Sulfonamide 127:

To a stirred solution of amine 126 (30.3 mmol) under nitrogen atmosphere was added pyridine (50 ml) at 0° C. and stirred for 10 min Quinoline-8-sulfonyl chloride 89 (8.94 gm, 39.4 mmol) was then added to the reaction mixture at the same temperature. The resulting mixture was stirred for 16 hr at RT. After completion of the reaction, the solvent was removed under low pressure. The traces of pyridine were removed by co-distillation with toluene. Diethylether was added to the resulting residue, and the solid product was filtered out and air-dried. The resulting crude product (8.0 gm, 74%) was taken to the next step without further purification.

General Procedure for the Synthesis of Acid 128:

To a stirred solution of sulfonamide 127 (22.4 mmol) in THF:$H_2O$ (1:1) under nitrogen atmosphere was added solid LiOH (9.4 gm, 224 mmol) at RT. The solution was then refluxed for 6 hr. After completion of the reaction, the reaction mixture was washed with ethyl acetate (2×100 ml) to remove non polar impurities. The aqueous layer was acidified (pH 4) with citric acid solution. The resultant precipitate was filtered out and air-dried. The traces of water were removed by co-distillation with toluene. The resultant off white solid (80%) was taken to the next step without further purification.

General Procedure for the Synthesis of Amine 129:

EDCI (3.8 g, 19.8 mmol) and HOBT (2.67 g, 19.8 mmol) were added to a stirred solution of the acid 128 (19.8 mmol) in anhydrous DMF. The temperature of the mixture was reduced to 0° C., at which time DIPEA (11 ml, 59.45 mmol) was added under nitrogen atmosphere and the resultant solution (or suspension) was stirred at room temperature for 30 min Boc-homopiperazine (19.8 mmol) was then added at 0° C. The reaction mixture was then brought to room temperature and stirred overnight. After completion of the reaction, the reaction mixture was diluted with water and extracted with ethyl acetate (3×70 ml). The organic layer was washed with water (3×50 ml), dried over anhydrous sodium sulfate, filtered and concentrated over the rotary evaporator to get the crude product. Crude product was purified by column chromatography (60-120 silica gel, 2% MeOH-DCM) to get pure product, Boc-129 (85%) as an off-white solid, which was subjected to the treatment with methanolic HCl (100 ml) for 2 hr at RT. After the complete cleavage of Boc-group, the solvent was removed under low pressure, to give the crude product as an HCl salt. The aqueous solution of the salt was washed with diethylether and basified with $NaHCO_3$ (pH 10). The desired product was then partitioned into ethyl acetate, dried with anhydrous $Na_2SO_4$ and the solvent removed under low pressure to get the free amine 129 as off white solid (92%).

General Procedure for the Synthesis of Amides 130a-r:

EDCI (48 mg, 0.2525 mmol) and HOBT (34 mg, 0.2525 mmol) were added to a stirred solution of the Ar—COOH (0.2525 mmol) in anhydrous DMF. The temperature of the mixture was reduced to 0° C., at which time DIPEA (139 μl, 0.7575 mmol) was added under nitrogen atmosphere and the resultant solution (or suspension) was stirred at room temperature for 30 min Amine 129 (0.2525 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (333 10 ml), dried over anhydrous sodium sulfate, filtered and concentrated over the rotary evaporator to get the crude product. Crude product was purified by either by silica column chromatography or preparative HPLC to obtain the pure products in 54-72% yields.

N-(4-(4-(2-(2-Fluorophenyl)acetyl)-1,4-diazepane-1-carbonyl)phenyl)quinoline-8-sulfonamide (130a)

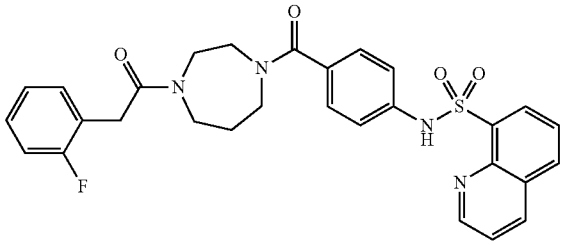

[$^1$H NMR (400 MHz, DMSOd$_6$) δ: 3.0-3.8 (m, 10H), 7.0-7.4 (m, 8H), 7.5-7.8 (m, 2H), 8.0-8.4 (m, 3H), 9.1 (m, 1H);] HPLC Purity: 98.1%; LCMS, m/z found 547.4 (M+1)$^+$.

N-(4-(4-(2-(5-Fluoropyridin-2-yl)-2-methylpropanoyl)-1,4-diazepane-1-carbonyl)phenyl)quinoline-8-sulfonamide (130b)

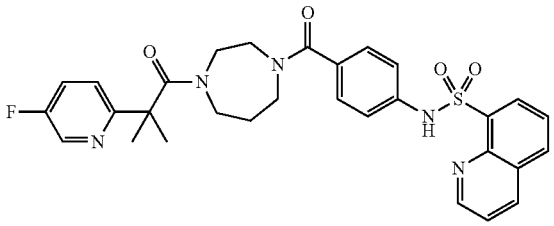

$^1$H NMR (400 MHz, DMSOd$_6$) δ: 1.4 (s, 6H), 3.0-3.8 (m, 10H), 7.0-7.2 (m, 6H), 7.6-7.8 (m, 2H), 8.0-8.4 (m, 3H), 9.1 (m, 1H); HPLC Purity: 98.6%; LCMS, m/z found 575.4 (M+1)$^+$.

N-(4-(4-(2-Fluoro-3-methoxybenzoyl)-1,4-diazepane-1-carbonyl)phenyl)quinoline-8-sulfonamide (130c)

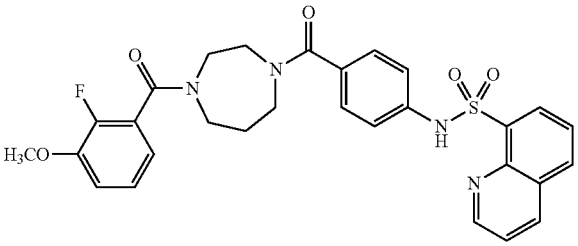

[$^1$H NMR (400 MHz, DMSOd$_6$) δ: 3.0-3.8 (m, 10H), 3.9 (s, 3H), 6.9-7.2 (m, 7H), 7.6-7.8 (m, 2H), 8.2-8.4 (m, 3H), 9.1 (m, 1H);] HPLC Purity: 98.2%[; LCMS, m/z found 561.5 (M+1)$^+$].

N-(4-(4-Picolinoyl-1,4-diazepane-1-carbonyl)phenyl)quinoline-8-sulfonamide (130d)

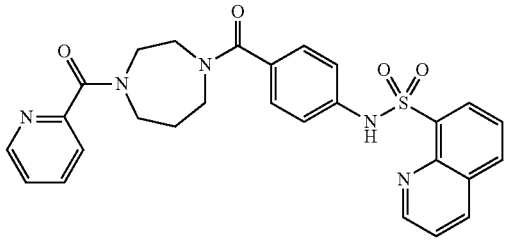

$^1$H NMR (400 MHz, DMSOd$_6$) δ: 1.4-1.6 (m, 2H), 3.0-3.8 (m, 8H), 7.0-8.0 (m, 8H), 8.2-8.4 (m, 5H), 9.1 (m, 1H); HPLC Purity: 99.4%; LCMS, m/z found 516.0 (M+1)$^+$.

N-(4-(4-(2,6-Difluorobenzoyl)-1,4-diazepane-1-carbonyl)-phenyl)quinoline-8-sulfonamide (130e)

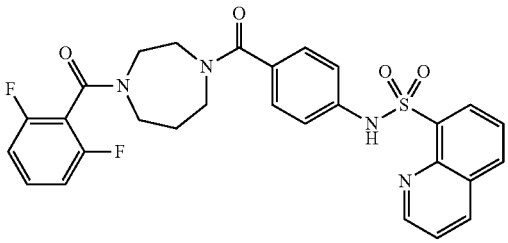

$^1$H NMR (400 MHz, DMSOd$_6$) δ: 1.4-1.6 (m, 2H), 3.0-3.8 (m, 8H), 7.0-8.0 (m, 8H), 8.2-8.4 (m, 4H), 9.1 (m, 1H); HPLC Purity: 98.7%; LCMS, m/z found 551.3 (M+1)$^+$.

N-(4-(4-(2-(4-Fluorophenyl)acetyl)-1,4-diazepane-1-carbonyl)phenyl)quinoline-8-sulfonamide (130f)

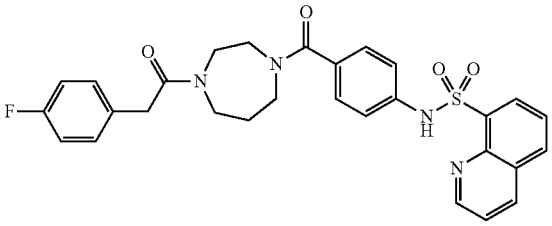

$^1$H NMR (400 MHz, DMSOd$_6$) δ: 1.4-1.6 (m, 2H), 3.0-3.8 (m, 8H), 7.0-8.0 (m, 8H), 8.2-8.4 (m, 5H), 9.1 (m, 1H); HPLC Purity: 99.6%; LCMS, m/z found 547.2 (M+1)$^+$.

N-(4-(4-(4-Chlorobenzoyl)-1,4-diazepane-1-carbonyl)phenyl)quinoline-8-sulfonamide (130g)

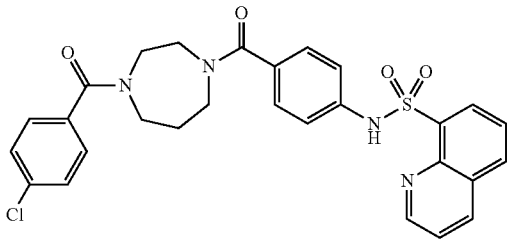

[$^1$H NMR (400 MHz, DMSO$d_6$) δ: 1.4-1.6 (m, 2H), 3.0-3.8 (m, 8H), 7.0-8.0 (m, 8H), 8.2-8.4 (m, 5H), 9.1 (m, 1H);] HPLC Purity: 99.4%; LCMS, m/z found 549.3 $(M+1)^+$.

N-(4-(4-(2-(4-(Trifluoromethyl)phenyl)acetyl)-1,4-diazepane-1-carbonyl)phenyl)quinoline-8-sulfonamide (130h)

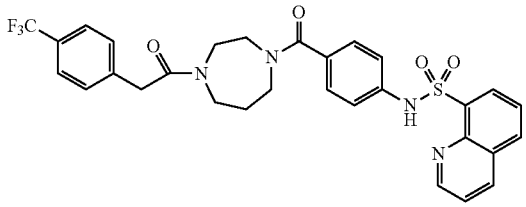

$^1$H NMR (400 MHz, DMSO$d_6$) δ: 1.4-1.6 (m, 2H), 3.0-3.8 (m, 8H), 7.0-8.0 (m, 8H), 8.2-8.4 (m, 5H), 9.1 (m, 1H); HPLC Purity: 99.2%; LCMS, m/z found 597.2 $(M+1)^+$.

N-(4-(4-(2,4-Dichlorobenzoyl)-1,4-diazepane-1-carbonyl)phenyl)quinoline-8-sulfonamide 2,2,2-trifluoroacetate (130i)

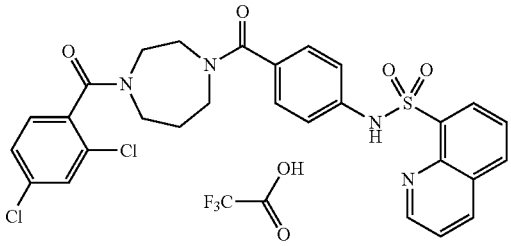

$^1$H NMR (400 MHz, DMSO$d_6$) δ: 1.4-1.6 (m, 2H), 3.0-3.8 (m, 8H), 7.0-8.0 (m, 8H), 8.2-8.4 (m, 3H), 8.5 (s, 1H), 9.1 (m, 1H), HPLC Purity: 94.4%; LCMS, m/z found 582.47 $(M+1)^+$.

N-(4-(4-(2,3-Difluorobenzoyl)-1,4-diazepane-1-carbonyl)phenyl)quinoline-8-sulfonamide (130j)

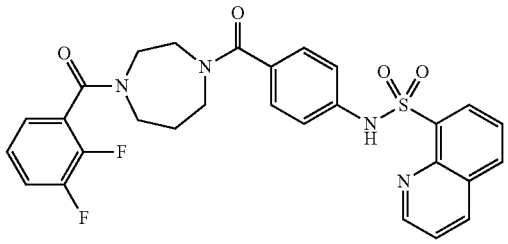

$^1$H NMR (400 MHz, $CD_3OD$) δ: 1.4-1.6 (m, 2H), 3.0-3.8 (m, 8H), 7.0-8.0 (m, 8H), 8.2-8.4 (m, 4H), 9.1 (m, 1H); HPLC Purity: 98.6%; LCMS, m/z found 549.5 $(M+1)^+$.

N-(4-(4-(3,4-Difluorobenzoyl)-1,4-diazepane-1-carbonyl)phenyl)quinoline-8-sulfonamide 2,2,2-trifluoroacetate (130k)

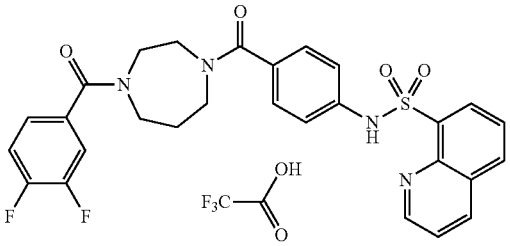

$^1$H NMR (400 MHz, $CD_3OD$) δ: 1.4-1.6 (m, 2H), 3.0-3.8 (m, 8H), 7.0-8.0 (m, 8H), 8.2-8.4 (m, 4H), 9.1 (m, 1H); HPLC Purity: 99.4%; LCMS, m/z found 549.3 $(M-1)^+$.

N-(4-(4-(2-Methylnicotinoyl)-1,4-diazepane-1-carbonyl)phenyl)quinoline-8-sulfonamide (130l)

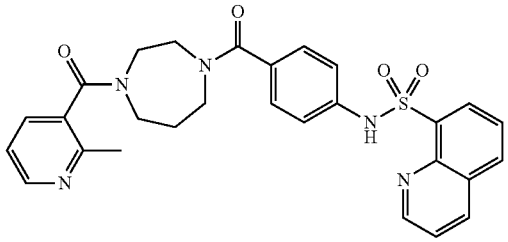

$^1$H NMR (400 MHz, $CD_3OD$) δ: 1.4-1.6 (m, 2H), 2.1 (s, 3H), 3.0-3.8 (m, 8H), 7.0-8.0 (m, 8H), 8.2-8.4 (m, 4H), (m, 1H); HPLC Purity: 98.0%; LCMS, m/z found 530.4 $(M+1)^+$.

N-(4-(4-(2-Phenylacetyl)-1,4-diazepane-1-carbonyl)phenyl)quinoline-8-sulfonamide 2,2,2-trifluoroacetate (130m)

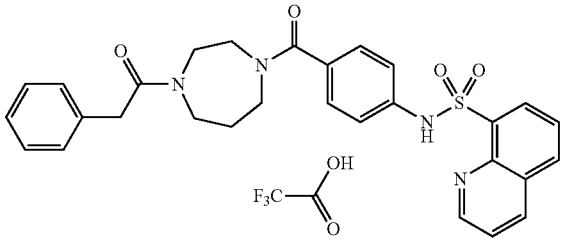

$^1$H NMR (400 MHz, $CD_3OD$) δ: 1.4-1.6 (m, 2H), 1.6-2.0 (s, 2H), 3.0-3.8 (m, 8H), 7.0-8.0 (m, 8H), 8.2-8.4 (m, 6H), 9.1 (m, 1H); HPLC Purity: 98.8%; LCMS, m/z found 529.1 $(M+1)^+$.

N-(4-(4-(1,2,3-Thiadiazole-4-carbonyl)-1,4-diazepane-1-carbonyl)phenyl)quinoline-8-sulfonamide 2,2,2-trifluoroacetate (130n)

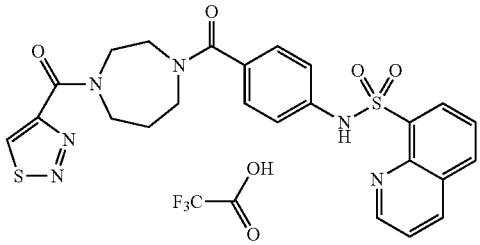

$^1$H NMR (400 MHz, $CD_3OD$) δ: 1.4-1.6 (m, 2H), 3.0-3.8 (m, 8H), 7.0-8.0 (m, 6H), 8.2-8.4 (m, 4H), 9.1 (s, 1H); HPLC Purity: 98.5%; LCMS, m/z found 523.1 $(M+1)^+$.

N-(4-(4-(3-Phenylpropanoyl)-1,4-diazepane-1-carbonyl)phenyl)quinoline-8-sulfonamide (130o)

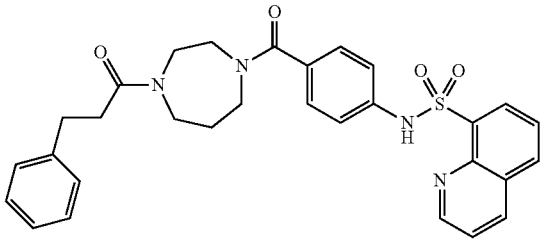

$^1$H NMR (400 MHz, $CD_3OD$) δ: 1.4-1.6 (m, 2H), 1.7 (t, 2H), 1.8 (t, 2H), 3.0-3.8 (m, 8H), 7.0-8.0 (m, 8H), 8.2-8.4 (m, 6H), 9.1 (s, 1H); HPLC Purity: 98.2%; LCMS, m/z found 543.1 $(M+1)^+$.

N-(4-(4-(2-Phenylpropanoyl)-1,4-diazepane-1-carbonyl)phenyl)quinoline-8-sulfonamide (130p)

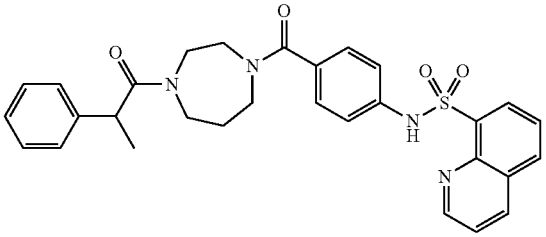

$^1$H NMR (400 MHz, $DMSOd_6$) δ: 1.2 (s, 3H), 1.3 (m, 2H), 3.0-3.8 (m, 8H), 4.0 (m, 1H), 7.0-8.0 (m, 8H), 8.2-8.4 (m, 6H), 9.1 (s, 1H); HPLC Purity: 97.1%; LCMS, m/z found 543.1 $(M+1)^+$.

N-(2-Methyl-4-(4-picolinoyl-1,4-diazepane-1-carbonyl)phenyl)quinoline-8-sulfonamide (130q)

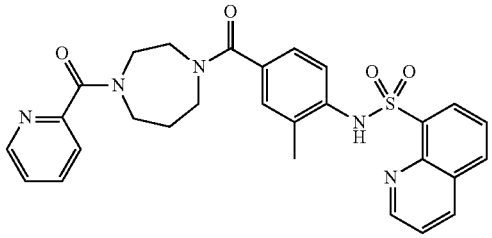

$^1$H NMR (400 MHz, $DMSOd_6$) δ: 1.2 (s, 3H), 1.3 (m, 2H), 3.0-3.8 (m, 8H), 7.0-8.0 (m, 8H), 8.2-8.4 (m, 4H), 9.1 (s, 1H); HPLC Purity: 96.3%; LCMS, m/z found 530.1 $(M+1)^+$.

N-(2-Hydroxy-4-(4-picolinoyl-1,4-diazepane-1-carbonyl)phenyl)quinoline-8-sulfonamide (130r)

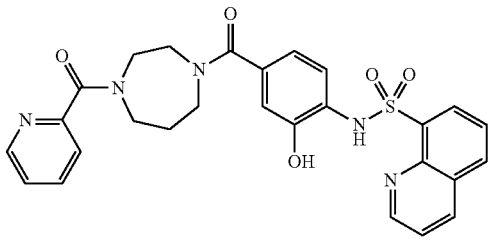

$^1$H NMR (400 MHz, $DMSOd_6$) δ: 1.3-1.8 (m, 2H), 3.0-3.8 (m, 8H), 5.8 (s, 1H), 7.0-8.0 (m, 8H), 8.2-8.4 (m, 4H), 9.1 (s, 1H); 10.2 (s, 1H), HPLC Purity: 98.0%; LCMS, m/z found 532.2 $(M+1)^+$.

Synthesis of Piperazine Based Reverse Sulfonamides

Scheme 20

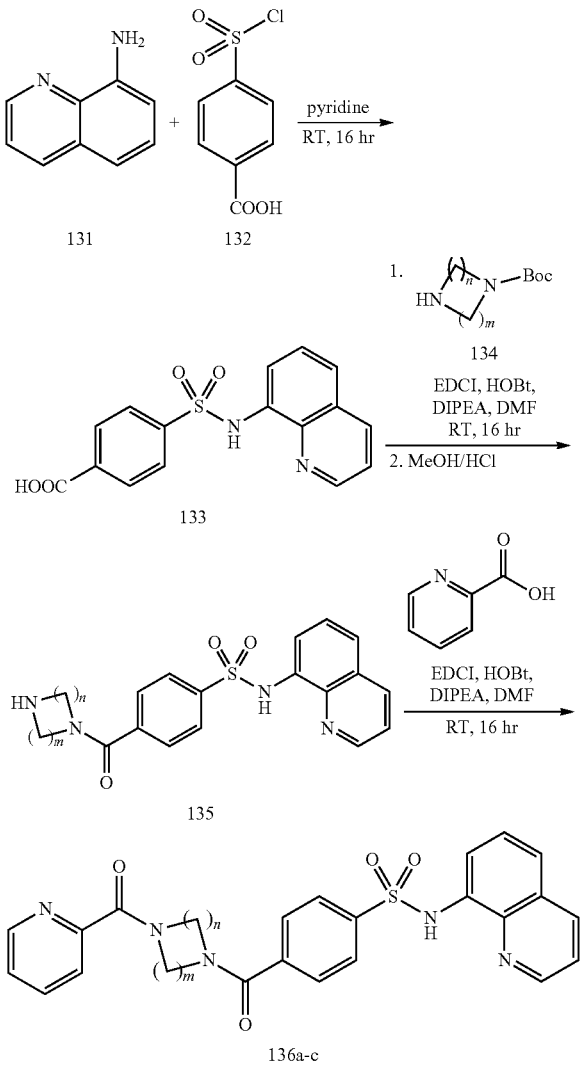

General Procedure for the Synthesis of Sulfonamide 133:

To a stirred solution of Quinoline-8-amine 131 (30.3 mmol) under nitrogen atmosphere was added pyridine (50 ml) at 0° C. and stirred for 10 min 4-(Chlorosulfonyl) benzoic acid (132, 30.3 mmol) was then added to the reaction mixture at the same temperature. The resulting mixture was stirred for 16 hr at RT. After completion of the reaction, the solvent was removed under low pressure. The traces of pyridine were removed by co-distillation with toluene. Diethylether was added to the resulting residue, and the solid product was filtered out and air-dried. The resulting crude product (74%) was then to the next step without further purification.

General Procedure for the Synthesis of Sulfonamide 135:

EDCI (3.8 g, 19.8 mmol) and HOBT (2.67 g, 19.8 mmol) were added to a stirred solution of the acid 133 (19.8 mmol) in anhydrous DMF. The temperature of the mixture was reduced to 0° C., at which time DIPEA (11 ml, 59.45 mmol) was added under nitrogen atmosphere and the resultant solution (or suspension) was stirred at room temperature for 30 min Secondary amine 134 (19.8 mmol) was then added at 0° C. The reaction mixture was then brought to room temperature and stirred overnight. After completion of the reaction, the reaction mixture was diluted with water and extracted with ethyl acetate (3×70 ml). The organic layer was washed with water (3×50 ml), dried over anhydrous sodium sulfate, filtered and concentrated over the rotary evaporator to get the crude product. Crude product was purified by column chromatography (60-120 silica gel, 2% MeOH-DCM) to get pure product, Boc-135 (83%) as an off-white solid, which was subjected to the treatment with methanolic HCl (100 ml) for 2 hr at RT. After the complete cleavage of Boc-group, the solvent was removed under low pressure, to give the crude product as an HCl salt. The aqueous solution of the salt was washed with diethylether and basified with $NaHCO_3$ (pH 10). The desired product was then partitioned into ethyl acetate, dried with anhydrous $Na_2SO_4$ and the solvent removed under low pressure to get the free amine 135 as off white solid (95%)

General Procedure for the Synthesis of Amides 136a-c:

EDCI (48 mg, 0.2525 mmol) and HOBT (34 mg, 0.2525 mmol) were added to a stirred solution of the picolinic acid (0.2525 mmol) in anhydrous DMF. The temperature of the mixture was reduced to 0° C., at which time DIPEA (139 μl, 0.7575 mmol) was added under nitrogen atmosphere and the resultant solution (or suspension) was stirred at room temperature for 30 min Amine 135 (100 mg, 0.2525 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (3×10 ml), dried over anhydrous sodium sulfate, filtered and concentrated over the rotary evaporator to get the crude product. Crude product was purified by either by silica column chromatography or preparative HPLC to obtain the pure products in 55-76% yields.

4-(4-Picolinoylpiperazine-1-carbonyl)-N-(quinolin-8-yl)benzenesulfonamide (136a)

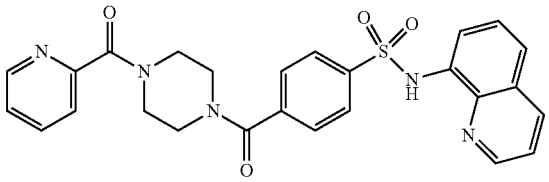

[$^1$H NMR (400 MHz, $DMSOd_6$) δ: 1.4-1.6 (m, 2H), 3.2-3.8 (m, 8H), 7.0-8.0 (m, 10H), 8.2 (m, 1H), 8.5 (d, 2H), 8.8 (d, 2H), 10.2 (s, 1H);] HPLC Purity: 99.4%; LCMS, m/z found 502.1 $(M+1)^+$.

4-(4-Picolinoyl-1,4-diazepane-1-carbonyl)-N-(quinolin-8-yl)benzenesulfonamide (136b)

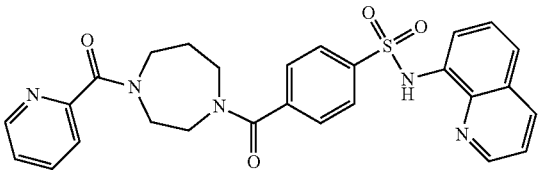

$^1$H NMR (400 MHz, DMSO$d_6$) δ: 3.2 (m, 2H), 3.5 (m, 2H), 3.8 (m, 6H), 7.0-7.4 (m, 6H), 7.6-8.0 (m, 4H), 8.2-9.0 (m, 4H), 10.2 (s, 1H); HPLC Purity: 97.8%; LCMS, m/z found 516.2 $(M+1)^+$.

Synthesis of Benzyl Series—Piperazine Based Compounds with Substituted Phenyl Rings Scheme 21

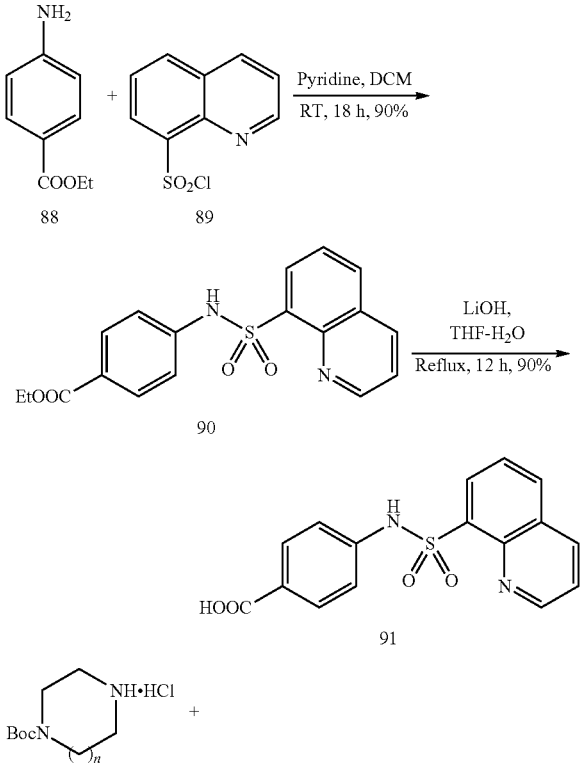

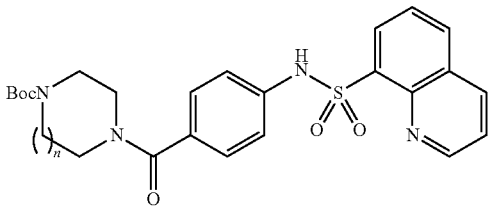

138 $\xrightarrow{\text{Methanolic HCl/0° C.-RT}}$

-continued

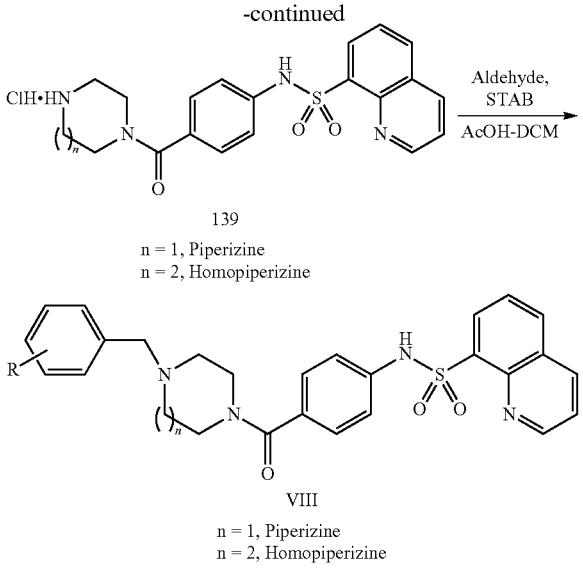

STAB = Sodium tri-acetoxy borohydride

Synthesis of ethyl 4-(quinoline-8-sulfonamido)benzoate (90)

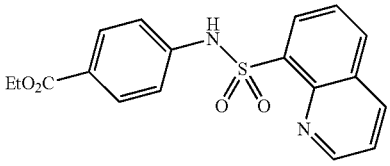

To a solution of amine 88 (16 gm, 96.85 mmol) in a mixture (1:1) of DCM and pyridine, sulfonyl chloride 89 (27.56 gm, 121.07 mmol) was added at room temperature under $N_2$ atmosphere. The resulting mixture was allowed to stir for 16 hrs. After completion of reaction, the crude mixture was diluted with DCM, washed with water followed by 1N HCl. The organic layer was then dried over $Na_2SO_4$ and concentrated under reduced pressure to afford product 90 in 98% yields (34 gm).

Synthesis of 4-(quinoline-8-sulfonamido)benzoic acid (91)

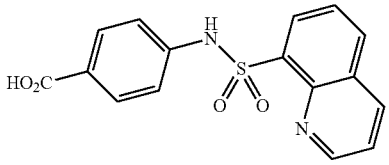

To a solution of sulfonamide 90 (34 gm, 95.5 mmol) in THF and water (1:1), LiOH (20 gm, 47.66 mmol) was added and the resulting mixture was allowed to stir at 80° C. overnight. After completion of reaction, the crude mixture was washed with EtOAc. The aqueous layer was acidified with citric acid and filtered. Thus obtained solid was washed with $Et_2O$ and azeotroped by toluene, under reduced pressure to afford acid 91 (30 gm, 95.8% yield) which was taken forward for the next step without further purification.

Synthesis of tert-butyl 4-(4-(quinoline-8-sulfonamido)benzoyl)piperazine-1-carboxylate (138)

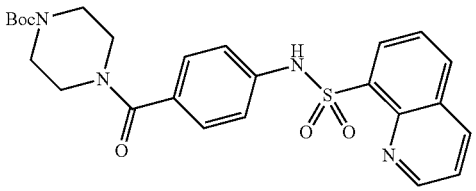

To a solution of acid 91 (2 gm, 6.09 mmol) in DMF, PyBoP (Benzotriazole-1-yl-oxy-tris-(dimethylamino)-phosphonium hexafluorophosphate) (4.75 gm, 9.14 mmol) was added at 0° C. and allowed to stir for 5 minutes. Then Boc protected piperizine/homopiperizine 137 (1.13 gm, 6.09 mmol) was added to the reaction mixture at the same temperature under $N_2$ atmosphere and stirred overnight at room temperature. After completion of reaction, mixture was diluted with water and extracted with EtOAc. The organic layer was washed with water, dried over $Na_2SO_4$, and evaporated under reduced pressure. The residue was purified by column chromatography (silica gel, 60-120 mesh; MeOH-DCM, 2:8) to afford product 138 in 66% yield (2 gm).

Synthesis of N-(4-(piperazine-1-carbonyl)phenyl) quinoline-8-sulfonamide (139)

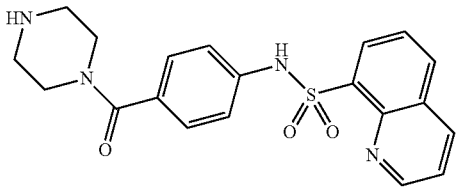

To a solution of MeOH.HCl, Boc protected amine 138 (2 gm, 4.03 mmol) was added and the resulting mixture was stirred for 1 hr. After completion of reaction, solvent was so removed under reduced pressure, washed with water followed by addition of $NaHCO_3$ and extracted with DCM. The organic layer was dried over $Na_2SO_4$ and evaporated under reduced pressure to afford product 139 (1.5 gm, 94.30% yield).

General Procedure for the Synthesis of Compound (VIII-1)-(VIII-216):

To a solution of amine 139 (0.25 mmoles) and appropriate aldehyde (0.27 mmol) in DCM, acetic acid (0.2 mL) was added at room temperature and the resulting mixture was allowed to stir for 30 min Then STAB (0.26 gm, 1.26 mmol) was added to reaction mixture and the resulting mixture was allowed to stir at 50° C. for 1 hr. After completion of reaction, the crude mixture was diluted with DCM washed with water, dried over $Na_2SO_4$ and concentrated under reduced pressure. The residue was purified by column chromatography (silica gel, 60-120 mesh; MeOH-DCM, 2:8) to afford product (VIII-1)-(VIII-216) in 32-45% yield.

N-(4-(4-benzylpiperazine-1-carbonyl)phenyl)quinoline-8-sulfonamide (VIII-1)

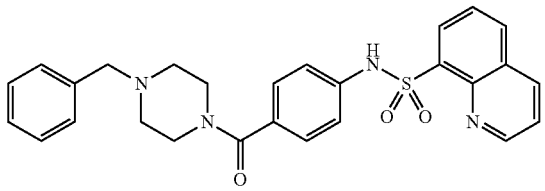

$^1$H NMR (400 MHz, $CDCl_3$) δ: 1.8 (s, 2H), 2.40 (br d, 4H), 3.38 (br d, 2H), 3.48 (d, 2H), 6.79-7.04 (m, 6H), 7.1-7.2 (m, 4H), 7.59-7.64 (m, 2H), 8.03-8.28 (m, 2H), 9.18 (s, 1H), 10.4 (s, 1H); HPLC Purity: 98.7%; LCMS: 487 (M+1).

N-(4-(4-(2-cyanobenzyl)piperazine-1-carbonyl)phenyl)quinoline-8-sulfonamide (VIII-2)

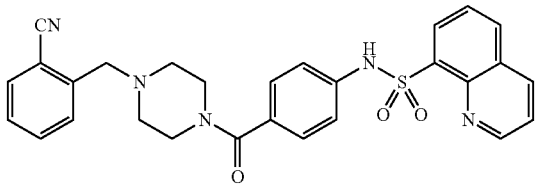

$^1$H NMR (400 MHz, $CDCl_3$) δ: 1.8 (s, 2H), 2.40 (br d, 4H), 3.38 (br d, 2H), 3.48 (d, 2H), 6.79-7.04 (m, 6H), 7.1-7.2 (m, 4H), 7.59-8.1 (m, 4H), 9.18 (s, 1H); HPLC Purity: 99.2%; LCMS: 512.3 (M+1).

N-(4-(4-(4-acetylbenzyl)piperazine-1-carbonyl)phenyl)quinoline-8-sulfonamide (VIII-3)

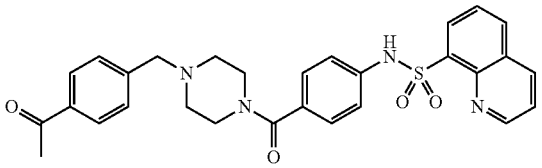

$^1$H NMR (400 MHz, $CDCl_3$) δ: 1.8 (s, 2H), 2.6 (s, 3H), 2.40 (br d, 4H), 3.38 (br d, 2H), 3.48 (d, 2H), 6.79-7.04 (m, 6H), 7.1-7.2 (m, 4H), 7.60-7.71 (m, 2H), 8.01-8.28 (m, 2H), 9.18 (s, 1H); HPLC Purity: 97.8%; LCMS: 529.2 (M+1).

N-(4-(4-(4-cyanobenzyl)piperazine-1-carbonyl)phenyl)quinoline-8-sulfonamide (VIII-4)

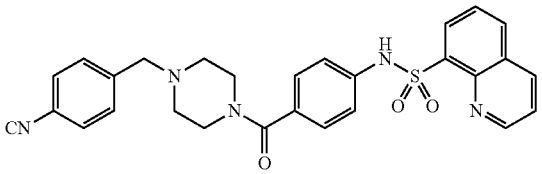

$^1$H NMR (400 MHz, $CDCl_3$) δ: 1.8 (s, 2H), 2.40 (br d, 4H), 3.38 (br d, 2H), 3.48 (d, 2H), 6.79-7.04 (m, 6H), 7.1-7.2 (m, 4H), 7.59-7.64 (m, 2H), 8.03-8.28 (m, 2H), 9.18 (s, 1H); HPLC Purity: 97.8%; LCMS: 512.3 (M+1).

N-(4-(4-(4-bromobenzyl)piperazine-1-carbonyl)phenyl)quinoline-8-sulfonamide (VIII-5)

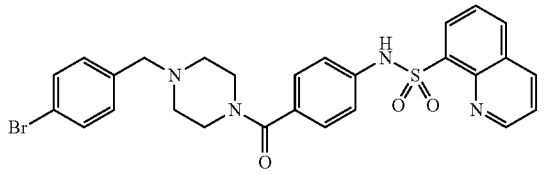

$^1$H NMR (400 MHz, $CDCl_3$) δ: 1.8 (s, 2H), 2.40 (br d, 4H), 3.38 (br d, 2H), 3.48 (d, 2H), 6.79-7.04 (m, 6H), 7.1-7.2 (m, 4H), 7.59-7.64 (m, 2H), 8.03-8.28 (m, 2H), 10.4 (s, 1H); HPLC Purity: 98.3%; LCMS: 566.1 (M+1).

N-(4-(4-(3-chlorobenzyl)piperazine-1-carbonyl)phenyl)quinoline-8-sulfonamide (VIII-6) 40

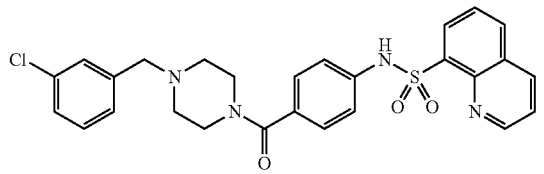

$^1$H NMR (400 MHz, $CDCl_3$) δ: 1.8 (s, 2H), 2.40 (br d, 4H), 3.38 (br d, 2H), 3.48 (d, 2H), 6.8-7.04 (m, 4H), 7.1-7.2 (m, 3H), 7.59-7.64 (m, 4H), 8.0-8.6 (m, 3H), 10.4 (s, 1H); HPLC Purity: 96.5%; LCMS: 522.1 (M+1).

N-(4-(4-(3-methoxybenzyl)piperazine-1-carbonyl)phenyl)quinoline-8-sulfonamide (VIII-7)

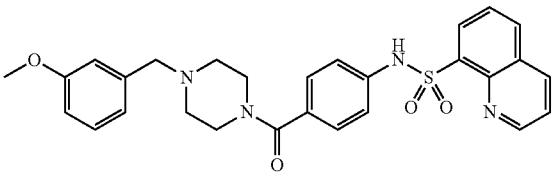

$^1$H NMR (400 MHz, $CDCl_3$) δ: 2.40 (s, 2H), 3.9 (s, 3H), 3.68 (br s, 4H), 3.4-3.6 (m, 4H), 7.06 (m, 4H), 7.18 (m, 3H), 7.25 (m, 2H), 7.42 (m, 2H), 8.58 (s, 1H), 9.18 (s, 1H); HPLC Purity: 97.8%; LCMS: 517.1 (M+1).

[N-(4-(4-(cyclopropylmethyl)piperazine-1-carbonyl)phenyl)quinoline-8-sulfonamide (VIII-8)]

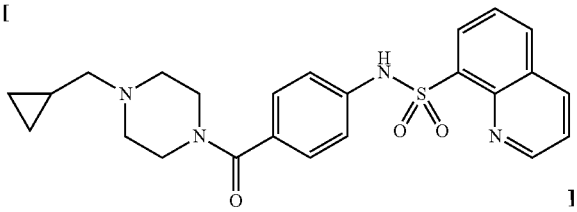

[$^1$H NMR (400 MHz, DMSO-$d_6$) δ: 1.2 (t, 2H), 1.3 (t, 2H), 1.31-1.35 (m, 1H), 2.40 (s, 2H), 3.68 (br s, 4H), 3.4-3.6 (m, 4H), 7.06 (m, 6H), 7.25-7.42 (m, 3H), 9.18 (s, 1H) 10.4 (s, 1H); HPLC Purity: 97.81%; LCMS: 451.3 (M+1).]

N-(4-(4-butylpiperazine-1-carbonyl)phenyl)quinoline-8-sulfonamide (VIII-9)

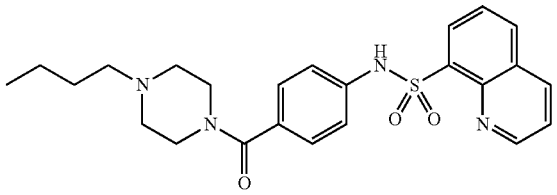

$^1$H NMR (400 MHz, DMSO-$d_6$) δ: 1.25-1.3 (m, 2H), 1.38-1.35 (m, 2H), 1.5 (t, 3H), 2.40 (s, 2H), 3.68 (br s, 4H), 3.4-3.6 (m, 4H), 7.06 (m, 6H), 7.25-7.42 (m, 3H), 9.18 (s, 1H) 10.4 (s, 1H); HPLC Purity: 99.7%; LCMS: 453.2 (M+1).

N-(4-(4-(pyridin-2-ylmethyl)piperazine-1-carbonyl)phenyl)quinoline-8-sulfonamide (VIII-10)

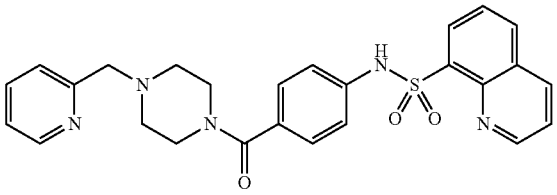

[$^1$H NMR (400 MHz, DMSO-$d_6$) δ: 2.5 (s, 2H), 3.68 (br s, 4H), 3.4-3.6 (m, 4H), 7.0-7.4 (m, 8H), 7.3-7.4 (m, 3H), 9.18 (s, 1H), 10.4 (s, 1H);] HPLC Purity: 95.8%; LCMS: 488.1 (M+1).

N-(4-(4-(2-chlorobenzyl)piperazine-1-carbonyl)phenyl)quinoline-8-sulfonamide (VIII-11)

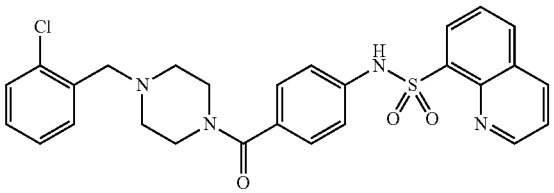

$^1$H NMR (400 MHz, DMSO-$d_6$) δ: 2.5 (s, 2H), 3.68 (br s, 4H), 3.4-3.6 (m, 4H), 7.0-7.4 (m, 6H), 7.3-7.4 (m, 4H), 8.0-8.35 (m, 3H), 9.18 (s, 1H), 10.4 (s, 1H); HPLC Purity: 98.8%; LCMS: 522.1 (M+1).

N-(4-(4-(2-acetylbenzyl)piperazine-1-carbonyl)phenyl)quinoline-8-sulfonamide (VIII-12)

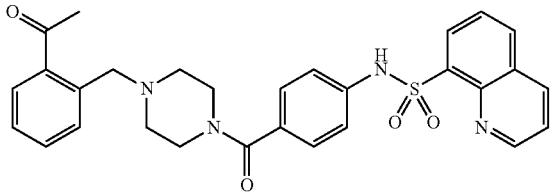

$^1$H NMR (400 MHz, $CDCl_3$ ) δ: 1.8 (s, 2H), 2.6 (s, 3H), 2.40 (br d, 4H), 3.38 (br d, 2H), 3.48 (d, 2H), 7.0-7.4 (m, 6H), 7.45-7.7 (m, 4H), 8.0-8.4 (m, 3H), 9.18 (s, 1H), 10.4 (s, 1H); HPLC Purity: 98.3%; LCMS: 529.2 (M+1).

N-(4-(4-(3-cyanobenzyl)piperazine-1-carbonyl)phenyl)quinoline-8-sulfonamide (VIII-13)

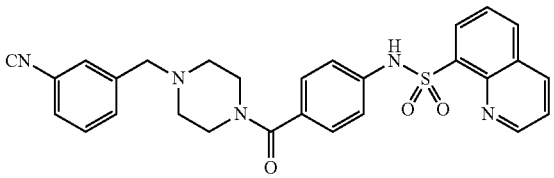

$^1$H NMR (400 MHz, $CDCl_3$) δ: 1.8 (s, 2H), 2.40 (br d, 4H), 3.38 (br d, 2H), 3.48 (d, 2H), 6.79-7.04 (m, 6H), 7.1-7.2 (m, 4H), 7.59-8.1 (m, 4H), 10.35 (s, 1H), HPLC Purity: 99.2%; MS: 512.3 (M+1).

N-(4-(4-(4-chlorobenzyl)piperazine-1-carbonyl)phenyl)quinoline-8-sulfonamide (VIII-14)

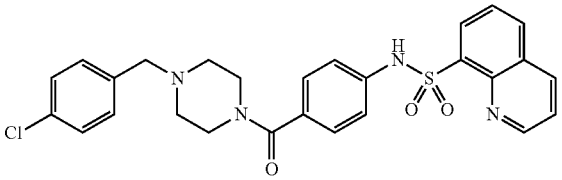

$^1$H NMR (400 MHz, $CDCl_3$) δ: 1.8 (s, 2H), 2.40 (br d, 4H), 3.38 (br d, 2H), 3.48 (d, 2H), 6.79-7.04 (m, 6H), 7.1-7.2 (m, 4H), 7.59-7.64 (m, 2H), 8.03-8.28 (m, 2H), 10.4 (s, 1H); HPLC Purity: 98.3%; LCMS: 522.3 (M+1).

N-(4-(4-(2-cyanobenzyl)piperazine-1-carbonyl)phenyl)quinoline-8-sulfonamide (VIII-15)

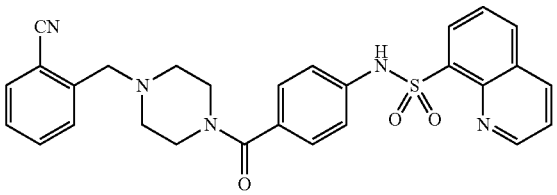

$^1$H NMR (400 MHz, DMSO$d_6$) δ: 2.5 (s, 2H), 3.68 (br s, 4H), 3.4-3.6 (m, 4H), 7.0-7.4 (m, 6H), 7.3-7.4 (m, 4H), 8.0-8.35 (m, 3H), 9.18 (s, 1H), 10.4 (s, 1H); HPLC Purity: 99.1%; LCMS: 512.3 (M+1).

N-(4-(4-(4-acetylbenzyl)piperazine-1-carbonyl)phenyl)quinoline-8-sulfonamide (VIII-16)

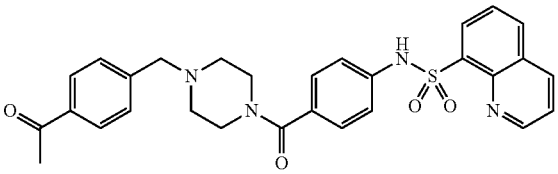

$^1$H NMR (400 MHz, $CDCl_3$) δ: 1.8 (s, 2H), 2.6 (s, 3H), 2.40 (br d, 4H), 3.38 (br d, 2H), 3.48 (d, 2H), 6.79-7.04 (m, 6H), 7.1-7.2 (m, 4H), 7.6-7.7 (m, 2H), 8.0-8.28 (m, 2H), 10.3 (s, 1H); HPLC Purity: 97.8%; LCMS: 529.2 (M+1).

N-(4-(4-(4-cyanobenzyl)piperazine-1-carbonyl)phenyl)quinoline-8-sulfonamide (VIII-17)

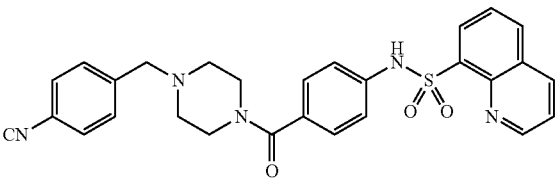

$^1$H NMR (400 MHz, $CDCl_3$) δ: 1.8 (s, 2H), 2.40 (br d, 4H), 3.38 (br d, 2H), 3.48 (d, 2H), 6.79-7.04 (m, 6H), 7.1-7.2 (m, 4H), 7.59-7.64 (m, 2H), 8.03-8.28 (m, 2H), 10.3 (s, 1H); HPLC Purity: 97.8%; LCMS: 512.3 (M+1).

N-(4-(4-(4-fluorobenzyl)piperazine-1-carbonyl)phenyl)quinoline-8-sulfonamide (VIII-18)

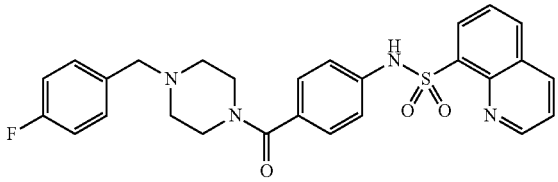

$^1$H NMR (400 MHz, $CDCl_3$) δ: 2.38 (br d, 4H), 3.31 (br s, 2H), 3.41 (s, 2H), 3.64 (br s, 2H), 6.94 (t, 2H), 7.02 (d, 2H), 7.17 (d, 2H), 7.20-7.26 (m, 2H), 7.56-7.64 (m, 2H), 8.03 (d, 1H), 8.28 (d, 1H), 8.38 (d, 1H), 8.58 (s, 1H), 9.18 (s, 1H); HPLC Purity: 97.62%; LCMS: 505 ($M^+$+1).

N-(4-(4-(4-bromobenzyl)piperazine-1-carbonyl)phenyl)quinoline-8-sulfonamide (VIII-19)

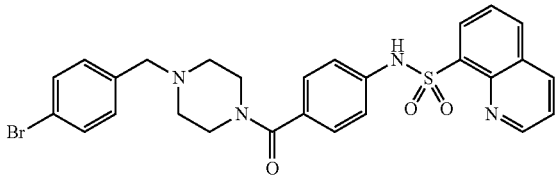

$^1$H NMR (400 MHz, $CDCl_3$) δ: 2.38 (br d, 4H), 3.31 (br s, 2H), 3.41 (s, 2H), 3.64 (br s, 2H), 6.94 (d, 2H), 7.06 (t, 4H), 7.40 (d, 2H), 7.56-7.63 (m, 2H), 8.01 (d, 1H), 8.28 (d, 1H), 8.38 (d, 1H), 8.56 (s, 1H), 9.18 (s, 1H); HPLC Purity: 94.21%; LCMS: 567 ($M^+$).

N-(4-(4-(3-chlorobenzyl)piperazine-1-carbonyl)phenyl)quinoline-8- sulfonamide (VIII-20)

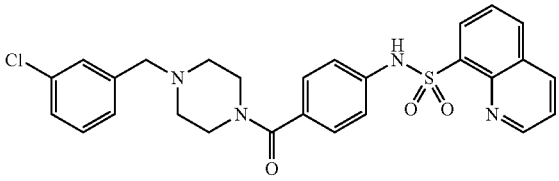

[$^1$H NMR (400 MHz, $CDCl_3$) δ: 2.38 (br d, 4H), 3.31 (br s, 2H), 3.41 (s, 2H), 3.64 (br s, 2H), 7.01 (d, 2H), 7.16 (t, 3H), 7.21-7.28 (m, 5H), 7.56-7.62 (m, 2H), 8.01 (d, 1H), 8.28 (d, 1H), 8.38 (d, 1H), 8.56 (s, 1H), 9.18 (s, 1H);] HPLC Purity: 99.41[%; LCMS: 567 ($M^+$+2)].

N-(4-(4-(3-methoxybenzyl)piperazine-1-carbonyl)phenyl)quinoline-8-sulfonamide (VIII-21)

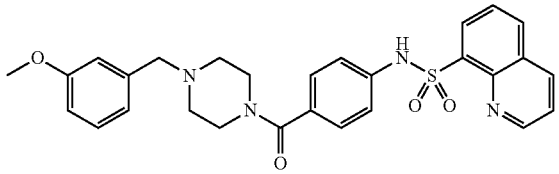

$^1$H NMR (400 MHz, $CDCl_3$) δ: 2.38 (br d, 4H), 3.38 (br s, 2H), 3.46 (s, 2H), 3.72 (br s, 2H), 3.82 (s, 3H), 6.79 (d, 1H), 6.82 (s, 2H), 7.10 (q, 4H), 7.21-7.29 (m, 2H), 7.59-7.66 (m, 2H), 8.01 (d, 1H), 8.28 (d, 1H), 8.38 (d, 1H), 8.56 (s, 1H), 9.18 (s, 1H); HPLC Purity: 98.26%; LCMS: 539 ($M^+$+23).

N-(4-(4-(3-chloro-4-fluorobenzyl)piperazine-1-carbonyl)phenyl)quinoline-8-sulfonamide (VIII-22)

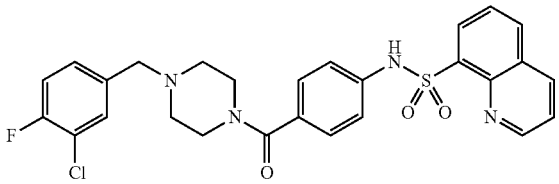

$^1$H NMR (400 MHz, $CDCl_3$) δ: 3.10 (br s, 4H), 3.84 (br s, 4H), 4.19 (s, 2H), 7.16 (d, 2H), 7.21 (d, 2H), 7.28-7.34 (m, 1H), 7.44 (d, 1H), 7.60-7.68 (m, 2H), 8.10 (d, 1H), 8.36 (d, 1H), 8.41 (d, 1H), 9.18 (d, 1H); HPLC Purity: 96.82%; LCMS: 539 ($M^+$).

N-(4-(4-(4-methoxy-2-methylbenzyl)piperazine-1-carbonyl)phenyl)quinoline-8-sulfonamide (VIII-23)

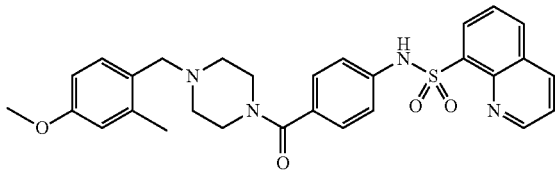

$^1$H NMR (400 MHz, $CDCl_3$) δ: 2.38 (s, 3H), 2.80 (br s, 4H), 3.80 (s, 3H), 3.88 (br s, 4H), 4.20 (s, 2H), 6.78 (d, 2H), 7.10 (d, 2H), 7.20 (d, 2H), 7.25 (d, 2H), 7.60-7.65 (m, 2H), 8.03 (d, 1H), 8.32 (d, 1H), 8.38 (d, 1H), 9.18 (d, 1H); HPLC Purity: 96.98%; LCMS: 531 ($M^+$+1).

N-(4-(4-(2-chloro-3-methoxybenzyl)piperazine-1-carbonyl)phenyl)quinoline-8-sulfonamide (VIII-24)

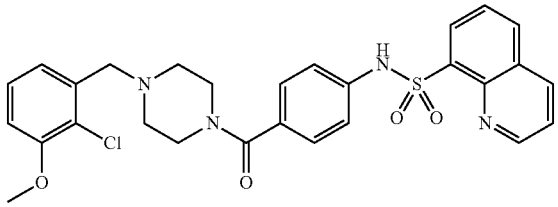

$^1$H NMR (400 MHz, $CDCl_3$) δ: 2.41 (br s, 4H), 3.18 (br s, 4H), 3.81 (br s, 3H), 3.98 (s, 2H), 7.02 (d, 1H), 7.13 (d, 2H), 7.18-7.22 (m, 2H), 7.30 (t, 1H), 7.60-7.67 (m, 2H), 8.04 (d, 1H), 8.36 (d, 1H), 8.38 (d, 1H), 9.18 (d, 1H); HPLC Purity: 99.46%; LCMS: 551 ($M^+$).

N-(4-(4-(4-chloro-3-fluorobenzyl)piperazine-1-carbonyl)phenyl)quinoline-8-sulfonamide (VIII-25)

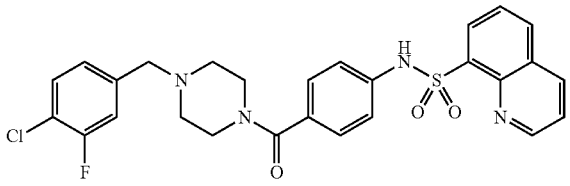

$^1$H NMR (400 MHz, $CDCl_3$) δ: 3.15 (br s, 4H), 3.84 (br s, 4H), 4.19 (s, 2H), 7.13-7.24 (m, 6H), 7.48 (t, 1H), 7.61-7.68 (m, 2H), 8.10 (d, 1H), 8.34 (d, 1H), 8.41 (d, 1H), 9.18 (d, 1H); HPLC Purity: 99.24%; LCMS: 539 ($M^+$).

N-(4-(4-(2-chloro-4-fluorobenzyl)piperazine-1-carbonyl)phenyl)quinoline-8-sulfonamide (VIII-26)

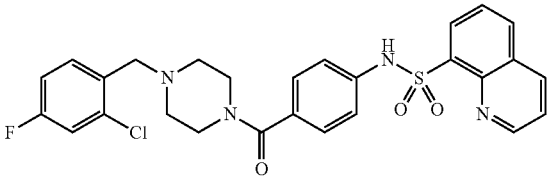

$^1$H NMR (400 MHz, $CDCl_3$) δ: 2.37 (s, 4H), 3.21 (br s, 2H), 3.78 (br s, 2H), 4.39 (s, 2H), 7.18 (d, 2H), 7.21 (d, 2H), 7.61-7.65 (m, 2H), 8.05 (d, 1H), 8.36 (d, 1H), 8.41 (d, 1H), 9.18 (d, 1H); HPLC Purity: 99.56%; LCMS: 539 ($M^+$).

N-(4-(4-(2,6-difluorobenzyl)piperazine-1-carbonyl)phenyl)quinoline-8-sulfonamide (VIII-27)

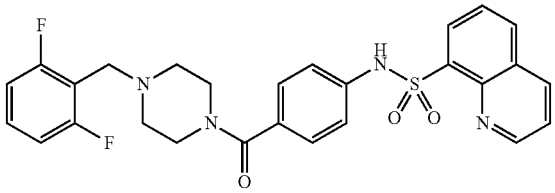

$^1$H NMR (400 MHz, $CDCl_3$) δ: 3.07 (br s, 4H), 3.81 (s, 4H), 4.38 (s, 2H), 7.06 (t, 2H), 7.12 (d, 2H), 7.18 (d, 2H), 7.54 (s, 1H), 7.60-7.64 (m, 2H), 8.01 (d, 1H), 8.36 (d, 1H), 8.38 (d, 1H), 9.18 (d, 1H); HPLC Purity: 98.26%; LCMS: 523 ($M^+$+1).

N-(4-(4-(2,3-dimethoxybenzyl)piperazine-1-carbonyl)phenyl)quinoline-8-sulfonamide (VIII-28)

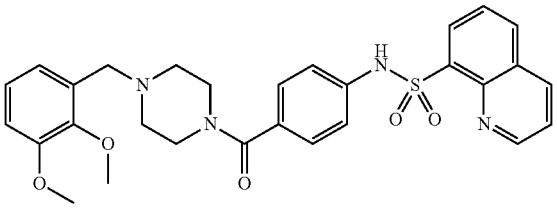

$^1$H NMR (400 MHz, $CDCl_3$) δ: 2.63 (br s, 4H), 3.57 (br s, 4H), 3.90 (d, 6H), 4.18 (s, 2H), 6.98 (d, 2H), 7.00 (d, 1H), 7.14-7.19 (m, 6H), 7.58-7.64 (m, 2H), 8.06 (d, 1H), 8.38 (d, 1H), 8.40 (d, 1H), 9.18 (d, 1H); HPLC Purity: 99.41%; LCMS: 547 ($M^+$+1).

N-(4-(4-(3,4-dimethoxybenzyl)piperazine-1-carbonyl)phenyl)quinoline-8-sulfonamide (VIII-29)

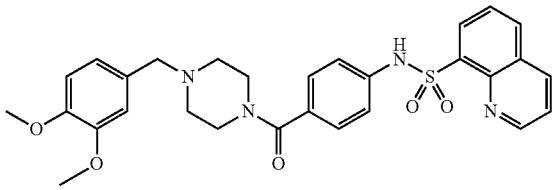

$^1$H NMR (400 MHz, $CDCl_3$) δ: 2.63 (br s, 4H), 3.57 (br s, 4H), 3.90 (d, 6H), 4.18 (s, 2H), 6.83 (s, 2H), 7.00 (s, 1H), 7.14 (d, 2H), 7.21 (d, 2H), 7.62-7.68 (m, 2H), 8.04 (d, 1H), 8.38 (d, 1H), 8.40 (d, 1H), 9.18 (d, 1H); HPLC Purity: 92.46%; LCMS: 547 ($M^+$+1).

N-(4-(4-(3-fluorobenzyl)piperazine-1-carbonyl)phenyl)quinoline-8-sulfonamide (VIII-30)

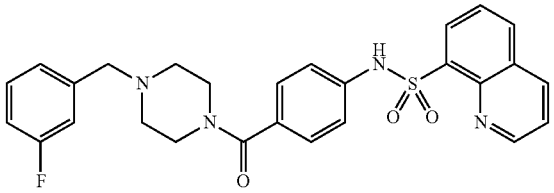

$^1$H NMR (400 MHz, $CDCl_3$) δ: 3.09 (br s, 4H), 3.85 (s, 4H), 4.19 (s, 2H), 6.94 (d, 2H), 7.06-7.21 (m, 6H), 7.40-7.44 (m, 1H), 7.62-7.68 (m, 2H), 8.08 (d, 1H), 8.38 (d, 1H), 8.40 (d, 1H), 9.18 (d, 1H); HPLC Purity: 98.92%; LCMS: 505 ($M^+$+1).

N-(4-(4-(2-ethylbenzyl)piperazine-1-carbonyl)phenyl)quinoline-8-sulfonamide (VIII-31)

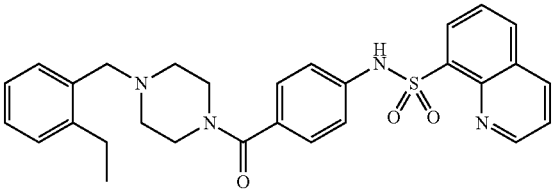

$^1$H NMR (400 MHz, $CDCl_3$) δ: 1.22 (t, 3H), 2.41 (br s, 4H), 2.68 (q, 2H), 3.64 (br s, 4H), 7.06 (d, 2H), 7.20 (d, 2H), 7.22-7.26 (m, 2H), 7.40 (d, 2H), 7.61-7.68 (m, 2H), 8.01 (d, 1H), 8.32 (d, 1H), 8.41 (d, 1H), 9.18 (d, 1H); HPLC Purity: 99.22%; LCMS: 515 ($M^+$+1).

N-(4-(4-(4-(trifluoromethyl)benzyl)piperazine-1-carbonyl)phenyl)quinoline-8-sulfonamide (VIII-32)

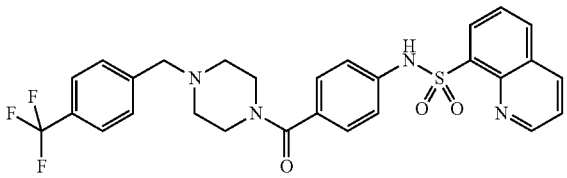

$^1$H NMR (400 MHz, $CDCl_3$) δ: 3.18 (br s, 4H), 3.83 (br s, 4H), 4.25 (s, 2H), 7.06 (d, 2H), 7.22 (d, 2H), 7.56 (d, 2H), 7.60-7.78 (m, 4H), 8.07 (d, 1H), 8.36 (d, 1H), 8.40 (d, 1H), 9.18 (s, 1H); HPLC Purity: 96.72%; LCMS: 555 ($M^+$+1).

N-(4-(4-(pyridin-4-ylmethyl)piperazine-1-carbonyl)phenyl)quinoline-8-sulfonamide (VIII-33)

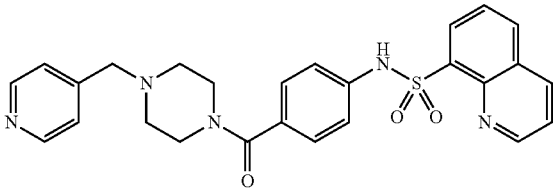

$^1$H NMR (400 MHz, $CDCl_3$) δ: 2.40 (br s, 4H), 3.33 (br s, 2H), 3.41 (s, 2H), 3.64 (br s, 2H), 7.06 (d, 2H), 7.18 (d, 2H), 7.26 (d, 3H), 7.58-7.63 (m, 2H), 8.01 (d, 1H), 8.28 (d, 1H), 8.38 (d, 1H), 8.79 (br s, 2H), 9.18 (s, 1H); HPLC Purity: 97.4%; LCMS: 488.3 ($M^+$+1).

N-(4-(4-(pyridin-3-ylmethyl)piperazine-1-carbonyl)phenyl)quinoline-8-sulfonamide (VIII-34) 30

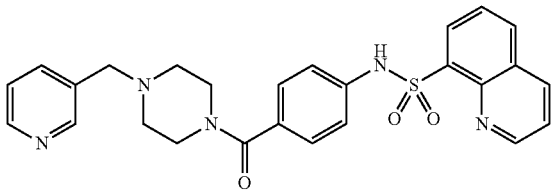

$^1$H NMR (400 MHz, $CDCl_3$) δ: 2.40 (br s, 4H), 3.33 (br s, 2H), 3.41 (s, 2H), 3.64 (br s, 2H), 7.06 (d, 2H), 7.18 (d, 2H), 7.26 (d, 3H), 7.58-7.63 (m, 2H), 8.01 (d, 1H), 8.28 (d, 1H), 8.38 (d, 1H), 8.51-8.59 (m, 2H), 9.18 (s, 1H); HPLC Purity: 98.50%; LCMS: 488.0 ($M^+$+1).

N-(4-(4-(2-methoxybenzyl)piperazine-1-carbonyl)phenyl)quinoline-8-sulfonamide (VIII-35)

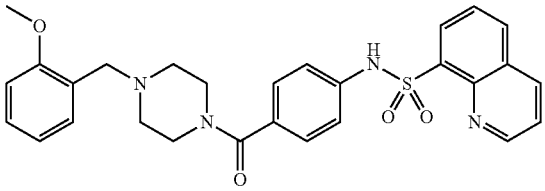

$^1$H NMR (400 MHz, $CDCl_3$) δ: 2.42 (br d, 4H), 3.38 (br s, 2H), 3.58 (s, 2H), 3.70 (br s, 2H), 3.80 (s, 3H), 6.83-6.93 (m, 2H), 7.06 (d, 2H), 7.18 (d, 2H), 7.20-7.26 (m, 2H), 7.58-7.63 (m, 2H), 8.01 (d, 1H), 8.28 (d, 1H), 8.38 (d, 1H), 8.51-8.59 (m, 2H), 9.18 (s, 1H); HPLC Purity: 98.9%; LCMS: 517.1 ($M^+$+1).

N-(4-(4-((2-chloropyridin-3-yl)methyl)piperazine-1-carbonyl)phenyl)quinoline-8-sulfonamide (VIII-36)

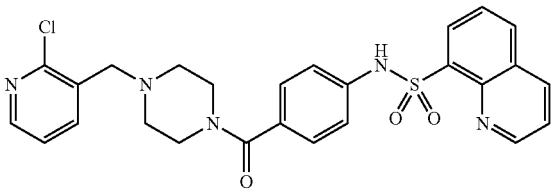

[$^1$H NMR (400 MHz, $CDCl_3$) δ: 2.44 (br s, 4H), 3.41 (br s, 2H), 3.60 (s, 2H), 3.74 (br s, 2H), 7.06 (d, 2H), 7.20 (d, 2H), 7.22-7.28 (m, 2H), 7.59-7.66 (m, 2H), 7.81 (d, 1H), 8.01 (d, 1H), 8.35 (d, 2H), 8.39 (d, 1H), 8.59 (s, 1H), 9.18 (s, 1H);] HPLC Purity: 98.6%; LCMS: 522 [($M^+$)] (*M+1*).

N-(4-(4-((6-chloropyridin-3-yl)methyl)piperazine-1-carbonyl)phenyl)quinoline-8-sulfonamide (VIII-37)

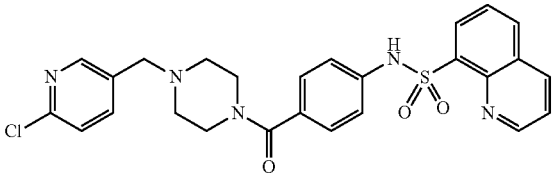

$^1$H NMR (400 MHz, $CDCl_3$) δ: 2.44 (br s, 4H), 3.41 (br s, 2H), 3.54 (s, 2H), 3.74 (br s, 2H), 7.06 (d, 2H), 7.20 (d, 2H), 7.22-7.28 (m, 2H), 7.59-7.66 (m, 3H), 8.01 (d, 1H), 8.35 (d, 2H), 8.39 (d, 1H), 8.59 (s, 1H), 9.18 (s, 1H); HPLC Purity: 99.22%; LCMS: 522 ($M^+$).

N-(4-(4-(2-chlorobenzyl)piperazine-1-carbonyl)phenyl)quinoline-8-sulfonamide (VIII-38)

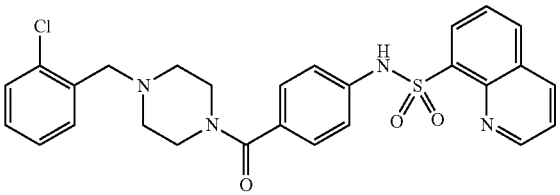

$^1$H NMR (400 MHz, $CDCl_3$) δ: 2.44 (br d, 4H), 3.41 (br s, 2H), 3.61 (s, 2H), 3.74 (br s, 2H), 7.06 (d, 2H), 7.08-7.24 (m, 4H), 7.32 (d, 1H), 7.39 (d, 1H), 7.59-7.7.65 (m, 2H), 8.01 (d, 1H), 8.35 (d, 1H), 8.39 (d, 1H), 8.58 (s, 1H), 9.18 (s, 1H); HPLC Purity: 94.42%; LCMS: 521 ($M^+$).

N-(4-(4-(2-acetylbenzyl)piperazine-1-carbonyl)phenyl)quinoline-8-sulfonamide (VIII-39)

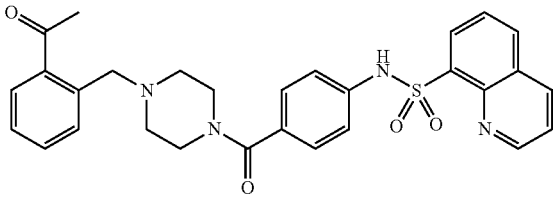

$^1$H NMR (400 MHz, $CDCl_3$) δ: 2.38 (br d, 4H), 2.58 (s, 3H), 3.31 (br s, 2H), 3.60 (s, 2H), 3.64 (br s, 2H), 7.03 (d, 2H), 7.15 (d, 2H), 7.30-7.41 (m, 3H), 7.43 (d, 1H), 7.59-7.64 (m, 2H), 8.01 (d, 1H), 8.30 (d, 1H), 8.38 (d, 1H), 8.56 (s, 1H), 9.18 (s, 1H); HPLC Purity: 96.32%; LCMS: 529 ($M^+$).

N-(4-(4-(3-cyanobenzyl)piperazine-1-carbonyl)phenyl)quinoline-8-sulfonamide (VIII-40)

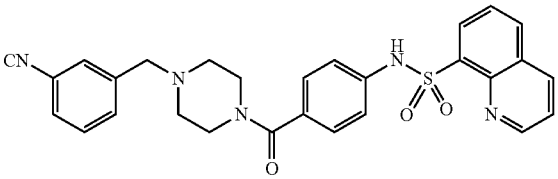

$^1$H NMR (400 MHz, $CDCl_3$) δ: 2.43 (br d, 4H), 3.38 (br s, 2H), 3.68 (s, 4H), 7.08 (d, 2H), 7.18 (d, 2H), 7.40 (t, 1H), 7.45-7.70 (m, 5H), 8.01 (d, 1H), 8.28 (d, 1H), 8.38 (d, 1H), 8.56 (s, 1H), 9.18 (s, 1H); HPLC: 98.2%; LCMS: 512 ($M^+$+1).

N-(4-(4-(4-chlorobenzyl)piperazine-1-carbonyl)phenyl)quinoline-8-sulfonamide (VIII-41)

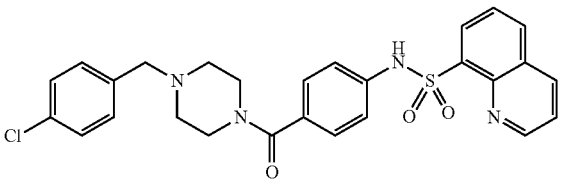

$^1$H NMR (400 MHz, $CDCl_3$) δ: 2.39 (br d, 4H), 3.39 (br s, 2H), 3.50 (s, 2H), 3.64 (br s, 2H), 7.06 (d, 2H), 7.17 (d, 2H), 7.40 (d, 2H), 7.44 (d, 1H), 7.56-7.63 (m, 4H), 8.01 (d, 1H), 8.28 (d, 1H), 8.38 (d, 1H), 8.56 (s, 1H), 9.18 (s, 1H); HPLC Purity: 96.9%; LCMS: 521 ($M^+$+1).

N-(4-(4-(2-cyanobenzyl)piperazine-1-carbonyl)phenyl)quinoline-8-sulfonamide (VIII-42)

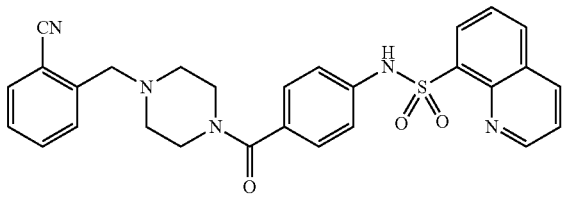

$^1$H NMR (400 MHz, $CDCl_3$) δ: 2.39 (br s, 4H), 3.38 (br s, 2H), 3.50 (s, 2H), 3.68 (br s, 2H), 7.03 (d, 2H), 7.18 (d, 2H), 7.40 (t, 1H), 7.51-7.64 (m, 4H), 8.01 (d, 1H), 8.28 (d, 1H), 8.38 (d, 1H), 8.56 (s, 1H), 9.18 (s, 1H); HPLC Purity: 97.70%; ESMS: 5.12 ($M^+$+1).

N-(4-(4-(4-acetylbenzyl)piperazine-1-carbonyl)phenyl)quinoline-8-sulfonamide (VIII-43)

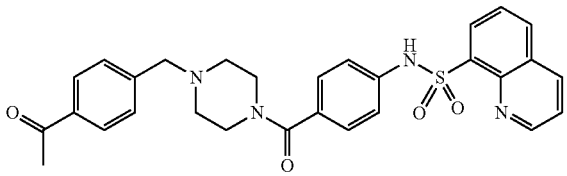

$^1$H NMR (400 MHz, $CDCl_3$) δ: 2.38 (br d, 4H), 2.58 (s, 3H), 3.34 (br s, 2H), 3.58 (s, 2H), 3.68 (br s, 2H), 7.03 (d, 2H), 7.15 (d, 2H), 7.40 (d, 2H), 7.43 (d, 1H), 7.59-7.64 (m, 2H), 7.91 (d, 2H), 8.01 (d, 1H), 8.30 (d, 1H), 8.38 (d, 1H), 8.56 (s, 1H), 9.18 (s, 1H); HPLC Purity: 92.23%; ESMS: 529 ($M^+$+1).

N-(4-(4-(4-cyanobenzyl)piperazine-1-carbonyl)phenyl)quinoline-8-sulfonamide (VIII-44)

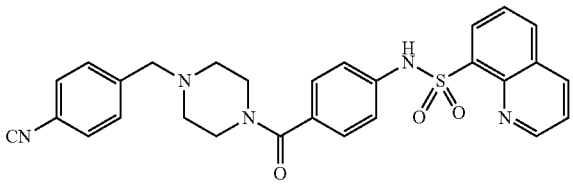

$^1$H NMR (400 MHz, $CDCl_3$) δ: 2.39 (br s, 4H), 3.38 (br s, 2H), 3.52 (s, 2H), 3.68 (br s, 2H), 7.03 (d, 2H), 7.18 (d, 2H), 7.40 (d, 1H), 7.59-7.64 (m, 4H), 8.01 (d, 1H), 8.28 (d, 1H), 8.38 (d, 1H), 8.56 (s, 1H), 9.18 (s, 1H); HPLC Purity: 98.71%; LCMS: 512 ($M^+$+1).

N-(4-(4-(4-fluorobenzyl)piperazine-1-carbonyl)phenyl)quinoline-8-sulfonamide (VIII-45)

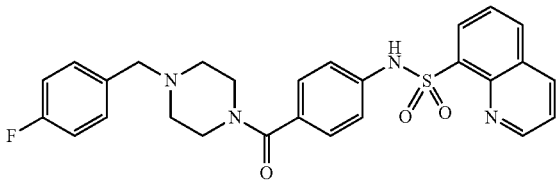

$^1$H NMR (400 MHz, $CDCl_3$) δ: 2.38 (br d, 4H), 3.35 (br s, 2H), 3.46 (s, 2H), 3.64 (br s, 2H), 6.94 (t, 2H), 7.06 (t, 2H), 7.18 (d, 2H), 7.24-7.28 (m, 2H), 7.56-7.63 (m, 2H), 8.01 (d, 1H), 8.28 (d, 1H), 8.38 (d, 1H), 8.56 (s, 1H), 9.18 (s, 1H); HPLC Purity: 94.7%; LCMS: 505 ($M^+$+1).

N-(4-(4-(4-bromobenzyl)piperazine-1-carbonyl)phenyl)quinoline-8-sulfonamide (VIII-46)

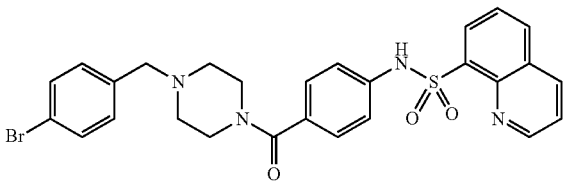

[$^1$H NMR (400 MHz, $CDCl_3$) δ: 2.38 (br d, 4H), 3.31 (br s, 2H), 3.41 (s, 2H), 3.64 (br s, 2H), 7.06 (d, 2H), 7.18 (t, 3H), 7.40 (d, 2H), 7.56-7.63 (m, 2H), 8.01 (d, 1H), 8.28 (d, 1H), 8.38 (d, 1H), 8.56 (s, 1H), 9.18 (s, 1H);] HPLC Purity: 99.7%[; LCMS: 567 ($M^+$+2)].

N-(4-(4-(3-chlorobenzyl)piperazine-1-carbonyl)phenyl)quinoline-8-sulfonamide (VIII-47)

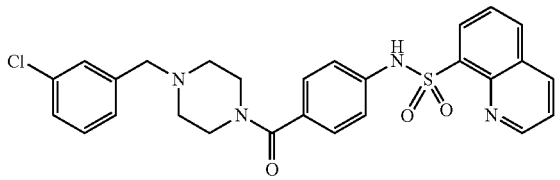

$^1$H NMR (400 MHz, $CDCl_3$) δ: 2.39 (br d, 4H), 3.39 (br s, 2H), 3.48 (s, 2H), 3.64 (br s, 2H), 7.06 (d, 2H), 7.17 (d, 2H), 7.40 (d, 2H), 7.44 (d, 1H), 7.58-7.63 (m, 2H), 8.01 (d, 1H), 8.28 (d, 1H), 8.38 (d, 1H), 8.56 (s, 1H), 9.18 (s, 1H); HPLC Purity: 98.98%; ESMS: 521 ($M^+$+1).

N-(4-(4-(2,4-dichloro-5-hydroxybenzyl)piperazine-1-carbonyl)phenyl)quinoline-8-sulfonamide (VIII-49)

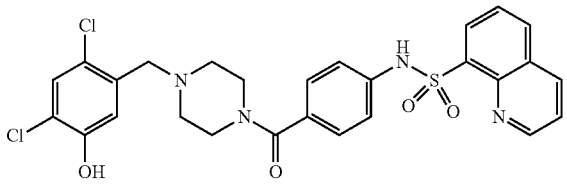

$^1$H NMR (400 MHz, DMSO-d6) δ: 2.39 (br s, 4H), 3.48 (br s, 4H), 3.70 (s, 2H), 6.98 (s, 1H), 7.01 (s, 1H), 7.10-7.20 (m, 4H), 7.70-7.79 (m, 2H), 8.28 (d, 1H), 8.43 (d, 1H), 8.55 (d, 1H), 9.18 (s, 1H), 10.41 (s, 1H); HPLC Purity: 95.42%; LCMS: 571 ($M^+$).

N-(4-(4-(2-fluoro-6-hydroxybenzyl)piperazine-1-carbonyl)phenyl)quinoline-8-sulfonamide (VIII-50)

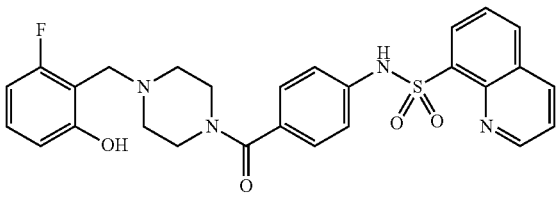

$^1$H NMR (400 MHz, DMSO-d6) δ: 2.39 (s, 4H), 3.42 (br s, 4H), 3.63 (s, 3H), 6.56-6.62 (m, 2H), 7.10-7.19 (m, 4H), 7.70-7.79 (m, 2H), 8.28 (d, 1H), 8.43 (d, 1H), 8.55 (d, 1H), 9.18 (s, 1H), 10.41 (s, 1H); HPLC Purity: 99.89%; LCMS: 521 ($M^+$+1).

N-(4-(4-(2-(methylthio)benzyl)piperazine-1-carbonyl)phenyl)quinoline-8-sulfonamide (VIII-51)

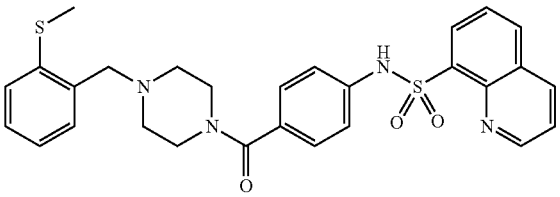

$^1$H NMR (400 MHz, DMSO-d6) δ: 2.35 (br s, 4H), 2.39 (s, 3H), 3.43 (s, 4H), 3.61 (s, 2H), 7.10-7.19 (m, 4H), 7.26 (s, 3H), 7.30 (q, 1H), 7.70-7.79 (m, 2H), 8.28 (d, 1H), 8.43 (d, 1H), 8.55 (d, 1H), 9.18 (s, 1H), 10.41 (s, 1H); HPLC Purity: 91.14%; LCMS: 533 ($M^+$+1).

N-(4-(4-(2-fluoro-6-methoxybenzyl)piperazine-1-carbonyl)phenyl)quinoline-8-sulfonamide (VIII-52)

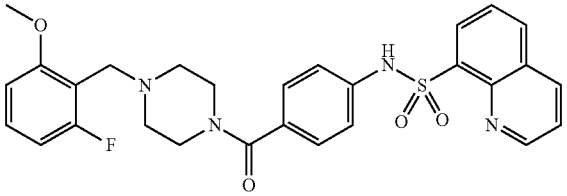

$^1$H NMR (400 MHz, DMSO-d6) δ: 2.32 (br s, 4H), 3.55 (s, 3H), 3.62 (br s, 4H), 3.80 (s, 2H), 6.78 (t, 1H), 6.84 (d, 1H), 7.13 (s, 4H), 7.30 (q, 1H), 7.70-7.79 (m, 2H), 8.28 (d, 1H), 8.43 (d, 1H), 8.55 (d, 1H), 9.18 (s, 1H), 10.41 (s, 1H); HPLC Purity: 98.18%; LCMS: 535 ($M^+$+1).

N-(4-(4-(2-(tert-butylthio)benzyl)piperazine-1-carbonyl)phenyl)quinoline-8-sulfonamide (VIII-53)

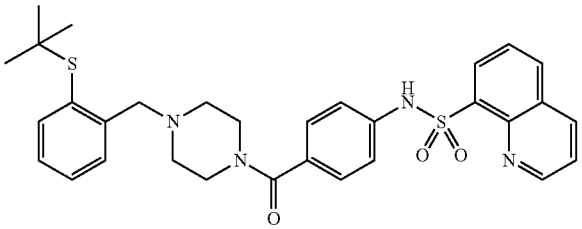

$^1$H NMR (400 MHz, DMSO-d6) δ: 1.24 (s, 9H), 2.37 (br s, 4H), 3.30 (br s, 4H), 3.78 (s, 2H), 7.08-7.18 (m, 4H), 7.25 (t, 1H), 7.41 (t, 1H), 7.50-7.59 (m, 2H), 7.70-7.79 (m, 2H), 8.29 (d, 1H), 8.43 (d, 1H), 8.48 (d, 1H), 9.18 (s, 1H), 10.41 (s, 1H); HPLC Purity: 97.92%; LCMS: 575 ($M^+$+1).

N-(4-(4-(3-chloro-4-fluorobenzyl)piperazine-1-carbonyl)phenyl)quinoline-8-sulfonamide (VIII-54)

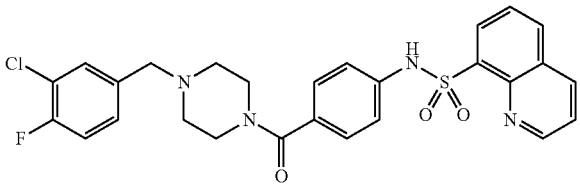

$^1$H NMR (400 MHz, DMSO-d6) δ: 2.29 (br s, 4H), 3.43 (s, 4H), 3.62 (s, 2H), 7.06-7.18 (m, 4H), 7.25-7.39 (m, 2H), 7.46 (d, 1H), 7.70-7.79 (m, 2H), 8.29 (d, 1H), 8.43 (d, 1H), 8.48 (d, 1H), 9.18 (s, 1H), 10.41 (s, 1H); HPLC Purity: 96.47%; LCMS: 539 ($M^+$).

N-(4-(4-(2,6-dimethoxybenzyl)piperazine-1-carbonyl)phenyl)quinoline-8-sulfonamide (VIII-55)

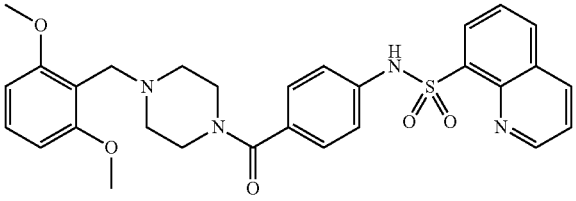

$^1$H NMR (400 MHz, DMSO-d6) δ: 2.32 (br s, 4H), 3.50 (br s, 4H), 3.76 (s, 6H), 3.81 (s, 2H), 6.60 (d, 2H), 7.10 (s, 3H), 7.22 (t, 1H), 7.70-7.79 (m, 2H), 8.28 (d, 1H), 8.43 (d, 1H), 8.54 (d, 1H), 9.18 (s, 1H), 10.41 (br s, 1H); HPLC purity: 94.09%; LCMS: 547 ($M^+$+1).

N-(4-(4-(3,5-difluorobenzyl)piperazine-1-carbonyl)phenyl)quinoline-8-sulfonamide (VIII-56)

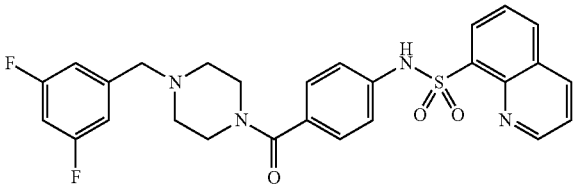

$^1$H NMR (400 MHz, DMSO-d6) δ: 2.30 (br s, 4H), 3.45 (s, 3H), 7.01 (d, 2H), 7.10-7.21 (m, 4H), 7.70-7.79 (m, 2H), 8.29 (d, 1H), 8.43 (d, 1H), 8.48 (d, 1H), 9.18 (s, 1H), 10.41 (s, 1H); HPLC Purity: 96.47%; LCMS: 523 ($M^+$+1).

N-(4-(4-(3-fluorobenzyl)piperazine-1-carbonyl)phenyl)quinoline-8-sulfonamide (VIII-57)

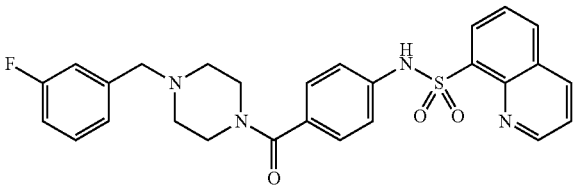

$^1$H NMR (400 MHz, DMSO-d6) δ: 2.36 (br s, 4H), 3.41 (br s, 2H), 3.59 (s, 2H), 7.10-7.21 (m, 6H), 7.37-7.40 (m, 1H), 7.70-7.79 (m, 2H), 8.31 (d, 1H), 8.43 (d, 1H), 8.48 (d, 1H), 9.18 (s, 1H), 10.41 (s, 1H); HPLC Purity: 94.31%; LCMS: 505 ($M^+$+1).

N-(4-(4-(3-fluoro-4-(trifluoromethyl)benzyl)piperazine-1-carbonyl)phenyl)quinoline-8-sulfonamide (VIII-58)

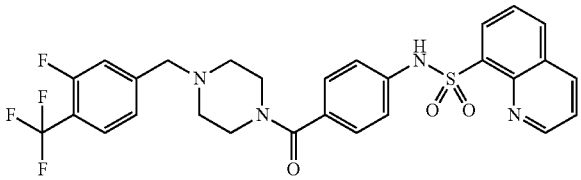

$^1$H NMR (400 MHz, DMSO-d6) δ: 2.36 (br s, 4H), 3.42 (br s, 4H), 3.59 (s, 3H), 7.10-7.21 (m, 4H), 7.39 (d, 1H), 7.42 (d, 1H), 7.70-7.79 (m, 2H), 8.32 (d, 1H), 8.43 (d, 1H), 8.48 (d, 1H), 9.18 (s, 1H), 10.41 (s, 1H); HPLC Purity: 96.69%; LCMS: 595 ($M^+$+23).

methyl 4-((4-(4-(quinoline-8-sulfonamido)benzoyl)piperazin-1-yl)methyl)benzoate (VIII-59)

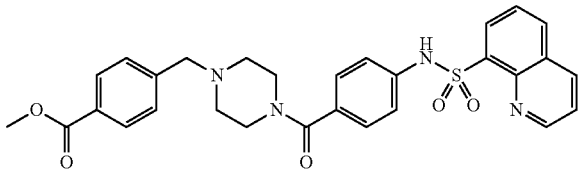

$^1$H NMR (400 MHz, DMSO-d6) δ: 2.36 (br s, 4H), 3.43 (br s, 4H), 3.59 (s, 2H), 3.83 (s, 3H), 7.10-7.21 (m, 4H), 7.46 (d, 2H), 7.70-7.79 (m, 2H), 7.95 (d, 2H), 8.32 (d, 1H), 8.43 (d, 1H), 8.48 (d, 1H), 9.18 (s, 1H), 10.41 (s, 1H); HPLC Purity: 97.92%; LCMS: 545 ($M^+$+1)

N-(4-(4-(2,5-dimethylbenzyl)piperazine-1-carbonyl)phenyl)quinoline-8-sulfonamide (VIII-60)

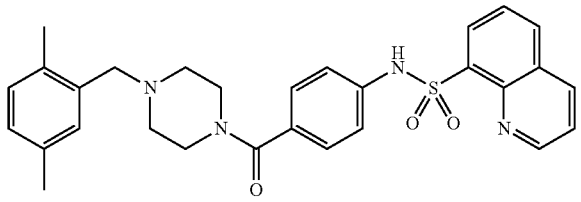

$^1$H NMR (400 MHz, DMSO-d6) δ: 2.38 (s, 6H), 2.41 (br s, 4H), 3.41 (br s, 4H), 6.97-7.02 (m, 2H), 7.10-7.21 (m, 3H), 7.31 (s, 1H), 7.70-7.79 (m, 2H), 8.29 (d, 1H), 8.43 (d, 1H), 8.56 (d, 1H), 9.18 (s, 1H), 10.41 (br s, 1H); HPLC Purity: 99.73%; LCMS: 515 ($M^+$+1).

N-(4-(4-(2,4-dichlorobenzyl)piperazine-1-carbonyl) phenyl)quinoline-8-sulfonamide (VIII-61)

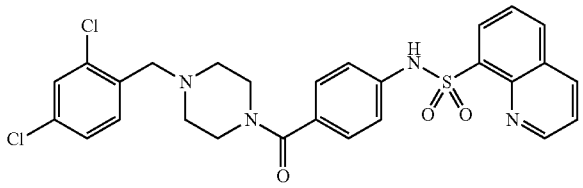

$^1$H NMR (400 MHz, DMSO-d6) δ 2.38 (br s, 4H), 3.41 (br s, 4H), 3.59 (s, 2H), 7.10 (q, 4H), 7.39 (d, 1H), 7.43 (d, 1H), 7.59 (s, 1H), 7.70-7.79 (m, 2H), 8.29 (d, 1H), 8.43 (d, 1H), 8.56 (d, 1H), 9.18 (s, 1H), 10.41 (br s, 1H); HPLC Purity: 99.34%; LCMS: 555 ($M^+$).

N-(4-(4-(4-methoxybenzyl)piperazine-1-carbonyl) phenyl)quinoline-8-sulfonamide (VIII-62)

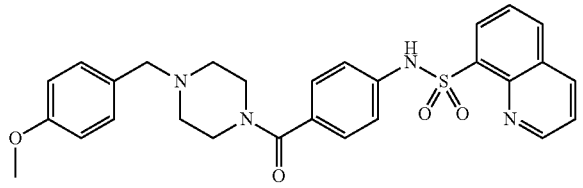

$^1$H NMR (400 MHz, DMSO-d6) δ: 2.32 (br s, 4H), 3.52 (br s, 4H), 3.79 (s, 2H), 6.81 (d, 2H), 7.10-7.21 (m, 5H), 7.31 (s, 1H), 7.70-7.79 (m, 2H), 8.28 (d, 1H), 8.43 (d, 1H), 8.56 (d, 1H), 9.18 (s, 1H), 10.41 (br s, 1H); HPLC Purity: 96.49%; LCMS: 539 ($M^+$+23).

N-(4-(4-(5-chloro-2-hydroxybenzyl)piperazine-1-carbonyl)phenyl)quinoline-8-sulfonamide (VIII-63)

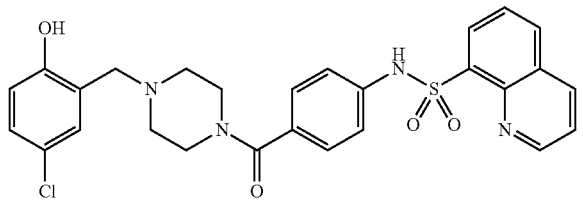

[$^1$H NMR (400 MHz, DMSO-d6) δ: 2.38 (br s, 4H), 3.59 (s, 4H), 3.62 (s, 2H), 6.79 (d, 2H), 7.06-7.21 (m, 6H), 7.70-7.81 (m, 2H), 8.31 (d, 1H), 8.28 (d, 1H), 8.38 (d, 1H), 8.56 (s, 1H), 9.18 (s, 1H), 10.41 (s, 1H);] HPLC Purity: 97.02%; LCMS: 537 [($M^+$)] (*M+1*).

N-(4-(4-(4-methylbenzyl)piperazine-1-carbonyl) phenyl)quinoline-8-sulfonamide (VIII-64)

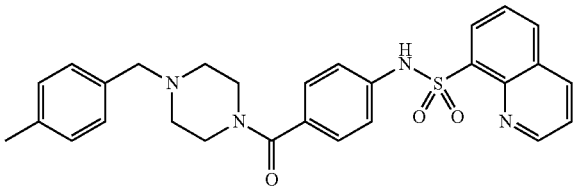

$^1$H NMR (400 MHz, DMSO-d6) δ: 2.30 (s, 4H), 3.42 (s, 4H), 3.46 (s, 2H), 7.06-7.20 (m, 8H), 7.70-7.79 (m, 2H), 8.28 (d, 1H), 8.43 (d, 1H), 8.56 (d, 1H), 9.18 (s, 1H), 10.41 (br s, HPLC Purity: 98.59%; LCMS: 501 ($M^+$+1).

N-(4-(4-(3-chloro-4-methoxybenzyl)piperazine-1-carbonyl)phenyl)quinoline-8-sulfonamide (VIII-65)

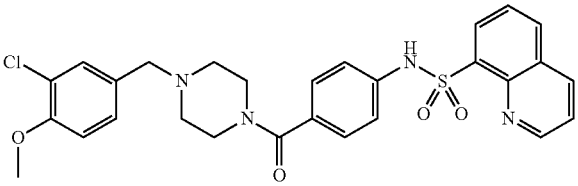

$^1$H NMR (400 MHz, DMSO-d6) δ: 2.30 (br s, 4H), 3.45 (br s, 6H), 3.81 (s, 3H), 7.04-7.21 (m, 6H), 7.31 (s, 1H), 7.70-7.79 (m, 2H), 8.28 (d, 1H), 8.43 (d, 1H), 8.56 (d, 1H), 9.18 (s, 1H), 10.41 (br s, 1H); HPLC Purity: 99.70%; LCMS: 551 ($M^+$).

2-methoxy-4-((4-(4-(quinoline-8-sulfonamido)benzoyl)piperazin-1-yl)methyl)phenyl acetate (VIII-66)

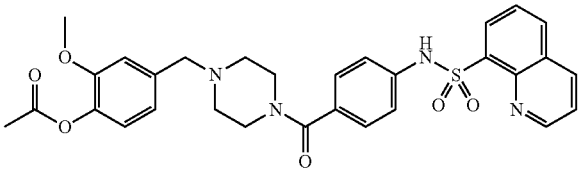

$^1$H NMR (400 MHz, DMSO-d6) δ: 2.22 (s, 3H), 2.38 (br s, 4H), 3.31 (br s, 2H), 3.51 (s, 4H), 3.80 (s, 3H), 6.89 (d, 1H), 7.04 (d, 2H), 7.10-7.23 (m, 4H), 7.71-7.79 (m, 2H), 8.31 (d, 1H), 8.45 (d, 1H), 8.56 (d, 1H), 9.18 (d, 1H), 10.42 (s, 1H); HPLC Purity: 91.90%; LCMS: 575 ($M^+$+1).

N-(4-(4-(4-cyanobenzyl)piperazine-1-carbonyl)phenyl)quinoline-8-sulfonamide (VIII-67)

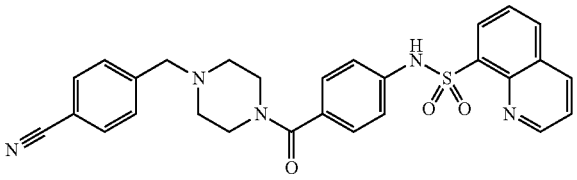

$^1$H NMR (400 MHz, DMSO-d6) δ: 2.23 (br s, 4H), 3.41 (br s, 2H), 3.54 (s, 2H), 7.06 (q, 4H), 7.22 (s, 2H), 7.62-7.76 (m, 4H), 8.22 (d, 1H), 8.38 (d, 1H), 8.44 (d, 1H), 9.08 (s, 1H), 10.40 (s, 1H); HPLC Purity: 99.87%; MS: 512 ($M^+$+1).

N-(4-(4-(3,5-dichlorobenzyl)piperazine-1-carbonyl)phenyl)quinoline-8-sulfonamide (VIII-68)

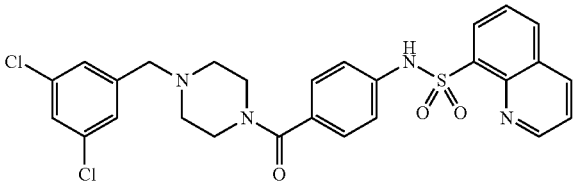

$^1$H NMR (400 MHz, DMSO-d6) δ: 2.24 (br s, 4H), 3.41 (br s, 4H), 3.44 (s, 2H), 7.08 (q, 3H), 7.30 (2H), 7.41 (s, 1H), 7.60-7.66 (m, 2H), 8.21 (d, 1H), 8.38 (d, 1H), 8.44 (d, 1H), 9.08 (s, 1H), 10.38 (s, 1H); HPLC Purity: 99.83%; LCMS: 555 ($M^+$).

N-(4-(4-(2,5-dimethoxybenzyl)piperazine-1-carbonyl)phenyl)quinoline-8-sulfonamide (VIII-69)

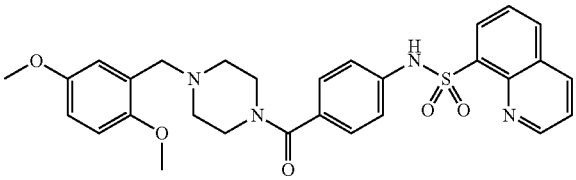

$^1$H NMR (400 MHz, DMSO-d6) δ: 2.23 (br s, 4H), 3.40 (s, 4H), 3.61 (d, 6H), 3.72 (s, 2H), 6.82 (d, 3H), 7.02-7.10 (m, 4H), 7.60-7.68 (m, 2H), 8.22 (d, 1H), 8.38 (d, 1H), 8.44 (d, 1H), 9.08 (s, 1H), 10.40 (s, 1H); HPLC Purity: 98.63%; LCMS: 547 ($M^+$1).

N-(4-(4-(2-hydroxy-6-methoxybenzyl)piperazine-1-carbonyl)phenyl)quinoline-8-sulfonamide (VIII-70)

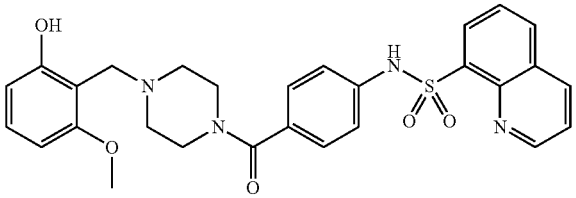

$^1$H NMR (400 MHz, DMSO-d6) δ: 2.36 (br s, 4H), 3.54 (s, 4H), 3.61 (s, 2H), 3.64 (s, 3H), 6.36 (d, 1H), 7.00-7.10 (m, 5H), 7.60-7.68 (m, 2H), 8.20 (d, 1H), 8.38 (d, 1H), 8.44 (d, 1H), 9.08 (s, 1H), 10.40 (s, 1H); HPLC Purity: 98.03%; LCMS: 533 ($M^+$1).

N-(4-(4-(5-chloro-2-hydroxy-4-methylbenzyl)piperazine-1-carbonyl)phenyl)quinoline-8-sulfonamide (VIII-71)

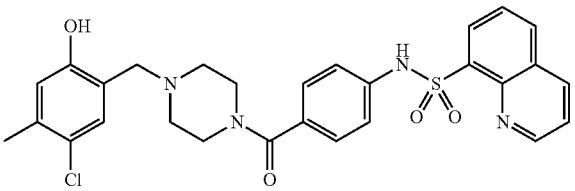

[$^1$H NMR (400 MHz, DMSO-d6) δ: 2.18 (s, 3H), 2.30 (br s, 4H), 3.41 (s, 4H), 3.46 (s, 2H), 6.68 (s, 1H), 7.10-7.19 (m, 4H), 7.65-7.78 (m, 2H), 8.24 (d, 1H), 8.41 (d, 1H), 8.51 (d, 1H), 9.12 (s, 1H), 10.40 (s, 1H);] HPLC Purity: 96.25%; LCMS: 551 [($M^+$)] (*M+1*).

N-(4-(4-(4-(hex-1-ynyl)benzyl)piperazine-1-carbonyl)phenyl)quinoline-8-sulfonamide (VIII-72)

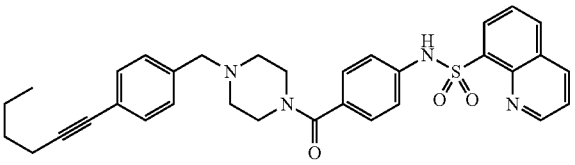

$^1$H NMR (400 MHz, DMSO-d6) δ: 0.93 (t, 3H), 1.38-1.41 (m, 4H), 2.22 (br s, 6H), 2.38 (t, 2H), 2.80 (s, 3H), 3.44 (s, 2H), 6.22 (d, 1H), 7.00-7.12 (m, 4H), 7.22 (dd, 2H), 7.62-7.70 (m, 2H), 8.24 (d, 1H), 8.38 (d, 1H), 8.44 (d, 1H), 9.08 (s, 1H), 9.60 (br s, 1H), 10.36 (s, 1H); HPLCPpurity: 99.84%; LCMS: 567 ($M^+$1).

N-(4-(4-(2-ethylbenzyl)piperazine-1-carbonyl)phenyl)quinoline-8-sulfonamide (VIII-73)

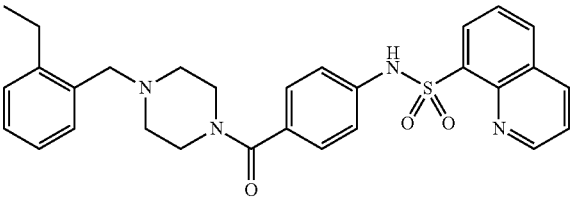

$^1$H NMR (400 MHz, DMSO-d6) δ: 1.12 (t, 3H), 2.23 (br s, 4H), 2.62 (q, 2H), 3.40 (s, 2H), 3.43 (br s, 4H), 7.04-7.20 (m, 5H), 7.65-7.70 (m, 2H), 8.25 (d, 1H), 8.41 (d, 1H), 8.50 (d, 1H), 9.10 (s, 1H), 10.40 (s, 1H); HPLC Purity: 98.83%; LCMS: 515 ($M^+$+1).

N-(4-(4-(4-(dimethylamino)benzyl)piperazine-1-carbonyl)phenyl)quinoline-8-sulfonamide (VIII-74)

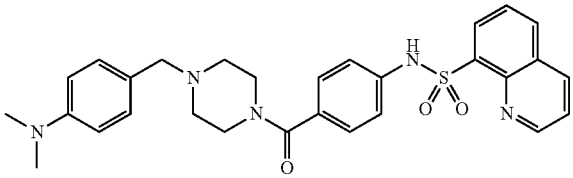

$^1$H NMR (400 MHz, DMSO-d6) δ: 2.21 (br s, 4H), 2.81 (s, 6H), 3.41 (br s, 6H), 6.61 (d, 2H), 7.01-7.11 (m, 6H), 7.48 (d, 2H), 7.63-7.70 (m, 2H), 8.22 (d, 1H), 8.38 (d, 1H), 8.45 (d, 1H), 9.08 (s, 1H), 10.40 (br s, 1H); HPLC Purity: 96.86%; LCMS: 552 ($M^+$+23).

N-(4-(4-(2-hydroxy-3-methoxybenzyl)piperazine-1-carbonyl)phenyl)quinoline-8-sulfonamide (VIII-75)

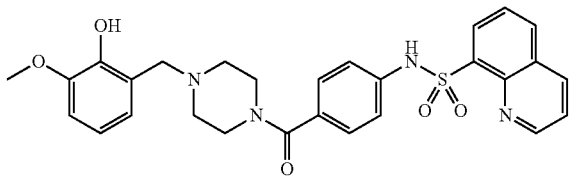

[$^1$H NMR (400 MHz, DMSO-d6) δ: 2.30 (br s, 4H), 3.41 (br s, 4H), 3.54 (s, 2H), 3.75 (s, 3H), 6.66 (s, 2H), 6.80 (d, 1H), 7.20 (q, 4H), 7.48 (d, 2H), 7.62-7.70 (m, 2H), 8.24 (d, 1H), 8.38 (d, 1H), 8.48 (d, 1H), 9.10 (s, 1H), 10.40 (s, 1H);] HPLC Purity: 99.76%[; LCMS: 555 ($M^+$+23)].

N-(4-(4-(3,4-dichlorobenzyl)piperazine-1-carbonyl)phenyl)quinoline-8-sulfonamide (VIII-76)

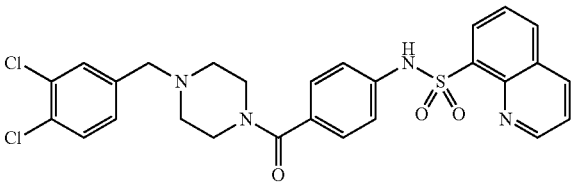

$^1$H NMR (400 MHz, DMSO-d6) δ: 2.24 (br s, 4H), 3.41 (s, 4H), 3.45 (s, 2H), 7.05 (q, 4H), 7.24 (d, 1H), 7.52-7.58 (m, 2H), 7.66-7.74 (m, 4H), 8.24 (d, 1H), 8.38 (d, 1H), 8.48 (d, 1H), 9.10 (s, 1H), 10.40 (br s, 1H); HPLC Purity: 97.35%; LCMS: 555 ($M^+$).

N-(4-(4-(3-(2-hydroxyethoxy)benzyl)piperazone-1-carbonyl)phenyl)quinoline-8-sulfonamide (VIII-77)

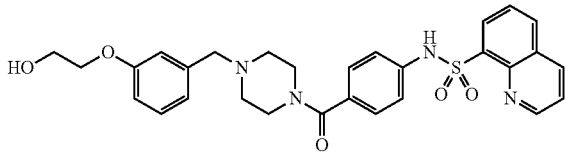

$^1$H NMR (400 MHz, DMSO-d6) δ: 2.23 (br s, 4H), 3.40 (s, 4H), 3.69 (q, 2H), 3.98 (t, 2H), 4.78 (s, 2H), 6.79-7.01 (m, 3H), 7.12 (q, 4H), 7.18 (t, 1H), 7.62-7.70 (m, 2H), 8.26 (d, 1H), 8.38 (d, 1H), 8.46 (s, 1H), 9.10 (s, 1H), 10.38 (s, 1H); HPLC Purity: 97.11%; LCMS: 547 ($M^+$1).

N-(4-(4-(4-(trifluoromethyl)benzyl)piperazine-1-carbonyl)phenyl)quinoline-8-sulfonamide (VIII-78)

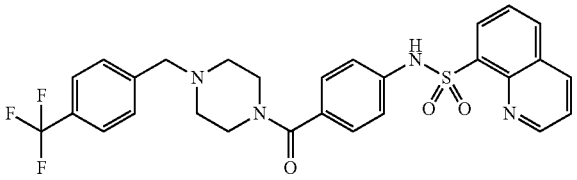

$^1$H NMR (400 MHz, DMSO-d6) δ: 2.24 (br s, 4H), 3.46 (br s, 4H), 3.55 (s, 2H), 7.08 (q, 4H), 7.48 (d, 2H), 7.60-7.70 (m, 4H), 8.24 (d, 1H), 8.38 (d, 1H), 8.48 (d, 1H), 9.10 (s, 1H), 10.40 (s, 1H); HPLC Purity: 99.28%; LCMS: 555 ($M^+$+1).

N-(4-(4-(2,4,5-trimethylbenzyl)piperazine-1-carbonyl)phenyl)quinoline-8-sulfonamide (VIII-79)

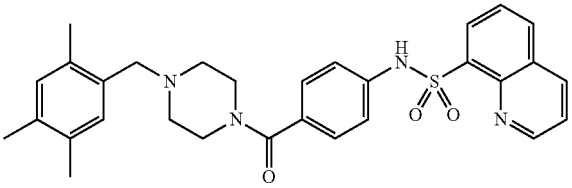

$^1$H NMR (400 MHz, DMSO-d6) δ: 2.12 (s, 6H), 2.20 (s, 3H), 2.23 (br s, 4H), 3.41 (br s, 4H), 3.46 (s, 2H), 6.88 (d, 2H), 7.08 (q, 4H), 7.62-7.70 (m, 2H), 8.28 (d, 1H), 8.40 (d, 1H), 8.48 (d, 1H), 9.10 (s, 1H), 10.40 (s, 1H); HPLC Purity: 99.58%; LCMS: 529 ($M^+$+1).

N-(4-(4-(4-(pentyloxy)benzyl)piperazine-1-carbonyl)phenyl)quinoline-8-sulfonamide (VIII-80)

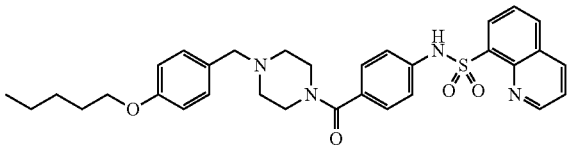

$^1$H NMR (400 MHz, DMSO-d6) δ: 0.85 (t, 3H), 1.25-1.39 (m, 4H), 1.65 (pentet, 2H), 2.22 (br s, 4H), 3.38 (s, 4H), 3.41 (s, 2H), 3.90 (t, 2H), 6.80 (d, 2H), 7.08-7.14 (m, 6H), 7.68-7.75 (m, 2H), 8.28 (d, 1H), 8.40 (d, 1H), 8.50 (s, 1H), 9.10 (s, 1H), 10.40 (s, 1H); HPLC Purity: 99.80%; LCMS: 573 ($M^+$+1).

N-(4-(4-(2-methylbenzyl)piperazine-1-carbonyl) phenyl)quinoline-8-sulfonamide (VIII-81)

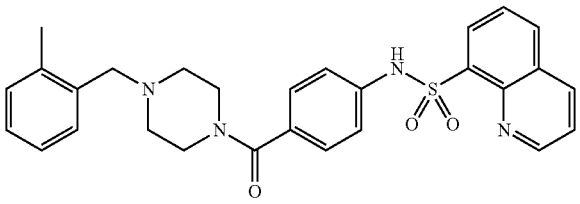

[$^1$H NMR (400 MHz, DMSO-d6) δ: 2.24 (s, 3H), 2.36 (br s, 4H), 3.38 (s, 4H), 3.40 (s, 2H), 7.05-7.20 (m, 6H), 7.65-7.74 (m, 2H), 8.26 (d, 1H), 8.39 (d, 1H), 8.46 (s, 1H), 9.10 (s, 1H), 10.40 (s, 1H);] HPLC Purity: 98.75%; LCMS: 501 [($M^+$1)] (*M+1*).

N-(4-(4-(4-chlorobenzyl)piperazine-1-carbonyl)phenyl)quinoline-8-sulfonamide (VIII-82) 20

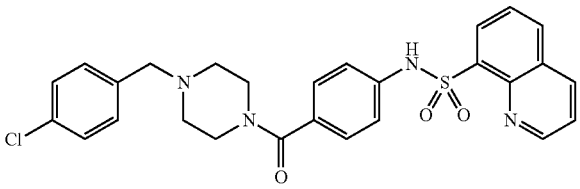

$^1$H NMR (400 MHz, $CDCl_3$) δ: 2.38 (br d, 4H), 3.31 (br s, 2H), 3.41 (s, 2H), 3.64 (br s, 2H), 6.94 (d, 2H), 7.06 (t, 4H), 7.40 (d, 2H), 7.56-7.63 (m, 2H), 8.01 (d, 1H), 8.28 (m, 2H), 9.18 (s, 1H); HPLC purity: 97.61%; LCMS: 522.0 ($M^+$).

N-(4-(4-(3-propoxybenzyl)piperazine-1-carbonyl) phenyl)quinoline-8-sulfonamide (VIII-83)

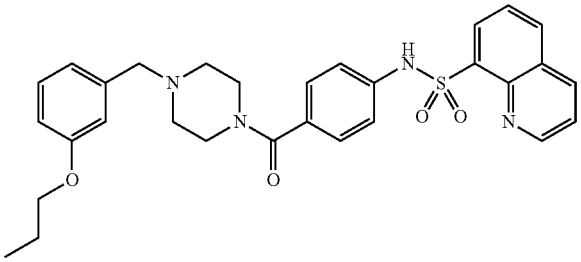

$^1$H NMR (400 MHz, DMSO-d6) δ: 0.97 (t, 3H), 1.70 (q, 2H), 2.32 (s, 4H), 3.41 (br s, 4H), 3.90 (t, 2H), 4.22 (br s, 2H), 6.99 (d, 2H), 7.17 (dd, 4H), 7.36 (t, 1H), 7.68-7.74 (m, 2H), 8.28 (d, 1H), 8.39 (d, 1H), 8.50 (d, 1H), 9.16 (s, 1H), 10.50 (s, 1H); HPLC Purity: 99.57%; LCMS: 545 ($M^+$+1).

N-(4-(4-(2-propoxybenzyl)piperazine-1-carbonyl) phenyl)quinoline-8-sulfonamide (VIII-84)

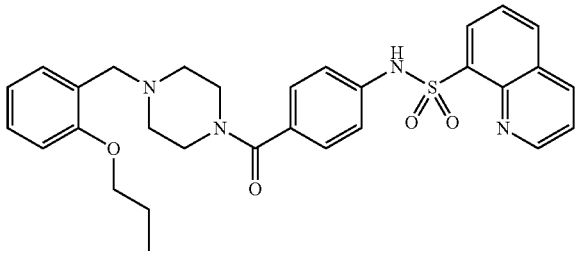

$^1$H NMR (400 MHz, DMSO-d6) δ: 0.97 (t, 3H), 1.70 (q, 2H), 2.36 (br s, 4H), 3.42 (br s, 4H), 3.90 (t, 2H), 4.22 (br s, 2H), 6.99 (d, 2H), 7.17 (dd, 4H), 7.40 (br s, 1H), 7.68-7.74 (m, 2H), 8.28 (d, 1H), 8.39 (d, 1H), 8.50 (d, 1H), 9.16 (s, 1H), 10.50 (s, 1H); HPLC Purity: 99.12%; LCMS: 545 ($M^+$+1).

N-(4-(4-(2-isopropoxybenzyl)piperazine-1-carbonyl) phenyl)quinoline-8-sulfonamide (VIII-85)

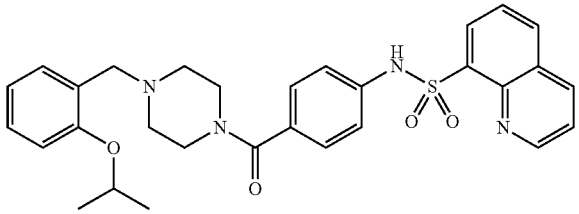

[$^1$H NMR (400 MHz, DMSO-d6) δ: 1.37 (d, 6H), 3.12 (br s, 3H), 4.25 (br s, 2H), 4.71-4.75 (m, 1H), 7.01 (t, 2H), 7.17 (d, 2H), 7.22 (d, 2H), 7.42 (br s, 2H), 7.70-7.79 (m, 2H), 8.30 (d, 1H), 8.42 (d, 1H), 8.51 (d, 1H), 9.14 (s, 1H), 9.50 (br s, 1H), 10.55 (s, 1H);] HPLC Purity: 99.17%; LCMS: 545 ($M^+$+1).

N-(4-(4-(3-isopropoxybenzyl)piperazine-1-carbonyl) phenyl)quinoline-8-sulfonamide (VIII-86)

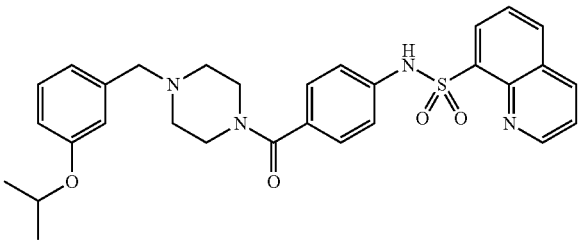

$^1$H NMR (400 MHz, DMSO-d6) δ: 1.29 (d, 6H), 2.36 (br s, 4H), 3.02 (br s, 4H), 4.25 (s, 2H), 4.62 (sextet, 1H), 6.99-7.09 (m, 3H), 7.20 (dd, 4H), 7.39 (t, 1H), 7.70-7.79 (m, 2H), 8.30 (d, 1H), 8.42 (d, 1H), 8.51 (d, 1H), 9.14 (s, 1H), 9.79 (br s, 1H), 10.57 (s, 1H); HPLC Purity: 99.11%; LCMS: 545 ($M^+$+1).

N-(4-(4-(3-butoxybenzyl)piperazine-1-carbonyl) phenyl)quinoline-8-sulfonamide (VIII-87)

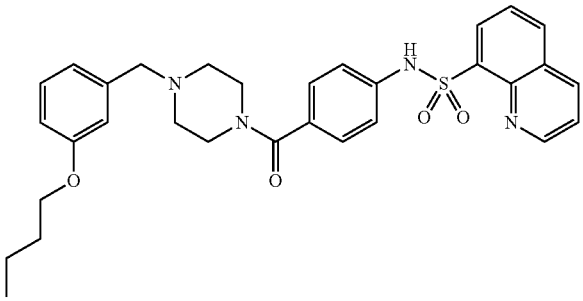

$^1$H NMR (400 MHz, DMSO-d6) δ: 0.90 (t, 3H), 1.21 (sextet, 2H), 1.64 (pentet, 2H), 2.31 (br s, 4H), 3.36 (br s, 4H), 3.92 (t, 2H), 4.23 (s, 2H), 6.93-7.01 (m, 2H), 7.17 (q, 4H), 7.31 (s, 2H), 7.63-7.74 (m, 2H), 8.28 (d, 1H), 8.40 (d, 1H), 8.51 (d, 1H), 9.10 (s, 1H), 9.50 (br s, 1H), 10.55 (s, 1H); HPLC Purity: 99.06%; LCMS: 559 ($M^+$+1).

N-(4-(4-(2-isopropylbenzyl)piperazine-1-carbonyl) phenyl)quinoline-8-sulfonamide (VIII-88)

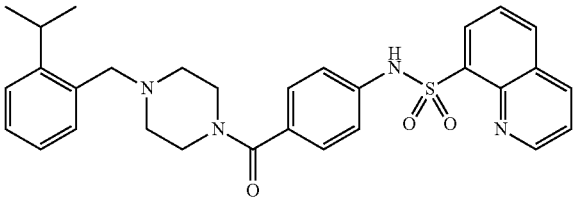

$^1$H NMR (400 MHz, DMSO-d6) δ: 1.17 (d, 6H), 3.10 (br s, 4H), 3.21 (br s, 4H), 4.35 (s, 2H), 4.62 (sextate, 1H), 7.18 (dd, 4H), 7.17 (d, 2H), 7.21 (br s, 1H), 7.20 (s, 2H), 7.68-7.74 (m, 2H), 8.28 (d, 1H), 8.40 (d, 1H), 8.51 (d, 1H), 9.14 (s, 1H), 9.50 (br s, 1H), 10.55 (s, 1H); HPLC Purity: 99.16%; LCMS: 529 ($M^+$+1).

N-(4-(4-(4-isobutoxybenzyl)piperazine-1-carbonyl) phenyl)quinoline-8-sulfonamide (VIII-89)

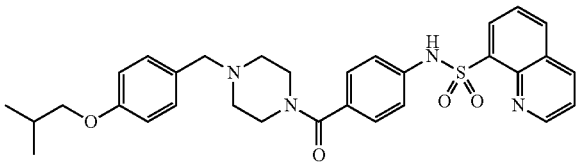

$^1$H NMR (400 MHz, DMSO-d6) δ: 0.96 (d, 6H), 2.00 (septet, 1H), 2.99 (br s, 2H), 3.18 (br s, 2H), 3.22 (br s, 2H), 3.70 (d, 2H), 4.20 (s, 2H), 6.99 (d, 2H), 7.18 (dd, 4H), 7.35 (d, 2H), 7.65-7.73 (m, 2H), 8.28 (d, 1H), 8.40 (d, 1H), 8.51 (d, 1H), 9.10 (s, 1H), 9.50 (br s, 1H), 10.55 (s, 1H); HPLC Purity: 99.06%; LCMS: 559 ($M^+$+1).

N-(4-(4-(2-phenylpropyl)piperazine-1-carbonyl) phenyl)quinoline-8-sulfonamide (VIII-90)

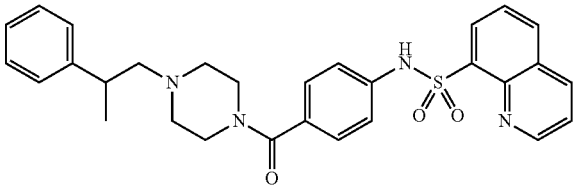

[$^1$H NMR (400 MHz, DMSO-d6) δ: 1.21 (d, 3H), 2.99 (br s, 3H), 3.21 (br s, 2H), 7.17 (d, 4H), 7.21-7.35 (m, 4H), 7.63-7.74 (m, 2H), 8.28 (d, 1H), 8.40 (d, 1H), 8.51 (d, 1H), 9.10 (s, 1H), 9.24 (br s, 1H), 10.55 (s, 1H);] HPLC Purity: 99.88%; LCMS: 515 ($M^+$+1).

N-(4-(4-(4-methoxy-3-methylbenzyl)piperazine-1-carbonyl)phenyl)quinoline-8-sulfonamide (VIII-91)

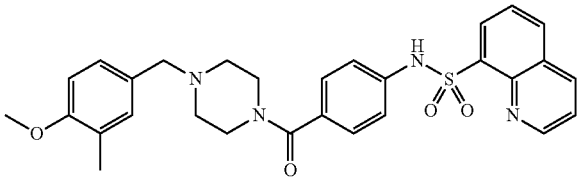

$^1$H NMR (400 MHz, DMSO-d6) δ: 2.19 (s, 3H), 3.02 (br s, 2H), 3.20 (br s, 2H), 3.30 (br s, 4H), 3.80 (s, 3H), 4.21 (s, 2H), 7.01 (d, 1H), 7.16-7.29 (m, 4H), 7.70-7.79 (m, 2H), 8.28 (d, 1H), 8.44 (d, 1H), 8.57 (d, 1H), 9.14 (s, 1H), 9.78 (br s, 1H), 10.55 (s, 1H); HPLC Purity: 99.86%; LCMS: 531 ($M^+$+1).

N-(4-(4-(4-isopropylbenzyl)piperazine-1-carbonyl) phenyl)quinoline-8-sulfonamide (VIII-92)

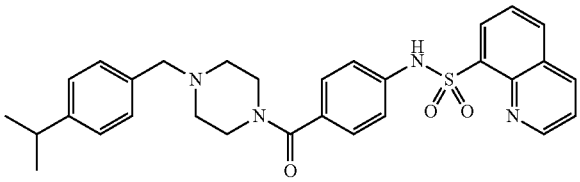

$^1$H NMR (400 MHz, DMSO-d6) δ: 1.20 (d, 6H), 2.31 (br s, 4H), 2.95 (pentet, 1H), 3.42 (br s, 4H), 4.22 (br s, 2H), 7.20 (dd, 4H), 7.39 (q, 4H), 7.70-7.78 (m, 2H), 8.28 (d, 1H), 8.46 (d, 1H), 8.53 (d, 1H), 9.14 (s, 1H), 9.60 (br s, 1H), 10.58 (s, 1H); HPLC Purity: 97.92%; LCMS: 529 ($M^+$+1).

N-(4-(4-(2,6-difluorobenzyl)piperazine-1-carbonyl) phenyl)quinoline-8-sulfonamide compound (VIII-93)

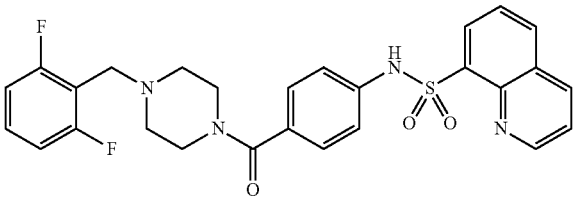

$^1$H NMR (400 MHz, DMSO-d6) δ: 2.31 (br s, 4H), 3.44 (br s, 4H), 3.61 (s, 2H), 7.02-7.26 (m, 5H), 7.56 (br s, 1H), 7.70-7.78 (m, 2H), 8.28 (d, 1H), 8.43 (d, 1H), 8.50 (d, 1H), 9.14 (s, 1H), 10.42 (s, 1H); HPLC Purity: 99.64%; LCMS: 523 ($M^+$+1).

N-(4-(4-(4-butylbenzyl)piperazine-1-carbonyl)phenyl)quinoline-8-sulfonamide (VIII-94)

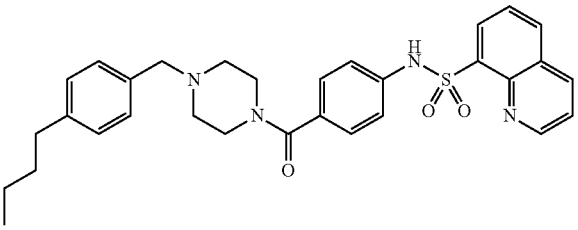

[$^1$H NMR (400 MHz, DMSO-d6) δ: 0.85 (t, 3H), 1.25 (sextet, 2H), 1.32 (pentet, 2H), 2.59 (t, 2H), 3.01 (br s, 4H), 3.12 (br s, 2H), 3.22 (br s, 2H), 4.21 (s, (2H), 7.11 (d, 2H), 7.21 (d, 2H), 7.25 (d, 2H), 7.30 (d, 2H), 7.63-7.71 (m, 2H), 8.28 (d, 1H), 8.40 (d, 1H), 8.51 (d, 1H), 9.10 (s, 1H), 9.78 (br s, 1H), 10.50 (s, 1H);] HPLC Purity: 99.98%; LCMS: 543 ($M^+$+1).

N-(4-(4-(2,6-dimethylbenzyl)piperazine-1-carbonyl) phenyl)quinoline-8-sulfonamide (VIII-95)

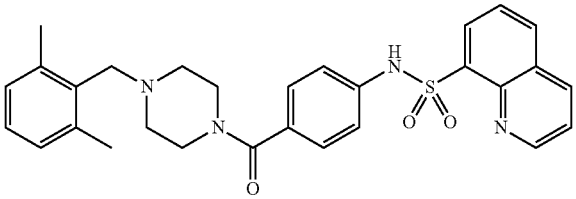

$^1$H NMR (400 MHz, DMSO-d6) δ: 2.25 (s, 6H), 2.41 (br s, 4H), 3.02 (br s, 2H), 3.20 (br s, 2H), 4.21 (br s, 2H), 7.05 (d, 3H), 7.17 (d, 2H), 7.24 (d, 2H), 7.70-7.79 (m, 2H), 8.28 (d, 1H), 8.44 (d, 1H), 8.57 (d, 1H), 9.14 (s, 1H), 9.78 (br s, 1H), 10.55 (s, 1H); HPLC Purity: 98.76%; LCMS: 515 ($M^+$+1).

N-(4-(4-(3,5-dimethoxybenzyl)piperazine-1-carbonyl)phenyl)quinoline-8-sulfonamide (VIII-96)

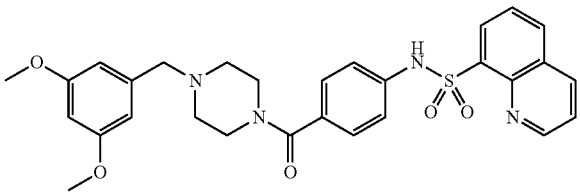

$^1$H NMR (400 MHz, DMSO-d6) δ: 2.32 (br s, 4H), 3.44 (br s, 4H), 3.72 (d, 6H), 4.19 (s, 2H), 6.59 (d, 1H), 7.18 (dd, 4H), 7.69-7.75 (m, 2H), 8.28 (d, 1H), 8.42 (d, 1H), 8.50 (d, 1H), 9.14 (s, 1H), 9.78 (br s, 1H), 10.51 (s, 1H); HPLC Purity: 93.00%; LCMS: 547 ($M^+$1).

N-(4-(4-(4-chloro-2-fluorobenzyl)piperazine-1-carbonyl)phenyl)quinoline-8-sulfonamide (VIII-97)

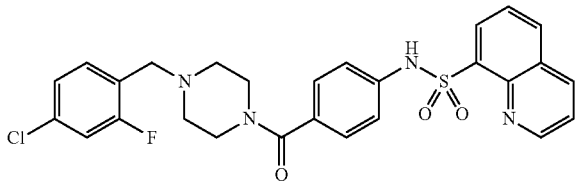

$^1$H NMR (400 MHz, DMSO-d6) δ: 2.38 (br s, 4H), 3.46 (br s, 4H), 3.77 (s, 3H), 4.40 (s, 2H), 7.22 (q, 4H), 7.34-7.44 (m, 2H), 7.55 (t, 1H), 7.63-7.70 (m, 2H), 8.20 (d, 1H), 8.42 (d, 2H), 9.14 (s, 1H); HPLC Purity: 98.85%; LCMS: 539 ($M^+$).

N-(4-(4-(4-ethoxybenzyl)piperazine-1-carbonyl) phenyl)quinoline-8-sulfonamide (VIII-98)

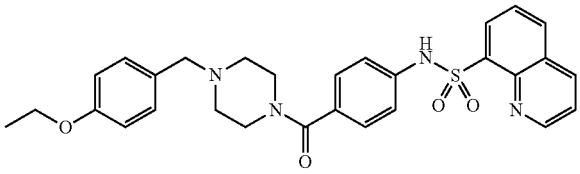

$^1$H NMR (400 MHz, DMSO-d6) δ: 1.23 (t, 2H), 4.00 (q, 2H), 4.20 (s, 2H), 6.97 (d, 2H), 7.17 (dd, 4H), 7.36 (d, 1H), 7.69-7.75 (m, 2H), 8.28 (d, 1H), 8.41 (d, 1H), 8.51 (d, 1H), 9.10 (s, 1H), 9.50 (br s, 1H), 10.50 (s, 1H); HPLC Purity: 96.83%; LCMS: 531 ($M^+$1).

N-(4-(4-(4-chlorobenzyl)piperazine-1-carbonyl)phenyl)quinoline-8-sulfonamide (VIII-99)

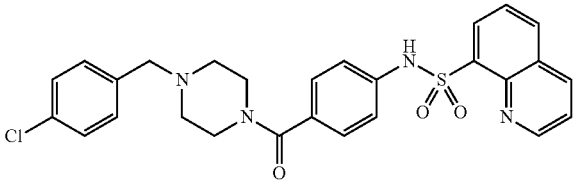

$^1$H NMR (400 MHz, $CD_3OD$) δ: 2.34 (br s, 4H), 3.23 (br s, 2H), 3.62 (br s, 2H), 4.30 (s, 2H), 7.16-7.20 (m, 4H), 7.37-7.57 (m, 4H), 7.79-7.84 (m, 2H), 8.15 (d, 1H), 8.40 (d, 1H), 9.10 (s, 1H), 9.50 (br s, 1H); HPLC Purity: 99.75%; LCMS: 521 ($M^+$).

N-(4-(4-(2,3-dichlorobenzyl)piperazine-1-carbonyl)phenyl)quinoline-8-sulfonamide (VIII-100)

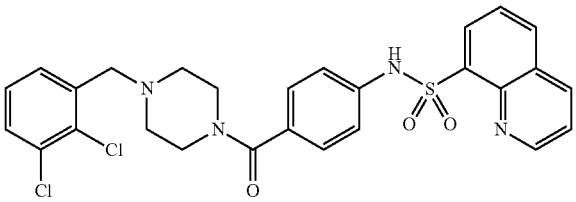

$^1$H NMR (400 MHz, $CD_3OD$) δ: 2.32 (br s, 4H), 3.62 (br s, 4H), 3.81 (s, 2H), 7.21 (q, 4H), 7.42 (t, 2H), 7.58 (d, 2H), 7.61-7.72 (m, 2H), 8.18 (d, 1H), 8.41 (d, 1H), 9.18 (s, 1H); HPLC Purity: 99.15%; LCMS: 555 ($M^+$1).

N-(4-(4-(2-hydroxy-5-methylbenzyl)piperazine-1-carbonyl)phenyl)quinoline-8-sulfonamide (VIII-101)

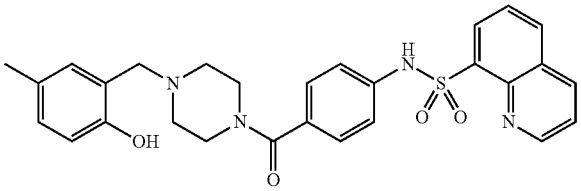

[$^1$H NMR (400 MHz, $CD_3OD$-d6) δ: 2.08 (s, 3H), 2.22 (s, 4H), 3.32 (s, 4H), 3.72 (s, 2H), 4.21 (s, 1H), 6.80 (d, 1H), 7.10 (s, 2H), 7.18-7.25 (m, 3H), 7.61-7.68 (m, 2H), 8.18 (d, 1H), 8.40 (d, 2H), 9.14 (s, 1H);] HPLC Purity: 98.02%; LCMS: 517 ($M^+$+1).

N-(4-(4-(5-fluoro-2-hydroxybenzyl)piperazine-1-carbonyl)phenyl)quinoline-8-sulfonamide (VIII-102)

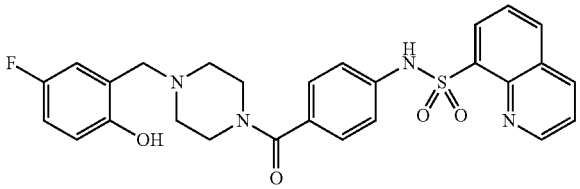

$^1$H NMR (400 MHz, $DMSOd_6$) δ: 2.30 (br s, 4H), 3.31 (br s, 4H), 3.72 (s, 2H), 6.90-6.95 (m, 3H), 7.04-7.18 (m, 2H), 7.20-7.25 (m, 3H), 7.60-7.65 (m, 2H), 8.41 (d, 2H), 9.10 (s, 1H); HPLC Purity: 98.95%; LCMS: 521 ($M^{30}$ +1).

N-(4-(4-(2,4-difluorobenzyl)piperazine-1-carbonyl)phenyl)quinoline-8-sulfonamide (103)

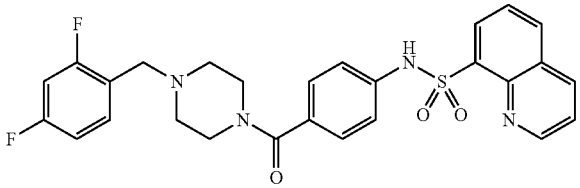

$^1$H NMR (400 MHz, $DMSOd_6$) δ: 2.36 (br s, 4H), 3.3 (br s, 4H), 3.7 (s, 2H), 7.05-7.22 (m, 5H), 7.55 (d, 2H), 7.60-7.65 (m, 2H), 8.18 (d, 1H), 8.40 (d, 2H), 9.10 (s, 1H); HPLC Purity: 99.24%; LCMS: 523.1 ($M^+$+1).

N-(4-(4-(3,5-dichloro-2-hydroxybenzyl)piperazine-1-carbonyl)phenyl)quinoline-8-sulfonamide (VIII-104)

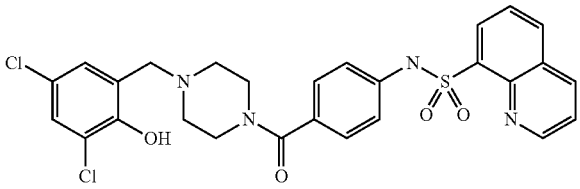

$^1$H NMR (400 MHz, $DMSOd_6$) δ: 2.37 (br s, 4H), 3.32 (br s, 4H), 3.71 (s, 2H), 4.2 (s, 1H), 7.19-7.23 (m, 4H), 7.39 (s, 1H), 7.56 (s, 1H), 7.62-7.68 (m, 2H), 8.18 (d, 2H), 8.40 (d, 1H), 9.13 (s, 1H); HPLC Purity: 99.95%; LCMS: 572.3 ($M^+$+1).

N-(4-(4-(2,3-dihydroxybenzyl)piperazine-1-carbonyl)phenyl)quinoline-8-sulfonamide (VIII-105)

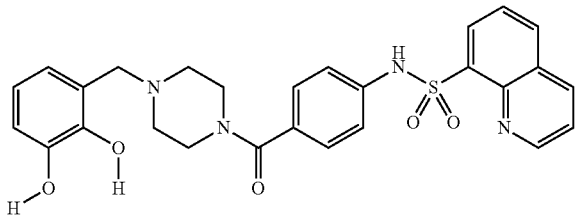

[$^1$H NMR (400 MHz, DMSO$d_6$) δ: 2.30 (br s, 4H), 3.32 (br s, 4H), 3.76 (s, 2H), 4.2 (br s, 2H), 7.19-7.23 (m, 4H), 7.39 (s, 1H), 7.56 (s, 1H), 7.62-7.68 (m, 3H), 8.18 (d, 2H), 8.40 (d, 1H), 9.13 (s, 1H);] HPLC Purity: 91.9%; LCMS: 519.1 ($M^+$+1).

N-(4-(4-(3-hydroxy-4-methoxybenzyl)piperazine-1-carbonyl)phenyl)quinoline-8-sulfonamide (VIII-106)

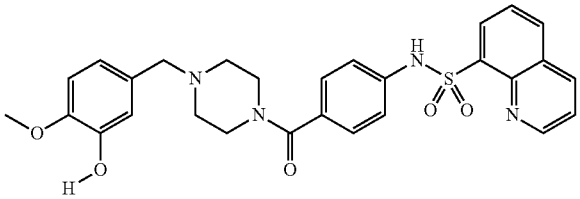

$^1$H NMR (400 MHz, DMSO$d_6$) δ: 3.19 (br s, 4H), 3.3-3.6 (m, 4H), 3.7 (s, 2H), 3.81 (s, 3H), 6.85 (d, 2H), 6.97 (d, 1H), 7.18-7.24 (m, 5H), 7.60-7.66 (m, 2H), 8.18 (d, 1H), 8.41 (d, 1H), 9.13 (s, 1H); HPLC Purity: 97.5%; LCMS: 533.1 ($M^+$+1).

N-(4-(4-(2-(difluoromethoxy)benzyl)piperazine-1-carbonyl)phenyl)quinoline-8-sulfonamide (VIII-107)

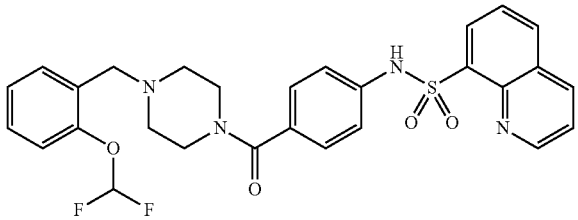

$^1$H NMR (400 MHz, DMSO$d_6$) δ: 2.7 (s, 1H), 3.19 (br s, 4H), 3.3-3.6 (m, 4H), 3.7 (s, 2H), 6.97-7.0 (m, 4H), 7.18-7.24 (m, 5H), 7.60-7.66 (m, 2H), 8.18 (d, 1H), 8.41 (d, 1H), 9.13 (s, 1H); HPLC Purity: 99.4%; LCMS: 553.1 ($M^+$+1).

N-(4-(4-(2-ethoxybenzyl)piperazine-1-carbonyl)phenyl)quinoline-8-sulfonamide (VIII-108)

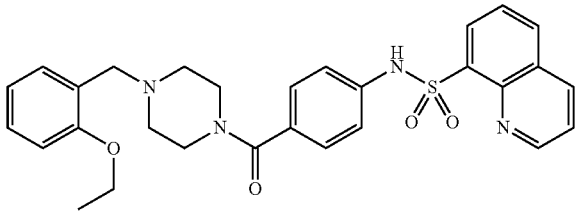

$^1$H NMR (400 MHz, DMSO$d_6$) δ: 1.89 (t, 3H), 3.19 (br s, 4H), 3.3-3.6 (m, 4H), 3.7 (s, 2H), 3.91 (q, 2H), 6.97-7.0 (m, 4H), 7.18-7.24 (m, 5H), 7.60-7.66 (m, 2H), 8.18 (d, 1H), 8.41 (d, 1H), 9.13 (s, 1H); HPLC Purity: 96.2%; LCMS: 553.1 ($M^+$+1).

N-(4-(4-(4-hydroxy-3,5-dimethylbenzyl)piperazine-1-carbonyl)phenyl)quinoline-8-sulfonamide (VIII-109)

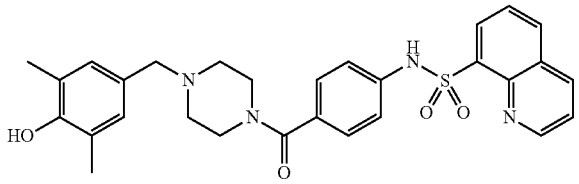

$^1$H NMR (400 MHz, DMSO$d_6$) δ: 2.2 (s, 6H), 3.19 (br s, 4H), 3.3-3.6 (m, 4H), 3.7 (s, 2H), 6.97-7.0 (m, 4H), 7.18-7.24 (m, 3H), 7.60-7.66 (m, 2H), 8.18 (d, 1H), 8.41 (d, 1H), 9.13 (s, 1H); HPLC Purity: 98.4%; LCMS: 531.1 ($M^+$+1).

N-(4-(4-(3-ethoxy-4-hydroxybenzyl)piperazine-1-carbonyl)phenyl)quinoline-8-sulfonamide (VIII-110)

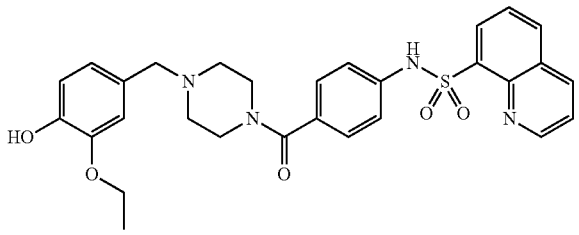

$^1$H NMR (400 MHz, $CDCl_3$) δ: 1.41 (t, 3H), 2.42 (br s, 4H), 3.25-3.95 (m, 4H), 3.42 (q, 2H), 3.60 (br s, 2H), 4.21 (s, 1H), 6.75 (s, 2H), 6.90 (s, 1H), 7.19 (s, 4H), 7.62-7.67 (m, 2H), 8.18 (d, 1H), 8.40 (d, 2H), 9.18 (s, 1H); HPLC Purity: 99.29%; LCMS: 546.1 ($M^+$+1).

N-(4-(4-(4-(tert-butyl)benzyl)piperazine-1-carbonyl)phenyl)quinoline-8-sulfonamide (VIII-111)

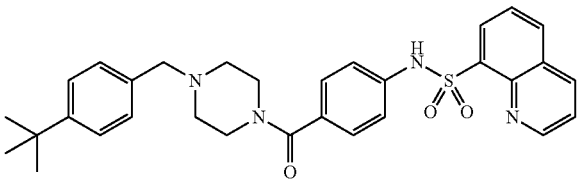

$^1$H NMR (400 MHz, $CD_3OD$) δ: 1.30 (s, 9H), 2.56 (br s, 4H), 3.30 (br s, 4H), 3.68 (s, 2H), 7.20 (dd, 4H), 7.45 (dd, 4H), 7.70-7.80 (m, 2H), 8.45 (d, 2H), 8.55 (d, 1H), 9.18 (s, 1H), 10.54 (s, 1H); HPLC Purity: 98.47%; LCMS: 543.0 ($M^+$+1).

N-(4-(4-(5-fluoro-2-(trifluoromethyl)benzyl)piperazine-1-carbonyl)phenyl)quinoline-8-sulfonamide (VIII-112)

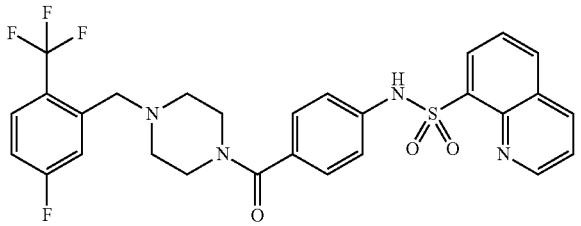

$^1$H NMR (400 MHz, $CDCl_3$) δ: 2.45 (br s, 4H), 3.2-3.6 (m, 4H), 3.70 (s, 2H), 7.20 (s, 4H), 7.59-7.74 (m, 4H), 8.18 (d, 2H), 8.40 (m, 2H), 9.16 (s, 1H); HPLC Purity: 99.35%; LCMS: 573.1 ($M^+$+1).

N-(4-(4-(4-chloro-2-fluoro-5-methoxybenzyl)piperazine-1-carbonyl)phenyl)quinoline-8-sulfonamide (VIII-113)

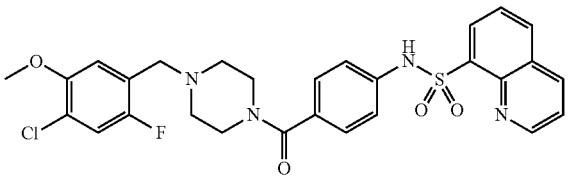

[$^1$H NMR (400 MHz, $CD_3OD$) δ: 2.91 (br s, 4H), 3.77 (br s, 4H), 3.92 (s, 2H), 4.01 (s, 3H), 7.20-7.25 (m, 4H), 7.40 (d, 1H), 7.62-7.68 (m, 3H), 8.18 (d, 1H), 8.41 (d, 2H), 9.13 (s, 1H);] HPLC Purity: 99.42%; LCMS: 569 ($M^+$+1).

N-(4-((4-(4-(quinoline-8-sulfonamido)benzoyl)piperazin-1-yl)methyl)phenyl)acetamide (VIII-114)

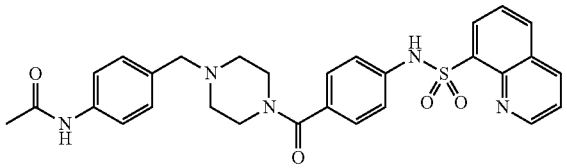

$^1$H NMR (400 MHz, DMSO-d6) δ: 2.01 (s, 3H), 3.01 (br s, 4H), 3.20 (br s, 2H), 3.30 (br s, 2H), 4.24 (s, 2H), 7.20 (dd, 4H), 7.40 (d, 2H), 7.65 (d, 2H), 7.70-7.80 (m, 2H), 8.30 (d, 1H), 8.45 (d, 1H), 8.52 (d, 1H), 9.18 (s, 1H), 10.60 (s, 1H); HPLC Purity: 95.84%; LCMS: 544.1 ($M^{30}$ +1).

N-(4-(4-(2-fluorobenzyl)piperazine-1-carbonyl)phenyl)quinoline-8-sulfonamide (VIII-115)

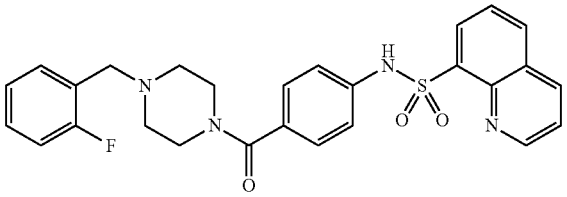

$^1$H NMR (400 MHz, $CD_3OD$-d6) δ: 3.01 (br s, 4H), 3.20 (br s, 2H), 3.30 (br s, 2H), 3.82 (s, 2H), 7.02-7.20 (m, 5H), 7.24-7.41 (m, 2H), 7.61-7.67 (m, 2H), 8.18 (d, 1H), 8.41 (t, 2H), 9.12 (s, 1H); HPLC Purity: 99.03%; LCMS: 505 ($M^+$1).

N-(4-(4-(2,3-difluorobenzyl)piperazine-1-carbonyl)phenyl)quinoline-8-sulfonamide (VIII-116)

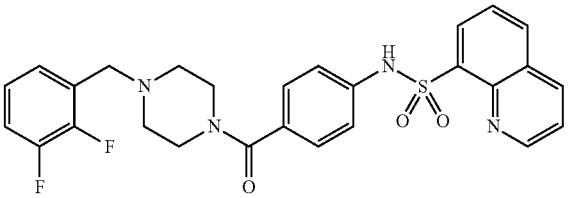

$^1$H NMR (400 MHz, $CD_3OD$-d6) δ: 3.01 (br s, 4H), 3.20 (br s, 2H), 3.30 (br s, 2H), 4.24 (s, 2H), 7.16-7.34 (m, 6H), 7.39-7.47 (m, 2H), 7.61-7.67 (m, 2H), 8.18 (d, 1H), 8.41 (d, 1H), 9.12 (s, 1H); HPLC Purity: 97.11%; LCMS: 523.2 ($M^+$1).

N-(4-(4-(2-hydroxy-4,6-dimethoxybenzyl)piperazine-1-carbonyl)phenyl)quinoline-8-sulfonamide (VIII-117)

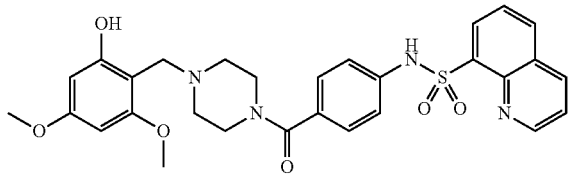

$^1$H NMR (400 MHz, $CDCl_3$) δ: 3.15 (br s, 2H), 3.2-3.6 (br s, 6H), 3.39 (br s, 2H), 3.78 (s, 3H), 3.81 (s, 3H), 6.17 (d, 2H), 7.22 (q, 4H), 7.62-7.68 (m, 2H), 8.18 (d, 1H), 8.41 (d, 1H), 9.17 (s, 1H); HPLC Purity: 97.92%; LCMS: 563 ($M^+$).

N-(4-(4-(3,5-dichloro-4-hydroxybenzyl)piperazine-1-carbonyl)phenyl)quinoline-8-sulfonamide (VIII-118)

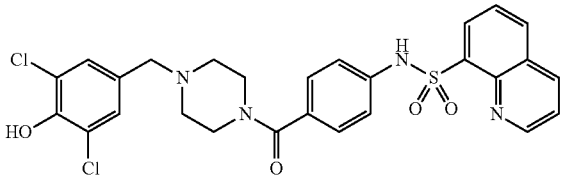

$^1$H NMR (400 MHz, DMSO-d6) δ: 3.04 (br s, 2H), 3.30 (br s, 4H), 4.12 (s, 4H), 4.2 (s, 1H), 7.21 (dd, 4H), 7.27 (s, 1H), 7.50 (s, 2H), 7.69-7.78 (m, 2H), 8.30 (d, 1H), 8.50 (d, 2H), 10.59 (s, 1H); HPLC Purity: 93.26%; LCMS: 571.3 ($M^+$).

N-(4-(4-(2,6-dimethylbenzyl)piperazine-1-carbonyl)phenyl)quinoline-8-sulfonamide (VIII-119)

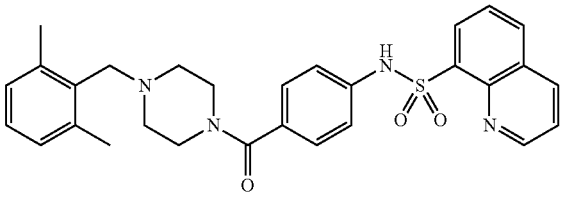

$^1$H NMR (400 MHz, DMSO-d6) δ: 2.44 (s, 6H), 3.34 (s, 6H), 3.39 (br s, 2H), 4.45 (s, 2H), 7.19-7.30 (m, 6H), 7.63-7.70 (m, 3H), 8.20 (d, 1H), 8.42 (d, 2H), 9.18 (s, 1H); HPLC Purity: 98.10%; LCMS: 515 ($M^+$1).

N-(4-(4-(3,4-dimethoxybenzyl)piperazine-1-carbonyl)phenyl)quinoline-8-sulfonamide (VIII-120)

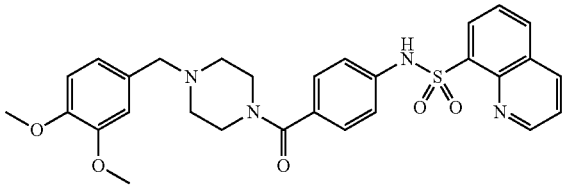

$^1$H NMR (400 MHz, $CD_3OD$) δ: 3.4-3.6 (br s, 2H), 3.85 (d, 6H), 4.1 (s, 6H), 4.29 (s, 2H), 7.02 (d, 3H), 7.21-7.27 (m, 4H), 7.63-7.72 (m, 2H), 8.20 (d, 1H), 8.42 (d, 1H), 9.14 (s, 1H); HPLC Purity: 99.44%; LCMS: 547 ($M^+$1).

N-(4-(4-(3-methoxybenzyl)piperazine-1-carbonyl)phenyl)quinoline-8-sulfonamide (VIII-121)

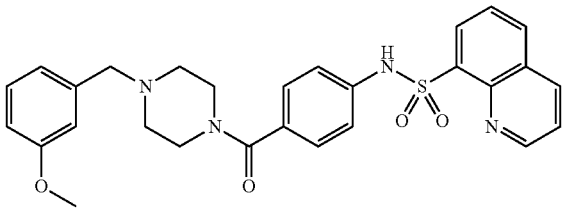

$^1$H NMR (400 MHz, $CD_3OD$) δ: 2.81 (br s, 4H), 3.20 (br s, 4H), 3.78 (s, 3H), 4.25 (s, 2H), 7.01 (t, 2H), 7.20 (t, 3H), 7.39 (t, 1H), 7.61-7.67 (m, 2H), 8.18 (d, 1H), 8.41 (d, 2H), 9.14 (s, 1H); HPLC Purity: 97.82%; LCMS: 517 ($M^+$+1).

N-(4-(4-(4-propoxybenzyl)piperazine-1-carbonyl)phenyl)quinoline-8-sulfonamide (VIII-122)

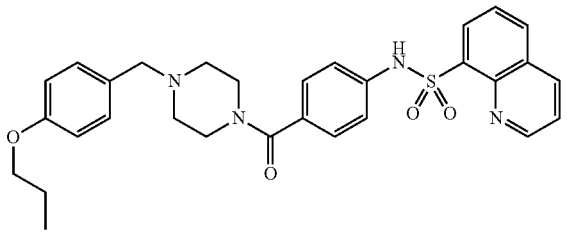

[$^1$H NMR (400 MHz, $CD_3OD$) δ: 1.01 (t, 3H), 1.78 (sextet, 2H), 3.2-3.85 (br s, 4H), 3.9-4.0 (br s, 4H), 3.92 (t, 2H), 4.22 (s, 2H), 6.97 (d, 2H), 7.21 (q, 4H), 7.38 (d, 2H), 7.61-7.67 (m, 2H), 8.18 (d, 1H), 8.40 (d, 2H), 9.10 (s, 1H);] HPLC Purity: 98.67%; LCMS: 545 ($M^+$+1).

N-(4-(4-phenethylpiperazine-1-carbonyl)phenyl) quinoline-8-sulfonamide (VIII-123)

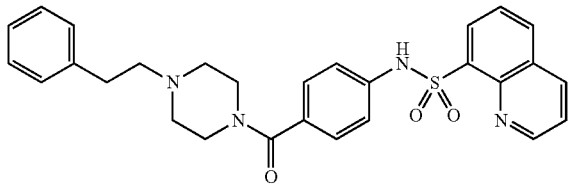

$^1$H NMR (400 MHz, DMSO-d6) δ: 2.01 (t, 2H), 2.20 (t, 2H), 2.8 (br s, 2H), 3.2-3.89 (m, 6H), 7.04-7.32 (m, 4H), 7.59-7.63 (m, 6H), 8.01 (d, 1H), 8.25 (dd, 2H), 8.41 (d, 1H), 9.18 (s, 1H); HPLC Purity: 99.43%; LCMS: 501 ($M^+$+1).

N-(4-(4-(2,3,4-trimethoxybenzyl)piperazine-1-carbonyl)phenyl)quinoline-8-sulfonamide (VIII-124)

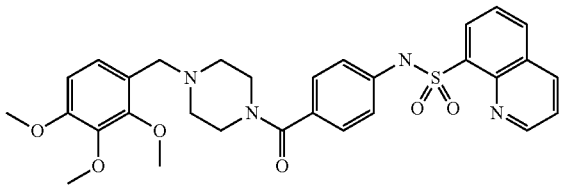

$^1$H NMR (400 MHz, DMSO-d6) δ: 3.01 (br s, 2H), 3.32-3.71 (m, 6H), 3.78 (s, 3H), 3.84 (s, 3H), 3.86 (s, 3H), 4.22 (br s, 2H), 6.89 (d, 1H), 7.18 (d, 3H), 7.25 (d, 2H), 7.72-7.80 (m, 2H), 8.30 (d, 1H), 8.45 (d, 1H), 8.55 (d, 1H), 9.18 (d, 1H), 10.59 (s, 1H); HPLC Purity: 99.84%; LCMS: 577 ($M^+$+1).

N-(4-(4-(4-hydroxy-3,5-dimethoxybenzyl)piperazine-1-carbonyl)phenyl)quinoline-8-sulfonamide (VIII-125)

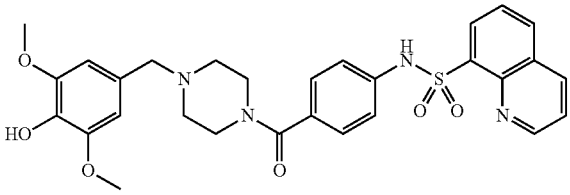

$^1$H NMR (400 MHz, DMSO-d6) δ: 3.01 (br s, 2H), 3.21 (br s, 2H), 3.3-3.7 (m, 6H), 3.79 (s, 6H), 6.75 (s, 2H), 7.20 (dd, 4H), 7.70-7.80 (m, 2H), 8.31 (d, 1H), 8.46 (d, 2H), 8.55 (d, 1H), 10.59 (s, 1H); HPLC Purity: 99.21%; LCMS: 563 ($M^+$+1).

N-(4-(4-(2-hydroxy-3,4-dimethoxy-6-methylbenzyl) piperazine-1-carbonyl)phenyl)quinoline-8-sulfonamide (VIII-126)

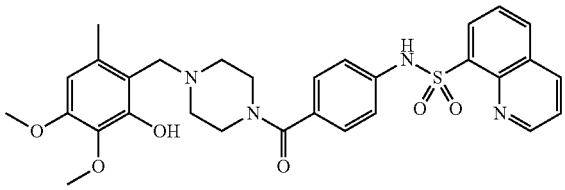

[$^1$H NMR (400 MHz, DMSO-d6) δ: 2.11 (s, 3H), 3.18 (br s, 4H), 3.30 (br s, 4H), 3.66 (s, 3H), 3.75 (s, 3H), 4.18 (s, 2H), 6.48 (s, 1H), 7.20 (dd, 4H), 7.70-7.80 (m, 2H), 8.31 (d, 1H), 8.44 (d, 2H), 8.52 (d, 1H), 8.78 (br s, 1H), 9.10 (br s, 1H), 9.19 (s, 1H), 9.60 (br s, 1H), 10.53 (s, 1H);] HPLC Purity: 97.01%; LCMS: 577 ($M^+$+1).

N-(4-(4-(4-butoxybenzyl)piperazine-1-carbonyl) phenyl)quinoline-8-sulfonamide (VIII-127)

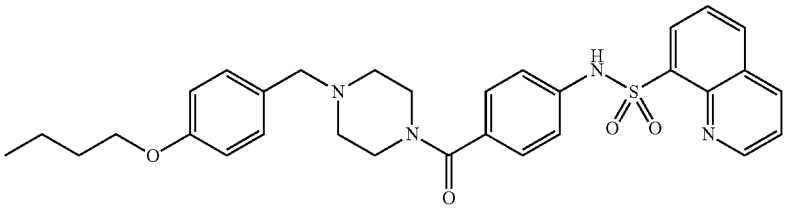

$^1$H NMR (400 MHz, DMSO-d6) δ: 0.92 (t, 3H), 1.41 (sextet, 2H), 1.68 (pentate, 2H), 3.00 (br s, 2H), 3.15 (br s, 2H), 3.25 (br s, 4H), 3.92 (t, 2H), 4.22 (s, 2H), 6.97 (d, 2H), 7.20 (dd, 4H), 7.38 (d, 2H), 7.70-7.79 (m, 2H), 8.44 (d, 1H), 8.50 (d, 1H), 9.12 (s, 1H), 9.64 (br s, 1H), 10.50 (s, 1H); HPLC Purity: 98.86%; LCMS: 559 ($M^+$+1).

N-(4-(4-(3-hydroxybenzyl)piperazine-1-carbonyl) phenyl)quinoline-8-sulfonamide (VIII-128)

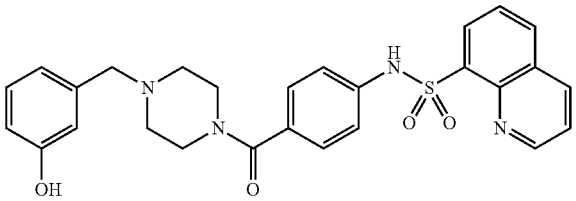

$^1$H NMR (400 MHz, DMSO-d6) δ: 2.81 (br s, 2H), 3.00 (br s, 6H), 4.20 (br s, 2H), 6.80 (s, 2H), 7.20 (dd, 4H), 7.70-7.80 (m, 2H), 8.31 (d, 1H), 8.46 (d, 2H), 8.55 (d, 1H), 9.17 (s, 1H), 9.70 (br s, 1H), 10.56 (s, 1H); HPLC Purity: 99.28%; LCMS: 503 ($M^+$+1).

4-((4-(4-(quinoline-8-sulfonamido)benzoyl)piperazin-1-yl)methyl)phenyl butyrate (VIII-129)

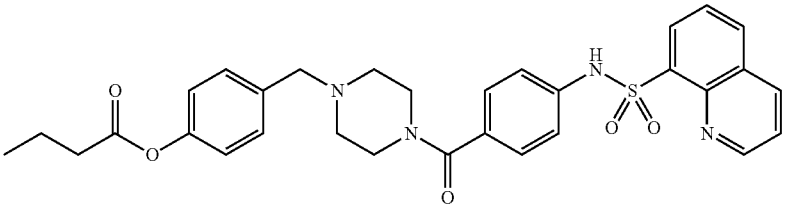

$^1$H NMR (400 MHz, DMSO-d6) δ: 0.99 (t, 3H), 1.61 (sextet, 2H), 2.56 (t, 2H), 3.03 (br s, 4H), 3.61 (br s, 4H), 4.24 (br s, 2H), 7.10-7.20 (m, 5H), 7.45 (d, 2H), 7.65-7.72 (m, 2H), 8.23 (d, 1H), 8.41 (d, 2H), 8.51 (d, 1H), 9.10 (s, 1H), 9.78 (br s, 1H), 10.50 (s, 1H); HPLC Purity: 99.17%; LCMS: 573 ($M^+$+1).

4-((4-(4-(quinoline-8-sulfonamido)benzoyl)piperazin-1-yl)methyl)phenyl acetate (VIII-130)

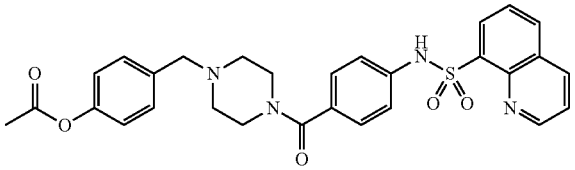

$^1$H NMR (400 MHz, DMSO-d6) δ 2.24 (s, 3H), 2.38 (br s, 4H), 3.42 (br s, 4H), 3.78 (s, 2H), 7.10 (d, 2H), 7.20 (d, 2H), 7.44 (d, 2H), 7.63-7.71 (m, 2H), 8.25 (d, 1H), 8.41 (d, 2H), 8.45 (d, 1H), 9.10 (s, 1H), 9.70 (br s, 1H), 10.50 (s, 1H); HPLC Purity: 95.24%; LCMS: 545 ($M^+$+1).

N-(4-(4-(3,4,5-trimethoxybenzyl)piperazine-1-carbonyl)phenyl)quinoline-8-sulfonamide (VIII-131)

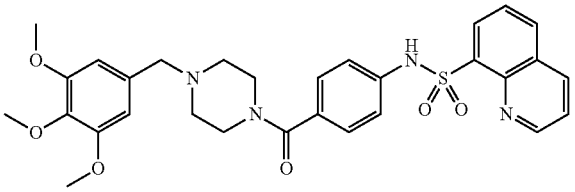

$^1$H NMR (400 MHz, DMSO-d6) δ: 3.75 (s, 3H), 3.81 (s, 6H), 4.22 (s, 2H), 6.78 (s, 2H), 7.21 (q, 4H), 7.63-7.68 (m, 2H), 8.16 (d, 1H), 8.40 (d, 2H), 9.10 (s, 1H); HPLC Purity: 98.81%; LCMS: 577 ($M^+$+1).

N-(4-(4-(3-isobutoxybenzyl)piperazine-1-carbonyl) phenyl)quinoline-8-sulfonamide (VIII-132)

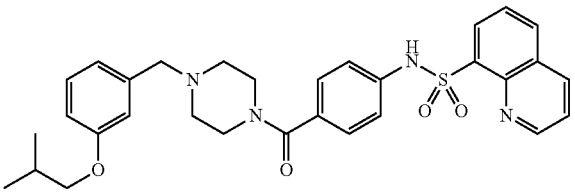

$^1$H NMR (400 MHz, DMSO-d6) δ: 1.00 (d, 6H), 2.02 (septet, 1H), 3.05 (br s, 4H), 3.30 (br s, 4H), 3.80 (d, 2H), 3.91 (d, 2H), 7.00-7.08 (m, 2H), 7.20 (dd, 4H), 7.39 (t, 1H), 7.71-7.80 (m, 2H), 8.30 (d, 1H), 8.45 (d, 1H), 8.58 (d, 1H), 9.15 (s, 1H), 9.90 (br s, 1H), 10.58 (s, 1H); HPLCPpurity: 99.17%; LCMS: 559 ($M^+$+1).

N-(4-(4-(2,3-dimethoxybenzyl)piperazine-1-carbonyl)phenyl)quinoline-8-sulfonamide (VIII-133)

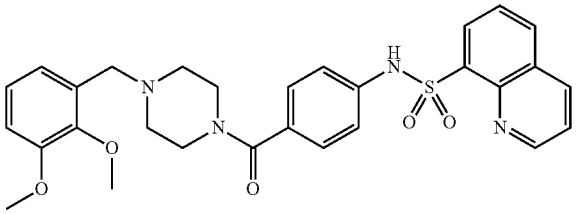

$^1$H NMR (400 MHz, DMSO-d6) δ: 2.25 (br s, 4H), 3.41 (br s, 4H), 3.64 (s, 3H), 3.72 (s, 2H), 3.78 (s, 3H), 6.80-7.05 (m, 6H), 7.21 (q, 1H), 7.59-7.70 (m, 2H), 8.14 (d, 1H), 8.38-8.42 (m, 2H), 9.01 (s, 1H); HPLC Purity: 98.50%; LCMS: 547 ($M^+$+1).

N-(4-(4-(3-fluoro-4-methoxybenzyl)piperazine-1-carbonyl)phenyl)quinoline-8-sulfonamide (VIII-134)

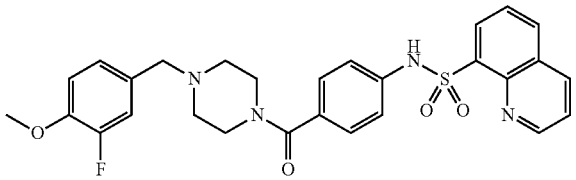

$^1$H NMR (400 MHz, DMSO-d6) δ: 2.81 (br s, 2H), 3.01 (br s, 2H), 3.25 (br s, 4H), 3.82 (s, 2H), 3.90 (s, 3H), 7.17 (d, 2H), 7.21 (d, 3H), 7.35 (1H), 7.70-7.78 (m, 2H), 8.30 (d, 1H), 8.43 (d, 2H), 8.55 (d, 1H), 9.12 (br s, 1H), 10.58 (s, 1H); HPLC Purity: 95.38%; LCMS: 535 ($M^+$+1).

N-(4-(4-(3-fluoro-2-hydroxybenzyl)piperazine-1-carbonyl)phenyl)quinoline-8-sulfonamide (VIII-135)

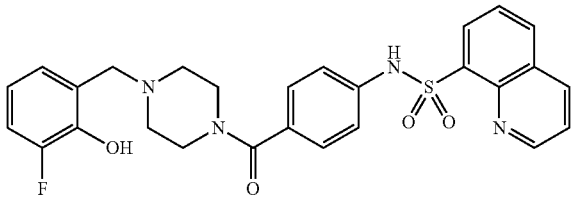

$^1$H NMR (400 MHz, DMSO-d6) δ: 2.38 (br s, 4H), 3.43 (br s, 4H), 3.62 (s, 2H), 4.38 (s, 1H), 6.90 (q, 1H), 7.10-7.28 (m, 6H), 7.62 (d, 2H), 8.18 (d, 1H), 8.40 (d, 2H), 9.10 (s, 1H); HPLC purity: 98.81%; LCMS: 521 ($M^+$+1).

N-(4-(4-(2,4-dimethoxybenzyl)piperazine-1-carbonyl)phenyl)quinoline-8-sulfonamide (VIII-136)

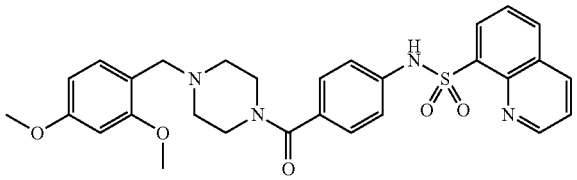

$^1$H NMR (400 MHz, DMSO-d6) δ: 2.52 (br s, 4H), 3.30 (br s, 4H), 3.70-3.98 (m, 8H), 6.58-6.64 (m, 2H), 7.16 (d, 2H), 7.22 (d, 2H), 7.33 (d, 1H), 7.70-7.79 (m, 2H), 8.28 (d, 1H), 8.44 (d, 2H), 8.55 (d, 1H), 9.10 (s, 1H), 9.50 (br s, 1H), 10.51 (s, 1H); HPLC Purity: 92.62%; LCMS: 547 ($M^+$+1).

N-(4-(4-(3,4-dimethylbenzyl)piperazine-1-carbonyl)phenyl)quinoline-8-sulfonamide (VIII-137)

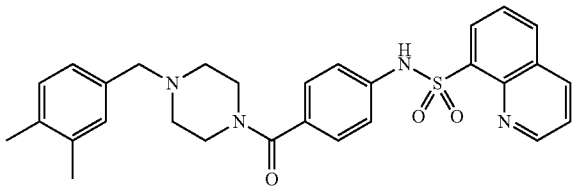

$^1$H NMR (400 MHz, DMSO-d6) δ: 2.20 (s, 3H), 2.25 (br s, 4H), 2.50 (s, 3H), 3.42 (br s, 4H), 3.81 (s, 2H), 6.96-7.20 (m, 7H), 7.68-7.76 (m, 2H), 8.26 (d, 1H), 8.40 (d, 2H), 8.54 (d, 1H), 9.13 (s, 1H), 10.40 (br s, 1H); HPLC Purity: 96.74%; LCMS: 515 ($M^+$+1).

N-(4-(4-(3-phenylpropyl)piperazine-1-carbonyl)phenyl)quinoline-8-sulfonamide (VIII-138)

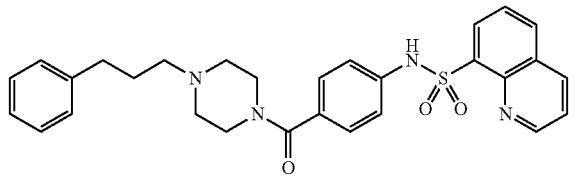

[$^1$H NMR (400 MHz, DMSO-d6) δ: 1.70 (t, 2H), 2.24 (br s, 4H), 2.48-2.60 (m, 4H), 3.44 (br s, 4H), 7.18-7.24 (m, 8H), 7.70-7.79 (m, 2H), 8.30 (d, 1H), 8.42 (d, 1H), 8.58 (d, 1H), 9.16 (s, 1H), 10.41 (s, 1H);] HPLC Purity: 93.22%; LCMS: 515 ($M^+$+1).

3-((4-(4-(quinoline-8-sulfonamido)benzoyl)piperazin-1-yl)methyl)phenyl acetate (VIII-139)

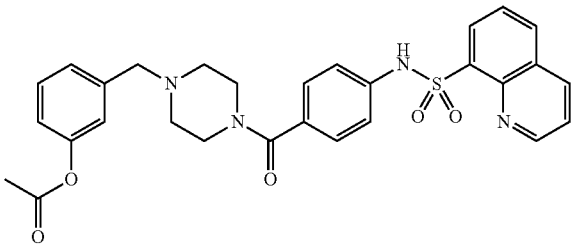

$^1$H NMR (400 MHz, DMSO-d6) δ: 2.24 (s, 4H), 2.30 (br s, 2H), 3.40 (br s, 4H), 3.52 (s, 2H), 7.01-7.21 (m, 6H), 7.38 (t, 1H), 7.70-7.79 (m, 2H), 8.29 (d, 1H), 8.42 (d, 1H), 8.58 (d, 1H), 9.15 (s, 1H), 10.41 (s, 1H); HPLC Purity: 93.39%; LCMS: 545 ($M^+$+1).

N-(4-(4-(1-phenylethyl)piperazine-1-carbonyl)phenyl)quinoline-8-sulfonamide (VIII-140)

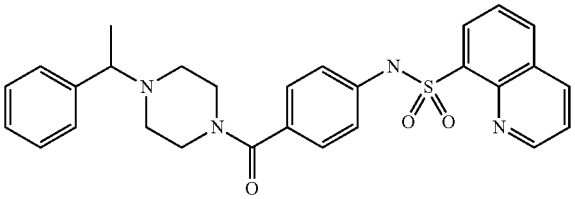

$^1$H NMR (400 MHz, DMSO-d6) δ 1.22 (d, 3H), 2.20 (br s, 2H), 2.24 (br s, 2H), 3.42 (br s, 4H), 3.68 (s, 2H), 7.04 (s, 3H), 7.17-7.26 (m, 4H), 7.66-7.74 (m, 2H), 8.24 (d, 1H), 8.39 (d, 1H), 8.50 (d, 1H), 9.16 (s, 1H), 10.40 (s, 1H); HPLC Purity: 99.27%; LCMS: 501 ($M^+$+1).

N-(4-(4-((1-phenylcyclopropyl)methyl)piperazine-1-carbonyl)phenyl)quinoline-8-sulfonamide (VIII-141)

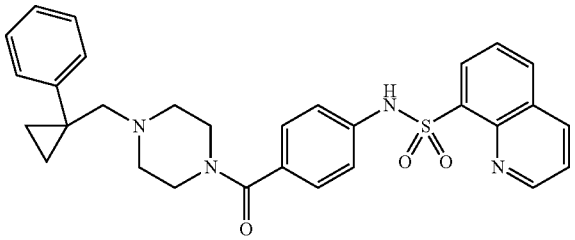

$^1$H NMR (400 MHz, DMSO-d6) δ: 1.03 (d, 4H), 2.38 (br s, 2H), 2.61 (s, 2H), 3.50 (br s, 4H), 7.19 (s, 4H), 7.25 (t, 1H), 7.36 (t, 2H), 7.42 (d, 2H), 7.60-7.65 (m, 2H), 8.18 (d, 1H), 8.40 (d, 1H), 9.12 (s, 1H); HPLC Purity: 94.05%; LCMS: 527 ($M^+$+1).

N-(4-(4-(2-hydroxy-3,4-dimethoxybenzyl)piperazine-1-carbonyl)phenyl)quinoline-8-sulfonamide (VIII-142)

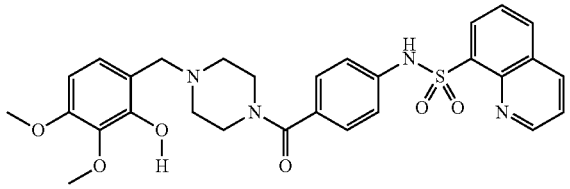

$^1$H NMR (400 MHz, DMSO-d6) δ: 2.38 (brs, 4H), 3.06 (br s, 4H), 3.65 (s, 2H), 3.70 (s, 3H), 3.80 (s, 3H), 4.18 (s, 1H), 6.59 (d, 1H), 7.00 (d, 1H), 7.18 (dd, 4H), 7.68-7.77 (m, 2H), 8.26 (d, 1H), 8.48 (d, 3H), 8.53 (d, 1H), 9.18 (s, 1H), 9.42 (br s, 1H), 9.61 (s, 1H), 10.51 (s, 1H); HPLC Purity: 93.10%; LCMS: 563 ($M^+$+1).

N-(4-(4-(2-fluoro-4-methoxybenzyl)piperazine-1-carbonyl)phenyl)quinoline-8-sulfonamide (VIII-143)

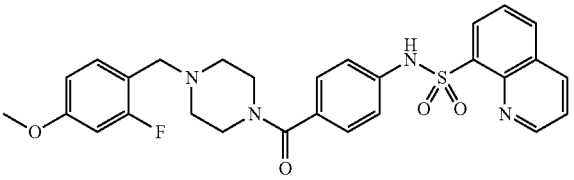

$^1$H NMR (400 MHz, DMSO-d6) δ: 2.39 (br s, 4H), 3.20 (br s, 4H), 3.72 (s, 2H), 3.80 (s, 3H), 6.79 (s, 1H), 6.90-7.01 (m, 2H), 7.18-7.24 (m, 2H), 7.44 (br s, 1H), 7.71-7.80 (m, 2H), 8.30 (d, 1H), 8.49 (d, 1H), 8.57 (d, 1H), 9.18 (s, 1H), 9.82 (br s, 1H), 10.48 (s, 1H); HPLC Purity: 96.28%; LCMS: 435 ($M^+$+1).

N-(4-(4-(4-hydroxybenzyl)piperazine-1-carbonyl)phenyl)quinoline-8-sulfonamide (VIII-144)

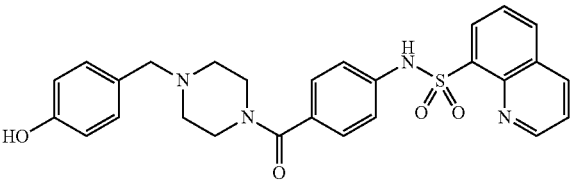

$^1$H NMR (400 MHz, DMSO-d6) δ: 2.42 (br s, 4H), 3.20 (br s, 4H), 3.71 (s, 2H), 6.77 (d, 1H), 6.84 (d, 2H), 7.18-7.24 (m, 5H), 7.61-7.67 (m, 2H), 8.17 (d, 1H), 8.40 (d, 2H), 9.10 (s, 1H); HPLC Purity: 92.29%; LCMS: 503 ($M^+$+1).

N-(4-(4-(2,5-dihydroxybenzyl)piperazine-1-carbonyl)phenyl)quinoline-8-sulfonamide (VIII-145)

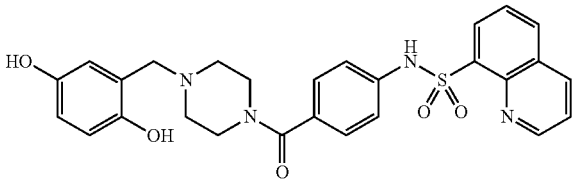

$^1$H NMR (400 MHz, DMSO-d6) δ: 2.38 (br s, 4H), 3.38 (br s, 4H), 3.50 (s, 2H), 6.45-6.59 (m, 3H), 7.04-7.18 (m, 4H), 7.65-7.77 (m, 2H), 8.24 (d, 1H), 8.40 (d, 1H), 8.50 (d, 1H), 8.61 (s, 1H), 9.18 (s, 1H), 10.41 (s, 1H); HPLC Purity: 98.19%; LCMS: 519 ($M^+$+1).

N-(4-(4-(pyridin-3-ylmethyl)piperazine-1-carbonyl)phenyl)quinoline-8-sulfonamide (VIII-146)

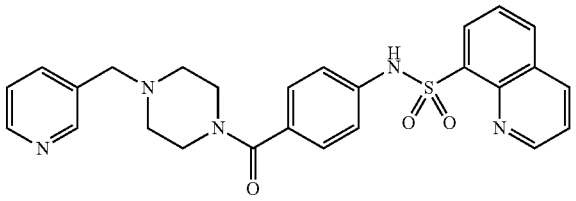

[$^1$H NMR (400 MHz, DMSO-d6) δ: 2.25 (br s, 4H), 3.30 (br s, 4H), 3.59 (s, 2H), 7.06-7.18 (s, 3H), 7.35-7.40 (m, 1H), 7.65-7.77 (m, 2H), 8.26 (d, 1H), 8.40-8.56 (m, 3H), 9.18 (s, 1H), 10.41 (s, 1H);] HPLC Purity: 99.48%; LCMS: 488 ($M^+$+1).

[N-(4-(4-(cyclopropylmethyl)piperazine-1-carbonyl)phenyl)quinoline-8-sulfonamide (VIII-147)

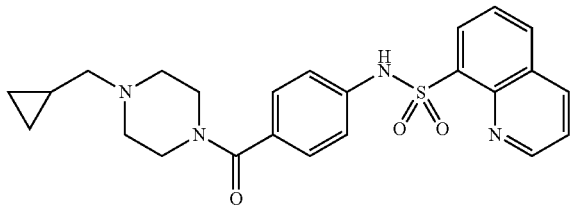

]

[$^1$H NMR (400 MHz, DMSO-d6) δ: 0.03 (s, 2H), 0.43 (s, 2H), 0.78-0.84 (m, 1H), 2.18 (d, 2H), 2.39 (br s, 4H), 3.25 (br s, 2H), 3.46 (br s, 2H), 7.10-7.19 (m, 3H), 7.76-7.80 (m, 2H), 8.26 (d, 1H), 8.43 (d, 1H), 8.58 (d, 1H), 9.17 (s, 1H), 10.41 (s, 1H); HPLC Purity: 98.98%; LCMS: 451 ($M^+$+1).]

N-(4-(4-(3-fluoropyridin-2-yl)methyl)piperazine-1-carbonyl)phenyl)quinoline-8-sulfonamide (VIII-148)

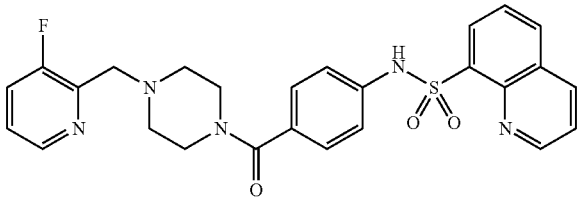

$^1$H NMR (400 MHz, DMSO-d6) δ: 2.37 (br s, 4H), 3.21 (br s, 2H), 3.46 (br s, 4H), 3.62 (s, 2H), 7.06-7.11 (m, 3H), 7.40 (t, 1H), 7.62-7.77 (m, 2H), 8.21 (d, 1H), 8.25 (dd, 2H), 8.50 (d, 1H), 9.18 (s, 1H), 10.41 (s, 1H); HPLC Purity: 98.83%; LCMS: 506 ($M^+$+1).

N-(4-(4-((4-(trifluoromethyl)pyridin-3-yl)methyl)piperazine-1-carbonyl)phenyl)quinoline-8-sulfonamide (VIII-149)

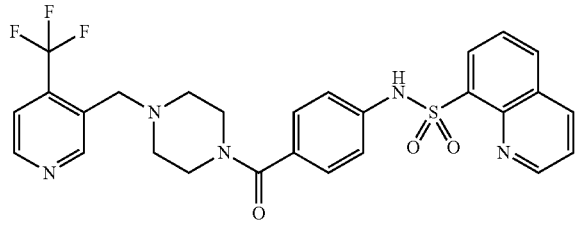

[$^1$H NMR (400 MHz, DMSO-d6) δ: 2.37 (br s, 4H), 3.31 (br s, 4H), 3.62 (s, 2H), 7.06-7.17 (m, 3H), 7.62-7.77 (m, 2H), 8.21 (d, 1H), 8.38 (d, 1H), 8.50 (d, 1H), 8.72 (s, 1H), 8.90 (s, 1H), 9.10 (s, 1H), 10.40 (s, 1H);] HPLC Purity: 99.86%; LCMS: 556 ($M^+$+1).

N-(4-(4-((3-(trifluoromethyl)pyridin-2-yl)methyl)piperazine-1-carbonyl)phenyl)quinoline-8-sulfonamide (VIII-150)

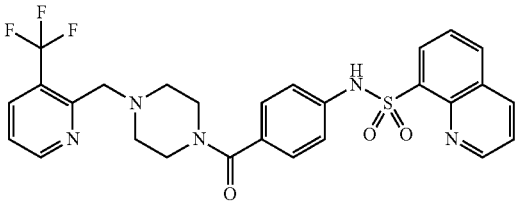

$^1$H NMR (400 MHz, DMSO-d6) δ: 2.37 (br s, 4H), 3.21 (br s, 2H), 3.46 (br s, 2H), 3.70 (s, 2H), 7.06-7.11 (m, 4H), 7.50 (t, 1H), 7.68-7.77 (m, 2H), 8.15 (d, 1H), 8.25 (d, 1H), 8.40 (d, 1H), 8.50 (d, 1H), 8.76 (s, 1H), 9.18 (s, 1H), 10.41 (s, 1H); HPLC Purity: 98.67%; LCMS: 556 ($M^+$+1).

N-(4-(4-((5-chloropyridin-3-yl)methyl)piperazine-1-carbonyl)phenyl)quinoline-8-sulfonamide (VIII-151)

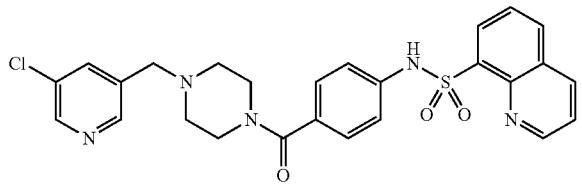

$^1$H NMR (400 MHz, DMSOd$_6$) δ: 2.31 (br s, 4H), 83.38 (br s, 4H), 3.72 (s, 2H), 6.91-7.06 (m, 4H), 7.40 (d, 2H), 7.56-7.63 (m, 2H), 8.0-8.3 (m, 4H), 9.18 (s, 1H); HPLC: 98.2%; LCMS: 523.2 (M$^+$+1).

N-(4-(4-((4-methoxypyridin-3-yl)methyl)piperazine-1-carbonyl)phenyl)quinoline-8-sulfonamide (VIII-152)

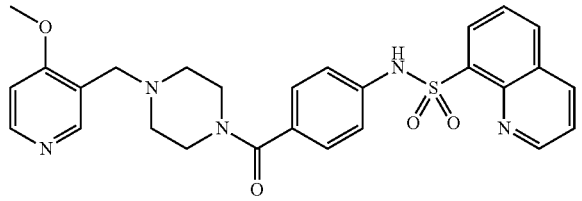

$^1$H NMR (400 MHz, DMSOd$_6$) δ: 2.38 (br s, 4H), 3.51 (br s, 4H), 3.61 (s, 2H), 7.21-7.81 (m, 6H), 7.40 (m, 2H), 7.56-7.63 (m, 2H), 8.01 (m, 1H), 8.56 (m, 1H), 9.18 (s, 1H); HPLC Purity: 98.2%; LCMS: 518.1 (M$^+$+1).

N-(4-(4-((3-fluoropyridin-4-yl)methyl)piperazine-1-carbonyl)phenyl)quinoline-8-sulfonamide (VIII-153)

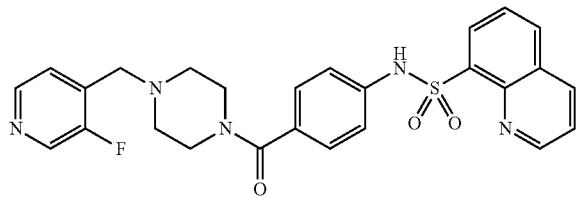

$^1$H NMR (400 MHz, CDCl$_3$) δ: 2.38 (s, 4H), 3.31 (br s, 4H), 3.64 (m, 2H), 7.0-7.6 (m, 6H), 7.40 (m, 2H), 7.0-7.6 (m, 2H), 8.56 (m, 2H), 9.18 (s, 1H); HPLC Purity: 96.5% LCMS: 506.1 (M$^+$+1).

N-(4-(4-((5-fluoropyridin-3-yl)methyl)piperazine-1-carbonyl)phenyl)quinoline-8-sulfonamide (VIII-154)

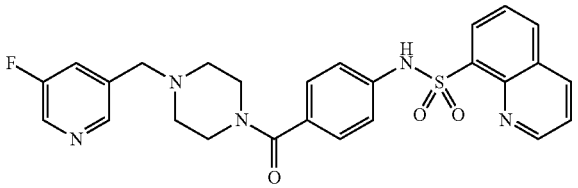

$^1$H NMR (400 MHz, DMSOd$_6$) δ: 2.38 (s, 2H), 3.31 (m, 2H), 3.41 (m, 2H), 3.64 (m, 2H), 7.0-7.6 (m, 6H), 7.40 (m, 2H), 7.0-7.6(d, 2H), 8.56 (d, 2H), 918 (m, 1H), 10.3 (m, 1H); HPLC Purity: 98.5%; LCMS: 506.1 (M$^+$+1).

N-(4-(4-((5-fluoropyridin-2-yl)methyl)piperazine-1-carbonyl)phenyl)quinoline-8-sulfonamide (VIII-155)

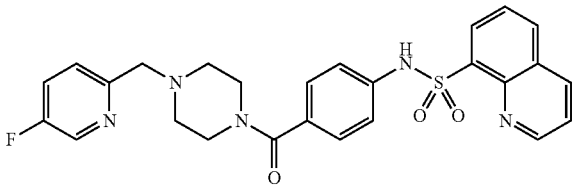

$^1$H NMR (400 MHz, DMSOd$_6$) δ: 2.38 (s, 4H), 3.32 (br s, 2H), 3.52 (br s, 2H), 3.8 (s, 2H), 7.0-7.6 (m, 6H), 7.40 (m, 2H), 7.0-7.6 (d, 2H), 8.56 (d, 2H), 9.18 (m, 1H); HPLC Purity: 99.3%; LCMS: 506.1 (M$^+$+1).

N-(4-(4-((3-methoxypyridin-2-yl)methyl)piperazine-1-carbonyl)phenyl)quinoline-8-sulfonamide (VIII-156)

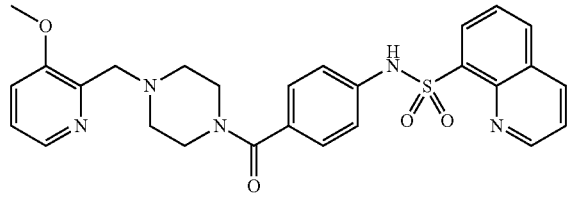

$^1$H NMR (400 MHz, DMSO-d$_6$) δ: 2.38 (s, 4H), 3.41 (m, 4H), 3.8 (m, 2H), 3.91 (s, 3H), 7.0-7.7 (m, 8H), 8.0-8.51 (m, 4H), 9.12 (m, 1H), 10.4 (s, 1H); HPLC Purity: 97.3%; LCMS: 518.3 (M$^+$+1).

N-(4-(4-(4-fluorobenzyl)piperazine-1-carbonyl)phenyl)quinoline-8-sulfonamide (VIII-157)

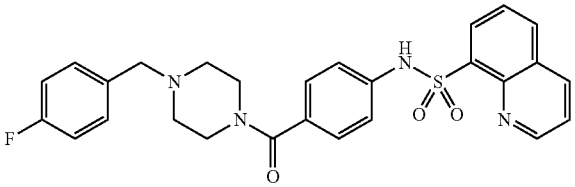

$^1$H NMR (400 MHz, DMSO-$d_6$) δ: 2.41 (br s, 4H), 3.21 (m, 4H), 3.3-3.8 (m, 2H), 7.05-7.71 (m, 8H), 8.22-8.62 (m, 5H), 9.12 (m, 1H), 10.4 (s, 1H); HPLC Purity: 99.3%; LCMS: 505.2 ($M^+$+1).

N-(4-(4-((2-methoxypyridin-3-yl)methyl)piperazine-1-carbonyl)phenyl)quinoline-8-sulfonamide (VIII-158)

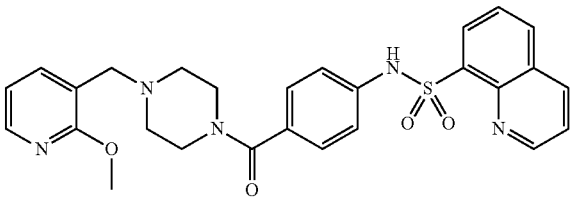

$^1$H NMR (400 MHz, DMSO-$d_6$) δ: 2.41 (br s, 4H), 3.21 (s, 4H), 3.3-3.8 (br s, 2H), 7.05-7.72 (m, 10H), 8.22-8.61 (m, 3H), 9.12 (m, 1H), 10.41 (s, 1H); HPLC Purity: 98.6%; LCMS: 505.2 ($M^+$+1).

[N-(4-(4-(cyclopropylmethyl)piperazine-1-carbonyl)phenyl)quinoline-8-sulfonamide (VIII-159)

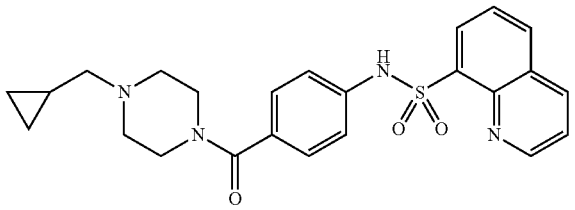

]

[$^1$H NMR (400 MHz, DMSO-$d_6$) δ: 0.04-0.45 (m, 2H), 0.61-0.66 (m, 2H), 1.4-1.6 (m, 1H), 2.21-2.38 (m, 4H), 2.61 (d, 2H), 3.31-3.61 (br s, 4H), 6.94-7.06 (m, 4H), 7.40 (d, 2H), 7.56-7.63 (m, 2H), 8.28 (d, 1H), 9.18 (s, 1H), 10.4 (s, 1H); HPLC Purity: 99.6%; LCMS: 451.3 ($M^+$+1).]

N-(4-(4-(cyclohexylmethyl)piperazine-1-carbonyl)phenyl)quinoline-8-sulfonamide (VIII-160)

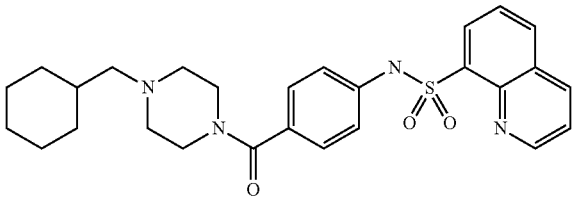

$^1$H NMR (400 MHz, DMSO-$d_6$) δ: 0.8 (m, 2H), 1.2 (m, 4H), 1.4 (s, 1H), 1.7 (m, 4H), 2.32 (m, 4H), 2.62 (br s, 2H), 3.42 (br s, 4H), 7.0-7.4 (m, 4H), 7.5-7.7 (m, 2H), 8.3-8.6 (m, 3H), 9.1 (d, 1H), 10.4 (s, 1H); HPLC Purity: 99.3%; MS: 493.3 ($M^+$+1).

N-(4-(4-(4-chloro-3-fluorobenzyl)piperazine-1-carbonyl)phenyl)quinoline-8-sulfonamide (VIII-161)

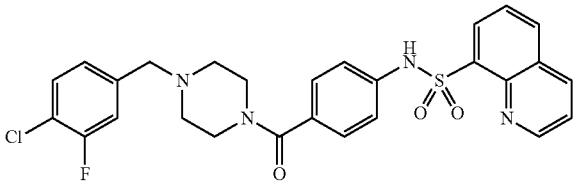

$^1$H NMR (400 MHz, DMSO-$d_6$) δ: 2.22-2.41 (m, 4H), 3.21-3.81 (m, 6H), 7.02-7.51 (m, 7H), 7.61-7.72 (m, 2H), 8.31-8.62 (m, 3H), 9.12 (d, 1H), 10.4 (s, 1H); HPLC Purity: 96.8%; LCMS: 539.0 ($M^+$+1).

N-(4-(4-(cyclopentylmethyl)piperazine-1-carbonyl)phenyl)quinoline-8-sulfonamide (VIII-162)

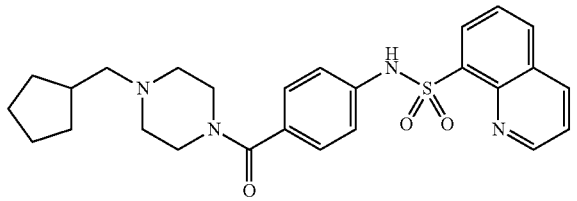

$^1$H NMR (400 MHz, DMSO-d6) δ: 1.10 (sextet, 2H), 140-153 (m, 4H), 1.60 (br s, 2H), 1.99 (pentate, 1H), 2.20 (d, 4H), 2.43 (br s, 2H), 3.32 (br s, 4H), 7.10 (t, 4H), 7.62-7.69 (m, 5H), 8.25 (d, 1H), 8.40 (d, 1H), 8.47 (d, 1H), 9.10 (d, 1H), 10.28 (s, 1H); HPLC Purity: 98.26%; LCMS: 479 ($M^+$+1).

N-(4-(4-((tetrahydrofuran-3-yl)methyl)piperazine-1-carbonyl)phenyl)quinoline-8-sulfonamide (VIII-163)

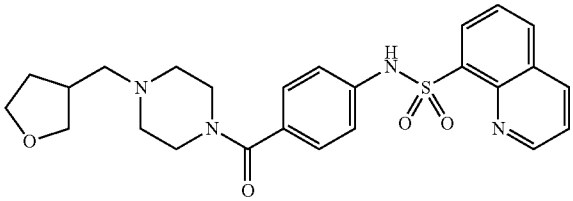

$^1$H NMR (400 MHz, DMSO-d6) δ 1.42 (sextet, 1H), 1.6-1.8 (m, 2H), 2.20-2.40 (m, 4H), 3.42-3.52 (m, 4H), 3.61-3.75 (m, 4H), 3.80-4.05 (m, 2H), 7.04-7.14 (m, 4H), 7.62-7.69 (m, 2H), 8.25 (d, 1H), 8.40 (d, 1H), 8.47 (d, 1H), 9.10 (d, 1H); HPLC Purity: 98.26%; LCMS: 479 ($M^+$+1).

N-(4-(4-((3-chloropyridin-4-yl)methyl)piperazine-1-carbonyl)phenyl)quinoline-8-sulfonamide (VIII-164)

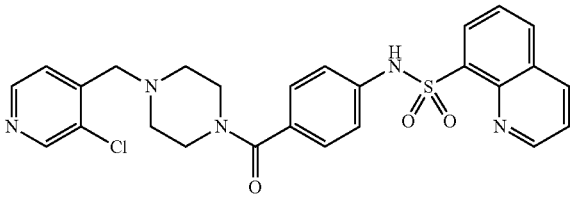

$^1$H NMR (400 MHz, DMSO-d6) δ 2.37 (br s, 4H), 3.42 (br s, 4H), 3.59 (s, 2H), 7.10 (q, 4H), 7.50 (s, 1H), 7.62-7.69 (m, 2H), 8.25 (d, 1H), 8.42 (d, 1H), 8.46-8.52 (m, 2H), 8.58 (s, 1H), 9.10 (d, 1H), 10.30 (s, 1H); HPLC Purity: 96.59%; LCMS: 522 ($M^+$).

N-(4-(4-((tetrahydrofuran-3-yl)methyl)piperazine-1-carbonyl)phenyl)quinoline-8-sulfonamide (VIII-165)

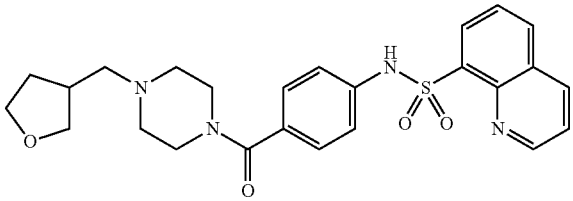

$^1$H NMR (400 MHz, DMSO-d6) δ 1.62 (sextet, 1H), 1.72-1.92 (m, 2H), 2.20-2.40 (m, 4H), 3.41-3.52 (m, 4H), 3.62-3.75 (m, 4H), 3.82-4.05 (m, 2H), 7.04-7.14 (m, 4H), 7.62-7.69 (m, 2H), 8.25 (d, 1H), 8.40 (d, 1H), 8.47 (d, 1H), 9.10 (d, 1H), 10.4 (s, 1H); HPLC Purity: 99.2%; LCMS: 479 ($M^+$+1).

N-(4-(4-((5-(trifluoromethyl)pyridin-2-yl)methyl) piperazine-1-carbonyl)phenyl)quinoline-8-sulfonamide (VIII-166)

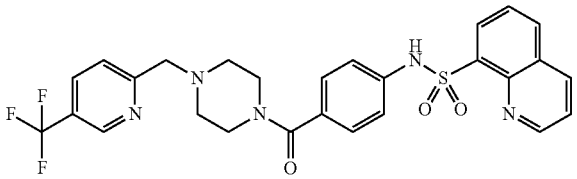

$^1$H NMR (400 MHz, DMSO-d6) δ: 2.37 (br s, 4H), 3.5-3.7 (m, 4H), 3.7-4.0 (m, 2H), 7.1-7.3 (m, 6H), 7.50-7.62 (m, 4H), 8.0-8.3 (m, 2H), 9.10 (d, 1H), 10.30 (s, 1H); HPLC Purity: 96.59%; LCMS: 522 ($M^+$).

N-(4-(4-benzyl-1,4-diazepane-1-carbonyl)phenyl) uinoline-8-sulfonamide (VIII-167)

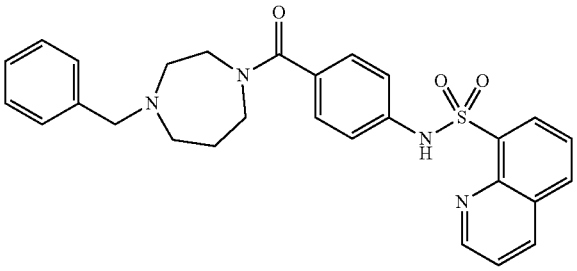

[$^1$H NMR (400 MHz, DMSO-d6) δ: 1.72 (dd, 2H), 2.41-2.72 (m, 2H), 3.22-3.42 (m, 4H), 3.5-3.7 (m, 4H), 7.0-7.4 (m, 5H), 7.5-7.8 (m, 4H), 8.0-8.6 (m, 3H), 9.1 (d, 1H), 10.4 (s, 1H);] HPLC Purity: 98.59%; LCMS: 501.2 [($M^+$1)] (*M+1*).

N-(4-(4-(2-methoxybenzyl)-1,4-diazepane-1-carbonyl)phenyl)quinoline-8-sulfonamide (VIII-168)

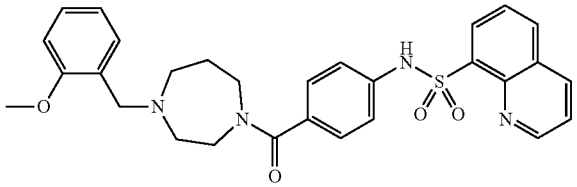

$^1$H NMR (400 MHz, $CDCl_3$) δ: 2.06 (br s, 2H), 2.42 (br s, 4H), 3.62 (s, 4H), 3.72 (br s, 3H), 3.80 (d, 2H), 6.82-6.97 (m, 2H), 7.06 (t, 2H), 7.18 (t, 2H), 7.22-7.39 (m, 2H), 7.58-7.63 (m, 2H), 8.01 (d, 1H), 8.28 (d, 1H), 8.38 (d, 1H), 8.56 (m, 2H), 9.18 (d, 1H); HPLC Purity: 98.10%; LCMS: 531 ($M^+$1).

N-(4-(4-(4-propoxybenzyl)-1,4-diazepane-1-carbonyl)phenyl)quinoline-8-sulfonamide (VIII-169)

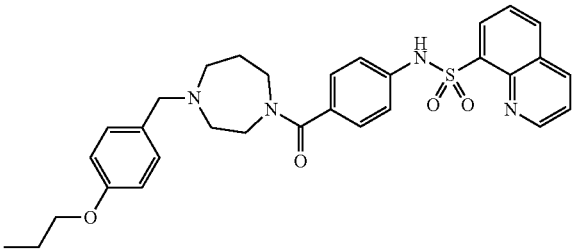

$^1$H NMR (400 MHz, $CD_3OD$) δ: 1.04 (t, 3H), 1.80 (q, 2H), 2.06 (br s, 2H), 3.55 (br s, 4H), 3.99 (t, 4H), 4.35 (s, 2H), 7.00-7.10 (m, 2H), 7.19-7.28 (m, 3H), 7.66-7.70 (m, 2H), 8.19 (d, 1H), 8.42 (d, 2H), 9.18 (d, 1H); HPLC Purity: 98.74%; LCMS: 559 ($M^+$+1).

N-(4-(4-(2-propoxybenzyl)-1,4-diazepane-1-carbonyl)phenyl)quinoline-8-sulfonamide (VIII-170)

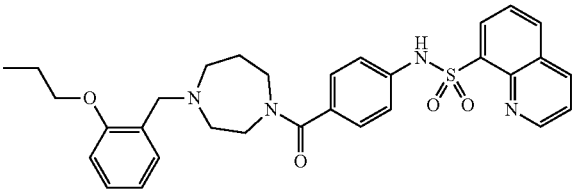

[$^1$H NMR (400 MHz, $CD_3OD$) δ: 1.04 (t, 3H), 1.84 (br s, 2H), 2.16 (br s, 2H), 3.58 (br s, 4H), 4.08 (br s, 2H), 4.25 (br d, 1H), 4.40 (s, 2H), 7.04 (t, 1H), 7.19 (d, 1H), 7.20-7.28 (m, 4H), 7.44 (d, 1H), 7.53 (t, 1H), 7.68-7.72 (m, 2H), 8.21 (d, 1H), 8.42 (d, 2H), 9.18 (d, 1H);] HPLC Purity: 97.74%; LCMS: 559 ($M^+$+1).

N-(4-(4-(2-isopropoxybenzyl)-1,4-diazepane-1-carbonyl)phenyl)quinoline-8-sulfonamide (VIII-171)

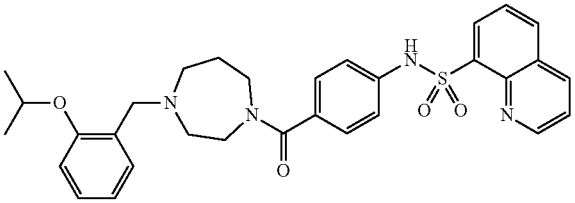

$^1$H NMR (400 MHz, $CD_3OD$) δ: 1.38 (s, 6H), 2.16 (br s, 2H), 3.55 (br s, 3H), 4.18 (br d, 1H), 4.38 (s, 2H), 4.79 (s, 1H), 7.04 (t, 1H), 7.19 (d, 1H), 7.21-7.34 (m, 4H), 7.40-7.52 (m, 2H), 7.53 (t 1H), 7.67-7.72 (m, 2H), 8.21 (d, 1H), 8.44 (d, 2H), 9.18 (s, 1H); LCMS: 559 ($M^+$+1); HPLC Purity: 98.99%.

N-(4-(4-(3-isopropoxybenzyl)-1,4-diazepane-1-carbonyl)phenyl)quinoline-8-sulfonamide (VIII-172)

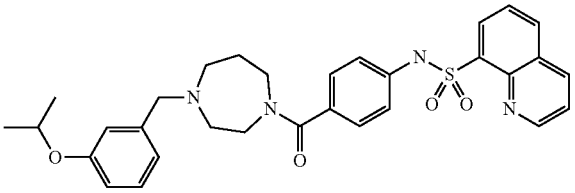

$^1$H NMR (400 MHz, $CD_3OD$) δ: 1.38 (d, 6H), 1.4 (m, 1H), 2.08 (br s, 2H), 3.18 (br s, 2H), 3.56 (br s, 4H), 4.38 (s, 2H), 4.68 (m, 2H), 6.99-7.10 (m, 2H), 7.20-7.30 (m, 5H), 7.40 (t, 1H), 7.65-7.70 (m, 2H), 8.20 (d, 1H), 8.43 (d, 2H), 9.18 (d, 1H); HPLC Purity: 99.68%; LCMS: 559 ($M^+$+1).

N-(4-(4-(3-butoxybenzyl)-1,4-diazepane-1-carbonyl)phenyl)quinoline-8-sulfonamide (VIII-173)

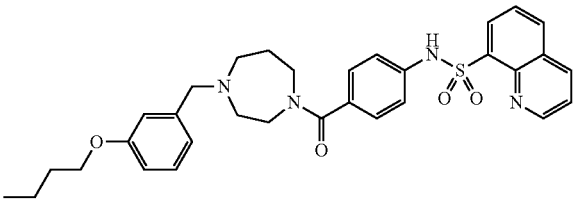

$^1$H NMR (400 MHz, $CD_3OD$) δ: 1.01 (t, 3H), 1.50 (sextet, 2H), 1.79 (pentate, 2H), 2.06 (br s, 2H), 3.58 (br s, 4H), 3.6-3.9 (m, 4H), 4.03 (t, 2H), 4.38 (s, 2H), 7.00-7.08 (m, 3H), 7.19-7.26 (m, 4H), 7.41 (t, 1H), 7.63-7.69 (m, 2H), 8.19 (d, 1H), 8.42 (d, 2H), 9.18 (d, 1H); HPLC Purity: 99.75%; LCMS: 573 ($M^+$+1).

N-(4-(4-(2-hydroxy-3,4-dimethoxybenzyl)-1,4-diazepane-1-carbonyl)phenyl)quinoline-8-sulfonamide (VIII-174)

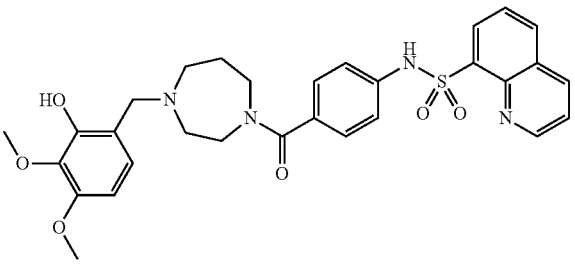

$^1$H NMR (400 MHz, $CD_3OD$) δ: 2.18 (br s, 2H), 3.18 (br s, 2H), 3.56 (br s, 4H), 3.80 (s, 3H), 3.84 (s, 3H), 4.18 (br s, 2H), 4.30 (s, 2H), 6.61 (d, 2H), 7.03 (d, 2H), 7.19-7.27 (m, 2H), 7.61-7.66 (m, 2H), 8.19 (d, 1H), 8.42 (d, 2H), 9.18 (d, 1H); HPLC Purity: 97.61%; LCMS: 577 ($M^+$+1).

N-(4-(4-(2-isopropylbenzyl)-1,4-diazepane-1-carbonyl)phenyl)quinoline-8-sulfonamide (VIII-175)

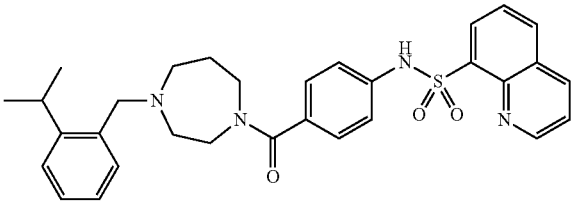

$^1$H NMR (400 MHz, $CD_3OD$) δ: 1.22 (d, 6H), 2.05 (br s, 1H), 3.56 (br s, 8H), 4.50 (s, 4H), 7.20-7.39 (m, 5H), 7.40-7.56 (m, 3H), 7.64-7.69 (m, 2H), 8.20 (d, 1H), 8.42 (d, 2H), 9.18 (d, 1H); HPLC Purity: 98.73%; LCMS: 543 ($M^+$+1).

N-(4-(4-(4-isobutoxybenzyl)-1,4-diazepane-1-carbonyl)phenyl)quinoline-8-sulfonamide (VIII-176)

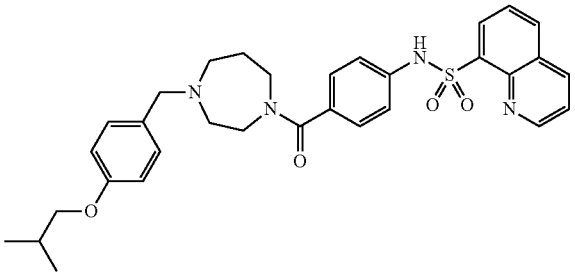

$^1$H NMR (400 MHz, $CD_3OD$) δ: 1.04 (d, 6H), 2.02-2.17 (m, 3H), 3.15 (br d, 2H), 3.56 (br d, 4H), 3.79 (d, 2H), 4.20 (br d, 2H), 4.35 (s, 2H), 7.02 (d, 2H), 7.24 (t, 3H), 7.41 (d, 2H), 7.68-7.74 (m, 2H), 8.21 (d, 2H), 8.42 (d, 2H), 9.18 (d, 1H); HPLC Purity: 98.56%; LCMS: 573 ($M^+$+1).

N-(4-(4-(2-hydroxy-3-methoxybenzyl)-1,4-diazepane-1-carbonyl)phenyl)quinoline-8-sulfonamide (VIII-177)

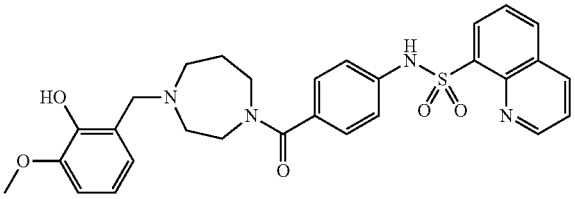

$^1$H NMR (400 MHz, DMSO-d6) δ: 1.61 (br s, 1H), 1.77 (br s, 1H), 2.60 (br s, 4H), 2.70 (br s, 2H), 3.58 (br s, 2H), 3.78 (s, 2H), 3.9 (s, 3H), 6.63 (d, 3H), 6.80 (br s, 1H), 7.12 (d, 2H), 7.77 (br s. 2H), 8.28 (s, 1H), 8.42 (d, 2H), 8.58 (s, 1H), 9.18 (s, 1H), 10.40 (s, 1H); HPLC Purity: 98.72%; LCMS: 547 ($M^+$+1).

N-(4-(4-(2-(tert-butylthio)benzyl)-1,4-diazepane-1-carbonyl)phenyl)quinoline-8-sulfonamide (VIII-178)

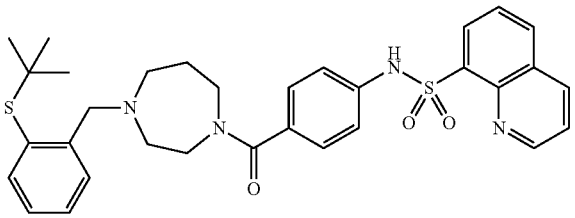

$^1$H NMR (400 MHz, DMSO-d6) δ: 1.20 (d, 9H), 1.61 (br s, 1H), 1.77 (br s, 1H), 2.60 (br s, 1H), 2.70 (br s, 1H), 3.25 (br s, 2H), 3.58 (br s, 4H), 3.83 (d, 2H), 7.10 (d, 3H), 7.20 (br s, 2H), 7.49 (br s, 1H), 7.77 (br s. 4H), 8.28 (s, 1H), 8.42 (d, 1H), 8.58 (s, 1H), 9.18 (s, 1H), 10.40 (s, 1H); HPLC Purity: 91.52%; LCMS: 589 ($M^+$+1).

N-(4-(4-(2-fluoro-6-methoxybenzyl)-1,4-diazepane-1-carbonyl)phenyl)quinoline-8-sulfonamide (VIII-179)

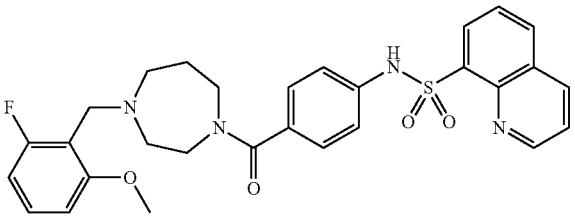

$^1$H NMR (400 MHz, DMSO-d6) δ: 1.61 (br s, 1H), 1.77 (br s, 1H), 2.60 (br s, 2H), 3.10 (br s, 2H), 3.45-3.55 (m, 4H), 3.64 (s, 3H), 3.81 (s, 2H), 6.77-6.87 (m, 2H), 7.08-7.20 (m, 4H), 7.30 (br s, 1H), 7.77-7.80 (m. 2H), 8.28 (d, 1H), 8.42 (d, 1H), 8.58 (d, 1H), 9.18 (s, 1H), 10.40 (s, 1H); HPLC Purity: 99.88%; LCMS: 549 ($M^+$+1).

N-(4-(4-(2-(methylthio)benzyl)-1,4-diazepane-1-carbonyl)phenyl)quinoline-8-sulfonamide (VIII-180)

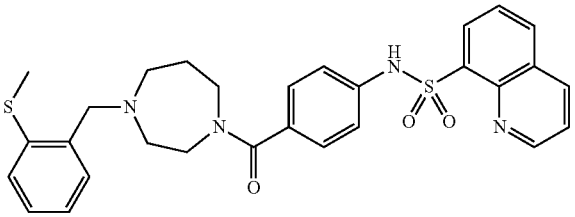

$^1$H NMR (400 MHz, DMSO-d6) δ: 1.61 (br s, 1H), 1.77 (br s, 1H), 2.38 (d, 4H), 2.60 (br s, 2H), 3.25 (br s, 2H), 3.58 (s, 2H), 3.6 (s, 3H), 7.00-7.18 (m, 5H), 7.24 (d, 2H), 7.77-7.80 (d, 2H), 8.28 (d, 1H), 8.42 (d, 2H), 8.58 (s, 1H), 9.18 (s, 1H), 10.40 (s, 1H); HPLC Purity: 99.77%; LCMS: 547 ($M^+$+1).

N-(4-(4-(5-chloro-2-hydroxy-4-methylbenzyl)-1,4-diazepane-1-carbonyl)phenyl)quinoline-8-sulfonamide (VIII-181)

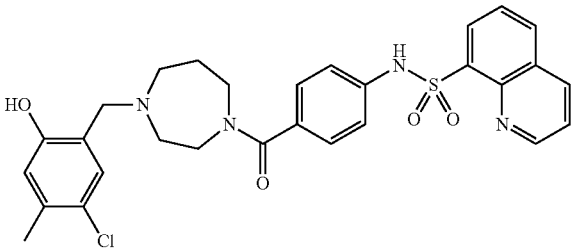

$^1$H NMR (400 MHz, DMSO-d6) δ: 1.61 (br s, 1H), 1.77 (br s, 1H), 2.25 (s, 4H), 2.78 (br s, 2H), 3.50-3.78 (m, 4H), 6.78 (d, 1H), 7.10-7.20 (m, 4H), 7.77-7.80 (m. 2H), 8.28 (s, 1H), 8.42 (d, 2H), 8.58 (s, 1H), 9.18 (s, 1H), 10.40 (s, 1H); HPLC Purity: 99.85%; LCMS: 565 ($M^+$+1).

N-(4-(4-(3-phenylpropyl)-1,4-diazepane-1-carbonyl)phenyl)quinoline-8-sulfonamide (VIII-182)

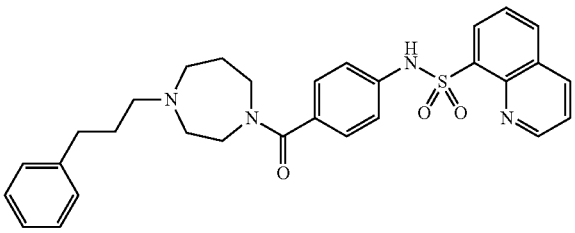

$^1$H NMR (400 MHz, DMSO-d6) δ: 1.32 (m, 2H), 1.61 (br s, 2H), 1.77 (br s, 2H), 2.1 (t, 2H), 2.38 (d, 2H), 2.60 (br s, 1H), 3.28 (br s, 3H), 3.58 (br s, 2H), 7.05-7.31 (m, 7H), 7.77-7.80 (m, 3H), 8.28 (d, 1H), 8.42 (d, 2H), 8.58 (d, 1H), 9.18 (s, 1H), 10.40 (s, 1H); HPLC Purity: 99.73%; LCMS: 529 ($M^+$+1).

N-(4-(4-(3-chloro-4-methoxybenzyl)-1,4-diazepane-1-carbonyl)phenyl)quinoline-8-sulfonamide (VIII-183)

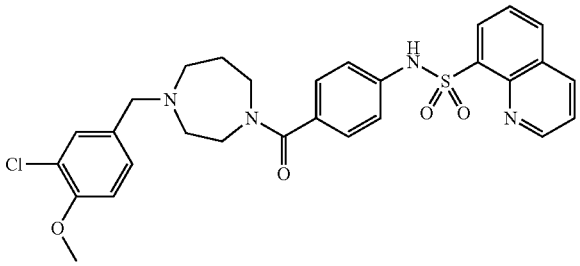

$^1$H NMR (400 MHz, DMSO-d6) δ: 1.61 (br s, 1H), 1.77 (br s, 1H), 2.60 (br s, 2H), 3.22 (br s, 2H), 3.57 (s, 4H), 3.82 (s, 2H), 7.01-7.38 (m, 6H), 7.77 (br s. 2H), 8.28 (s, 1H), 8.42 (d, 1H), 8.58 (s, 1H), 9.18 (s, 1H), 10.40 (s, 1H); HPLC Purity: 99.50%; LCMS: 565 ($M^+$+1).

3-((4-(4-(quinoline-8-sulfonamido)benzoyl)-1,4-diazepan-1-yl)methyl)phenyl acetate (VIII-184)

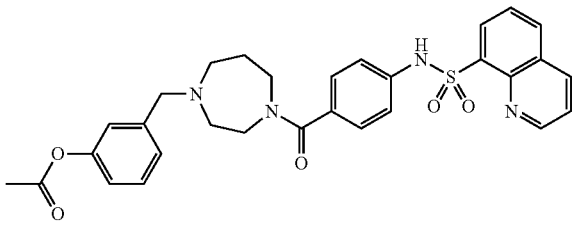

$^1$H NMR (400 MHz, DMSO-d6) δ: 1.61 (br s, 1H), 1.77 (br s, 1H), 2.60 (br s, 4H), 2.70 (br s, 2H), 3.58 (br s, 2H), 3.78 (s, 2H), 6.63 (d, 2H), 6.80 (br s, 2H), 7.12 (d, 2H), 7.77 (br s. 2H), 8.28 (s, 1H), 8.42 (d, 2H), 8.58 (s, 1H), 9.18 (s, 1H), 10.40 (s, 1H); HPLC Purity: 98.72%; LCMS: 547 ($M^+$+1).

N-(4-(4-(4-methylbenzyl)-1,4-diazepane-1-carbonyl)phenyl)quinoline-8-sulfonamide (VIII-185)

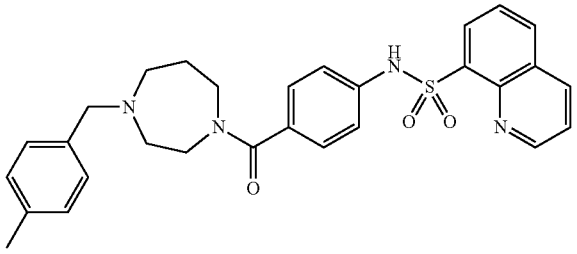

$^1$H NMR (400 MHz, DMSO-d6) δ: 1.61 (br s, 1H), 1.77 (br s, 1H), 2.26 (s, 3H), 2.39-2.62 (m, 4H), 3.10 (br s, 2H), 3.50 (br s, 4H), 7.01-7.20 (m, 7H), 7.77-7.80 (m, 2H), 8.28 (br s, 1H), 8.42 (d, 1H), 8.58 (d, 2H), 9.18 (s, 1H), 10.41 (s, 1H); HPLC Purity: 97.70%; LCMS: 515 ($M^+$+1).

N-(4-(4-(2,4-dichlorobenzyl)-1,4-diazepane-1-carbonyl)phenyl)quinoline-8-sulfonamide (VIII-186)

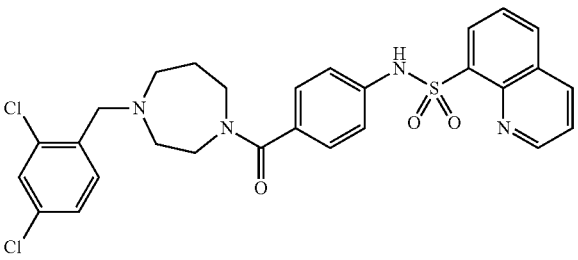

$^1$H NMR (400 MHz, DMSO-d6) δ: 1.61 (br s, 1H), 1.77 (br s, 1H), 2.50-2.76 (m, 2H), 3.45-3.70 (m, 4H), 3.7-3.9 (m, 4H), 7.05-7.20 (m, 2H), 7.36-7.60 (m, 4H), 7.77-7.80 (m, 2H), 8.28 (d, 1H), 8.42 (d, 1H), 8.58 (d, 2H), 9.18 (s, 1H), 10.41 (s, 1H); HPLC Purity: 99.76%; LCMS: 569 ($M^+$+1).

N-(4-(4-(4-(trifluoromethyl)benzyl)-1,4-diazepane-1-carbonyl)phenyl)quinoline-8-sulfonamide (VIII-187)

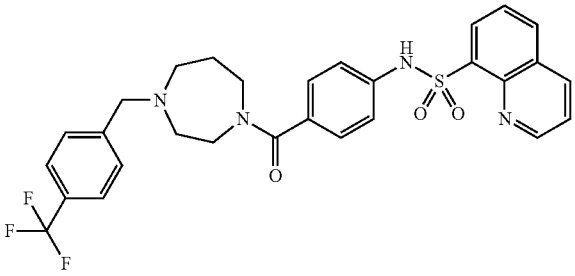

$^1$H NMR (400 MHz, DMSO-d6) δ: 1.61 (br s, 1H), 1.77 (br s, 1H), 2.50-2.60 (m, 2H), 3.10 (br s, 2H), 3.50 (br s, 4H), 3.55-3.9 (m, 2H), 7.10 (s, 4H), 7.20-7.38 (m, 3H), 7.77-7.80 (m, 2H), 8.28 (br s, 1H), 8.42 (d, 1H), 8.58 (d, 2H), 9.18 (s, 1H), 10.41 (s, 1H); MS: 569 ($M^+$+1); HPLC Purity: 99.47%; LCMS: 569 ($M^+$+1).

N-(4-(4-(2-phenylpropyl)-1,4-diazepane-1-carbonyl)phenyl)quinoline-8-sulfonamide (VIII-188)

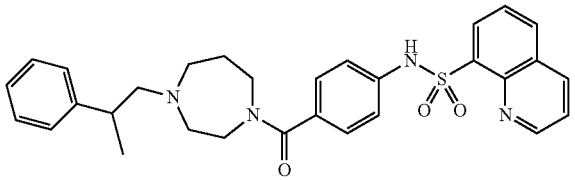

$^1$H NMR (400 MHz, $CD_3OD$) δ: 1.0 (q, 1H), 1.36 (d, 3H), 2.04 (br s, 2H), 3.10 (br s, 2H), 3.44 (br s, 4H), 3.56 (br s, 2H), 4.09 (br s, 2H), 7.10 (s, 4H), 7.24-7.40 (m, 4H), 7.62-7.68 (m, 3H), 8.18 (d, 1H), 8.42 (d, 2H), 9.18 (s, 1H); HPLC Purity: 99.86%; LCMS: 529 ($M^+$+1).

N-(4-(4-phenethyl-1,4-diazepane-1-carbonyl)phenyl)quinoline-8-sulfonamide (VIII-189)

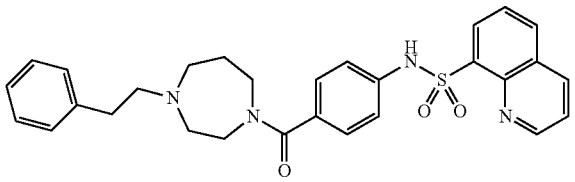

$^1$H NMR (400 MHz, $CD_3OD$) δ: 2.10 (br s, 2H), 3.06 (br s, 2H), 3.40 (br s, 4H), 3.62 (br s, 2H), 3.79 (t, 2H), 4.09 (br s, 2H), 7.20-7.39 (m, 8H), 7.62-7.68 (m, 2H), 8.18 (d, 1H), 8.42 (d, 2H), 9.18 (s, 1H); HPLC Purity: 97.56%; LCMS: 515 ($M^+$+1).

N-(4-(4-(4-butylbenzyl)-1,4-diazepane-1-carbonyl)phenyl)quinoline-8-sulfonamide (VIII-190)

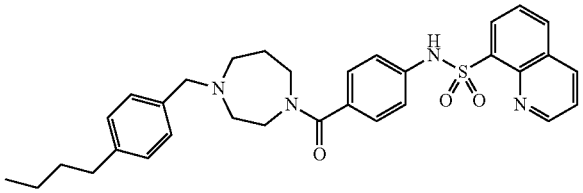

$^1$H NMR (400 MHz, $CD_3OD$) δ: 0.92 (t, 3H), 1.37 (sextet, 2H), 1.58 (sextet, 2H), 2.03 (br s, 2H), 2.62 (t, 2H), 3.16 (br s, 2H), 3.50 (br s, 4H), 4.19 (br s, 2H), 4.24 (s, 2H), 7.17-7.23 (m, 4H), 7.25-7.38 (m, 4H), 7.61-7.65 (m, 2H), 8.18 (d, 1H), 8.41 (d, 2H), 9.16 (s, 1H); HPLC Purity: 99.72%; LCMS: 557 ($M^+$+1).

N-(4-(4-(3,5-dimethylbenzyl)-1,4-diazepane-1-carbonyl)phenyl)quinoline-8-sulfonamide (VIII-191)

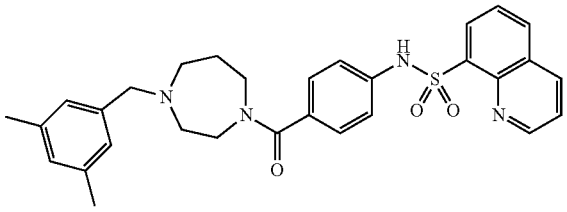

$^1$H NMR (400 MHz, $CD_3OD$) δ: 2.01 (br s, 2H), 2.28 (s, 6H), 3.10 (br s, 2H), 3.44 (br s, 4H), 3.18 (br s, 1H), 4.12 (s, 2H), 7.02 (s, 2H), 7.10 (s, 1H), 7.14-7.22 (m, 4H), 7.60-7.65 (m, 2H), 8.18 (d, 1H), 8.42 (d, 2H), 9.18 (s, 1H); HPLC Purity: 99.81%; LCMS: 529 ($M^+$+1).

N-(4-(4-(2-hydroxy-3,4-dimethoxy-6-methylbenzyl)-1,4-diazepane-1-carbonyl)phenyl)quinoline-8-sulfonamide (VIII-192)

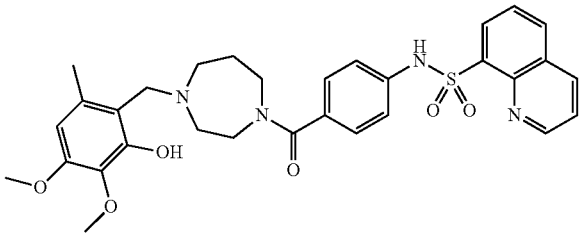

$^1$H NMR (400 MHz, $CD_3OD$) δ: 2.12 (br s, 2H), 2.38 (s, 3H), 3.58 (br s, 5H), 3.79 (s, 3H), 3.83 (s, 3H), 3.85-3.9 (m, 2H), 4.21 (br s, 1H), 4.38 (s, 2H), 6.50 (s, 1H), 7.20-7.30 (m, 4H), 7.62-7.68 (m, 2H), 8.18 (d, 1H), 8.42 (d, 2H), 9.18 (s, 1H); HPLC Purity: 98.77%; LCMS: 591 ($M^+$+1).

N-(4-(4-(3,5-dimethoxybenzyl)-1,4-diazepane-1-carbonyl)phenyl)quinoline-8-sulfonamide (VIII-193)

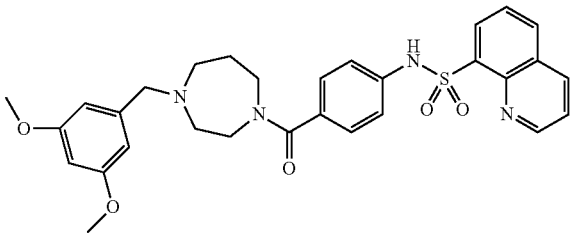

$^1$H NMR (400 MHz, $CD_3OD$) δ: 2.02 (br s, 2H), 3.51 (br s, 3H), 3.2-3.7 (m, 3H), 3.79 (s, 2H), 3.81 (s, 6H), 4.28 (s, 2H), 6.63 (d, 2H), 7.20-7.27 (m, 5H), 7.62-7.68 (m, 2H), 8.18 (d, 1H), 8.42 (d, 2H), 9.18 (s, 1H); HPLC Purity: 94.85%; LCMS: 561 ($M^+$+1).

N-(4-(4-(4-chloro-2-fluorobenzyl)-1,4-diazepane-1-carbonyl)phenyl)quinoline-8-sulfonamide (VIII-193)

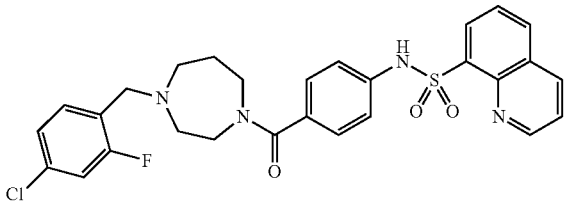

$^1$H NMR (400 MHz, $CD_3OD$) δ 2.03 (br s, 2H), 3.40 (br s, 4H), 3.61 (br s, 2H), 4.38 (s, 2H), 6.63 (d, 2H), 7.15-7.27 (m, 4H), 7.32-7.38 (m, 2H), 7.52 (t, 1H), 7.60-7.65 (m, 2H), 8.18 (d, 1H), 8.41 (d, 2H), 9.18 (s, 1H); HPLC Purity: 99.99%; LCMS: 553 ($M^+$).

N-(4-(4-(4-ethoxybenzyl)-1,4-diazepane-1-carbonyl)phenyl)quinoline-8-sulfonamide (VIII-194)

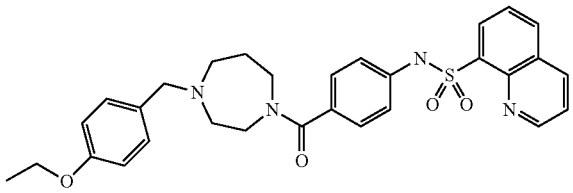

$^1$H NMR (400 MHz, $CD_3OD$) δ: 1.39 (t, 3H), 2.03 (br s, 2H), 3.10 (br s, 1H), 3.57 (br s, 5H), 3.71 (br s, 2H), 4.06 (q, 2H), 4.19 (br s, 1H), 4.30 (s, 1H), 6.63 (d, 2H), 7.00 (d, 2H), 7.18-7.27 (m, 2H), 7.38 (d, 2H), 7.62-7.68 (m, 2H), 8.18 (d, 1H), 8.42 (d, 2H), 9.18 (s, 1H); HPLC Purity: 98.87%; LCMS: 545.0 ($M^+$+1).

N-(4-(4-(3-hydroxybenzyl)-1,4-diazepane-1-carbonyl)phenyl)quinoline-8-sulfonamide (VIII-195)

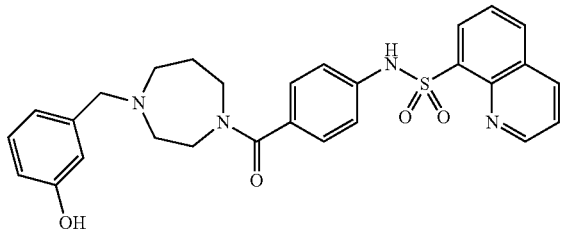

$^1$H NMR (400 MHz, $CD_3OD$) δ: 2.02 (br s, 2H), 3.18 (br s, 2H), 3.59 (s, 4H), 4.20 (br s, 2H), 4.31 (s, 2H), 6.90 (d, 3H), 7.19-7.32 (m, 5H), 7.62-7.68 (m, 2H), 8.18 (d, 1H), 8.42 (d, 2H), 9.18 (s, 1H); HPLC Purity: 96.26%; LCMS: 517.2 ($M^+$+1).

N-(4-(4-(2,3-dichlorobenzyl)-1,4-diazepane-1-carbonyl)phenyl)quinoline-8-sulfonamide (VIII-196)

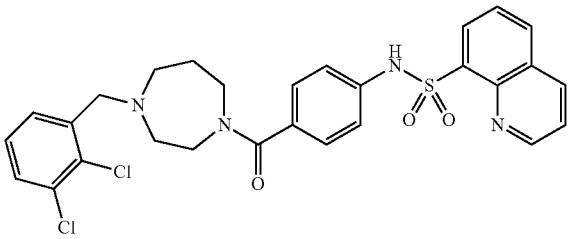

$^1$H NMR (400 MHz, $CD_3OD$) δ: 2.12 (br s, 2H), 3.53 (br s, 6H), 3.73 (br s, 2H), 4.59 (s, 2H), 6.63 (d, 2H), 7.20-7.30 (m, 3H), 7.44 (t, 1H), 7.59 (s, 1H), 7.63-7.68 (m, 2H), 7.78 (d, 1H), 8.18 (d, 1H), 8.42 (d, 1H), 9.18 (s, 1H); HPLC Purity: 99.29%; LCMS: 569 ($M^+$1).

N-(4-(4-(3,4-dichlorobenzyl)-1,4-diazepane-1-carbonyl)phenyl)quinoline-8-sulfonamide (VIII-197)

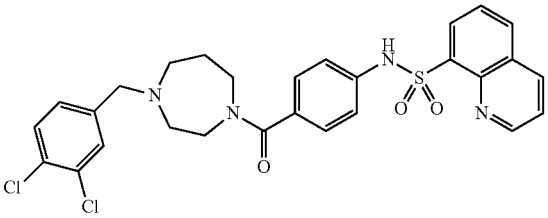

$^1$H NMR (400 MHz, $DMSOd_6$) δ: 1.60 (br s, 1H), 1.78 (br s, 1H), 2.60 (br s, 2H), 2.62 (br s, 2H), 3.23 (br s, 2H), 3.58 (br s, 2H), 3.50-3.62 (m, 2H), 7.07-7.18 (m, 3H), 7.24 (dd, 1H), 7.43-7.60 (m, 2H), 7.70-7.79 (m, 2H), 8.24 (d, 1H), 8.42 (d, 2H), 8.55 (d, 1H), 9.18 (s, 1H), 10.42 (s, 1H); HPLC Purity: 99.76%; LCMS: 569.1 ($M^+$+1).

N-(4-(4-(3,5-difluorobenzyl)-1,4-diazepane-1-carbonyl)phenyl)quinoline-8-sulfonamide (VIII-198)

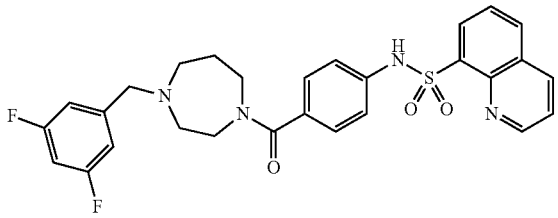

$^1$H NMR (400 MHz, DMSOd$_6$) δ: 1.60 (br s, 1H), 1.78 (br s, 1H), 2.60 (br s, 2H), 2.62 (br s, 2H), 3.23 (br s, 4H), 3.50-3.62 (m, 2H), 6.95-7.20 (m, 6H), 7.74 (s, 2H), 8.24 (d, 1H), 8.42 (d, 2H), 8.55 (d, 1H), 9.18 (s, 1H), 10.42 (s, 1H); HPLC Purity: 98.49%; LCMS: 559.1 (M$^+$+23).

N-(4-(4-(2,6-dimethoxybenzyl)-1,4-diazepane-1-carbonyl)phenyl)quinoline-8-sulfonamide (VIII-199)

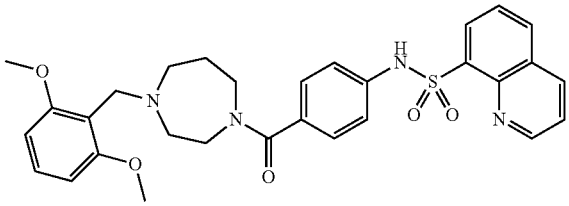

$^1$H NMR (400 MHz, DMSO-d6) δ: 1.60 (br s, 1H), 1.71 (br s, 1H), 2.62 (br s, 3H), 3.21 (br s, 2H), 3.50 (s, 3H), 3.59 (s, 3H), 3.79 (s, 2H), 6.58 (d, 1H), 6.61 (d, 2H), 7.02-7.21 (m, 4H), 7.62-7.68 (m, 2H), 8.18 (d, 1H), 8.42 (d, 2H), 9.18 (s, 1H), 10.39 (s, 1H); HPLC Purity: 99.26%; LCMS: 561 (M$^+$+1).

N-(4-(4-(3-chloro-4-fluorobenzyl)-1,4-diazepane-1-carbonyl)phenyl)quinoline-8-sulfonamide (VIII-200)

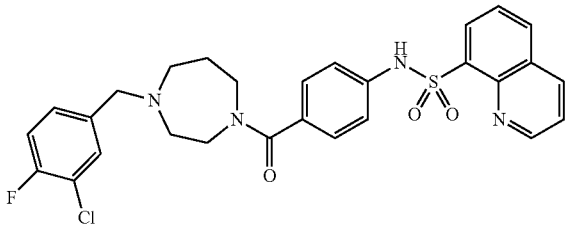

$^1$H NMR (400 MHz, DMSO-d6) δ: 1.61 (br s, 1H), 1.80 (br s, 1H), 3.42 (dd, 6H), 7.08-7.18 (m, 3H), 7.20-7.55 (m, 3H), 7.70-7.80 (m, 2H), 8.28 (d, 1H), 8.42 (d, 2H), 8.58 (d, 1H), 9.18 (s, 1H), 10.40 (s, 1H); HPLC Purity: 99.54%; LCMS: 561 (M$^+$).

N-(4-(4-(4-(1-amino-2-cyanopropyl)benzyl)-1,4-diazepane-1-carbonyl)phenyl)quinoline-8-sulfonamide (VIII-201)

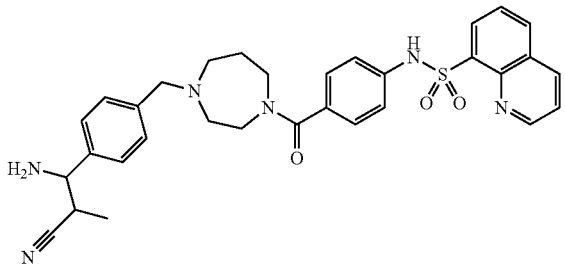

$^1$H NMR (400 MHz, DMSO-d6) δ: 1.61 (br s, 1H), 1.7 (s, 1H), 1.80 (br s, 1H), 2.70 (t, 2H), 2.93 (s, 3H), 3.23 (br s, 2H), 3.40-3.59 (m, 4H), 3.64 (t, 1H), 6.68 (t, 2H), 7.01-7.18 (m, 5H), 7.70 (br s, 2H), 8.28 (t, 1H), 8.42 (d, 2H), 8.58 (t, 1H), 9.18 (s, 1H), 10.40 (s, 1H); HPLC Purity: 96.64%; LCMS: 605 (M$^+$+23).

N-(4-(4-(2-ethylbenzyl)-1,4-diazepane-1-carbonyl)phenyl)quinoline-8-sulfonamide (VIII-202)

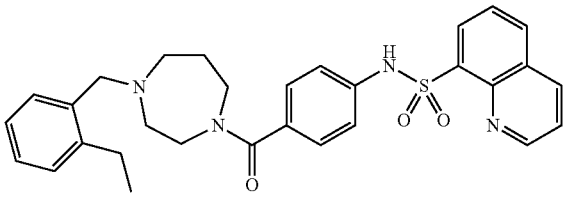

$^1$H NMR (400 MHz, DMSO-d6) δ: 1.0-1.17 (m, 2H), 1.2 (t, 3H), 1.59 (br s, 1H), 1.74 (br s, 1H), 2.1 (m, 2H), 2.42-2.75 (m, 5H), 3.2-3.6 (m, 3H), 7.01-7.22 (m, 7H), 7.75 (s, 2H), 8.28 (d, 1H), 8.42 (d, 2H), 8.58 (d, 1H), 9.18 (s, 1H), 10.40 (s, 1H); HPLC Purity: 99.16%; LCMS: 529 (M$^+$+1).

N-(4-(4-(4-(hex-1-yn-1-yl)benzyl)-1,4-diazepane-1-carbonyl)phenyl)quinoline-8-sulfonamide (VIII-203)

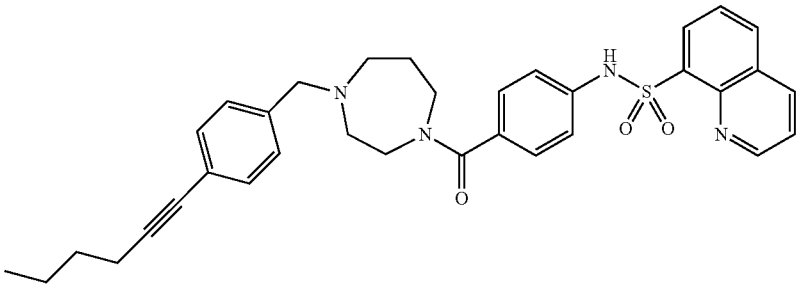

$^1$H NMR (400 MHz, DMSO-d6) δ: 0.92 (t, 3H), 1.40-1.60 (m, 5H), 1.77 (br s, 2H), 3.20 (br s, 4H), 3.50 (br s, 6H), 7.03-7.38 (m, 7H), 7.78 (br s, 2H), 8.28 (br s, 1H), 8.42 (d, 2H), 8.58 (d, 1H), 9.18 (s, 1H), 10.40 (s, 1H); HPLC Purity: 99.77%; LCMS: 581 ($M^+$+1).

N-(4-(4-(2-fluoro-6-hydroxybenzyl)-1,4-diazepane-1-carbonyl)phenyl)quinoline-8-sulfonamide (VIII-204)

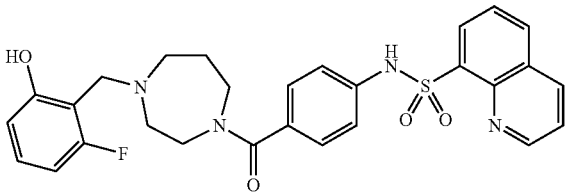

$^1$H NMR (400 MHz, DMSO-d6) δ: 1.61 (br s, 1H), 1.77 (br s, 1H), 2.60 (br s, 2H), 2.78 (br s, 1H), 3.20-3.42 (m, 3H), 3.58 (d, 2H), 3.79 (d, 2H), 4.1 (s, 1H), 6.59 (br s, 2H), 7.10-7.20 (m, 4H), 7.71-7.80 (m. 2H), 8.28 (d, 1H), 8.42 (d, 1H), 8.58 (d, 1H), 9.18 (s, 1H), 10.40 (s, 1H); HPLC Purity: 99.78%; LCMS: 535 ($M^+$+1).

N-(4-(4-(2,4-dichloro-6-hydroxybenzyl)-1,4-diazepane-1-carbonyl)phenyl)quinoline-8-sulfonamide (VIII-205)

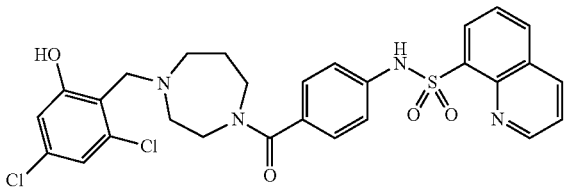

$^1$H NMR (400 MHz, DMSO-d6) δ: 1.61 (br s, 1H), 1.77 (br s, 1H), 2.58-2.80 (m, 3H), 3.20-3.68 (m, 5H), 3.79 (d, 2H), 6.78 (d, 1H), 6.99 (d, 1H), 7.09-7.20 (m, 4H), 7.71-7.80 (m. 2H), 8.28 (d, 1H), 8.42 (d, 1H), 8.58 (d, 1H), 9.18 (s, 1H), 10.40 (s, 1H); HPLC Purity: 99.58%. LCMS: 585 ($M^+$+1).

N-(4-(4-(2-hydroxy-6-methoxybenzyl)-1,4-diazepane-1-carbonyl)phenyl)quinoline-8-sulfonamide (VIII-206)

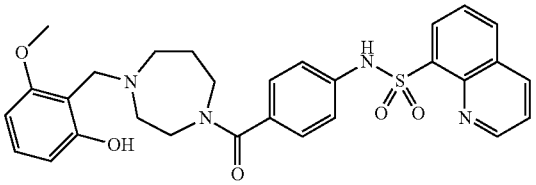

$^1$H NMR (400 MHz, DMSO-d6) δ: 1.61 (br s, 1H), 1.77 (br s, 1H), 2.60 (br s, 2H), 3.21 (br s, 2H), 3.42-3.58 (m, 2H), 3.53 (s, 2H), 3.68 (d, 2H), 6.26-6.45 (m, 2H), 7.03-7.20 (m, 3H), 7.71-7.80 (m, 2H), 8.28 (s, 2H), 8.42 (d, 2H), 8.58 (s, 1H), 9.18 (s, 1H), 10.41 (s, 1H); HPLC Purity: 99.89%; LCMS: 547 ($M^+$+1).

N-(4-(4-(4-cyanobenzyl)-1,4-diazepane-1-carbonyl)phenyl)quinoline-8-sulfonamide (VIII-207)

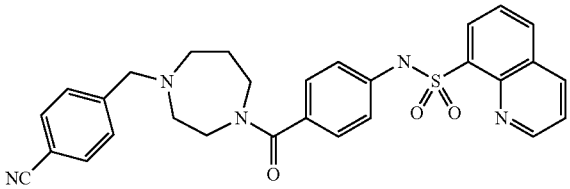

$^1$H NMR (400 MHz, DMSO-d6) δ: 1.61 (br s, 1H), 1.77 (br s, 1H), 2.60 (br s, 2H), 3.21 (br s, 2H), 3.42-3.58 (m, 2H), 3.53 (s, 2H), 3.68 (d, 2H), 7.10-7.20 (m, 3H), 7.41-7.58 (m, 2H), 7.71-7.81 (m. 3H), 8.28 (d, 1H), 8.42 (d, 2H), 8.58 (d, 1H), 9.18 (s, 1H), 10.40 (s, 1H); HPLC Purity: 97.75%; LCMS: 526.2 ($M^+$+1).

N-(4-(4-(5-chloro-2-hydroxybenzyl)-1,4-diazepane-1-carbonyl)phenyl)quinoline-8-sulfonamide (VIII-208)

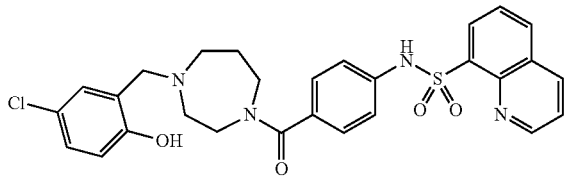

$^1$H NMR (400 MHz, DMSO-d6) δ: 1.61 (br s, 1H), 1.77 (br s, 1H), 2.60-2.78 (m, 2H), 3.21 (br s, 2H), 3.42-3.58 (m, 2H), 3.50-3.71 (m, 4H), 6.74-6.80 (m, 1H), 7.08-7.20 (m, 5H), 7.71-7.80 (m. 2H), 8.28 (br s, 1H), 8.42 (d, 2H), 8.58 (br s, 1H), 9.18 (s, 1H), 10.40 (s, 1H); HPLC Purity: 99.40%; LCMS: 551.1 ($M^+$).

N-(4-(4-(4-methoxybenzyl)-1,4-diazepane-1-carbonyl)phenyl)quinoline-8-sulfonamide (VIII-208)

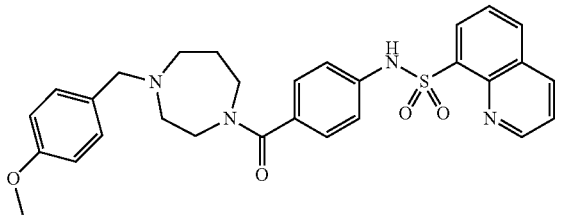

$^1$H NMR (400 MHz, DMSO-d6) δ: 1.61 (br s, 1H), 1.77 (br s, 1H), 2.40 (br s, 1H), 2.60 (br s, 1H), 3.21 (br s, 2H), 3.42-3.58 (m, 4H), 3.77 (s, 2H), 6.80-6.91 (m, 2H), 7.06-7.20 (m, 4H), 7.71-7.79 (m. 2H), 8.28 (br s, 1H), 8.42 (d, 2H), 8.58 (br s, 1H), 9.18 (s, 1H), 10.40 (s, 1H); HPLC Purity: 99.04%; LCMS: 531 ($M^+$1).

N-(4-(4-(2,5-dimethylbenzyl)-1,4-diazepane-1-carbonyl)phenyl)quinoline-8-sulfonamide (VIII-209)

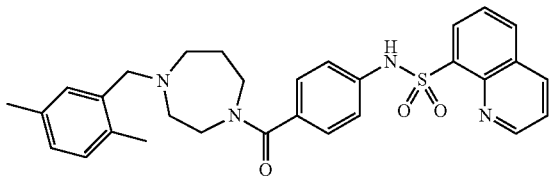

$^1$H NMR (400 MHz, DMSO-d6) δ: 1.61 (br s, 1H), 1.77 (br s, 1H), 2.10-2.25 (m, 2H), 2.24 (s, 2H), 2.60-2.67 (m, 2H), 2.60 (br s, 2H), 3.20-3.60 (m, 2H), 6.90-7.20 (m, 5H), 7.71-7.80 (m. 2H), 8.28 (d, 1H), 8.42 (d, 2H), 8.58 (d, 1H), 9.18 (s, 1H), 10.40 (s, 1H); HPLC Purity: 98.86%; LCMS: 529 ($M^+$+1).

N-(4-(4-(3,5-dichlorobenzyl)-1,4-diazepane-1-carbonyl)phenyl)quinoline-8-sulfonamide (VIII-210)

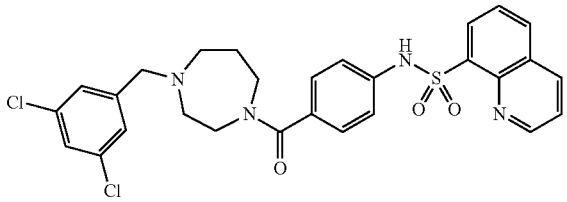

$^1$H NMR (400 MHz, DMSO-d6) δ: 1.61 (br s, 1H), 1.77 (br s, 1H), 2.24 (s, 2H), 2.60-2.67 (m, 2H), 3.20-3.60 (br s, 2H), 3.8-3.9 (m, 4H), 7.09-7.20 (m, 3H), 7.25-7.50 (m, 3H), 7.71-7.80 (m. 2H), 8.28 (d, 1H), 8.42 (d, 1H), 8.58 (d, 1H), 9.18 (s, 1H), 10.40 (s, 1H); HPLC Purity: 99.29%; LCMS: 569 ($M^+$−1).

N-(4-(4-(3-fluoro-4-(trifluoromethyl)benzyl)-1,4-diazepane-1-carbonyl)phenyl)quinoline-8-sulfonamide (VIII-211)

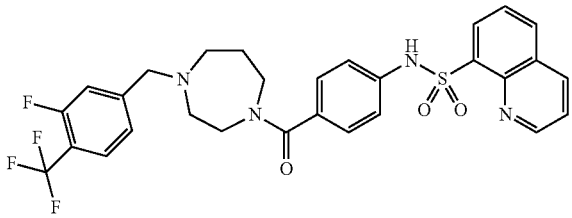

$^1$H NMR (400 MHz, DMSO-d6) δ: 1.61 (br s, 1H), 1.77 (br s, 1H), 2.24 (s, 2H), 2.40-2.60 (m, 2H), 3.20 (br s, 2H), 3.59 (br s, 2H), 3.58 (d, 2H), 7.10-7.20 (m, 3H), 7.25-7.42 (m, 2H), 7.71-7.80 (m. 2H), 8.28 (d, 1H), 8.42 (d, 2H), 8.58 (d, 1H), 9.18 (s, 1H), 10.40 (s, 1H); HPLC Purity: 99.71%; LCMS: 587 ($M^+$+1).

N-(4-(4-(2,4,5-trimethylbenzyl)-1,4-diazepane-1-carbonyl)phenyl)quinoline-8-sulfonamide (VIII-212)

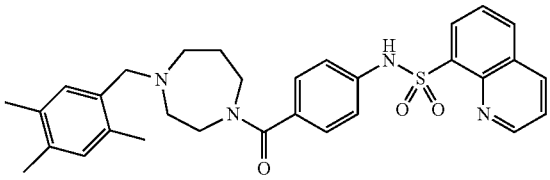

$^1$H NMR (400 MHz, DMSO-d6) δ: 2.10 (s, 3H), 2.18 (s, 6H), 2.24 (s, 2H), 2.40-2.60 (m, 4H), 3.20 (br s, 2H), 3.59 (br s, 2H), 3.58 (d, 2H), 6.80-6.99 (m, 2H), 7.04-7.18 (m, 2H), 7.71-7.80 (m, 2H), 8.28 (d, 1H), 8.42 (d, 2H), 8.58 (d, 1H), 9.18 (s, 1H), 10.40 (s, 1H); HPLC Purity: 99.80%; LCMS: 543 ($M^+$+1).

N-(4-(4-(4-chlorobenzyl)-1,4-diazepane-1-carbonyl)phenyl)quinoline-8-sulfonamide (VIII-213)

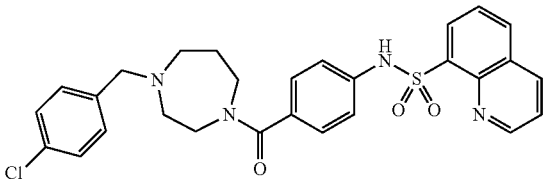

$^1$H NMR (400 MHz, DMSO-d6) δ: 1.59 (s, 1H), 1.78 (s, 1H), 2.41 (s, 1H), 2.52-2.64 (m, 2H), 3.25 (br s, 2H), 3.55 (s, 2H), 3.59 (s, 2H), 7.08-7.17 (m, 3H), 7.20-7.40 (m, 4H), 7.68-7.75 (m, 2H), 8.28 (d, 1H), 8.42 (d, 1H), 8.53 (d, 1H), 9.18 (s, 1H), 10.39 (s, 1H); HPLC Purity: 97.45%; LCMS: 535.1 ($M^+$).

N-(4-(4-(2,5-dimethoxybenzyl)-1,4-diazepane-1-carbonyl)phenyl)quinoline-8-sulfonamide (VIII-214)

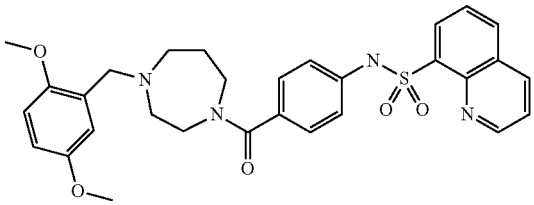

[$^1$H NMR (400 MHz, DMSO-d6) δ: 1.63 (br s, 1H), 1.78 (br s, 1H), 2.2 (br s, 2H), 2.62 (br s, 2H), 3.24 (br s, 2H), 3.48-3.66 (m, 4H), 3.7-3.86 (s, 6H), 6.71-6.81 (m, 1H), 6.82-6.99 (m, 2H), 7.05-7.17 (m, 3H), 7.70-7.79 (m, 2H), 8.28 (d, 1H), 8.42 (d, 1H), 8.56 (d, 1H), 9.18 (s, 1H), 10.39 (s, 1H);] HPLC Purity: 98.43%; LCMS: 561 ($M^+$+1).

Synthesis of Corresponding Salts:

General Procedure for Making Salts:

To a solution of N-(4-(4-benzylpiperazine-1 -carbonyl) phenyl)quinoline-8-sulfonamide (0.25 mmol) in methanol (5 ml) added Sodium hydroxide/methanesulfonic acid (0.25 mmol, 1.0 eq) and the reaction mixture was stirred for 3 h at room temperature. The solvent was removed under reduced pressure and azeotroped with pentane to get the salts as pale yellow solid.

Sodium (4-(4-benzylpiperazine-1-carbonyl)phenyl)(quinolin-8-ylsulfonyl)amide (VIII-215)

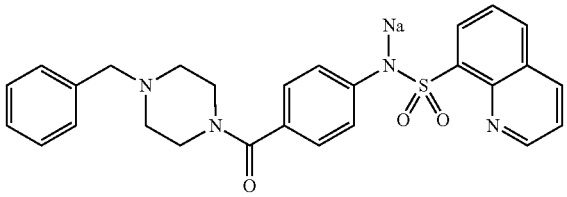

[$^1$H NMR (400 MHz, $CDCl_3$) δ: 2.38 (br d, 4H), 3.31 (br s, 2H), 3.41 (s, 2H), 3.64 (br s, 2H), 6.94 (d, 2H), 7.06 (t, 4H), 7.40 (d, 2H), 7.56-7.63 (m, 2H), 8.01 (d, 1H), 8.28 (d, 1H), 8.38 (d, 1H), 8.56 (s, 1H), 9.18 (s, 1H); LCMS: 508.5 ($M^+$+23)].

8-(N-(4-(4-benzylpiperazine-1-carbonyl)phenyl)sulfamoyl)quinolin-1-ium methanesulfonate (VIII-216)

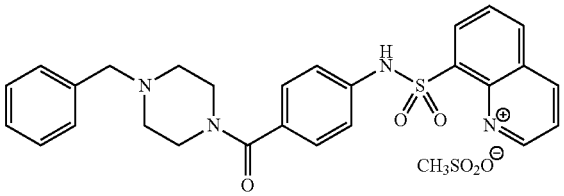

$^1$H NMR (400 MHz, $CDCl_3$) δ: 2.38 (br d, 4H), 3.31 (br s, 2H), 3.41 (s, 2H), 3.64 (br s, 2H), 6.94 (d, 2H), 7.06 (t, 4H), 7.40 (d, 2H), 7.56-7.63 (m, 2H), 8.01 (d, 1H), 8.28 (d, 1H), 8.38 (d, 1H), 8.56 (s, 1H), 9.18 (s, 1H); LCMS: 487.0 ($M^+$+1).

Synthesis of Piperazine Based Benzyl Derivatives with 3-Methyl, 2-Methyl, 3-Fluoro, 3-Chloro, 3-Methoxy and 2-Methoxy Substituted Phenyl Rings Scheme 22

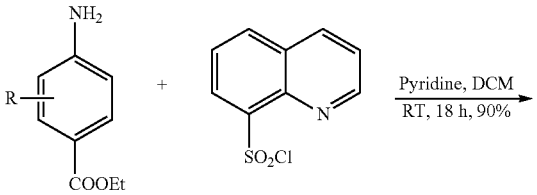

140
R = Me, F, 2-OMe, 3-OMe

89

-continued

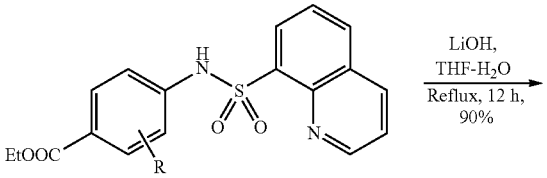

141
R = Me, F, 2-OMe, 3-OMe

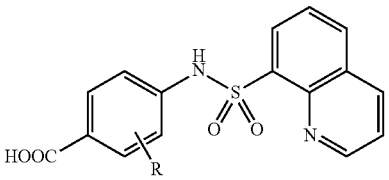

14

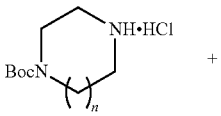

137
n = 1, Piperizine
n = 2, Homopiperizine

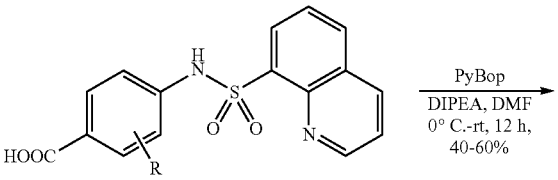

143

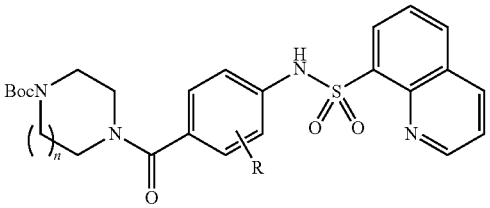

144
n = 1, Piperizine
n = 2, Homopiperizine
R = Me, F, 2-OMe, 3-OMe

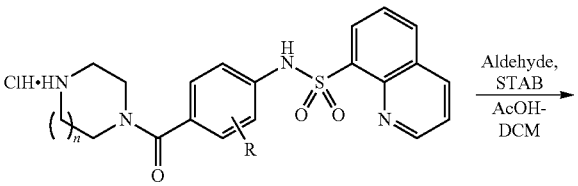

145
n = 1, Piperizine
n = 2, Homopiperizine
R = Me, F, 2-OMe, 3-OMe

-continued

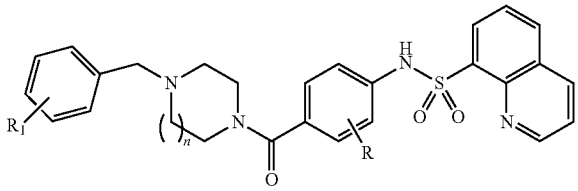

XIV n = 1, Piperizine n = 2, Homopiperizine

R = Me, F, 2-OMe, 3-OMe $R_1$ = Different A ring variations

STAB = Sodium tri-acetoxy borohydride

The synthesis of compounds 140-145 and compound of formula (XIV) was carried out starting from aniline 140 (0.25 mmol) by following the similar procedure as mentioned in Scheme 21 for compounds of formula (VIII) with respective key steps such as sulfonamide formation, ester hydrolysis, amide bond formation and reductive amination.

N-(4-(4-benzylpiperazine-1-carbonyl)-2-methylphenyl)quinoline-8-sulfonamide (XIV-1)

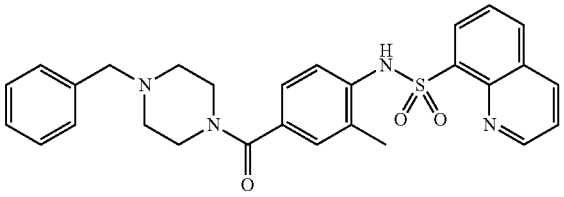

[$^1$H NMR (400 MHz, $CDCl_3$) δ: 2.22 (s, 3H), 2.65 (br s, 4H), 3.50 (br s, 4H), 4.20 (s, 2H), 7.01 (d, 1H), 7.12 (s, 1H), 7.39 (t, 2H), 7.48 (q, 2H), 7.60-7.68 (m, 2H), 8.18 (d, 1H), 8.28 (d, 1H), 8.43 (d, 1H), 9.18 (d, 1H);] HPLC Purity: 98.75%; LCMS: 501 ($M^+$+1).

N-(4-(4-benzylpiperazine-1-carbonyl)-2-fluorophenyl)quinoline-8-sulfonamide (XIV-2)

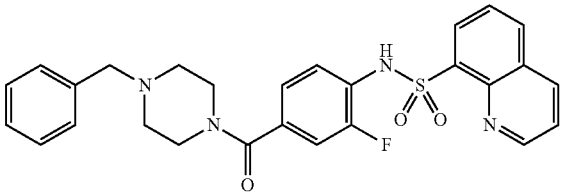

$^1$H NMR (400 MHz, $CDCl_3$) δ: 2.62 (br s, 4H), 3.80 (br s, 4H), 4.20 (s, 2H), 6.99 (d, 1H), 7.03 (d, 1H), 7.39 (d, 2H), 7.40-7.48 (m, 3H), 7.60-7.68 (m, 2H), 7.80 (t, 1H), 8.18 (d, 1H), 8.26 (d, 1H), 8.43 (d, 1H), 9.18 (d, 1H); HPLC Purity: 97.86%; LCMS: 505 ($M^+$+1).

N-(4-(4-benzylpiperazine-1-carbonyl)-2-methoxyphenyl)quinoline-8-sulfonamide (XIV-3)

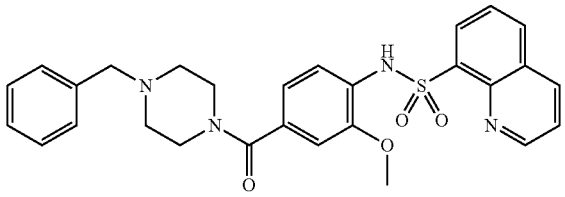

$^1$H NMR (400 MHz, $CDCl_3$) δ: 2.46 (br s, 4H), 3.50 (br s, 4H), 3.66 (s, 3H), 4.20 (br s, 2H), 6.40 (br s, 1H), 6.94 (br s, 1H), 7.39 (d, 2H), 7.42-7.48 (m, 3H), 7.61-7.66 (m, 2H), 8.18 (d, 1H), 8.36 (d, 1H), 8.41 (d, 1H), 9.18 (d, 1H); HPLC Purity:

99.99%; LCMS: 517 ($M^+$+1).

N-(4-(4-benzylpiperazine-1-carbonyl)-3-chlorophenyl)quinoline-8-sulfonamide (XIV-4)

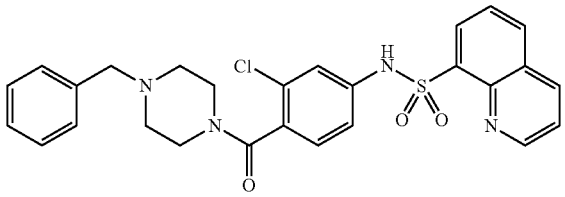

$^1$H NMR (400 MHz, $CDCl_3$) δ: 2.32 (br s, 4H), 3.42 (br s, 4H), 4.38 (s, 2H), 7.16 (q, 2H), 7.30 (s, 1H), 7.49 (s, 4H), 7.64-7.73 (m, 2H), 8.21 (d, 1H), 8.42 (t, 2H), 9.18 (d, 1H); HPLC Purity: 96.62% LCMS: 521 ($M^+$).

N-(4-(4-(4-chlorobenzyl)piperazine-1-carbonyl)-2-methylphenyl)quinoline-8-sulfonamide (XIV-5)

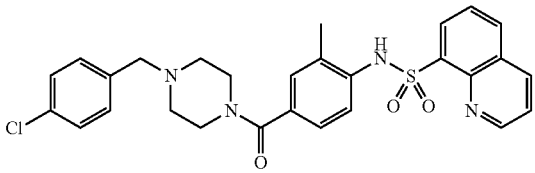

$^1$H NMR (400 MHz, DMSO-d6) δ: 2.01 (s, 3H), 2.37 (br s, 4H), 3.41 (br s, 4H), 3.50 (s, 2H), 6.97 (s, 2H), 7.06 (s, 1H), 7.39 (dd, 2H), 7.54 (s, 1H), 7.62-7.77 (m, 2H), 8.21-8.30 (m, 3H), 8.52 (d, 1H), 9.18 (s, 1H); 9.34 (s, 1H), HPLC Purity: 97.97%; LCMS: 535 ($M^+$).

N-(4-(4-(2,4-dichlorobenzyl)piperazine-1-carbonyl)-2-methylphenyl)quinoline-8-sulfonamide (XIV-6)

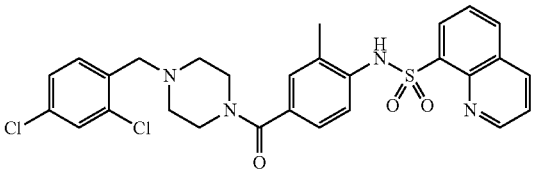

$^1$H NMR (400 MHz, DMSO-d6) δ: 2.01 (s, 3H), 2.37 (br s, 4H), 3.42 (br s, 4H), 3.50 (s, 2H), 6.97 (s, 2H), 7.06 (s, 1H), 7.39 (dd, 2H), 7.54 (s, 1H), 7.62-7.77 (m, 2H), 8.21-8.30 (m, 2H), 8.52 (d, 1H), 9.18 (s, 1H); HPLC Purity: 97.97%; LCMS: 569 ($M^+$).

N-(2-methyl-4-(4-(4-(trifluoromethyl)benzyl)piperazine-1-carbonyl)phenyl)quinoline-8-sulfonamide (XIV-7)

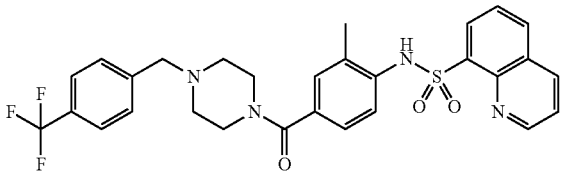

$^1$H NMR (400 MHz, DMSO-d6) δ: 2.01 (s, 3H), 2.37 (br s, 4H), 3.41 (br s, 4H), 3.53 (s, 2H), 6.97 (s, 2H), 7.06 (s, 1H), 7.46 (d, 2H), 7.62-7.77 (m, 4H), 8.21-8.30 (m, 2H), 8.57 (d, 1H), 9.18 (s, 1H), 9.21 (br s, 1H); HPLC Purity: 96.00%; LCMS: 569 ($M^+$+1).

N-(4-(4-(3,5-dichlorobenzyl)piperazine-1-carbonyl)-2-methylphenyl)quinoline-8-sulfonamide (XIV-8)

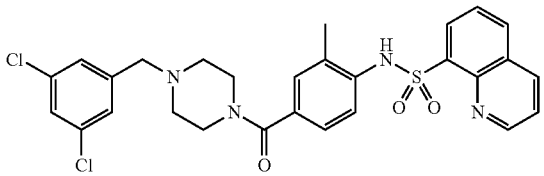

$^1$H NMR (400 MHz, DMSO-d6) δ: 2.01 (s, 3H), 2.37 (br s, 4H), 3.46 (s, 4H), 6.97 (s, 2H), 7.06 (s, 1H), 7.31 (s, 2H), 7.46 (s, 1H), 7.62-7.77 (m, 3H), 8.21-8.30 (m, 2H), 8.57 (d, 1H), 9.18 (s, 1H), 9.39 (s, 1H); HPLC Purity: 99.45%; LCMS: 569 ($M^+$)

N-(4-(4-(3-fluorobenzyl)piperazine-1-carbonyl)-2-methylphenyl)quinoline-8-sulfonamide (XIV-9)

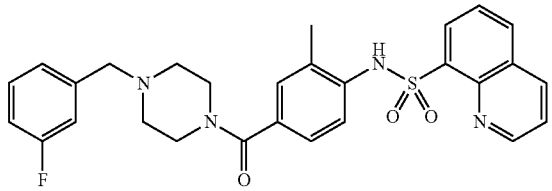

$^1$H NMR (400 MHz, DMSO-d6) δ: 2.01 (s, 3H), 2.30 (br s, 4H), 3.41 (br s, 4H), 3.47 (s, 2H), 6.97 (s, 2H), 6.99-7.16 (m, 4H), 7.25-7.34 (m, 1H) 7.62-7.77 (m, 2H), 8.21-8.30 (m, 2H), 8.57 (d, 1H), 9.18 (s, 1H), 9.21 (s, 1H); HPLC Purity: 97.71%; LCMS: 519 ($M^+$+1).

N-(4-(4-(3,4-dichlorobenzyl)piperazine-1-carbonyl)-2-methylphenyl)quinoline-8-sulfonamide (XIV-10)

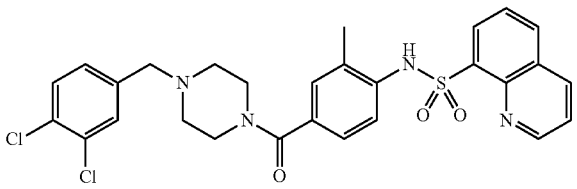

$^1$H NMR (400 MHz, DMSO-d6) δ 2.01 (s, 3H), 2.25 (br s, 4H), 3.45 (s, 4H), 6.97 (s, 2H), 7.06 (m, 1H), 7.25 (d, 1H) 7.58 (t, 2H), 7.62-7.77 (m, 2H), 8.21-8.30 (m, 2H), 8.57 (d, 1H), 9.18 (s, 1H), 9.21 (s, 1H); HPLC Purity: 94.90%; LCMS: 569 ($M^+$).

N-(4-(4-(3,5-difluorobenzyl)piperazine-1-carbonyl)-2-methylphenyl)quinoline-8-sulfonamide (XIV-11)

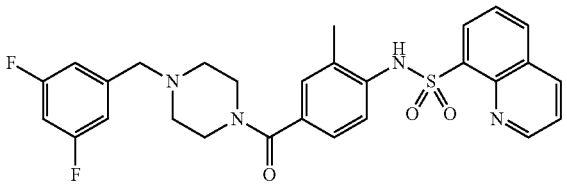

$^1$H NMR (400 MHz, DMSO-d6) δ: 2.01 (s, 3H), 2.25 (br s, 4H), 3.45 (s, 4H), 3.52 (s, 2H), 6.97-7.10 (m, 5H), 7.62-7.77 (m, 3H), 8.21-8.30 (m, 2H), 8.57 (d, 1H), 9.18 (s, 1H), 9.21 (s, 1H); HPLC Purity: 97.84%; LCMS: 536 ($M^+$+23).

N-(4-(4-(3-chloro-4-fluorobenzyl)piperazine-1-carbonyl)-2-methylphenyl)quinoline-8-sulfonamide (XIV-12)

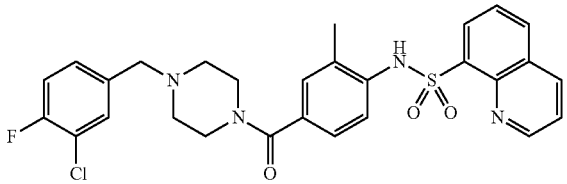

$^1$H NMR (400 MHz, DMSO-d6) δ: 2.01 (s, 3H), 2.25 (br s, 4H), 3.43 (s, 4H), 3.46 (s, 2H), 6.97 (s, 2H), 7.06 (s, 1H), 7.21-7.35 (m, 2H), 7.42 (d, 1H), 7.62-7.77 (m, 2H), 8.21-8.30 (m, 2H), 8.53 (d, 1H), 9.18 (s, 1H), 9.21 (s, 1H); HPLC Purity: 94.61%; LCMS: 553 ($M^+$).

N-(4-(4-(4-chloro-2-fluorobenzyl)piperazine-1-carbonyl)-2-methylphenyl)quinoline-8-sulfonamide (XIV-13)

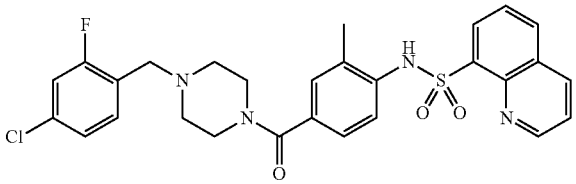

$^1$H NMR (400 MHz, DMSO-d6) δ: 2.01 (s, 3H), 2.25 (br s, 4H), 3.20 (br s, 2H), 3.45 (s, 4H), 6.97 (s, 2H), 7.06 (s, 1H), 7.21 (d, 1H), 7.31-7.39 (m, 2H), 7.62-7.77 (m, 2H), 8.21-8.30 (m, 2H), 8.57 (d, 1H), 9.18 (s, 1H), 9.21 (s, 1H); HPLC Purity: 96.23%; LCMS: 553 ($M^+$).

N-(4-(4-(2,4-difluorobenzyl)piperazine-1-carbonyl)-2-methylphenyl)quinoline-8-sulfonamide (XIV-14)

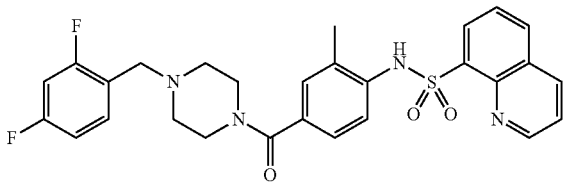

$^1$H NMR (400 MHz, DMSO-d6) δ: 2.01 (s, 3H), 2.25 (br s, 4H), 3.20 (br s, 2H), 3.45 (s, 4H), 6.97-7.06 (m, 4H), 7.20 (t, 1H), 7.31-7.39 (m, 1H), 7.62-7.77 (m, 2H), 8.21-8.30 (m, 2H), 8.57 (d, 1H), 9.18 (s, 1H), 9.21 (s, 1H); HPLC Purity: 99.12%; LCMS: 537 ($M^+$+1).

N-(4-(4-(2,3-dichlorobenzyl)piperazine-1-carbonyl)-2-methylphenyl)quinoline-8-sulfonamide (XIV-15)

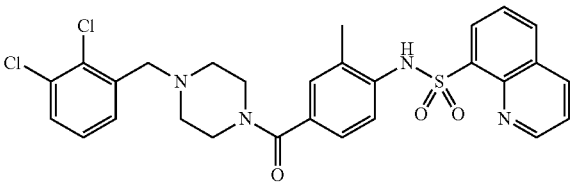

$^1$H NMR (400 MHz, DMSO-d6) δ: 2.01 (s, 3H), 2.25 (br s, 4H), 3.37 (s, 4H), 3.45 (s, 2H), 6.97 (s, 2H), 7.06 (s, 1H), 7.25 (t, 1H) 7.42 (d, 1H), 7.50 (d, 1H), 7.62-7.77 (m, 2H), 8.21-8.30 (m, 2H), 8.57 (d, 1H), 9.18 (s, 1H), 9.21 (s, 1H); HPLC Purity: 98.43%; LCMS: 569 ($M^+$).

N-(4-(4-(2-fluorobenzyl)piperazine-1-carbonyl)-2-methylphenyl)quinoline-8-sulfonamide (XIV-16)

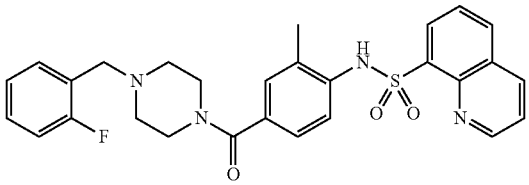

$^1$H NMR (400 MHz, DMSO-d6) δ: 2.01 (s, 3H), 2.30 (br s, 4H), 3.25 (s, 4H), 3.47 (s, 2H), 6.97 (s, 2H), 7.06 (s, 1H), 7.10-7.20 (m, 2H), 7.24-7.38 (m, 2H) 7.62-7.77 (m, 2H), 8.21-8.30 (m, 2H), 8.57 (d, 1H), 9.18 (s, 1H), 9.21 (s, 1H); HPLC Purity: 98.71%; LCMS: 519 ($M^+$+1).

N-(4-(4-(3-chlorobenzyl)piperazine-1-carbonyl)-2-methylphenyl)quinoline-8-sulfonamide (XIV-17)

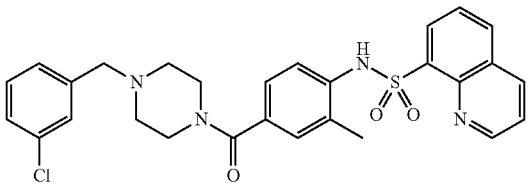

$^1$H NMR (400 MHz, DMSO-d6) δ 2.01 (s, 3H), 2.37 (br s, 4H), 3.37 (br s, 4H), 3.44 (s, 2H), 6.97 (s, 2H), 7.06 (s, 1H), 7.20-7.29 (m, 4H), 7.62-7.77 (m, 2H), 8.21-8.30 (m, 2H), 8.56 (d, 1H), 9.18 (s, 1H), 9.34 (s, 1H); HPLC Purity: 99.25%; LCMS: 535 ($M^+$).

N-(4-(4-(2,3-difluorobenzyl)piperazine-1-carbonyl)-2-methylphenyl)quinoline-8-sulfonamide (XIV-18)

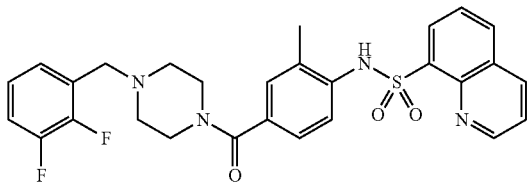

$^1$H NMR (400 MHz, DMSO-d6) δ 2.01 (s, 3H), 2.25 (br s, 4H), 3.46 (br s, 4H), 3.59 (s, 2H), 6.97 (s, 2H), 7.06 (s, 1H), 7.25-7.36 (m, 2H), 7.63-7.77 (m, 2H), 8.21-8.30 (m, 2H), 8.57 (d, 1H), 9.18 (s, 1H), 9.21 (s, 1H); HPLC Purity: 96.79%; LCMS: 537 ($M^+$+1).

N-(4-(4-(cyclopropylmethyl)piperazine-1-carbonyl)-2-methylphenyl)quinoline-8-sulfonamide (XIV-19)

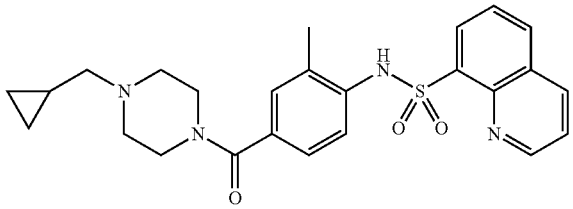

[$^1$H NMR (400 MHz, DMSO-d6) δ: 0.03-0.05 (m, 2H), 0.30-0.31 (m, 2H), 0.45-0.47 (m, 1H), 2.01 (s, 3H), 2.17 (d, 2H), 2.25 (br s, 4H), 3.22 (br s, 4H), 3.59 (s, 2H), 6.97 (s, 2H), 7.06 (s, 1H), 7.63-7.77 (m, 2H), 8.21-8.30 (m, 2H), 8.57 (d, 1H), 9.18 (s, 1H), 9.21 (s, 1H);] HPLC Purity: 98.31%; LCMS: 465 ($M^+$+1).

N-(2-methyl-4-(4-(pyridin-4-ylmethyl)piperazine-1-carbonyl)phenyl)quinoline-8-sulfonamide (XIV-20)

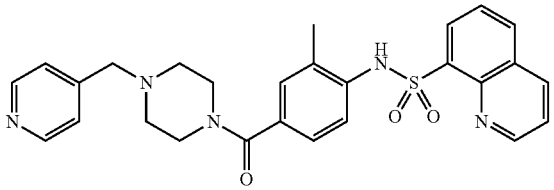

$^1$H NMR (400 MHz, DMSO-d6) δ: 2.01 (s, 3H), 2.25 (br s, 4H), 3.46 (br s, 4H), 3.50 (s, 2H), 6.97 (s, 2H), 7.06 (s, 1H), 7.31 (m, 2H), 7.63-7.77 (m, 3H), 8.21-8.30 (m, 2H), 8.54 (d, 1H), 8.58 (d, 1H), 9.18 (s, 1H), 9.21 (br s, 1H); HPLC Purity: 94.88%; LCMS: 502 ($M^+$+1).

N-(4-(4-(3,5-difluorobenzyl)piperazine-1-carbonyl)-2-fluorophenyl)quinoline-8-sulfonamide (XIV-21)

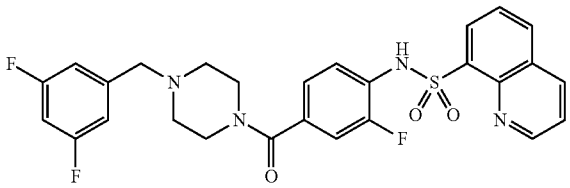

$^1$H NMR (400 MHz, DMSO-d6) δ: 2.38 (br s, 4H), 3.52 (br s, 4H), 3.58 (s, 2H), 7.01-7.18 (m, 4H), 7.38 (t, 1H), 7.71-7.82 (m, 3H), 8.32 (t, 2H), 8.60 (d, 1H), 9.12 (s, 1H), 9.98 (s, 1H); HPLC Purity: 98.93%; LCMS: 541 ($M^+$+1).

N-(4-(4-(4-chlorobenzyl)piperazine-1-carbonyl)-2-fluorophenyl)quinoline-8-sulfonamide (XIV-22)

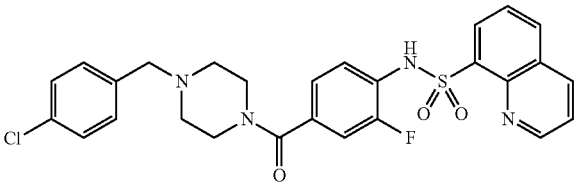

$^1$H NMR (400 MHz, DMSO-d6) δ: 2.38 (br s, 4H), 3.28 (br s, 4H), 3.55 (br s, 2H), 7.08 (t, 2H), 7.35-7.40 (m, 4H), 7.71-7.80 (m, 3H), 8.32 (t, 2H), 8.60 (d, 1H), 9.18 (s, 1H), 9.98 (s, 1H); HPLC Purity: 98.58%; LCMS: 539 ($M^+$).

N-(4-(4-(2,4-dichlorobenzyl)piperazine-1-carbonyl)-2-fluorophenyl)quinoline-8-sulfonamide (XIV-23)

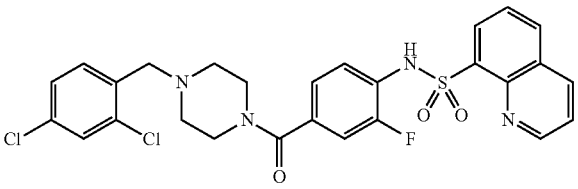

$^1$H NMR (400 MHz, DMSO-d6) δ: 2.38 (br s, 3H), 3.46 (br s, 4H), 3.58 (s, 2H), 7.08 (t, 2H), 7.35 (t, 1H), 7.40 (d, 1H), 7.50 (d, 1H), 7.60 (s, 1H), 7.71-7.79 (m, 2H), 8.32 (t, 2H), 8.60 (d, 1H), 9.18 (s, 1H), 9.98 (s, 1H); HPLC Purity: 98.58%; LCMS: 573 ($M^+$).

N-(4-(4-(3,5-dichlorobenzyl)piperazine-1-carbonyl)-2-fluorophenyl)quinoline-8-sulfonamide (XIV-24)

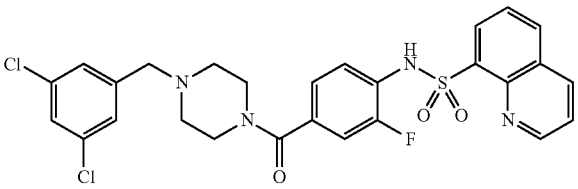

$^1$H NMR (400 MHz, DMSO-d6) δ: 2.38 (br s, 4H), 3.28 (br s, 4H), 3.55 (br s, 2H), 7.10 (t, 2H), 7.30-7.38 (m, 3H), 7.50 (s, 1H), 7.71-7.80 (m, 2H), 8.32 (t, 2H), 8.58 (d, 1H), 9.18 (s, 1H), 9.98 (s, 1H); HPLC Purity: 97.63%; LCMS: 573 ($M^+$).

N-(4-(4-(3-chloro-4-fluorobenzyl)piperazine-1-carbonyl)-2-fluorophenyl)quinoline-8-sulfonamide (XIV-25)

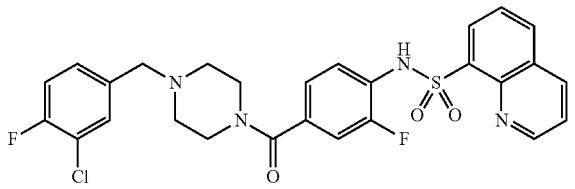

$^1$H NMR (400 MHz, DMSO-d6) δ: 2.38 (br s, 3H), 3.28 (br s, 4H), 3.55 (s, 2H), 7.10 (t, 2H), 7.29-7.40 (m, 3H), 7.50 (d, 1H), 7.71-7.80 (m, 2H), 8.30 (t, 2H), 8.60 (d, 1H), 9.18 (s, 1H), 9.98 (s, 1H); HPLC Purity: 96.66%; LCMS: 557 ($M^+$).

N-(2-fluoro-4-(4-(4-(trifluoromethyl)benzyl)piperazine-1-carbonyl)phenyl)quinoline-8-sulfonamide (XIV-26)

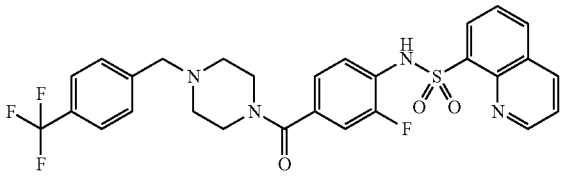

$^1$H NMR (400 MHz, DMSO-d6) δ: 2.38 (br s, 4H), 3.46 (br s, 4H), 3.60 (s, 2H), 7.10 (t, 2H), 7.35 (t 1H), 7.59 (d, 2H), 7.63-7.78 (m, 4H), 8.32 (t, 2H), 8.60 (d, 1H), 9.18 (s, 1H), 9.98 (s, 1H); HPLC Purity: 99.96%; LCMS: 573 ($M^+$+1).

N-(4-(4-(3,4-dichlorobenzyl)piperazine-1-carbonyl)-2-fluorophenyl)quinoline-8-sulfonamide (XIV-27)

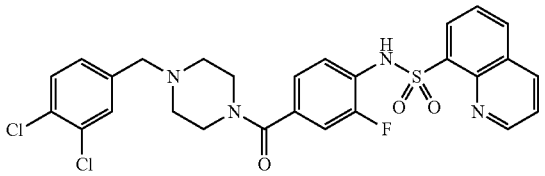

$^1$H NMR (400 MHz, DMSO-d6) δ: 2.38 (br s, 3H), 3.28 (br s, 4H), 3.55 (s, 2H), 7.10 (t, 2H), 7.28-7.40 (m, 2H), 7.58 (t, 2H), 7.70-7.79 (m, 2H), 8.32 (t, 2H), 8.60 (d, 1H), 9.18 (s, 1H), 9.98 (s, 1H); HPLC Purity: 98.23%; LCMS: 573 ($M^+$).

N-(2-fluoro-4-(4-(2-fluorobenzyl)piperazine-1-carbonyl)phenyl)quinoline-8-sulfonamide (XIV-28)

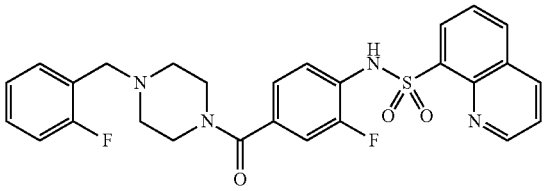

$^1$H NMR (400 MHz, DMSO-d6) δ: 2.38 (br s, 4H), 3.48 (br s, 4H), 3.58 (s, 2H), 7.05-7.20 (m, 3H), 7.28-7.40 (m, 2H), 7.70-7.79 (m, 2H), 8.32 (t, 2H), 8.60 (d, 1H), 9.18 (s, 1H), 9.98 (s, 1H); HPLC Purity: 96.54%; LCMS: 523 ($M^+$+1).

N-(4-(4-(2,4-difluorobenzyl)piperazine-1-carbonyl)-2-fluorophenyl)quinoline-8-sulfonamide (XIV-29)

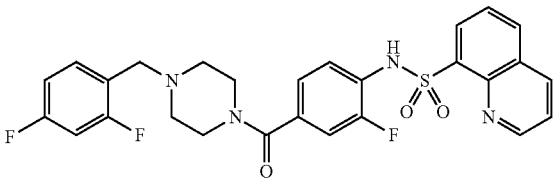

$^1$H NMR (400 MHz, DMSO-d6) δ: 2.38 (br s, 4H), 3.22 (br s, 4H), 3.58 (s, 2H), 7.03-7.20 (m, 3H), 7.20 (t, 1H), 7.38 (t, 1H), 7.44 (q, 1H), 7.70-7.79 (m, 2H), 8.32 (t, 2H), 8.60 (d, 1H), 9.18 (s, 1H), 9.98 (s, 1H); HPLC Purity: 99.52%; LCMS: 541 ($M^+$+1).

N-(4-(4-(2,3-dichlorobenzyl)piperazine-1-carbonyl)-2-fluorophenyl)quinoline-8-sulfonamide (XIV-30)

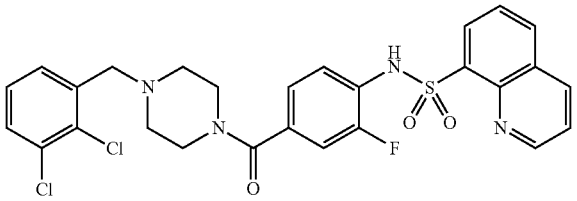

$^1$H NMR (400 MHz, DMSO-d6) δ: 2.38 (br s, 4H), 3.22 (br s, 4H), 3.58 (s, 2H), 7.12 (m, 3H), 7.31-7.40 (m, 1H), 7.44 (d, 1H), 7.60 (d, 1H), 7.70-7.79 (m, 2H), 8.32 (t, 2H), 8.60 (d, 1H), 9.12 (s, 1H), 9.98 (s, 1H); HPLC Purity: 97.43%; LCMS: 573 ($M^+$).

N-(4-(4-(4-chloro-2-fluorobenzyl)piperazine-1-carbonyl)-2-fluorophenyl)quinoline-8-sulfonamide (XIV-31)

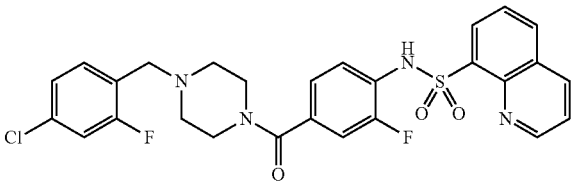

$^1$H NMR (400 MHz, DMSO-d6) δ: 2.38 (br s, 3H), 3.22 (br s, 4H), 3.58 (s, 2H), 7.10 (t, 2H), 7.23-7.46 (m, 4H), 7.70-7.79 (m, 2H), 8.32 (t, 2H), 8.60 (d, 1H), 9.18 (s, 1H), 9.98 (s, 1H); HPLC Purity: 99.89%; LCMS: 557 ($M^+$).

N-(4-(4-(2,3-difluorobenzyl)piperazine-1-carbonyl)-2-fluorophenyl)quinoline-8-sulfonamide (XIV-32)

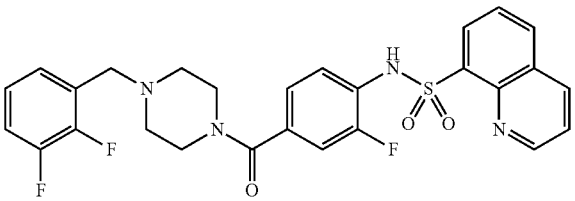

$^1$H NMR (400 MHz, DMSO-d6) δ: 2.38 (br s, 3H), 3.26 (br s, 4H), 3.58 (s, 2H), 7.03-7.25 (m, 4H), 7.38 (t, 2H), 7.70-7.79 (m, 2H), 8.32 (t, 2H), 8.60 (d, 1H), 9.12 (s, 1H), 9.98 (s, 1H); HPLC Purity: 99.04%; LCMS: 541 ($M^+$+1).

N-(4-(4-(cyclopropylmethyl)piperazine-1-carbonyl)-2-fluorophenyl)quinoline-8-sulfonamide (XIV-33)

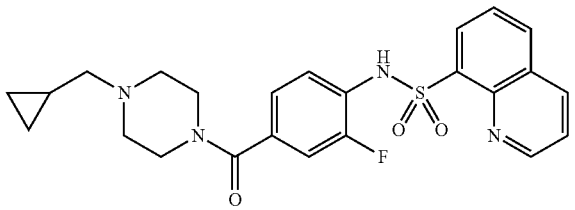

$^1$H NMR (400 MHz, DMSO-d6) δ: 0.03-0.035 (m, 2H), 0.64-0.66 (m, 2H), 0.81-0.83 (m, 1H), 2.20 (s, 2H), 2.38 (br s, 4H), 3.52 (br s, 4H), 7.10 (m, 2H), 7.38 (t, 1H), 7.70-7.79 (m, 2H), 8.32 (t, 2H), 8.60 (d, 1H), 9.12 (s, 1H), 9.98 (s, 1H); HPLC Purity: 97.67%; LCMS: 469 ($M^+$+1).

N-(2-fluoro-4-(4-(pyridin-4-ylmethyl)piperazine-1-carbonyl)phenyl)quinoline-8-sulfonamide (XIV-34)

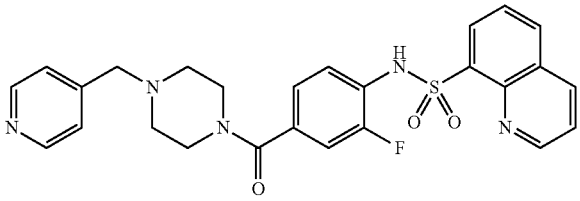

$^1$H NMR (400 MHz, DMSO-d6) δ: 2.38 (br s, 4H), 3.48 (br s, 4H), 3.59 (s, 2H), 7.12 (t, 2H), 7.38 (s, 3H), 7.70-7.79 (m, 2H), 8.32 (t, 2H), 8.57 (d, 2H), 8.60 (d, 1H), 9.10 (s, 1H), 9.98 (s, 1H); HPLC Purity: 97.70%; LCMS: 506 ($M^+$+1).

N-(2-fluoro-4-(4-(pyridin-2-ylmethyl)piperazine-1-carbonyl)phenyl)quinoline-8-sulfonamide (XIV-35)

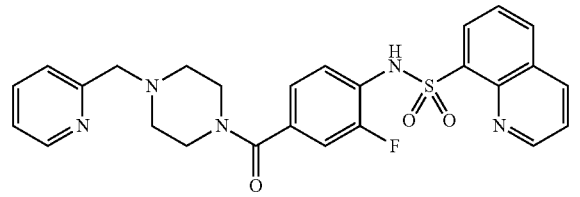

$^1$H NMR (400 MHz, DMSO-d6) δ: 2.38 (br s, 4H), 3.22 (br s, 4H), 3.62 (s, 2H), 7.13 (t, 2H), 7.22-7.38 (m, 2H), 7.42 (d, 1H), 7.70-7.79 (m, 3H), 8.32 (t, 2H), 8.50 (s, 1H), 8.60 (d, 1H), 9.18 (s, 1H), 9.98 (s, 1H); HPLC Purity: 99.74%; LCMS: 506 ($M^+$+1).

N-(2-methyl-4-(4-(pyridin-2-ylmethyl)piperazine-1-carbonyl)phenyl)quinoline-8-sulfonamide (XIV-36)

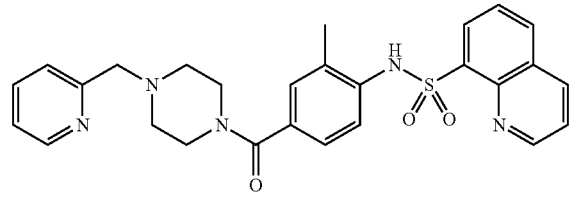

$^1$H NMR (400 MHz, DMSO-d6) δ: 2.01 (s, 3H), 2.38 (br s, 4H), 3.52 (br s, 4H), 3.60 (s, 2H), 6.97 (s, 2H), 7.03 (s, 1H), 7.23 (t, 1H), 7.40 (d, 1H), 7.64-7.78 (m, 4H), 8.25 (dd, 2H), 8.46 (d, 1H), 8.58 (d, 1H), 9.08 (s, 1H); HPLC Purity: 98.36%; LCMS: 502 ($M^+$+1).

N-(2-methyl-4-(4-(1-phenylethyl)piperazine-1-carbonyl)phenyl)quinoline-8-sulfonamide (XIV-37)

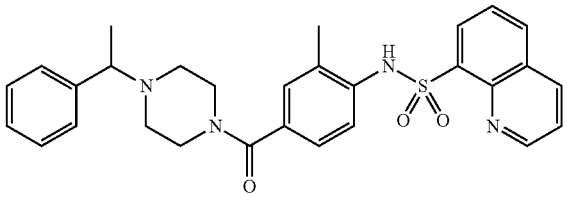

$^1$H NMR (400 MHz, DMSO-d6) δ: 1.21 (d, 3H), 2.01 (s, 3H), 2.18-2.40 (m, 4H), 3.42 (br s, 4H), 3.46 (q, 1H), 6.90 (s, 2H), 7.01 (s, 1H), 7.18-7.34 (m, 5H), 7.64-7.78 (m, 2H), 8.25 (dd, 2H), 8.38 (d, 1H), 9.18 (s, 1H), 9.31 (s, 1H); HPLC Purity: 99.85%; LCMS: 515 ($M^+$+1).

N-(2-methyl-4-(4-(2-phenylpropyl)piperazine-1-carbonyl)phenyl)quinoline-8-sulfonamide (XIV-38)

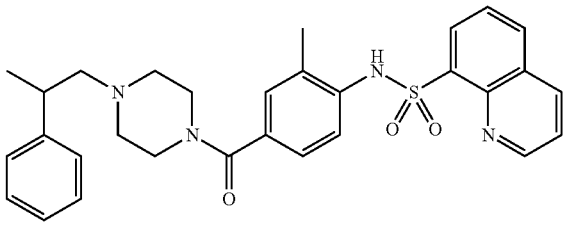

$^1$H NMR (400 MHz, DMSO-d6) δ: 1.15 (d, 3H), 2.01 (s, 3H), 2.20-2.38 (m, 6H), 3.48 (br s, 4H), 3.85 (q, 1H), 6.97 (s, 2H), 7.01 (s, 1H), 7.05-7.30 (m, 5H), 7.62-7.76 (m, 2H), 8.25 (dd, 2H), 8.58 (d, 1H), 9.18 (s, 1H), 9.31 (br s, 1H); HPLC Purity: 95.95%; LCMS: 529 ($M^+$+1).

N-(2-methyl-4-(4-(3-phenylpropyl)piperazine-1-carbonyl)phenyl)quinoline-8-sulfonamide (XIV-39)

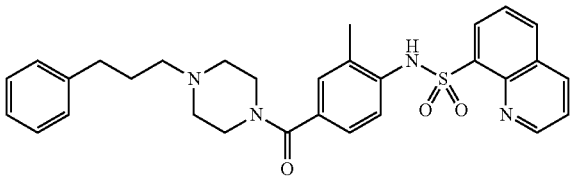

$^1$H NMR (400 MHz, DMSO-d6) δ: 1.62 (m, 2H), 2.01 (s, 3H), 2.18-2.40 (m, 6H), 2.56 (br s, 2H), 3.43-3.56 (m, 4H), 6.97 (s, 2H), 7.01 (s, 1H), 7.13-7.28 (m, 5H), 7.64-7.78 (m, 2H), 8.25 (dd, 2H), 8.56 (d, 1H), 9.10 (s, 1H), 9.31 (s, 1H); HPLC Purity: 98.98%; LCMS: 529 ($M^+$+1).

N-(2-methyl-4-(4-phenethylpiperazine-1-carbonyl)phenyl)quinoline-8-sulfonamide (XIV-40) 25

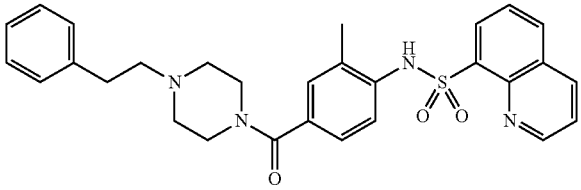

$^1$H NMR (400 MHz, $CDCl_3$) δ 2.01 (s, 3H), 2.38 (br s, 4H), 2.58 (t, 2H), 2.65 (t, 2H), 3.50 (br s, 4H), 6.97 (s, 2H), 7.01 (s, 1H), 7.15-7.28 (m, 5H), 7.62-7.78 (m, 2H), 8.25 (dd, 2H), 8.38 (d, 1H), 9.18 (s, 1H), 9.31 (br s, 1H); LCMS: 515 ($M^+$+1); HPLC Purity: 97.07%.

N-(3-methoxy-4-(4-phenethylpiperazine-1-carbonyl)phenyl)quinoline-8-sulfonamide (XIV-41)

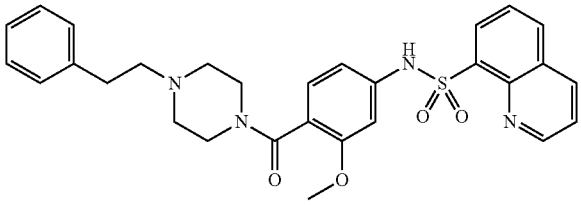

[$^1$H NMR (400 MHz, DMSO-d6) δ 2.21-2.58 (m, 6H), 2.73-2.79 (m, 2H), 3.18 (d, 2H), 3.66 (s, 3H), 6.38 (d, 1H), 6.87 (d, 2H), 7.19-7.30 (m, 4H), 7.59-7.62 (m, 2H), 8.02 (d, 1H), 8.25 (d, 2H), 8.35 (d, 1H), 8.42 (s, 2H), 9.18 (d, 1H);] HPLC Purity: 99.42%; LCMS: 531 ($M^+$+1).

N-(3-methoxy-4-(4-(1-phenylethyl)piperazine-1-carbonyl)phenyl)quinoline-8-sulfonamide (XIV-42)

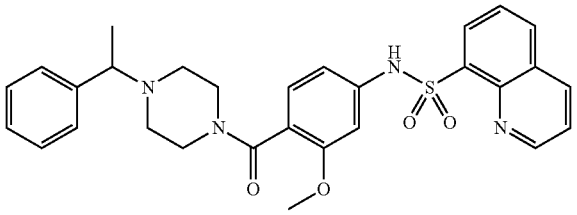

$^1$H NMR (400 MHz, $CDCl_3$) δ: 1.34 (d, 3H), 2.15-2.40 (m, 4H), 3.20 (br s, 4H), 3.35 (q, 1H), 3.62 (s, 3H), 6.35 (d, 1H), 6.82 (d, 2H), 7.18-7.28 (m, 3H), 7.58-7.62 (m, 2H), 8.02 (d, 1H), 8.28 (d, 1H), 8.35 (d, 1H), 8.41 (s, 1H), 9.18 (d, 1H); HPLC Purity: 97.00%; LCMS: 531 ($M^+$+1).

N-(3-methoxy-4-(4-(2-phenylpropyl)piperazine-1-carbonyl)phenyl)quinoline-8-sulfonamide (XIV-43)

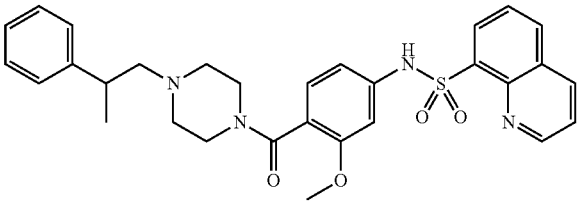

$^1$H NMR (400 MHz, $CDCl_3$) δ: 1.21 (d, 3H), 2.12-2.45 (m, 6H), 2.84-2.93 (m, 1H), 3.10 (br s, 4H), 3.62 (s, 3H), 6.37 (d, 1H), 6.82 (d, 2H), 7.18 (d, 2H), 7.28 (d, 2H), 7.58-7.62 (m, 2H), 8.02 (d, 1H), 8.28 (d, 1H), 8.35 (d, 1H), 8.41 (s, 1H), 9.18 (d, 1H); HPLC Purity: 99.00%; LCMS: 545 ($M^+$+1).

N-(3-methoxy-4-(4-(3-phenylpropyl)piperazine-1-carbonyl)phenyl)quinoline-8-sulfonamide (XIV-44)

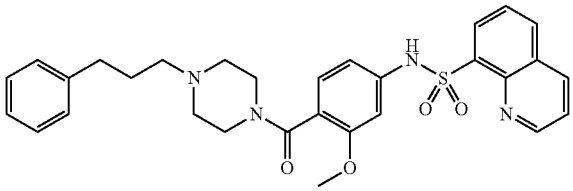

$^1$H NMR (400 MHz, $CDCl_3$) δ: 1.78 (pentate, 2H), 2.20 (br s, 2H), 2.35 (t, 4H), 2.60 (t, 2H), 3.15 (m, 4H), 3.62 (s, 3H), 6.35 (d, 1H), 6.84 (d, 2H), 7.10-7.28 (m, 4H), 7.58-7.62 (m, 2H), 8.02 (d, 1H), 8.28 (d, 1H), 8.35 (d, 1H), 8.41 (s, 1H), 9.18 (d, 1H); HPLC Purity: 99.00%; LCMS: 545 ($M^+$+1).

N-(2-fluoro-4-(4-phenethylpiperazine-1-carbonyl)phenyl)quinoline-8-sulfonamide (XIV-45)

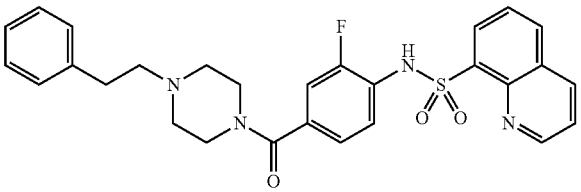

[$^1$H NMR (400 MHz, $CDCl_3$) δ: 2.44 (m, 4H), 2.59 (br s, 2H), 2.76 (d, 2H), 3.40 (br s, 2H), 3.62 (br s, 2H), 6.90 (d, 1H), 7.01 (d, 1H), 7.12-7.30 (m, 4H), 7.58-7.62 (m, 2H), 7.70 (t, 1H), 8.02 (d, 1H), 8.28 (d, 1H), 8.37 (d, 1H), 8.81 (br s, 1H), 9.18 (d, 1H);] HPLC Purity: 96.00%; LCMS: 519 ($M^+$+1).

N-(2-fluoro-4-(4-(1-phenylethyl)piperazine-1-carbonyl)phenyl)quinoline-8-sulfonamide (XIV-46)

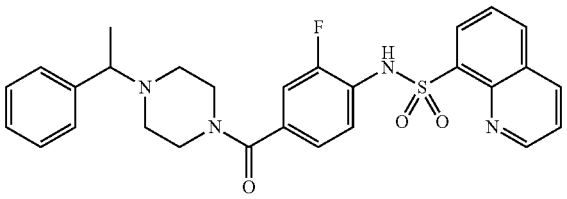

$^1$H NMR (400 MHz, $CDCl_3$) δ: 1.31 (d, 3H), 2.38 (br s, 4H), 3.36 (q, 3H), 3.58 (br s, 2H), 6.82 (d, 1H), 7.00 (d, 1H), 7.18-7.30 (d, 5H), 7.58-7.62 (m, 2H), 7.70 (t, 1H), 8.02 (d, 1H), 8.28 (d, 1H), 8.35 (d, 1H), 8.41 (s, 1H), 8.80 (br s, 1H), 9.18 (d, 1H); HPLC Purity: 99.00%; LCMS: 519 ($M^+$+).

N-(2-fluoro-4-(4-(2-phenylpropyl)piperazine-1-carbonyl)phenyl)quinoline-8-sulfonamide (XIV-47)

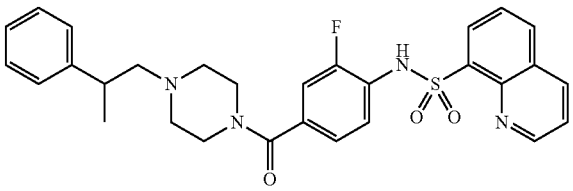

$^1$H NMR (400 MHz, $CDCl_3$) δ: 1.21 (d, 3H), 2.20-2.55 (m, 6H), 2.84 (m, 1H), 3.35 (br s, 2H), 3.58 (br s, 2H), 6.82 (d, 1H), 7.01 (d, 1H), 7.12-7.28 (m, 4H), 7.58-7.62 (m, 3H), 7.70 (t, 1H), 8.02 (d, 1H), 8.28 (d, 1H), 8.35 (d, 1H), 8.80 (br s, 1H), 9.18 (d, 1H); HPLC Purity: 97.00%; LCMS: 533 ($M^+$+1).

N-(2-fluoro-4-(4-(3-phenylpropyl)piperazine-1-carbonyl)phenyl)quinoline-8-sulfonamide (XIV-48)

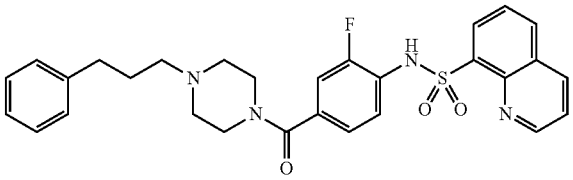

$^1$H NMR (400 MHz, $CDCl_3$) δ: 1.77 (pentate, 2H), 2.20-2.42 (m, 6H), 2.62 (t, 2H), 3.40 (br s, 2H), 3.60 (br s, 2H), 6.90 (d, 1H), 7.01 (d, 1H), 7.12-7.30 (m, 4H), 7.58-7.62 (m, 2H), 7.70 (t, 1H), 8.02 (d, 1H), 8.28 (d, 1H), 8.37 (d, 1H), 8.81 (br s, 1H), 9.18 (d, 1H); HPLC Purity: 98.00%; LCMS: 533 ($M^+$+1).

N-(2-methyl-4-(4-((3-(trifluoromethyl)pyridin-2-yl)methyl)piperazine-1-carbonyl)phenyl)quinoline-8-sulfonamide (XIV-49)

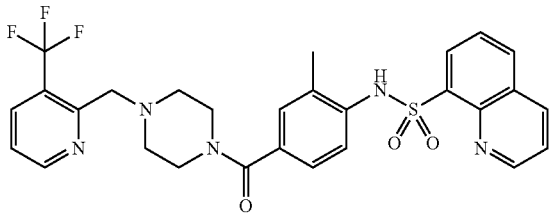

$^1$H NMR (400 MHz, DMSO-d6) δ: 2.01 (s, 3H), 2.37 (br s, 4H), 3.14 (br s, 2H), 3.46 (s, 2H), 6.97 (s, 2H), 7.06 (s, 1H), 7.51 (t, 1H), 7.62-7.77 (m, 2H), 8.17 (d, 1H), 8.25 (dd, 2H), 8.58 (d, 1H), 8.78 (s, 1H), 9.18 (s, 1H), 9.39 (s, 1H); HPLC Purity: 97.97%; LCMS: 592 ($M^+$+23).

N-(2-methyl-4-(4-((4-(trifluoromethyl)pyridin-3-yl)methyl)piperazine-1-carbonyl)phenyl)quinoline-8-sulfonamide (XIV-50)

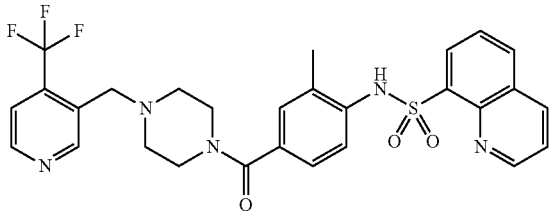

$^1$H NMR (400 MHz, DMSO-d6) δ: 2.01 (s, 3H), 2.37 (br s, 4H), 3.46 (br s, 4H), 3.64 (s, 2H), 6.97 (s, 2H), 7.06 (s, 1H), 7.62-7.77 (m, 3H), 8.20-8.30 (m, 2H), 8.56 (d, 1H), 8.78 (s, 1H), 8.90 (s, 1H), 9.18 (s, 1H), 9.39 (br s, 1H); HPLC Purity: 98.71%; LCMS: 570 ($M^+$+1).

N-(4-(4-((5-chloropyridin-3-yl)methyl)piperazine-1-carbonyl)-2-methylphenyl)quinoline-8-sulfonamide (XIV-51)

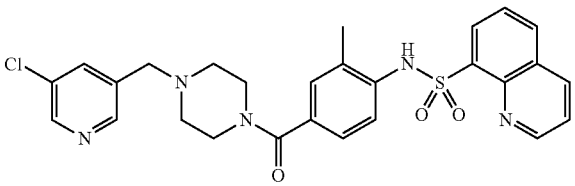

$^1$H NMR (400 MHz, DMSO-d6) δ: 2.01 (s, 3H), 2.37 (br s, 4H), 3.26 (br s, 4H), 3.51 (s, 2H), 6.98 (s, 2H), 7.06 (s, 1H), 7.62-7.77 (m, 2H), 7.81 (s, 1H), 8.25 (dd, 2H), 8.41 (s, 1H), 8.50 (s, 1H), 8.58 (d, 1H), 9.11 (s, 1H), 9.39 (s, 1H); HPLC Purity: 99.11%; LCMS: 536 ($M^+$).

N-(4-(4-((3-fluoropyridin-2-yl)methyl)piperazine-1-carbonyl)-2-methylphenyl)quinoline-8-sulfonamide (XIV-52)

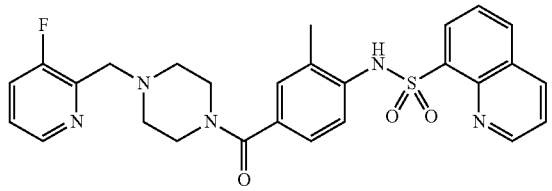

$^1$H NMR (400 MHz, DMSO-d6) δ: 2.01 (s, 3H), 2.37 (br s, 4H), 3.21 (br s, 2H), 3.46 (br s, 2H), 3.64 (s, 2H), 6.97 (s, 2H), 7.06 (s, 1H), 7.37-7.41 (m, 1H), 7.62-7.77 (m, 3H), 8.22 (d, 1H), 8.27 (d, 1H), 8.36 (s, 1H), 8.58 (d, 1H), 9.10 (s, 1H), 9.38 (s, 1H); HPLC Purity: 99.15%; LCMS: 520 ($M^+$+1).

N-(4-(4-(cyclohexylmethyl)piperazine-1-carbonyl)-2-methylphenyl)quinoline-8-sulfonamide (XIV-53)

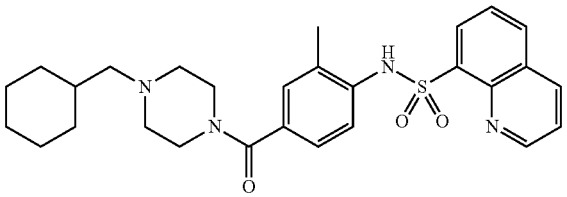

$^1$H NMR (400 MHz, DMSO-d6) δ: 0.72-0.90 (m, 2H), 1.05-1.21 (m, 4H), 1.41 (br s, 1H), 1.56-1.74 (m, 4H), 2.01 (s, 3H), 2.25 (br s, 5H), 3.20 (br s, 2H), 3.46 (br s, 2H), 6.97 (s, 2H), 7.06 (s, 1H), 7.62-7.77 (m, 2H), 8.25 (dd, 2H), 8.58 (d, 1H), 9.18 (s, 1H), 9.39 (br s, 1H); HPLC Purity: 94.98%; LCMS: 507 ($M^+$+1).

N-(2-methyl-4-(4-(pyridin-3-ylmethyl)piperazine-1-carbonyl)phenyl)quinoline-8-sulfonamide (XIV-54)

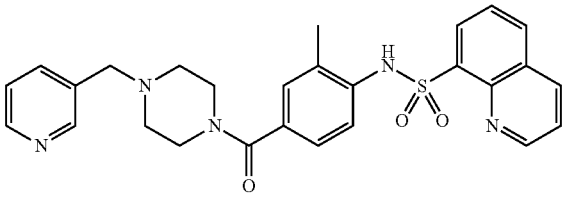

$^1$H NMR (400 MHz, DMSO-d6) δ: 2.01 (s, 3H), 2.30 (br s, 4H), 3.41 (br s, 4H), 3.46 (s, 2H), 6.97 (s, 2H), 7.06 (s, 1H), 7.31 (t, 1H), 7.62-7.77 (m, 2H), 8.25 (dd, 2H), 8.42 (s, 2H), 8.58 (d, 1H), 9.18 (s, 1H), 9.39 (s, 1H); HPLC Purity: 96.73%; LCMS: 502 ($M^+$+1).

N-(2 -methyl-4-(4-((1 -phenylcyclopropyl)methyl) piperazine-1-carbonyl)phenyl)quinoline-8-sulfonamide (XIV-55)

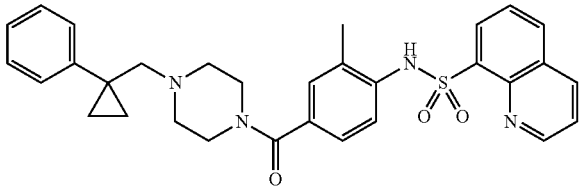

$^1$H NMR (400 MHz, DMSO-d6) δ: 0.65 (s, 2H), 0.78 (s, 2H), 2.01 (s, 3H), 2.36 (br s, 4H), 2.63 (br s, 2H), 3.41 (br s, 4H), 6.97 (s, 2H), 7.06 (s, 1H), 7.12 (t, 1H), 7.20-7.28 (m, 4H), 7.62-7.77 (m, 2H), 8.25 (dd, 2H), 8.58 (d, 1H), 9.18 (s, 1H), 9.39 (s, 1H); HPLC Purity: 96.19%; LCMS: 541 ($M^+$+1).

N-(2-fluoro-4-(4-(3-fluorobenzyl)piperazine-1-carbonyl)phenyl)quinoline-8-sulfonamide (XIV-56)

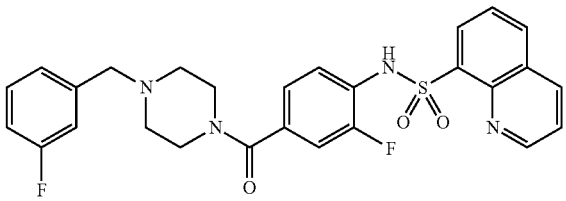

$^1$H NMR (400 MHz, DMSO-d6) δ: 2.45 (s, 4H), 3.56 (br s, 4H), 3.66 (s, 2H), 7.06-7.26 (m, 4H), 7.28-7.39 (m, 2H), 7.62-7.79 (m, 3H), 8.21-8.36 (m, 2H), 8.57 (d, 1H), 9.18 (s, 1H), 9.85 (s, 1H); HPLC Purity: 93.25%; LCMS: 522.57 ($M^+$).

N-(4-(4-(3-chlorobenzyl)piperazine-1-carbonyl)-2-fluorophenyl)quinoline-8-sulfonamide (XIV-57)

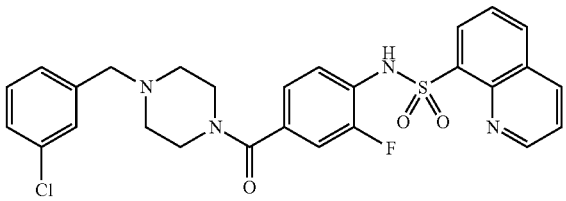

$^1$H NMR (400 MHz, DMSO-d6) δ: 2.25 (s, 4H), 3.41 (br s, 4H), 3.47 (s, 2H), 7.01-7.09 (m, 2H), 7.22-7.36 (m, 5H), 7.61-7.78 (m, 2H), 8.21-8.38 (m, 2H), 8.55-8.60 (m, 1H), 9.01 (s, 1H), 9.9 (s, 1H) HPLC Purity: 97.30%; LCMS: 539 ($M^+$).

N-(4-(4-(2,4-dichlorobenzyl)piperazine-1-carbonyl)-3-methoxyphenyl)quinoline-8-sulfonamide (XIV-58)

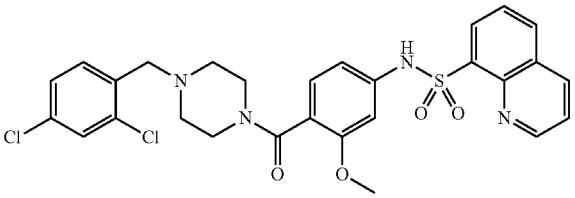

$^1$H NMR (400 MHz, DMSO-d6) δ: 2.20-2.39 (m, 4H), 3.41 (br s, 4H), 3.46 (s, 2H), 3.56 (s, 3H), 6.61-6.81 (m, 3H), 7.36-7.60 (m, 3H), 7.62-7.67 (m, 2H), 8.25 (d, 1H), 8.41-8.58 (m, 2H), 9.18 (s, 1H), 10.25 (s, 1H); HPLC Purity: 98.16%; LCMS: 585.50 ($M^+$).

N-(4-(4-(3,5-dichlorobenzyl)piperazine-1-carbonyl)-3-methoxyphenyl)quinoline-8-sulfonamide (XIV-59)

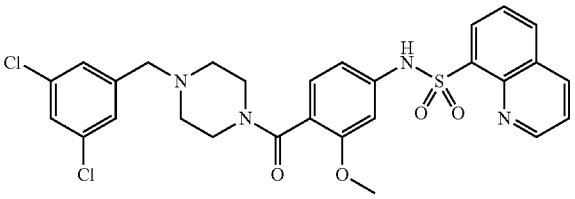

$^1$H NMR (400 MHz, DMSO-d6) δ: 2.20-2.39 (m, 4H), 3.26 (br s, 4H), 3.46 (s, 2H), 3.56 (s, 3H) 6.61-6.85 (m, 3H), 7.26 (s, 2H), 7.45 (s, 1H), 7.63-7.78 (m, 2H), 8.20-8.60 (m, 3H), 9.18 (s, 1H), 10.25 (s, 1H); HPLC Purity: 97.92%; LCMS: 584.1 ($M^+$).

N-(4-(4-(3-chloro-4-fluorobenzyl)piperazine-1-carbonyl)-3-methoxyphenyl)quinoline-8-sulfonamide (XIV-60)

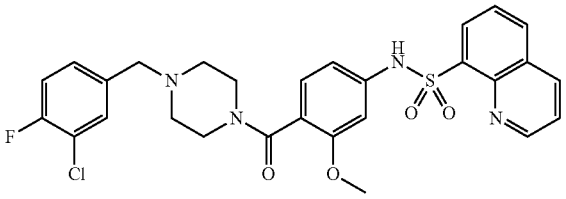

$^1$H NMR (400 MHz, DMSO-d6) δ: 2.20-2.39 (m, 4H), 3.26 (br s, 4H), 3.46 (s, 2H), 3.56 (s, 3H), 6.61-6.85 (m, 3H), 7.21-7.55 (m, 3H), 7.62-7.75 (m, 2H), 8.21-8.60 (m, 3H), 9.18 (s, 1H), 10.25 (s, 1H); HPLC Purity: 98.4%; LCMS: 569 ($M^+$).

N-(3-methoxy-4-(4-(4-(trifluoromethyl)benzyl)piperazine-1-carbonyl)phenyl)quinoline-8-sulfonamide (XIV-61)

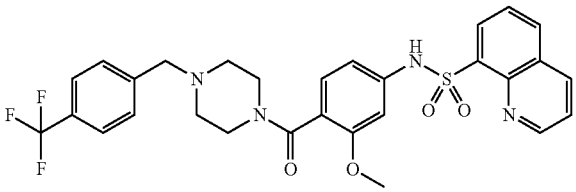

$^1$H NMR (400 MHz, DMSO-d6) δ: 2.20-2.39 (m, 4H), 2.97 (br s, 4H), 3.46 (s, 2H), 3.56 (s, 3H), 6.61-6.85 (m, 3H), 7.42-7.58 (m, 2H), 7.61-7.78 (m, 4H), 8.21-8.60 (m, 3H), 9.18 (s, 1H), 10.25 (s, 1H); HPLC Purity: 99.24%; LCMS: 584.6 ($M^+$).

N-(4-(4-(3,4-dichlorobenzyl)piperazine-1-carbonyl)-3-methoxyphenyl)quinoline-8-sulfonamide (XIV-62)

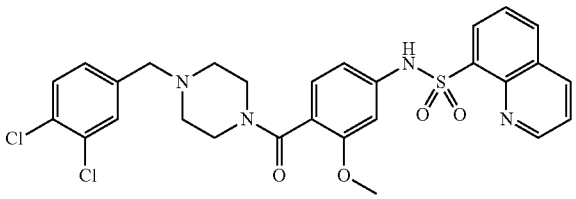

$^1$H NMR (400 MHz, DMSO-d6) δ: 2.08-2.39 (m, 4H), 2.97 (br s, 4H), 3.46 (s, 2H), 3.56 (s, 3H), 6.61-6.85 (m, 3H), 7.25 (d, 1H), 7.45-7.60 (m, 2H), 7.63-7.80 (m, 2H), 7.62-7.77 (m, 3H), 8.21-8.60 (m, 3H), 9.18 (s, 1H), 10.25 (s, 1H), HPLC Purity: 98.45%; LCMS: 585.50 ($M^+$).

N-(4-(4-(2-fluorobenzyl)piperazine-1-carbonyl)-3-methoxyphenyl)quinoline-8-sulfonamide (XIV-63)

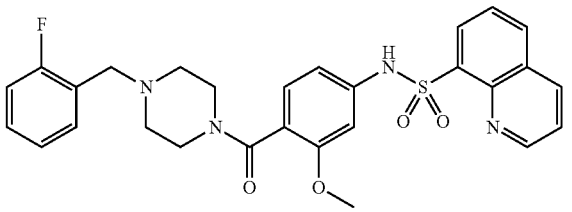

$^1$H NMR (400 MHz, DMSO-d6) δ: 2.08-2.39 (m, 4H), 2.97 (br s, 4H), 3.46 (s, 2H), 3.56 (s, 3H), 6.61-6.85 (m, 3H), 7.06-7.45 (m, 4H), 7.71 (s, 2H), 8.21-8.60 (m, 3H), 9.18 (s, 1H), 10.25 (s, 1H) HPLC Purity: 98.29%; LCMS: 534.8 ($M^+$).

N-(4-(4-(2,4-difluorobenzyl)piperazine-1-carbonyl)-3-methoxyphenyl)quinoline-8-sulfonamide (XIV-64)

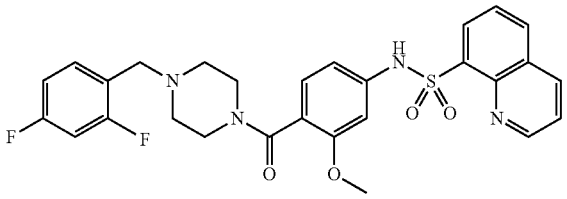

$^1$H NMR (400 MHz, DMSO-d6) δ: 2.08-2.39 (m, 4H), 2.97 (br s, 4H), 3.46 (s, 2H), 3.56 (s, 3H), 6.61-6.85 (m, 3H), 7.01-7.21 (m, 2H), 7.35-7.42 (m, 1H), 7.62-7.78 (m, 2H), 8.21-8.60 (m, 3H), 9.18 (s, 1H), 10.25 (s, 1H) HPLC Purity: 99.00%; LCMS: 552.59 ($M^+$).

N-(4-(4-(2,3-dichlorobenzyl)piperazine-1-carbonyl)-3-methoxyphenyl)quinoline-8-sulfonamide (XIV-65)

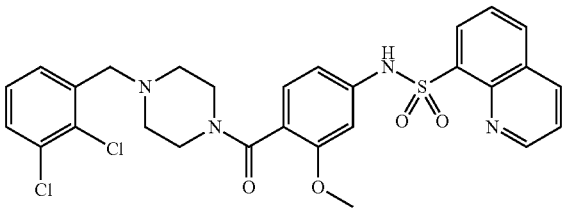

$^1$H NMR (400 MHz, DMSO-d6) δ: 2.08-2.39 (m, 4H), 3.21 (br s, 4H), 3.46 (s, 2H), 3.61 (s, 3H), 6.61-6.85 (m, 3H), 7.35-7.59 (m, 3H), 7.63-7.75 (m, 2H), 8.21-8.60 (m, 3H), 9.18 (s, 1H), 10.25 (s, 1H); HPLC Purity: 99.17%; LCMS: 585.50 ($M^+$).

N-(4-(4-(4-chloro-2-fluorobenzyl)piperazine-1-carbonyl)-3-methoxyphenyl)quinoline-8-sulfonamide (XIV-66)

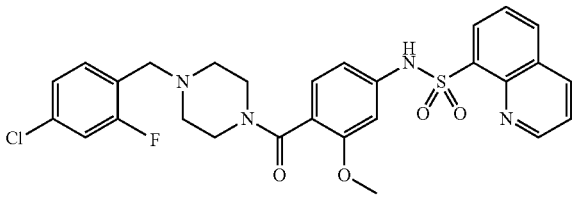

$^1$H NMR (400 MHz, DMSO-d6) δ: 2.08-2.39 (m, 4H), 3.25 (br s, 4H), 3.46 (s, 2H), 3.61 (s, 3H), 6.61-6.85 (m, 3H), 7.22-7.42 (m, 3H), 7.65-7.75 (m, 2H), 8.21-8.60 (m, 3H), 9.18 (s, 1H), 10.25 (s, 1H); HPLC Purity: 91.3%; LCMS: 569 ($M^+$).

N-(4-(4-(2,3-difluorobenzyl)piperazine-1-carbonyl)-3-methoxyphenyl)quinoline-8-sulfonamide (XIV-67)

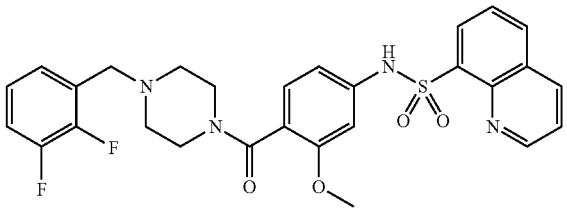

$^1$H NMR (400 MHz, DMSO-d6) δ: 2.08-2.39 (m, 4H), 3.21 (br s, 4H), 3.46 (s, 2H), 3.61 (s, 3H), 6.61-6.85 (m, 3H), 7.12-7.40 (m, 3H), 7.65-7.75 (m, 2H), 8.21-8.62 (m, 3H), 9.18 (s, 1H), 10.25 (s, 1H); HPLC Purity: 98.39%; LCMS: 552.5 ($M^+$).

N-(4-(4-(cyclopropylmethyl)piperazine-1-carbonyl)-3-methoxyphenyl)quinoline-8-sulfonamide (XIV-68)

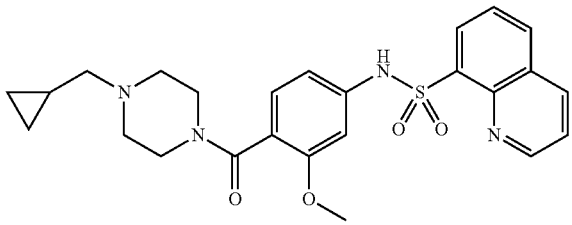

$^1$H NMR (400 MHz, DMSO-d6) δ: 0.10-0.15 (m, 2H), 0.70-0.82 (m, 1H), 1.20-1.30 (m, 2H), 2.02-2.42 (m, 6H), 2.90-3.05 (m, 4H), 3.63 (s, 3H), 6.61-6.85 (m, 3H), 7.65-7.75 (m, 2H), 8.21-8.60 (m, 3H), 9.18 (s, 1H), 10.25 (s, 1H), HPLC Purity: 98%; LCMS: 480.5 ($M^+$).

N-(4-(4-((5-chloropyridin-3-yl)methyl)piperazine-1-carbonyl)-3-methoxyphenyl)quinoline-8-sulfonamide (XIV-69)

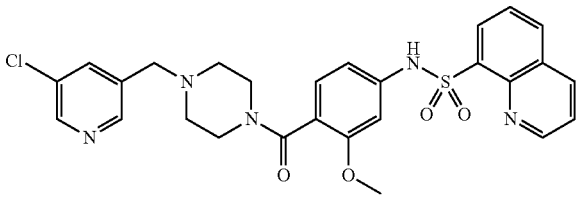

$^1$H NMR (400 MHz, DMSO-d6) δ: 2.08-2.39 (m, 4H), 3.21 (br s, 4H), 3.46 (s, 2H), 3.61 (s, 3H), 6.61-6.85 (m, 3H), 7.62-7.83 (m, 3H), 8.21-8.60 (m, 5H), 9.18 (s, 1H), 10.25 (s, 1H); HPLC Purity: 96.1%; LCMS: 551 ($M^+$).

N-(4-(4-((3-fluoropyridin-2-yl)methyl)piperazine-1-carbonyl)-3-methoxyphenyl)quinoline-8-sulfonamide (XIV-70)

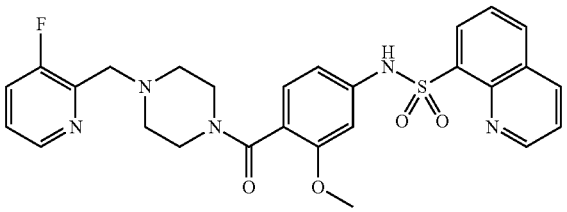

$^1$H NMR (400 MHz, DMSO-d6) δ: 2.08-2.39 (m, 4H), 3.21 (br s, 4H), 3.46 (s, 2H), 3.61 (s, 3H), 6.61-6.85 (m, 3H), 7.38-4.42 (m, 1H), 7.61-7.78 (m, 3H), 8.21-8.60 (m, 4H), 9.18 (s, 1H), 10.25 (s, 1H); HPLC Purity: 99.54%; LCMS: 535.5 ($M^+$).

N-(3-methoxy-4-(4-((4-(trifluoromethyl)pyridin-3-yl)methyl)piperazine-1-carbonyl)phenyl)quinoline-8-sulfonamide (XIV-71)

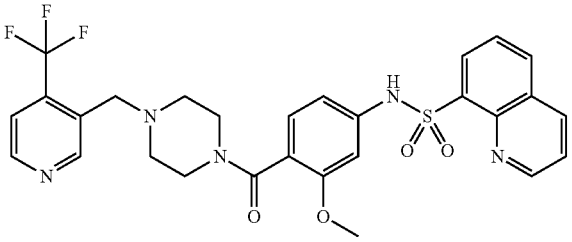

$^1$H NMR (400 MHz, DMSO-d6) δ: 2.08-2.39 (m, 4H), 3.15 (br s, 4H), 3.46 (s, 2H), 3.61 (s, 3H), 6.61-6.85 (m, 3H), 7.62-7.77 (m, 3H), 8.21-8.60 (m, 3H), 8.70-8.90 (m, 2H), 9.18 (s, 1H), 10.25 (s, 1H); HPLC Purity: 98.48%; LCMS: 585.6 ($M^+$).

N-(3-methoxy-4-(4-((3-(trifluoromethyl)pyridin-2-yl)methyl)piperazine-1-carbonyl)phenyl)quinoline-8-sulfonamide (XIV-72)

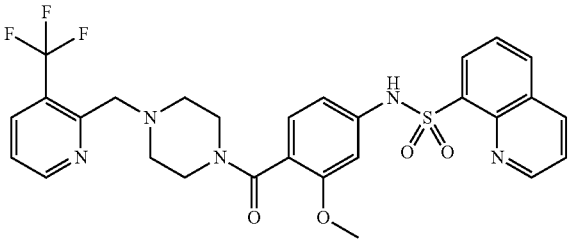

$^1$H NMR (400 MHz, DMSO-d6) δ: 2.25 (br s, 4H), 2.85 (br s, 2H), 3.42 (br s, 2H), 3.58 (s, 3H), 3.76 (br s, 2H), 6.60 (d, 1H), 6.78 (s, 1H), 6.92 (d, 1H), 7.46 (t, 1H), 7.63-7.70 (m, 2H), 8.18 (d, 1H), 8.22 (d, 1H), 8.37-8.45 (dd, 2H), 8.78 (d, 1H), 9.18 (s, 1H), 10.29 (s, 1H); HPLC Purity: 95.85%; LCMS: 586.1 ($M^+$+1).

N-(4-(4-((3-methoxypyridin-2-yl)methyl)piperazine-1-carbonyl)-2-methylphenyl)quinoline-8-sulfonamide (XIV-73)

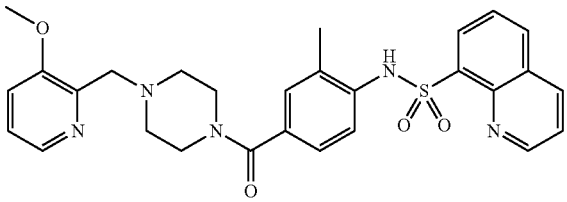

$^1$H NMR (400 MHz, DMSO-d6) δ: 2.01 (s, 3H), 2.39 (br s, 4H), 3.46 (s, 4H), 3.61 (s, 2H), 3.79 (s, 3H), 6.97 (s, 2H), 7.06 (s, 1H), 7.22-7.32 (s, 1H), 7.39 (d, 1H), 7.64-7.81 (m, 2H), 8.12 (d, 1H), 8.21-8.36 (m, 2H), 8.57 (d, 1H), 9.18 (s, 1H), 9.39 (s, 1H); HPLC Purity: 99.29%; LCMS: 532 ($M^+$).

N-(4-(4-((4-methoxypyridin-3-yl)methyl)piperazine-1-carbonyl)-2-methylphenyl)quinoline-8-sulfonamide (XIV-74)

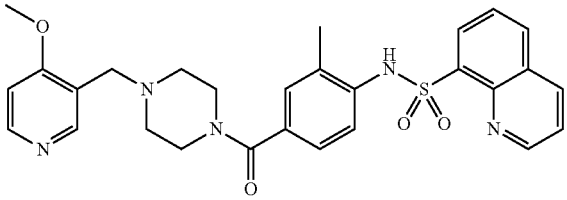

$^1$H NMR (400 MHz, DMSO-d6) δ: 2.01 (s, 3H), 2.37 (br s, 4H), 3.46 (br s, 6H), 3.79 (s, 3H), 6.97-7.06 (m, 3H), 7.10 (s, 1H), 7.66-7.79 (m, 2H), 8.21-8.38 (m, 4H), 8.57 (d, 1H), 9.16 (s, 1H), 9.39 (s, 1H); HPLC Purity: 98.22%; LCMS: 532 ($M^+$+1).

N-(4-(4-((5-fluoropyridin-3-yl)methyl)piperazine-1-carbonyl)-2-methylphenyl)quinoline-8-sulfonamide (XIV-75)

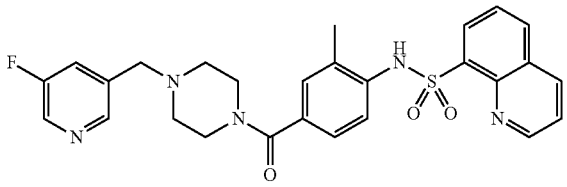

$^1$H NMR (400 MHz, DMSO-d6) δ: 2.01 (s, 3H), 2.37 (br s, 4H), 3.25 (s, 4H), 3.58 (s, 2H), 6.96 (s, 2H), 7.06 (s, 1H), 7.60-7.79 (m, 3H), 8.21-8.30 (m, 3H), 8.43 (s, 1H), 8.57 (d, 1H), 9.16 (s, 1H), 9.39 (s, 1H); HPLC Purity: 94.48%; LCMS: 520.3 ($M^+$+1).

N-(4-(4-((5-fluoropyridin-3-yl)methyl)piperazine-1-carbonyl)-2-methylphenyl)quinoline-8-sulfonamide (XIV-76)

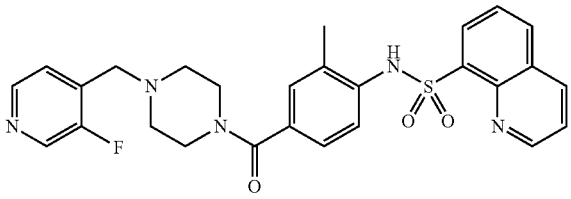

$^1$H NMR (400 MHz, DMSO-d6) δ: 2.01 (s, 3H), 2.37 (br s, 4H), 3.25 (s, 4H), 3.58 (s, 2H), 6.96 (s, 2H), 7.06 (s, 1H), 7.42 (t, 1H), 7.60-7.79 (m, 2H), 8.21-8.30 (m, 3H), 8.46 (s, 1H), 8.57 (d, 1H), 9.16 (s, 1H), 9.39 (s, 1H); HPLC Purity: 99.87%; LCMS: 520.3 ($M^+$+1).

N-(4-(4-(2-fluoro-4-methoxybenzyl)piperazine-1-carbonyl)-2-methylphenyl)quinoline-8-sulfonamide (XIV-77)

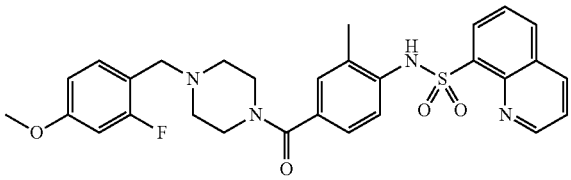

$^1$H NMR (400 MHz, DMSO-d6) δ: 2.01 (s, 3H), 2.37 (br s, 4H), 3.25 (br s, 4H), 3.58 (s, 2H), 3.76 (s, 3H), 6.65-6.78 (m, 2H), 6.96 (s, 2H), 7.06 (s, 1H), 7.21 (t 1H), 7.61-7.79 (m, 2H), 8.21-8.30 (m, 2H), 8.57 (d, 1H), 9.16 (s, 1H), 9.39 (s, 1H); HPLC Purity: 99.37%; LCMS: 549.3 ($M^+$+1).

N-(4-(4-((3-chloropyridin-4-yl)methyl)piperazine-1-carbonyl)-2-methylphenyl)quinoline-8-sulfonamide (XIV-78)

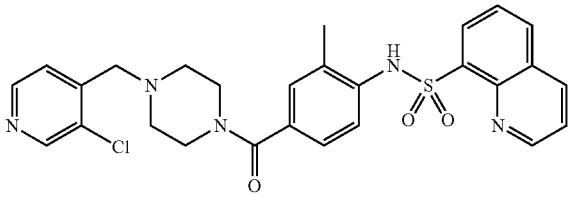

$^1$H NMR (400 MHz, DMSO-d6) δ: 2.01 (s, 3H), 2.37 (br s, 4H), 3.24 (br s, 4H), 3.59 (br s, 2H), 6.97 (s, 2H), 7.06 (s, 1H), 7.46 (d, 1H), 7.62-7.77 (m, 2H), 8.21-8.30 (m, 2H), 8.44 (d, 1H), 8.52-8.60 (m, 2H), 9.16 (s, 1H), 9.39 (s, 1H); HPLC Purity: 99.46%; LCMS: 536 ($M^+$).

N-(4-(4-(3-fluoro-4-methoxybenzyl)piperazine-1-carbonyl)-2-methylphenyl)quinoline-8-sulfonamide (XIV-79)

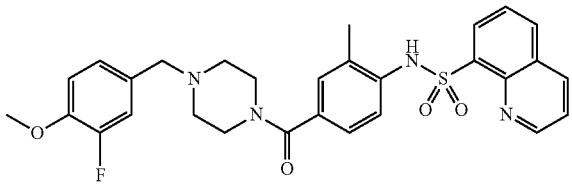

$^1$H NMR (400 MHz, DMSO-d6) δ: 2.01 (s, 3H), 2.37 (br s, 4H), 3.25 (s, 4H), 3.58 (s, 2H), 3.79 (s, 3H), 6.96-7.18 (m, 6H), 7.60-7.78 (m, 2H), 8.21-8.36 (m, 2H), 8.57 (d, 1H), 9.16 (s, 1H), 9.39 (s, 1H); HPLC Purity: 99.01%; LCMS: 549.3 ($M^+$+1).

N-(4-(4-(2,4-difluorobenzyl)piperazine-1-carbonyl)-2-methoxyphenyl)quinoline-8-sulfonamide (XIV-80)

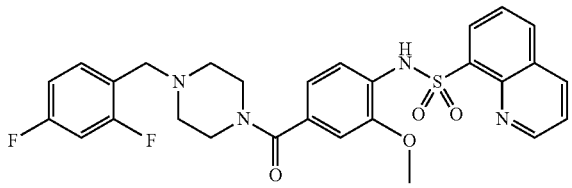

$^1$H NMR (400 MHz, DMSO-d6) δ: 2.37 (br s, 4H), 3.31 (s, 6H), 3.56 (s, 3H), 6.75 (s, 1H), 6.81 (d, 1H), 7.05 (t 1H), 7.20 (t 1H), 7.37-7.42 (m, 2H), 7.66-7.79 (m, 2H), 8.25 (d, 2H), 8.57 (d, 1H), 9.13 (s, 1H), 9.21 (s, 1H); HPLC Purity: 99.51%; LCMS: 553 ($M^+$).

N-(4-(4-(2,3-difluorobenzyl)piperazine-1-carbonyl)-2-methoxyphenyl)quinoline-8-sulfonamide (XIV-81)

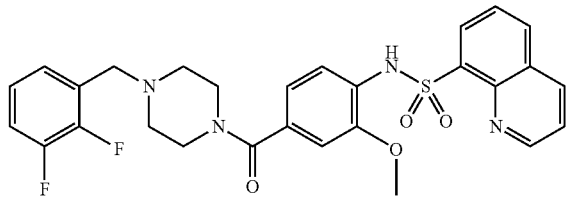

$^1$H NMR (400 MHz, DMSO-d6) δ: 2.37 (br s, 4H), 3.31 (br s, 6H), 3.58 (s, 3H), 6.75 (s, 1H), 6.81 (d, 1H), 7.05-7.12 (m, 1H), 7.22-7.38 (m, 1H), 7.41 (d, 1H), 7.66-7.79 (m, 2H), 8.25 (d, 2H), 8.57 (d, 1H), 9.13 (s, 1H), 9.21 (s, 1H); HPLC Purity: 96.99%; LCMS: 553 ($M^+$).

N-(4-(4-(4-chloro-2-fluorobenzyl)piperazine-1-carbonyl)-2-methoxyphenyl)quinoline-8-sulfonamide (XIV-82)

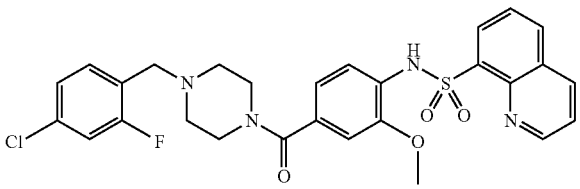

$^1$H NMR (400 MHz, DMSO-d6) δ: 2.37 (br s, 4H), 3.31 (s, 6H), 3.58 (s, 3H), 6.75 (s, 1H), 6.81 (d, 1H), 7.21 (d, 1H), 7.33-7.44 (m, 3H), 7.66-7.79 (m, 2H), 8.25 (d, 2H), 8.57 (d, 1H), 9.13 (s, 1H), 9.21 (s, 1H); HPLC Purity: 97.45%; LCMS: 553 ($M^+$).

N-(4-(4-(3,4-dichlorobenzyl)piperazine-1-carbonyl)-2-methoxyphenyl)quinoline-8-sulfonamide (XIV-83)

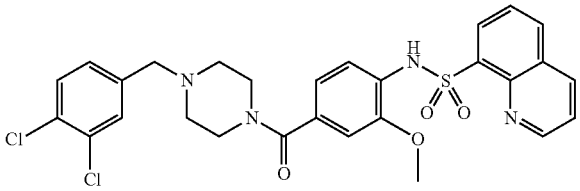

$^1$H NMR (400 MHz, DMSO-d6) δ: 2.37 (br s, 4H), 3.31 (br s, 6H), 3.55 (s, 3H), 6.75 (s, 1H), 6.81 (d, 1H), 7.23 (d, 1H), 7.42 (d, 1H), 7.55-7.61 (m, 2H), 7.66-7.79 (m, 2H), 8.25 (d, 2H), 8.57 (d, 1H), 9.13 (s, 1H), 9.21 (s, 1H); HPLC Purity: 99.49%; LCMS: 585 ($M^+$).

N-(4-(4-(3,5-dichlorobenzyl)piperazine-1-carbonyl)-2-methoxyphenyl)quinoline-8-sulfonamide (XIV-84)

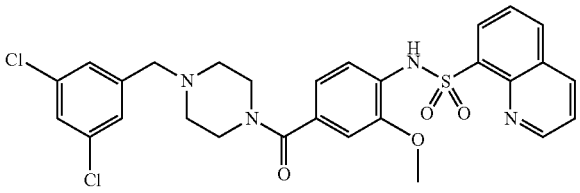

$^1$H NMR (400 MHz, DMSO-d6) δ 2.37 (br s, 4H), 3.31 (br s, 6H), 3.55 (s, 3H), 6.75 (s, 1H), 6.81 (d, 1H), 7.38 (s, 1H), 7.42-7.50 (m, 3H), 7.66-7.79 (m, 2H), 8.25 (d, 2H), 8.59 (d, 1H), 9.13 (s, 1H), 9.21 (s, 1H); HPLC Purity: 99.43%; LCMS: 585 ($M^+$).

N-(4-(4-(2,4-dichlorobenzyl)piperazine-1-carbonyl)-2-methoxyphenyl)quinoline-8-sulfonamide (XIV-85)

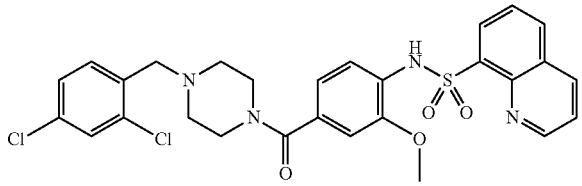

$^1$H NMR (400 MHz, DMSO-d6) δ 2.37 (br s, 4H), 3.31 (br s, 4H), 3.41 (s, 2H), 3.57 (s, 3H), 6.75 (s, 1H), 6.81 (d, 1H), 7.38-7.59 (m, 4H), 7.64-7.79 (m, 2H), 8.25 (d, 2H), 8.59 (d, 1H), 9.13 (s, 1H), 9.21 (s, 1H); HPLC Purity: 99.87%; LCMS: 585 ($M^+$).

N-(2-methoxy-4-(4-(2-phenylpropyl)piperazine-1-carbonyl)phenyl)quinoline-8-sulfonamide (XIV-86)

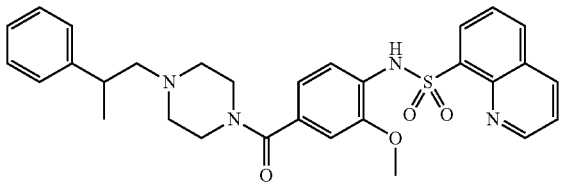

$^1$H NMR (400 MHz, DMSO-d6) δ: 1.18 (d, 3H), 2.37 (br s, 4H), 2.41 (m, 1H), 2.46 (br s, 4H), 3.36 (br s, 2H), 3.41 (s, 3H), 6.75 (s, 1H), 6.81 (d, 1H), 7.16-7.36 (m, 5H), 7.41 (d, 1H), 7.62-7.77 (m, 2H), 8.24 (d, 2H), 8.57 (d, 1H), 9.18 (s, 1H), 9.39 (s, 1H); HPLC Purity: 99.41%; LCMS: 545 ($M^+$).

N-(2-methoxy-4-(4-(3-phenylpropyl)piperazine-1-carbonyl)phenyl)quinoline-8-sulfonamide (XIV-87)

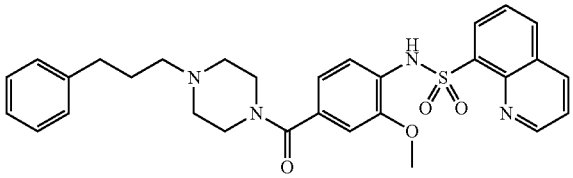

$^1$H NMR (400 MHz, DMSO-d6) δ: 1.65 (t, 2H), 2.27-2.38 (m, 6H), 2.52-2.58 (m, 2H), 3.36 (br s, 6H), 3.41 (br s, 5H), 6.75 (s, 1H), 6.81 (d, 1H), 7.16-7.32 (m, 5H), 7.41 (d, 1H), 7.62-7.77 (m, 2H), 8.24 (d, 2H), 8.57 (d, 1H), 9.18 (s, 1H), 9.39 (s, 1H); HPLC Purity: 99.69%; LCMS: 545 ($M^+$).

N-(2-methoxy-4-(4-phenethylpiperazine-1-carbonyl)phenyl)quinoline-8-sulfonamide (XIV-88)

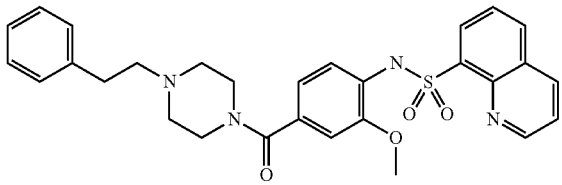

$^1$H NMR (400 MHz, DMSO-d6) δ: 2.39 (s, 4H), 2.61-2.72 (m, 2H), 3.36 (br s, 6H), 3.41 (s, 3H), 6.75 (s, 1H), 6.81 (d, 1H), 7.16-7.32 (m, 5H), 7.41 (d, 1H), 7.62-7.77 (m, 2H), 8.24 (d, 2H), 8.57 (d, 1H), 9.18 (s, 1H), 9.39 (s, 1H); HPLC Purity: 99.41%; LCMS: 545 ($M^+$+1).

N-(4-(4-((5-fluoropyridin-2-yl)methyl)piperazine-1-carbonyl)-2-methylphenyl)quinoline-8-sulfonamide (XIV-89)

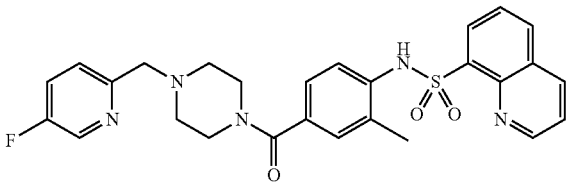

$^1$H NMR (400 MHz, DMSO-d6) δ: 2.01 (s, 3H), 2.39 (br s, 4H), 3.31 (br s, 4H), 3.61 (s, 2H), 6.98-7.08 (m, 3H), 7.44-7.56 (m, 2H), 7.62-7.79 (m, 3H), 8.21-8.32 (m, 2H), 8.41 (s, 1H), 8.56-8.60 (m, 1H), 9.16 (s, 1H), 9.38 (s, 1H); HPLC Purity: 99.82%; LCMS: 520 ($M^+$+1).

N-(4-(4-(2,4-dimethoxybenzyl)piperazine-1-carbonyl)-2-methylphenyl)quinoline-8-sulfonamide (XIV-90)

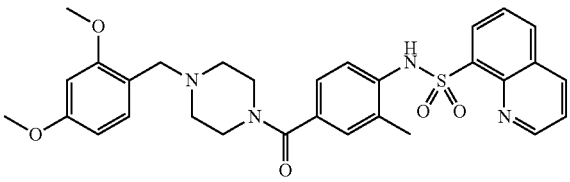

$^1$H NMR (400 MHz, DMSO-d6) δ: 2.01 (s, 3H), 2.37 (br s, 4H), 3.31 (br s, 4H), 3.42 (s, 2H), 3.76 (s, 6H), 6.42 (d, 1H), 6.52 (s, 1H), 6.97-7.18 (m, 4H), 7.64-7.79 (m, 2H), 8.21-8.36 (m, 2H), 8.59 (d, 1H), 9.16 (s, 1H), 9.39 (s, 1H); HPLC Purity: 94.33%; LCMS: 561 ($M^+$+1).

N-(4-(4-(2-fluorobenzyl)piperazine-1-carbonyl)-2-methoxyphenyl)quinoline-8-sulfonamide (XIV-91)

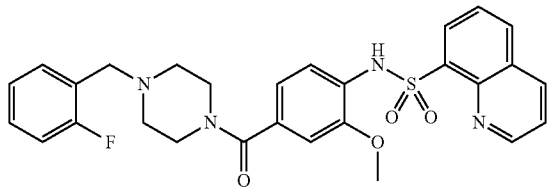

$^1$H NMR (400 MHz, DMSO-d6) δ: 2.37 (br s, 4H), 3.36 (s, 4H), 3.42 (s, 2H), 3.56 (s, 3H), 6.79 (s, 1H), 6.82 (d, 1H), 7.15-7.19 (m, 4H), 7.21-7.44 (m, 3H), 8.24 (m, 2H), 8.57 (d, 1H), 9.18 (s, 1H), 9.39 (s, 1H); HPLC Purity: 97.44%; LCMS: 535 ($M^+$).

N-(4-(4-(3-chloro-4-fluorobenzyl)piperazine-1-carbonyl)-2-methoxyphenyl)quinoline-8-sulfonamide (XIV-92)

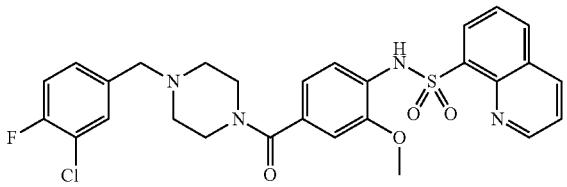

$^1$H NMR (400 MHz, DMSO-d6) δ: 2.37 (br s, 4H), 3.36 (s, 4H), 3.42 (s, 2H), 3.56 (s, 3H), 6.79 (s, 1H), 6.82 (d, 1H), 7.21-7.45 (m, 4H), 7.62-7.78 (m, 2H), 8.24 (d, 2H), 8.57 (d, 1H), 9.16 (s, 1H), 9.19 (s, 1H); HPLC Purity: 99.19%; LCMS: 569 ($M^+$).

N-(4-(4-(2,3-dichlorobenzyl)piperazine-1-carbonyl)-2-methoxyphenyl)quinoline-8-sulfonamide (XIV-93)

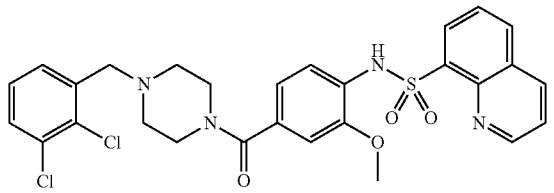

$^1$H NMR (400 MHz, DMSO-d6) δ: 2.37 (br s, 4H), 3.36 (s, 4H), 3.42 (s, 2H), 3.59 (s, 3H), 6.79 (s, 1H), 6.82 (d, 1H), 7.24-7.58 (m, 4H), 7.62-7.78 (m, 2H), 8.24 (d, 2H), 8.57 (d, 1H), 9.16 (s, 1H), 9.19 (s, 1H); HPLC Purity: 99.80%; LCMS: 585 ($M^+$).

N-(2-methoxy-4-(4-(pyridin-3-ylmethyl)piperazine-1-carbonyl)phenyl)quinoline-8-sulfonamide (XIV-94)

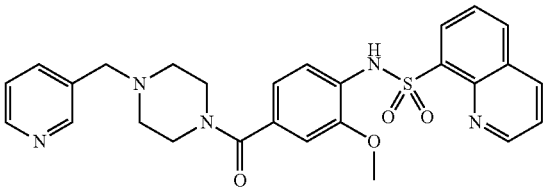

$^1$H NMR (400 MHz, DMSO-d6) δ: 2.37 (br s, 4H), 3.32 (s, 4H), 3.42 (s, 3H), 3.56 (s, 2H), 6.79 (s, 1H), 6.82 (d, 1H), 7.30-7.46 (m, 2H), 7.62-7.79 (m, 3H), 8.24 (d, 2H), 8.40-8.59 (m, 2H), 9.10 (s, 1H), 9.19 (s, 1H); HPLC Purity: 98.45%; LCMS: 518 ($M^+$1).

N-(4-(4-(3-chlorobenzyl)piperazine-1-carbonyl)-2-methoxyphenyl)quinoline-8-sulfonamide (XIV-95)

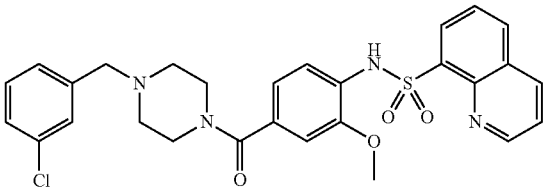

$^1$H NMR (400 MHz, DMSO-d6) δ: 2.37 (br s, 4H), 3.36 (s, 4H), 3.42 (s, 3H), 3.59 (s, 2H), 6.79 (s, 1H), 6.82 (d, 1H), 7.21-7.44 (m, 5H), 7.62-7.78 (m, 2H), 8.24 (d, 2H), 8.57 (d, 1H), 9.16 (s, 1H), 9.19 (s, 1H); HPLC Purity: 98.92%; LCMS: 551 ($M^+$).

N-(4-(4-(cyclopentylmethyl)piperazine-1-carbonyl)-2-methoxyphenyl)quinoline-8-sulfonamide (XIV-96)

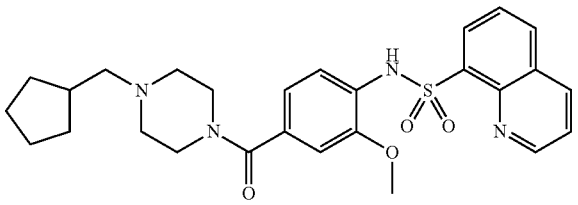

$^1$H NMR (400 MHz, DMSO-d6) δ: 1.15-1.19 (m, 2H), 1.40-1.71 (m, 6H), 2.01-2.05 (m, 1H), 2.30-2.37 (br s, 6H), 3.36 (s, 4H), 3.42 (s, 3H), 6.79 (s, 1H), 6.82 (d, 1H), 7.41 (d, 1H), 7.62-7.78 (m, 2H), 8.24 (d, 2H), 8.57 (d, 1H), 9.12 (s, 1H), 9.19 (s, 1H); HPLC Purity: 99.58%; LCMS: 509 ($M^+$+1).

N-(4-(4-(2,4-dimethoxybenzyl)piperazine-1-carbonyl)-2-methoxyphenyl)quinoline-8-sulfonamide (XIV-97)

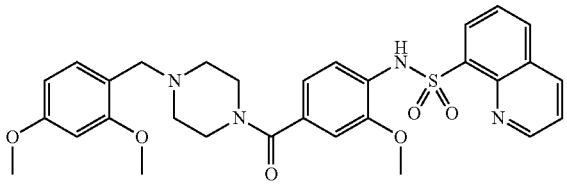

$^1$H NMR (400 MHz, DMSO-d6) δ: 2.37 (br s, 4H), 3.36 (br s, 6H), 3.42 (s, 3H), 3.78 (s, 6H), 6.42-6.51 (m, 2H), 6.79 (s, 1H), 6.82 (d, 1H), 7.41 (d, 1H), 7.62-7.78 (m, 2H), 8.24 (d, 2H), 8.57 (d, 1H), 9.12 (s, 1H), 9.19 (s, 1H); HPLC Purity: 96.10%; LCMS: 577 ($M^+$+1).

N-(4-(4-(3,5-difluorobenzyl)piperazine-1-carbonyl)-2-methoxyphenyl)quinoline-8-sulfonamide (XIV-98)

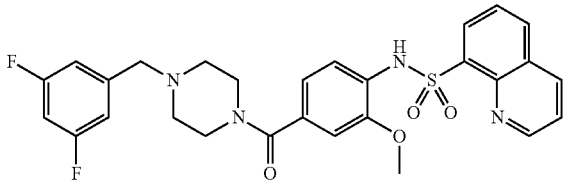

$^1$H NMR (400 MHz, DMSO-d6) δ: 2.37 (br s, 4H), 3.36 (s, 4H), 3.41 (s, 3H), 3.52 (s, 2H), 6.78 (s, 1H), 6.81 (d, 1H), 6.97-7.16 (m, 3H), 7.41 (d, 1H), 7.62-7.80 (m, 2H), 8.21-8.30 (m, 2H), 8.57 (d, 1H), 9.08 (s, 1H), 918 (s, 1H); HPLC Purity: 99.30%; LCMS: 553 ($M^+$+1).

N-(2-methoxy-4-(4-((4-(trifluoromethyl)pyridin-3-yl)methyl)piperazine-1-carbonyl)phenyl)quinoline-8-sulfonamide (XIV-99)

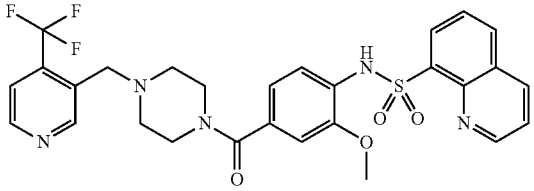

$^1$H NMR (400 MHz, DMSO-d6) δ: 2.37 (br s, 4H), 3.36 (s, 4H), 3.41 (s, 3H), 3.62 (s, 2H), 6.78 (s, 1H), 6.81 (d, 1H), 6.97-7.16 (m, 3H), 7.41 (d, 1H), 7.64-7.80 (m, 3H), 8.21-8.30 (m, 2H), 8.57 (d, 1H), 8.76 (d, 1H), 8.84 (s, 1H), 9.08 (s, 1H), 9.18 (s, 1H); HPLC Purity: 96.90%; LCMS: 586 ($M^+$+1).

N-(4-(4-((5-fluoropyridin-2-yl)methyl)piperazine-1-carbonyl)-2-methoxyphenyl)quinoline-8-sulfonamide (XIV-100)

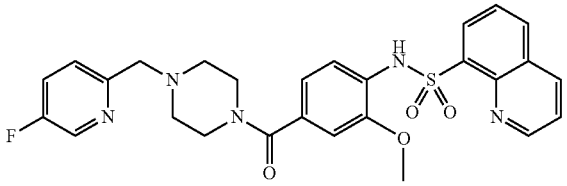

[$^1$H NMR (400 MHz, DMSO-d6) δ: 2.37 (br s, 4H), 3.36 (s, 4H), 3.41 (s, 3H), 3.59 (s, 2H), 6.78 (s, 1H), 6.81 (d, 1H), 7.41-7.52 (m, 2H), 7.64-7.80 (m, 3H), 8.21-8.30 (m, 2H), 8.41 (s, 2H), 8.57 (d, 2H), 9.08 (s, 1H), 9.18 (s, 1H);] HPLC Purity: 98.81%; LCMS: 536 ($M^+$+1).

N-(2-methoxy-4-(4-((3-methoxypyridin-2-yl)methyl)piperazine-1-carbonyl)phenyl)quinoline-8-sulfonamide (XIV-101)

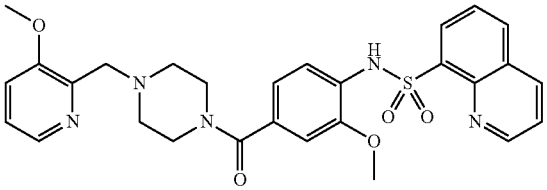

$^1$H NMR (400 MHz, DMSO-d6) δ: 2.39 (br s, 4H), 3.36 (s, 4H), 3.41 (s, 3H), 3.59 (s, 2H), 3.79 (s, 3H), 6.78 (s, 1H), 6.81 (d, 1H), 7.21-7.43 (m, 3H), 7.64-7.80 (m, 2H), 8.05 (s, 1H), 8.24-8.30 (m, 2H), 8.57 (d, 1H), 9.08 (s, 1H), 9.18 (s, 1H); HPLC Purity: 99.08%; LCMS: 548 ($M^+$+1).

N-(2-methoxy-4-(4-((4-methoxypyridin-3-yl)methyl)piperazine-1-carbonyl)phenyl)quinoline-8-sulfonamide (XIV-102)

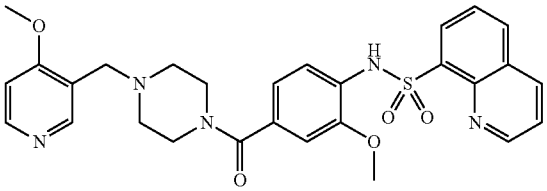

$^1$H NMR (400 MHz, DMSO-d6) δ: 2.39 (br s, 4H), 3.36 (s, 4H), 3.41 (s, 3H), 3.55 (s, 2H), 3.81 (s, 3H), 6.78 (s, 1H), 6.81 (d, 1H), 7.01 (s, 1H), 7.41 (s, 1H), 7.64-7.80 (m, 2H), 8.24-8.39 (m, 4H), 8.59 (d, 1H), 9.08 (s, 1H), 9.18 (s, 1H); HPLC Purity: 97.31%; LCMS: 548 ($M^+$+1).

N-(4-(4-(cyclopentylmethyl)piperazine-1-carbonyl)-2-methylphenyl)quinoline-8-sulfonamide (XIV-103)

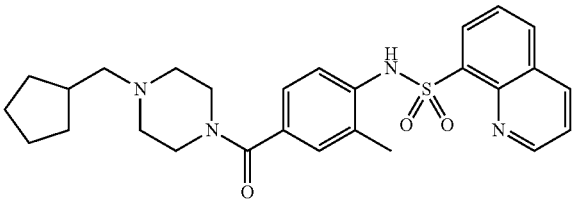

$^1$H NMR (400 MHz, DMSO-d6) δ: 0.81-0.84 (m, 1H), 1.1-1.32 (m, 3H), 1.4-1.75 (m, 5H), 2.1 (s, 3H), 2.12-2.4 (br s, 6H), 3.18-3.62 (br s, 4H), 6.9-7.14 (s, 3H), 7.62-7.77 (m, 2H), 8.21-8.35 (m, 2H), 8.57 (d, 1H), 9.18 (s, 1H), 9.39 (s, 1H); HPLC Purity: 99.55%; LCMS: 493.3 ($M^+$+1).

N-(4-(4-(4-fluorobenzyl)piperazine-1-carbonyl)-2-methylphenyl)quinoline-8-sulfonamide (XIV-104)

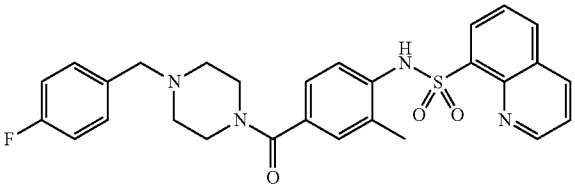

$^1$H NMR (400 MHz, DMSO-d6) δ: 2.01 (s, 3H), 2.2-2.37 (br s, 4H), 3.18-3.34 (br s, 2H), 3.42-3.59 (br s, 4H), 6.96 (s, 2H), 7.06-7.16 (m, 3H), 7.31 (t, 2H), 7.61-7.79 (m, 2H), 8.21-8.30 (m, 2H), 8.57 (d, 1H), 9.16 (s, 1H), 9.39 (s, 1H); HPLC Purity: 99.31%; LCMS: 519.3 ($M^+$+1).

N-(4-(4-(4-methoxybenzyl)piperazine-1-carbonyl)-2-methylphenyl)quinoline-8-sulfonamide (XIV-105)

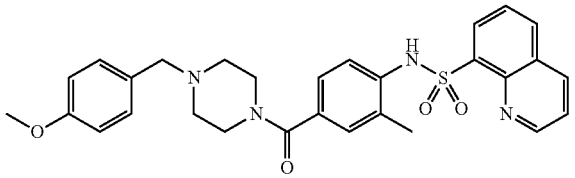

$^1$H NMR (400 MHz, DMSO-d6) δ: 2.01 (s, 3H), 2.37 (br s, 4H), 3.18-3.28 (br s, 4H), 3.46 (s, 2H), 3.71 (s, 3H), 6.82 (d, 2H), 6.96 (d, 2H), 7.06 (s, 1H), 7.19 (d, 2H), 7.62-7.77 (m, 2H), 8.21-8.30 (m, 2H), 8.57 (d, 1H), 9.18 (s, 1H), 9.39 (s, 1H); HPLC Purity: 94.41%. LCMS: 531.15 ($M^+$+1).

N-(2-methyl-4-(4-((6-methylpyridin-2-yl)methyl)piperazine-1-carbonyl)phenyl)quinoline-8-sulfonamide (XIV-106)

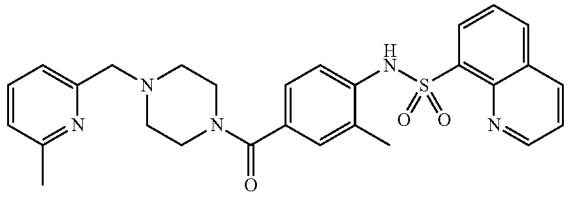

$^1$H NMR (400 MHz, DMSO-d6) δ: 2.01 (s, 3H), 2.34 (br s, 4H), 2.39 (s, 3H), 3.21 (br s, 4H), 3.58 (s, 2H), 6.97-7.16 (m, 4H), 7.21 (d, 2H), 7.62-7.77 (m, 3H), 8.21-8.34 (m, 2H), 8.57 (d, 1H), 9.18 (s, 1H); HPLC Purity: 95.18%; LCMS: 516.35 ($M^+$+1).

N-(2-methyl-4-(4-((tetrahydrofuran-3-yl)methyl)piperazine-1-carbonyl)phenyl)quinoline-8-sulfonamide (XIV-107)

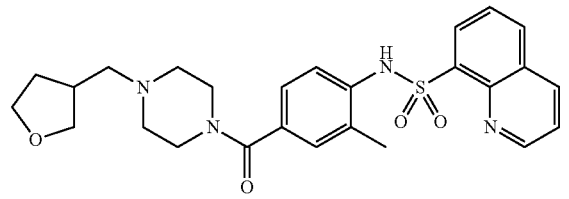

$^1$H NMR (400 MHz, DMSO-d6) δ: 0.82-0.84 (m, 1H), 1.22 (s, 2H), 1.42-1.58 (br s, 1H), 1.82-1.96 (m, 1H), 2.04 (s, 3H), 2.21-2.31 (m, 5H), 3.16-3.51 (br s, 5H), 3.72-3.85 (m, 2H), 6.97-7.04 (m, 3H), 7.62-7.77 (m, 2H), 8.21-8.30 (m, 2H), 8.57 (d, 1H), 9.18 (s, 1H), 9.39 (s, 1H); HPLC Purity: 98.714%; LCMS: 495.35 ($M^+$+1).

N-(4-(4-(cyclopropylmethyl)piperazine-1-carbonyl)-2-methoxyphenyl)quinoline-8-sulfonamide (XIV-108)

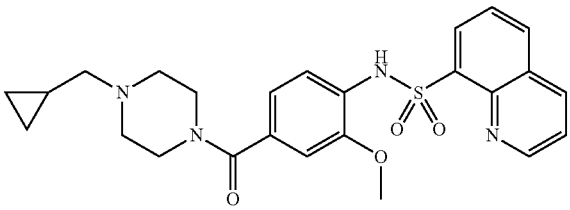

$^1$H NMR (400 MHz, DMSO-d6) δ: 0.21 (s, 2H), 0.41 (s, 2H), 0.91 (br s, 1H), 2.12 (s, 2H), 2.39 (br s, 4H), 3.36 (s, 4H), 3.41 (s, 3H), 6.78 (s, 1H). 6.81 (d, 1H), 7.41 (d, 1H), 7.62-7.82 (m, 2H), 8.21-8.30 (m, 2H), 8.57 (d, 1H), 9.08 (s, 1H), 9.19 (s, 1H); HPLC Purity: 99.74%; LCMS: 481 ($M^+$+1).

N-(4-(4-(4-chlorobenzyl)piperazine-1-carbonyl)-2-methoxyphenyl)quinoline-8-sulfonamide (XIV-109)

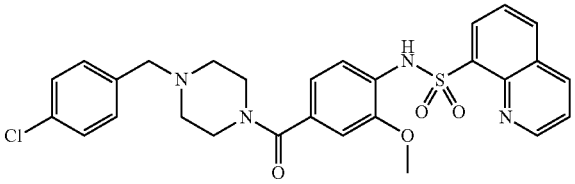

$^1$H NMR (400 MHz, DMSO-d6) δ: 2.31 (br s, 4H), 3.36 (s, 4H), 3.41 (s, 3H), 3.44 (s, 2H), 6.78 (s, 1H), 6.81 (d, 1H), 7.21-7.43 (m, 5H), 7.62-7.78 (m, 2H), 8.21-8.30 (m, 2H), 8.55 (d, 1H), 9.08 (s, 1H), 9.19 (s, 1H); HPLC Purity: 94.85%; LCMS: 551 ($M^+$).

N-(2-methoxy-4-(4-(4-(trifluoromethyl)benzyl)piperazine-1-carbonyl)phenyl)quinoline-8-sulfonamide (XIV-110)

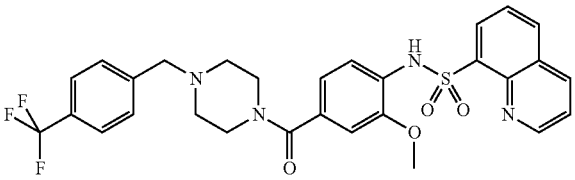

$^1$H NMR (400 MHz, DMSO-d6) δ: 2.37 (br s, 4H), 3.36 (s, 4H), 3.41 (s, 3H), 3.59 (s, 2H), 6.78 (s, 1H), 6.81 (d, 1H), 7.41-7.56 (m, 3H), 7.62-7.78 (m, 4H), 8.21-8.30 (m, 2H), 8.58 (d, 1H), 9.08 (s, 1H), 9.19 (s, 1H); HPLC Purity: 98.62%; LCMS: 585 ($M^+$+1).

N-(2-methoxy-4-(4-(4-methoxybenzyl)piperazine-1-carbonyl)phenyl)quinoline-8-sulfonamide (XIV-111)

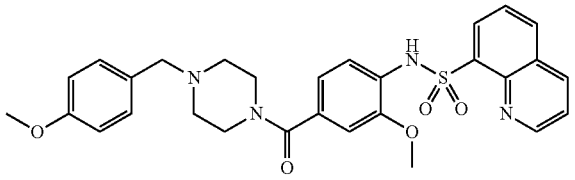

$^1$H NMR (400 MHz, DMSO-d6) δ: 2.35 (br s, 4H), 3.36 (s, 4H), 3.41 (s, 3H), 3.43 (s, 2H), 3.66 (s, 3H), 6.76-6.90 (m, 4H), 7.19 (d, 2H), 7.41 (s, 1H), 7.62-7.78 (m, 2H), 8.21-8.30 (m, 2H), 8.58 (d, 1H), 9.05 (s, 1H), 9.19 (s, 1H); HPLC Purity: 97.73%; LCMS: 547 ($M^+$+1).

N-(4-(4-((5-chloropyridin-3-yl)methyl)piperazine-1-carbonyl)-2-methoxyphenyl)quinoline-8-sulfonamide (XIV-112)

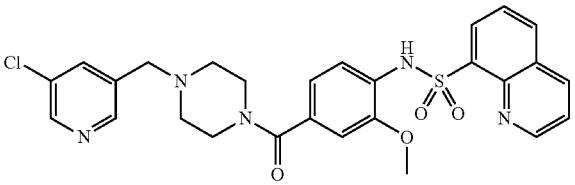

$^1$H NMR (400 MHz, DMSO-d6) δ: 2.31 (br s, 4H), 3.37 (s, 4H), 3.41 (s, 3H), 3.55 (s, 2H), 6.78 (s, 1H), 6.81 (d, 1H), 7.41 (d, 1H), 7.62-7.82 (m, 3H), 8.21-8.30 (m, 2H), 8.41-8.61 (m, 3H), 9.05 (s, 1H), 9.19 (s, 1H); HPLC Purity: 99.46%; LCMS: 553 ($M^+$+1).

N-(4-(4-((3-fluoropyridin-2-yl)methyl)piperazine-1-carbonyl)-2-methoxyphenyl)quinoline-8-sulfonamide (XIV-113)

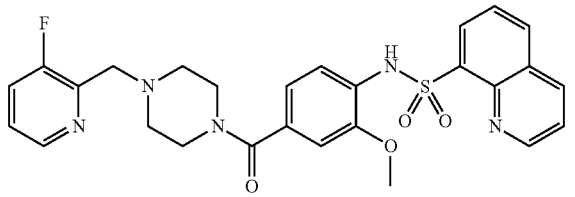

$^1$H NMR (400 MHz, DMSO-d6) δ 2.39 (br s, 4H), 3.37 (s, 4H), 3.41 (s, 3H), 3.61 (s, 2H), 6.78 (s, 1H), 6.81 (d, 1H), 7.41-7.45 (m, 2H), 7.62-7.80 (m, 4H), 8.21-8.39 (m, 3H), 8.59 (s, 1H), 9.18 (s, 1H); HPLC Purity: 96.15%; LCMS: 536 ($M^+$).

N-(2-methoxy-4-(4-((3-(trifluoromethyl)pyridin-2-yl)methyl)piperazine-1-carbonyl)phenyl)quinoline-8-sulfonamide (XIV-114)

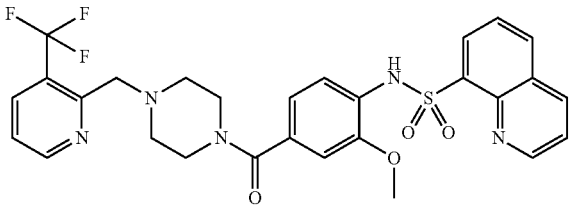

$^1$H NMR (400 MHz, DMSO-d6) δ: 2.39 (br s, 4H), 3.37 (s, 4H), 3.43 (s, 3H), 3.70 (s, 2H), 6.78 (s, 1H), 6.81 (d, 1H), 7.41-7.59 (m, 2H), 7.64-7.80 (m, 2H), 8.18 (d, 1H), 8.24-8.29 (m, 2H), 8.59 (d, 1H), 8.79 (d, 1H), 9.08 (s, 1H), 9.18 (s, 1H); HPLC Purity: 99.41%; LCMS: 586 ($M^+$+1).

N-(4-(4-((3-fluoropyridin-4-yl)methyl)piperazine-1-carbonyl)-2-methoxyphenyl)quinoline-8-sulfonamide (XIV-115)

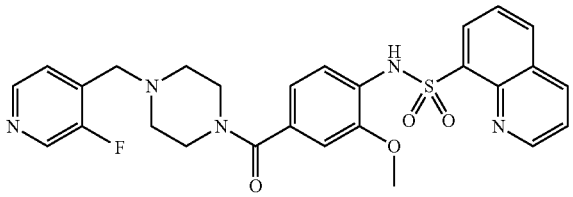

$^1$H NMR (400 MHz, DMSO-d6) δ: 2.45 (s, 4H), 3.47 (s, 4H), 3.56 (s, 3H), 3.61 (s, 2H), 6.72-6.85 (m, 2H), 7.38-7.42 (m, 2H), 7.62-7.81 (m, 2H), 8.21-8.40 (m, 3H), 8.57 (d, 2H), 9.08 (s, 1H), 9.21 (s, 1H); HPLC Purity: 99.2%; LCMS: 535 ($M^+$).

N-(4-(4-((5-fluoropyridin-3-yl)methyl)piperazine-1-carbonyl)-2-methoxyphenyl)quinoline-8-sulfonamide (XIV-116)

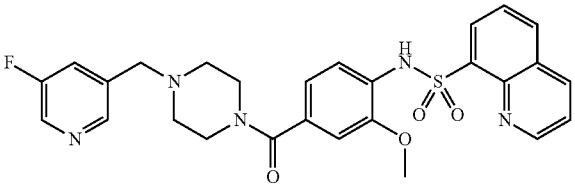

$^1$H NMR (400 MHz, DMSO-d6) δ: 2.45 (s, 4H), 3.47 (s, 4H), 3.56 (s, 3H), 3.61 (s, 2H), 6.72-6.85 (m, 2H), 7.42 (d, 1H), 7.58-7.81 (m, 3H), 8.21-8.40 (m, 3H), 8.57 (d, 2H), 9.08 (s, 1H), 9.21 (s, 1H); HPLC Purity: 99.8%; LCMS: 535 ($M^+$).

N-(4-(4-(cyclohexylmethyl)piperazine-1-carbonyl)-2-methoxyphenyl)quinoline-8-sulfonamide (XIV-117)

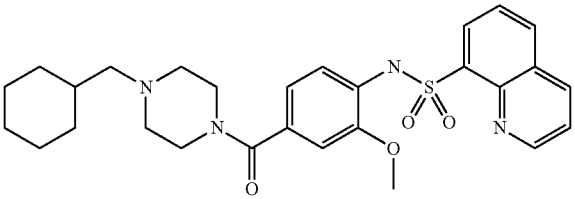

$^1$H NMR (400 MHz, DMSO-d6) δ: 0.70-0.84 (m, 2H), 1.01-1.21 (m, 3H), 1.35-1.42 (m, 1H), 1.61-1.74 (m, 5H), 2.02 (d, 2H), 2.25 (br s, 4H), 3.47 (s, 2H), 3.56 (s, 3H), 3.61 (s, 2H), 6.65-6.82 (m, 2H), 7.42 (d, 1H), 7.65-7.80 (m, 2H), 8.35 (d, 2H), 8.60 (d, 1H), 9.08 (s, 1H), 9.19 (d, 1H); HPLC Purity: 99.7%; LCMS: 522 ($M^+$).

N-(4-(4-((2-methoxypyridin-3-yl)methyl)piperazine-1-carbonyl)-2-methylphenyl)quinoline-8-sulfonamide (XIV-118)

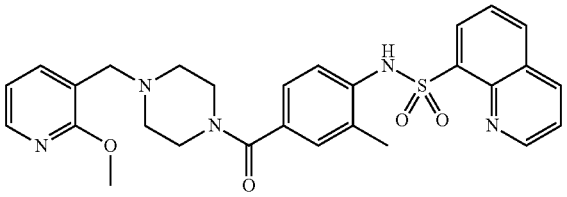

$^1$H NMR (400 MHz, DMSO-d6) δ: 2.01 (s, 3H), 2.37 (br s, 4H), 3.46 (s, 4H), 3.56 (s, 2H), 3.86 (s, 3H), 6.96-7.02 (m, 3H), 7.61-7.79 (m, 3H), 8.0 (d, 1H), 8.22-8.35 (m, 2H), 8.58 (d, 1H), 9.15 (s, 1H), 9.35 (s, 1H); HPLC Purity: 97.2%; LCMS: 531 ($M^+$).

N-(3-methoxy-4-(4-(pyridin-3-ylmethyl)piperazine-1-carbonyl)phenyl)quinoline-8-sulfonamide (XIV-119)

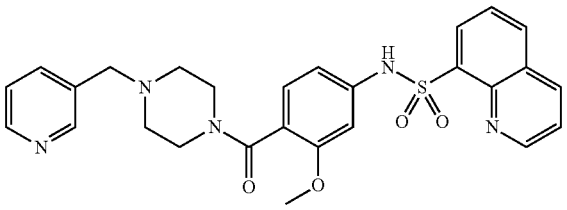

$^1$H NMR (400 MHz, DMSO-d6) δ: 2.01-2.38 (s, 4H), 2.97 (br s, 2H), 3.46 (s, 4H), 3.56 (s, 3H), 6.65-6.97 (m, 3H), 7.36 (m, 1H), 7.61-7.78 (m, 3H), 8.20-8.58 (m, 5H), 9.18 (s, 1H), 10.25 (s, 1H); HPLC Purity: 99.09%; LCMS: 517.6 ($M^+$).

N-(4-(4-(3,5-difluorobenzyl)piperazine-1-carbonyl)-3-methoxyphenyl)quinoline-8-sulfonamide (XIV-120)

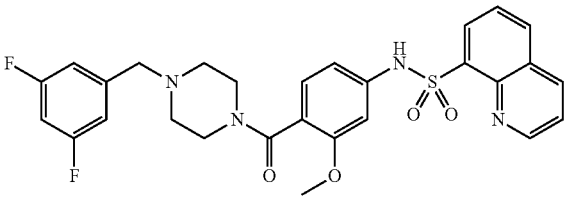

$^1$H NMR (400 MHz, DMSO-d6) δ: 2.31 (br s, 4H), 3.02 (br s, 2H), 3.46 (br s, 4H), 3.59 (s, 3H), 6.81 (d, 1H), 6.78 (s, 1H), 6.85 (d, 1H), 7.06-7.18 (m, 3H), 7.71-7.76 (m, 2H), 8.24 (d, 1H), 8.42-8.58 (m, 2H), 9.18 (s, 1H), 10.28 (s, 1H); HPLC Purity: 99.20%; LCMS: 553 ($M^+$+1).

N-(4-(4-(4-chlorobenzyl)piperazine-1-carbonyl)-3-methoxyphenyl)quinoline-8-sulfonamide (XIV-121)

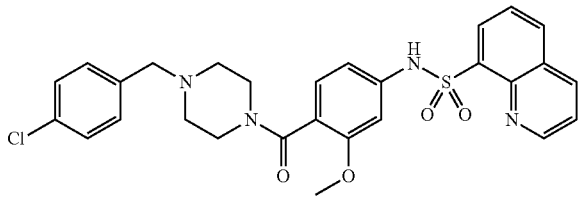

$^1$H NMR (400 MHz, DMSO-d6) δ: 2.36 (br s, 4H), 3.37 (s, 4H), 3.42 (s, 3H), 3.46 (s, 2H), 6.78 (s, 1H), 6.81 (d, 1H), 7.24-7.43 (m, 5H), 7.62-7.78 (m, 2H), 8.21-8.30 (m, 2H), 8.57 (d, 1H), 9.08 (s, 1H), 9.19 (s, 1H); HPLC Purity: 95.65%; LCMS: 551 ($M^+$).

N-(4-(4-((5-fluoropyridin-3-yl)methyl)piperazine-1-carbonyl)-3-methoxyphenyl)quinoline-8-sulfonamide (XIV-122)

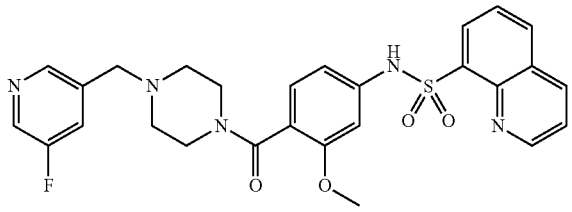

$^1$H NMR (400 MHz, DMSO-d6) δ: 2.19 (s, 2H), 2.25 (br s, 2H), 2.95 (br s, 2H), 3.52 (d, 5H), 6.61 (d, 1H), 6.78 (s, 1H), 6.83 (d, 1H), 7.60 (d, 1H), 7.70-7.79 (m, 2H), 8.28 (d, 1H), 8.34 (s, 1H), 8.39-8.48 (m, 3H), 9.16 (d, 1H), 10.30 (s, 1H); HPLC Purity: 99.58%; LCMS: 536 ($M^+$+1).

N-(4-(4-((3-fluoropyridin-4-yl)methyl)piperazine-1-carbonyl)-3-methoxyphenyl)quinoline-8-sulfonamide (XIV-123)

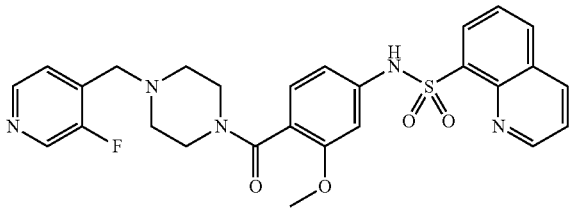

$^1$H NMR (400 MHz, DMSO-d6) δ: 2.21 (br s, 2H), 2.30 (br s, 2H), 3.00 (br s, 2H), 3.58 (d, 5H), 6.61 (d, 1H), 6.78 (s, 1H), 6.84 (d, 1H), 7.44 (t, 1H), 7.70-7.79 (m, 2H), 8.28 (d, 1H), 8.40 (d, 1H), 8.44 (d, 2H), 8.51 (s, 2H), 9.16 (d, 1H), 10.30 (s, 1H); HPLC Purity: 90.34%; LCMS: 536 ($M^+$+1).

N-(4-(4-((5-fluoropyridin-2-yl)methyl)piperazine-1-carbonyl)-3-methoxyphenyl)quinoline-8-sulfonamide (XIV-124)

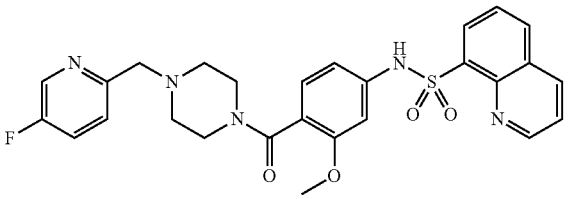

$^1$H NMR (400 MHz, DMSO-d6) δ: 2.19 (br s, 2H), 2.25 (br s, 2H), 2.95 (br s, 2H), 3.41 (br s, 2H), 3.58 (s, 3H), 6.61 (d, 1H), 6.78 (s, 1H), 6.83 (d, 1H), 7.47 (t, 1H), 7.60-7.78 (m, 2H), 8.24 (d, 1H), 8.39-8.48 (m, 3H), 9.16 (d, 1H), 10.30 (s, 1H); HPLC Purity: 99.57%; LCMS: 536 ($M^+$+1).

N-(4-(4-(3-fluorobenzyl)piperazine-1-carbonyl)-3-methoxyphenyl)quinoline-8-sulfonamide (XIV-125)

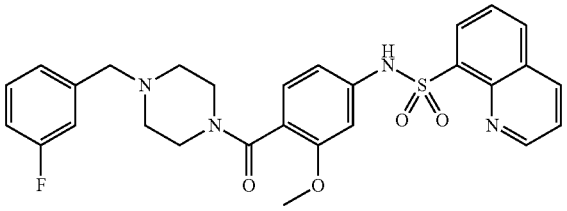

[$^1$H NMR (400 MHz, DMSO-d6) δ: 2.19 (br s, 2H), 2.25 (br s, 2H), 2.95 (br s, 2H), 3.42 (s, 2H), 3.52 (s, 3H), 6.60 (d, 1H), 6.78 (s, 1H), 6.82 (d, 1H), 7.00-7.16 (m, 3H), 7.30 (q, 1H), 7.64-7.71 (m, 2H), 8.28 (d, 1H), 8.34 (s, 1H), 8.38 (d, 1H), 9.16 (d, 1H), 10.30 (s, 1H);] HPLC Purity: 99.82%; LCMS: 535 ($M^+$+1).

N-(4-(4-(3-chlorobenzyl)piperazine-1-carbonyl)-3-methoxyphenyl)quinoline-8-sulfonamide (XIV-126)

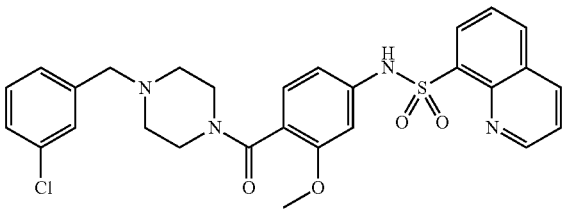

$^1$H NMR (400 MHz, DMSO-d6) δ: 2.19 (br s, 2H), 2.25 (br s, 2H), 2.97 (br s, 2H), 3.42 (s, 2H), 3.52 (s, 3H), 6.61 (d, 1H), 6.78 (s, 1H), 6.82 (d, 1H), 7.24 (d, 1H), 7.28-7.37 (m, 2H), 8.28 (d, 1H), 8.39 (s, 1H), 8.50 (d, 1H), 9.16 (d, 1H), 10.30 (s, 1H); HPLC Purity: 99.53%; LCMS: 551 ($M^+$).

N-(3-methoxy-4-(4-(4-methoxybenzyl)piperazine-1-carbonyl)phenyl)quinoline-8-sulfonamide (XIV-127)

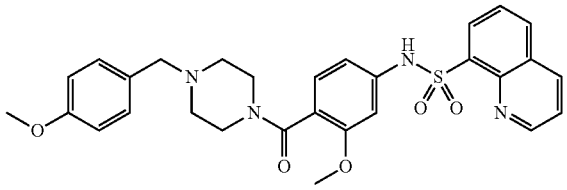

$^1$H NMR (400 MHz, DMSO-d6) δ: 2.19 (br s, 2H), 2.25 (br s, 2H), 2.97 (br s, 2H), 3.31 (br s, 2H), 3.59 (s, 2H), 3.63 (s, 3H), 6.61 (d, 1H), 6.78 (s, 1H), 6.82 (d, 3H), 7.12-7.21 (m, 2H), 7.62-7.70 (m, 2H), 8.28 (d, 1H), 8.39 (s, 1H), 8.50 (d, 1H), 9.16 (d, 1H), 10.26 (s, 1H); HPLC Purity: 90.80%; LCMS: 546 ($M^+$+1).

N-(4-(4-(2,4-dimethoxybenzyl)piperazine-1-carbonyl)-3-methoxyphenyl)quinoline-8-sulfonamide (XIV-128)

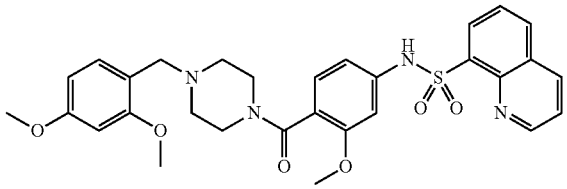

$^1$H NMR (400 MHz, DMSO-d6) δ: 2.25 (br s, 2H), 2.97 (br s, 2H), 3.42 (br s, 4H), 3.59 (s, 2H), 3.63 (s, 3H), 3.73 (s, 6H), 6.45 (d, 1H), 6.50 (s, 1H), 6.64 (d, 1H), 6.78 (s, 1H), 6.82 (d, 1H), 7.12 (d, 1H), 7.65-7.72 (m, 2H), 8.28 (d, 1H), 8.40 (s, 1H), 8.50 (d, 1H), 9.16 (d, 1H), 10.26 (s, 1H); HPLC Purity: 99.78%; LCMS: 577 ($M^+$+1).

N-(4-(4-(cyclohexylmethyl)piperazine-1-carbonyl)-3-methoxyphenyl)quinoline-8-sulfonamide (XIV-129)

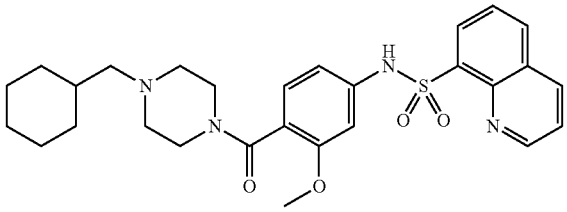

$^1$H NMR (400 MHz, DMSO-d6) δ: 0.78 (q, 2H), 1.11 (d, 2H), 1.40 (br s, 1H), 1.54-1.71 (m, 2H), 1.99-2.30 (m, 8H), 2.90 (br s, 4H), 3.45 (d, 1H), 3.59 (s, 3H), 3.70 (s, 1H), 6.61 (d, 1H), 6.76 (s, 1H), 6.82 (d, 3H), 7.62-7.70 (m, 2H), 8.28 (d, 1H), 8.40 (s, 1H), 8.47 (m, 1H), 9.10 (d, 1H), 10.26 (s, 1H); HPLC Purity: 98.50%; LCMS: 546 ($M^+$+1).

N-(3-methoxy-4-(4-((3-methoxypyridin-2-yl)methyl)piperazine-1-carbonyl)phenyl)quinoline-8-sulfonamide (XIV-130)

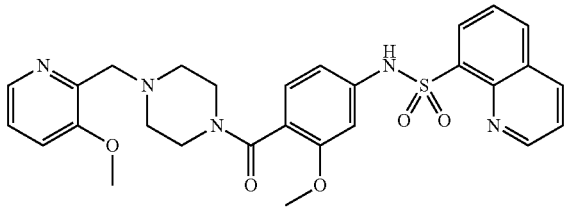

[$^1$H NMR (400 MHz, DMSO-d6) δ: 2.22 (br s, 2H), 2.38 (br s, 2H), 2.87 (br s, 4H), 3.41 (s, 3H), 3.59 (br s, 5H), 3.73 (s, 2H), 6.76 (s, 1H), 6.82 (d, 1H), 7.21 (s, 1H), 7.40 (d, 1H), 7.62-7.69 (m, 2H), 8.03 (s, 1H), 8.27 (d, 1H), 8.39 (s, 1H), 8.50 (m, 1H), 9.10 (d, 1H), 10.23 (s, 1H);] HPLC Purity: 99.86%; LCMS: 548 ($M^+$+1).

N-(3-methoxy-4-(4-((4-methoxypyridin-3-yl)methyl)piperazine-1-carbonyl)phenyl)quinoline-8-sulfonamide (XIV-131)

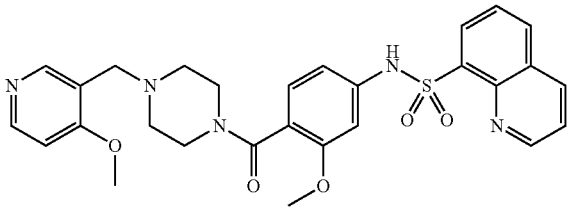

$^1$H NMR (400 MHz, DMSO-d6) δ: 2.22 (br s, 2H), 2.38 (br s, 2H), 2.90 (br s, 4H), 3.41 (s, 3H), 3.55 (s, 3H), 3.80 (s, 2H), 6.60 (d, 1H), 6.72 (s, 1H), 6.82 (d, 1H), 7.00 (d, 1H), 7.62-7.69 (m, 2H), 8.29 (s, 2H), 8.35 (d, 1H), 8.39 (s, 1H), 8.50 (m, 1H), 9.10 (d, 1H); HPLC Purity: 92.10%; LCMS: 548 ($M^+$+1).

N-(4-(4-(4-fluorobenzyl)piperazine-1-carbonyl)-3-methoxyphenyl)quinoline-8-sulfonamide (XIV-132)

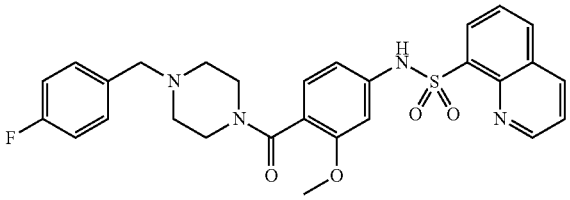

$^1$H NMR (400 MHz, DMSO-d6) δ: 2.19 (br s, 2H), 2.25 (br s, 2H), 2.95 (br s, 4H), 3.42 (s, 2H), 3.52 (s, 3H), 6.60 (d, 1H), 6.78 (s, 1H), 6.82 (d, 1H), 7.10 (t, 2H), 7.23 (t, 2H), 7.63-7.71 (m, 2H), 8.25 (d, 1H), 8.40 (d, 1H), 8.48 (d, 1H), 9.16 (d, 1H), 10.30 (s, 1H); HPLC Purity: 99.62%; LCMS: 535 ($M^+$+1).

N-(4-(4-((3-chloropyridin-4-yl)methyl)piperazine-1-carbonyl)-3-methoxyphenyl)quinoline-8-sulfonamide (XIV-133)

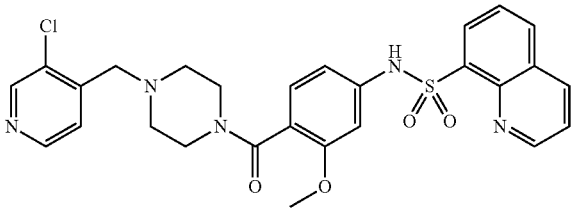

$^1$H NMR (400 MHz, DMSO-d6) δ: 2.24 (br s, 2H), 2.25 (br s, 2H), 2.95 (br s, 4H), 3.58 (s, 5H), 6.61 (d, 1H), 6.74 (s, 1H), 6.83 (d, 1H), 7.47 (d, 1H), 7.63-7.72 (m, 2H), 8.23 (d, 1H), 8.39-8.49 (m, 3H), 8.54 (s, 1H), 9.16 (d, 1H), 10.30 (s, 1H); HPLC Purity: 98.63%; LCMS: 552 ($M^+$).

N-(3-methoxy-4-(4-((tetrahydrofuran-3-yl)methyl)piperazine-1-carbonyl)phenyl)quinoline-8-sulfonamide (XIV-134)

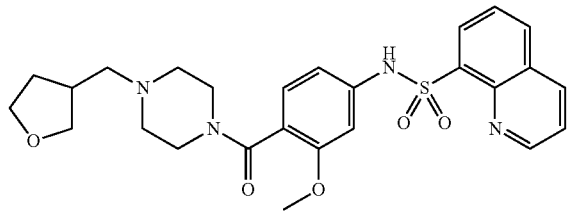

$^1$H NMR (400 MHz, DMSO-d6) δ: 1.42 (m, 2H), 1.83 (m, 2H), 2.19 (d, 2H), 2.24-2.39 (m, 4H), 2.95 (br s, 4H), 3.48 (d, 1H), 3.56 (s, 3H), 3.63 (q, 2H), 6.60 (d, 1H), 6.76 (s, 1H), 6.81 (d, 1H), 7.63-7.70 (m, 2H), 8.24 (d, 1H), 8.40 (d, 1H), 8.50 (d, 1H), 9.10 (d, 1H), 10.26 (s, 1H); HPLC Purity: 98.40%; LCMS: 511 ($M^+$+1).

N-(3-methoxy-4-(4-((2-methoxypyridin-3-yl)methyl)piperazine-1-carbonyl)phenyl)quinoline-8-sulfonamide (XIV-135)

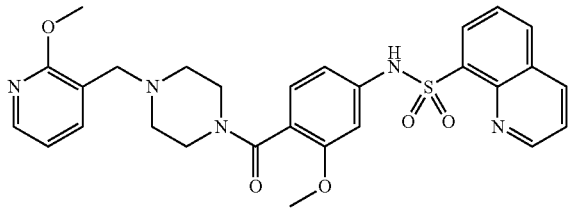

$^1$H NMR (400 MHz, DMSO-d6) δ: 2.22 (br s, 2H), 2.38 (br s, 4H), 2.90 (br s, 4H), 3.41 (s, 3H), 3.55 (s, 3H), 3.80 (s, 2H), 6.61 (d, 1H), 6.75 (s, 1H), 6.82 (d, 1H), 6.97 (t, 1H), 7.60-7.73 (m, 3H), 8.02 (s, 1H), 8.27 (d, 1H), 8.39 (s, 1H), 8.50 (m, 1H), 9.10 (d, 1H), 10.28 (s, 1H); HPLC Purity: 99.85%; LCMS: 548 ($M^+$+1).

N-(3-methoxy-4-(4-((5-(trifluoromethyl)pyridin-2-yl)methyl)piperazine-1-carbonyl)phenyl)quinoline-8-sulfonamide (XIV-136)

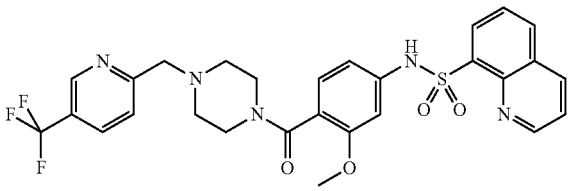

$^1$H NMR (400 MHz, DMSO-d6) δ 2.22 (br s, 2H), 2.38 (br s, 2H), 2.99 (br s, 4H), 3.58 (s, 3H), 3.67 (s, 2H), 6.61 (d, 1H), 6.74 (s, 1H), 6.82 (d, 1H), 7.62-7.73 (m, 3H), 8.19 (d, 1H), 8.26 (d, 1H), 8. d, 1H), 8.50 (m, 1H), 8.82 (s, 1H), 9.10 (d, 1H), 10.30 (s, 1H); HPLC Purity: 94.67%; LCMS: 586 ($M^+$+1).

N-(4-(4-(cyclopentylmethyl)piperazine-1-carbonyl)-3-methoxyphenyl)quinoline-8-sulfonamide (XIV-137)

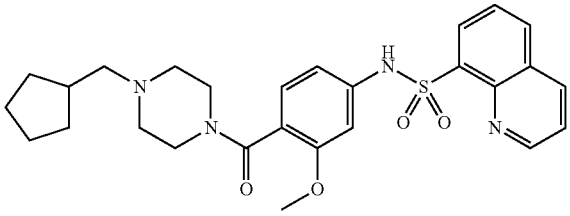

$^1$H NMR (400 MHz, DMSO-d6) δ: 1.10 (sextet, 2H), 1.38-1.50 (m, 3H), 1.55-1.61 (m, 3H), 1.99 (pentet, 1H), 2.07 (d, 2H), 2.30 (br s, 4H), 2.90 (br s, 4H), 3.59 (s, 3H), 6.60 (d, 1H), 6.72 (s, 1H), 6.82 (d, 1H), 7.62-7.69 (m, 2H), 8.25 (s, 1H), 8.40 (d, 1H), 8.47 (d, 1H), 9.10 (d, 1H), 10.24 (s, 1H); HPLC Purity: 99.86%; LCMS: 509 ($M^+$+1).

N-(4-(4-(2-fluoro-4-methoxybenzyl)piperazine-1-carbonyl)-3-methoxyphenyl)quinoline-8-sulfonamide (XIV-138)

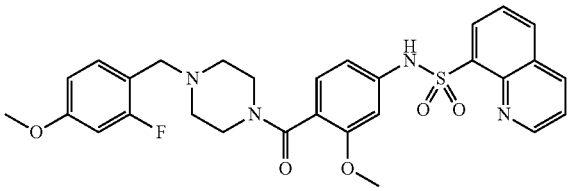

$^1$H NMR (400 MHz, DMSO-d6) δ: 2.20 (br s, 2H), 2.35 (br s, 2H), 2.90 (br s, 4H), 3.41 (s, 3H), 3.60 (s, 3H), 3.78 (s, 2H), 6.61 (d, 1H), 6.70-6.80 (m, 2H), 6.84 (d, 1H), 7.22 (t, 1H), 7.70-7.80 (m, 2H), 8.26 (d, 1H), 8.42 (d, 1H), 8.50 (d, 1H), 9.16 (s, 1H), 10.28 (s, 1H); HPLC Purity: 90.48%; LCMS: 565 ($M^+$+1).

N-(4-(4-(3-fluoro-4-methoxybenzyl)piperazine-1-carbonyl)-3-methoxyphenyl)quinoline-8-sulfonamide (XIV-139)

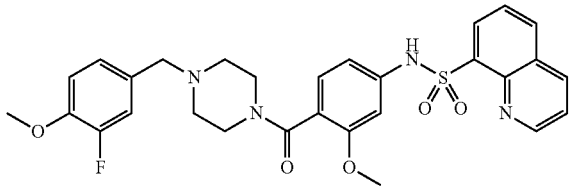

$^1$H NMR (400 MHz, DMSO-d6) δ: 2.20 (br s, 2H), 2.35 (br s, 2H), 2.97 (br s, 4H), 3.42 (s, 3H), 3.59 (s, 3H), 3.82 (s, 2H), 6.61 (d, 1H), 6.80 (s, 1H), 6.84 (d, 1H), 7.02-7.18 (m, 3H), 7.70-7.80 (m, 2H), 8.26 (d, 1H), 8.42 (d, 1H), 8.50 (d, 1H), 9.16 (s, 1H), 10.28 (s, 1H); HPLC Purity: 99.65%; LCMS: 565 ($M^+$+1).

N-(4-(4-(4-fluorobenzyl)piperazine-1-carbonyl)-2-methoxyphenyl)quinoline-8-sulfonamide (XIV-140)

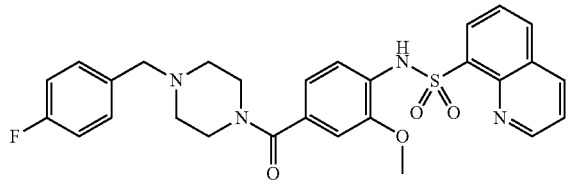

$^1$H NMR (400 MHz, DMSO-d6) δ: 2.24 (br s, 4H), 3.20-3.45 (m, 6H), 3.61 (s, 3H), 6.77 (s, 1H), 6.82 (d, 1H), 7.21 (t, 2H), 7.28 (t, 2H), 7.40 (d, 1H), 7.65-7.77 (m, 2H), 8.26 (d, 2H), 8.56 (d, 1H), 9.07 (s, 1H), 9.20 (s, 1H); HPLC Purity: 95.43%; LCMS: 535 ($M^+$+1).

N-(2-methoxy-4-(4-((tetrahydrofuran-3-yl)methyl) piperazine-1-carbonyl)phenyl)quinoline-8-sulfonamide (XIV-141)

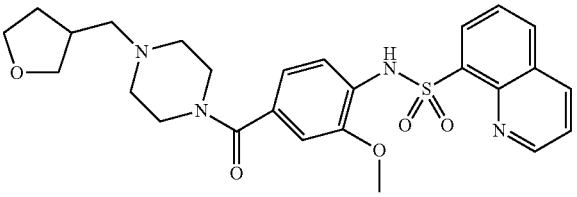

$^1$H NMR (400 MHz, DMSO-d6) δ: 1.45 (m, 2H), 1.86 (m, 2H), 2.20 (d, 2H), 2.24-2.39 (m, 4H), 2.95 (br s, 4H), 3.48 (d, 1H), 3.56 (s, 3H), 3.63 (q, 2H), 6.79 (s, 1H), 6.83 (d, 1H), 7.42 (d, 1H), 7.70-7.80 (m, 2H), 8.42 (d, 2H), 8.59 (d, 1H), 9.04 (br s, 1H), 9.18 (s, 1H); HPLC Purity: 98.88%; LCMS: 511 ($M^+$+1).

N-(4-(4-(4-chloro-3-fluorobenzyl)piperazine-1-carbonyl)-2-methoxyphenyl)quinoline-8-sulfonamide (XIV-142)

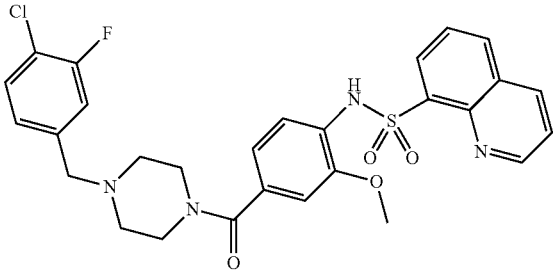

$^1$H NMR (400 MHz, DMSO-d6) δ: 2.37 (br s, 4H), 3.36 (s, 4H), 3.42 (s, 3H), 3.56 (s, 2H), 6.78 (s, 1H), 6.84 (d, 1H), 7.18 (s, 1H), 7.31-7.56 (m, 3H), 7.63-7.81 (m, 2H), 8.24-8.30 (m, 2H), 8.57 (d, 1H), 9.08 (s, 1H), 9.19 (d, 1H); HPLC Purity: 97.47%; LCMS: 569 ($M^+$).

N-(4-(4-((3-chloropyridin-4-yl)methyl)piperazine-1-carbonyl)-2-methoxyphenyl)quinoline-8-sulfonamide (XIV-143)

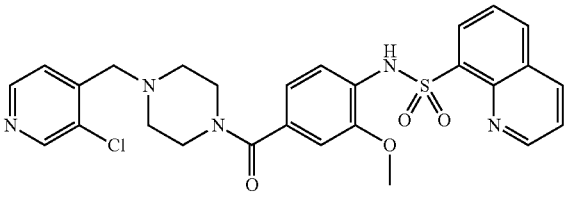

$^1$H NMR (400 MHz, DMSO-d6) δ: 2.41 (br s, 4H), 3.36 (s, 4H), 3.44 (s, 3H), 3.60 (s, 2H), 6.78 (s, 1H), 6.82 (d, 1H), 7.41-7.51 (m, 2H), 7.65-7.80 (m, 2H), 8.22-8.30 (m, 2H), 8.42-8.58 (m, 3H), 9.08 (s, 1H), 9.18 (d, 1H); HPLC Purity: 99.17%; LCMS: 552 ($M^+$).

N-(4-(4-(3-fluorobenzyl)piperazine-1-carbonyl)-2-methoxyphenyl)quinoline-8-sulfonamide (XIV-144)

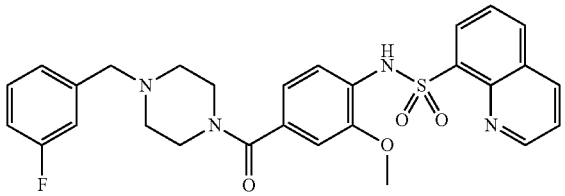

$^1$H NMR (400 MHz, DMSO-d6) δ: 2.37 (br s, 4H), 3.36 (s, 4H), 3.42 (s, 3H), 3.56 (s, 2H), 6.78 (s, 1H), 6.84 (d, 1H), 7.18 (s, 1H), 7.31-7.56 (m, 3H), 7.63-7.81 (m, 2H), 8.24-8.30 (m, 2H), 8.57 (d, 1H), 9.08 (s, 1H), 9.19 (d, 1H); HPLC Purity: 97.47%; LCMS: 535 ($M^+$).

N-(2-methoxy-4-(4-((2-methoxypyridin-3-yl)methyl) piperazine-1-carbonyl)phenyl)quinoline-8-sulfonamide (XIV-145)

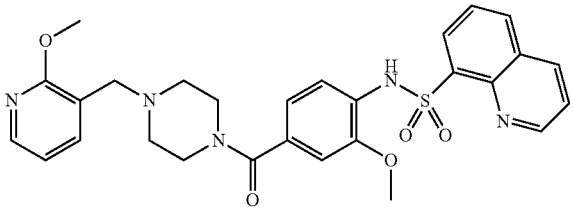

$^1$H NMR (400 MHz, DMSO-d6) δ: 2.37 (br s, 4H), 3.36 (s, 4H), 3.41 (s, 3H), 3.46 (s, 2H), 3.81 (s, 3H), 6.78 (s, 1H), 6.81 (d, 1H), 6.97-7.01 (m, 1H), 7.41 (d, 1H), 7.62-7.78 (m, 3H), 8.01 (d, 1H), 8.21-8.30 (m, 2H), 8.57 (d, 1H), 9.08 (s, 1H), 9.19 (d, 1H); HPLC Purity: 99.95%; LCMS: 548 ($M^+$).

N-(2-methoxy-4-(4-(1-phenylethyl)piperazine-1-carbonyl)phenyl)quinoline-8-sulfonamide (XIV-146)

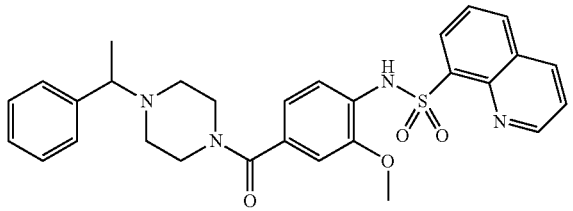

$^1$H NMR (400 MHz, DMSO-d6) δ: 1.21 (d, 3H), 2.37 (br s, 4H), 3.36-3.41 (m, 8H), 6.71 (s, 1H), 6.78 (d, 1H), 7.11-7.29 (m, 5H), 7.36 (d, 1H), 7.60-7.76 (m, 2H), 8.21-8.30 (m, 2H), 8.48 (d, 1H), 9.01 (s, 1H), 9.12 (s, 1H); HPLC Purity: 95.62%; LCMS: 531 ($M^+$+1).

N-(2-methoxy-4-(4-((1-phenylcyclopropyl)methyl) piperazine-1-carbonyl)phenyl)quinoline-8-sulfonamide (XIV-147)

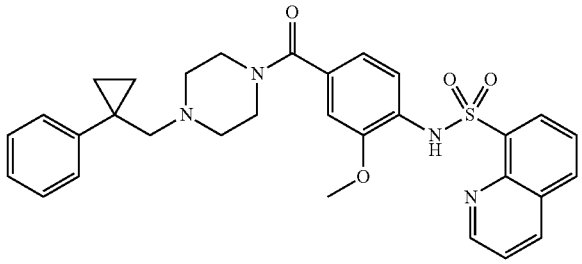

$^1$H NMR (400 MHz, DMSO-d6) δ: 0.06 (s, 2H), 0.08 (s, 2H), 2.37 (br s, 4H), 3.16 (s, 4H), 3.41 (br s, 5H), 6.78 (s, 1H), 6.81 (s, 1H), 7.12 (s, 2H), 7.19-7.26 (m, 4H), 7.42 (d, 1H), 7.65-7.80 (m, 2H), 8.25-8.31 (m, 2H), 8.58 (d, 1H), 9.10 (s, 1H), 9.19 (s, 1H); HPLC Purity: 99.97%; LCMS: 557 ($M^+$+1).

N-(4-(4-(3-fluoro-4-methoxybenzyl)piperazine-1-carbonyl)-2-methoxyphenyl)quinoline-8-sulfonamide (XIV-148)

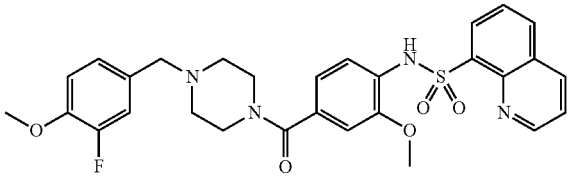

[$^1$H NMR (400 MHz, DMSO-d6) δ: 2.31 (br s, 4H), 3.32 (s, 4H), 3.41 (s, 2H), 3.43 (s, 3H), 3.80 (s, 3H), 6.78 (s, 1H), 6.82 (d, 1H), 6.98-7.18 (m, 3H), 7.21 (d, 1H), 7.31 (s, 2H), 7.64-7.80 (m, 2H), 8.21-8.30 (m, 2H), 8.57 (d, 1H), 9.08 (s, 1H), 9.19 (s, 1H);] HPLC Purity: 92.22%; LCMS: 565 ($M^+$+1).

N-(2-methoxy-4-(4-(pyridin-4-ylmethyl)piperazine-1-carbonyl)phenyl)quinoline-8-sulfonamide (XIV-149)

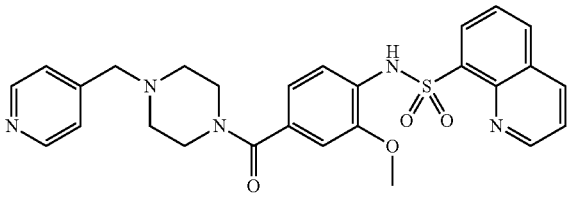

$^1$H NMR (400 MHz, DMSO-d6) δ: 2.32 (br s, 4H), 3.41 (s, 3H), 3.50 (s, 4H), 3.62 (s, 2H), 6.75 (s, 1H), 6.82 (d, 1H), 7.28 (d, 2H), 7.41 (d, 1H), 7.66-7.80 (d, 2H), 8.30 (s, 2H), 8.50 (d, 2H), 8.59 (d, 1H), 9.18 (s, 1H); HPLC Purity: 97.52%; LCMS: 518 ($M^+$+1).

N-(2-methoxy-4-(4-((tetrahydrofuran-2-yl)methyl) piperazine-1-carbonyl)phenyl)quinoline-8-sulfonamide (XIV-150)

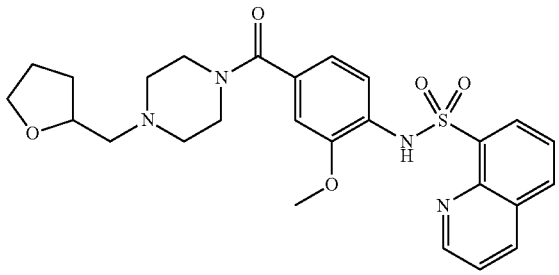

$^1$H NMR (400 MHz, DMSO-d6) δ: 1.45 (pentet, 2H), 1.78 (pentet, 2H), 1.90 (sextet, 1H), 2.30-2.41 (m, 7H), 3.41 (s, 3H), 3.60 (q, 2H), 3.70 (q, 2H), 3.95 (pentet, 1H), 6.78 (s, 1H), 6.82 (d, 1H), 7.42 (d, 1H), 7.70-7.81 (m, 2H), 8.30 (d, 1H), 8.60 (d, 1H), 9.10 (s, 1H), 9.20 (s, 1H); HPLC Purity: 99.24%; LCMS: 511 ($M^+$+1).

N-(4-(4-(4-chloro-3-fluorobenzyl)piperazine-1-carbonyl)-3-methoxyphenyl)quinoline-8-sulfonamide (XIV-151)

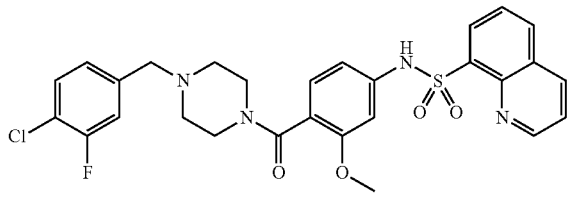

$^1$H NMR (400 MHz, DMSO-d6) δ: 2.19 (br s, 2H), 2.28 (br s, 2H), 2.97 (br s, 4H), 3.44 (s, 3H), 3.58 (s, 2H), 6.61 (d, 1H), 6.78 (s, 1H), 6.83 (d, 1H), 7.15 (1H), 7.30 (d, 1H), 7.49 (d, 1H), 7.70-7.78 (m, 2H), 8.24 (d, 1H), 8.42 (d, 1H), 8.50 (d, 1H), 9.10 (s, 1H), 10.30 (s, 1H); HPLC Purity: 98.63%; LCMS: 569 ($M^+$).

N-(3-methoxy-4-(4- ((1 -phenylcyclopropyl)methyl) piperazine-1-carbonyl)phenyl)quinoline-8-sulfonamide (XIV-152)

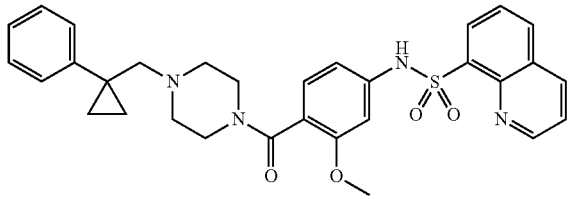

[$^1$H NMR (400 MHz, DMSO-d6) δ: 0.64 (s, 2H), 0.78 (s, 2H), 2.18 (br s, 4H), 2.39 (s, 2H), 2.81 (br s, 4H), 3.41 (s, 3H), 6.61 (d, 1H), 6.78 (s, 1H), 6.82 (d, 1H), 7.10 (q, 1H), 7.12 (t 1H), 7.20-7.28 (m, 4H), 7.70-7.80 (m, 2H), 8.23 (d, 1H), 8.41 (d, 1H), 8.50 (d, 1H), 9.13 (s, 1H), 10.30 (s, 1H);] HPLC Purity: 99.99%; LCMS: 557 ($M^+$+1).

N-(3-methoxy-4-(4-(pyridin-2-ylmethyl)piperazine-1-carbonyl)phenyl)quinoline-8-sulfonamide (XIV-153)

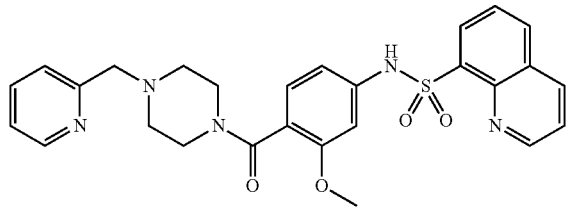

$^1$H NMR (400 MHz, DMSO-d6) δ: 2.22 (br s, 2H), 2.39 (br s, 2H), 2.98 (br s, 2H), 3.57 (br s, 2H), 3.60 (s, 5H), 6.62 (d, 1H), 6.78 (s, 1H), 6.82 (d, 1H), 7.20 (s, 1H), 7.40 (d, 1H), 7.66-7.79 (m, 3H), 8.21-8.30 (m, 2H), 8.40-8.50 (m, 2H), 9.16 (s, 1H), 10.30 (s, 1H); HPLC Purity: 98.14%; LCMS: 518 ($M^+$+1).

N-(3-methoxy-4-(4-(pyridin-4-ylmethyl)piperazine-1-carbonyl)phenyl)quinoline-8-sulfonamide (XIV-154)

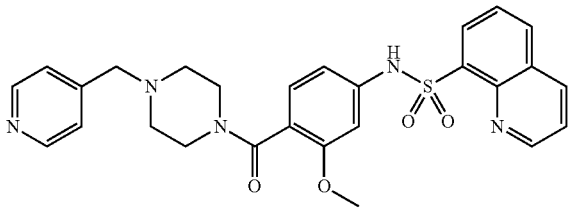

$^1$H NMR (400 MHz, DMSO-d6) δ: 2.20 (br s, 2H), 2.30 (br s, 2H), 2.98 (br s, 4H), 3.50 (s, 3H), 3.58 (s, 2H), 6.62 (d, 1H), 6.78 (s, 1H), 6.82 (d, 1H), 7.24 (s, 2H), 7.65-7.73 (m, 2H), 8.21-8.30 (m, 2H), 8.40 (d, 1H), 8.43-8.50 (m, 2H), 9.10 (s, 1H), 10.23 (br s, 1H); HPLC Purity: 99.69%; LCMS: 518 ($M^+$+1).

N-(4-(4-(4-chloro-3-fluorobenzyl)piperazine-1-carbonyl)-2-methylphenyl)quinoline-8-sulfonamide (XIV-155)

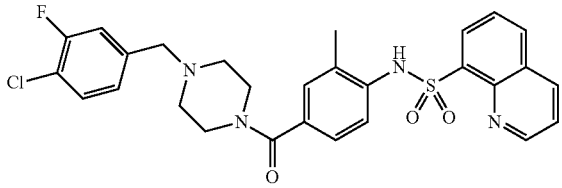

$^1$H NMR (400 MHz, DMSO-d6) δ: 2.01 (s, 3H), 2.38 (br s, 4H), 3.50 (s, 4H), 3.56 (s, 2H), 7.00 (s, 2H), 7.06 (s, 1H), 7.18 (d, 1H), 7.35 (d, 1H), 7.52 (t 1H), 7.70-7.80 (m, 2H), 8.29 (q, 2H), 8.59 (d, 1H), 9.15 (s, 1H), 9.38 (s, 1H); HPLC Purity: 99.25%; LCMS: 553 ($M^+$).

N-(4-(4-benzyl-1,4-diazepane-1-carbonyl)-2-methoxyphenyl)quinoline-8-sulfonamide (XIV-156)

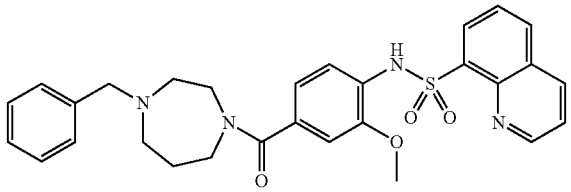

$^1$H NMR (400 MHz, DMSO-d6) δ: 2.22 (br s, 2H), 3.01 (br s, 2H), 3.52-3.58 (m, 9H), 4.39 (br s, 2H), 6.66 (d, 1H), 6.80 (s, 1H), 7.50 (br s, 4H), 7.74-7.79 (m, 2H), 8.30 (d, 1H), 8.47 (d, 2H), 8.59 (d, 1H), 9.18 (d, 1H), 10.40 (s, 1H); HPLC Purity: 99.00%; LCMS: 531 ($M^+$+1).

N-(4-(4-benzyl-1,4-diazepane-1-carbonyl)-2-methylphenyl)quinoline-8-sulfonamide (XIV-157)

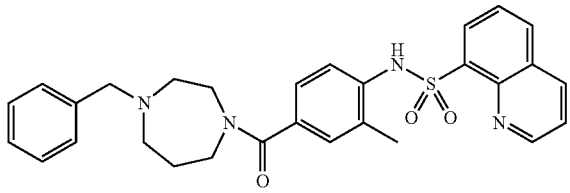

$^1$H NMR (400 MHz, $CD_3OD$) δ: 2.06 (s, 3H), 2.14 (br s, 2H), 2.22 (s, 4H), 3.58 (br s, 4H), 4.40 (s, 2H), 7.10 (br s, 1H), 7.22 (d, 2H), 7.50 (s, 4H), 7.68-7.77 (m, 2H), 8.21 (d, 1H), 8.38 (d, 1H), 8.51 (d, 1H), 9.18 (d, 1H); HPLC Purity: 99.04%; LCMS: 515 ($M^+$+1).

N-(4-(4-benzyl-1,4-diazepane-1-carbonyl)-2-fluorophenyl)quinoline-8-sulfonamide (XIV-158)

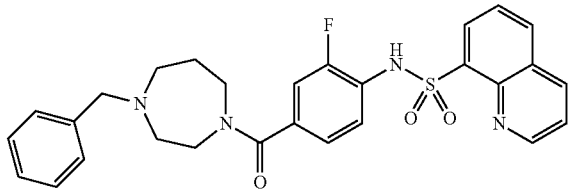

$^1$H NMR (400 MHz, $CDCl_3$) δ: 2.21 (br s, 6H), 3.43 (br s, 4H), 4.21 (s, 2H), 6.97 (d, 1H), 7.08 (br s, 1H), 7.42 (t, 4H), 7.63-7.68 (m, 2H), 7.79 (t, 1H), 8.09 (d, 1H), 8.28 (d, 1H), 8.38 (d, 1H), 9.18 (d, 1H); HPLC Purity: 96.67%; LCMS: 519 ($M^+$+1).

N-(4-(4-benzyl-1,4-diazepane-1-carbonyl)-3-chlorophenyl)quinoline-8-sulfonamide (XIV-159)

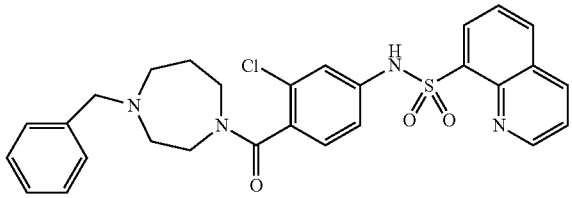

$^1$H NMR (400 MHz, $CDCl_3$) δ: 2.12 (br s, 1H), 2.50 (br s, 1H), 3.09 (br s, 2H), 3.29 (br s, 1H), 3.58 (br s, 2H), 3.67 (br s, 2H), 4.20 (s, 2H), 4.41 (br s, 1H), 6.99 (d, 2H), 7.28-7.39 (m, 4H), 7.66 (t, 2H), 8.21 (d, 1H), 8.38 (d, 1H), 8.42 (d, 1H), 9.18 (s, 1H); HPLC Purity: 95.33%; LCMS: 535 ($M^+$).

Synthesis of Reverse Sulfonamide Benzyl and Alkyl Derivatives

Scheme 23

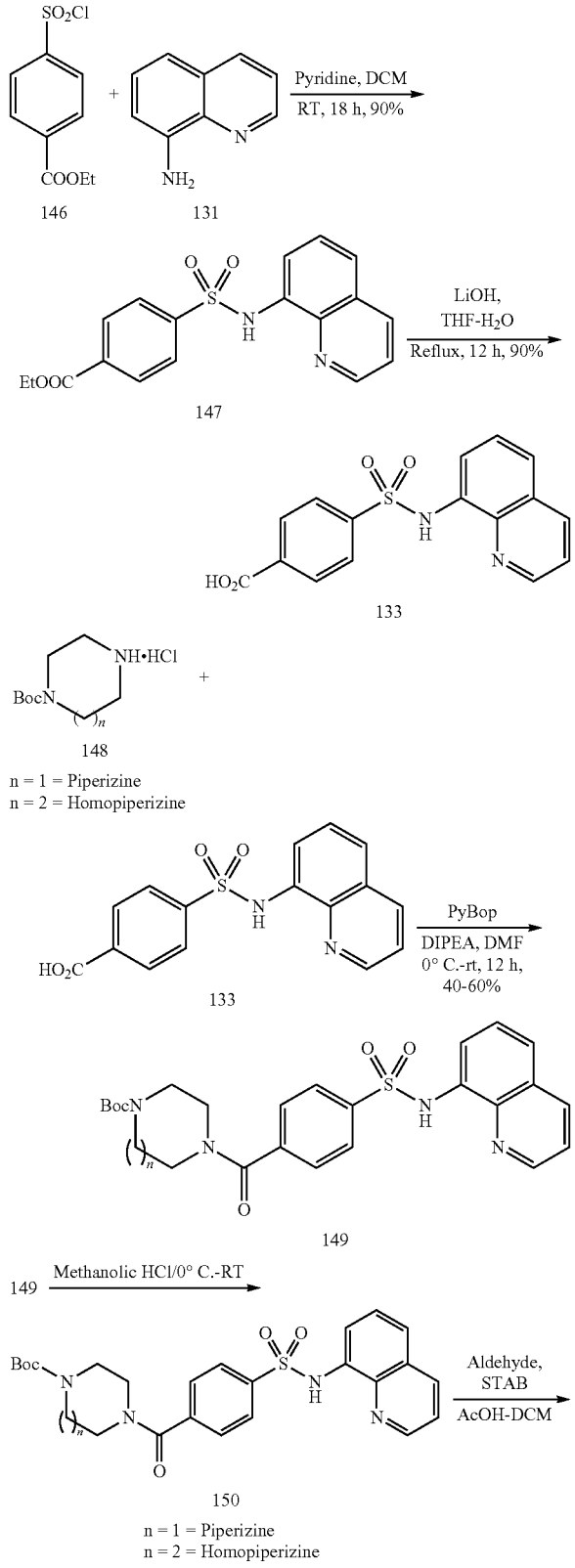

-continued

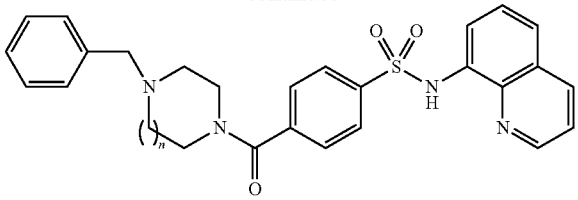

151 n = 1 = Piperizine
n = 2 = Homopiperizine

STAB = Sodium tri-acetoxy borohydride

The synthesis of compound 151 was carried out from aniline 131 (0.25 mmol) by following the similar procedure as mentioned in Scheme 21 for compounds of formula (VIII) with respective key steps such as ester hydrolysis, amide bond formation in the presence of PyBop following reductive amination in the presence of sodium tri-acetoxy borohydride.

4-(4-benzylpiperazine-1-carbonyl)-N-(quinolin-8-yl) benzenesulfonamide (151a)

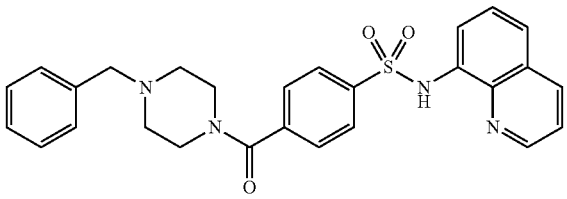

[$^1$H NMR (400 MHz, DMSO-d6) δ: 2.24 (br s, 2H), 2.40 (br s, 2H), 3.10 (br s, 2H), 3.55 (s, 2H), 3.59 (s, 2H), 7.21-7.39 (m, 4H), 7.42 (d, 2H), 7.58 (d, 2H), 7.91 (d. 2H), 8.37 (d, 1H), 8.81 (s, 1H), 10.15 (br s, 1H);] HPLC: 99.26%; LCMS: 487 ($M^+$+1).

4-(4-benzyl-1,4-diazepane-1-carbonyl)-N-(quinolin8-yl)benzenesulfonamide (151b)

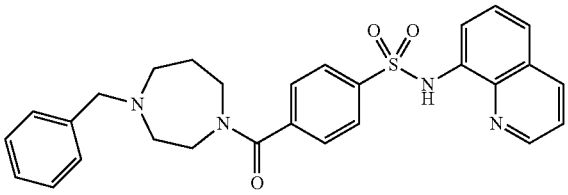

$^1$H NMR (400 MHz, DMSO-d6) δ: 1.55 (s, 1H), 1.75 (s, 1H), 2.41 (s, 2H), 2.52-2.64 (m, 2H), 3.05 (d, 2H), 3.58-3.62 (m, 4H), 7.19-7.32 (m, 3H), 7.36-7.47 (m, 2H), 7.58 (d, 1H), 7.63-7.77 (m, 2H), 7.81-7.89 (m, 2H), 8.30 (dd, 1H), 8.78 (dd, 1H), 10.05 (s, 1H); HPLC Purity: 99.89%; LCMS: 501 ($M^+$+1).

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A compound of formula II or a pharmaceutically acceptable salt thereof, wherein:

(II)

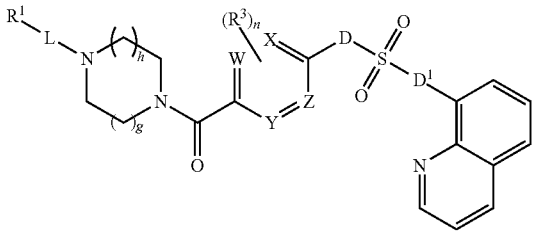

W, X, Y and Z are each independently selected from CH or N;

D and $D^1$ are independently selected from a bond or $NR^b$;

L is a bond, —C(O)—, —$(CR^cR^c)_m$—, —OC(O)—, —$(CR^cR^c)_m$—OC(O)—, —$(CR^cR^c)_m$—C(O)—, —$NR^bC(S)$—, or —$NR^bC(O)$— (wherein the point of the attachment to $R^1$ is on the left-hand side);

$R^1$ is selected from alkyl, cycloalkyl, aryl, heteroaryl, and heterocyclyl; each of which is substituted with 0-5 occurrences of $R^d$;

each $R^3$ is independently selected from halo, haloalkyl, alkyl, hydroxyl and —$OR^a$ or two adjacent $R^3$ taken together with the carbon atoms to which they are attached form an optionally substituted heterocyclyl;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —$C(O)R^a$, —$OC(O)R^a$, —$C(O)OR^a$, —$SR^a$, —$NR^aR^b$ and —$OR^a$, or two $R^d$ taken together with the carbon atoms to which they are attached form an optionally substituted heterocyclyl;

n is 0, 1, or 2;

m is 1, 2 or 3;

h is 1; and g is 1.

2. The compound of claim 1, wherein W, X, Y and Z are CH.

3. The compound of claim 2, wherein D is $NR^b$ and $D^1$ is a bond.

4. The compound of claim 3, wherein $R^b$ is H, methyl or ethyl.

5. The compound of claim 1, wherein L is a bond, —$(CR^cR^c)_m$—, —$NR^bC(O)$—, —$(CR^cR^c)_m$—C(O)—, —C(O)—, or [—O(CO)—] —*OC(O)*—.

6. The compound of claim 5, wherein L is a bond.

7. The compound of claim 6, wherein $R^1$ is alkyl, aryl or heteroaryl, each substituted with 0-5 occurrences of $R^d$.

8. The compound of claim 5, wherein L is —$(CR^cR^c)_m$—.

9. The compound of claim 8, wherein $R^1$ is cycloalkyl, aryl, heteroaryl or heterocyclyl, each substituted with 0-5 occurrences of $R^d$.

10. The compound of claim 5, wherein L is —$NR^bC(O)$— and $R^b$ is hydrogen.

11. The compound of claim 10, wherein $R^1$ is aryl substituted with 0-5 occurrences of $R^d$.

12. The compound of claim 5, wherein L is —$(CR^cR^c)_m$—C(O)—.

13. The compound of claim 12, wherein $R^1$ is cycloalkyl, aryl or heteroaryl, each substituted with 0-5 occurrences of $R^d$.

14. The compound of claim 5, wherein L is —C(O)—.

15. The compound of claim 14, wherein $R^1$ is aryl, alkyl, or heteroaryl, each substituted with 0-5 occurrences of $R^d$.

16. The compound of claim 5, wherein L is —OC(O)—.

17. The compound of claim 16, wherein $R^1$ is alkyl, aryl or heterocyclyl, each substituted with 0-5 occurrences of $R^d$.

18. The compound of claim 1, wherein L is —$(CR^cR^c)_m$—OC(O)—.

19. The compound of claim 18, wherein $R^1$ is heterocyclyl or cycloalkyl, each substituted with 0-5 occurrences of $R^d$.

20. The compound of claim 5, wherein n is 0.

21. The compound of claim 5, wherein n is 1 and $R^3$ is $CH_3$, $CH_2CH_3$, $OCH_3$, $OCH_2CH_3$, OH, F, Cl, or $CF_3$.

22. A pharmaceutical composition comprising a compound *of* formula II or a pharmaceutically acceptable salt thereof, wherein:

(II)

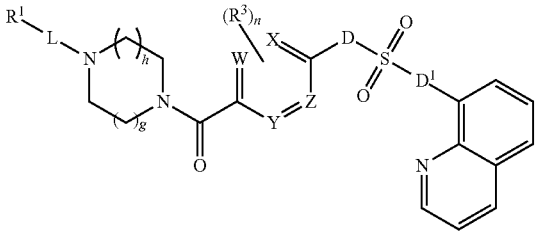

W, X, Y and Z are each independently selected from CH or N;

D and $D^1$ are independently selected from a bond or $NR^b$;

L is a bond, —C(O)—, —$(CR^cR^c)_m$—, —OC(O)—, —$(CR^cR^c)_m$—OC(O)—, —$(CR^cR^c)_m$—C(O)—, —$NR^bC(S)$—, or —$NR^bC(O)$— (wherein the point of the attachment to $R^1$ is on the left-hand side);

$R^1$ is selected from alkyl, cycloalkyl, aryl, heteroaryl, and heterocyclyl; each of which is substituted with 0-5 occurrences of $R^d$;

each $R^3$ is independently selected from halo, haloalkyl, alkyl, hydroxyl and —$OR^a$, or two adjacent $R^3$ taken together with the carbon atoms to which they are attached form an optionally substituted heterocyclyl;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —$C(O)R^a$, —$OC(O)R^a$, —$C(O)OR^a$, —$SR^a$, —$NR^aR^b$ and —$OR^a$, or two $R^d$ taken together with the carbon atoms to which they are attached form an optionally substituted heterocyclyl;

n is 0, 1, or 2;

m is 1, 2 or 3;

h is 1; and g is 1.

23. The pharmaceutical composition of claim 22, wherein the compound is a compound of formula:

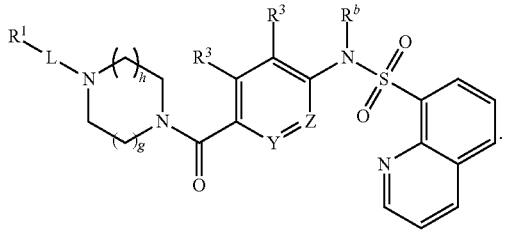

24. The compound of claim 1, wherein the compound is selected from the following:

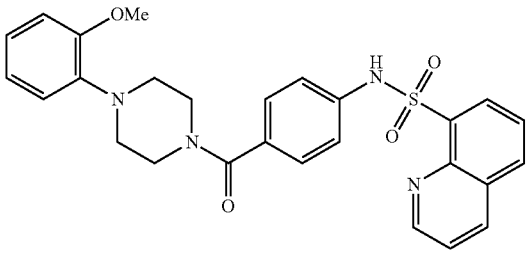

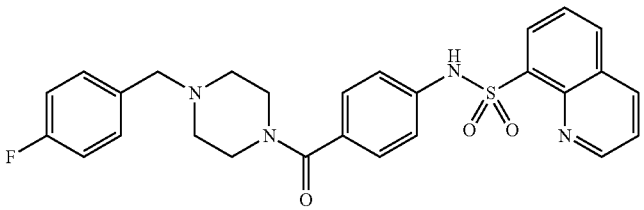

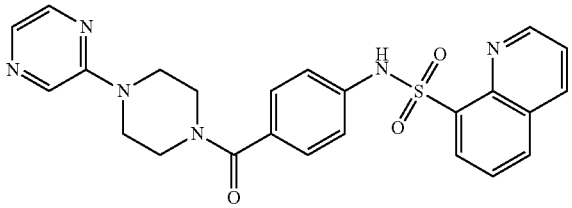

-continued
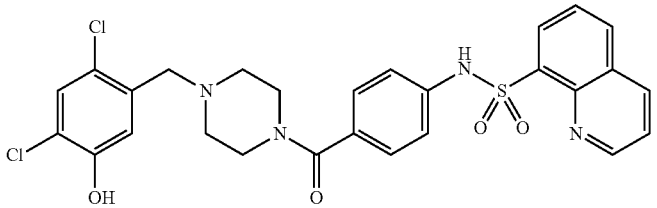
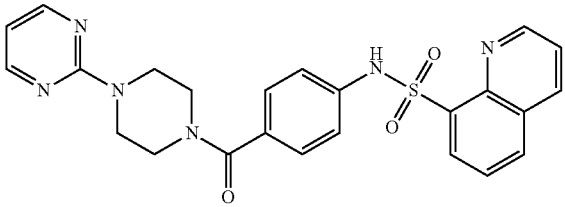
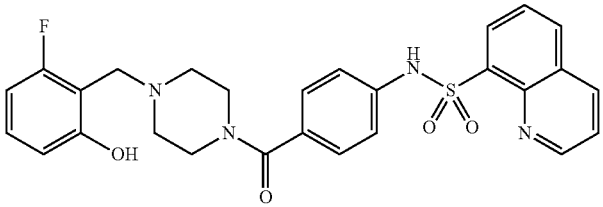
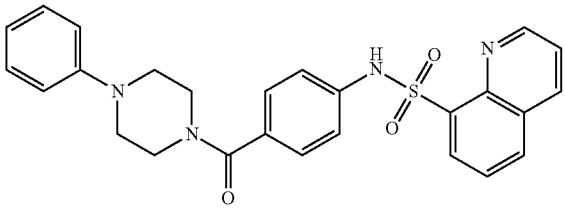
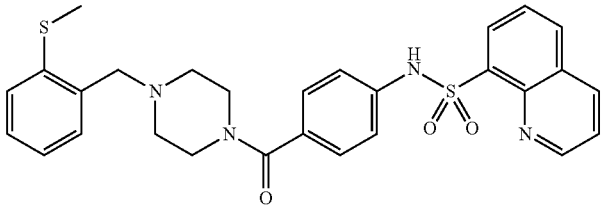
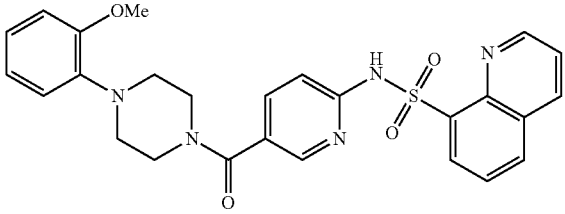
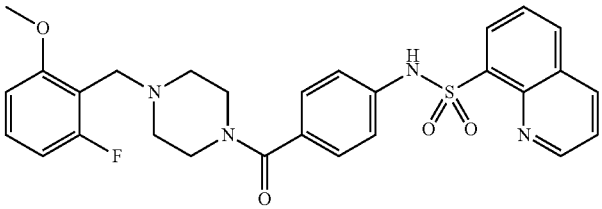
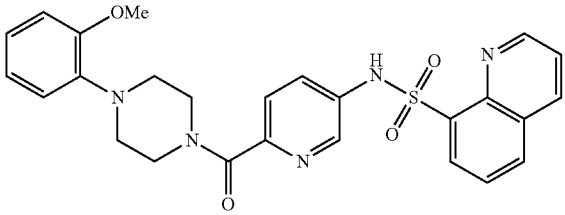
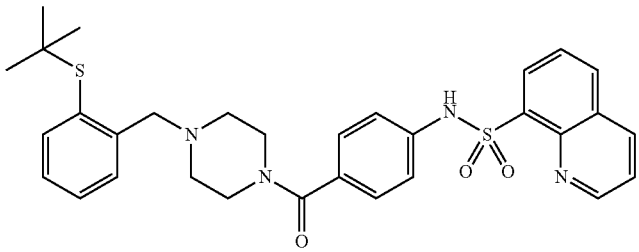
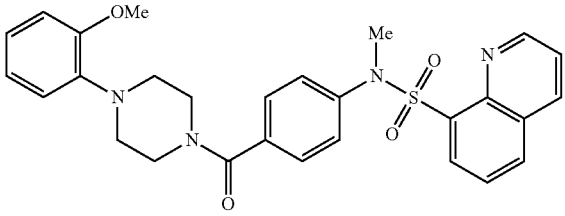
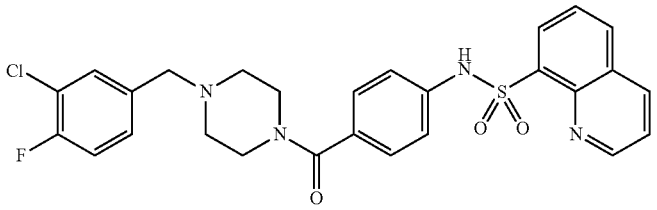

-continued
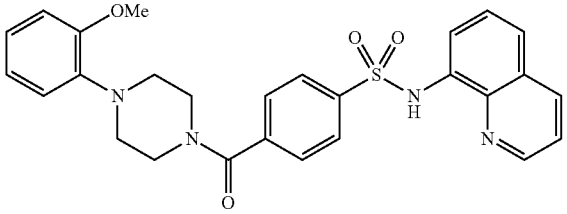
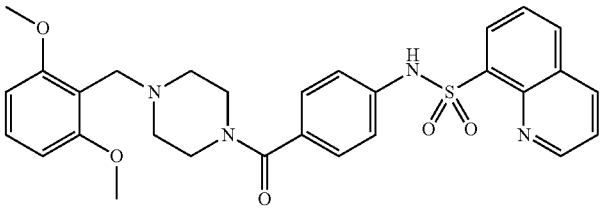
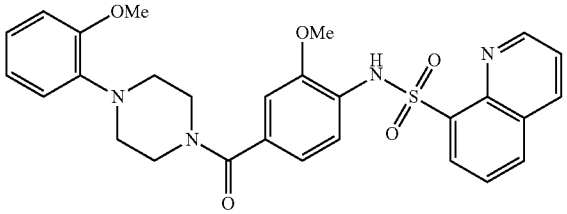
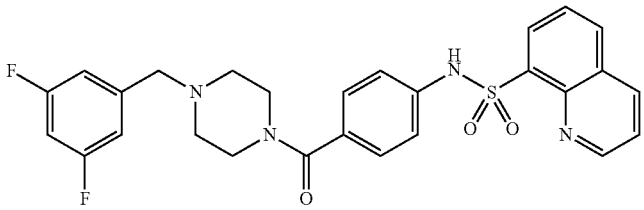
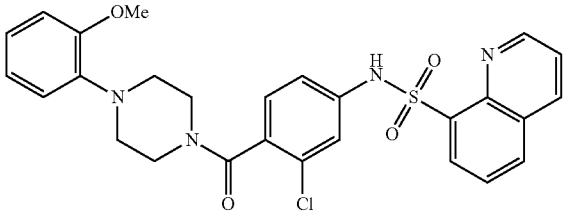
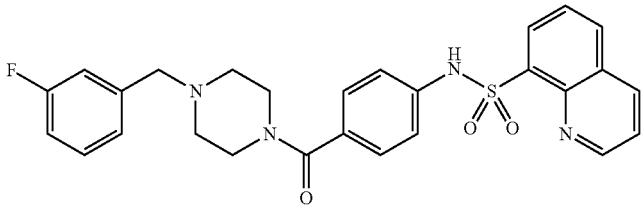
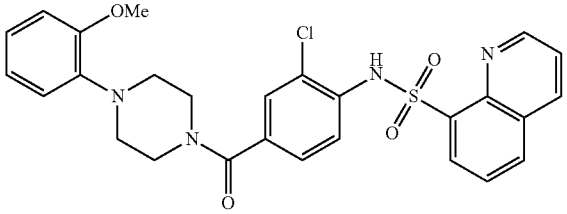
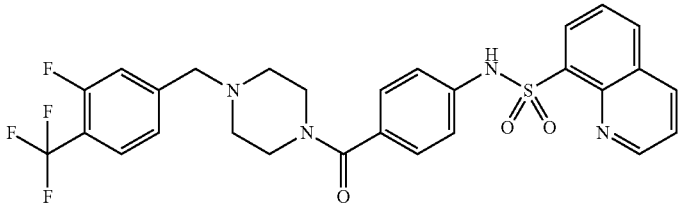
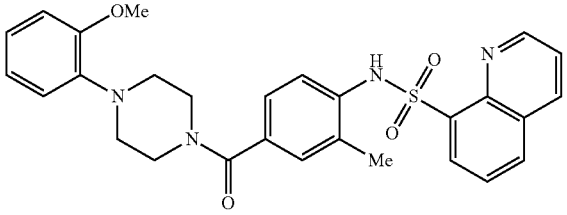

-continued
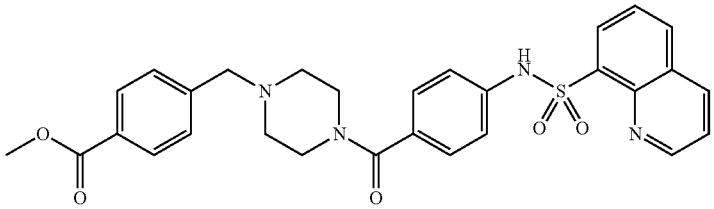
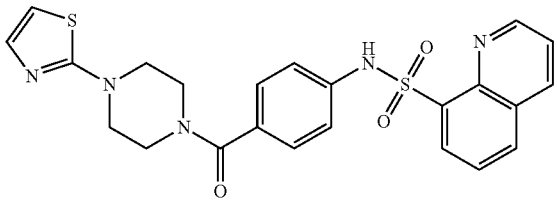
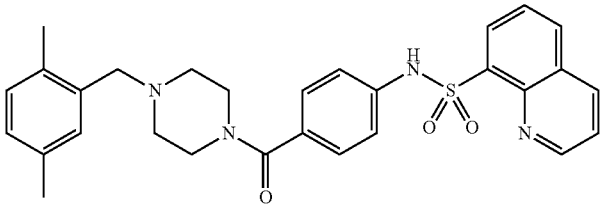
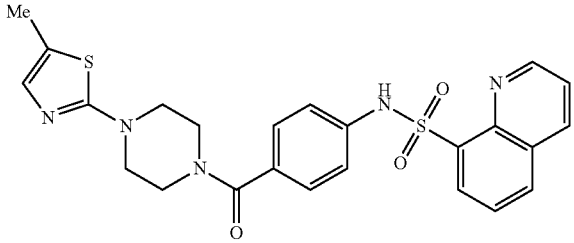
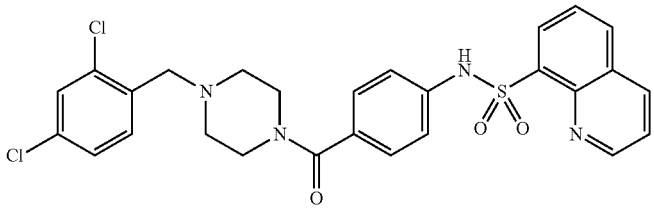
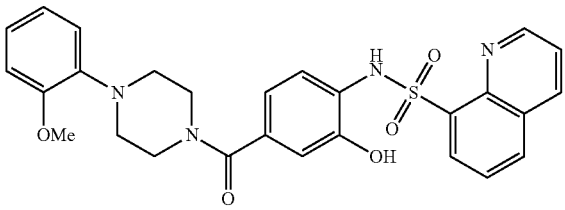
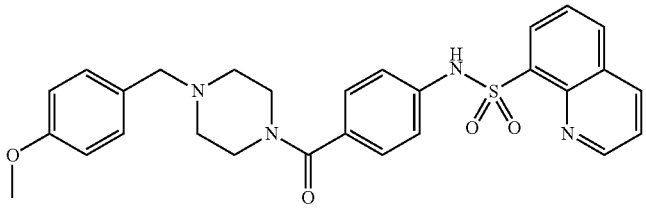
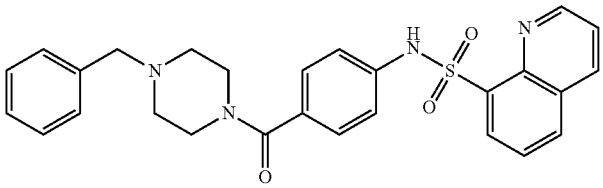
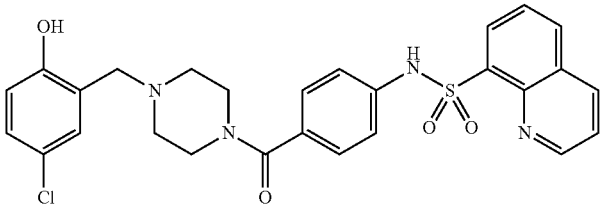

-continued
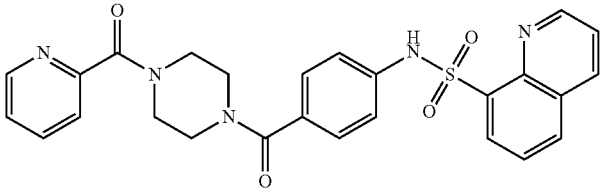
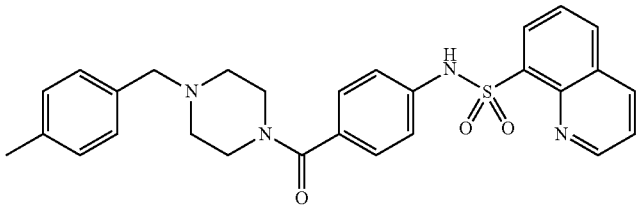
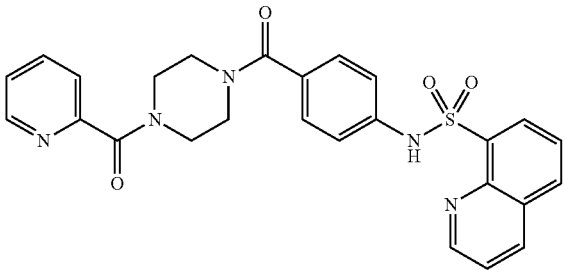
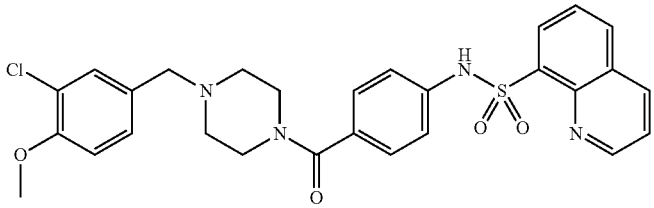
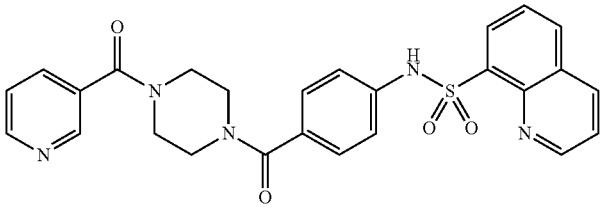
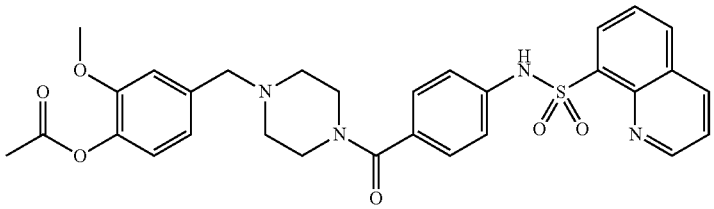
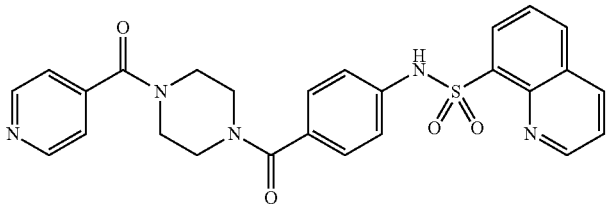
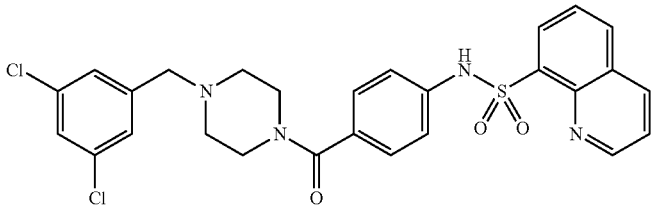

-continued
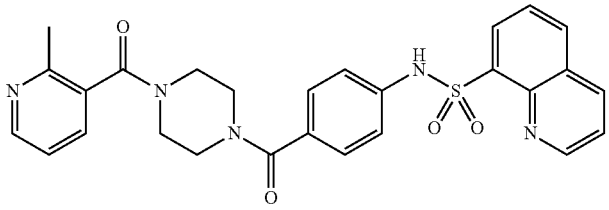
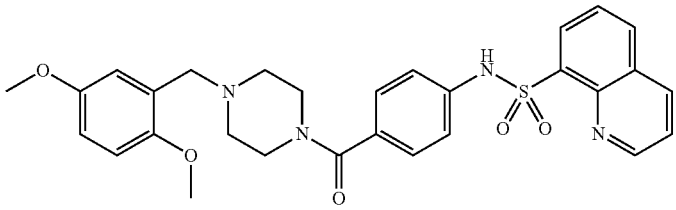
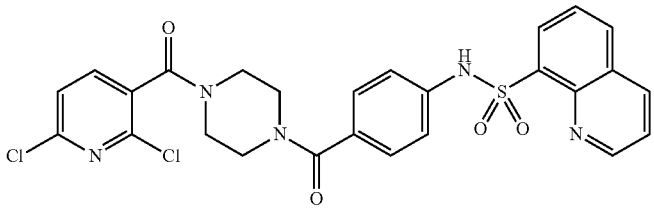
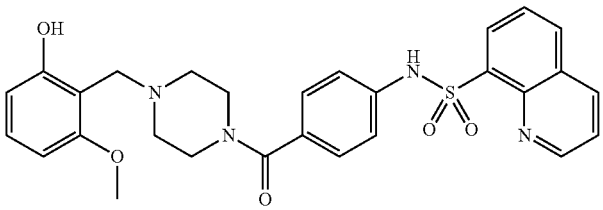
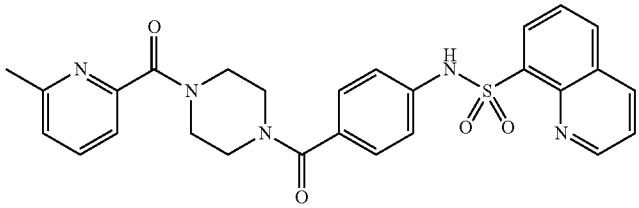
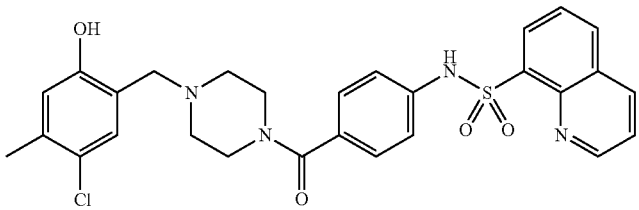
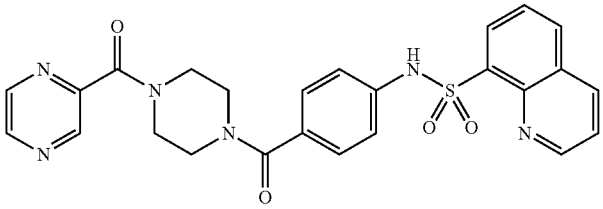
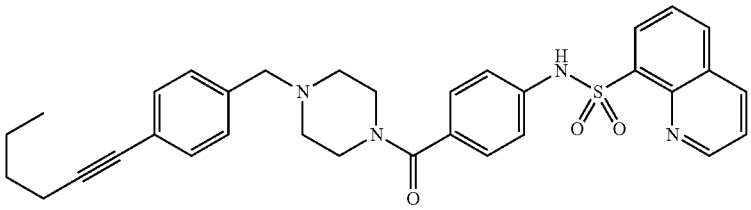

-continued
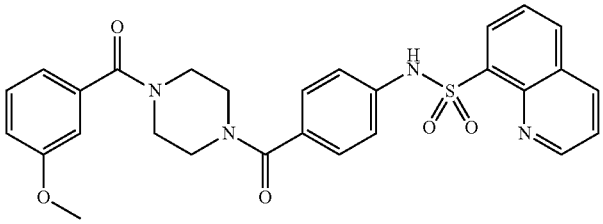
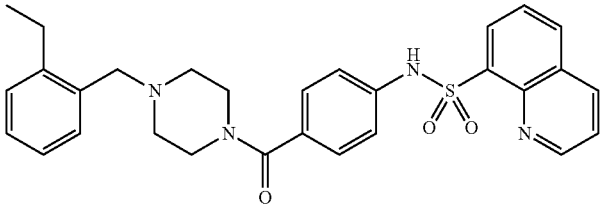
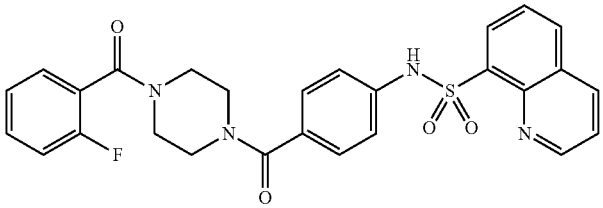
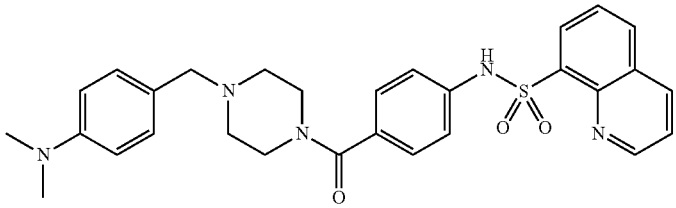
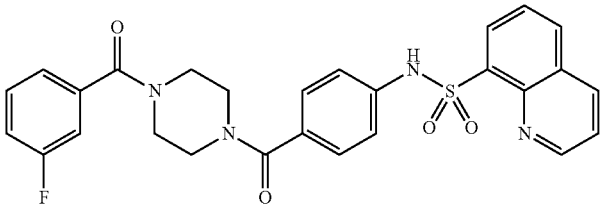
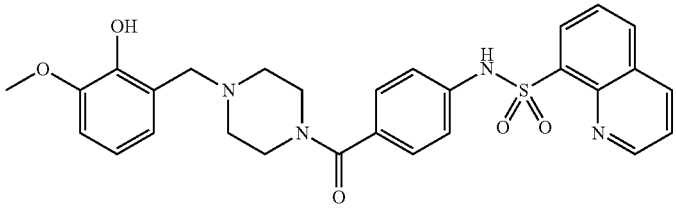
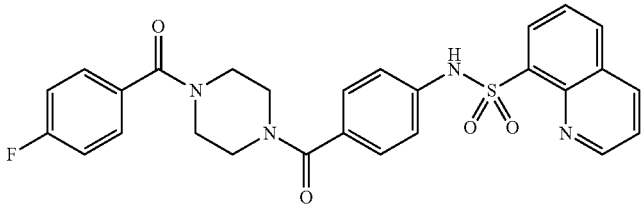
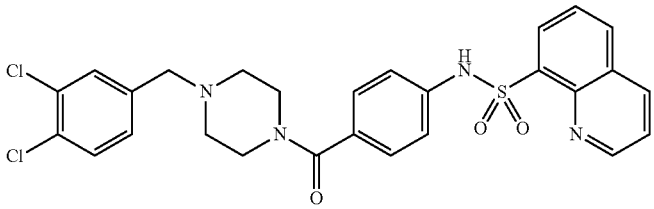

-continued
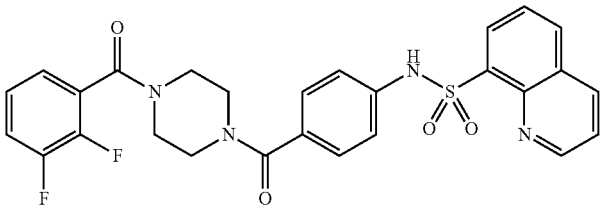
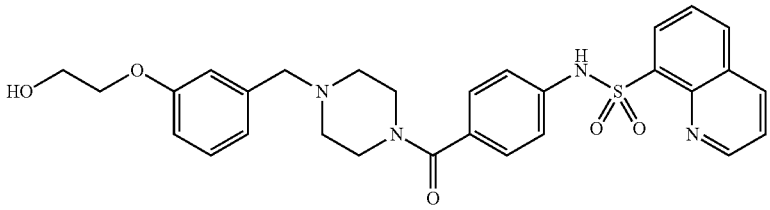
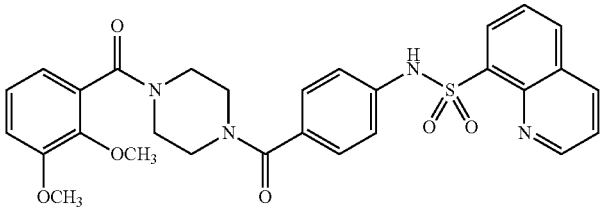
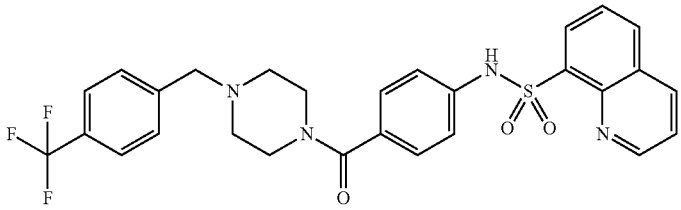
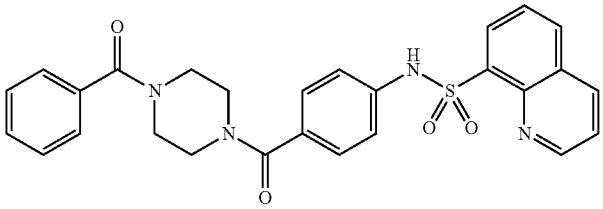
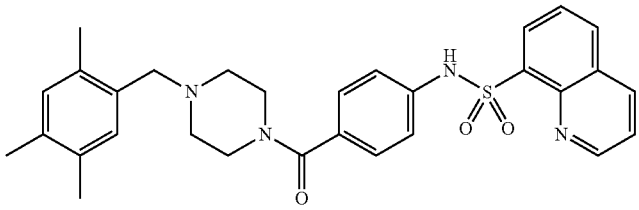
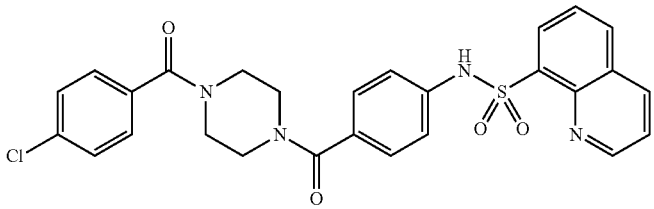
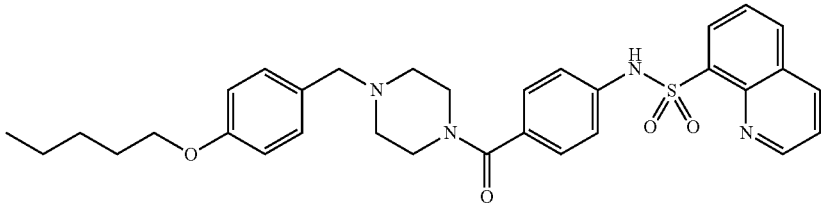

-continued
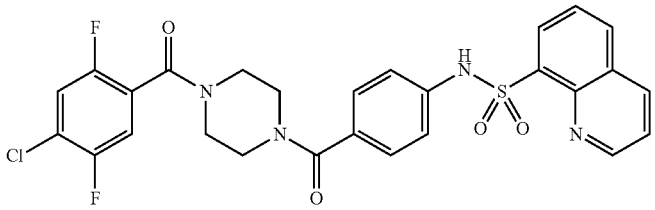
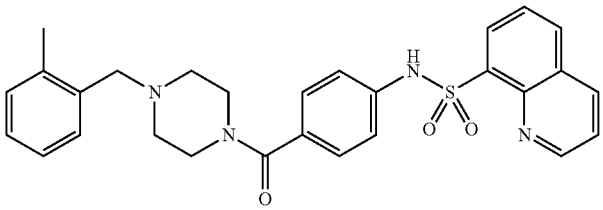
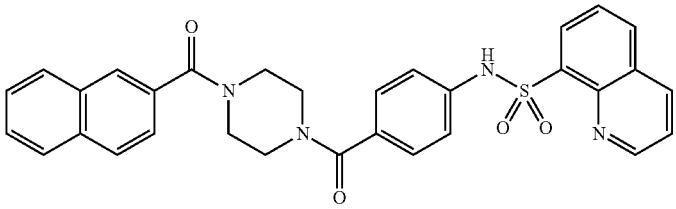
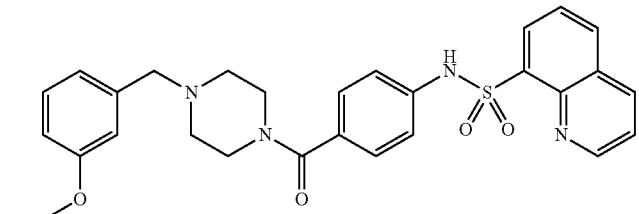
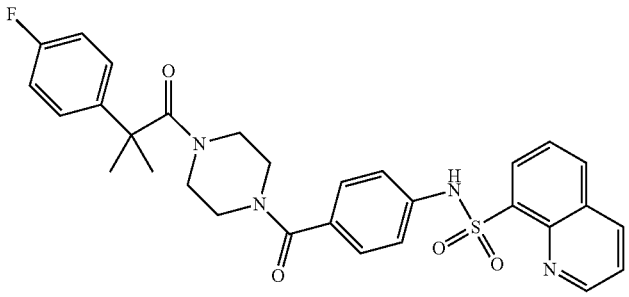
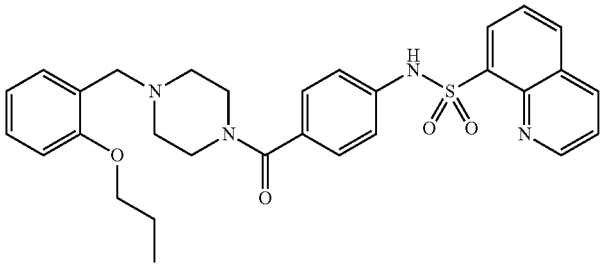

-continued
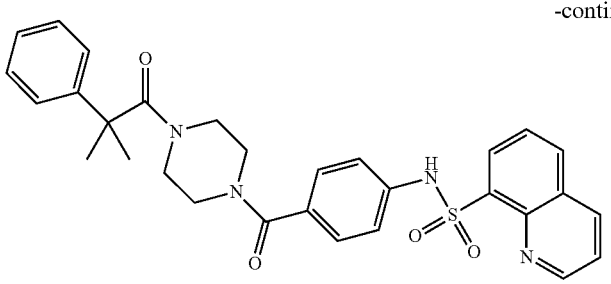
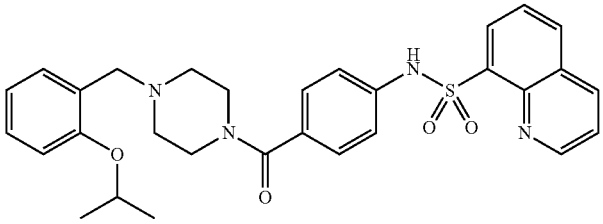
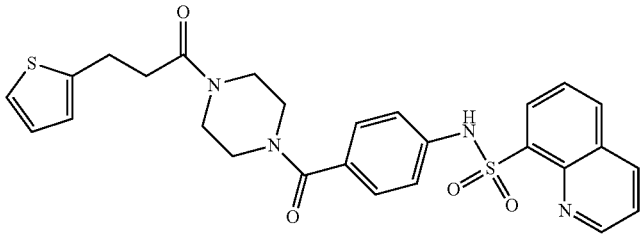
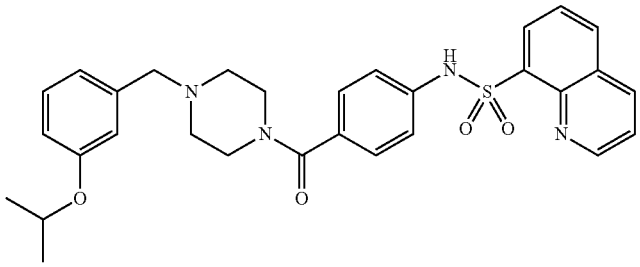
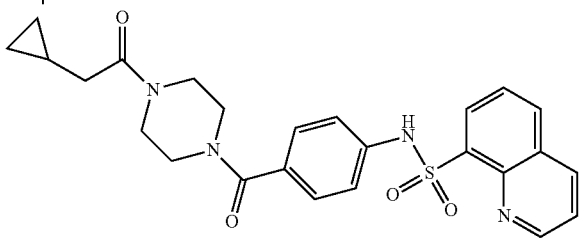
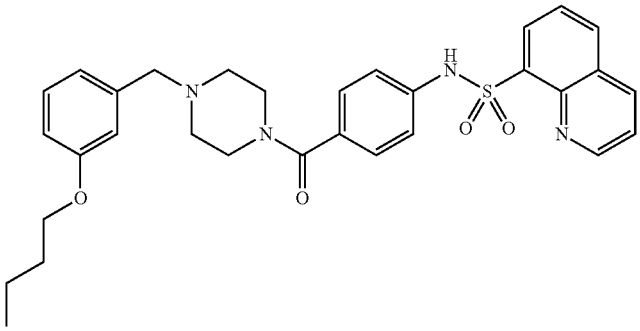

-continued
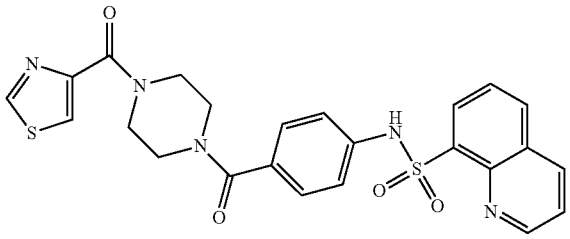
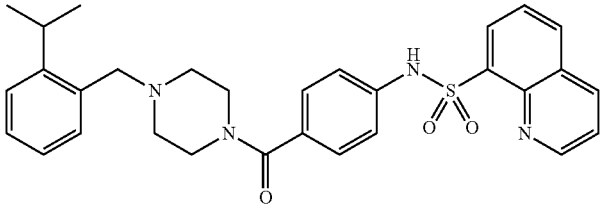
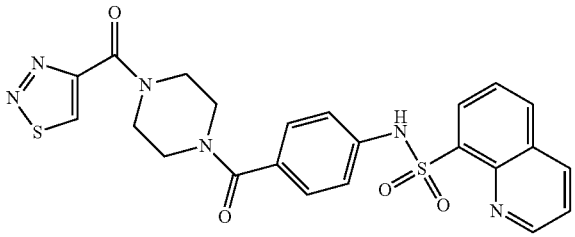
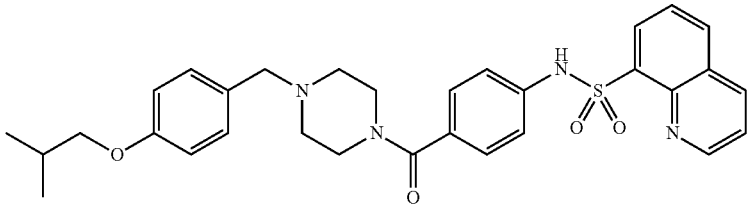
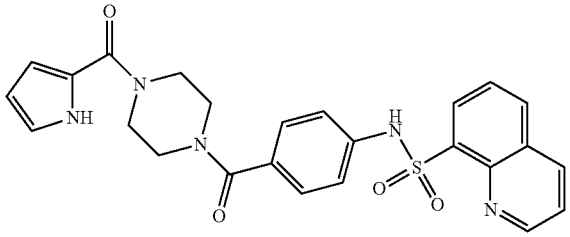
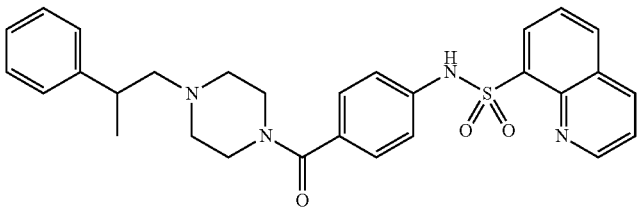
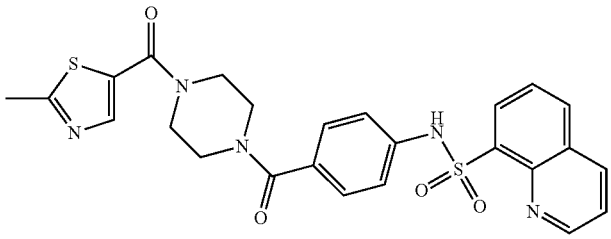
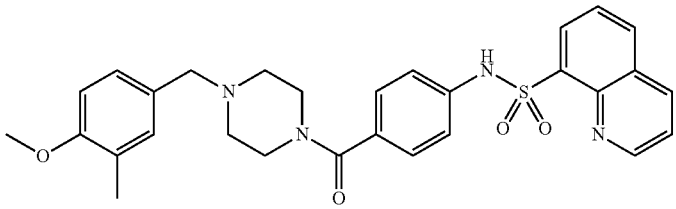

-continued
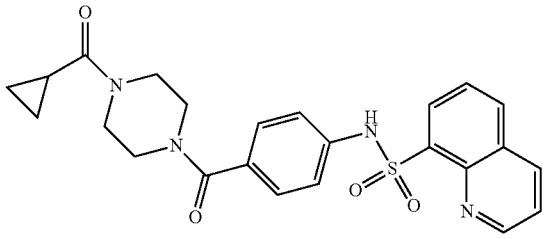
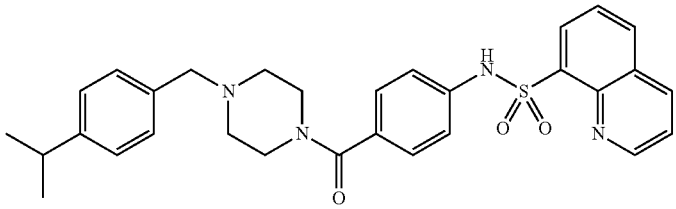
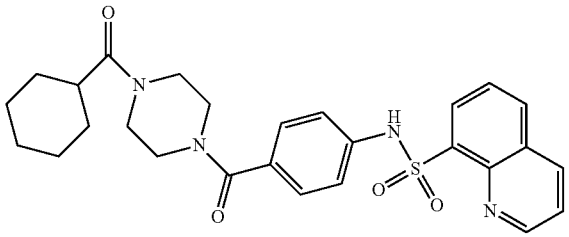
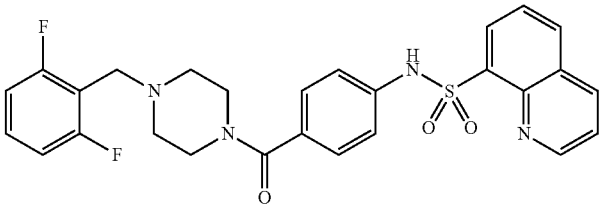
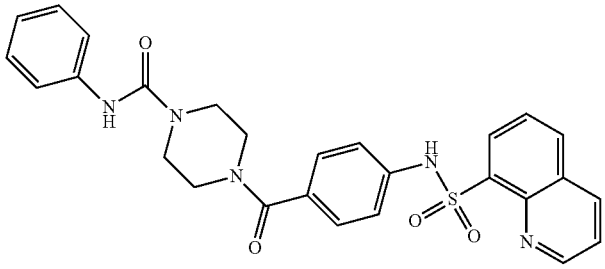
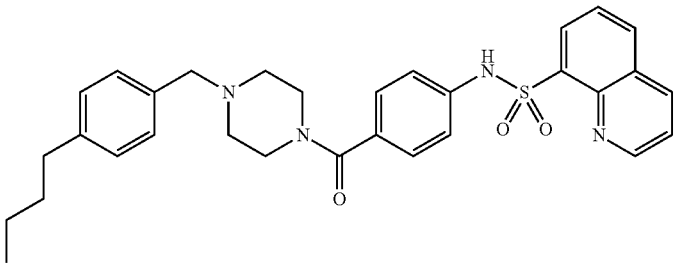
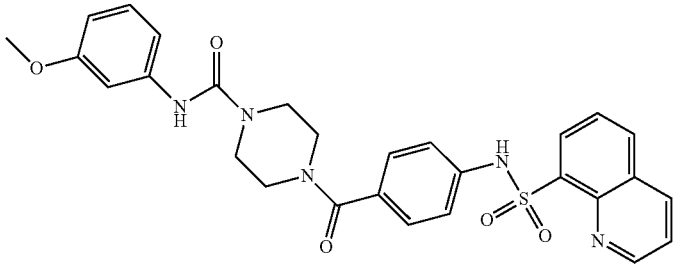
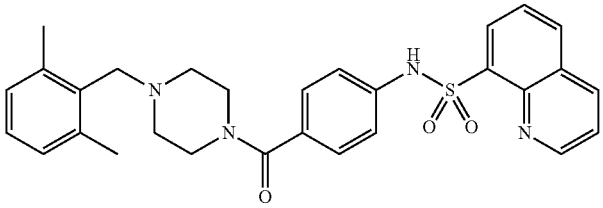

-continued
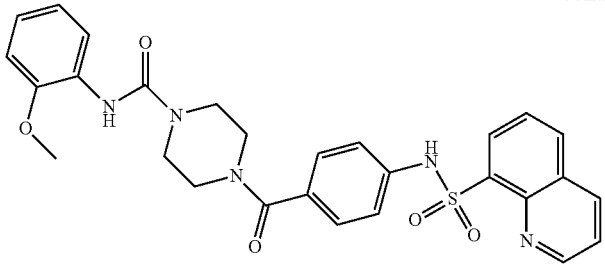
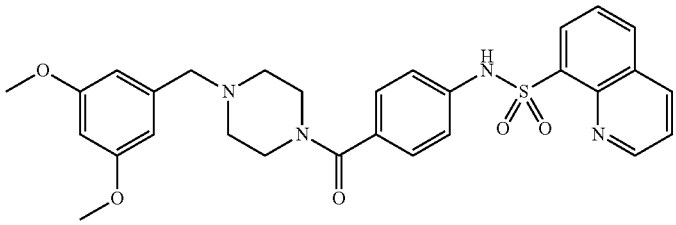
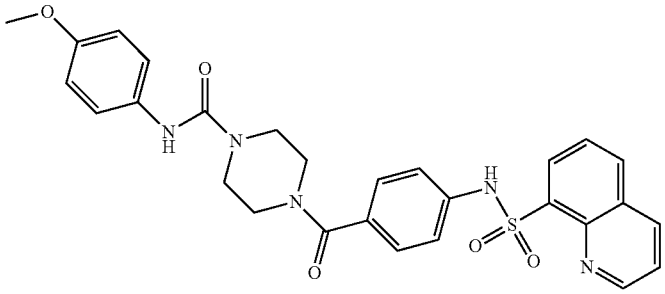
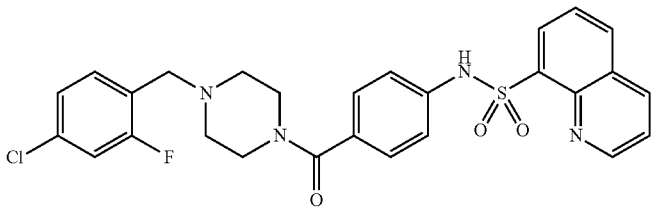
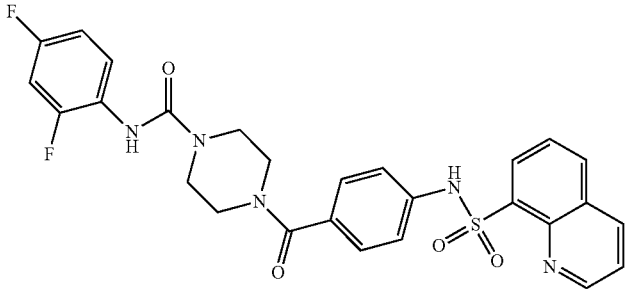
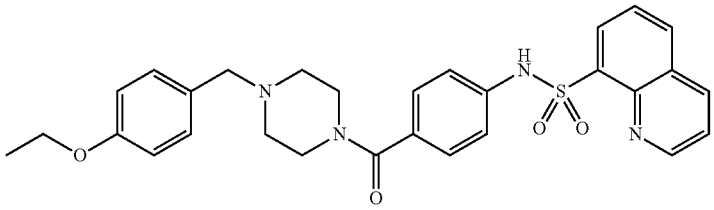

-continued
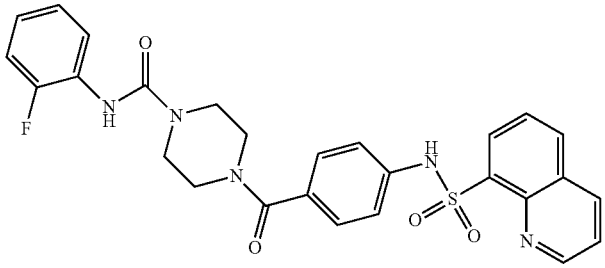
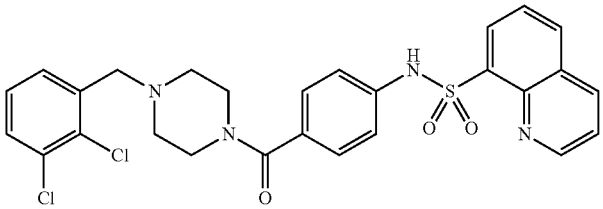
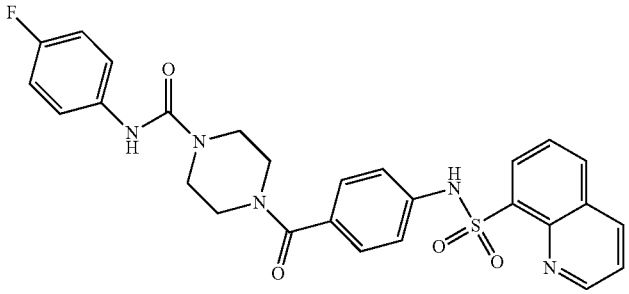
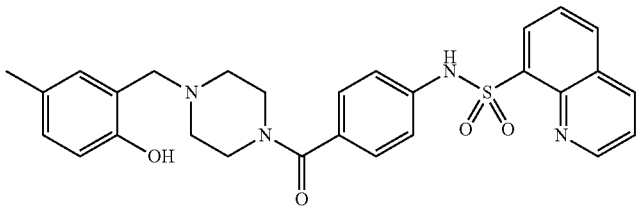
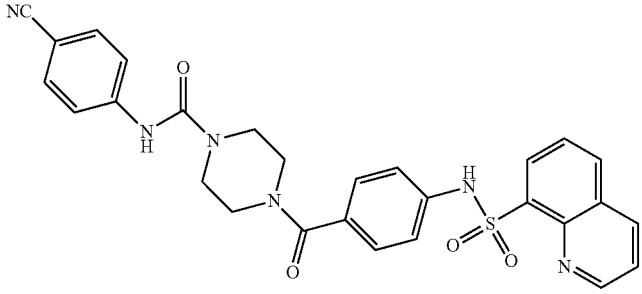
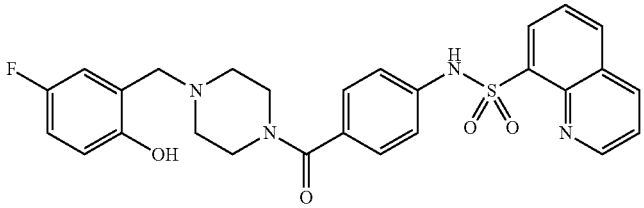

-continued
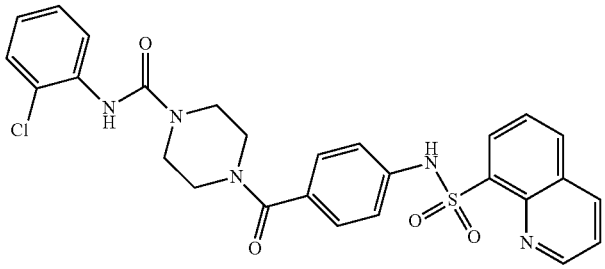
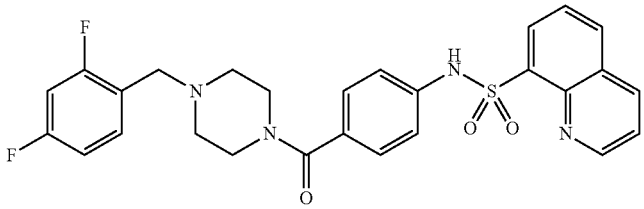
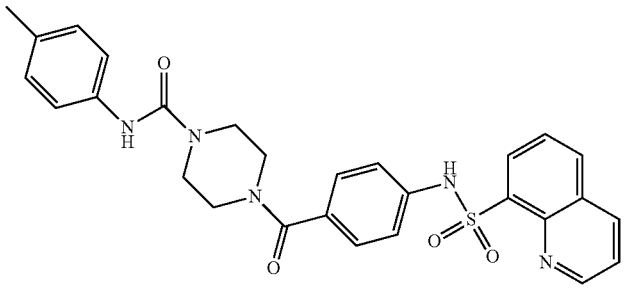
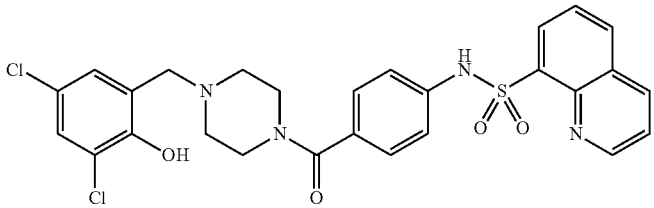
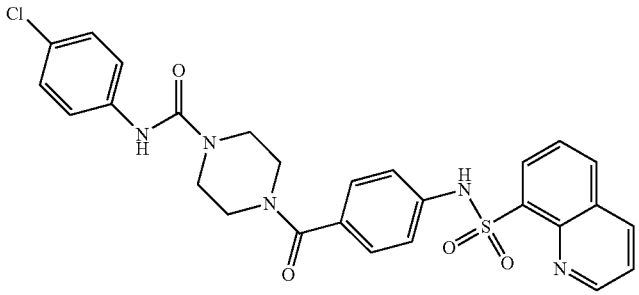
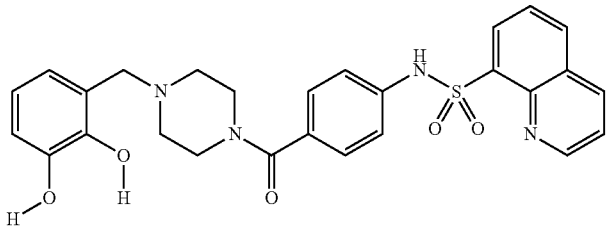

-continued
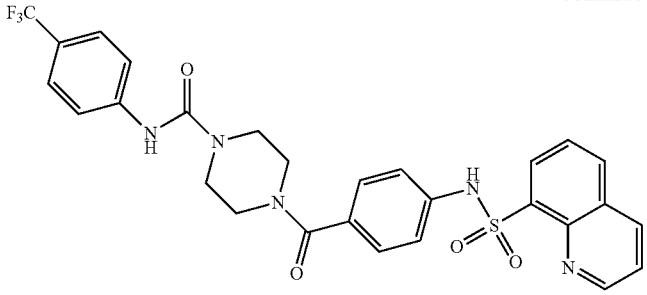
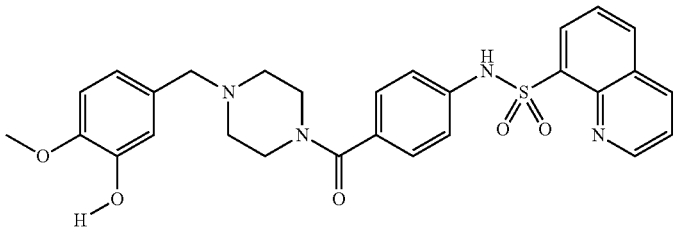
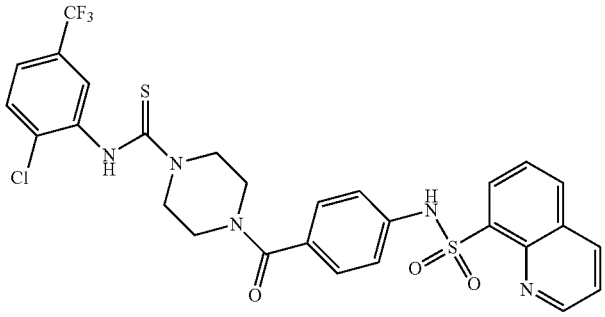
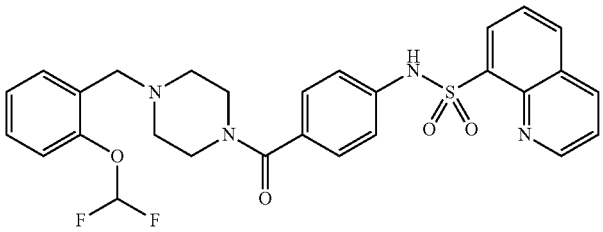
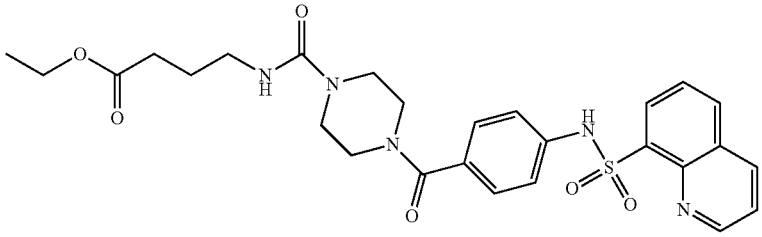
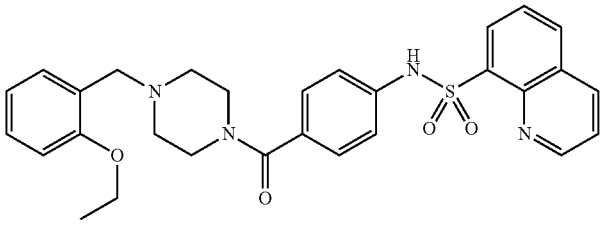

-continued
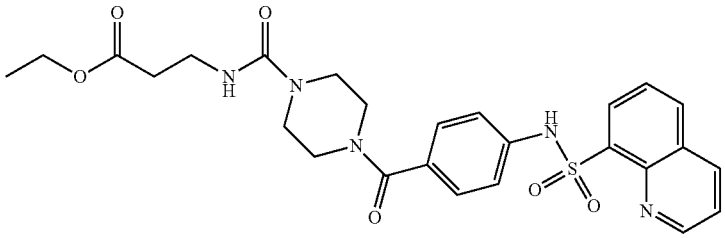
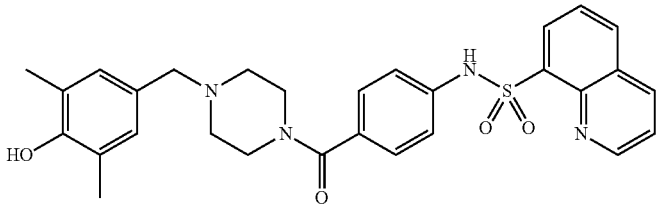
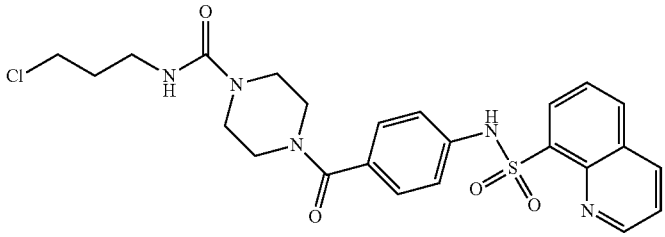
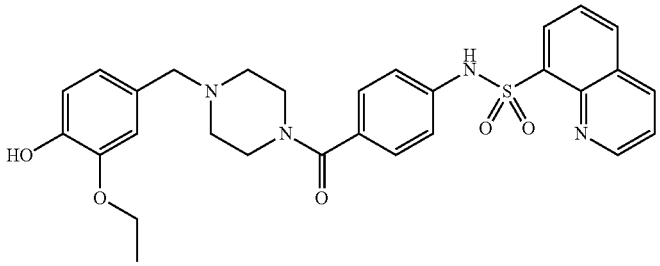
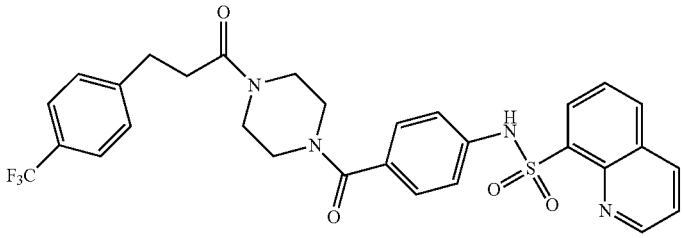
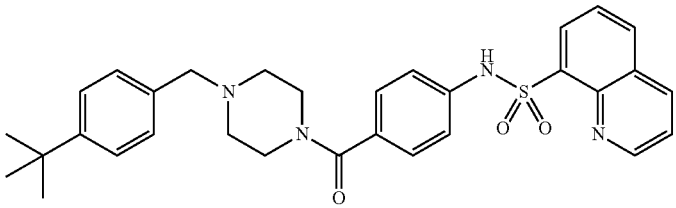
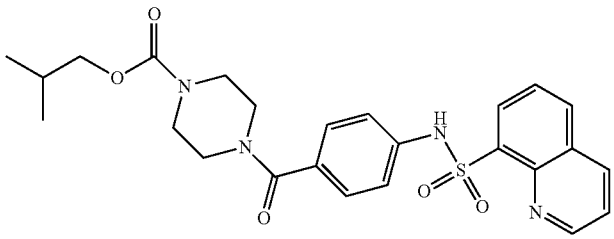

-continued
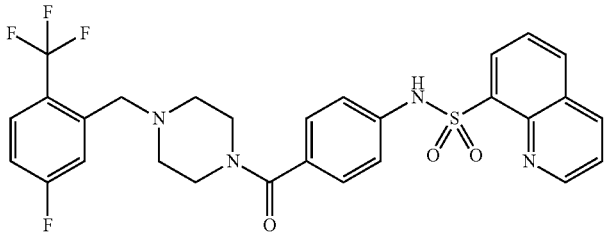
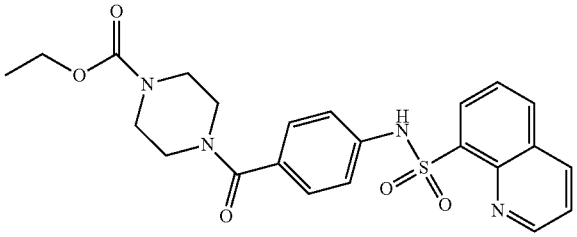
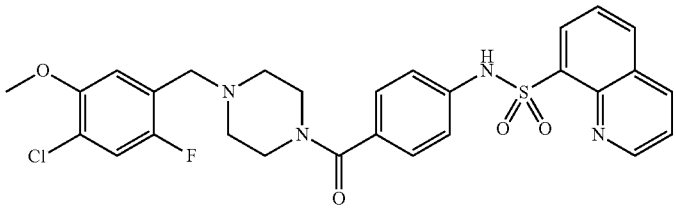
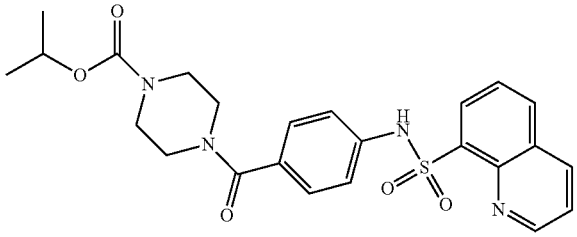
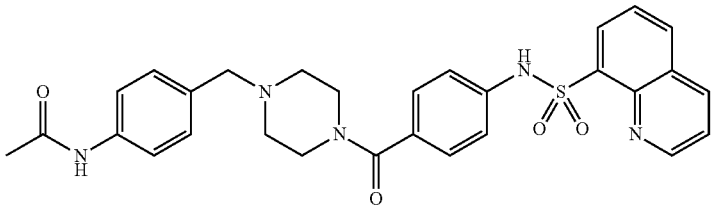
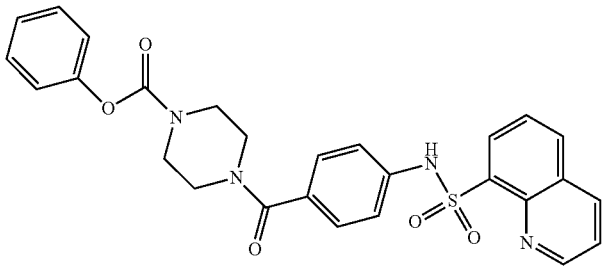
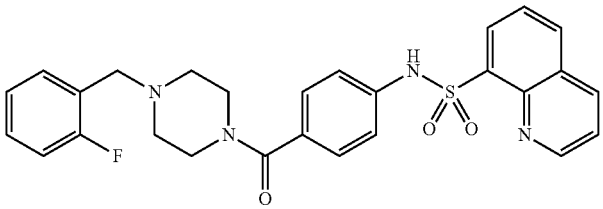
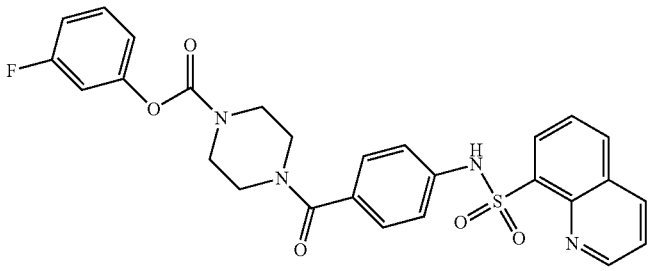

-continued
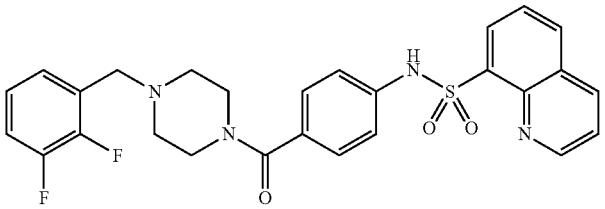
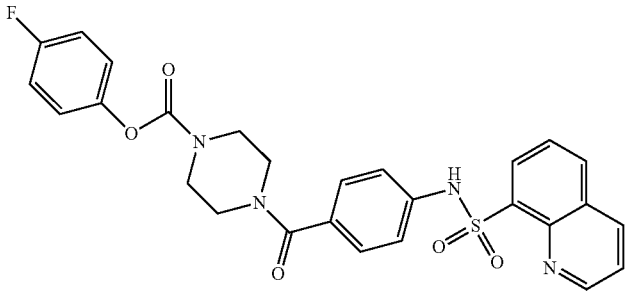
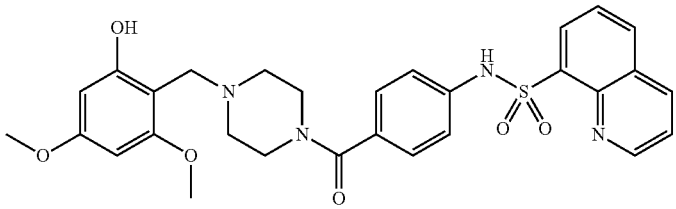
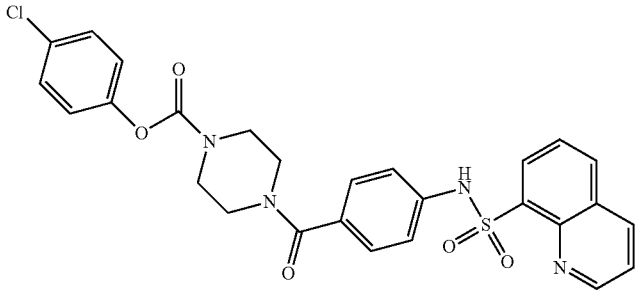
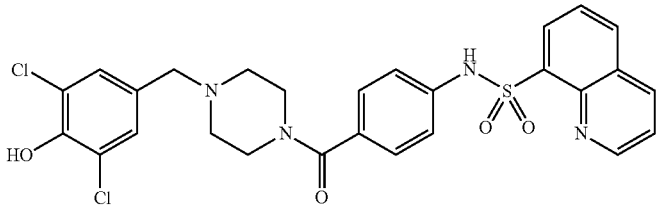
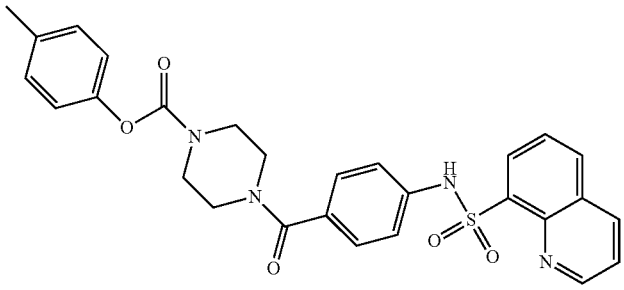
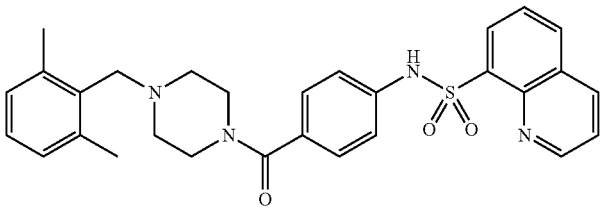

-continued
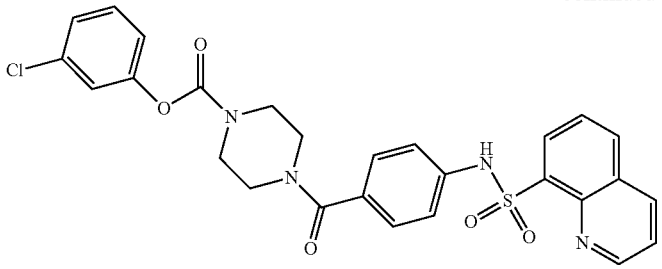
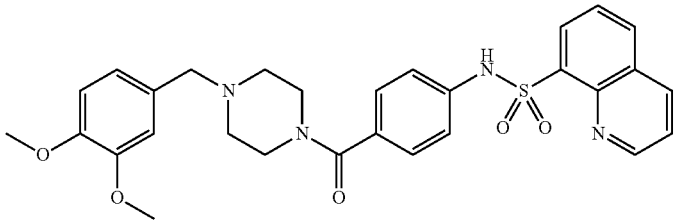
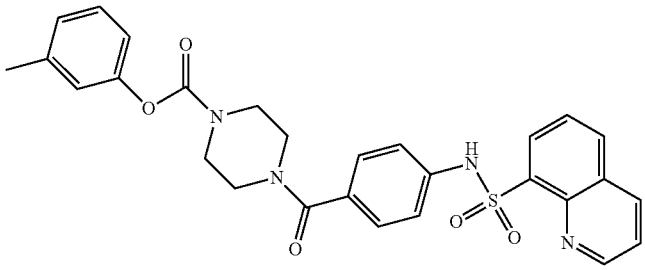
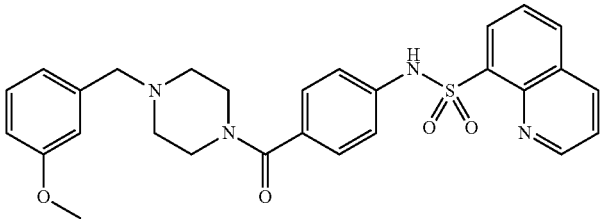
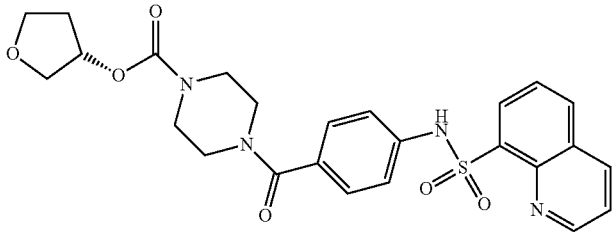
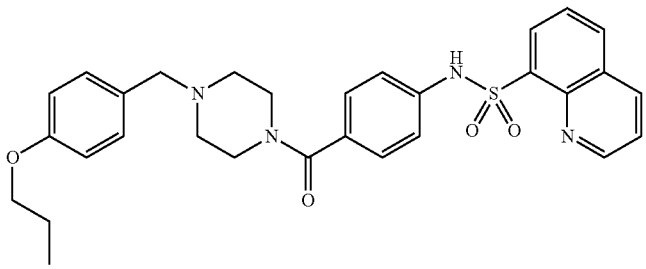
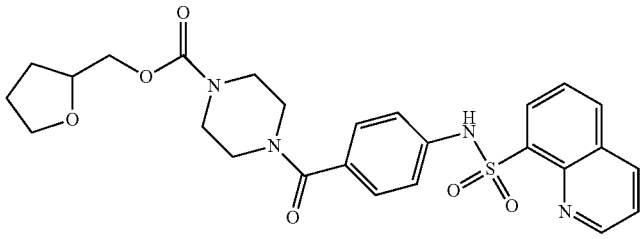

-continued
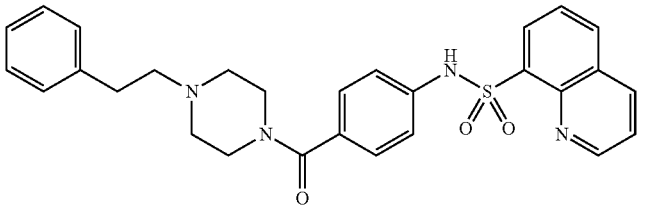
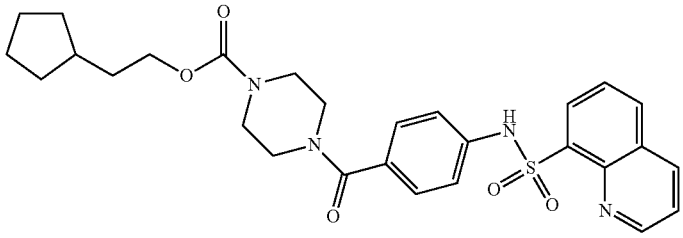
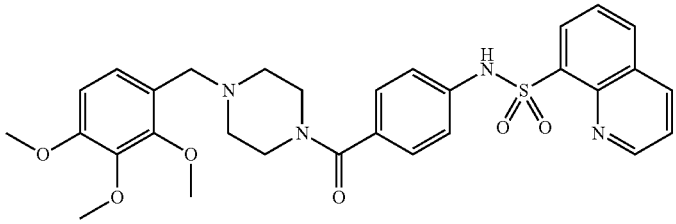
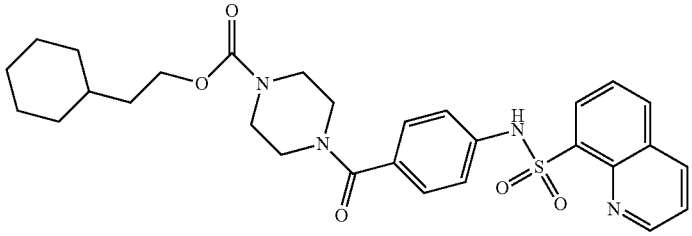
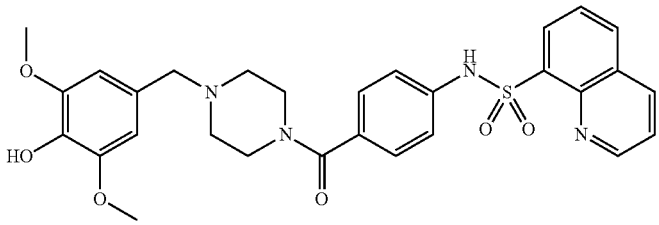
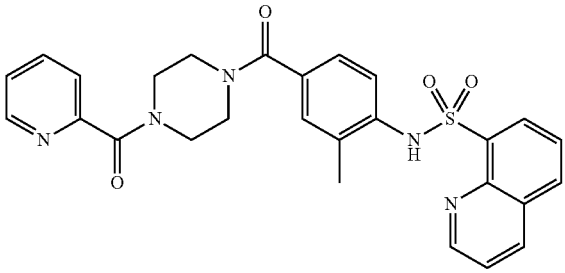
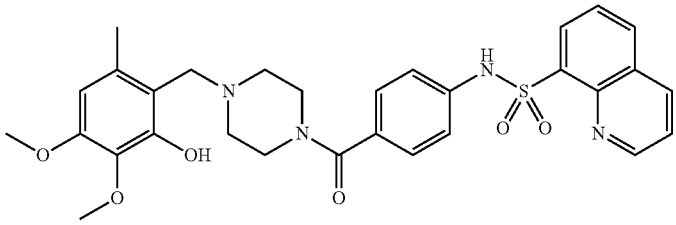

-continued
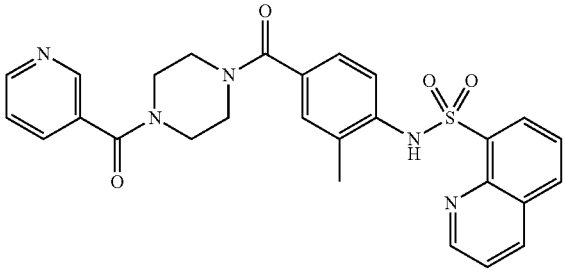
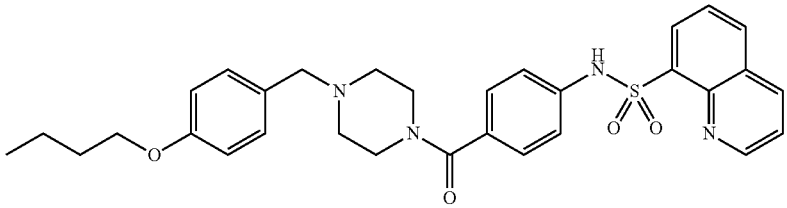
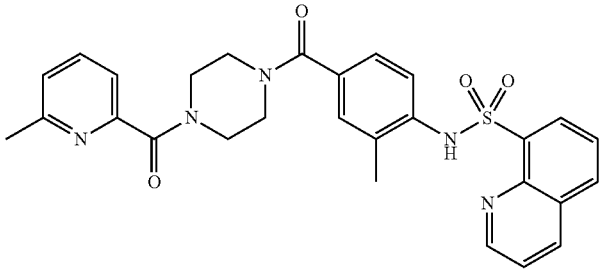
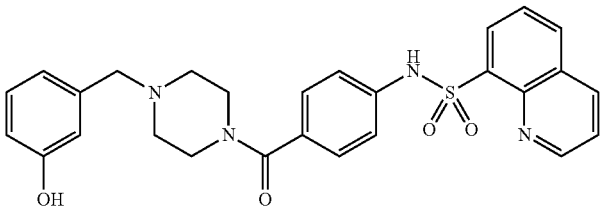
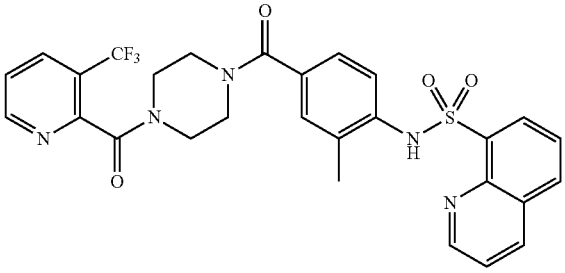
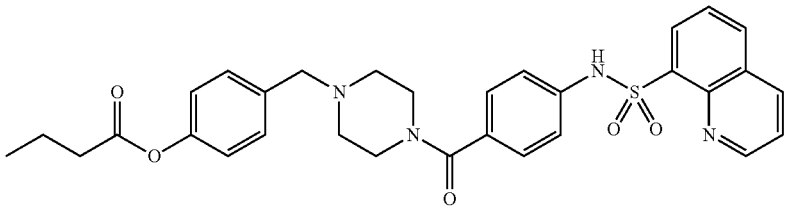
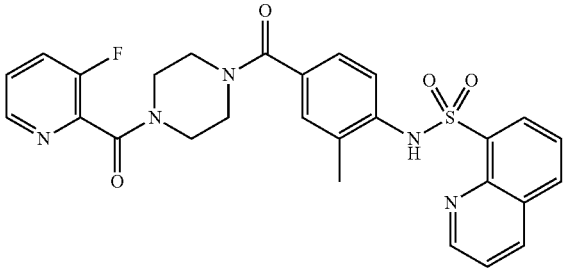
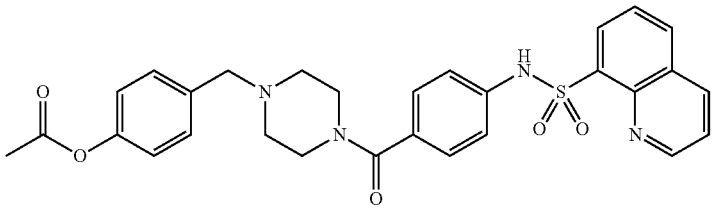

-continued
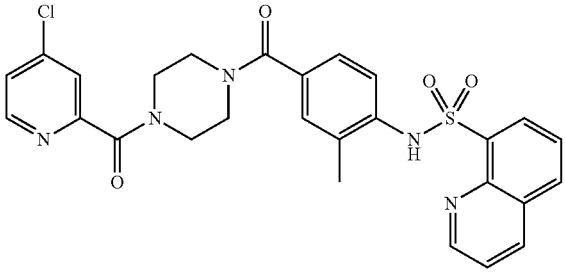
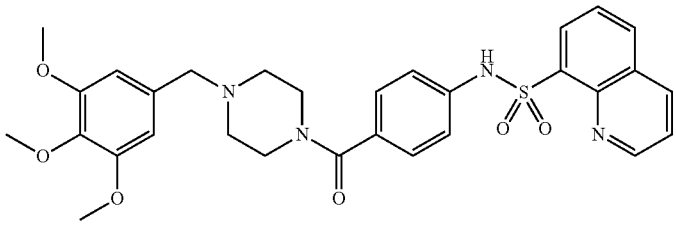
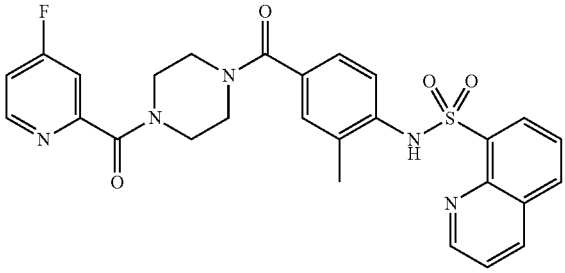
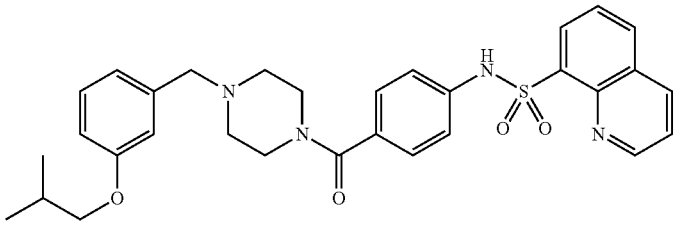
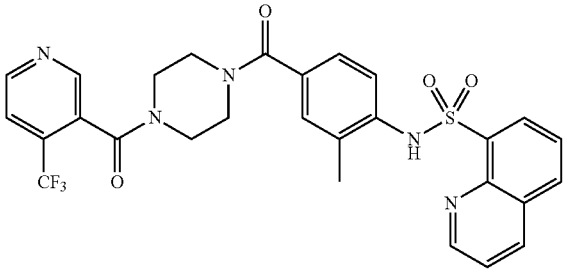
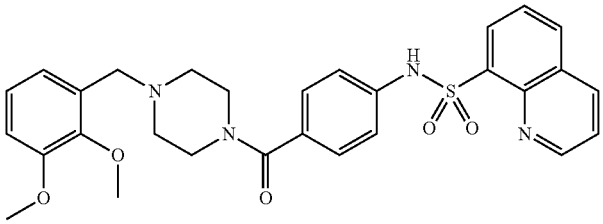
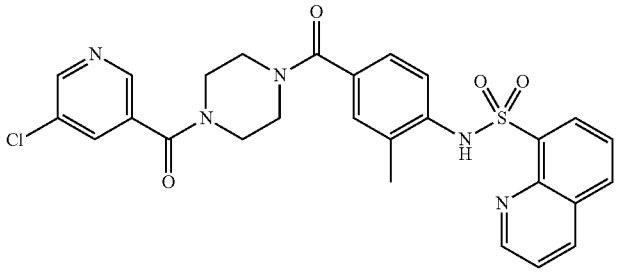

-continued
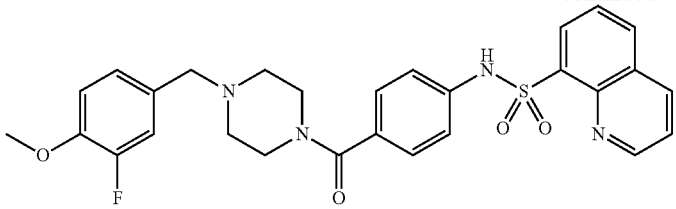
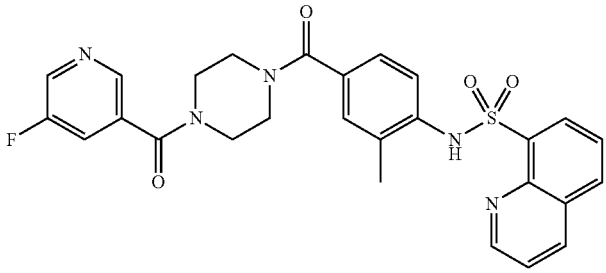
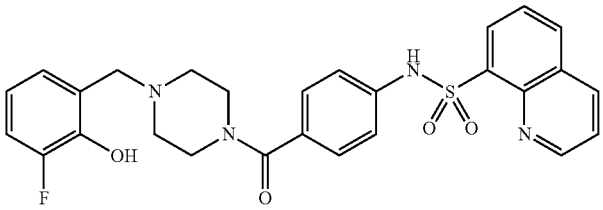
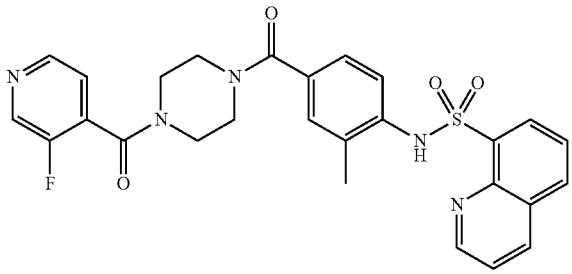
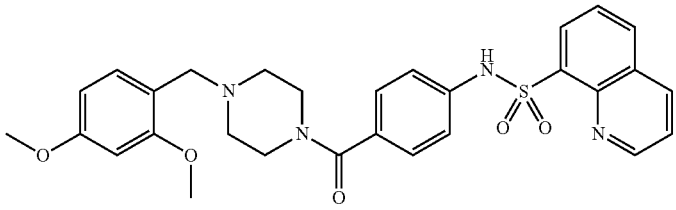
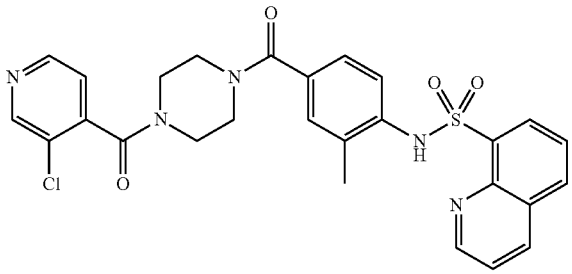
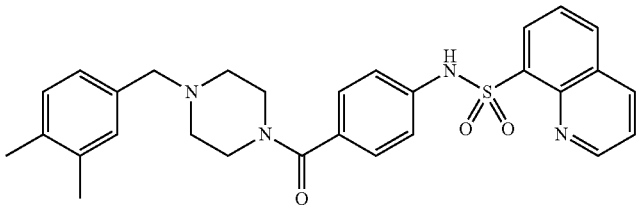
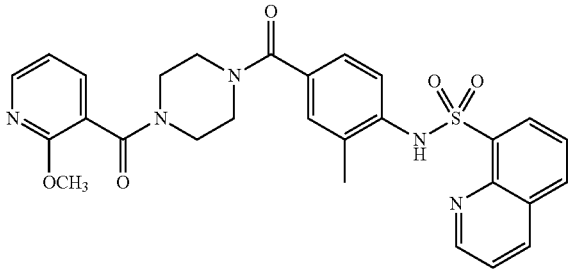

-continued
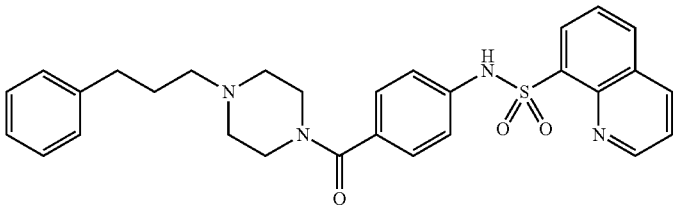
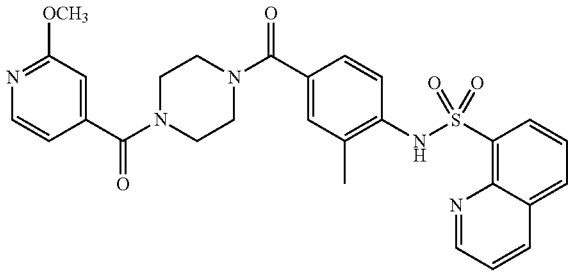
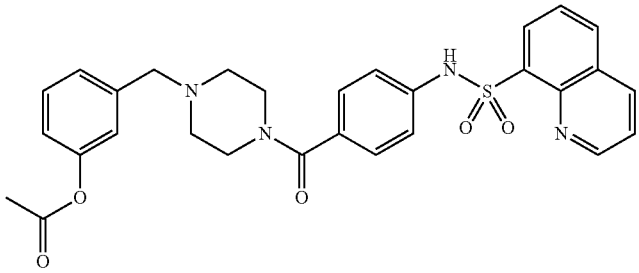
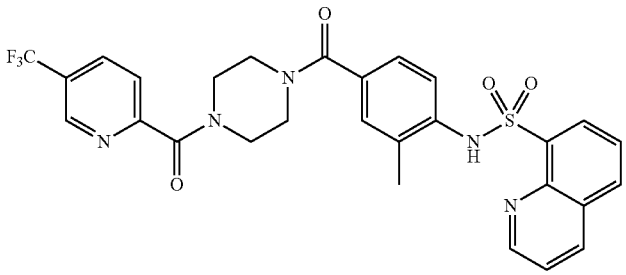
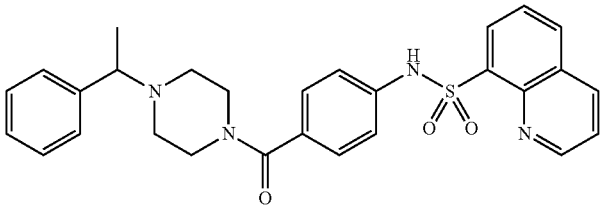
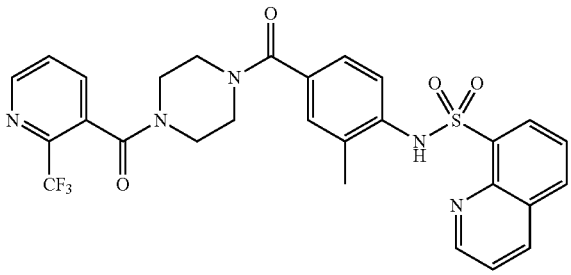
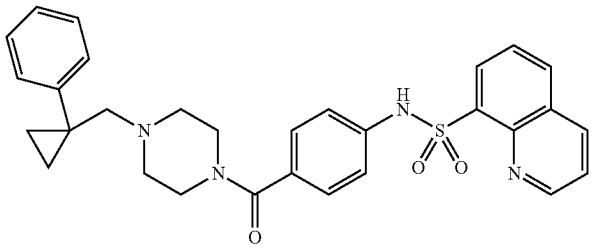
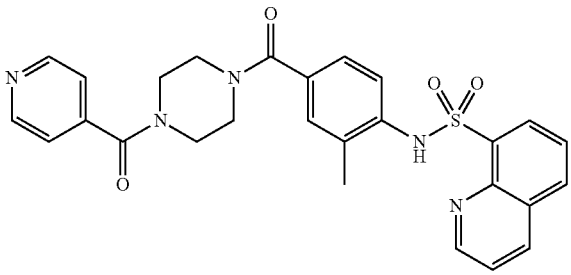

-continued
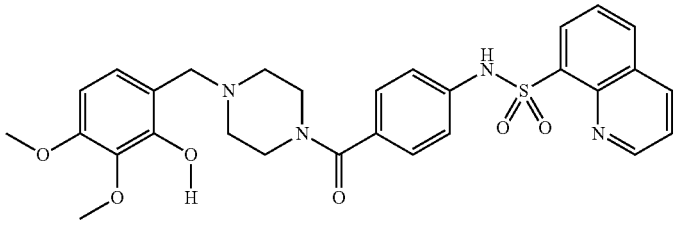
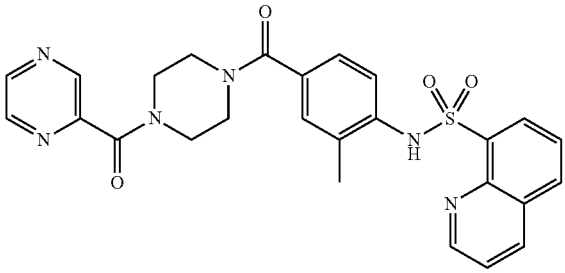
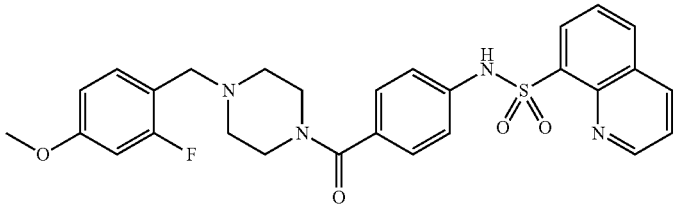
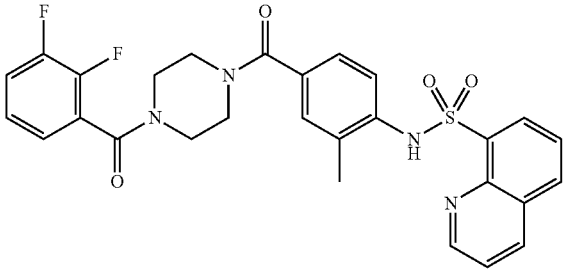
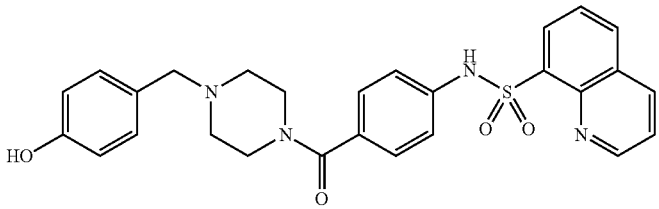
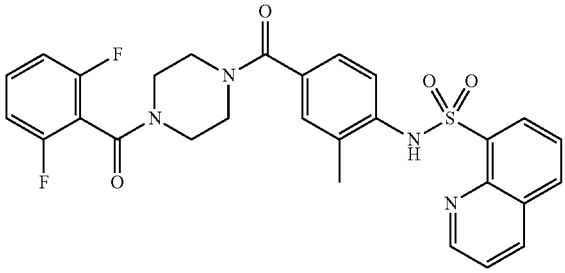
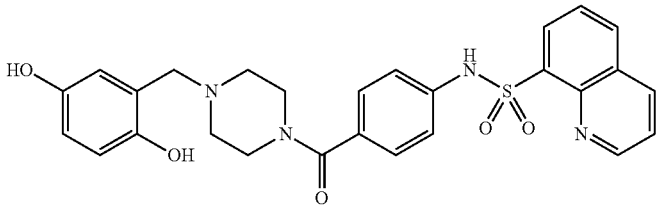

-continued
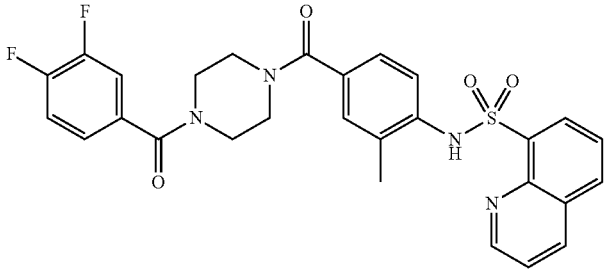
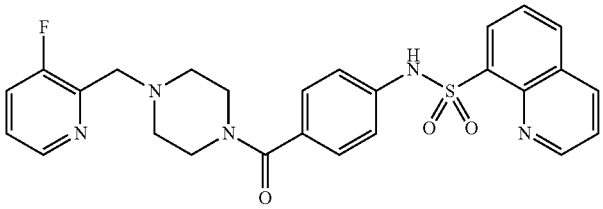
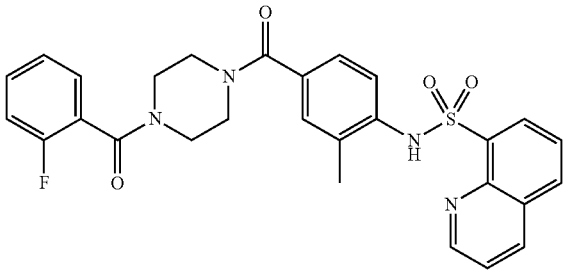
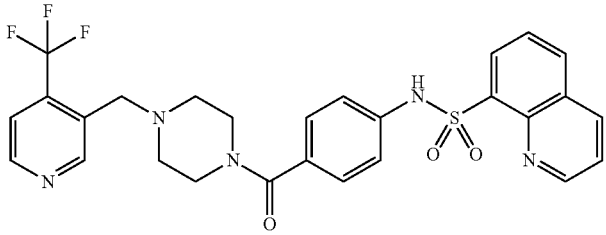
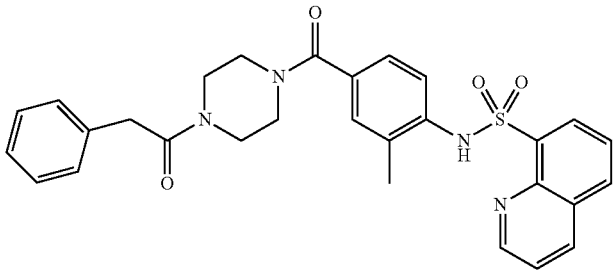
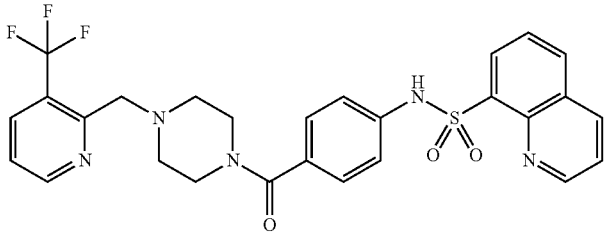
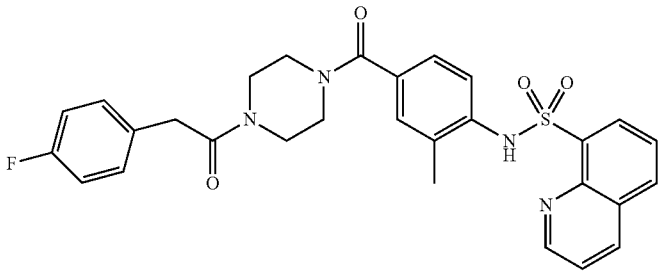

-continued
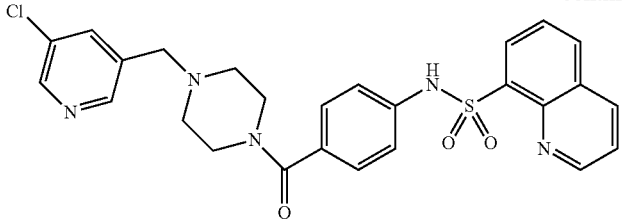
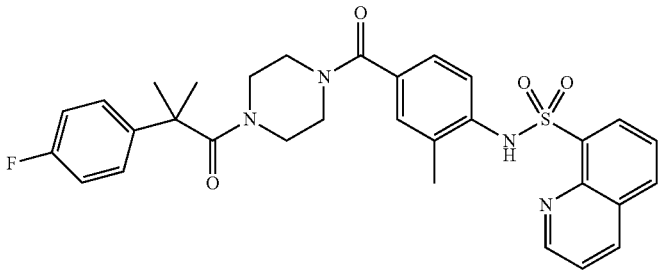
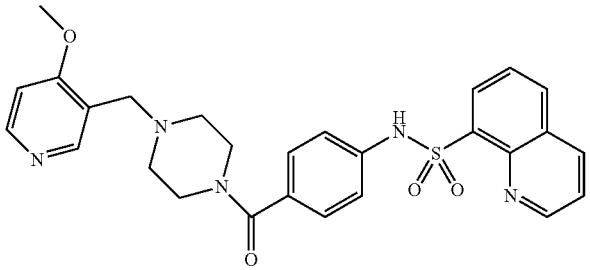
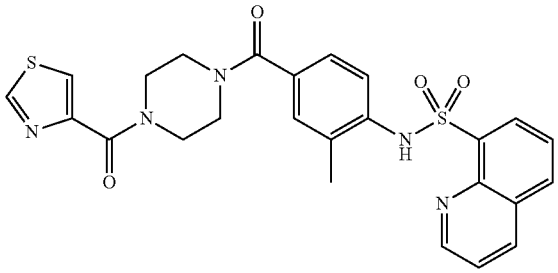
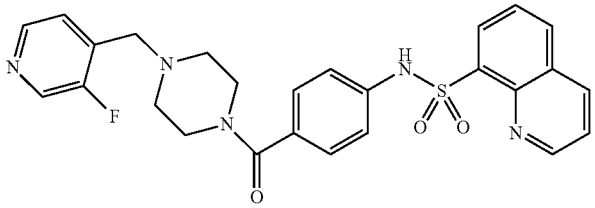
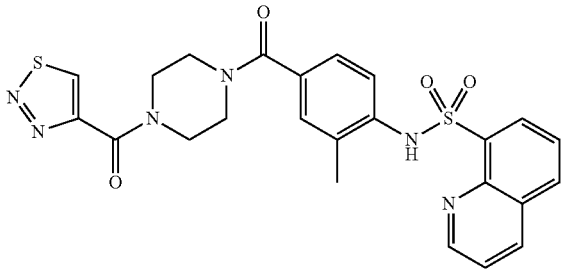
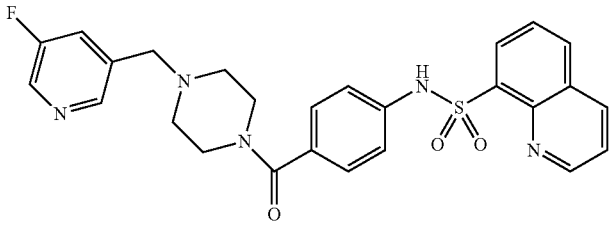
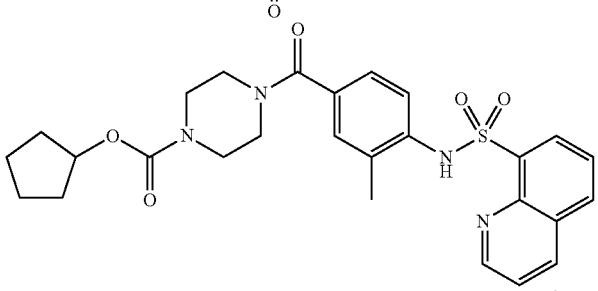
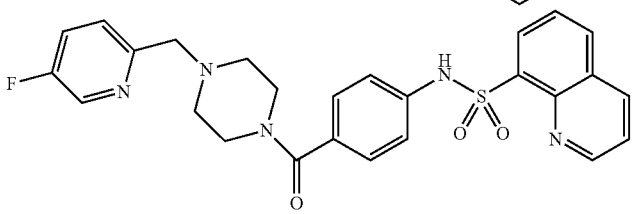

-continued
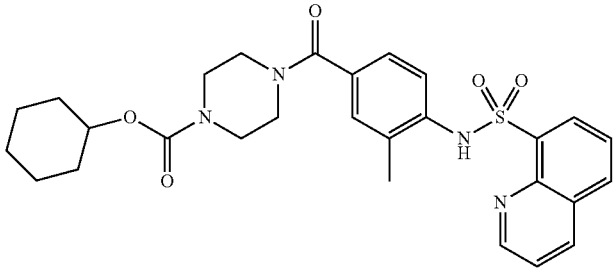
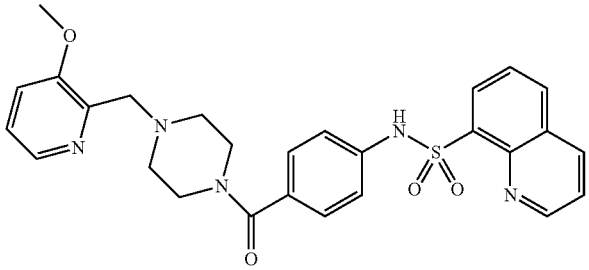
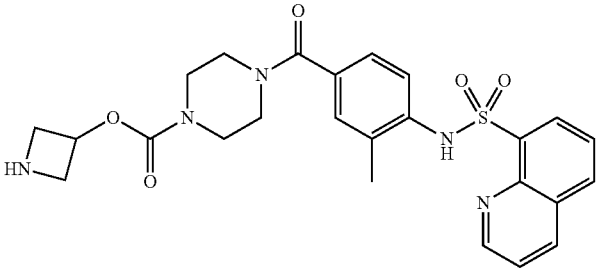
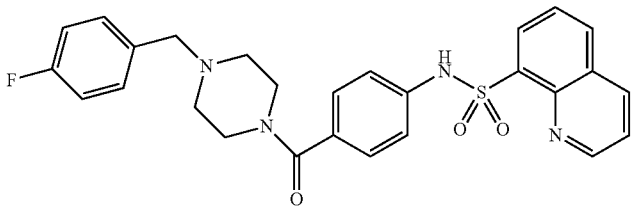
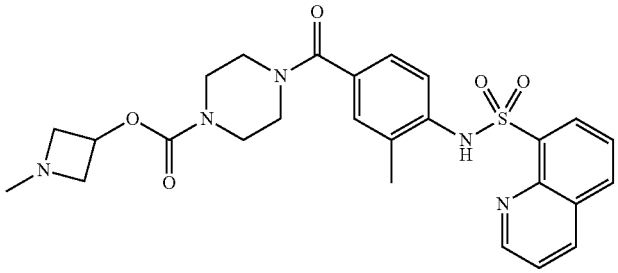
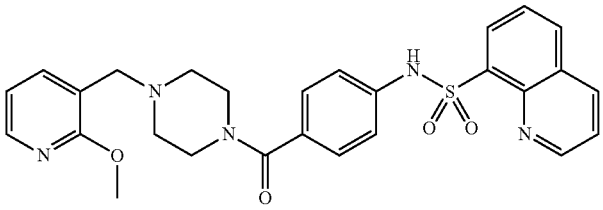
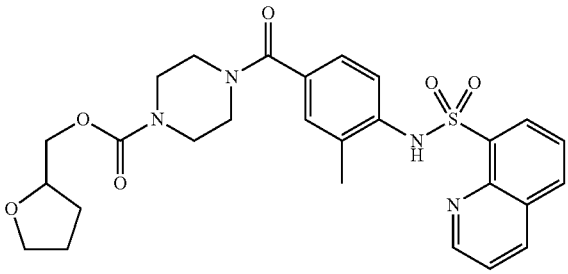
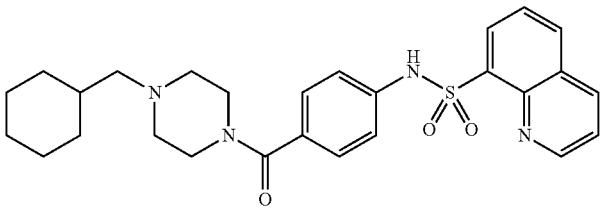

-continued
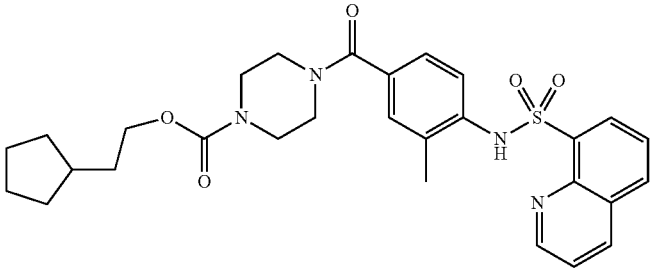
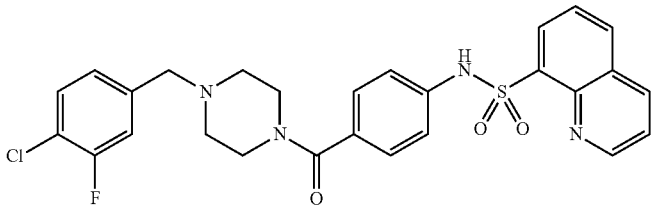
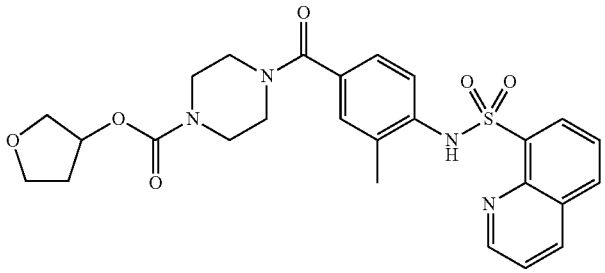
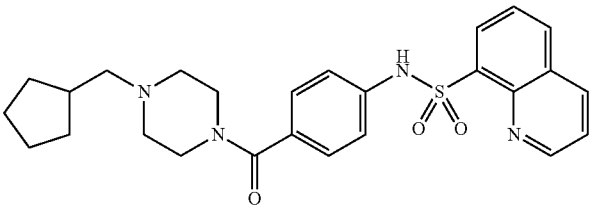
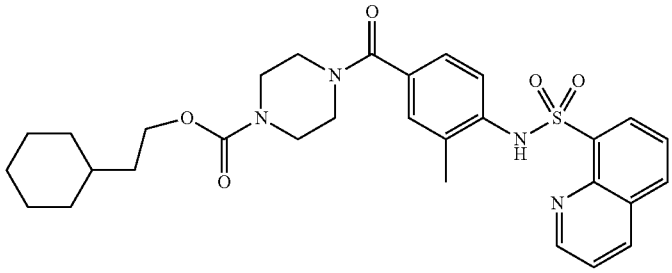
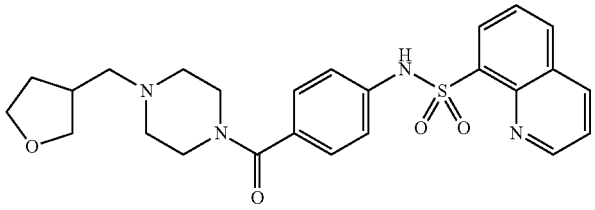
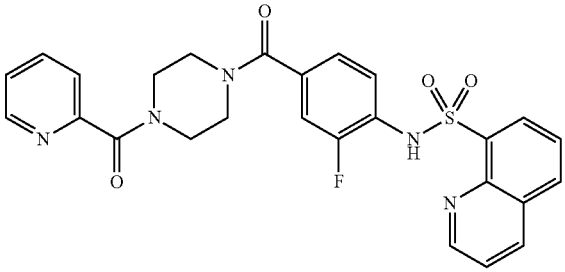
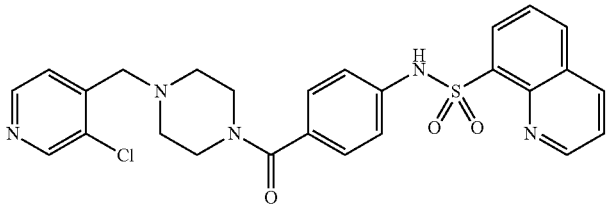
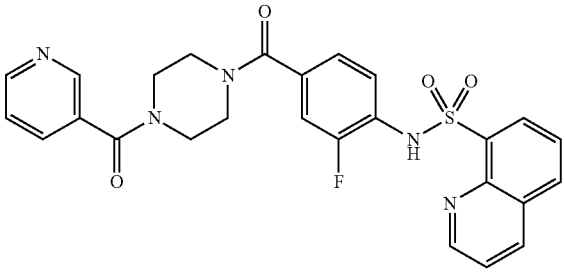

-continued
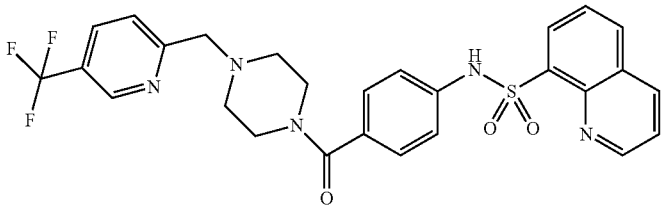
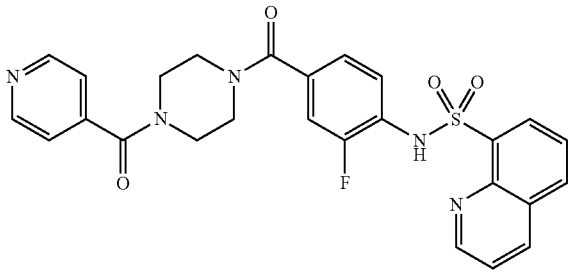
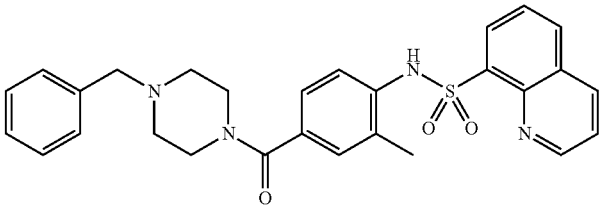
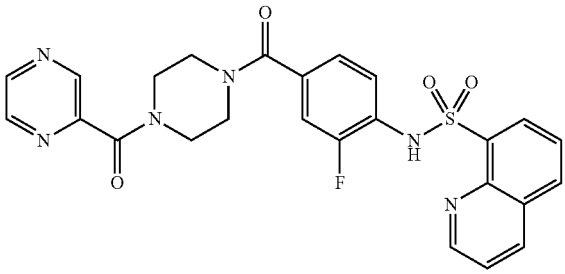
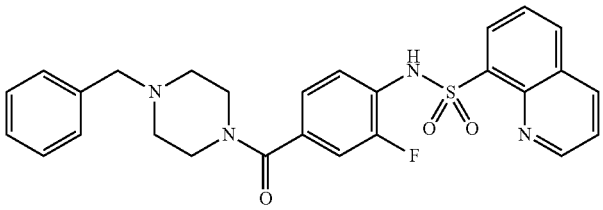
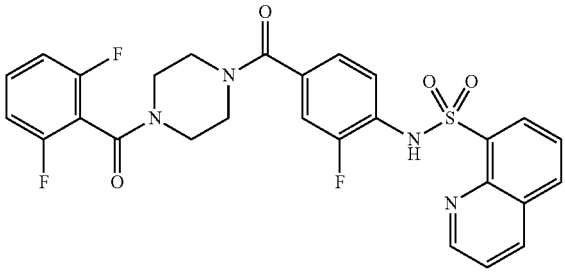
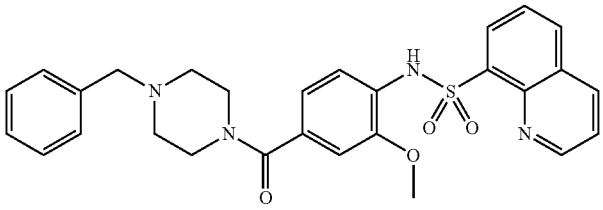
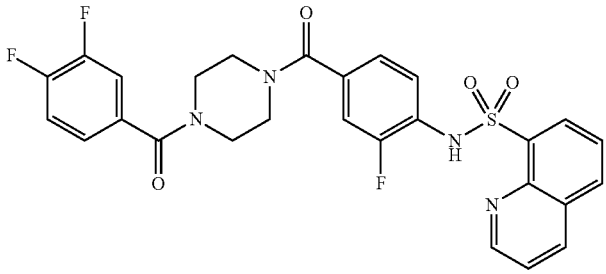
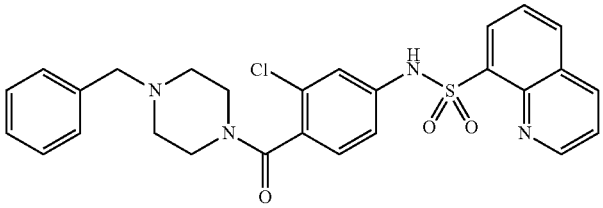
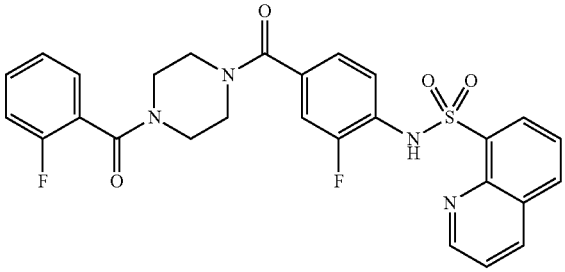

-continued
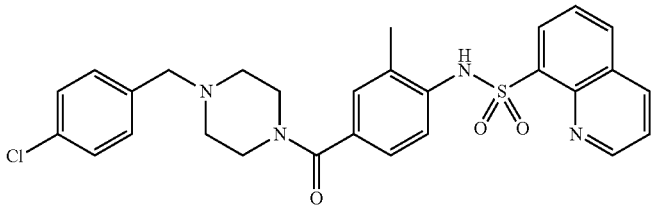
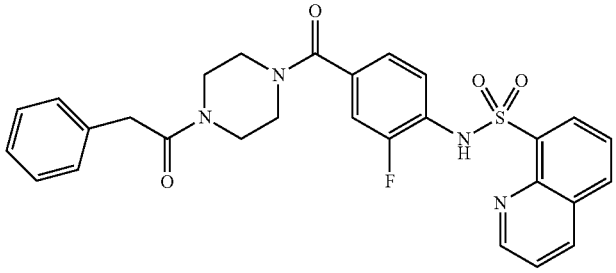
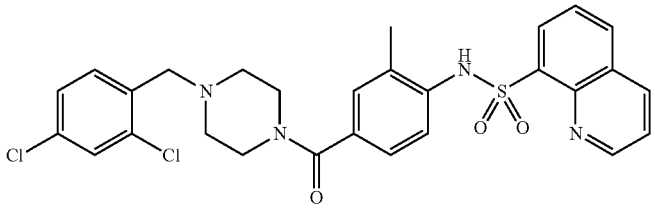
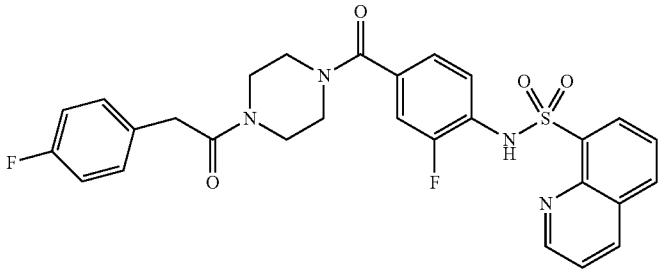
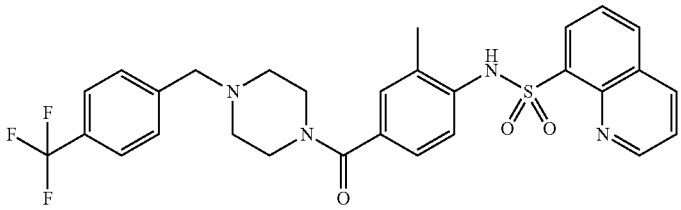
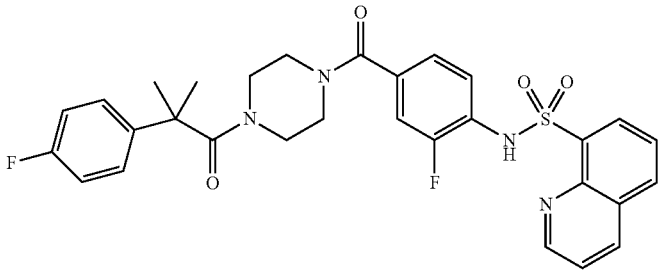
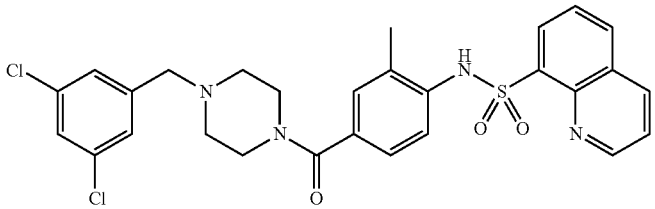

-continued
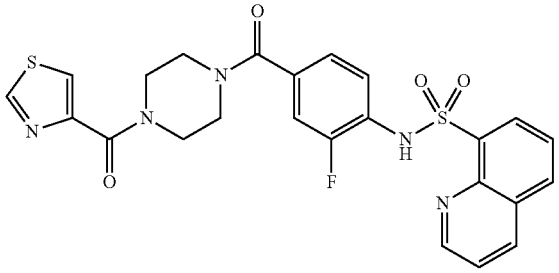
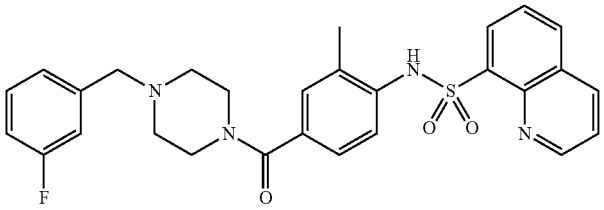
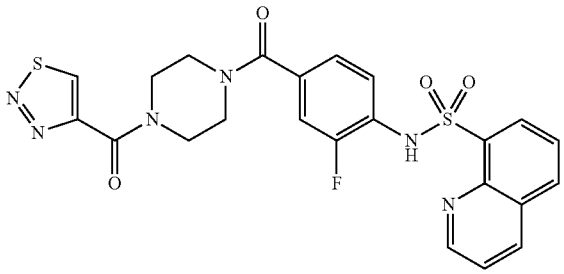
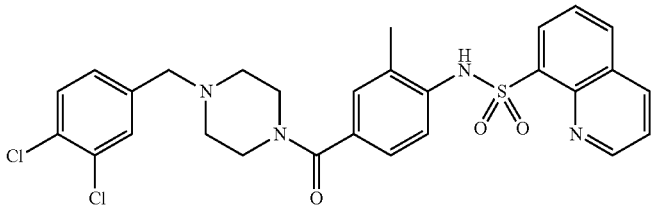
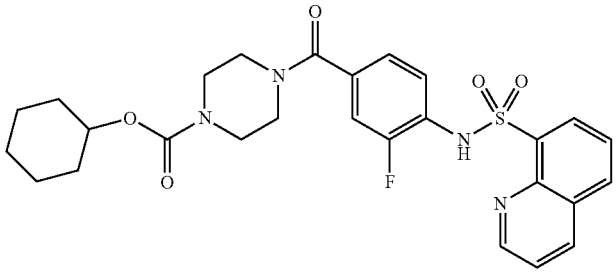
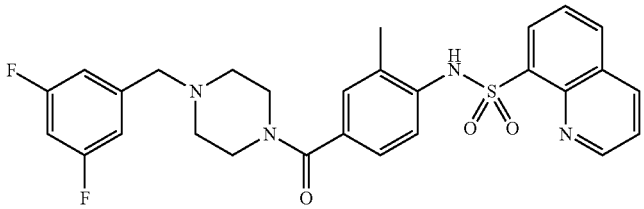
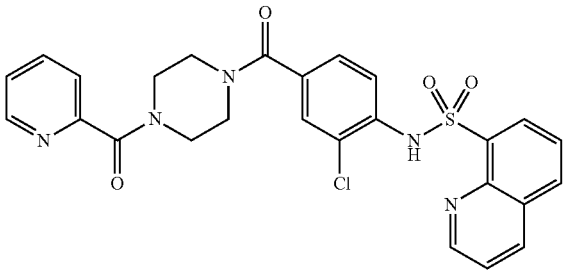
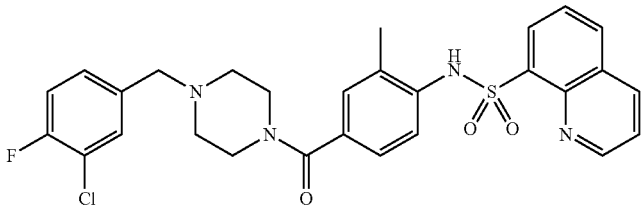

-continued
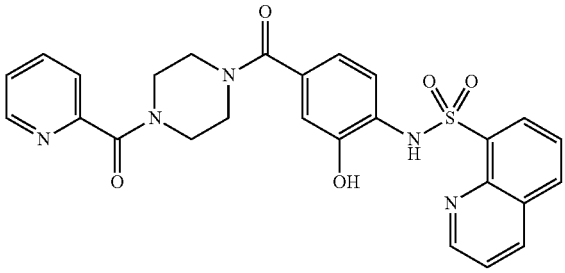
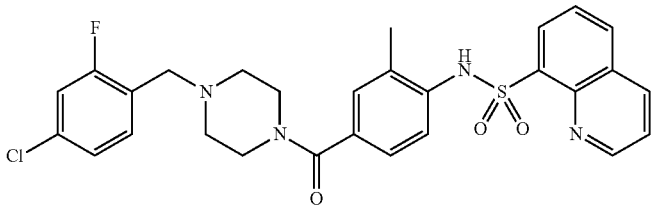
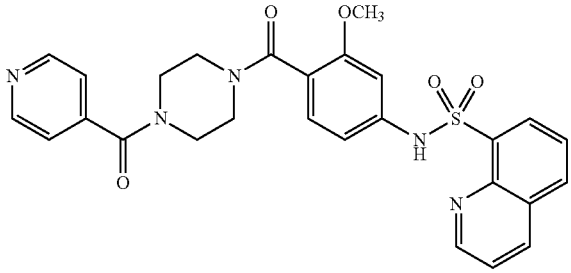
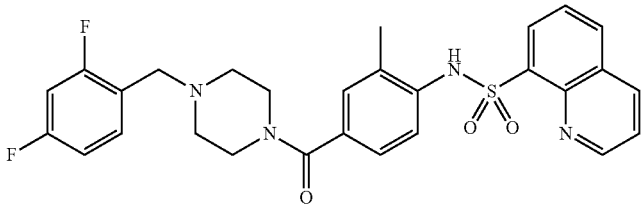
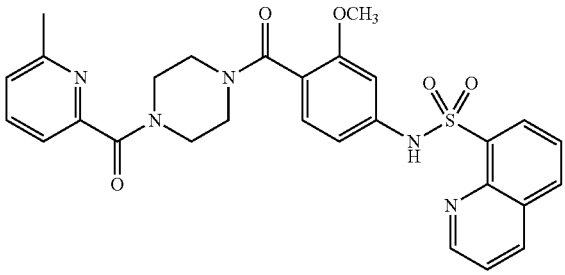
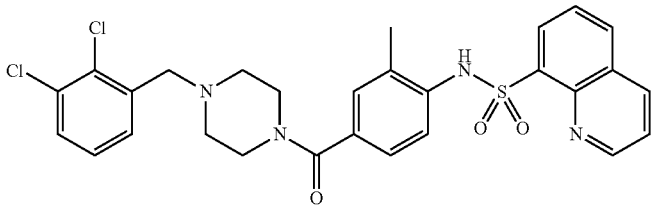
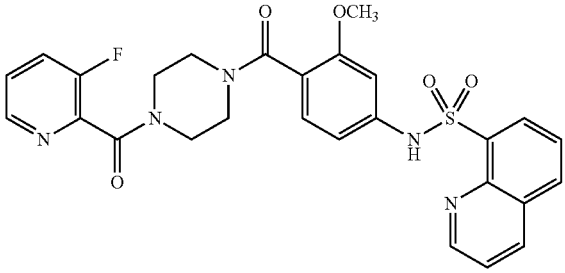
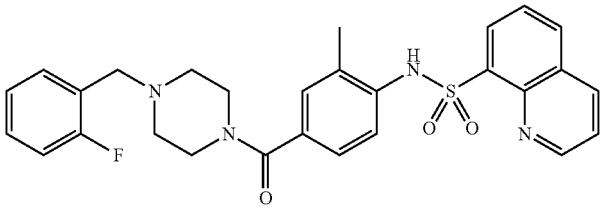

-continued
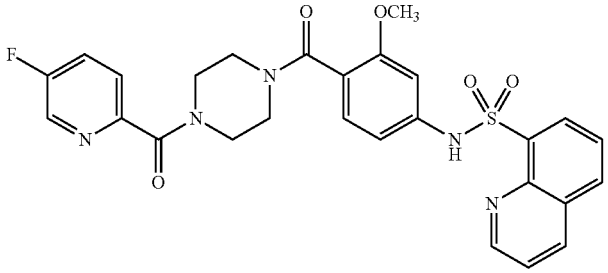
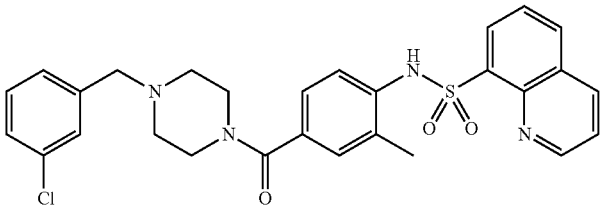
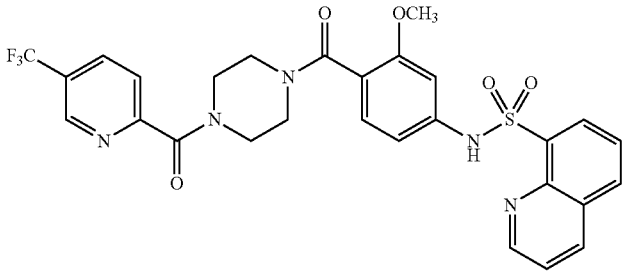
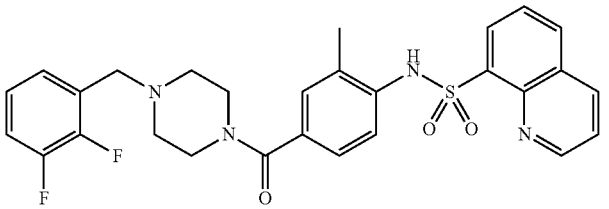
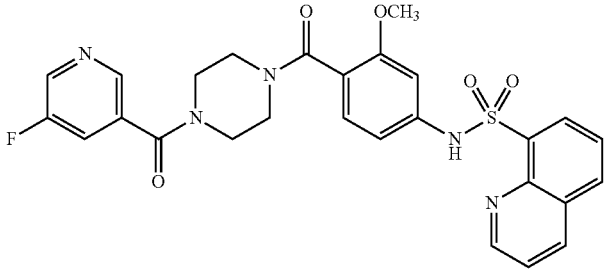
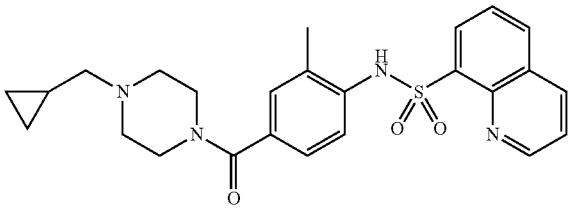
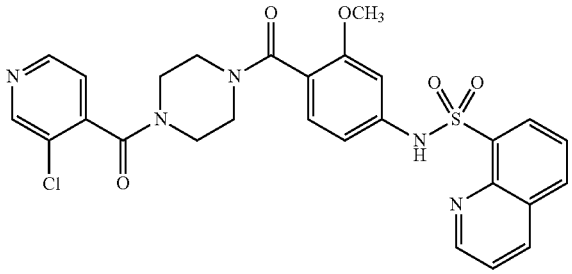
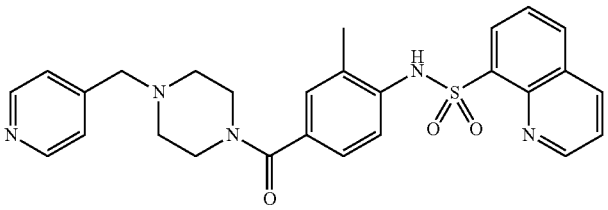

-continued
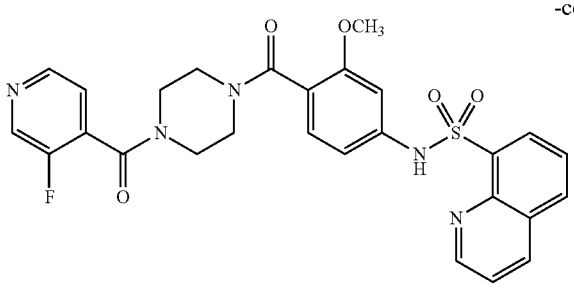
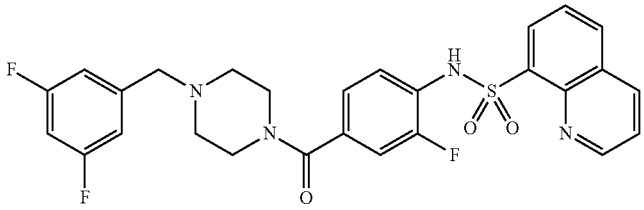
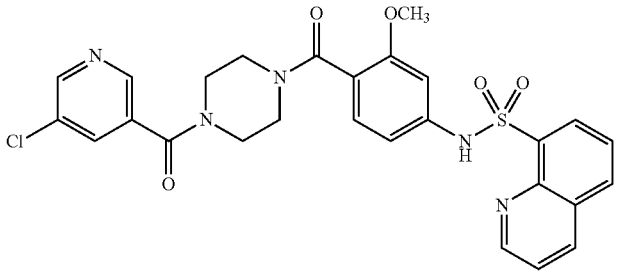
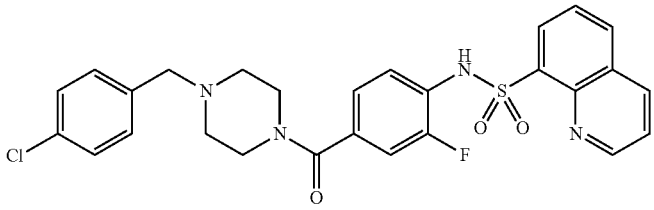
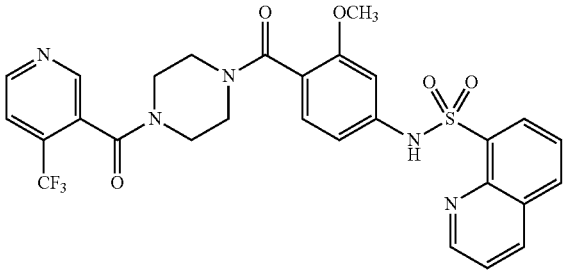
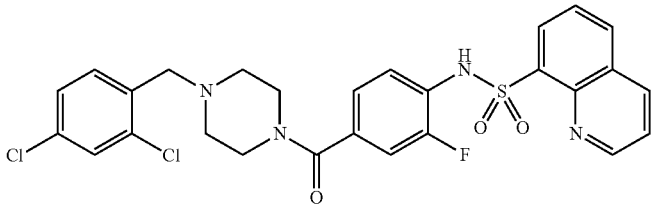
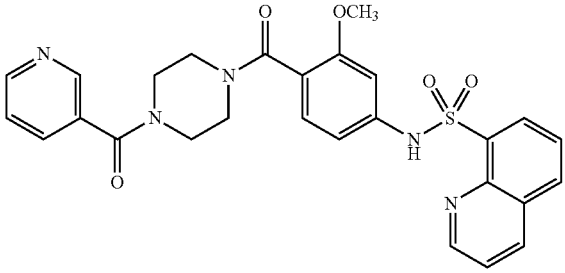

-continued
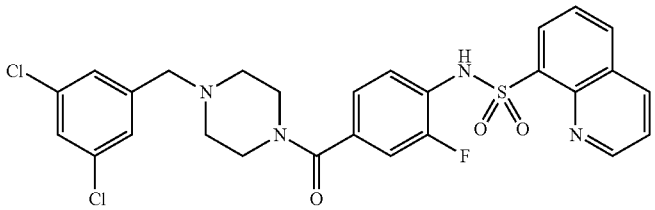
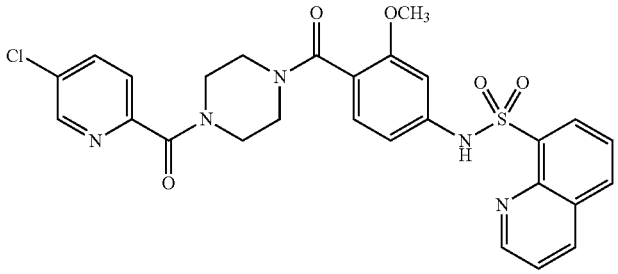
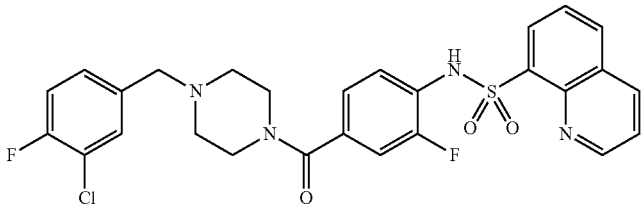
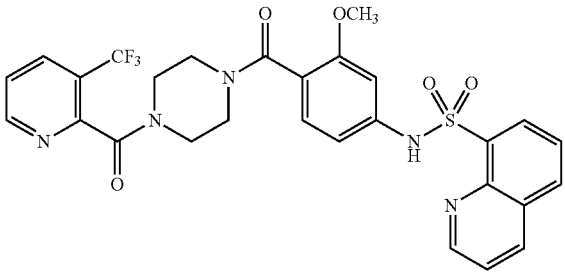
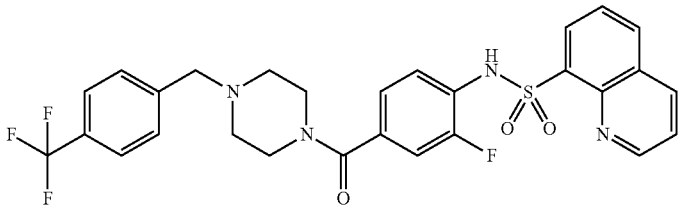
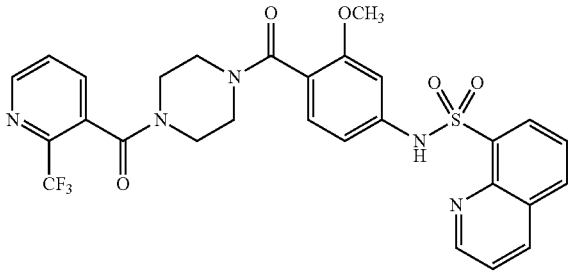
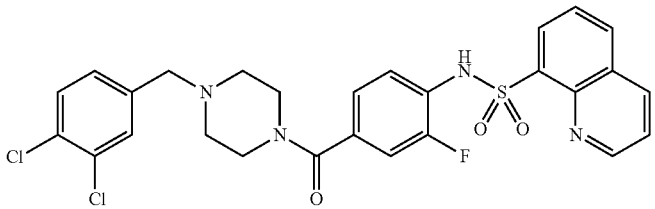

-continued
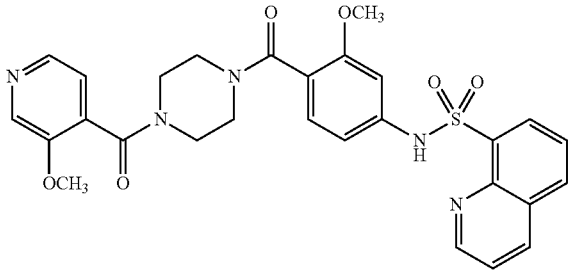
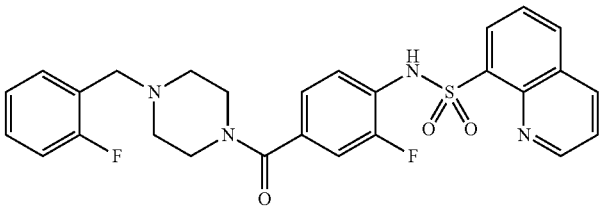
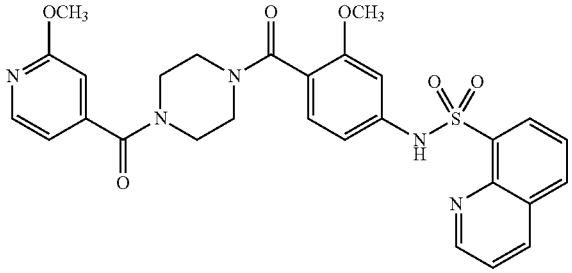
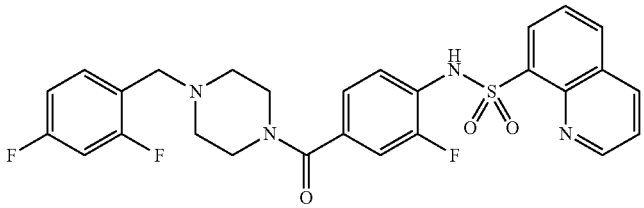
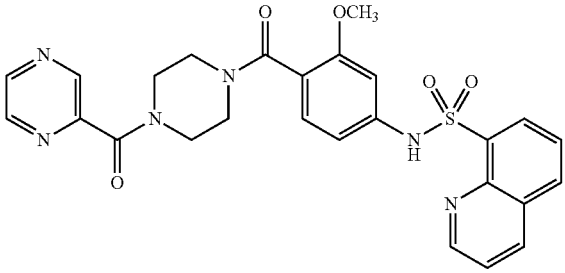
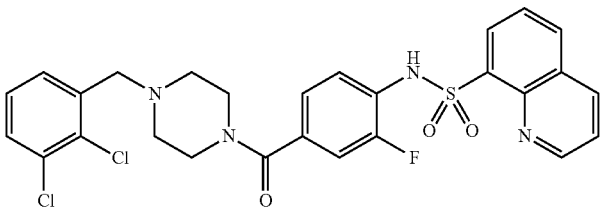
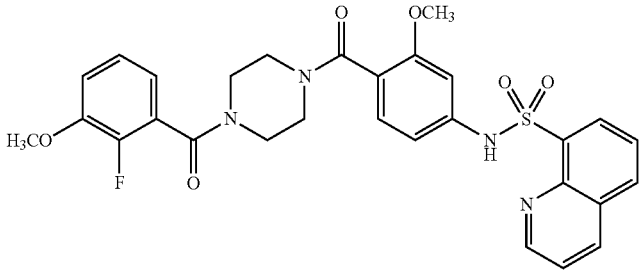
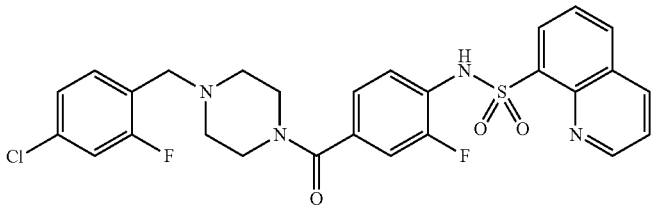

-continued
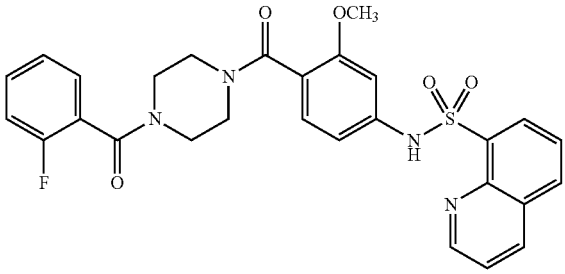
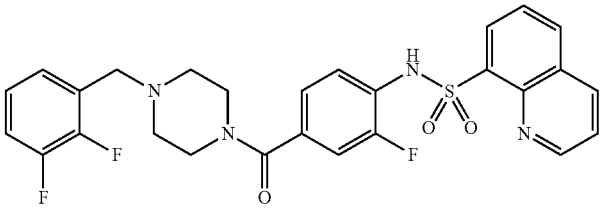
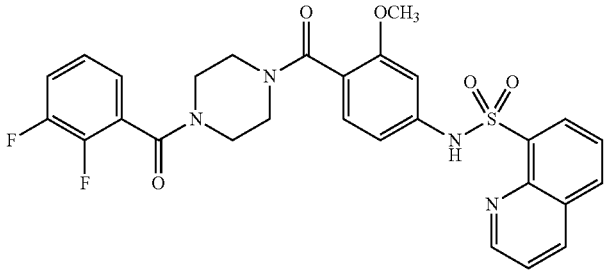
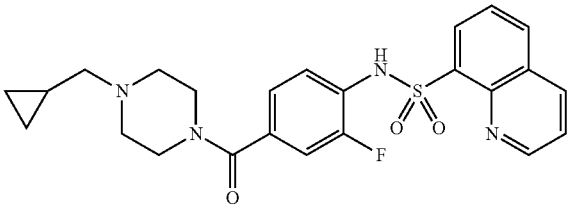
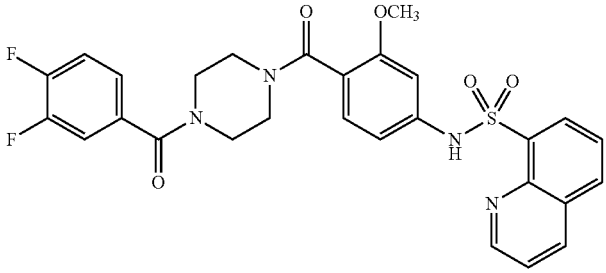
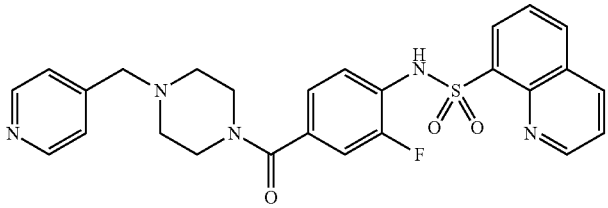
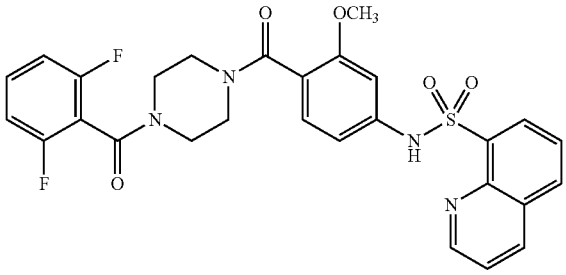
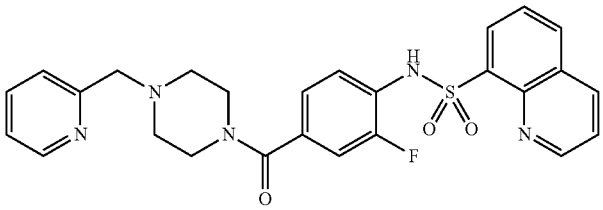
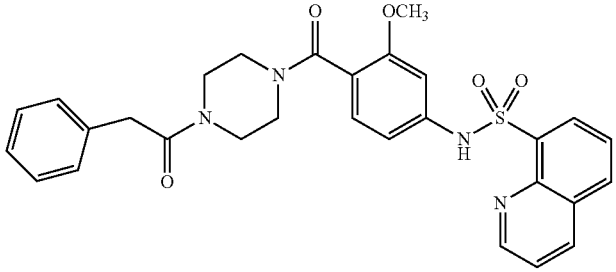

-continued
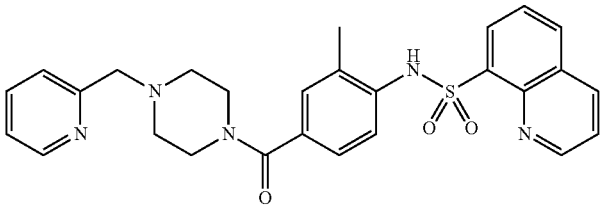
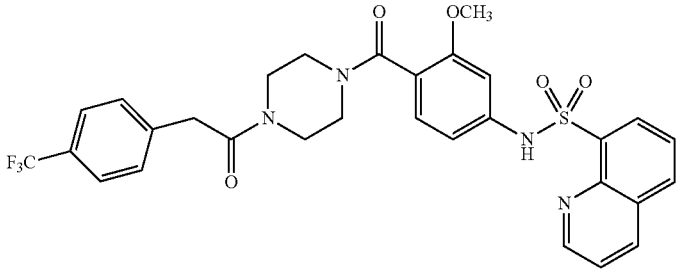
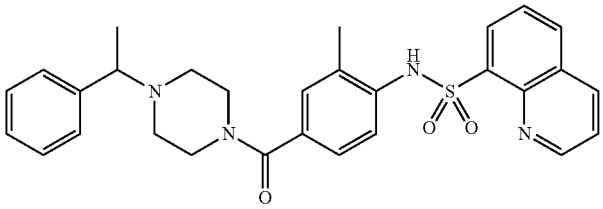
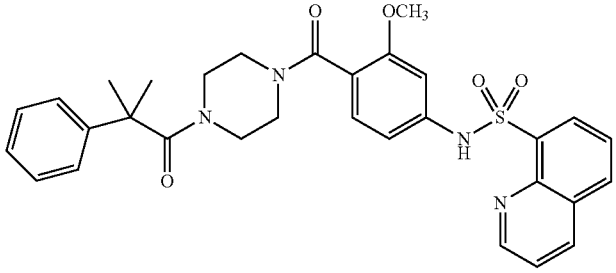
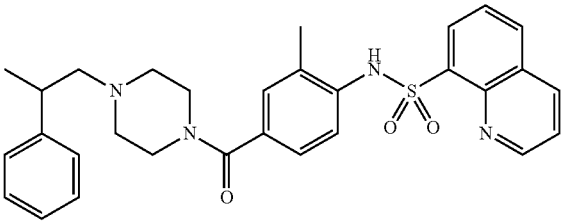
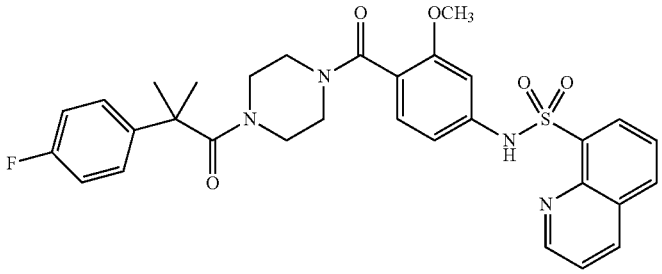
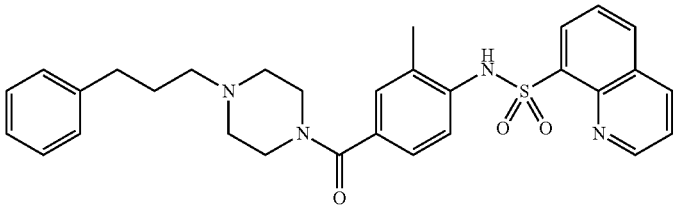
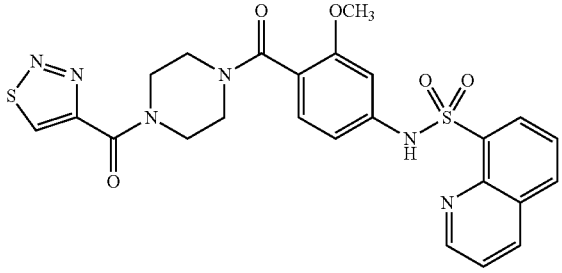
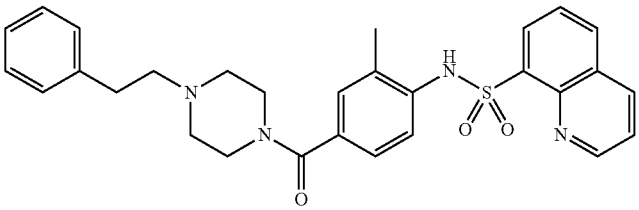

-continued
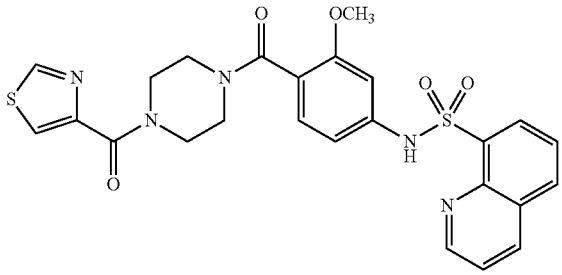
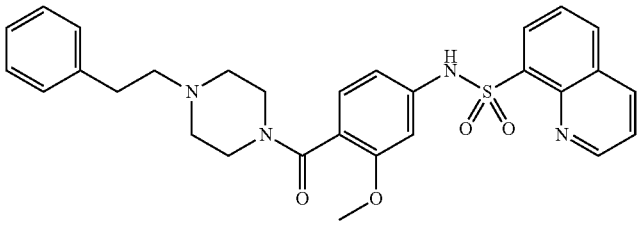
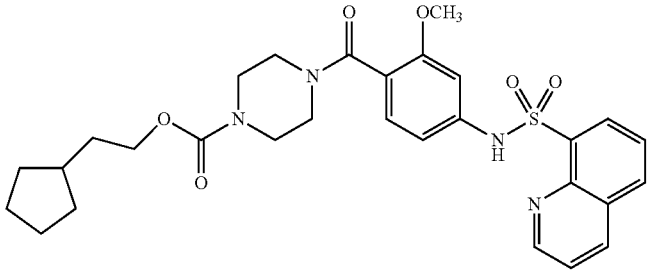
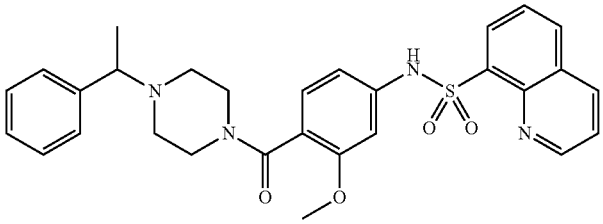
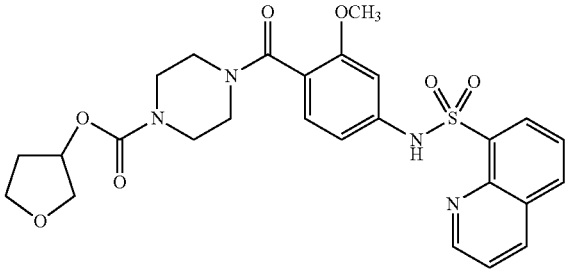
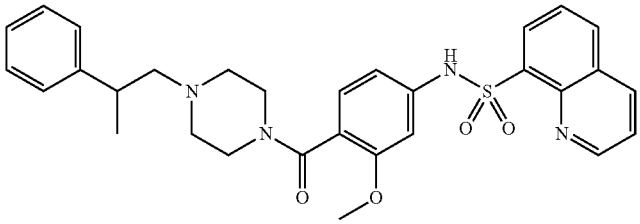
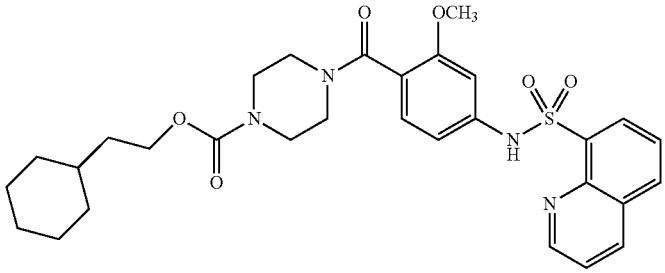

-continued
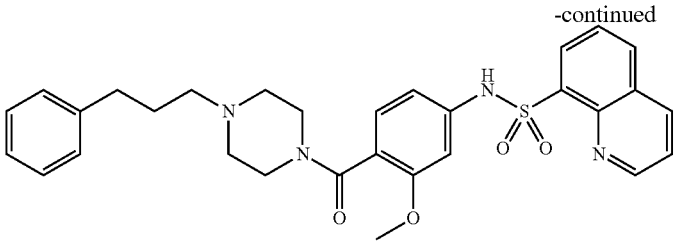
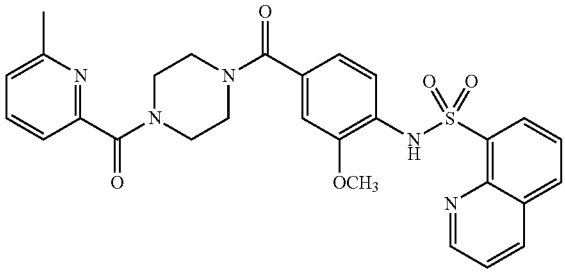
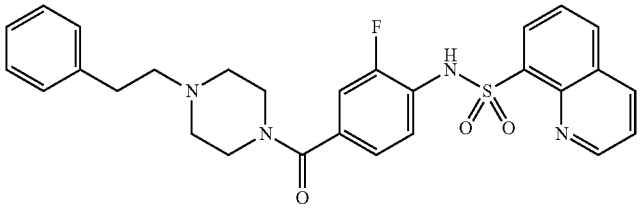
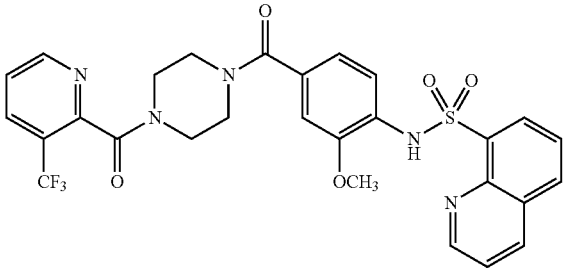
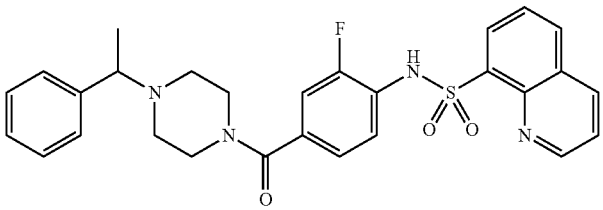
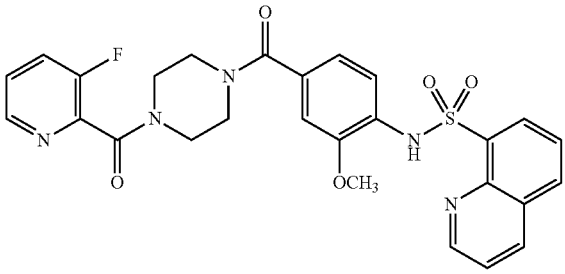
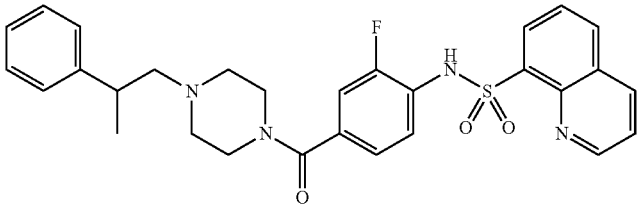
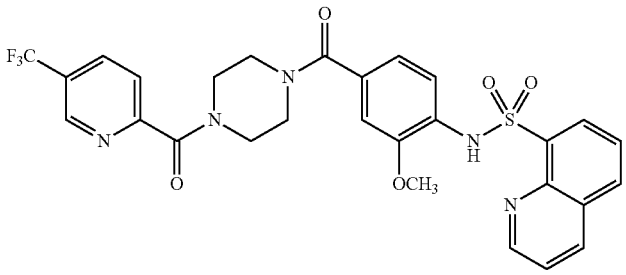

-continued
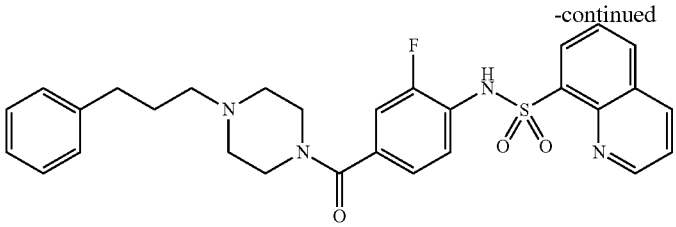
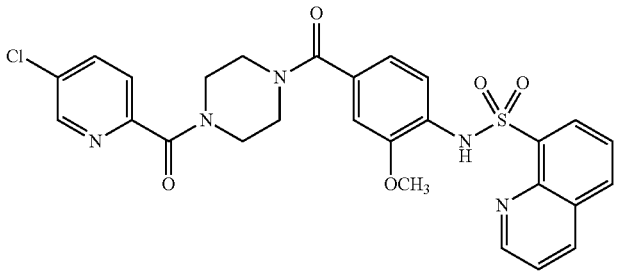
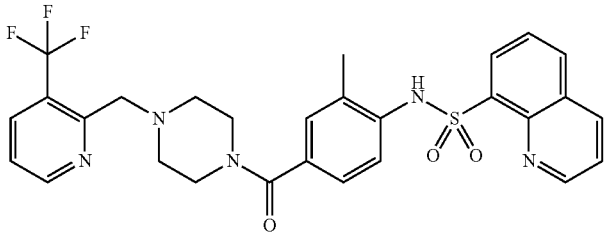
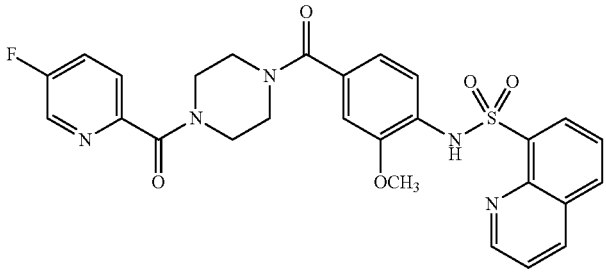
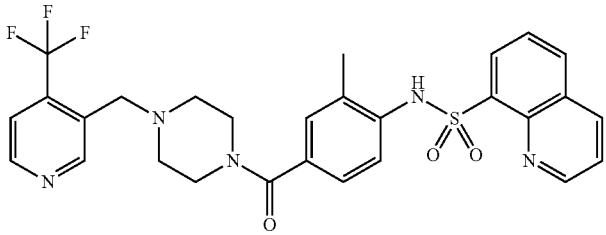
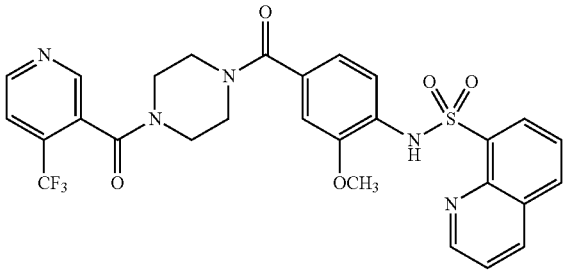
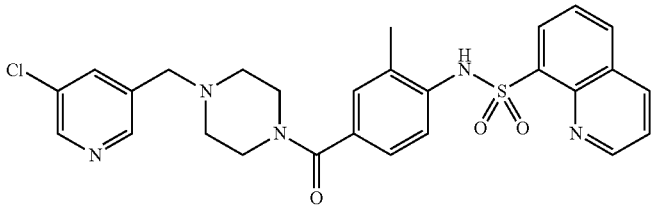
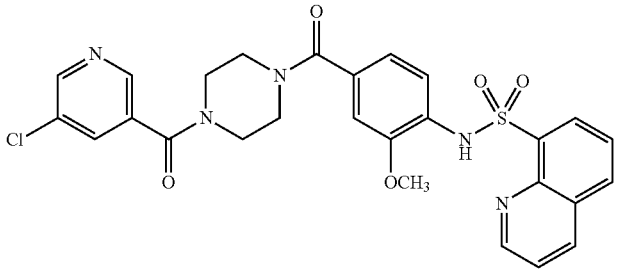

-continued
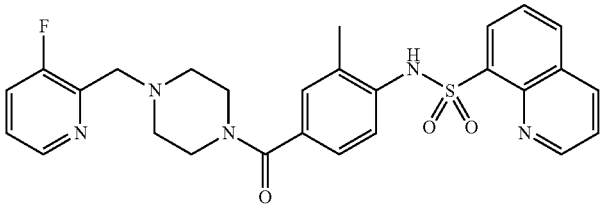
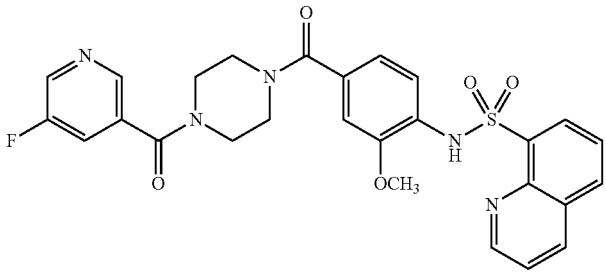
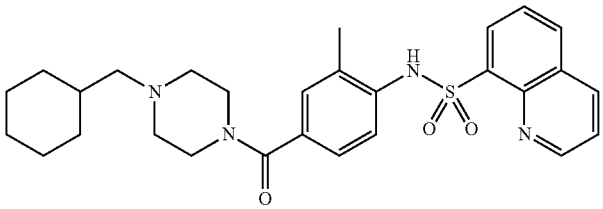
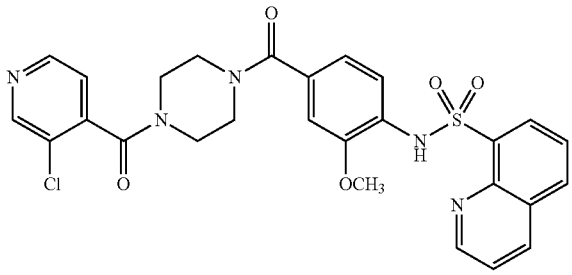
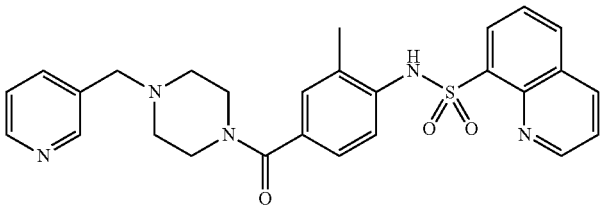
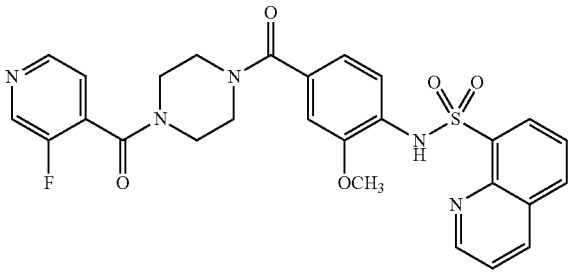
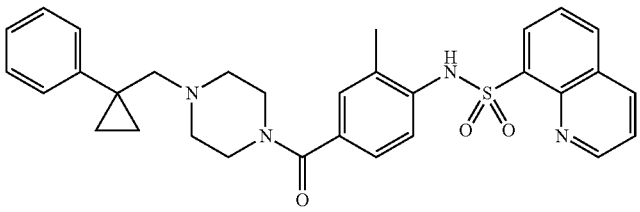
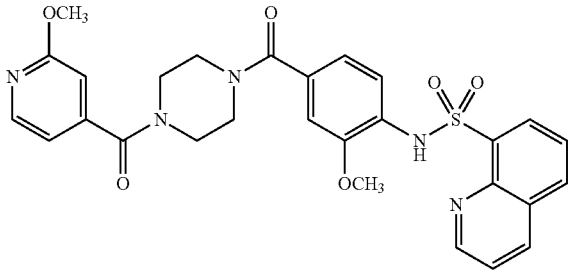
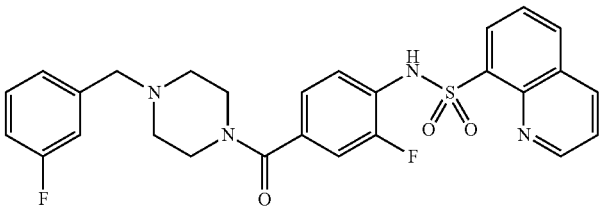

-continued
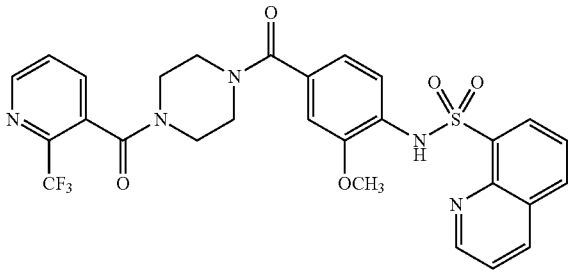
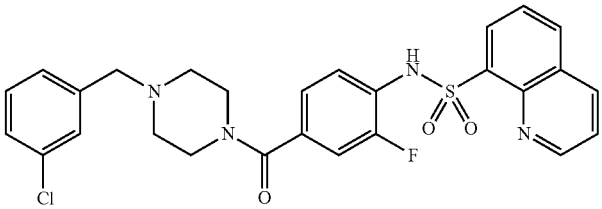
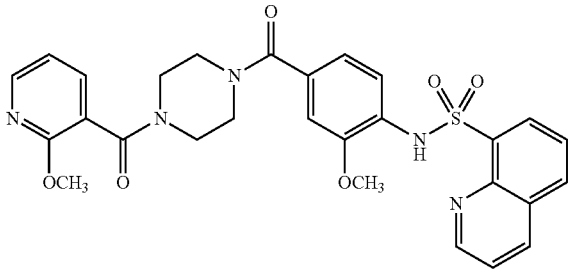
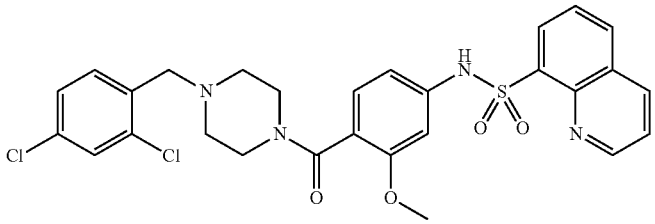
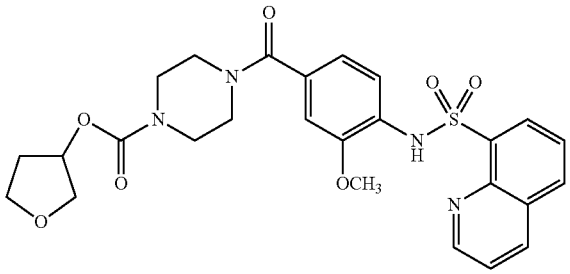
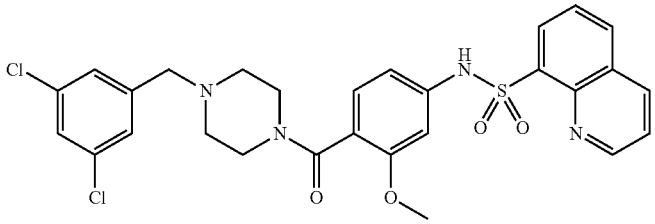
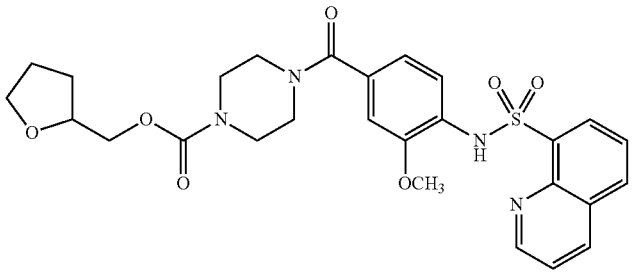

-continued
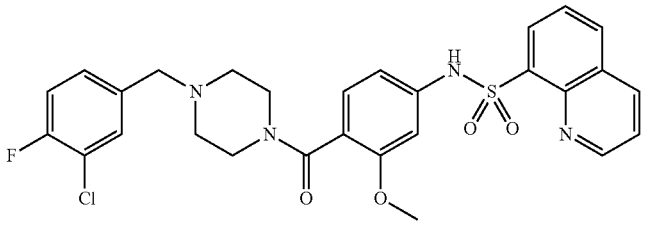
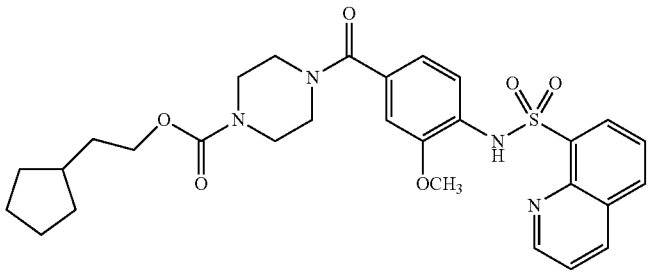
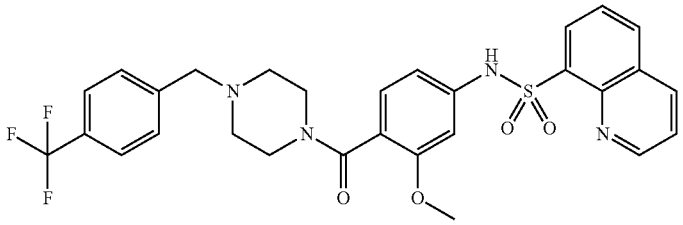
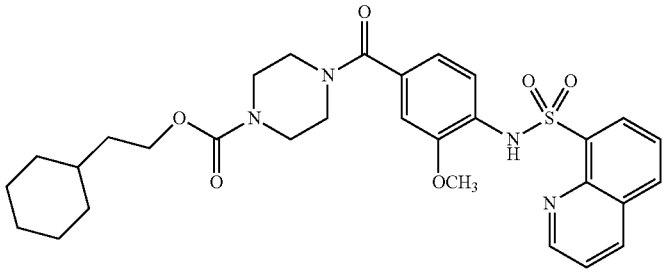
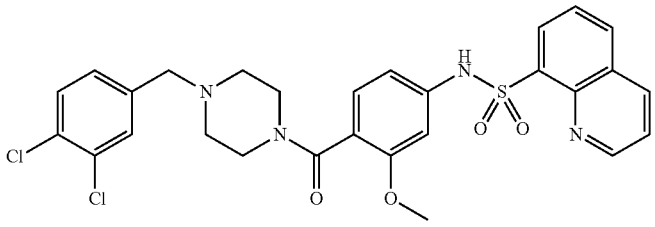
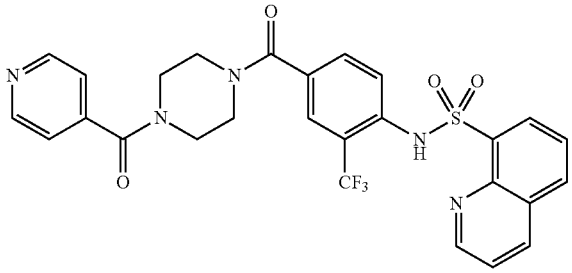
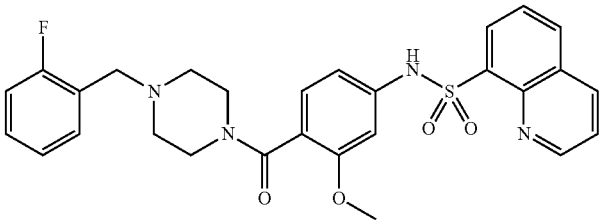

-continued
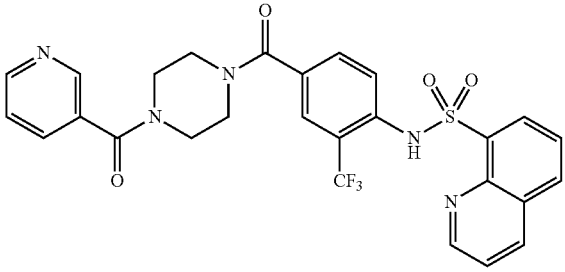
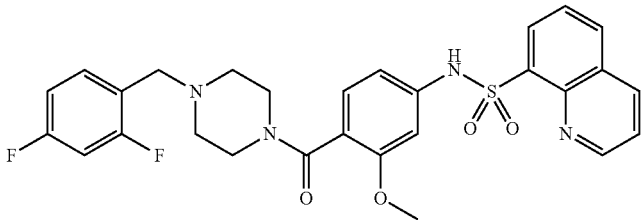
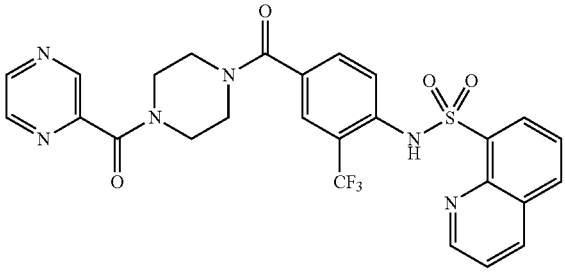
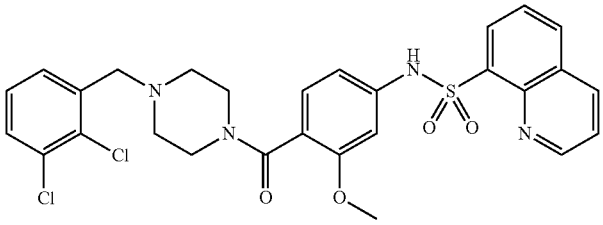
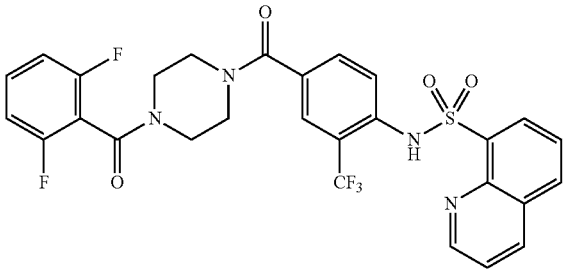
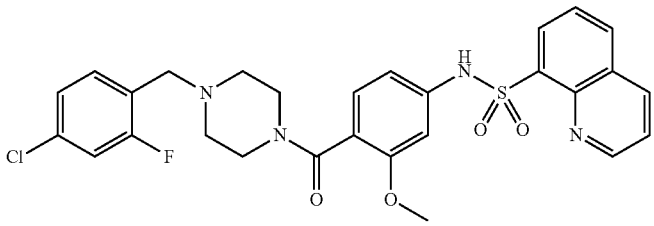
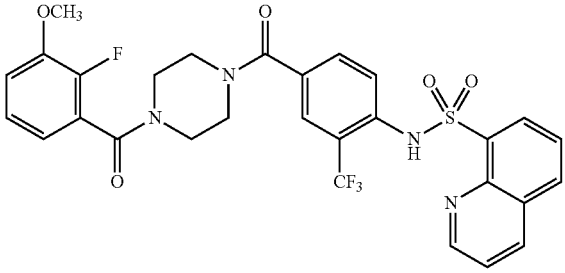
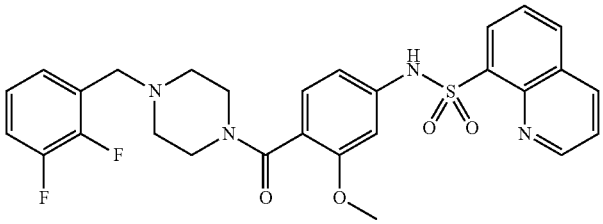

-continued
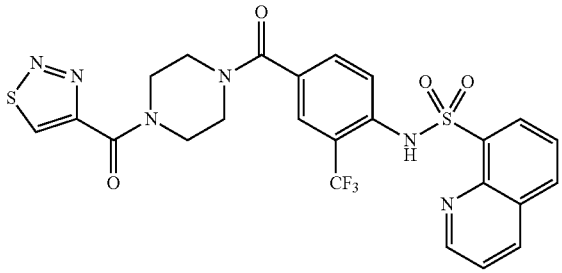
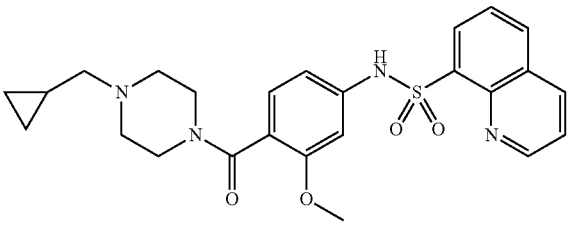
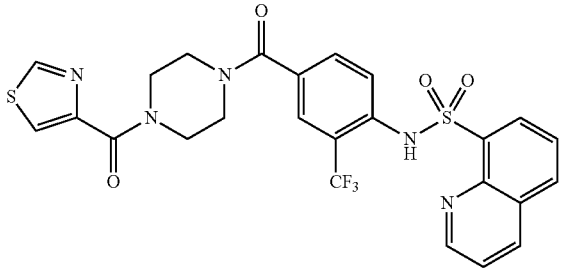
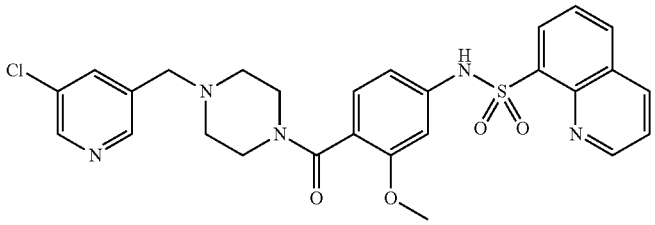
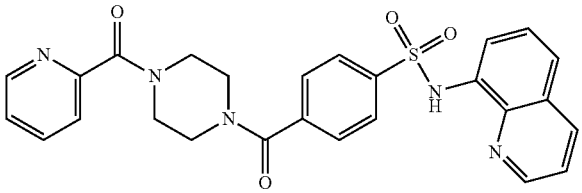
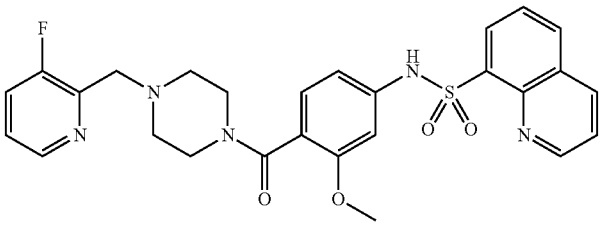
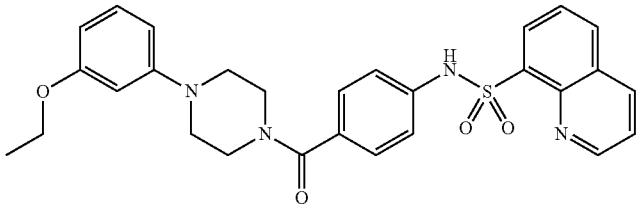
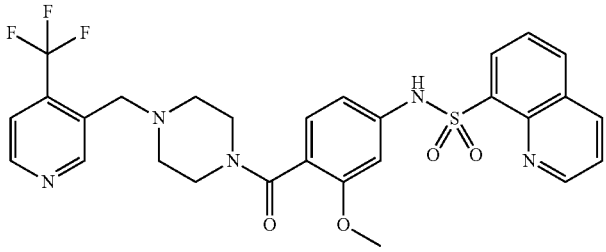
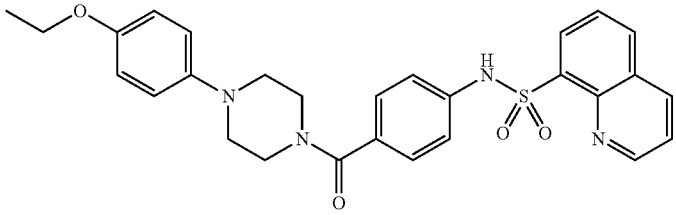

-continued
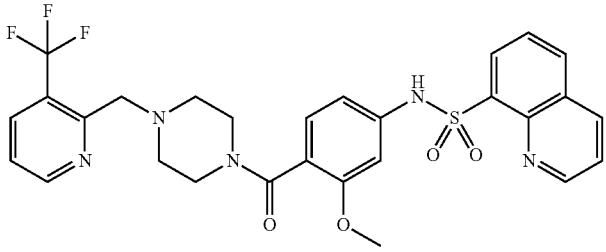
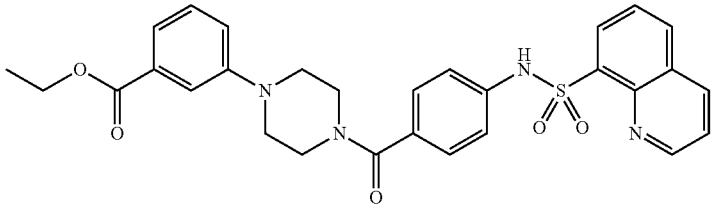
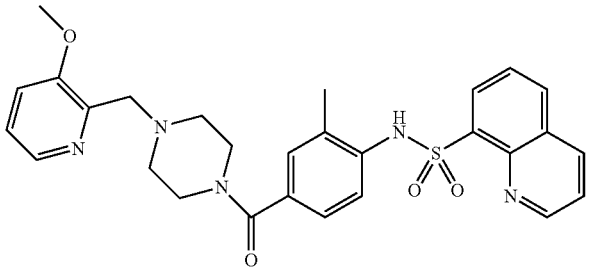
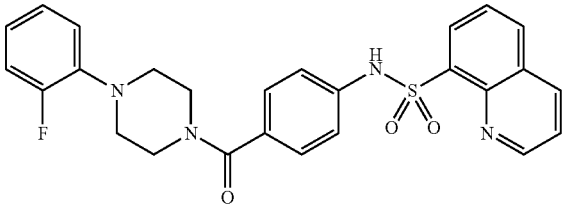
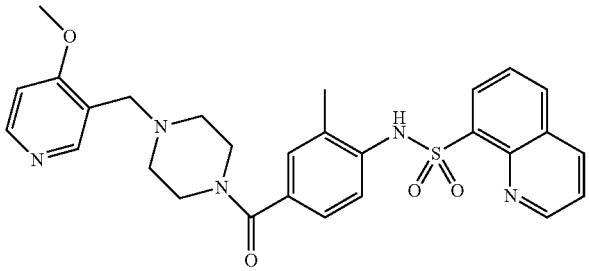
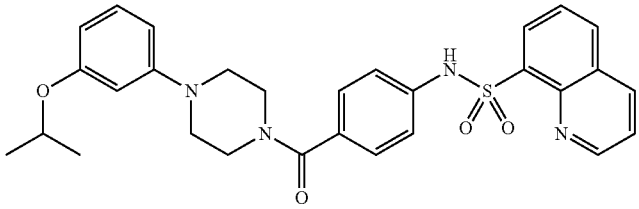
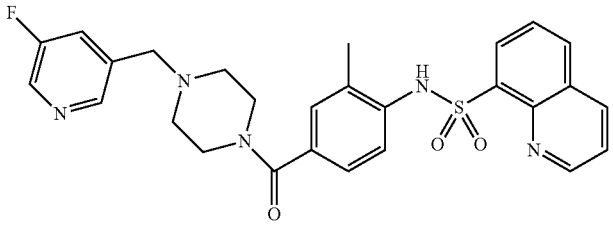
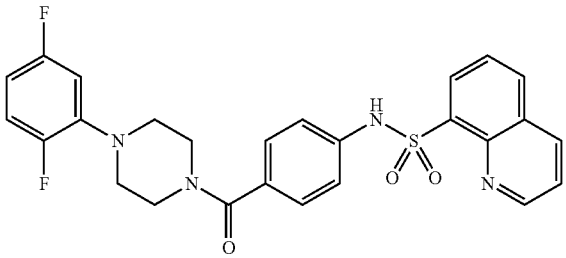
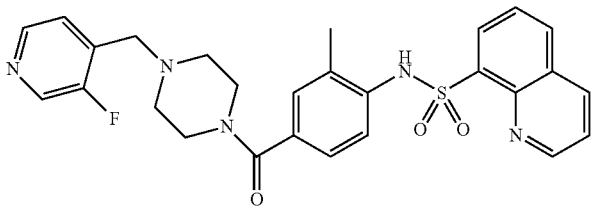

-continued
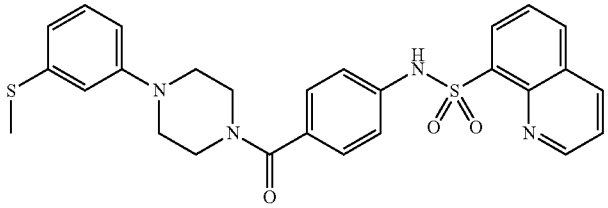
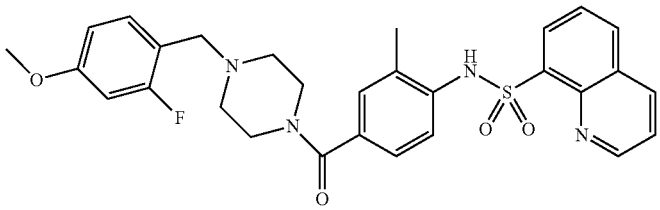
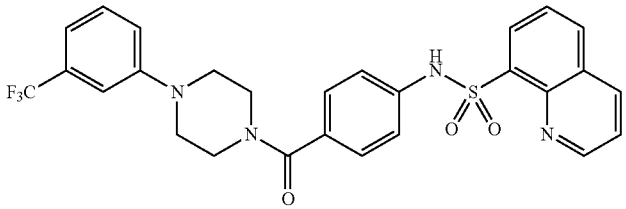
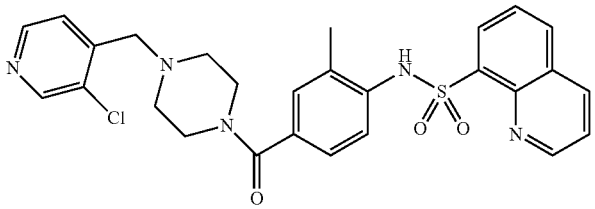
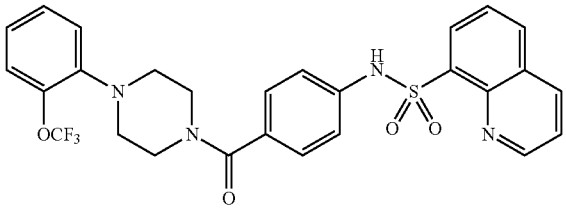
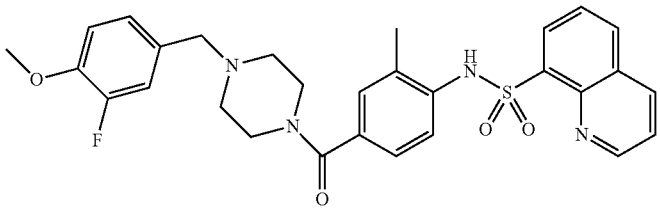
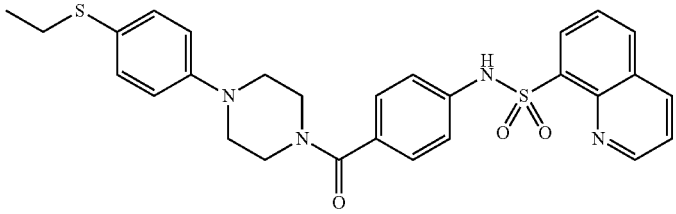
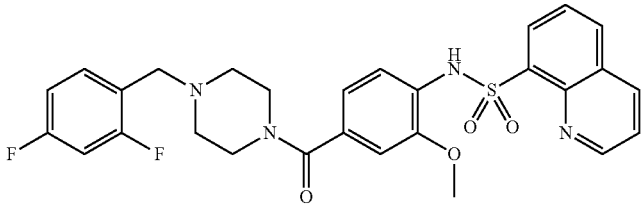
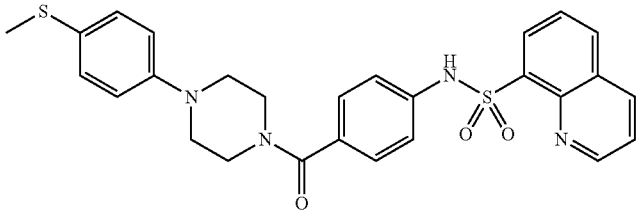

-continued
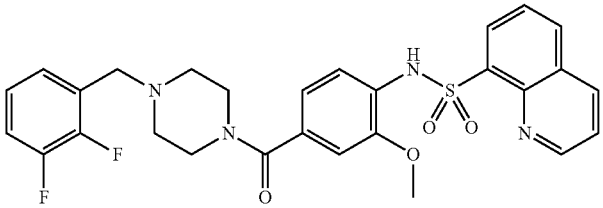
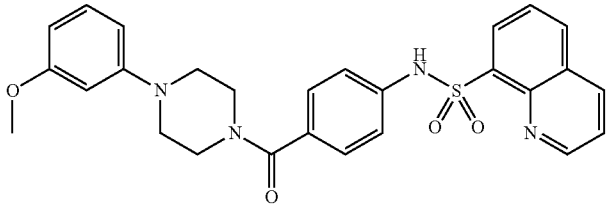
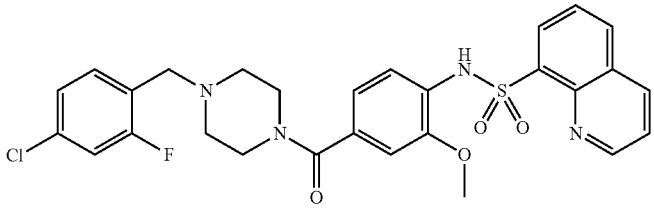
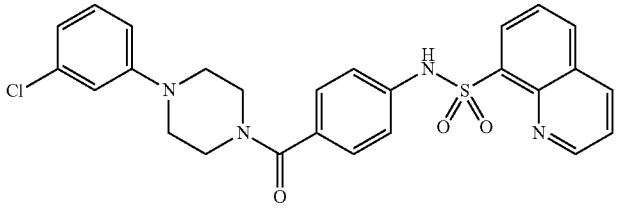
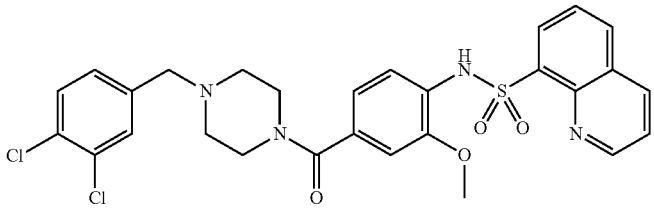
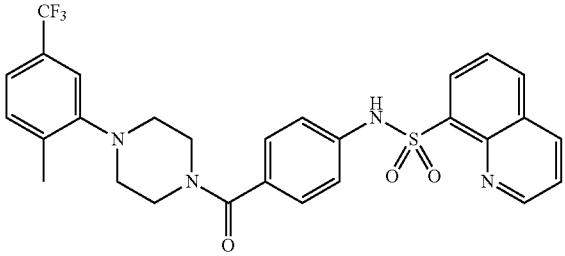
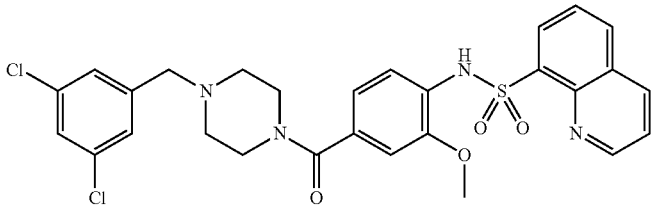
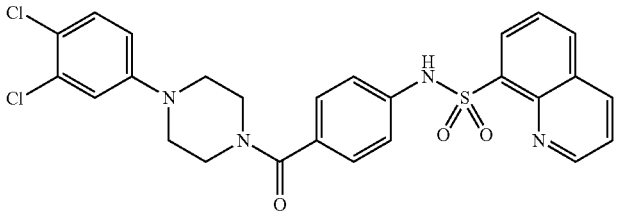

-continued
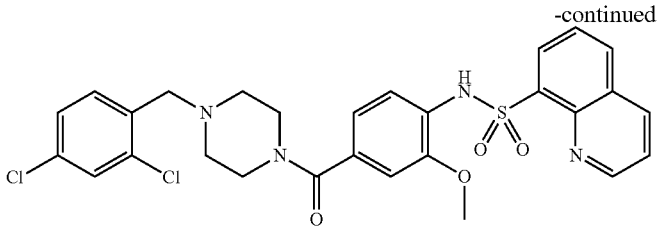
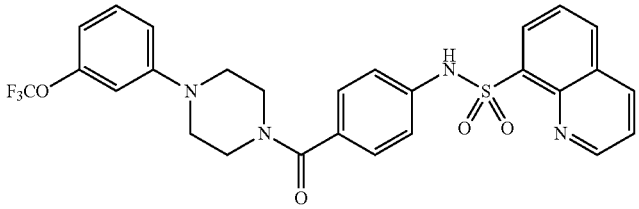
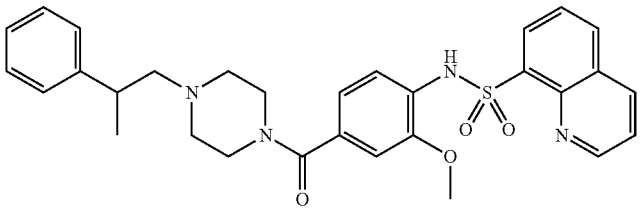
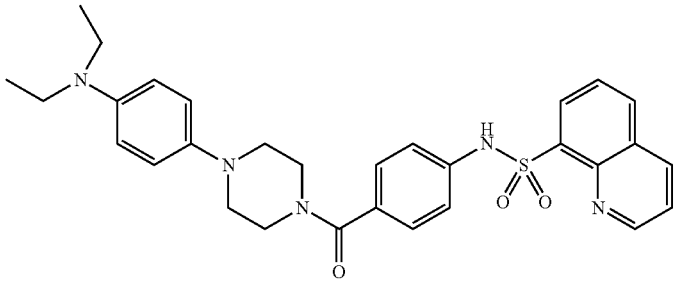
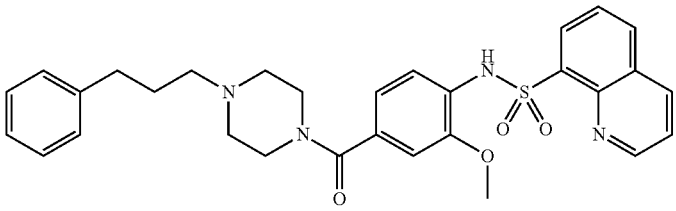
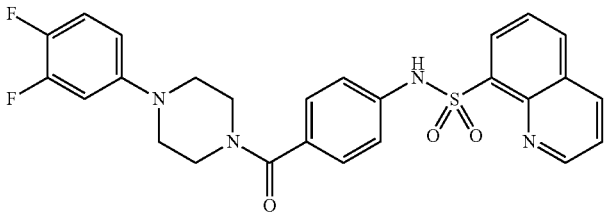
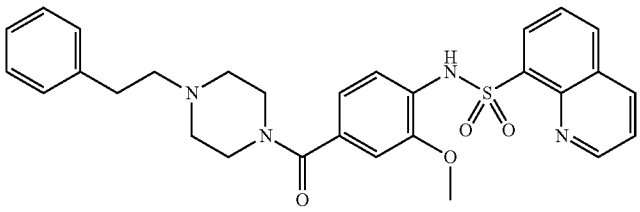

-continued
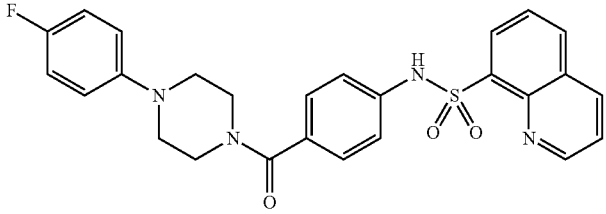
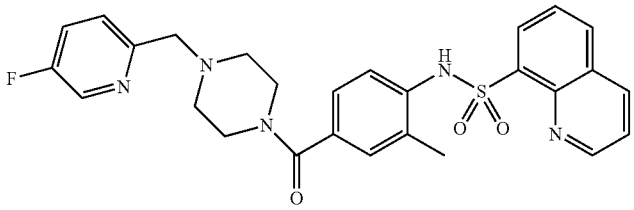
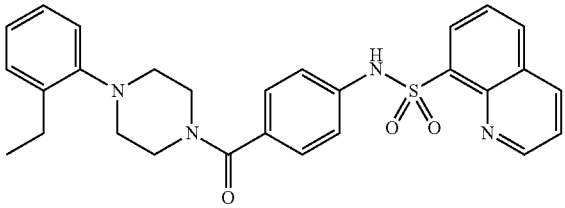
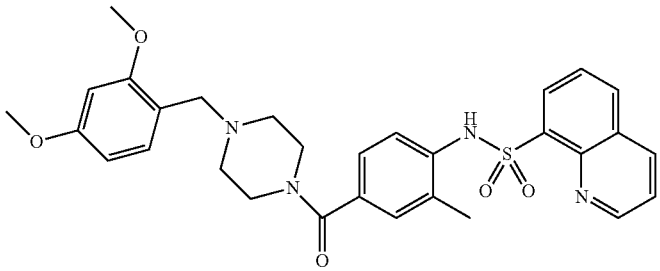
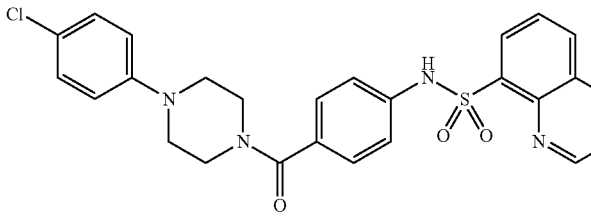
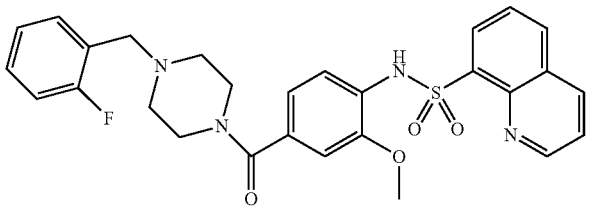
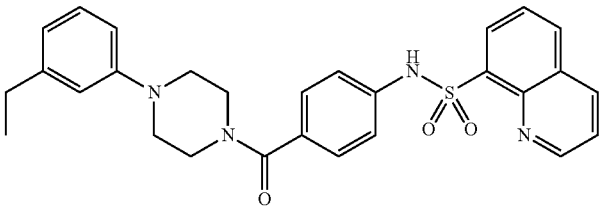
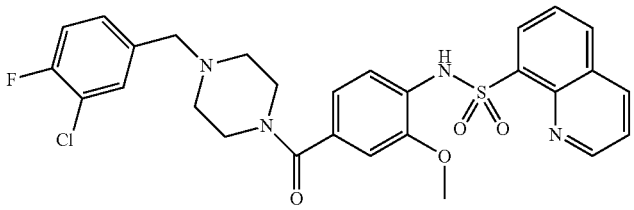

-continued
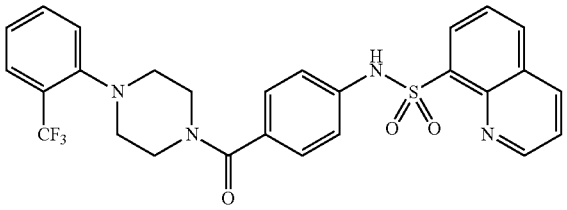
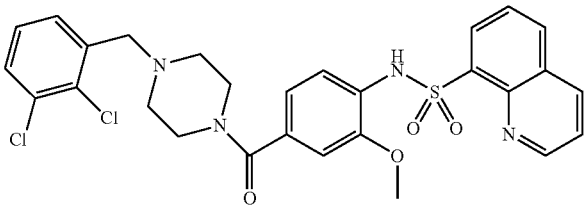
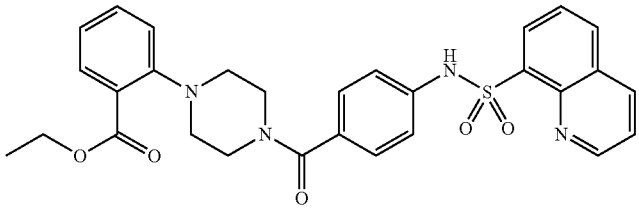
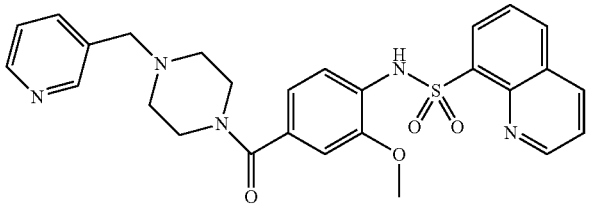
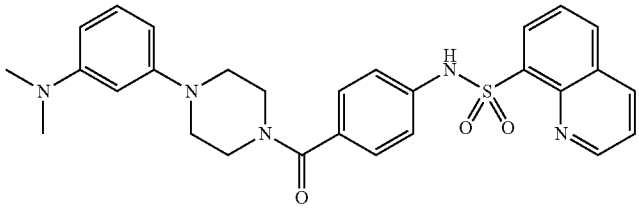
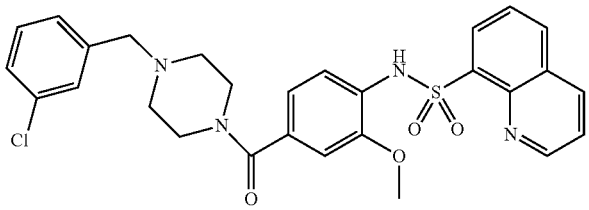
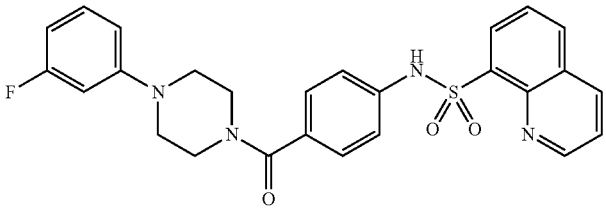
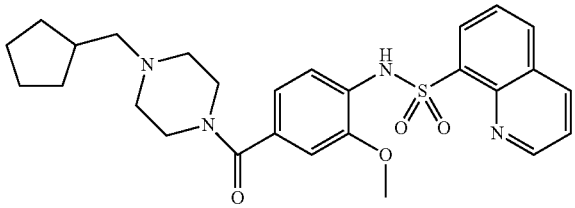
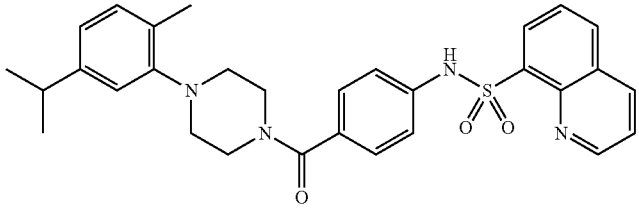
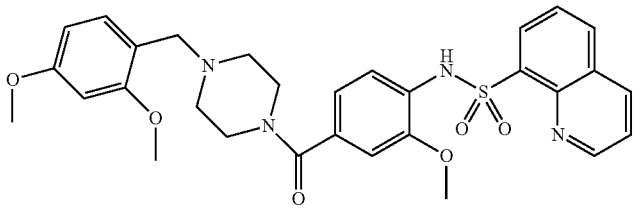

-continued
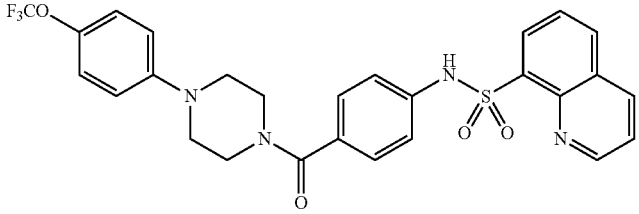
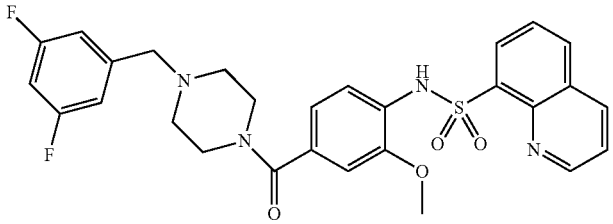
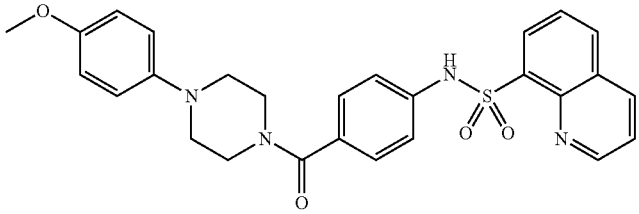
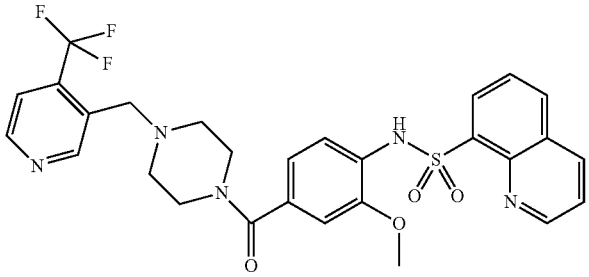
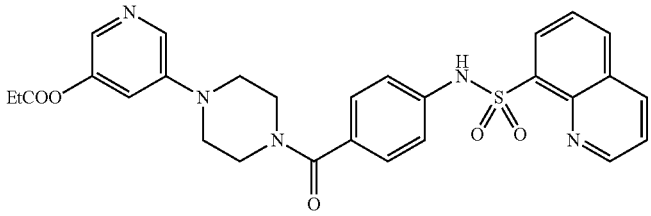
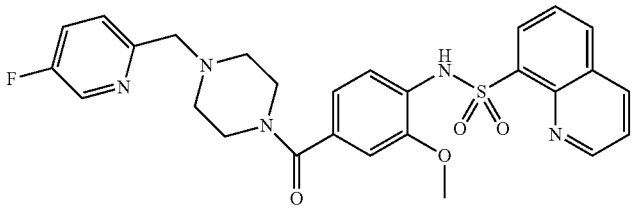
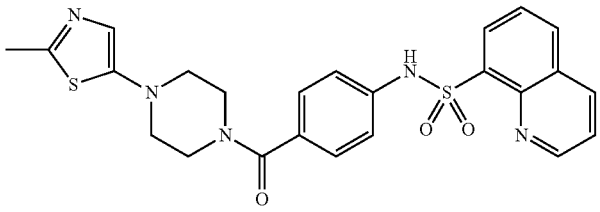
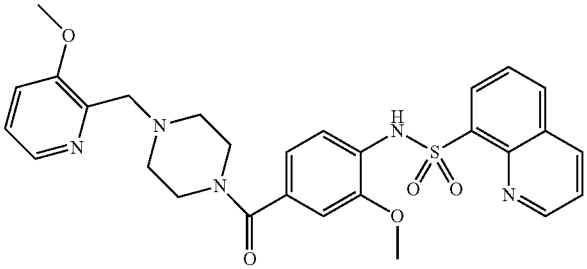

-continued
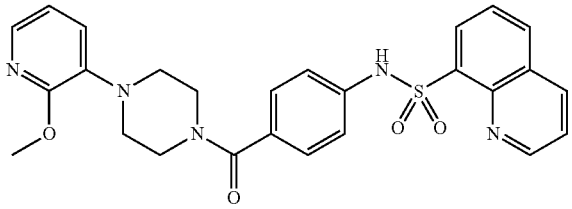
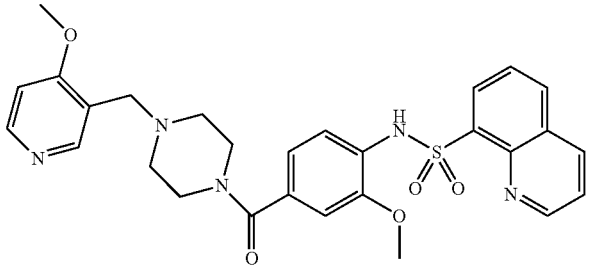
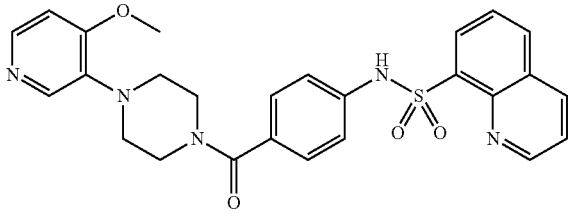
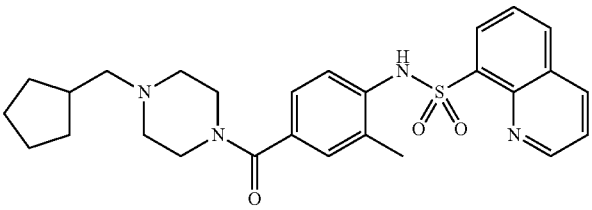
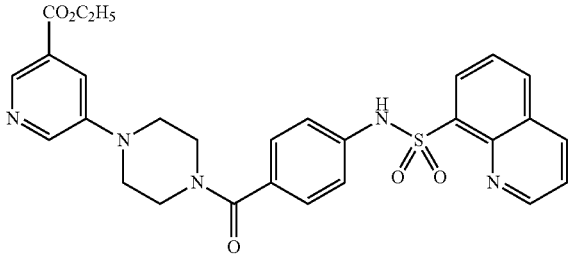
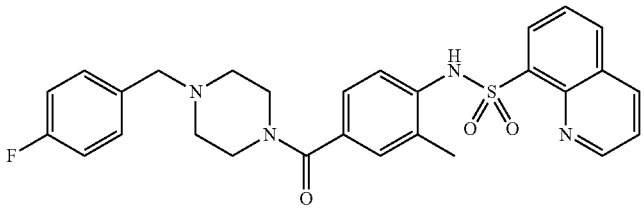
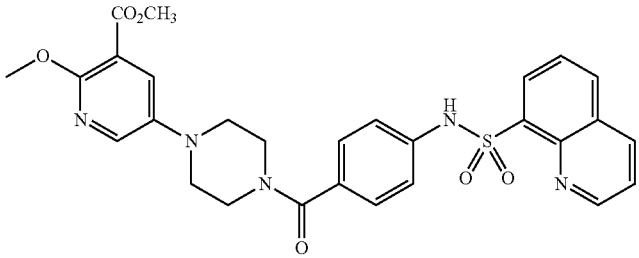
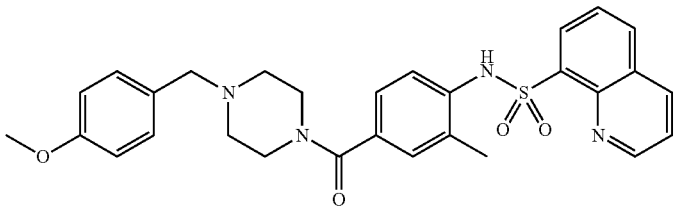
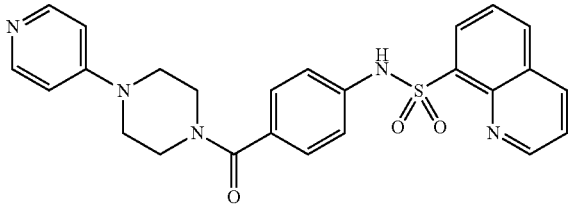
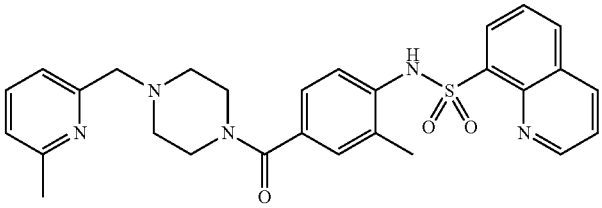

-continued
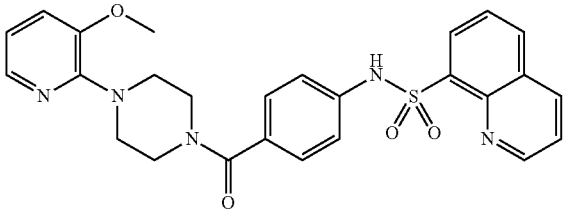
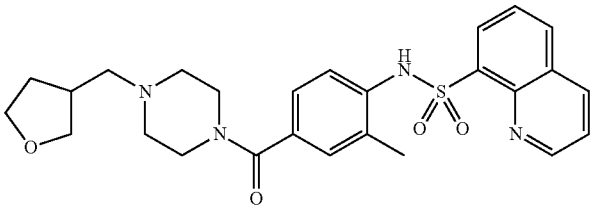
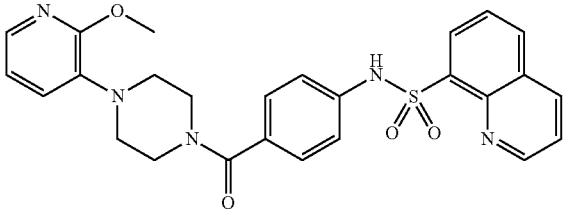
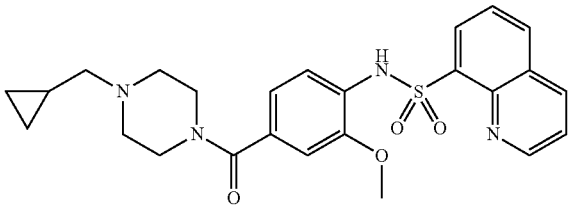
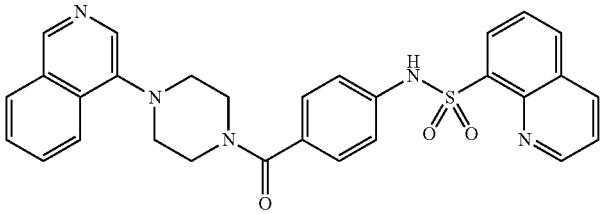
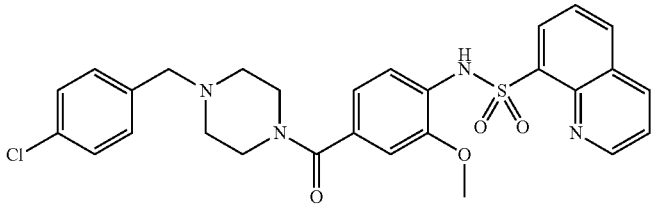
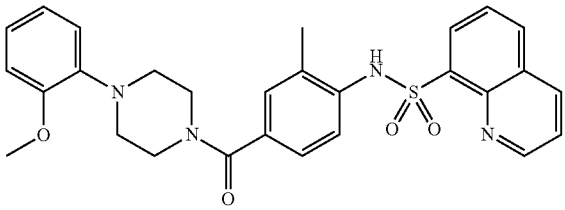
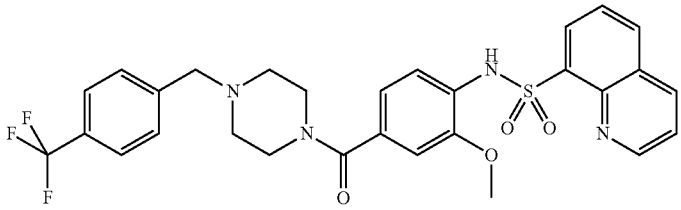
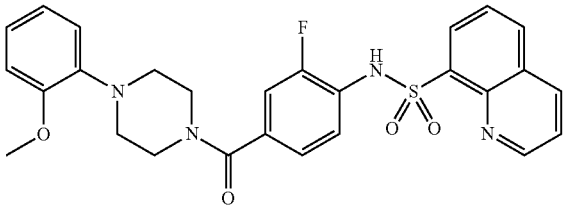
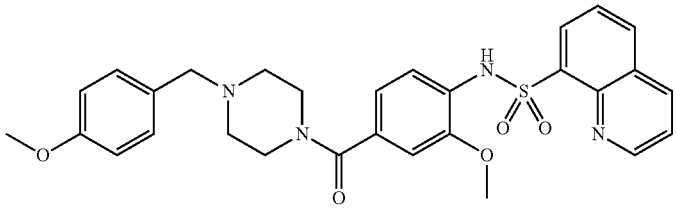

-continued
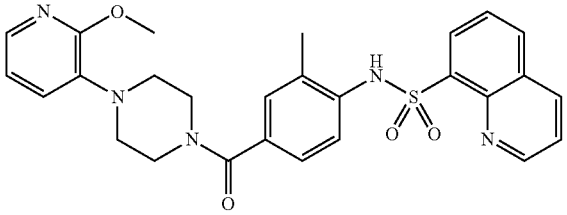
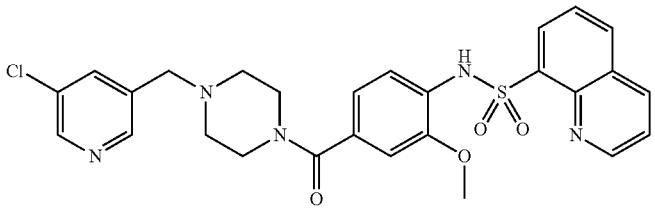
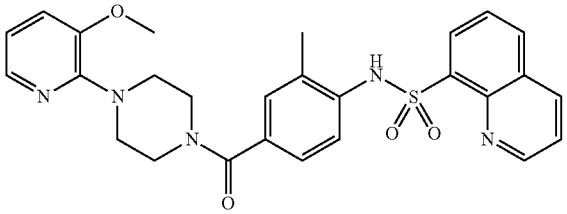
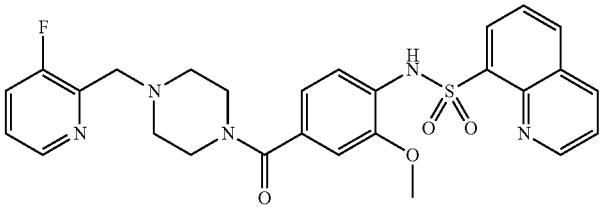
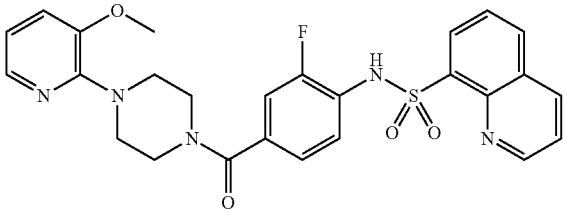
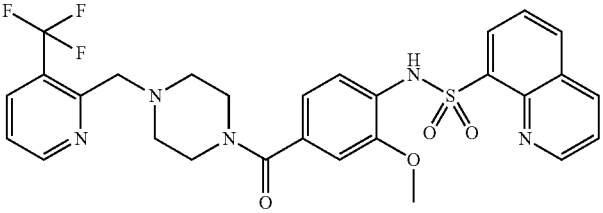
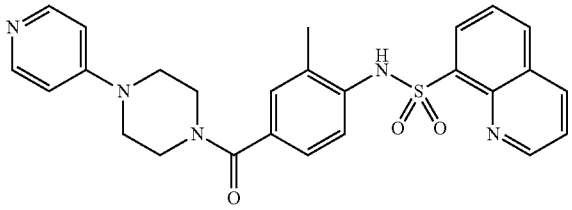
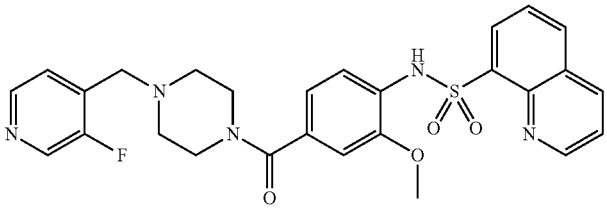
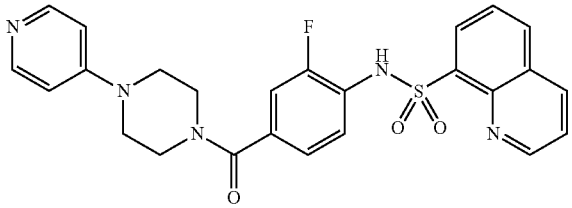
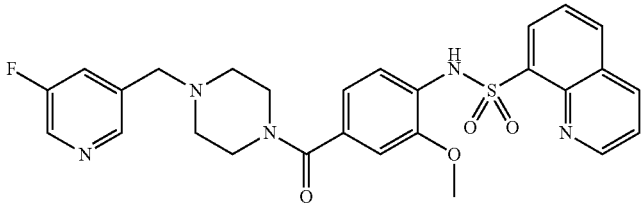
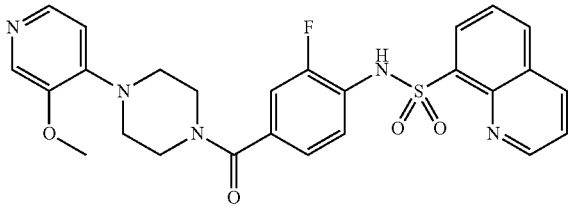

-continued
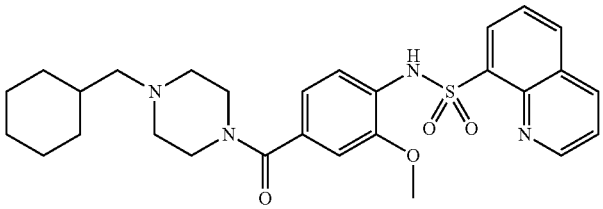
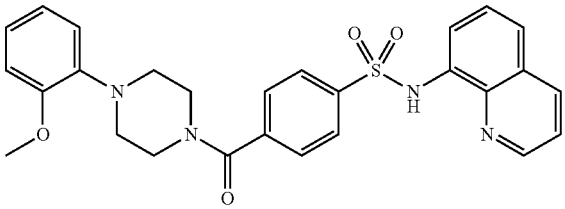
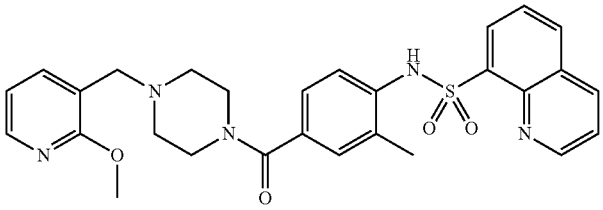
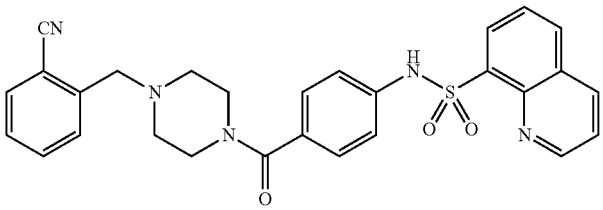
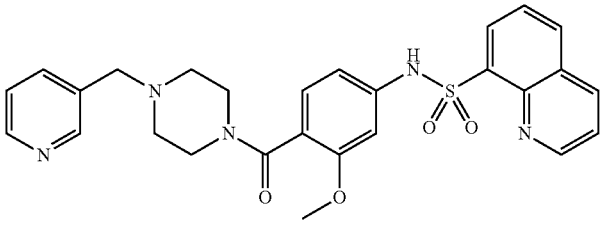
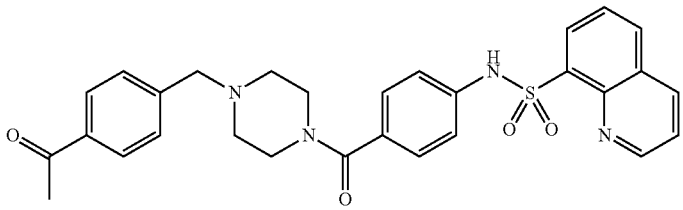
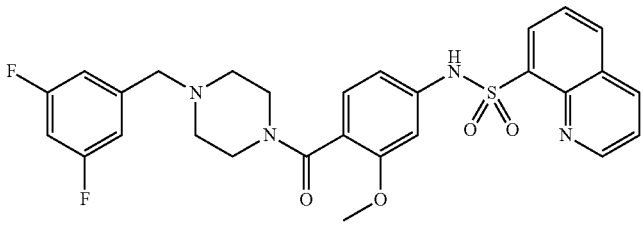
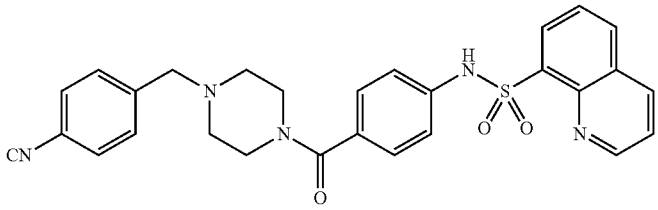
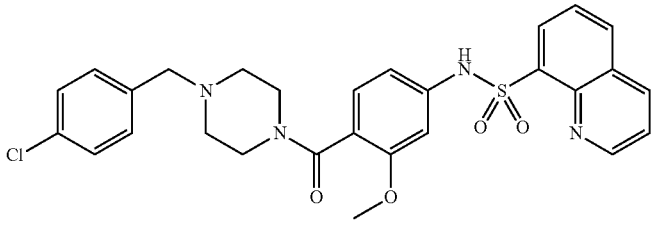

-continued
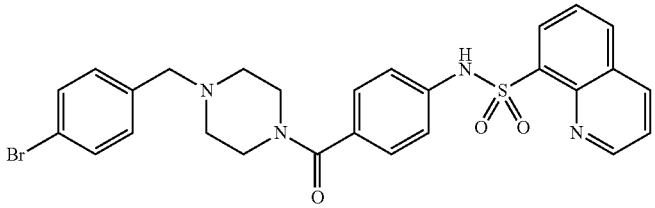
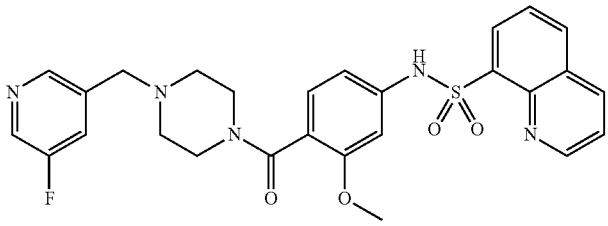
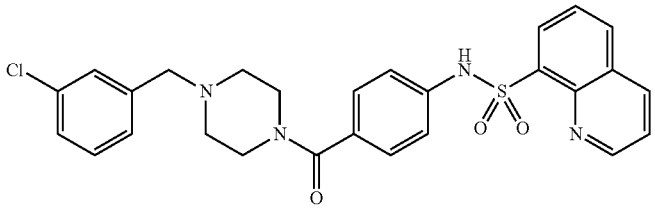
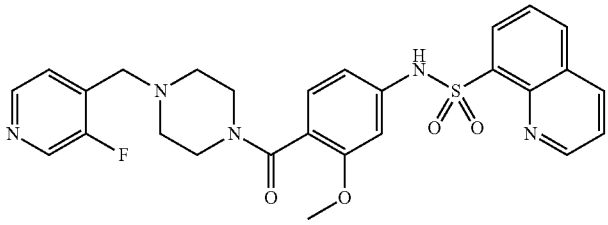
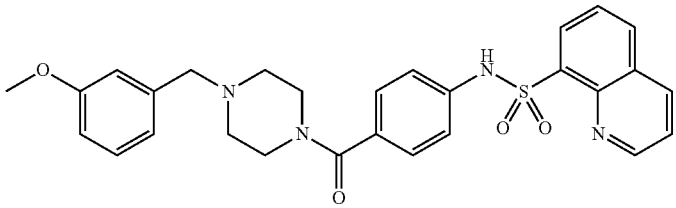
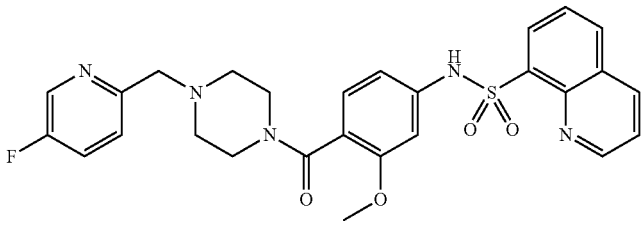
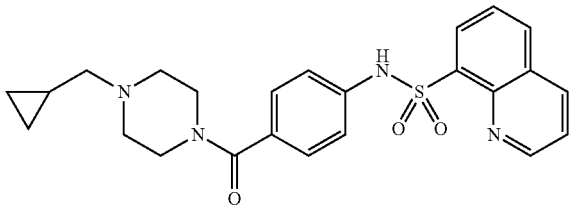
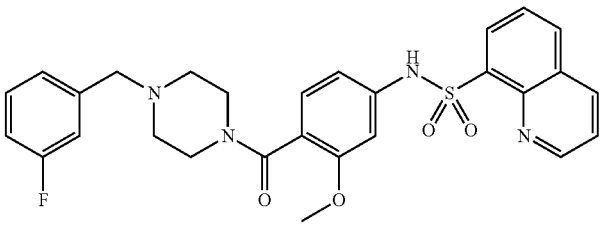
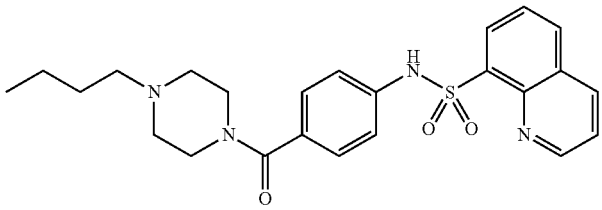

-continued
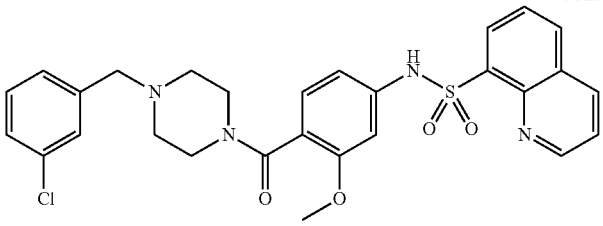
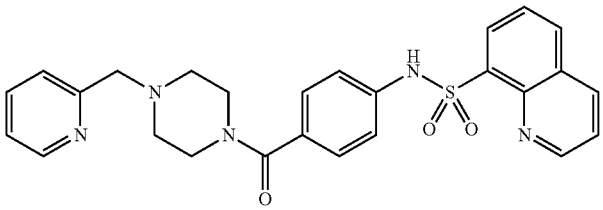
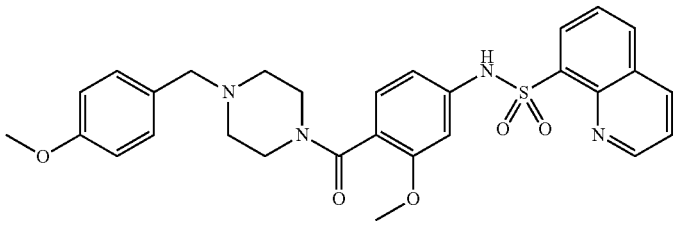
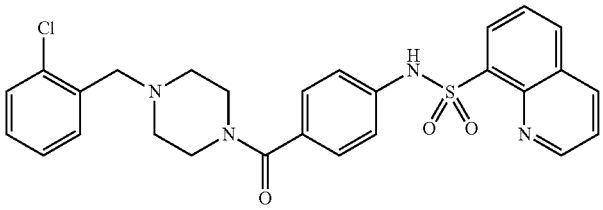
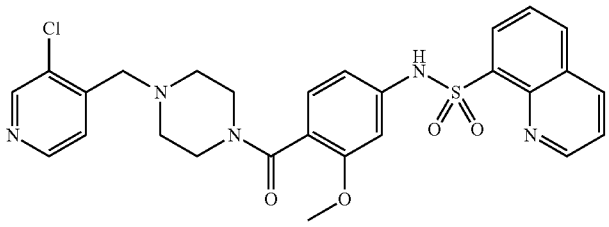
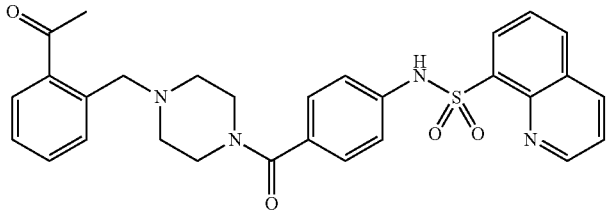
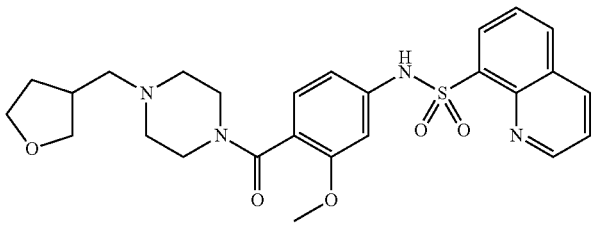
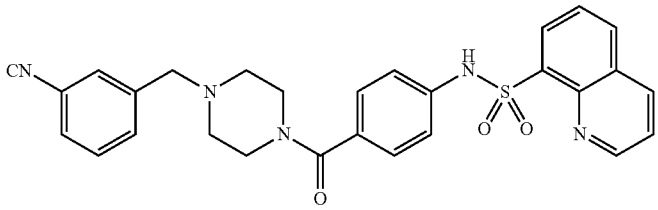

-continued
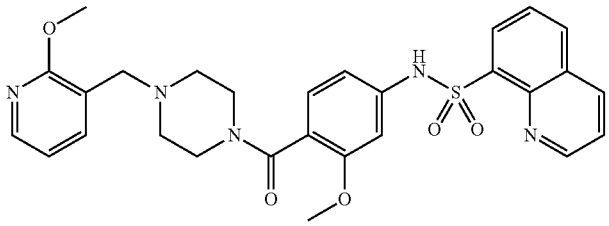
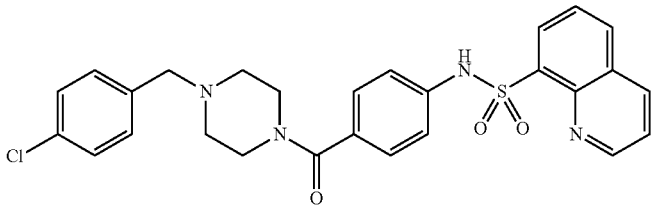
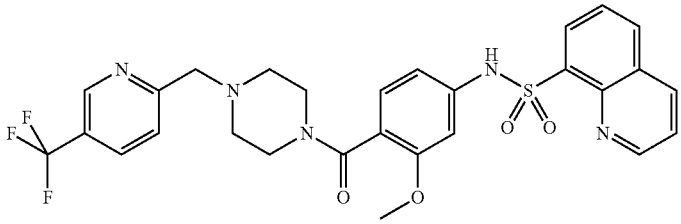
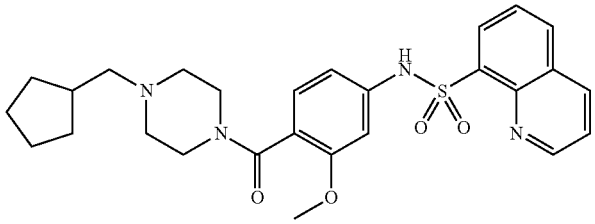
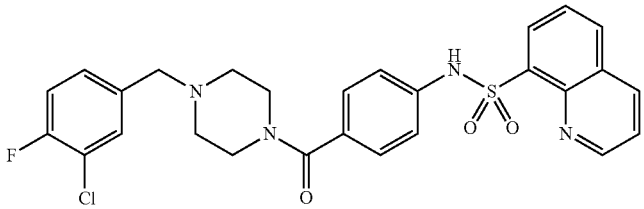
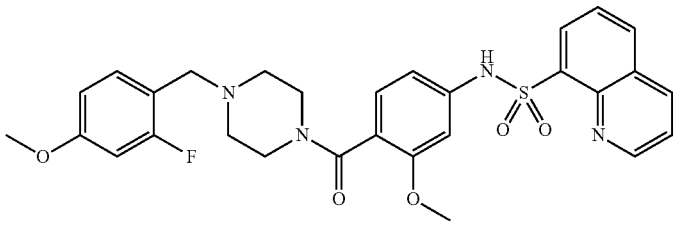
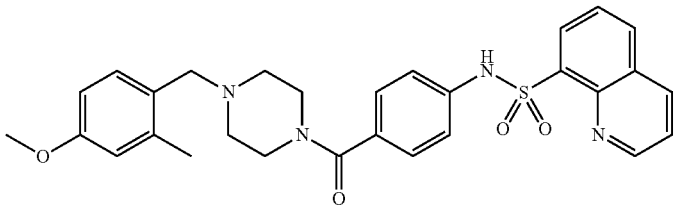

-continued
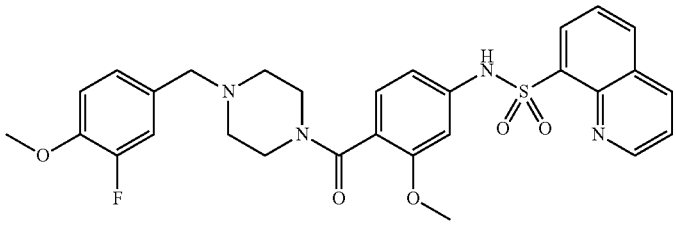
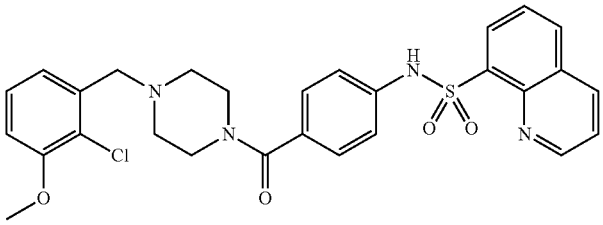
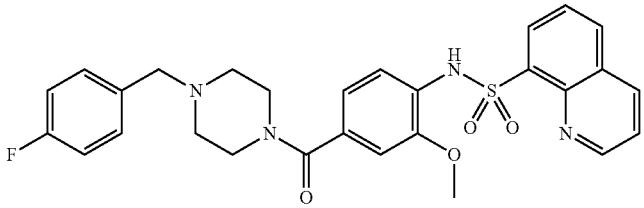
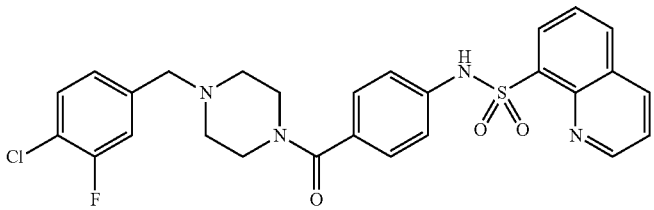
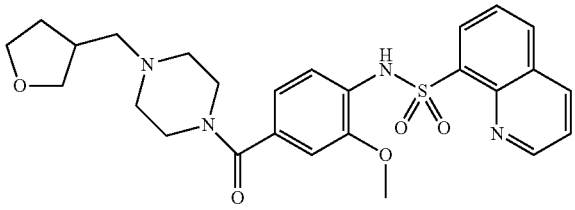
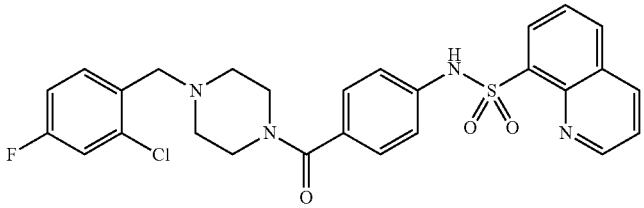
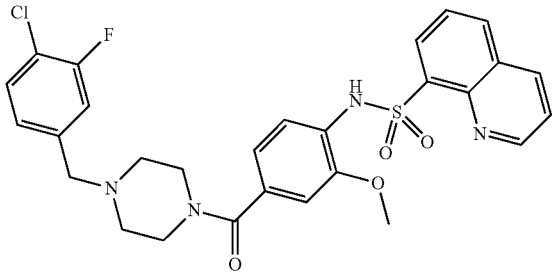
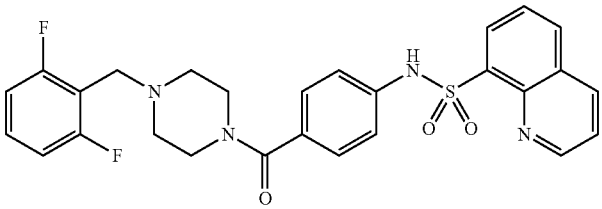

-continued
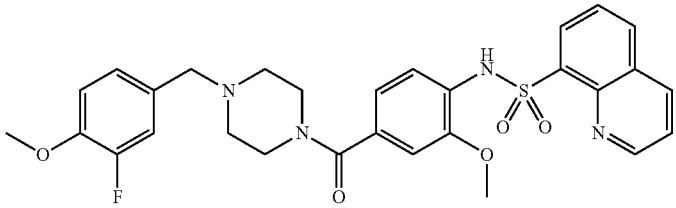
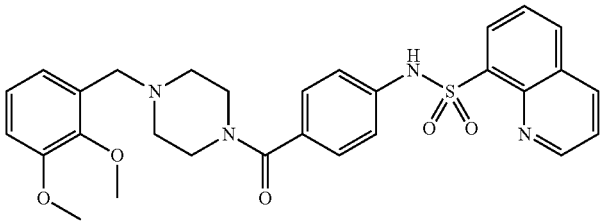
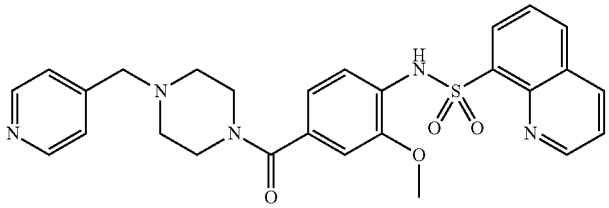
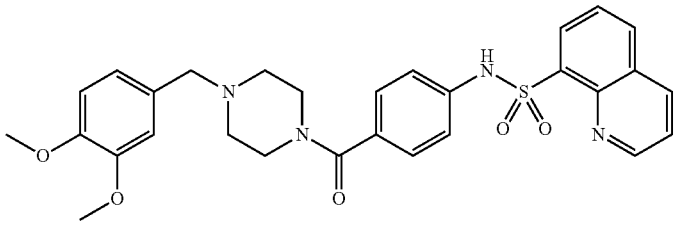
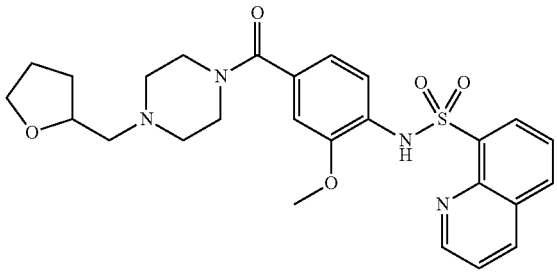
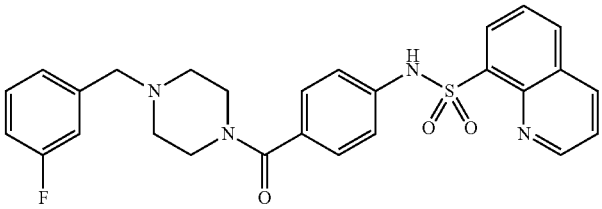
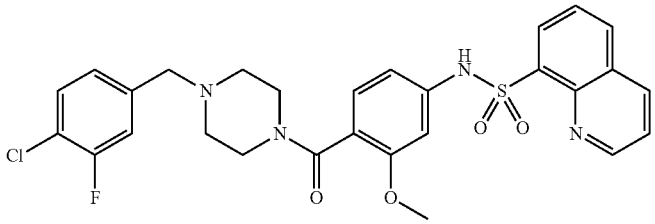
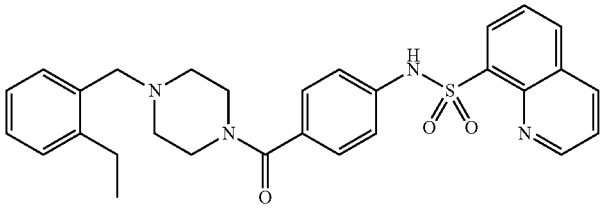

-continued
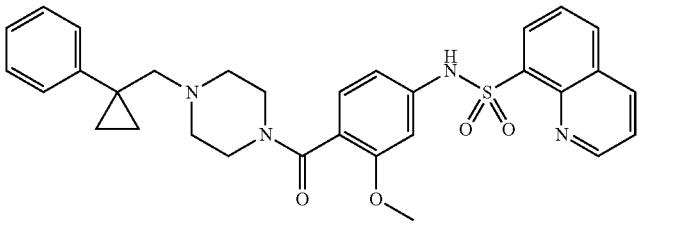
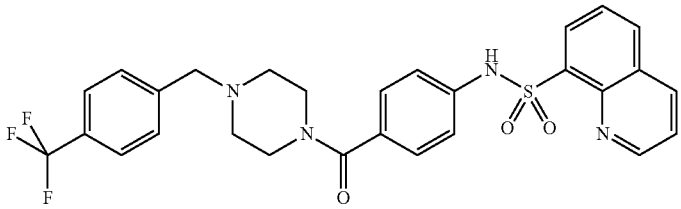
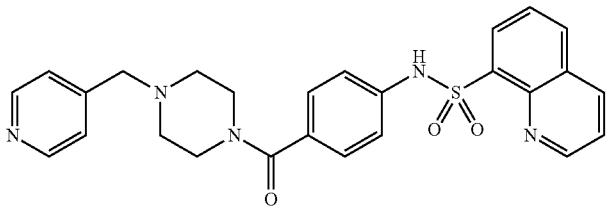
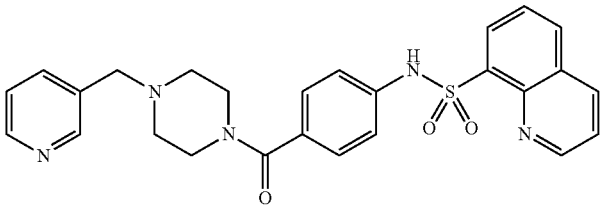
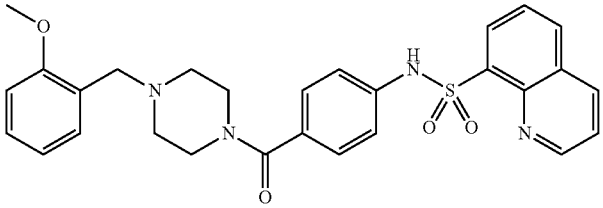
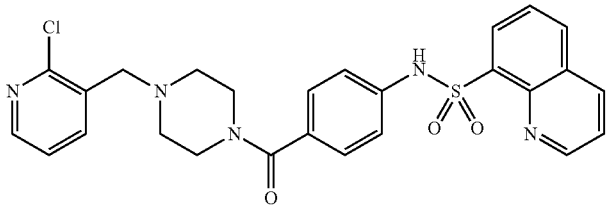
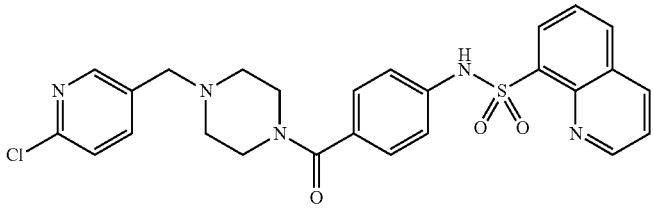
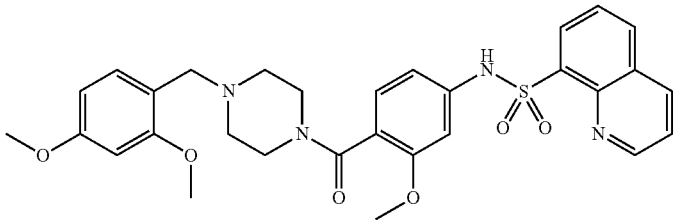

-continued
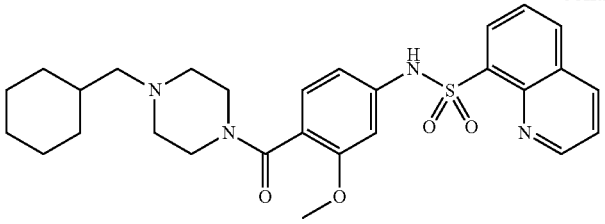
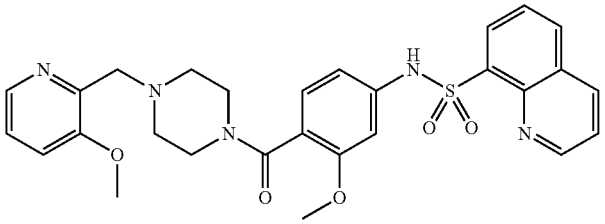
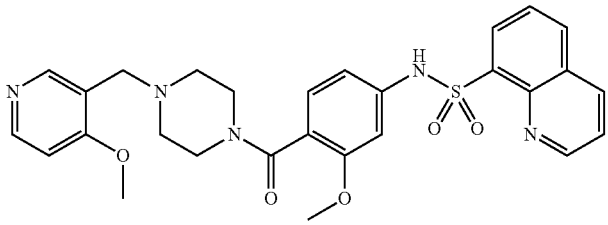
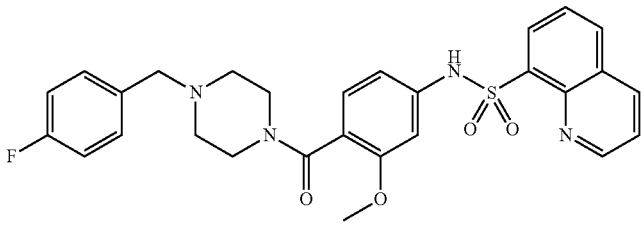
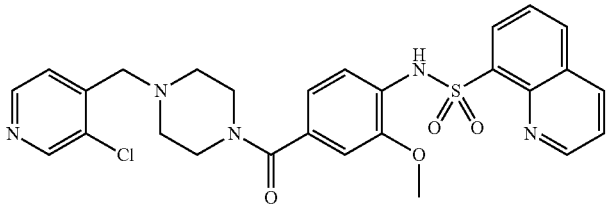
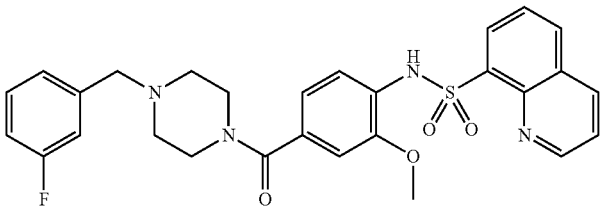
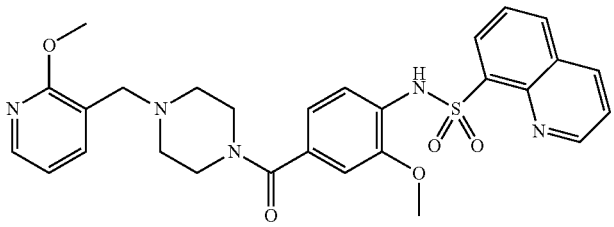

-continued
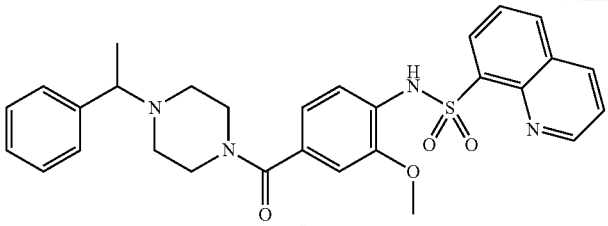
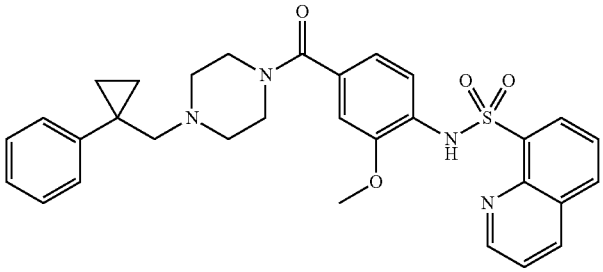
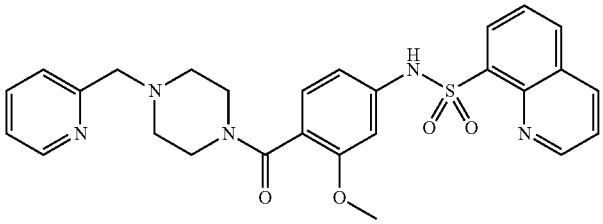
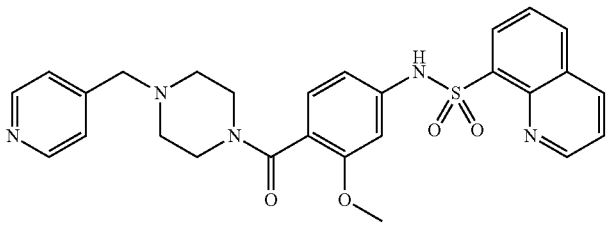
and
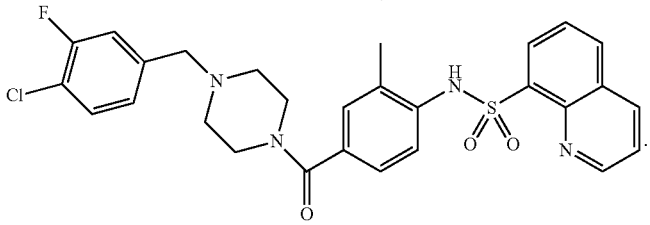
25. The compound of claim 1 selected from the following:
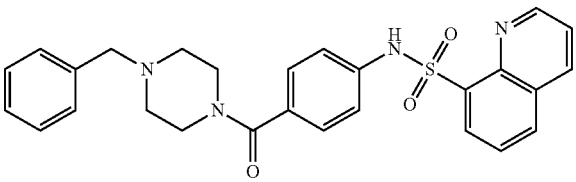
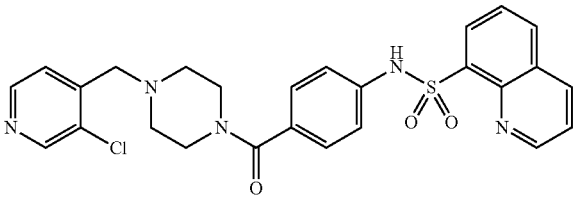
-continued
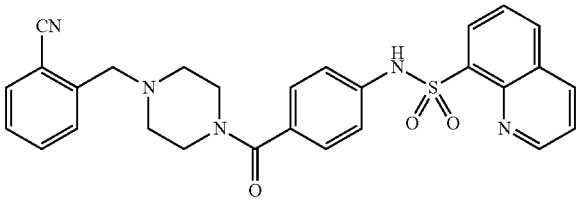
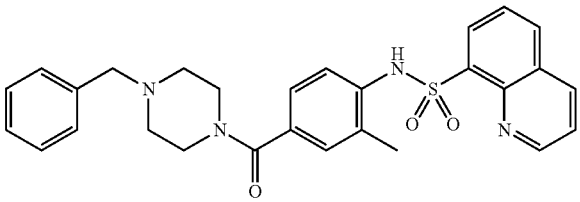

-continued
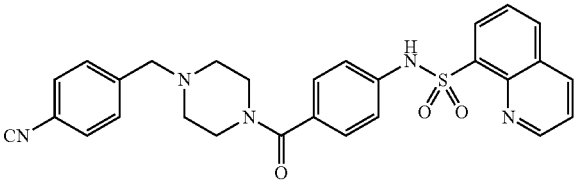
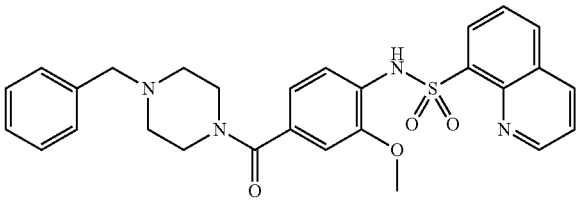
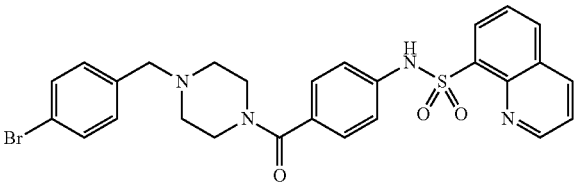
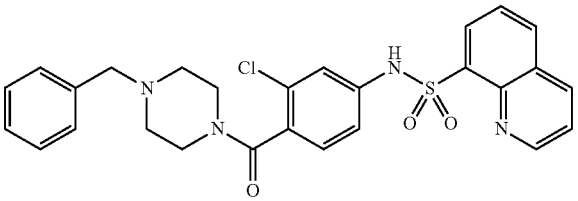
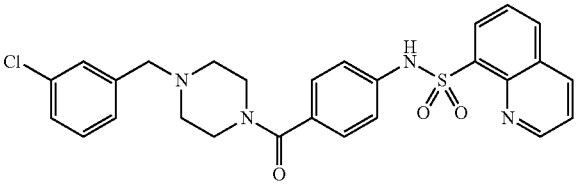
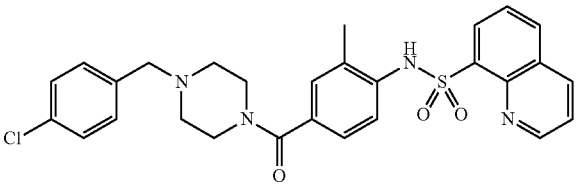
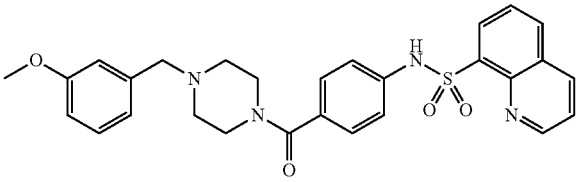
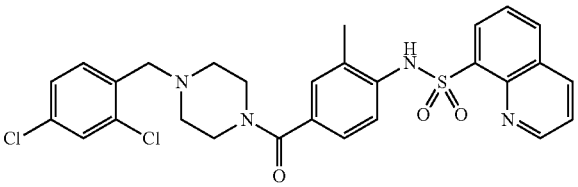
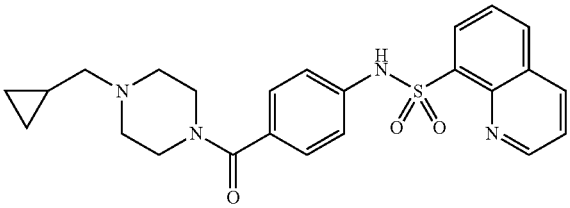
-continued
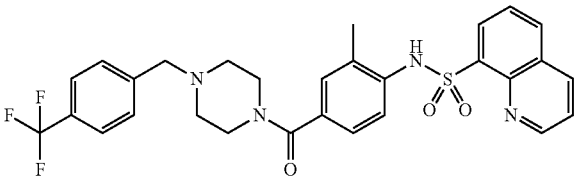
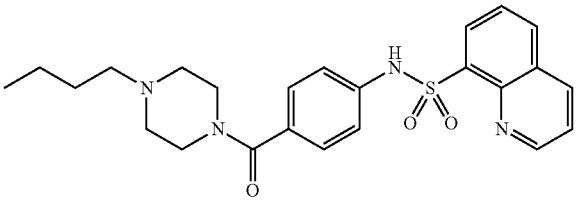
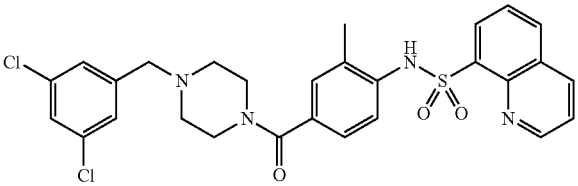
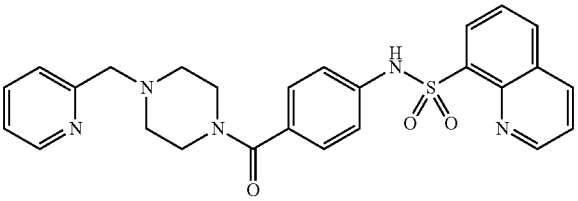
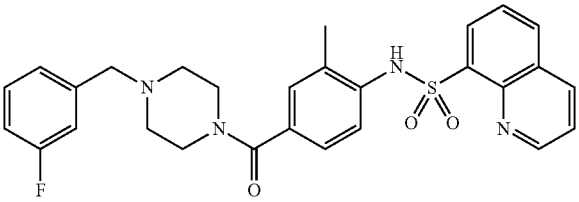
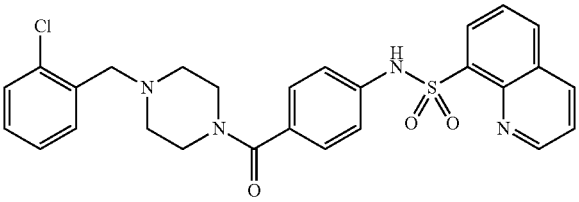
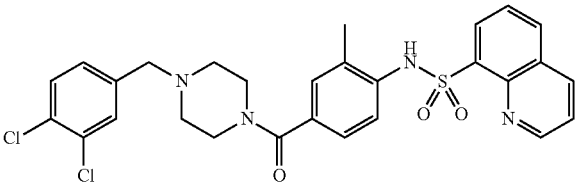
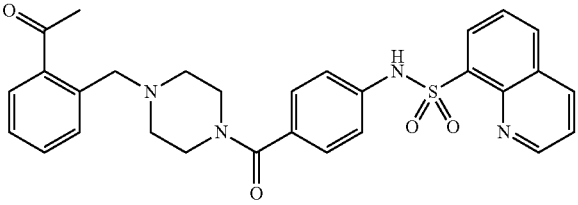

-continued
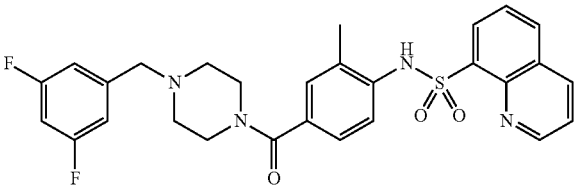
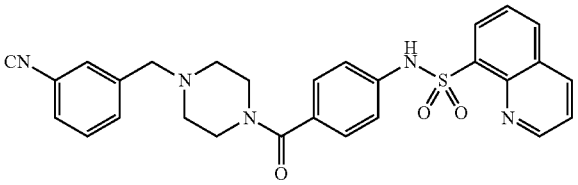
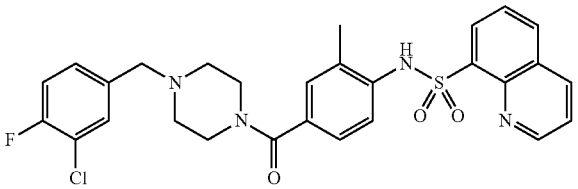
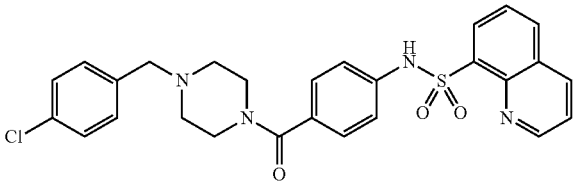
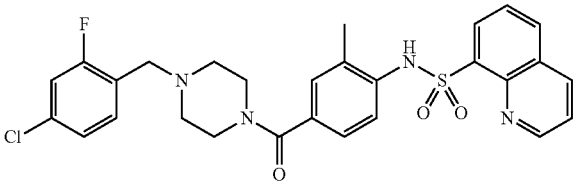
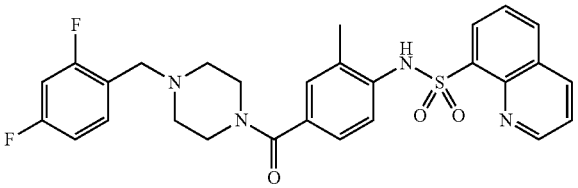
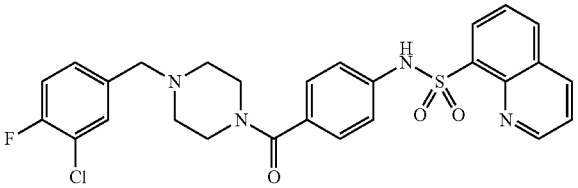
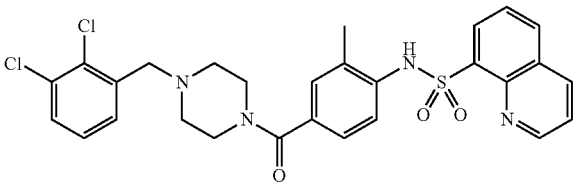
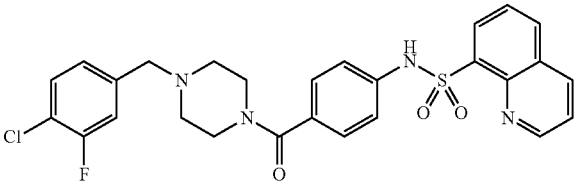
-continued
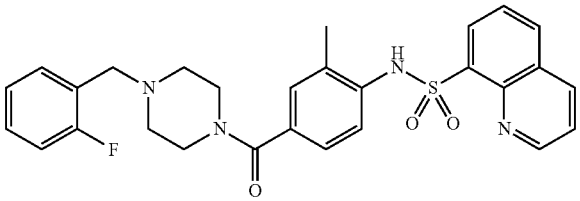
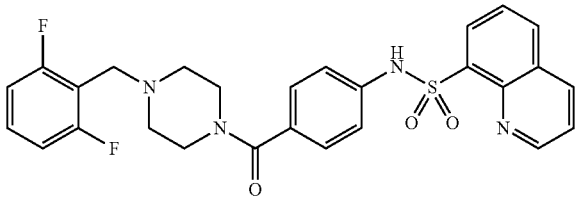
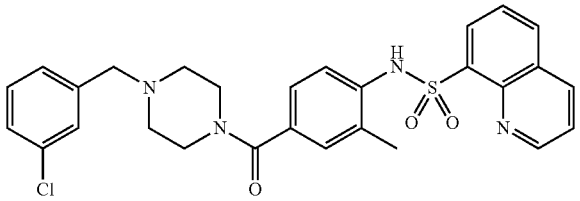
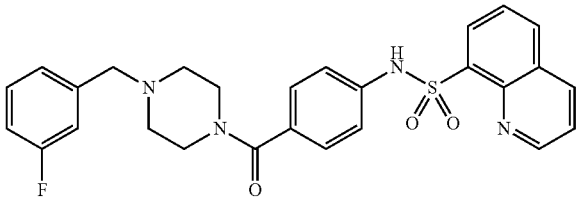
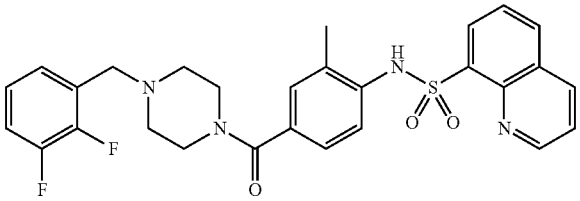
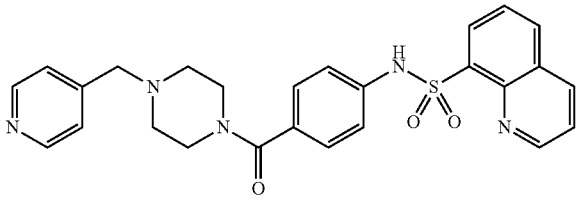
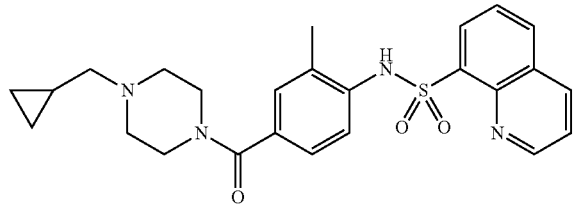
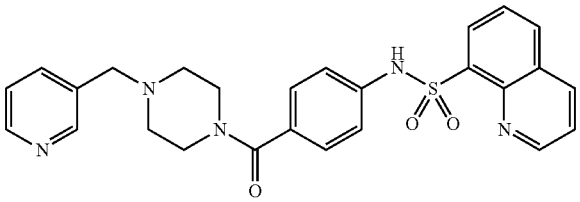

-continued
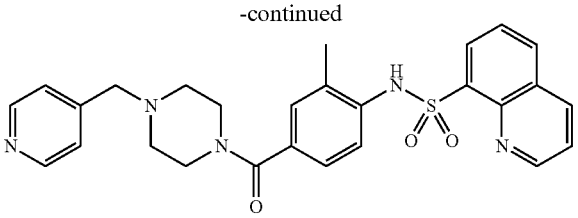
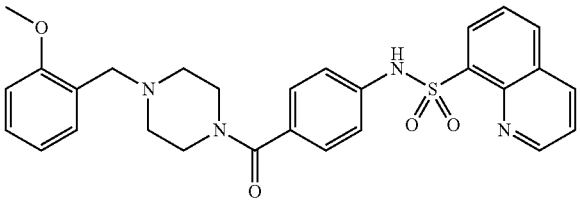
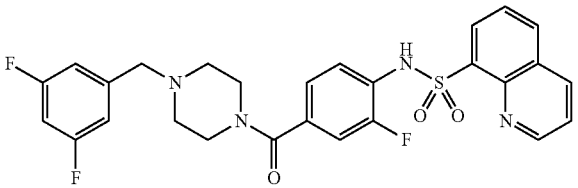
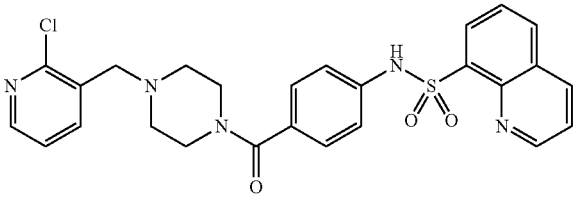
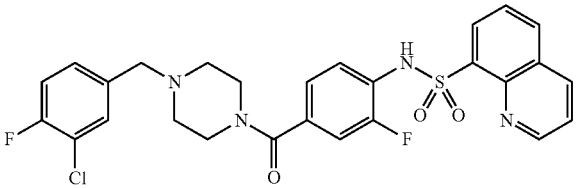
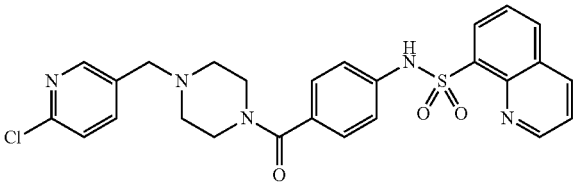
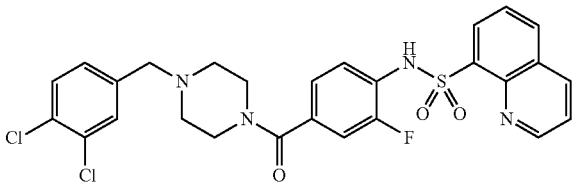
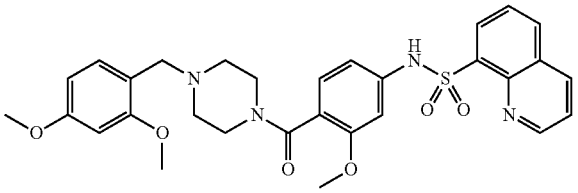
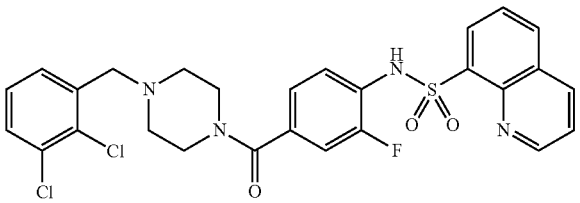
-continued
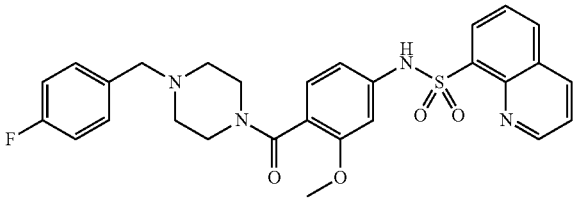
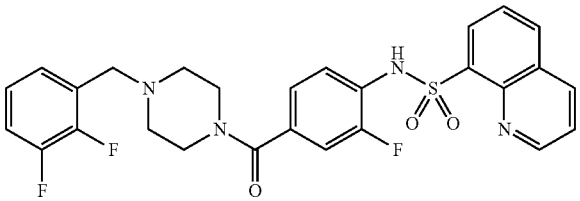
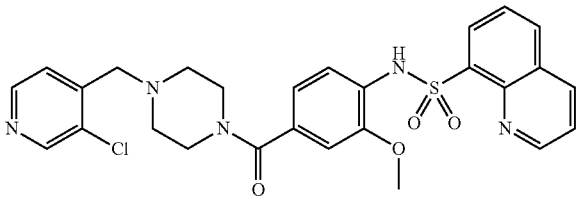
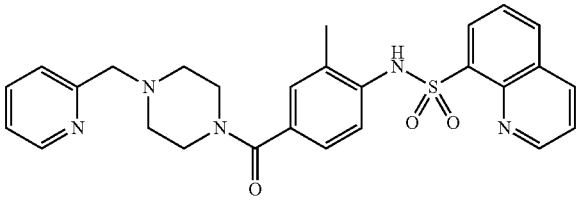
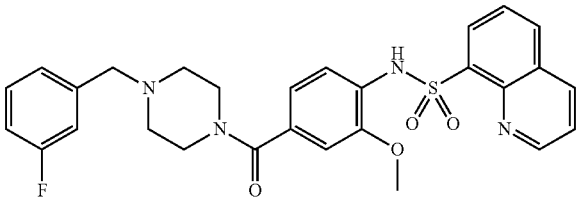
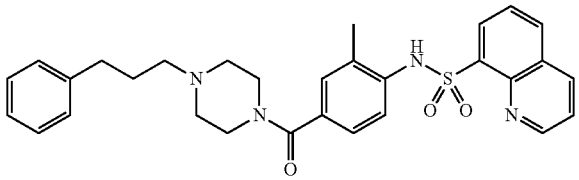
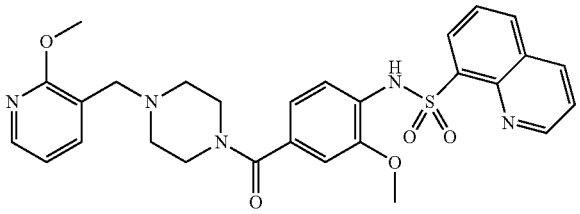
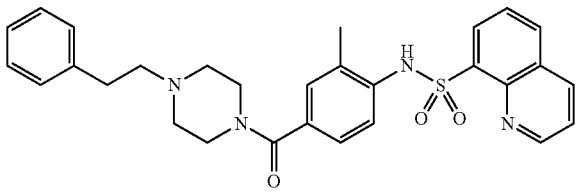

-continued
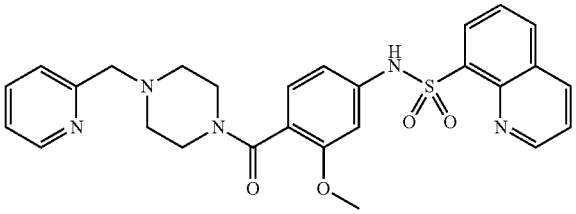
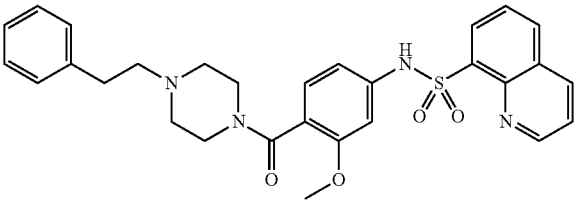
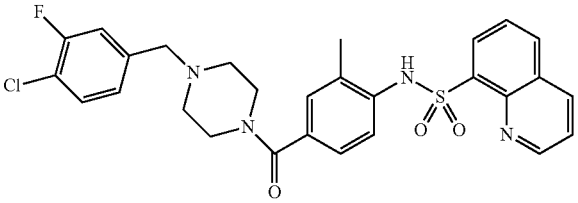
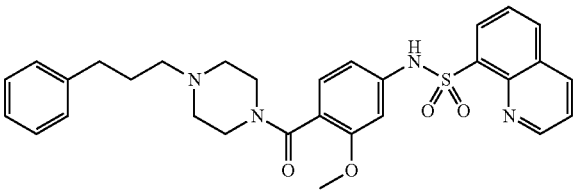
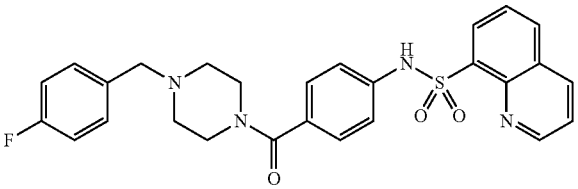
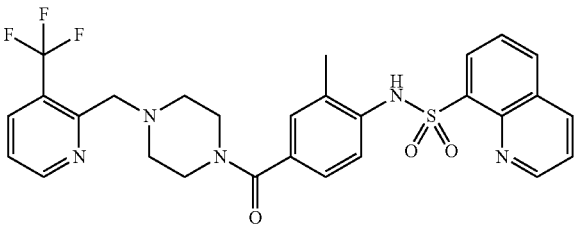
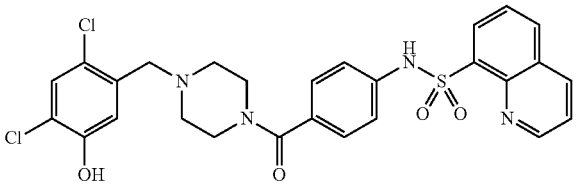
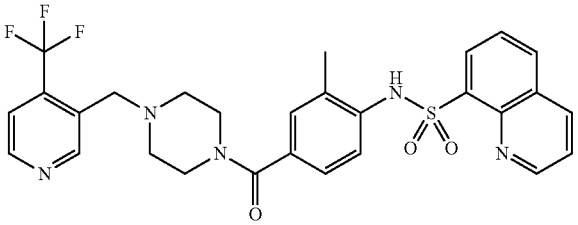
-continued
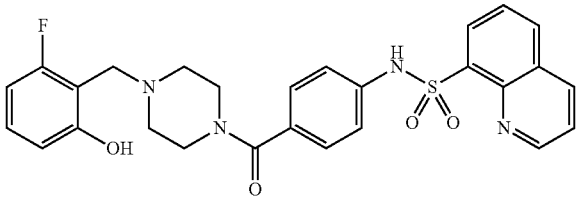
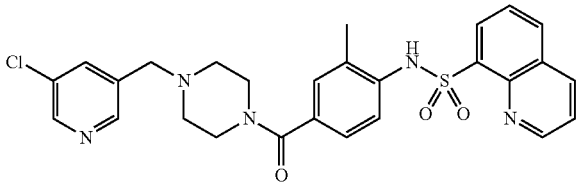
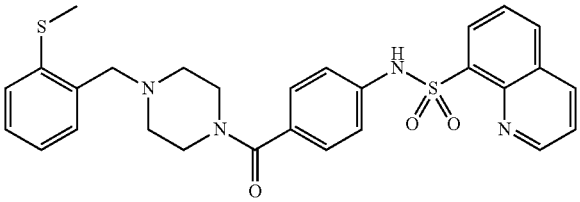
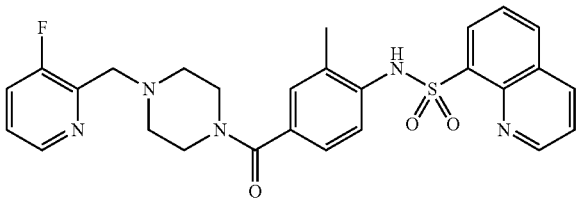
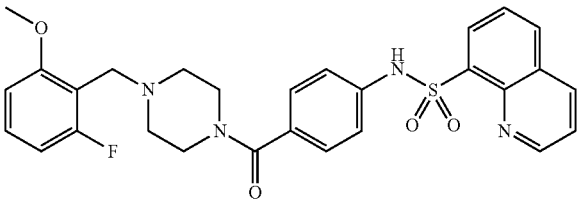
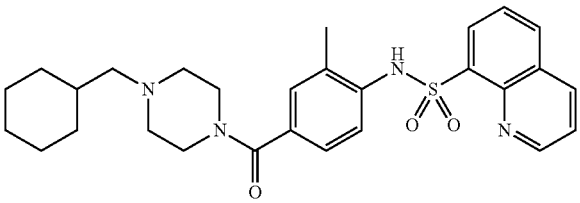
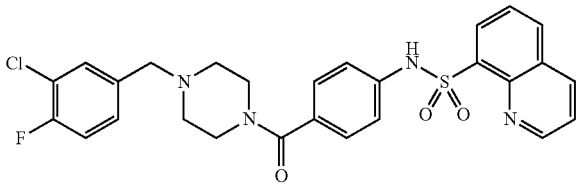
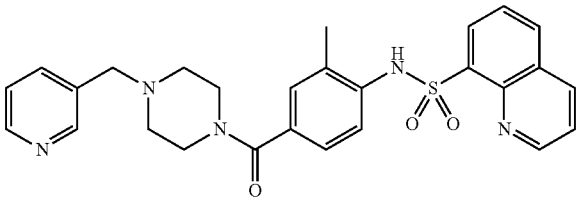

-continued
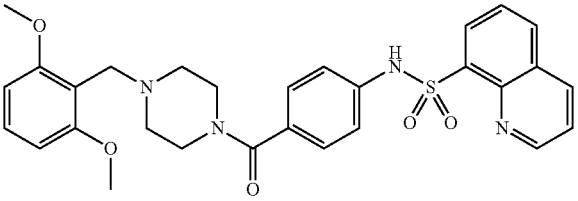
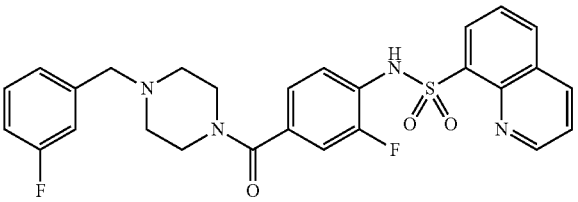
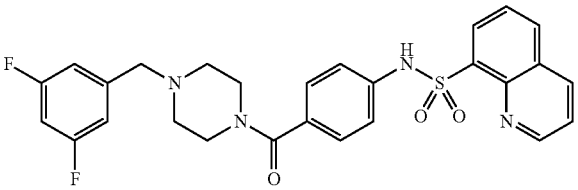
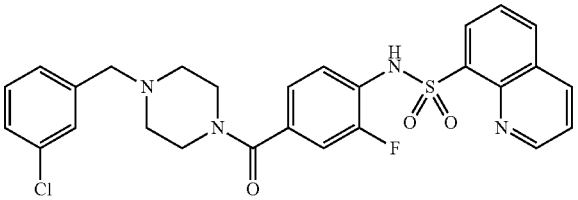
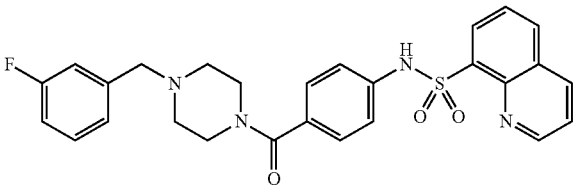
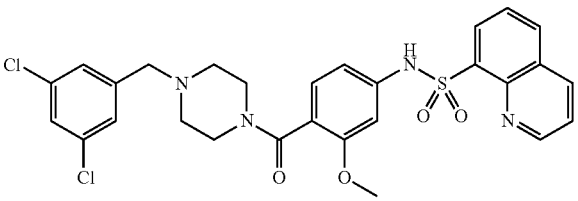
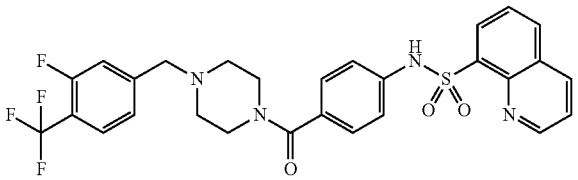
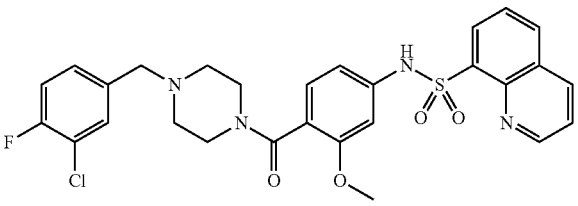
-continued
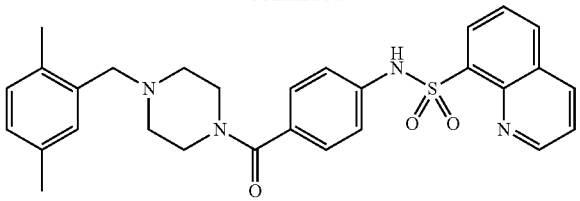
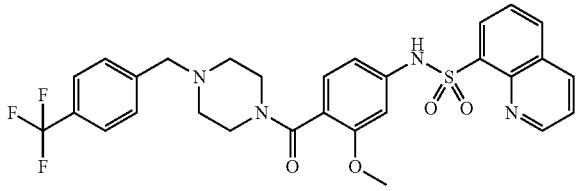
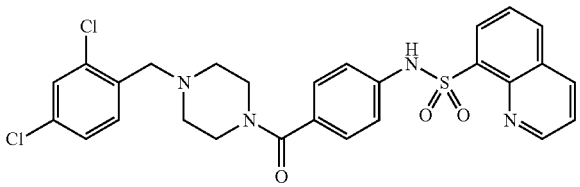
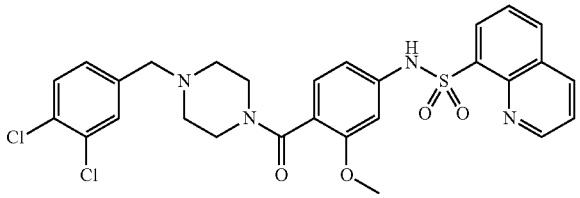
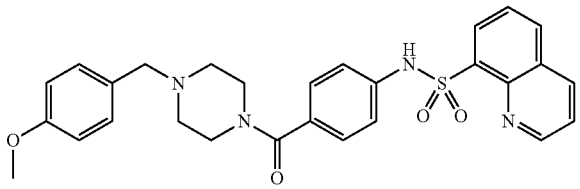
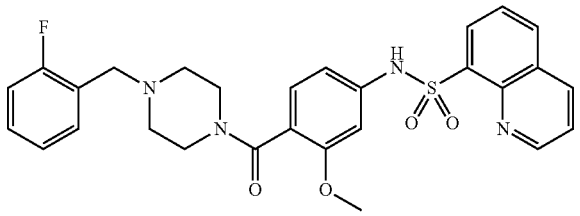
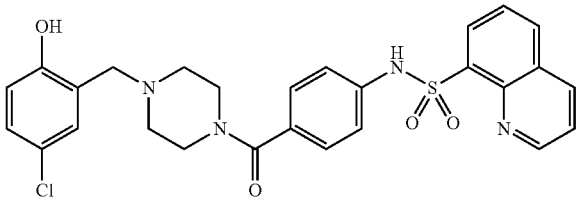
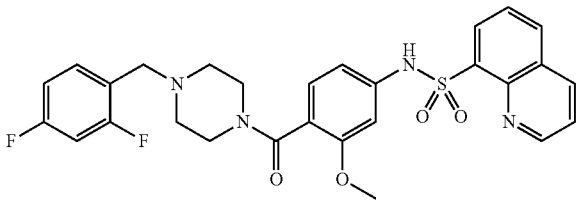

-continued
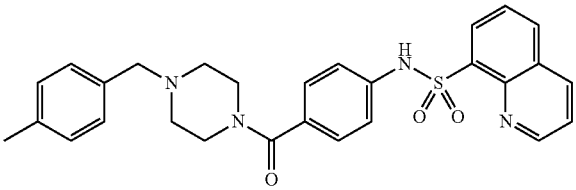
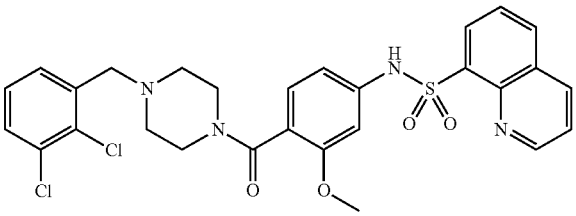
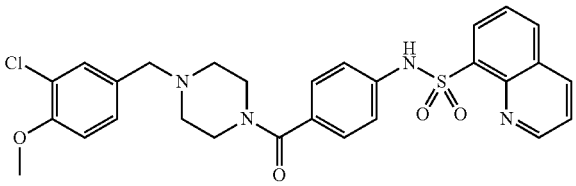
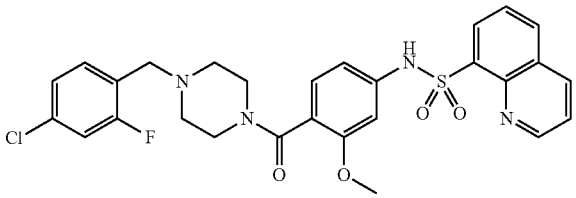
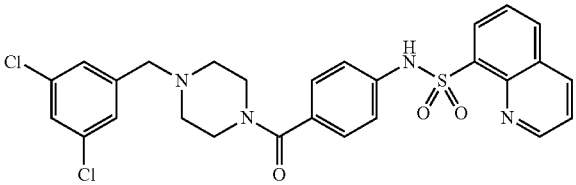
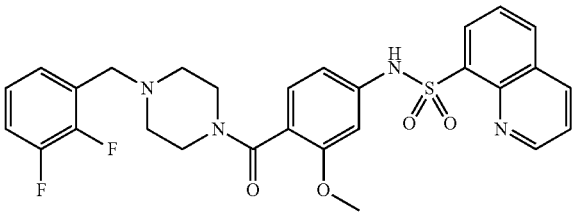
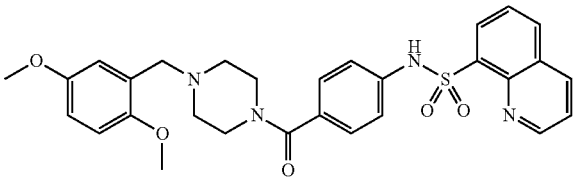
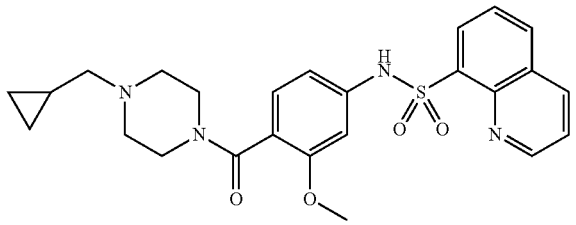
-continued
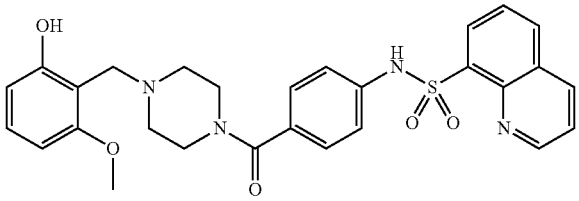
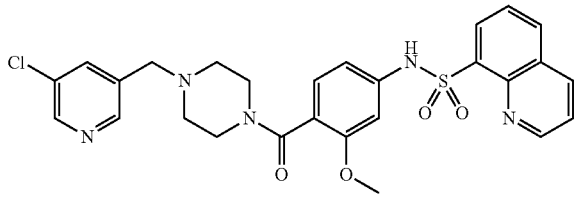
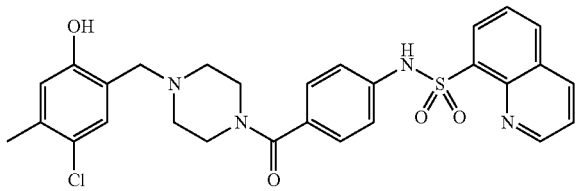
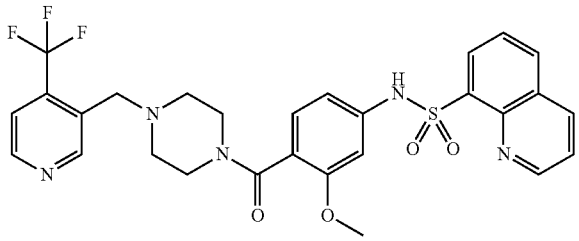
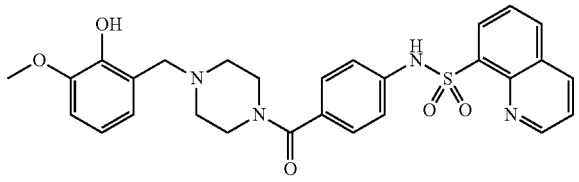
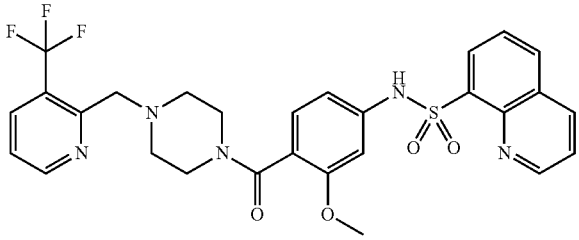
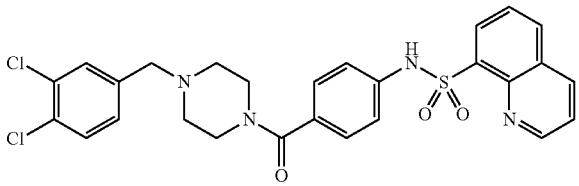
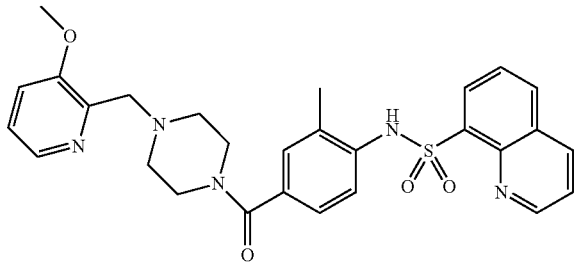

-continued
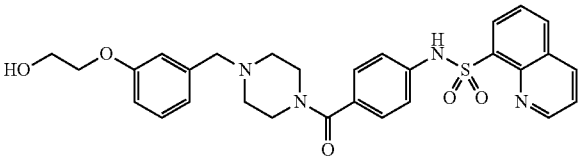
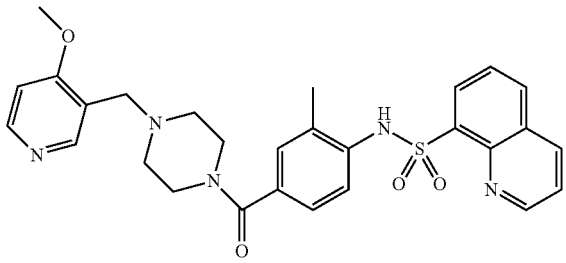
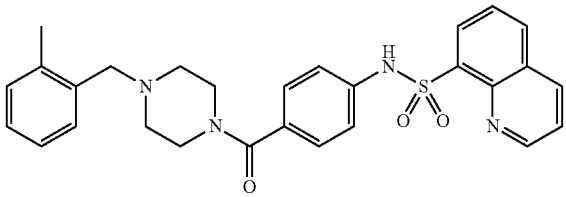
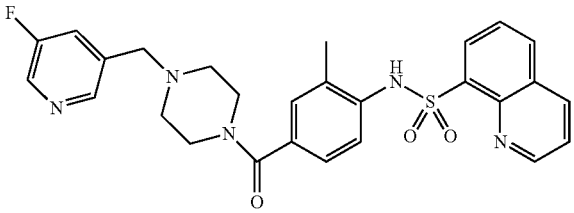
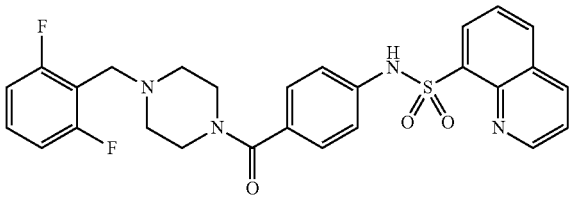
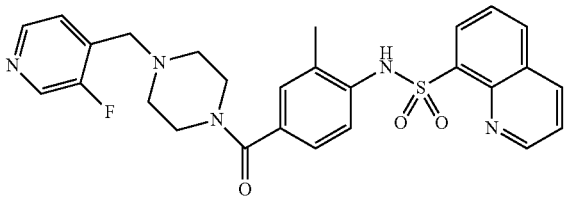
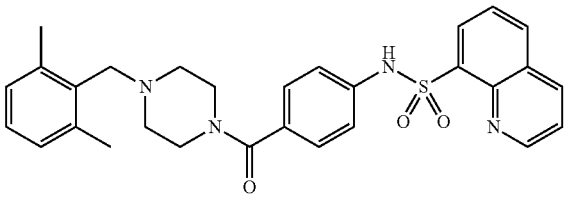
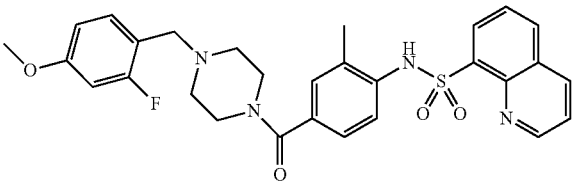
-continued
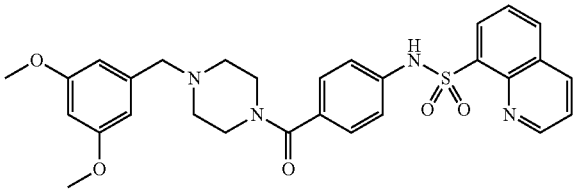
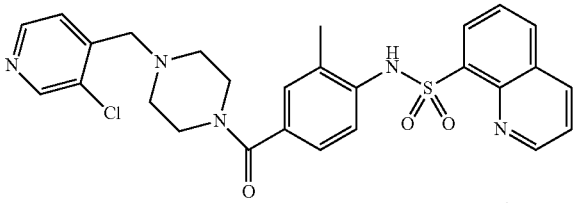
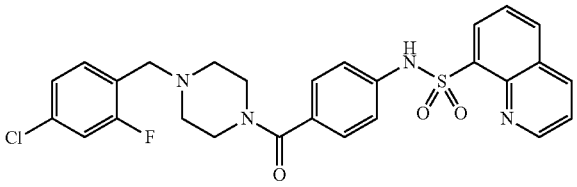
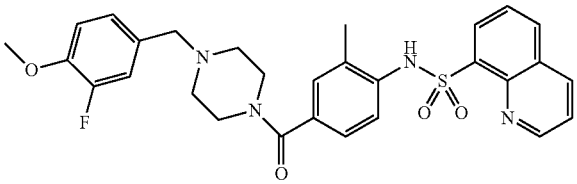
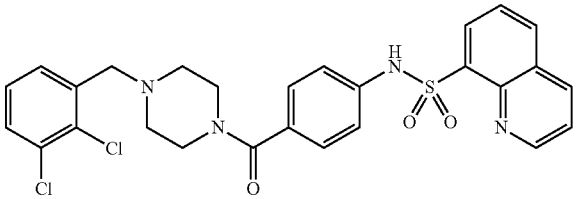
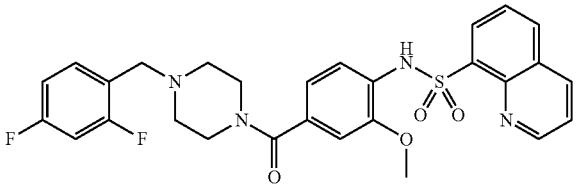
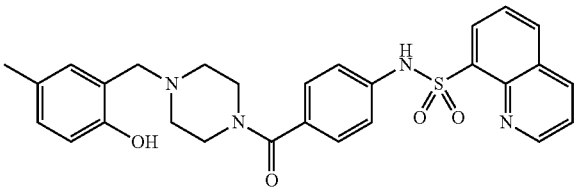
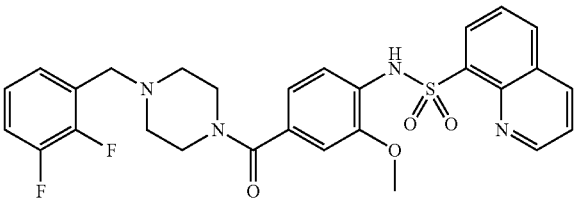
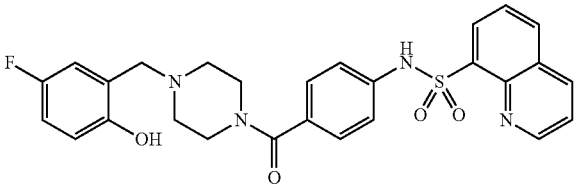

-continued
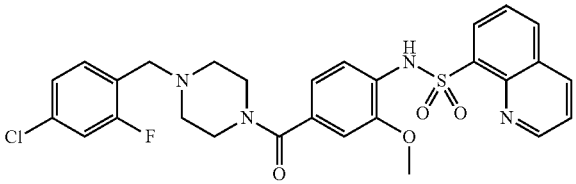
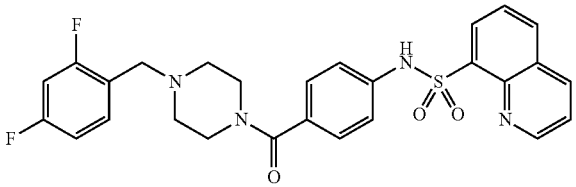
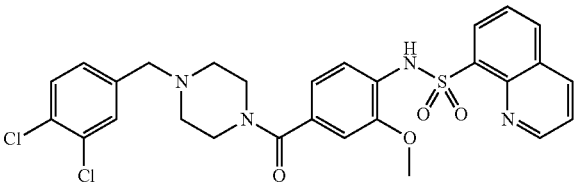
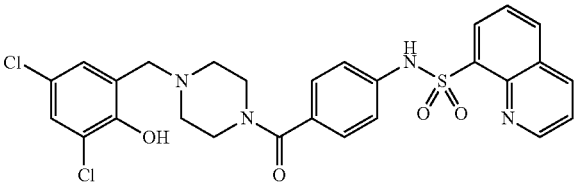
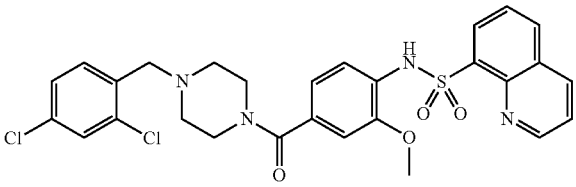
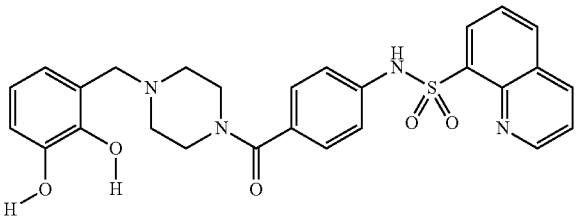
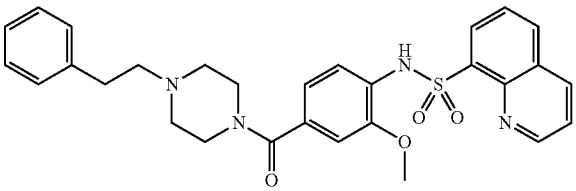
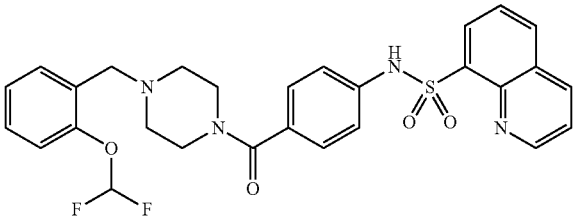
-continued
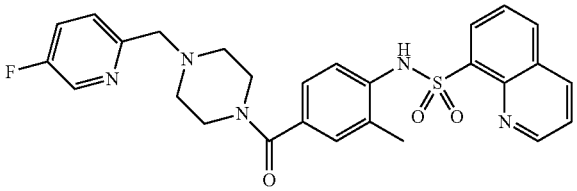
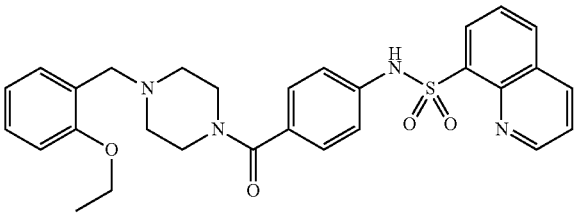
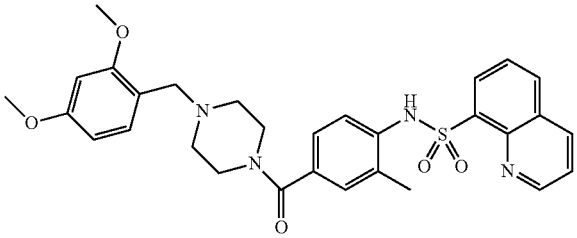
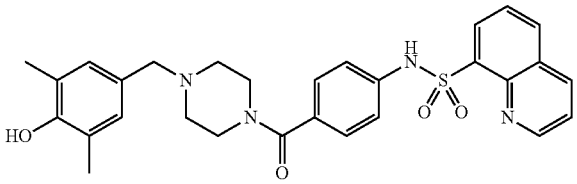
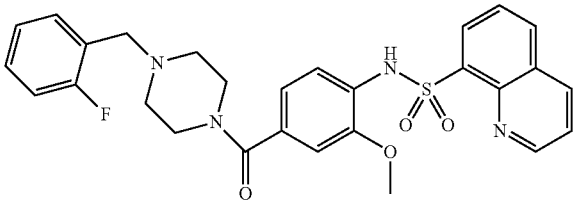
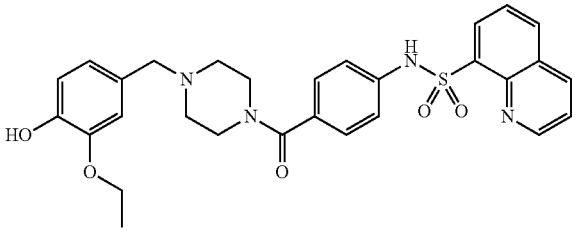
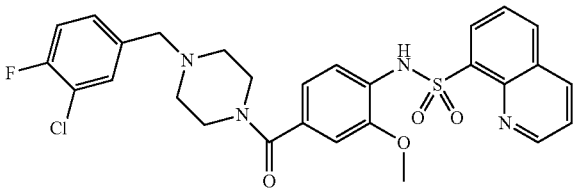
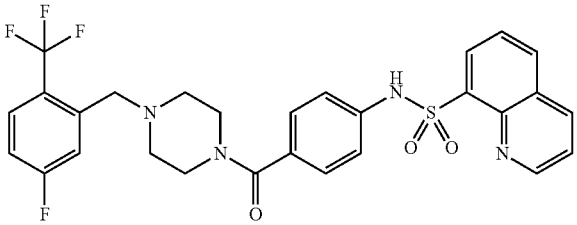

-continued
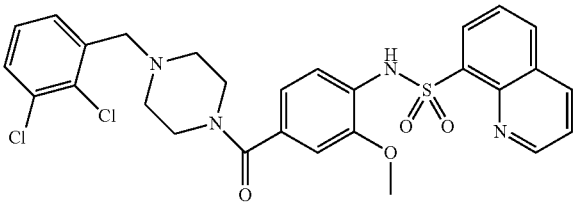
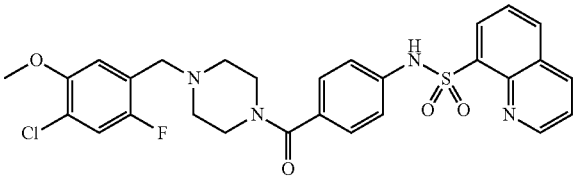
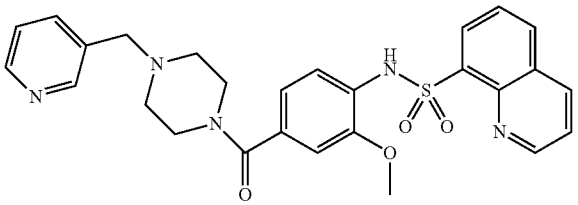
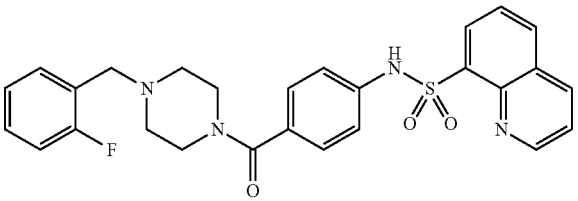
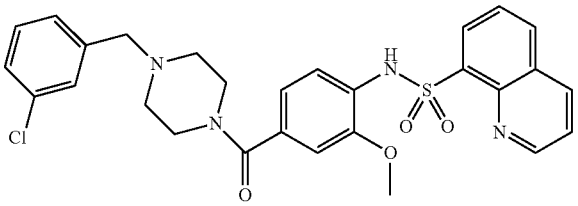
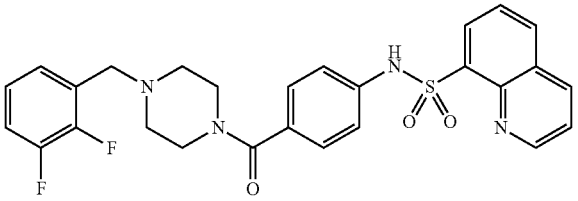
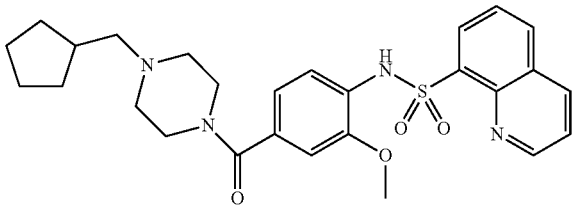
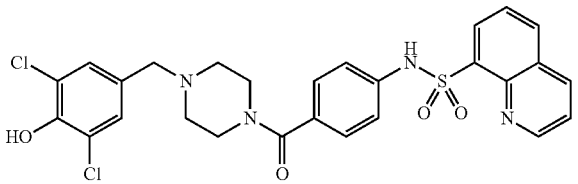
-continued
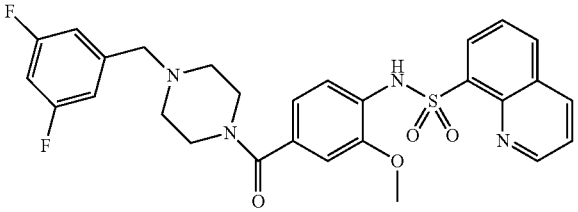
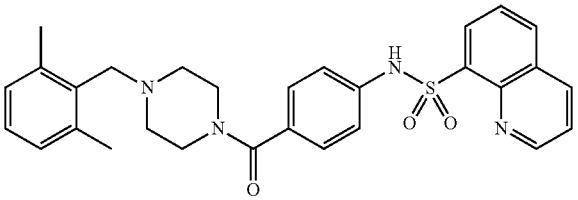
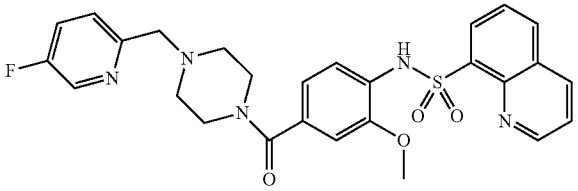
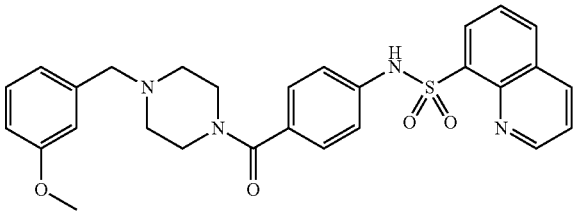
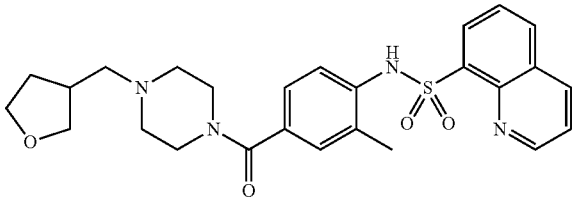
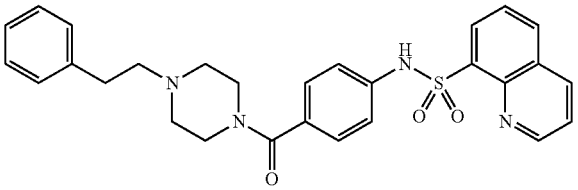
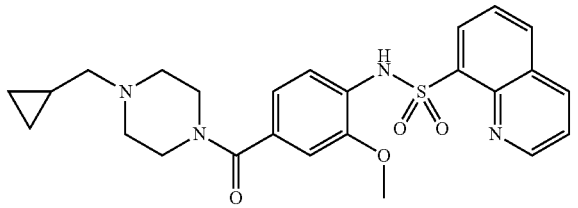
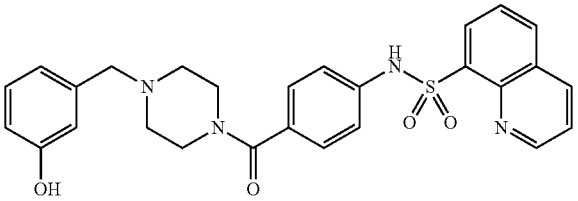

-continued
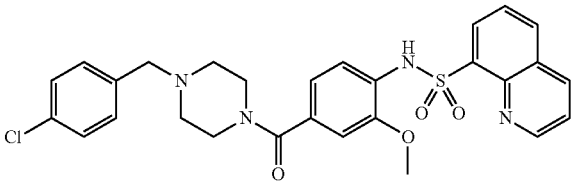
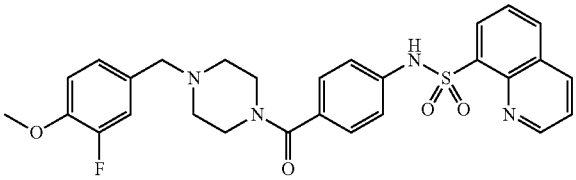
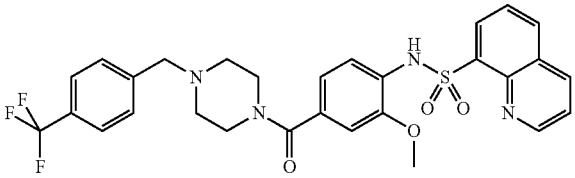
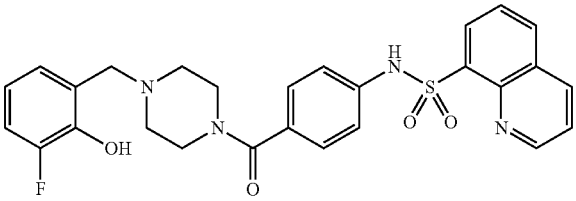
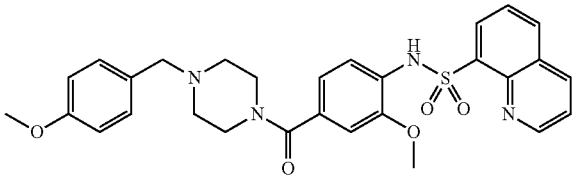
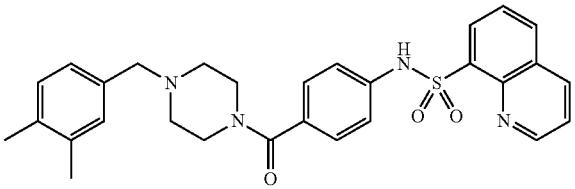
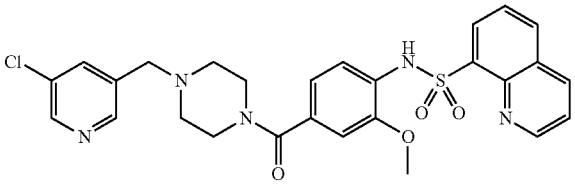
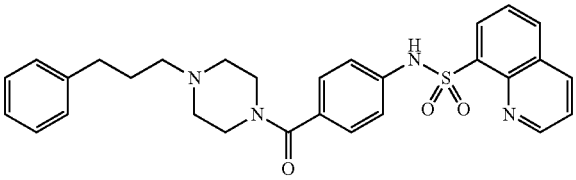
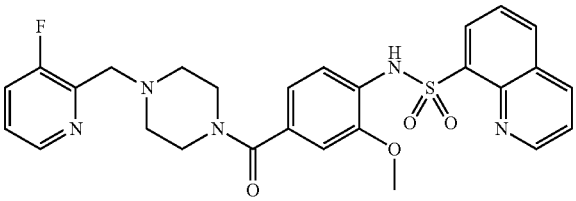
-continued
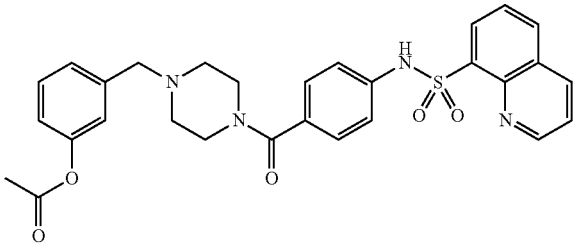
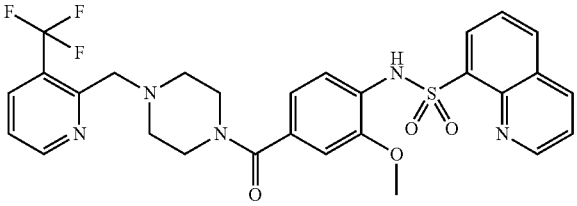
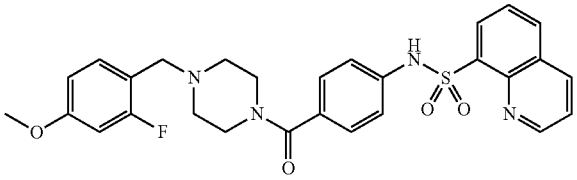
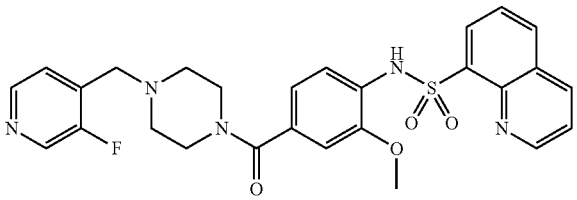
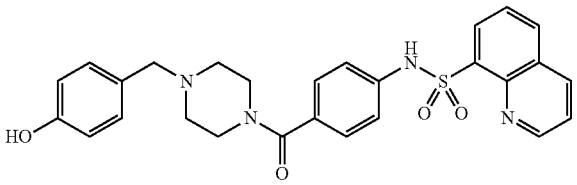
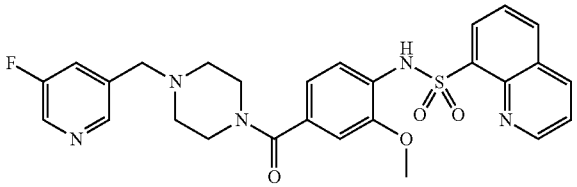
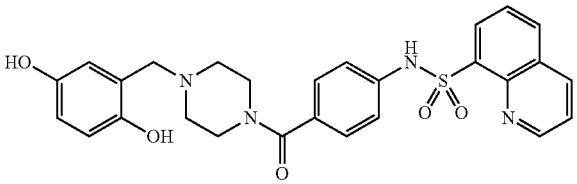
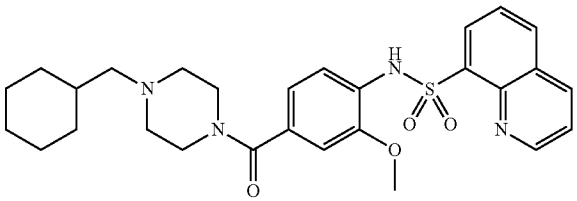

-continued
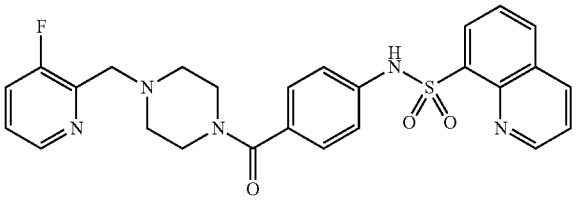
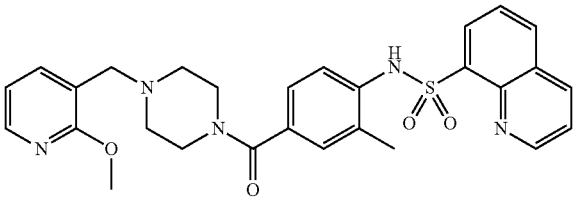
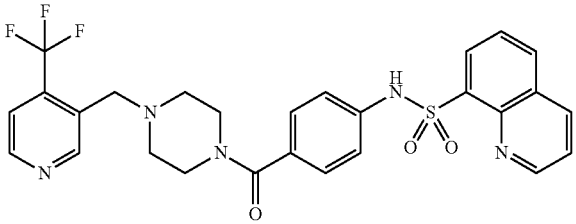
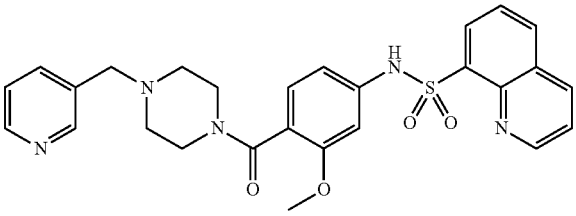
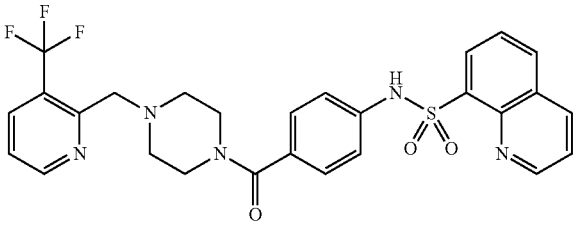
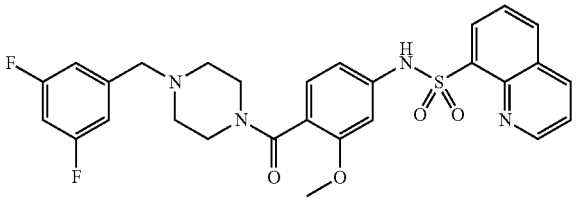
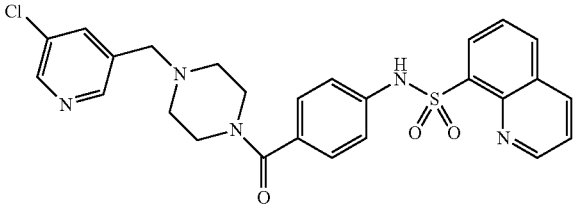
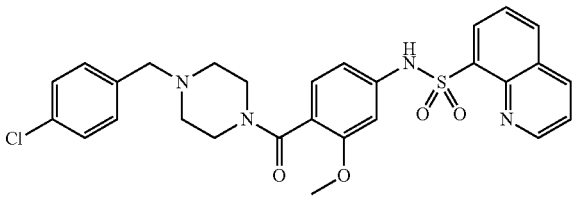
-continued
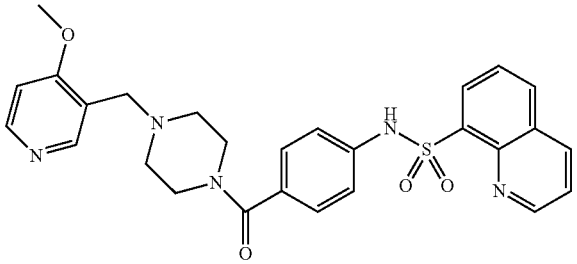
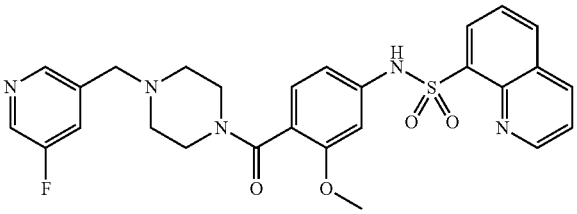
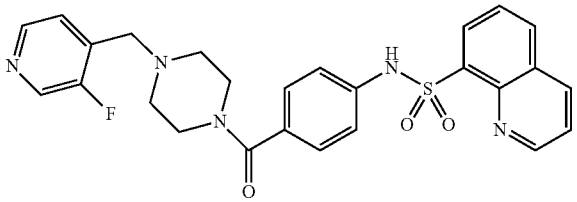
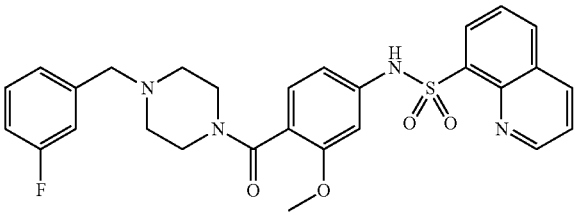
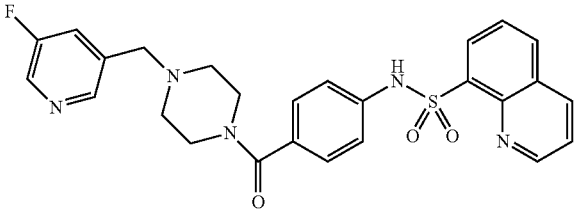
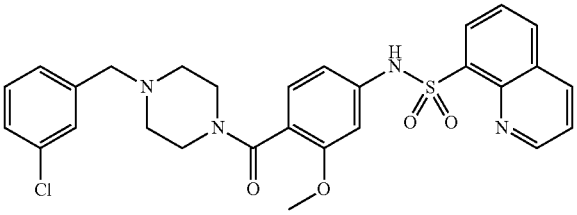
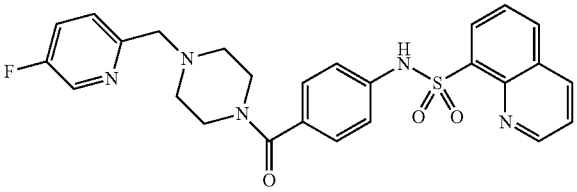
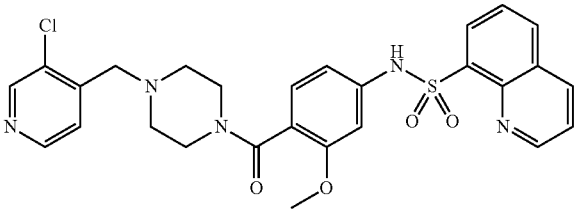

-continued
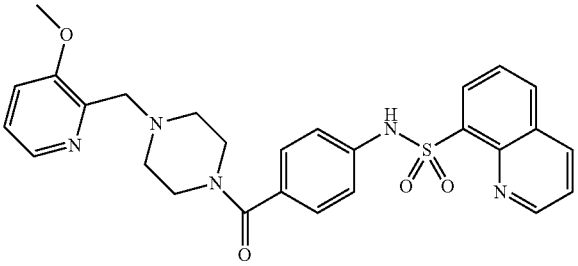
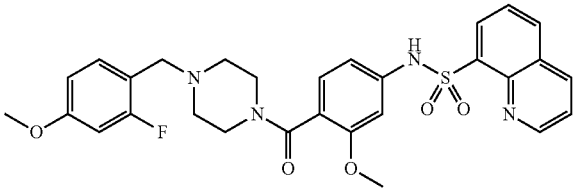
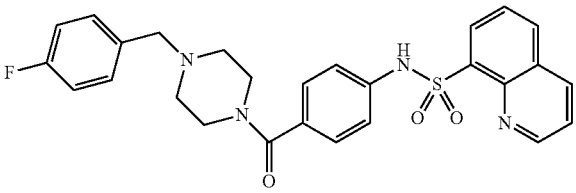
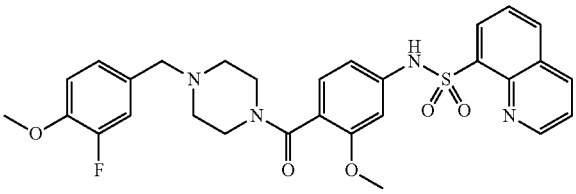
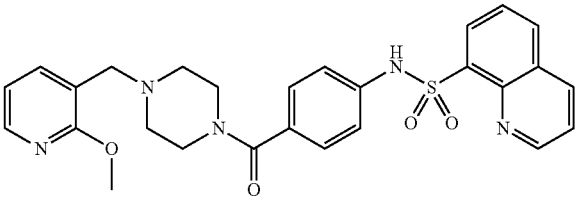
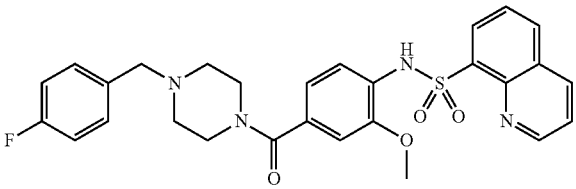
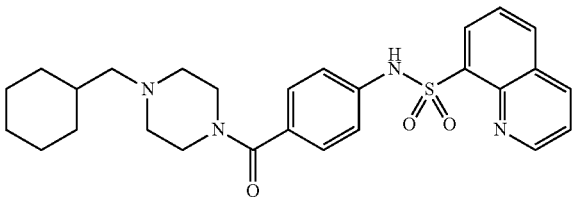
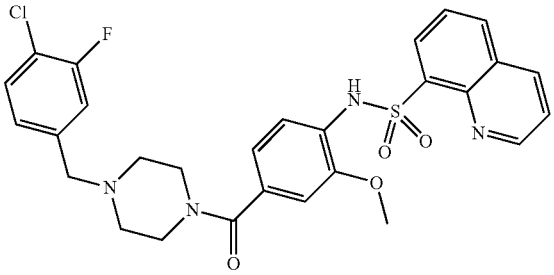
-continued
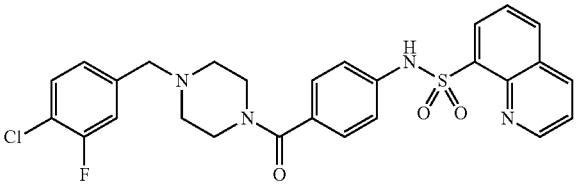
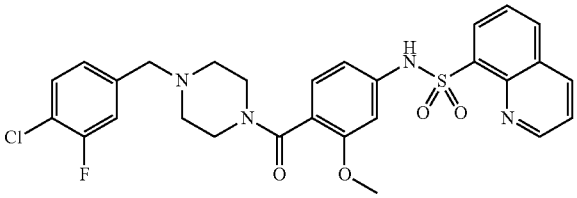
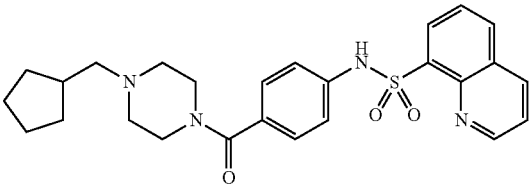
and
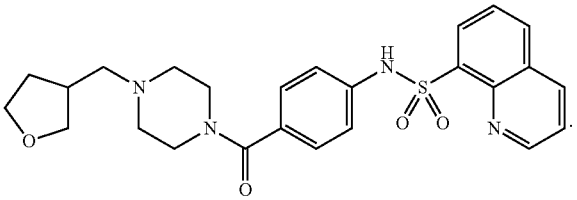
26. The compoud of claim 1 selected from:
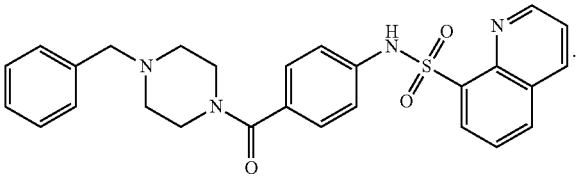
27. The compound of claim 1 selected from:
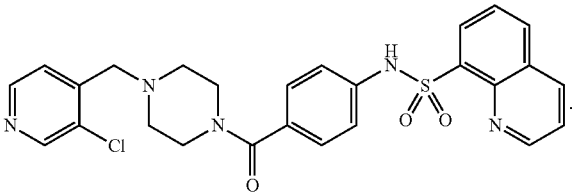
28. The compound of claim 1 selected from:
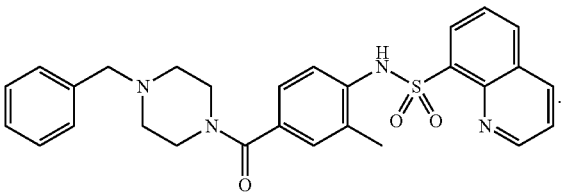

29. The compound of claim 1 selected from:

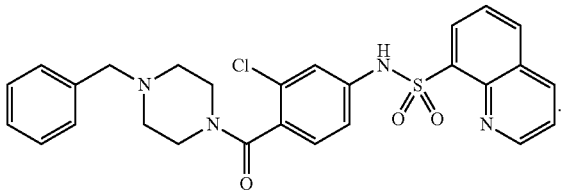

30. The compound of claim 1 selected from:

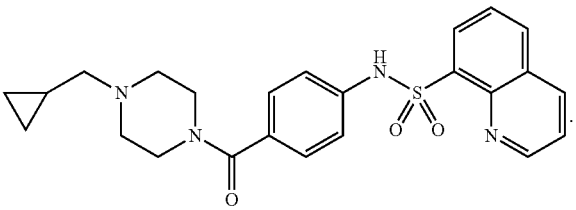

31. The compound of claim 1 selected from:

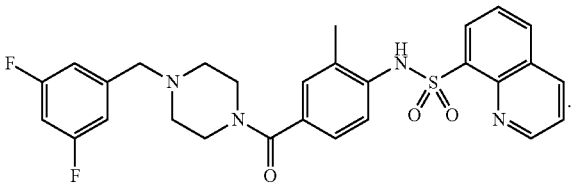

32. The compound of claim 1 selected from:

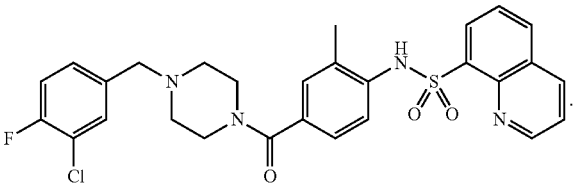

33. The compound of claim 1 selected from:

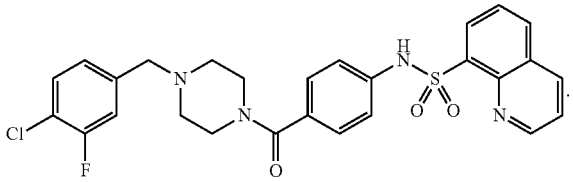

34. The compound of claim 1 selected from:

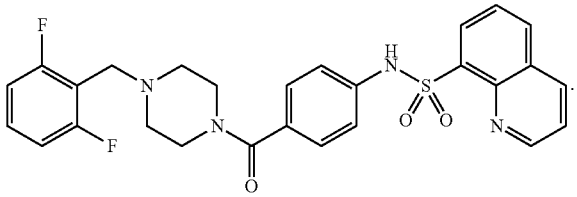

35. The compound of claim 1 selected from:

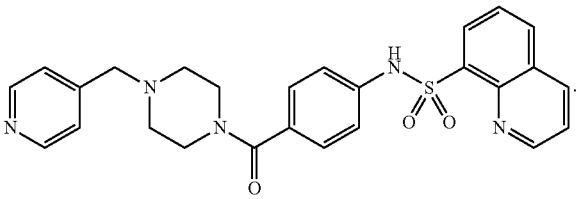

36. The compound of claim 1 selected from:

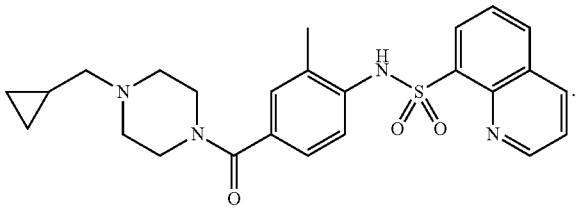

37. The compound of claim 1 selected from:

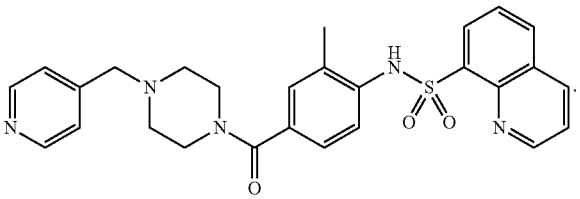

38. The compound of claim 1 selected from:

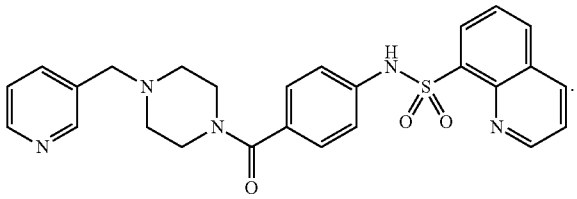

39. The compound of claim 1 selected from:

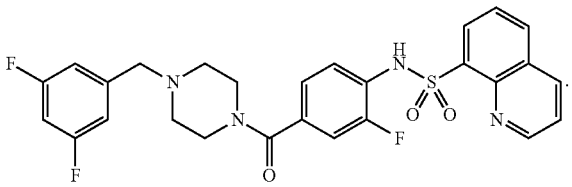

40. The compound of claim 1 selected from:

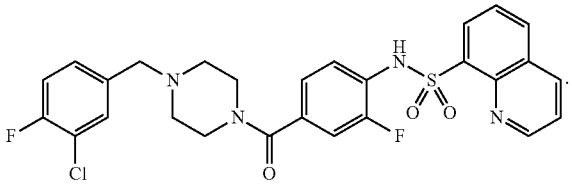

41. The compound of claim 1 selected from:

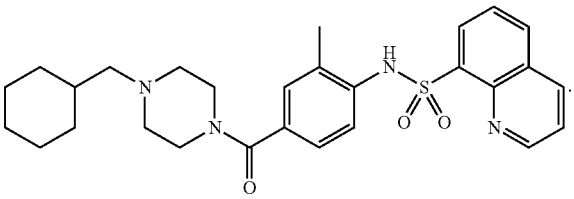

42. The compound of claim 1 selected from:

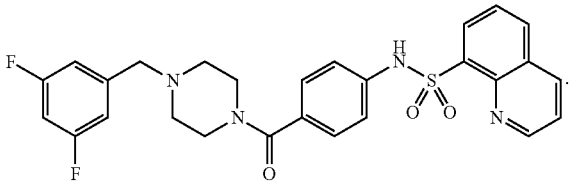

43. The compound of claim 1 selected from:

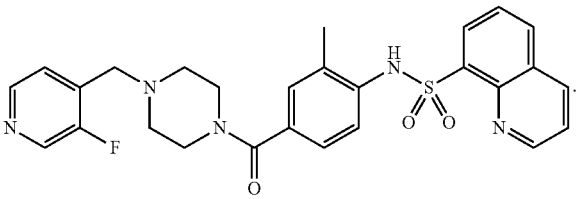

44. The compound of claim 1 selected from:

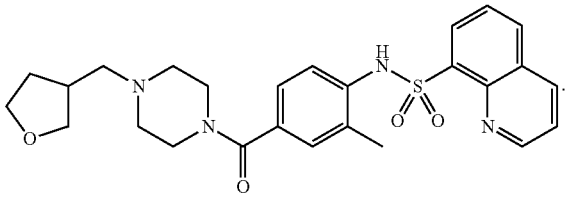

45. The compound of claim 1 selected from:

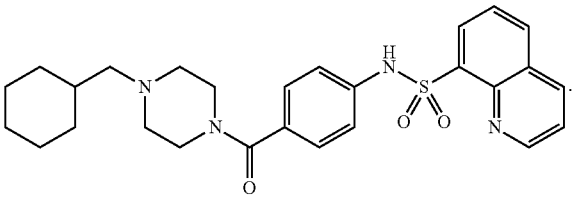

46. The compound of claim 1 selected from:

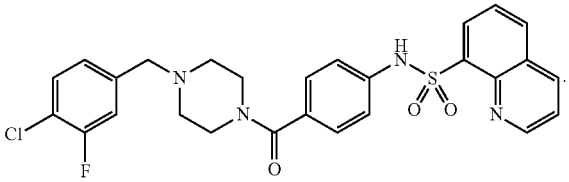

47. The compound of claim 1 selected from:

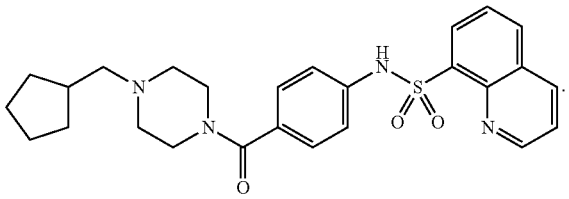

48. The compound of claim 1 selected from:

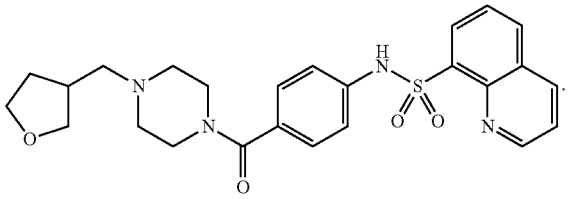

49. A compound selected from one of the following:
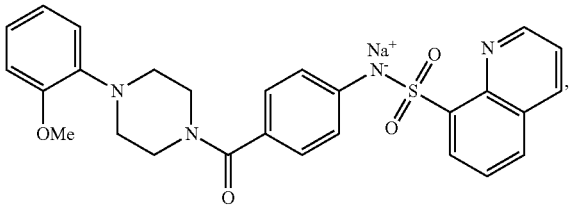
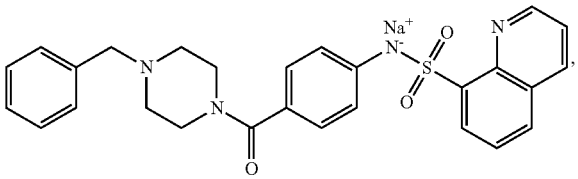
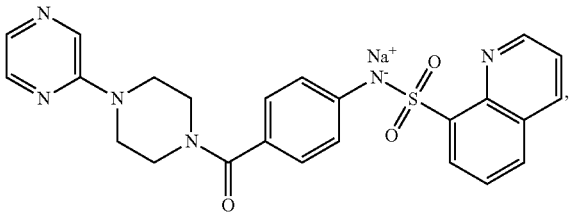
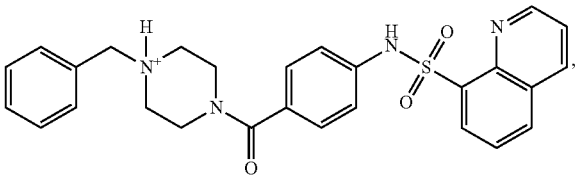
-continued
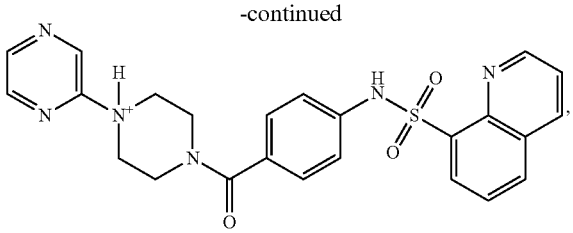
and
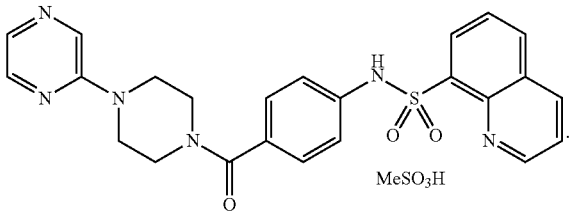
50. A pharmaceutical composition comprising a compound of any one of claims 2 to 21, or a pharmaceutically acceptable salt thereof, or a compound of claim 49.
51. A pharmaceutical composition comprising a compound [of claim 24] *selected from the following:*
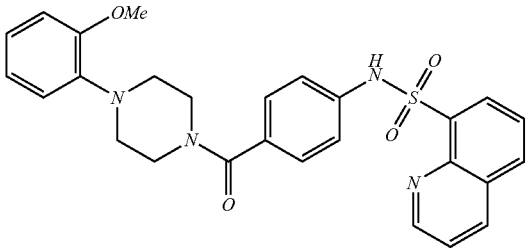
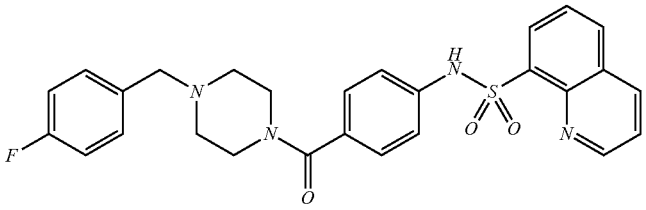
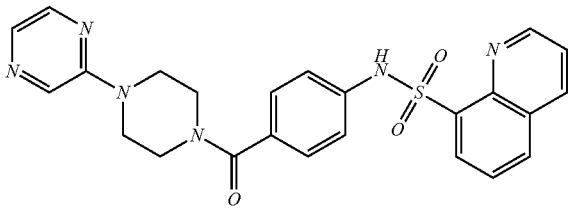
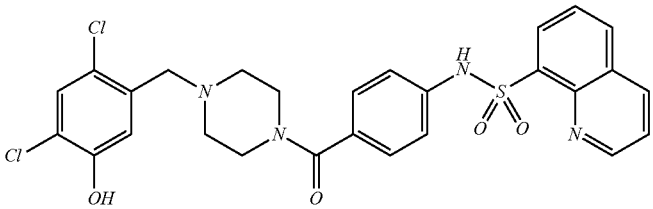

*-continued*
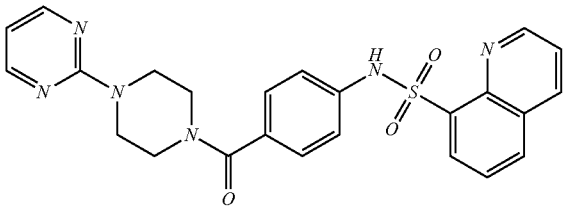
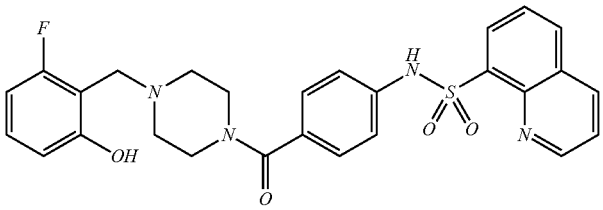
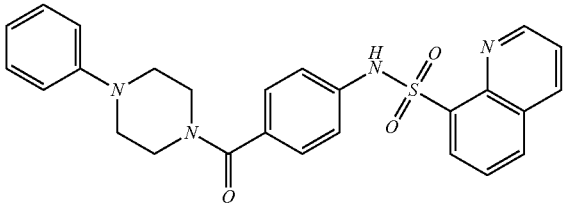
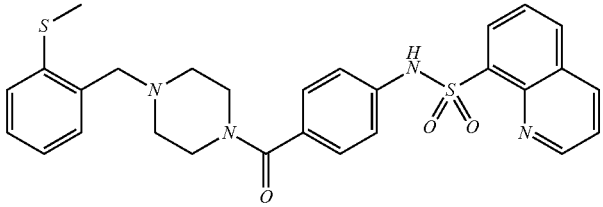
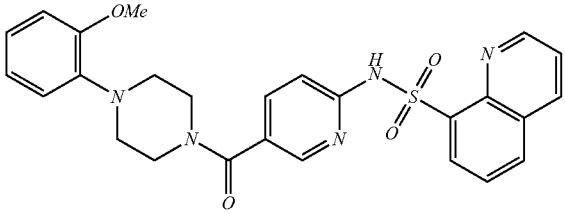
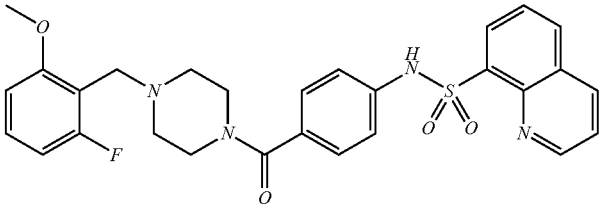
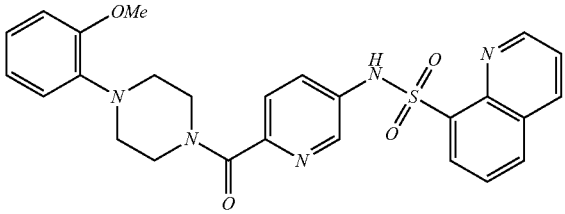
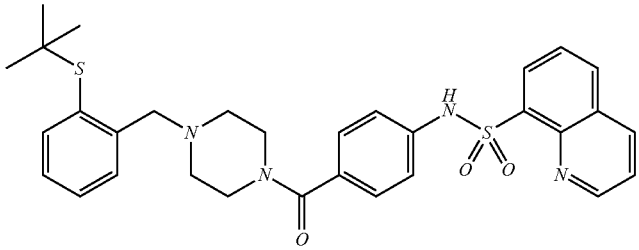
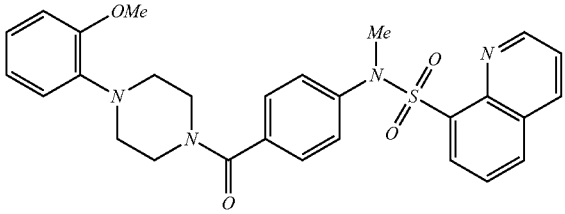
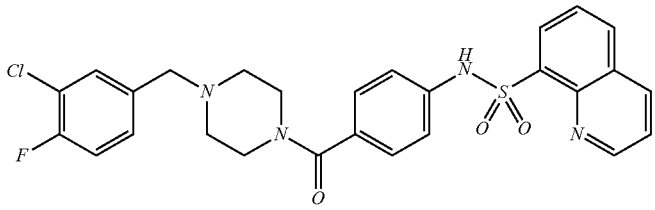

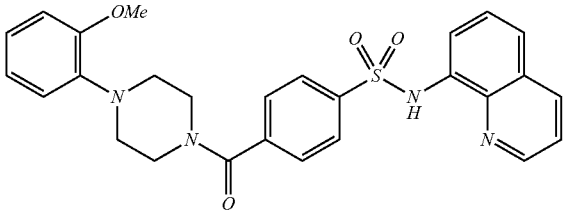
-continued
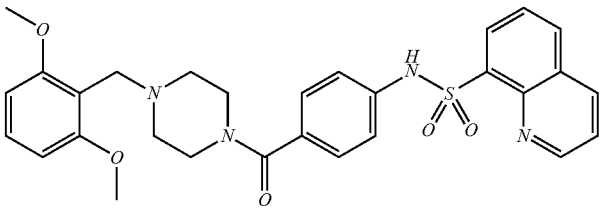
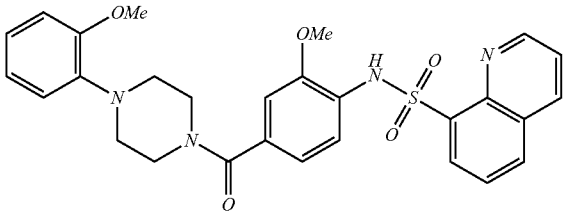
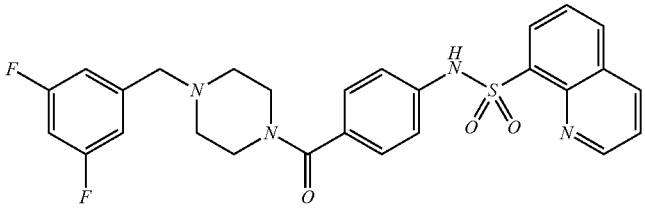
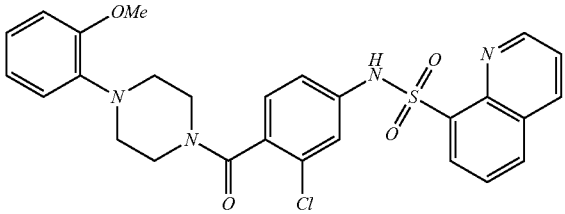
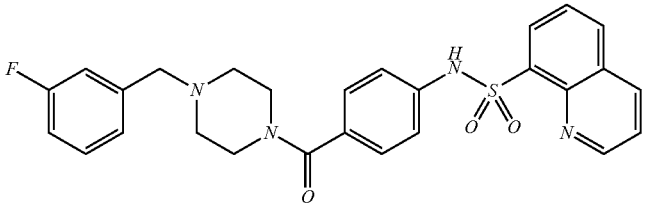
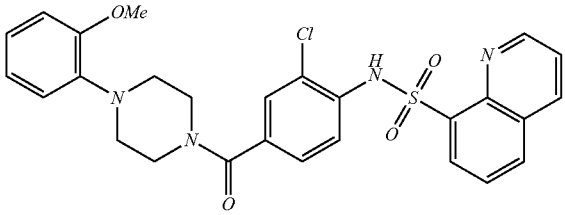
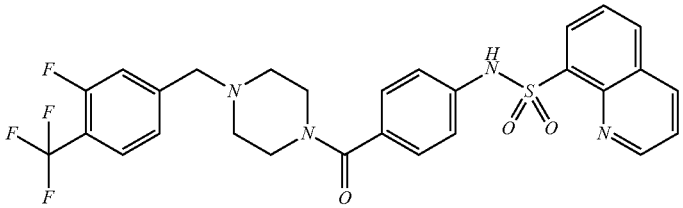
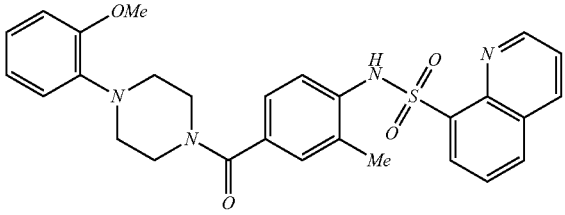

*-continued*
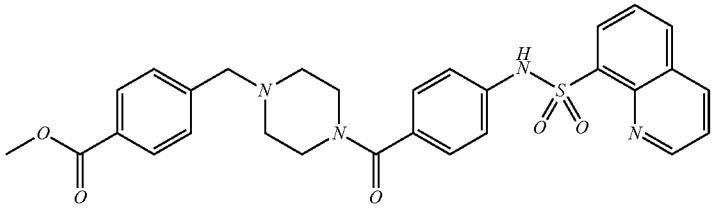
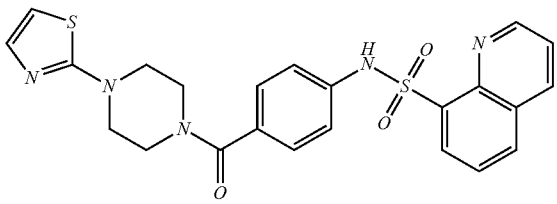
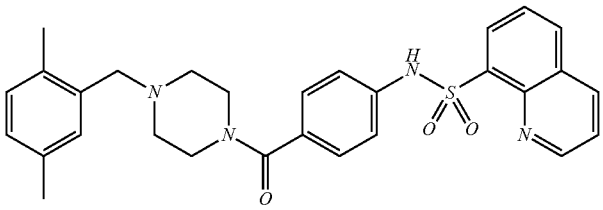
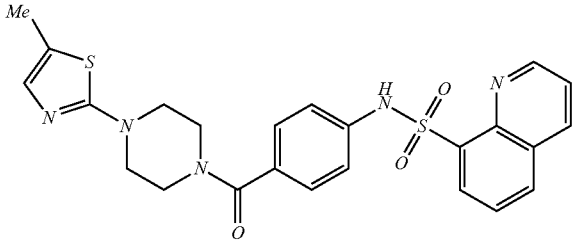
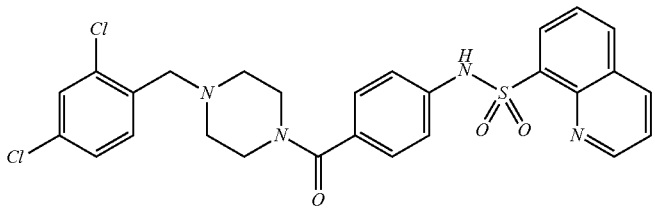
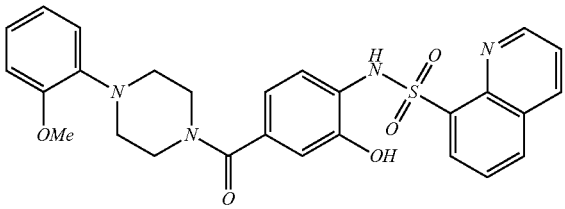
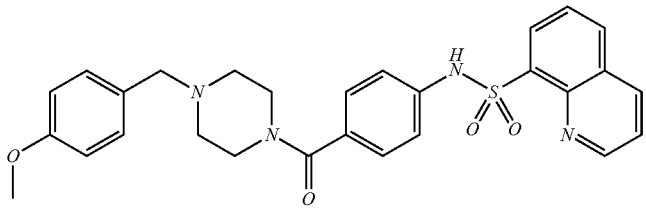
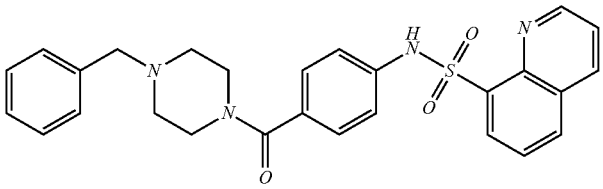
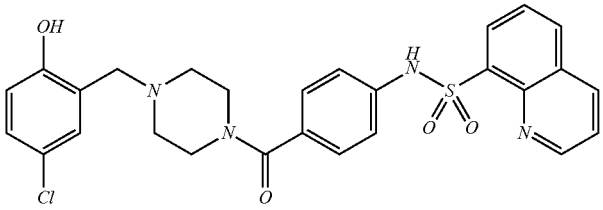

*-continued*
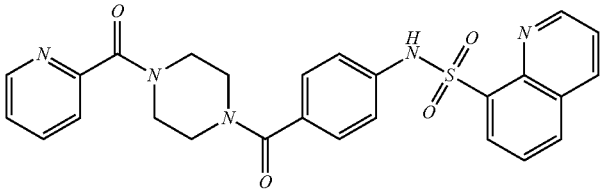
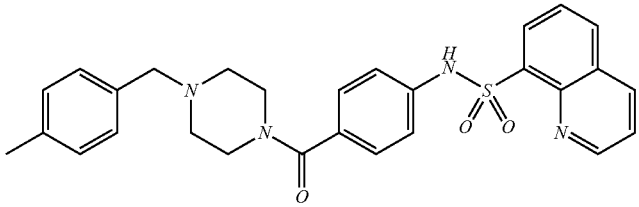
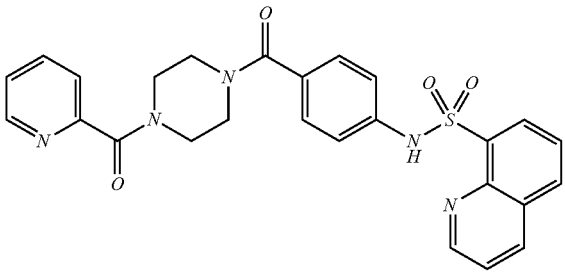
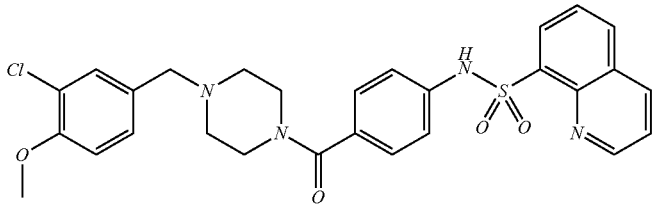
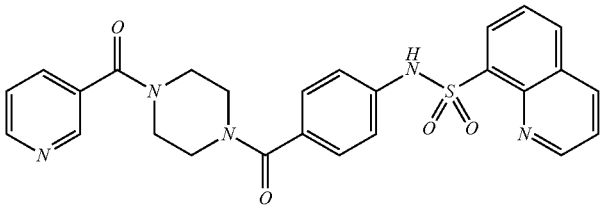
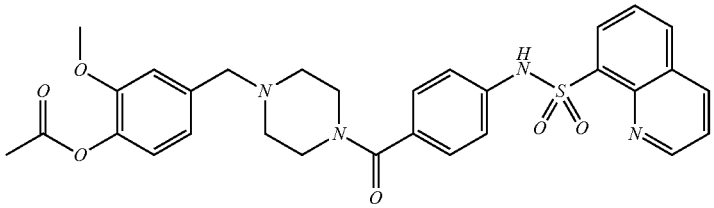
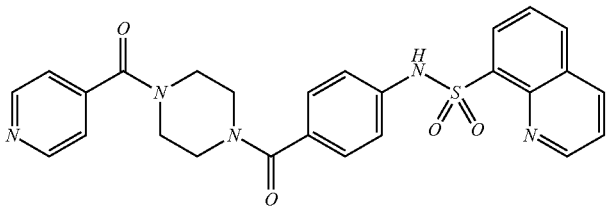

*-continued*
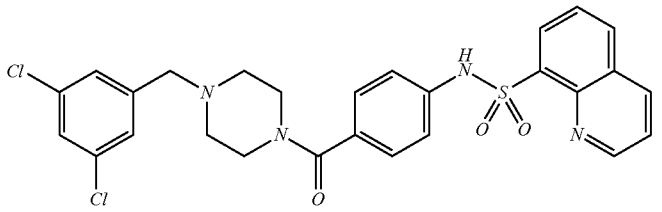
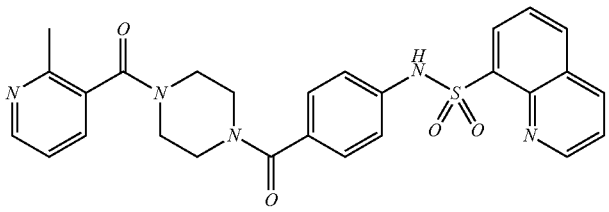
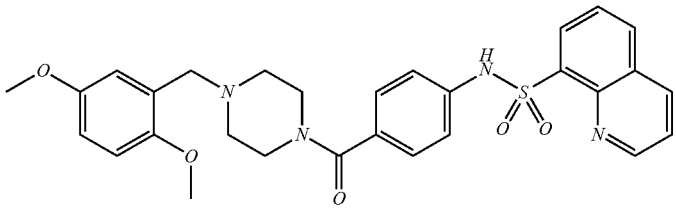
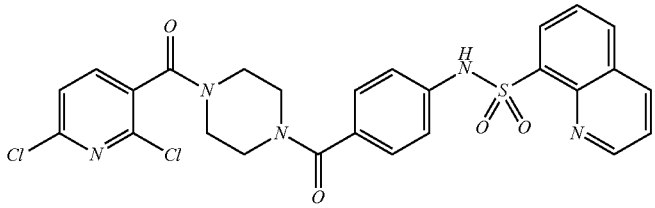
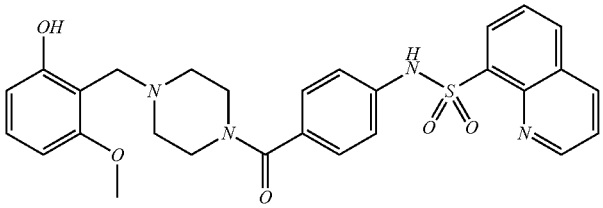
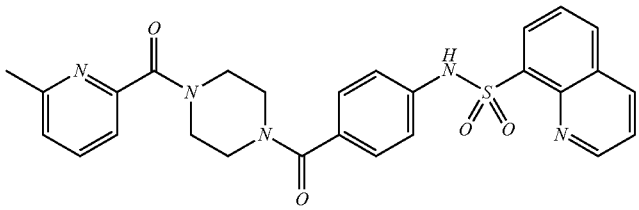
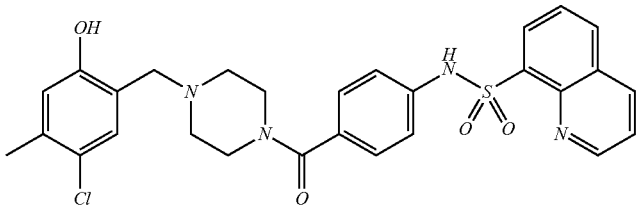
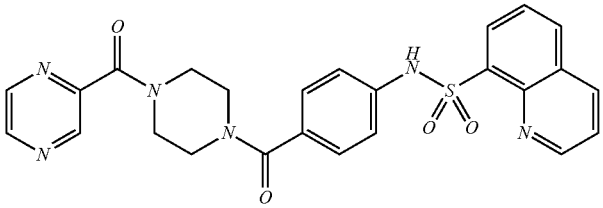

*-continued*
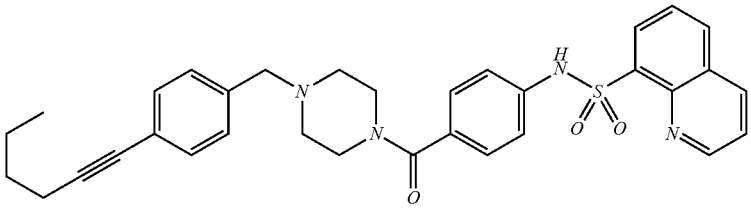
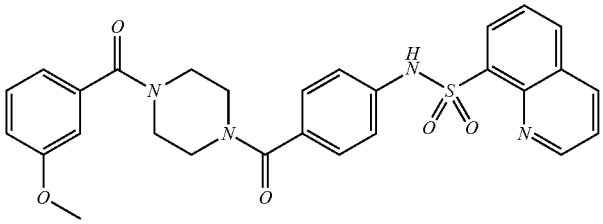
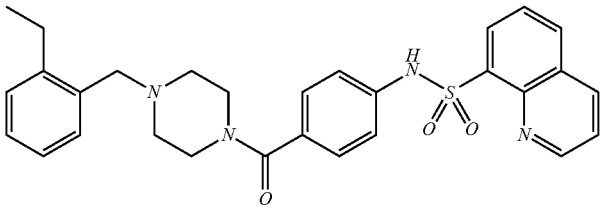
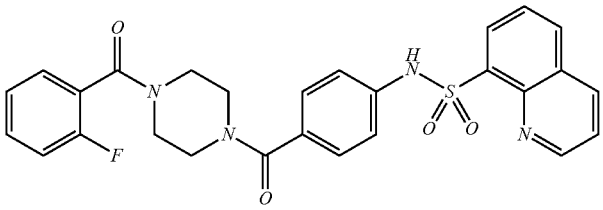
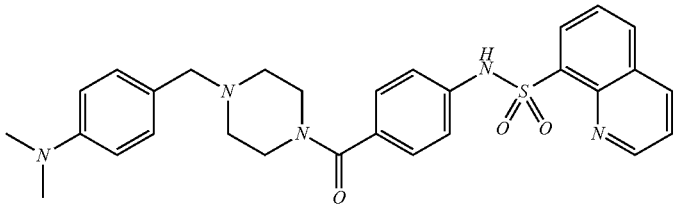
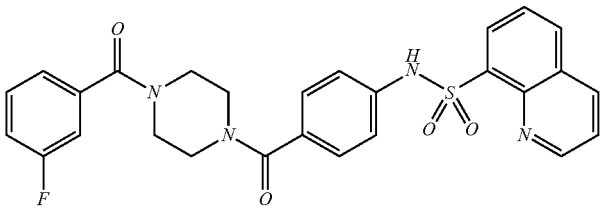
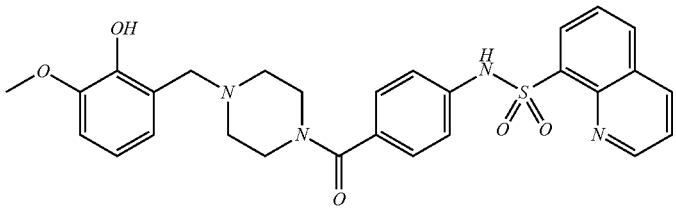
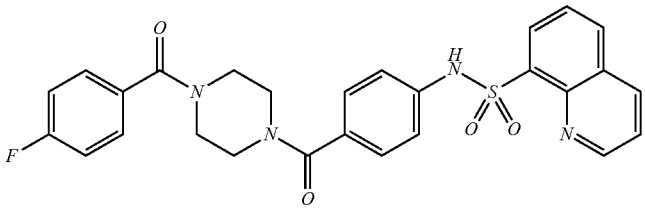

*-continued*
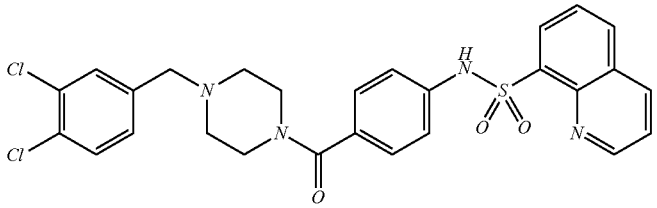
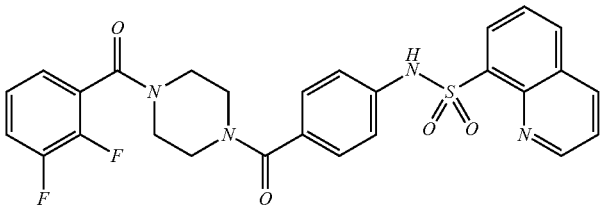
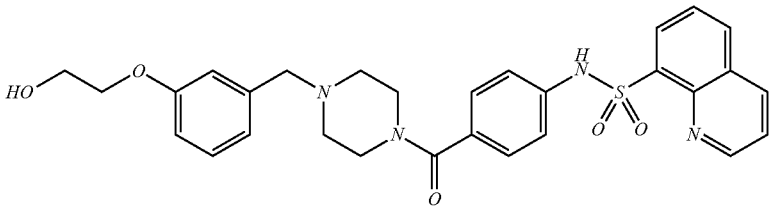
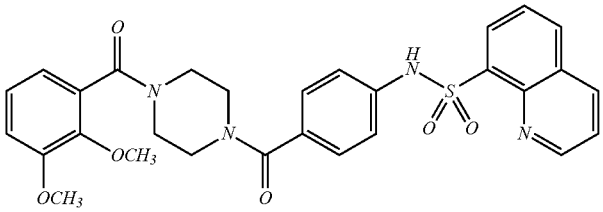
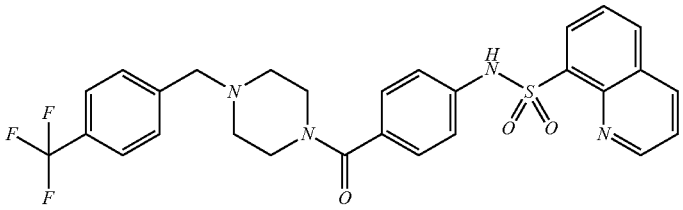
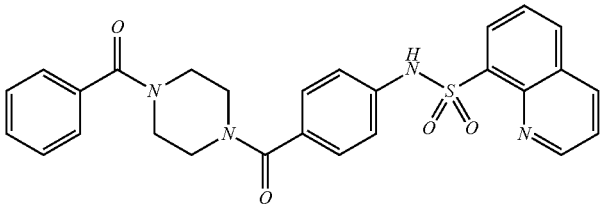
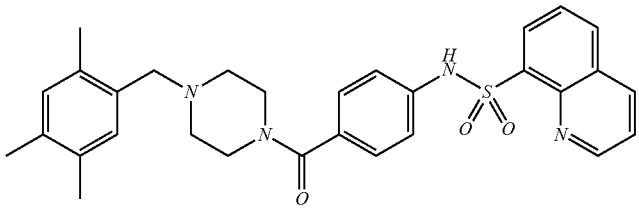
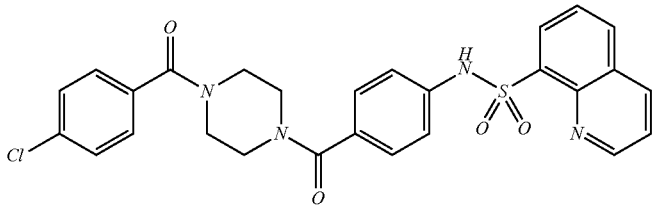

*-continued*
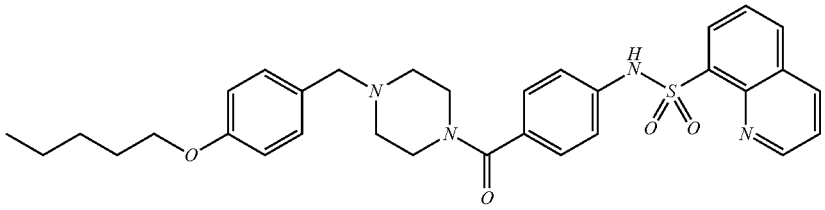
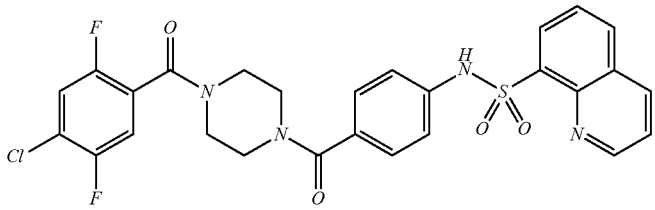
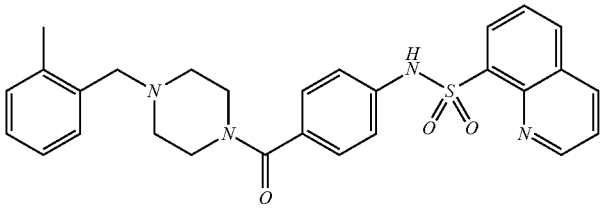
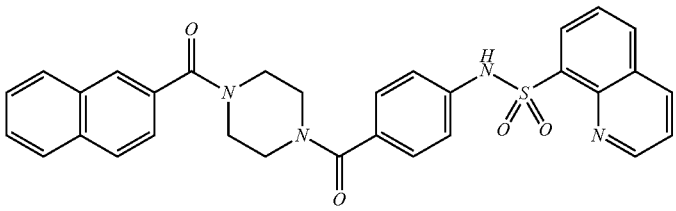
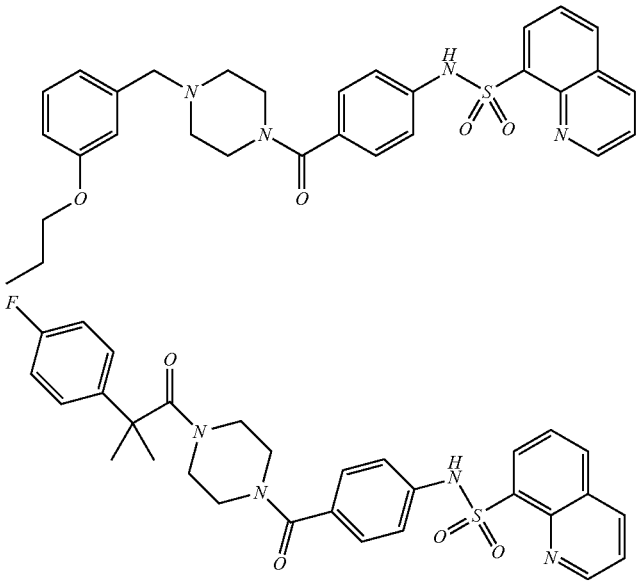
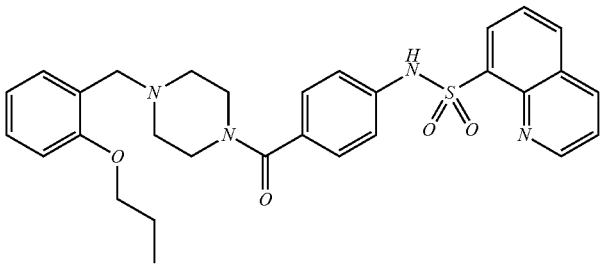

*-continued*
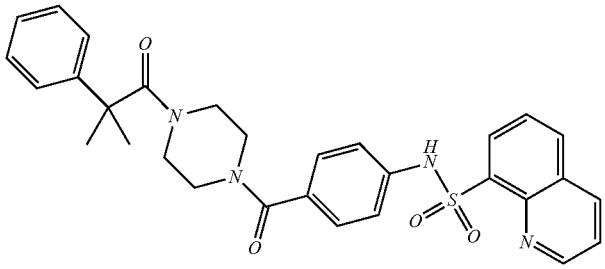
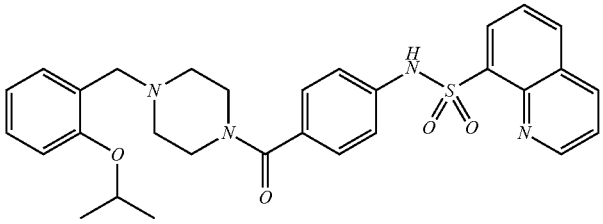
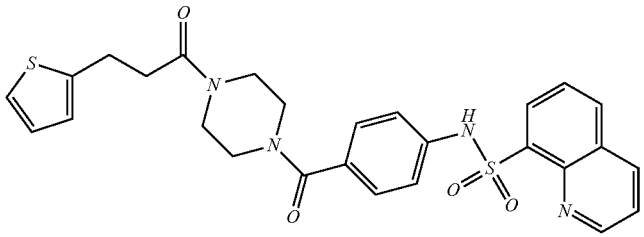
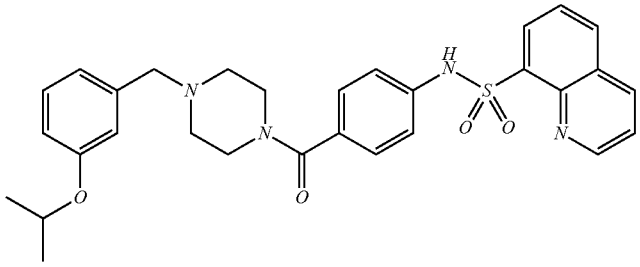
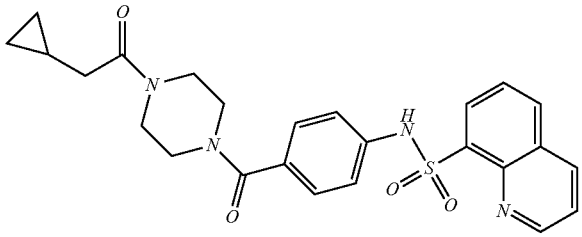
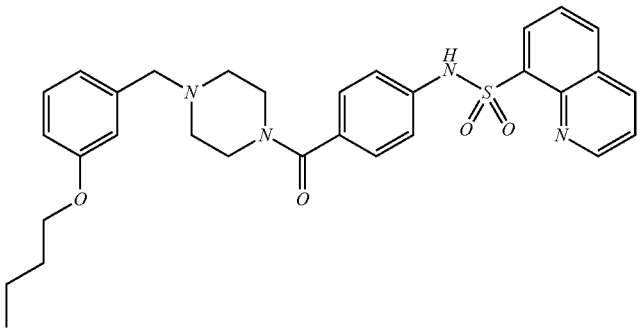

*-continued*
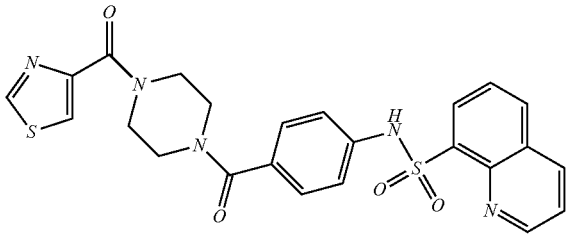
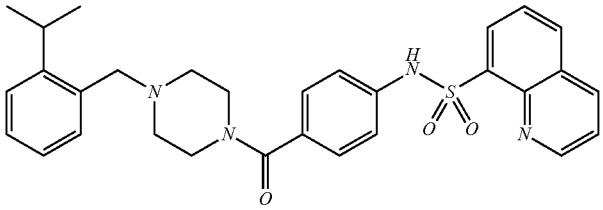
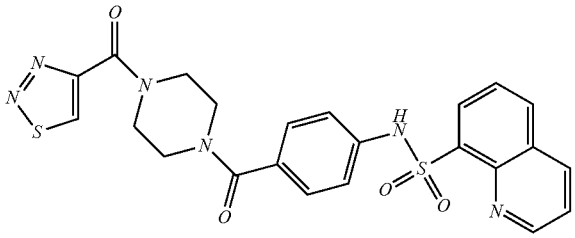
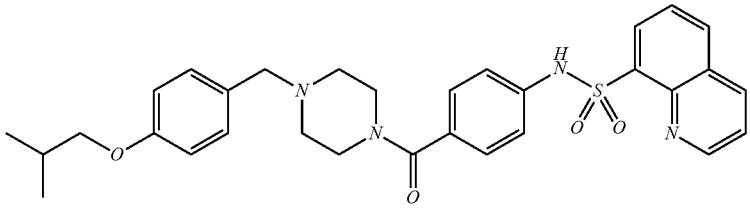
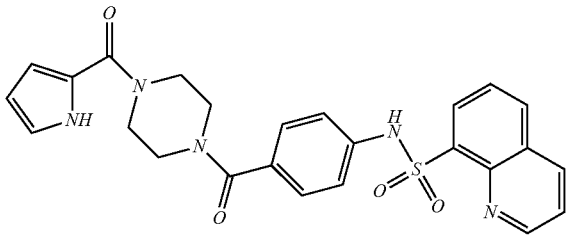
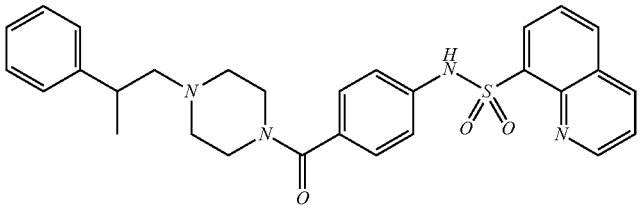
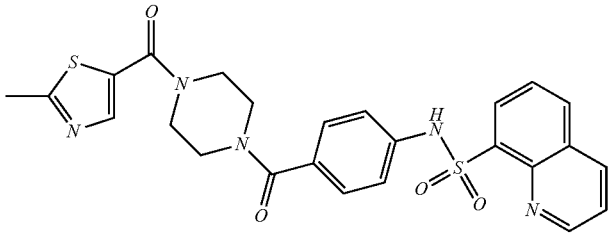
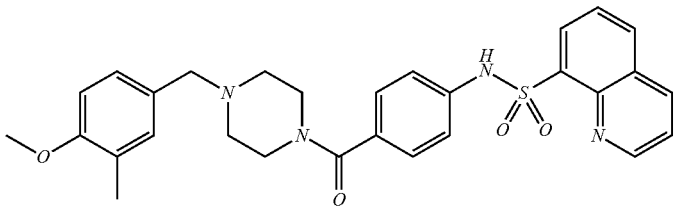

*-continued*
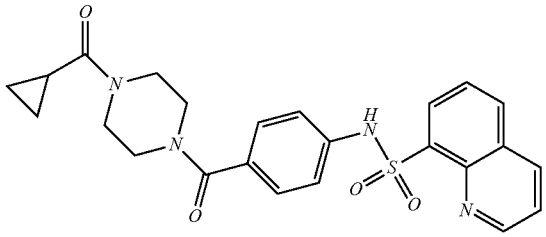
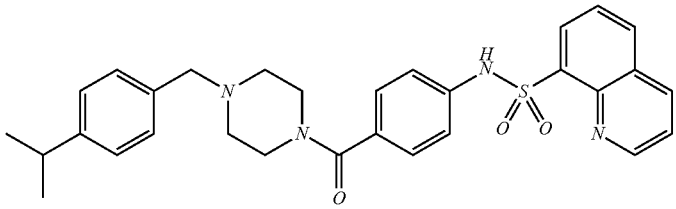
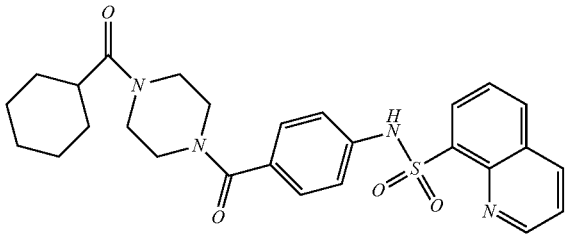
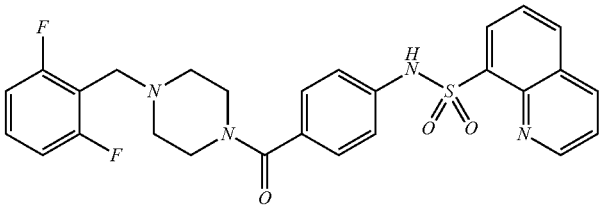
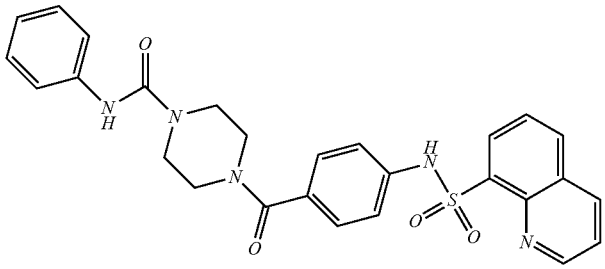
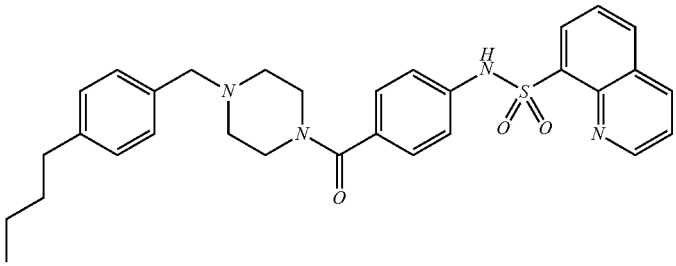
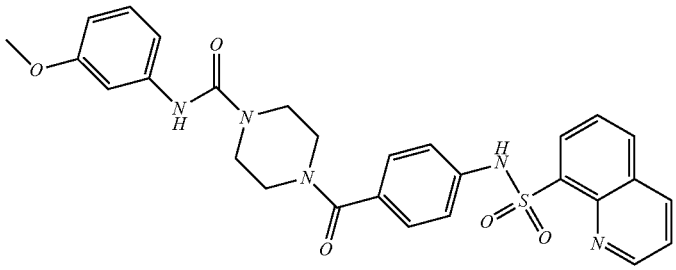
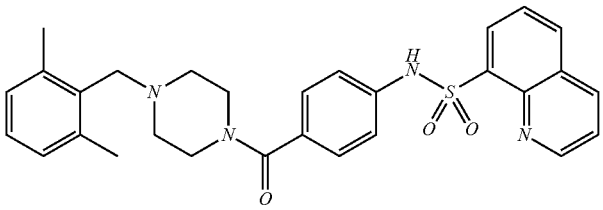

*-continued*
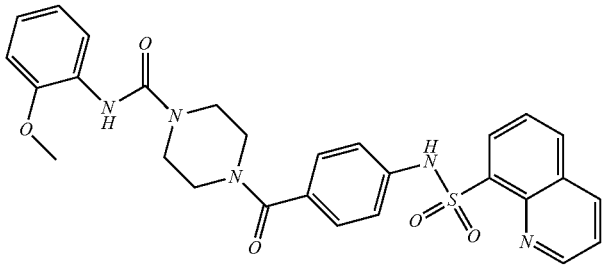
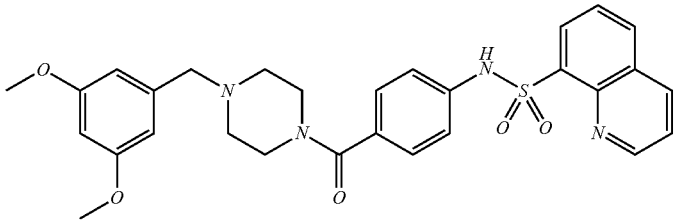
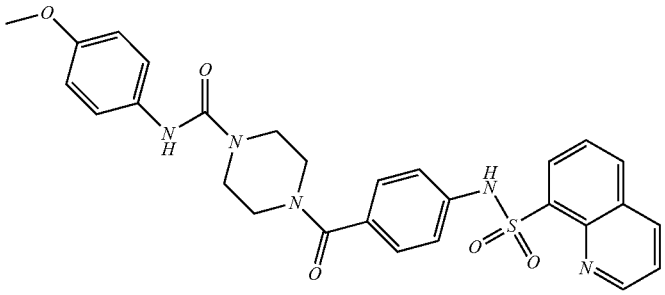
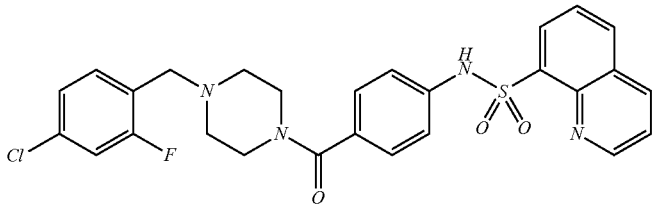
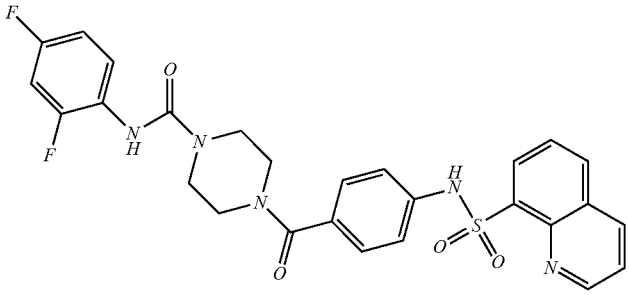
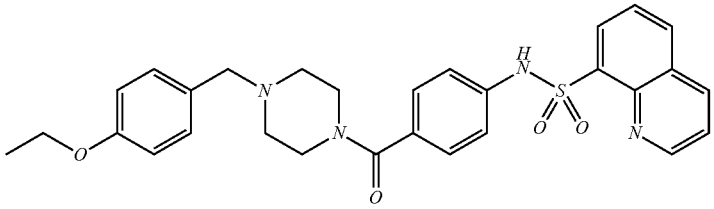

*-continued*
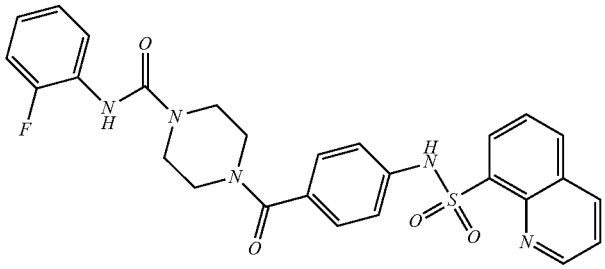
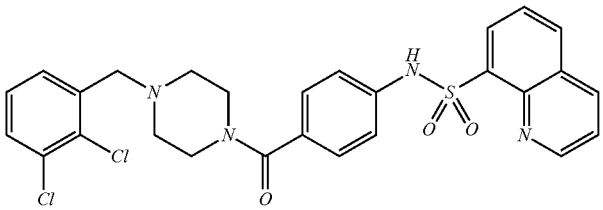
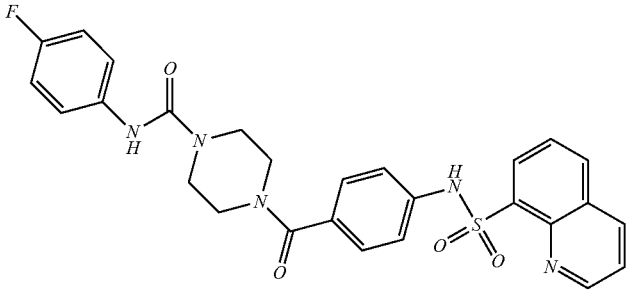
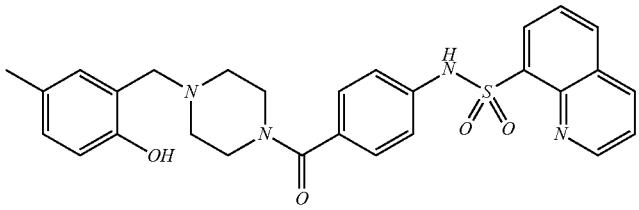
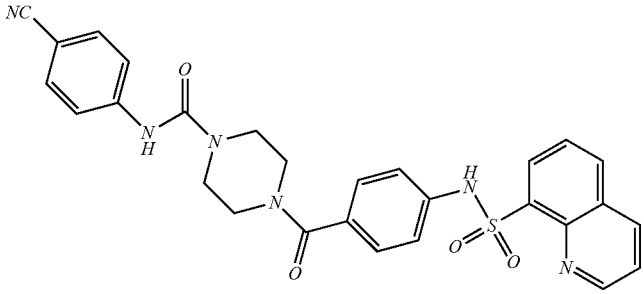
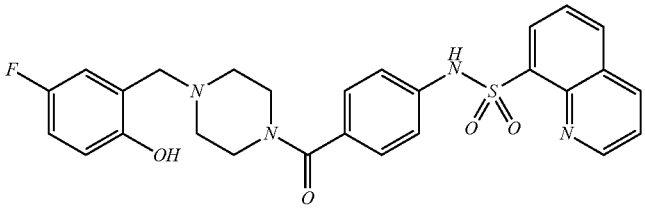

*-continued*
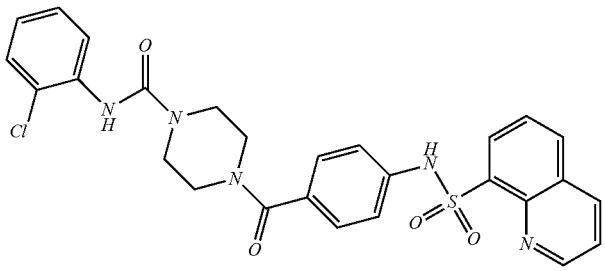
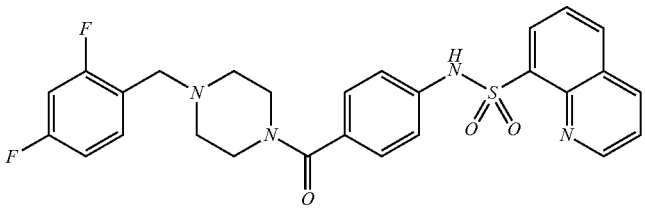
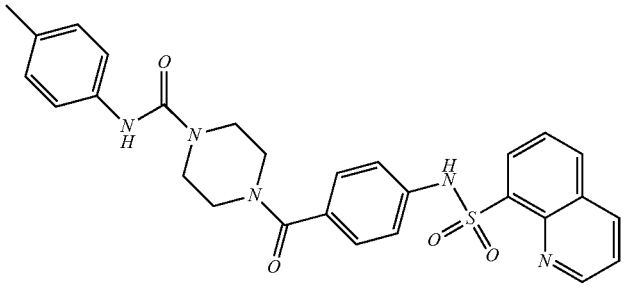
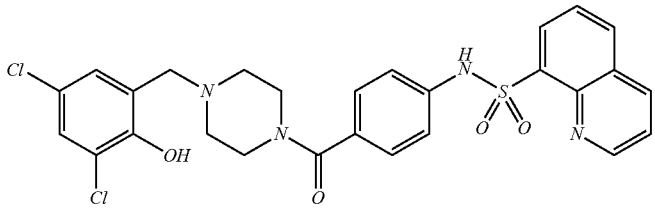
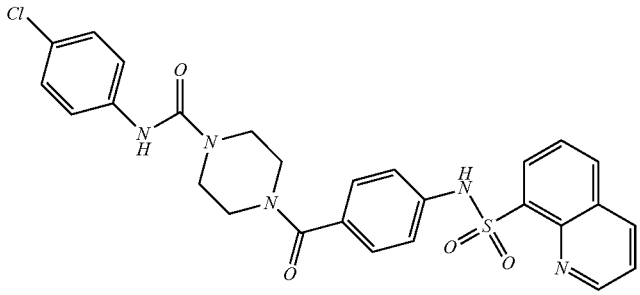
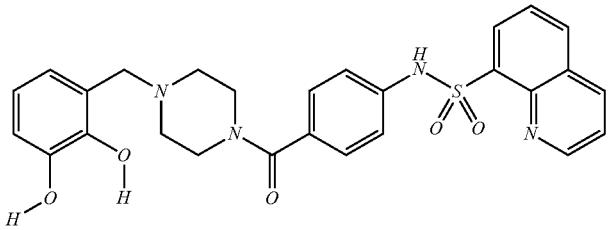

*-continued*
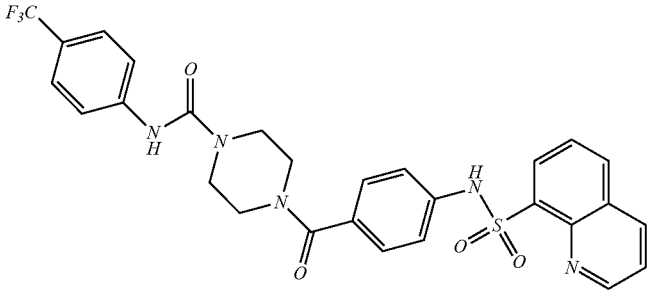
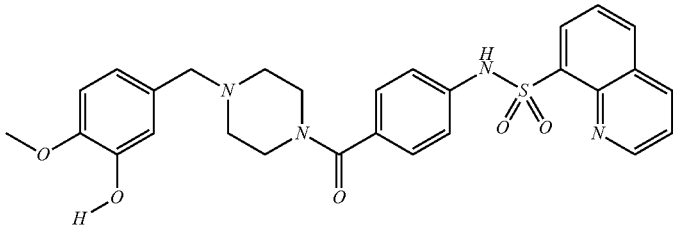
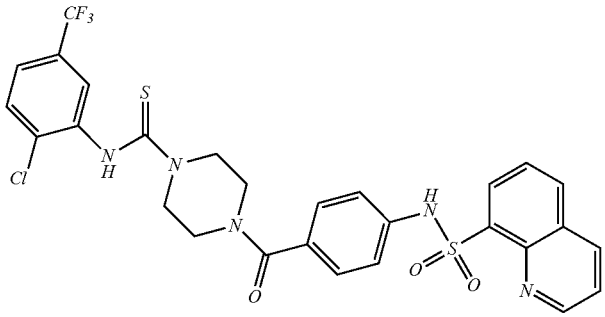
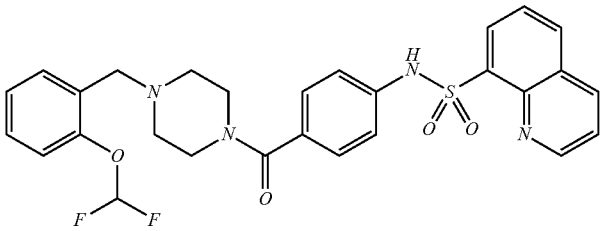
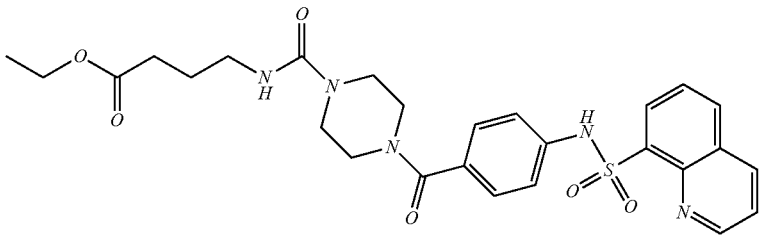
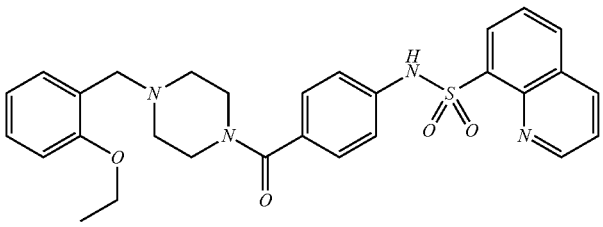

*-continued*
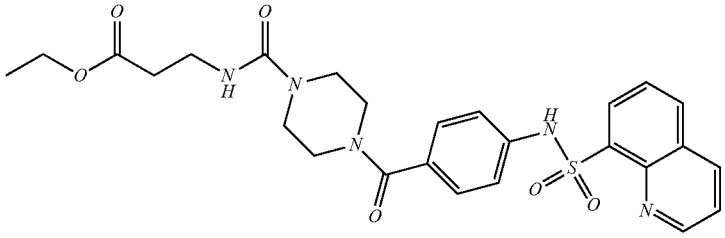
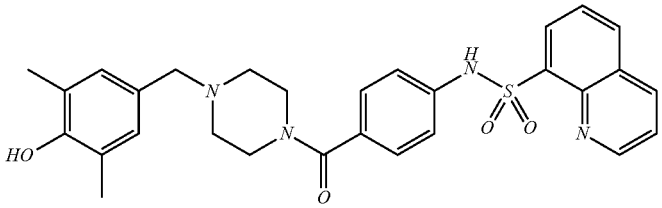
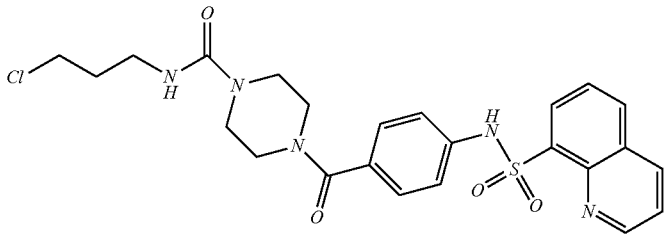
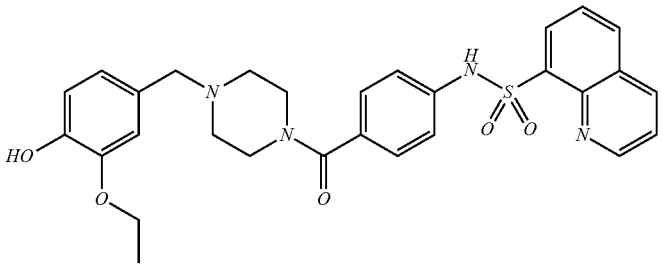
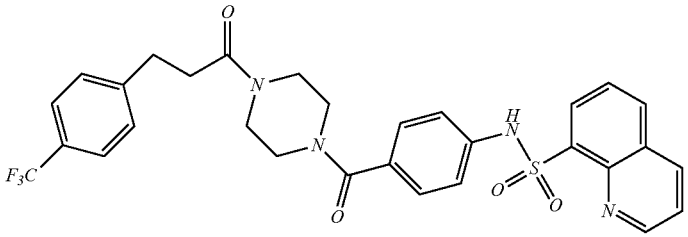
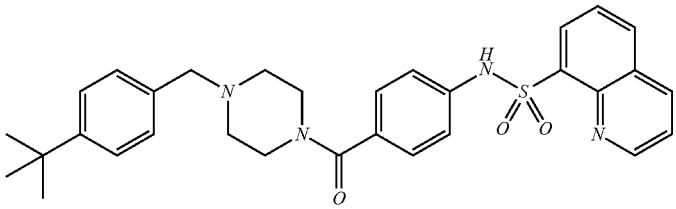
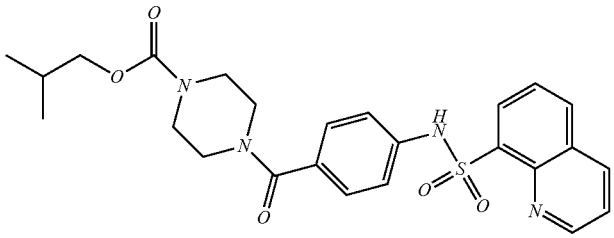

*-continued*
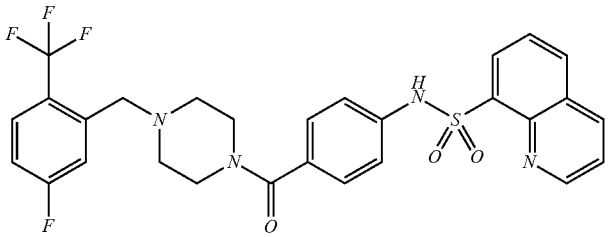
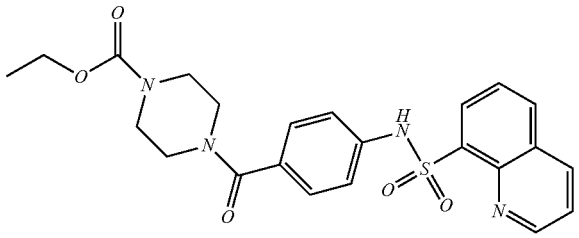
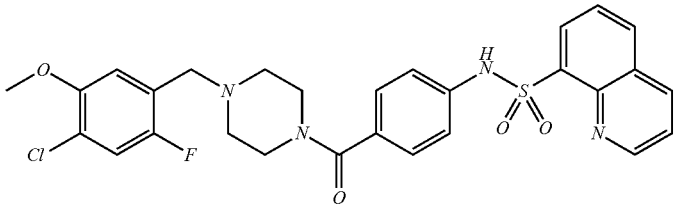
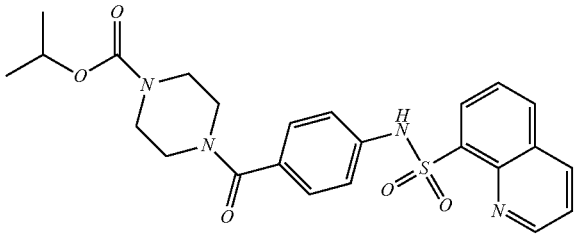
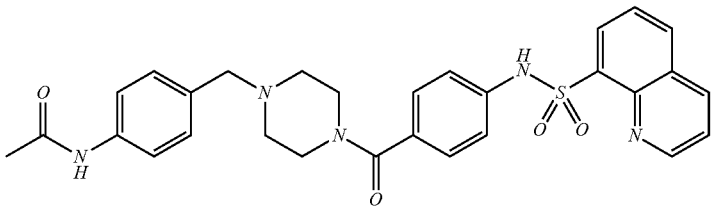
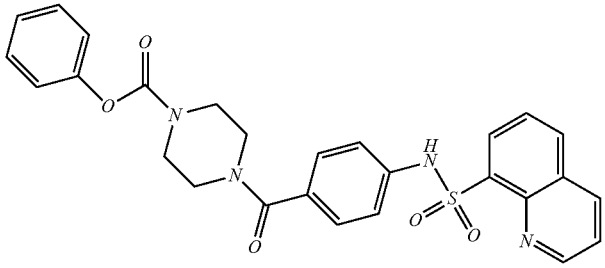
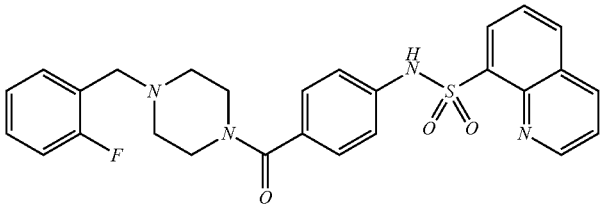
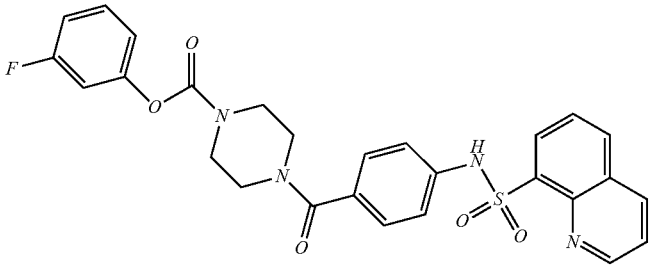

*-continued*
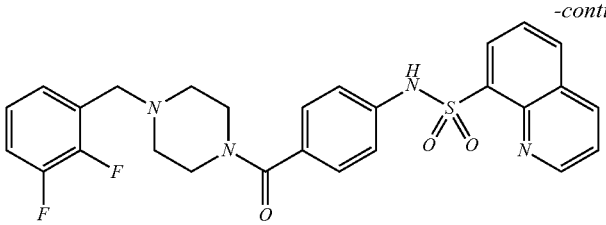
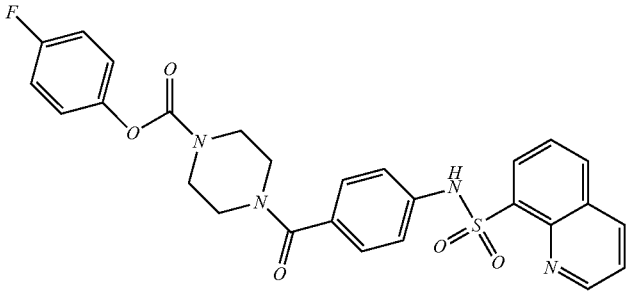
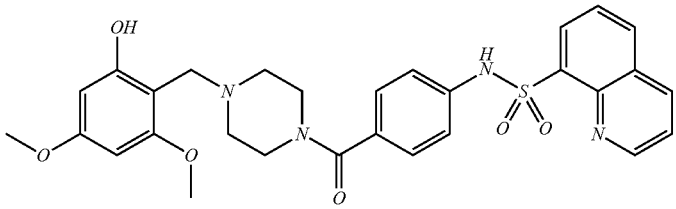
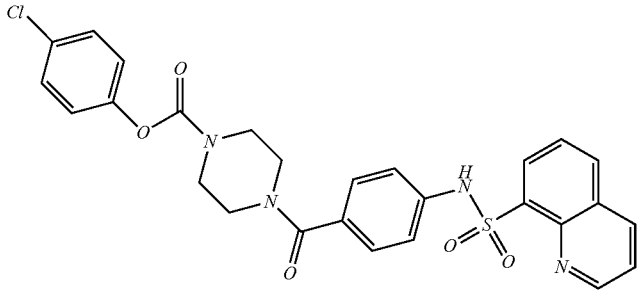
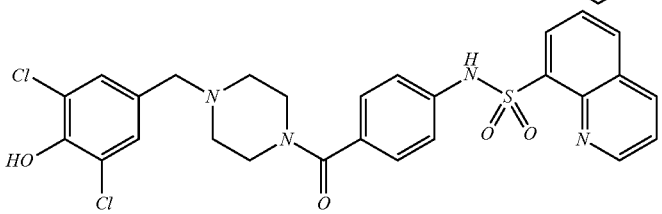
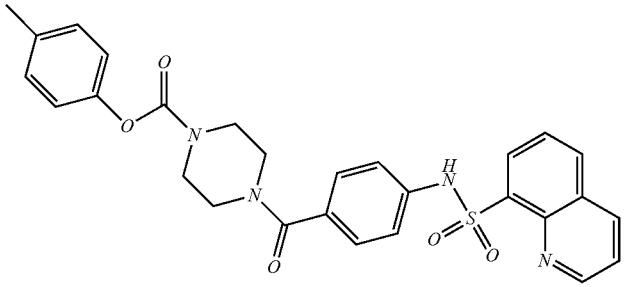
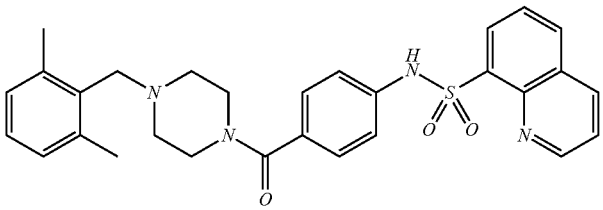

*-continued*
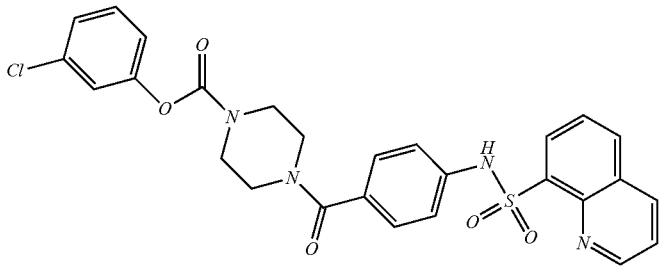
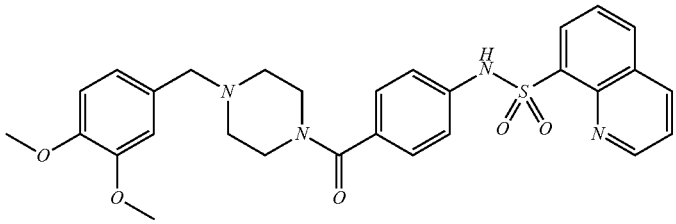
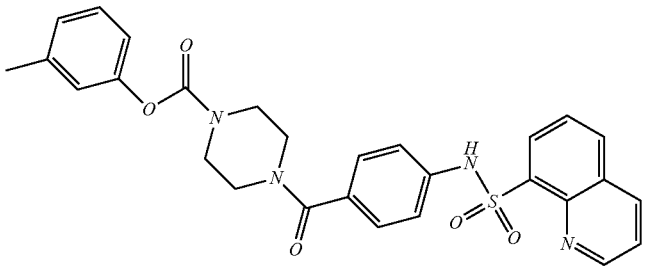
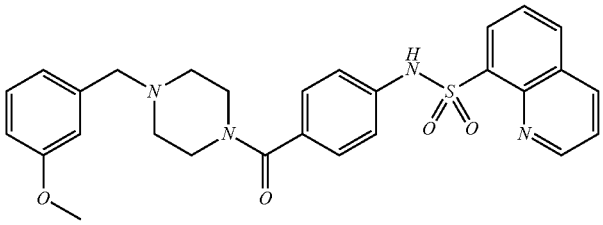
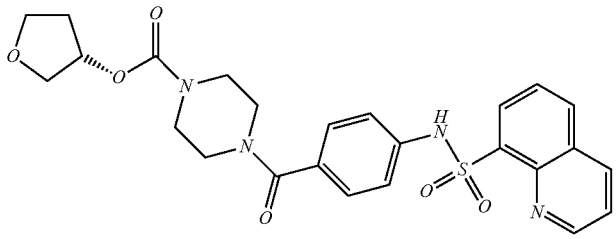
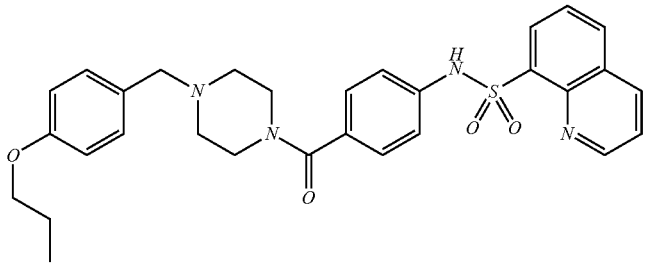

*-continued*
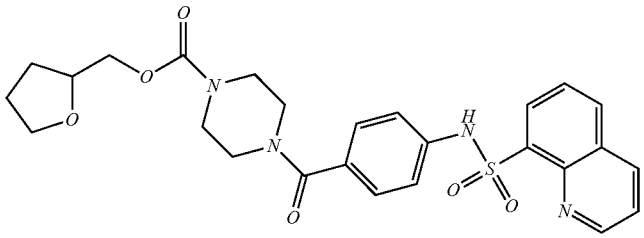
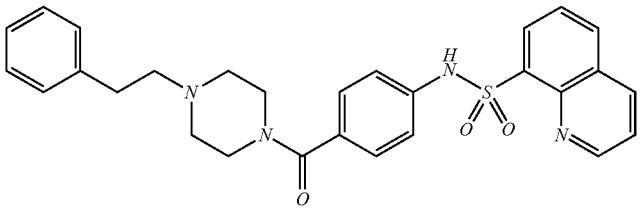
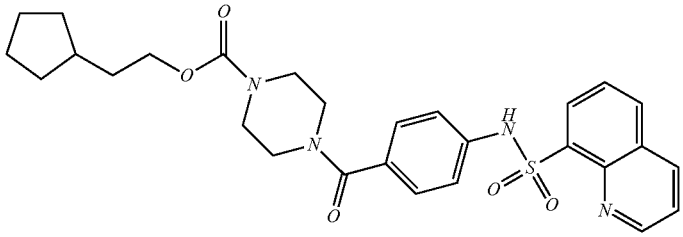
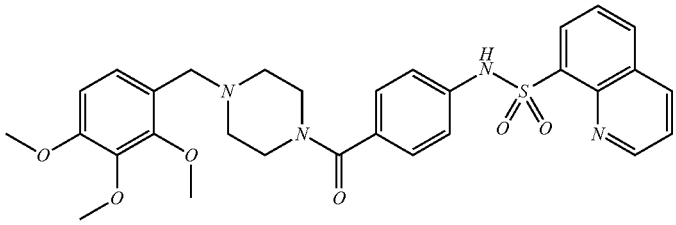
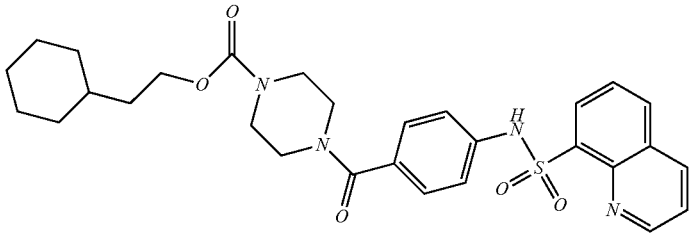
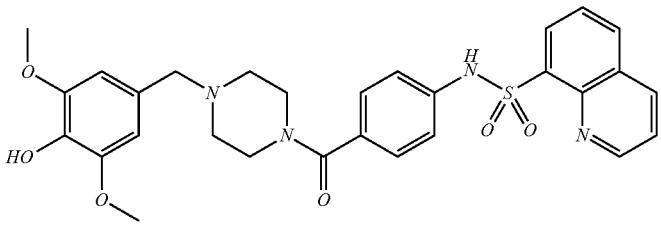
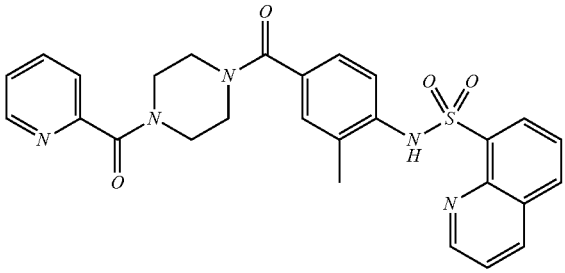

*-continued*
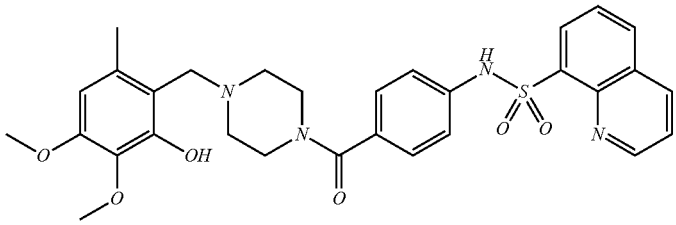
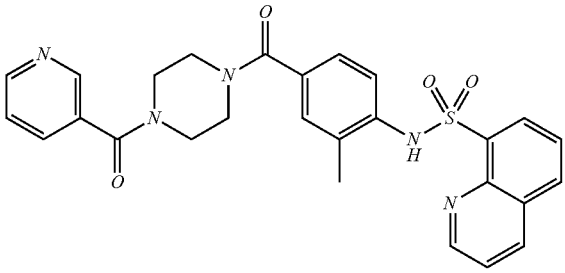
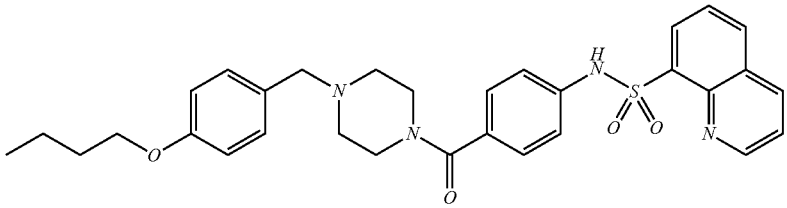
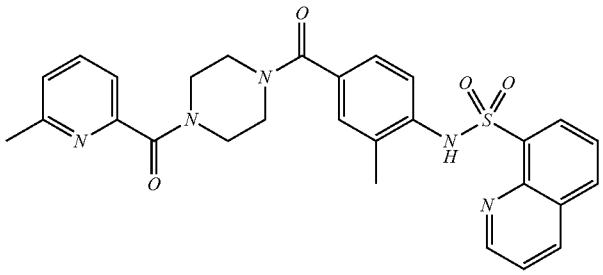
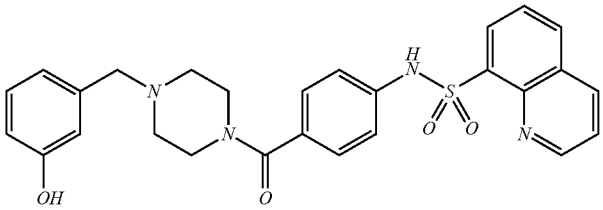
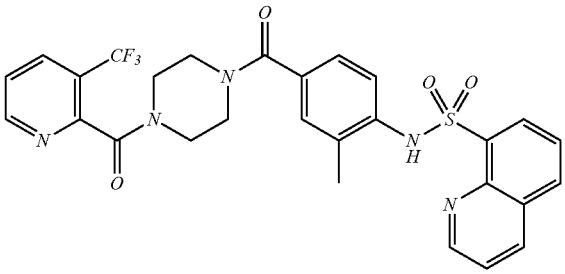
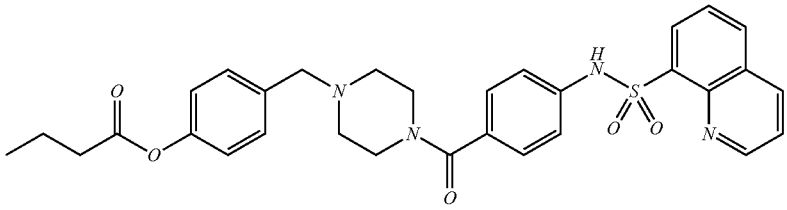

*-continued*
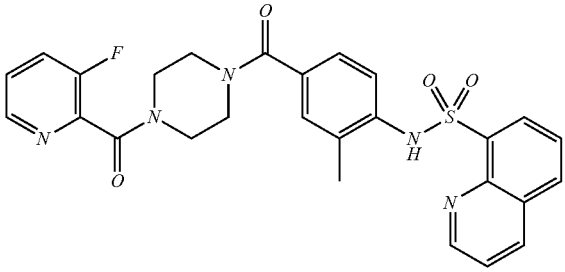
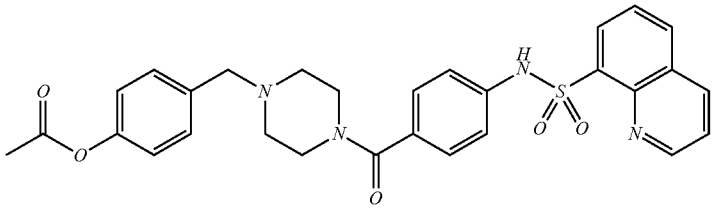
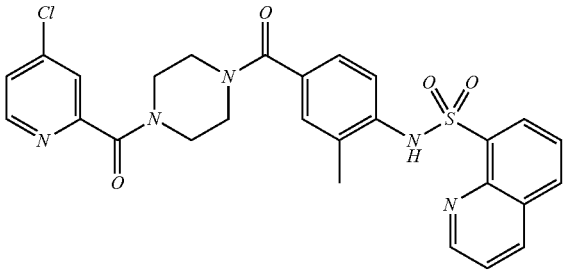
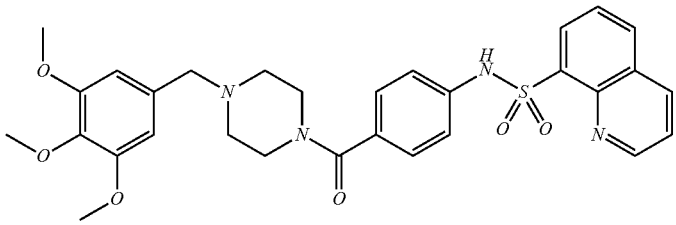
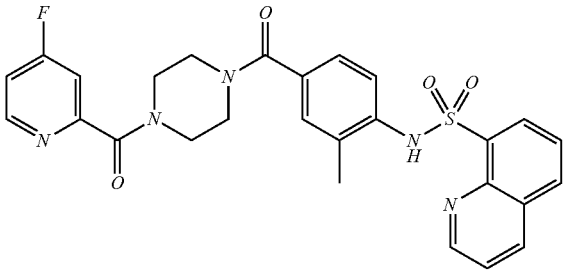
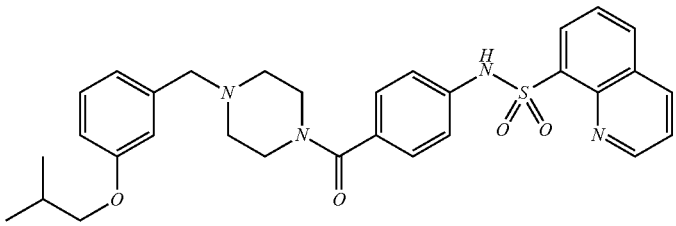

*-continued*
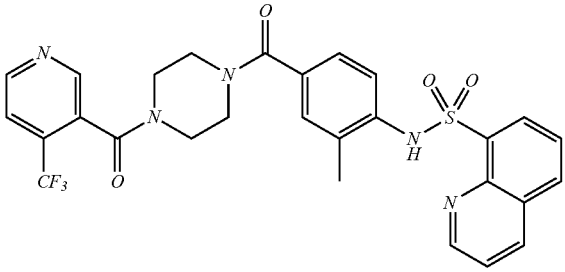
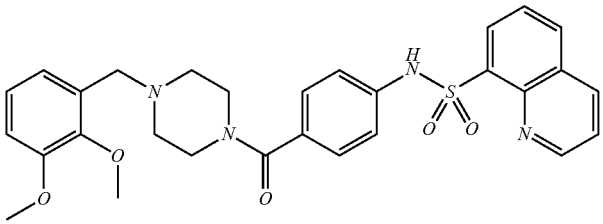
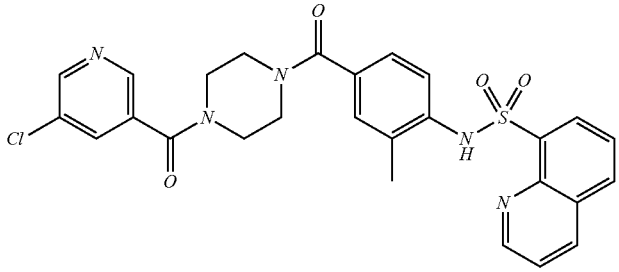
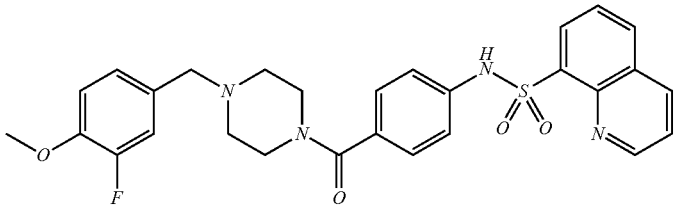
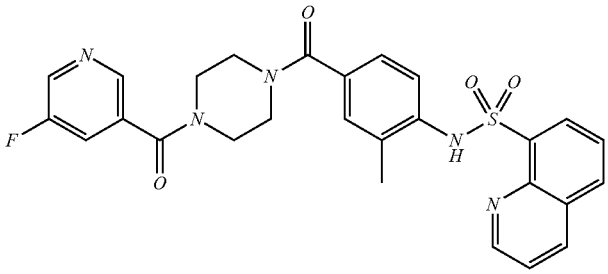
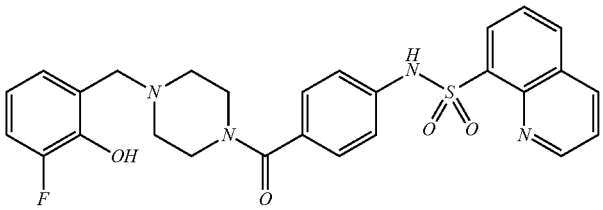
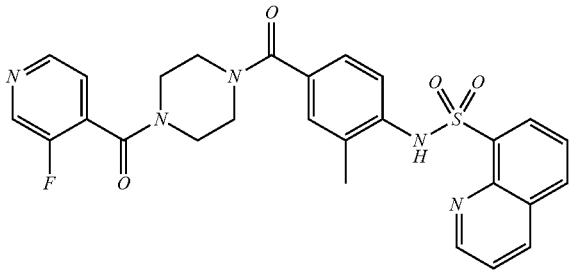
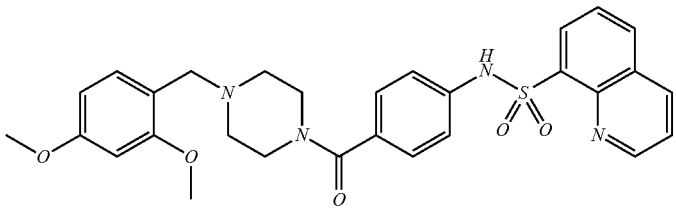

*-continued*
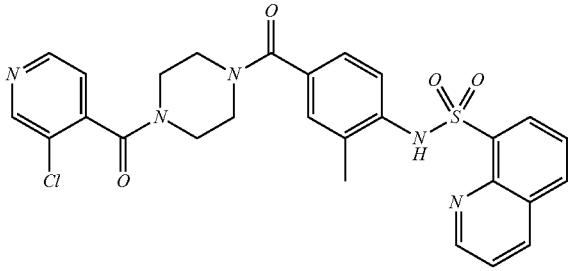
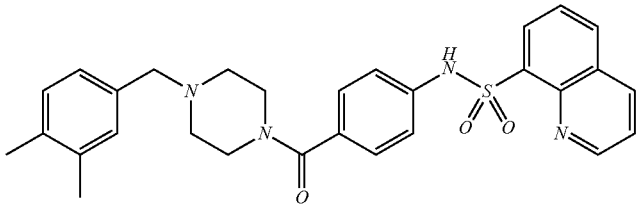
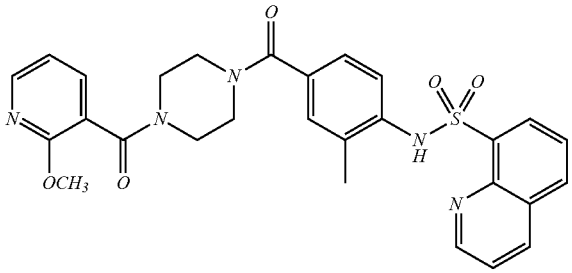
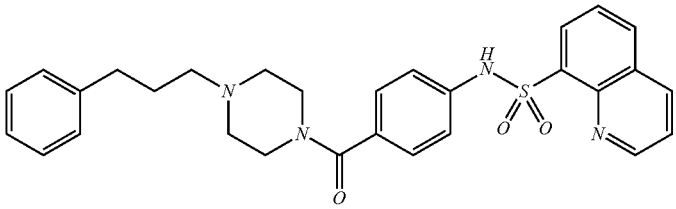
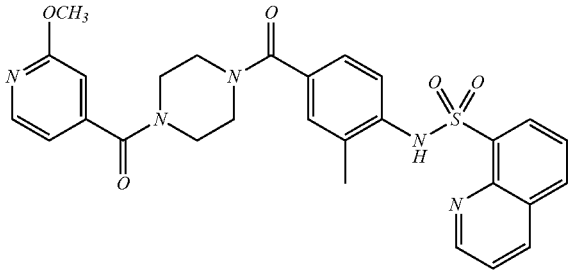
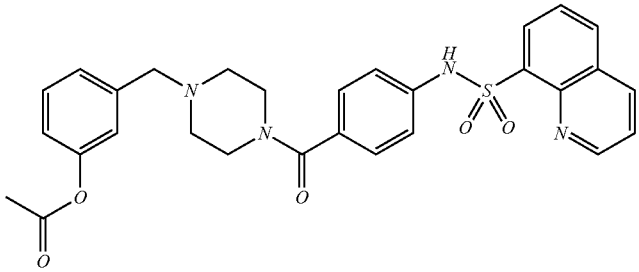

*-continued*
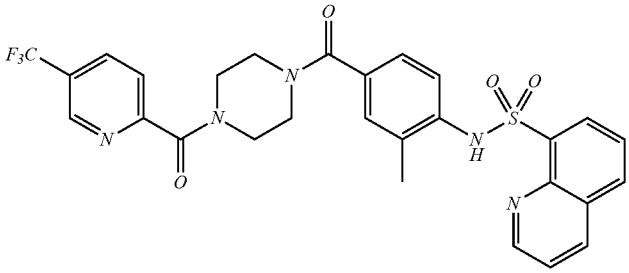
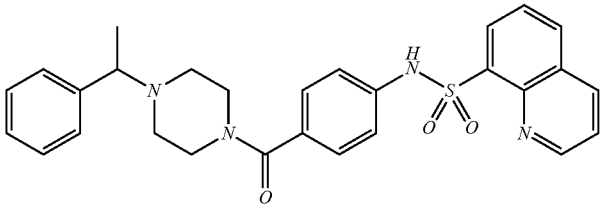
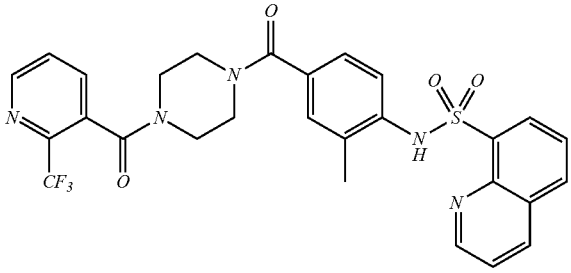
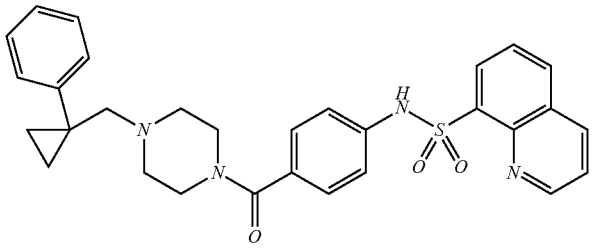
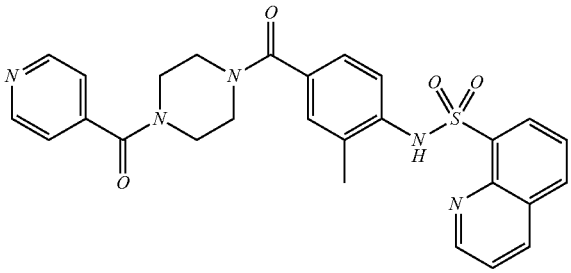
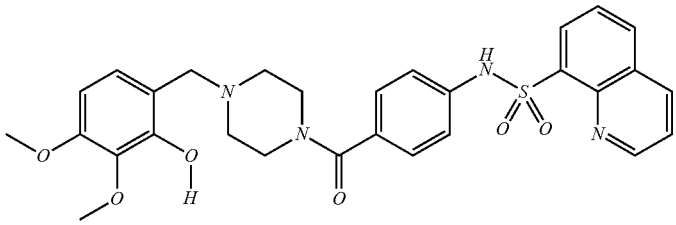
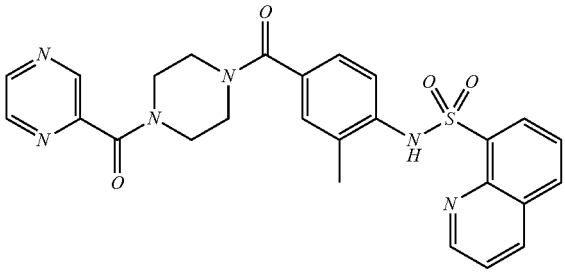
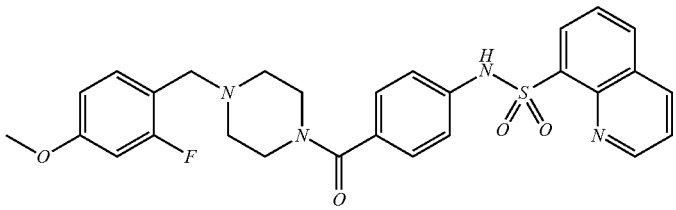

*-continued*
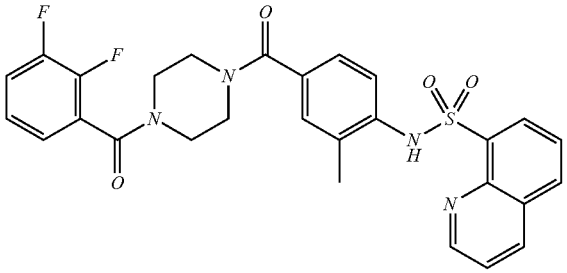
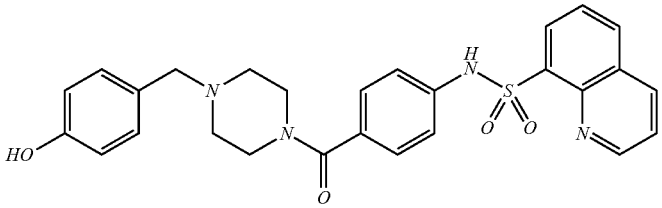
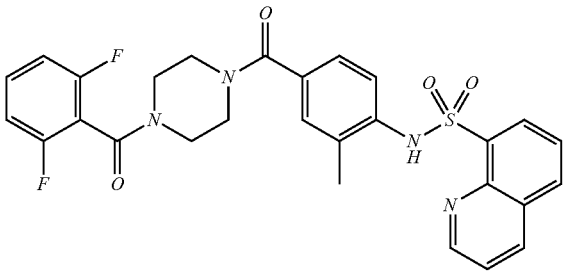
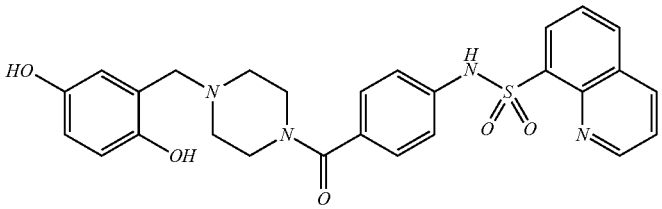
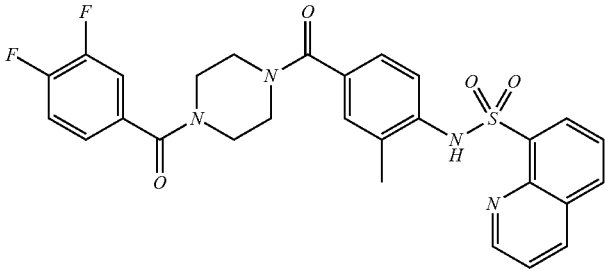
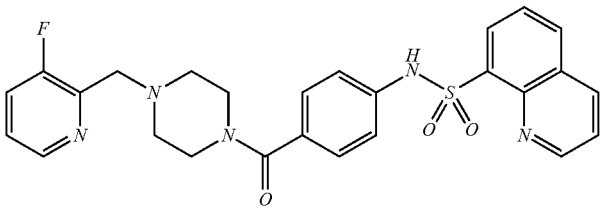
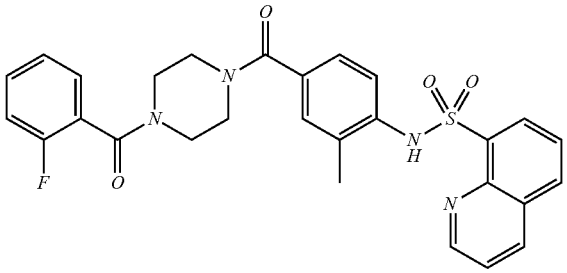

*-continued*
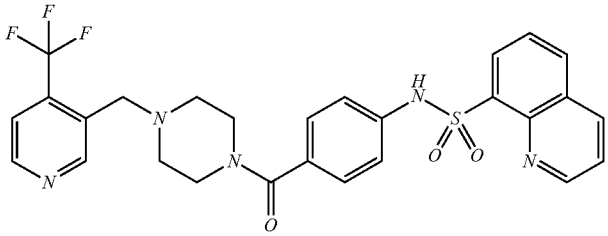
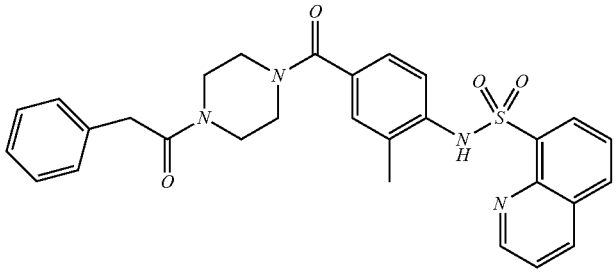
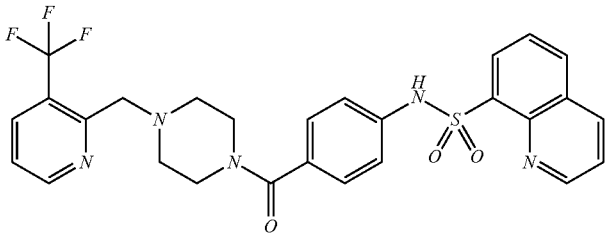
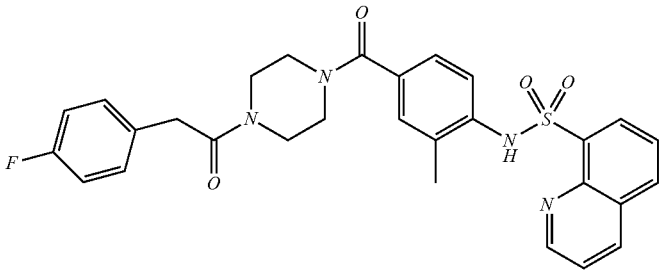
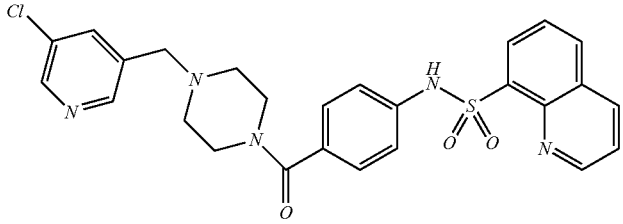
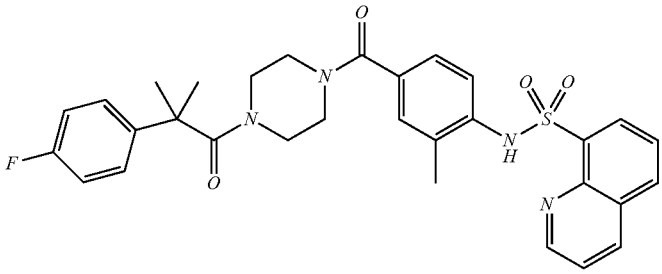

*-continued*
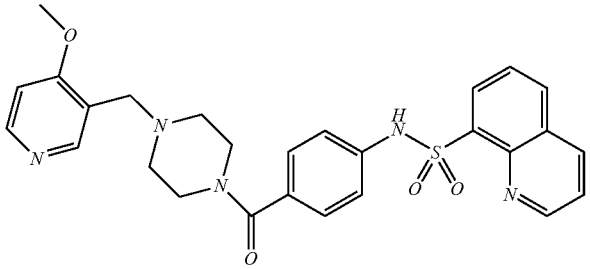
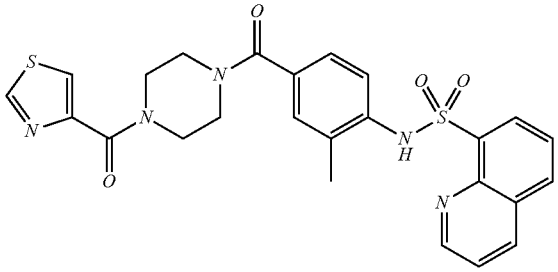
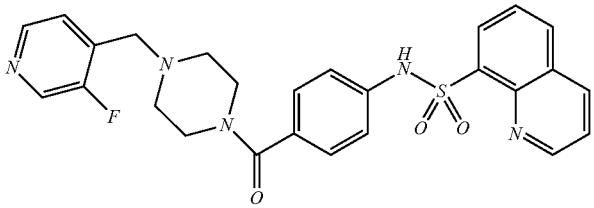
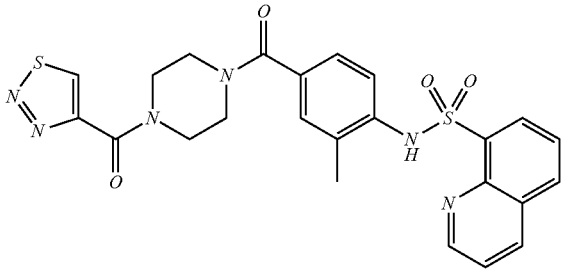
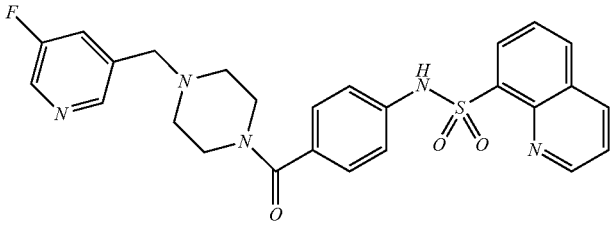
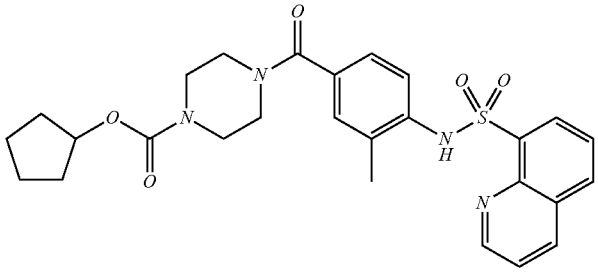
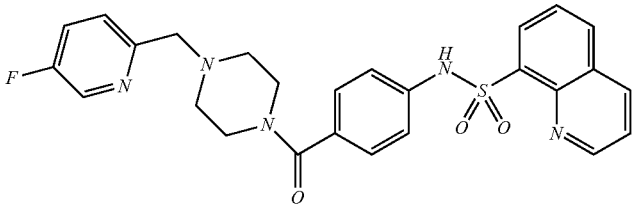
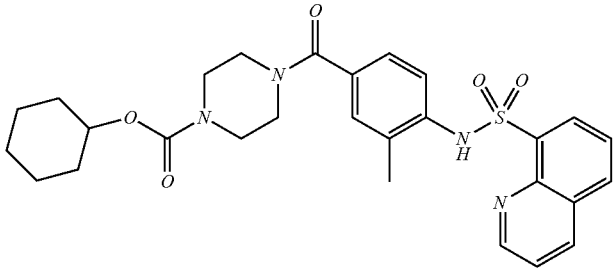

*-continued*
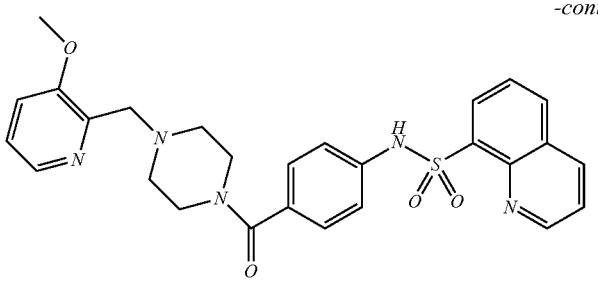
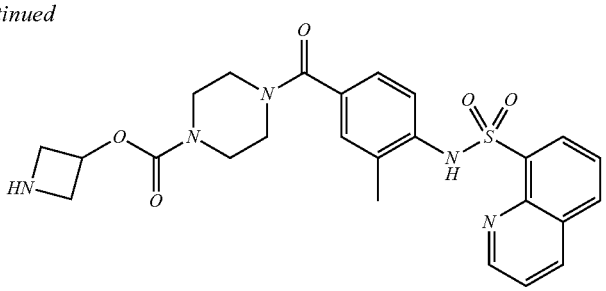
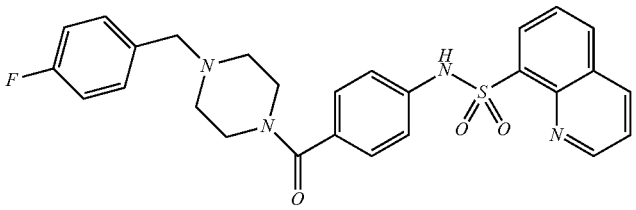
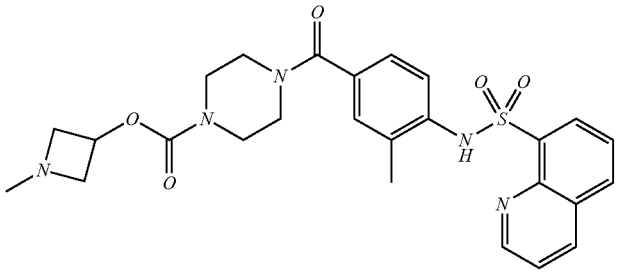
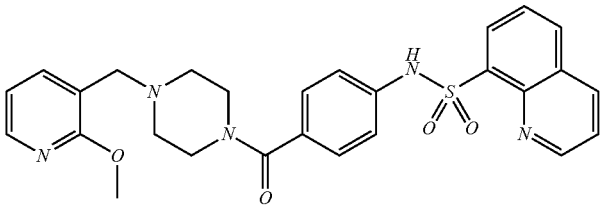
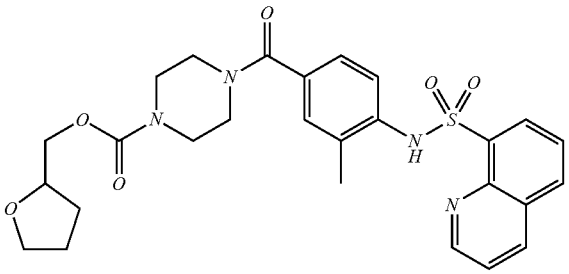
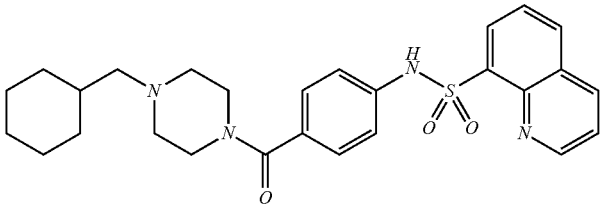
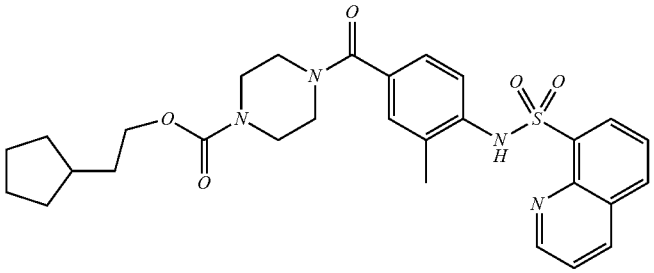
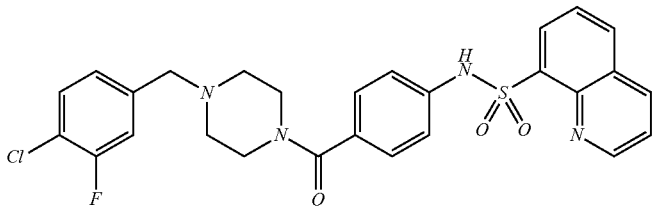

*-continued*
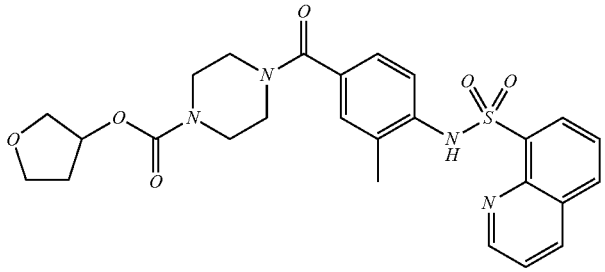
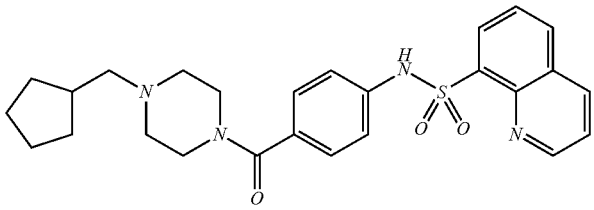
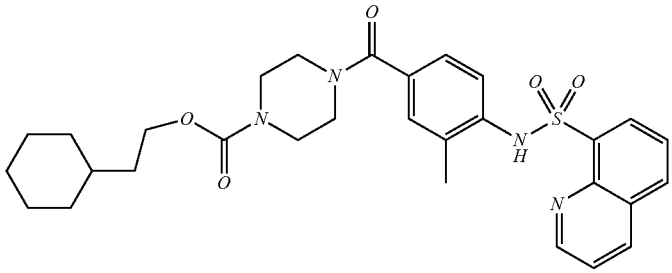
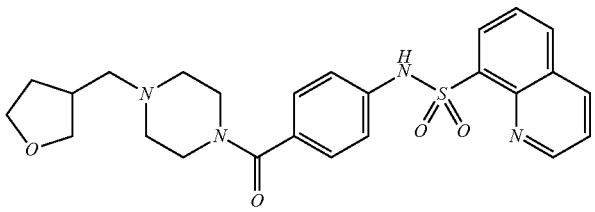
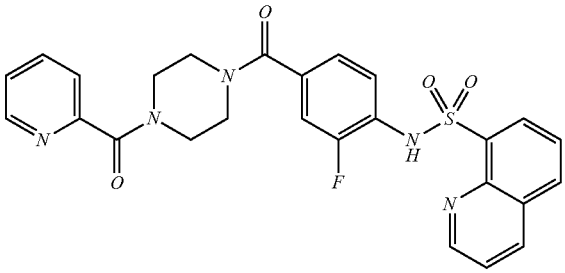
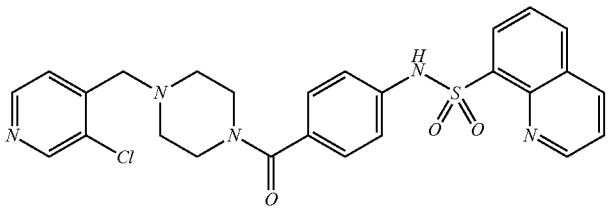
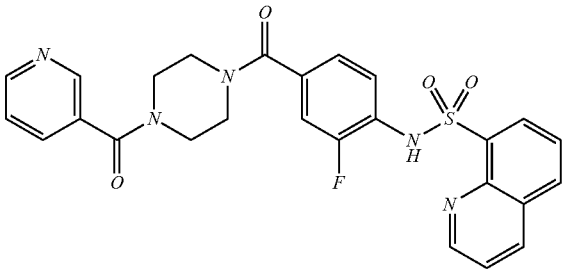
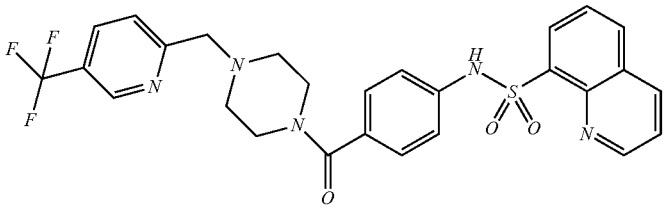
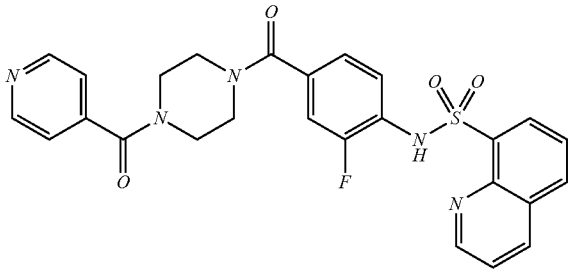
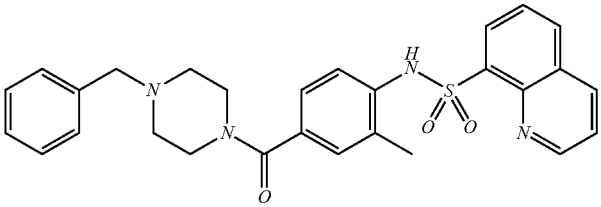

*-continued*
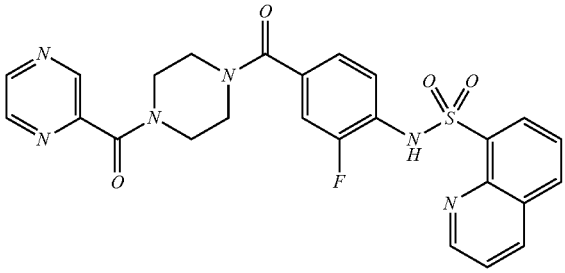
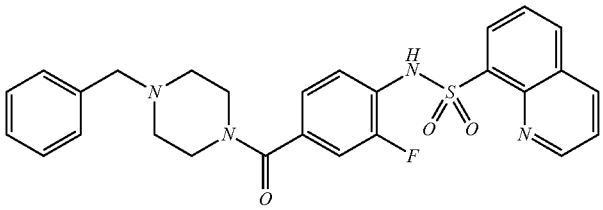
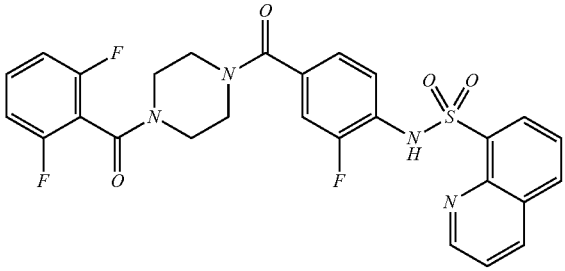
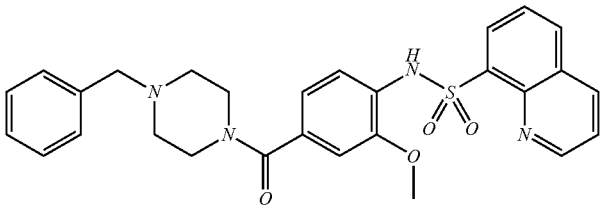
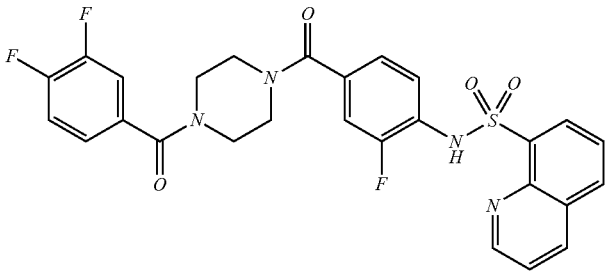
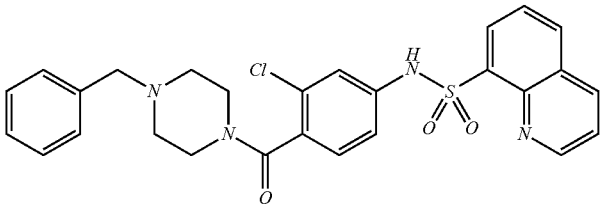
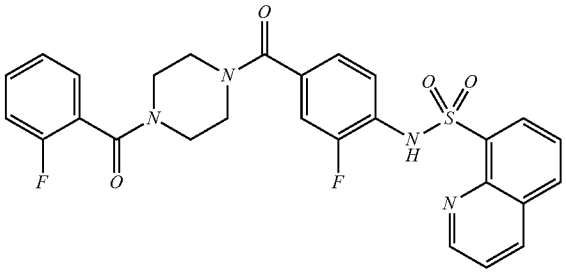
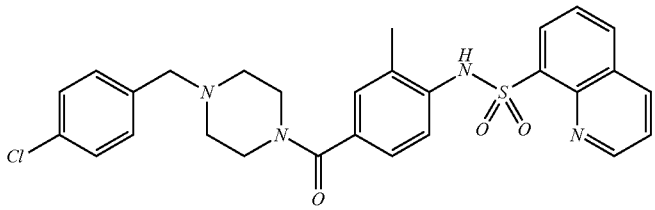
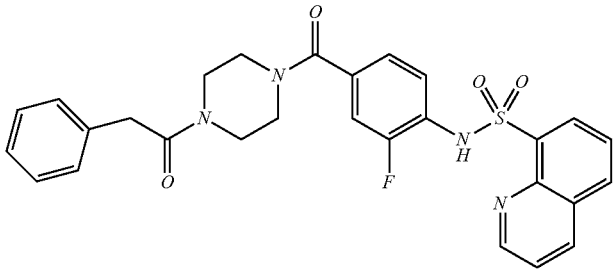

*-continued*
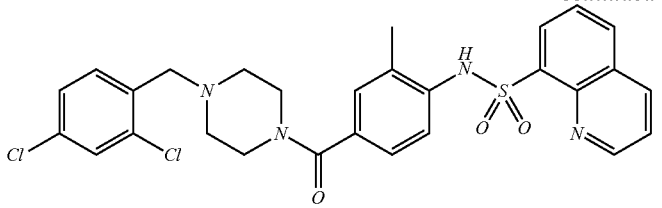
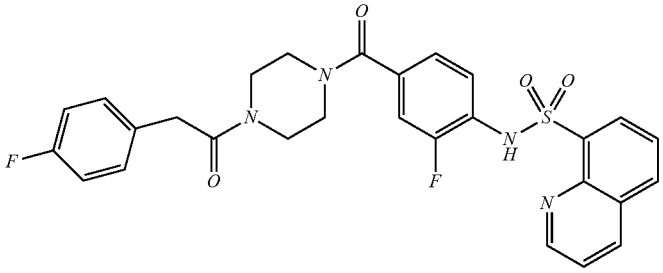
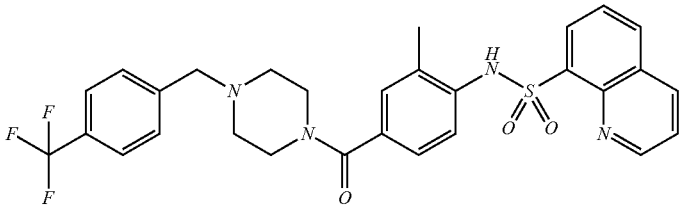
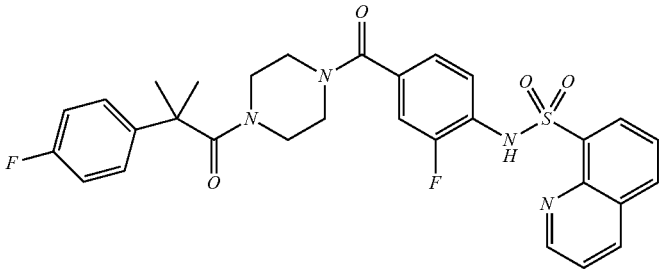
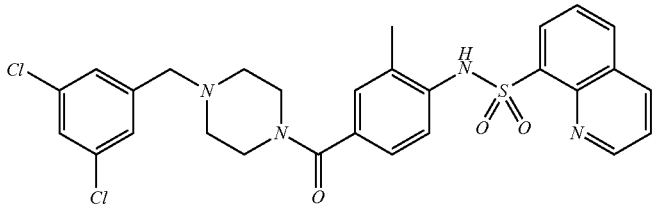
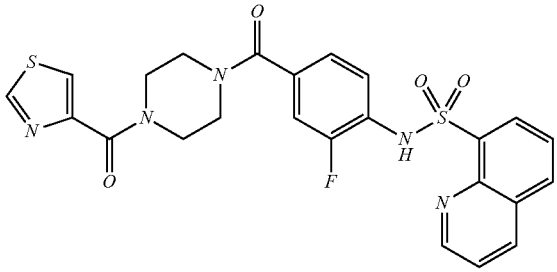
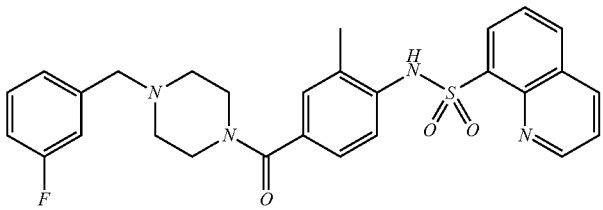
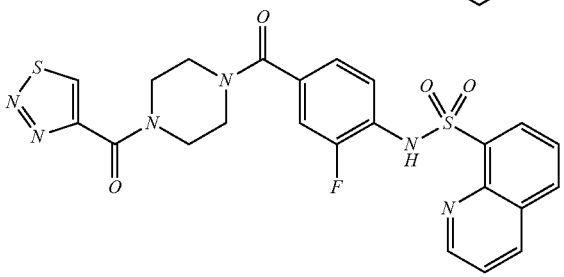

*-continued*
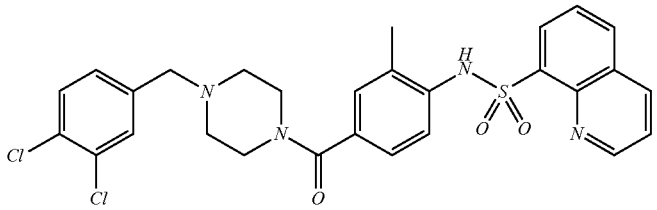
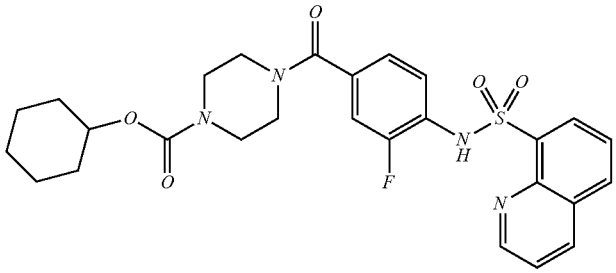
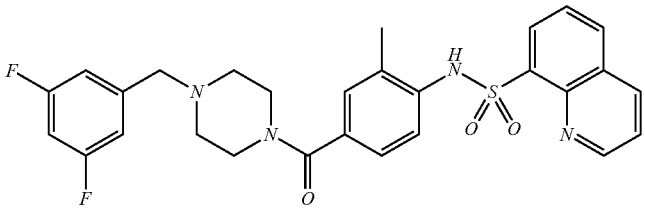
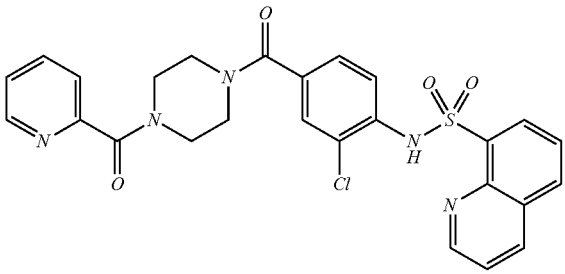
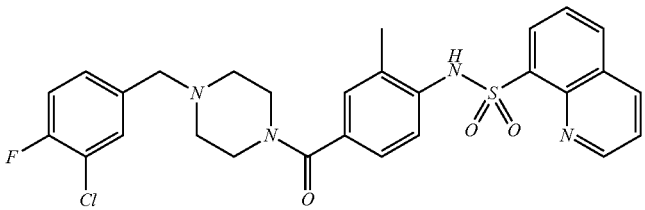
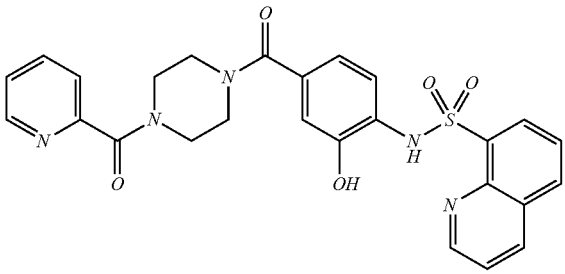
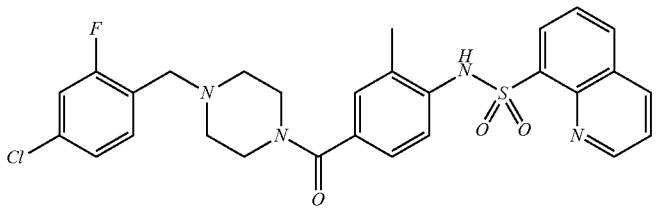

*-continued*
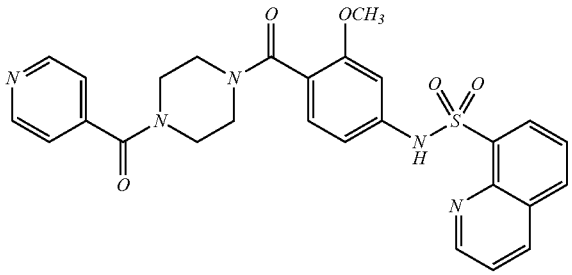
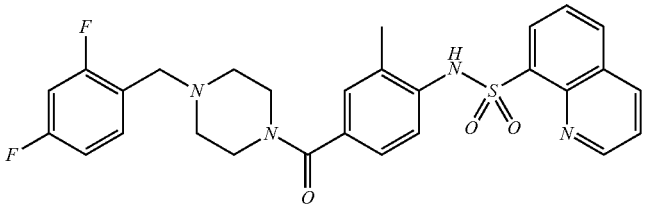
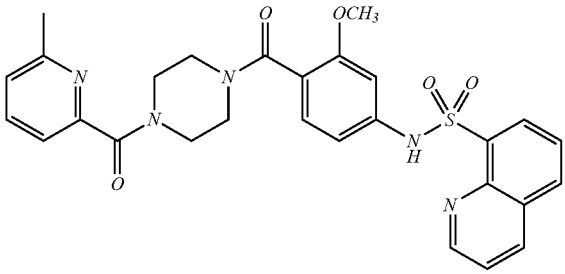
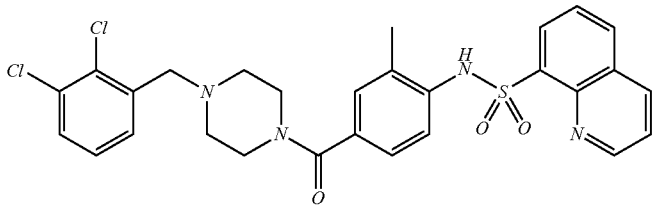
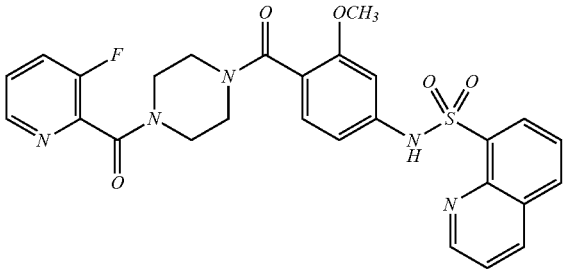
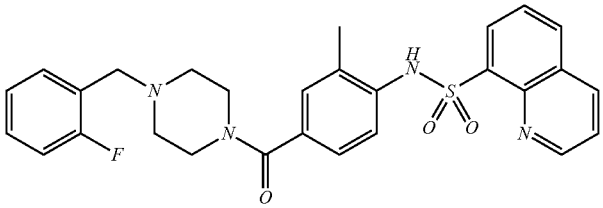
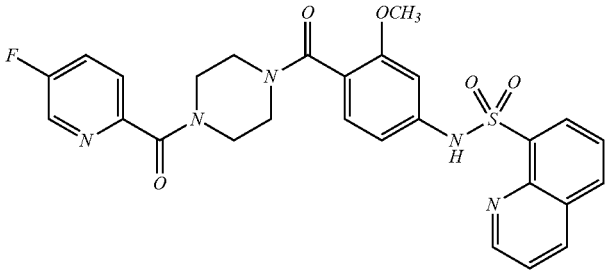

*-continued*
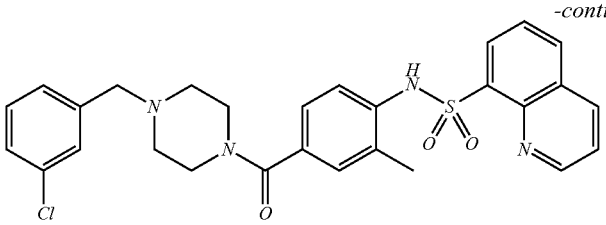
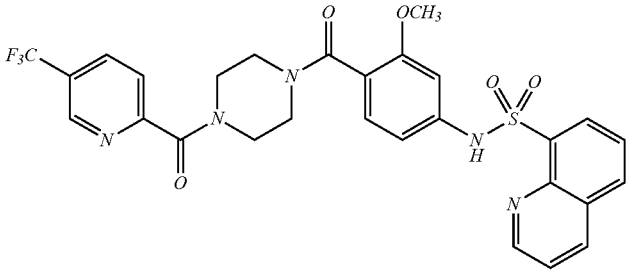
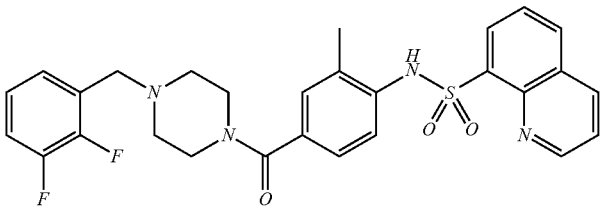
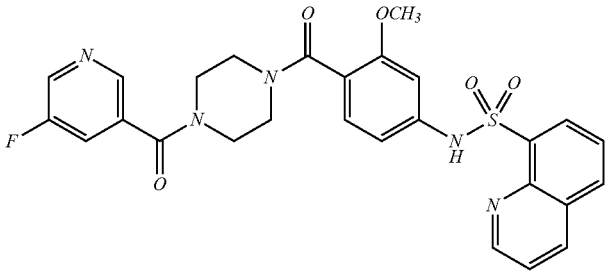
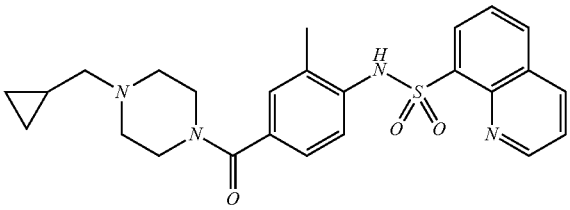
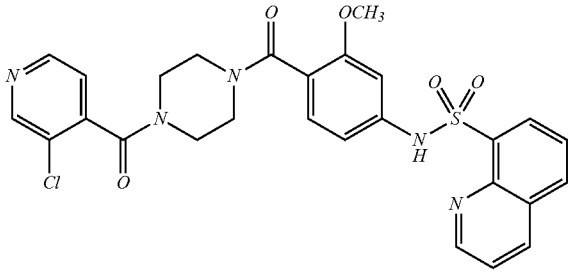
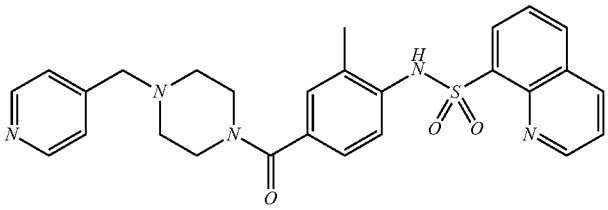
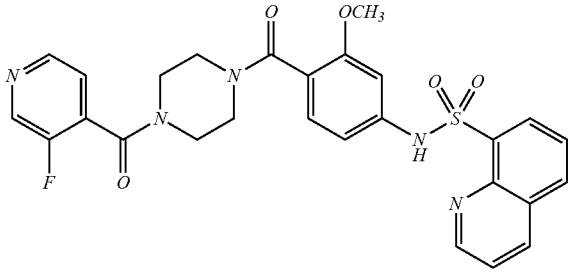
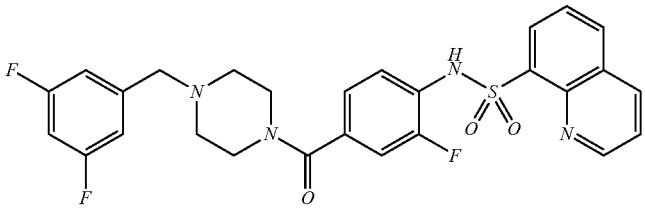

*-continued*
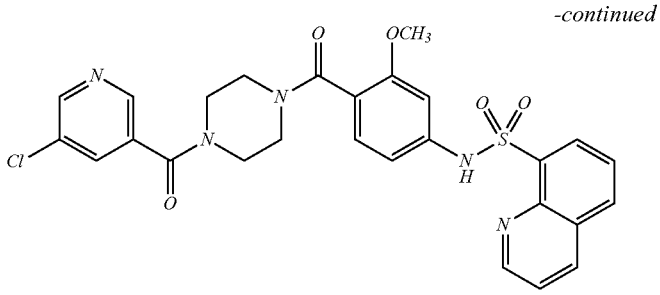
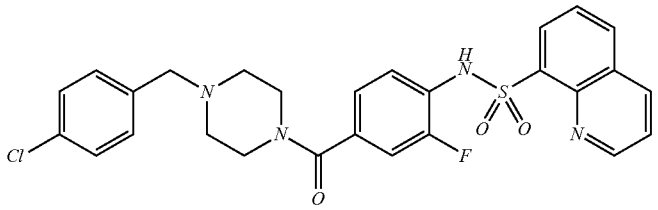
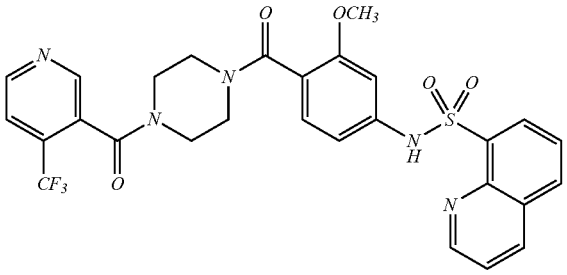
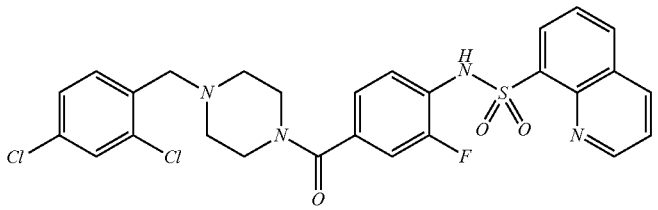
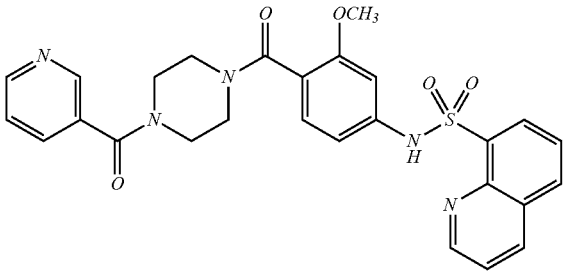
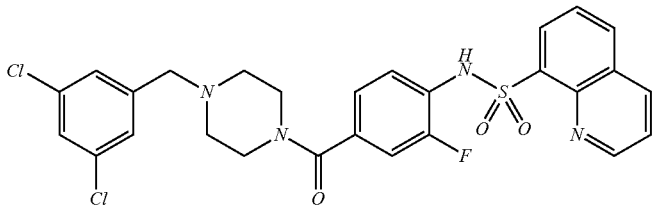
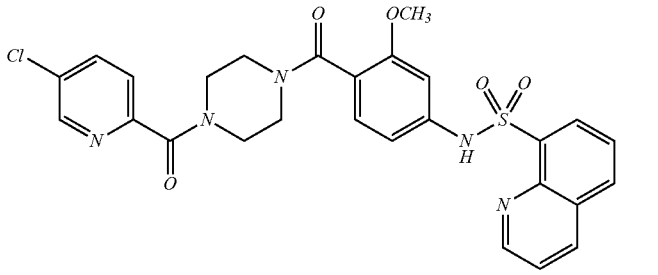

-continued
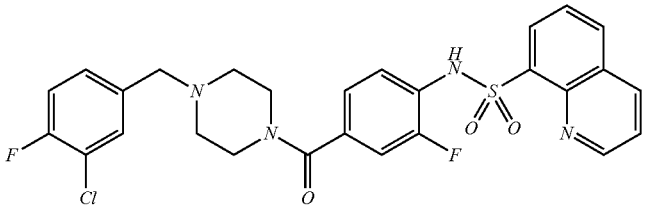
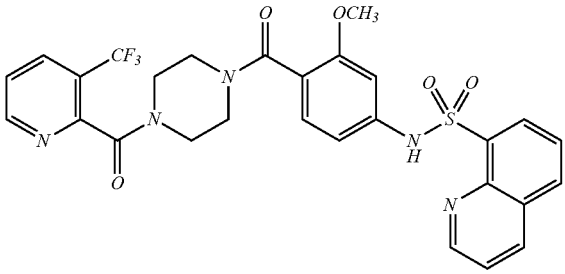
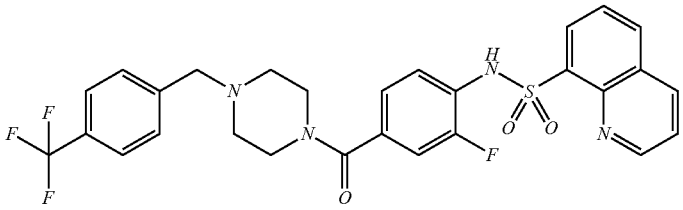
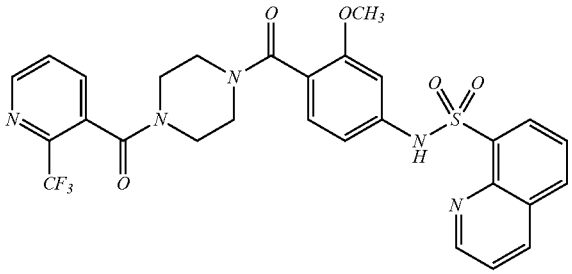
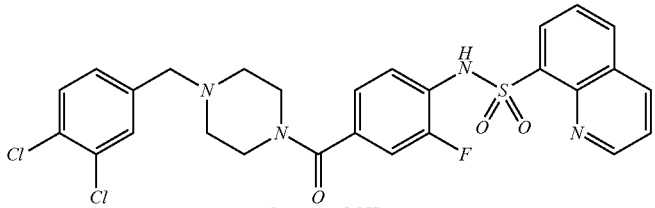
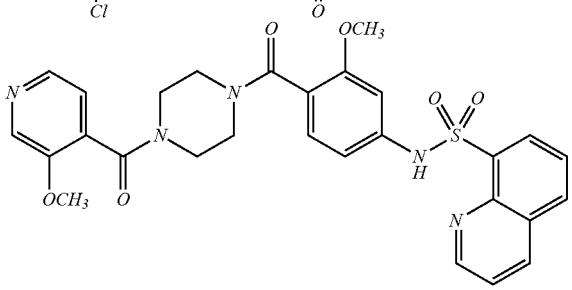
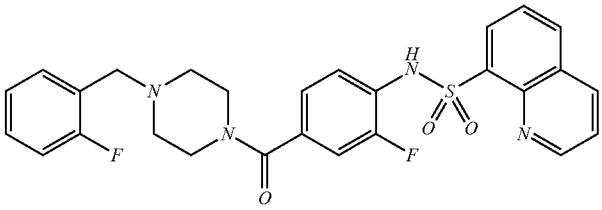
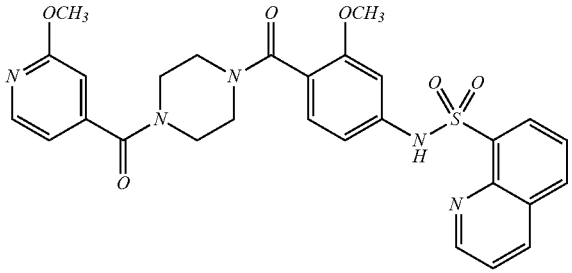

*-continued*
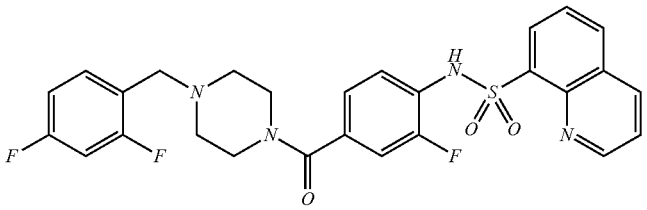
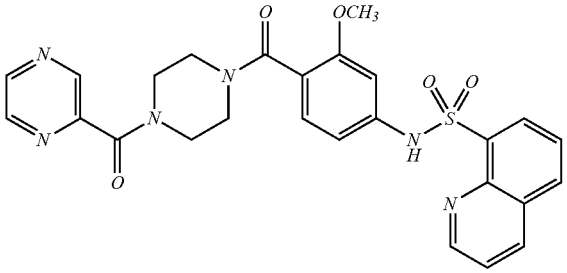
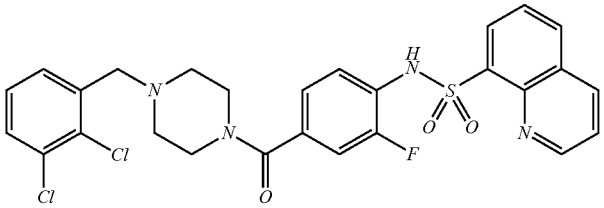
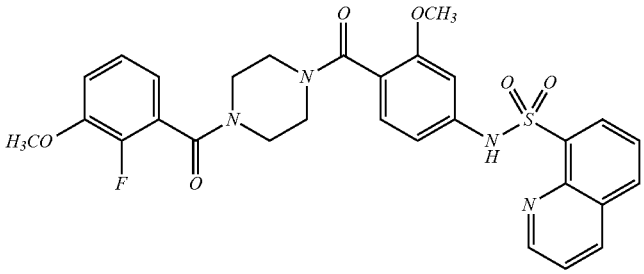
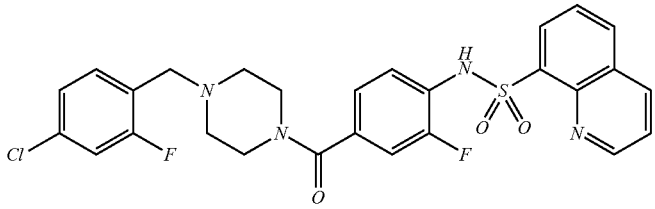
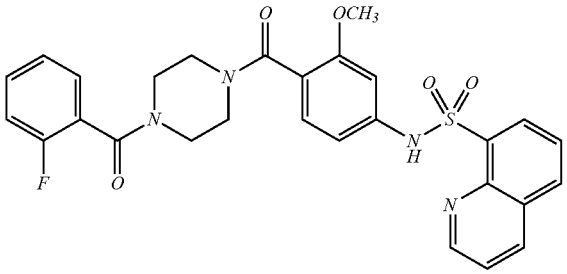
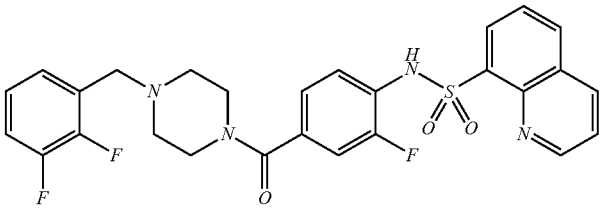
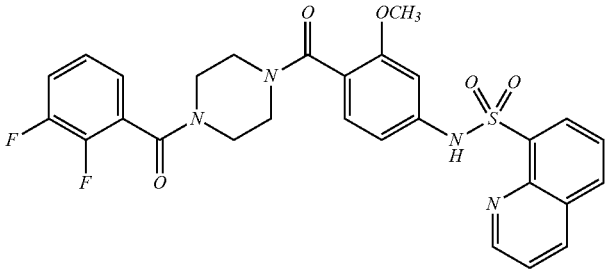
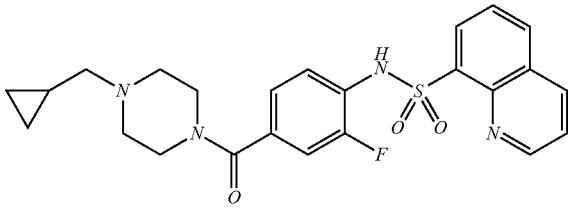

*-continued*
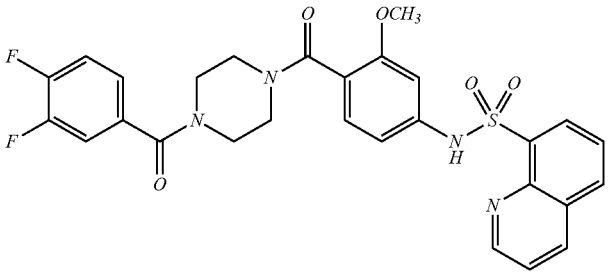
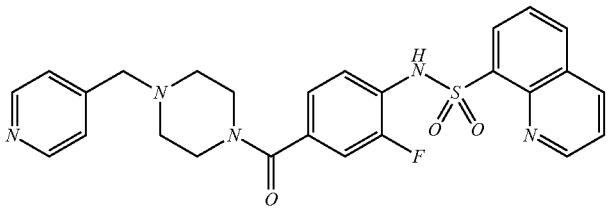
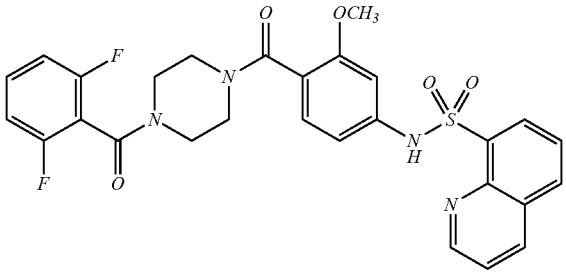
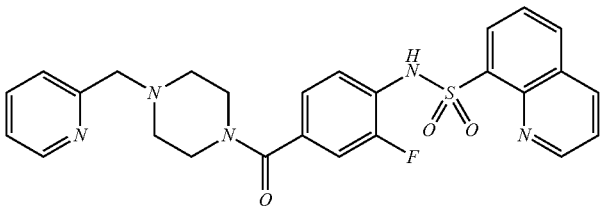
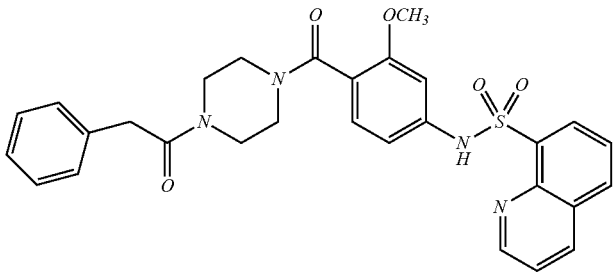
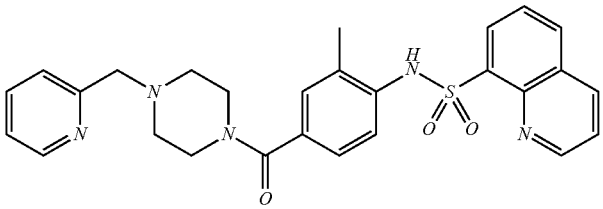
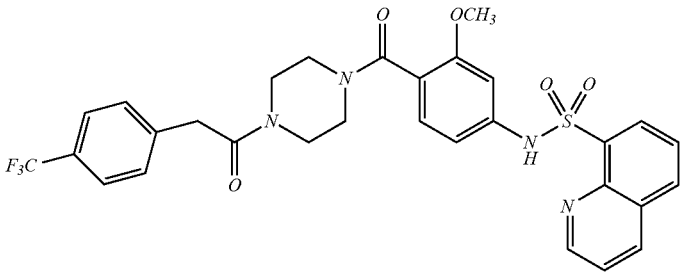

*-continued*
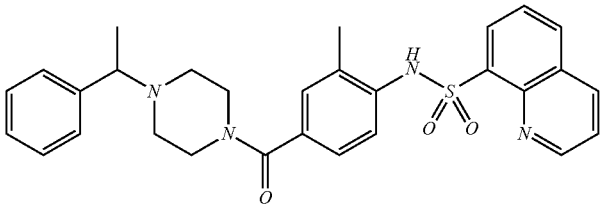
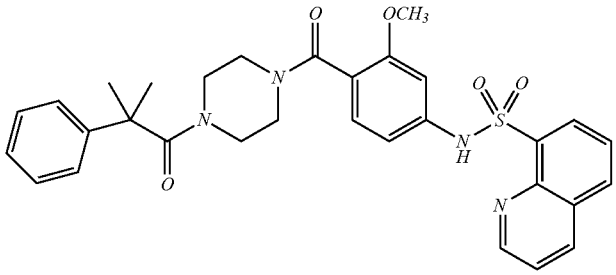
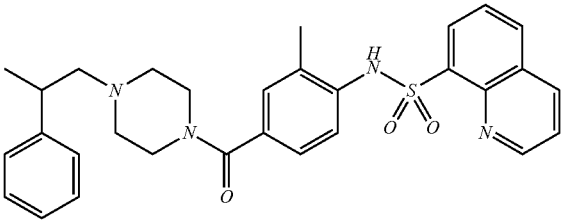
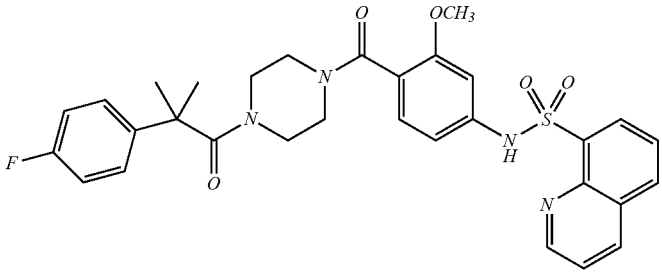
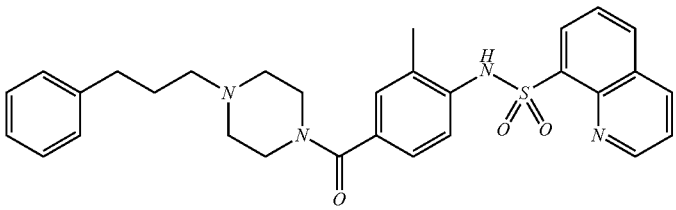
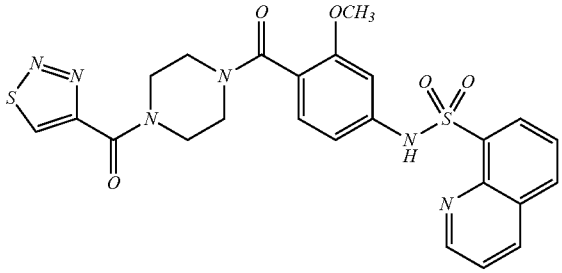
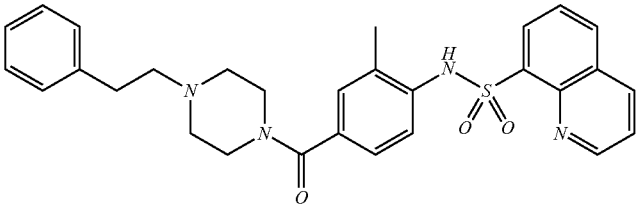
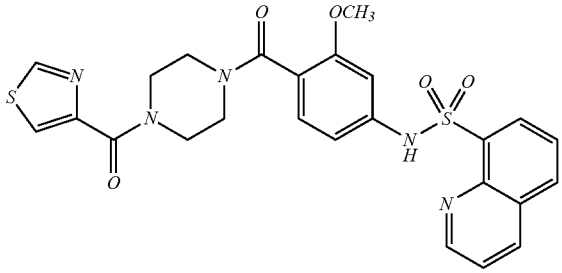

*-continued*
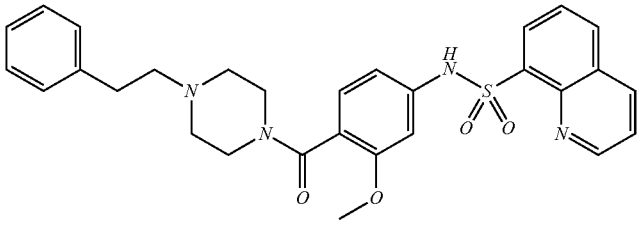
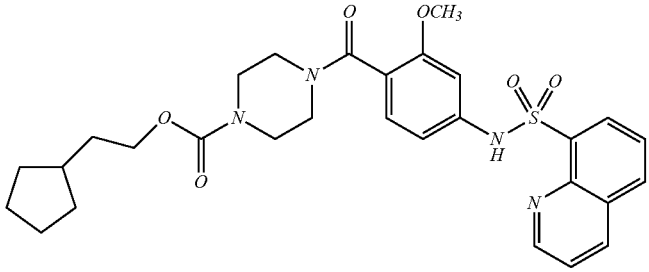
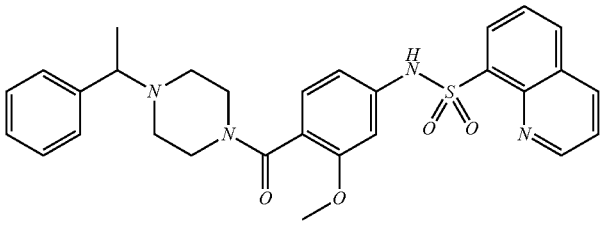
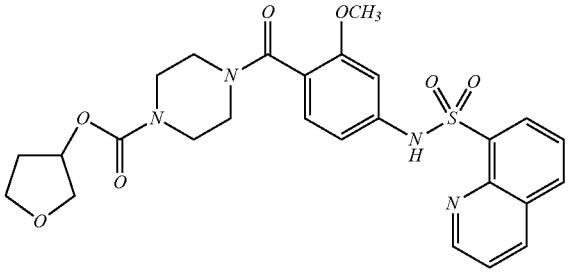
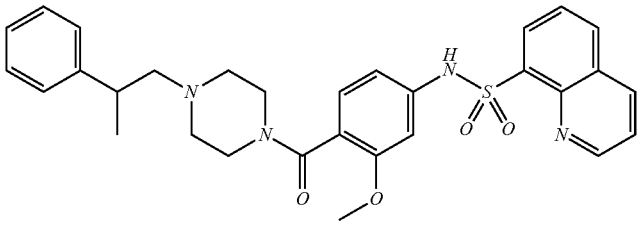
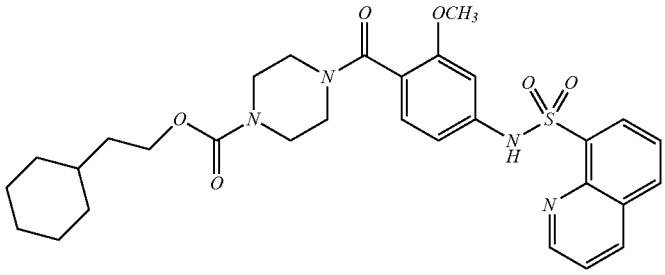
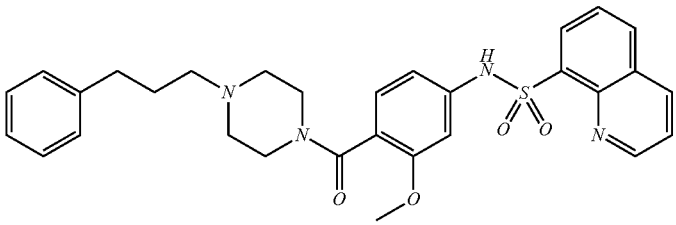

*-continued*
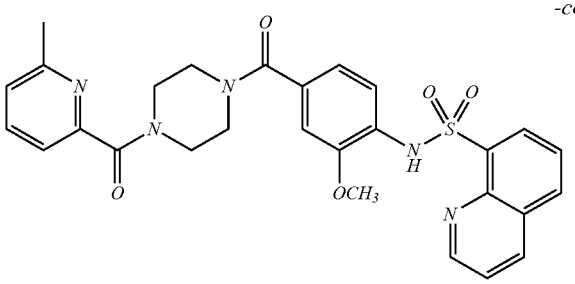
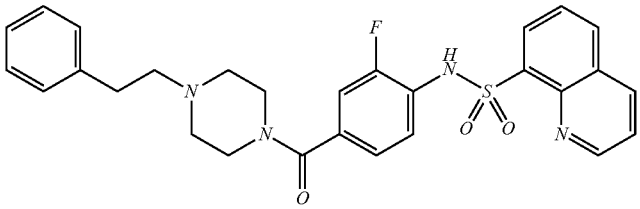
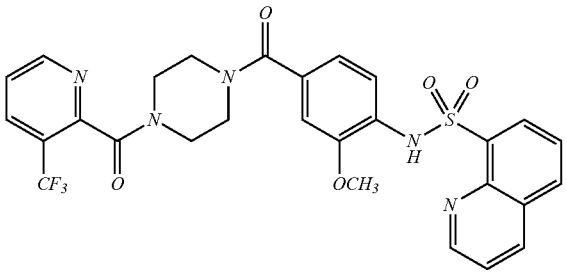
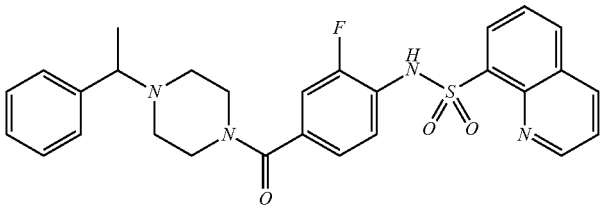
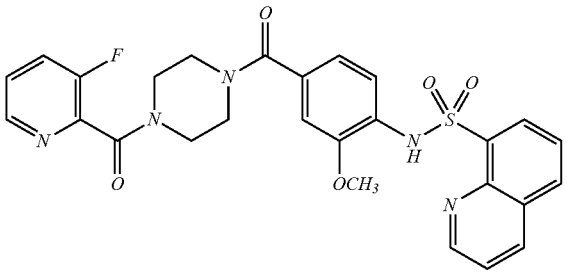
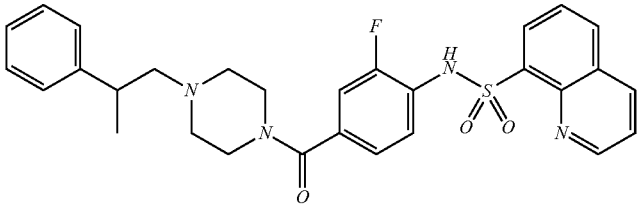
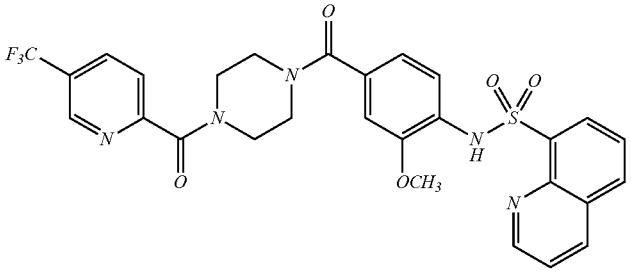
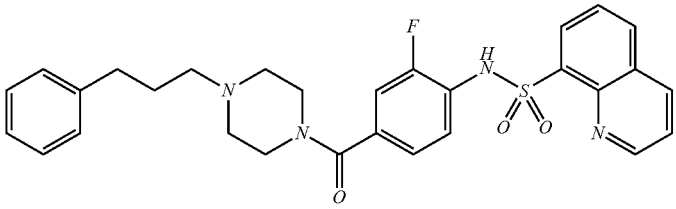

*-continued*
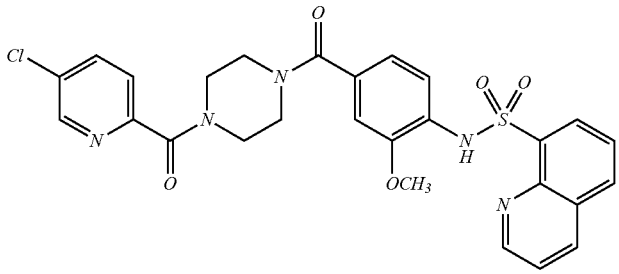
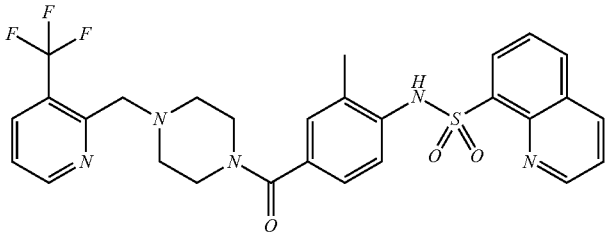
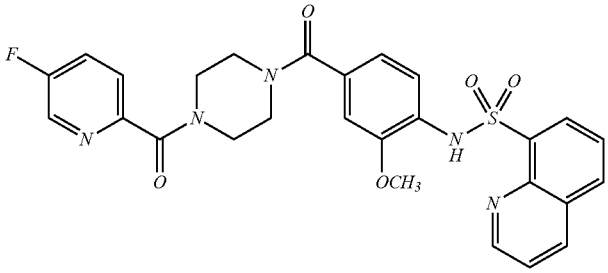
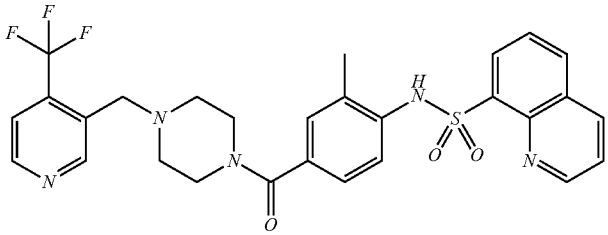
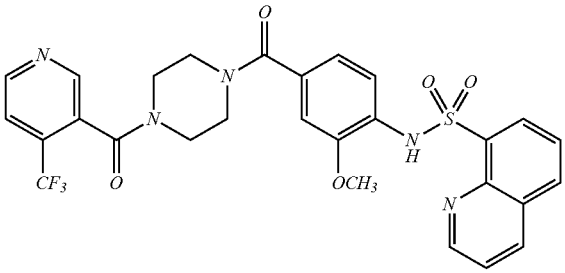
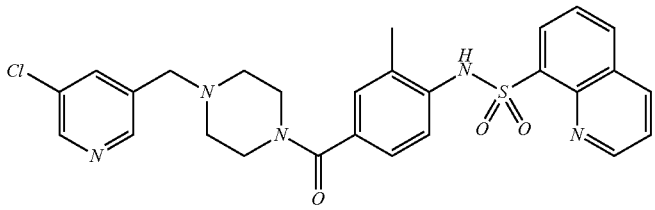
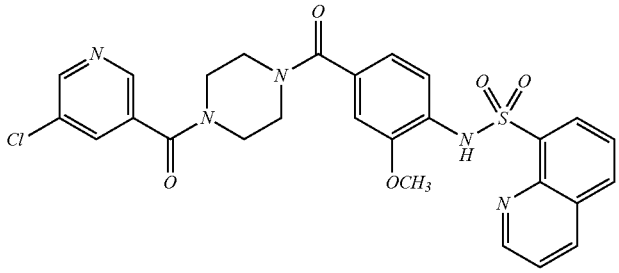

*-continued*
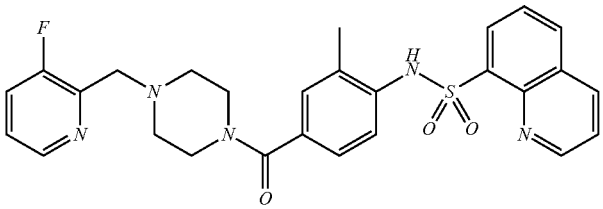
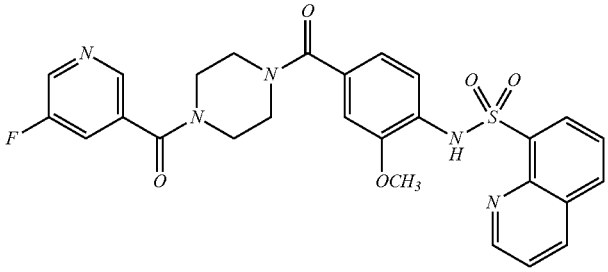
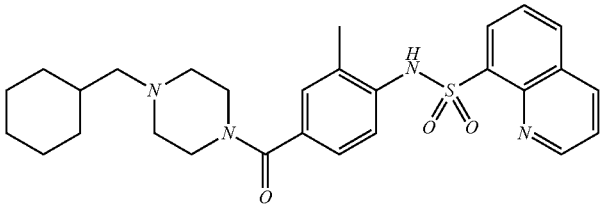
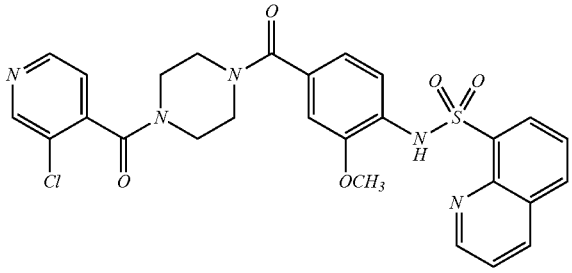
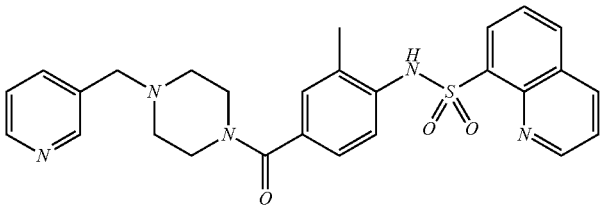
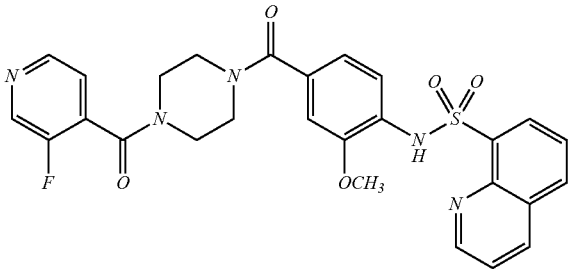
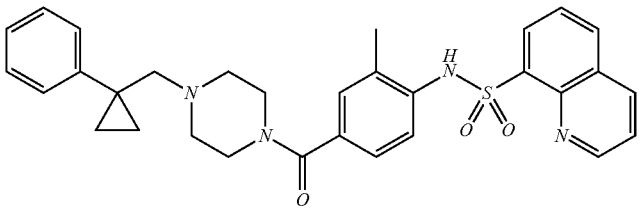
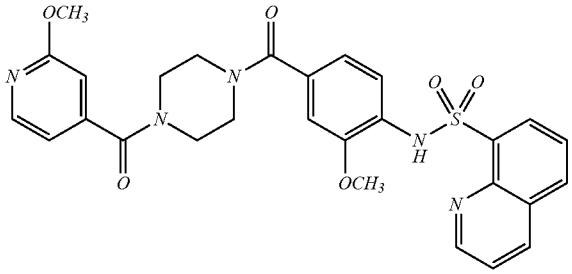
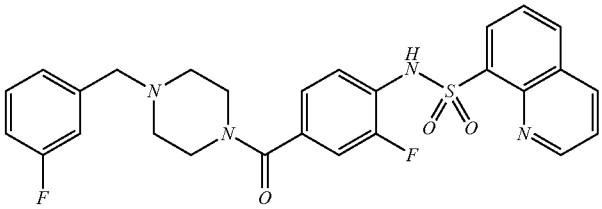

*-continued*
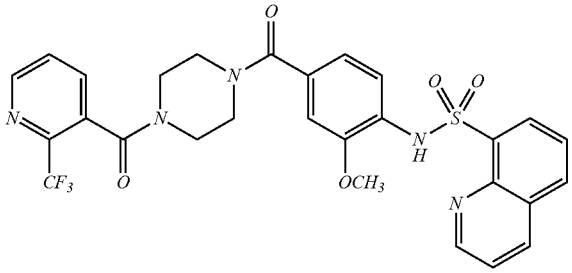
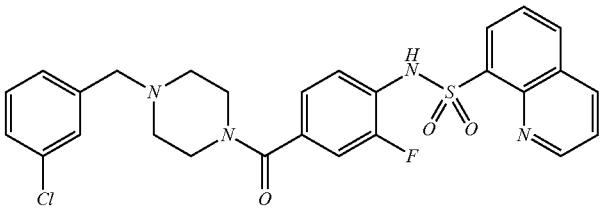
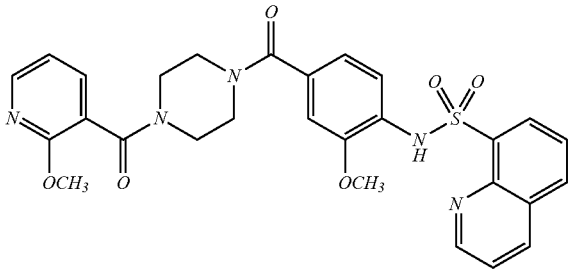
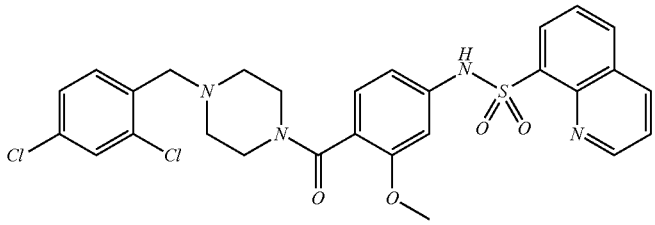
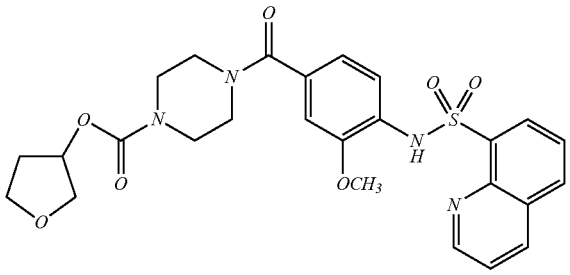
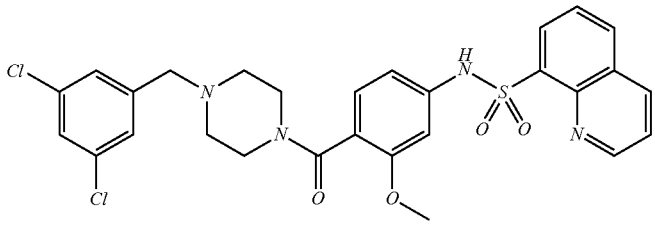
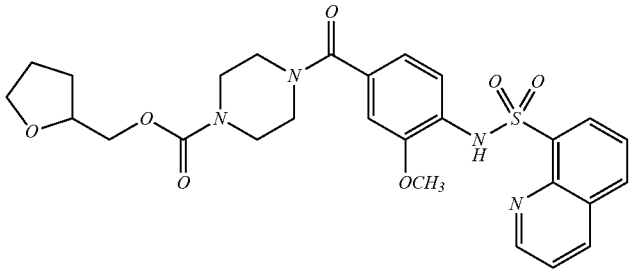

*-continued*
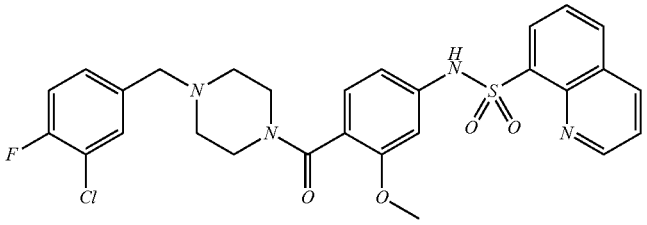
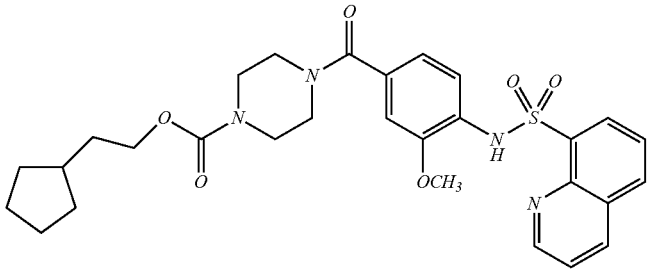
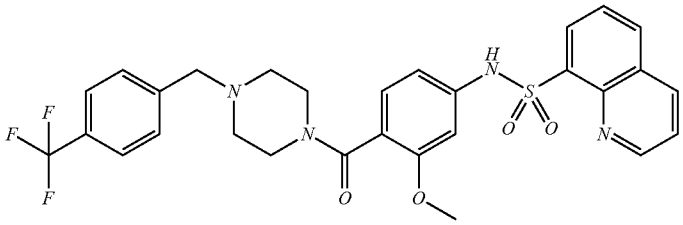
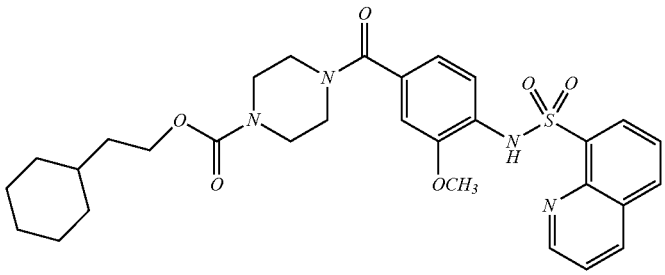
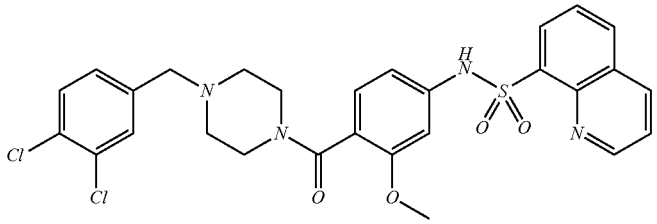
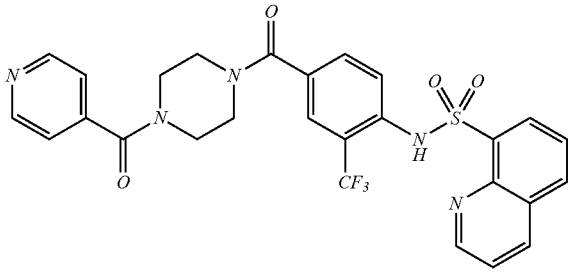
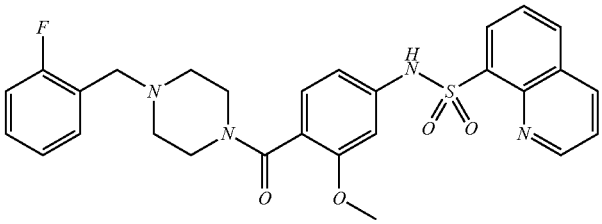

*-continued*
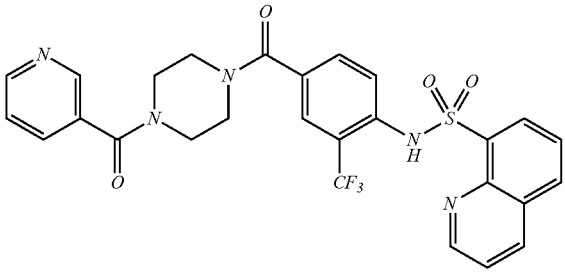
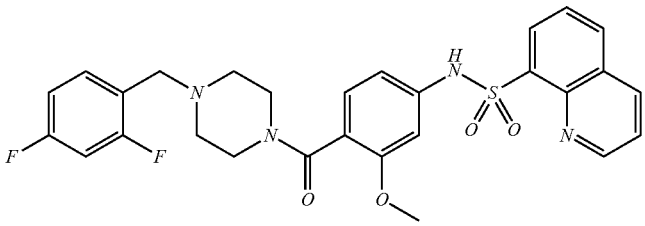
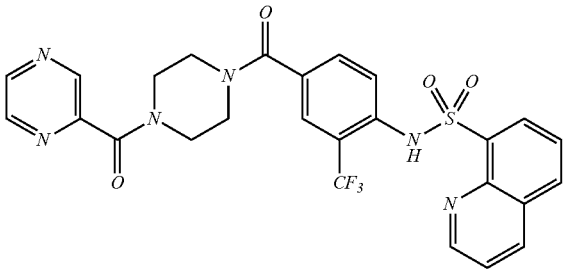
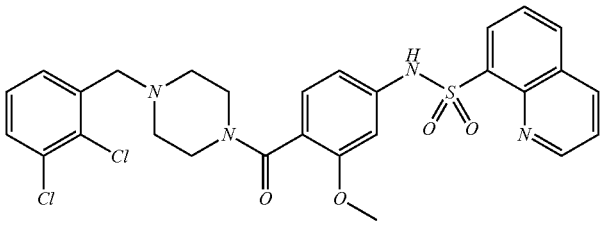
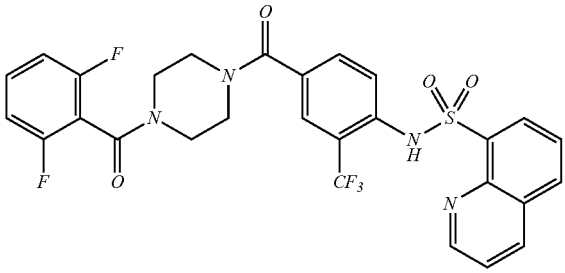
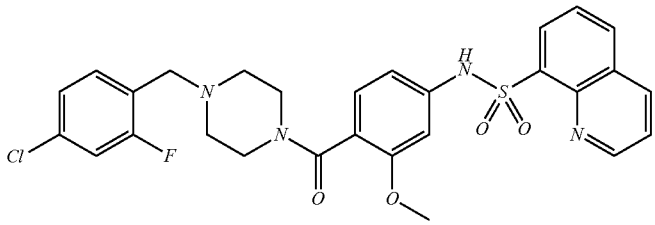
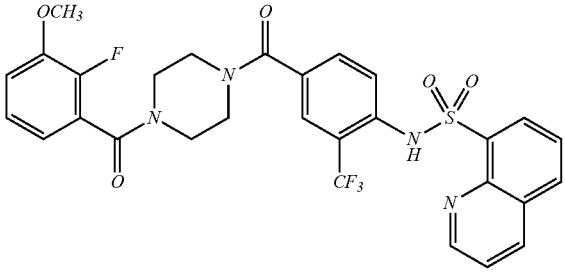
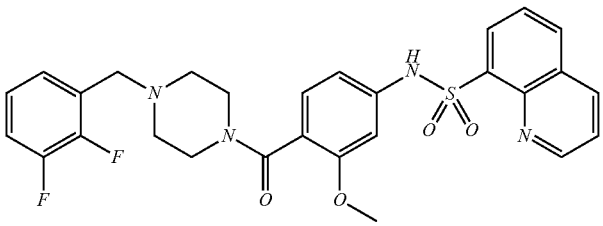

*-continued*
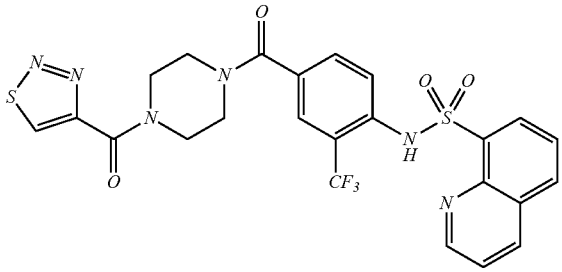
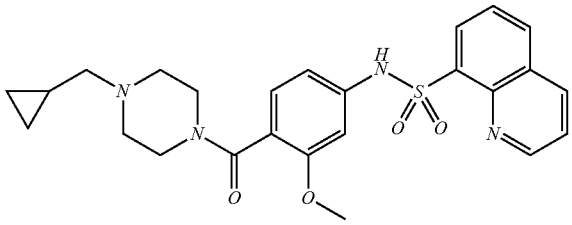
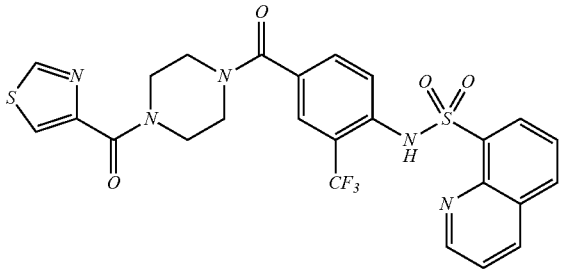
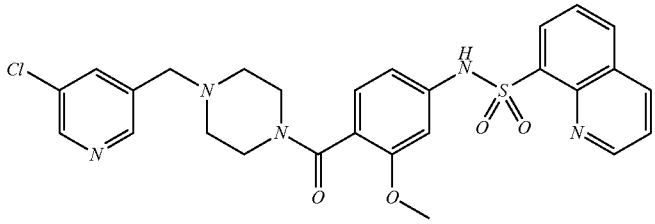
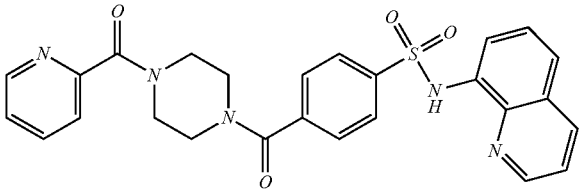
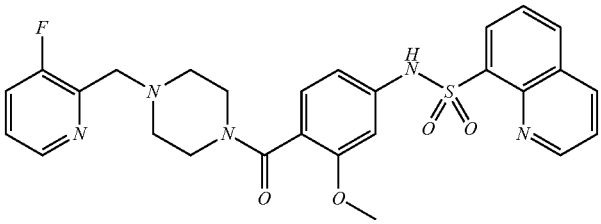
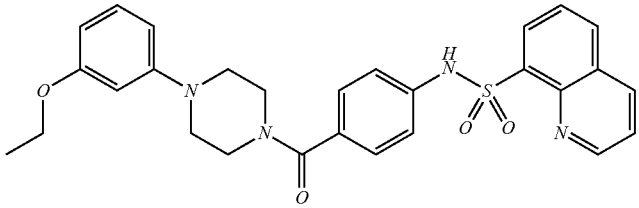
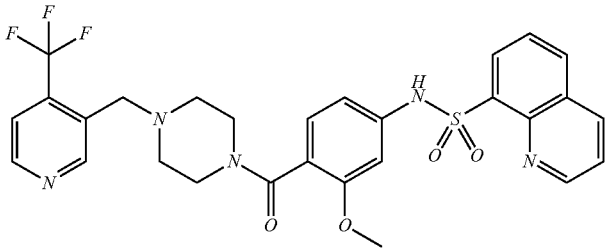
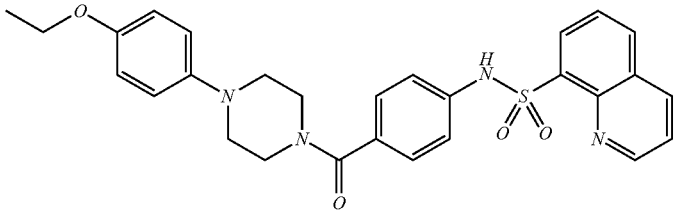

*-continued*
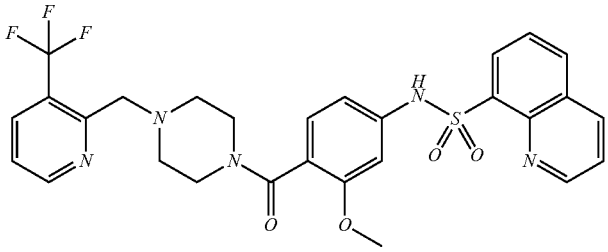
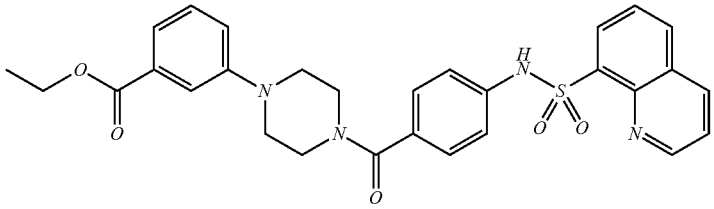
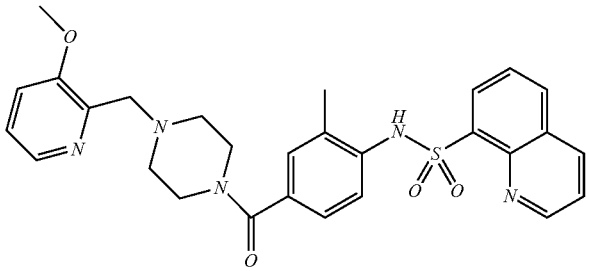
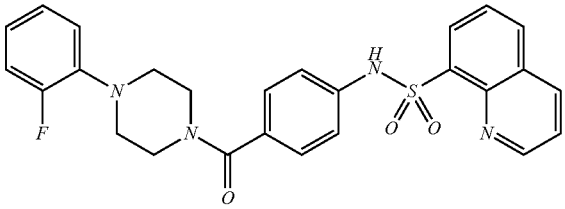
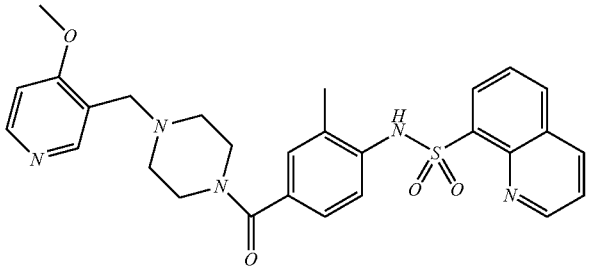
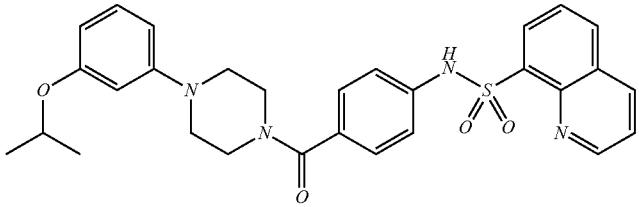
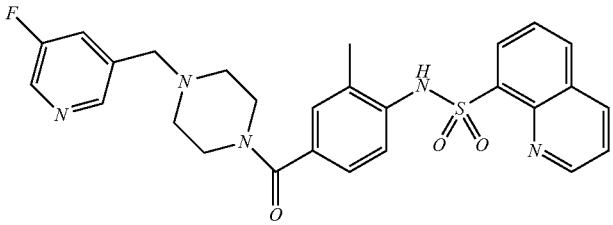
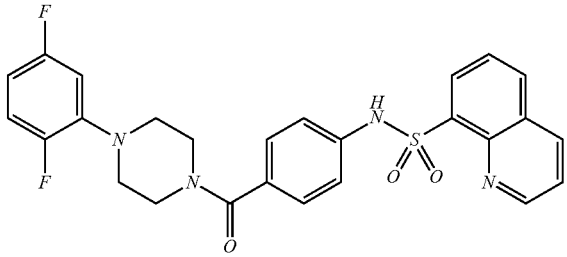
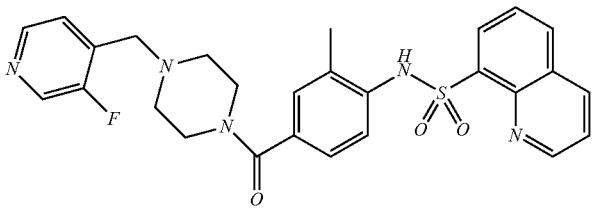

*-continued*
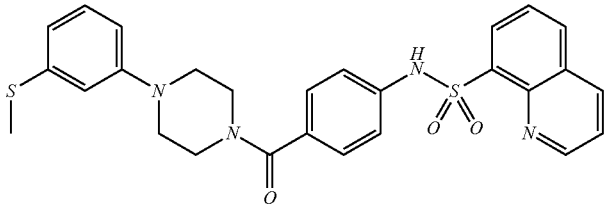
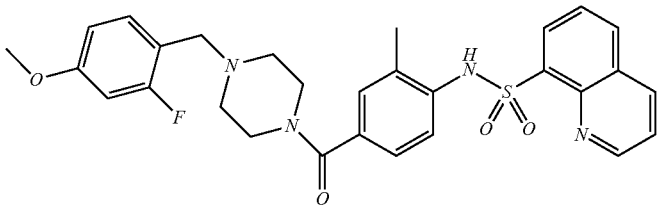
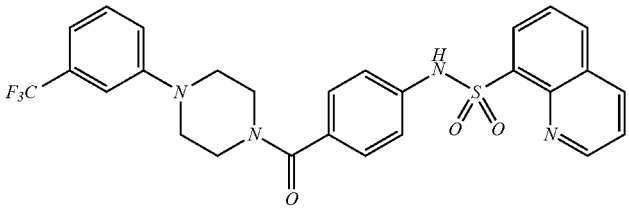
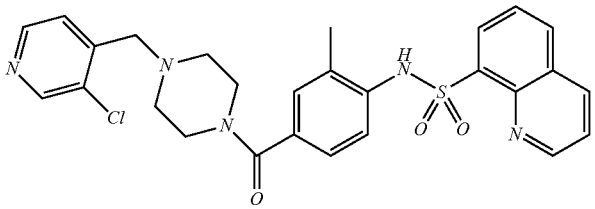
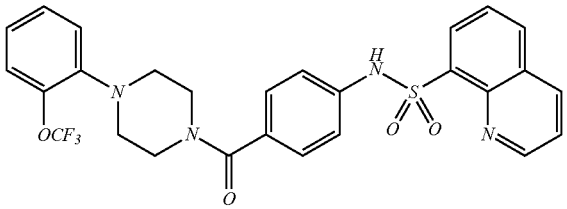
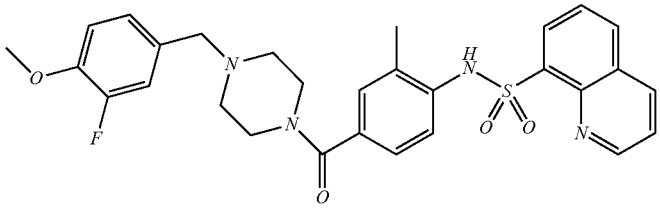
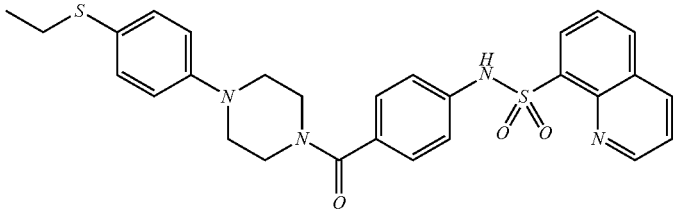
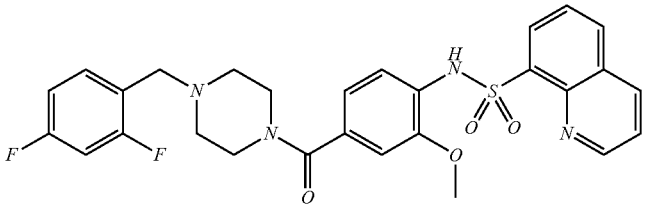
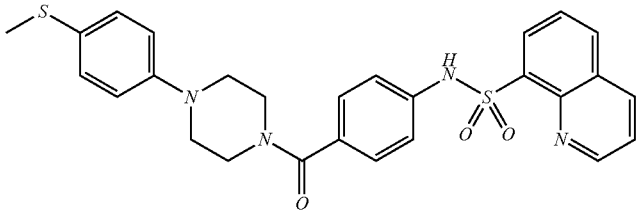

*-continued*
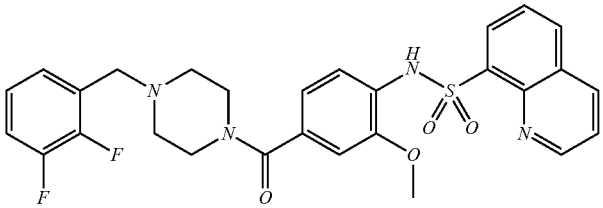
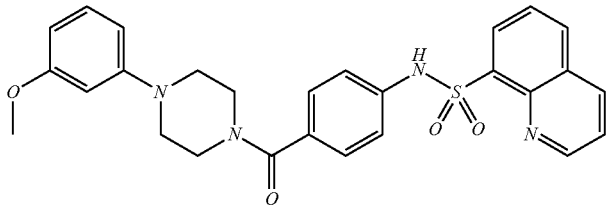
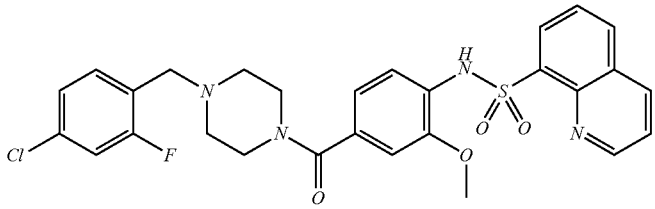
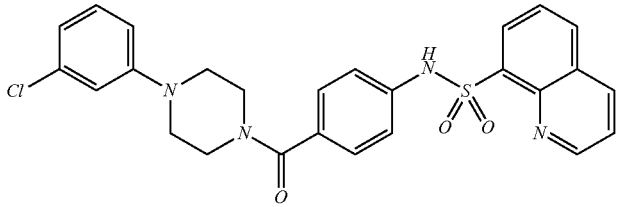
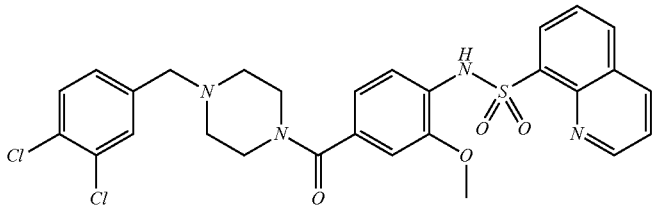
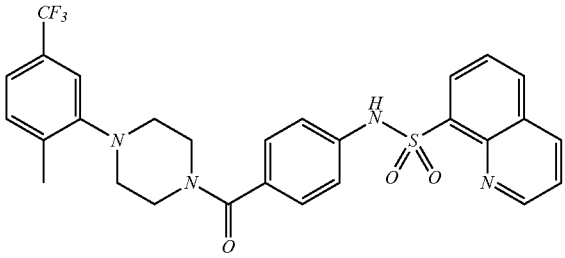
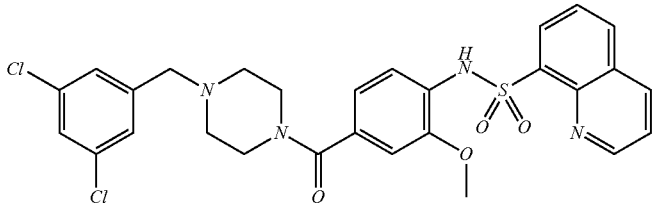

*-continued*
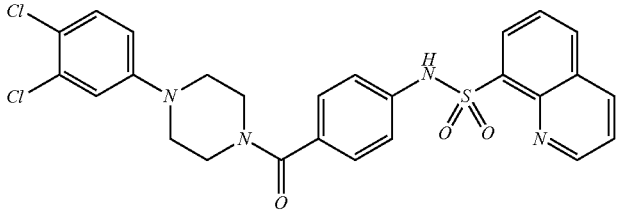
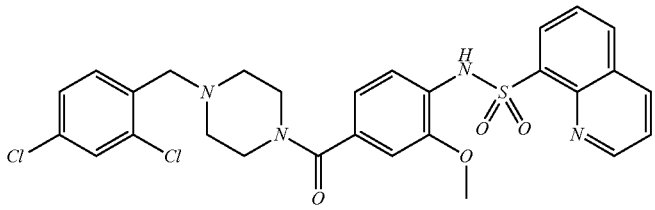
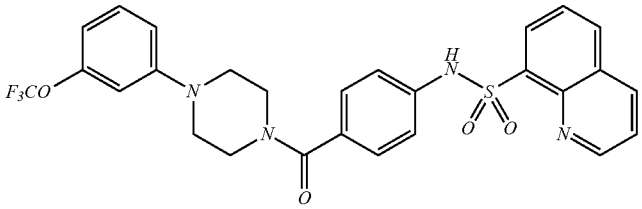
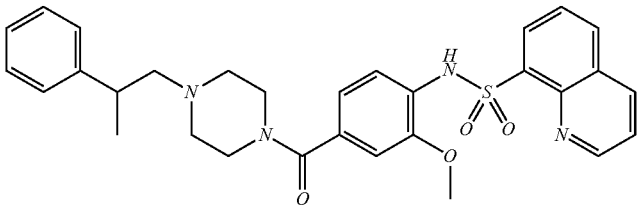
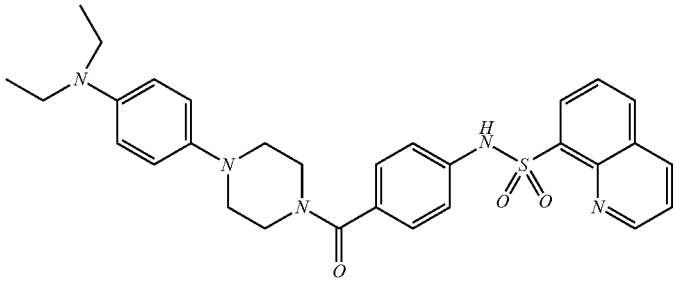
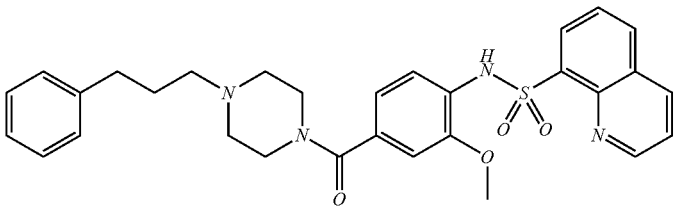
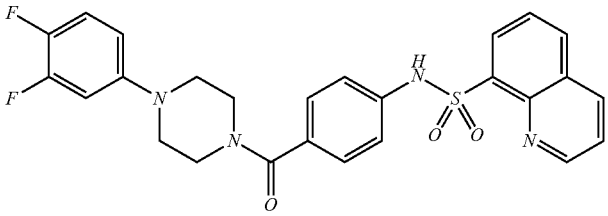

*-continued*
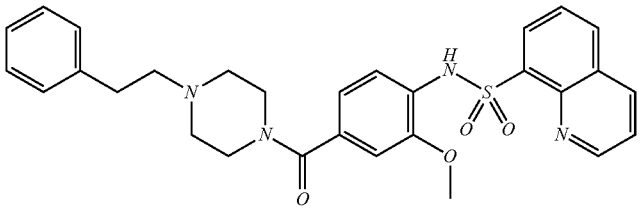
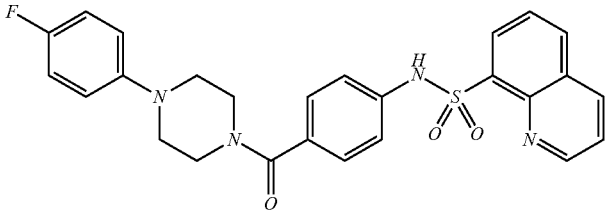
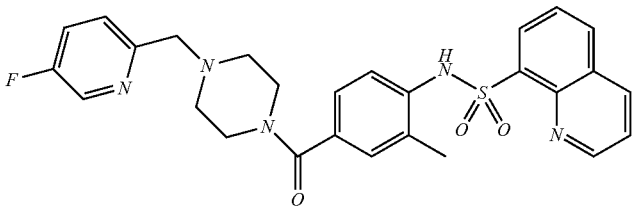
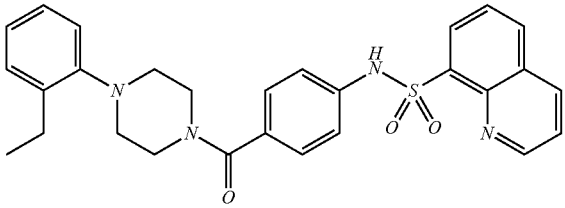
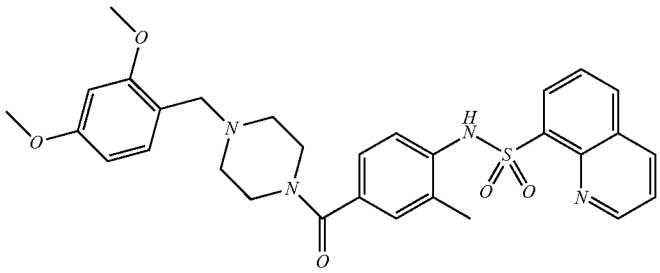
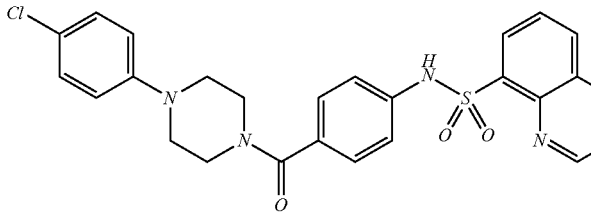
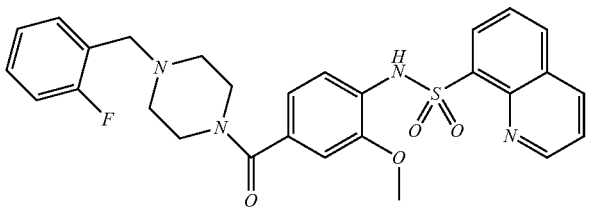
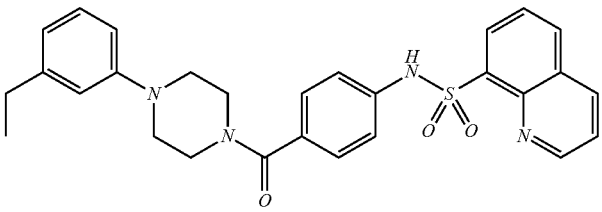

*-continued*
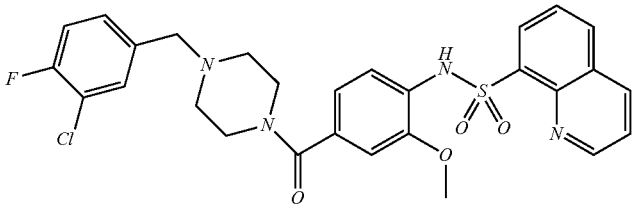
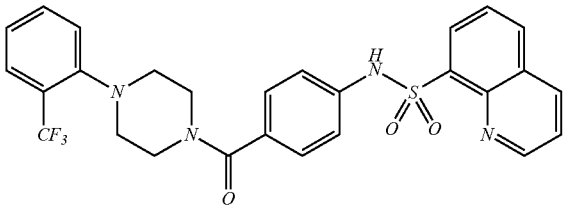
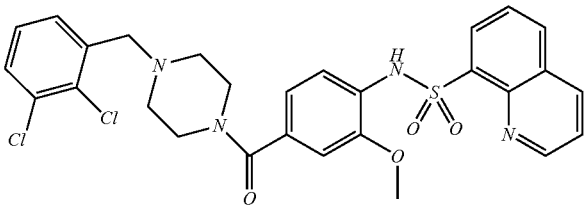
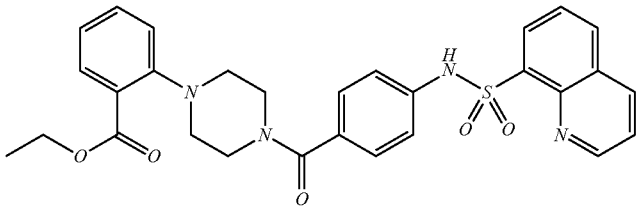
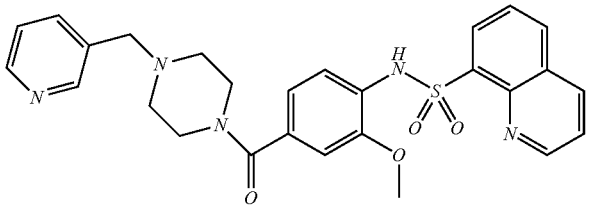
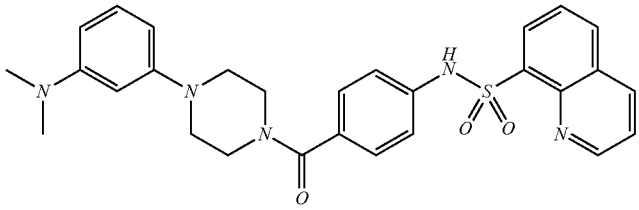
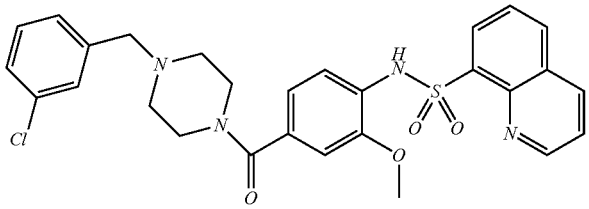
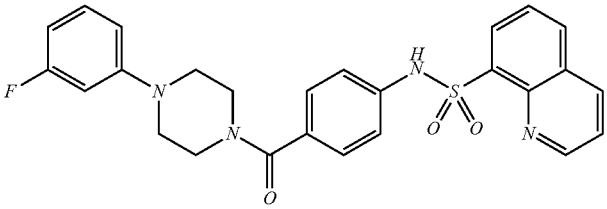
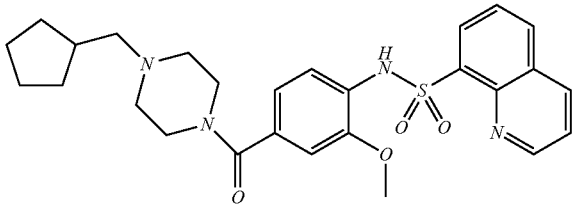
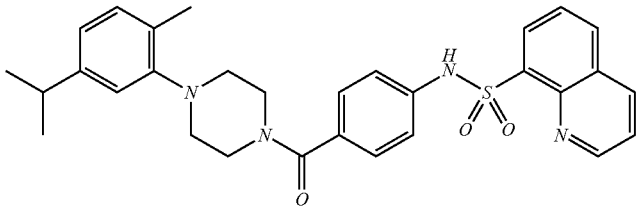

*-continued*
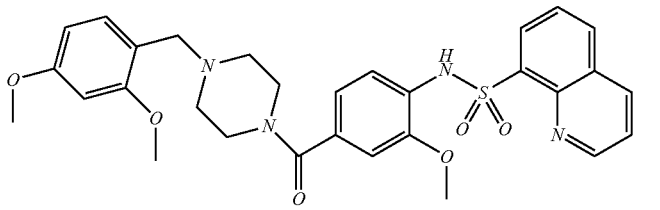
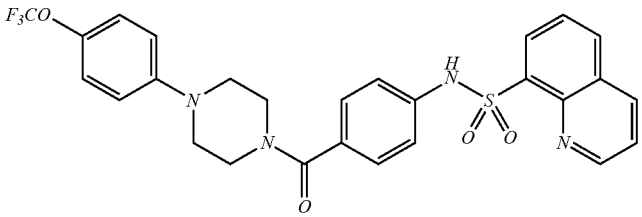
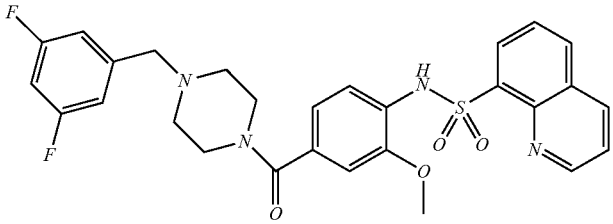
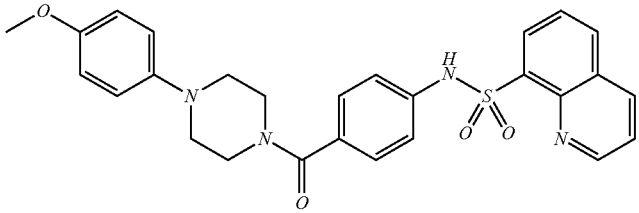
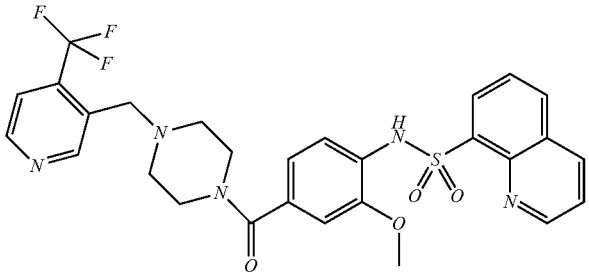
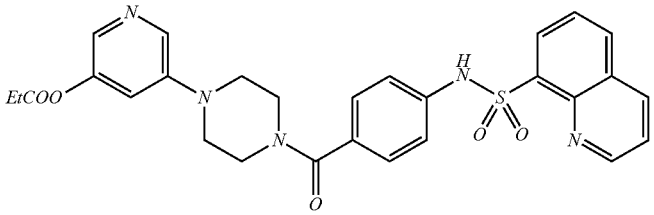
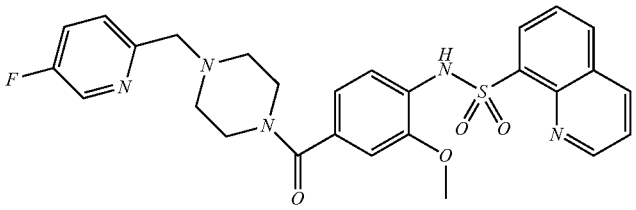

*-continued*
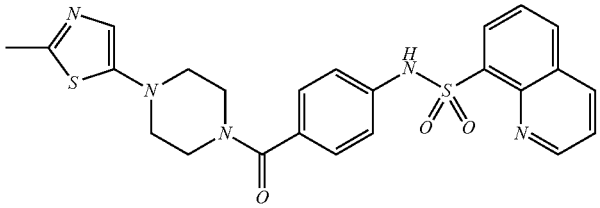
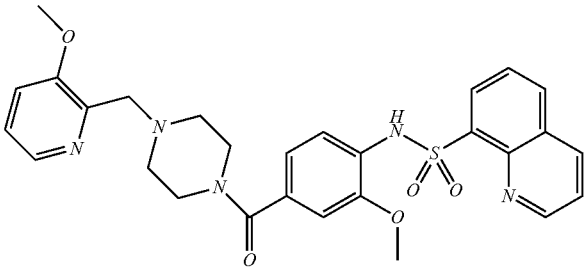
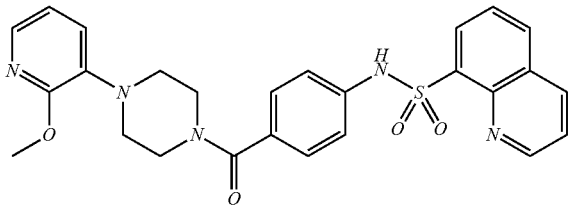
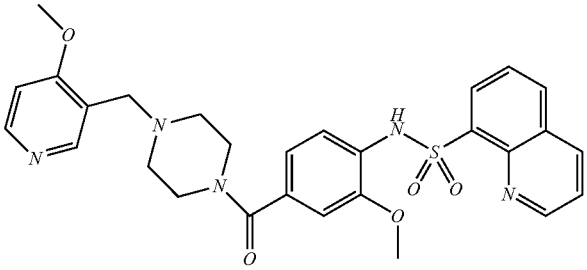
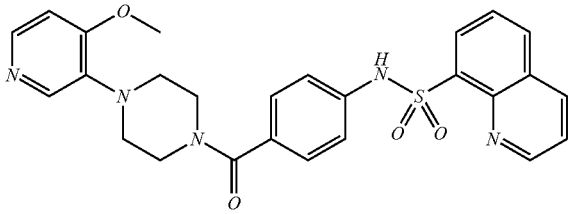
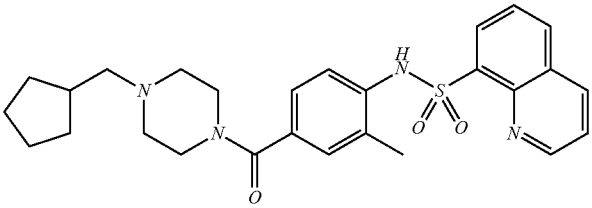
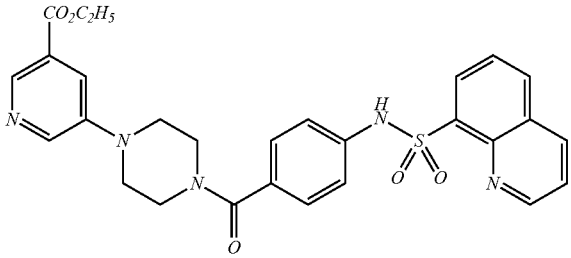
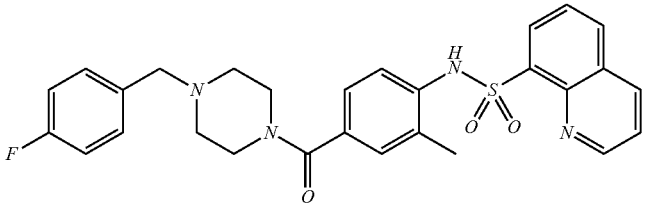
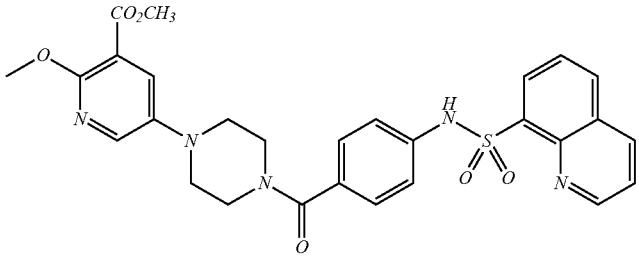
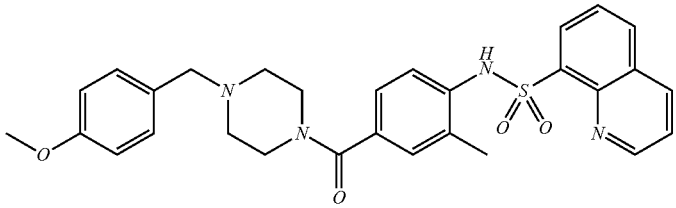

*-continued*
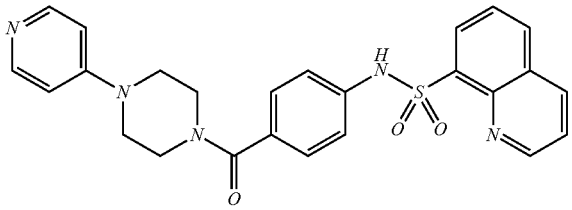
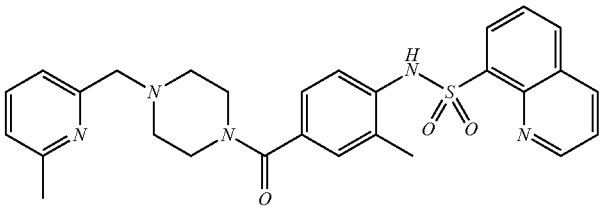
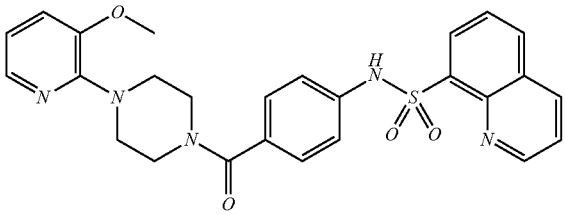
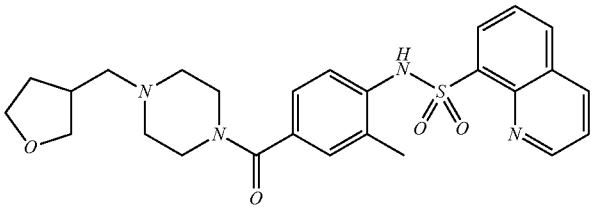
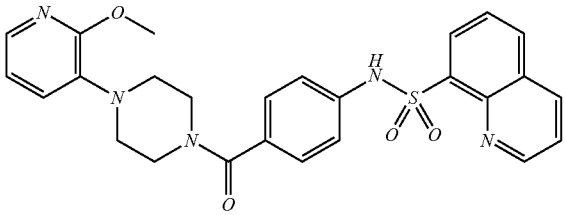
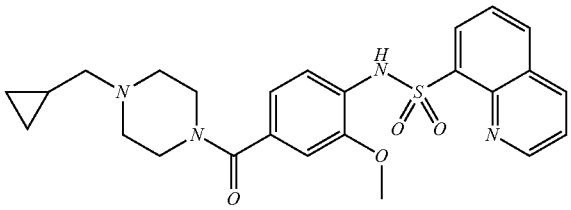
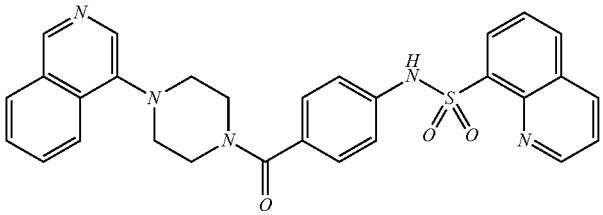
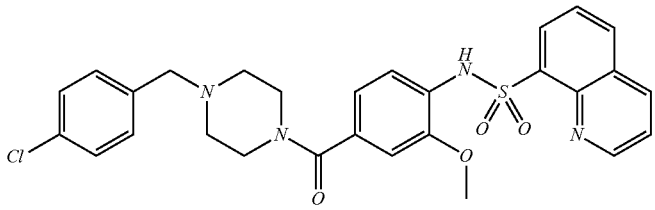
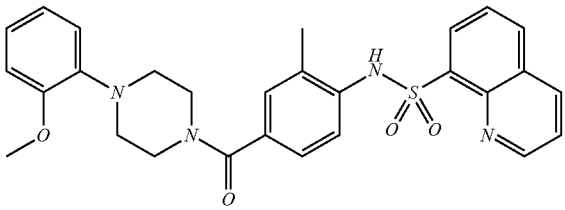
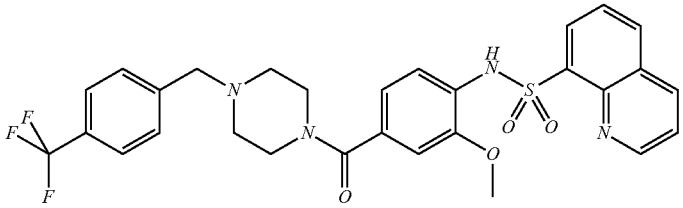

*-continued*
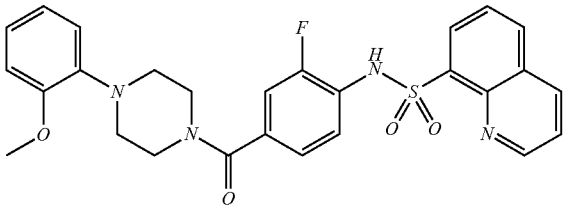
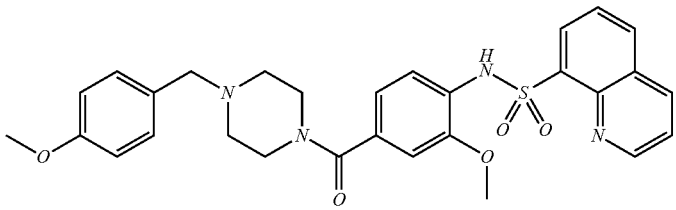
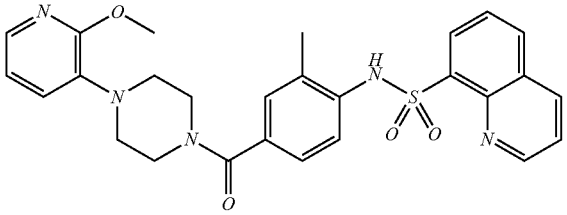
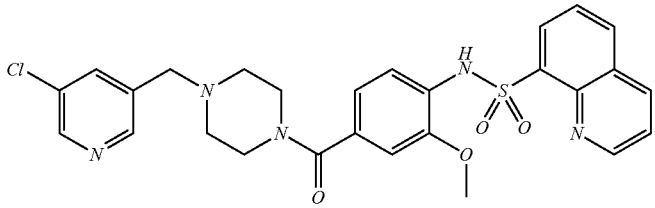
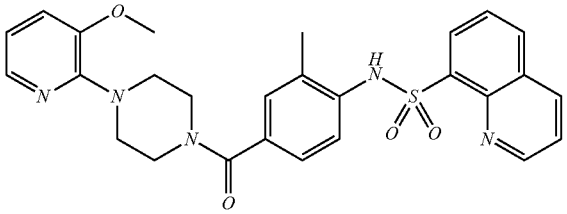
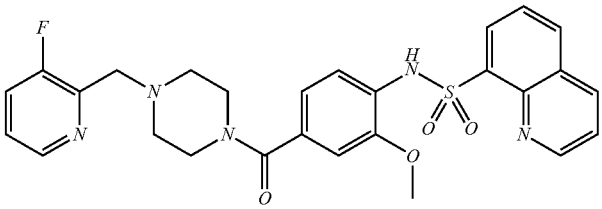
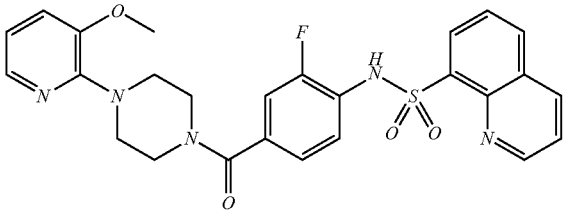
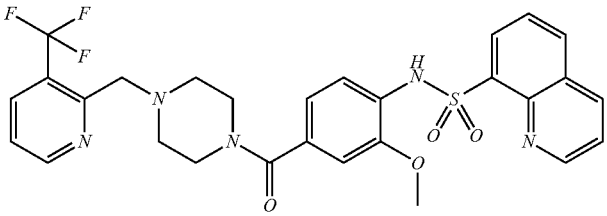
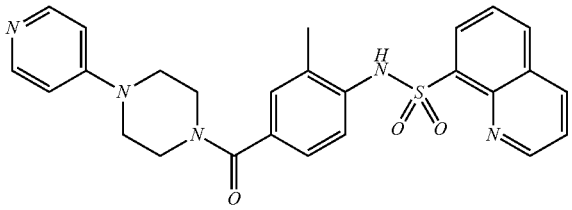
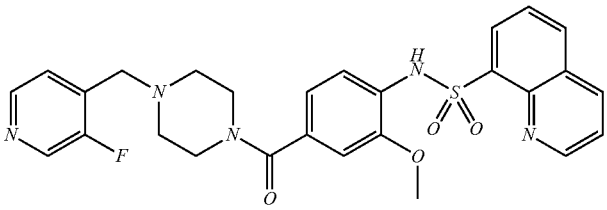
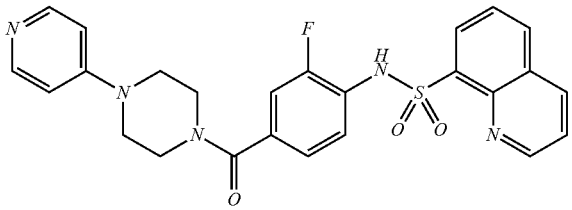

*-continued*
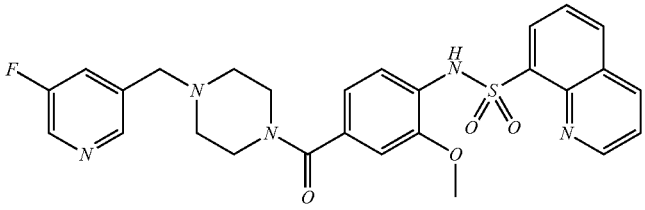
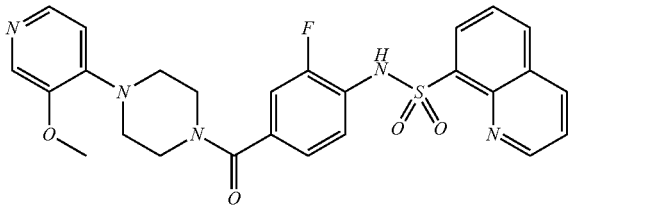
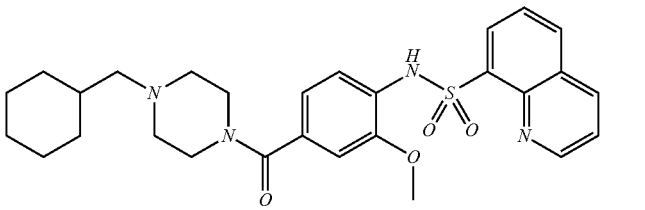
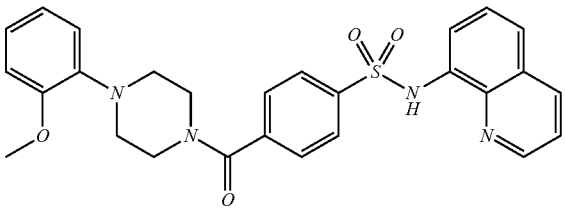
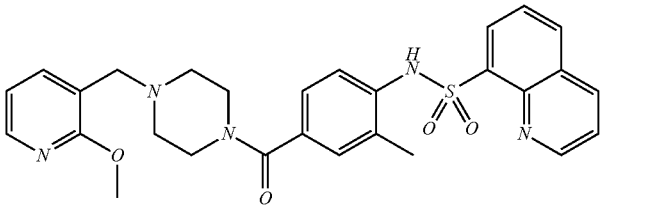
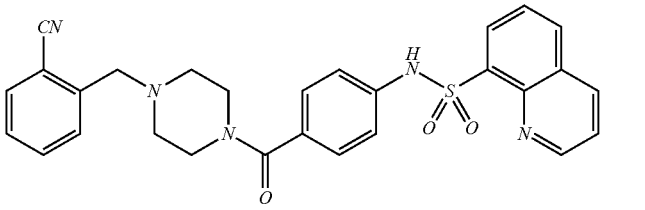
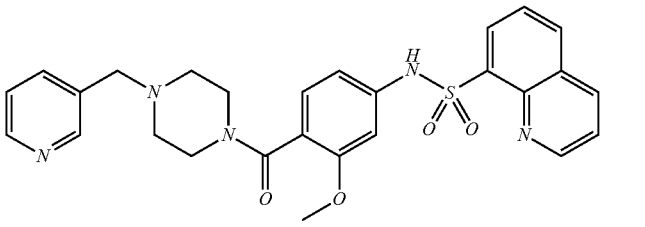
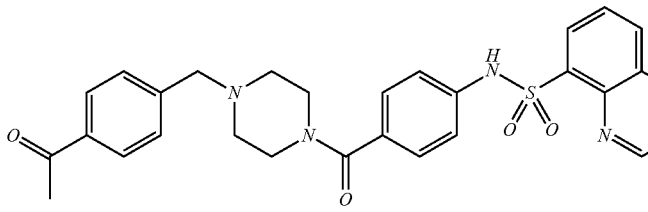
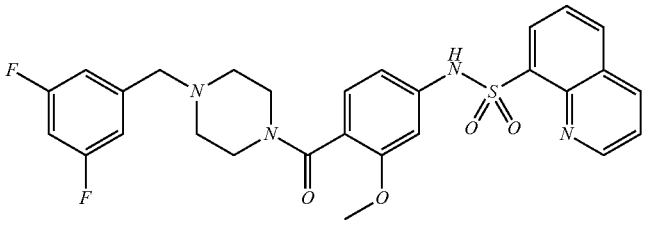

*-continued*
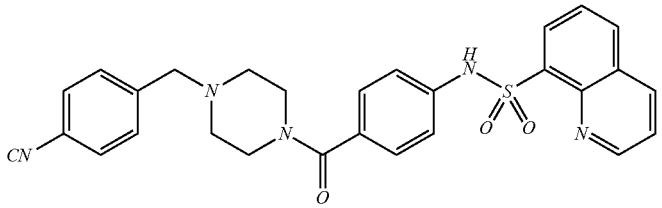
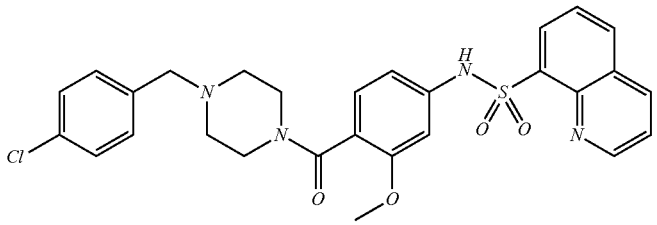
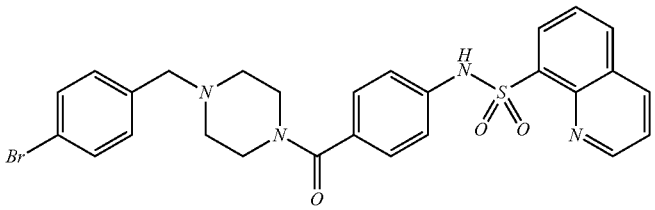
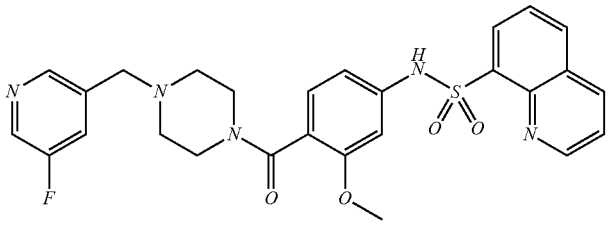
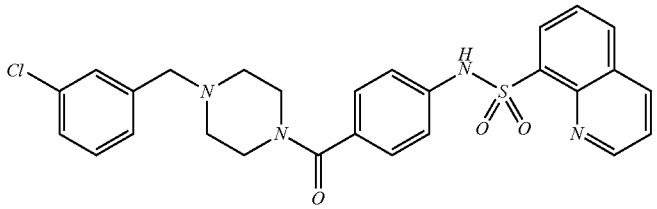
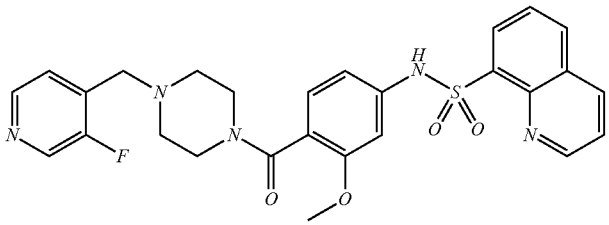
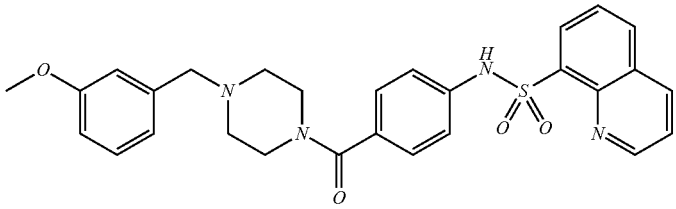

*-continued*
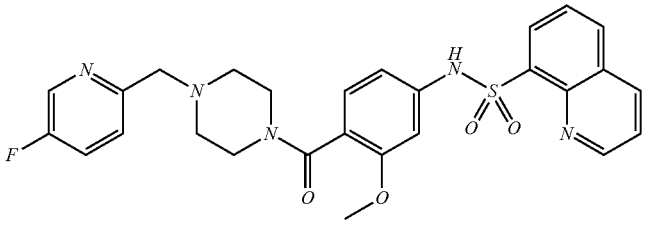
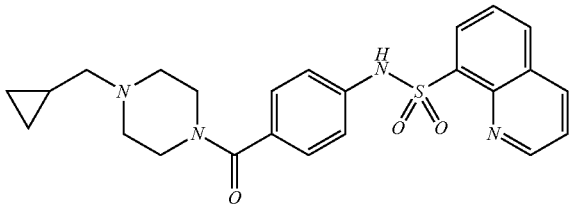
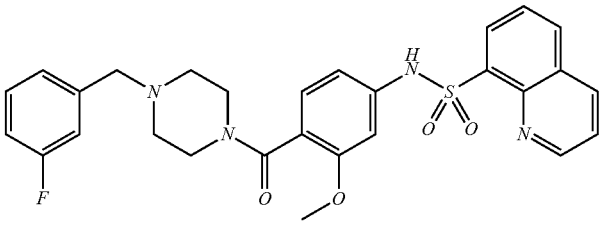
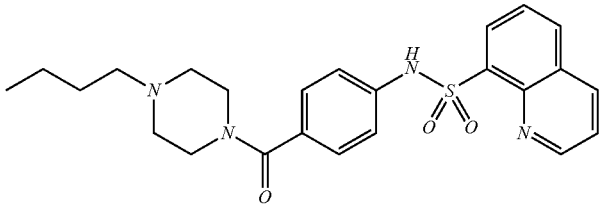
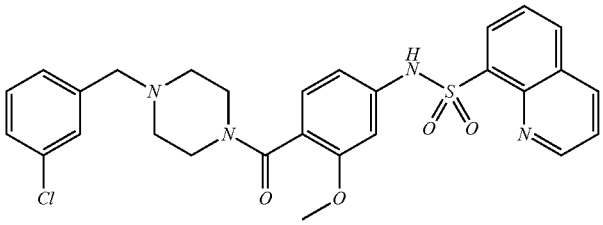
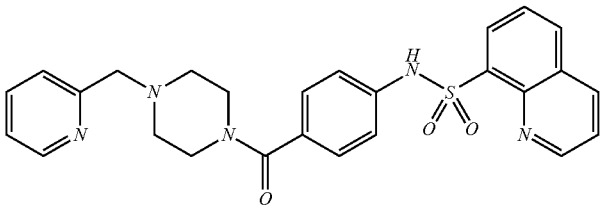
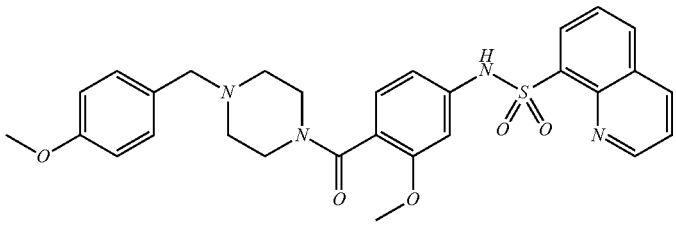
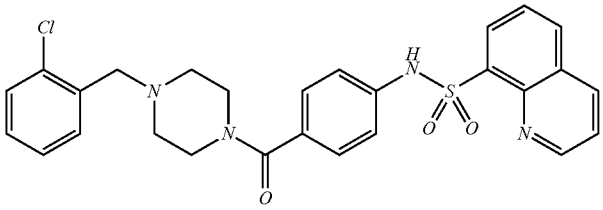

*-continued*
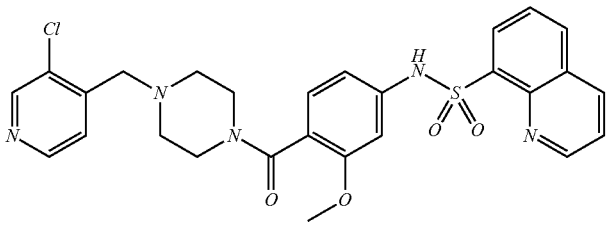
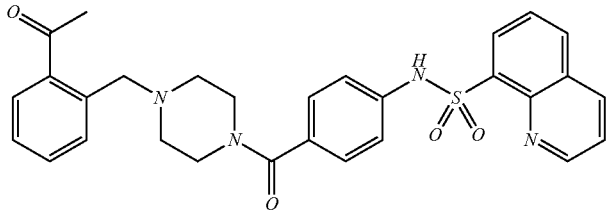
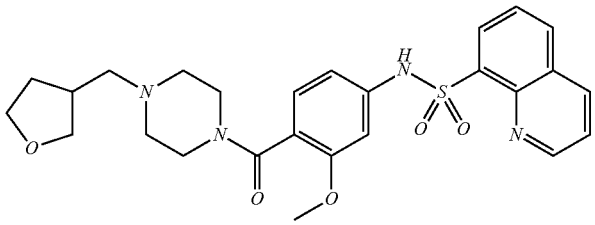
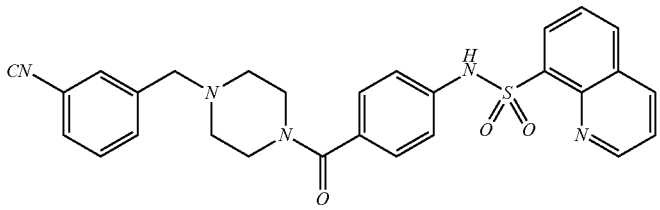
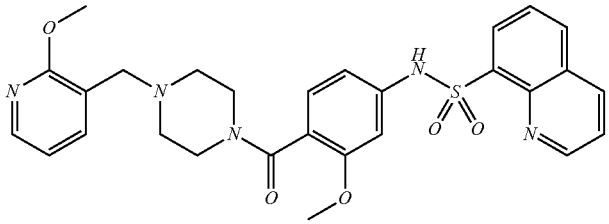
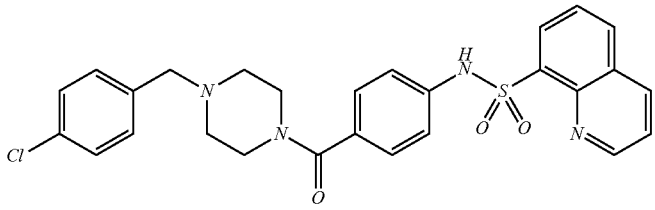
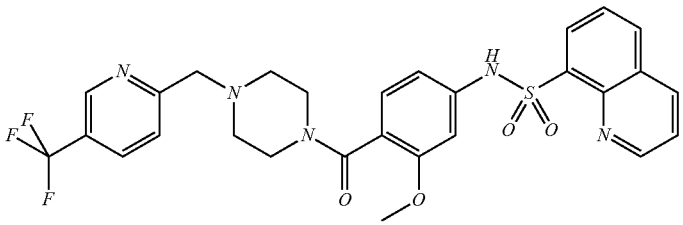

*-continued*
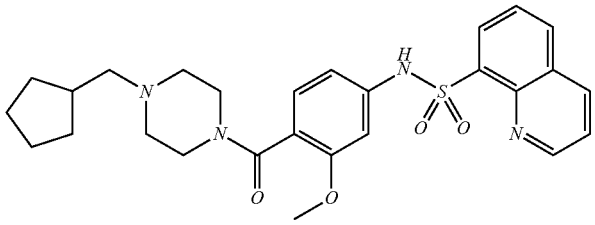
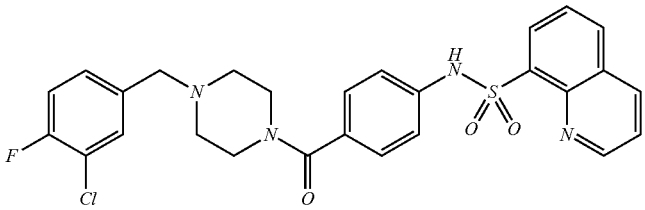
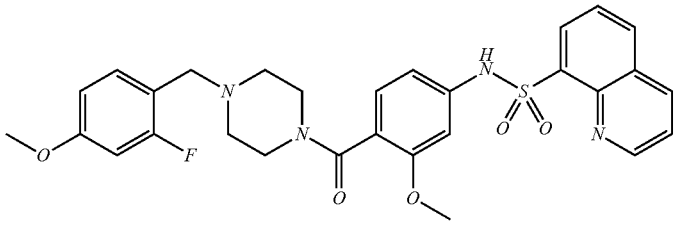
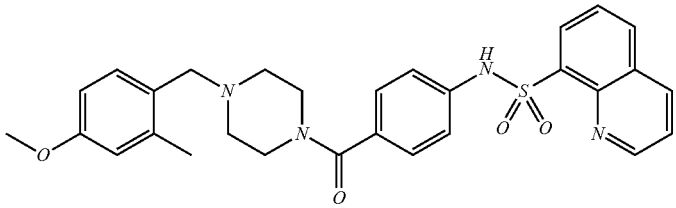
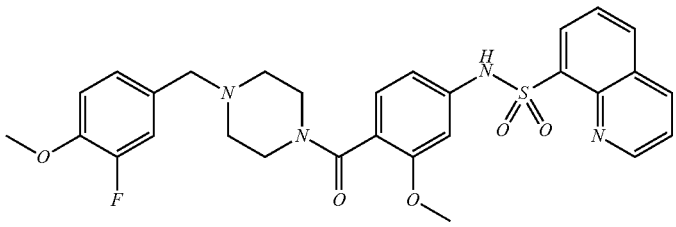
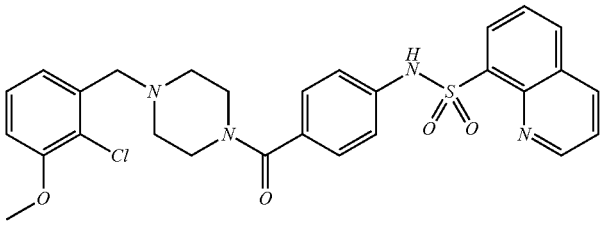
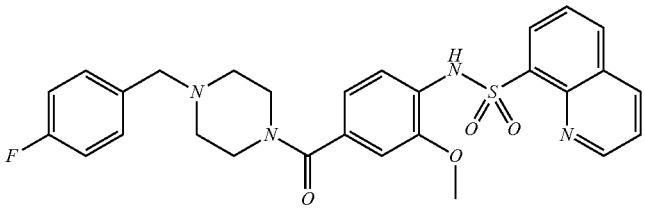

*-continued*
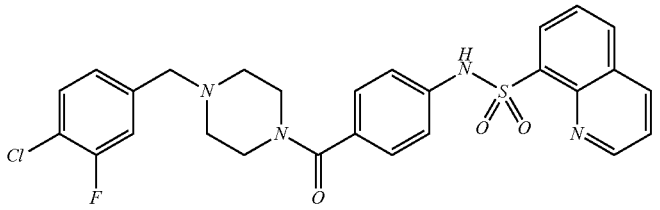
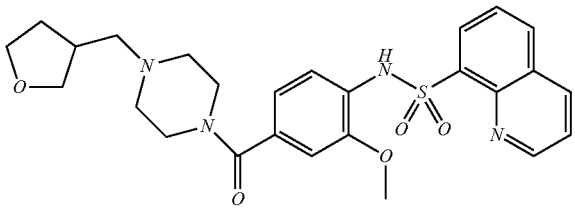
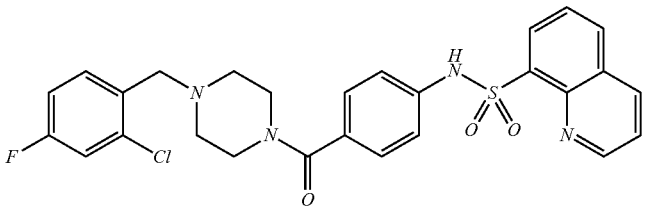
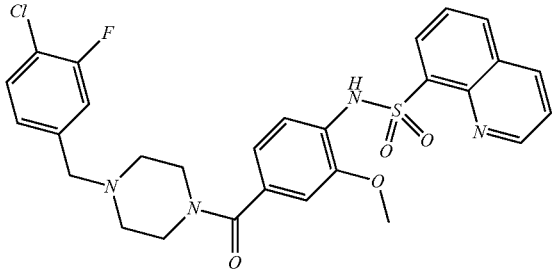
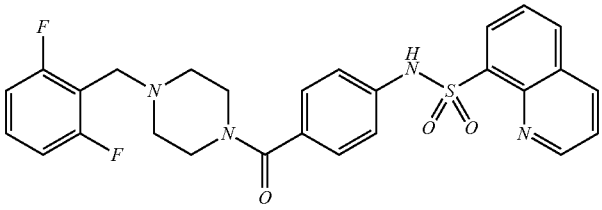
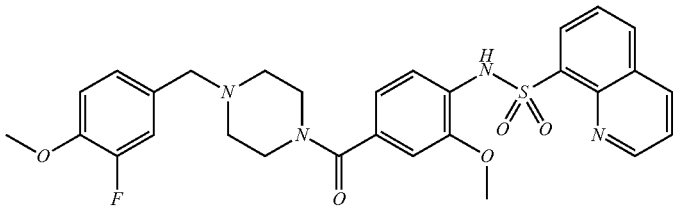
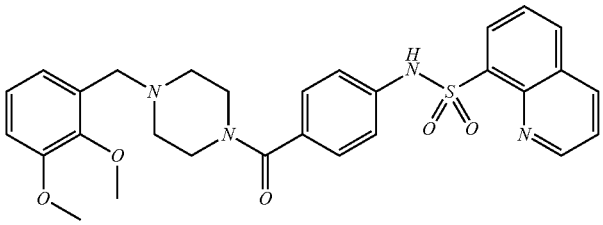
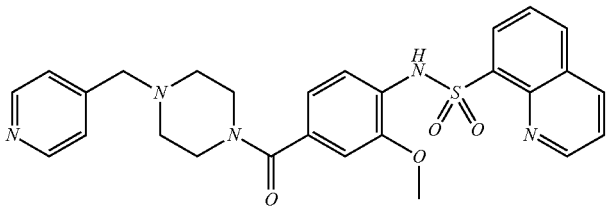

*-continued*
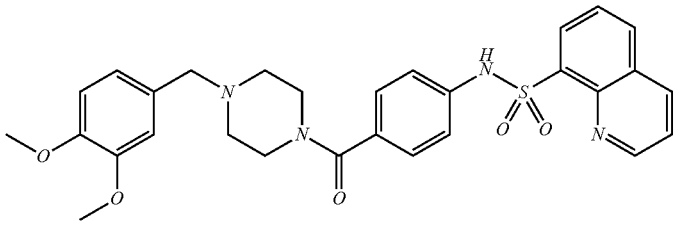
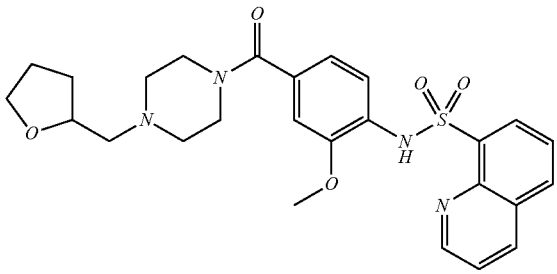
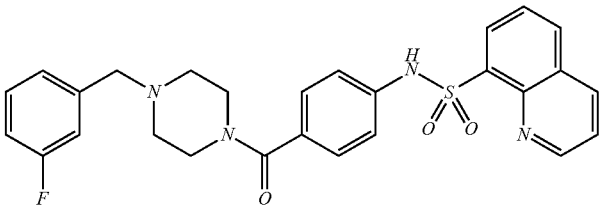
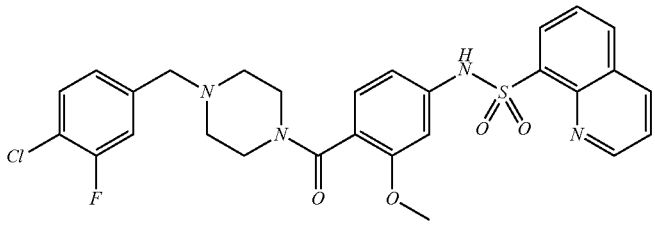
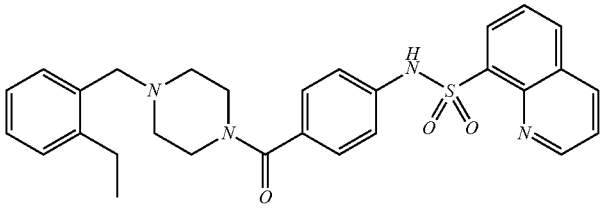
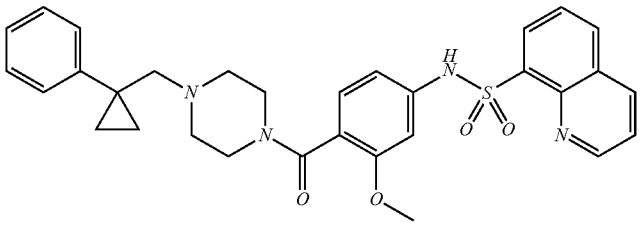
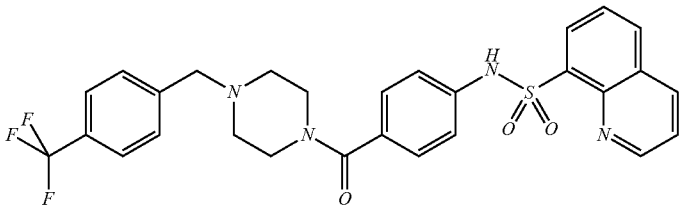
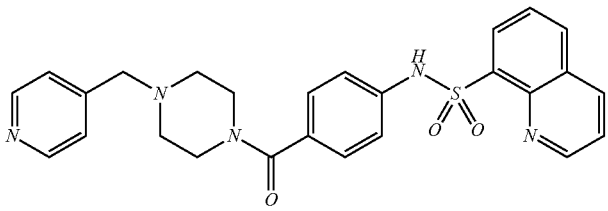

*-continued*
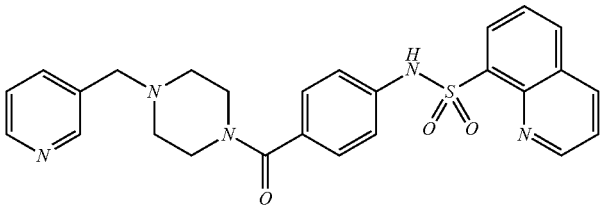
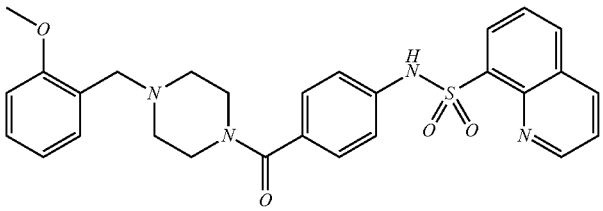
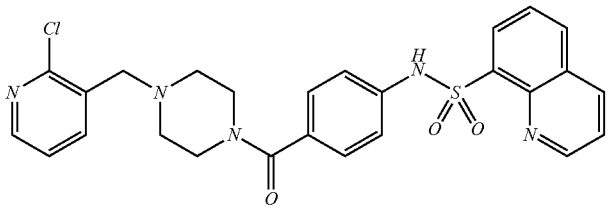
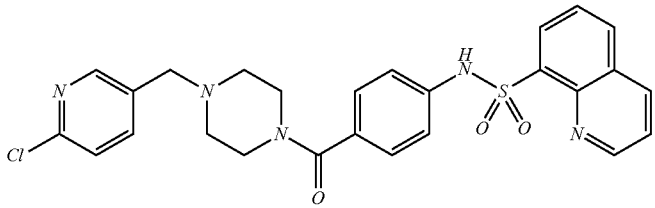
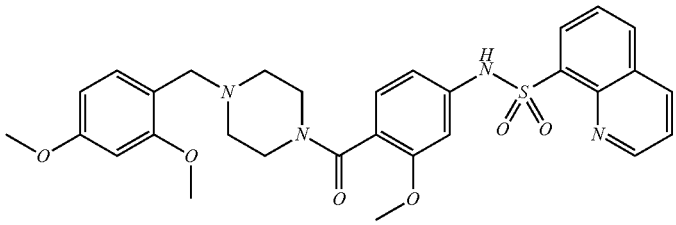
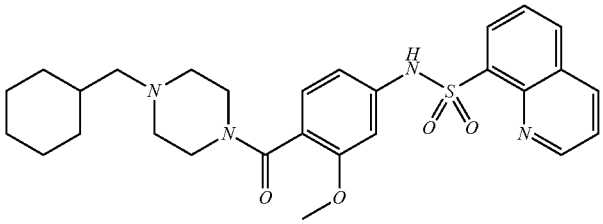
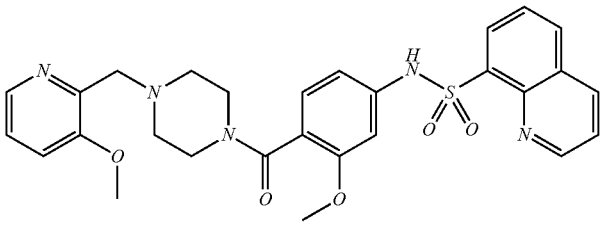

*-continued*
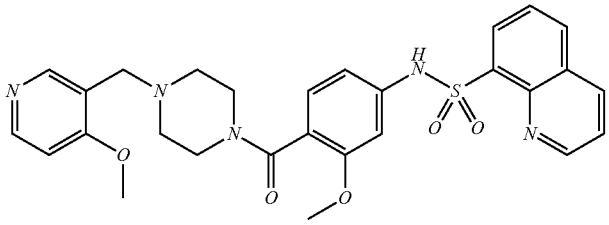
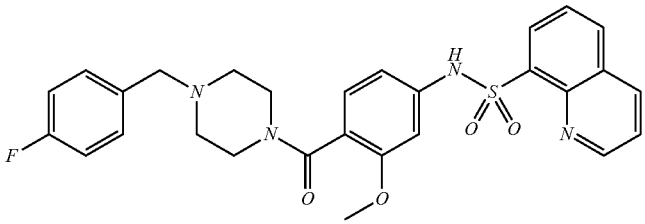
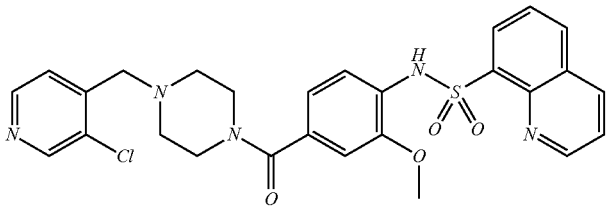
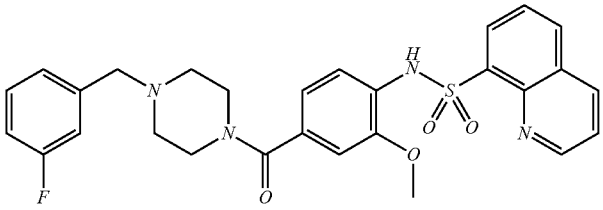
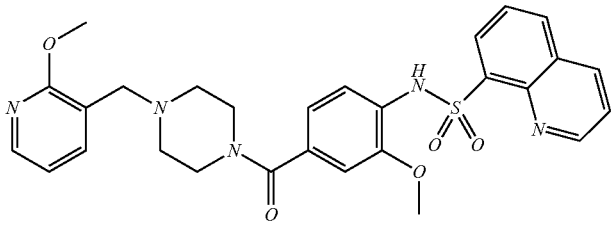
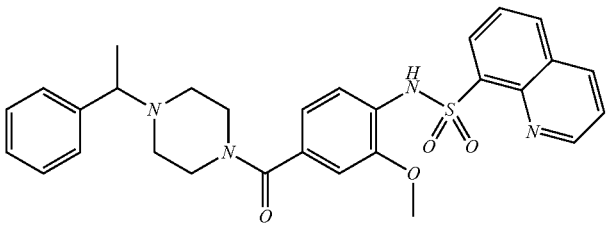
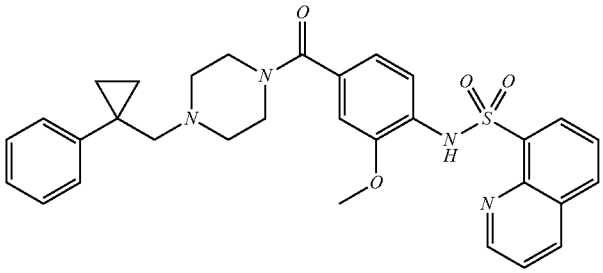

*-continued*

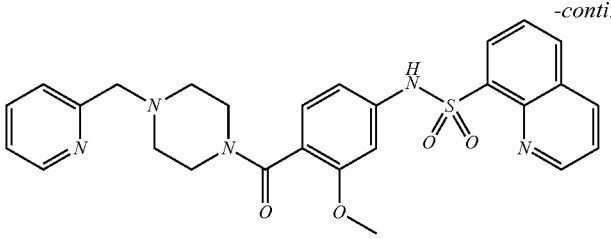

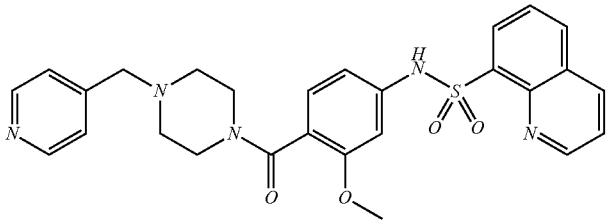

, *and*

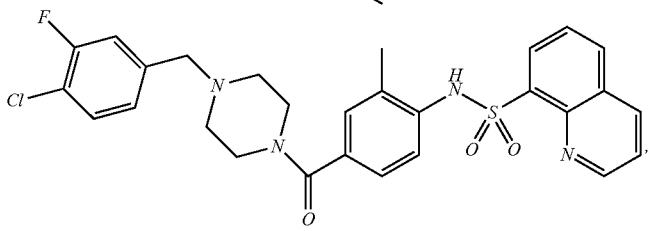

, or a pharmaceutically acceptable salt thereof.

*52. A pharmaceutically acceptable salt of the compound:*

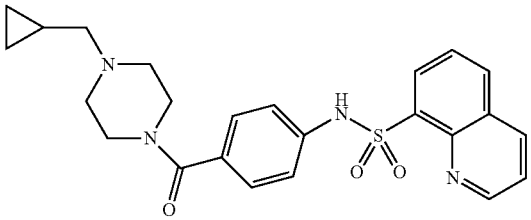

.

*53. A compound or a pharmaceutically acceptable salt thereof, wherein the compound is:*

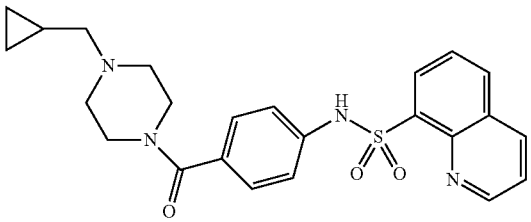

.

*54. A pharmaceutical composition comprising a pharmaceutically acceptable salt of the compound:*

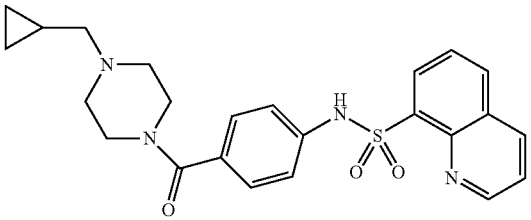

.

*55. A pharmaceutical composition comprising a compound or a pharmaceutically acceptable salt thereof, wherein the compound is:*

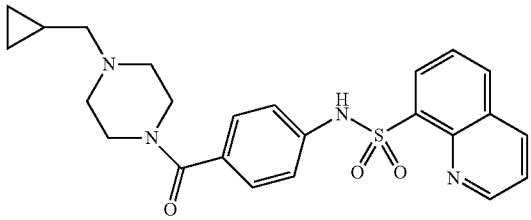

.

*56. The pharmaceutical composition of claim 54 further comprising a pharmaceutically acceptable carrier.*

*57. The pharmaceutical composition of claim 55 further comprising a pharmaceutically acceptable carrier.*

* * * * *